United States Patent
Kubo et al.

(10) Patent No.: US 9,586,951 B2
(45) Date of Patent: Mar. 7, 2017

(54) MORPHOLINE DERIVATIVE OR SALT THEREOF

(71) Applicant: FUJIFILM Corporation, Tokyo (JP)

(72) Inventors: Yohei Kubo, Kanagawa (JP); Makoto Ando, Kanagawa (JP); Hidehiko Tanaka, Kanagawa (JP); Shuhei Osaka, Kanagawa (JP); Takuya Matsumoto, Kanagawa (JP); Hiyoku Nakata, Kanagawa (JP); Daisuke Terada, Kanagawa (JP); Tatsuya Nitabaru, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/052,252

(22) Filed: Feb. 24, 2016

(65) Prior Publication Data

US 2016/0168139 A1 Jun. 16, 2016

Related U.S. Application Data

(63) Continuation of application No. PCT/JP2014/072445, filed on Aug. 27, 2014.

(30) Foreign Application Priority Data

Aug. 29, 2013 (JP) .................. 2013-177934

(51) Int. Cl.
*C07D 413/14* (2006.01)
*C07D 401/14* (2006.01)
(Continued)

(52) U.S. Cl.
CPC ........ *C07D 413/14* (2013.01); *A61K 31/5377* (2013.01); *A61K 31/5383* (2013.01);
(Continued)

(58) Field of Classification Search
None
See application file for complete search history.

(56) References Cited

U.S. PATENT DOCUMENTS

| 2004/0002492 | A1 | 1/2004 | Murray Smith et al. |
| 2005/0054657 | A1 | 3/2005 | Smith et al. |
| 2009/0043091 | A1* | 2/2009 | Smith .......... C07D 409/04 540/575 |

FOREIGN PATENT DOCUMENTS

| JP | 2005-521689 A | 7/2005 |
| JP | 2007-501836 A | 2/2007 |

(Continued)

OTHER PUBLICATIONS

Bakkenist et al., "DNA damage activates ATM through intermolecular autophosphorylation and dimer dissociation", Nature, Jan. 30, 2003, vol. 421, pp. 499-506.
Daniel et al., "Wortmannin Potentiates Integrase-Mediated Killing of Lymphocytes and Reduces the Efficiency of Stable Transduction by Retroviruses", Molecular and Cellular Biology, Feb. 2001, vol. 21, No. 4, pp. 1164-1172.
Gaudio et al., "Tcl1 interacts with Atm and enhances NF-κB activation in hematologic malignancies", Blood, Jan. 5, 2012, vol. 119, No. 1, pp. 180-187.
Herzog et al., "Requirement for Atm in Ionizing Radiation-Induced Cell Death in the Developing Central Nervous System", Science, May 15, 1998, vol. 280, pp. 1089-1091.
International Search Report, issued in PCT/JP2014/072445, dated Oct. 21, 2014.
Ito et al., "Regulation of oxidative stress by ATM is required for self-renewal of haematopoietic stem cells", Nature, Oct. 21, 2004, vol. 431, pp. 997-1002.

(Continued)

*Primary Examiner* — Karl J Puttlitz
(74) *Attorney, Agent, or Firm* — Birch, Stewart, Kolasch & Birch, LLP

(57) ABSTRACT

There is provided a morpholine derivative represented by General Formula [1A] or a salt thereof

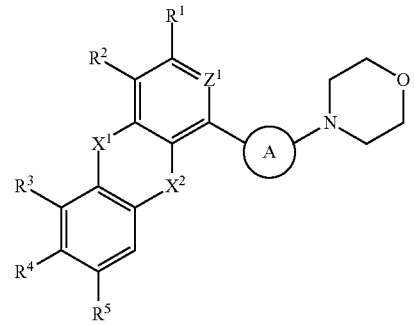

[1A]

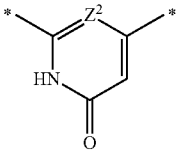

[I]

(In the formula, a ring A represents a ring represented by General Formula [I]; * represents a bonding position; $Z^2$ represents CH or the like; $Z^1$ represents $CR^6$ or the like; $R^6$ represents a hydrogen atom or the like; $X^1$ represents $CHR^7$ or the like; $R^7$ represents a hydrogen atom or the like; $X^2$ represents $CH_2$ or the like; $R^1$ and $R^2$ are the same as or different from each other, and each of $R^1$ and $R^2$ represents a hydrogen atom or the like; $R^3$, $R^4$, and $R^5$ are the same as or different from each other, and each of $R^3$, $R^4$, and $R^5$ represents a hydrogen atom, $NR^aR^b$, or the like; and each of $R^a$ and $R^b$ represents a hydrogen atom, a $C_{1-8}$ alkyl group which may have a substituent, or the like).

23 Claims, No Drawings

(51) Int. Cl.

| | |
|---|---|
| *C07D 405/14* | (2006.01) |
| *A61K 31/5377* | (2006.01) |
| *A61K 31/5383* | (2006.01) |
| *A61K 31/5386* | (2006.01) |
| *A61K 31/541* | (2006.01) |
| *A61K 31/55* | (2006.01) |
| *A61K 31/553* | (2006.01) |
| *C07D 405/04* | (2006.01) |
| *C07D 409/04* | (2006.01) |
| *C07D 409/14* | (2006.01) |
| *C07D 411/04* | (2006.01) |
| *C07D 411/14* | (2006.01) |
| *C07D 417/14* | (2006.01) |
| *C07D 491/048* | (2006.01) |
| *C07D 491/052* | (2006.01) |
| *C07D 491/056* | (2006.01) |
| *C07D 491/107* | (2006.01) |
| *C07D 498/04* | (2006.01) |
| *C07D 498/08* | (2006.01) |

(52) U.S. Cl.
CPC ........ *A61K 31/5386* (2013.01); *A61K 31/541* (2013.01); *A61K 31/55* (2013.01); *A61K 31/553* (2013.01); *C07D 401/14* (2013.01); *C07D 405/04* (2013.01); *C07D 405/14* (2013.01); *C07D 409/04* (2013.01); *C07D 409/14* (2013.01); *C07D 411/04* (2013.01); *C07D 411/14* (2013.01); *C07D 417/14* (2013.01); *C07D 491/048* (2013.01); *C07D 491/052* (2013.01); *C07D 491/056* (2013.01); *C07D 491/107* (2013.01); *C07D 498/04* (2013.01); *C07D 498/08* (2013.01)

(56) References Cited

FOREIGN PATENT DOCUMENTS

| JP | 2008-529995 A | 8/2008 |
|---|---|---|
| WO | WO 03/070726 A1 | 8/2003 |
| WO | WO 2005/016919 A1 | 2/2005 |
| WO | WO 2007/026157 A1 | 3/2007 |

OTHER PUBLICATIONS

Miyasaka et al., "The Role of the DNA Damage Checkpoint Pathway in Intraductal Papillary Mucinous Neoplasms of the Pancreas", Clinical Cancer Research, Aug. 1, 2007, vol. 13, No. 15, pp. 4371-4377.

Morrison et al., "The controlling rold of ATM in homologous recombinational repair of DNA damage", The EMBO Journal, 2000, vol. 19, No. 3, pp. 463-471.

Savitsky et al., "A Single Ataxia Telangiectasia Gene with a Product Similar to PI-3 Kinase", Science, Jun. 23, 1995, vol. 268, pp. 1749-1753.

Suzuki et al., "Recruitment of ATM Protein to Double Strand DNA Irradiated with Ionizing Radiation", The Journal of Biological Chemistry, 1999, vol. 274, No. 36, Issue of Sep. 3, pp. 25571-25575.

Tominaga et al., "Role of Human Cds1 (Chk2) Kinase in DNA Damage Checkpoint and Its Regulation by p53", The Journal of Biological Chemistry, 1999, vol. 274, No. 44, Issue of Oct. 29, pp. 31463-31467.

Written Opinion of the International Searching Authority, issued in PCT/JP2014/072445, dated Oct. 21, 2014.

Finlay et al., "Modulation of DNA Repair by Pharmacological Inhibitors of the PIKK Protein Kinase Family", Bioorganic & Medicinal Chemistry Letters, vol. 22 (2012) pp. 5352-5359.

Hollick et al., "Pyranone, Thiopyranone, and Pyridone Inhibitors of Phosphatidylinositol 3-Kinase Related Kinases. Structure-Activity Relationships for DNA-Dependent Protein Kinase Inhibition, and Identification of the First Potent and Selective Inhibitor of the Ataxia Telangiectasia Mutated Kinase", J. Med. Chem., vol. 50 (2007) pp. 1958-1972.

Partial Supplementary European Search Report issued in European Patent Application No. 14840352.0 on Oct. 6, 2016.

Japanese Office Action issued in Japanese Application No. 2015-534262 on Sep. 20, 2016, with partial English translation.

Extended European Search Report issued in European Patent Application No. 14840352.0 on Jan. 19, 2017.

\* cited by examiner

MORPHOLINE DERIVATIVE OR SALT THEREOF

CROSS-REFERENCE TO RELATED APPLICATIONS

This application is a continuation application of International Application No. PCT/JP2014/072445, filed Aug. 27, 2014, which is incorporated herein by reference. Further, this application claims priority from Japanese Patent Application No. 2013-177934, filed Aug. 29, 2013, which is incorporated herein by reference.

BACKGROUND OF THE INVENTION

1. Field of the Invention

The present invention relates to a novel morpholine derivative or a salt thereof having an ATM (ataxia telangiectasia mutated) inhibitory action.

2. Description of the Related Art

ATM consists of 3056 amino acids that have been identified as a gene responsible for ataxia telangiectasia (A-T), and is a serine/threonine kinase of about 350 kDa belonging to a PI3K (Phosphoinisitide 3-kinase) family (The Journal of biological chemistry, Vol. 274, pp. 25571-25575). ATM senses DNA double-strand break (DSB) induced in the cells by irradiation with an ionizing radiation or by a certain type of anticancer agent treatment, and serine 1981 is autophosphorylated, and as a result, becomes an activator. It is known that the phosphorylated ATM performs a homologous recombination, repairs DSB, and phosphorylates a downstream protein such as Chk2 or p53, and as a result, arrest of a cell cycle, induction of a DNA repair factor, or the like is suppressed (The Journal of biological chemistry, Vol. 274, pp. 25571-25575, 1999; Nature, Vol. 421, pp. 499-506, 2003; EMBO Journal, Vol. 19, pp. 463-471, 2000; and The Journal of biological chemistry, Vol. 274, pp. 31463-31467, 1999). In an A-T patient, ATM inactivation mutation is observed, and, as clinical symptoms, progressive cerebellar degeneration, oculocutaneous telangiectasia, delay of growth, immunodeficiency, predisposition of cancer, and premature senility are observed. In addition, at a cellular level, high sensitivity to an ionizing radiation or a treatment having effects similar to the ionizing radiation is observed (Science, Vol. 268, pp. 1749-1753, 1995). Based on the above description, it is expected that the compound having an ATM inhibitory action has an action of enhancing the effects on a cancer cure in which an ionizing radiation or an anticancer agent having effects similar to the ionizing radiation is applied. On the other hand, nerve cells in which ATM is deficient exhibit resistance to apoptosis through p53 induced by radiation (Science, Vol. 280, pp. 1089-1091, 1998), and thus, in a certain type of cell including nerve cells, there is a possibility that a radiation protection ability is exhibited. In addition, by exhibiting temporary immunodeficiency caused by the compound having an ATM inhibitory action, there is a possibility that the action of a disease in which an immune function is involved is reduced.

It is known that, when a retrovirus introduces its DNA produced by reverse transcription into a host cell, the retrovirus uses an ATM function of the host (Molecular Cell Biology, Vol. 21, pp. 1164-1172, 2001). Thus, it is expected that the compound having an ATM inhibitory action is useful in the prevention and cure of a disease caused by retroviral infection.

It is reported that ATM is involved in functional maintenance or proliferation through an ATM downstream signal, alone or by an interaction with other proteins (Nature, Vol. 431, pp. 997-1002, 2004; Blood, Vol. 119, pp. 180-187, 2012). Thus, it is expected that, by a use of an ATM inhibitor alone or by a combined use with an inhibitor to a protein that interacts with the ATM, cell killing effects are exhibited in a certain type of cancers.

It is reported that, in precancerous lesion in an onset process of cancer, expression of activated ATM is observed (Clinical Cancer Research, Vol. 15, pp. 4371-4377, 2007). It is thought that, by the cell killing effects of immune cells or active cell proliferation in a carcinogenic process, DNA repair through ATM is performed. Thus, it is expected that, in the period of a carcinogenic process, cancer onset can be prevented by a compound having an ATM inhibitory action.

On the other hand, a morpholine derivative having ATM inhibitory activity is known (WO2005/016919A).

SUMMARY OF THE INVENTION

Although compounds having ATM inhibitory activity are known, a compound and a pharmaceutical composition having more excellent ATM inhibitory activity have been desired.

As a result of intensive studies to solve the above-described problem, the inventors found that a morpholine derivative represented by General Formula [1A] or the salt thereof has excellent ATM inhibitory activity, and completed the present invention.

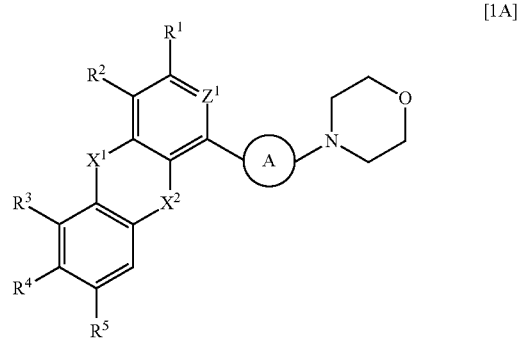

[1A]

(In the formula, the ring A represents a ring represented by General Formula [I] or a ring represented by General Formula [II]

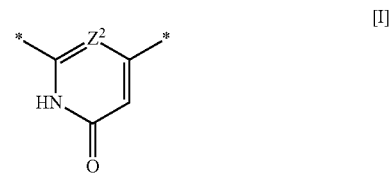

[I]

(in the formula, * represents a bonding position; and $Z^2$ represents CH or N)

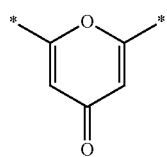

(in the formula, * has the same meaning as that described above);

$Z^1$ represents $CR^6$ (in the formula, $R^6$ represents a hydrogen atom, a halogen atom, or a $C_{1-8}$ alkyl group which may have a substituent) or N;

$X^1$ represents $CHR^7$ (in the formula, $R^7$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent), $CHR^8$—$CHR^9$ (in the formula, $R^8$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent; $R^9$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent; and a carbon atom to which $R^8$ is bonded is bonded to the ring having $R^1$ and $R^2$), O, or S;

$X^2$ represents $CH_2$, O, S, or $NR^{10}$ (in the formula, $R^{10}$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent);

$R^1$ and $R^2$ are the same as or different from each other, and each of $R^1$ and $R^2$ represents a hydrogen atom, a halogen atom, a hydroxyl group which may have a protecting group, a $C_{1-8}$ alkyl group which may have a substituent, or a $C_{1-6}$ alkoxy group which may have a substituent;

$R^3$, $R^4$, and $R^5$ are the same as or different from each other, and each of $R^3$, $R^4$, and $R^5$ represents a hydrogen atom, a halogen atom, a nitro atom, a hydroxyl group which may have a protecting group, a $C_{1-8}$ alkyl group which may have a substituent, a $C_{2-6}$ alkenyl group which may have a substituent, a $C_{2-6}$ alkynyl group which may have a substituent, a $C_{1-6}$ alkoxy group which may have a substituent, an acyl group which may have a substituent, an aryl group which may have a substituent, a heterocyclic group which may have a substituent, or $NR^aR^b$ (in the formula, $R^a$ and $R^b$ are the same as or different from each other, and each of $R^a$ and $R^b$ represents a hydrogen atom, a $C_{1-8}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, an aryl group which may have a substituent, an ar $C_{1-6}$ alkyl group which may have a substituent, an acyl group which may have a substituent, a $C_{1-6}$ alkylsulfonyl group which may have a substituent, a heterocyclic group which may have a substituent, or a heterocyclic $C_{1-8}$ alkyl group which may have a substituent);

here, when the ring A is a ring represented by General Formula [II], $R^4$ represents $NR^{a1}R^{b1}$ (in the formula, $R^{a1}$ represents a hydrogen atom, a $C_{1-8}$ alkyl group which may have one or more substituents selected from the substituent group f, a $C_{2-6}$ alkenyl group which may have one or more substituents selected from the substituent group f, a $C_{2-6}$ alkynyl group which may have one or more substituents selected from the substituent group f, a $C_{3-8}$ cycloalkyl group which may have one or more substituents selected from the substituent group f, an aryl group which may have one or more substituents selected from the substituent group f, an ar $C_{1-6}$ alkyl group which may have one or more substituents selected from the substituent group f, an acyl group which may have one or more substituents selected from the substituent group f, a $C_{1-6}$ alkylsulfonyl group which may have one or more substituents selected from the substituent group f, a heterocyclic group which may have one or more substituents selected from the substituent group f, or a heterocyclic $C_{1-8}$ alkyl group which may have one or more substituents selected from the substituent group f; and $R^{b1}$ represents a $C_{1-8}$ alkyl group which may have one or more substituents selected from the substituent group f, a $C_{2-6}$ alkenyl group which may have one or more substituents selected from the substituent group f, a $C_{2-6}$ alkynyl group which may have one or more substituents selected from the substituent group f, a $C_{3-8}$ cycloalkyl group which may have one or more substituents selected from the substituent group f, an aryl group which may have one or more substituents selected from the substituent group f, an ar $C_{1-6}$ alkyl group which may have one or more substituents selected from the substituent group f, a $C_{1-6}$ alkylsulfonyl group which may have one or more substituents selected from the substituent group f, a heterocyclic group which may have one or more substituents selected from the substituent group f, or a heterocyclic $C_{1-8}$ alkyl group which may have one or more substituents selected from the substituent group f).)

<Substituent Group f>

A deuterium atom, a halogen atom, a cyano group, a nitro group, a hydroxyl group which may have a protecting group, an amino group which may have a protecting group, a carboxyl group which may have a protecting group, a $C_{1-8}$ alkyl group which may have one or more substituents selected from the substituent group d, a $C_{2-6}$ alkenyl group which may have one or more substituents selected from the substituent group d, a $C_{2-6}$ alkynyl group which may have one or more substituents selected from the substituent group d, a $C_{3-8}$ cycloalkyl group which may have one or more substituents selected from the substituent group d, a $C_{3-8}$ cycloalkenyl group which may have one or more substituents selected from the substituent group d, an aryl group which may have one or more substituents selected from the substituent group d, an ar $C_{1-6}$ alkyl group which may have one or more substituents selected from the substituent group d, an $C_{1-6}$ alkoxy group which may have one or more substituents selected from the substituent group d, an acyl group which may have one or more substituents selected from the substituent group d, a $C_{1-6}$ alkylamino group which may have one or more substituents selected from the substituent group d, a di($C_{1-6}$ alkyl)amino group which may have one or more substituents selected from the substituent group d, a heterocyclic group which may have one or more substituents selected from the substituent group d, a heterocyclic $C_{1-8}$ alkyl group which may have one or more substituents selected from the substituent group d, a heterocyclic oxy group which may have one or more substituents selected from the substituent group d, $CONR^cR^d$ (in the formula, $R^c$ and $R^d$ are the same as or different from each other, and each of $R^c$ and $R^d$ represents a hydrogen atom, a $C_{1-8}$ alkyl group which may have one or more substituents selected from the substituent group d, a $C_{2-6}$ alkenyl group which may have one or more substituents selected from the substituent group d, or a $C_{2-6}$ alkynyl group which may have one or more substituents selected from the substituent group d; or $R^c$ and $R^d$ may form a cyclic amino group which may be substituted with one or more substituents selected from the substituent group d, together with the nitrogen atom to which $R^c$ and $R^d$ are bonded), and NHCONR$^e$R$^f$ (in the formula, $R^e$ and $R^f$ are the same as or different from each other, and each of $R^e$ and $R^f$ represents a hydrogen atom, a $C_{1-8}$ alkyl group which may have one or more substituents selected from the substituent group d, a $C_{2-6}$ alkenyl group which may have one or more substituents selected from the substituent group d, or a $C_{2-6}$ alkynyl group which may have one or more substituents selected from the substituent group d; or $R^e$ and $R^f$ may form a cyclic amino group which may have one or more substituents selected from the substituent group d, together with the nitrogen atom to which $R^e$ and $R^f$ are bonded)

<Substituent Group d>

A halogen atom, a cyano group, a nitro group, an oxo group, a hydroxyl group which may have a protecting group, an amino group which may have a protecting group, a carboxyl group which may have a protecting group, a $C_{1-8}$ alkyl group which may have one or more substituents selected from the substituent group e, a $C_{2-6}$ alkenyl group which may have one or more substituents selected from the substituent group e, a $C_{2-6}$ alkynyl group which may have one or more substituents selected from the substituent group e, a $C_{3-8}$ cycloalkyl group which may have one or more substituents selected from the substituent group e, an aryl group which may have one or more substituents selected from the substituent group e, a $C_{1-6}$ alkoxy group which may have one or more substituents selected from the substituent group e, an acyl group which may have one or more substituents selected from the substituent group e, a $C_{1-6}$ alkylamino group which may have one or more substituents selected from the substituent group e, a di($C_{1-6}$ alkyl)amino group which may have one or more substituents selected from the substituent group e, a heterocyclic group which may have one or more substituents selected from the substituent group e, and a heterocyclic oxy group which may have one or more substituents selected from the substituent group e <Substituent Group e>

A halogen atom, a hydroxyl group which may have a protecting group, a $C_{1-6}$ alkoxy group, CONR$^g$R$^h$ (in the formula, $R^g$ and $R^h$ are the same as or different from each other, and each of $R^g$ and $R^h$ represents a hydrogen atom, a $C_{1-8}$ alkyl group, a $C_{2-6}$ alkenyl group, or a $C_{2-6}$ alkynyl group; or $R^g$ and $R^h$ may form a cyclic amino group together with the nitrogen atom to which $R^g$ and $R^h$ are bonded)

That is, the present invention provides the following.

(1) A morpholine derivative represented by General Formula [1A] defined above or a salt thereof.

(2) The morpholine derivative or a salt thereof according to (1), in which the morpholine derivative is represented by General Formula [1].

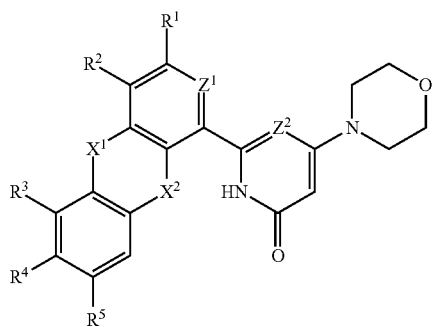

[1]

(In the formula, each of $Z^1$, $Z^2$, $X^1$, $X^2$, $R^1$, $R^2$, $R^3$, $R^4$, and $R^5$ has the same meaning as that described above.)

(3) The morpholine derivative or a salt thereof according to (1) or (2), in which $Z^1$ is CH.

(4) The morpholine derivative or a salt thereof according to any one of (1) to (3), in which $X^1$ is CH$_2$ or S.

(5) The morpholine derivative or a salt thereof according to any one of (1) to (4), in which $X^2$ is O or S.

(6) The morpholine derivative or a salt thereof according to any one of (1) to (5), in which $R^1$ is a hydrogen atom; and $R^2$ is a hydrogen atom.

(7) The morpholine derivative or a salt thereof according to any one of (2) to (6), in which $R^3$ is a hydrogen atom; one of $R^4$ or $R^5$ is NR$^a$R$^b$ (in the formula, each of $R^a$ and $R^b$ has the same meaning as that described above); and the other $R^4$ or $R^5$ is a hydrogen atom.

(8) The morpholine derivative or a salt thereof according to any one of (2) to (7), in which $R^3$ is a hydrogen atom; $R^4$ is NR$^a$R$^b$ (in the formula, each of $R^a$ and $R^b$ has the same meaning as that described above); and $R^5$ is a hydrogen atom.

(9) The morpholine derivative or a salt thereof according to any one of (2) to (8), in which $R^a$ is a hydrogen atom; and $R^b$ is a hydrogen atom, a $C_{1-8}$ alkyl group which may have a substituent, a $C_{3-8}$ cycloalkyl group which may have a substituent, an ar $C_{1-6}$ alkyl group which may have a substituent, an acyl group which may have a substituent, a $C_{1-6}$ alkylsulfonyl group which may have a substituent, a heterocyclic group which may have a substituent, or a heterocyclic $C_{1-8}$ alkyl group which may have a substituent.

(10) The morpholine derivative or a salt thereof according to any one of (2) to (9), in which $R^a$ is a hydrogen atom; and $R^b$ is a $C_{3-8}$ cycloalkyl group which may have a substituent, a heterocyclic group which may have a substituent, or a heterocyclic $C_{1-8}$ alkyl group which may have a substituent.

(11) The morpholine derivative or a salt thereof according to (1), in which the morpholine derivative is represented by General Formula [1α].

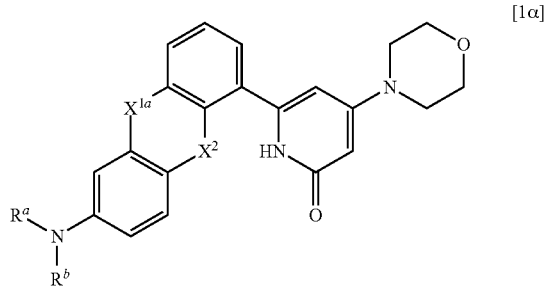

[1α]

(In the formula, $X^{1a}$ represents CHR$^7$ (in the formula, $R^7$ has the same meaning as that described above), O, or S; and each of $X^2$, $R^a$, and $R^b$ has the same meaning as that described above.)

(12) The morpholine derivative or a salt thereof according to (11), in which $X^{1a}$ is CH$_2$ or S.

(13) The morpholine derivative or a salt thereof according to (11) or (12), in which $X^2$ is O or S.

(14) The morpholine derivative or a salt thereof according to any one of (11) to (13), in which $R^a$ is a hydrogen atom; and $R^b$ is a hydrogen atom, a $C_{1-8}$ alkyl group which may have a substituent, a $C_{3-8}$ cycloalkyl group which may have a substituent, an ar $C_{1-6}$ alkyl group which may have a substituent, an acyl group which may have a substituent, a $C_{1-6}$ alkylsulfonyl group which may have a substituent, a heterocyclic group which may have a substituent, or a heterocyclic $C_{1-8}$ alkyl group which may have a substituent.

(15) The morpholine derivative or a salt thereof according to any one of (11) to (14), in which $R^a$ is a hydrogen atom; and $R^b$ is a $C_{3-8}$ cycloalkyl group which may have a substituent, a heterocyclic group which may have a substituent, or a heterocyclic $C_{1-8}$ alkyl group which may have a substituent.

(16) The morpholine derivative or a salt thereof according to (1), in which the morpholine derivative is represented by General Formula [1β].

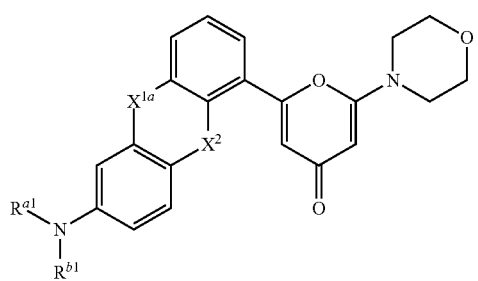

[1β]

(In the formula, each of $X^{1a}$, $X^2$, $R^{a1}$, and $R^{b1}$ has the same meaning as that described above.)

(17) The morpholine derivative or a salt thereof according to (16), in which $X^{1a}$ is $CH_2$ or S.

(18) The morpholine derivative or a salt thereof according to (16) or (17), in which $X^2$ is O or S.

(19) The morpholine derivative or a salt thereof according to any one of (16) to (18), in which $R^{a1}$ is a hydrogen atom; and $R^{b1}$ is a $C_{1-8}$ alkyl group which may have one or more substituents selected from the substituent group f, a $C_{3-8}$ cycloalkyl group which may have one or more substituents selected from the substituent group f, an ar $C_{1-6}$ alkyl group which may have one or more substituents selected from the substituent group f, a $C_{1-6}$ alkylsulfonyl group which may have one or more substituents selected from the substituent group f, a heterocyclic group which may have one or more substituents selected from the substituent group f, or a heterocyclic $C_{1-8}$ alkyl group which may have one or more substituents selected from the substituent group f.

(20) The morpholine derivative or a salt thereof according to any one of (16) to (19), in which $R^{a1}$ is a hydrogen atom; and $R^{b1}$ is a $C_{3-8}$ cycloalkyl group which may have one or more substituents selected from the substituent group f, a heterocyclic group which may have one or more substituents selected from the substituent group f, or a heterocyclic $C_{1-8}$ alkyl group which may have one or more substituents selected from the substituent group f.

(21) A pharmaceutical composition containing the morpholine derivative or a salt thereof according to any one of (1) to (20).

(22) The pharmaceutical composition according to (21), which is an agent for treating a disease in which ATM is involved.

(23) The pharmaceutical composition according to (21), which is an agent for treating a disease or cancer caused by retroviral infection.

(24) The pharmaceutical composition according to (21), which is a sensitivity-enhancing agent to an ionizing radiation or an anticancer agent having effects similar to the ionizing radiation.

The present invention further provides the following.

(A) The morpholine derivative represented by General Formula [1A] defined above or a salt thereof for use as a medicine.

(B) The morpholine derivative represented by General Formula [1A] or a salt thereof for use in treatment for a disease in which ATM is involved, and preferably for use in treatment for a disease or cancer caused by retroviral infection.

(C) A pharmaceutical composition including a pharmacologically acceptable additive together with the morpholine derivative represented by General Formula [1A] or a salt thereof.

(D) A use of the morpholine derivative represented by General Formula [1A] or a salt thereof in preparing a medicine for use in treatment for a disease in which ATM is involved, and preferably for use in treatment for a disease or cancer caused by retroviral infection.

(E) A method which is a method for treating a disease in which ATM is involved, and preferably for treating a disease or cancer caused by retroviral infection, and includes a step of administering an effective amount of the morpholine derivative represented by General Formula [1A] or a salt thereof to a subject (mammal including humans) that requires such a treatment.

(F) The morpholine derivative represented by General Formula [1A] or a salt thereof for use in enhancing the sensitivity to an ionizing radiation or an anticancer agent having effects similar to the ionizing radiation.

(G) A use of the morpholine derivative represented by General Formula [1A] or a salt thereof in preparing a medicine for use in enhancing the sensitivity to an ionizing radiation or an anticancer agent having effects similar to the ionizing radiation.

(H) A method which is a method for enhancing the sensitivity to an ionizing radiation or an anticancer agent having effects similar to the ionizing radiation, and includes a step of administering an effective amount of the morpholine derivative represented by General Formula [1A] or a salt thereof to a subject (mammal including humans) that requires a treatment by an ionizing radiation or an anticancer agent having effects similar to the ionizing radiation.

(a) The morpholine derivative represented by General Formula [1] defined above or a salt thereof for use as a medicine.

(b) The morpholine derivative represented by General Formula [1] or a salt thereof for use in treatment for a disease in which ATM is involved, and preferably for use in treatment for a disease or cancer caused by retroviral infection.

(c) A pharmaceutical composition including a pharmacologically acceptable additive together with the morpholine derivative represented by General Formula [1] or a salt thereof.

(d) A use of the morpholine derivative represented by General Formula [1] or a salt thereof in preparing a medicine for use in treatment for a disease in which ATM is involved, and preferably for use in treatment for a disease or cancer caused by retroviral infection.

(e) A method which is a method for treating a disease in which ATM is involved, and preferably for treating a disease or cancer caused by retroviral infection, and includes a step of administering an effective amount of the morpholine derivative represented by General Formula [1] or a salt thereof to a subject (mammal including humans) that requires such a treatment.

(f) The morpholine derivative represented by General Formula [1] or a salt thereof for use in enhancing the sensitivity to an ionizing radiation or an anticancer agent having effects similar to the ionizing radiation.

(g) A use of the morpholine derivative represented by General Formula [1] or a salt thereof in preparing a medicine for use in enhancing the sensitivity to an ionizing radiation or an anticancer agent having effects similar to the ionizing radiation.

(h) A method which is a method for enhancing the sensitivity to an ionizing radiation or an anticancer agent having effects similar to the ionizing radiation, and includes a step of administering an effective amount of the morpholine derivative represented by General Formula [1] or a salt thereof to a subject (mammal including humans) that requires a treatment by an ionizing radiation or an anticancer agent having effects similar to the ionizing radiation.

The novel morpholine derivative of the present invention or a salt thereof has excellent ATM inhibitory activity, and is useful as an agent for treating a disease in which ATM is involved. In addition, the novel morpholine derivative of the present invention or a salt thereof is useful as a sensitivity-enhancing agent to an ionizing radiation or an anticancer agent having effects similar to the ionizing radiation.

DESCRIPTION OF THE PREFERRED EMBODIMENTS

Hereinafter, the present invention will be described in detail.

In the present invention, each term has the following meaning, unless specified otherwise.

A halogen atom means a fluorine atom, a chlorine atom, a bromine atom, or an iodine atom.

A $C_{1-6}$ alkyl group means a linear or branched $C_{1-6}$ alkyl group such as a methyl group, an ethyl group, a propyl group, an isopropyl group, a butyl group, a sec-butyl group, an isobutyl group, a tert-butyl group, a pentyl group, an isopentyl group, a 2-methylbutyl group, a 2-pentyl group, a 3-pentyl group, or a hexyl group.

A $C_{1-8}$ alkyl group means a linear or branched $C_{1-8}$ alkyl group such as a methyl group, an ethyl group, a propyl group, an isopropyl group, a butyl group, a sec-butyl group, an isobutyl group, a tert-butyl group, a pentyl group, an isopentyl group, a 2-methylbutyl group, a 2-pentyl group, a 3-pentyl group, a hexyl group, a heptyl group, a 2-methyl-heptyl group, a 2-methyl-4-heptyl group, or an octyl group.

A $C_{2-6}$ alkenyl group means a linear or branched $C_{2-6}$ alkenyl group such as a vinyl group, an allyl group, a propenyl group, an isopropenyl group, a butenyl group, an isobutenyl group, a 1,3-butadienyl group, a pentenyl group, or a hexenyl group.

A $C_{2-6}$ alkynyl group means a linear or branched $C_{2-6}$ alkynyl group such as an ethynyl group, a propynyl group, a butynyl group, a pentynyl group, or a hexynyl group.

A $C_{3-8}$ cycloalkyl group means a $C_{3-8}$ cycloalkyl group such as a cyclopropyl group, a cyclobutyl group, a cyclopentyl group, a cyclohexyl group, or a cycloheptyl group.

A $C_{3-8}$ cycloalkenyl group means a $C_{3-8}$ cycloalkenyl group such as a cyclopropenyl group, a cyclobutenyl group, a cyclopentenyl group, or a cyclohexenyl group.

A $C_{2-6}$ alkylene group means a linear or branched $C_{2-6}$ alkylene group such as an ethylene group, a propylene group, a butylene group, or a hexylene group.

An aryl group means a phenyl group or a naphthyl group.

An ar $C_{1-6}$ alkyl group means an ar $C_{1-6}$ alkyl group (aralkyl group in which the alkyl portion is a $C_{1-6}$ alkyl group) such as a benzyl group, a diphenylmethyl group, a trityl group, a phenethyl group, a 2-phenylpropyl group, a 3-phenylpropyl group, or a naphthylmethyl group.

A $C_{1-6}$ alkoxy group means a linear, cyclic, or branched $C_{1-6}$ alkyloxy group such as a methoxy group, an ethoxy group, a propoxy group, an isopropoxy group, a cyclopropoxy group, a butoxy group, an isobutoxy group, a sec-butoxy group, a tert-butoxy group, a cyclobutoxy group, a pentyloxy group, or a hexyloxy group.

A $C_{1-6}$ alkoxy $C_{1-6}$ alkyl group means a $C_{1-6}$ alkyloxy $C_{1-6}$ alkyl group such as a methoxymethyl group or a 1-ethoxyethyl group.

An ar $C_{1-6}$ alkoxy $C_{1-6}$ alkyl group means an ar $C_{1-6}$ alkyloxy $C_{1-6}$ alkyl group such as a benzyloxymethyl group or a phenethyloxymethyl group.

A $C_{2-6}$ alkanoyl group means a linear or branched $C_{2-6}$ alkanoyl group such as an acetyl group, a propionyl group, a valeryl group, an isovaleryl group, or a pivaloyl group.

An aroyl group means a benzoyl group, a naphthoyl group, or the like.

A heterocyclic carbonyl group means a furoyl group, a thenoyl group, a pyrrolidinylcarbonyl group, a piperidinylcarbonyl group, a piperazinylcarbonyl group, a morpholinylcarbonyl group, or a pyridinylcarbonyl group.

An (α-substituted) aminoacetyl group means an (α-substituted) aminoacetyl group in which the N-terminal, which is derived from an amino acid (glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline, or hydroxyproline), may be protected.

An acyl group means a formyl group, a succinyl group, a glutaryl group, a maleoyl group, a phthaloyl group, a $C_{2-6}$ alkanoyl group, an aroyl group, a heterocyclic carbonyl group, an (α-substituted) aminoacetyl group, or the like.

An acyl $C_{1-6}$ alkyl group means an acyl $C_{1-6}$ alkyl group such as an acetyl methyl group, a benzoylmethyl group, or a 1-benzoylethyl group.

An acyloxy $C_{1-6}$ alkyl group means an acyloxy $C_{1-6}$ alkyl group such as an acetoxymethyl group, a propionyloxymethyl group, a pivaloyloxymethyl group, a benzoyloxymethyl group, and a 1-(benzoyloxy)ethyl group.

A $C_{1-6}$ alkoxycarbonyl group means a linear or branched $C_{1-6}$ alkyloxycarbonyl group such as a methoxycarbonyl group, an ethoxycarbonyl group, an isopropoxycarbonyl group, a tert-butoxycarbonyl group, or a 1,1-dimethylpropoxycarbonyl group.

An ar $C_{1-6}$ alkoxycarbonyl group means an ar $C_{1-6}$ alkyloxycarbonyl group such as a benzyloxycarbonyl group or a phenethyloxycarbonyl group.

An aryloxycarbonyl group means a phenyloxycarbonyl group or a naphthyloxycarbonyl group.

A $C_{1-6}$ alkylamino group means a linear, branched, or cyclic $C_{1-6}$ alkylamino group such as a methylamino group, an ethylamino group, a propylamino group, an isopropylamino group, a cyclopropylamino group, a butylamino group, a sec-butylamino group, a tert-butylamino group, a cyclobutylamino group, a pentylamino group, a cyclopentylamino group, a hexylamino group, or a cyclohexylamino group.

A di($C_{1-6}$ alkyl)amino group means a linear, branched, or cyclic di($C_{1-6}$ alkyl)amino group such as a dimethylamino group, a diethylamino group, a dipropylamino group, a diisopropylamino group, a dibutylamino group, a di(tert-butyl)amino group, a dipentylamino group, a dihexylamino group, an (ethyl)(methyl)amino group, a (methyl)(propyl)

amino group, a (cyclopropyl)(methyl)amino group, a (cyclobutyl)(methyl)amino group, or a (cyclohexyl)(methyl) amino group.

A $C_{1-6}$ alkylsulfonyl group means a $C_{1-6}$ alkylsulfonyloxy group such as a methylsulfonyl group, an ethylsulfonyl group, or a propylsulfonyl group.

An arylsulfonyl group means a benzenesulfonyl group, a p-toluenesulfonyl group, or a naphthalenesulfonyl group.

A $C_{1-6}$ alkylsulfonyloxy group means a $C_{1-6}$ alkylsulfonyloxy group such as a methylsulfonyloxy group or an ethylsulfonyloxy group.

An arylsulfonyloxy group means a benzenesulfonyloxy group or a p-toluenesulfonyloxy group.

A cyclic amino group means a cyclic amino group which includes one or more nitrogen atoms as a heteroatom forming a ring, and may further include one or more oxygen atoms or sulfur atoms, such as an azetidinyl group, a pyrrolidinyl group, a pyrrolinyl group, a pyrrolyl group, a piperidinyl group, a tetrahydropyridyl group, a homopiperidinyl group, an imidazolidinyl group, an imidazolinyl group, an imidazolyl group, a pyrazolidinyl group, a pyrazolinyl group, a pyrazolyl group, a piperazinyl group, a homopiperazinyl group, a triazolyl group, a tetrazolyl group, a morpholinyl group, a thiomorpholinyl group, a tetrahydroquinolinyl group, a tetrahydroisoquinolinyl group, or a quinuclidinyl group.

A monocyclic nitrogen-containing heterocyclic group means a monocyclic nitrogen-containing heterocyclic group which includes only nitrogen atom as a heteroatom forming a ring, such as an aziridinyl group, an azetidinyl group, a pyrrolidinyl group, a pyrrolinyl group, a pyrrolyl group, a piperidyl group, a tetrahydropyridyl group, a dihydropyridyl group, a pyridyl group, a homopiperidinyl group, an octahydroazocinyl group, an imidazolidinyl group, an imidazolinyl group, an imidazolyl group, a pyrazolidinyl group, a pyrazolinyl group, a pyrazolyl group, a piperazinyl group, a pyrazinyl group, a pyridazinyl group, a pyrimidinyl group, a homopiperazinyl group, a triazolyl group, or a tetrazolyl group.

A monocyclic oxygen-containing heterocyclic group means a monocyclic oxygen-containing heterocyclic group which includes only oxygen atom as a heteroatom forming a ring, such as an oxetanyl group, a tetrahydrofuranyl group, a furanyl group, a tetrahydropyranyl group, a pyranyl group, a 1,3-dioxanyl group, or a 1,4-dioxanyl group.

A monocyclic sulfur-containing heterocyclyl group means a thienyl group or the like.

A monocyclic nitrogen- and oxygen-containing heterocyclic group means a monocyclic nitrogen- and oxygen-containing heterocyclic group which includes only nitrogen atom and oxygen atom as a heteroatom forming a ring, such as an oxazolyl group, an isoxazolyl group, an oxadiazolyl group, a morpholinyl group, or an oxazepanyl group.

A monocyclic nitrogen- and sulfur-containing heterocyclic group means a monocyclic nitrogen- and sulfur-containing heterocyclic group which includes only nitrogen atom and sulfur atom as a heteroatom forming a ring, such as a thiazolyl group, an isothiazolyl group, a thiadiazolyl group, a thiomorpholinyl group, a 1-oxidethiomorpholinyl group, or a 1,1-dioxidethiomorpholinyl group.

A monocyclic heterocyclic group means a monocyclic nitrogen-containing heterocyclic group, a monocyclic oxygen-containing heterocyclic group, a monocyclic sulfur-containing heterocyclyl group, a monocyclic nitrogen- and oxygen-containing heterocyclic group, or a monocyclic nitrogen- and sulfur-containing heterocyclic group.

A bicyclic nitrogen-containing heterocyclic group means a bicyclic nitrogen-containing heterocyclic group which includes only nitrogen atom as a heteroatom forming a ring, such as an indolinyl group, an indolyl group, an isoindolinyl group, an isoindolyl group, a benzimidazolyl group, an indazolyl group, a benzotriazolyl group, a pyrazolopyridinyl group, a quinolyl group, a tetrahydroquinolinyl group, a quinolyl group, a tetrahydroisoquinolinyl group, an isoquinolinyl group, a quinolizinyl group, a cinnolinyl group, a phthalazinyl group, a quinazolinyl group, a dihydroquinoxalinyl group, a quinoxalinyl group, a naphthyridinyl group, a purinyl group, a pteridinyl group, or a quinuclidinyl group.

A bicyclic oxygen-containing heterocyclic group means a bicyclic oxygen-containing heterocyclic group which includes only oxygen atom as a heteroatom forming a ring, such as a 2,3-dihydrobenzofuranyl group, a benzofuranyl group, an isobenzofuranyl group, a chromanyl group, a chromenyl group, an isochromanyl group, a 1,3-benzodioxolyl group, a 1,3-benzodioxanyl group, or a 1,4-benzodioxanyl group.

A bicyclic sulfur-containing heterocyclic group means a bicyclic sulfur-containing heterocyclic group which includes only sulfur atom as a heteroatom forming a ring, such as a 2,3-dihydrobenzothienyl group or a benzothienyl group.

A bicyclic nitrogen- and oxygen-containing heterocyclic group means a bicyclic nitrogen- and oxygen-containing heterocyclic group which includes only nitrogen atom and oxygen atom as a heteroatom forming a ring, such as a benzoxazolyl group, a benzisoxazolyl group, a benzoxadiazolyl group, a benzomorpholinyl group, a dihydropyranopyridyl group, a dioxolopyridyl group, a furopyridinyl group, a dihydrodioxinopyridyl group, or a dihydropyridoxadinyl group.

A bicyclic nitrogen- and sulfur-containing heterocyclic group means a bicyclic nitrogen- and sulfur-containing heterocyclic group which includes only sulfur atom as a heteroatom forming a ring, such as an benzothiazolyl group, a benzisothiazolyl group, or a benzothiadiazolyl group.

A bicyclic heterocyclic group means a bicyclic nitrogen-containing heterocyclic group, a bicyclic oxygen-containing heterocyclic group, a bicyclic sulfur-containing heterocyclyl group, a bicyclic nitrogen- and oxygen-containing heterocyclic group, or a bicyclic nitrogen- and sulfur-containing heterocyclic group.

A spiro type heterocyclic group means a spiro type heterocyclic group which includes one or more nitrogen atoms, oxygen atoms, or sulfur atoms as a heteroatom forming a ring, such as a 2-oxa-6-azaspiro[3.3]heptyl group, a 1,4-dioxaspiro[4.5]decyl group, a 1-oxa-8-azaspiro[4.5]decyl group, or a 1-thia-8-azaspiro[4.5]decyl group.

A crosslinking type heterocyclic group means a crosslinking type heterocyclic group which includes one or more nitrogen atoms as a heteroatom forming a ring, and may further include one or more oxygen atoms or sulfur atoms, such as a 3-oxa-8-azabicyclo[3.2.1]octyl group, a 8-oxa-3-azabicyclo[3.2.1]octyl group, or a quinuclidinyl group.

The heterocyclic group means a monocyclic heterocyclic group, a bicyclic heterocyclic group, a spiro type heterocyclic group, or a crosslinking type heterocyclic group.

The heterocyclic oxy group means a hydroxyl group substituted with a heterocyclic group.

A heterocyclic amino group means an amino group substituted with a heterocyclic group.

The heterocyclic $C_{1-8}$ alkyl group means a $C_{1-8}$ alkyl group substituted with a heterocyclic group.

A silyl group means a trimethylsilyl group, a triethylsilyl group, a tributylsilyl group, or the like.

Examples of a leaving group include a halogen atom, a $C_{1-6}$ alkylsulfonyloxy group, and an arylsulfonyloxy group. The $C_{1-6}$ alkylsulfonyloxy group or the arylsulfonyloxy group may be substituted.

Examples of an amino protecting group include all groups that can be used as a protecting group of a typical amino group, and for example, the groups described in "Protective Groups in Organic Synthesis" written by T. W. Greene et al., 4th edition, pp. 696-926, 2007 (John Wiley & Sons, INC.) can be mentioned. Specific examples thereof include an ar $C_{1-6}$ alkyl group, a $C_{1-6}$ alkoxy $C_{1-6}$ alkyl group, an acyl group, a $C_{1-6}$ alkoxycarbonyl group, an ar $C_{1-6}$ alkoxycarbonyl group, an aryloxycarbonyl group, a $C_{1-6}$ alkylsulfonyl group, an arylsulfonyl group, and a silyl group.

Examples of a hydroxyl protecting group include all groups that can be used as a protecting group of a typical hydroxyl group, and for example, the groups described in "Protective Groups in Organic Synthesis" written by T. W. Greene et al., 4th edition, pp. 16-299, 2007 (John Wiley & Sons, INC.) can be mentioned. Specific examples thereof include a $C_{1-6}$ alkyl group, a $C_{2-6}$ alkenyl group, an ar $C_{1-6}$ alkyl group, a $C_{1-6}$ alkoxy $C_{1-6}$ alkyl group, an ar $C_{1-6}$ alkoxy $C_{1-6}$ alkyl group, an acyl group, a $C_{1-6}$ alkoxycarbonyl group, an ar $C_{1-6}$ alkoxycarbonyl group, a $C_{1-6}$ alkylsulfonyl group, an arylsulfonyl group, a silyl group, a tetrahydrofuranyl group, and a tetrahydropyranyl group.

Examples of a carboxyl protecting group include all groups that can be used as a protecting group of a typical carboxyl group, and for example, the groups described in "Protective Groups in Organic Synthesis" written by T. W. Greene et al., 4th edition, pp. 533-643, 2007 (John Wiley & Sons, INC.) can be mentioned. Specific examples thereof include a $C_{1-6}$ alkyl group, a $C_{2-6}$ alkenyl group, an aryl group, an ar $C_{1-6}$ alkyl group, a $C_{1-6}$ alkoxy $C_{1-6}$ alkyl group, an ar $C_{1-6}$ alkoxy $C_{1-6}$ alkyl group, an acyl $C_{1-6}$ alkyl group, an acyloxy $C_{1-6}$ alkyl group, or a silyl group.

Aliphatic hydrocarbons mean pentane, hexane, heptane, cyclohexane, methyl cyclohexane, ethylcyclohexane, and the like.

Halogenated hydrocarbons mean dichloromethane, chloroform, dichloroethane, and the like.

Ethers mean diethyl ether, diisopropyl ether, dioxane, tetrahydrofuran, anisole, ethylene glycol dimethyl ether, diethylene glycol dimethyl ether, diethylene glycol diethyl ether, and the like.

Alcohols mean methanol, ethanol, propanol, 2-propanol, butanol, 2-methyl-2-propanol, and the like.

Glycols mean ethylene glycol, propylene glycol, diethylene glycol, and the like.

Ketones mean acetone, 2-butanone, 4-methyl-2-pentanone, methyl isobutyl ketone, and the like.

Esters mean methyl acetate, ethyl acetate, propyl acetate, butyl acetate, and the like.

Amides mean N,N-dimethylformamide, N,N-dimethyl acetamide, N-methyl pyrrolidone, and the like.

Nitriles mean acetonitrile, propionitrile, and the like.

Sulfoxides mean dimethyl sulfoxide, sulfolane, and the like.

Aromatic hydrocarbons mean benzene, toluene, xylene, and the like.

An organic acid means formic acid, acetic acid, propionic acid, trifluoroacetic acid, or the like.

An inorganic base means sodium hydroxide, potassium hydroxide, sodium methoxide, sodium tert-butoxide, potassium tert-butoxide, sodium hydrogen carbonate, sodium carbonate, potassium carbonate, tripotassium phosphate, potassium acetate, cesium fluoride, cesium carbonate, or the like.

An organic base means triethylamine, N,N-diisopropyl ethylamine, 1,8-diazabicyclo(5.4.0)undec-7-ene (DBU), pyridine, 4-dimethylaminopyridine, N-methylmorpholine, or the like.

Examples of a palladium catalyst include metallic palladiums such as palladium-carbon and palladium black; inorganic palladium salts such as palladium chloride; organic palladium salts such as palladium acetate; chloro(2-(dicyclohexylphosphino)-3,6-dimethoxy-2',4',6'-triisopropyl-1,1'-biphenyl)(2-(2-aminoethyl)phenyl)palladium (II); and organic palladium complexes such as tetrakis(triphenylphosphine)palladium (0), bis(triphenylphosphine)palladium (II) dichloride, bis(di-tert-butyl (4-dimethylaminophenyl)phosphine)dichloropalladium (II), 1,1'-bis(diphenylphosphino)ferrocene palladium (II) dichloride, (E)-di(μ-acetate)bis(o-(di-o-tolylphosphino)benzyl)dipalladium (II), and tris(dibenzylideneacetone)dipalladium (0), and polymer-supported organic palladium complexes such as polymer-supported bis(acetate)triphenylphosphine palladium (II) and polymer-supported di(acetate)dicyclohexylphenylphosphine palladium (II).

Examples of a ligand include trialkylphosphines such as trimethylphosphine and tri-tert-butylphosphine; alkyl biscycloalkylphosphines such as butyl bis(1-adamantyl)phosphine; tricycloalkyphosphines such as tricyclohexylphosphine; triarylphosphines such as triphenylphosphine and tritolylphosphine; aryldialkylphosphines such as (4-(N,N-dimethylamino)phenyl)di-tert-butylphosphine; trialkylphosphites such as trimethylphosphite, triethylphosphite, and tributylphosphite; tricycloalkylphosphites such as tricyclohexylphosphite; triarylphosphites such as triphenylphosphite; imidazolium salts such as 1,3-bis(2,4,6-trimethylphenyl)imidazolium chloride; diketones such as acetylacetone and occtafluoroacetyl acetone; amines such as trimethylamine, triethylamine, tripropylamine, and triisopropylamine; and 1,1'-bis(diphenylphosphino)ferrocene, 2,2'-bis(diphenylphosphino)-1,1'-binaphthyl, 2-dicyclohexylphosphino-2',6'-dimethoxybiphenyl, 2-dicyclohexylphosphino-2',4',6'-triisopropylbiphenyl, 2-(dicyclohexylphosphino)-3,6-dimethoxy-2',4',6'-triisopropyl-1,1'-biphenyl, 2-(di-tert-butylphosphino)-2',4',6'-triisopropyl biphenyl, 4,5'-bis(diphenylphosphino)-9,9'-dimethylxanthene, and 2-(di-tert-butylphosphino)biphenyl.

Examples of a salt of the compound represented by General Formula [1A] include typical salts of a basic group such as an amino group and an acidic group such as a hydroxyl group or a carboxyl group.

Examples of the salts of the basic group include salts of mineral acids such as hydrochloric acid, hydrobromic acid, nitric acid, and sulfuric acid; salts of organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts of sulfonic acids such as methanesulfonic acid, benzenesulfonic acid, p-toluenesulfonic acid, mesitylenesulfonic acid, and naphthalenesulfonic acid.

Examples of the salts of the acidic group include salts of alkali metals such as sodium and potassium; salts of alkali earth metals such as calcium and magnesium; an ammonium salt; and salts of nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-3-phenethylamine, 1-ephenamine, and N,N'-dibenzylethylenediamine.

Among the above-described salts, examples of a preferable salt include pharmacologically acceptable salts.

Prevention means inhibition of onset, reduction of onset risk, delay of onset, or the like.

A cure means amelioration of a target disease or conditions, suppression of progress, or the like.

A treatment means prevention or a cure for various diseases.

An agent for treating means a substance which is provided for the purpose of prevention or a cure for various diseases.

A disease in which ATM is involved means all diseases which can be prevented or cured by inhibiting ATM. A disease or cancer caused by retroviral infection is exemplified.

A sensitivity-enhancing agent to an ionizing radiation or an anticancer agent having effects similar to the ionizing radiation means a substance enhancing the sensitivity toward an ionizing radiation or an anticancer agent having effects similar to the ionizing radiation, regardless of the action mechanism. By using an ionizing radiation or an anticancer agent having effects similar to the ionizing radiation and the novel morpholine derivative of the present invention or a salt thereof in combination, the efficacy of a cancer cure can be improved.

The cancer cure by an ionizing radiation is not particularly limited as long as it is a cancer cure by a typical ionizing radiation, and, for example, irradiation with electromagnetic waves such as X-rays or γ-rays, or particle beams such as an electron beam, β-rays, π-mesons, neutrons, or baryon, is performed at an irradiation amount of about 0.1 Gy to 100 Gy per irradiation such that the total irradiation amount becomes 10 Gy to 500 Gy, over a period of 1 week to 6 months. In the cancer cure by an ionizing radiation, the whole body can be irradiated with an ionizing radiation or only tumor tissues can be locally irradiated with an ionizing radiation, and it is preferable that tumor tissues are locally irradiated.

The anticancer agent having effects similar to the ionizing radiation is not particularly limited as long as it is an anticancer agent which induces DNA damage, and directly or indirectly causes DBS, and examples thereof include a platinum-based drug, a taxane-based drug, a vinca alkaloid-based drug, a topoisomerase inhibitor, an antimetabolic agent, and an alkylating agent. Specific examples thereof include cisplatin, carboplatin, oxaliplatin, paclitaxel (taxol), docetaxel (taxotere), vincristine, vinblastine, vinorelbine, vindesine, irinotecan hydrochloride, topotecan, etoposide, teniposide, doxorubicin, tegafur, gemcitabine, cytarabine, methotrexate, pemetrexed (alimta), cyclophosphamide, adriamycin, and mitomycin. These may be, for example, salts or hydrates.

As the sensitivity-enhancing agent to an ionizing radiation or an anticancer agent having effects similar to the ionizing radiation, a subject to which the novel morpholine derivative of the present invention or a salt thereof can be effectively used is not particularly limited as long as it is cancer on which a cancer cure in which a typical ionizing radiation or an anticancer agent having effects similar to the ionizing radiation is applied can be performed, and examples thereof include a head and neck cancer, a sophageal cancer, a stomach cancer, a colorectal cancer, a liver cancer, a gallbladder and bile duct cancer, a pancreatic cancer, a lung cancer, a breast cancer, a bladder cancer, a prostate cancer, a cervical cancer, a basal cell carcinoma, a squamous cell carcinoma, a thyroid cancer, an ovarian cancer, a salivary gland cancer, and a renal cell carcinoma.

The morpholine derivative of the present invention is represented by General Formula [1A].

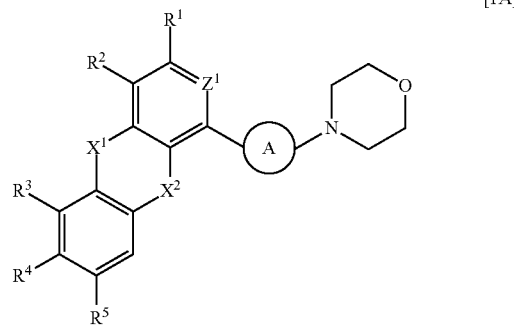

[1A]

(In the formula, each of the ring A, $Z^1$, $Z^2$, $X^1$, $X^2$, $R^1$, $R^2$, $R^3$, $R^4$, and $R^5$ has the same meaning as that described above.)

The ring A is a ring represented by General Formula [I] or a ring represented by General Formula [II].

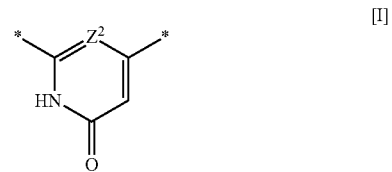

[I]

(In the formula, each of * and $Z^2$ has the same meaning as that described above.)

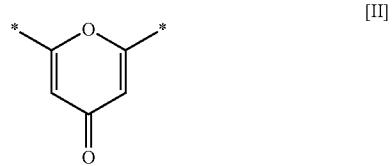 [SMILES: *c1cc(=O)cc(*)o1]

[II]

(In the formula, * has the same meaning as that described above.)

$Z^1$ represents $CR^6$ (in the formula, $R^6$ has the same meaning as that described above) or N.

$Z^1$ is preferably $CR^6$ (in the formula, $R^6$ has the same meaning as that described above), more preferably $CR^{6a}$ (in the formula, $R^{6a}$ represents a hydrogen atom or a halogen atom), and still more preferably CH.

$R^6$ represents a hydrogen atom, a halogen atom, or a $C_{1-8}$ alkyl group which may have a substituent.

$R^6$ is preferably a hydrogen atom or a halogen atom, and more preferably a hydrogen atom.

As a substituent in a $C_{1-8}$ alkyl group represented by $R^6$, one or more substituents selected from the substituent group a are preferable.

<Substituent Group a>

A halogen atom, a hydroxyl group which may have a protecting group, an amino group which may have a protecting group, a carboxyl group which may have a protecting group, a $C_{1-8}$ alkyl group which may have one or more substituents selected from the substituent group b, a $C_{3-8}$ cycloalkyl group which may have one or more substituents selected from the substituent group b, a $C_{1-6}$ alkoxy group which may have one or more substituents selected from the substituent group b, a $C_{1-6}$ alkylamino group which may have one or more substituents selected from the substituent group b, a di($C_{1-6}$ alkylamino) group which may have one or more substituents selected from the substituent group b, a heterocyclic group which may have one or more substituents selected from the substituent group b, a heterocyclic amino group which may have one or more substituents selected from the substituent group b, a heterocyclic $C_{1-8}$ alkyl group which may have one or more substituents selected from the substituent group b <Substituent Group b>

A halogen atom, a hydroxyl group which may have a protecting group, an amino group which may have a protecting group, a carboxyl group which may have a protecting group, a $C_{1-8}$ alkyl group $Z^2$ represents CH or N.

$Z^2$ is preferably CH.

$X^1$ represents $CHR^7$ (in the formula, $R^7$ has the same meaning as that described above), $CHR^8$—$CHR^9$ (in the formula, each of $R^8$ and $R^9$ has the same meaning as that described above), O, or S.

$X^1$ is preferably $CHR^7$ (in the formula, $R^7$ has the same meaning as that described above), O, or S, more preferably $CHR^7$ (in the formula, $R^7$ has the same meaning as that described above) or S, still more preferably $CH^2$ or S, and particularly preferably S.

$R^7$ represents a $C_{1-8}$ alkyl group which may have a substituent, a $C_{2-6}$ alkenyl group which may have a substituent, a $C_{2-6}$ alkynyl group which may have a substituent, or an aryl group which may have a substituent.

$R^7$ is preferably a hydrogen atom or an aryl group which may have a substituent, and more preferably a hydrogen atom.

As a substituent in a $C_{1-8}$ alkyl group, a $C_{2-6}$ alkenyl group, a $C_{2-6}$ alkynyl group, and an aryl group represented by $R^7$, one or more substituents selected from the substituent group a are preferable.

$R^8$ represents a $C_{1-8}$ alkyl group which may have a substituent, a $C_{2-6}$ alkenyl group which may have a substituent, a $C_{2-6}$ alkynyl group which may have a substituent, or an aryl group which may have a substituent.

$R^8$ is preferably a hydrogen atom.

As a substituent in a $C_{1-8}$ alkyl group, a $C_{2-6}$ alkenyl group, a $C_{2-6}$ alkynyl group, or an aryl group represented by $R^8$, one or more substituents selected from the substituent group a are preferable.

$R^9$ represents a $C_{1-8}$ alkyl group which may have a substituent, a $C_{2-6}$ alkenyl group which may have a substituent, a $C_{2-6}$ alkynyl group which may have a substituent, or an aryl group which may have a substituent.

$R^9$ is preferably a hydrogen atom.

As a substituent in a $C_{1-8}$ alkyl group, a $C_{2-6}$ alkenyl group, a $C_{2-6}$ alkynyl group, or an aryl group represented by $R^9$, one or more substituents selected from the substituent group a are preferable.

As a combination of $R^8$ and $R^9$, a combination in which $R^8$ is a hydrogen atom, and $R^9$ is a hydrogen atom is preferable.

$X^2$ represents $CH_2$, O, S, or $NR^{10}$ (in the formula, $R^{10}$ has the same meaning as that described above).

$X^2$ is preferably O or S, and more preferably S.

$R^{10}$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent.

$R^{10}$ is preferably a $C_{1-8}$ alkyl group which may have a substituent, a $C_{2-6}$ alkenyl group which may have a substituent, or a $C_{2-6}$ alkynyl group which may have a substituent, and more preferably a $C_{1-8}$ alkyl group which may have a substituent.

As a substituent in a $C_{1-8}$ alkyl group, a $C_{2-6}$ alkenyl group, a $C_{2-6}$ alkynyl group, or an aryl group represented by $R^{10}$, one or more substituents selected from the substituent group a are preferable.

As a combination of $X^1$ and $X^2$, a combination in which $X^1$ is $CH_2$ or S, and $X^2$ is O or S is preferable, and a combination in which $X^1$ is S, and $X^2$ is S is more preferable.

$R^1$ represents a hydrogen atom, a halogen atom, a hydroxyl group which may have a protecting group, a $C_{1-8}$ alkyl group which may have a substituent, or a $C_{1-6}$ alkoxy group which may have a substituent.

$R^1$ is preferably a hydrogen atom, a halogen atom, a hydroxyl group, a $C_{1-8}$ alkyl group, or a $C_{1-6}$ alkoxy group which may have a substituent, and more preferably a hydrogen atom.

As a substituent in a $C_{1-8}$ alkyl group or a $C_{1-6}$ alkoxy group represented by $R^1$, one or more substituents selected from the substituent group a are preferable.

$R^2$ represents a hydrogen atom, a halogen atom, a hydroxyl group which may have a protecting group, a $C_{1-8}$ alkyl group which may have a substituent, or a $C_{1-6}$ alkoxy group which may have a substituent.

$R^2$ is preferably a hydrogen atom or a halogen atom, and more preferably a hydrogen atom.

As a substituent in a $C_{1-8}$ alkyl group or a $C_{1-6}$ alkoxy group represented by $R^2$, one or more substituents selected from the substituent group a are preferable.

$R^3$ represents a hydrogen atom, a halogen atom, a nitro group, a hydroxyl group which may have a protecting group, a $C_{1-8}$ alkyl group which may have a substituent, a $C_{2-6}$ alkenyl group which may have a substituent, a $C_{2-6}$ alkynyl group which may have a substituent, a $C_{1-6}$ alkoxy group which may have a substituent, an acyl group which may have a substituent, an aryl group which may have a substituent, a heterocyclic group which may have a substituent, or $NR^aR^b$ (in the formula, each of $R^a$ and $R^b$ has the same meaning as that described above).

$R^3$ is preferably a hydrogen atom, an aryl group which may have a substituent, a heterocyclic group which may have a substituent, or $NR^aR^b$ (in the formula, each of $R^a$ and $R^b$ has the same meaning as that described above), more preferably a hydrogen atom or $NR^aR^b$ (in the formula, each of $R^a$ and $R^b$ has the same meaning as that described above), and still more preferably a hydrogen atom.

As a substituent in a $C_{1-8}$ alkyl group, a $C_{2-6}$ alkenyl group, a $C_{2-6}$ alkynyl group, a $C_{1-6}$ alkoxy group, an acyl group, an aryl group, or a heterocyclic group represented by $R^3$, one or more substituents selected from the substituent group a are preferable.

$R^4$ represents a hydrogen atom, a halogen atom, a nitro group, a hydroxyl group which may have a protecting group, a $C_{1-8}$ alkyl group which may have a substituent, a $C_{2-6}$ alkenyl group which may have a substituent, a $C_{2-6}$ alkynyl group which may have a substituent, a $C_{1-6}$ alkoxy group which may have a substituent, an acyl group which may have a substituent, an aryl group which may have a substituent, a heterocyclic group which may have a substituent, or $NR^aR^b$ (in the formula, each of $R^a$ and $R^b$ has the same meaning as that described above).

$R^4$ is preferably a hydrogen atom or $NR^aR^b$ (in the formula, each of $R^a$ and $R^b$ has the same meaning as that described above), and more preferably $NR^aR^b$ (in the formula, each of $R^a$ and $R^b$ has the same meaning as that described above).

As a substituent in a $C_{1-8}$ alkyl group, a $C_{2-6}$ alkenyl group, a $C_{2-6}$ alkynyl group, a $C_{1-6}$ alkoxy group, an acyl group, an aryl group, or a heterocyclic group represented by $R^4$, one or more substituents selected from the substituent group a are preferable.

$R^5$ represents a hydrogen atom, a halogen atom, a nitro group, a hydroxyl group which may have a protecting group, a $C_{1-8}$ alkyl group which may have a substituent, a $C_{2-6}$ alkenyl group which may have a substituent, a $C_{2-6}$ alkynyl group which may have a substituent, a $C_{1-6}$ alkoxy group which may have a substituent, an acyl group which may have a substituent, an aryl group which may have a substituent, a heterocyclic group which may have a substituent, or $NR^aR^b$ (in the formula, each of $R^a$ and $R^b$ has the same meaning as that described above).

$R^5$ is preferably a hydrogen atom or $NR^aR^b$ (in the formula, each of $R^a$ and $R^b$ has the same meaning as that described above), and more preferably a hydrogen atom.

As a substituent in a $C_{1-8}$ alkyl group, a $C_{2-6}$ alkenyl group, a $C_{2-6}$ alkynyl group, a $C_{1-6}$ alkoxy group, an acyl group, an aryl group, or a heterocyclic group represented by $R^5$, one or more substituents selected from the substituent group a are preferable.

$R^a$ represents a hydrogen atom, a $C_{1-8}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, an aryl group which may have a substituent, an ar $C_{1-6}$ alkyl group which may have a substituent, an acyl group which may have a substituent, a $C_{1-6}$ alkylsulfonyl group which may have a substituent, a heterocyclic group which may have a substituent, or a heterocyclic $C_{1-8}$ alkyl group which may have a substituent.

$R^a$ is preferably a hydrogen atom, a $C_{1-8}$ alkyl group which may have a substituent, an acyl group which may have a substituent, or a heterocyclic $C_{1-8}$ alkyl group which may have a substituent, and more preferably a hydrogen atom.

As a substituent in a $C_{1-8}$ alkyl group, a $C_{2-6}$ alkenyl group, a $C_{2-6}$ alkynyl group, a $C_{3-8}$ cycloalkyl group, an aryl group, an ar $C_{1-6}$ alkyl group, an acyl group, a $C_{1-6}$ alkylsulfonyl group, a heterocyclic group, or a heterocyclic $C_{1-8}$ alkyl group represented by $R^a$, one or more substituents selected from the substituent group c are preferable.

<Substituent Group c>

A deuterium atom, a halogen atom, a cyano group, a nitro group, an azide group, an oxo group, a hydroxyl group which may have a protecting group, an amino group which may have a protecting group, a carboxyl group which may have a protecting group, a $C_{1-8}$ alkyl group which may have one or more substituents selected from the substituent group d, a $C_{2-6}$ alkenyl group which may have one or more substituents selected from the substituent group d, a $C_{2-6}$ alkynyl group which may have one or more substituents selected from the substituent group d, a $C_{3-8}$ cycloalkyl group which may have one or more substituents selected from the substituent group d, a $C_{3-8}$ cycloalkenyl group which may have one or more substituents selected from the substituent group d, an aryl group which may have one or more substituents selected from the substituent group d, an ar $C_{1-6}$ alkyl group which may have one or more substituents selected from the substituent group d, an $C_{1-6}$ alkoxy group which may have one or more substituents selected from the substituent group d, an acyl group which may have one or more substituents selected from the substituent group d, a $C_{1-6}$ alkylamino group which may have one or more substituents selected from the substituent group d, a di($C_{1-6}$ alkyl)amino group which may have one or more substituents selected from the substituent group d, a heterocyclic group which may have one or more substituents selected from the substituent group d, a heterocyclic $C_{1-8}$ alkyl group which may have one or more substituents selected from the substituent group d, a heterocyclic oxy group which may have one or more substituents selected from the substituent group d, $CONR^cR^d$ (in the formula, $R^c$ and $R^d$ are the same as or different from each other, and each of $R^c$ and $R^d$ represents a hydrogen atom, a $C_{1-8}$ alkyl group which may have one or more substituents selected from the substituent group d, a $C_{2-6}$ alkenyl group which may have one or more substituents selected from the substituent group d, or a $C_{2-6}$ alkynyl group which may have one or more substituents selected from the substituent group d; or $R^c$ and $R^d$ may form a cyclic amino group which may be substituted with one or more substituents selected from the substituent group d, together with the nitrogen atom to which $R^c$ and $R^d$ are bonded), $NHCONR^eR^f$ (in the formula, $R^e$ and $R^f$ are the same as or different from each other, and each of $R^e$ and $R^f$ represents a hydrogen atom, a $C_{1-8}$ alkyl group which may have one or more substituents selected from the substituent group d, a $C_{2-6}$ alkenyl group which may have one or more substituents selected from the substituent group d, or a $C_{2-6}$ alkynyl group which may have one or more substituents selected from the substituent group d; or $R^e$ and $R^f$ may form a cyclic amino group which may be substituted with one or more substituents selected from the substituent group d, together with the nitrogen atom to which $R^e$ and $R^f$ are bonded)

<Substituent Group d>

A halogen atom, a cyano group, a nitro group, an oxo group, a hydroxyl group which may have a protecting group, an amino group which may have a protecting group, a carboxyl group which may have a protecting group, a $C_{1-8}$ alkyl group which may have one or more substituents selected from the substituent group e, a $C_{2-6}$ alkenyl group which may have one or more substituents selected from the substituent group e, a $C_{2-6}$ alkynyl group which may have one or more substituents selected from the substituent group e, a $C_{3-8}$ cycloalkyl group which may have one or more substituents selected from the substituent group e, an aryl group which may have one or more substituents selected from the substituent group e, a $C_{1-6}$ alkoxy group which may have one or more substituents selected from the substituent group e, an acyl group which may have one or more substituents selected from the substituent group e, a $C_{1-6}$ alkylamino group which may have one or more substituents selected from the substituent group e, a di($C_{1-6}$ alkyl)amino group which may have one or more substituents selected from the substituent group e, a heterocyclic group which may have one or more substituents selected from the substituent group e, a heterocyclic oxy group which may have one or more substituents selected from the substituent group e <Substituent Group e>

A halogen atom, a hydroxyl group which may have a protecting group, a $C_{1-6}$ alkoxy group, $CONR^gR^h$ (in the formula, $R^g$ and $R^h$ are the same as or different from each other, and each of $R^g$ and $R^h$ represents a hydrogen atom, a $C_{1-8}$ alkyl group, a $C_{2-6}$ alkenyl group, or a $C_{2-6}$ alkynyl group; or $R^g$ and $R^h$ may form a cyclic amino group together with the nitrogen atom to which $R^g$ and $R^h$ are bonded)

$R^{a1}$ represents a hydrogen atom, a $C_{1-8}$ alkyl group which may have one or more substituents selected from the substituent group f, a $C_{2-6}$ alkenyl group which may have one or more substituents selected from the substituent group f, a $C_{2-6}$ alkynyl group which may have one or more substituents selected from the substituent group f, a $C_{3-8}$ cycloalkyl group which may have one or more substituents selected from the substituent group f, an aryl group which may have one or more substituents selected from the substituent group f, an ar $C_{1-6}$ alkyl group which may have one or more substituents selected from the substituent group f, an acyl group which may have one or more substituents selected from the substituent group f, a $C_{1-6}$ alkylsulfonyl group which may have one or more substituents selected from the substituent group f, a heterocyclic group which may have one or more substituents selected from the substituent group f, or a heterocyclic $C_{1-8}$ alkyl group which may have one or more substituents selected from the substituent group f.

$R^{a1}$ is preferably a hydrogen atom.

<Substituent Group f>

A deuterium atom, a halogen atom, a cyano group, a nitro group, a hydroxyl group which may have a protecting group, an amino group which may have a protecting group, a carboxyl group which may have a protecting group, a $C_{1-8}$ alkyl group which may have one or more substituents selected from the substituent group d, a $C_{2-6}$ alkenyl group which may have one or more substituents selected from the substituent group d, a $C_{2-6}$ alkynyl group which may have one or more substituents selected from the substituent group d, a $C_{3-8}$ cycloalkyl group which may have one or more substituents selected from the substituent group d, a $C_{3-8}$ cycloalkenyl group which may have one or more substituents selected from the substituent group d, an aryl group which may have one or more substituents selected from the substituent group d, an ar $C_{1-6}$ alkyl group which may have one or more substituents selected from the substituent group d, an $C_{1-6}$ alkoxy group which may have one or more substituents selected from the substituent group d, an acyl group which may have one or more substituents selected from the substituent group d, a $C_{1-6}$ alkylamino group which may have one or more substituents selected from the substituent group d, a di($C_{1-6}$ alkyl)amino group which may have one or more substituents selected from the substituent group d, a heterocyclic group which may have one or more substituents selected from the substituent group d, a heterocyclic $C_{1-8}$ alkyl group which may have one or more substituents selected from the substituent group d, a heterocyclic oxy group which may have one or more substituents selected from the substituent group d, CONR$^c$R$^d$ (in the formula, $R^c$ and $R^d$ are the same as or different from each other, and each of $R^c$ and $R^d$ represents a hydrogen atom, a $C_{1-8}$ alkyl group which may have one or more substituents selected from the substituent group d, a $C_{2-6}$ alkenyl group which may have one or more substituents selected from the substituent group d, or a $C_{2-6}$ alkynyl group which may have one or more substituents selected from the substituent group d; or $R^c$ and $R^d$ may form a cyclic amino group which may be substituted with one or more substituents selected from the substituent group d, together with the nitrogen atom to which $R^c$ and $R^d$ are bonded), NHCONR$^e$R$^f$ (in the formula, $R^e$ and $R^f$ are the same as or different from each other, and each of $R^e$ and $R^f$ represents a hydrogen atom, a $C_{1-8}$ alkyl group which may have one or more substituents selected from the substituent group d, a $C_{2-6}$ alkenyl group which may have one or more substituents selected from the substituent group d, or a $C_{2-6}$ alkynyl group which may have one or more substituents selected from the substituent group d; or $R^e$ and $R^f$ may form a cyclic amino group which may be substituted with one or more substituents selected from the substituent group d, together with the nitrogen atom to which $R^e$ and $R^f$ are bonded)

$R^b$ represents a hydrogen atom, a $C_{1-8}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, an aryl group which may have a substituent, an ar $C_{1-6}$ alkyl group which may have a substituent, an acyl group which may have a substituent, a $C_{1-6}$ alkylsulfonyl group which may have a substituent, a heterocyclic group which may have a substituent, or a heterocyclic $C_{1-8}$ alkyl group which may have a substituent.

$R^b$ is preferably a hydrogen atom, a $C_{1-8}$ alkyl group which may have a substituent, a $C_{3-8}$ cycloalkyl group which may have a substituent, an ar $C_{1-6}$ alkyl group which may have a substituent, an acyl group which may have a substituent, a $C_{1-6}$ alkylsulfonyl group which may have a substituent, a heterocyclic group which may have a substituent, or a heterocyclic $C_{1-8}$ alkyl group which may have a substituent, and more preferably a $C_{3-8}$ cycloalkyl group which may have a substituent, a heterocyclic group which may have a substituent, or a heterocyclic $C_{1-8}$ alkyl group which may have a substituent.

As a substituent in a $C_{1-8}$ alkyl group, a $C_{2-6}$ alkenyl group, a $C_{2-6}$ alkynyl group, a $C_{3-8}$ cycloalkyl group, an aryl group, an ar $C_{1-6}$ alkyl group, an acyl group, a $C_{1-6}$ alkylsulfonyl group, a heterocyclic group, or a heterocyclic $C_{1-8}$ alkyl group represented by $R^b$, one or more substituents selected from the substituent group c are preferable.

$R^{b1}$ represents a $C_{1-8}$ alkyl group which may have one or more substituents selected from the substituent group f, a $C_{2-6}$ alkenyl group which may have one or more substituents selected from the substituent group f, a $C_{2-6}$ alkynyl group which may have one or more substituents selected from the substituent group f, a $C_{3-8}$ cycloalkyl group which may have one or more substituents selected from the substituent group f, an aryl group which may have one or more substituents selected from the substituent group f, an ar $C_{1-6}$ alkyl group which may have one or more substituents selected from the substituent group f, a $C_{1-6}$ alkylsulfonyl group which may have one or more substituents selected from the substituent group f, a heterocyclic group which may have one or more substituents selected from the substituent group f, or a heterocyclic $C_{1-8}$ alkyl group which may have one or more substituents selected from the substituent group f.

$R^{b1}$ is preferably a $C_{1-8}$ alkyl group which may have one or more substituents selected from the substituent group f, a $C_{3-8}$ cycloalkyl group which may have one or more substituents selected from the substituent group f, an ar $C_{1-6}$ alkyl group which may have one or more substituents selected from the substituent group f, a $C_{1-6}$ alkylsulfonyl group which may have one or more substituents selected from the substituent group f, a heterocyclic group which may have one or more substituents selected from the substituent group f, or a heterocyclic $C_{1-8}$ alkyl group which may have one or more substituents selected from the substituent group f, more preferably a $C_{3-8}$ cycloalkyl group which may have one or more substituents selected from the substituent group f, a heterocyclic group which may have one or more substituents selected from the substituent group f, or a heterocyclic $C_{1-8}$ alkyl group which may have one or more substituents selected from the substituent group f, and still more preferably a heterocyclic $C_{1-8}$ alkyl group which may have one or more substituents selected from the substituent group f.

When the ring A is a ring represented by General Formula [I], as a combination of $R^3$, $R^4$, and $R^5$, a combination in which $R^3$ is a hydrogen atom, one of $R^4$ or $R^5$ is $NR^aR^b$ (in the formula, each of $R^a$ and $R^b$ has the same meaning as that described above), and the other $R^4$ or $R^5$ is a hydrogen atom is preferable, and a combination in which $R^3$ is a hydrogen atom, $R^4$ is $NR^aR^b$ (in the formula, each of $R^a$ and $R^b$ has the same meaning as that described above), and $R^5$ is a hydrogen atom is more preferable.

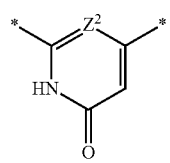

[I]

(In the formula, each of * and $Z^2$ has the same meaning as that described above.)

When the ring A is a ring represented by General Formula [II], as a combination of $R^3$, $R^4$, and $R^5$, a combination in which $R^3$ is a hydrogen atom, $R^4$ is $NR^{a1}R^{b1}$ (in the formula, each of $R^{a1}$ and $R^{b1}$ has the same meaning as that described above), and $R^5$ is a hydrogen atom is preferable.

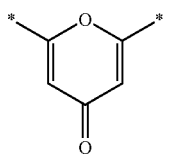

[II]

(in the formula, * has the same meaning as that described above)

As a combination of $R^a$ and $R^b$, a combination in which $R^a$ is a hydrogen atom, and $R^b$ is a hydrogen atom, a $C_{1-8}$ alkyl group which may have a substituent, a $C_{3-8}$ cycloalkyl group which may have a substituent, an ar $C_{1-6}$ alkyl group which may have a substituent, an acyl group which may have a substituent, a $C_{1-6}$ alkylsulfonyl group which may have a substituent, a heterocyclic group which may have a substituent, or a heterocyclic $C_{1-8}$ alkyl group which may have a substituent is preferable, and a combination in which $R^a$ is a hydrogen atom, and $R^b$ is a $C_{3-8}$ cycloalkyl group which may have a substituent, a heterocyclic group which may have a substituent, or a heterocyclic $C_{1-8}$ alkyl group which may have a substituent is more preferable.

As a combination of $R^{a1}$ and $R^{b1}$, a combination in which $R^{a1}$ is a hydrogen atom, and $R^{b1}$ is a $C_{1-8}$ alkyl group which may have one or more substituents selected from the substituent group f, a $C_{3-8}$ cycloalkyl group which may have one or more substituents selected from the substituent group f, an ar $C_{1-6}$ alkyl group which may have one or more substituents selected from the substituent group f, a $C_{1-6}$ alkylsulfonyl group which may have one or more substituents selected from the substituent group f, a heterocyclic group which may have one or more substituents selected from the substituent group f, or a heterocyclic $C_{1-8}$ alkyl group which may have one or more substituents selected from the substituent group f is preferable, a combination in which $R^{a1}$ is a hydrogen atom, and $R^{b1}$ is a $C_{3-8}$ cycloalkyl group which may have one or more substituents selected from the substituent group f, a heterocyclic group which may have one or more substituents selected from the substituent group f, or a heterocyclic $C_{1-8}$ alkyl group which may have one or more substituents selected from the substituent group f is more preferable, and a combination in which $R^{a1}$ is a hydrogen atom, and $R^{b1}$ is a heterocyclic $C_{1-8}$ alkyl group which may have one or more substituents selected from the substituent group f is still more preferable.

As the morpholine derivative of the present invention, the compound represented by General Formula [1] is preferable.

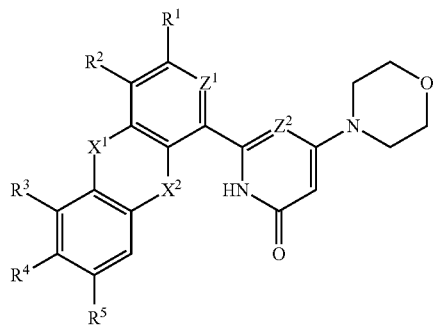

[1]

(In the formula, each of $Z^1$, $Z^2$, $X^1$, $X^2$, $R^1$, $R^2$, $R^3$, $R^4$, and $R^5$ has the same meaning as that described above.)

The preferable range of each of $Z^1$, $Z^2$, $X^1$, $X^2$, $R^1$, $R^2$, $R^3$, $R^4$, and $R^5$ in General Formula [1] is the same as that described above.

The preferable range of the combination of $R^a$ and $R^b$ is the same as that described above.

As the morpholine derivative of the present invention, a compound represented by General Formula [1α] is more preferable.

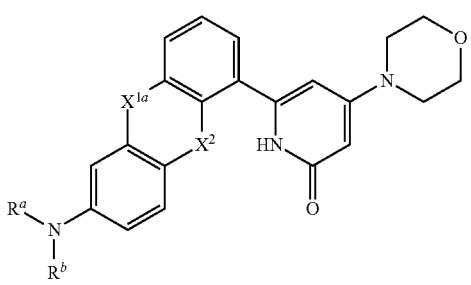

[1α]

(In the formula, each of X', $X^2$, $R^a$, and $R^b$ has the same meaning as that described above.)

$X^{1a}$ represents $CHR^7$ (in the formula, $R^7$ has the same meaning as that described above), O, or S.

$X^{1a}$ is preferably $CHR^7$ (in the formula, $R^7$ has the same meaning as that described above) or S, more preferably $CH^2$ or S, and still more preferably S.

The preferable range of each of $X^2$, $R^7$, $R^a$, and $R^b$ in General Formula [1α] is the same as that described above.

As a combination of $X^{1a}$ and $X^2$, a combination in which $X^{1a}$ is $CH_2$ or S, and $X^2$ is O or S is preferable, and a combination in which $X^{1a}$ is S, and $X^2$ is S is more preferable.

The preferable range of the combination of $R^a$ and $R^b$ is the same as that described above.

In addition, in another aspect, as the morpholine derivative of the present invention, a compound represented by General Formula [1β] is preferable.

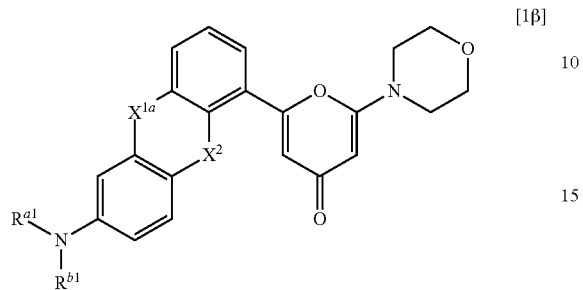
[1β]

(In the formula, each of $X^{1a}$, $X^2$, $R^{a1}$, and $R^{b1}$ has the same meaning as that described above.)

The preferable range of each of $X^{1a}$, $X^2$, $R^{a1}$, and $R^{b1}$ in General Formula [1β] is the same as that described above.

The preferable range of the combination of $X^{1a}$ and $X^2$ is the same as that described above.

The preferable range of the combination of $R^{a1}$ and $R^{b1}$ is the same as that described above.

In the compounds represented by General Formulas [1A] and [1], tautomers represented by the following General Formulas [Aa], [Ab], [Ac] to [Ae] are present in the group represented by the following General Formula [A]. The present invention also includes these tautomers.

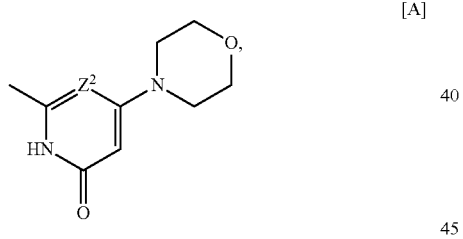
[A]

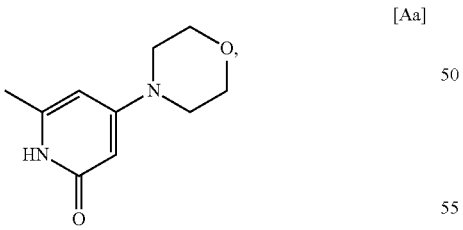
[Aa]

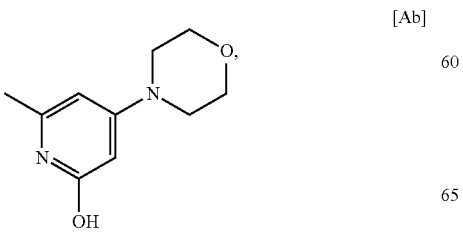
[Ab]

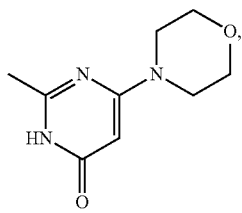
[Ac]

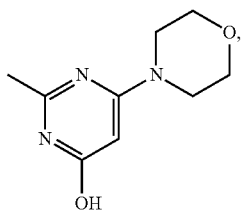
[Ad]

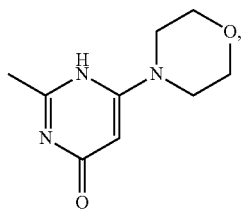
[Ae]

In the compound represented by General Formula [1α], tautomers represented by the following Formula [Ba] are present in the group represented by the following Formula [B]. The present invention also includes the tautomers.

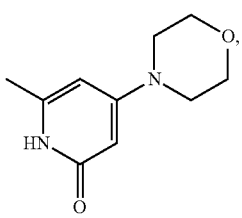
[B]

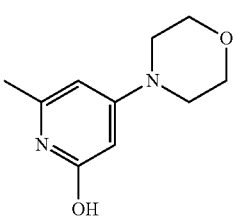
[Ba]

In the compound represented by General Formula [1A], [1], [1α], or [1β] or a salt thereof, in a case where isomers (for example, optical isomers or geometrical isomers) are present, the present invention includes these isomers, and includes a solvate, a hydrate, and various shapes of crystal.

Next, the preparation methods of the compound of the present invention will be described.

The compound of the present invention is prepared by combining known methods, and for example, can be prepared according to the following preparation methods.

[Preparation Method 1]

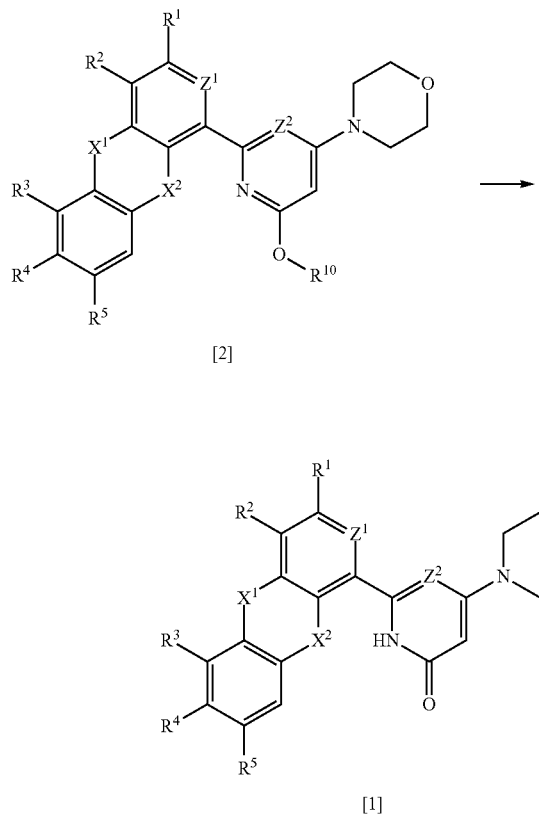

(In the formula, $R^{10}$ represents a hydroxyl protecting group; and each of $Z^1$, $Z^2$, $X^1$, $X^2$, $R^1$, $R^2$, $R^3$, $R^4$, and $R^5$ has the same meaning as that described above.)

The compound represented by General Formula [1] or a salt thereof can be prepared by deprotecting the compound represented by General Formula [2] or a salt thereof.

This reaction may be performed, for example, according to the method described in "Protective Groups in Organic Synthesis" written by W. Greene et al., 4th edition, pp. 16-430, 2007 (John Wiley & Sons, INC.).

[Preparation Method 2]

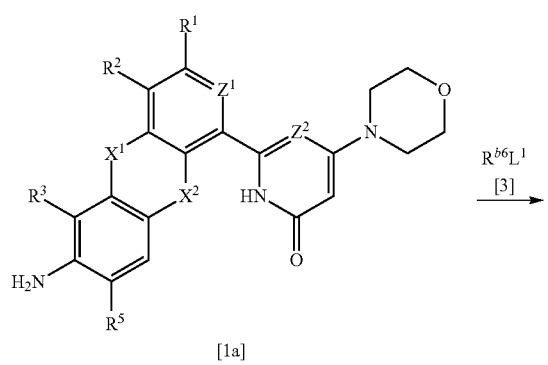

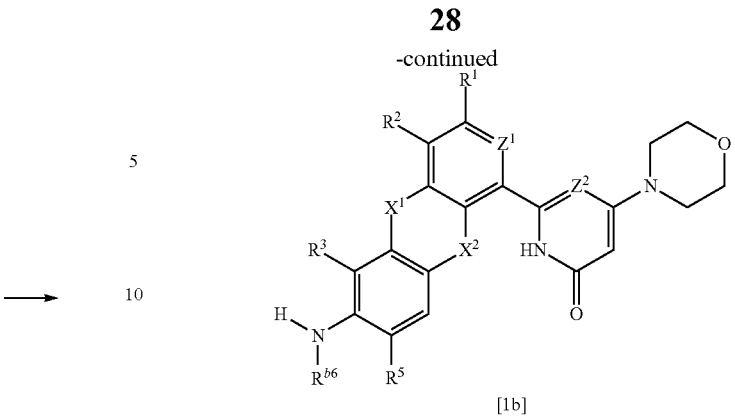

(In the formula, $R^{b6}$ represents a $C_{1-8}$ alkyl group which may have a substituent, a $C_{2-6}$ alkenyl group which may have a substituent, a $C_{2-6}$ alkynyl group which may have a substituent, ar $C_{1-6}$ alkyl group which may have a substituent, an acyl group which may have a substituent, a $C_{1-6}$ alkylsulfonyl group which may have a substituent, or a heterocyclic $C_{1-8}$ alkyl group which may have a substituent; $L^1$ represents a leaving group; and each of Z, $Z^2$, $X^1$, $X^2$, $R^1$, $R^2$, $R^3$, and $R^5$ has the same meaning as that described above.)

In this preparation method, conversion of $R^4$ in the compound represented by General Formula [1] will be described. In the same manner as this method, conversion of $R^3$ or $R^5$ can also be performed.

As the compound represented by General Formula [3], for example, chloroacetyl chloride, 3-bromopropanoyl chloride, ethyl 2-bromoacetate, and the like are known.

The compound represented by General Formula [1b] or a salt thereof can be prepared by reacting the compound represented by General Formula [3] with the compound represented by General Formula [1a] or a salt thereof in the presence of a base or in the absence thereof.

The solvent used in this reaction is not particularly limited as long as it does not affect the reaction, and examples thereof include aliphatic hydrocarbons, halogenated hydrocarbons, ethers, ketones, esters, amides, nitriles, sulfoxides, and aromatic hydrocarbons, and these may be used in combination.

Examples of a preferable solvent include esters and amides.

Although the amount of solvent used is not particularly limited, the amount used is preferably 1 time to 100 times (v/w), more preferably 1 time to 50 times (v/w), and still more preferably 1 time to 10 times (v/w) the amount of compound represented by General Formula [1a] or a salt thereof.

The amount of compound represented by General Formula [3] or a salt thereof used is preferably 1-fold by mole to 10-fold by mole and more preferably 1-fold by mole to 5-fold by mole, with respect to the compound represented by General Formula [1a] or a salt thereof.

Examples of the base used in this reaction as desired include an inorganic base and an organic base.

Examples of a preferable base include inorganic bases such as sodium hydrogen carbonate, sodium carbonate, potassium carbonate, cesium carbonate, and tripotassium phosphate, and organic bases such as pyridine, 4-(dimethylamino)pyridine, triethylamine, and diisopropyl ethylamine.

The amount of base used is preferably 1-fold by mole to 10-fold by mole and more preferably 1-fold by mole to 5-fold by mole, with respect to the compound represented by General Formula [1a] or a salt thereof.

This reaction, typically, may be performed at a temperature of 0° C. to 200° C., and preferably at a temperature of 0° C. to 100° C., for 10 minutes to 48 hours.

[Preparation Method 3]

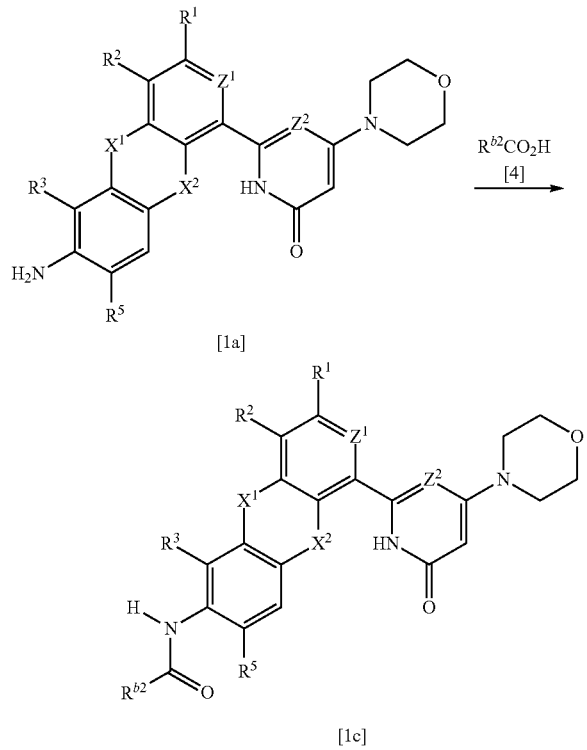

[1a]

[1c]

(In the formula, $R^{b2}$ represents a $C_{1-8}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, an aryl group which may have a substituent, or a heterocyclic group which may have a substituent; and each of $Z^1$, $Z^2$, $X^1$, $X^2$, $R^1$, $R^2$, $R^3$, and $R^5$ has the same meaning as that described above.)

In this preparation method, conversion of $R^4$ in the compound represented by General Formula [1] will be described. In the same manner as this method, conversion of $R^3$ or $R^5$ can also be performed.

As the compound represented by General Formula [4], for example, 2-fluoroisopicolinic acid, 4-bromopicolinic acid, and the like are known.

The compound represented by General Formula [1c] or a salt thereof can be prepared by reacting the compound represented by General Formula [4] or a salt thereof with the compound represented by General Formula [1a] or a salt thereof in the presence of a base or in the absence thereof.

This reaction may be performed, for example, according to the method described in "Organic Compound Synthesis IV, carboxylic acid, amino acid, peptide", 5th edition, Experimental Chemistry, Vol. 16, pp. 258-267 (Maruzen Publishing Co., Ltd.).

[Preparation Method 4]

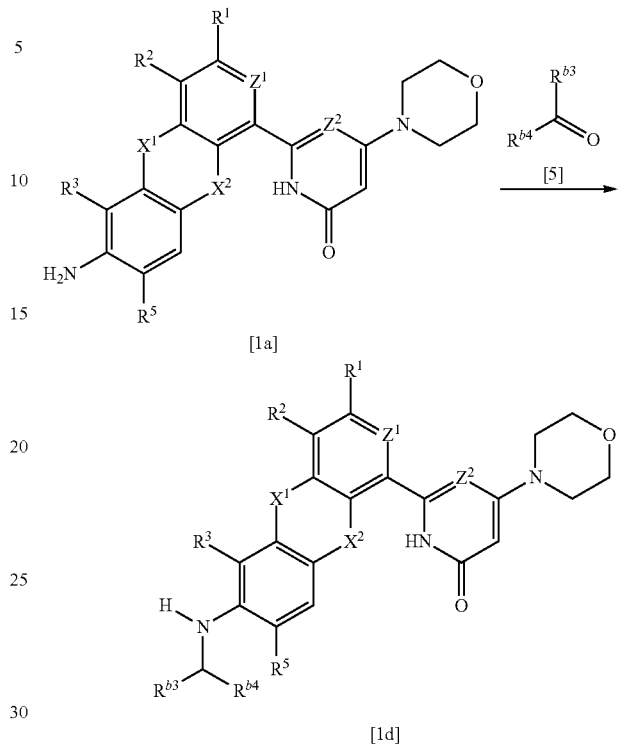

[1a]

[1d]

(In the formula, $R^{b3}$ represents a hydrogen atom, a $C_{1-8}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, an aryl group which may have a substituent, or a heterocyclic group which may have a substituent; $R^{b4}$ represents a $C_{1-8}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, an aryl group which may have a substituent, or a heterocyclic group which may have a substituent; and each of $Z^1$, $Z^2$, $X^1$, $X^2$, $R^1$, $R^2$, $R^3$, and $R^5$ has the same meaning as that described above.)

In this preparation method, conversion of $R^4$ in the compound represented by General Formula [1] will be described. In the same manner as this method, conversion of $R^3$ or $R^5$ can also be performed.

As the compound represented by General Formula [5], for example, 1-(pyrimidin-2-yl)ethanone and 5-methylpyrazine-2-carbaldehyde, and the like are known.

The compound represented by General Formula [1d] or a salt thereof can be prepared by reacting the compound represented by General Formula [5] with the compound represented by General Formula [1a] or a salt thereof in the presence of a reductant.

The solvent used in this reaction is not particularly limited as long as it does not affect the reaction, and examples thereof include aliphatic hydrocarbons, halogenated hydrocarbons, alcohols, glycols, ethers, ketones, esters, amides, nitriles, organic acids, sulfoxides, and aromatic hydrocarbons, and these may be used in combination.

Examples of a preferable solvent include organic acids, halogenated hydrocarbons, and alcohols.

Although the amount of solvent used is not particularly limited, the amount used is preferably 1 time to 1000 times (v/w), more preferably 1 time to 500 times (v/w), and still more preferably 1 time to 100 times (v/w) the amount of compound represented by General Formula [1a] or a salt thereof.

The amount of compound represented by General Formula [5] or a salt thereof used is preferably 1-fold by mole to 50-fold by mole and more preferably 1-fold by mole to 20-fold by mole, with respect to the compound represented by General Formula [1a] or a salt thereof.

Examples of the reductant used in this reaction include sodium triacetoxyborohydride, sodium cyanoborohydride, and 2-picoline borane.

The amount of reductant used is preferably 0.01-fold by mole to 10-fold by mole and more preferably 0.1-fold by mole to 10-fold by mole, with respect to the compound represented by General Formula [1a] or a salt thereof.

This reaction, typically, may be performed at a temperature of 0° C. to 200° C., and preferably at a temperature of 0° C. to 100° C., for 10 minutes to 72 hours.

[Preparation Method 5]

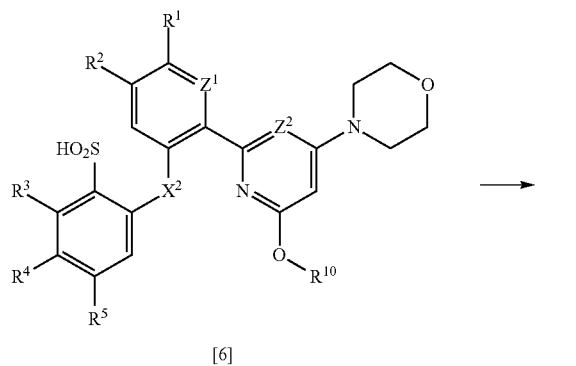

(In the formula, each of $Z^1$, $Z^2$, $X^2$, $R^1$, $R^2$, $R^3$, $R^5$, and $R^{10}$ has the same meaning as that described above.)

The compound represented by General Formula [1e] or a salt thereof can be prepared by reacting a dehydrating agent with the compound represented by General Formula [6] or a salt thereof.

The solvent used in this reaction is not particularly limited as long as it does not affect the reaction, and examples thereof include aliphatic hydrocarbons, halogenated hydrocarbons, ethers, and aromatic hydrocarbons, and these may be used in combination.

Examples of the dehydrating agent used in this reaction include polyphosphoric acid and an Eaton reagent.

The amount of dehydrating agent used is preferably 1 time to 500 times (v/w), more preferably 1 time to 100 times (v/w), and still more preferably 1 time to 30 times (v/w) the amount of compound represented by General Formula [6] or a salt thereof.

The dehydrating agent is preferably used as a solvent.

This reaction, typically, may be performed at a temperature of 20° C. to 200° C., and preferably at a temperature of 20° C. to 100° C., for 10 minutes to 72 hours.

[Preparation Method 6]

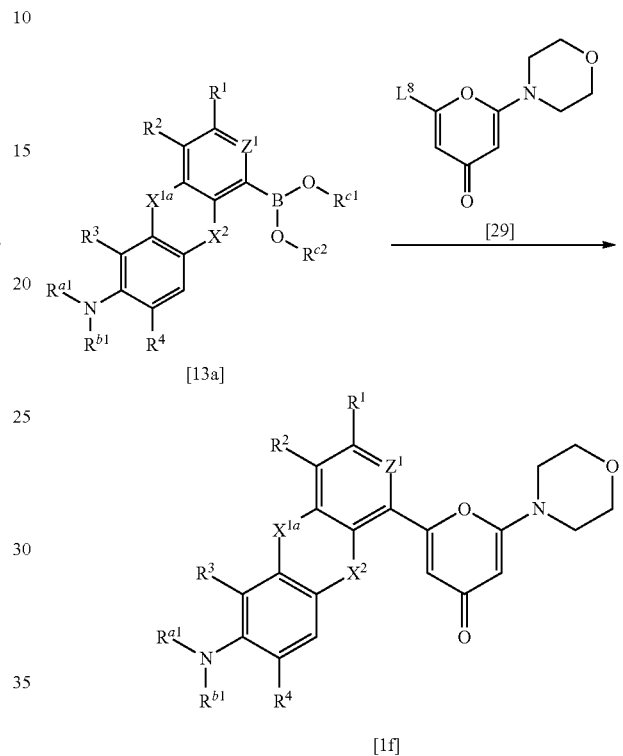

(In the formula, $R^{c1}$ represents a $C_{1-6}$ alkyl group which may have a substituent; $R^{c2}$ represents a $C_{1-6}$ alkyl group which may have a substituent; or both $R^{c1}$ and $R^{c2}$ represent $C_{2-6}$ alkylene groups which may have a substituent; $L^8$ represents a leaving group; and each of $Z^1$, $X^{1a}$, $X^2$, $R^{a1}$, $R^{b1}$, R, $R^2$, $R^3$, and $R^5$ has the same meaning as that described above.)

As the compound represented by General Formula [29], for example, 2-chloro-6-morpholino-4H-pyran-4-one and the like are known.

The compound represented by General Formula [1f] or a salt thereof can be prepared by reacting the compound represented by General Formula [29] or a salt thereof with the compound represented by General Formula [13a] or a salt thereof in the presence of a base or in the absence thereof, in the presence of a palladium catalyst, and in the presence of a ligand or in the absence thereof.

The solvent used in this reaction is not particularly limited as long as it does not affect the reaction, and examples thereof include aliphatic hydrocarbons, halogenated hydrocarbons, alcohols, glycols, ethers, ketones, esters, amides, nitriles, sulfoxides, aromatic hydrocarbons, and water, and these may be used in combination.

Examples of a preferable solvent include alcohols, esters, amides, nitriles, ethers, aromatic hydrocarbons, water, and mixed solvents thereof.

Although the amount of solvent used is not particularly limited, the amount used is preferably 0.1 time to 10000 times (v/w), more preferably 0.1 time to 5000 times (v/w), and still more preferably 0.1 time to 1000 times (v/w) the amount of compound represented by General Formula [13a] or a salt thereof.

The amount of compound represented by General Formula [29] or a salt thereof used is preferably 1-fold by mole to 10-fold by mole and more preferably 1-fold by mole to 5-fold by mole, with respect to the compound represented by General Formula [13a] or a salt thereof.

Examples of the base used in this reaction as desired include an inorganic base and an organic base.

Examples of a preferable base include inorganic bases such as sodium hydrogen carbonate, sodium carbonate, potassium carbonate, sodium acetate, potassium acetate, cesium carbonate, sodium tert-butoxide, potassium tert-butoxide, trisodium phosphate, and tripotassium phosphate, and organic bases such as pyridine, 4-(dimethylamino)pyridine, triethylamine, and diisopropyl ethylamine.

The amount of base used is preferably 1-fold by mole to 20-fold by mole, more preferably 1-fold by mole to 15-fold by mole, and still more preferably 1-fold by mole to 10-fold by mole, with respect to the compound represented by General Formula [13a] or a salt thereof.

The amount of palladium catalyst used is preferably 0.00001-fold by mole to 1-fold by mole and more preferably 0.001-fold by mole to 1-fold by mole, with respect to the compound represented by General Formula [13] or a salt thereof.

The amount of ligand used is preferably 0.00001-fold by mole to 5-fold by mole and more preferably 0.001-fold by mole to 2-fold by mole, with respect to the compound represented by General Formula [13a] or a salt thereof.

Preferably, this reaction may be performed at a temperature of 20° C. to 170° C. for 1 minute to 1 week in an inert gas (for example, nitrogen or argon) atmosphere.

This reaction may be performed under microwave irradiation.

The compounds represented by General Formulas [1], [1b], [1c], [1d], [1e], and [1f] obtained in these manners and salts thereof can be derived to other compounds or salts thereof, for example, by a known reaction such as condensation, addition, oxidation, reduction, rearrangement, substitution, halogenation, dehydration, or hydrolysis, or by suitably combining these reactions.

Next, the preparation method of raw materials for the compound of the present invention will be described.

[Preparation Method A]

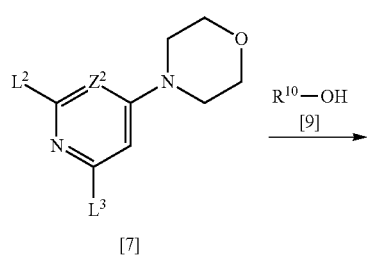

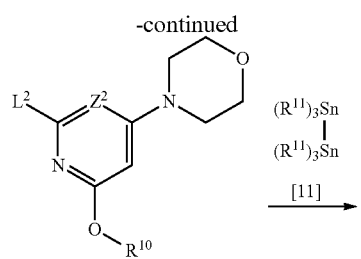

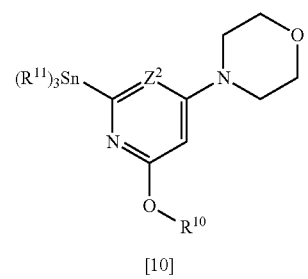

(In the formula, $R^{11}$ represents a $C_{1-8}$ alkyl group which may have a substituent; $L^2$ represents a leaving group; $L^3$ represents a leaving group; and each of $Z^2$ and $R^{10}$ has the same meaning as that described above.)

(1)

As the compound represented by General Formula [9], for example, methanol, 4-methoxybenzyl alcohol, and the like are known.

The compound represented by General Formula [8] or a salt thereof can be prepared by reacting the compound represented by General Formula [7] or a salt thereof with the compound represented by General Formula [9] in the presence of a base.

The solvent used in this reaction is not particularly limited as long as it does not affect the reaction, and examples thereof include aliphatic hydrocarbons, halogenated hydrocarbons, alcohols, ethers, ketones, amides, nitriles, sulfoxides, and aromatic hydrocarbons, and these may be used in combination.

Although the amount of solvent used is not particularly limited, the amount used is preferably 1 time to 1000 times (v/w), more preferably 1 time to 500 times (v/w), and still more preferably 1 time to 100 times (v/w) the amount of compound represented by General Formula [7].

The amount of compound represented by General Formula [9] used is preferably 1-fold by mole to 100-fold by mole and more preferably 1-fold by mole to 20-fold by mole, with respect to the compound represented by General Formula [7] or a salt thereof.

Examples of the base used in this reaction include an inorganic base.

Examples of a preferable base include sodium hydrogen carbonate, sodium carbonate, potassium carbonate, sodium methoxide, sodium hydride, and potassium tert-butoxide.

The amount of base used is preferably 1-fold by mole to 20-fold by mole and more preferably 1-fold by mole to 10-fold by mole, with respect to the compound represented by General Formula [7] or a salt thereof.

This reaction, typically, may be performed at a temperature of 0° C. to 200° C. for 10 minutes to 72 hours.

This reaction may be performed under microwave irradiation.

(2)

As the compound represented by General Formula [11], for example, 1,1,1,2,2,2-hexabutyldistannane and the like are known.

The compound represented by General Formula [10] or a salt thereof can be prepared by reacting the compound represented by General Formula [11] with the compound represented by General Formula [8] or a salt thereof in the presence of a base or in the absence thereof, in the presence of a palladium catalyst, and in the presence of a ligand or in the absence thereof.

The solvent used in this reaction is not particularly limited as long as it does not affect the reaction, and examples thereof include aliphatic hydrocarbons, halogenated hydrocarbons, alcohols, glycols, ethers, ketones, esters, amides, nitriles, sulfoxides, aromatic hydrocarbons, and water, and these may be used in combination.

Examples of a preferable solvent include alcohols, esters, amides, nitriles, ethers, and aromatic hydrocarbons.

Although the amount of solvent used is not particularly limited, the amount used is preferably 1 time to 500 times (v/w) and more preferably 1 time to 100 times (v/w) the amount of compound represented by General Formula [8] or a salt thereof.

The amount of compound represented by General Formula [11] used is preferably 1-fold by mole to 50-fold by mole and more preferably 1-fold by mole to 10-fold by mole, with respect to the compound represented by General Formula [8] or a salt thereof.

Examples of the base used in this reaction as desired include an inorganic base and an organic base.

Examples of a preferable base include inorganic bases such as sodium hydrogen carbonate, sodium carbonate, potassium carbonate, cesium carbonate, potassium tert-butoxide, sodium tert-butoxide, cesium fluoride, and tripotassium phosphate, and organic bases such as pyridine, 4-(dimethylamino)pyridine, triethylamine, and diisopropyl ethylamine.

The amount of base used is preferably 0.1-fold by mole to 10-fold by mole, more preferably 0.1-fold by mole to 5-fold by mole, and still more preferably 0.1-fold by mole to 3-fold by mole, with respect to the compound represented by General Formula [8] or a salt thereof.

The amount of palladium catalyst used is preferably 0.00001-fold by mole to 1-fold by mole and more preferably 0.001-fold by mole to 0.5-fold by mole, with respect to the compound represented by General Formula [8] or a salt thereof.

The amount of ligand used is preferably 0.00001-fold by mole to 2-fold by mole and more preferably 0.0001-fold by mole to 1-fold by mole, with respect to the compound represented by General Formula [8] or a salt thereof.

In this reaction, an additive such as lithium chloride or the like is preferably added.

The amount of additive used is preferably 1-fold by mole to 50-fold by mole and more preferably 1-fold by mole to 10-fold by mole, with respect to the compound represented by General Formula [8] or a salt thereof.

Preferably, this reaction may be performed at a temperature of 0° C. to 170° C. for 1 minute to 1 week in an inert gas (for example, nitrogen or argon) atmosphere.

This reaction may be performed under microwave irradiation.

[Preparation Method B]

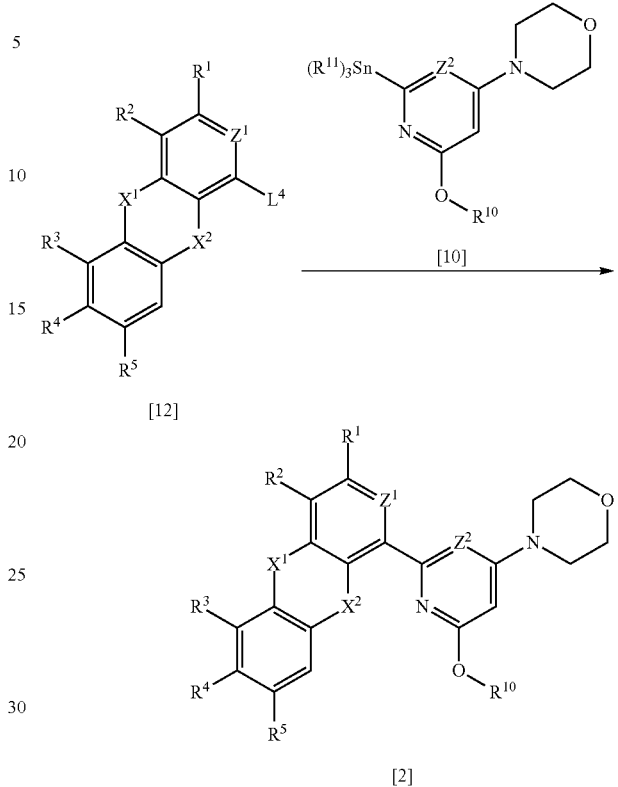

(In the formula, $L^4$ represents a leaving group; and each of $Z^1$, $Z^2$, $X^1$, $X^2$, $R^1$, $R^2$, $R^3$, $R^4$, $R^5$, $R^{10}$, and $R^{11}$ has the same meaning as that described above.)

The compound represented by General Formula [2] or a salt thereof can be prepared by reacting the compound represented by General Formula [10] or a salt thereof with the compound represented by General Formula [12] or a salt thereof in the presence of a base or in the absence thereof, in the presence of a palladium catalyst, and in the presence of a ligand or in the absence thereof.

The solvent used in this reaction is not particularly limited as long as it does not affect the reaction, and examples thereof include aliphatic hydrocarbons, halogenated hydrocarbons, alcohols, glycols, ethers, ketones, esters, amides, nitriles, sulfoxides, aromatic hydrocarbons, and water, and these may be used in combination.

Examples of a preferable solvent include alcohols, esters, amides, nitriles, ethers, and aromatic hydrocarbons.

Although the amount of solvent used is not particularly limited, the amount used is preferably 1 time to 500 times (v/w) and more preferably 1 time to 100 times (v/w) the amount of compound represented by General Formula [12] or a salt thereof.

The amount of compound represented by General Formula [10] or a salt thereof used is preferably 1-fold by mole to 10-fold by mole and more preferably 1-fold by mole to 5-fold by mole, with respect to the compound represented by General Formula [12] or a salt thereof.

Examples of the base used in this reaction as desired include an inorganic base and an organic base.

Examples of a preferable base include inorganic bases such as sodium hydrogen carbonate, sodium carbonate, potassium carbonate, cesium carbonate, potassium tert-butoxide, sodium tert-butoxide, cesium fluoride, and tripotassium phosphate, and organic bases such as pyridine, 4-(dimethylamino)pyridine, triethylamine, and diisopropyl ethylamine.

The amount of base used is preferably 0.1-fold by mole to 10-fold by mole, more preferably 0.1-fold by mole to 5-fold by mole, and still more preferably 0.1-fold by mole to 3-fold by mole, with respect to the compound represented by General Formula [12] or a salt thereof.

The amount of palladium catalyst used is preferably 0.00001-fold by mole to 1-fold by mole and more preferably 0.0001-fold by mole to 0.5-fold by mole, with respect to the compound represented by General Formula [12] or a salt thereof.

The amount of ligand used is preferably 0.00001-fold by mole to 5-fold by mole and more preferably 0.0001-fold by mole to 1-fold by mole, with respect to the compound represented by General Formula [12] or a salt thereof.

Preferably, this reaction may be performed at a temperature of 20° C. to 170° C. for 1 minute to 1 week in an inert gas (for example, nitrogen or argon) atmosphere.

This reaction may be performed under microwave irradiation.

[Preparation Method C]

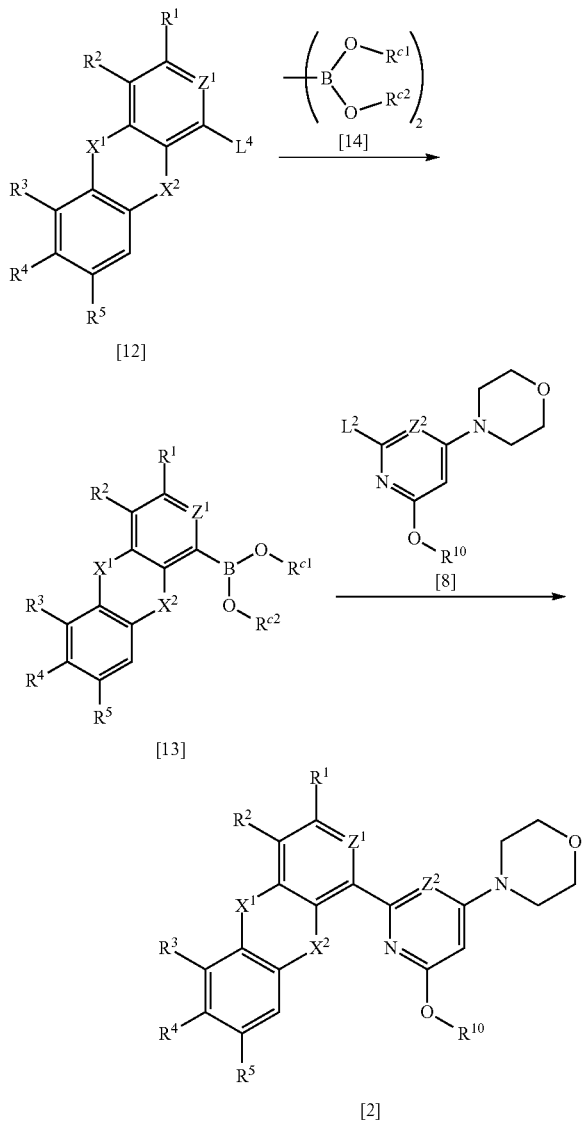

(In the formula, $R^{c1}$ represents a $C_{1-6}$ alkyl group which may have a substituent; $R^{c2}$ represents a $C_{1-6}$ alkyl group which may have a substituent; or both $R^{c1}$ and $R^{c2}$ represent $C_{2-6}$ alkylene groups which may have a substituent; and each of $Z^1$, $Z^2$, $X^1$, $X^2$, $R^1$, $R^2$, $R^3$, $R^4$, $R^5$, $R^{10}$, and $L^2$ has the same meaning as that described above.)

(1)

As the compound represented by General Formula [14], for example, bispinacolatodiboron and the like are known.

The compound represented by General Formula [13] or a salt thereof can be prepared by reacting the compound represented by General Formula [14] with the compound represented by General Formula [12] or a salt thereof in the presence of a base or in the absence thereof, in the presence of a palladium catalyst, and in the presence of a ligand or in the absence thereof.

The solvent used in this reaction is not particularly limited as long as it does not affect the reaction, and examples thereof include aliphatic hydrocarbons, halogenated hydrocarbons, alcohols, glycols, ethers, ketones, esters, amides, nitriles, sulfoxides, aromatic hydrocarbons, and water, and these may be used in combination.

Examples of a preferable solvent include alcohols, esters, amides, nitriles, ethers, and aromatic hydrocarbons.

Although the amount of solvent used is not particularly limited, the amount used is preferably 0.1 time to 1000 times (v/w), more preferably 0.1 time to 500 times (v/w), and still more preferably 0.1 time to 100 times (v/w) the amount of compound represented by General Formula [12] or a salt thereof.

The amount of compound represented by General Formula [14] or a salt thereof used is preferably 1-fold by mole to 10-fold by mole and more preferably 1-fold by mole to 3-fold by mole, with respect to the compound represented by General Formula [12] or a salt thereof.

Examples of the base used in this reaction as desired include an inorganic base and an organic base.

Examples of a preferable base include inorganic bases such as sodium hydrogen carbonate, sodium carbonate, potassium carbonate, sodium acetate, potassium acetate, cesium carbonate, sodium tert-butoxide, potassium tert-butoxide, and tripotassium phosphate, and organic bases such as pyridine, 4-(dimethylamino)pyridine, triethylamine, and diisopropyl ethylamine.

The amount of base used is preferably 1-fold by mole to 20-fold by mole, more preferably 1-fold by mole to 10-fold by mole, and still more preferably 1-fold by mole to 5-fold by mole, with respect to the compound represented by General Formula [12] or a salt thereof.

The amount of palladium catalyst used is preferably 0.00001-fold by mole to 1-fold by mole and more preferably 0.0001-fold by mole to 0.5-fold by mole, with respect to the compound represented by General Formula [12] or a salt thereof.

The amount of ligand used is preferably 0.00001-fold by mole to 5-fold by mole and more preferably 0.0001-fold by mole to 1-fold by mole, with respect to the compound represented by General Formula [12] or a salt thereof.

Preferably, this reaction may be performed at a temperature of 20° C. to 170° C. for 1 minute to 1 week in an inert gas (for example, nitrogen or argon) atmosphere.

This reaction may be performed under microwave irradiation.

(2)

The compound represented by General Formula [2] or a salt thereof can be prepared by reacting the compound represented by General Formula [8] or a salt thereof with the compound represented by General Formula [13] or a salt thereof in the presence of a base or in the absence thereof, in the presence of a palladium catalyst, and in the presence of a ligand or in the absence thereof.

The solvent used in this reaction is not particularly limited as long as it does not affect the reaction, and examples thereof include aliphatic hydrocarbons, halogenated hydrocarbons, alcohols, glycols, ethers, ketones, esters, amides, nitriles, sulfoxides, aromatic hydrocarbons, and water, and these may be used in combination.

Examples of a preferable solvent include alcohols, esters, amides, nitriles, ethers, and aromatic hydrocarbons.

Although the amount of solvent used is not particularly limited, the amount used is preferably 0.1 time to 1000 times (v/w), more preferably 0.1 time to 500 times (v/w), and still more preferably 0.1 time to 100 times (v/w) the amount of compound represented by General Formula [13] or a salt thereof.

The amount of compound represented by General Formula [8] or a salt thereof used is preferably 1-fold by mole to 10-fold by mole and more preferably 1-fold by mole to 3-fold by mole, with respect to the compound represented by General Formula [13] or a salt thereof.

Examples of the base used in this reaction as desired include an inorganic base and an organic base.

Examples of a preferable base include inorganic bases such as sodium hydrogen carbonate, sodium carbonate, potassium carbonate, sodium acetate, potassium acetate, cesium carbonate, sodium tert-butoxide, potassium tert-butoxide, and tripotassium phosphate, and organic bases such as pyridine, 4-(dimethylamino)pyridine, triethylamine, and diisopropyl ethylamine.

The amount of base used is preferably 1-fold by mole to 20-fold by mole, more preferably 1-fold by mole to 10-fold by mole, and still more preferably 1-fold by mole to 5-fold by mole, with respect to the compound represented by General Formula [13] or a salt thereof.

The amount of palladium catalyst used is preferably 0.00001-fold by mole to 1-fold by mole and more preferably 0.001-fold by mole to 0.5-fold by mole, with respect to the compound represented by General Formula [13] or a salt thereof.

The amount of ligand used is preferably 0.00001-fold by mole to 5-fold by mole and more preferably 0.001-fold by mole to 1-fold by mole, with respect to the compound represented by General Formula [13] or a salt thereof.

Preferably, this reaction may be performed at a temperature of 20° C. to 170° C. for 1 minute to 1 week in an inert gas (for example, nitrogen or argon) atmosphere.

This reaction may be performed under microwave irradiation.

[Preparation Method D]

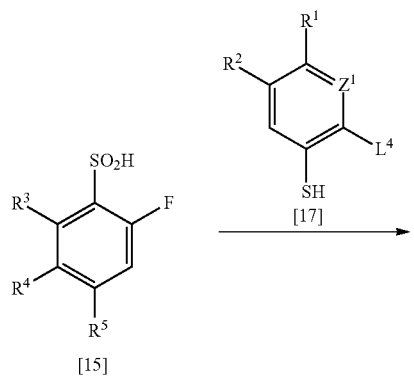

[15]

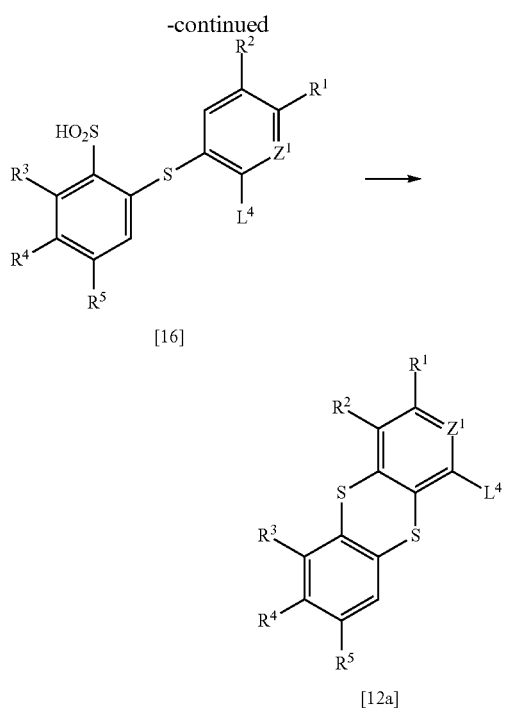

(In the formula, each of $Z^1$, $R^1$, $R^2$, $R^3$, $R^4$, $R^5$, and $L^4$ has the same meaning as that described above.)

(1)

As the compound represented by General Formula [15], for example, 2-fluoro-5-nitrobenzenesulfinic acid and the like are known.

As the compound represented by General Formula [17], for example, 2-bromonitrobenzenethiol and the like are known.

The compound represented by General Formula [16] or a salt thereof can be prepared by reacting the compound represented by General Formula [17] with the compound represented by General Formula [15] or a salt thereof in the presence of a base or in the absence thereof.

The solvent used in this reaction is not particularly limited as long as it does not affect the reaction, and examples thereof include aliphatic hydrocarbons, halogenated hydrocarbons, alcohols, glycols, ethers, ketones, esters, amides, nitriles, sulfoxides, aromatic hydrocarbons, and water, and these may be used in combination.

Examples of a preferable solvent include water.

Although the amount of solvent used is not particularly limited, the amount used is preferably 1 time to 100 times (v/w), more preferably 1 time to 50 times (v/w), and still more preferably 1 time to 30 times (v/w) the amount of compound represented by General Formula [15] or a salt thereof.

The amount of compound represented by General Formula [17] or a salt thereof used is preferably 1-fold by mole to 10-fold by mole and more preferably 1-fold by mole to 1.5-fold by mole, with respect to the compound represented by General Formula [15] or a salt thereof.

Examples of the base used in this reaction as desired include an inorganic base.

Examples of a preferable base include sodium hydroxide, potassium carbonate, cesium carbonate, and tripotassium phosphate.

The amount of base used is preferably 1-fold by mole to 10-fold by mole and more preferably 1-fold by mole to 5-fold by mole, with respect to the compound represented by General Formula [15] or a salt thereof.

This reaction, typically, may be performed at a temperature of 20° C. to 180° C., and preferably at a temperature of 20° C. to 130° C., for 10 minutes to 48 hours.

(2)

The compound represented by General Formula [12a] or a salt thereof can be prepared by reacting a dehydrating agent with the compound represented by General Formula [16] or a salt thereof.

The reaction may be performed according to Preparation Method 5.

[Preparation Method E]

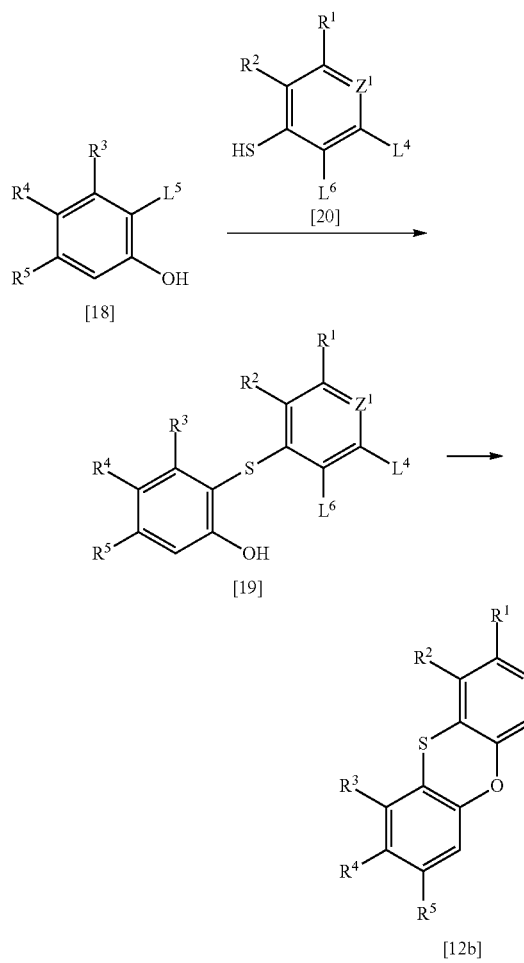

(In the formula, $L^5$ represents a leaving group; $L^6$ represents a leaving group; and each of $Z^1$, $R^1$, $R^2$, $R^3$, $R^4$, $R^5$, and $L^4$ has the same meaning as that described above.)

(1)

As the compound represented by General Formula [20], for example, 2,3-dichlorobenzenethiol and the like are known.

The compound represented by General Formula [19] or a salt thereof can be prepared by reacting the compound represented by General Formula [20] or a salt thereof with the compound represented by General Formula [18] or a salt thereof in the presence of a base or in the absence thereof.

The solvent used in this reaction is not particularly limited as long as it does not affect the reaction, and examples thereof include aliphatic hydrocarbons, halogenated hydrocarbons, alcohols, glycols, ethers, ketones, esters, amides, nitriles, sulfoxides, aromatic hydrocarbons, and water, and these may be used in combination.

Examples of a preferable solvent include water.

Although the amount of solvent used is not particularly limited, the amount used is preferably 1 time to 100 times (v/w), more preferably 1 time to 50 times (v/w), and still more preferably 1 time to 30 times (v/w) the amount of compound represented by General Formula [18] or a salt thereof.

The amount of compound represented by General Formula [20] or a salt thereof used is preferably 1-fold by mole to 10-fold by mole and more preferably 1-fold by mole to 2-fold by mole, with respect to the compound represented by General Formula [18] or a salt thereof.

Examples of the base used in this reaction as desired include an inorganic base.

Examples of a preferable base include inorganic bases such as sodium hydroxide, potassium carbonate, cesium carbonate, and tripotassium phosphate.

The amount of base used is preferably 1-fold by mole to 10-fold by mole and more preferably 1-fold by mole to 5-fold by mole, with respect to the compound represented by General Formula [18] or a salt thereof.

This reaction, typically, may be performed at a temperature of 20° C. to 180° C., and preferably at a temperature of 20° C. to 130° C., for 10 minutes to 48 hours.

This reaction may be performed under microwave irradiation.

(2)

The compound represented by General Formula [12b] or a salt thereof can be prepared by reacting a dehydrating agent with the compound represented by General Formula [19] or a salt thereof.

The reaction may be performed according to Preparation Method A(1).

[Preparation Method F]

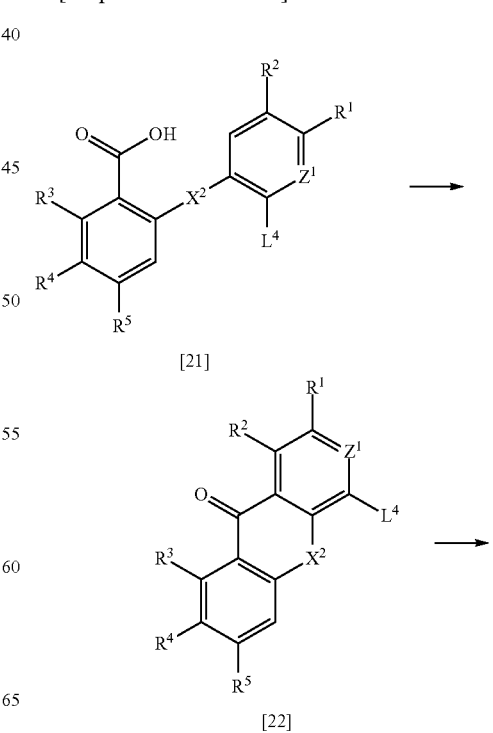

43
-continued

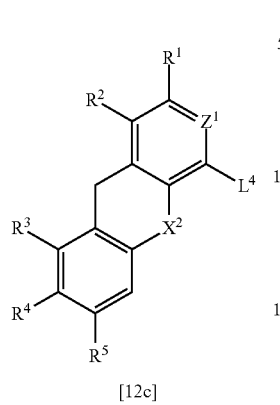

[12c]

(In the formula, each of $Z^1$, $R^1$, $R^2$, $R^3$, $R^4$, $R^5$, $X^2$, and $L^4$ has the same meaning as that described above.)

(1)

The compound represented by General Formula [22] or a salt thereof can be prepared by reacting a dehydrating agent with the compound represented by General Formula [21] or a salt thereof.

The reaction may be performed according to Preparation Method 5.

(2)

The compound represented by General Formula [12c] or a salt thereof can be prepared by reacting a reductant with the compound represented by General Formula [22] or a salt thereof.

The solvent used in this reaction is not particularly limited as long as it does not affect the reaction, and examples thereof include aliphatic hydrocarbons, halogenated hydrocarbons, alcohols, glycols, ethers, ketones, esters, amides, nitriles, sulfoxides, and aromatic hydrocarbons, and these may be used in combination.

Examples of a preferable solvent include ethers.

Although the amount of solvent used is not particularly limited, the amount used is preferably 1 time to 1000 times (v/w), more preferably 1 time to 500 times (v/w), and still more preferably 1 time to 100 times (v/w) the amount of compound represented by General Formula [22] or a salt thereof.

Examples of the reductant used in this reaction include a borane-tetrahydrofuran complex.

The amount of reductant used is preferably 0.5-fold by mole to 10-fold by mole and more preferably 0.5-fold by mole to 2-fold by mole, with respect to the compound represented by General Formula [22] or a salt thereof.

This reaction, typically, may be performed at a temperature of 0° C. to 200° C., and preferably at a temperature of 0° C. to 150° C., for 10 minutes to 48 hours.

44
[Preparation Method G]

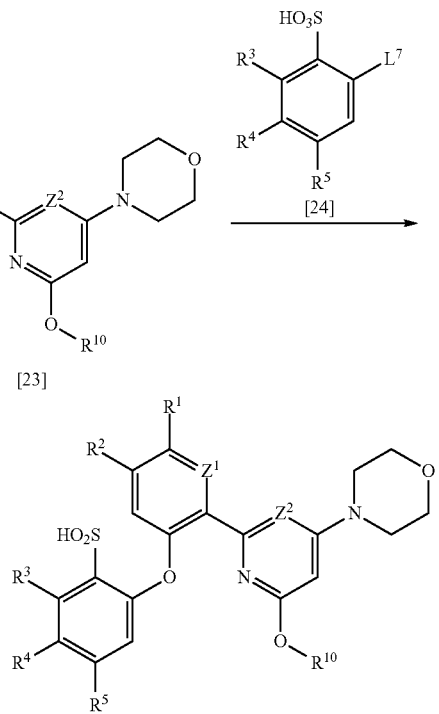

(In the formula, $L^7$ represents a leaving group; and each of $Z^1$, $Z^2$, $R^1$, $R^2$, $R^3$, $R^4$, $R^5$, and $R^{10}$ has the same meaning as that described above.)

As the compound represented by General Formula [24], for example, 2-fluoro-5-nitrobenzenesulfonic acid and the like are known.

The compound represented by General Formula [6a] or a salt thereof can be prepared by reacting the compound represented by General Formula [24] with the compound represented by General Formula [23] or a salt thereof in the presence of a base.

The solvent used in this reaction is not particularly limited as long as it does not affect the reaction, and examples thereof include aliphatic hydrocarbons, halogenated hydrocarbons, alcohols, glycols, ethers, ketones, esters, amides, nitriles, sulfoxides, aromatic hydrocarbons, and water, and these may be used in combination.

Examples of a preferable solvent include amides.

Although the amount of solvent used is not particularly limited, the amount used is preferably 1 time to 100 times (v/w), more preferably 1 time to 50 times (v/w), and still more preferably 1 time to 30 times (v/w) the amount of compound represented by General Formula [23] or a salt thereof.

The amount of compound represented by General Formula [24] or a salt thereof used is preferably 1-fold by mole to 10-fold by mole and more preferably 1-fold by mole to 2-fold by mole, with respect to the compound represented by General Formula [23] or a salt thereof.

Examples of the base used in this reaction include an inorganic base.

Examples of a preferable base include inorganic bases such as sodium hydroxide, potassium carbonate, cesium carbonate, and tripotassium phosphate.

The amount of base used is preferably 1-fold by mole to 10-fold by mole and more preferably 1-fold by mole to 5-fold by mole, with respect to the compound represented by General Formula [23] or a salt thereof.

This reaction, typically, may be performed at a temperature of 20° C. to 200° C., and preferably at a temperature of 60° C. to 180° C., for 10 minutes to 48 hours.

[Preparation Method H]

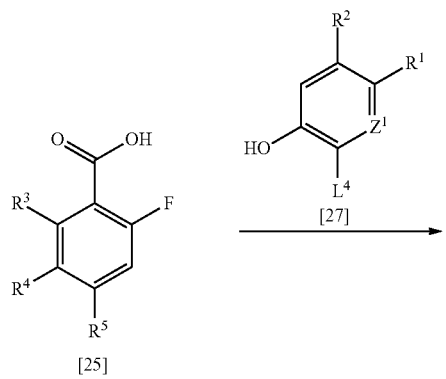

[25]

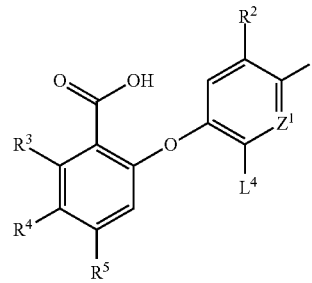

[26]

(In the formula, each of $Z^1$, $R^1$, $R^2$, $R^3$, $R^4$, $R^5$, and $L^4$ has the same meaning as that described above.)

As the compound represented by General Formula [25], for example, 2-fluoro-5-nitrobenzoic acid and the like are known.

As the compound represented by General Formula [27], for example, 2-bromophenol and the like are known.

The compound represented by General Formula [26] or a salt thereof can be prepared by reacting the compound represented by General Formula [27] or a salt thereof with the compound represented by General Formula [25] or a salt thereof in the presence of a base.

The solvent used in this reaction is not particularly limited as long as it does not affect the reaction, and examples thereof include aliphatic hydrocarbons, halogenated hydrocarbons, alcohols, glycols, ethers, ketones, esters, amides, nitriles, sulfoxides, aromatic hydrocarbons, and water, and these may be used in combination.

Examples of a preferable solvent include amides.

Although the amount of solvent used is not particularly limited, the amount used is preferably 1 time to 100 times (v/w), more preferably 1 time to 50 times (v/w), and still more preferably 1 time to 30 times (v/w) the amount of compound represented by General Formula [25] or a salt thereof.

The amount of compound represented by General Formula [27] or a salt thereof used is preferably 1-fold by mole to 10-fold by mole and more preferably 1-fold by mole to 2-fold by mole, with respect to the compound represented by General Formula [25] or a salt thereof.

Examples of the base used in this reaction include an inorganic base.

Examples of a preferable base include inorganic bases such as sodium hydroxide, potassium carbonate, cesium carbonate, and tripotassium phosphate.

The amount of base used is preferably 1-fold by mole to 10-fold by mole and more preferably 1-fold by mole to 5-fold by mole, with respect to the compound represented by General Formula [25] or a salt thereof.

This reaction, typically, may be performed at a temperature of 20° C. to 200° C., and preferably at a temperature of 60° C. to 150° C., for 10 minutes to 48 hours.

[Preparation Method I]

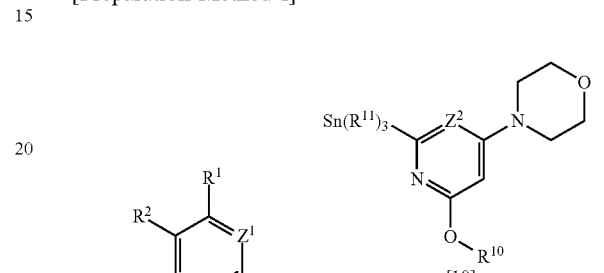

[12d]

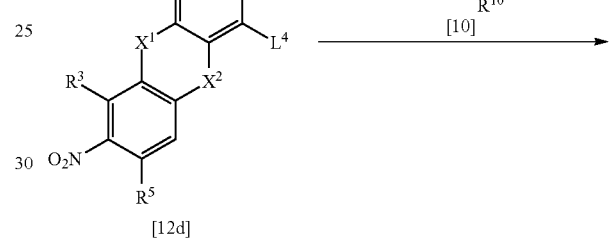

[2a]

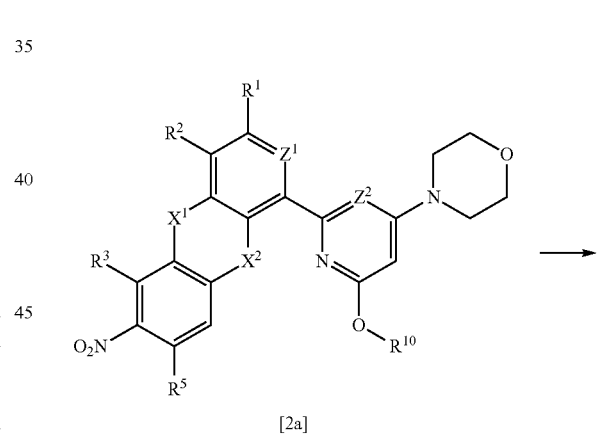

[2b]

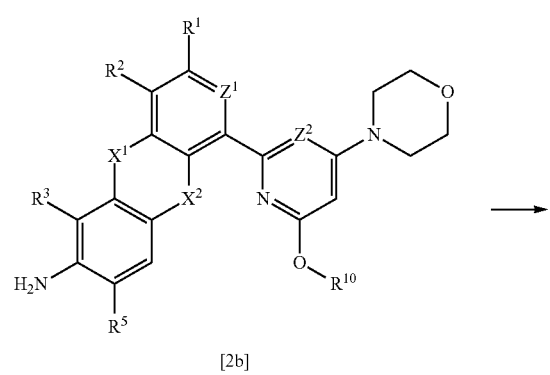

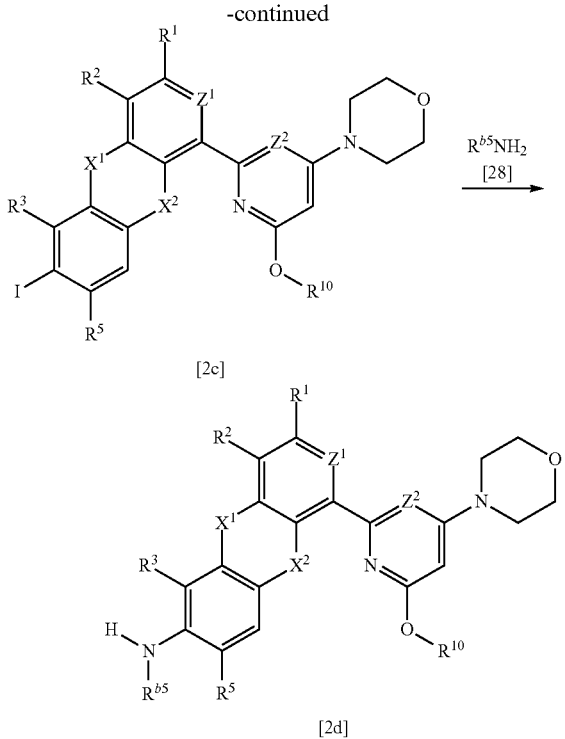

(In the formula, $R^{b5}$ represents an aryl group which may have a substituent or a heterocyclic group which may have a substituent; and each of $Z^1$, $Z^2$, $R^1$, $R^2$, $R^3$, $R^5$, $R^{10}$, $R^{11}$, $X^1$, $X^2$, and $L^4$ has the same meaning as that described above.)

In this preparation method, conversion of $R^4$ in the compound represented by General Formula [1] will be described. In the same manner as this method, conversion of $R^3$ or $R^5$ can also be performed.

(1)

The compound represented by General Formula [2a] or a salt thereof can be prepared by reacting the compound represented by General Formula [10] or a salt thereof with the compound represented by General Formula [12d] or a salt thereof in the presence of a base or in the absence thereof, in the presence of a palladium catalyst, and in the presence of a ligand or in the absence thereof.

The solvent used in this reaction is not particularly limited as long as it does not affect the reaction, and examples thereof include aliphatic hydrocarbons, halogenated hydrocarbons, alcohols, glycols, ethers, ketones, esters, amides, nitriles, sulfoxides, aromatic hydrocarbons, and water, and these may be used in combination.

Examples of a preferable solvent include alcohols, esters, amides, nitriles, ethers, and aromatic hydrocarbons.

Although the amount of solvent used is not particularly limited, the amount used is preferably 0.1 time to 1000 times (v/w), more preferably 0.1 time to 500 times (v/w), and still more preferably 0.1 time to 100 times (v/w) the amount of compound represented by General Formula [12d] or a salt thereof.

The amount of compound represented by General Formula [10] or a salt thereof used is preferably 1-fold by mole to 10-fold by mole and more preferably 1-fold by mole to 5-fold by mole, with respect to the compound represented by General Formula [12d] or a salt thereof.

Examples of the base used in this reaction as desired include an inorganic base and an organic base.

Examples of a preferable base include inorganic bases such as sodium hydrogen carbonate, sodium carbonate, potassium carbonate, cesium carbonate, potassium tert-butoxide, sodium tert-butoxide, cesium fluoride, and tripotassium phosphate, and organic bases such as pyridine, 4-(dimethylamino)pyridine, triethylamine, and diisopropyl ethylamine.

The amount of base used is preferably 0.1-fold by mole to 10-fold by mole, more preferably 0.1-fold by mole to 5-fold by mole, and still more preferably 0.1-fold by mole to 2-fold by mole, with respect to the compound represented by General Formula [12d] or a salt thereof.

The amount of palladium catalyst used is preferably 0.00001-fold by mole to 1-fold by mole and more preferably 0.0001-fold by mole to 0.5-fold by mole, with respect to the compound represented by General Formula [12d] or a salt thereof.

The amount of ligand used is preferably 0.00001-fold by mole to 2-fold by mole and more preferably 0.0001-fold by mole to 1-fold by mole, with respect to the compound represented by General Formula [12d] or a salt thereof.

Preferably, this reaction may be performed at a temperature of 20° C. to 170° C. for 1 minute to 1 week in an inert gas (for example, nitrogen or argon) atmosphere.

This reaction may be performed under microwave irradiation.

(2)

The compound represented by General Formula [2b] or a salt thereof can be prepared by reducing the compound represented by General Formula [2a] or a salt thereof.

This reaction may be performed, for example, according to the method described in "Comprehensive Organic Transformations" written by Richard C. Larock et al., 2nd edition, pp. 823-827, 1999 (John Wiley & Sons, INC.).

(3)

The compound represented by General Formula [2c] or a salt thereof can be prepared by reacting nitrous acid ester with the compound represented by General Formula [2b] or a salt thereof in the presence of copper iodide and in the presence of diiodomethane.

The solvent used in this reaction is not particularly limited as long as it does not affect the reaction, and examples thereof include aliphatic hydrocarbons, halogenated hydrocarbons, alcohols, glycols, ethers, ketones, esters, amides, nitriles, sulfoxides, aromatic hydrocarbons, and water, and these may be used in combination.

Examples of a preferable solvent include ethers and nitriles.

Examples of the copper iodide used in this reaction include copper (I) iodide.

The amount of copper iodide used is preferably 0.5-fold by mole to 20-fold by mole and more preferably 0.5-fold by mole to 10-fold by mole, with respect to the compound represented by General Formula [2b] or a salt thereof.

The amount of diiodomethane used in this reaction as desired is preferably 0.5-fold by mole to 20-fold by mole and more preferably 1-fold by mole to 10-fold by mole, with respect to the compound represented by General Formula [2b] or a salt thereof.

Examples of the nitrous acid ester used in this reaction include isoamyl nitrite.

The amount of nitrous acid ester used is preferably 0.5-fold by mole to 20-fold by mole and more preferably 1-fold by mole to 10-fold by mole, with respect to the compound represented by General Formula [2b] or a salt thereof.

This reaction, typically, may be performed at a temperature of 20° C. to 150° C., and preferably at a temperature of 20° C. to 100° C., for 30 minutes to 24 hours.

(4)

The compound represented by General Formula [2d] or a salt thereof can be prepared by reacting the compound represented by General Formula [28] or a salt thereof with the compound represented by General Formula [2c] or a salt thereof in the presence of a base, in the presence of a copper catalyst, and in the presence of a ligand.

The solvent used in this reaction is not particularly limited as long as it does not affect the reaction, and examples thereof include aliphatic hydrocarbons, halogenated hydrocarbons, alcohols, glycols, ethers, ketones, esters, amides, nitriles, sulfoxides, aromatic hydrocarbons, and water, and these may be used in combination.

Examples of a preferable solvent include alcohols, sulfoxides, and amides.

Although the amount of solvent used is not particularly limited, the amount used is preferably 0.1 time to 100 times (v/w), more preferably 0.1 time to 50 times (v/w), and still more preferably 0.1 time to 10 times (v/w) the amount of compound represented by General Formula [2c] or a salt thereof.

The amount of compound represented by General Formula [28] or a salt thereof used is preferably 1-fold by mole to 10-fold by mole and more preferably 1-fold by mole to 5-fold by mole, with respect to the compound represented by General Formula [2c] or a salt thereof.

Examples of the base used in this reaction include an inorganic base.

Examples of a preferable base include sodium hydrogen carbonate, sodium carbonate, potassium carbonate, potassium tert-butoxide, sodium tert-butoxide, cesium carbonate, and tripotassium phosphate.

The amount of base used is preferably 1-fold by mole to 50-fold by mole and more preferably 1-fold by mole to 10-fold by mole, with respect to the compound represented by Formula [2c] or a salt thereof.

Examples of the copper catalyst used in this reaction include copper powder, copper (I) iodide, copper (I) chloride, copper (II) chloride, copper (I) oxide, copper (II) oxide, copper (I) bromide, and copper (II) bromide, and these may be used in combination.

Examples of a preferable copper catalyst include copper (I) iodide.

The amount of copper catalyst used is preferably 0.1-fold by mole to 10-fold by mole and more preferably 0.5-fold by mole to 5-fold by mole, with respect to the compound represented by General Formula [2c] or a salt thereof.

Examples of the ligand used in this reaction include ethylene glycol, 2-acetylcyclohexanone, 2-propionylcyclohexanone, 2-isobutyryl cyclohexanone, 1,10-phenanthroline, trans-1,2-cyclohexanediamine, and trans-N,N'-dimethylcyclohexane-1,2-diamine, and these may be used in combination.

Examples of a preferable ligand include 2-isobutyryl cyclohexanone.

The amount of ligand used is preferably 0.2-fold by mole to 10-fold by mole and more preferably 1-fold by mole to 6-fold by mole, with respect to the compound represented by General Formula [2c] or a salt thereof.

Preferably, this reaction may be performed at a temperature of 0° C. to 200° C. for 1 minute to 48 hours in an inert gas (for example, nitrogen or argon) atmosphere.

This reaction may be performed under microwave irradiation.

In the preparation methods described above, protecting groups of a hydroxyl group, an amino group, or a carboxyl group can be suitably changed.

The compounds obtained the preparation methods described above can be isolated and purified by typical methods such as extraction, crystallization, distillation, and column chromatography. In addition, the compounds obtained the preparation methods described above may be used in the next reaction as it is without isolation.

In the compounds obtained the preparation methods described above, tautomers or enantiomers are present in some cases. The present invention includes these isomers.

In addition, in a case where a crystal polymorphism substance, a salt, a hydrate, or a solvate is present, the present invention includes all the crystal form substance, the salt, the hydrate, or the solvate.

In a case where the compound of the present invention is used as a medicine, typically, a pharmacologically acceptable additive may be suitable mixed.

Examples of the additive include an excipient, a disintegrating agent, a binding agent, a lubricant, a flavoring agent, a colorant, an aromatizer, a surfactant, a coating agent, and a plasticizer.

Examples of the excipient include sugar alcohols such as erythritol, mannitol, xylitol, and sorbitol; sugars such as white sugar, powdered sugar, lactose, and glucose; cyclodextrins such as α-cyclodextrin, β-cyclodextrin, γ-cyclodextrin, hydroxypropyl β-cyclodextrin, and sodium sulfobutylether β-cyclodextrin; celluloses such as crystalline cellulose and microcrystalline cellulose; and starches such as a corn starch, a potato starch, and a pregelatinized starch.

Examples of the disintegrating agent include carmellose, carmellose calcium, croscarmellose sodium, sodium carboxymethyl starch, crospovidone, low substituted hydroxypropyl cellulose, and a partly pregelatinized starch.

Examples of the binding agent include hydroxypropyl cellulose, carmellose sodium, and methylcellulose.

Examples of the lubricant include stearic acid, magnesium stearate, calcium stearate, talc, hydrated silicon dioxide, light anhydrous silicic acid, and sucrose fatty acid ester.

Examples of the flavoring agent include aspartame, saccharin, stevia, thaumatin, and acesulfame potassium.

Examples of the colorant include titanium dioxide, ferric oxide, yellow ferric oxide, black iron oxide, Food Red No. 102, Food Yellow No. 4, and Food Yellow No. 5.

Examples of the aromatizer include an essential oil such as an orange oil, a lemon oil, a peppermint oil, or a pine oil; an essence such as an orange essence or a peppermint essence; a flavor such as a cherry flavor, a vanilla flavor, or fruit flavor; a powder fragrance such as an apple micron, a banana micron, a peach micron, a strawberry micron, or an orange micron; vanillin; and ethyl vanillin.

Examples of the surfactant include sodium lauryl sulfate, dioctyl sodium sulfosuccinate, polysorbate, and polyoxyethylene hydrogenated castor oil.

Examples of the coating agent include hydroxypropyl methyl cellulose, an aminoalkyl methacrylate copolymer E, an aminoalkyl methacrylate copolymer RS, ethyl cellulose, cellulose acetate phthalate, hydroxypropyl methyl cellulose phthalate, a methacrylic acid copolymer L, a methacrylic acid copolymer LD, and a methacrylic acid copolymer S.

Examples of the plasticizer include triethyl citrate, macrogol, triacetin, and propylene glycol.

These additives may be used singly, or in combination of two or more kinds thereof.

Although the blending amount of the additives is not particularly limited, the additives may be suitably blended such that the effects thereof are sufficiently exhibited depending on the respective purposes.

These can be administered orally or parenterally according to a method in the related art in a form such as a tablet, a capsule, a powder, a syrup, a granule, a pill, a suspension, an emulsion, a solution, a powdered formulation, a suppository, an eye drop, a nasal drop, an ear drop, a patch, an ointment, or an injection.

In addition, an administration method, a dose, and a number of administration can be suitably selected depending on a patient's age, body weight, and symptom. In a case where an ionizing radiation or an anticancer agent having effects similar to the ionizing radiation is used in combination, it is possible to administer before or after a ionizing radiation cure, or before or after administration of the anticancer agent having effects similar to the ionizing radiation.

Typically, for an adult, 0.01 mg/kg to 1000 mg/kg may be administered orally or parenterally (for example, an injection, a drip, or administration to a colorectal portion) once or several times per day.

Next, the utility of the representative compound of the invention will be described in the following Test Examples.

Test Example 1

ATM Inhibition Test

ATM inhibitory effects of a test compound were measured by detecting phosphorylation of Chk2 in a human non-small cell lung cancer cell line NCI-H460 (ATCC company). The level of phosphorylated Chk2 generated by an ionizing radiation was measured using AlphaScreen SureFire (TGR Biosciences).

NCI-H460 cells were cultured in a RPMI-1640 medium containing penicillin/streptomycin and FBS having a final concentration of 10%. The cultured NCI-H460 cells were collected by a 0.25% trypsin treatment, and counted. The cells were seeded by 40000 cells per well in 96-well CellBIND® plates (Corning International Inc.), and incubated at 37° C. overnight in 5% $CO_2$. Thereafter, the medium was removed, and replaced with 100 μL of a medium to which a test compound had been added. 1 hour after a test compound treatment, half of the plates were irradiated with ionizing radiation 8Gy (Faxitron Bioptics, LLC, RX-650 type). The plates irradiated with ionizing radiation and the plates not being irradiated with ionizing radiation were incubated at 37° C. for 1 hour in 5% $CO_2$. Thereafter, the medium was removed, and 50 μL of a lysis buffer (5× Lysis Buffer having a final concentration of 18% (PerkinElmer Inc., AlphaScreen SureFire), Activation Buffer having a final concentration of 10% (PerkinElmer Inc., AlphaScreen SureFire), Benzonase having a final concentration of 0.1% (Novagen Inc.)) was added to each well, followed by incubating at room temperature for 10 minutes while stirring. Subsequent operations were performed according to the instruction book of AlphaScreen SureFire. Measurement was performed by using a Perkin Elmer EnVision plate reader provided with Turbo Module, using standard AlphaScreen setting (Ex 680 nm and Em 520 nm to 620 nm). The inhibition ratio was calculated by the following equation.

Inhibition ratio (%)=((signal of drug untreated wells in the plates irradiated with ionizing radiation−signal of drug treated wells in the plates irradiated with ionizing radiation)/(signal of drug untreated wells in the plates irradiated with ionizing radiation−signal of drug untreated wells in the plates not being irradiated with ionizing radiation))×100

IC50 values were calculated by nonlinear regression fit (FitModel (205)) by a sigmoidal dose-response equation using XLfit software (IDBS).

The results will be described below.

~Evaluation Criteria~
+++0.1 μmol/L>$IC_{50}$
++0.1 μmol/L≤$IC_{50}$<0.5 μmol/L
+0.5 μmol/L≤$IC_{50}$<2 μmol/L

TABLE 1

| Example No. | ATM inhibitory activity |
|---|---|
| 1-1 | +++ |
| 1-2-1 | ++ |
| 1-2-2 | ++ |
| 1-3 | ++ |
| 1-4 | ++ |
| 1-5 | ++ |
| 1-6-1 | ++ |
| 1-6-2 | ++ |
| 1-7-1 | + |
| 1-7-2 | ++ |
| 1-7-3 | + |
| 1-7-4 | ++ |
| 1-8 | + |
| 1-9-1 | ++ |
| 1-9-2-1 | +++ |
| 1-9-2-2 | ++ |
| 1-9-2-3 | ++ |
| 1-9-3 | +++ |
| 1-9-4 | ++ |
| 1-10-1 | ++ |
| 1-10-2 | ++ |
| 1-10-3 | ++ |
| 1-10-4 | ++ |
| 1-10-5 | +++ |
| 1-10-6 | ++ |
| 1-10-7 | +++ |
| 1-10-8 | + |
| 1-10-9 | +++ |
| 1-10-10 | +++ |
| 1-10-11 | ++ |
| 1-10-12 | ++ |
| 1-10-13 | + |
| 1-10-14 | +++ |
| 1-10-15 | ++ |
| 1-11 | ++ |
| 1-12-1 | ++ |
| 1-12-2 | +++ |
| 1-12-3 | +++ |
| 1-12-4 | +++ |
| 1-12-5 | +++ |
| 1-12-6 | +++ |
| 1-12-7 | ++ |
| 1-12-8 | ++ |
| 1-12-9 | +++ |
| 1-12-10 | ++ |
| 1-12-11 | +++ |
| 1-12-12 | ++ |
| 1-12-13 | +++ |
| 1-12-14 | +++ |
| 1-12-15 | +++ |
| 1-12-16 | ++ |
| 1-12-17 | ++ |
| 1-12-18 | +++ |

TABLE 1-continued

| Example No. | ATM inhibitory activity |
|---|---|
| 1-12-19 | +++ |
| 1-12-20 | +++ |
| 1-12-21 | +++ |
| 1-12-22 | ++ |
| 1-12-23 | ++ |
| 1-12-24 | ++ |
| 1-12-25 | ++ |
| 1-12-26 | ++ |
| 1-12-27 | + |
| 1-12-28 | +++ |
| 1-12-29 | +++ |
| 1-12-30 | +++ |
| 1-12-31 | ++ |
| 1-12-32 | ++ |
| 1-12-33 | ++ |
| 1-12-34 | + |
| 1-12-35 | ++ |
| 1-12-36 | ++ |
| 1-12-37 | ++ |
| 1-12-38 | +++ |
| 1-12-39 | + |
| 1-12-40 | ++ |
| 1-12-41 | ++ |
| 1-12-42 | ++ |
| 1-12-43 | + |
| 1-12-44 | ++ |
| 1-12-45 | + |
| 1-12-46 | +++ |
| 1-12-47 | ++ |
| 1-12-48 | ++ |
| 1-12-49 | +++ |
| 1-12-50 | +++ |
| 1-12-51 | ++ |
| 1-12-52 | ++ |
| 1-12-53 | ++ |
| 1-12-54 | ++ |
| 1-12-55 | ++ |
| 1-12-56 | ++ |
| 1-12-57 | ++ |
| 1-12-58 | ++ |
| 1-12-59 | + |
| 1-12-60 | ++ |
| 1-12-61 | ++ |
| 1-12-62 | +++ |
| 1-12-63 | +++ |
| 1-12-64 | +++ |
| 1-12-65 | +++ |
| 1-12-66 | ++ |
| 1-12-67 | ++ |
| 1-12-68 | ++ |
| 1-12-69 | +++ |
| 1-12-70 | +++ |
| 1-12-71 | +++ |
| 1-12-72 | + |
| 1-12-73 | +++ |
| 1-12-74 | ++ |
| 1-12-75 | +++ |
| 1-12-76 | ++ |
| 1-12-77 | +++ |
| 1-12-78 | ++ |
| 1-12-79 | ++ |
| 1-12-80 | ++ |
| 1-12-81 | ++ |
| 1-12-82 | ++ |
| 1-12-83 | ++ |
| 1-12-84 | ++ |
| 1-12-85 | +++ |
| 1-12-86 | ++ |
| 1-12-87 | +++ |
| 1-12-88 | ++ |
| 1-12-89 | +++ |
| 1-12-90 | +++ |
| 1-12-91 | +++ |
| 1-12-92 | ++ |
| 1-12-93 | +++ |
| 1-12-94 | ++ |
| 1-12-95 | ++ |

TABLE 1-continued

| Example No. | ATM inhibitory activity |
|---|---|
| 1-12-96 | +++ |
| 1-12-97 | +++ |
| 1-12-98 | +++ |
| 1-12-99 | ++ |
| 1-12-100 | +++ |
| 1-12-101 | ++ |
| 1-12-102 | +++ |
| 1-12-104 | ++ |
| 1-12-106 | ++ |
| 1-12-107 | +++ |
| 1-12-108 | +++ |
| 1-12-109 | ++ |
| 1-12-110 | + |
| 1-12-111 | ++ |
| 1-12-112 | ++ |
| 1-12-113 | +++ |
| 1-12-114 | +++ |
| 1-12-115 | ++ |
| 1-12-116 | ++ |
| 1-12-117 | ++ |

TABLE 2

| Example No. | ATM inhibitory activity |
|---|---|
| 1-12-118 | +++ |
| 1-12-119 | ++ |
| 1-12-120 | ++ |
| 1-12-121 | +++ |
| 1-12-122 | ++ |
| 1-12-123 | +++ |
| 1-12-124 | ++ |
| 1-12-125 | ++ |
| 1-12-126 | + |
| 1-12-128 | ++ |
| 1-12-129 | + |
| 1-12-130 | +++ |
| 1-12-131 | +++ |
| 1-12-132 | +++ |
| 1-12-133 | ++ |
| 1-12-134 | +++ |
| 1-12-135-1 | +++ |
| 1-12-135-2 | +++ |
| 1-12-136-1 | +++ |
| 1-12-136-2 | +++ |
| 1-12-137-1 | +++ |
| 1-12-137-2 | +++ |
| 1-12-138-1 | ++ |
| 1-12-138-2 | +++ |
| 1-12-139-1 | +++ |
| 1-12-139-2 | +++ |
| 1-12-140-1 | ++ |
| 1-12-140-2 | +++ |
| 1-12-141-1 | +++ |
| 1-12-141-2 | ++ |
| 1-12-142-1 | +++ |
| 1-12-142-2 | ++ |
| 1-12-143-1 | +++ |
| 1-12-143-2 | ++ |
| 1-12-144-1 | +++ |
| 1-12-144-2 | ++ |
| 1-12-145-1 | +++ |
| 1-12-145-2 | +++ |
| 1-12-146-1 | +++ |
| 1-12-146-2 | ++ |
| 1-13-1 | +++ |
| 1-13-2-1 | +++ |
| 1-13-2-2 | +++ |
| 1-13-2-3 | ++ |
| 1-13-3-1 | +++ |
| 1-13-3-2 | +++ |
| 1-13-3-3 | ++ |
| 1-13-4 | +++ |

TABLE 2-continued

| Example No. | ATM inhibitory activity |
|---|---|
| 1-13-5 | ++ |
| 1-13-6 | ++ |
| 1-13-7 | ++ |
| 1-13-8 | ++ |
| 1-13-9 | ++ |
| 1-13-10 | ++ |
| 1-13-11 | +++ |
| 1-13-12 | +++ |
| 1-13-13 | ++ |
| 1-13-14 | ++ |
| 1-13-15 | +++ |
| 1-13-16 | ++ |
| 1-13-17 | +++ |
| 1-13-18 | + |
| 1-14 | + |
| 1-15-1 | ++ |
| 1-15-2 | ++ |
| 1-15-3 | ++ |
| 1-15-4 | ++ |
| 1-16-1-1 | +++ |
| 1-16-1-2 | +++ |
| 1-16-1-3 | ++ |
| 1-16-2 | ++ |
| 1-16-3 | +++ |
| 1-16-4 | +++ |
| 1-16-5 | + |
| 1-16-6 | +++ |
| 1-16-7 | +++ |
| 1-16-8 | ++ |
| 1-17-1-1 | +++ |
| 1-17-1-2 | +++ |
| 1-17-1-3 | ++ |
| 1-17-2 | ++ |
| 1-17-3 | ++ |
| 1-18-1 | ++ |
| 1-18-2 | ++ |
| 1-18-3 | + |
| 1-18-4 | ++ |
| 1-18-5 | + |
| 1-18-6 | ++ |
| 1-19-1 | +++ |
| 1-19-2 | ++ |
| 1-19-3 | +++ |
| 1-19-4-1 | ++ |
| 1-19-4-2 | + |
| 1-20-1 | ++ |
| 1-20-2 | ++ |
| 1-20-3 | ++ |
| 1-20-4 | + |
| 1-20-5 | ++ |
| 1-20-6 | ++ |
| 1-20-7 | + |
| 1-20-8 | ++ |
| 1-20-9 | ++ |
| 1-20-10 | ++ |
| 1-20-11 | + |
| 1-20-12 | ++ |
| 1-20-13 | + |
| 1-20-14 | ++ |
| 1-21-1 | ++ |
| 1-21-2 | ++ |
| 1-21-3 | ++ |
| 1-21-4 | ++ |
| 1-21-5 | ++ |
| 1-22-1 | +++ |
| 1-22-2 | +++ |
| 1-22-3 | +++ |
| 1-22-4 | +++ |
| 1-22-5 | +++ |
| 1-22-6 | +++ |
| 1-22-7 | +++ |
| 1-22-8 | ++ |
| 1-22-9 | +++ |
| 1-22-10 | +++ |
| 1-22-11-1 | +++ |
| 1-22-11-2 | +++ |
| 1-22-12-1 | +++ |

TABLE 2-continued

| Example No. | ATM inhibitory activity |
|---|---|
| 1-22-12-2 | +++ |
| 1-23-1 | +++ |
| 1-23-2 | +++ |
| 1-24-1 | ++ |
| 1-24-2 | +++ |
| 1-24-3 | ++ |
| 1-24-4 | +++ |
| 1-24-5 | ++ |
| 1-24-6 | ++ |
| 1-24-7 | ++ |
| 1-24-8 | ++ |
| 1-24-9 | ++ |
| 1-24-10 | ++ |
| 1-24-11 | +++ |
| 1-24-12 | ++ |
| 1-24-13 | ++ |
| 1-24-14 | ++ |
| 1-24-15 | +++ |
| 1-24-16 | ++ |
| 1-24-17 | +++ |
| 1-24-18 | +++ |
| 1-24-19 | ++ |
| 1-24-20 | ++ |
| 1-24-21 | ++ |
| 1-25 | ++ |

TABLE 3

| Example No. | ATM inhibitory activity |
|---|---|
| 1-26-1 | +++ |
| 1-26-2 | +++ |
| 1-27 | ++ |
| 1-28 | + |
| 1-29-1 | ++ |
| 1-29-2 | ++ |
| 1-30 | + |
| 1-31-1 | ++ |
| 1-31-2 | +++ |
| 1-32 | ++ |
| 1-33 | ++ |
| 1-34-1 | ++ |
| 1-34-2 | ++ |
| 1-34-3 | +++ |
| 1-34-4 | +++ |
| 1-34-5 | ++ |
| 1-34-6 | ++ |
| 1-35 | +++ |
| 1-36-1 | ++ |
| 1-36-2 | ++ |
| 1-37-1 | ++ |
| 1-37-2 | ++ |
| 1-37-3 | + |
| 1-37-4 | ++ |
| 1-37-5 | ++ |
| 1-37-6 | ++ |
| 1-37-7 | + |
| 1-38 | ++ |
| 1-39 | ++ |
| 1-40 | ++ |
| 1-41-1-1 | +++ |
| 1-41-1-2 | +++ |
| 1-41-1-3 | ++ |
| 1-41-2 | +++ |
| 1-42-1 | +++ |
| 1-42-2 | ++ |
| 1-42-3 | ++ |
| 1-42-4 | ++ |
| 1-43-1 | ++ |
| 1-43-2 | ++ |
| 1-43-4 | ++ |
| 1-43-7 | ++ |
| 1-43-8 | + |

TABLE 3-continued

| Example No. | ATM inhibitory activity |
|---|---|
| 1-44-1 | +++ |
| 1-44-2 | +++ |
| 1-44-3 | ++ |
| 1-44-4 | +++ |
| 1-44-5 | +++ |
| 1-44-6 | +++ |
| 1-45 | ++ |
| 1-46-2 | ++ |
| 1-46-3 | ++ |
| 1-46-4 | +++ |
| 1-46-5 | +++ |
| 1-46-6 | +++ |
| 1-46-7 | +++ |
| 1-46-8 | +++ |
| 1-46-9 | +++ |
| 1-46-10 | +++ |
| 1-46-11 | +++ |
| 1-46-12 | ++ |
| 1-46-13 | ++ |
| 1-46-14 | ++ |
| 1-47 | ++ |
| 1-48-1 | +++ |
| 1-48-2 | +++ |
| 1-49 | + |
| 1-50-1 | +++ |
| 1-50-2 | +++ |
| 1-50-3 | ++ |
| 1-50-4 | +++ |
| 1-50-5 | +++ |
| 1-50-6 | + |
| 1-50-7 | +++ |
| 1-50-8 | +++ |
| 1-50-9 | +++ |
| 1-51-1 | +++ |
| 1-51-2 | +++ |
| 1-51-3 | +++ |
| 1-51-4 | ++ |
| 1-51-5 | +++ |
| 1-51-6 | +++ |
| 1-51-7 | +++ |
| 1-51-8 | +++ |
| 1-51-9 | +++ |
| 1-51-10 | +++ |
| 1-51-11 | +++ |
| 1-51-12 | +++ |
| 1-52-1 | +++ |
| 1-52-2 | +++ |
| 1-53 | + |
| 1-55-1 | +++ |
| 1-55-2 | +++ |
| 1-56-1 | +++ |
| 1-56-2 | ++ |
| 1-56-3 | +++ |
| 1-56-4 | ++ |
| 1-56-5 | +++ |
| 1-56-6 | +++ |
| 1-56-7 | +++ |
| 1-56-8 | +++ |
| 1-56-9 | +++ |
| 1-56-10 | +++ |
| 1-56-11 | +++ |
| 1-56-12 | +++ |
| 1-56-13 | +++ |
| 1-56-14 | +++ |
| 1-56-15 | +++ |
| 1-56-16 | +++ |
| 1-57-1 | +++ |
| 1-57-2 | +++ |
| 1-58 | +++ |
| 1-59-1 | +++ |
| 1-59-2 | ++ |
| 1-60 | +++ |
| 1-61 | +++ |
| 2-1-1 | + |
| 2-2-1 | +++ |
| 2-2-2 | +++ |
| 2-2-3 | ++ |
| 2-2-4 | + |
| 2-2-5 | ++ |
| 2-2-6 | ++ |
| 2-2-7 | ++ |
| 2-2-8 | ++ |
| 2-2-9 | ++ |
| 2-2-10 | ++ |
| 2-2-11 | +++ |
| 2-2-12 | +++ |
| 2-2-13 | + |
| 2-2-14 | +++ |
| 2-2-15 | + |
| 2-2-16 | ++ |
| 2-2-17 | +++ |
| 2-2-18 | ++ |
| 2-2-19 | ++ |
| 2-2-20 | +++ |
| 2-2-21 | ++ |
| 2-2-22 | +++ |
| 2-2-23 | ++ |
| 2-2-24 | ++ |
| 2-2-25 | ++ |
| 2-2-26 | ++ |
| 2-2-27 | ++ |
| 2-2-28 | ++ |
| 2-2-29 | +++ |
| 2-2-30 | ++ |
| 2-2-31 | ++ |
| 2-2-32 | ++ |
| 2-2-33 | ++ |

TABLE 4

| Example No. | ATM inhibitory activity |
|---|---|
| 2-2-34 | + |
| 2-2-35 | +++ |
| 2-2-36 | ++ |
| 2-2-37 | +++ |
| 2-2-38 | +++ |
| 2-2-39 | +++ |
| 2-2-40 | +++ |
| 2-2-41 | ++ |
| 2-2-42 | ++ |
| 2-2-43 | ++ |
| 2-2-44 | +++ |
| 2-2-45 | + |
| 2-2-46 | +++ |
| 2-2-47 | + |
| 2-2-48 | +++ |
| 2-2-49 | ++ |
| 2-2-50 | +++ |
| 2-2-51 | +++ |
| 2-2-52 | +++ |
| 2-2-53 | +++ |
| 2-2-54 | + |
| 2-2-55 | ++ |
| 2-2-56 | ++ |
| 2-2-57 | ++ |
| 2-2-58 | +++ |
| 2-2-59 | ++ |
| 2-2-60 | +++ |
| 2-2-61 | ++ |
| 2-2-62 | ++ |
| 2-2-63 | ++ |
| 2-2-64 | +++ |
| 2-2-65 | ++ |
| 2-2-66 | +++ |
| 2-2-67 | ++ |
| 2-2-68 | ++ |
| 2-2-69 | +++ |
| 2-2-70 | ++ |
| 2-2-71 | +++ |

TABLE 4-continued

| Example No. | ATM inhibitory activity |
|---|---|
| 2-2-72 | +++ |
| 2-2-73 | + |
| 2-2-74 | +++ |
| 2-2-75 | ++ |
| 2-2-76 | +++ |
| 2-3-1 | ++ |
| 2-3-2 | ++ |
| 2-3-4 | + |
| 2-3-5 | ++ |
| 2-3-7 | + |
| 2-3-8 | ++ |
| 2-3-11 | ++ |
| 2-3-12 | ++ |
| 2-3-14 | ++ |
| 2-3-15 | ++ |
| 2-4 | +++ |
| 2-5 | + |
| 2-6-1 | ++ |
| 2-6-2 | ++ |
| 2-7-1 | + |
| 2-8-2 | ++ |
| 2-9-2 | ++ |
| 2-10 | + |
| 2-11-1 | ++ |
| 2-11-2 | ++ |
| 2-12 | ++ |
| 2-13-1 | ++ |
| 2-13-2 | ++ |
| 2-13-3 | + |
| 2-13-4 | +++ |
| 2-13-5 | +++ |
| 2-13-6 | +++ |
| 2-13-7 | +++ |
| 2-13-8 | +++ |
| 2-13-9 | +++ |
| 2-13-10 | +++ |
| 2-13-11 | +++ |
| 2-13-12 | ++ |
| 2-14-1 | ++ |
| 2-14-2 | ++ |
| 2-14-3 | ++ |
| 2-14-4 | ++ |
| 2-14-5 | ++ |
| 2-14-6 | ++ |
| 2-14-7 | +++ |
| 2-14-8 | ++ |
| 2-14-9 | ++ |
| 2-14-10 | +++ |
| 2-14-11 | +++ |
| 2-14-12 | +++ |
| 2-14-13 | +++ |
| 2-14-14 | ++ |
| 2-14-15 | ++ |
| 2-14-16 | +++ |
| 2-14-17 | ++ |
| 2-14-18 | ++ |
| 2-14-19 | ++ |
| 2-14-20 | +++ |
| 2-14-21 | +++ |
| 2-14-22 | ++ |
| 2-14-23 | +++ |
| 2-14-24 | +++ |
| 2-14-25 | ++ |
| 2-14-26 | +++ |
| 2-14-27 | ++ |
| 2-14-28 | ++ |
| 2-14-29 | ++ |
| 2-14-30 | ++ |
| 2-14-31 | ++ |
| 2-14-32 | +++ |
| 2-14-33 | ++ |
| 2-14-34 | ++ |
| 2-14-35 | ++ |
| 2-14-36 | ++ |
| 2-14-37 | + |
| 2-14-38 | ++ |
| 2-14-39 | ++ |
| 2-14-40 | + |
| 2-14-41 | ++ |
| 2-14-42 | ++ |
| 2-14-43 | ++ |
| 2-14-44 | ++ |
| 2-14-45 | +++ |
| 2-14-46 | ++ |
| 2-14-47 | ++ |
| 2-14-48 | ++ |
| 2-14-49 | ++ |
| 2-14-50 | + |
| 2-14-51 | +++ |
| 2-14-52 | ++ |
| 2-14-53 | ++ |
| 2-14-54 | ++ |
| 2-14-55 | ++ |
| 2-14-56 | ++ |
| 2-14-57 | ++ |
| 2-14-58 | ++ |
| 2-14-59 | ++ |
| 2-14-60 | ++ |
| 2-14-61 | +++ |
| 2-14-62 | +++ |
| 2-14-63 | ++ |
| 2-14-64 | ++ |
| 2-14-65 | ++ |
| 2-14-66 | + |
| 2-14-67 | + |
| 2-14-68 | + |
| 2-14-69 | ++ |
| 2-14-70 | + |
| 2-14-71 | ++ |
| 2-14-72 | ++ |
| 2-14-73 | ++ |
| 2-14-74 | ++ |

TABLE 5

| Example No. | ATM inhibitory activity |
|---|---|
| 2-14-75 | ++ |
| 2-14-76 | ++ |
| 2-14-77 | ++ |
| 2-14-78 | ++ |
| 2-14-79 | ++ |
| 2-14-80 | +++ |
| 2-14-81 | ++ |
| 2-14-82 | + |
| 2-14-83 | ++ |
| 2-14-84 | + |
| 2-14-85-1 | ++ |
| 2-14-85-2 | +++ |
| 2-14-86-1 | ++ |
| 2-14-86-2 | +++ |
| 2-14-87-1 | +++ |
| 2-14-87-2 | ++ |
| 2-14-88-1 | ++ |
| 2-14-88-2 | ++ |
| 2-14-89-1 | ++ |
| 2-14-89-2 | +++ |
| 2-14-90-1 | + |
| 2-14-90-2 | +++ |
| 2-14-91 | ++ |
| 2-14-92-1 | + |
| 2-14-92-2 | ++ |
| 2-14-93-1 | ++ |
| 2-14-93-2 | +++ |
| 2-14-94-1 | +++ |
| 2-14-94-2 | ++ |
| 2-15 | ++ |
| 2-16 | + |
| 2-17 | + |
| 2-18 | ++ |

TABLE 5-continued

| Example No. | ATM inhibitory activity |
|---|---|
| 2-19-1 | ++ |
| 2-19-2 | + |
| 2-19-3 | + |
| 2-19-4 | ++ |
| 2-19-5 | ++ |
| 2-19-6 | ++ |
| 2-19-7 | ++ |
| 2-19-8 | ++ |
| 2-20-2 | + |
| 2-21-2 | +++ |
| 2-21-3 | + |
| 2-21-4 | ++ |
| 2-21-5 | + |
| 2-21-6 | +++ |
| 2-21-7 | +++ |
| 2-21-8 | + |
| 2-21-9 | +++ |
| 2-22-1 | ++ |
| 2-22-2 | ++ |
| 2-23-2 | + |
| 2-24 | + |
| 2-26 | + |
| 2-28-1 | + |
| 2-28-2 | + |
| 2-28-3 | + |
| 2-28-4 | ++ |
| 2-28-5 | +++ |
| 2-28-6 | ++ |
| 2-28-7 | + |
| 2-28-8 | ++ |
| 2-28-9 | ++ |
| 2-28-10 | ++ |
| 2-28-11 | ++ |
| 2-28-12 | + |
| 2-28-13 | ++ |
| 2-28-14 | ++ |
| 2-28-15 | + |
| 2-28-16 | ++ |
| 2-28-17 | ++ |
| 2-28-18 | ++ |
| 2-28-19 | ++ |
| 2-28-20 | ++ |
| 2-28-21 | ++ |
| 2-28-22 | ++ |
| 2-28-23 | +++ |
| 2-28-24 | ++ |
| 2-28-25 | ++ |
| 2-28-26 | ++ |
| 2-28-27 | ++ |
| 2-28-28 | ++ |
| 2-28-29 | ++ |
| 2-28-30 | ++ |
| 2-28-31 | ++ |
| 2-28-32 | +++ |
| 2-28-33 | ++ |
| 2-28-34 | + |
| 2-28-35 | ++ |
| 2-28-36 | ++ |
| 2-28-37 | ++ |
| 2-28-38 | ++ |
| 2-29 | + |
| 2-30-1 | ++ |
| 2-30-2 | ++ |
| 2-30-3 | + |
| 2-30-4 | ++ |
| 2-30-5 | + |
| 2-30-6 | + |
| 2-30-7 | ++ |
| 2-30-8 | + |
| 2-30-9 | ++ |
| 2-30-10 | + |
| 2-30-11 | ++ |
| 2-30-12 | + |
| 2-30-13 | ++ |
| 2-30-14 | ++ |
| 2-30-15 | + |
| 2-30-16 | ++ |

TABLE 5-continued

| Example No. | ATM inhibitory activity |
|---|---|
| 2-30-17 | ++ |
| 2-30-18 | ++ |
| 2-30-19 | + |
| 2-30-20 | + |
| 2-31 | ++ |
| 2-32 | ++ |
| 2-33 | ++ |
| 2-34 | ++ |
| 2-36-1 | + |
| 2-36-2 | ++ |
| 2-37 | ++ |
| 2-40 | ++ |
| 2-41-1 | ++ |
| 2-41-2 | +++ |
| 2-41-3 | +++ |
| 2-41-4 | +++ |
| 2-41-5 | ++ |
| 2-41-6 | ++ |
| 2-41-7 | ++ |
| 2-41-8 | ++ |
| 2-41-9 | ++ |
| 2-41-10 | ++ |
| 2-41-11 | ++ |
| 2-41-12 | + |
| 2-41-13 | ++ |
| 2-41-14 | ++ |
| 2-41-15 | ++ |
| 2-41-16 | ++ |
| 2-41-17 | ++ |
| 2-42-1 | + |
| 2-42-2 | ++ |
| 2-42-3 | ++ |
| 2-42-4 | ++ |
| 2-42-5 | ++ |
| 2-42-6 | ++ |
| 2-42-7 | + |
| 2-43 | + |
| 2-44-1 | ++ |
| 2-44-2 | ++ |
| 2-44-3 | ++ |

TABLE 6

| Example No. | ATM inhibitory activity |
|---|---|
| 2-45 | ++ |
| 2-46-1 | +++ |
| 2-46-2 | +++ |
| 2-46-3 | +++ |
| 2-46-4 | +++ |
| 2-46-5 | +++ |
| 2-47 | ++ |
| 2-48-1 | + |
| 2-48-2 | ++ |
| 2-48-3 | ++ |
| 2-48-4 | ++ |
| 2-49-1 | + |
| 2-49-2 | ++ |
| 2-50 | + |
| 2-51-2 | ++ |
| 2-51-3 | + |
| 2-52-1 | ++ |
| 2-52-2 | ++ |
| 2-52-3 | ++ |
| 2-52-4 | ++ |
| 2-56-4 | ++ |
| 2-60 | ++ |
| 2-61 | + |
| 2-66 | ++ |
| 2-67 | +++ |
| 3-1 | + |
| 3-4-1 | + |
| 3-4-3 | + |

TABLE 6-continued

| Example No. | ATM inhibitory activity |
|---|---|
| 3-4-4 | + |
| 3-6 | + |
| 3-8-1 | ++ |
| 3-8-2 | + |
| 3-8-5 | + |
| 3-8-6 | ++ |
| 3-8-8 | + |
| 3-8-9 | ++ |
| 3-8-10 | +++ |
| 3-8-12 | + |
| 3-8-13 | ++ |
| 3-10 | + |
| 4-1 | + |
| 4-2 | ++ |
| 4-3 | ++ |
| 4-4-1 | ++ |
| 4-4-2 | +++ |
| 4-4-3 | ++ |
| 4-4-4 | +++ |
| 4-4-5 | ++ |
| 4-4-6 | +++ |
| 4-4-7 | +++ |
| 4-4-8 | +++ |
| 4-4-9 | +++ |
| 4-4-10 | ++ |
| 4-4-11 | ++ |
| 4-4-12 | +++ |
| 4-4-13 | +++ |
| 4-4-14 | +++ |
| 4-4-15 | +++ |
| 4-4-16 | +++ |
| 4-4-17 | +++ |
| 4-4-18 | ++ |
| 4-4-19 | ++ |
| 4-4-20 | +++ |
| 4-4-21 | ++ |
| 4-4-22 | +++ |
| 4-4-23 | ++ |
| 4-4-24 | ++ |
| 4-4-25 | +++ |
| 4-4-26 | ++ |
| 4-4-27 | ++ |
| 4-4-28 | +++ |
| 4-4-29 | +++ |
| 4-4-30 | +++ |
| 4-5 | + |
| 4-6-1 | ++ |
| 4-6-2 | ++ |
| 4-6-3 | ++ |
| 4-7 | ++ |
| 4-8-1 | +++ |
| 4-8-2 | ++ |
| 4-8-3 | ++ |
| 4-8-4 | ++ |
| 4-8-5 | +++ |
| 4-8-6 | ++ |
| 4-8-7 | ++ |
| 4-8-8 | +++ |
| 4-8-9 | ++ |
| 4-8-10 | ++ |
| 4-8-11 | ++ |
| 4-8-12 | +++ |
| 4-8-13 | +++ |
| 4-8-14 | ++ |
| 4-8-15 | +++ |
| 4-8-16 | ++ |
| 4-8-17 | +++ |
| 4-8-18 | +++ |
| 4-8-19 | +++ |
| 4-8-20 | + |
| 4-8-21 | ++ |
| 4-8-22 | +++ |
| 4-8-23 | +++ |
| 4-8-24 | +++ |
| 4-8-25 | +++ |
| 4-8-26 | ++ |
| 4-9 | ++ |

TABLE 6-continued

| Example No. | ATM inhibitory activity |
|---|---|
| 4-10 | +++ |
| 4-11 | ++ |
| 4-12 | + |
| 6 | + |
| 7 | + |
| 8-1 | ++ |
| 8-2 | ++ |
| 8-3 | + |
| 8-4 | ++ |
| 9-1 | ++ |
| 9-2 | ++ |
| 9-3 | + |
| 10-1 | ++ |
| 10-2 | +++ |
| 10-3-1 | +++ |
| 10-3-2 | +++ |
| 10-3-3 | +++ |
| 10-3-4 | +++ |
| 10-3-5 | +++ |
| 10-3-6 | +++ |
| 10-4-1 | +++ |
| 10-4-2 | ++ |
| 10-5-1 | +++ |
| 10-5-2 | ++ |
| 10-6 | ++ |
| 10-7 | +++ |
| 10-8 | +++ |
| 10-9 | +++ |
| 11-1 | ++ |
| 11-2 | ++ |
| 11-3 | +++ |
| 11-4 | ++ |
| 12-1 | ++ |
| 12-2 | ++ |
| 12-3 | ++ |
| 12-4 | +++ |
| 12-5 | ++ |
| 12-6 | ++ |

The compound of the present invention exhibited excellent ATM inhibitory activity.

Test Example 2

Cell Proliferation Inhibition Test by Sensitivity-Enhancing to Ionizing Radiation A human non-small cell lung cancer cell line NCI-H460 (ATCC company) was adjusted so as to be $2 \times 10^3$ cells/mL in a RPMI-1640 medium containing penicillin/streptomycin and FBS having a final concentration of 10%, and this was seeded by 100 µL per well in 96-well CellBIND® plates (Corning International Inc.). After 24 hours, the medium of cells was replaced with 100 µL of a medium including serially diluted liquid of the test compound or DMSO having a final concentration of 0.1%. 30 minutes after the medium was replaced, half of the plates were irradiated with ionizing radiation 2 Gy (Faxitron Bioptics, LLC, RX-650 type). The cells of the plates irradiated with ionizing radiation and the plates not being irradiated with ionizing radiation were cultured at 37° C. for 120 hour in 5% $CO_2$. After a Cell Titer Glo reaction liquid of an equal volume was added to each well, the amount of luminescence was measured, according to the instruction book of Cell Titer Glo (Promega Corporation). Since the amount of luminescence is proportional to the ATP concentration in cells, the amount of luminescence was used as an indicator of the number of viable cells. Sensitivity-enhancing effects (SER) to ionizing radiation by the test compound was calculated by the following equation.

SER=(amount of luminescence of wells including DMSO having a final concentration of 0.1% in the plates irradiated with ionizing radiation× amount of luminescence of wells including a compound in the plates not being irradiated with ionizing radiation)/(amount of luminescence of wells including the test compound in the plates irradiated with ionizing radiation× amount of luminescence of wells including DMSO having a final concentration of 0.1% in the plates not being irradiated with ionizing radiation)

SER at each compound concentration was plotted by nonlinear regression fit (FitModel (205)) by a sigmoidal dose-response equation using XLfit software (IDBS), and the concentration (SER2) in which SER became 2 was calculated. SER2 corresponds to the compound concentration which resulted in 50% inhibition of cell growth at the time of ionizing radiation irradiation.

The results will be described below.

~Evaluation Criteria~
+++0.1 µmol/L>IC$_{50}$
++0.1 µmol/L≤IC$_{50}$<0.5 µmol/L
+0.5 µmol/L≤IC$_{50}$<2 µmol/L

TABLE 7

| Example No. | SER2 |
| --- | --- |
| 1-1 | + |
| 1-9-2-1 | ++ |
| 1-10-5 | ++ |
| 1-10-7 | ++ |
| 1-10-9 | ++ |
| 1-10-10 | ++ |
| 1-10-14 | ++ |
| 1-12-2 | +++ |
| 1-12-3 | ++ |
| 1-12-4 | ++ |
| 1-12-5 | ++ |
| 1-12-6 | ++ |
| 1-12-9 | ++ |
| 1-12-11 | ++ |
| 1-12-13 | ++ |
| 1-12-14 | ++ |
| 1-12-15 | ++ |
| 1-12-18 | ++ |
| 1-12-28 | ++ |
| 1-12-29 | +++ |
| 1-12-30 | +++ |
| 1-12-38 | +++ |
| 1-12-46 | ++ |
| 1-12-50 | ++ |
| 1-12-62 | ++ |
| 1-12-63 | ++ |
| 1-12-64 | +++ |
| 1-12-65 | ++ |
| 1-12-69 | +++ |
| 1-12-70 | +++ |
| 1-12-71 | ++ |
| 1-12-73 | +++ |
| 1-12-75 | ++ |
| 1-12-77 | ++ |
| 1-12-85 | +++ |
| 1-12-87 | ++ |
| 1-12-89 | ++ |
| 1-12-90 | ++ |
| 1-12-91 | ++ |
| 1-12-93 | ++ |
| 1-12-96 | ++ |
| 1-12-97 | ++ |
| 1-12-98 | ++ |
| 1-12-100 | +++ |
| 1-12-102 | ++ |
| 1-12-107 | ++ |
| 1-12-108 | ++ |
| 1-12-113 | ++ |
| 1-12-114 | ++ |

TABLE 7-continued

| Example No. | SER2 |
| --- | --- |
| 1-12-118 | ++ |
| 1-12-121 | ++ |
| 1-12-123 | ++ |
| 1-12-130 | ++ |
| 1-12-131 | ++ |
| 1-12-132 | ++ |
| 1-12-134 | ++ |
| 1-12-135-1 | +++ |
| 1-12-135-2 | ++ |
| 1-12-136-1 | +++ |
| 1-12-136-2 | ++ |
| 1-12-137-1 | +++ |
| 1-12-137-2 | ++ |
| 1-12-138-2 | +++ |
| 1-12-139-1 | +++ |
| 1-12-139-2 | ++ |
| 1-12-140-2 | +++ |
| 1-12-141-1 | ++ |
| 1-12-142-1 | ++ |
| 1-12-143-1 | +++ |
| 1-12-144-1 | +++ |
| 1-12-145-1 | ++ |
| 1-12-145-2 | ++ |
| 1-12-146-1 | ++ |
| 1-13-1 | ++ |
| 1-13-2-1 | ++ |
| 1-13-2-2 | +++ |
| 1-13-3-1 | ++ |
| 1-13-3-2 | ++ |
| 1-13-4 | ++ |
| 1-13-12 | ++ |
| 1-13-15 | ++ |
| 1-13-17 | ++ |
| 1-16-1-1 | +++ |
| 1-16-1-2 | +++ |
| 1-16-3 | ++ |
| 1-16-6 | ++ |
| 1-16-7 | ++ |
| 1-17-1-1 | +++ |
| 1-17-1-2 | +++ |
| 1-19-1 | ++ |
| 1-19-3 | ++ |
| 1-22-1 | ++ |
| 1-22-2 | ++ |
| 1-22-3 | +++ |
| 1-22-4 | +++ |
| 1-22-5 | ++ |
| 1-22-6 | +++ |
| 1-22-7 | +++ |
| 1-22-9 | +++ |
| 1-22-10 | ++ |
| 1-22-11-1 | ++ |
| 1-22-11-2 | +++ |
| 1-22-12-1 | ++ |
| 1-22-12-2 | +++ |
| 1-23-1 | ++ |
| 1-23-2 | ++ |
| 1-24-2 | ++ |
| 1-24-17 | ++ |
| 1-24-18 | ++ |
| 1-26-1 | ++ |
| 1-31-2 | ++ |
| 1-34-4 | +++ |
| 1-35 | +++ |
| 1-41-1-1 | +++ |
| 1-41-1-2 | +++ |
| 1-41-2 | ++ |
| 1-42-1 | ++ |
| 1-44-1 | + |
| 1-44-4 | + |
| 1-44-5 | + |
| 1-46-4 | ++ |
| 1-46-5 | ++ |
| 1-46-6 | +++ |
| 1-46-7 | ++ |
| 1-46-8 | ++ |
| 1-46-9 | ++ |
| 1-46-10 | ++ |

TABLE 7-continued

| Example No. | SER2 |
|---|---|
| 1-46-11 | +++ |
| 1-48-1 | ++ |
| 1-48-2 | +++ |
| 1-50-1 | +++ |
| 1-50-2 | ++ |
| 1-50-4 | ++ |
| 1-50-5 | ++ |
| 1-50-7 | ++ |
| 1-50-8 | +++ |
| 1-50-9 | +++ |
| 1-51-1 | +++ |
| 1-51-2 | ++ |
| 1-51-3 | ++ |
| 1-52-1 | +++ |
| 1-52-2 | +++ |
| 2-2-1 | ++ |
| 2-2-3 | ++ |
| 2-2-7 | ++ |
| 2-2-11 | ++ |
| 2-2-12 | ++ |
| 2-2-14 | ++ |
| 2-2-16 | ++ |
| 2-2-17 | + |

TABLE 8

| Example No. | SER2 |
|---|---|
| 2-2-18 | + |
| 2-2-20 | + |
| 2-2-35 | + |
| 2-2-36 | + |
| 2-2-37 | + |
| 2-2-38 | ++ |
| 2-2-40 | ++ |
| 2-2-41 | ++ |
| 2-2-48 | + |
| 2-2-50 | ++ |
| 2-2-51 | + |
| 2-2-52 | + |
| 2-2-53 | + |
| 2-2-58 | + |
| 2-2-60 | + |
| 2-2-64 | ++ |
| 2-2-69 | + |
| 2-2-71 | ++ |
| 2-2-72 | ++ |
| 2-2-74 | ++ |
| 2-13-1 | + |
| 2-13-4 | ++ |
| 2-13-5 | + |
| 2-13-6 | + |
| 2-13-7 | + |
| 2-13-8 | + |
| 2-13-9 | + |
| 2-13-10 | ++ |
| 2-13-11 | ++ |
| 2-14-7 | + |
| 2-14-10 | ++ |
| 2-14-11 | ++ |
| 2-14-12 | ++ |
| 2-14-13 | ++ |
| 2-14-16 | +++ |
| 2-14-18 | ++ |
| 2-14-19 | ++ |
| 2-14-20 | +++ |
| 2-14-21 | ++ |
| 2-14-23 | ++ |
| 2-14-24 | ++ |
| 2-14-45 | ++ |
| 2-14-51 | ++ |
| 2-14-61 | +++ |
| 2-14-62 | ++ |
| 2-14-80 | ++ |
| 2-14-85-2 | +++ |

TABLE 8-continued

| Example No. | SER2 |
|---|---|
| 2-14-86-2 | ++ |
| 2-14-87-1 | ++ |
| 2-14-89-2 | +++ |
| 2-14-90-2 | +++ |
| 2-14-92-2 | +++ |
| 2-14-94-1 | +++ |
| 2-21-2 | ++ |
| 2-21-6 | + |
| 2-21-7 | + |
| 2-21-9 | + |
| 2-28-5 | + |
| 2-28-23 | + |
| 2-28-32 | + |
| 2-41-2 | ++ |
| 2-41-3 | ++ |
| 2-41-4 | ++ |
| 2-46-1 | +++ |
| 2-46-2 | ++ |
| 2-46-3 | +++ |
| 2-46-4 | ++ |
| 2-46-5 | ++ |
| 3-8-10 | ++ |
| 4-4-2 | ++ |
| 4-4-4 | + |
| 4-4-6 | + |
| 4-4-7 | ++ |
| 4-4-8 | ++ |
| 4-4-9 | ++ |
| 4-4-12 | ++ |
| 4-4-13 | ++ |
| 4-4-14 | ++ |
| 4-4-15 | ++ |
| 4-4-16 | ++ |
| 4-4-17 | ++ |
| 4-4-20 | ++ |
| 4-4-22 | + |
| 4-4-25 | + |
| 4-4-28 | ++ |
| 4-4-29 | ++ |
| 4-4-30 | ++ |
| 4-8-1 | ++ |
| 4-8-5 | ++ |
| 4-8-8 | ++ |
| 4-8-12 | ++ |
| 4-8-13 | ++ |
| 4-8-15 | + |
| 4-8-17 | ++ |
| 4-8-18 | ++ |
| 4-8-19 | ++ |
| 4-8-22 | ++ |
| 4-8-23 | ++ |
| 4-8-24 | ++ |
| 4-8-25 | ++ |
| 4-10 | ++ |
| 10-1 | +++ |
| 10-2 | +++ |

The compound of the present invention exhibited excellent sensitivity-enhancing effects to ionizing radiation.

Test Example 3

Evaluation of Sensitivity-Enhancing Effects to Ionizing Radiation in Subcutaneously Transplanted Tumor of Mouse A 6-week male Balb/c nu/nu mouse (Clea Japan, Inc.) was used. A human lung cancer cell line NCI-H460 a (ATCC company) was suspended in serum-free medium, and the resultant product was subcutaneously transplanted into the right limb femoral region of a mouse. 10 days after transplantation, grouping into a test compound nonadministration group (control group) and a test compound administration group was performed such that the average tumor volume became 200 mm³ to 250 mm³, and an X-ray irradiation treatment and test compound administration were started. Using radiation irradiation apparatus (Precision X-RAY, X-RAD225) for small animals, irradiation conditions were set such that one irradiation per mouse became 225 kV and 13.3 mA (about 1.9 Gy/min). All except for the vicinity of the tumor transplanted portion are shielded by a lead plate, and local irradiation was performed. The test compound was dissolved in a solubilizing solvent, the resultant product was administered intravenously to a mouse in the test compound administration group once a day at a dose of 3 mg/kg to 50 mg/kg. After an X-ray irradiation treatment, the tumor diameter was measured over date, and the tumor volume was calculated. For the tumor volume, the major axis and the minor axis of the tumor were measured, and the tumor volume was calculated by the following equation.

Tumor volume (mm³)=major axis (mm)×minor axis (mm)×minor axis (mm)/2

The day when the average tumor volume of the control group exceeded 2000 mm³ was set to the test end date, and the tumor volume ratio of the test compound administration group to the control group on the test end date was calculated. The tumor volume ratio was calculated by the following equation.

Tumor volume ratio (%)=100×((average tumor volume of the test compound administration group of the test end date)−(average tumor volume of the test compound administration group of the test start date))/((average tumor volume of the control group of the test end date)−(average tumor volume of the control group of the test start date))

The tumor volume of ratio of the test compound administration group, to which each compound of Example 1-12-2, Example 1-12-137-1, Example 1-12-139-1, Example 1-12-140-2, Example 1-12-144-1, Example 1-13-2-2, Example 1-13-3-2, Example 1-17-1-2, Example 1-22-12-2, Example 1-41-1-2, Example 2-2-24, Example 2-14-2, Example 2-14-94-1, Example 2-28-2, Example 4-8-5, Example 4-8-19, and Example 4-8-23 was administered, was 80% or less, and this value was a low value by 20% or greater compared to that of the control group.

The compound of the present invention exhibited excellent sensitivity-enhancing effects to ionizing radiation.

Next, the present invention will be described with reference to reference examples and examples, but the present invention is not limited thereto.

Unless otherwise specified, in purification by column chromatography, an automated purification apparatus ISOLERA (Biotage) or a medium-pressure liquid chromatograph YFLC W-prep 2XY (YAMAZEN CORPORATION) was used.

Unless otherwise specified, as a carrier in silica gel column chromatography, a SNAP KP-Sil Cartridge (Biotage), HIGH FLASH COLUMN W001, W002, W003, W004, or W005 (YAMAZEN CORPORATION) was used.

As NH silica, a SNAP KP-NH Cartridge (Biotage) was used.

The mixing ratio in the eluent was a volume ratio.

For example, "chloroform:methanol=90:10→50:50" means that an eluent of "chloroform:methanol=90:10" was changed to an eluent of "chloroform:methanol=50:50".

As a supercritical fluid chromatography, SFC 30 (Waters) was used.

In preparative thin layer silica gel chromatography, PLC glass plate silica gel $F_{60}$ (Merck KGaA) was used.

As NH silica, PLC05 Plates NH (Fuji Silysia Chemical Ltd.) was used.

In preparative reversed phase HPLC, a Waters 2998 Photodiode Array (PDA) Detector (Waters), a Waters 600 Controller (Waters), a Waters 2767 Sample Manager (Waters) set, and a YMC-Actus ProC18, 30×50 mm column (YMC Co., Ltd.) were used.

A MS spectrum was measured by an ionization method in which ACQUITY SQD LC/MS System (Waters, ionization method: ElectroSpray Ionization method (ESI)) and LCMS-2010EV (Shimadzu Corporation, ionization method: ESI and Atomospheric Pressure Chemical Ionization (APCI)) were performed at the same time.

Unless otherwise specified, MS in the table means MS(ESI m/z):(M+H).

As a microwave reaction apparatus, Initiator Sixty (Biotage) was used.

As a flow-type hydrogenation reaction apparatus, H-Cube (ThaLesNano Inc.) was used.

In the measurement of an NMR spectrum, tetramethylsilane was used as an internal standard, Bruker AV300 (Bruker Corporation) was used, and all δ values were shown in ppm.

Unless otherwise specified, the solvent of the NMR spectrum in the table is DMSO-$d_6$. In a case where a solvent other than DMSO-$d_6$ was used, the solvent name was described in parentheses.

The retention time (RT) was measured by using a SQD (Waters), and shown in minutes (min).

Column: BEHC 181.7 um, 2.1×30 mm, manufactured by Waters

Solvent: A liquid: 0.1% formic acid-water

B liquid: 0.1% formic acid-acetonitrile

Gradient cycle: 0.00 min (A liquid/B liquid=95/5), 2.00 min (A liquid/B liquid=5/95), 3.00 min (A liquid/B liquid=5/95), 3.01 min (A liquid/B liquid=100/0), 3.80 min (A liquid/B liquid=100/0)

Flow rate: 0.5 mL/min

Column temperature: room temperature

Detection wavelength: 254 nm

Abbreviations in respective examples have the following meanings.

Boc: tert-Butoxycarbonyl

Bn: Benzyl

Bu: Butyl

Bz: Benzoyl

Cbz: Benzyloxycarbonyl

Et: Ethyl

MPM: 4-Methoxybenzyl

Ms: Methylsulfonyl

Ph: Phenyl

RaNi: Raney nickel

SEM: (2-(Trimethylsilyl)ethoxy)methyl

TBS: tert-Butyldimethylsilyl t-Bu: tert-Butyl

Tf: Trifluoromethylsulfonyl

TMS: Trimethylsilyl

Ts: p-Toluenesulfonyl

DMSO-$d_6$: Hexadeuterodimethylsulfoxide

TBDPS: tert-Butyldimethylsilyl

RT (min): Retention time (min)

Reference Example 1

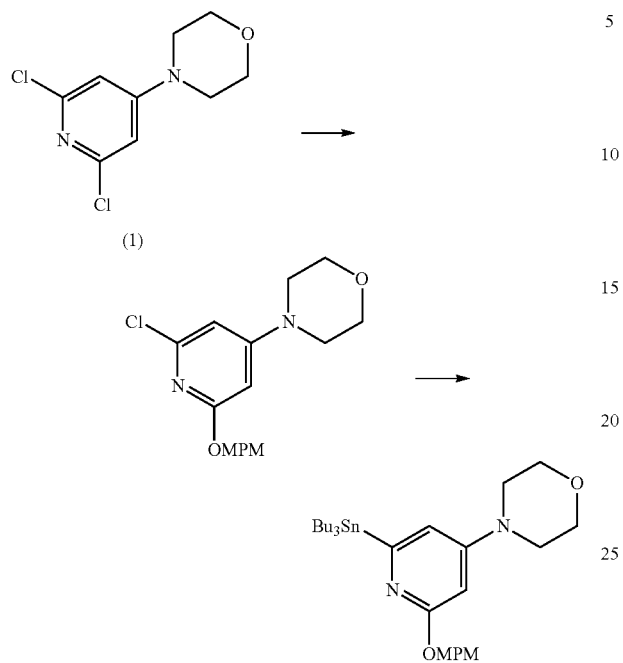

Sodium hydride (103 mg, 60%, dispersed in liquid paraffin) was added to a solution of 4-methoxybenzyl alcohol (196 mg) in tetrahydrofuran (5 mL) under ice-cooling, followed by stirring for 0.5 hours. 4-(2,6-Dichloropyridin-4-yl)morpholine (300 mg) was added to the reaction mixture, followed by refluxing for 18 hours. After the reaction mixture was cooled to 0° C., water was added thereto, and extraction was performed by using ethyl acetate. The organic layer was washed with a saturated sodium chloride aqueous solution, and dried over anhydrous sodium sulfate, and the solvent was distilled off under reduced pressure. The obtained residues were purified by silica gel column chromatography (hexane:ethyl acetate=1:0→4:1), whereby 4-(2-chloro-6-((4-methoxybenzyl)oxy)pyridin-4-yl)morpholine (418 mg) was obtained as a colorless oily material.

MS(ESI m/z): 335 (M+H)

RT(min): 1.69

(2)

Lithium chloride (5.3 g), 1,1,1,2,2,2-hexabutyldistannane (53 mL), and tetrakis(triphenylphosphine)palladium (0) (2.3 g) were added to a solution of 4-(2-chloro-6-((4-methoxy benzyl) oxy) pyridin-4-yl)morpholine (7.0 g) obtained in Reference Example 1 (1) in 1,4-dioxane (350 mL), followed by refluxing for 62 hours under a nitrogen gas flow. The reaction mixture was cooled to room temperature, and filtered using Celite, whereby the insoluble materials were removed. Silica gel (50 g) was added to the filtrate, and the solvent was distilled off under reduced pressure. The obtained residues were purified by silica gel column chromatography (hexane:ethyl acetate=7:3), whereby 4-(2-((4-methoxybenzyl)oxy)-6-(tributylstannyl)pyridin-4-yl)morpholine (560 mg) was obtained as a yellow oily material.

MS(ESI m/z): 591 (M+H)

RT(min): 1.77

Reference Example 2

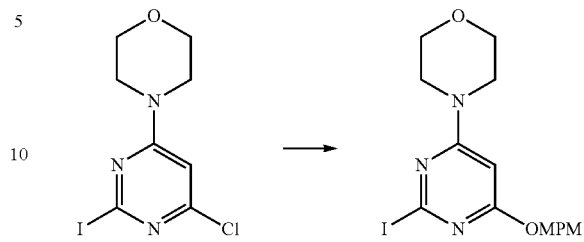

The following compound was obtained using 4-(6-chloro-2-iodopyrimidin-4-yl)morpholine in the same manner as in Reference Example 1 (1).

4-(2-Iodo-6-((4-methoxybenzyl)oxy)pyrimidin-4-yl)morpholine

MS(ESI m/z): 428 (M+H)

RT(min): 1.74

Reference Example 3

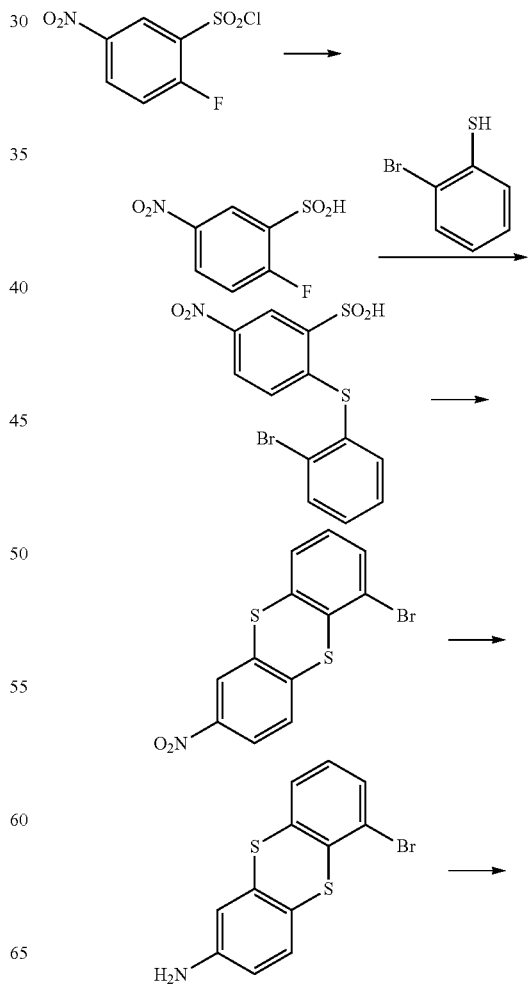

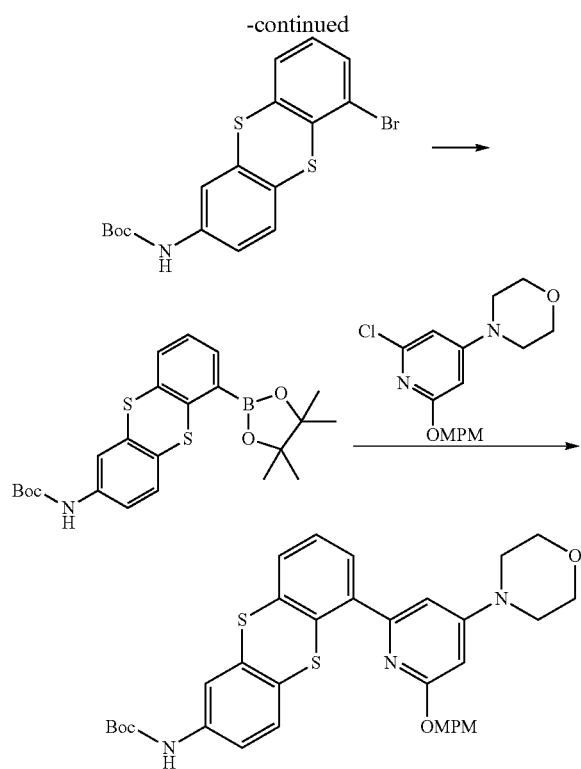

(1)

Sodium sulfite (4.4 g) was added to a solution of 2 fluoro 5-5-nitrobenzenesulfonyl chloride (2.4 g) in water (15 mL) under ice-cooling, followed by stirring at room temperature for 1 hour. Concentrated hydrochloric acid was added to the reaction mixture, and extraction was performed by using ethyl acetate. The organic layer was washed with a saturated aqueous sodium chloride solution, and dried over anhydrous sodium sulfate. The solvent was distilled off under reduced pressure, whereby 2-fluoro-5-nitrobenzenesulfinic acid (1.4 g) was obtained as a white solid.

MS(ESI m/z): 204 (M−H)
RT(min): 0.51

(2)

Sodium hydroxide (810 mg) and 2-bromobenzenethiol (1.2 g) were added to a solution of 2-fluoro-5-nitrobenzenesulfinic acid (1.4 g) obtained in Reference Example 3 (1) in water (10 mL), followed by refluxing for 0.5 hours under a nitrogen gas flow. After the reaction mixture was cooled to 0° C., concentrated hydrochloric acid was added thereto, and extraction was performed by using ethyl acetate. The organic layer was washed with a saturated aqueous sodium chloride solution, and dried over anhydrous sodium sulfate. The solvent was distilled off under reduced pressure, whereby 2-((2-bromophenyl)thio)-5-nitrobenzenesulfinic acid (2.3 g) was obtained as a brown solid.

MS(ESI m/z): 372 (M−H)
RT(min): 1.06

(3)

Under a nitrogen gas flow, a mixture of 2-((2-bromophenyl)thio)-5-nitrobenzenesulfinic acid (2.3 g) obtained in Reference Example 3 (2) and an Eaton reagent (30 mL) was stirred at 50° C. for 1.5 hours. After the reaction mixture was cooled to room temperature, a 5.0 mol/L sodium hydroxide aqueous solution was added thereto, and extraction was performed by using ethyl acetate. The organic layer was washed with a saturated aqueous sodium chloride solution, and dried over anhydrous sodium sulfate. The solvent was distilled off under reduced pressure, and the obtained solid was washed with ethanol, whereby 1-bromo-7-nitro thianthrene (840 mg) was obtained as a brown solid.

MS(ESI m/z): 341 (M+H)
RT(min): 2.04

(4)

A mixture of 1-bromo-7-nitrothianthrene (840 mg) obtained in Reference Example 3 (3), iron powder (480 mg), ammonium chloride (260 mg), tetrahydrofuran (10 mL), ethanol (10 mL), and water (2 mL) was stirred at 90° C. for 1 hour, and further stirred at 120° C. for 2 hours. The reaction mixture was cooled to room temperature, and filtered using Celite, whereby the insoluble materials were removed. After the solvent was distilled off under reduced pressure, the residues were dissolved in ethyl acetate, and washed sequentially with water and a saturated sodium chloride aqueous solution, and dried over anhydrous sodium sulfate. The solvent was distilled off under reduced pressure, and the obtained solid was purified by silica gel column chromatography (hexane:ethyl acetate=9:1→1:1, NH silica), whereby 6-bromo thianthrene-2-amine (500 mg) was obtained.

MS(ESI m/z): 312 (M+H+2)
RT(min): 1.69

(5)

Di-tert-butyl dicarbonate (700 mg) was added to a solution of 6-bromothianthrene-2-amine (500 mg) obtained in Reference Example 3 (4) in tetrahydrofuran (5 mL), followed by refluxing for 5 hours. The reaction mixture was cooled to room temperature, the solvent was distilled off under reduced pressure, and the obtained residues were purified by silica gel column chromatography (hexane:ethyl acetate=1:0→1:1), whereby tert-butyl(6-bromothianthren-2-yl)carbamate (390 mg) was obtained as a colorless oily material.

MS(ESI m/z): 411 (M+H)
RT(min): 2.14

(6)

Under a nitrogen gas flow, tert-butyl(6-bromothianthren-2-yl)carbamate (580 mg) obtained in Reference Example 3 (5), bispinacolatodiboron (430 mg), potassium acetate (420 mg), and a 1,1'-bis(diphenylphosphino)ferrocene palladium (II) dichloride-dichloromethane complex (170 mg) were added a mixed solvent of 1,4-dioxane (8 mL) and dimethyl sulfoxide (0.8 mL), followed by stirring at 90° C. for 19 hours. The reaction mixture was cooled to room temperature, ethyl acetate was added thereto, and the insoluble materials were filtered off. The solvent was distilled off under reduced pressure, and the obtained residues were purified by silica gel column chromatography (hexane; ethyl acetate=9:1→1:1), whereby tert-butyl(6-(4,4,5,5-tetramethyl-1,3,2-dioxaborolan-2-yl)thianthren-2-yl)carbamate (580 mg) was obtained as a brown solid.

MS(ESI m/z): 458 (M+H)
RT(min): 2.19

(7)

Under a nitrogen gas flow, tert-butyl(6-(4,4,5,5-tetramethyl-1,3,2-dioxaborolan-2-yl)thianthren-2-yl)carbamate (580 mg) obtained in Reference Example 3 (6), sodium carbonate (400 mg), 4-(2-chloro-6-((4-methoxybenzyl)oxy) pyridin-4-yl)morpholine (430 mg), and bis(di-tert-butyl(4-dimethylaminophenyl)phosphine)dichloropalladium (II) (45 mg) were added to a mixed solvent of 1,2-dimethoxyethane (20 mL) and water (5 mL), followed by stirring at 120° C. for 1.5 hours. After the reaction mixture was cooled to room temperature, ethyl acetate was added thereto, and the resultant product was washed sequentially with water and a saturated sodium chloride aqueous solution, and dried over anhydrous sodium sulfate. The solvent was distilled off under reduced pressure, and the obtained residues were purified by silica gel column chromatography (hexane:ethyl acetate=9:1→1:1), whereby tert-butyl(6-(6-((4-methoxybenzyl)oxy)-4-morpholinopyridin-2-yl)thianthren-2-yl)carbamate (300 mg) was obtained as a brown oily material.

MS(ESI m/z): 630 (M+H)
RT(min): 2.02

Reference Example 4

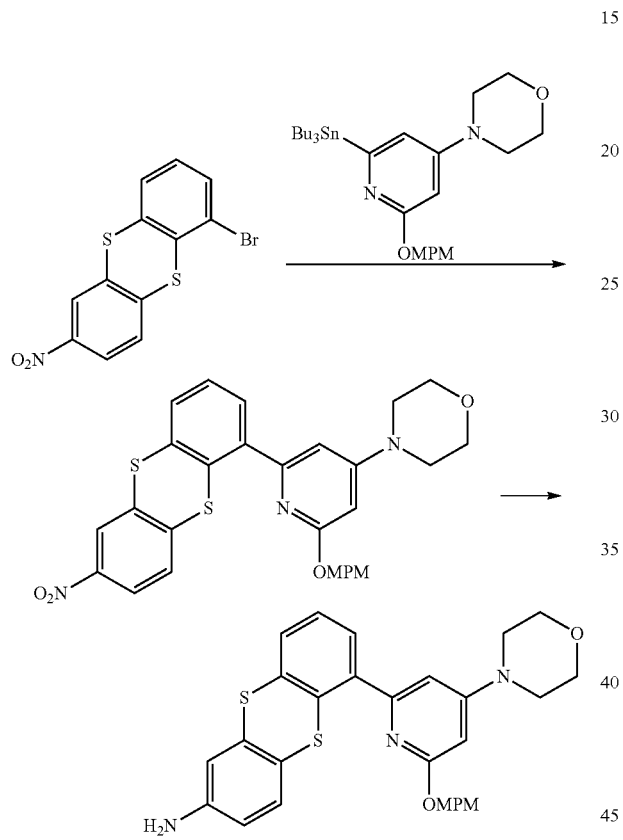

(1)
Under a nitrogen gas flow, 4-(2-((4-methoxybenzyl)oxy)-6-(tributylstannyl)pyridin-4-yl)morpholine (1.1 g) and bis(di-tert-butyl(4-dimethylaminophenyl)phosphine)dichloropalladium (II) (21 mg) were added to a solution of 1-bromo-7-nitrothianthrene (500 mg) in 1,4-dioxane (15 mL), followed by stirring at 110° C. for 4 hours. The reaction mixture was cooled to room temperature, and the insolubles were filtered off. The solvent was distilled off under reduced pressure, and the obtained residues were purified by silica gel column chromatography (hexane:ethyl acetate=1:0→3:1), whereby 4-(2-((4-methoxybenzyl)oxy)-6-(7-nitrothianthren-1-yl)pyridin-4-yl)morpholine (630 mg) was obtained as a yellow solid.

MS(ESI m/z): 560 (M+H)
RT(min): 2.11

(2)
In the same manner as in Reference Example 3 (4), the following compound was obtained.

6-(6-((4-Methoxybenzyl)oxy)-4-morpholinopyridin-2-yl)thianthrene-2-amine

MS(ESI m/z): 530 (M+H)
RT(min): 1.60

Reference Example 5

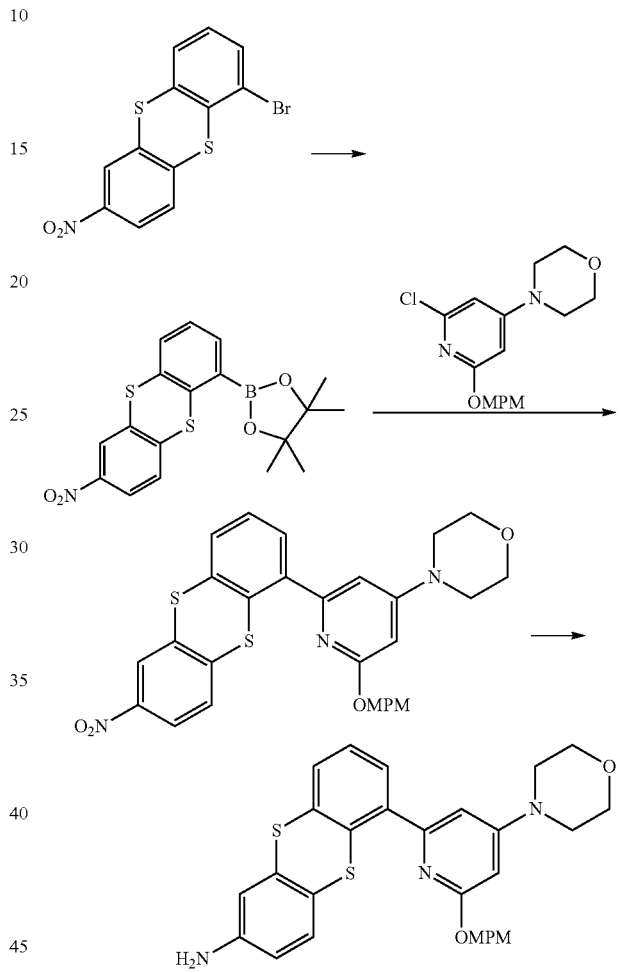

(1)
Bispinacolatodiboron (9.0 g), a 1,1'-bis(diphenylphosphino)ferrocene palladium (II) dichloride-dichloromethane complex (1.2 g), and potassium acetate (8.7 g) were added to a solution of 1-bromo-7-nitrothianthrene (10.0 g) in 1,4-dioxane (147 mL), followed by stirring at 90° C. for 2 hours under a nitrogen gas flow. A 1,1'-bis(diphenylphosphino)ferrocene palladium (II) dichloride-dichloromethane complex (1.2 g) was added thereto, and the resultant product was stirred at 90° C. for 1 hour, and further stirred at 100° C. for 1.5 hours. A 1,1'-bis(diphenylphosphino)ferrocene palladium (II) dichloride-dichloromethane complex (1.2 g) was added thereto, followed by stirring at 100° C. for 1.5 hours. 4-(2-Chloro-6-((4-methoxy benzyl)oxy)pyridin-4-yl)morpholine (11.8 g), potassium carbonate (12.2 g), 2-dicyclohexylphosphino-2',4',6'-triisopropylbiphenyl (5.1 g), and water (29 mL) were added to the reaction mixture, followed by stirring at 110° C. for 1 hour. After the reaction mixture was cooled to room temperature, ethyl acetate was added thereto, and the resultant product was washed with water, and dried over anhydrous sodium sulfate. The solvent was distilled off under reduced pressure, and the obtained residues were purified by silica gel column chromatography (hexane:ethyl acetate=1:0→3:1), whereby 4-(2-((4-methoxy benzyl)oxy)-6-(7-nitrothianthren-1-yl)pyridin-4-yl)morpholine (16.4 g) was obtained as a yellow solid.

MS(ESI m/z): 560 (M+H)
RT(min): 2.11

(2)

In the same manner as in Reference Example 3 (4), the following compound was obtained.

6-(6-((4-Methoxy benzyl)oxy)-4-morpholinopyridin-2-yl)thianthrene-2-amine

MS(ESI m/z): 530 (M+H)
RT(min): 1.60

Reference Example 6

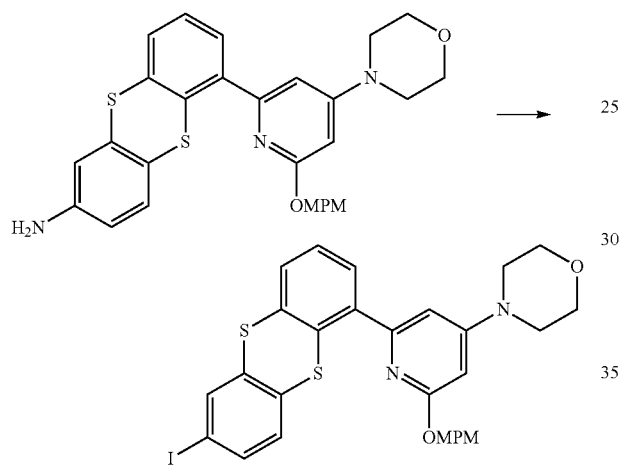

Copper iodide (I) (2.8 g), diiodomethane (5.9 mL), and isoamyl nitrite (5.9 mL) were added to a solution of 6-(6-((4-methoxybenzyl)oxy)-4-morpholinopyridin-2-yl)thianthrene-2-amine (7.9 g) in tetrahydrofuran (73 mL), followed by stirring at 85° C. for 0.5 hours. The reaction mixture was cooled to room temperature, the solvent was distilled off under reduced pressure, and the obtained residues were purified by silica gel column chromatography (hexane:ethyl acetate=1:0→7:3), whereby 4-(2-(7-iodothianthren-1-yl)-6-((4-methoxybenzyl)oxy)pyridin-4-yl)morpholine (4.6 g) was obtained as a yellow solid.

MS(ESI m/z): 641 (M+H)
RT(min): 2.33

Reference Example 7

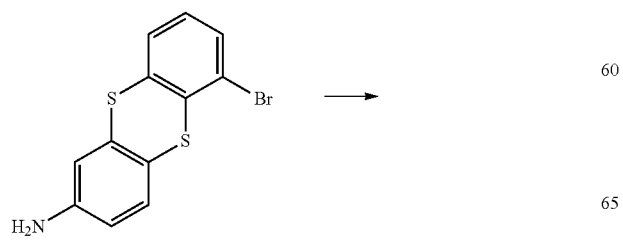

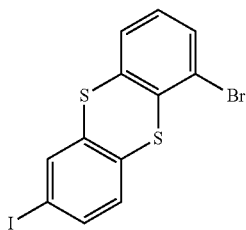

In the same manner as in Reference Example 6, the following compound was obtained.

1-Bromo-7-iodothianthrene

MS(ESI m/z): 422 (M+H)
RT(min): 2.38

Reference Example 8

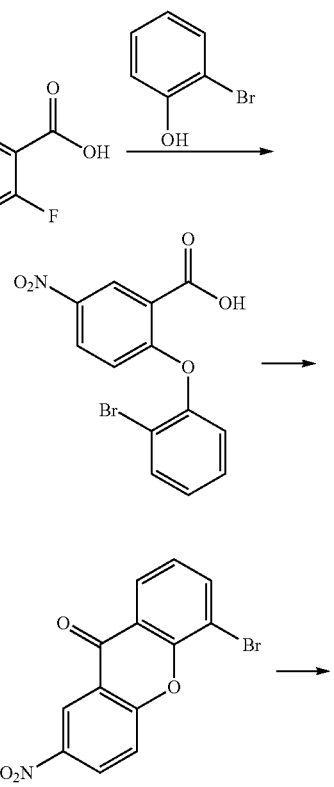

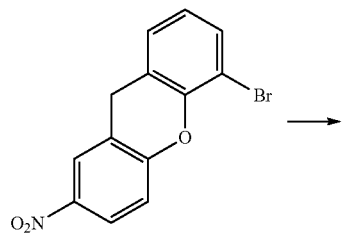

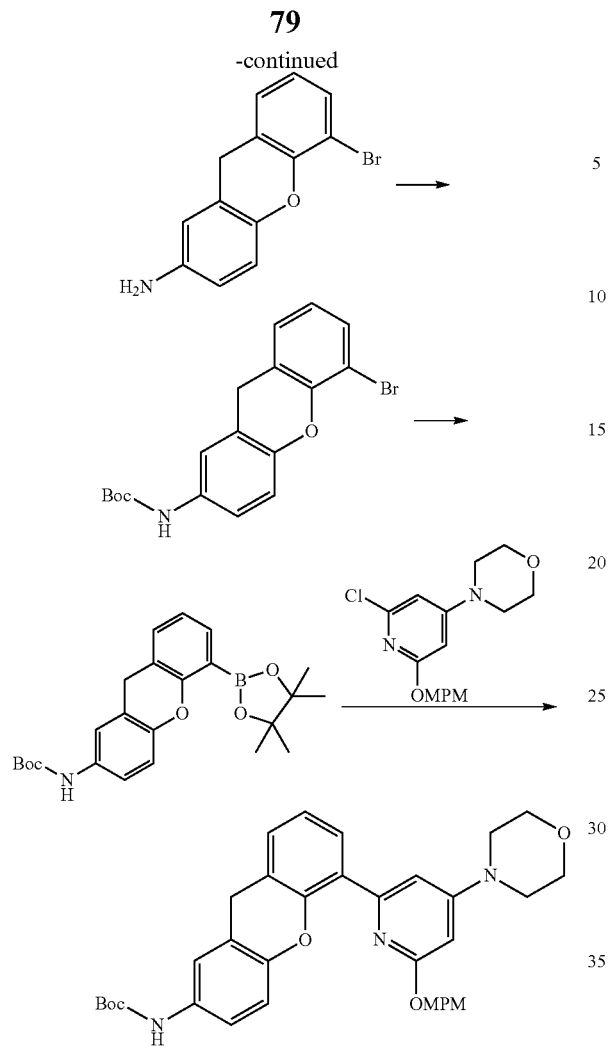

(1)

Potassium carbonate (3.5 g) and 2-bromophenol (1.0 g) were added to a solution of 2-fluoro-5-nitrobenzoic acid (1.0 g) in N,N-dimethyl acetamide (20 mL), and the resultant product was stirred at 90° C. for 5 hours, and further stirred at 100° C. for 1 hour. After the reaction mixture was cooled to room temperature, ethyl acetate was added thereto, and the resultant product was washed sequentially with 1 mol/L hydrochloric acid and a saturated sodium chloride aqueous solution, and dried over anhydrous sodium sulfate. The solvent was distilled off under reduced pressure, and the obtained residues were purified by silica gel column chromatography (methanol:ethyl acetate=0:1→1:4), whereby 2-(2-bromophenoxy)-5-nitrobenzoic acid (1.8 g) was obtained as a brown solid.

(2)

Under a nitrogen gas flow, a mixture of 2-(2-bromophenoxy)-5-nitrobenzoic acid (100 mg) obtained in Reference Example 8 (1) and an Eaton reagent (2 mL) was stirred at 50° C. for 1.5 hours, then, at 100° C. for 1 hour, and at 150° C. for 1 hour. After the reaction mixture was cooled to room temperature, ice was added thereto, and the precipitated solid was collected by filtration. The obtained solid was washed sequentially with water and ethanol, whereby 5-bromo-2-nitro-9H-xanthen-9-one (81 mg) was obtained as a white solid.

MS(ESI m/z): 320 (M+H)

RT(min): 1.66

(3)

Under ice-cooling, a 1.0 mol/L borane-tetrahydrofuran complex/tetrahydrofuran solution (2 mL) was added to a solution of 5-bromo-2-nitro-9H-xanthen-9-one (3.0 g) in tetrahydrofuran (15 mL) obtained in Reference Example 8 (2), and the resultant product was stirred at room temperature for 0.75 hours, and refluxed for 2 hours. After the reaction mixture was cooled to room temperature, ethanol was added thereto, and the solvent was distilled off under reduced pressure. Chloroform was added to the obtained residues, and the resultant product was washed with a saturated sodium hydrogen carbonate aqueous solution, and dried over anhydrous magnesium sulfate. The solvent was distilled off under reduced pressure, whereby 5-bromo-2-nitro-9H-xanthene (2.8 g) was obtained.

MS(ESI m/z): 306 (M+H)

RT(min): 1.88

(4) to (7)

In the same manner as in Reference Examples 3 (4) to 3 (7), the following compounds were obtained.

5-Bromo-9H-xanthene-2-amine

MS(ESI m/z): 276 (M+H)

RT(min): 1.12 tert-Butyl (5-bromo-9H-xanthen-2-yl)carbamate

MS(ESI m/z): 376 (M+H)

RT(min): 2.00 tert-Butyl (5-(4,4,5,5-tetramethyl-1,3,2-dioxaborolan-2-yl)-9H-xanthen-2-yl)carbamate MS(ESI m/z): 424 (M+H)

RT(min): 2.03 tert-Butyl (5-(6-((4-methoxybenzyl)oxy)-4-morpholinopyridin-2-yl)-9H-xanthen-2-yl)carbamate Reference Example 9-1

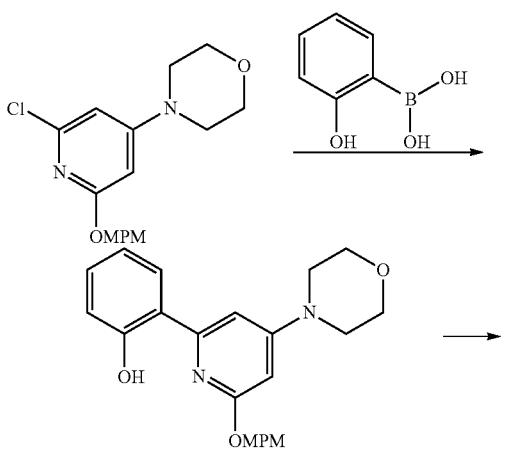

-continued

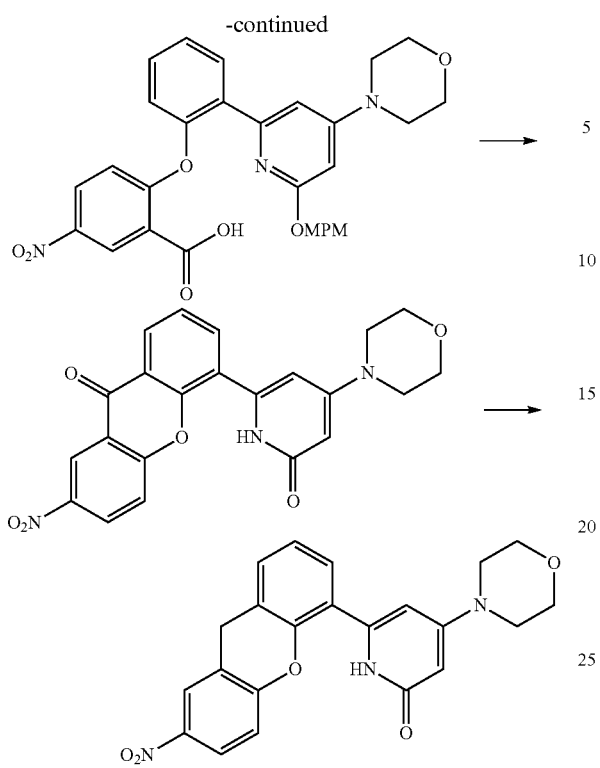

(1)
Under a nitrogen gas flow, (2-hydroxyphenyl)boronic acid (2.3 g), sodium carbonate (3.2 g), 4-(2-chloro-6-((4-methoxybenzyl)oxy)pyridin-4-yl)morpholine (5 g), and bis(di-tert-butyl(4-dimethylaminophenyl)phosphine)dichloropalladium (II) (110 mg) were added to a mixed solvent of 1,2-dimethoxyethane (50 mL) and water (15 mL), followed by stirring at 90° C. for 2 hours. After the reaction mixture was cooled to room temperature, ethyl acetate was added thereto, and the resultant product was washed with a saturated sodium chloride aqueous solution, and dried over anhydrous sodium sulfate. The solvent was distilled off under reduced pressure, and the obtained solid was washed with ethanol, whereby 2-(6-((4-methoxybenzyl)oxy)-4-morpholinopyridin-2-yl)phenol (5.4 g) was obtained as a white solid.
MS(ESI m/z): 393 (M+H)
RT(min): 1.62
(2)
Potassium carbonate (4.8 g) and 2-fluoro-5-nitrobenzoic acid (3.1 g) were added to a solution of 2-(6-((4-methoxybenzyl)oxy)-4-morpholinopyridin-2-yl)phenol (5.4 g) obtained in Reference Example 9-1 (1) in N,N-dimethyl acetamide (30 mL), followed by stirring at 140° C. for 5.5 hours. 2-Fluoro-5-nitrobenzoic acid (260 mg) was further added thereto, followed by stirring at 150° C. for 4 hours. After the reaction mixture was cooled to room temperature, water was added thereto, then, the pH of the resultant product was adjusted to 3.5 with 6 mol/L hydrochloric acid, and the precipitated solid was collected by filtration, whereby 2-(2-(6-((4-methoxybenzyl)oxy)-4-morpholinopyridin-2-yl)phenoxy)-5-nitrobenzoic acid (8.3 g) was obtained as a white solid.
(3)
Under a nitrogen gas flow, a mixture of 2-(2-(6-((4-methoxybenzyl)oxy)-4-morpholinopyridin-2-yl)phenoxy)-5-nitrobenzoic acid (7.7 g) obtained in Reference Example 9-1 (2) and an Eaton reagent (45 mL) was stirred at 50° C. for 2 hours. After the reaction mixture was cooled to room temperature, ice was added thereto, then, the resultant product was neutralized with 28% ammonia water, and the precipitated solid was collected by filtration. The obtained solid was washed with methanol, whereby 4-morpholino-6-(7-nitro-9-oxo-9H-xanthen-4-yl)pyridin-2(1H)-one (7.1 g) was obtained.
(4)
In the same manner as in Reference Example 8 (3), the following compound was obtained.

4-Morpholino-6-(7-nitro-9H-xanthen-4-yl)pyridin-2(1H)-one

Reference Example 9

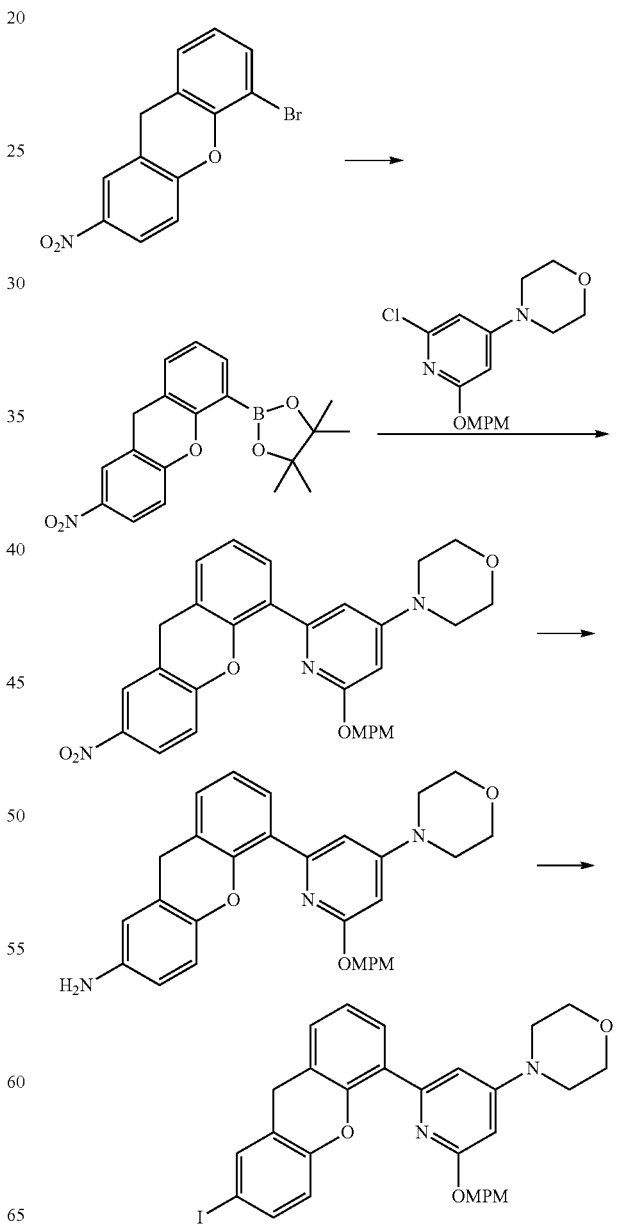

(1)

Bispinacolatodiboron (2.0 g), a 1,1'-bis(diphenylphosphino)ferrocene palladium (II) dichloride-dichloromethane complex (0.80 g), and potassium acetate (1.9 g) were added to a solution of 5-bromo-2-nitro-9H-xanthene (2.0 g) in 1,4-dioxane (33 mL), followed by stirring at 90° C. for 3 hours under a nitrogen gas flow. 4-(2-Chloro-6-((4-methoxybenzyl)oxy)pyridin-4-yl)morpholine (2.6 g), potassium carbonate (2.7 g), 2-dicyclohexylphosphino-2',4',6'-triisopropylbiphenyl (1.1 g), and water (6.6 mL) were added to the reaction mixture, followed by stirring at 110° C. for 1 hour. After the reaction mixture was cooled to room temperature, ethyl acetate was added thereto, and the resultant product was washed with water, and dried over anhydrous sodium sulfate. The solvent was distilled off under reduced pressure, and ethyl acetate and methanol were added to the obtained residues. The precipitated solid was collected by filtration, whereby 4-(2-((4-methoxybenzyl)oxy)-6-(7-nitro-9H-xanthen-4-yl)pyridin-4-yl)morpholine (3.4 g) was obtained as a brown solid.

MS(ESI m/z): 526 (M+H)
RT(min): 1.53

(2)

In the same manner as in Reference Example 3 (4), the following compound was obtained.

5-(6-((4-Methoxybenzyl)oxy)-4-morpholinopyridin-2-yl)-9H-xanthene-2-amine

MS(ESI m/z): 496 (M+H)
RT(min): 1.03

(3)

In the same manner as in Reference Example 6, the following compound was obtained.

4-(2-(7-Iodo-9H-xanthen-4-yl)-6-((4-methoxybenzyl)oxy)pyridin-4-yl)morpholine

MS(ESI m/z): 607 (M+H)
RT(min): 1.72

Reference Example 10

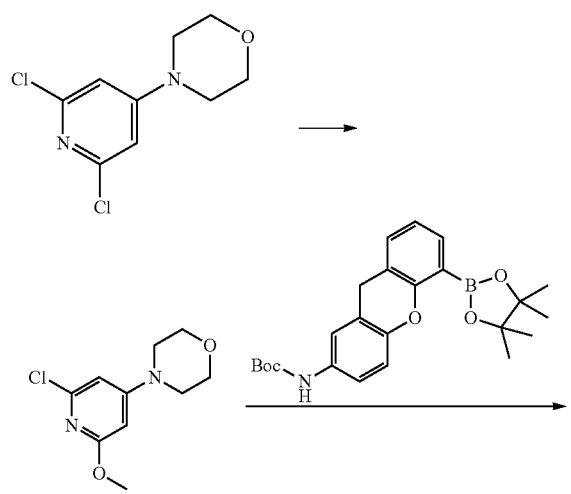

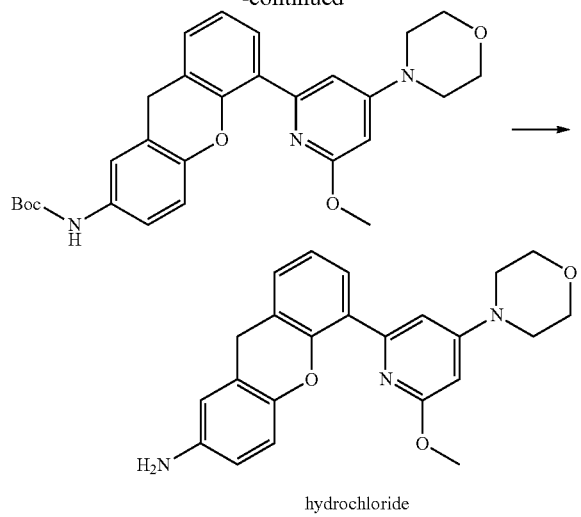

(1)

A 28% sodium methoxide/methanol solution (2 mL) was added to a solution of 4-(2,6-dichloropyridin-4-yl)morpholine (1.0 g) in methanol (2 mL), and the resultant product was irradiated with microwaves (microwave reaction apparatus, 120° C., 0.5 hours, 2.45 GHz, 0 W to 240 W). After the reaction mixture was cooled to room temperature, water was added thereto, and the precipitated solid was collected by filtration, whereby 4-(2-chloro-6-methoxy pyridin-4-yl)morpholine (1.0 g) was obtained as a white solid.

$^1$H-NMR (CDCl$_3$, 300 MHz) δ: 6.40 (1H, d, J=1.8 Hz), 5.95 (1H, d, J=1.8 Hz), 3.89 (3H, s), 3.81 (4H, t, J=5.0 Hz), 3.24 (4H, t, J=5.0 Hz).

(2)

In the same manner as in Reference Example 3 (7), the following compound was obtained.

tert-Butyl (5-(6-methoxy-4-morpholinopyridin-2-yl)-9H-xanthen-2-yl)carbamate (3)

A mixture of tert-butyl (5-(6-methoxy-4-morpholinopyridin-2-yl)-9H-xanthen-2-yl)carbamate obtained in Reference Example 10 (2) and 4.0 mol/L hydrogen chloride/1,4-dioxane (20 mL) was stirred at room temperature for 0.5 hours. The solvent was distilled off under reduced pressure, and the obtained solid was washed with ethyl acetate, whereby hydrochloride (370 mg) of 5-(6-methoxy-4-morpholinopyridin-2-yl)-9H-xanthen-2-amine was obtained as a pale yellow solid.

MS(ESI m/z): 390 (M+H)
RT(min): 0.67

Reference Example 11

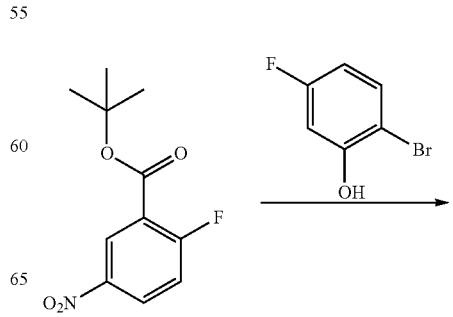

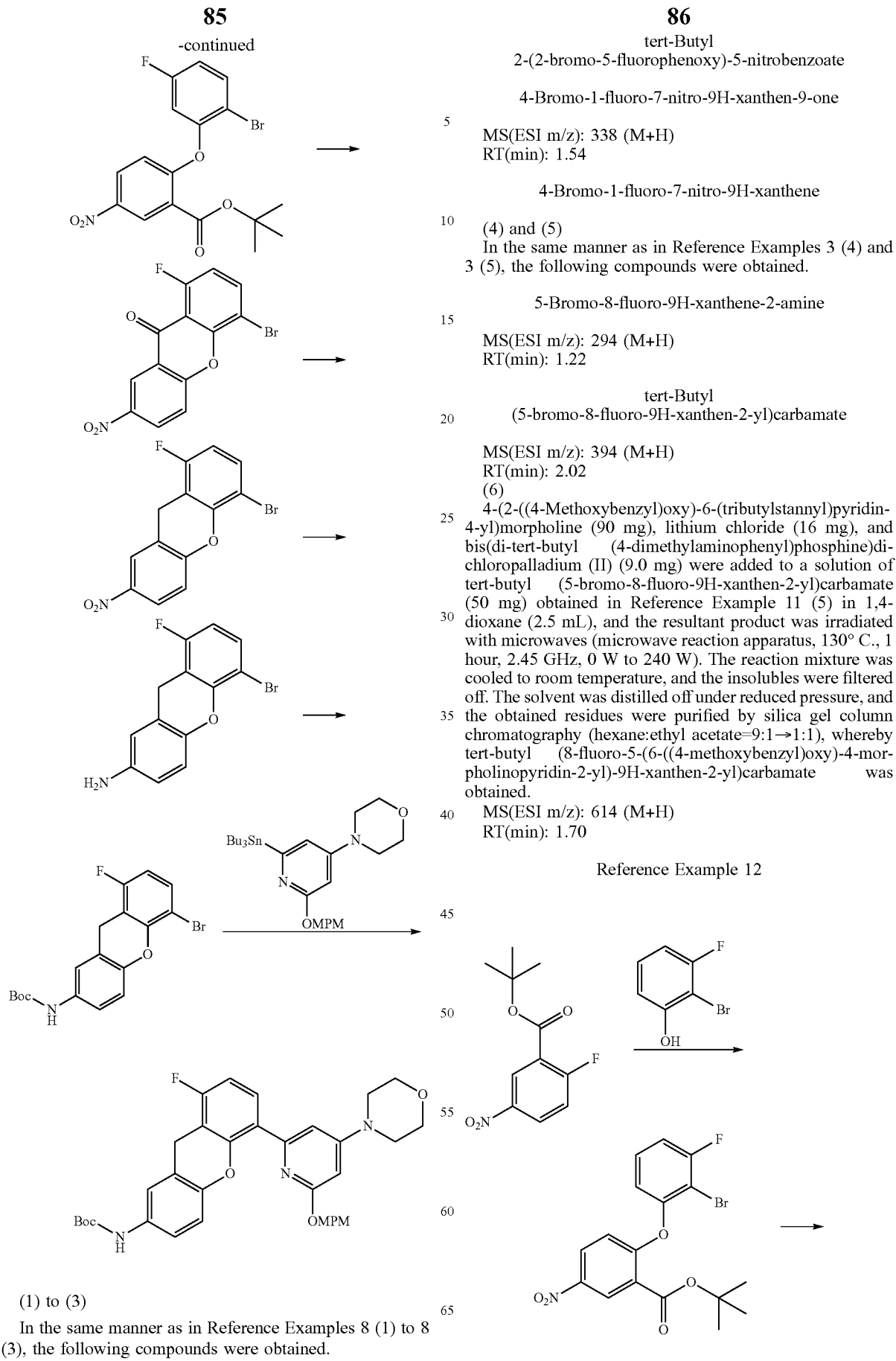

tert-Butyl 2-(2-bromo-5-fluorophenoxy)-5-nitrobenzoate

4-Bromo-1-fluoro-7-nitro-9H-xanthen-9-one

MS(ESI m/z): 338 (M+H)
RT(min): 1.54

4-Bromo-1-fluoro-7-nitro-9H-xanthene (4) and (5)
In the same manner as in Reference Examples 3 (4) and 3 (5), the following compounds were obtained.

5-Bromo-8-fluoro-9H-xanthene-2-amine

MS(ESI m/z): 294 (M+H)
RT(min): 1.22 tert-Butyl (5-bromo-8-fluoro-9H-xanthen-2-yl)carbamate

MS(ESI m/z): 394 (M+H)
RT(min): 2.02

(6)
4-(2-((4-Methoxybenzyl)oxy)-6-(tributylstannyl)pyridin-4-yl)morpholine (90 mg), lithium chloride (16 mg), and bis(di-tert-butyl (4-dimethylaminophenyl)phosphine)dichloropalladium (II) (9.0 mg) were added to a solution of tert-butyl (5-bromo-8-fluoro-9H-xanthen-2-yl)carbamate (50 mg) obtained in Reference Example 11 (5) in 1,4-dioxane (2.5 mL), and the resultant product was irradiated with microwaves (microwave reaction apparatus, 130° C., 1 hour, 2.45 GHz, 0 W to 240 W). The reaction mixture was cooled to room temperature, and the insolubles were filtered off. The solvent was distilled off under reduced pressure, and the obtained residues were purified by silica gel column chromatography (hexane:ethyl acetate=9:1→1:1), whereby tert-butyl (8-fluoro-5-(6-((4-methoxybenzyl)oxy)-4-morpholinopyridin-2-yl)-9H-xanthen-2-yl)carbamate was obtained.

MS(ESI m/z): 614 (M+H)
RT(min): 1.70

Reference Example 12

(1) to (3)
In the same manner as in Reference Examples 8 (1) to 8 (3), the following compounds were obtained.

87

-continued

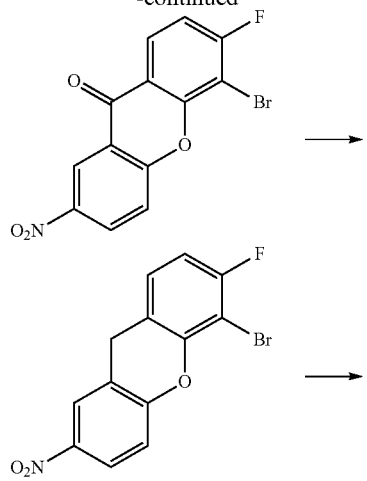

(1) to (6)

In the same manner as in Reference Example 11, the following compounds were obtained.

tert-Butyl 2-(2-bromo-3-fluorophenoxy)-5-nitrobenzoate

5-Bromo-6-fluoro-2-nitro-9H-xanthen-9-one

5-Bromo-6-fluoro-2-nitro-9H-xanthene

MS(ESI m/z): 324 (M+H)
RT(min): 1.84

88

5-Bromo-6-fluoro-9H-xanthene-2-amine

MS(ESI m/z): 294 (M+H)
RT(min): 1.17 tert-Butyl (5-bromo-6-fluoro-9H-xanthen-2-yl)carbamate tert-Butyl (6-fluoro-5-(6-((4-methoxybenzyl)oxy)-4-morpholinopyridin-2-yl)-9H-xanthen-2-yl)carbamate MS(ESI m/z): 614 (M+H)
RT(min): 1.63

Reference Example 13

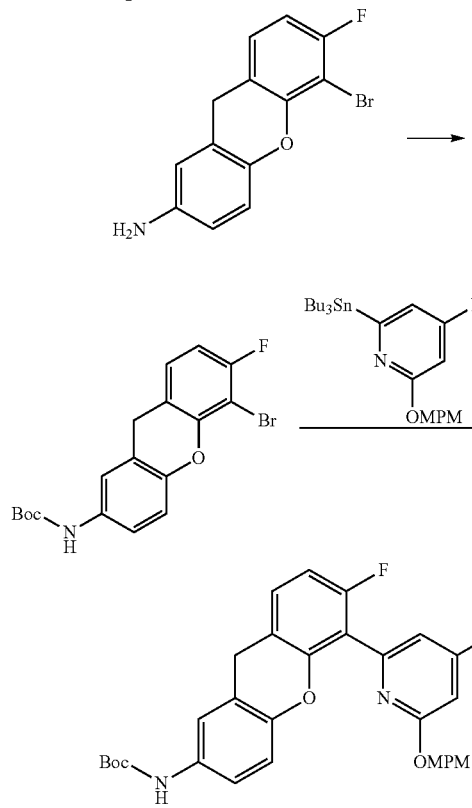

89

-continued

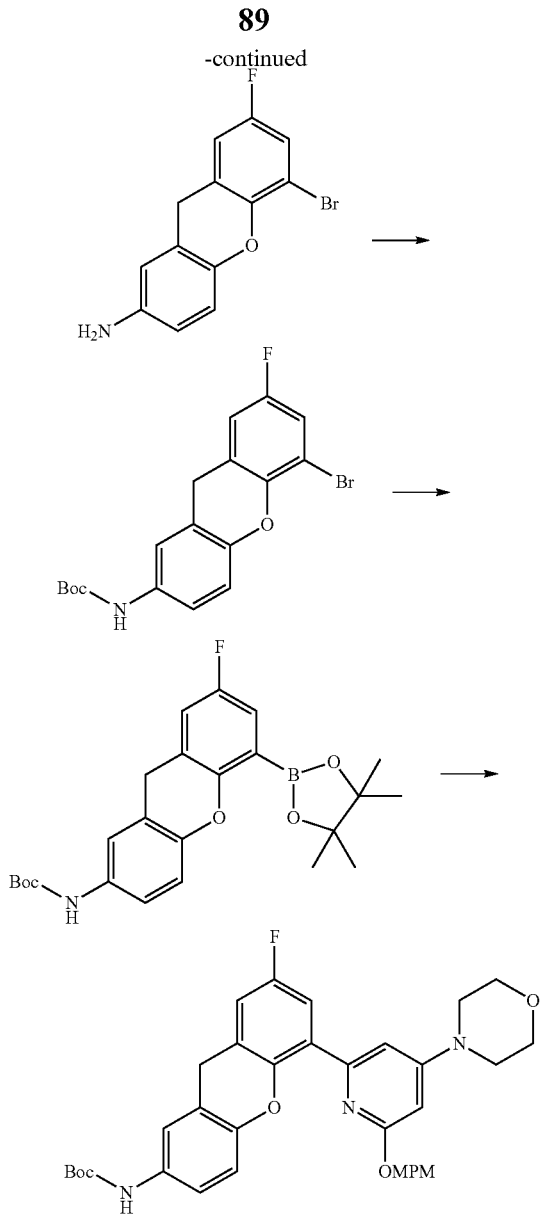

(1) to (5)

In the same manner as in Reference Examples 11 (1) to 11 (5), the following compounds were obtained.

2-(2-Bromo-4-fluorophenoxy)-5-nitrobenzoic acid

MS(ESI m/z): 356 (M+H)
RT(min): 1.37

4-Bromo-2-fluoro-7-nitro-9H-xanthen-9-one

4-Bromo-2-fluoro-7-nitro-9H-xanthene

MS(ESI m/z): 325 (M+H)
RT(min): 1.87

5-Bromo-7-fluoro-9H-xanthene-2-amine

MS(ESI m/z): 294 (M+H)
RT(min): 1.19

90 tert-Butyl (5-bromo-7-fluoro-9H-xanthen-2-yl)carbamate

MS(ESI m/z): 394 (M+H)
RT(min): 2.00

(6)

Under a nitrogen gas flow, tert-butyl (5-bromo-7-fluoro-9H-xanthen-2-yl)carbamate (180 mg) obtained in Reference Example 13 (5), bispinacolatodiboron (128 mg), potassium acetate (112 mg), and a 1,1'-bis(diphenylphosphino)ferrocenepalladium (II) dichloride-dichloromethane complex (56 mg) were added a mixed solvent of 1,4-dioxane (2 mL) and dimethyl sulfoxide (0.2 mL), and the resultant product was irradiated with microwaves (microwave reaction apparatus, 130° C., 0.5 hours, 2.45 GHz, 0 W to 240 W). After the reaction mixture was cooled to room temperature, ethyl acetate was added thereto, and the resultant product was washed sequentially with water and a saturated sodium chloride aqueous solution. The solvent was distilled off under reduced pressure, and the obtained residues were purified by silica gel column chromatography (hexane; ethyl acetate=1:0→0:1), whereby tert-butyl (7-fluoro-5-(4,4,5,5-tetramethyl-1,3,2-dioxaborolan-2-yl)-9H-xanthen-2-yl)carbamate (197 mg) was obtained.

(7)

Under a nitrogen gas flow, tert-butyl (7-fluoro-5-(4,4,5,5-tetramethyl-1,3,2-dioxaborolan-2-yl)-9H-xanthen-2-yl)carbamate (197 mg) obtained in Reference Example 13 (6), sodium carbonate (95 mg), 4-(2-chloro-6-((4-methoxybenzyl)oxy)pyridin-4-yl)morpholine (164 mg), and bis(di-tert-butyl(4-dimethylaminophenyl)phosphine)dichloropalladium (II) (32 mg) were added to a mixed solvent of 1,2-dimethoxyethane (1.78 mL) and water (0.45 mL), and the resultant product was irradiated with microwaves (microwave reaction apparatus, 130° C., 0.5 hours, 2.45 GHz, 0 W to 240 W). After the reaction mixture was cooled to room temperature, ethyl acetate was added thereto, and the resultant product was washed with a saturated sodium chloride aqueous solution. The solvent was distilled off under reduced pressure, and the obtained residues were purified by silica gel column chromatography (hexane:ethyl acetate=1:0→0:1), whereby tert-butyl (7-fluoro-5-(6-((4-methoxybenzyl)oxy)-4-morpholinopyridin-2-yl)-9H-xanthen-2-yl)carbamate (181 mg) was obtained.

MS(ESI m/z): 614 (M+H)
RT(min): 1.84

Reference Example 14

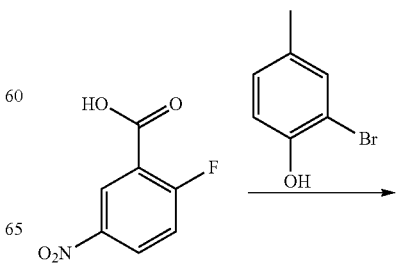

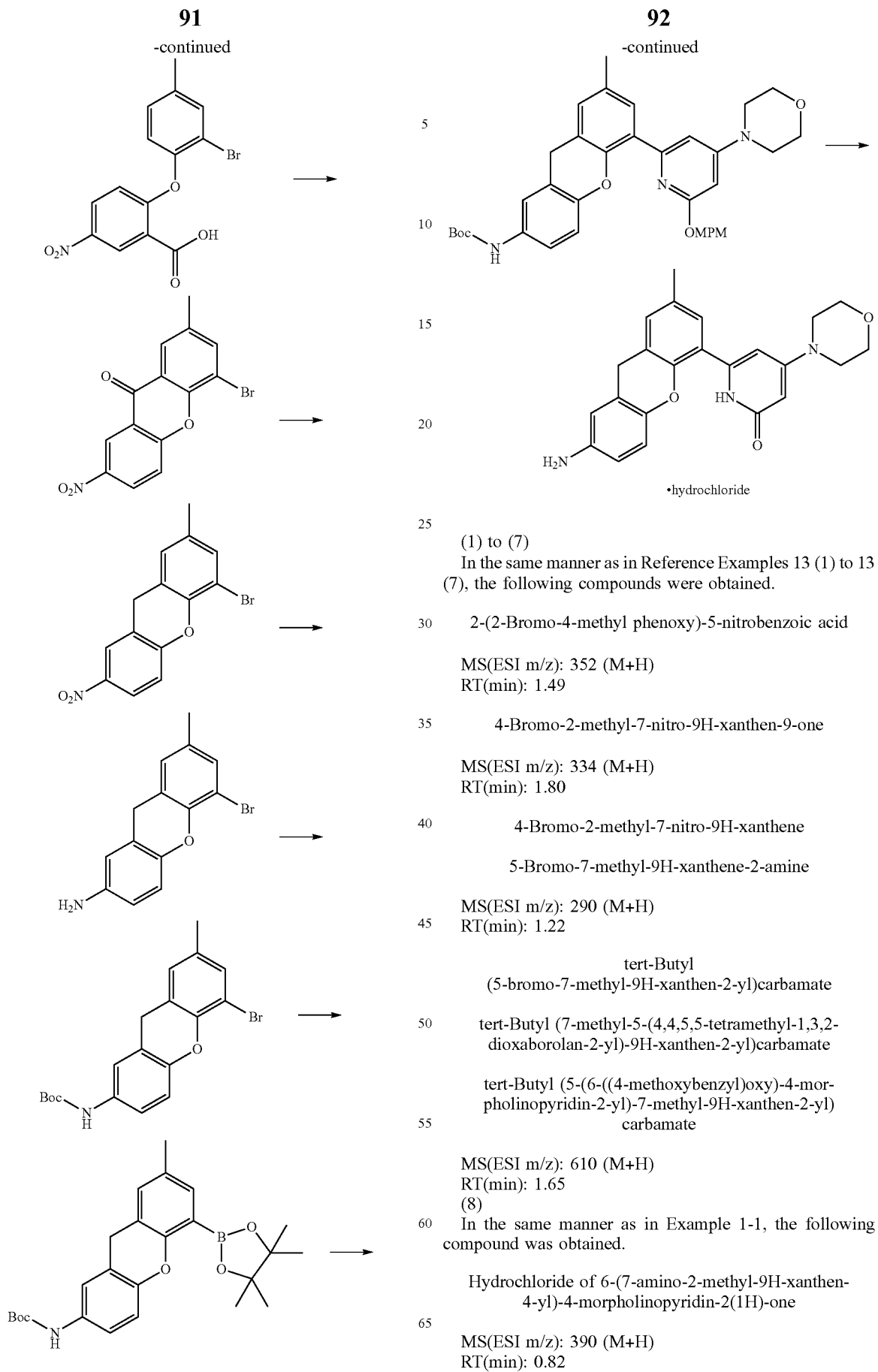

(1) to (7)

In the same manner as in Reference Examples 13 (1) to 13 (7), the following compounds were obtained.

2-(2-Bromo-4-methyl phenoxy)-5-nitrobenzoic acid

MS(ESI m/z): 352 (M+H)
RT(min): 1.49

4-Bromo-2-methyl-7-nitro-9H-xanthen-9-one

MS(ESI m/z): 334 (M+H)
RT(min): 1.80

4-Bromo-2-methyl-7-nitro-9H-xanthene

5-Bromo-7-methyl-9H-xanthene-2-amine

MS(ESI m/z): 290 (M+H)
RT(min): 1.22 tert-Butyl
(5-bromo-7-methyl-9H-xanthen-2-yl)carbamate tert-Butyl (7-methyl-5-(4,4,5,5-tetramethyl-1,3,2-dioxaborolan-2-yl)-9H-xanthen-2-yl)carbamate tert-Butyl (5-(6-((4-methoxybenzyl)oxy)-4-morpholinopyridin-2-yl)-7-methyl-9H-xanthen-2-yl) carbamate MS(ESI m/z): 610 (M+H)
RT(min): 1.65

(8)

In the same manner as in Example 1-1, the following compound was obtained.

Hydrochloride of 6-(7-amino-2-methyl-9H-xanthen-4-yl)-4-morpholinopyridin-2(1H)-one MS(ESI m/z): 390 (M+H)
RT(min): 0.82

93

Reference Example 15

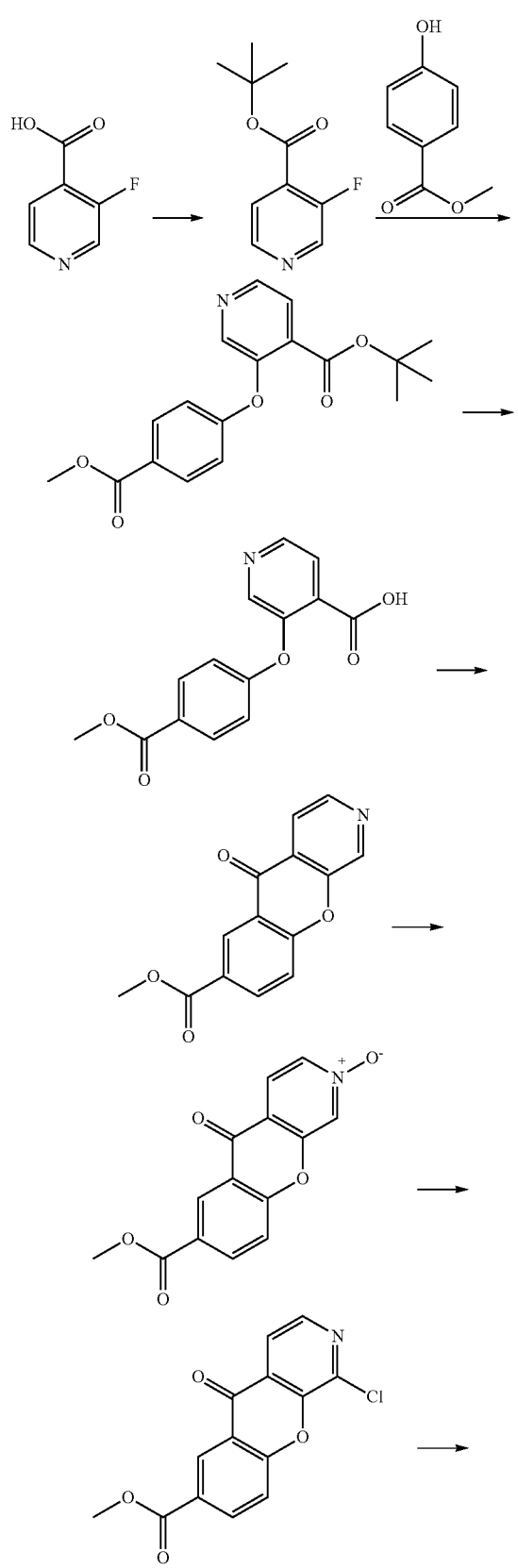

94

-continued

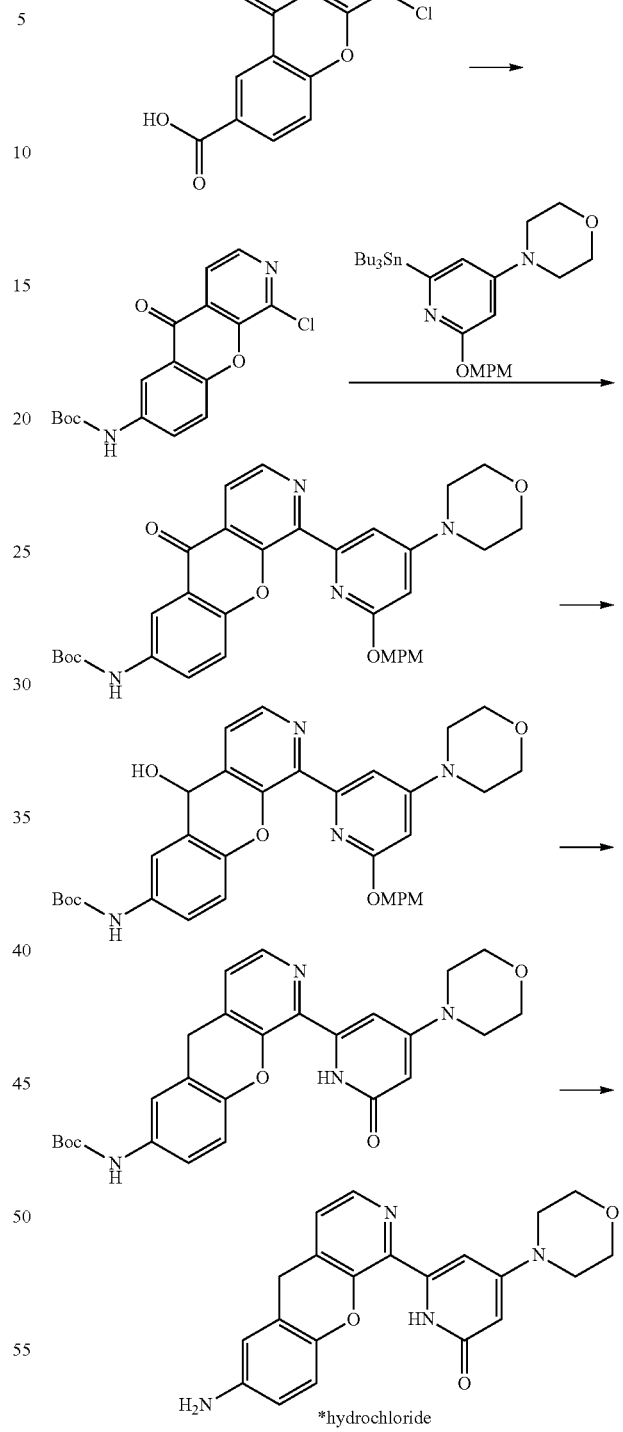

*hydrochloride (1)
N,N-dimethyl-4-amino pyridine (87 mg), tert-butanol (5 mL), and di-tert-butyl dicarbonate (3.1 g) were added to a solution of 3-fluoroisonicotinic acid (1.0 g) in tetrahydrofuran (5 mL), followed by stirring at 75° C. for 5 hours. After the reaction mixture was cooled to room temperature, a saturated sodium hydrogen carbonate aqueous solution was added thereto, then, the resultant product was extracted with ethyl acetate, and the organic layer was dried over anhydrous sodium sulfate. The solvent was distilled off under reduced pressure, and the obtained residues were purified by silica gel column chromatography (hexane:ethyl acetate=1:0→7:3), whereby tert-butyl 3-fluoroisonicotinate (1.3 g) was obtained as a colorless oily material.

MS(ESI m/z): 198 (M+H)

(2)

In the same manner as in Reference Example 8 (1), the following compound was obtained.

tert-Butyl 3-(4-(methoxycarbonyl)phenoxy)isonicotinate

MS(ESI m/z): 330 (M+H)

(3)

Concentrated hydrochloric acid (2 mL) was added to a solution of tert-butyl 3-(4-(methoxycarbonyl)phenoxy)isonicotinate (556 mg) obtained in Reference Example 15 (2) in 1,4-dioxane (10 mL), followed by stirring at 50° C. for 4 hours. After the reaction mixture was cooled to room temperature, the solvent was distilled off under reduced pressure, whereby 3-(4-(methoxycarbonyl)phenoxy)isonicotinic acid was obtained as a white solid.

MS(ESI m/z): 274 (M+H)

(4)

A mixture of 3-(4-(methoxycarbonyl)phenoxy)isonicotinic acid obtained in Reference Example 15 (3) and an Eaton reagent (10 mL) was stirred at 50° C. for 1 hour, at 80° C. for 3 hours, at 100° C. for 60 hours, at 120° C. for 24 hours, and at 130° C. for 24 hours. The reaction mixture was cooled to room temperature, and poured into methanol (50 mL), followed by refluxing for 3 hours. After the reaction mixture was cooled to 0° C., 25% ammonia water was added thereto, and the solvent was distilled off under reduced pressure. A saturated sodium hydrogen carbonate aqueous solution was added to the obtained residues, then, the resultant product was extracted with ethyl acetate, and the organic layer was dried over anhydrous sodium sulfate. The solvent was distilled off under reduced pressure, and the obtained solid was washed with diisopropyl ether, whereby methyl 5-oxo-5H-chromeno[2,3-c]pyridine-7-carboxylate (296 mg) was obtained as a brown solid.

MS(ESI m/z): 256 (M+H)

(5)

Metachloroperbenzoic acid (300 mg) was added to a solution of methyl 5-oxo-5H-chromeno[2,3-c]pyridine-7-carboxylate (296 mg) obtained in Reference Example 15 (4) in chloroform (5 mL), followed by stirring at room temperature for 60 hours. A sodium sulfite aqueous solution was added to the reaction mixture, followed by stirring at room temperature for 0.5 hours. A saturated sodium hydrogen carbonate aqueous solution was added thereto, then, the resultant product was extracted with chloroform, and the organic layer was dried over anhydrous sodium sulfate. The solvent was distilled off under reduced pressure, whereby 7-(methoxycarbonyl)-5-oxo-5H-chromeno[2,3-c]pyridine 2-oxide (265 mg) was obtained as a pale yellow solid.

MS(ESI m/z): 272 (M+H)

(6)

Phosphorus oxychloride (20 mL) was added to a solution of 7-(methoxycarbonyl)-5-oxo-5H-chromeno[2,3-c]pyridine 2-oxide (4.0 g) obtained in Reference Example 15 (5) in chloroform (30 mL), followed by stirring for 1.5 hours. Chloroform (20 mL) was added thereto, followed by refluxing for 1 hour, and phosphorus oxychloride (10 mL) and chloroform (30 mL) were further added thereto, followed by refluxing for 3 hours. The reaction mixture was cooled to room temperature, and the solvent was distilled off under reduced pressure. Chloroform was added to the obtained residues, and the resultant product was neutralized with a potassium carbonate aqueous solution, and extracted with chloroform. The organic layer was dried over anhydrous sodium sulfate, and the solvent was distilled off under reduced pressure. The obtained residues were washed with a mixed solvent of hexane/ethyl acetate=1/1, whereby methyl 1-chloro-5-oxo-5H-chromeno[2,3-c]pyridine-7-carboxylate (3.0 g) was obtained as a brown solid.

MS(ESI m/z): 290 (M+H)

(7)

A 1 mol/L sodium hydroxide aqueous solution (21 mL) was added to a solution of methyl 1-chloro-5-oxo-5H-chromeno[2,3-c]pyridine-7-carboxylate (3.0 g) obtained in Reference Example 15 (6) in methanol (30 mL), followed by stirring at room temperature for 12 hours. Methanol (50 mL) and water (30 mL) were added thereto, followed by stirring at 50° C. for 4 hours. The reaction mixture was cooled to room temperature, and the solvent was distilled off under reduced pressure. Water was added to the obtained residues, and 2 mol/L hydrochloric acid was added dropwise. The precipitated solid was collected by filtration, whereby 1-chloro-5-oxo-5H-chromeno[2,3-c]pyridine-7-carboxylic acid (2.8 g) was obtained as a brown solid.

MS(ESI m/z): 276 (M+H)

(8)

Triethylamine (1.8 mL) was added to a solution of 1-chloro-5-oxo-5H-chromeno[2,3-c]pyridine-7-carboxylic acid (1.5 g) obtained in Reference Example 15 (7) in tert-butanol (100 mL), and diphenylphosphoryl azide (1.4 mL) was added thereto at 80° C., followed by refluxing for 13 hours. After the reaction mixture was cooled to room temperature, the solvent was distilled off under reduced pressure, and the obtained residues were washed with methanol. Toluene was added to the obtained solid, followed by stirring at 100° C. for 0.5 hours, then, the resultant product was filtered while hot, and washed with a 25% methanol aqueous solution, whereby tert-butyl (1-chloro-5-oxo-5H-chromeno[2,3-c]pyridin-7-yl)carbamate (819 mg) was obtained as a yellow solid.

MS(ESI m/z): 347 (M+H)

(9)

4-(2-((4-Methoxybenzyl)oxy)-6-(tributylstannyl)pyridin-4-yl)morpholine (275 mg), lithium chloride (60 mg), and bis(di-tert-butyl (4-dimethylaminophenyl)phosphine)dichloropalladium (II) (33 mg) were added to a solution of tert-butyl (1-chloro-5-oxo-5H-chromeno[2,3-c]pyridin-7-yl)carbamate (163 mg) obtained in Reference Example 15 (8) in 1,4-dioxane (15 mL), and the resultant product was irradiated with microwaves (microwave reaction apparatus, 130° C., 1 hour, 2.45 GHz, 0 W to 240 W). The reaction mixture was cooled to room temperature, and the solvent was distilled off under reduced pressure. Chloroform was added to the obtained residues, and the resultant product was filtered using Celite. The solvent was distilled off under reduced pressure, and the obtained residues were purified by silica gel column chromatography (chloroform:methanol=1:0→19:1), whereby tert-butyl (1-(6-((4-methoxybenzyl)oxy)-4-morpholinopyridin-2-yl)-5-oxo-5H-chromeno[2,3-c]pyridin-7-yl)carbamate (103 mg) was obtained as a yellow solid.

MS(ESI m/z): 611 (M+H)

(10)

Methanol (20 mL) and sodium borohydride (15 mg) were added to a solution of tert-butyl (1-(6-((4-methoxybenzyl)

oxy)-4-morpholinopyridin-2-yl)-5-oxo-5H-chromeno[2,3-c]pyridin-7-yl)carbamate (121 mg) obtained in Reference Example 15 (9) in tetrahydrofuran (20 mL), followed by stirring at room temperature for 1 hour. A saturated ammonium chloride aqueous solution was added to the reaction mixture, followed by stirring at room temperature for 0.5 hours. The solvent was distilled off under reduced pressure, a saturated sodium hydrogen carbonate aqueous solution was added to the obtained residues, the resultant product was extracted with chloroform, and the solvent was distilled off under reduced pressure, whereby tert-butyl (5-hydroxy-1-(6-((4-methoxybenzyl)oxy)-4-morpholinopyridin-2-yl)-5H-chromeno[2,3-c]pyridin-7-yl)carbamate was obtained as a yellow solid.

(11)

Dichloromethane (3 mL), triethylsilane (0.3 mL), and trifluoroacetic acid (0.12 mL) were added to tert-butyl (5-hydroxy-1-(6-((4-methoxybenzyl)oxy)-4-morpholinopyridin-2-yl)-5H-chromeno[2,3-c]pyridin-7-yl)carbamate obtained in Reference Example 15 (10), followed by stirring at room temperature for 0.5 hours. A saturated sodium hydrogen carbonate aqueous solution was added to the reaction mixture, then, the resultant product was extracted with chloroform, and the solvent was distilled off under reduced pressure. The obtained residues were purified by silica gel column chromatography (chloroform:methanol=1:0→97:3), whereby tert-butyl (1-(4-morpholino-6-oxo-1,6-dihydro pyridin-2-yl)-5H-chromeno[2,3-c]pyridin-7-yl)carbamate (32 mg) was obtained as an orange solid.

MS(ESI m/z): 477 (M+H)

RT(min): 1.30

(12)

4.0 mol/L hydrogen chloride/1,4-dioxane (5.0 mL) was added to a solution of tert-butyl (1-(4-morpholino-6-oxo-1,6-dihydro pyridin-2-yl)-5H-chromeno[2,3-c]pyridin-7-yl)carbamate (32 mg) obtained in Reference Example 15 (11) in methanol (1 mL), followed by stirring at 50° C. for 1 hour. The reaction mixture was cooled to room temperature, and the solvent was distilled off under reduced pressure, whereby hydrochloride (32 mg) of 6-(7-amino-5H-chromeno[2,3-c]pyridin-1-yl)-4-morpholinopyridin-2(1H)-one was obtained as a brown solid.

Reference Example 16

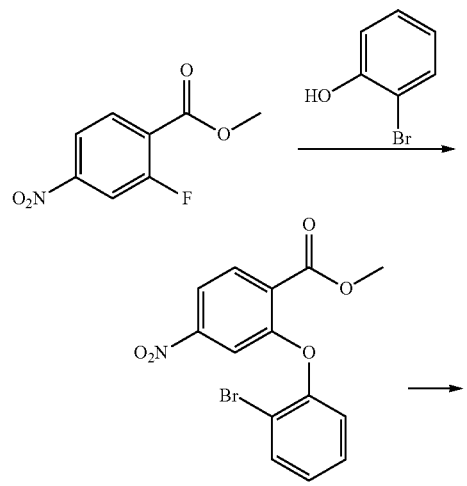

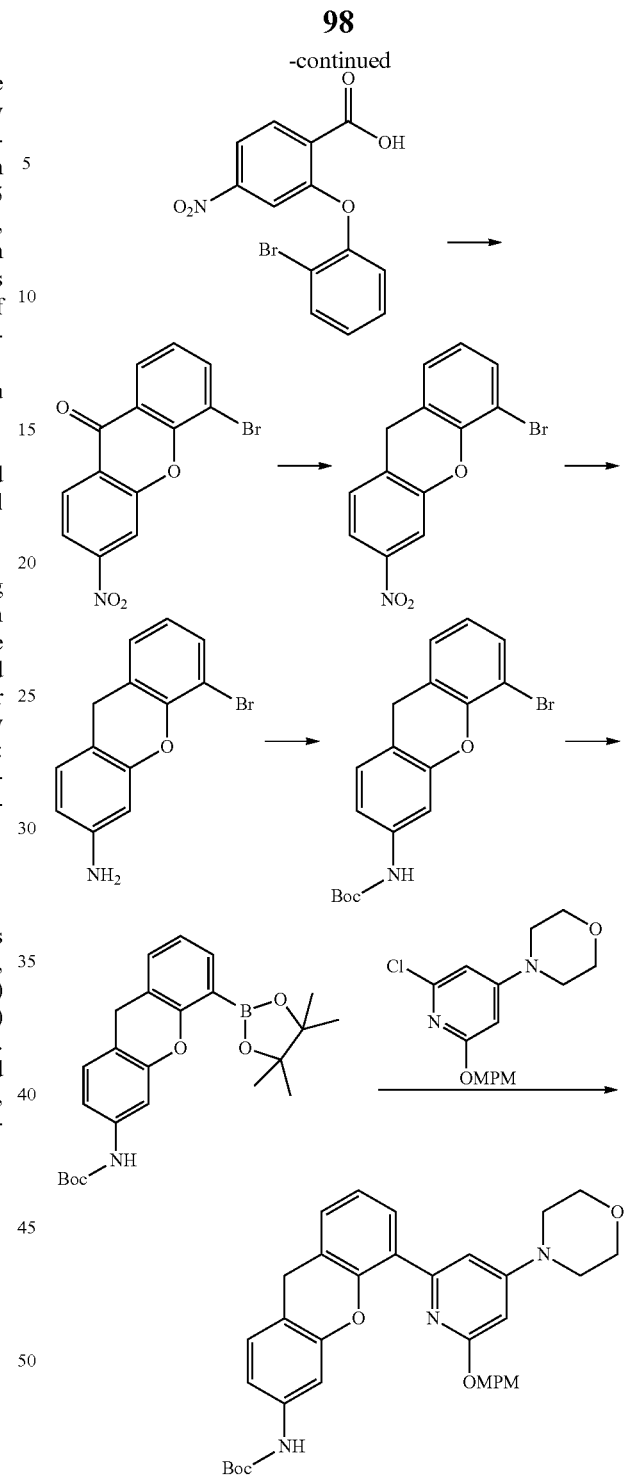

(1)

In the same manner as in Reference Example 8 (1), the following compound was obtained.

Methyl 2-(2-bromophenoxy)-4-nitrobenzoate $^1$H-NMR (CDCl$_3$, 300 MHz) δ: 8.06 (1H, d, J=8.6 Hz), 7.98 (1H, dd, J=8.6, 2.0 Hz), 7.70 (1H, dd, J=7.9, 1.7 Hz), 7.56 (1H, d, J=2.0 Hz), 7.36 (1H, td, J=7.8, 1.5 Hz), 7.15 (1H, td, J=7.8, 1.3 Hz), 7.05 (1H, dd, J=8.1, 1.5 Hz), 3.93 (3H, s).

(2)

Methanol (10 mL) and a 2 mol/L sodium hydroxide aqueous solution (50 mL) were added to a solution of methyl 2-(2-bromophenoxy)-4-nitrobenzoate (12.5 g) obtained in Reference Example 16 (1) in dichloromethane (10 mL), followed by stirring at 110° C. for 5 hours. The reaction liquid was cooled to room temperature, and washed with dichloromethane, and after 2 mol/L hydrochloric acid was added to the aqueous layer until the pH thereof became 2, the resultant product was extracted with ethyl acetate. The organic layer was washed with a saturated sodium chloride aqueous solution, and dried over anhydrous sodium sulfate. The solvent was distilled off under reduced pressure, whereby 2-(2-bromophenoxy)-4-nitrobenzoic acid (11.8 g) was obtained.

$^1$H-NMR (CDCl$_3$, 300 MHz) δ: 8.30 (1H, d, J=8.6 Hz), 8.01 (1H, dd, J=8.6, 2.0 Hz), 7.73 (1H, dd, J=7.9, 1.7 Hz), 7.48 (1H, dd, J=7.6, 2.0 Hz), 7.43 (1H, dd, J=7.8, 1.5 Hz), 7.27-7.22 (1H, m), 7.20 (1H, dd, J=8.1, 1.5 Hz).

(3)

A mixture of 2-(2-bromophenoxy)-4-nitrobenzoic acid (4.8 g) obtained in Reference Example 16 (2) and methanesulfonic acid (30 mL) was stirred at 100° C. for 17 hours. The reaction mixture was cooled to room temperature, and poured into ice. The precipitated solid was collected by filtration, and the resultant product was washed with methanol, whereby 5-bromo-3-nitro-9H-xanthen-9-one (2.0 g) was obtained as a brown solid.

$^1$H-NMR (DMSO-d$_6$, 300 MHz) δ: 8.49 (1H, d, J=2.0 Hz), 8.43 (1H, d, J=8.6 Hz), 8.28 (1H, d, J=2.0 Hz), 8.25 (1H, t, J=1.5 Hz), 8.22 (1H, dd, J=8.1, 1.5 Hz), 7.48 (1H, t, J=7.9 Hz).

(4)

In the same manner as in Reference Example 8 (3), the following compound was obtained.

5-Bromo-3-nitro-9H-xanthene $^1$H-NMR (DMSO-d$_6$, 300 MHz) δ: 8.00 (1H, dd, J=8.6, 2.3 Hz), 7.86 (1H, d, J=2.3 Hz), 7.63-7.55 (2H, m), 7.32 (1H, dd, J=7.6, 1.3 Hz), 7.08 (1H, t, J=7.8 Hz), 4.26 (2H, s).

(5) to (8)

In the same manner as in Reference Examples 3 (4) to 3 (7), the following compounds were obtained.

5-Bromo-9H-xanthene-3-amine $^1$H-NMR (CDCl$_3$, 300 MHz) δ: 7.41 (1H, dd, J=7.9, 1.3 Hz), 7.09 (1H, dd, J=7.6, 1.3 Hz), 6.94 (1H, d, J=7.9 Hz), 6.87 (1H, t, J=7.8 Hz), 6.53 (1H, d, J=2.3 Hz), 6.42 (1H, dd, J=8.3, 2.3 Hz), 3.95 (2H, s), 3.66 (2H, brs).

tert-Butyl (5-bromo-9H-xanthen-3-yl)carbamate $^1$H-NMR (CDCl$_3$, 300 MHz) δ: 7.42 (1H, dd, J=7.8, 1.5 Hz), 7.33 (1H, d, J=1.7 Hz), 7.13-7.03 (2H, m), 6.98 (1H, dd, J=8.3, 2.3 Hz), 6.88 (1H, t, J=7.8 Hz), 6.46 (1H, brs), 4.00 (2H, s), 1.53 (9H, s).

tert-Butyl (5-(4,4,5,5-tetramethyl-1,3,2-dioxaborolan-2-yl)-9H-xanthen-3-yl)carbamate $^1$H-NMR (CDCl$_3$, 300 MHz) δ: 7.54 (1H, dd, J=7.1, 1.5 Hz), 7.30-7.21 (2H, m), 7.05 (1H, d, J=8.3 Hz), 7.01 (1H, t, J=7.3 Hz), 6.91 (1H, d, J=2.6 Hz), 6.41 (1H, brs), 3.95 (2H, s), 1.53 (9H, s), 1.40 (12H, s).

tert-Butyl (5-(6-((4-methoxybenzyl)oxy)-4-morpholinopyridin-2-yl)-9H-xanthen-3-yl)carbamate $^1$H-NMR (CDCl$_3$, 300 MHz) δ: 7.88 (1H, dd, J=7.3, 2.0 Hz), 7.49 (1H, s), 7.42 (2H, d, J=8.6 Hz), 7.34 (1H, d, J=2.0 Hz), 7.17 (1H, dd, J=7.6, 2.0 Hz), 7.13 (1H, d, J=7.6 Hz), 7.07 (1H, d, J=8.3 Hz), 6.90 (2H, d, J=8.9 Hz), 6.73 (1H, dd, J=8.1, 2.1 Hz), 6.47 (1H, brs), 6.12 (1H, d, J=2.3 Hz), 5.40 (2H, s), 4.02 (2H, s), 3.91 (4H, t, J=5.0 Hz), 3.81 (3H, s), 3.38 (4H, t, J=4.8 Hz), 1.51 (9H, s).

Reference Example 17

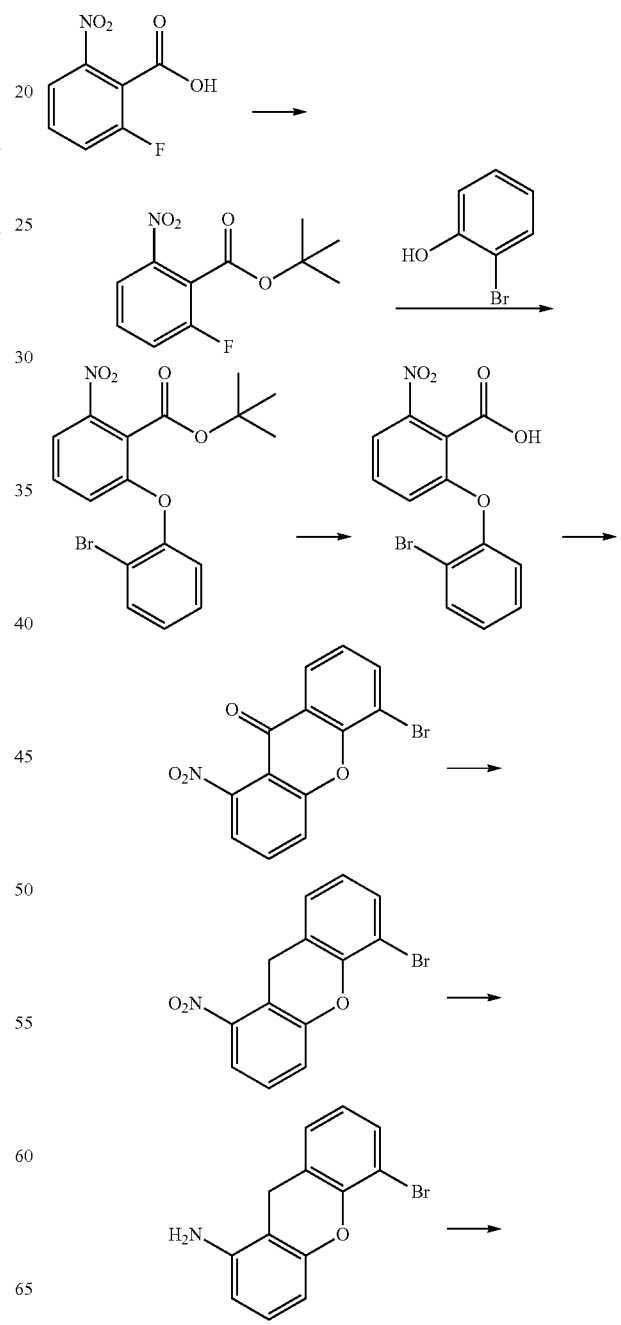

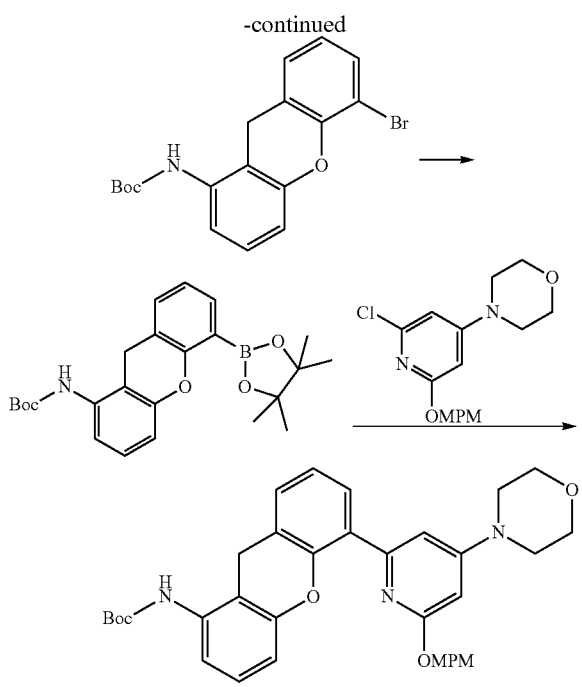

(1)

In the same manner as in Reference Example 15 (1), the following compound was obtained.

tert-Butyl 2-fluoro-6-nitrobenzoate $^1$H-NMR (CDCl$_3$, 300 MHz) δ: 7.96 (1H, d, J=8.3 Hz), 7.55 (1H, td, J=8.3, 5.5 Hz), 7.45 (1H, td, J=8.3, 1.2 Hz), 1.62 (9H, s).

(2)

In the same manner as in Reference Example 8 (1), the following compound was obtained.

tert-Butyl 2-(2-bromophenoxy)-6-nitrobenzoate $^1$H-NMR (CDCl$_3$, 300 MHz) δ: 7.91 (1H, dd, J=8.3, 1.0 Hz), 7.66 (1H, dd, J=7.9, 1.7 Hz), 7.43 (1H, t, J=8.3 Hz), 7.32 (1H, td, J=7.8, 1.4 Hz), 7.10 (1H, td, J=7.8, 1.5 Hz), 7.07-7.00 (2H, m), 1.58 (9H, s).

(3)

A mixture of tert-butyl 2-(2-bromophenoxy)-6-nitrobenzoate (2.6 g) obtained in Reference Example 17 (2) and 4.0 mol/L hydrogen chloride/1,4-dioxane (5 mL) was stirred at room temperature for 1 hour. 2 mol/L hydrochloric acid (1 mL) was added thereto, and the resultant product was stirred at room temperature for 3 hours, and further stirred at 100° C. for 1 hour. Ethyl acetate was added to the reaction mixture, and the resultant product was washed sequentially with water and a saturated sodium chloride aqueous solution. The organic layer was dried over anhydrous sodium sulfate, then, the solvent was distilled off under reduced pressure, and the obtained residues were purified by silica gel column chromatography (ethyl acetate:methanol=1:0→8:2), whereby 2-(2-bromophenoxy)-6-nitrobenzoic acid (1.5 g) was obtained.

$^1$H-NMR (DMSO-d$_6$, 300 MHz) δ: 7.97 (1H, dd, J=8.3, 0.7 Hz), 7.79 (1H, dd, J=7.9, 1.7 Hz), 7.65 (1H, t, J=8.4 Hz), 7.45 (1H, td, J=7.8, 1.3 Hz), 7.25-7.19 (2H, m), 7.13 (1H, dd, J=8.1, 1.5 Hz).

(4)

In the same manner as in Reference Example 3 (3), the following compound was obtained.

5-Bromo-1-nitro-9H-xanthen-9-one $^1$H-NMR (DMSO-d$_6$, 300 MHz) δ: 8.25 (1H, dd, J=7.9, 1.7 Hz), 8.13 (1H, dd, J=8.1, 1.5 Hz), 8.07 (1H, dd, J=8.6, 7.6 Hz), 7.99 (1H, dd, J=8.8, 1.2 Hz), 7.84 (1H, dd, J=7.3, 1.3 Hz), 7.46 (1H, t, J=7.9 Hz).

(5)

In the same manner as in Reference Example 8 (3), the following compound was obtained.

5-Bromo-1-nitro-9H-xanthene $^1$H-NMR (DMSO-d$_6$, 300 MHz) δ: 7.86 (1H, t, J=4.6 Hz), 7.58-7.52 (3H, m), 7.34 (1H, dd, J=7.6, 1.3 Hz), 7.06 (1H, t, J=7.8 Hz), 4.41 (2H, s).

(6) to (9)

In the same manner as in Reference Examples 3 (4) to 3 (7), the following compounds were obtained.

5-Bromo-9H-xanthene-1-amine $^1$H-NMR (DMSO-d$_6$, 300 MHz) δ: 7.49 (1H, dd, J=7.9, 1.3 Hz), 7.21 (1H, dd, J=7.6, 1.3 Hz), 6.97 (1H, t, J=7.6 Hz), 6.91 (1H, t, J=8.11 Hz), 6.40 (1H, dd, J=8.3, 1.0 Hz), 6.28 (1H, dd, J=8.1, 0.8 Hz), 5.19 (2H, s), 3.78 (2H, s).

tert-Butyl (5-bromo-9H-xanthen-1-yl)carbamate $^1$H-NMR (DMSO-d$_6$, 300 MHz) δ: 8.74 (1H, s), 7.51 (1H, dd, J=7.9, 1.3 Hz), 7.28 (1H, dd, J=7.8, 1.5 Hz), 7.22 (1H, s), 7.20 (1H, d, J=1.0 Hz), 7.01 (1H, t, J=7.8 Hz), 6.90 (1H, t, J=4.8 Hz), 3.99 (2H, s), 1.48 (9H, s).

tert-Butyl (5-(4,4,5,5-tetramethyl-1,3,2-dioxaborolan-2-yl)-9H-xanthen-1-yl)carbamate $^1$H-NMR (CDCl$_3$, 300 MHz) δ: 7.55 (1H, dd, J=7.3, 1.7 Hz), 7.50 (1H, d, J=8.3 Hz), 7.24 (1H, d, J=2.0 Hz), 7.16 (1H, t, J=8.1 Hz), 7.01 (1H, t, J=7.4 Hz), 6.83 (1H, dd, J=8.3, 1.0 Hz), 6.26 (1H, s), 3.88 (2H, s), 1.53 (9H, s), 1.40 (12H, s).

tert-Butyl (5-(6-((4-methoxybenzyl)oxy)-4-morpholinopyridin-2-yl)-9H-xanthen-1-yl)carbamate $^1$H-NMR (CDCl$_3$, 300 MHz) δ: 7.78 (1H, dd, J=7.6, 1.7 Hz), 7.54 (1H, d, J=8.3 Hz), 7.41 (2H, d, J=8.6 Hz), 7.23-7.08 (4H, m), 6.90 (2H, d, J=8.6 Hz), 6.72 (1H, dd, J=8.3, 1.0 Hz), 6.30 (1H, s), 6.13 (1H, d, J=2.0 Hz), 5.38 (2H, s), 3.98 (2H, s), 3.85 (4H, t, J=5.0 Hz), 3.81 (3H, s), 3.33 (4H, t, J=4.8 Hz), 1.55 (9H, s).

Reference Example 18

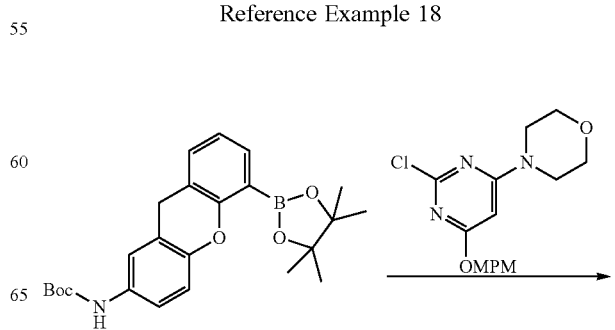

-continued

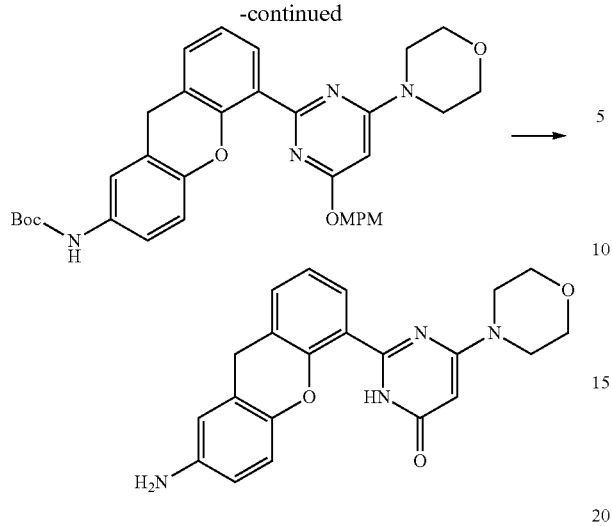

(1)

In the same manner as in Reference Example 3 (7), the following compound was obtained.

tert-Butyl (5-(4-((4-methoxybenzyl)oxy)-6-morpholino pyrimidin-2-yl)-9H-xanthen-2-yl)carbamate MS(ESI m/z): 597 (M+H)

RT(min): 2.01

(2)

4.0 mol/L hydrogen chloride/1,4-dioxane (5.0 mL) was added to a solution of tert-butyl (5-(4-((4-methoxybenzyl)oxy)-6-morpholinopyrimidin-2-yl)-9H-xanthen-2-yl)carbamate (734 mg) obtained in Reference Example 18 (1) in methanol (5.0 mL), followed by stirring at 60° C. for 1.5 hours. The reaction mixture was cooled to room temperature, and the solvent was distilled off under reduced pressure. The obtained residues were washed with ethyl acetate, dissolved in a mixed solvent of dichloromethane and methanol, and washed with a sodium carbonate aqueous solution. The organic layer was dried over anhydrous sodium sulfate, and the solvent was distilled off under reduced pressure. Chloroform and diisopropyl ether were added to the obtained residues, and the solid was collected by filtration, whereby 2-(7-amino-9H-xanthen-4-yl)-6-morpholino pyrimidin-4(3H)-one (208 mg) was obtained as a yellow solid.

MS(ESI m/z): 377 (M+H)

RT(min): 0.82

Reference Example 19

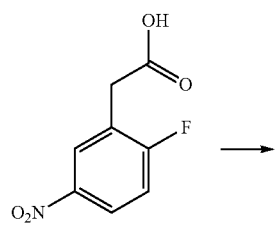

-continued

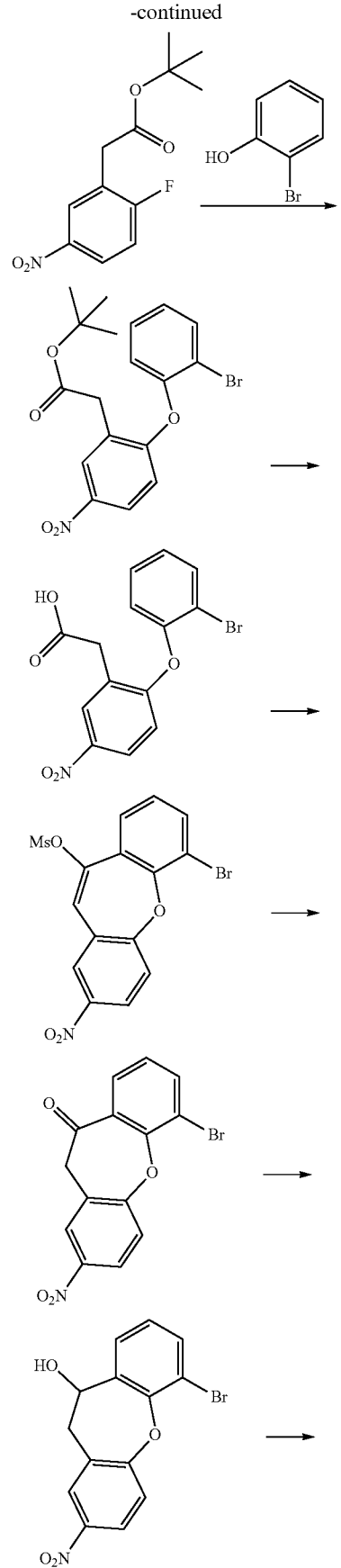

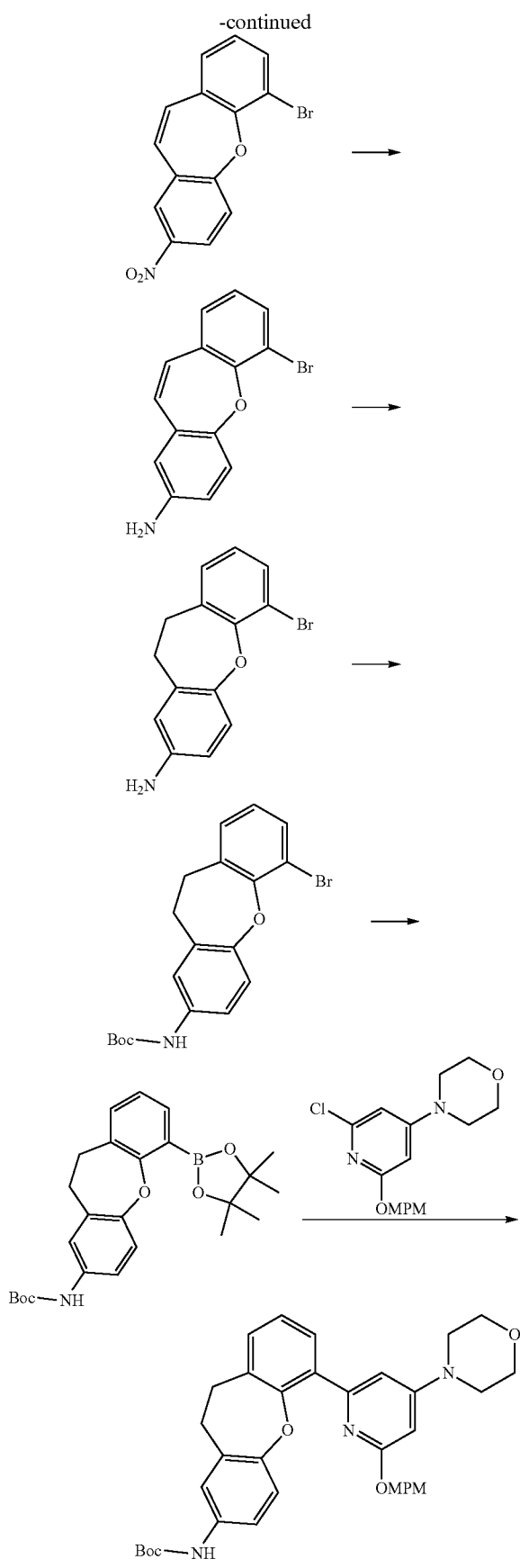

(1)

In the same manner as in Reference Example 15 (1), the following compound was obtained.

tert-Butyl 2-(2-fluoro-5-nitrophenyl)acetate

MS(ESI m/z): 256 (M+H)
RT(min): 1.65

(2)

In the same manner as in Reference Example 8 (1), the following compound was obtained.

tert-Butyl 2-(2-(2-bromophenoxy)-5-nitrophenyl)acetate

MS(ESI m/z): 408 (M+H)
RT(min): 2.01

(3)

In the same manner as in Reference Example 15 (3), the following compound was obtained.

2-(2-(2-Bromophenoxy)-5-nitrophenyl)acetate

MS(ESI m/z): 352 (M+H)
RT(min): 1.46

(4)

A mixture of 2-(2-(2-bromophenoxy)-5-nitrophenyl)acetate (7.80 g) obtained in Reference Example 19 (3) and an Eaton reagent (30 mL) was stirred at 100° C. for 1 hour. The reaction mixture was cooled to 0° C., and ethyl acetate was added thereto. The organic layer was washed sequentially with water and a saturated sodium chloride aqueous solution, and dried over anhydrous sodium sulfate. The solvent was distilled off under reduced pressure, and the obtained solid was washed with ethyl acetate, whereby 6-bromo-2-nitrodibenz[b,f]oxepin-10-ylmethanesulfonate (2.47 g) was obtained.

MS(ESI m/z): 412 (M+H)
RT(min): 1.71

(5)

Chloroform (100 mL), methanol (10 mL), and a 5 mol/L sodium hydroxide aqueous solution (2 mL) were added to 6-bromo-2-nitrodibenz[b,f]oxepin-10-yl methanesulfonate (4.6 g) obtained in Reference Example 19 (4), followed by stirring at room temperature for 20 hours. The reaction mixture was washed with 1 mol/L hydrochloric acid, and dried over anhydrous sodium sulfate. The solvent was distilled off under reduced pressure, and the obtained residues were purified by silica gel column chromatography (hexane:ethyl acetate=23:2→7:3), whereby 6-bromo-2-nitrodibenz[b,f]oxepin-10(11H)-one (1.8 g) was obtained as a white solid.

MS(ESI m/z): 334 (M+H)
RT(min): 1.73

(6)

In the same manner as in Reference Example 8 (3), the following compound was obtained.

6-Bromo-2-nitro-10,11-dihydrodibenz[b,f]oxepin-10-ol

MS(ESI m/z): 336 (M+H)
RT(min): 1.58

(7)

Toluene (15 mL) and paratoluenesulfonic acid monohydrate (717 mg) were added to 6-bromo-2-nitro-10,11-dihydrodibenz[b,f]oxepin-10-ol (1.4 g) obtained in Reference Example 19 (6), followed by heating to reflux for 2.5 hours. The reaction mixture was cooled to room temperature, and ethyl acetate was added thereto. The organic layer was washed sequentially with water and a saturated sodium chloride aqueous solution, and dried over anhydrous sodium sulfate. The solvent was distilled off under reduced pressure, and the obtained residues were washed with hexane, whereby 6-bromo-2-nitrodibenz[b,f]oxepin (1.2 g) was obtained as a white solid.

MS(ESI m/z): 318 (M+H)
RT(min): 1.93

(8)
In the same manner as in Reference Example 3 (4), the following compound was obtained.

6-Bromodibenz[b,f]oxepin-2-amine

MS(ESI m/z): 288 (M+H)
RT(min): 1.33

(9)
6-Bromodibenz[b,f]oxepin-2-amine (300 mg) obtained in Reference Example 19 (8) was subjected to a hydrogenation reaction (50° C., 1 bar, flow rate of 1 mL/min, 5% Rh/C) using a flow type hydrogenation reaction apparatus. The solvent was distilled off under reduced pressure, and the obtained residues were purified by silica gel column chromatography (hexane:ethyl acetate=39:11→14:11), whereby 6-bromo-10,11-dihydrodibenz[b,f]oxepin-2-amine (350 mg) was obtained as a colorless oily material.

MS(ESI m/z): 290 (M+H)
RT(min): 1.24

(10) to (12)
In the same manner as in Reference Examples 3 (5) to 3 (7), the following compounds were obtained.

tert-Butyl (6-bromo-10,11-dihydrodibenz[b,f]oxepin-2-yl)carbamate

MS(ESI m/z): 390 (M+H)
RT(min): 2.04 tert-Butyl (6-(4,4,5,5,-tetra methyl-1,3,2-dioxaboran-2-yl)-10,11-dihydrodibenz[b,f]oxepin-2-yl)carbamate MS(ESI m/z): 438 (M+H)
RT(min): 2.12 tert-Butyl (6-(6-((4-methoxybenzyl)oxy)-4-morpholinopyridin-2-yl)-10,11-dihydrodibenz[b,f]oxepin-2-yl)carbamate MS(ESI m/z): 610 (M+H)
RT(min): 1.62

Reference Example 20

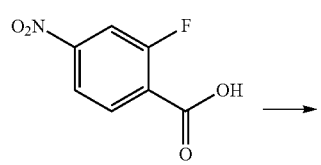

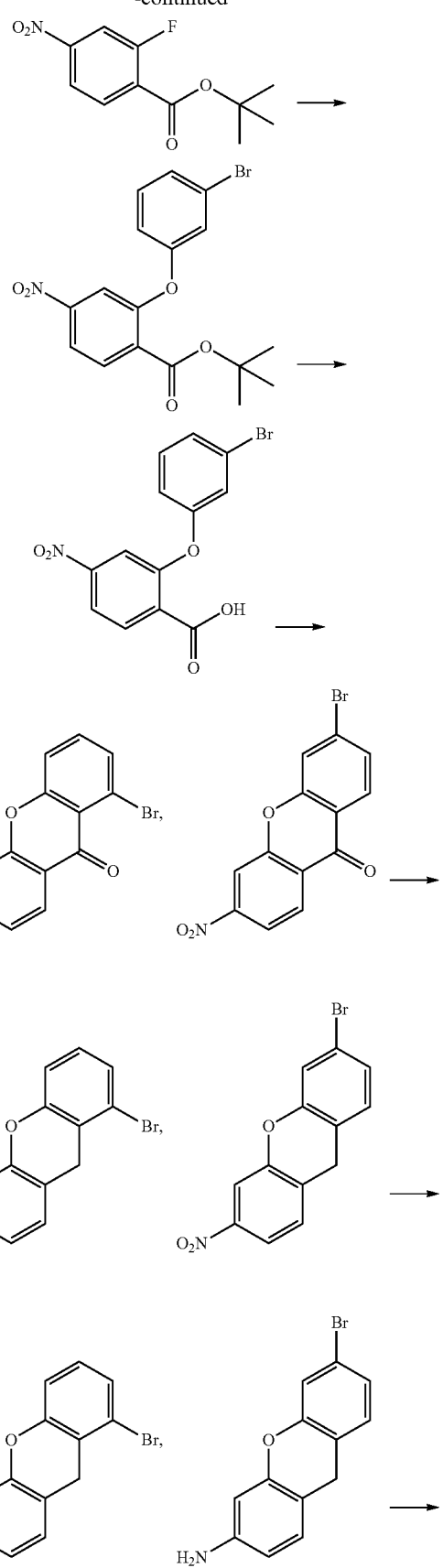

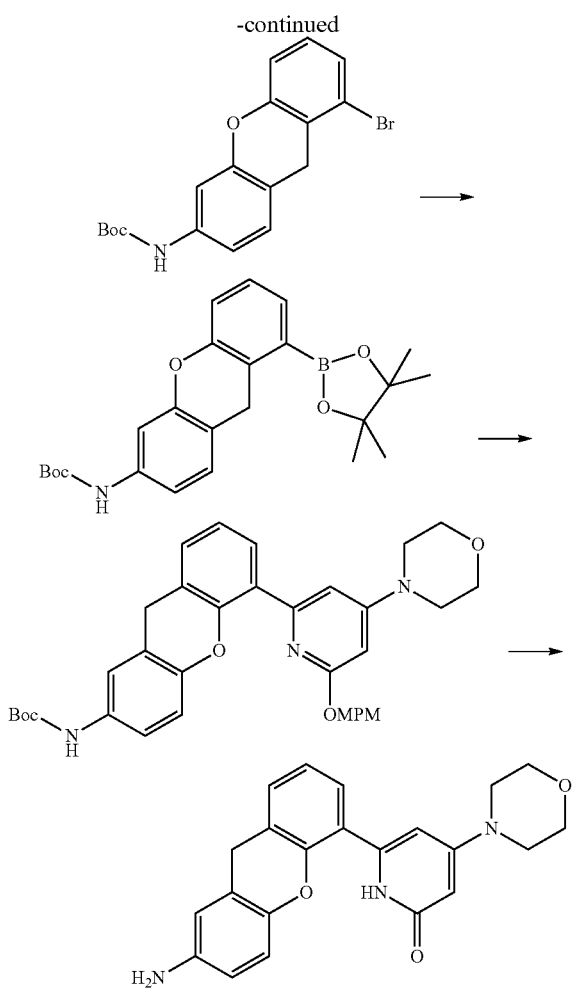

(1)

In the same manner as in Reference Example 15 (1), the following compound was obtained.

tert-Butyl 2-fluoro-4-nitrobenzoate

MS(ESI m/z): 242 (M+H)
RT(min): 1.66

(2)

In the same manner as in Reference Example 8 (1), the following compound was obtained.

tert-Butyl 2-(3-bromophenoxy)-4-nitrobenzoate

MS(ESI m/z): 395 (M+H)
RT(min): 2.03

(3)

In the same manner as in Reference Example 17 (3), the following compound was obtained.

2-(3-Bromophenoxy)-4-nitrobenzoic acid

MS(ESI m/z): 339 (M+H)
RT(min): 1.43

(4)

In the same manner as in Reference Example 3 (3), the following compound was obtained.

A mixture of 1-bromo-6-nitro-9H-xanthen-9-one and 3-bromo-6-nitro-9H-xanthen-9-one MS(ESI m/z): 321 (M+H)
RT(min): 1.62, 1.73

(5)

In the same manner as in Reference Example 8 (3), the following compound was obtained.

A mixture of 1-bromo-6-nitro-9H-xanthene and 3-bromo-6-nitro-9H-xanthene

MS(ESI m/z): 307 (M+H)
RT(min): 1.47, 1.94

(6)

In the same manner as in Reference Example 3 (4), the following compound was obtained.

A mixture of 8-bromo-9H-xanthene-3-amine and 6-bromo-9H-xanthene-3-amine

MS(ESI m/z): 277 (M+H)
RT(min): 1.44, 1.46

(7)

Di-tert-butyl dicarbonate (2.3 g) was added to a solution of the mixture (1.5 g) of 8-bromo-9H-xanthene-3-amine and 6-bromo-9H-xanthene-3-amine in Reference Example 20 (6) in tetrahydrofuran (10 mL), followed by refluxing for 1.5 hours. The reaction mixture was cooled to room temperature, the solvent was distilled off under reduced pressure, and the obtained residues were washed with hexane, and purified by silica gel column chromatography (hexane:ethyl acetate=1:0→17:3), whereby tert-butyl (8-bromo-9H-xanthen-3-yl)carbamate was obtained as a white solid.

MS(ESI m/z): 377 (M+H)
RT(min): 2.08

(8) and (9)

In the same manner as in Reference Examples 3 (6) and 3 (7), the following compounds were obtained.

tert-Butyl (8-(4,4,5,5-tetra methyl-1,3,2-dioxaborolan-2-yl)-9H-xanthen-3-yl)carbamate MS(ESI m/z): 424 (M+H)
RT(min): 2.19 tert-Butyl (8-(6-((4-methoxybenzyl)oxy)-4-morpholinopyridin-2-yl)-9H-xanthen-3-yl)carbamate MS(ESI m/z): 596 (M+H)
RT(min): 1.73

(10)

In the same manner as in Reference Example 18 (2), the following compound was obtained.

6-(6-Amino-9H-xanthen-1-yl)-4-morpholinopyridin-2(1H)-one

MS(ESI m/z): 376 (M+H)
RT(min): 0.81

Reference Example 21-1-1

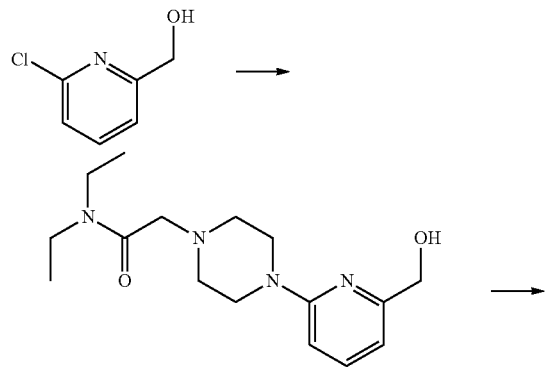

N,N-diethyl-2-(piperazin-1-yl)acetamide (350 μL) was added to a solution of (6-chloropyridin-2-yl)methanol (29 mg) in ethanol (0.5 mL), and the resultant product was irradiated with microwaves (microwave reaction apparatus, 200° C., 0.5 hours, 2.45 GHz, 0 W to 240 W). The solvent was distilled off under reduced pressure, whereby N,N-diethyl-2-(4-(6-(hydroxymethyl)pyridin-2-yl)piperazin-1-yl)acetamide (61 mg) was obtained.

(2)

Manganese dioxide (233 mg) was added to a solution of N,N-diethyl-2-(4-(6-(hydroxymethyl)pyridin-2-yl)piperazin-1-yl)acetamide (61 mg) obtained in Reference Example 21-1-1 (1) in chloroform (0.7 mL), followed by stirring at 80° C. for 1 hour. The reaction mixture was filtered using Celite, whereby the insoluble materials were removed. The solvent was distilled off under reduced pressure, whereby N,N-diethyl-2-(4-(6-formylpyridin-2-yl)piperazin-1-yl)acetamide (61 mg) was obtained.

Reference Example 21-1-2

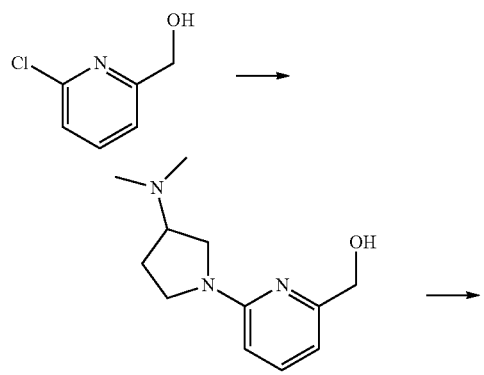

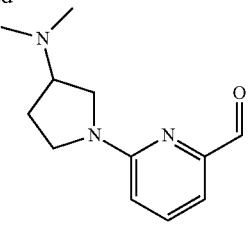

In the same manner as in Reference Example 21-1-1, the following compounds were obtained.

6-(3-(Dimethyl amino)pyrrolidin-1-yl)picolinic aldehyde

Reference Example 21-2-1

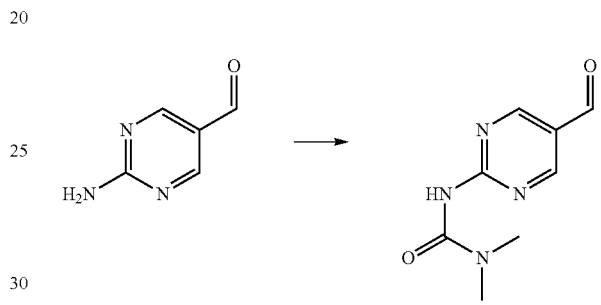

Sodium hydride (48 mg, 60%, dispersed in liquid paraffin) and N,N-dimethyl carbamoyl chloride (0.5 mL) were added to a solution of 2-amino-5-formylpyrimidine (123 mg) in N,N-dimethyl formamide (4 mL), followed by stirring at room temperature for 1 hour. A saturated sodium hydrogen carbonate aqueous solution was added to the reaction mixture, and the resultant product was extracted with ethyl acetate. The solvent was distilled off under reduced pressure, and the obtained residues were purified by silica gel column chromatography (hexane:ethyl acetate=1:1→0:1), whereby 3-(5-formyl pyrimidin-2-yl)-1,1-dimethylurea (194 mg) was obtained.

MS(ESI m/z): 195 (M+H)
RT(min): 0.43

Reference Example 21-2-2

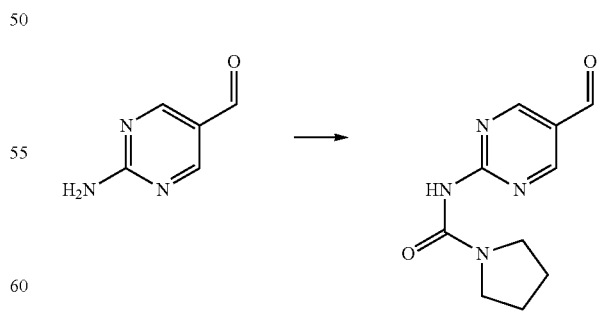

In the same manner as in Reference Example 21-2-1, N-(5-formylpyrimidin-2-yl)pyrrolidine-1-carboxamide was obtained.

MS(ESI m/z): 221 (M+H)
RT(min): 0.55

Reference Example 21-3

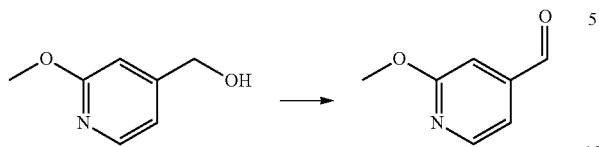

Manganese dioxide (1.04 g) was added to a solution of (2-methoxypyridin-4-yl)methanol (417 mg) in ethyl acetate (5 mL), followed by refluxing for 1.5 hours. Manganese dioxide (1.04 g) was added thereto, followed by refluxing for 1.5 hours. The reaction mixture was cooled to room temperature, the insoluble materials were filtered off, and the solvent was distilled off under reduced pressure. The obtained residues were purified by silica gel column chromatography (hexane:ethyl acetate=9:1→4:6), whereby 2-methoxyisonicotinic aldehyde (260 mg) was obtained as a colorless oily material.

Reference Example 21-4-1

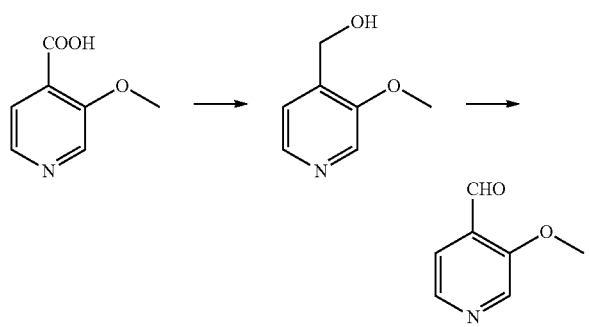

(1)

A 1.0 mol/L borane-tetrahydrofuran complex tetrahydrofuran solution (15 mL) was added to a solution of 3-methoxyisonicotinic acid (766 mg) in tetrahydrofuran (10 mL), followed by refluxing for 2.5 hours. 2.0 mol/L hydrochloric acid (3 mL) was added thereto, followed by refluxing for 2.5 hours. The reaction mixture was cooled to room temperature, and extracted with ethyl acetate. The organic layer was washed with a saturated sodium chloride aqueous solution, and dried over anhydrous sodium sulfate, and the solvent was distilled off under reduced pressure. The obtained residues were purified by silica gel column chromatography (ethyl acetate:methanol=1:0→4:1), whereby (3-methoxypyridin-4-yl)methanol (270 mg) was obtained as a white solid.

MS(ESI m/z): 140 (M+H)
RT(min): 0.75

(2)

Manganese dioxide (843 mg) was added to a solution of (3-methoxypyridin-4-yl)methanol (270 mg) in ethyl acetate (10 mL), followed by refluxing for 2 hours. Manganese dioxide (167 mg) was added thereto, followed by refluxing for 1 hour. The reaction mixture was cooled to room temperature, the insoluble materials were filtered off, and the solvent was distilled off under reduced pressure. The obtained residues were purified by silica gel column chromatography (hexane:ethyl acetate=1:1→0:1), whereby 3-methoxyisonicotinic aldehyde (190 mg) was obtained as a white solid.

Reference Example 21-4-2

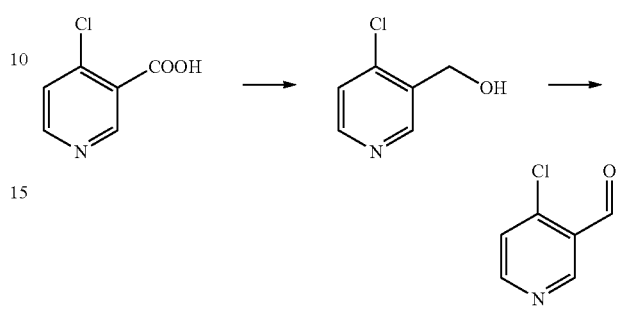

(1)

A 1.0 mol/L borane-tetrahydrofuran complex tetrahydrofuran solution (30 mL) was added to a solution of 4-chloronicotinic acid (1.58 g) in tetrahydrofuran (20 mL), followed by refluxing for 1.5 hours. 2.0 mol/L hydrochloric acid (10 mL) was added thereto, followed by refluxing for 1 hour. The reaction mixture was cooled to room temperature, and extracted with ethyl acetate. The organic layer was washed sequentially with a sodium carbonate aqueous solution and a saturated sodium chloride aqueous solution, and dried over anhydrous sodium sulfate, and the solvent was distilled off under reduced pressure. The obtained residues were purified by silica gel column chromatography (ethyl acetate:methanol=1:0→9:1), whereby (4-chloro pyridin-3-yl)methanol (630 mg) was obtained as a white solid.

MS(ESI m/z): 144 (M+H)
RT(min): 0.77

(2)

Manganese dioxide (1.53 g) was added to a solution of (4-chloro pyridin-3-yl)methanol (630 mg) in ethyl acetate (15 mL), followed by refluxing for 2 hours. Manganese dioxide (382 mg) was added thereto, followed by refluxing for 2 hours. The reaction mixture was cooled to room temperature, the insoluble materials were filtered off, and the solvent was distilled off under reduced pressure. The obtained residues were purified by silica gel column chromatography (hexane:ethyl acetate=7:3→3:7), whereby 4-chloronicotinic aldehyde (480 mg) was obtained as a white solid.

Reference Example 21-4-3

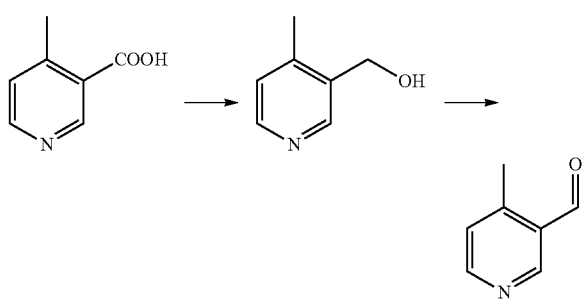

(1)

A 1.0 mol/L borane-tetrahydrofuran complex tetrahydrofuran solution (15 mL) was added to a solution of 4-methylnicotinic acid (686 mg) in tetrahydrofuran (15 mL), followed by refluxing for 2 hours. 2.0 mol/L hydrochloric acid (5 mL) was added thereto, followed by refluxing for 0.5 hours. The reaction mixture was cooled to room temperature, and extracted with ethyl acetate. The organic layer was washed sequentially with a sodium carbonate aqueous solution and a saturated sodium chloride aqueous solution, and dried over anhydrous sodium sulfate, and the solvent was distilled off under reduced pressure. The obtained residues were purified by silica gel column chromatography (ethyl acetate:methanol=1:0→9:1), whereby (4-methylpyridin-3-yl)methanol (270 mg) was obtained as a white solid.

MS(ESI m/z): 124 (M+H)

RT(min): 1.11

(2)

Manganese dioxide (572 mg) was added to a solution of (4-methyl pyridin-3-yl)methanol (270 mg) obtained in Reference Example 21-4-3 (1) in ethyl acetate (15 mL), followed by refluxing for 2 hours. Manganese dioxide (572 mg) was added thereto, followed by refluxing for 4 hours. The reaction mixture was cooled to room temperature, the insoluble materials were filtered off, and the solvent was distilled off under reduced pressure. The obtained residues were purified by silica gel column chromatography (hexane:ethyl acetate=7:3→3:7), whereby 4-methylnicotinic aldehyde (47 mg) was obtained as a white solid.

Reference Example 21-5

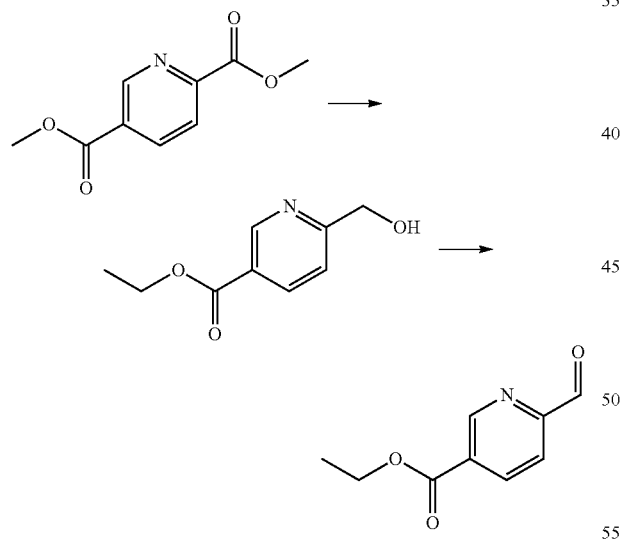

(1)

Calcium chloride (1.33 mg) was added to a mixed solvent of dimethyl pyridine-2,5-dicarboxylate (500 mg) in tetrahydrofuran (5 mL) and ethanol (5 mL), followed by stirring at room temperature for 0.5 hours. Under ice-cooling, sodium borohydride (227 mg) was added thereto, followed by stirring at room temperature for 12 hours. After the reaction mixture was cooled to 0° C., a saturated ammonium chloride aqueous solution was added thereto, followed by stirring at 0° C. for 0.5 hours. The resultant product was extracted with ethyl acetate, followed by drying over anhydrous sodium sulfate. The solvent was distilled off under reduced pressure, whereby ethyl 6-(hydroxymethyl)nicotinate (164 mg) was obtained as a yellow oily material.

(2)

Under ice-cooling, 1,1,1-triacetoxy-1,1-dihydro-1,2-benziodoxol-3-(1H)-one (420 mg) was added to a solution of ethyl 6-(hydroxymethyl)nicotinate obtained in Reference Example 21-5 (1) in dichloromethane (5 mL), followed by stirring at room temperature for 18 hours. A saturated sodium dithionite aqueous solution and a saturated sodium hydrogen carbonate aqueous solution were added thereto, and the resultant product was extracted with ethyl acetate. The organic layer was dried over anhydrous sodium sulfate, and the solvent was distilled off under reduced pressure. The obtained residues were purified by silica gel column chromatography (hexane:ethyl acetate=1:0→0:1), whereby ethyl 6-formylnicotinate (83 mg) was obtained as an orange oily material.

Reference Example 21-6

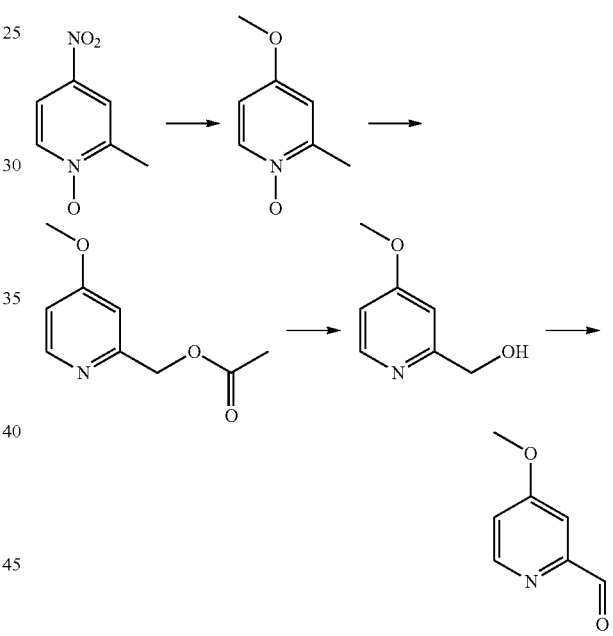

(1)

2-Methyl-4-nitro pyridine-N-oxide (2.3 g) was dissolved in methanol (20 mL), and 28% sodium methoxide/methanol (9 mL) was added thereto, followed by refluxing for 1.5 hours. After the reaction mixture was cooled to room temperature, 2 mol/L hydrochloric acid was added thereto, then, the resultant product was extracted with chloroform and dried over anhydrous sodium sulfate, and the solvent was distilled off under reduced pressure, whereby 2-methyl-4-methoxypyridine-N-oxide (2.5 g) was obtained as a yellow oily material.

(2)

2-Methyl-4-methoxypyridine-N-oxide (2.5 g) obtained in Reference Example 21-6 (1) was dissolved in acetic anhydride (10 mL), followed by stirring at 100° C. for 2 hours. After the reaction mixture was cooled to room temperature, ethanol was added thereto, and the solvent was distilled off under reduced pressure. The obtained residues were boiled with toluene, whereby (4-methoxypyridin-2-yl)methyl acetate was obtained as a brown oily material.

MS(ESI m/z): 182 (M+H)
RT(min): 0.38
(3)

Methanol (5 mL) and a 2 mol/L sodium hydroxide aqueous solution (5 mL) were added to (4-methoxypyridin-2-yl)methyl acetate obtained in Reference Example 21-6 (2), followed by refluxing for 3 hours. The reaction mixture was cooled to room temperature, 2 mol/L hydrochloric acid was added thereto, the resultant product was extracted with chloroform and dried over anhydrous sodium sulfate, and the solvent was distilled off under reduced pressure. The obtained residues were purified by silica gel column chromatography (ethyl acetate:methanol=1:0→9:1), whereby (4-methoxypyridin-2-yl)methanol (820 mg) was obtained as a white solid.

MS(ESI m/z): 140 (M+H)
RT(min): 0.25
(4)

Manganese dioxide (696 mg) was added to a solution of (4-methoxypyridin-2-yl)methanol (278 mg) obtained in Reference Example 21-6 (3) in ethyl acetate (5 mL), followed by refluxing for 1 hour. Manganese dioxide (696 mg) was added thereto, followed by refluxing for 2 hours. The reaction mixture was cooled to room temperature, the insoluble materials were filtered off, and the solvent was distilled off under reduced pressure. The obtained residues were purified by silica gel column chromatography (ethyl acetate), whereby 4-methoxypicolinic aldehyde (193 mg) was obtained as a colorless oily material.

Reference Example 21-7

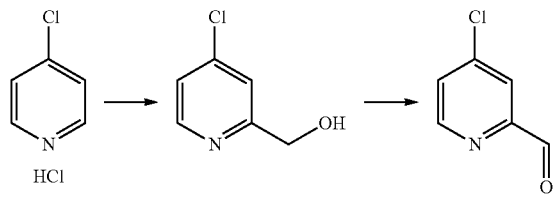 [SMILES: Clc1ccncc1 ; Cl ; OCc1cc(Cl)ccn1 ; O=Cc1cc(Cl)ccn1]

(1)
Concentrated sulfuric acid (0.25 mL) was added to a solution of 4-chloropyridine hydrochloride (3.00 g) in methanol (25 mL), followed by refluxing for 0.5 hours. An aqueous solution (25 mL) of ammonium persulfate (12.2 g) was added to the reaction mixture, followed by refluxing for 2.5 hours. The reaction mixture was cooled to room temperature, and the solvent was distilled off under reduced pressure. A sodium carbonate aqueous solution was added to the obtained residues, and the resultant product was extracted with ethyl acetate. The organic layer was dried over anhydrous sodium sulfate, and the solvent was distilled off under reduced pressure. The obtained residues were purified by silica gel column chromatography (hexane:ethyl acetate=1:1→0:1), whereby (4-chloro pyridin-2-yl)methanol (1.90 g) was obtained.

(2)
Manganese dioxide (3.03 g) was added to a solution of (4-chloropyridin-2-yl)methanol (1.00 g) obtained in Reference Example 21-7 (1) in ethyl acetate (20 mL), followed by refluxing for 3.5 hours. The reaction mixture was cooled to room temperature, the insoluble materials were filtered off, and the solvent was distilled off under reduced pressure. The obtained residues were purified by silica gel column chromatography (hexane:ethyl acetate=9:1→1:1), whereby 4-chloropicolinic aldehyde (425 mg) was obtained.

Reference Example 21-8-1

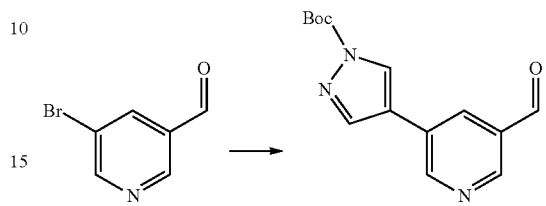

Bis(di-tert-butyl (4-dimethylamino phenyl)phosphine)dichloropalladium (II) was added to a suspension of 5-bromonicotinic aldehyde (100 mg), tert-butyl 4-(4,4,5,5-tetramethyl-1,3,2-dioxaborolan-2-yl)-1H-pyrazole-1-carboxylate (158 mg), and sodium carbonate (39 mg) in 1,2-dimethoxyethane (2.0 mL) and water (0.5 mL), followed by stirring at 80° C. for 1 hour. After the reaction mixture was cooled to room temperature, ethyl acetate was added thereto, and the organic layer was washed with a saturated sodium chloride aqueous solution, and dried over anhydrous sodium sulfate. The solvent was distilled off under reduced pressure, and the obtained residues were purified by silica gel column chromatography (hexane:ethyl acetate=9:1→1:3), whereby tert-butyl 4-(5-formylpyridin-3-yl)-1H-pyrazole-1-carboxylate (42 mg) was obtained.

Reference Example 21-8-2

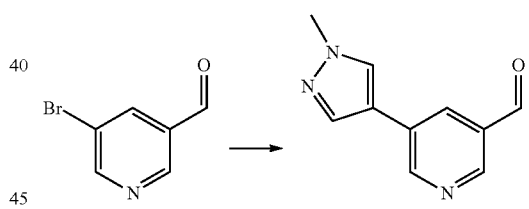

In the same manner as in Reference Example 21-8-1, the following compound was obtained.

5-(1-Methyl-1H-pyrazol-4-yl)nicotinic aldehyde

Reference Example 21-8-3

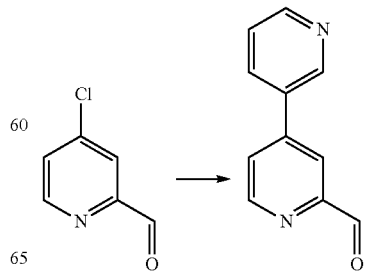

In the same manner as in Reference Example 21-8-1, the following compound was obtained.

[3,4'-bipyridine]-2'-carbaldehyde

Reference Example 21-8-4

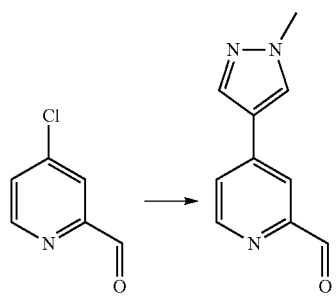

In the same manner as in Reference Example 21-8-1, the following compound was obtained.

4-(1-Methyl-1H-pyrazol-4-yl)picolinic aldehyde

Reference Example 21-9-1

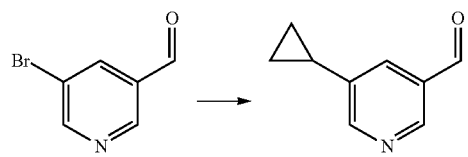 [SMILES: O=Cc1cncc(Br)c1 ; O=Cc1cncc(C2CC2)c1]

A mixture of 5-bromonicotinic aldehyde (372 mg), potassium cyclopropyltrifluoroboronic acid (325 mg), a 1,1'-bis(diphenylphosphino)ferrocene palladium (II) dichloride-dichloromethane complex (82 mg), tripotassium phosphate (1.49 g), tetrahydrofuran (9 mL), and water (3 mL) was irradiated with microwaves (microwave reaction apparatus, 150° C., 0.5 hours, 2.45 GHz, 0 W to 240 W). After the reaction mixture was cooled to room temperature, ethyl acetate was added thereto, the resultant product was washed sequentially with water and a saturated sodium chloride aqueous solution and dried over anhydrous sodium sulfate, and the solvent was distilled off under reduced pressure. The obtained residues were purified by silica gel column chromatography (hexane:ethyl acetate=9:1→0:1), whereby 5-cyclopropylnicotinic aldehyde (72 mg) was obtained as a colorless oily material.

Reference Example 21-9-2

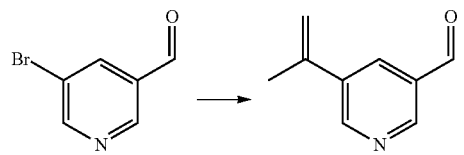

Potassium isopropenyltrifluoroboronic acid (175 mg), triethylamine (225 μL), and a 1,1'-bis(diphenylphosphino) ferrocene palladium (II) dichloride-dichloromethane complex (26 mg) were added to a solution of 5-bromonicotinic aldehyde (200 mg) in 2-propanol (2.0 mL) and water (1.0 mL), followed by refluxing for 4 hours. After the reaction mixture was cooled to room temperature, ethyl acetate was added thereto, and the organic layer was washed with a saturated sodium chloride aqueous solution, and dried over anhydrous sodium sulfate. The solvent was distilled off under reduced pressure, and the obtained residues were purified by silica gel column chromatography (hexane:ethyl acetate=1:0→1:1), whereby 5-(propen-2-yl)nicotinic aldehyde (140 mg) was obtained.

Reference Example 21-10

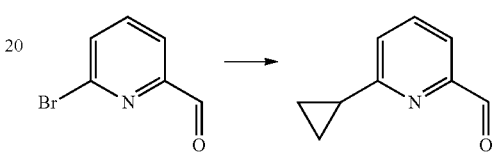

(1)

A mixture of 6-bromopicolinic aldehyde (200 mg), potassium cyclopropyltrifluoroboronic acid (320 mg), cesium carbonate (1.06 g), palladium acetate (25 mg), butyl bis(1-adamantyl)phosphine (51 mg), toluene (4.91 mL), and water (0.49 mL) was irradiated with microwaves (microwave reaction apparatus, 150° C., 20 minutes, 2.45 GHz, 0 W to 240 W). After the reaction mixture was cooled to room temperature, ethyl acetate was added thereto, the resultant product was washed sequentially with water and a saturated sodium chloride aqueous solution and dried over anhydrous sodium sulfate, and the solvent was distilled off under reduced pressure. The obtained residues were purified by silica gel column chromatography (hexane:ethyl acetate=9:1→0:1), whereby 6-cyclopropylpicolinic aldehyde (133 mg) was obtained.

Reference Example 21-11

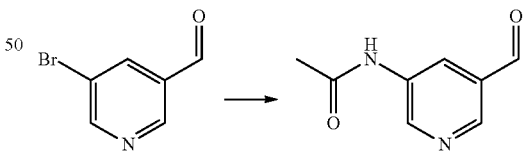

Acetamide (95 mg), tris(dibenzylidineacetone)dipalladium (0) (39 mg), 4,5-bis(diphenylphosphino)-9,9-dimethyl xanthene (57 mg), and cesium carbonate (525 mg) were added to a solution of 5-bromonicotinic aldehyde (200 mg) in 1,4-dioxane (2.0 mL), followed by stirring at 100° C. for 7 hours. The reaction mixture was cooled to room temperature, the insoluble materials were filtered off, and the solvent was distilled off under reduced pressure. The obtained residues were purified by silica gel column chromatography (chloroform:methanol=1:0→91:9), whereby N-(5-formylpyridin-3-yl)acetamide (118 mg) was obtained.

Reference Example 21-12-1

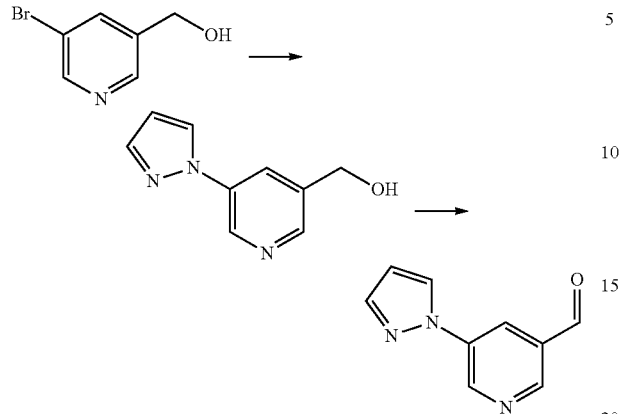

(1)

Pyrazole (217 mg), cesium carbonate (1040 mg), and copper iodide (I) (30 mg) were added to a solution of 5-bromo-3-pyridine methanol (300 mg) in N-methyl pyrrolidone (3.0 mL), and the resultant product was irradiated with microwaves (microwave reaction apparatus, 180° C., 0.25 hours, 2.45 GHz, 0 W to 240 W). After the reaction mixture was cooled to room temperature, ethyl acetate was added thereto, then, the resultant product was washed with water, and the insoluble materials were filtered off. The organic layer was collected by separation, and the aqueous layer was extracted with chloroform. The organic layer and the extraction liquid were combined, then, the resultant product was dried over anhydrous sodium sulfate, and the solvent was distilled off under reduced pressure. The obtained residues were purified by silica gel column chromatography (hexane:ethyl acetate=9:1→0:1, NH silica), whereby (5-(1H-pyrazol-1-yl)pyridin-3-yl)methanol (45 mg) was obtained.

(2)

Manganese dioxide (112 mg) was added to a dichloromethane solution (4.0 mL) of (5-(1H-pyrazol-1-yl)pyridin-3-yl)methanol (45 mg), and the resultant product was stirred at room temperature for 1.5 hours, and refluxed for 6 hours. The reaction mixture was cooled to room temperature, the insoluble materials were filtered off, and the solvent was distilled off under reduced pressure. The obtained residues were purified by silica gel column chromatography (chloroform:methanol=1:0→9:1), whereby 5-(1H-pyrazol-1-yl)nicotinic aldehyde (47 mg) was obtained.

Reference Example 21-12-2

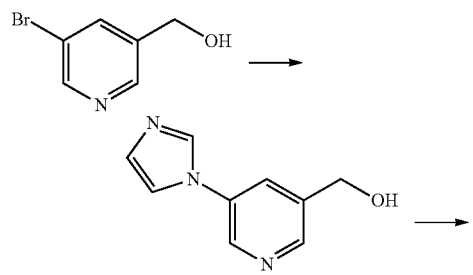

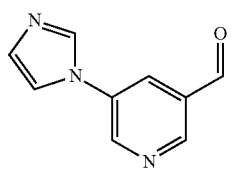

In the same manner as in Reference Example 21-12-1, the following compounds were obtained.

(5-(1H-imidazol-1-yl)pyridin-3-yl)methanol 5-(1H-imidazol-1-yl)nicotinic aldehyde

Reference Example 21-12-3

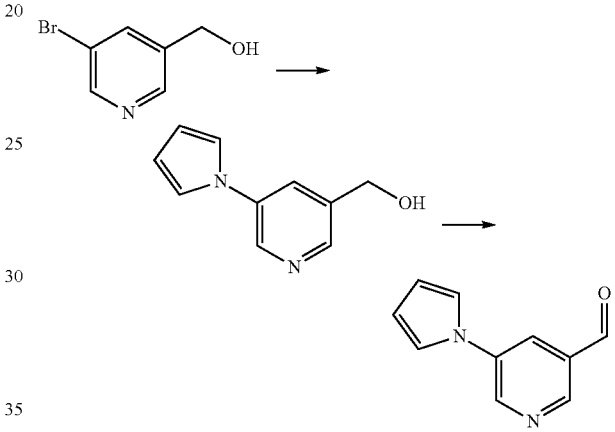

In the same manner as in Reference Example 21-12-1, the following compounds were obtained.

(5-(1H-pyrrol-1-yl)pyridin-3-yl)methanol 5-(1H-pyrrol-1-yl)nicotinic aldehyde

Reference Example 21-12-4

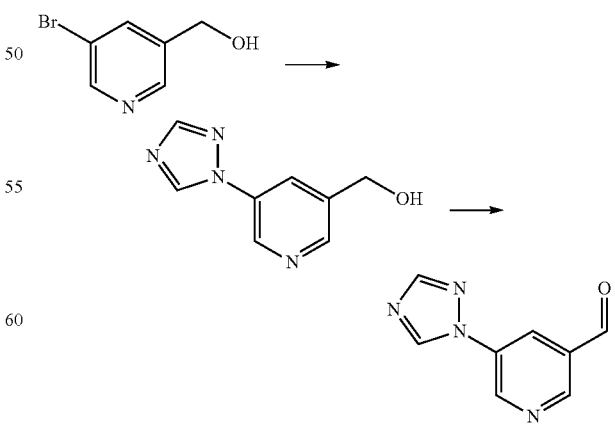

In the same manner as in Reference Example 21-12-1, the following compounds were obtained.

(5-(1H-1,2,4-triazol-1-yl)pyridin-3-yl)methanol 5-(1H-1,2,4-triazol-1-yl)nicotinic aldehyde Reference Example 21-13

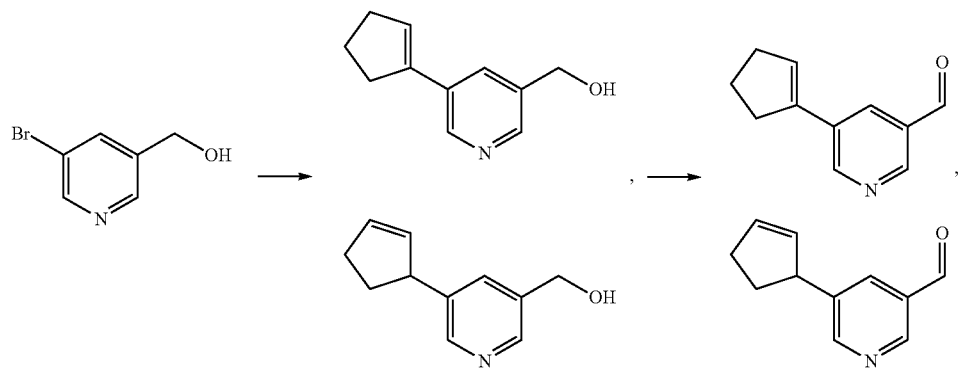 [SMILES: OCc1cncc(Br)c1 ; OCc1cncc(C2=CCCC2)c1 ; O=Cc1cncc(C2=CCCC2)c1 ; OCc1cncc(C2C=CCC2)c1 ; O=Cc1cncc(C2C=CCC2)c1]
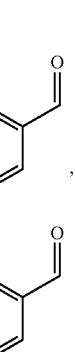

(1)

Cyclopentene (813 μL), triethylamine (519 μL), and bis(tri-tert-butyl phosphine)palladium (0) (19 mg) were added to a solution of 5-bromo-3-pyridine methanol (350 mg) in N-methyl pyrrolidone (3.0 mL), and the resultant product was irradiated with microwaves (microwave reaction apparatus, 130° C., 0.5 hours, 2.45 GHz, 0 W to 240 W). After the reaction mixture was cooled to room temperature, ethyl acetate was added thereto, the resultant product was washed with a saturated sodium chloride aqueous solution and dried over anhydrous sodium sulfate, and the solvent was distilled off under reduced pressure. The obtained residues were purified by silica gel column chromatography (hexane:ethyl acetate=9:1→0:1, NH silica), whereby a mixture (326 mg) of (5-(cyclopent-1-en-1-yl)pyridin-3-yl)methanol and (5-(cyclopent-2-en-1-yl)pyridin-3-yl)methanol was obtained.

(2)

Using the mixture (326 mg) obtained in Reference Example 21-13 (1), in the same manner as in Reference Example 21-12-1 (2), a mixture (140 mg) of 5-(cyclopent-1-en-1-yl)nicotinic aldehyde and 5-(cyclopent-2-en-1-yl)nicotinic aldehyde was obtained.

Reference Example 21-14

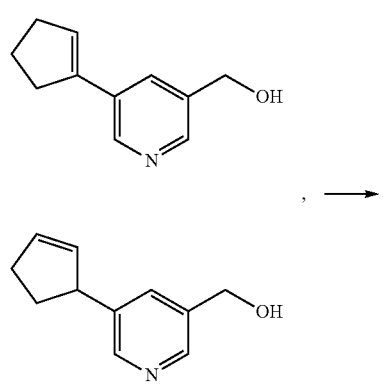

-continued

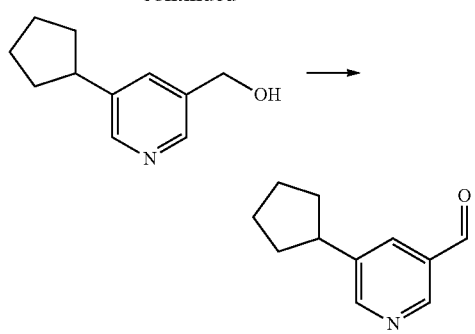

(1)

The mixture (186 mg) obtained in Reference Example 21-13 (1) was subjected to a hydrogenation reaction (70° C., 50 bar, flow rate of 2 mL/min, RaNi) using a flow type hydrogenation reaction apparatus, whereby (5-cyclopentylpyridin-3-yl)methanol (188 mg) was obtained.

(2)

In the same manner as in Reference Example 21-12-1 (2), the following compound was obtained.

5-Cyclopentylnicotinic aldehyde

Reference Example 21-15

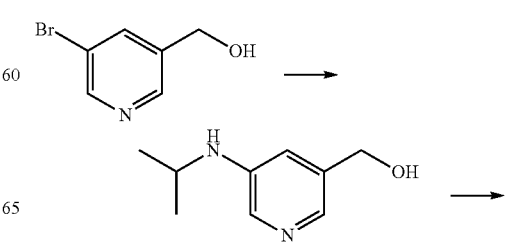

-continued

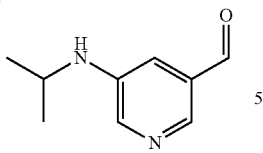

(1)

Isopropylamine (273 μL), potassium acetate (783 mg), copper iodide (I) (30 mg), and L-proline (37 mg) were added to a solution of 5-bromo-3-pyridine methanol (300 mg) in N,N-dimethyl acetamide (3.0 mL), and the resultant product was stirred at 90° C. for 13 hours. After the reaction mixture was cooled to room temperature, ethyl acetate was added thereto, the resultant product was washed with a saturated sodium chloride aqueous solution and dried over anhydrous sodium sulfate, and the solvent was distilled off under reduced pressure. The obtained residues were purified by silica gel column chromatography (hexane:ethyl acetate: methanol=1:1:0→0:1:0→0:9:1, NH silica), whereby (5-(isopropyl amino)pyridin-3-yl)methanol (60 mg) was obtained.

(2)

In the same manner as in Reference Example 21-5 (2), the following compound was obtained.

5-(Isopropyl amino)nicotinic aldehyde

Reference Example 21-16

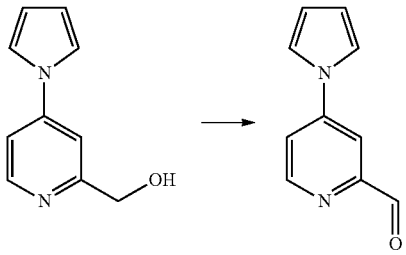 [SMILES: OCc1cc(-n2cccc2)ccn1 ; O=Cc1cc(-n2cccc2)ccn1]

In the same manner as in Reference Example 21-5 (2), the following compound was obtained.

4-(1H-pyrrol-1-yl)picolinic aldehyde

Reference Example 21-17

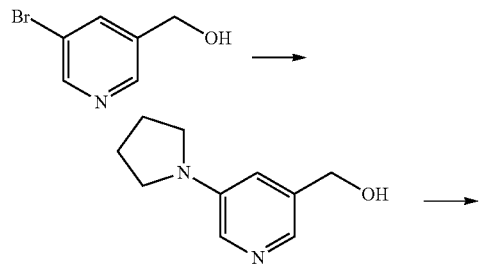

-continued

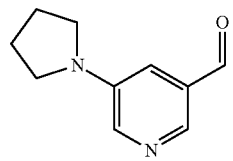

(1)

Pyrrolidine (106 μL), triethylamine (519 mg), tris(dibenzylidineacetone)dipalladium (0) (19 mg), 2-dicyclohexylphosphino-2',4',6'-triisopropylbiphenyl (15 mg), and cesium carbonate (485 mg) were added to a solution of 5-bromo-3-pyridine methanol (200 mg) in 1,4-dioxane (2.0 mL), and the resultant product was irradiated with microwaves (microwave reaction apparatus, 130° C., 0.5 hours, 2.45 GHz, 0 W to 240 W). The reaction mixture was cooled to room temperature, the insoluble materials were filtered off, and the solvent was distilled off under reduced pressure. The obtained residues were purified by silica gel column chromatography (chloroform:methanol=1:0→9:1), whereby (5-(pyrrolidin-1-yl)pyridin-3-yl)methanol (60 mg) was obtained.

(2)

1,1,1-Tris(acetyloxy)-1,1-dihydro-1,2-benziodoxol-3-(1H)-one (157 mg) was added to a solution (6.0 mL) of (5-(pyrrolidin-1-yl)pyridin-3-yl)methanol (60 mg) in dichloromethane, followed by stirring at room temperature for 17 hours. Ethyl acetate was added to the reaction mixture, and the resultant product was washed with a 1 mol/L sodium thiosulfate aqueous solution, and dried over anhydrous sodium sulfate. The solvent was distilled off under reduced pressure, and the obtained residues were purified by silica gel column chromatography (chloroform:methanol=1:0→9:1), whereby 5-(pyrrolidin-1-yl)nicotinic aldehyde (50 mg) was obtained.

Reference Example 21-18

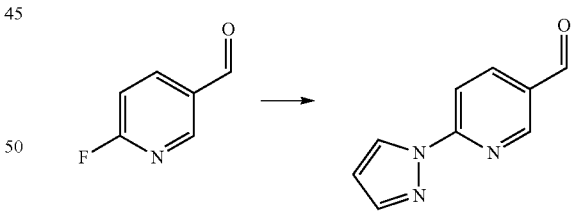

Pyrazole (41 mg) and cesium carbonate (195 mg) were added to a solution of 6-fluoronicotinic aldehyde (50 mg) in N-methyl pyrrolidone (1.0 mL), and the resultant product was irradiated with microwaves (microwave reaction apparatus, 150° C., 0.25 hours, 2.45 GHz, 0 W to 240 W). After the reaction mixture was cooled to room temperature, ethyl acetate was added thereto, and the resultant product was washed with a saturated sodium chloride aqueous solution, and dried over anhydrous sodium sulfate. The solvent was distilled off under reduced pressure, and the obtained residues were purified by silica gel column chromatography (hexane:ethyl acetate=1:0→1:1), whereby 6-(1H-pyrazol-1-yl)nicotinic aldehyde (10 mg) was obtained.

Reference Example 21-19

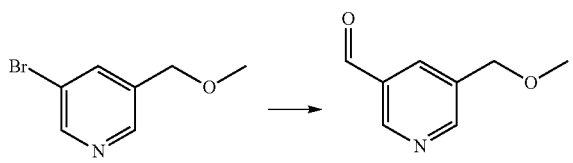

A 1.6 mol/L butyl lithium hexane solution (1.1 mL) was added to a solution of 3-bromo-5-methoxymethyl pyridine (295 mg) in tetrahydrofuran (6.0 mL) at −78° C., and N,N-dimethyl formamide (500 µL) was added thereto, followed by stirring at −78° C. for 15 minutes. Ethyl acetate was added to the reaction mixture, then, the resultant product was washed with a saturated ammonium chloride aqueous solution and dried over anhydrous sodium sulfate, and the solvent was distilled off under reduced pressure. The obtained residues were purified by silica gel column chromatography (hexane:ethyl acetate=9:1→1:4), whereby 5-(methoxy methyl)nicotinic aldehyde (29 mg) was obtained.

Reference Example 21-20

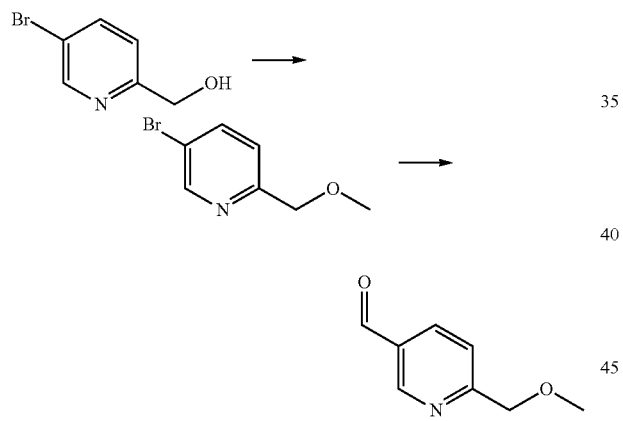

(1)
Under ice-cooling, sodium hydride (117 mg, 60%, dispersed in liquid paraffin) was added to a solution of 5-bromo-2-pyridine methanol (500 mg) in N,N-dimethyl formamide (5.0 mL), followed by stirring for 15 minutes, and methyl iodide (202 µL) was added thereto, followed by stirring for 1 hour. Ethyl acetate was added to the reaction mixture, then, the resultant product was washed with a saturated sodium chloride aqueous solution and dried over anhydrous sodium sulfate, and the solvent was distilled off under reduced pressure. The obtained residues were purified by silica gel column chromatography (hexane:ethyl acetate=1:0→2:1), whereby 5-bromo-2-(methoxy methyl) pyridine (425 mg) was obtained.

(2)
In the same manner as in Reference Example 21-19, the following compound was obtained.

6-(Methoxy methyl)nicotinic aldehyde

Reference Example 21-21-1

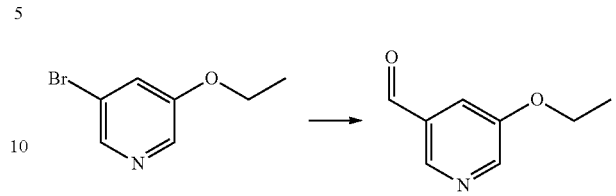

Under ice-cooling, a 1.0 mol/L isopropylmagnesium bromide-tetrahydrofuran solution (1.59 mL) was added to a solution of 3-bromo-5-ethoxy pyridine (200 mg) in tetrahydrofuran (2.0 mL), and the resultant product was stirred for 0.5 hours, and stirred at room temperature for 1.5 hours. N,N-dimethylformamide (500 µL) was added to the reaction mixture, followed by stirring for 0.5 hours. Ethyl acetate was added to the reaction mixture, then, the resultant product was washed with a saturated ammonium chloride aqueous solution and dried over anhydrous sodium sulfate, and the solvent was distilled off under reduced pressure. The obtained residues were purified by silica gel column chromatography (hexane:ethyl acetate=9:1→1:1), whereby 5-ethoxynicotinic aldehyde (61 mg) was obtained.

Reference Example 21-21-2

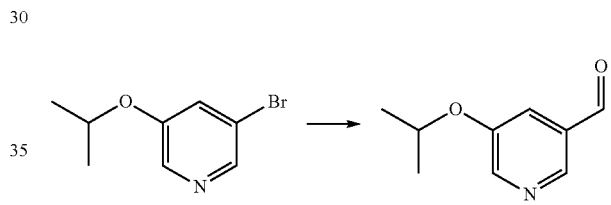

In the same manner as in Reference Example 21-21-1, the following compounds were obtained.

5-Isopropoxynicotinic aldehyde

Reference Example 2121-3

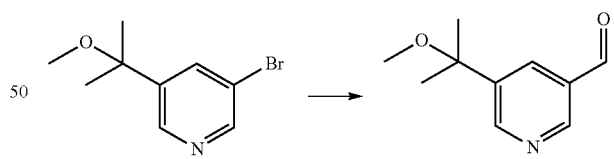

In the same manner as in Reference Example 21-21-1, the following compounds were obtained.

5-(2-Methoxy propan-2-yl)nicotinic aldehyde

Reference Example 21-22

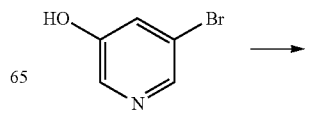

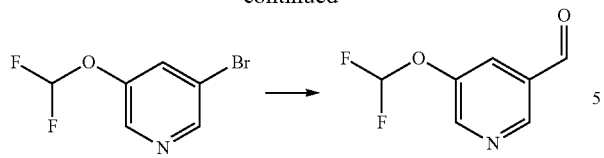

(1)

Sodium chlorodifluoroacetate (526 mg) and potassium carbonate (286 mg) were added to a solution of 5-bromo-3-hydroxypyridine (300 mg) in N,N-dimethyl formamide (6.0 mL) and water (500 μL), followed by stirring at 100° C. for 6 hours. After the reaction mixture was cooled to room temperature, ethyl acetate was added thereto, the resultant product was washed with a saturated sodium chloride aqueous solution and dried over anhydrous sodium sulfate, and the solvent was distilled off under reduced pressure. The obtained residues were purified by silica gel column chromatography (hexane:ethyl acetate=1:0→4:1), whereby 3-bromo-5-(difluoromethoxy)pyridine (60 mg) was obtained.

(2)

In the same manner as in Reference Example 21-21-1, the following compound was obtained.

5-(Difluoro methoxy)nicotinic aldehyde

Reference Example 21-23

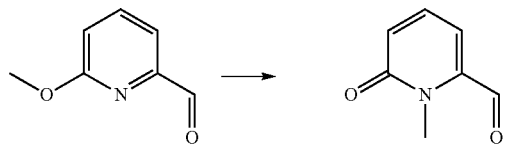

A solution of 6-methoxypicolinic aldehyde (500 mg) and methyl iodide (202 μL) in acetonitrile (1.5 mL) was irradiated with microwaves (microwave reaction apparatus, 140° C., 0.5 hours→170° C., 0.5 hours, 2.45 GHz, 0 W to 240 W). The reaction mixture was cooled to room temperature, the solvent was distilled off under reduced pressure, and the obtained residues were purified by silica gel column chromatography (hexane:ethyl acetate=1:1→0:1), whereby 1-methyl-6-oxo-1,6-dihydro pyridine-2-carbaldehyde (56 mg) was obtained.

Reference Example 21-24

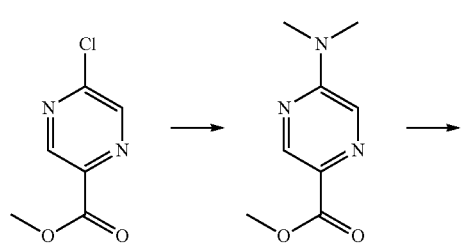

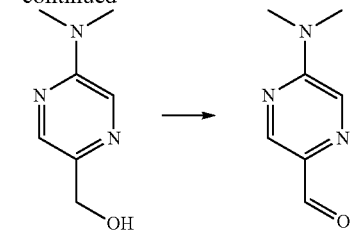

(1)

A 2 mol/L dimethylamine-tetrahydrofuran solution (2.32 mL) was added to a solution of methyl 5-chloropyrazine-2-carboxylate (400 mg) in tetrahydrofuran (12 mL), followed by stirring at 50° C. for 2 hours. A 2 mol/L dimethylamine-tetrahydrofuran solution (4.64 mL) was added thereto, followed by stirring at 50° C. for 0.5 hours. After the reaction mixture was cooled to room temperature, ethyl acetate was added thereto, then, the resultant product was washed with a saturated sodium chloride aqueous solution, and the solvent was distilled off under reduced pressure. The obtained residues were purified by silica gel column chromatography (hexane:ethyl acetate=1:0→0:1), whereby methyl 5-(dimethylamino)pyrazine-2-carboxylate (364 mg) was obtained.

$^{1}$H-NMR (CDCl$_3$) δ: 8.81 (1H, d, J=1.3 Hz), 8.04 (1H, d, J=1.3 Hz), 3.96 (3H, s), 3.23 (6H, s).

(2)

Under ice-cooling, a 3 mol/L lithium borohydride-tetrahydrofuran solution (1.22 mL) was added to a solution of methyl 5-(dimethylamino)pyrazine-2-carboxylate (300 mg) obtained in Example 21-24 (1) in tetrahydrofuran (8.3 mL), followed by stirring at room temperature for 24 hours. Methanol and water were added to the reaction mixture, and the resultant product was extracted with ethyl acetate. The organic layer was washed with a saturated sodium chloride aqueous solution, and dried over anhydrous sodium sulfate, and the solvent was distilled off under reduced pressure. The obtained residues were purified by silica gel column chromatography (hexane:ethyl acetate=1:0→0:1), whereby (5-(dimethylamino)pyrazin-2-yl)methanol (77.7 mg) was obtained.

MS(ESI m/z): 154 (M+H)

RT(min): 0.46

(3)

Manganese dioxide (227 mg) was added to a solution of (5-(dimethylamino)pyrazin-2-yl)methanol (40 mg) obtained in Example 21-24 (2) in dichloromethane (2.6 mL), followed by stirring for 21 hours. The insolubles were filtered off, and the solvent was distilled off under reduced pressure. The obtained residues were purified by silica gel column chromatography (hexane:ethyl acetate), whereby 5-(dimethylamino)pyrazine-2-carbaldehyde (30.5 mg) was obtained.

MS(ESI m/z): 152 (M+H)

RT(min): 0.62

Reference Example 22-1

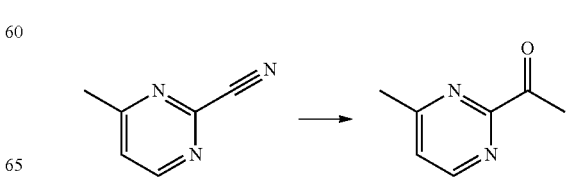

A 3.0 mol/L methylmagnesium bromide/tetrahydrofuran (0.86 mL) was added to a solution of 4-methyl pyrimidine-2-carbonitrile (159 mg) in tetrahydrofuran (4.5 mL) under ice-cooling, followed by stirring for 20 minutes. A saturated ammonium chloride aqueous solution and a saturated sodium chloride aqueous solution were added thereto, and the resultant product was extracted with ethyl acetate. The organic layer was dried over anhydrous sodium sulfate, then, the solvent was distilled off under reduced pressure, and the obtained residues were purified by silica gel column chromatography (hexane:ethyl acetate=1:1→1:2), whereby 1-(4-methyl pyrimidin-2-yl)ethanone (64 mg) was obtained.

MS(ESI m/z): 137 (M+H)
RT(min): 0.54

Reference Example 22-2-1

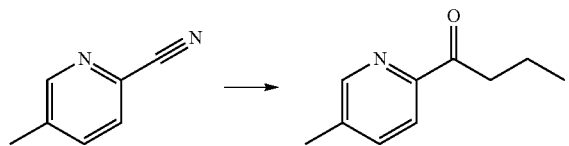

A solution of 1-bromopropane (185 mg) in tetrahydrofuran (0.8 mL) was added to a solution of magnesium (36 mg) and 1,2-dibromoethane (9 μL) in tetrahydrofuran (0.2 mL), followed by stirring at room temperature for 1 hour. The reaction mixture was added to a solution of 5-methyl pyridine-2-carbonitrile (118 mg) in tetrahydrofuran (1 mL) under ice-cooling, followed by stirring at room temperature for 1 hour. A saturated ammonium chloride aqueous solution and a saturated sodium chloride aqueous solution were added to the reaction mixture, and the resultant product was extracted with ethyl acetate. The organic layer was dried over anhydrous sodium sulfate, then, the solvent was distilled off under reduced pressure, and the obtained residues were purified by silica gel column chromatography (hexane:ethyl acetate=1:1→1:2), whereby 1-(5-methyl pyridin-2-yl)butanone (70 mg) was obtained.

MS(ESI m/z): 164 (M+H)
RT(min): 1.28

Reference Examples 22-2-2 to 22-2-14

In the same manner as in Reference Example 22-2-1, the following compounds were obtained.

TABLE 9

| Reference Example No. | R | MS | RT(min) |
|---|---|---|---|
| 22-2-2 | Isobutyl | 178 | 1.47 |
| 22-2-3 | Isopropyl | 164 | 1.29 |
| 22-2-4 | sec-Butyl | 178 | 1.49 |
| 22-2-5 | Cyclopropyl | 162 | 1.10 |
| 22-2-6 | Cyclobutyl | 176 | 1.31 |
| 22-2-7 | Cyclopentyl | 190 | 1.53 |
| 22-2-8 | Cyclohexyl | 204 | 1.67 |

TABLE 9-continued

| Reference Example No. | R | MS | RT(min) |
|---|---|---|---|
| 22-2-9 | Cycloheptyl | 218 | 1.82 |
| 22-2-10 | Cyclopropylmethyl | 176 | 1.37 |
| 22-2-11 | Cyclohexylmethyl | 218 | 1.83 |
| 22-2-12 | 3-Methoxy propyl | 194 | 1.04 |
| 22-2-13 | 2-(1,3-Dioxan-2-yl)ethyl | 236 | 1.07 |
| 22-2-14 | 1-Methyl piperidin-4-yl | 219 | 0.59 |

Reference Example 22-3

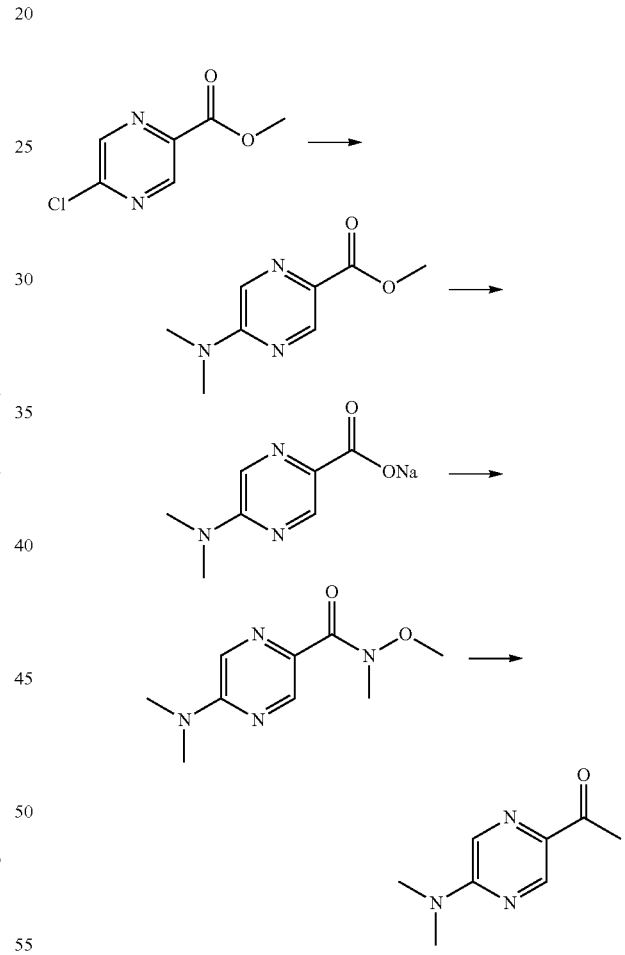

(1)
2.0 mol/L diethylamine/methanol (1.1 mL) was added to a solution of methyl 5-chloropyrazine-2-carboxylate (172 mg) in 1,4-dioxane (4 mL), followed by stirring at room temperature for 16 hours. The solvent was distilled off under reduced pressure, and the obtained residues were purified by silica gel column chromatography (hexane:ethyl acetate=1:1, NH silica), whereby methyl 5-(dimethylamino)pyrazine-2-carboxylate (179 mg) was obtained.

MS(ESI m/z): 182 (M+H)
RT(min): 0.74

(2)

A solution of sodium hydroxide (43 mg) in water (0.5 mL) was added to a solution of methyl 5-(dimethylamino)pyrazine-2-carboxylate (179 mg) obtained in Reference Example 22-3 (1) in 1,4-dioxane (1 mL), followed by stirring at room temperature for 0.5 hours. 1,4-Dioxane (1.5 mL) was added thereto, followed by stirring for 0.5 hours. The solvent was distilled off under reduced pressure, whereby sodium 5-(dimethylamino)pyrazine-2-carboxylate (190 mg) was obtained.

MS(ESI m/z): 168 (M+H)
RT(min): 0.57

(3)

N,O-dimethylhydroxylamine hydrochloride (145 mg) and 1-ethyl-3-(3-dimethylaminopropyl)carbodiimide hydrochloride (286 mg) were added to a mixed solution of sodium 5-(dimethylamino)pyrazine-2-carboxylate (190 mg) obtained in Reference Example 22-3 (2) in chloroform (5 mL) and pyridine (1 mL), followed by stirring at room temperature for 0.5 hours. The solvent was distilled off under reduced pressure, and the obtained residues were purified by silica gel column chromatography (hexane:ethyl acetate=1:1→0:1), whereby 5-(dimethylamino)-N-methoxy-N-methyl pyrazine-2-carboxamide (168 mg) was obtained.

MS(ESI m/z): 211 (M+H)
RT(min): 0.70

(4)

1.0 mol/L methyl lithium/diethyl ether (1.2 mL) was added to a solution of 5-(dimethyl amino)-N-methoxy-N-methyl pyrazine-2-carboxamide (168 mg) obtained in Reference Example 22-3 (3) in tetrahydrofuran (4 mL) under ice-cooling, followed by stirring for 0.5 hours. The solvent was distilled off under reduced pressure, and the obtained residues were purified by silica gel column chromatography (hexane:ethyl acetate=4:1→3:2), whereby 1-(5-(dimethylamino)pyrazin-2-yl)ethanone (89 mg) was obtained as a white solid.

MS(ESI m/z): 166 (M+H)
RT(min): 0.73

Reference Example 22-4

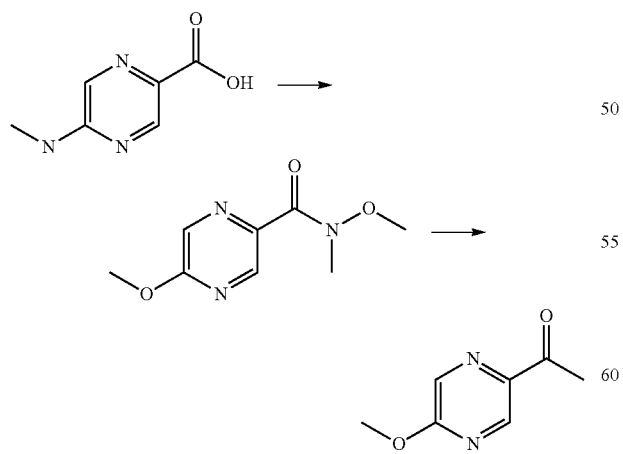

(1)
In the same manner as in Reference Example 22-3 (3), the following compound was obtained.

N,5-dimethoxy-N-methyl pyrazine-2-carboxamide

MS(ESI m/z): 198 (M+H)
RT(min): 0.72

(2)
In the same manner as in Reference Example 22-3 (4), the following compound was obtained.

1-(5-Methoxypyrazin-2-yl)ethanone

MS(ESI m/z): 153 (M+H)
RT(min): 0.82

Reference Example 22-5

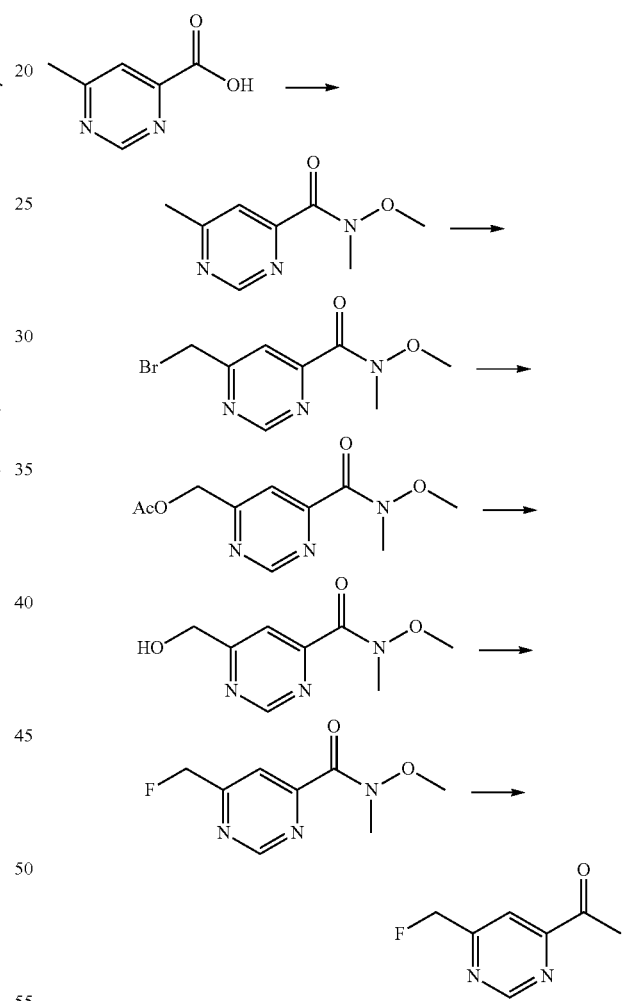

(1)
In the same manner as in Reference Example 22-3 (3), the following compound was obtained.

N-methoxy-N,6-dimethyl pyrimidine-4-carboxamide

MS(ESI m/z): 182 (M+H)
RT(min): 0.

(2)
Bromine (206 mg) was added to a solution of N-methoxy-N,6-dimethyl pyrimidine-4-carboxamide (224 mg) obtained in Reference Example 22-5 (1) in acetic acid (5 mL), and the resultant product was irradiated with microwaves (microwave reaction apparatus, 70° C., 0.5 hours, 2.45 GHz, 0 W to 240 W). After the reaction mixture was cooled to room temperature, ethyl acetate was added thereto, then, a sodium hydroxide aqueous solution was added dropwise thereto under ice-cooling, and the resultant product was extracted with ethyl acetate. The organic layer was dried over anhydrous sodium sulfate, and the solvent was distilled off under reduced pressure, whereby 6-(bromomethyl)-N-methoxy-N-methyl pyrimidine-4-carboxamide (195 mg) was obtained.

(3)

Sodium acetate (315 mg) was added to a solution of 6-(bromomethyl)-N-methoxy-N-methyl pyrimidine-4-carboxamide (195 mg) obtained in Reference Example 22-5 (2) in N,N-dimethyl formamide (4 mL), followed by stirring at room temperature for 5 hours. After water was added thereto, the resultant product was extracted with ethyl acetate, then, the organic layer was dried over anhydrous sodium sulfate, and the solvent was distilled off under reduced pressure, whereby (6-(methoxy(methyl)carbamoyl)pyrimidin-4-yl)methyl acetate was obtained.

MS(ESI m/z): 240 (M+H)
RT(min): 0.65

(4)

Sodium methoxide (15 mg) was added to a solution of (6-(methoxy(methyl)carbamoyl)pyrimidin-4-yl)methyl acetate obtained in Reference Example 22-5 (3) in methanol (4.5 mL), followed by stirring at room temperature for 15 minutes. The solvent was distilled off under reduced pressure, and the obtained residues were purified by silica gel column chromatography (hexane:ethyl acetate=1:1→0:1), whereby 6-(hydroxymethyl)-N-methoxy-N-methyl pyrimidine-4-carboxamide (122 mg) was obtained.

(5)

Bis(2-methoxyethyl)aminosulfur trifluoride (135 µL) was added to a solution of 6-(hydroxymethyl)-N-methoxy-N-methyl pyrimidine-4-carboxamide (111 mg) obtained in Reference Example 22-5 (4) in dichloromethane (5.6 mL) at −78° C., and the resultant product was stirred for 0.5 hours, and stirred at −35° C. for 1 hour. Bis(2-methoxyethyl)aminosulfur trifluoride (60 µL) was added thereto, followed by stirring at −35° C. for 1 hour. Bis(2-methoxyethyl)aminosulfur trifluoride (100 µL) was added thereto at 0° C., followed by stirring for 2 hours, then, a saturated sodium hydrogen carbonate aqueous solution was added thereto, and the resultant product was extracted with chloroform. The organic layer was dried over anhydrous sodium sulfate, and the solvent was distilled off under reduced pressure. The obtained residues were purified by silica gel column chromatography (hexane:ethyl acetate=2:1→1:1), whereby 6-(fluoromethyl)-N-methoxy-N-methyl pyrimidine-4-carboxamide (25 mg) was obtained.

MS(ESI m/z): 200 (M+H)
RT(min): 0.59

(6)

1.0 mol/L methylmagnesium bromide/tetrahydrofuran (0.25 mL) was added to a solution of 6-(fluoromethyl)-N-methoxy-N-methyl pyrimidine-4-carboxamide (25 mg) obtained in Reference Example 22-5 (5) in tetrahydrofuran (2.5 mL) at −30° C., followed by stirring for 10 minutes under ice-cooling. A saturated ammonium chloride aqueous solution was added thereto, then, the resultant product was extracted with ethyl acetate, and the organic layer was dried over anhydrous sodium sulfate. The solvent was distilled off under reduced pressure, and the obtained residues were purified by silica gel column chromatography (hexane:ethyl acetate=4:1→3:1), whereby 1-(6-(fluoromethyl)pyrimidin-4-yl)ethanone (11 mg) was obtained.

MS(ESI m/z): 155 (M+H)
RT(min): 0.68

Reference Example 22-6-1

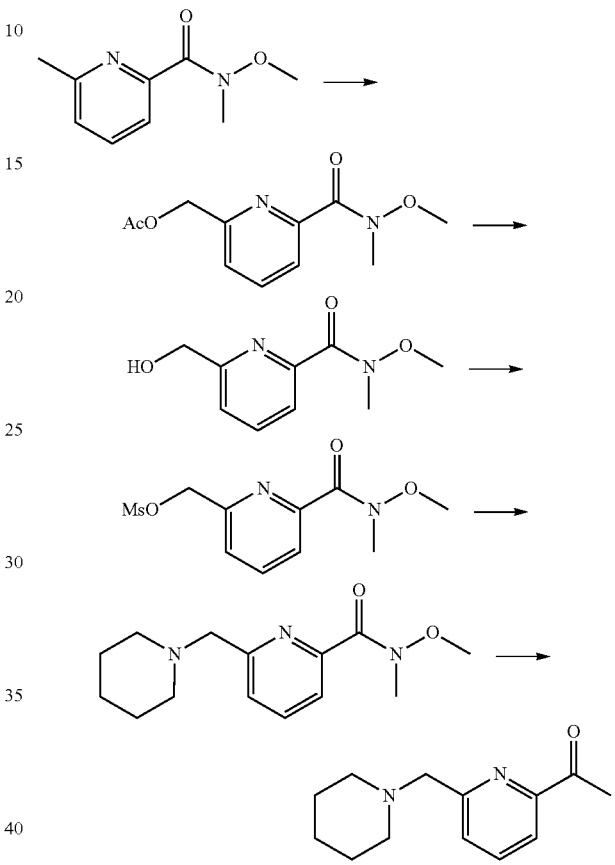

(1)

Metachloroperbenzoic acid (1.74 g) was added to a solution of N-methoxy-N,6-dimethyl picolinamide (980 mg) in dichloromethane (20 mL), and the resultant product was stirred at room temperature for 1.5 hours, and refluxed for 10 minutes. The reaction mixture was cooled to room temperature, and purified by silica gel column chromatography (chloroform:methanol=10:1). Acetic anhydride (10 mL) was added to the obtained residues, and the resultant product was irradiated with microwaves (Initiator™, 110° C., 0.5 hours, 2.45 GHz, 0 W to 240 W). The reaction mixture was purified by silica gel column chromatography (hexane:ethyl acetate=2:1→0:1), whereby (6-(methoxy(methyl)carbamoyl)pyridin-2-yl)methyl acetate (948 mg) was obtained.

MS(ESI m/z): 239 (M+H)
RT(min): 0.74

(2)

In the same manner as in Reference Example 22-5 (4), the following compound was obtained.

6-(Hydroxymethyl)-N-methoxy-N-methyl picolinamide

MS(ESI m/z): 197 (M+H)
RT(min): 0.49

(3)

Under ice-cooling, triethylamine (836 μL) and methanesulfonyl chloride (302 μL) were added to a solution of 6-(hydroxymethyl)-N-methoxy-N-methyl picolinamide (590 mg) obtained in Reference Example 22-6-1 (2) in dichloromethane (10 mL), followed by stirring for 0.5 hours. A saturated sodium hydrogen carbonate aqueous solution was added to the reaction mixture, then, the resultant product was extracted with chloroform, and the organic layer was dried over anhydrous sodium sulfate. The solvent was distilled off under reduced pressure, whereby (6-(methoxy (methyl)carbamoyl)pyridin-2-yl)methyl methanesulfonate was obtained.

MS(ESI m/z): 275 (M+H)
RT(min): 0.70

(4)

Piperidine (85 mg) was added to a solution of (6-(methoxy(methyl)carbamoyl)pyridin-2-yl)methyl methanesulfonate (137 mg) obtained in Reference Example 22-6-1 (3) in tetrahydrofuran (2 mL), followed by stirring at room temperature for 0.5 hours, then, sodium iodide (15 mg) was added thereto, and the resultant product was irradiated with microwaves (microwave reaction apparatus, 50° C., 10 minutes, 2.45 GHz, 0 W to 240 W). A saturated sodium hydrogen carbonate aqueous solution was added to the reaction mixture, then, the resultant product was extracted with chloroform, and the organic layer was dried over anhydrous sodium sulfate. The solvent was distilled off under reduced pressure, whereby obtaining N-methoxy-N-methyl-6-(piperidin-1-ylmethyl)picolinamide was obtained.

MS(ESI m/z): 264 (M+H)
RT(min): 0.46

(5)

In the same manner as in Reference Example 22-5 (6), the following compound was obtained.

1-(6-(Piperidin-1-ylmethyl)pyridin-2-yl)ethanone

MS(ESI m/z): 219 (M+H)
RT(min): 0.50

Reference Example 22-6-2

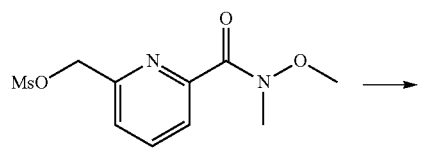

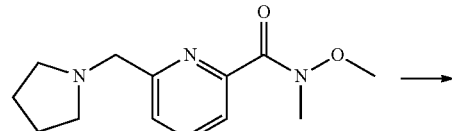

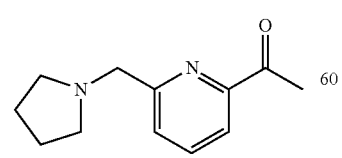

(1)

In the same manner as in Reference Example 22-6-1 (4), the following compound was obtained.

N-methoxy-N-methyl-6-(pyrrolidin-1-ylmethyl)picolinamide

MS(ESI m/z): 250 (M+H)
RT(min): 0.40

(2)

In the same manner as in Reference Example 22-5 (6), the following compound was obtained.

1-(6-(Pyrrolidin-1-ylmethyl)pyridin-2-yl)ethanone

MS(ESI m/z): 205 (M+H)
RT(min): 0.44

Reference Example 22-6-3

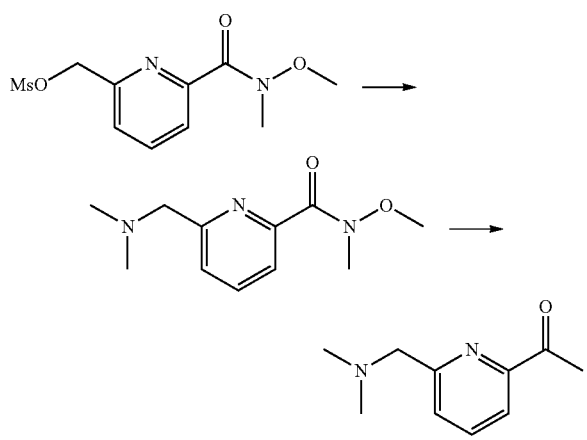

(1)

In the same manner as in Reference Example 22-6-1 (4), the following compound was obtained.

6-((Dimethylamino)methyl)-N-methoxy-N-methyl picolinamide

MS(ESI m/z): 224 (M+H)
RT(min): 0.35

(2)

In the same manner as in Reference Example 22-5 (6), the following compound was obtained.

1-(6-((Dimethylamino)methyl)pyridin-2-yl)ethanone

MS(ESI m/z): 179 (M+H)
RT(min): 0.37

Reference Example 22-6-4

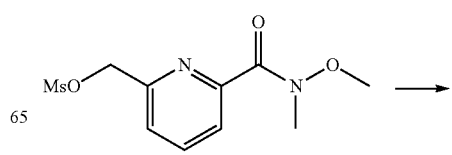

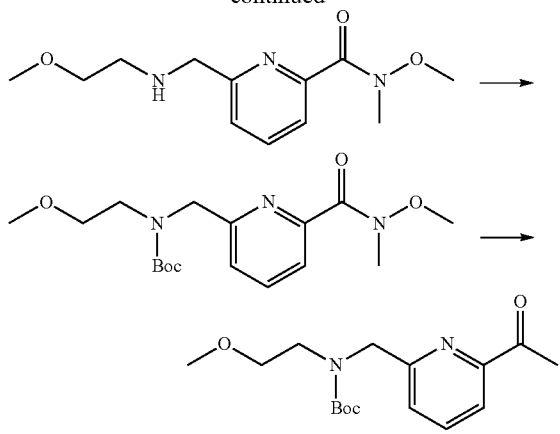

(1)

In the same manner as in Reference Example 22-6-1 (4), the following compound was obtained.

N-methoxy-6-(((2-methoxyethyl)amino)methyl)-N-methyl picolinamide

MS(ESI m/z): 254 (M+H)
RT(min): 0.42

(2)

Di-tert-butyl dicarbonate (218 mg) was added to a solution of N-methoxy-6-(((2-methoxyethyl)amino)methyl)-N-methyl picolinamide obtained in Reference Example 22-6-4 (1) in dichloromethane, followed by stirring at room temperature for 12 hours. Methanol was added thereto, then, the solvent was distilled off under reduced pressure, and the obtained residues were purified by silica gel column chromatography (hexane:ethyl acetate=1:1→1:2), whereby tert-butyl ((6-(methoxy(methyl)carbamoyl)pyridin-2-yl)methyl)(2-methoxyethyl)carbamate (80 mg) was obtained.

MS(ESI m/z): 354 (M+H)
RT(min): 1.16

(3)

In the same manner as in Reference Example 22-5 (6), the following compound was obtained.

tert-Butyl ((6-acetylpyridin-2-yl)methyl)(2-methoxyethyl)carbamate

MS(ESI m/z): 309 (M+H)
RT(min): 1.40

Reference Example 22-7-1

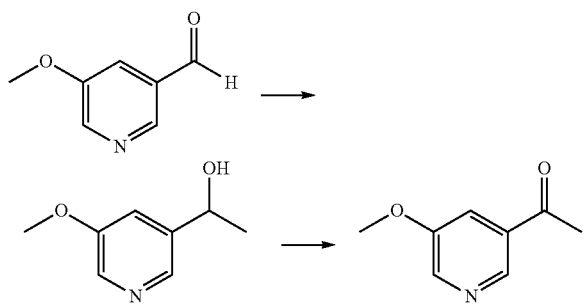

(1)

A 3.0 mol/L methyl magnesiumchloride tetrahydrofuran solution (2.6 mL) was added to a solution of 5-methoxynicotinic aldehyde (707 mg) in tetrahydrofuran (20 mL) at 0° C., followed by stirring for 1 hour. A saturated ammonium chloride aqueous solution (3 mL) was added to the reaction mixture, followed by stirring at 0° C. for 0.5 hours, and a saturated sodium hydrogen carbonate aqueous solution was added thereto. The resultant product was extracted with ethyl acetate, the organic layer was washed with a saturated sodium chloride aqueous solution and dried over anhydrous sodium sulfate, and the solvent was distilled off under reduced pressure, whereby 1-(5-methoxypyridin-3-yl)ethanol (560 mg) was obtained as an orange oily material.

$^1$H-NMR (CDCl$_3$, 300 MHz) δ: 8.27-8.17 (2H, m), 7.32-7.24 (1H, m), 5.04-4.91 (1H, m), 3.92-3.85 (3H, m), 2.09-1.96 (1H, m), 1.58-1.50 (3H, m).

MS(ESI m/z): 154 (M+H)
RT(min): 0.28

(2)

Dichloromethane (10 mL) was added to a mixture of 1-(5-methoxypyridin-3-yl)ethanol (560 mg) and manganese dioxide (1.59 g), followed by stirring at room temperature for 24 hours. Manganese dioxide (1.59 g) was added thereto, followed by stirring at room temperature for 24 hours. The insoluble materials were filtered off, and the solvent was distilled off under reduced pressure. The obtained residues were purified by silica gel column chromatography (hexane:ethyl aceate=1:0→3:7), whereby 1-(5-methoxypyridin-3-yl)ethanone (393 mg) was obtained as a pale yellow solid.

$^1$H-NMR (CDCl$_3$, 300 MHz) δ: 8.77 (1H, d, J=1.3 Hz), 8.50 (1H, d, J=3.0 Hz), 7.71 (1H, dd, J=3.0, 1.3 Hz), 3.91 (3H, s), 2.65 (3H, s).

Reference Example 22-7-2

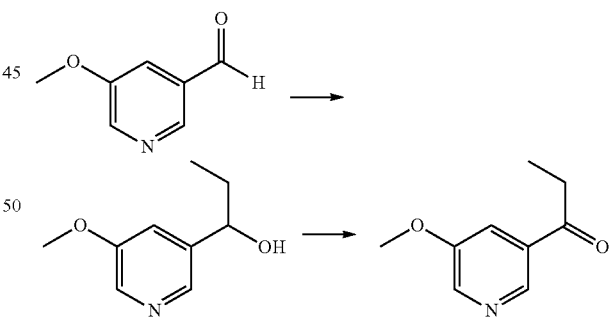

In the same manner as in Reference Example 22-7-1, the following compounds were obtained.

1-(5-Methoxypyridin-3-yl)propane-1-ol 1-(5-Methoxypyridin-3-yl)propan-1-one $^1$H-NMR (CDCl$_3$, 300 MHz) δ: 8.78 (1H, d, J=1.3 Hz), 8.48 (1H, d, J=3.3 Hz), 7.72 (1H, dd, J=3.3, 1.3 Hz), 3.91 (3H, s), 3.03 (2H, q, J=7.3 Hz), 1.25 (3H, t, J=7.3 Hz).

Reference Example 22-7-3

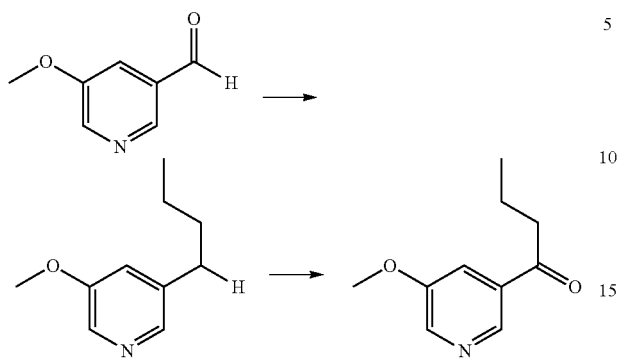

In the same manner as in Reference Example 22-7-1, the following compounds were obtained.

1-(5-Methoxypyridin-3-yl)butane-1-ol 1-(5-Methoxypyridin-3-yl)butan-1-one $^1$H-NMR (CDCl$_3$, 300 MHz) δ: 8.77 (1H, d, J=1.3 Hz), 8.48 (1H, d, J=3.0 Hz), 7.71 (1H, dd, J=3.0, 1.3 Hz), 3.91 (3H, s), 2.97 (2H, t, J=7.3 Hz), 1.79 (2H, tq, J=7.3, 7.3 Hz), 1.02 (3H, t, J=7.3 Hz).

Reference Example 22-7-4

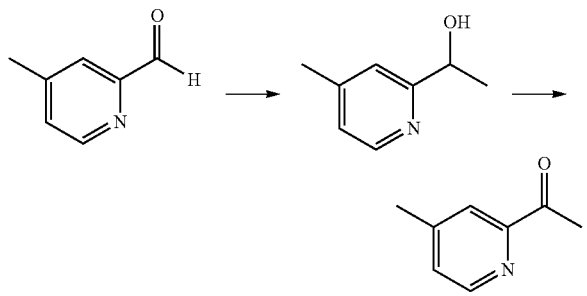

(1)
In the same manner as in Reference Example 22-7-1 (1), the following compound was obtained.

1-(4-Methylpyridin-2-yl)ethanol (2)
In the same manner as in Reference Example 21-3, the following compound was obtained.

1-(4-Methylpyridin-2-yl)ethanone $^1$H-NMR (CDCl$_3$, 300 MHz) δ: 8.54 (1H, d, J=5.3 Hz), 7.87 (1H, s), 7.29 (1H, d, J=5.3 Hz), 2.72 (3H, s), 2.43 (3H, s).

Reference Example 22-7-5

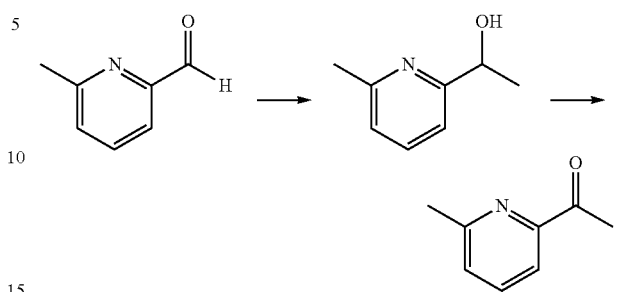

In the same manner as in Reference Example 22-7-4, the following compounds were obtained.

1-(6-Methylpyridin-2-yl)ethanol 1-(6-Methylpyridin-2-yl)ethanone $^1$H-NMR (CDCl$_3$, 300 MHz) δ: 7.84 (1H, d, J=7.9 Hz), 7.70 (1H, d, J=7.9, 7.9 Hz), 7.32 (1H, d, J=7.9 Hz), 2.72 (3H, s), 2.62 (3H, s).
MS(ESI m/z): 136 (M+H)
RT(min): 0.64

Reference Example 22-8

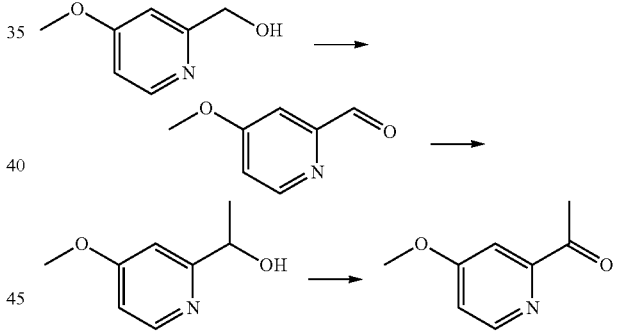

(1)
In the same manner as in Reference Example 21-1-1 (2), the following compound was obtained.

4-Methoxypicolinic aldehyde (2)
In the same manner as in Reference Example 22-7-1 (1), the following compound was obtained.

1-(4-Methoxypyridin-2-yl)ethanol (3)
In the same manner as in Reference Example 21-1-1 (2), the following compound was obtained.

1-(4-methoxypyridin-2-yl)ethanone

MS(ESI m/z): 152 (M+H)
RT(min): 0.43

Reference Example 22-9-1

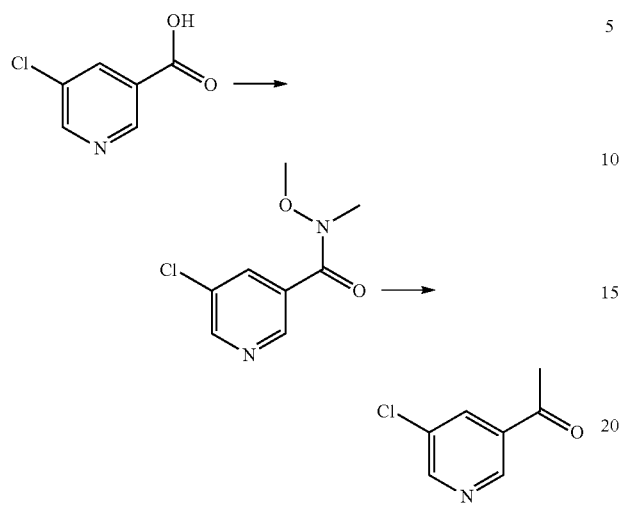

(1)
In the same manner as in Reference Example 22-3 (3), the following compound was obtained.

5-Chloro-N-methoxy-N-methyl nicotinamide

MS(ESI m/z): 201 (M+H)
RT(min): 0.81

(2)
In the same manner as in Reference Example 22-5 (6), the following compound was obtained.

1-(5-Chloro pyridin-3-yl)ethanone

Reference Example 22-9-2

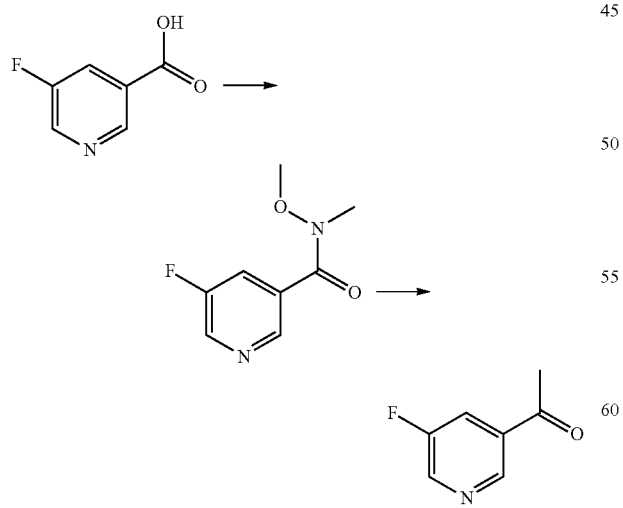

In the same manner as in Reference Example 22-9-1, the following compound was obtained.

5-Fluoro-N-methoxy-N-methyl nicotinamide 1-(5-Fluoro pyridin-3-yl)ethanone

Reference Example 22-10-1

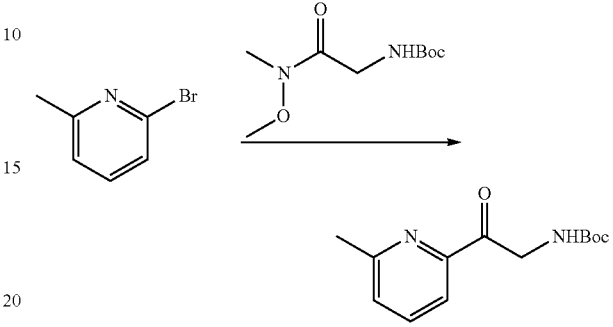

1.6 mol/L butyl lithium/hexane (2.9 mL) was added to a solution of 2-bromo-6-methyl pyridine (791 mg) in tetrahydrofuran (10 mL) at −78° C., followed by stirring at the same temperature for 0.5 hours. A solution of tert-butyl (2-(methoxy(methyl)amino)-2-oxoethyl)carbamate (500 mg) in tetrahydrofuran (5 mL) was added thereto at the same temperature, followed by stirring at room temperature for 24 hours. An aqueous saturated ammonium chloride solution was added to the reaction mixture, and extraction thereof was performed using ethyl acetate. The organic layer was washed with a saturated aqueous sodium chloride solution, and dried over anhydrous sodium sulfate. The solvent was distilled off under reduced pressure, and the obtained residues were purified by silica gel column chromatography (hexane:ethyl aceate=1:0→1:1), whereby tert-butyl (2-(6-methylpyridin-2-yl)-2-oxoethyl)carbamate (56 mg) was obtained as a yellow oily material.

$^1$H-NMR (CDCl$_3$, 300 MHz) δ: 7.84 (1H, d, J=7.9 Hz), 7.71 (1H, t, J=7.9 Hz), 7.34 (1H, d, J=7.3 Hz), 5.42 (1H, brs), 4.90 (2H, d, J=5.3 Hz), 2.59 (3H, s), 1.48 (9H, s).

Reference Example 22-10-2

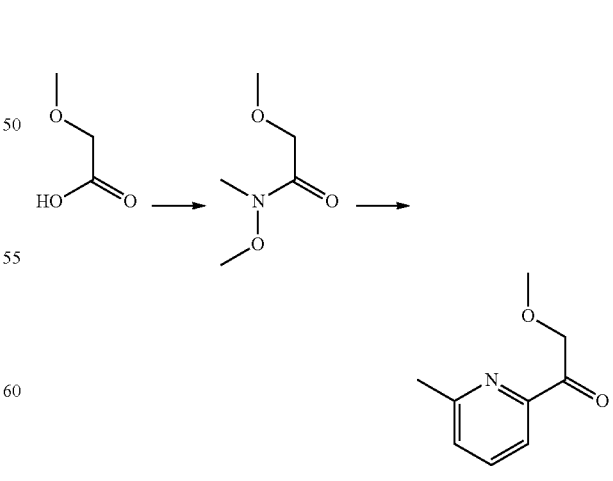

(1)
In the same manner as in Reference Example 22-3 (3), the following compound was obtained.

N,2-dimethoxy-N-methyl acetamide $^1$H-NMR (CDCl$_3$, 300 MHz) δ: 4.22 (2H, s), 3.69 (3H, s), 3.47 (3H, s), 3.20 (3H, s).

(2)
In the same manner as in Reference Example 22-10-1, the following compound was obtained.

2-Methoxy-1-(6-methyl pyridin-2-yl)ethanone

MS(ESI m/z): 166 (M+H)
RT(min): 0.82

Reference Example 22-11-1

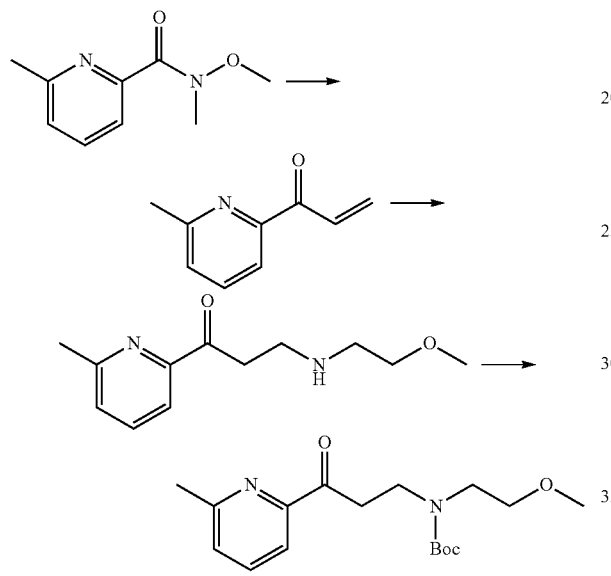

(1)
Under ice-cooling, 1.0 mol/L vinylmagnesium bromide/tetrahydrofuran (3.4 mL) was added to a solution of N-methoxy-N,6-dimethyl picolinamide (597 mg) in tetrahydrofuran (11 mL), followed by stirring for 10 minutes. A saturated sodium chloride aqueous solution and a saturated sodium hydrogen carbonate aqueous solution were added to the reaction mixture, then, the resultant product was extracted with ethyl acetate, and the organic layer was dried over anhydrous sodium sulfate. The solvent was distilled off under reduced pressure, and the obtained residues were purified by silica gel column chromatography (hexane:ethyl acetate=17:3→7:3), whereby 1-(6-methylpyridin-2-yl)-2-propen-1-one (85 mg) was obtained.
MS(ESI m/z): 148 (M+H)
RT(min): 0.98

(2)
2-Methoxyethylamine (97 mg) was added to a solution of 1-(6-methylpyridin-2-yl)-2-propen-1-one (20 mg) obtained in Reference Example 22-11-1 (1) in tetrahydrofuran (1 mL), followed by stirring at room temperature for 0.5 hours. A saturated ammonium chloride aqueous solution was added to the reaction mixture, then, the resultant product was extracted with chloroform, and the organic layer was dried over anhydrous sodium sulfate. The solvent was distilled off under reduced pressure, whereby 3-((2-methoxyethyl)amino)-1-(6-methylpyridin-2-yl)propan-1-one was obtained.

MS(ESI m/z): 223 (M+H)
RT(min): 0.52

(3)
Di-tert-butyl dicarbonate (296 mg), N,N-dimethyl-4-aminopyridine (4.8 mg), and triethylamine (190 μL) were added to a solution of 3-((2-methoxyethyl)amino)-1-(6-methylpyridin-2-yl)propan-1-one obtained in Reference Example 22-11-1 (2) in dichloromethane (5 mL), followed by stirring for 1 hour. Methanol (1 mL) was added to the reaction mixture, followed by stirring for 15 minutes, and the solvent was distilled off under reduced pressure. The obtained residues were purified by silica gel column chromatography (hexane:ethyl aceate=4:1→2:1), whereby tert-butyl (2-methoxyethyl)(3-(6-methylpyridin-2-yl)-3-oxo propyl)carbamate (25 mg) was obtained.
MS(ESI m/z): 323 (M+H)
RT(min): 1.47

Reference Example 22-11-2

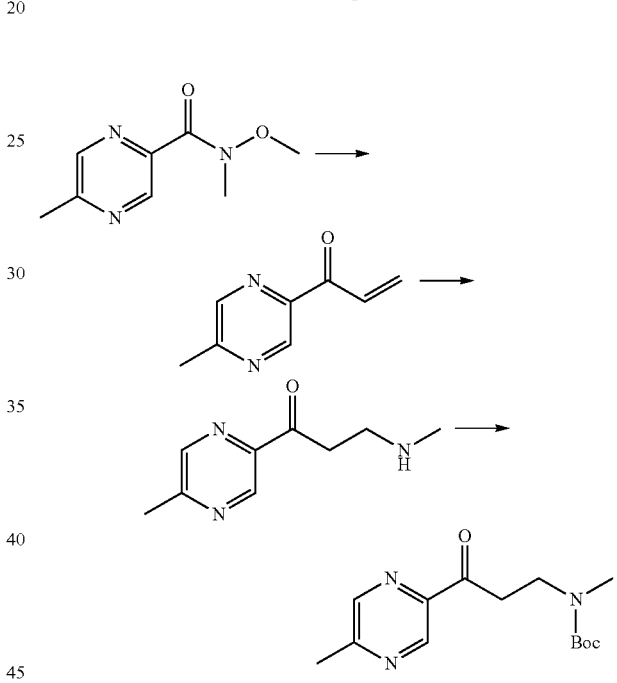

(1)
In the same manner as in Reference Example 22-11-1 (1), the following compound was obtained.

1-(5-Methyl pyrazin-2-yl)-2-propen-1-one

MS(ESI m/z): 149 (M+H)
RT(min): 0.99

(2)
2.0 mol/L methyl amine/methanol (1.3 mL) was added to a solution of 1-(5-methylpyrazin-2-yl)-2-propen-1-one (129 mg) obtained in Reference Example 22-11-2 (1) in tetrahydrofuran (10 mL), followed by stirring at room temperature for 10 minutes. The solvent was distilled off under reduced pressure, whereby 3-(methylamino)-1-(5-methylpyrazin-2-yl)propan-1-one was obtained.
MS(ESI m/z): 180 (M+H)
RT(min): 0.31

(3)
In the same manner as in Reference Example 22-11-1 (3), the following compound was obtained.

tert-Butyl methyl (3-(5-methylpyrazin-2-yl)-3-oxo-propyl)carbamate

MS(ESI m/z): 280 (M+H)
RT(min): 1.25

Reference Example 22-12

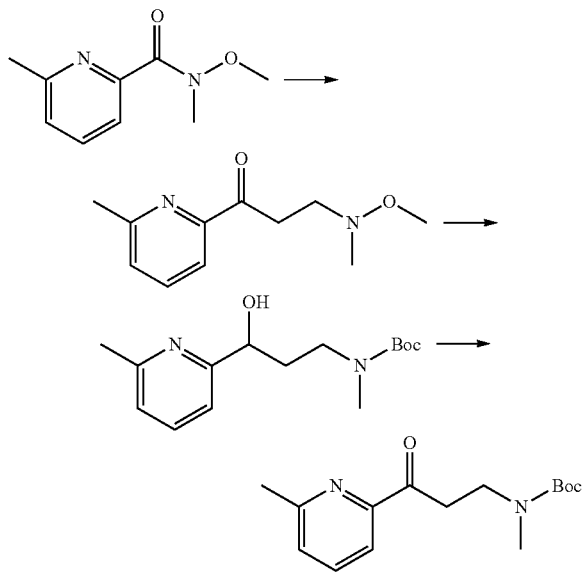

(1)
1.0 mol/L vinylmagnesium bromide/tetrahydrofuran (17 mL) was added to a solution of N-methoxy-N,6-dimethyl picolinamide (3.6 g) in tetrahydrofuran (50 mL), followed by stirring at −78° C. for 5 minutes. After acetic acid (1.5 mL) was added to the reaction mixture, the temperature was raised to room temperature, then, water was added thereto, and the resultant product was extracted with ethyl acetate. The organic layer was dried over anhydrous sodium sulfate, and the solvent was distilled off under reduced pressure. The obtained residues were purified by silica gel column chromatography (hexane:ethyl acetate=2:1→0:1), whereby 3-(methoxy(methyl)amino)-1-(6-methylpyridin-2-yl)propan-1-one (2.48 g) was obtained.

MS(ESI m/z): 209 (M+H)
RT(min): 0.89

(2)
A solution of 3-(methoxy(methyl)amino)-1-(6-methyl-pyridin-2-yl)propan-1-one (100 mg) obtained in Reference Example 22-12 (1) in methanol (10 mL) was subjected to a hydrogenation reaction (80° C., 60 bar, flow rate of 1 mL/min, RaNi) using a flow type hydrogenation reaction apparatus. The reaction mixture was cooled to room temperature, and the solvent was distilled off under reduced pressure. Triethylamine (100 μL) and di-tert-butyl dicarbonate (126 μL) were added to a solution of the obtained residues in dichloromethane (3 mL), followed by stirring at room temperature for 10 minutes. Methanol was added to the reaction mixture, then, the solvent was distilled off under reduced pressure, and the obtained residues were purified by silica gel column chromatography (hexane:ethyl acetate=1:1), whereby tert-butyl (3-hydroxy-3-(6-methylpyridin-2-yl)propyl)(methyl)carbamate (69 mg) was obtained.

MS(ESI m/z): 281 (M+H)
RT(min): 0.79

(3)
1,1,1-Triacetoxy-1,1-dihydro-1,2-benziodoxol-3-(1H)-one (125 mg) was added to a solution of tert-butyl (3-hydroxy-3-(6-methylpyridin-2-yl)propyl)(methyl)carbamate (69 mg) obtained in Reference Example 22-12 (2) in dichloromethane (2 mL), and the resultant product was irradiated with microwaves (microwave reaction apparatus, 50° C., 10 minutes, 2.45 GHz, 0 W to 240 W). A saturated sodium hydrogen carbonate aqueous solution and a sodium thiosulfate aqueous solution were added to the reaction mixture, then, the resultant product was extracted with chloroform, and the organic layer was dried over anhydrous sodium sulfate. The solvent was distilled off under reduced pressure, and the obtained residues were purified by silica gel column chromatography (hexane:ethyl aceate=4:1-3:1), whereby tert-butyl methyl (3-(6-methylpyridin-2-yl)-3-oxopropyl)carbamate (61 mg) was obtained.

MS(ESI m/z): 279 (M+H)
RT(min): 1.46

Reference Example 22-13-1

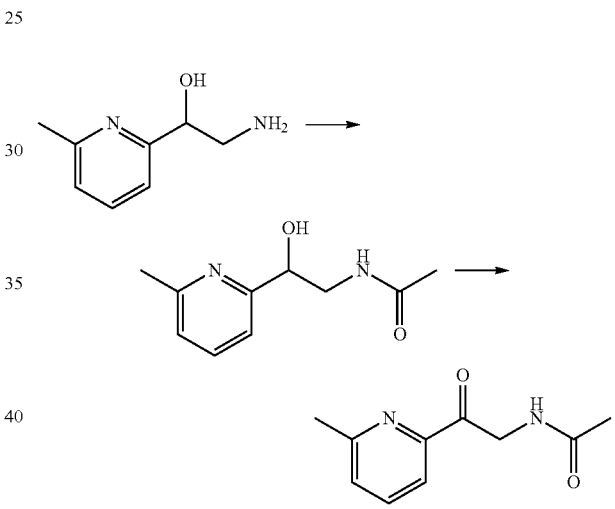

(1)
Triethylamine (183 μL) and acetic anhydride (73 mg) were added to a solution of 2-amino-1-(6-methylpyridin-2-yl)ethanol (100 mg) in ethyl acetate (6.5 mL), followed by stirring at room temperature for 5 minutes. The solvent was distilled off under reduced pressure, and the obtained residues were purified by silica gel column chromatography (ethyl acetate:methanol=1:0→19:1), whereby N-(2-hydroxy-2-(6-methylpyridin-2-yl)ethyl)acetamide (88 mg) was obtained.

MS(ESI m/z): 195 (M+H)

(2)
In the same manner as in Reference Example 22-12 (3), the following compound was obtained.

N-(2-(6-methylpyridin-2-yl)-2-oxoethyl)acetamide

MS(ESI m/z): 193 (M+H)
RT(min): 0.56

Reference Example 22-13-2

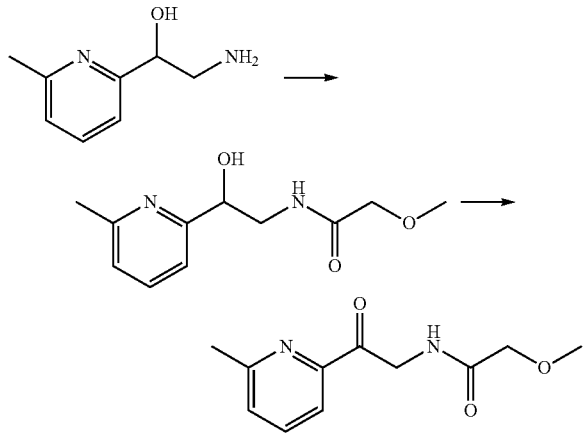

(1)

Using 2-methoxyacetyl chloride instead of acetic anhydride in Reference Example 22-13-1 (1), the following compound was obtained.

N-(2-hydroxy-2-(6-methylpyridin-2-yl)ethyl)-2-methoxyacetamide

MS(ESI m/z): 225 (M+H)

(2)

In the same manner as in Reference Example 22-12 (3), the following compound was obtained.

2-Methoxy-N-(2-(6-methylpyridin-2-yl)-2-oxoethyl)acetamide

MS(ESI m/z): 223 (M+H)
RT(min): 0.76

Reference Example 22-14-1

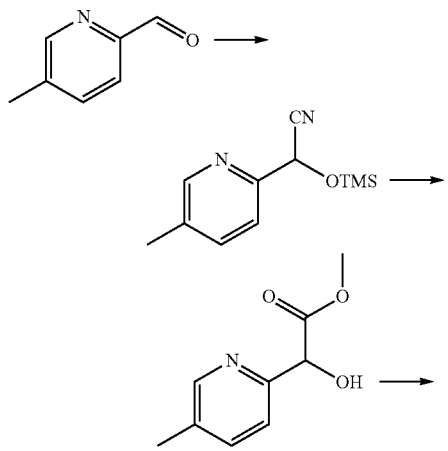

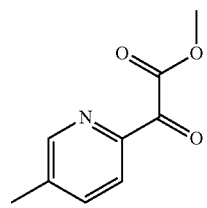

(1)

Under ice-cooling, zinc iodide (II) (1.2 g) and trimethyl silylcyanide (0.93 mL) were added to a solution of 5-methyl picolinic aldehyde (451 mg) in dichloromethane (10 mL), followed by stirring for 3 hours. The insolubles were filtered off, and the solvent was distilled off under reduced pressure. Methanol (6 mL) and concentrated hydrochloric acid (4 mL) were added to the obtained residues, followed by refluxing for 2 hours. After the reaction mixture was cooled to 0° C., potassium carbonate and water were added thereto, and the resultant product was extracted with ethyl acetate. The organic layer was dried over anhydrous sodium sulfate, and the solvent was distilled off under reduced pressure, whereby methyl 2-hydroxy-2-(5-methylpyridin-2-yl)acetate (317 mg) was obtained as a yellow solid.

MS(ESI m/z): 182 (M+H)
RT(min): 0.76

(2)

In the same manner as in Reference Example 21-5 (2), the following compound was obtained.

Methyl 2-(5-methylpyridin-2-yl)-2-oxoacetate $^1$H-NMR (CDCl$_3$, 300 MHz) δ: 8.57 (1H, s), 8.02 (1H, d, J=7.8 Hz), 7.70 (1H, d, J=7.8 Hz), 4.00 (3H, s), 2.45 (3H, s).

Reference Example 22-14-2

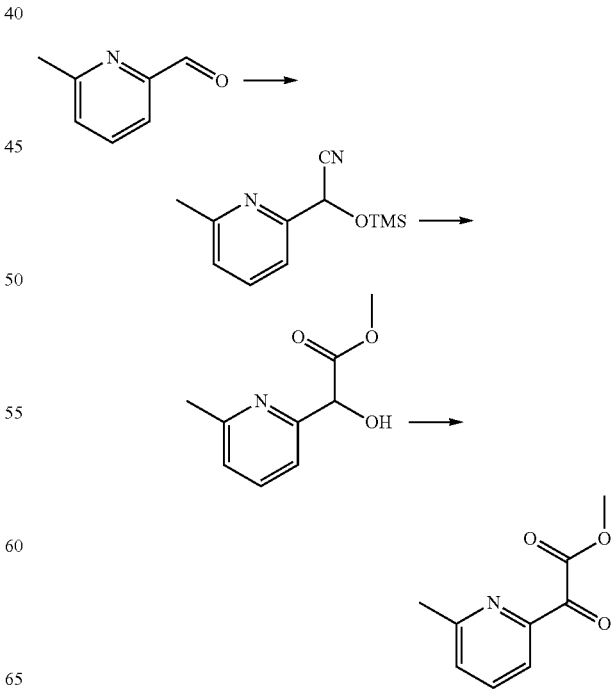

In the same manner as in Reference Example 22-14-1, the following compounds were obtained.

Methyl 2-hydroxy-2-(6-methylpyridin-2-yl)acetate

MS(ESI m/z): 182 (M+H)
RT(min): 0.36

Methyl 2-(6-methylpyridin-2-yl)-2-oxoacetate $^1$H-NMR (CDCl$_3$, 300 MHz) δ: 7.92 (1H, d, J=7.8 Hz), 7.77 (1H, t, J=7.5 Hz), 7.39 (1H, d, J=7.2 Hz), 4.00 (3H, s), 2.61 (3H, s).
MS(ESI m/z): 180 (M+H)
RT(min): 0.43

Reference Example 22-15

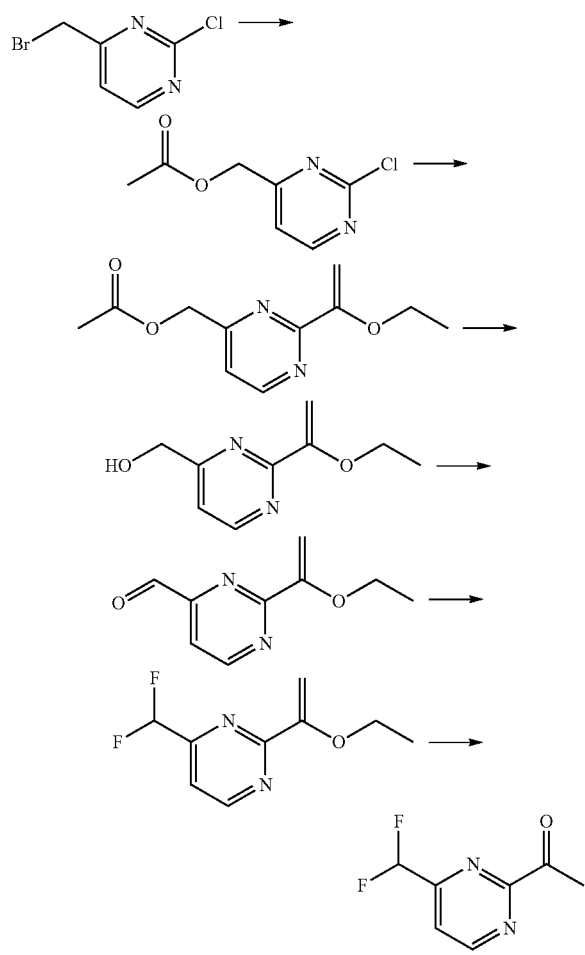

(1)
In the same manner as in Reference Example 22-5 (3), the following compound was obtained.

(2-Chloropyrimidin-4-yl)methyl acetate

MS(ESI m/z): 187 (M+H)
RT(min): 0.77

(2)
A solution of (2-chloropyrimidin-4-yl)methyl acetate (400 mg) obtained in Reference Example 22-15 (1), lithium chloride (109 mg), bis(triphenylphosphine)palladium (II) dichloride (45 mg), and tributyl (1-ethoxyvinyl) tin (800 μL) in 1-methyl-2-pyrrolidone (4 mL) was irradiated with microwaves (microwave reaction apparatus, 130° C., 0.5 hours, 2.45 GHz, 0 W to 240 W). After the reaction mixture was cooled to room temperature, a potassium fluoride aqueous solution was added thereto, and the resultant product was extracted with a mixed solvent of ethyl acetate and hexane. The organic layer was dried over anhydrous sodium sulfate, and the solvent was distilled off under reduced pressure. The obtained residues were purified by silica gel column chromatography (hexane:ethyl acetate=4:1→1:1), whereby (2-(1-ethoxyvinyl)pyrimidin-4-yl)methyl acetate (298 mg) was obtained.
MS(ESI m/z): 223 (M+H)
RT(min): 0.96

(3)
In the same manner as in Reference Example 22-5 (4), the following compound was obtained.

(2-(1-Ethoxyvinyl)pyrimidin-4-yl)methanol

MS(ESI m/z): 181 (M+H)
RT(min): 0.66

(4)
1,1,1-Triacetoxy-1,1-dihydro-1,2-benziodoxol-3-(1H)-one (119 mg) was added to a solution of (2-(1-ethoxyvinyl)pyrimidin-4-yl)methanol obtained in Reference Example 22-15 (3) in dichloromethane (3 mL) under ice-cooling, and the resultant product was stirred at the same temperature for 0.5 hours, and stirred at room temperature for 2 hours. A saturated sodium hydrogen carbonate aqueous solution was added to the reaction mixture, and the resultant product was extracted with ethyl acetate. The organic layer was dried over anhydrous sodium sulfate, and the solvent was distilled off under reduced pressure. The obtained residues were purified by silica gel column chromatography (hexane:ethyl acetate=1:1), whereby 2-(1-ethoxyvinyl)pyrimidine-4-carbaldehyde (27 mg) was obtained.

(5)
Bis(2-methoxyethyl)aminosulfur trifluoride (335 mg) was added to a solution of 2-(1-ethoxyvinyl)pyrimidine-4-carbaldehyde (27 mg) obtained in Reference Example 22-15 (4) in dichloromethane (1.3 mL) at −78° C., and the resultant product was stirred at the same temperature for 0.5 hours, and stirred for 0.5 hours under ice-cooling. A small amount of methanol and saturated sodium chloride aqueous solution was added to the reaction mixture, and the resultant product was extracted with chloroform. The organic layer was dried over anhydrous sodium sulfate, and the solvent was distilled off under reduced pressure. The obtained residues were purified by silica gel column chromatography (hexane:ethyl acetate=3:1→2:1), whereby 4-(difluoromethyl)-2-(1-ethoxyvinyl)pyrimidine (13 mg) was obtained.
MS(ESI m/z): 201 (M+H)
RT(min): 1.10

(6)
2 mol/L hydrochloric acid (0.5 mL) was added to a solution of 4-(difluoromethyl)-2-(1-ethoxyvinyl)pyrimidine (13 mg) obtained in Reference Example 22-15 (5) in acetone (0.75 mL), followed by stirring at room temperature for 1.5 hours. Saturated sodium hydrogen carbonate aqueous solution and a saturated sodium chloride aqueous solution were added to the reaction mixture, and the resultant product was extracted with ethyl acetate. The organic layer was dried over anhydrous sodium sulfate, and the solvent was distilled off under reduced pressure, whereby 1-(4-(difluoromethyl)pyrimidin-2-yl)ethanone was obtained.

MS(ESI m/z): 173 (M+H)
RT(min): 0.69

Reference Example 22-16

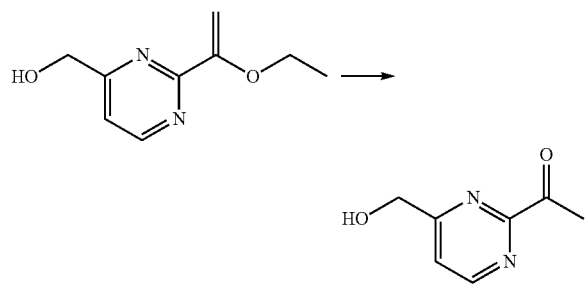

In the same manner as in Reference Example 22-15 (6), the following compound was obtained.

1-(4-(Hydroxymethyl)pyrimidin-2-yl)ethanone

MS(ESI m/z): 153 (M+H)
RT(min): 0.41

Reference Example 22-17

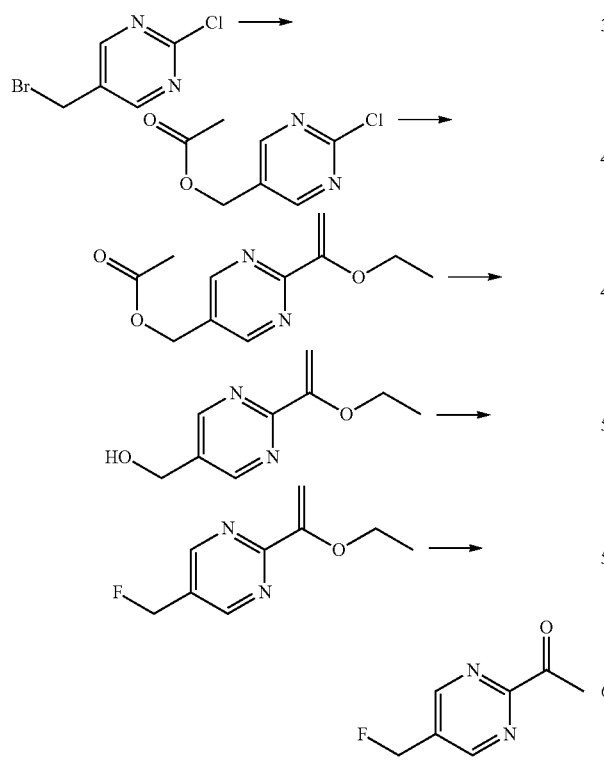

(1)
In the same manner as in Reference Example 22-5 (3), the following compound was obtained.

(2-Chloropyrimidin-5-yl)methyl acetate

MS(ESI m/z): 187 (M+H)
RT(min): 0.77

(2)
In the same manner as in Reference Example 22-15 (2), the following compound was obtained.

(2-(1-Ethoxyvinyl)pyrimidin-5-yl)methyl acetate

MS(ESI m/z): 223 (M+H)
RT(min): 0.94

(3)
In the same manner as in Reference Example 22-5 (4), the following compound was obtained.

(2-(1-Ethoxyvinyl)pyrimidin-5-yl)methanol

MS(ESI m/z): 181 (M+H)
RT(min): 0.65

(4)
Bis(2-methoxyethyl)aminosulfur trifluoride (59 mg) was added to a solution of (2-(1-ethoxyvinyl)pyrimidin-5-yl)methanol (25 mg) obtained in Reference Example 22-17 (3) in dichloromethane (1.3 mL), and the resultant product was stirred at −30° C. for 1 hour, and stirred for 15 minutes under ice-cooling. A saturated sodium hydrogen carbonate aqueous solution was added to the reaction mixture, and the resultant product was extracted with ethyl acetate. The organic layer was dried over anhydrous sodium sulfate, and the solvent was distilled off under reduced pressure. The obtained residues were purified by silica gel column chromatography (hexane:ethyl acetate=3:1→2:1), whereby 2-(1-ethoxyvinyl)-5-(fluoromethyl)pyrimidine (3.8 mg) was obtained.

MS(ESI m/z): 183 (M+H)
RT(min): 0.89

(5)
Using tetrahydrofuran instead of acetone in Reference Example 22-15 (6), the following compound was obtained.

1-(5-(Fluoro methyl)pyrimidin-2-yl)ethanone

MS(ESI m/z): 155 (M+H)
RT(min): 0.55

Reference Example 22-18

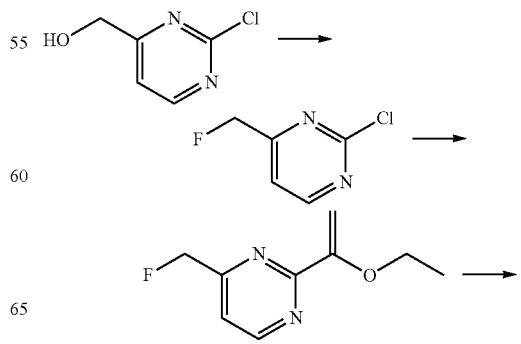

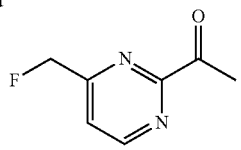

(1)

In the same manner as in Reference Example 22-17 (4), the following compound was obtained.

2-Chloro-4-(fluoromethyl)pyrimidine (2)

In the same manner as in Reference Example 22-15 (2), the following compound was obtained.

2-(1-Ethoxyvinyl)-4-(fluoro methyl)pyrimidine

MS(ESI m/z): 183 (M+H)
RT(min): 0.94

(3)

4-Methyl benzenesulfonic acid monohydrate (30 mg) was added to a solution of 2-(1-ethoxyvinyl)-4-(fluoromethyl) pyrimidine obtained in Reference Example 22-18 (2) in tetrahydrofuran (1.5 mL) and water (1.5 mL), followed by stirring at room temperature for 0.5 hours, and the resultant product was irradiated with microwaves (microwave reaction apparatus, 70° C., 15 minutes, 2.45 GHz, 0 W to 240 W). The reaction mixture was cooled to room temperature, then, an aqueous saturated sodium hydrogen carbonate solution was added thereto, and the resultant product was extracted with ethyl acetate. The organic layer was dried over anhydrous sodium sulfate, and the solvent was distilled off under reduced pressure. The obtained residues were purified by silica gel column chromatography (hexane:ethyl aceate=2:1→1:1), whereby 1-(4-(fluoromethyl)pyrimidin-2-yl)ethanone (4 mg) was obtained as a white solid.

MS(ESI m/z): 155 (M+H)
RT(min): 0.56

Reference Example 22-19

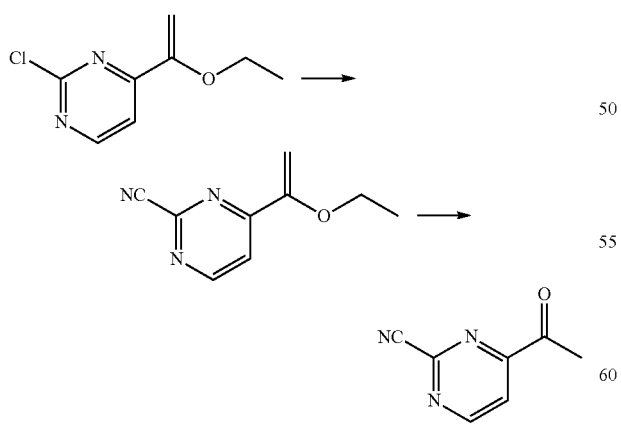

(1)

Zinc cyanide (II) (28 mg) and tetrakis(triphenylphosphine)palladium (0) (23 mg) were added to a solution of 2-chloro-4-(1-ethoxyvinyl)pyrimidine (73 mg) in 1-methyl-2-pyrrolidone (1 mL), and the resultant product was irradiated with microwaves (microwave reaction apparatus, 130° C., 1 hour, 2.45 GHz, 0 W to 240 W). After the reaction mixture was cooled to room temperature, a saturated sodium hydrogen carbonate aqueous solution was added thereto, and the resultant product was extracted with a mixed solvent of ethyl acetate and hexane. The organic layer was dried over anhydrous sodium sulfate, and the solvent was distilled off under reduced pressure. The obtained residues were purified by silica gel column chromatography (hexane:ethyl aceate=20:1→5:1), whereby 4-(1-ethoxyvinyl)pyrimidine-2-carbonitrile (16 mg) was obtained as a white solid.

MS(ESI m/z): 176 (M+H)
RT(min): 1.33

(2)

In the same manner as in Reference Example 22-15 (6), the following compound was obtained.

4-Acetyl pyrimidine-2-carbonitrile

Reference Example 22-20-1

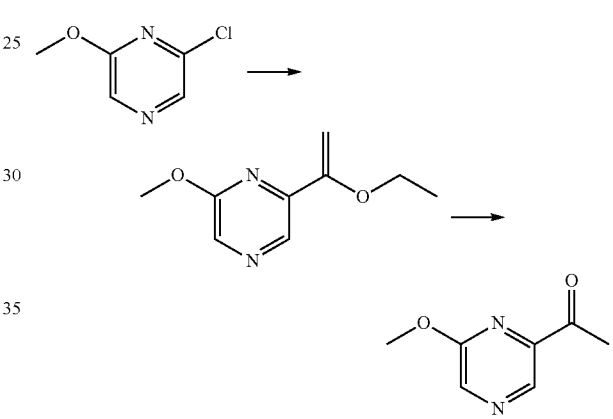

(1)

In the same manner as in Reference Example 22-15 (2), the following compound was obtained.

2-(1-Ethoxyvinyl)-6-methoxypyrazine

MS(ESI m/z): 181 (M+H)
RT(min): 1.41

(2)

In the same manner as in Reference Example 22-15 (6), the following compound was obtained.

1-(6-Methoxypyrazin-2-yl)ethanone

MS(ESI m/z): 153 (M+H)
RT(min): 0.85

Reference Example 22-20-2

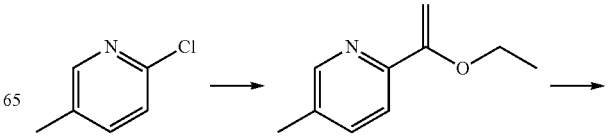

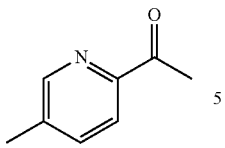

In the same manner as in Reference Example 22-20-1, the following compounds were obtained.

2-(1-Ethoxyvinyl)-5-methyl pyridine

MS(ESI m/z): 164 (M+H)
RT(min): 0.63

1-(5-Methylpyridin-2-yl)ethanone

MS(ESI m/z): 136 (M+H)
RT(min): 0.75

Reference Example 22-21

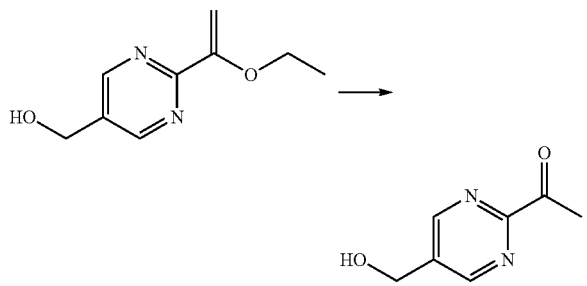

Using tetrahydrofuran instead of acetone, the following compound was obtained in the same manner as in Reference Example 22-15 (6).

1-(5-(Hydroxymethyl)pyrimidin-2-yl)ethanone

MS(ESI m/z): 153 (M+H)
RT(min): 0.40

Reference Example 22-22

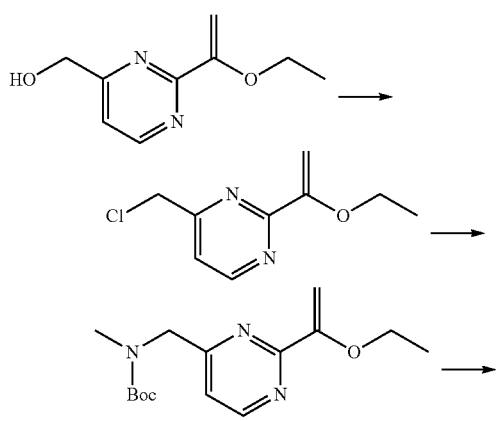

(1)

Triethylamine (0.598 mL) and methanesulfonyl chloride (0.221 mL) were added to a solution (1.4 mL) of (2-(1-ethoxyvinyl)pyrimidin-4-yl)methanol (129 mg) in dichloromethane, followed by stirring for 0.5 hours under ice-cooling. After the insoluble materials were filtered off, the filtrate was concentrated under reduced pressure, then, N,N-dimethyl formamide (1 mL), tert-butyl carbamate (186 mg), and triethylamine (0.3 mL) were added thereto, and the resultant product was irradiated with microwaves (microwave reaction apparatus, 80° C., 15 minutes, 2.45 GHz, 0 W to 240 W). After the reaction mixture was cooled to room temperature, water was added thereto, then, the resultant product was extracted with ethyl acetate, and the organic layer was dried over anhydrous sodium sulfate. The solvent was distilled off under reduced pressure, and the obtained residues were purified by silica gel column chromatography (hexane:ethyl acetate=4:1→3:1), whereby 4-chloromethyl-2-(1-ethoxyvinyl)pyrimidine (41 mg) was obtained.

MS(ESI m/z): 199 (M+H)

RT(min): 1.09

(2)

A solution of 4-chloro methyl-2-(1-ethoxyvinyl)pyrimidine (41 mg) obtained in Reference Example 22-22 (1) in tetrahydrofuran (5 mL) was added to 2.0 mol/L methyl amine/tetrahydrofuran (2 mL) under ice-cooling, followed by stirring for 1 hour. N,N-dimethyl formamide (4.5 mL), potassium carbonate (20 mg), and sodium iodide (20 mg) were added to the reaction mixture, and the resultant product was irradiated with microwaves (microwave reaction apparatus, 80° C., 10 minutes, 2.45 GHz, 0 W to 240 W). After the reaction mixture was cooled to room temperature, the solvent was distilled off under reduced pressure, and triethylamine (0.1 mL) and di-tert-butyl dicarbonate were added thereto, followed by stirring at room temperature for 10 minutes. After methanol was added to the reaction mixture, the solvent was distilled off under reduced pressure, then, water was added to the obtained residues, and the resultant product was extracted with a mixed solvent of ethyl acetate and hexane. The organic layer was dried over anhydrous sodium sulfate, then, the solvent was distilled off under reduced pressure, and the obtained residues were purified by silica gel column chromatography (hexane:ethyl aceate=4:1→1:1), whereby tert-butyl ((2-(1-ethoxyvinyl)pyrimidin-4-yl)methyl)(methyl)carbamate (38 mg) was obtained.

(3)

In the same manner as in Reference Example 22-21, the following compound was obtained.

tert-Butyl ((2-acetylpyrimidin-4-yl)methyl)(methyl)carbamate

MS(ESI m/z): 266 (M+H)
RT(min): 1.08

Reference Example 22-23

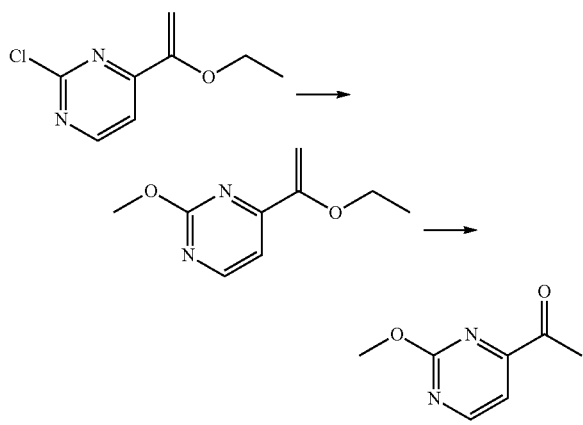

(1)
Sodium methoxide (43 mg) was added to a solution of 2-chloro-4-(1-ethoxyvinyl)pyrimidine (110 mg) in methanol (5 mL), and the resultant product was irradiated with microwaves (microwave reaction apparatus, 80° C., 15 minutes, 100° C., 2.45 GHz, 0 W to 240 W; 80° C., 0.5 hours, 110° C., 2.45 GHz, 0 W to 240 W). The reaction mixture was cooled to room temperature, then, tetrahydrofuran was added thereto, and the insoluble materials were filtered off. The filtrate was distilled off under reduced pressure, whereby 4-(1-ethoxyvinyl)-2-methoxypyrimidine was obtained.

(2)
In the same manner as in Reference Example 22-21, the following compound was obtained.

1-(2-Methoxypyrimidin-4-yl)ethanone

MS(ESI m/z): 153 (M+H)
RT(min): 0.75

Reference Example 22-24-1

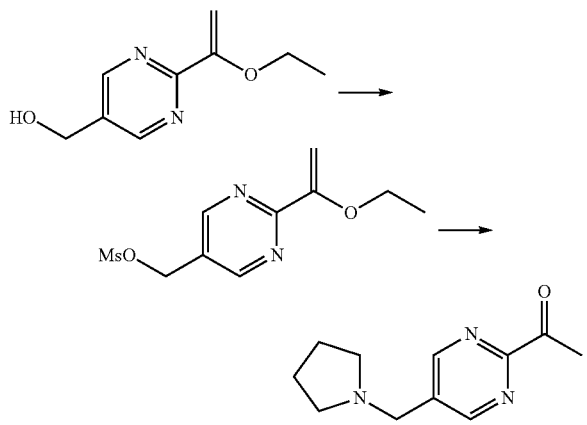

(1)
Under ice-cooling, methanesulfonyl chloride (52 μL) and triethylamine (141 μL) were added to a solution of (2-(1-ethoxyvinyl)pyrimidin-5-yl)methanol (61 mg) in dichloromethane (3.5 mL), followed by stirring for 0.5 hours. The solvent was distilled off under reduced pressure, then, a saturated ammonium chloride aqueous solution was added thereto, and the resultant product was extracted with ethyl acetate. The organic layer was dried over anhydrous sodium sulfate, and the solvent was distilled off under reduced pressure, whereby (2-(1-ethoxyvinyl)pyrimidin-5-yl)methyl methanesulfonate was obtained.

MS(ESI m/z): 259 (M+H)
RT(min): 0.90

(2)
Pyrrolidine (27 μL) was added to a solution of (2-(1-ethoxyvinyl)pyrimidin-5-yl)methyl methanesulfonate (28 mg) obtained in Reference Example 22-24-1 (1) in N,N-dimethyl formamide (0.5 mL), and the resultant product was irradiated with microwaves (microwave reaction apparatus, 100° C., 15 minutes, 2.45 GHz, 0 W to 240 W). The reaction mixture was cooled to room temperature, and purified by silica gel column chromatography (hexane:ethyl acetate=7:3, NH silica), and water was added to the obtained mixture, and the resultant product was extracted with ethyl acetate. The organic layer was dried over anhydrous sodium sulfate, and the solvent was distilled off under reduced pressure. 2 mol/L hydrochloric acid (1 mL) was added to a solution of the obtained residues in tetrahydrofuran (1.5 mL), followed by stirring at room temperature for 0.5 hours. The solvent was distilled off under reduced pressure, whereby 1-(5-(pyrrolidin-1-ylmethyl)pyrimidin-2-yl)ethanone was obtained.

Reference Example 22-24-2

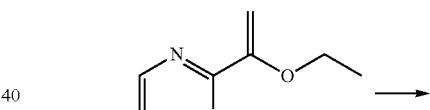

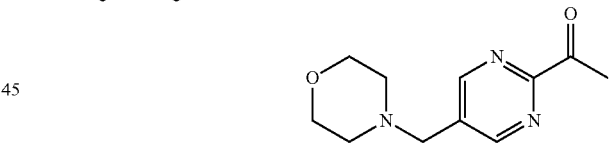

In the same manner as in Reference Example 22-24-1 (2), the following compound was obtained.

1-(5-(Morpholinomethyl)pyrimidin-2-yl)ethanone

Reference Example 22-25

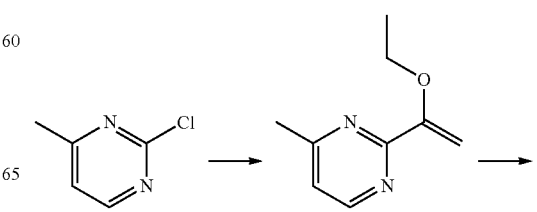

Reference Example 22-27

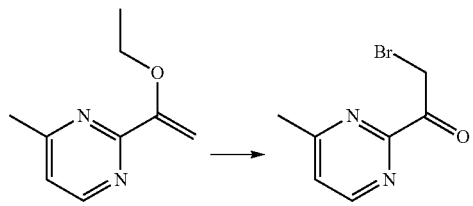

Water (3.5 mL) and N-bromosuccinimide (657 mg) were added to a solution of 2-(1-ethoxyvinyl)-4-methyl pyrimidine (605 mg) in tetrahydrofuran (31.5 mL), followed by stirring at room temperature for 0.5 hours. A sodium hydrogen carbonate aqueous solution was added to the reaction mixture, then, the resultant product was extracted with ethyl acetate, and the resultant product was washed sequentially with water and a saturated sodium chloride aqueous solution. The organic layer was dried over anhydrous sodium sulfate, and the solvent was distilled off under reduced pressure, whereby 2-bromo-1-(4-methylpyrimidin-2-yl)ethanone (820 mg) was obtained.

MS(ESI m/z): 215 (M+H)

RT(min): 0.80

Reference Example 22-28

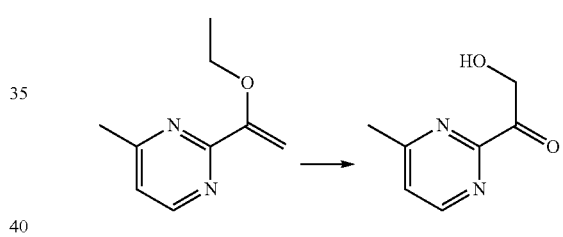

Metachloroperbenzoic acid (250 mg) was added to a solution of 2-(1-ethoxyvinyl)-4-methyl pyrimidine (605 mg) in dichloromethane (10 mL) under ice-cooling, followed by stirring at room temperature for 2 hours. 6.0 mol/L hydrochloric acid (2 mL) was added to the reaction mixture, followed by stirring at room temperature for 1 hour. The organic layer was collected by separation, and the aqueous layer was washed with chloroform. After the organic layer and the extraction liquid were combined, toluene (10 mL) was added thereto, then, the solvent was distilled off under reduced pressure, and the obtained residues were washed with chloroform, whereby 2-hydroxy-1-(4-methylpyrimidin-2-yl)ethanone (100 mg) was obtained.

MS(ESI m/z): 153 (M+H)

RT(min): 0.40

Reference Example 22-29

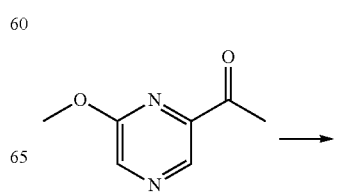

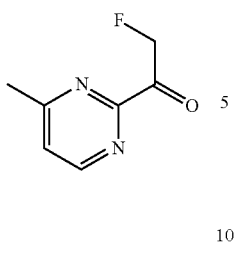

(1)

In the same manner as in Reference Example 22-15 (2), 2-(1-ethoxyvinyl)-4-methyl pyrimidine was obtained.

MS(ESI m/z): 165 (M+H)

RT(min): 0.83

(2)

1-Chloromethyl-4-fluoro-1,4-diazoniabicyclo[2,2,2]octane bis(tetrafluoroborate) (354 mg) was added to a solution of 2-(1-ethoxyvinyl)-4-methyl pyrimidine (164 mg) obtained in Reference Example 22-25 (1) in acetonitrile (1 mL), followed by stirring at room temperature for 18 hours. Ethyl acetate was added to the reaction mixture, then, the resultant product was filtered using Celite, and the solvent was distilled off under reduced pressure. The obtained residues were purified by silica gel column chromatography (hexane:ethyl aceate=1:1→0:1), whereby 2-fluoro-1-(4-methylpyrimidin-2-yl)ethanone (58 mg) was obtained.

MS(ESI m/z): 155 (M+H)

RT(min): 0.54

Reference Example 22-26

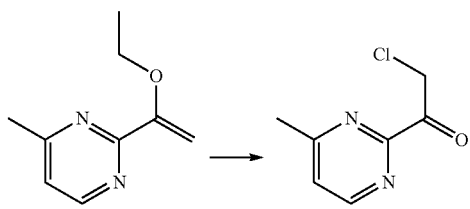

Water (4 mL) and N-chlorosuccinimide (534 mg) were added to a solution of 2-(1-ethoxyvinyl)-4-methyl pyrimidine (656 mg) obtained in Reference Example 22-25 (1) in tetrahydrofuran (36 mL), followed by stirring at 100° C. for 0.5 hours. After the reaction mixture was cooled to room temperature, a saturated sodium hydrogen carbonate aqueous solution was added thereto, then, the resultant product was extracted with ethyl acetate, and the resultant product was washed with a saturated sodium chloride aqueous solution. The organic layer was dried over anhydrous sodium sulfate, and the solvent was distilled off under reduced pressure, whereby 2-chloro-1-(4-methylpyrimidin-2-yl)ethanone (680 mg) was obtained.

MS(ESI m/z): 171 (M+H)

RT(min): 0.73

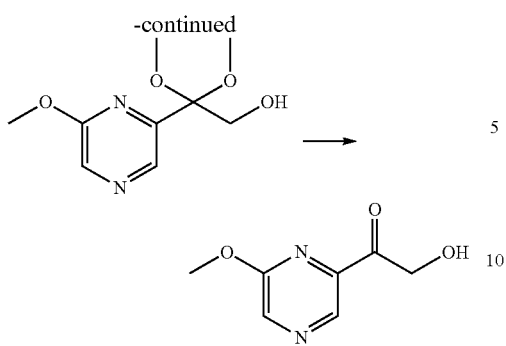

(1)

Potassium hydroxide (129 mg) was added to a solution of 1-(6-methoxypyrazin-2-yl)ethanone (71 mg) and iodobenzene diacetate (180 mg) in methanol (2.3 mL) at room temperature, followed by stirring for 0.5 hours. After the solvent was evaporated under reduced pressure, a saturated sodium chloride aqueous solution was added thereto, and the resultant product was extracted with chloroform. The organic layer was dried over anhydrous sodium sulfate, and the solvent was distilled off under reduced pressure. The obtained residues were purified by silica gel column chromatography (hexane:ethyl aceate=4:1→1:1), whereby 2,2-dimethoxy-2-(6-methoxypyrazin-2-yl)ethanol (55 mg) was obtained.

MS(ESI m/z): 215 (M+H)
RT(min): 0.69

(2)

4-Methyl benzenesulfonic acid monohydrate (5 mg) was added to a mixed solution of 2,2-dimethoxy-2-(6-methoxypyrazin-2-yl)ethanol (55 mg) obtained in Reference Example 22-29 (1) in tetrahydrofuran (2 mL) and water (0.5 mL), followed by stirring at room temperature for 1 hour, and the resultant product was irradiated with microwaves (microwave reaction apparatus, 100° C., 15 minutes, 2.45 GHz, 0 W to 240 W). The reaction mixture was cooled to room temperature, then, a saturated sodium chloride aqueous solution and saturated sodium hydrogen carbonate aqueous solution were added thereto, and the resultant product was extracted with ethyl acetate. The organic layer was dried over anhydrous sodium sulfate, and the solvent was distilled off under reduced pressure. The obtained residues were purified by silica gel column chromatography (hexane:ethyl aceate=2:1→1:1, NH silica), whereby 2-hydroxy-1-(6-methoxypyrazin-2-yl)ethanone was obtained as a white solid.

MS(ESI m/z): 169 (M+H)
RT(min): 0.57

Reference Example 22-30-1

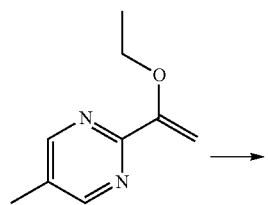

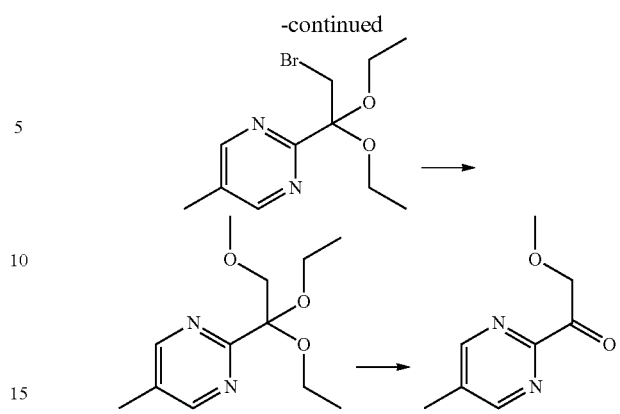

(1)

N-bromosuccinimide (344 mg) was added to an ethanol solution (9 mL) of 2-(1-ethoxyvinyl)-4-methyl pyrimidine (288 mg), followed by stirring at room temperature for 1 hour. A saturated sodium hydrogen carbonate aqueous solution was added to the reaction mixture, and the resultant product was extracted with ethyl acetate. The organic layer was washed with a saturated sodium chloride aqueous solution and dried over anhydrous sodium sulfate, then, the solvent was distilled off under reduced pressure, and the obtained residues were purified by silica gel column chromatography (hexane:ethyl acetate=1:1), whereby 2-(2-bromo-1,1-diethoxyethyl)-5-methyl pyrimidine (523 mg) was obtained.

MS(ESI m/z): 289 (M+H)
RT(min): 1.09

(2)

A 28% sodium methoxide/methanol solution (1 mL) was added to 2-(2-bromo-1,1-diethoxyethyl)-5-methyl pyrimidine (29 mg) obtained in Reference Example 22-30-1 (1), and the resultant product was irradiated with microwaves (microwave reaction apparatus, 160° C., 3 hours, 2.45 GHz, 0 W to 240 W). The reaction mixture was cooled to room temperature, and purified by silica gel column chromatography (hexane-ethyl acetate=1:1, NH silica), whereby 2-(1,1-diethoxy-2-methoxyethyl)-5-methyl pyrimidine (20 mg) was obtained.

MS(ESI m/z): 241 (M+H)
RT(min): 0.86

(3)

Water (0.4 mL) and concentrated hydrochloric acid (40 μL) were added to a solution (0.4 mL) of 2-(1,1-diethoxy-2-methoxyethyl)-5-methyl pyrimidine (20 mg) obtained in Reference Example 22-30-1 (2) in methanol, followed by stirring at 80° C. for 1 hour. The reaction mixture was cooled to room temperature, then, a saturated sodium hydrogen carbonate aqueous solution and a saturated sodium chloride aqueous solution were added thereto, and the resultant product was extracted with ethyl acetate. The organic layer was dried over anhydrous sodium sulfate, and the solvent was distilled off under reduced pressure, whereby 2-methoxy-1-(5-methylpyrimidin-2-yl)ethanone (10 mg) was obtained.

MS(ESI m/z): 167 (M+H)
RT(min): 0.55

Reference Example 22-30-2

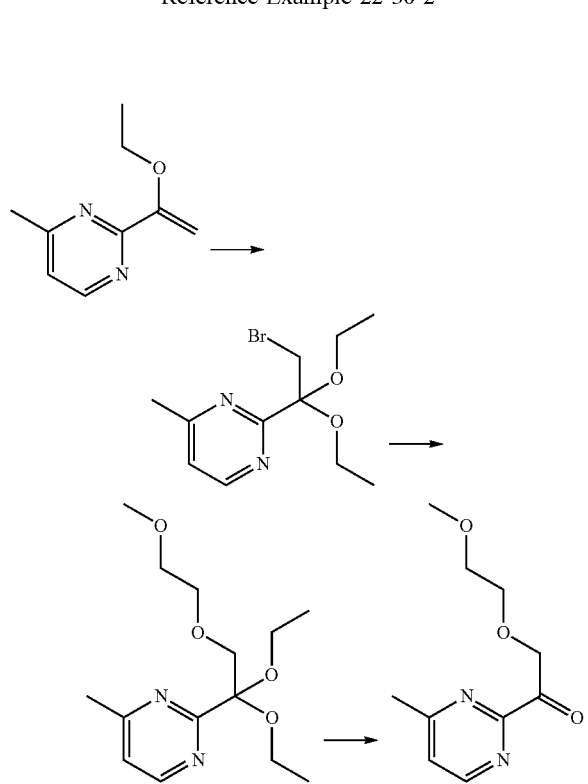

In the same manner as in Reference Example 22-30-1, the following compound was obtained.

2-(2-Methoxyethoxy)-1-(4-methyl pyrimidin-2-yl)ethanone

MS(ESI m/z): 211 (M+H)
RT(min): 0.62

Reference Example 22-30-3

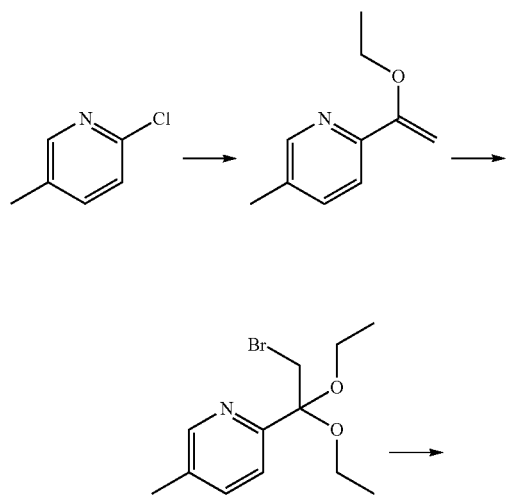

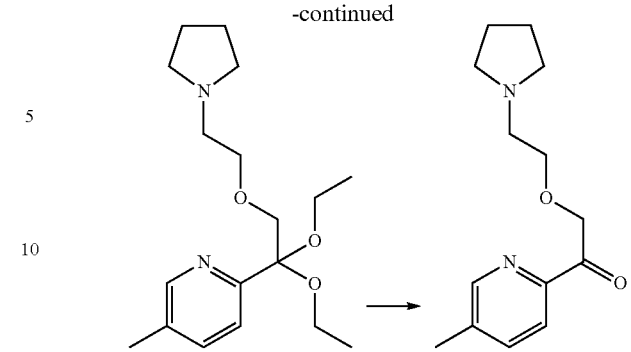

(1)
In the same manner as in Reference Example 22-15 (2), the following compound was obtained.

2-(1-Ethoxyvinyl)-5-methyl pyridine

MS(ESI m/z): 164 (M+H)
RT(min): 0.63

(2) to (4)
In the same manner as in Reference Example 22-30-1, the following compound was obtained.

1-(5-Methylpyridin-2-yl)-2-(2-(pyrrolidin-1-yl)ethoxy)ethanone

MS(ESI m/z): 249 (M+H)
RT(min): 0.63

Reference Example 22-30-4

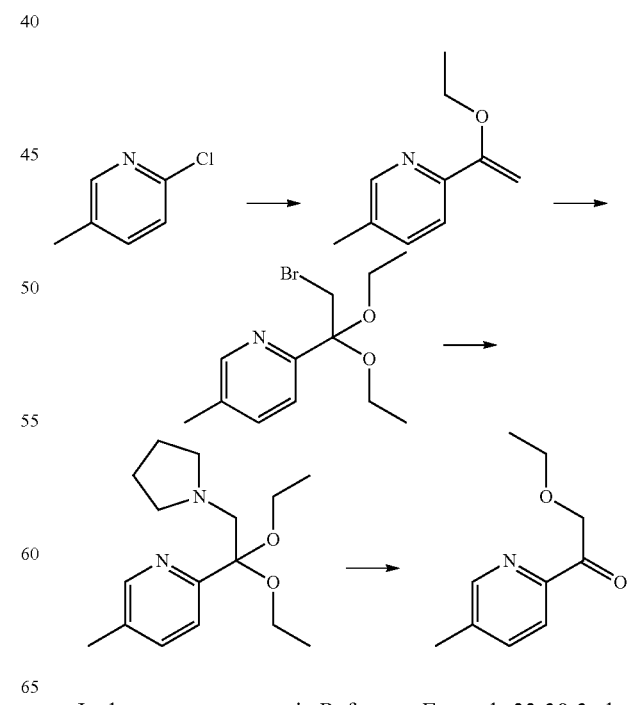

In the same manner as in Reference Example 22-30-3, the following compound was obtained.

2-Ethoxy-1-(5-methyl pyridin-2-yl)ethanon

MS(ESI m/z): 180 (M+H)
RT(min): 0.52

Reference Example 22-30-5

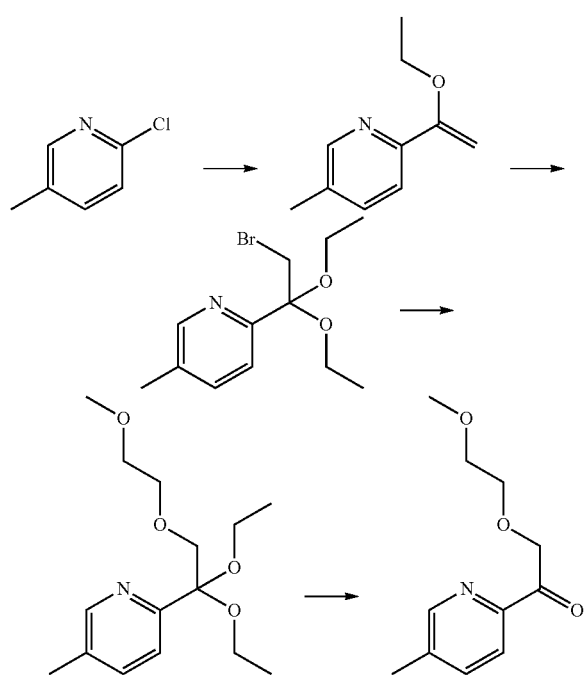

In the same manner as in Reference Example 22-30-3, the following compound was obtained.

2-(2-Methoxyethoxy)-1-(5-methylpyridin-2-yl)etha-none

MS(ESI m/z): 210 (M+H)
RT(min): 0.54

Reference Example 22-30-6

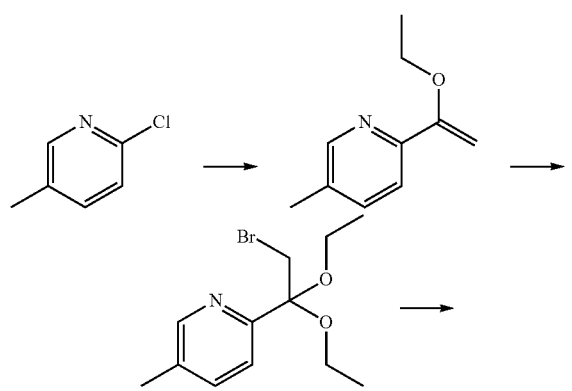

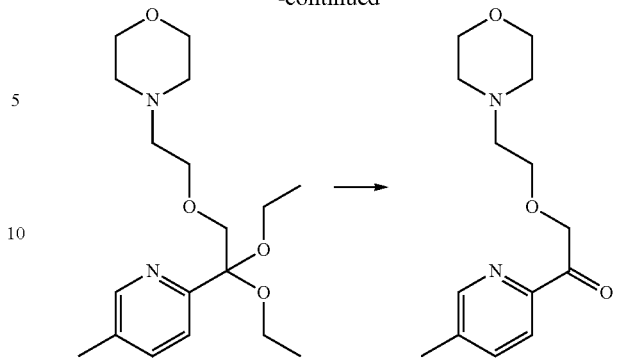

In the same manner as in Reference Example 22-30-3, the following compound was obtained.

1-(5-Methylpyridin-2-yl)-2-(2-morpholinoethoxy)ethanone

MS(ESI m/z): 265 (M+H)
RT(min): 0.63

Reference Example 22-30-7

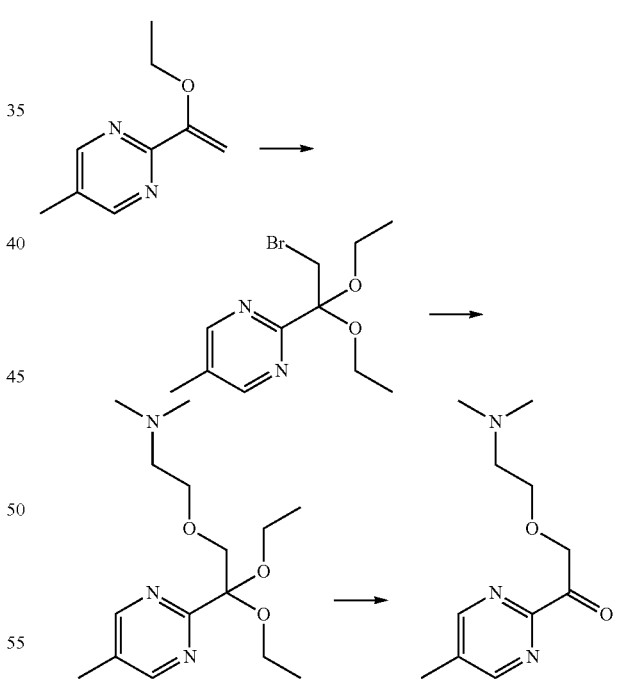

In the same manner as in Reference Example 22-30-1, the following compound was obtained.

2-(2-(Dimethyl amino)ethoxy)-1-(5-methylpyrimi-din-2-yl)ethanone

MS(ESI m/z): 224 (M+H)
RT(min): 0.44

Reference Example 22-30-8

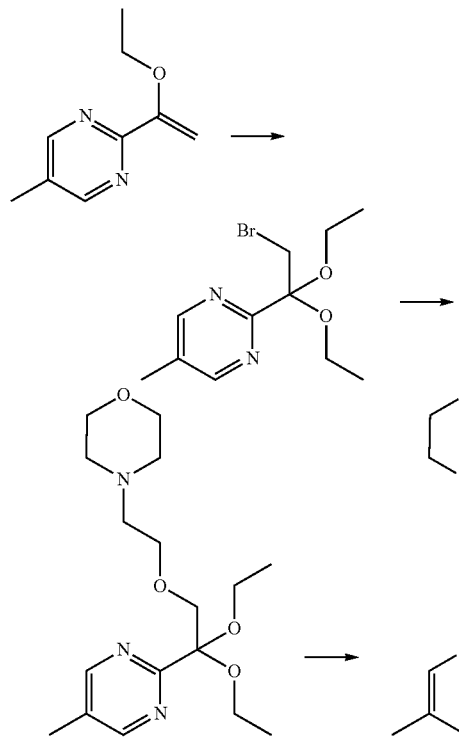

In the same manner as in Reference Example 22-30-1, the following compound was obtained.

1-(5-Methyl pyrimidin-2-yl)-2-(2-morpholinoethoxy)ethanone

MS(ESI m/z): 266 (M+H)
RT(min): 0.47

Reference Example 22-30-9

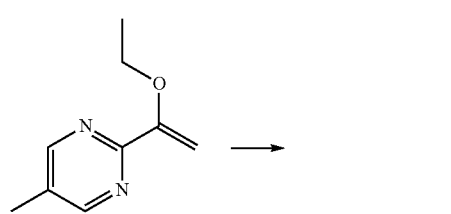

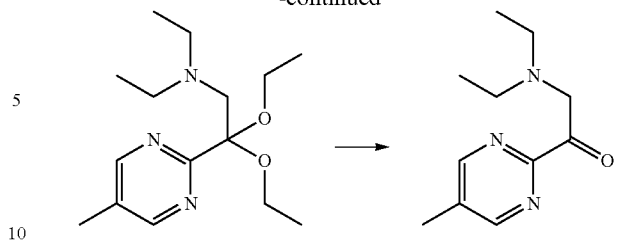

In the same manner as in Reference Example 22-30-1, the following compound was obtained.

2-(Diethylamino)-1-(5-methylpyrimidin-2-yl)ethanone

MS(ESI m/z): 208 (M+H)
RT(min): 0.59

Reference Example 22-31

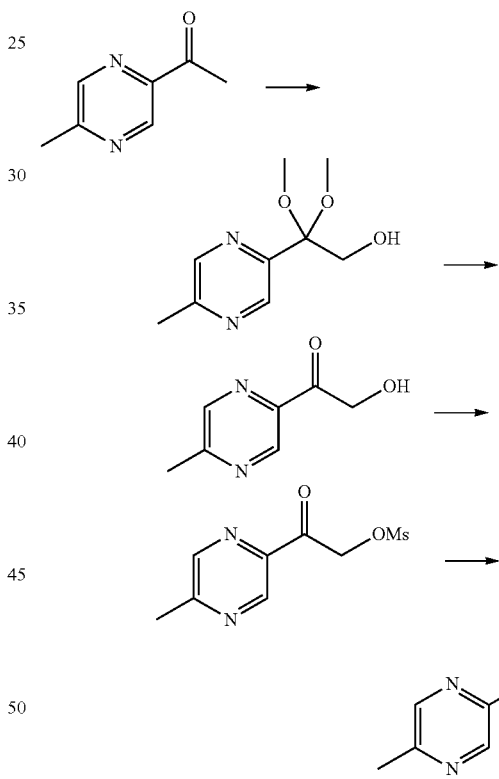

(1)
In the same manner as in Reference Example 22-29 (1), the following compound was obtained.

2,2-Dimethoxy-2-(5-methylpyrazin-2-yl)ethanol (2)
In the same manner as in Reference Example 22-29 (2), the following compound was obtained.

2-Hydroxy-1-(5-methylpyrazin-2-yl)ethanone

MS(ESI m/z): 153 (M+H)
RT(min): 0.45

(3)

Triethylamine (0.27 mL) and methanesulfonyl chloride (0.11 mL) were added to a solution of 2-hydroxy-1-(5-methylpyrazin-2-yl)ethanone (195 mg) obtained in Reference Example 22-31 (2) in dichloromethane (4 mL) under ice-cooling, followed by stirring for 0.5 hours. A saturated ammonium chloride aqueous solution was added to the reaction mixture, then, the resultant product was extracted with dichloromethane, and the organic layer was dried over anhydrous sodium sulfate. The solvent was distilled off under reduced pressure, whereby 2-(5-methylpyrazin-2-yl)-2-oxoethyl methanesulfonate (288 mg) was obtained.

MS(ESI m/z): 231 (M+H)

(4)

Sodium azide (0.12 g) was added to a mixed solution of 2-(5-methylpyrazin-2-yl)-2-oxo ethyl methanesulfonate (278 mg) obtained in Reference Example 22-31 (3) in N,N-dimethyl formamide (4 mL) and water (2 mL), followed by stirring at room temperature for 1 hour. A saturated sodium hydrogen carbonate aqueous solution was added to the reaction mixture, then, the resultant product was extracted with ethyl acetate, the organic layer was washed with water. The organic layer was dried over anhydrous sodium sulfate, and the solvent was distilled off under reduced pressure. The obtained residues were purified by silica gel column chromatography (hexane:ethyl aceate=2:1), whereby 2-azide-1-(5-methylpyrazin-2-yl)ethanone (111 mg) was obtained.

MS(ESI m/z): 178 (M+H)

RT(min): 0.87

Reference Example 22-32-1

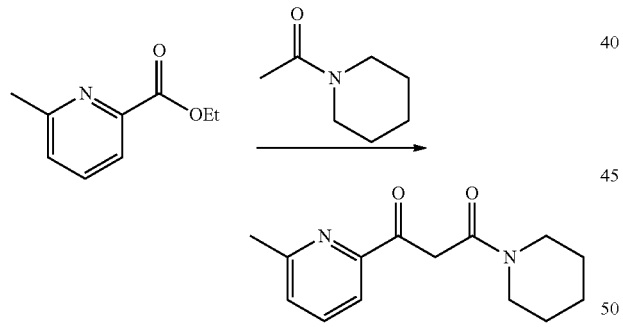

2.0 mol/L lithium diisopropyl amide/hexane/tetrahydrofuran/ethyl benzene (1.3 mL) was added to a solution of 1-(piperidin-1-yl)ethanone (330 mg) in tetrahydrofuran (3.5 mL), followed by stirring at −78° C. for 1 hour. The reaction mixture was added to a solution of ethyl 6-methyl picolinate (215 mg) in tetrahydrofuran (0.5 mL), followed by stirring at −78° C. for 0.5 hours, and acetic acid (0.1 mL) was added thereto, followed by raising the temperature to room temperature. A saturated sodium hydrogen carbonate aqueous solution was added to the reaction mixture, then, the resultant product was extracted with ethyl acetate, and the organic layer was dried over anhydrous sodium sulfate. The solvent was distilled off under reduced pressure, and the obtained residues were purified by silica gel column chromatography (hexane:ethyl acetate=7:3→1:1), whereby 1-(6-methylpyridin-2-yl)-3-(piperidin-1-yl)propane-1,3-dione (275 mg) was obtained.

MS(ESI m/z): 247 (M+H)

Reference Example 22-32-2

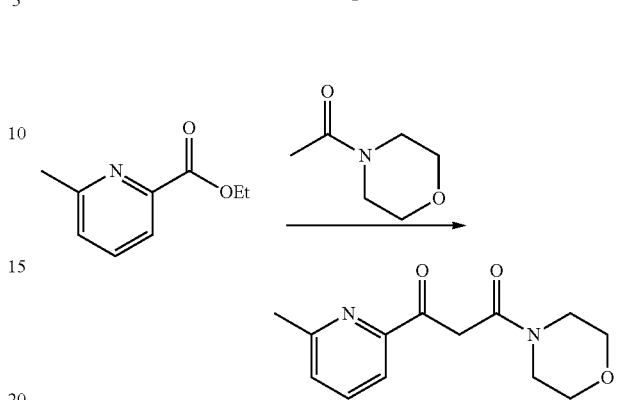

In the same manner as in Reference Example 22-32-1, the following compound was obtained.

1-(6-Methylpyridin-2-yl)-3-morpholino propane-1,3-dione

MS(ESI m/z): 249 (M+H)

Reference Example 22-32-3

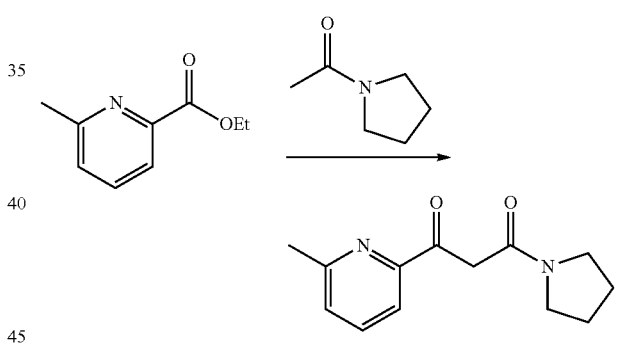

In the same manner as in Reference Example 22-32-1, the following compound was obtained.

1-(6-Methylpyridin-2-yl)-3-(pyrrolidin-1-yl)propane-1,3-dione

MS(ESI m/z): 233 (M+H)

Reference Example 22-33

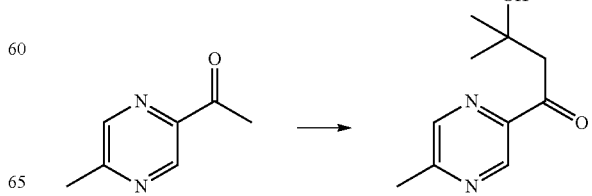

A 1.6 mol/L butyl lithium/hexane solution (0.69 mL) was added to a solution of diisopropylamine (157 µl) in tetrahydrofuran (3 mL) at −78° C., followed by stirring 0.5 hours. 1-(5-Methylpyrazin-2-yl)ethanone (136 mg) was added to the reaction mixture, followed by stirring at −78° C. for 0.5 hours, and acetone (88 µL) was added thereto, followed by stirring at room temperature for 1 hour. A saturated sodium chloride aqueous solution was added to the reaction mixture, and the resultant product was extracted with ethyl acetate. The organic layer was dried over anhydrous sodium sulfate, then, the solvent was distilled off under reduced pressure, and the obtained residues were purified by silica gel column chromatography (hexane:ethyl acetate=1:1), whereby 3-hydroxy-3-methyl-1-(5-methylpyrazin-2-yl)butan-1-one (120 mg) was obtained.

MS(ESI m/z): 195 (M+H)
RT(min): 0.74

Reference Example 22-34-1

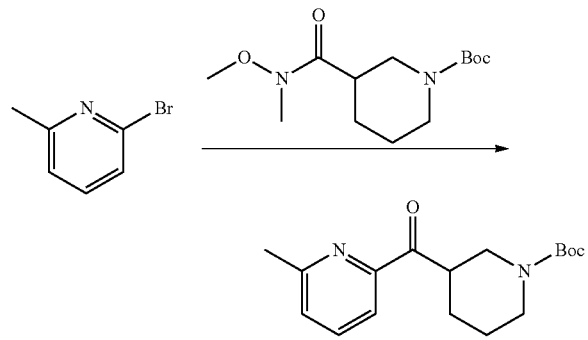

1.6 mol/L butyl lithium/hexane (2.2 mL) was added to a solution of 2-bromo-6-methyl pyridine (664 mg) in tetrahydrofuran (9 mL), followed by stirring at −78° C. for 1 hours. The reaction mixture (6 mL) was added to a solution of tert-butyl 3-(methoxy(methyl)carbamoyl)piperidine-1-carboxylate (470 mg) in tetrahydrofuran (10 mL), and the resultant product was stirred at −78° C. for 10 minutes, and stirred at room temperature for 10 minutes. An aqueous saturated ammonium chloride solution was added to the reaction mixture, and extraction thereof was performed using ethyl acetate. The organic layer was dried over anhydrous sodium sulfate, and the solvent was distilled off under reduced pressure. The obtained residues were purified by silica gel column chromatography (hexane:ethyl acetate=19:1→3:1), whereby tert-butyl 3-(6-methylpicolinoyl)piperidine-1-carboxylate (380 mg) was obtained.

MS(ESI m/z): 305 (M+H)
RT(min): 1.70

Reference Example 22-34-2

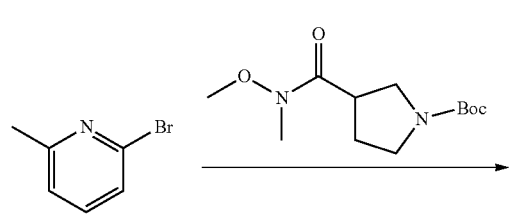

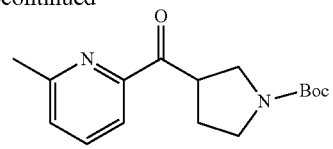

In the same manner as in Reference Example 22-34-1, the following compound was obtained.

tert-Butyl 3-(6-methylpicolinoyl)pyrrolidine-1-carboxylate

MS(ESI m/z): 291 (M+H)
RT(min): 1.61

Reference Example 22-34-3

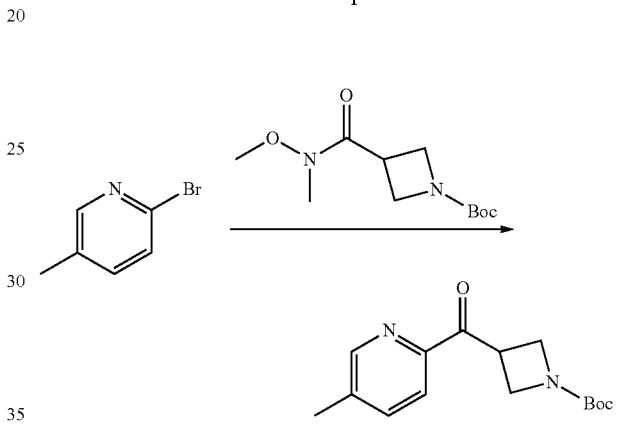

In the same manner as in Reference Example 22-34-1, the following compound was obtained.

tert-Butyl 3-(5-methylpicolinoyl)azetidine-1-carboxylate

MS(ESI m/z): 277 (M+H)
RT(min): 1.50

Reference Example 22-34-4

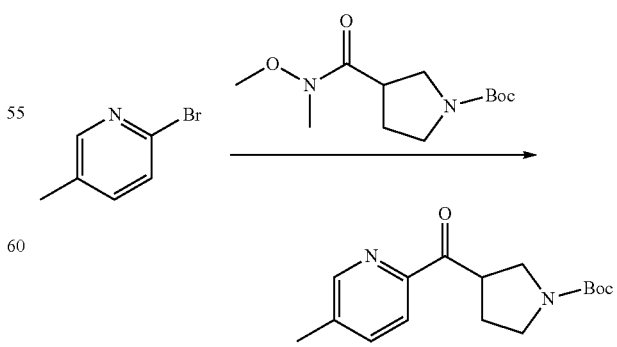

In the same manner as in Reference Example 22-34-1, the following compound was obtained.

tert-Butyl 3-(5-methylpicolinoyl)pyrrolidine-1-carboxylate

MS(ESI m/z): 291 (M+H)
RT(min): 1.55

Reference Example 22-35

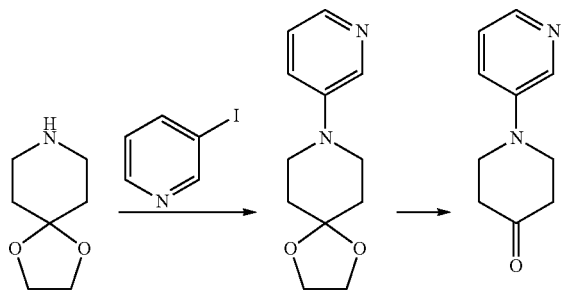

(1)
In a nitrogen atmosphere, a mixture of 1,4-dioxa-8-azaspiro[4.5]decane (573 mg), 3-iodopyridine (820 mg), 1,4-dioxane (10 mL), tris (dibenzylidineacetone)dipalladium (73 mg), 2-dicyclohexylphosphino-2',4',6'-triisopropylbiphenyl (57 mg), and cesium carbonate (1955 mg) was refluxed for 27 hours. After the reaction mixture was cooled to room temperature, ethyl acetate was added thereto, and the resultant product was washed sequentially with a sodium carbonate aqueous solution and a saturated sodium chloride aqueous solution. The organic layer was dried over anhydrous sodium sulfate, and the solvent was distilled off under reduced pressure. The obtained residues were purified by silica gel column chromatography (hexane:ethyl aceate=9:1→1:1, NH silica), whereby 8-(pyridin-3-yl)-1,4-dioxa-8-azaspiro[4.5]decane (122 mg) was obtained as a colorless oily material.

MS(ESI m/z): 221 (M+H)
RT(min): 0.50

(2)
8-(Pyridin-3-yl)-1,4-dioxa-8-azaspiro[4.5]decane (122 mg) was dissolved in a mixed solution of 4.0 mol/mL hydrogen chloride/1,4-dioxane (5 mL) and water (1 mL), followed by stirring at room temperature for 17 hours. Potassium carbonate was added to the reaction mixture, then, the pH of the resultant product was adjusted to 8, and the resultant product was extracted with ethyl acetate. The organic layer was dried over anhydrous sodium sulfate, and the solvent was distilled off under reduced pressure, whereby 1-(pyridin-3-yl)piperidin-4-one (116 mg) was obtained as a brown oily material.

Reference Example 22-36-1

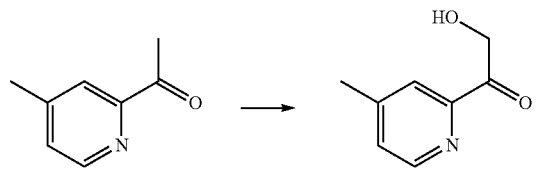

Potassium hydroxide and iodobenzene diacetate (141 mg) were added to a solution of 1-(4-methylpyridin-2-yl)ethanone (50 mg) in methanol (5.0 mL), followed by stirring at room temperature for 12 hours. The solvent was distilled off under reduced pressure, then, water was added to the obtained residues, and the resultant product was extracted with chloroform. The organic layer was dried over anhydrous sodium sulfate, and the solvent was distilled off under reduced pressure. The obtained residues were mixed with tetrahydrofuran (3.0 mL), water (1.0 mL), and p-toluenesulfonic acid (12.7 mg), and the resultant product was irradiated with microwaves (microwave reaction apparatus, 100° C., 0.5 hours, 2.45 GHz, 0 W to 240 W). After the reaction mixture was cooled to room temperature, the solvent was evaporated under reduced pressure, then, a saturated sodium hydrogen carbonate aqueous solution was added to the obtained residues, and the resultant product was extracted with chloroform. The organic layer was dried over anhydrous sodium sulfate, and the solvent was distilled off under reduced pressure. The obtained residues were purified by silica gel column chromatography (hexane:ethyl aceate=1:0→3:7), whereby 2-hydroxy-1-(4-methylpyridin-2-yl)ethanone (29 mg) was obtained as a colorless oily material.

MS(ESI m/z): 152 (M+H)
RT(min): 0.56

Reference Example 22-36-2

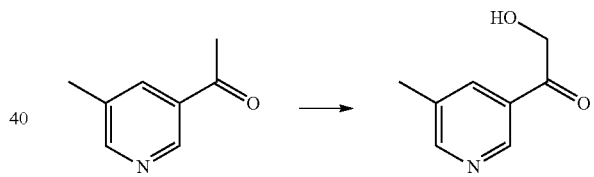

In the same manner as in Reference Example 22-36-1, the following compound was obtained.

2-Hydroxy-1-(5-methylpyridin-3-yl)ethanone

MS(ESI m/z): 152 (M+H)
RT(min): 0.32

Reference Example 22-36-3

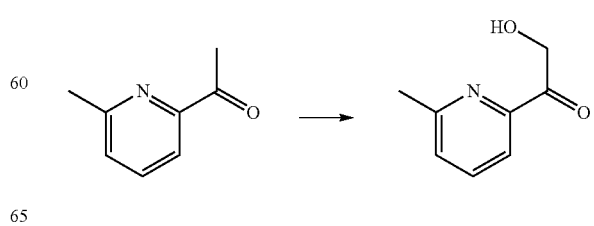

In the same manner as in Reference Example 22-36-1, the following compound was obtained.

2-Hydroxy-1-(6-methylpyridin-2-yl)ethanone

Reference Example 22-37

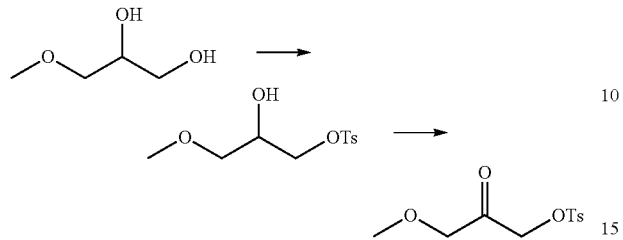

(1)
Under ice-cooling, p-toluenesulfonyl chloride (216 mg) and pyridine (186 µL) were added to a solution of 3-methoxypropane-1,2-diol (100 mg) in dichloromethane (2 mL), followed by stirring at room temperature for 13 hours. The solvent was distilled off under reduced pressure, and the obtained residues were purified by silica gel column chromatography (hexane:ethyl acetate=10:1→0:1), whereby 2-hydroxy-3-methoxypropyl 4-methylbenzene sulfonate (152 mg) was obtained.

MS(ESI m/z): 261 (M+H)
RT(min): 1.07

(2)
1,1,1-Triacetoxy-1,1-dihydro-1,2-benziodoxol-3-(1H)-one (318 mg) was added to a solution of 2-hydroxy-3-methoxy propyl 4-methyl benzene sulfonate (130 mg) obtained in Reference Example 22-37 (1) in dichloromethane (3 mL), followed by stirring for 1 hour. 1,1,1-Triacetoxy-1,1-dihydro-1,2-benziodoxol-3-(1H)-one (160 mg) was added to the reaction mixture, followed by stirring for 1.5 hours. A saturated sodium thiosulfate aqueous solution was added to the reaction mixture, and the resultant product was extracted with ethyl acetate. The organic layer was washed with a saturated sodium hydrogen carbonate aqueous solution, and dried over anhydrous sodium sulfate. The solvent was distilled off under reduced pressure, whereby 3-methoxy-2-oxopropyl 4-methylbenzene sulfonate (141 mg) was obtained.

Reference Example 22-38

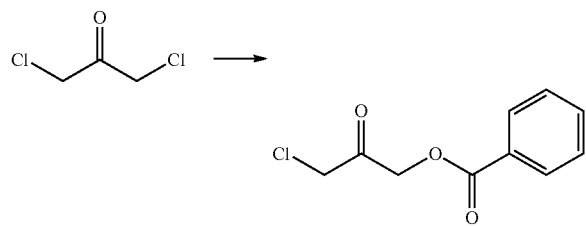

Sodium benzoate (750 mg) was added to a solution of 1,3-dichloroacetone (1 g) in N,N-dimethyl formamide (10 mL), followed by stirring for 12 hours. After water was added to the reaction mixture, the resultant product was extracted with ethyl acetate, and the organic layer was washed with a saturated sodium chloride aqueous solution. The solvent was distilled off under reduced pressure, and the obtained residues were purified by silica gel column chromatography (hexane:ethyl acetate=1:0→0:1), whereby 3-chloro-2-oxopropyl benzoate (200 mg) was obtained.

Reference Example 23-1

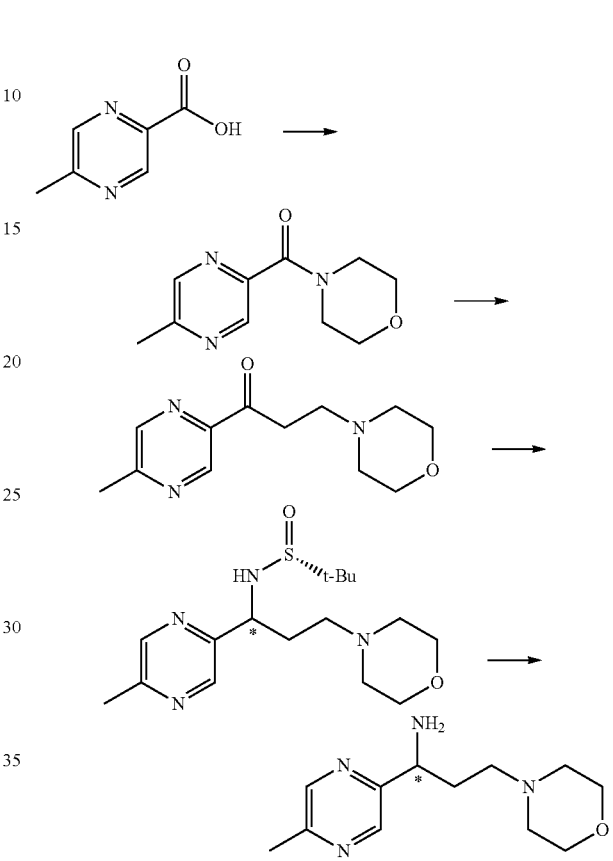

(1)
5-Methyl pyrazine-2-carboxylic acid (276 mg) was suspended in dichloromethane (5 mL), and N,N-dimethyl formamide (10 µL) and oxalyl chloride (258 µL) were added thereto at room temperature, followed by stirring for 15 minutes. The solvent was distilled off under reduced pressure, and dichloromethane (5 mL), triethylamine (1 mL), and morpholine (435 µL) were added to the obtained residues, followed by stirring at room temperature for 0.5 hours. A saturated ammonium chloride aqueous solution was added thereto, and the resultant product was extracted with chloroform. The organic layer was dried over anhydrous sodium sulfate, and the solvent was distilled off under reduced pressure. The obtained residues were purified by silica gel column chromatography (hexane:ethyl acetate=3:1→2:1, NH silica), whereby (5-methylpyrazin-2-yl)(morpholino)methanone (405 mg) was obtained.

MS(ESI m/z): 208 (M+H)
RT(min): 1.59

(2)
1.0 mol/L vinylmagnesium bromide/tetrahydrofuran (2 mL) was added to a solution of (5-methylpyrazin-2-yl)(morpholino)methanone (405 mg) obtained in Reference Example 23-1 (1) in tetrahydrofuran (5 mL), and the resultant product was stirred at −78° C. for 10 minutes, and stirred at room temperature for 20 minutes. Morpholine (0.1 mL) was added thereto, followed by stirring for 1 hour.

Water was added thereto, and the resultant product was extracted with chloroform. The organic layer was dried over anhydrous sodium sulfate, and the solvent was distilled off under reduced pressure. The obtained residues were purified by silica gel column chromatography (hexane:ethyl acetate=4:1→3:1, NH silica), whereby 1-(5-methylpyrazin-2-yl)-3-morpholinopropan-1-one (285 mg) was obtained.

MS(ESI m/z): 236 (M+H)
RT(min): 0.35

(3)
(R)-2-methyl propane-2-sulfinamide (111 mg) and tetraethyl orthotitanate (323 μL) were added to a solution of 1-(5-methylpyrazin-2-yl)-3-morpholinopropan-1-one (180 mg) obtained in Reference Example 23-1 (2) in toluene (2 mL), and the resultant product was irradiated with microwaves (microwave reaction apparatus, 120° C., 0.5 hours, 2.45 GHz, 0 W to 240 W). Ethyl acetate (3 mL) and a saturated sodium chloride aqueous solution (1 mL) were added thereto, the precipitated solid was filtered off using Celite. The filtrate was dried over anhydrous sodium sulfate, and the solvent was distilled off under reduced pressure. Tetrahydrofuran (7 mL) was added to the obtained residues, then, 1.0 mol/L diisobutyl aluminium hydride/toluene (1.76 mL) was added thereto at −78° C., and the resultant product was stirred at the same temperature for 0.5 hours, and stirred at room temperature for 0.5 hours. A saturated potassium sodium tartarate aqueous solution and a saturated sodium chloride aqueous solution were added thereto, followed by stirring for 1 hour, and the resultant product was extracted with ethyl acetate. The organic layer was dried over anhydrous sodium sulfate, and the solvent was distilled off under reduced pressure. The obtained residues were purified by silica gel column chromatography (hexane:ethyl acetate=1:1→0:1, NH silica), whereby (R)-2-methyl-N-(1-(5-methylpyrazin-2-yl)-3-morpholinopropyl)propane-2-sulfinamide (optically active substance A) was obtained.

MS(ESI m/z): 341 (M+H)
RT(min): 0.56

(4)
4.0 mol/L hydrogen chloride/1,4-dioxane (1 mL) was added to a mixed solution of (R)-2-methyl-N-(1-(5-methylpyrazin-2-yl)-3-morpholinopropyl)propane-2-sulfinamide (optically active substance A) obtained in Reference Example 23-1 (3) in dichloromethane (2 mL) and methanol (1 mL), followed by stirring at room temperature for 2 hours. A potassium hydroxide aqueous solution was added thereto, then, the solvent was distilled off, and the resultant product was extracted with chloroform. The organic layer was dried over anhydrous sodium sulfate, and the solvent was distilled off under reduced pressure. The obtained residues were purified by silica gel column chromatography (hexane:ethyl acetate=1:0→9:1, NH silica), whereby 1-(5-methylpyrazin-2-yl)-3-morpholinopropane-1-amine (optically active substance A) was obtained.

MS(ESI m/z): 237 (M+H)
RT(min): 0.20

Reference Example 23-2-1

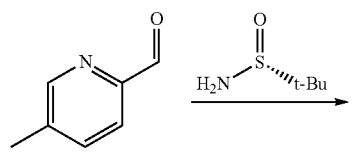

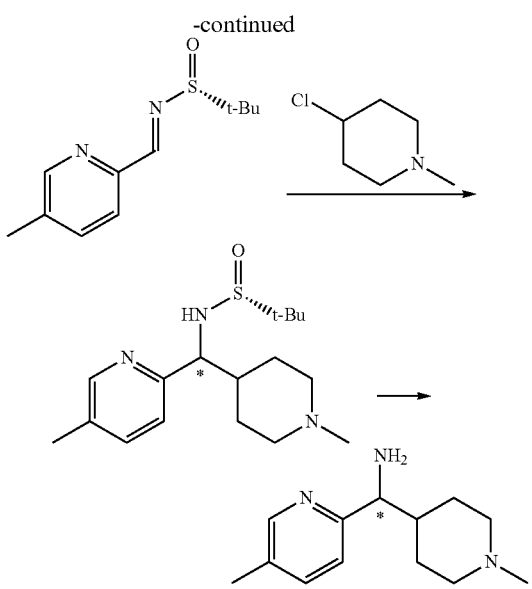

(1)
(R)-2-methyl propane-2-sulfinamide (133 mg) and tetraethyl orthotitanate (420 μL) were added to a solution of 5-methyl picolinic aldehyde (121 mg) in toluene (1.5 mL), and the resultant product was irradiated with microwaves (microwave reaction apparatus, 100° C., 15 minutes→110° C., 15 minutes, 2.45 GHz, 0 W to 240 W). Ethyl acetate (5 mL) and a saturated sodium chloride aqueous solution (1 mL) were added thereto, the precipitated solid was filtered off using Celite. The filtrate was dried over anhydrous sodium sulfate, and the solvent was distilled off under reduced pressure. The obtained residues were purified by silica gel column chromatography (hexane:ethyl acetate=4:1→2:1, NH silica), whereby (R,E)-2-methyl-N-((5-methyl-pyridin-2-yl)methylene)propane-2-sulfinamide was obtained.

This was dissolved in tetrahydrofuran (2 mL), whereby a solution of (R,E)-2-methyl-N-((5-methylpyridin-2-yl)methylene)propane-2-sulfinamide in tetrahydrofuran was obtained.

MS(ESI m/z): 225 (M+H)
RT(min): 1.16

(2)
Magnesium (36 mg) and 1,2-dibromoethane (4.3 μL) was added to tetrahydrofuran (1 mL), followed by stirring at room temperature until forming occurs no longer, and 4-chloro-1-methyl piperidine (133 mg) was added thereto, and the resultant product was stirred at room temperature for 0.5 hours, stirred at 50° C. for 10 minutes, and stirred for 10 minutes while refluxing. This reaction mixture was added to a solution (1 mL) of (R,E)-2-methyl-N-((5-methyl pyridin-2-yl)methylene)propane-2-sulfinamide obtained in Reference Example 23-2-1 (1) in tetrahydrofuran at −78° C., followed by stirring at room temperature for 10 minutes. A saturated sodium chloride aqueous solution was added thereto, then, the resultant product was extracted with ethyl acetate, and the organic layer was dried over anhydrous sodium sulfate. The solvent was distilled off under reduced pressure, whereby (R)-2-methyl-N-((1-methylpiperidin-4-yl)(5-methylpyridin-2-yl)methyl)propane-2-sulfinamide (optically active substance A) was obtained.

MS(ESI m/z): 324 (M+H)
RT(min): 0.53

(3)

Methanol (0.5 mL) and 4.0 mol/L hydrogen chloride/1,4-dioxane were added to a solution of (R)-2-methyl-N-((1-methylpiperidin-4-yl)(5-methylpyridin-2-yl)methyl)propane-2-sulfinamide (optically active substance A) obtained in Reference Example 23-2-1 (2) in dichloromethane (3.5 mL), followed by stirring at room temperature for 20 minutes. The solvent was distilled off under reduced pressure, then, a sodium chloride aqueous solution was added thereto, and the resultant product was extracted with 10% methanol/chloroform. The organic layer was dried over anhydrous sodium sulfate, and the solvent was distilled off under reduced pressure. The obtained residues were purified by silica gel column chromatography (hexane:ethyl acetate=1:0→19:1), whereby (1-methylpiperidin-4-yl)(5-methylpyridin-2-yl)methaneamine (88 mg) (optically active substance A) was obtained.

MS(ESI m/z): 220 (M+H)
RT(min): 0.21

Reference Example 23-2-2

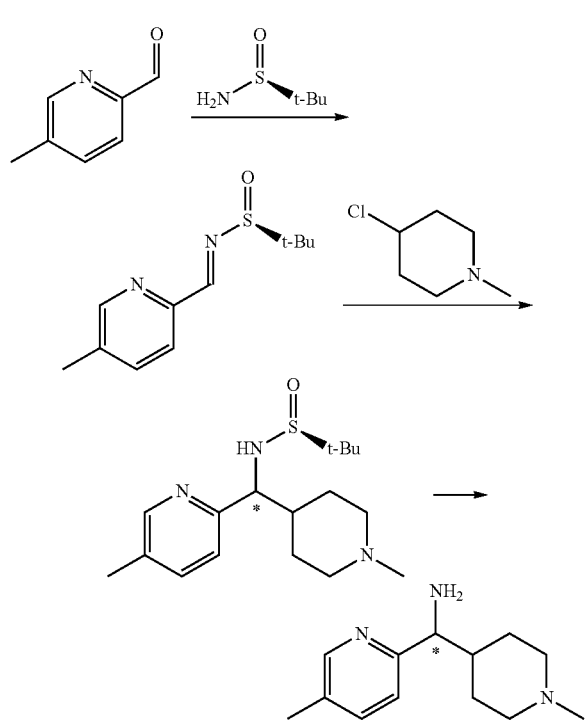

(1)

Using (S)-2-methyl propane-2-sulfinamide instead of (R)-2-methyl propane-2-sulfinamide in Reference Example 23-2-1 (1), the following compound was obtained in the same manner.

(S,E)-2-methyl-N-((5-methylpyridin-2-yl)methylene)propane-2-sulfinamide

MS(ESI m/z): 225 (M+H)
RT(min): 1.16

(2)

In the same manner as in Reference Example 23-2-1 (2), the following compound was obtained.

(S)-2-methyl-N-((1-methylpiperidin-4-yl)(5-methylpyridin-2-yl)methyl)propane-2-sulfinamide (optically active substance B)

MS(ESI m/z): 324 (M+H)
RT(min): 0.53

(3)

In the same manner as in Reference Example 23-2-1 (3), the following compound was obtained.

(1-Methyl piperidin-4-yl)(5-methyl pyridin-2-yl)methaneamine (88 mg) (optically active substance B)

MS(ESI m/z): 220 (M+H)
RT(min): 0.21

Reference Example 23-2-3

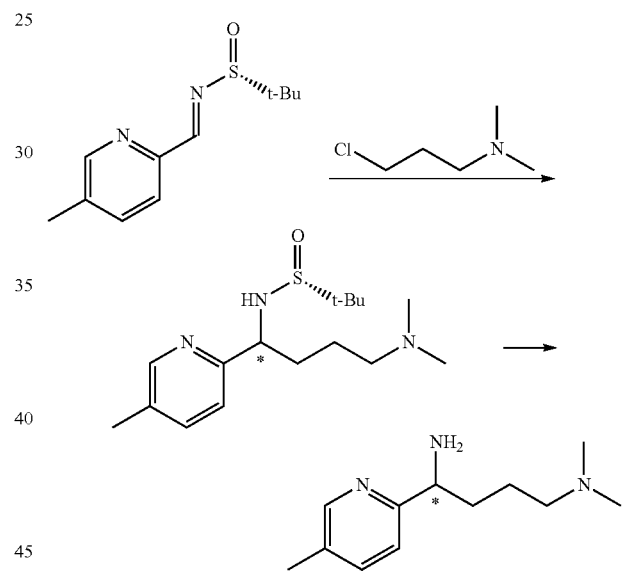

(1)

In the same manner as in Reference Example 23-2-1 (2), the following compound was obtained.

(R)—N-(4-(dimethylamino)-1-(5-methylpyridin-2-yl)butyl)-2-methyl propane-2-sulfinamide (optically active substance A)

MS(ESI m/z): 312 (M+H)
RT(min): 0.52

(2)

In the same manner as in Reference Example 23-2-1 (3), the following compound was obtained. $N^1,N^1$-dimethyl-4-(5-methylpyridin-2-yl)butane-1,4-diamine (optically active substance A)

MS(ESI m/z): 208 (M+H)
RT(min): 0.21

Reference Example 23-2-4

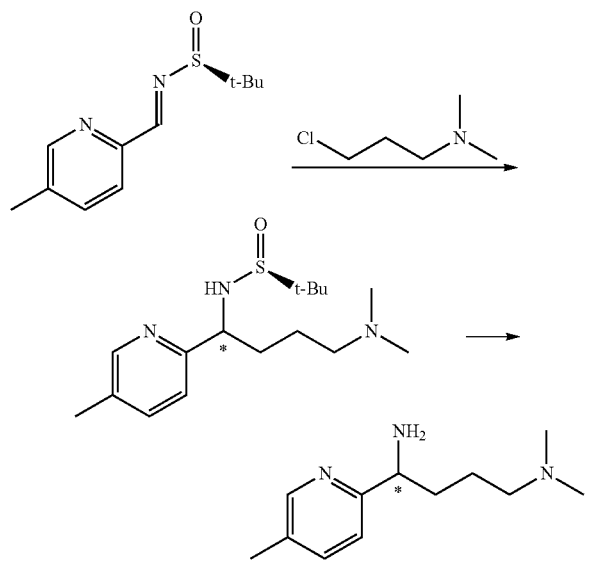

(1)

In the same manner as in Reference Example 23-2-1 (2), the following compound was obtained.

(S)—N-(4-(dimethylamino)-1-(5-methylpyridin-2-yl)butyl)-2-methyl propane-2-sulfinamide (optically active substance B)

MS(ESI m/z): 312 (M+H)
RT(min): 0.52

(2)

In the same manner as in Reference Example 23-2-1 (3), the following compound was obtained.

$N^1,N^1$-dimethyl-4-(5-methylpyridin-2-yl)butane-1,4-diamine (optically active substance B)

MS(ESI m/z): 208 (M+H)
RT(min): 0.21

Reference Example 23-3

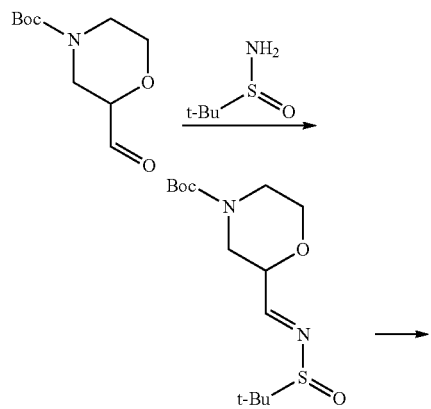

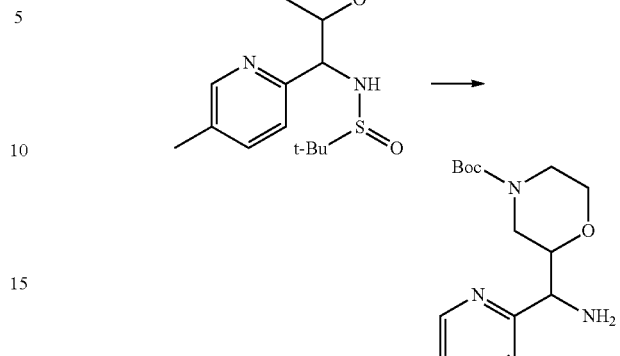

(1)

Cesium carbonate (820 mg), (R)-2-methyl propane-2-sulfinamide (151 mg), and (S)-2-methyl propane-2-sulfinamide (152 mg) were added to a solution of tert-butyl 2-formylmorpholine-4-carboxylate (536 mg) in dichloromethane (2 mL), followed by stirring at room temperature for 13 hours. The solid was separated from the reaction mixture by filtration, and the filtrate was concentrated under reduced pressure. The obtained residues were purified by silica gel column chromatography (hexane:ethyl acetate=4:1→2:1), whereby (E)-tert-butyl 2-(((tert-butyl sulfinyl)imino)methyl)morpholine-4-carboxylate (diastereomer mixture) (233 mg) was obtained.

(2)

1.6 mol/L butyl lithium/hexane (1.65 mL) was added to a solution of 2-bromo-5-methyl pyridine (567 mg) in tetrahydrofuran (10 mL) at −78° C., followed by stirring for 0.5 hours. The reaction mixture (7 mL) was added to a solution of (E)-tert-butyl 2-(((tert-butylsulfinyl)imino)methyl)morpholine-4-carboxylate (diastereomer mixture) (233 mg) obtained in Reference Example 23-3 (1) in tetrahydrofuran (3 mL) at −78° C. The resultant product was stirred at −78° C. for 0.5 hours, and stirred at room temperature for 0.5 hours, then, a saturated sodium chloride aqueous solution was added thereto, and the resultant product was extracted with ethyl acetate. The organic layer was dried over anhydrous sodium sulfate, and the solvent was distilled off under reduced pressure. The obtained residues were purified by silica gel column chromatography (hexane:methanol=1:1:0→0:1:0→0:9:1), whereby tert-butyl 2-((1,1-dimethylethylsulfinamide)(5-methylpyridin-2-yl)methyl)morpholine-4-carboxylate (diastereomer mixture) (235 mg) was obtained.

(3)

In the same manner as in Reference Example 23-2-1 (3), the following compound was obtained.

tert-Butyl 2-(amino(5-methylpyridin-2-yl)methyl)morpholine-4-carboxylate (diastereomer mixture)

MS(ESI m/z): 308 (M+H)
RT(min): 0.89

Reference Example 23-4-1

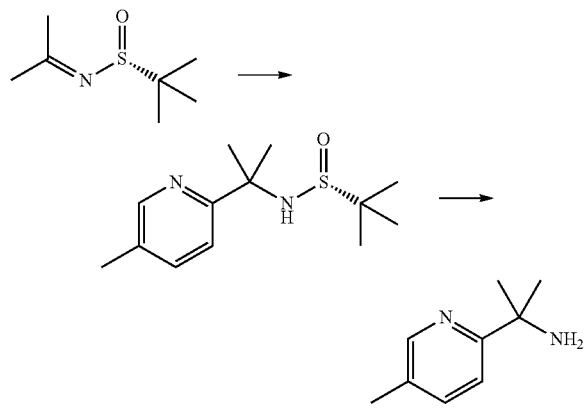

(1)

Using (R)-2-methyl-N-(propan-2-ylidene)propane-2-sulfinamide, in the same manner as in Reference Example 23-3 (2), (R)-2-methyl-N-(2-(5-methylpyridin-2-yl)propan-2-yl)propane-2-sulfinamide was obtained.

MS(ESI m/z): 255 (M+H)

RT(min): 0.75

(2)

Using (R)-2-methyl-N-(2-(5-methylpyridin-2-yl)propan-2-yl)propane-2-sulfinamide obtained in Reference Example 23-4-1 (1), in the same manner as in Reference Example 23-2-1 (3), 2-(5-methylpyridin-2-yl)propane-2-amine was obtained.

MS(ESI m/z): 151 (M+H)

RT(min): 0.53

Reference Example 23-4-2

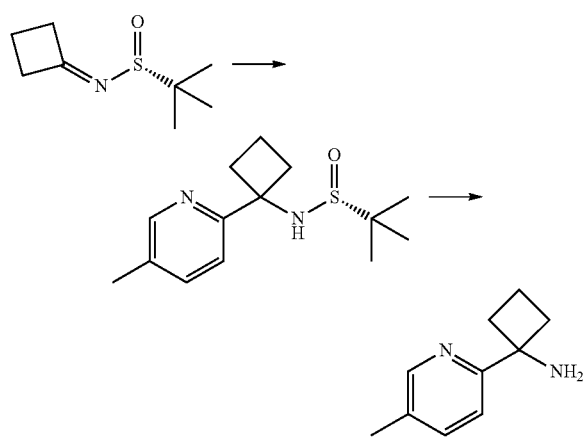

In the same manner as in Reference Example 23-4-1, 1-(5-methylpyridin-2-yl)cyclobutaneamine was obtained.

MS(ESI m/z): 163 (M+H)

RT(min): 0.55

Reference Example 23-4-3

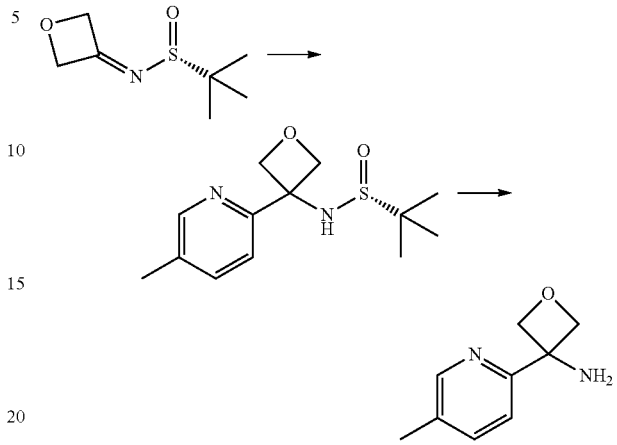

In the same manner as in Reference Example 23-4-1, 3-(5-methylpyridin-2-yl)oxetane-3-amine was obtained.

Reference Example 23-5

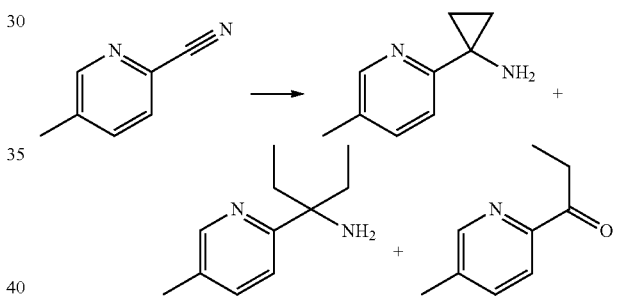

Titanium tetraisopropoxide (3.25 mL) and a 3.0 mol/L ethylmagnesium bromide/diethyl ether solution (7.3 mL) were added sequentially to a solution of 2-cyano-5-methyl pyridine (1.18 g) in tetrahydrofuran (55 mL) under ice-cooling, followed by stirring for 1 hour. A trifluoroborane-diethyl ether complex (4.5 mL) was added to the reaction mixture, followed by stirring at room temperature for 6 hours. A saturated sodium chloride aqueous solution was added to the reaction mixture, and the resultant product was extracted with ethyl acetate. After the organic layer was dried over anhydrous sodium sulfate, the solvent was distilled off under reduced pressure, then, the obtained residues were purified by silica gel column chromatography (ethyl acetate→chloroform:methanol=9:1, NH silica), and the following compound was obtained.

1-(5-Methylpyridin-2-yl)cyclopropane amine

MS(ESI m/z): 149 (M+H)
RT(min): 0.48

3-(5-Methylpyridin-2-yl)pentane-3-amine

MS(ESI m/z): 179 (M+H)
RT(min): 0.70

1-(5-Methylpyridin-2-yl)propan-1-one

MS(ESI m/z): 150 (M+H)
RT(min): 1.03

Reference Example 23-6

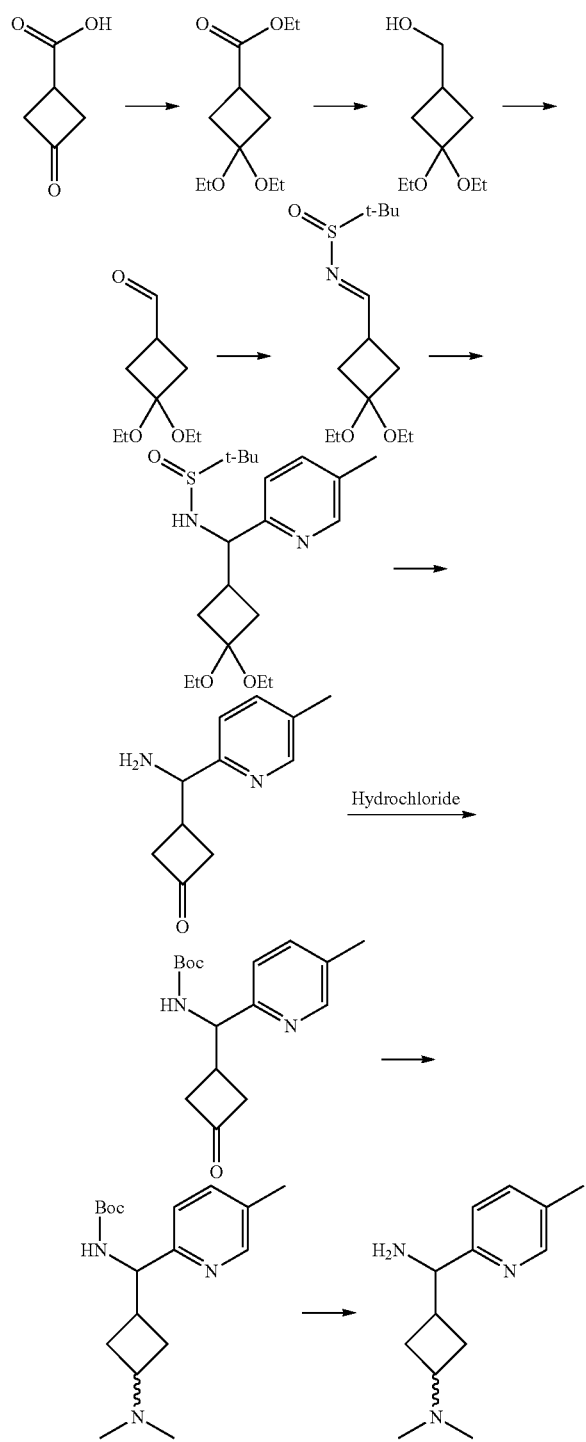

(1)
3-Oxocyclobutanecarboxylic acid (1.5 g) and 4-methyl benzenesulfonic acid monohydrate (0.25 g) were dissolved in a mixture of triethyl orthoformate (10 mL) and ethanol (5 mL), followed by refluxing for 13 hours. The solvent was distilled off under reduced pressure, and 4-methylbenzenesulfonic acid monohydrate (0.16 g), triethyl orthoformate (4 mL), and ethanol (3 mL) were added thereto, followed by refluxing for 4 hours. The solvent was distilled off under reduced pressure, then, a saturated sodium hydrogen carbonate aqueous solution was added thereto, and the resultant product was extracted with ethyl acetate. The organic layer was dried over anhydrous sodium sulfate, and the solvent was distilled off under reduced pressure. The obtained residues were purified by silica gel column chromatography (hexane:ethyl acetate=19:1→17:3), whereby ethyl 3,3-diethoxycyclobutanecarboxylate (1.84 g) was obtained.

MS(ESI m/z): 171 (M-EtOH)
RT(min): 1.41

(2)
Under ice-cooling, ethyl 3,3-diethoxycyclobutanecarboxylate (1.60 g) obtained in Reference Example 23-6 (1) was added dropwise to a mixed solution of 1.0 mol/L lithium aluminium hydride/tetrahydrofuran (11 mL) and tetrahydrofuran (25 mL), followed by stirring for 1 hour. A potassium sodium tartarate aqueous solution was added thereto, followed by stirring at room temperature for 5 hours. The resultant product was extracted with ethyl acetate, and the organic layer was dried over anhydrous sodium sulfate. The solvent was distilled off under reduced pressure, and the obtained residues were purified by silica gel column chromatography (hexane:ethyl acetate=4:1→1:1), whereby (3,3-diethoxycyclobutyl)methanol (1.13 g) was obtained.

(3)
2,2,6,6-Tetramethyl piperidine-1-oxyl (101 mg), iodobenzene diacetate (3.13 g), and sodium hydrogen carbonate (1 g) were added to a solution of (3,3-diethoxycyclobutyl) methanol (1.13 g) obtained in Reference Example 23-6 (2) in dichloromethane (21 mL), followed by stirring at room temperature for 2 hours. A saturated sodium hydrogen carbonate aqueous solution was added thereto, then, the resultant product was extracted with chloroform and ethyl acetate, and the organic layer was dried over anhydrous sodium sulfate. The solvent was distilled off under reduced pressure, and the obtained residues were purified by silica gel column chromatography (hexane:ethyl acetate=19:1→4:1), whereby 3,3-diethoxycyclobutanecarbaldehyde (707 mg) was obtained.

(4)
In the same manner as in Reference Example 23-3 (1), the following compound was obtained.

(E)-N-((3,3-diethoxycyclobutyl)methylene)-2-methyl propane-2-sulfinamide (5)
In the same manner as in Reference Example 23-3 (2), the following compound was obtained.

N-((3,3-diethoxycyclobutyl)(5-methylpyridin-2-yl)methyl)-2-methyl propane-2-sulfinamide (diastereomer mixture)

MS(ESI m/z): 323 (M-EtOH)
RT(min): 1.09

(6)
1 mol/L hydrogen chloride/1,4-dioxane/dichloromethane was added to a mixed solution of N-((3,3-diethoxycyclobutyl)(5-methylpyridin-2-yl)methyl)-2-methyl propane-2-sulfinamide (diastereomer mixture) (149 mg) obtained in Reference Example 23-6 (5) in dichloromethane (1 mL) and ethanol (0.5 mL), followed by stirring at room temperature for 0.5 hours. The solvent was distilled off under reduced pressure, whereby hydrochloride (racemic mixture) (68 mg) of 3-(amino(5-methylpyridin-2-yl)methyl)cyclobutanone was obtained.

MS(ESI m/z): 191 (M+H)
RT(min): 0.51

(7)

Triethylamine (167 μL) was added to a solution of hydrochloride (68 mg) of 3-(amino(5-methylpyridin-2-yl)methyl)cyclobutanone obtained in Reference Example 23-6 (6) and di-tert-butyl dicarbonate (131 mg) in dichloromethane (1 mL), followed by stirring at room temperature for 15 minutes. Methanol (2 mL) was added thereto, followed by stirring for 10 minutes, and the solvent was distilled off under reduced pressure. The obtained residues were purified by silica gel column chromatography (hexane:ethyl aceate=4:1→2:1), whereby tert-butyl ((5-methylpyridin-2-yl)(3-oxocyclobutyl)methyl)carbamate (racemic mixture) (46 mg) was obtained.

MS(ESI m/z): 291 (M+H)
RT(min): 0.92

(8)

In the same manner as in Example 1-12-1, the following compound was obtained.

tert-Butyl ((3-(dimethylamino)cyclo butyl)(5-methyl pyridin-2-yl)methyl)carbamate (diastereomer mixture)

MS(ESI m/z): 320 (M+H)
RT(min): 0.71, 1.21

(9)

Trifluoroacetic acid (0.3 mL) was added to a solution of tert-butyl ((3-(dimethylamino)cyclobutyl)(5-methylpyridin-2-yl)methyl)carbamate (diastereomer mixture) (43 mg) obtained in Reference Example 23-6 (8) in dichloromethane (0.1 mL), followed by stirring at room temperature for 2 hours. The solvent was distilled off under reduced pressure, then, a sodium chloride aqueous solution was added thereto, and the resultant product was extracted with 10% methanol/chloroform. The organic layer was dried over anhydrous sodium sulfate, and the solvent was distilled off under reduced pressure. The obtained residues were purified by silica gel column chromatography (hexane:ethyl acetate=1:0→19:1), whereby 3-(amino(5-methylpyridin-2-yl)methyl)-N,N-dimethyl cyclobutaneamine (diastereomer mixture) (23 mg) was obtained.

MS(ESI m/z): 220 (M+H)
RT(min): 0.21, 0.26

Reference Example 23-7

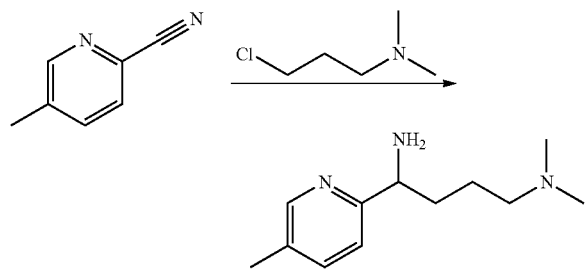

Magnesium (48 mg) and 1,2-dibromoethane (28 mg) were added to tetrahydrofuran (1 mL), followed by refluxing for 10 minutes. The resultant product was cooled to room temperature, and a solution of 3-chloro-N,N-dimethyl propane-1-amine (180 mg) in tetrahydrofuran (1 mL) was added thereto, followed by refluxing for 1 hour. The reaction mixture was added to a solution of 5-methyl picolinonitrile (118 mg) in tetrahydrofuran (1 mL) under ice-cooling, followed by stirring for 10 minutes. The reaction mixture (1 mL) was added to a solution of sodium borohydride (38 mg) in methanol (1 mL) under ice-cooling, followed by stirring for 1 hour. 1 mol/L hydrochloric acid was added thereto, and sodium hydrogen carbonate was added thereto, followed by stirring. The solvent was distilled off under reduced pressure, and the obtained residues were purified by silica gel column chromatography (chloroform:methanol=19:1), whereby $N^1,N^1$-dimethyl-4-(5-methylpyridin-2-yl)butane-1,4-diamine (19 mg) was obtained.

MS(ESI m/z): 208 (M+H)
RT(min): 0.70

Reference Example 23-8-1

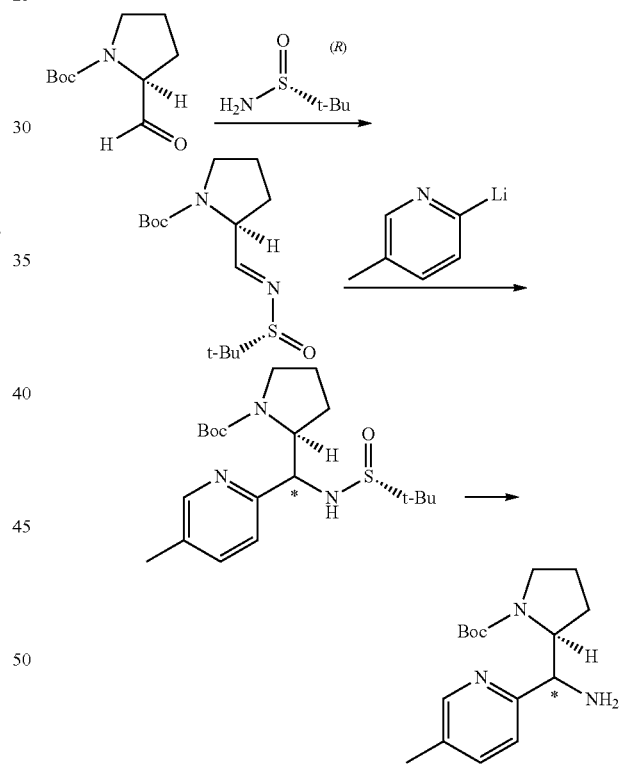

(1)

In the same manner as in Reference Example 23-2-1 (1), the following compound was obtained.

(S)-tert-butyl 2-((E)-(((R)-tert-butylsulfinyl)imino)methyl)pyrrolidine-1-carboxylate MS(ESI m/z): 303 (M+H)
RT(min): 1.47

(2)

In the same manner as in Reference Example 23-3 (2), the following compound was obtained.

(2S)-tert-butyl 2-(((R)-1,1-dimethylethylsulfina-mide)(5-methylpyridin-2-yl)methyl)pyrrolidine-1-carboxylate (optically active substance A)

MS(ESI m/z): 396 (M+H)
RT(min): 1.29
(3)
In the same manner as in Reference Example 23-2-1 (3), the following compound was obtained.

(2S)-tert-butyl 2-(amino(5-methylpyridin-2-yl)methyl)pyrrolidine-1-carboxylate (optically active substance A)

MS(ESI m/z): 292 (M+H)
RT(min): 0.96

Reference Example 23-8-2

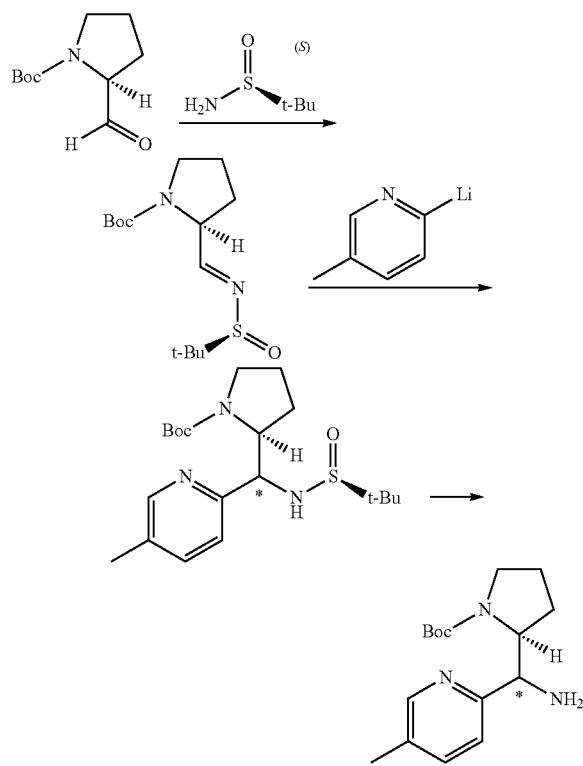

In the same manner as in Reference Example 23-8-1, the following compound was obtained.

(S)-tert-butyl 2-((E)-(((S)-tert-butylsulfinyl)imino)methyl)pyrrolidine-1-carboxylate MS(ESI m/z): 303 (M+H)
RT(min): 1.45

(2S)-tert-butyl 2-(((S)-1,1-dimethylethylsulfina-mide)(5-methylpyridin-2-yl)methyl)pyrrolidine-1-carboxylate (optically active substance B)

MS(ESI m/z): 396 (M+H)
RT(min): 1.39

(2S)-tert-butyl 2-(amino(5-methylpyridin-2-yl)methyl)pyrrolidine-1-carboxylate (optically active substance B)

MS(ESI m/z): 292 (M+H)
RT(min): 0.96

Reference Example 23-8-3

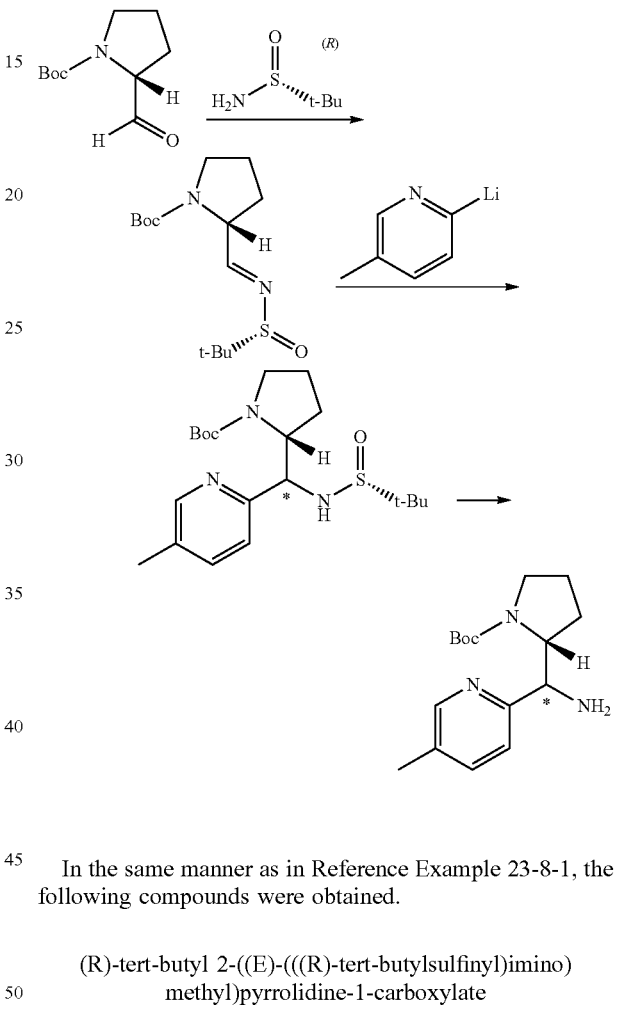

In the same manner as in Reference Example 23-8-1, the following compounds were obtained.

(R)-tert-butyl 2-((E)-(((R)-tert-butylsulfinyl)imino)methyl)pyrrolidine-1-carboxylate (2R)-tert-butyl 2-(((R)-1,1-dimethylethylsulfina-mide)(5-methylpyridin-2-yl)methyl)pyrrolidine-1-carboxylate (optically active substance C)

MS(ESI m/z): 396 (M+H)
RT(min): 1.39

(2R)-tert-butyl 2-(amino(5-methylpyridin-2-yl)methyl)pyrrolidine-1-carboxylate (optically active substance C)

MS(ESI m/z): 292 (M+H)
RT(min): 1.00

Reference Example 23-8-4

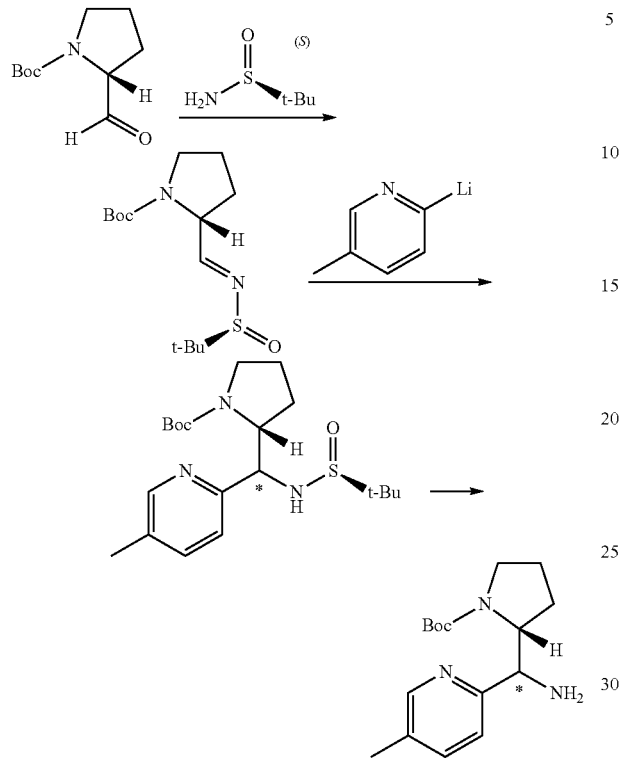

In the same manner as in Reference Example 23-8-1, the following compounds were obtained.

(R)-tert-butyl 2-((E)-(((S)-tert-butylsulfinyl)imino)methyl)pyrrolidine-1-carboxylate (2R)-tert-butyl 2-(((S)-1,1-dimethylethylsulfinamide)(5-methylpyridin-2-yl)methyl)pyrrolidine-1-carboxylate (optically active substance D)

MS(ESI m/z): 396 (M+H)
RT(min): 1.29

(2R)-tert-butyl 2-(amino(5-methylpyridin-2-yl)methyl)pyrrolidine-1-carboxylate (optically active substance D)

MS(ESI m/z): 292 (M+H)
RT(min): 0.99

Reference Example 23-8-5

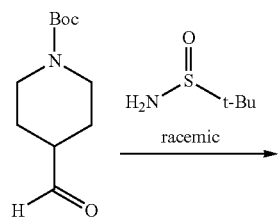

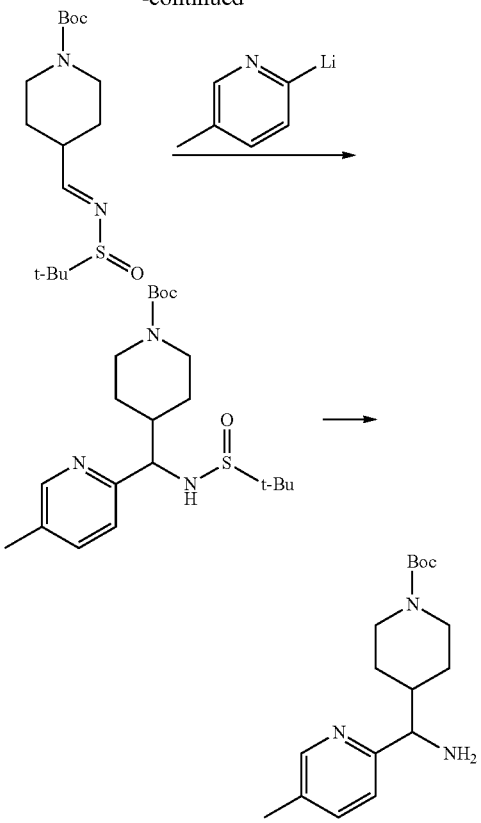

In the same manner as in Reference Example 23-8-1, the following compounds were obtained.

(E)-tert-butyl 4-(((tert-butyl sulfinyl)imino)methyl)piperidine-1-carboxylate

MS(ESI m/z): 317 (M+H)
RT(min): 1.55 tert-Butyl 4-((1,1-dimethylethylsulfinamide)(5-methylpyridin-2-yl)methyl)piperidine-1-carboxylate MS(ESI m/z): 410 (M+H)
RT(min): 1.22 tert-Butyl 4-(amino(5-methylpyridin-2-yl)methyl)piperidine-1-carboxylate

MS(ESI m/z): 306 (M+H)
RT(min): 0.94

Reference Example 23-8-6

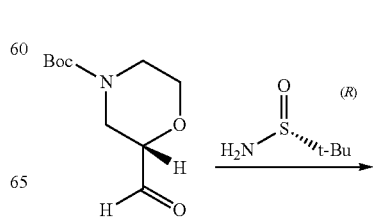

195

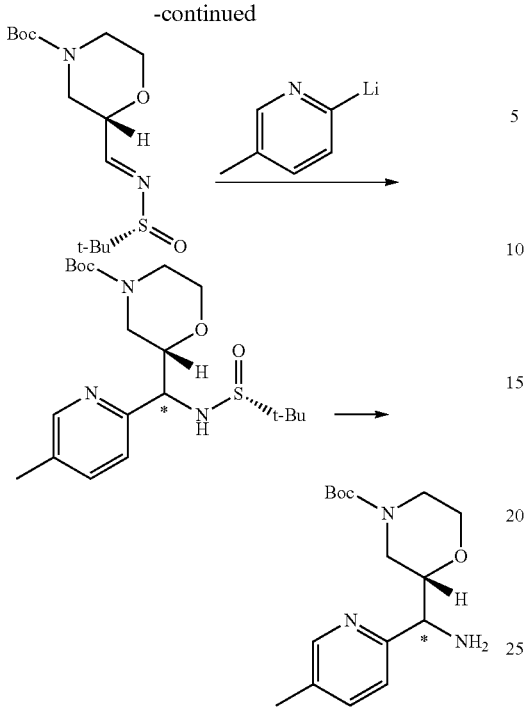

In the same manner as in Reference Example 23-8-1, the following compounds were obtained.

(S)-tert-butyl 2-((E)-(((R)-tert-butyl sulfinyl)imino)methyl)morpholine-4-carboxylate MS(ESI m/z): 319 (M+H)
RT(min): 1.38

(2S)-tert-butyl 2-(((R)-1,1-dimethylethylsulfinamide)(5-methylpyridin-2-yl)methyl)morpholine-4-carboxylate (optically active substance A)

MS(ESI m/z): 412 (M+H)
RT(min): 1.19

(2S)-tert-butyl 2-(amino(5-methylpyridin-2-yl)methyl)morpholine-4-carboxylate (optically active substance A)

MS(ESI m/z): 308 (M+H)
RT(min): 0.89

Reference Example 23-8-7

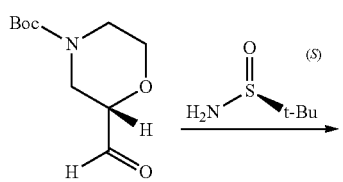

196

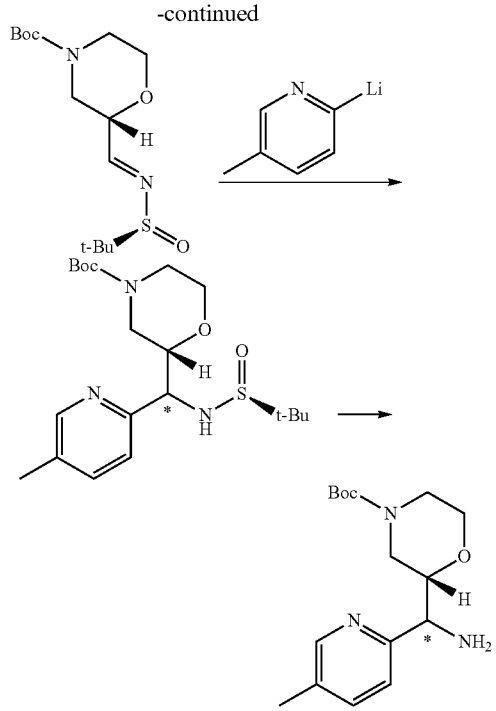

In the same manner as in Reference Example 23-8-1, the following compounds were obtained.

(S)-tert-butyl 2-((E)-(((S)-tert-butyl sulfinyl)imino)methyl)morpholine-4-carboxylate MS(ESI m/z): 319 (M+H)
RT(min): 1.38

(2S)-tert-butyl 2-(((S)-1,1-dimethylethylsulfinamide)(5-methylpyridin-2-yl)methyl)morpholine-4-carboxylate (optically active substance B)

MS(ESI m/z): 412 (M+H)
RT(min): 1.30

(2S)-tert-butyl 2-(amino(5-methylpyridin-2-yl)methyl)morpholine-4-carboxylate (optically active substance B)

MS(ESI m/z): 308 (M+H)
RT(min): 0.91

Reference Example 23-8-8

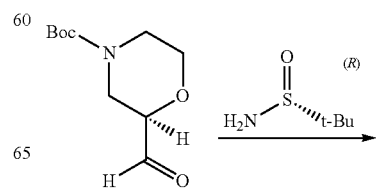

197

-continued

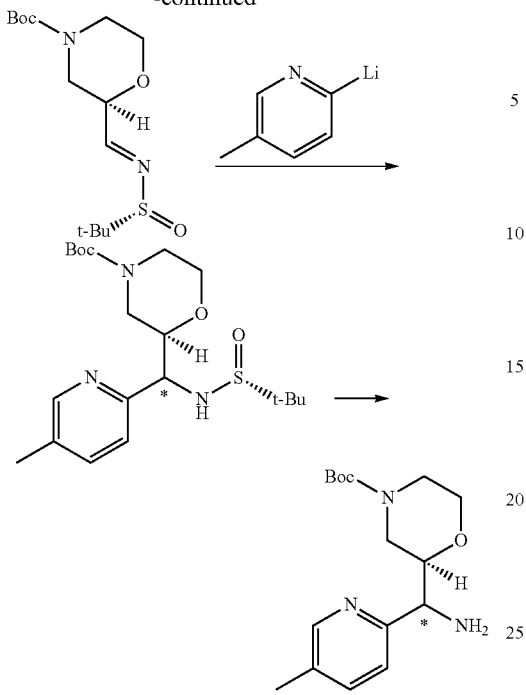

In the same manner as in Reference Example 23-8-1, the following compounds were obtained.

(R)-tert-butyl 2-((E)-(((R)-tert-butyl sulfinyl)imino)methyl)morpholine-4-carboxylate MS(ESI m/z): 319 (M+H)
RT(min): 1.38

(2R)-tert-butyl 2-(((R)-1,1-dimethylethylsulfinamide)(5-methylpyridin-2-yl)methyl)morpholine-4-carboxylate (optically active substance C)

MS(ESI m/z): 412 (M+H)
RT(min): 1.30

(2R)-tert-butyl 2-(amino (5-methylpyridin-2-yl)methyl)morpholine-4-carboxylate (optically active substance C)

MS(ESI m/z): 308 (M+H)
RT(min): 0.89

Reference Example 23-8-9

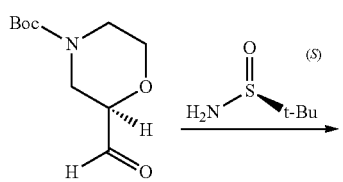

198

-continued

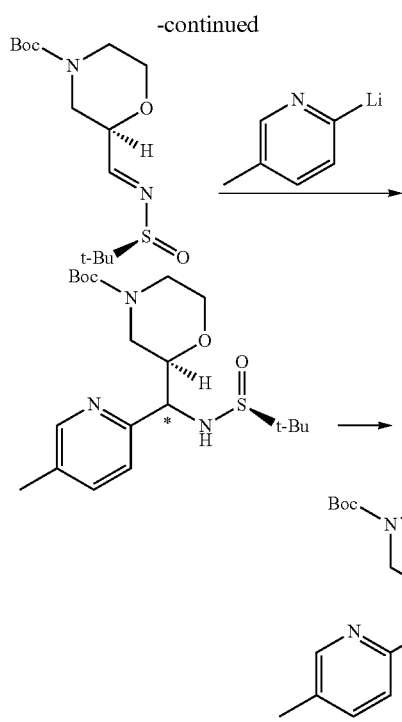

In the same manner as in Reference Example 23-8-1, the following compounds were obtained.

(R)-tert-butyl 2-((E)-(((S)-tert-butyl sulfinyl)imino)methyl)morpholine-4-carboxylate MS(ESI m/z): 319 (M+H)
RT(min): 1.39

(2R)-tert-butyl 2-(((S)-1,1-dimethylethylsulfinamide)(5-methyl pyridin-2-yl)methyl)morpholine-4-carboxylate (optically active substance D)

MS(ESI m/z): 412 (M+H)
RT(min): 1.19

(2R)-tert-butyl 2-(amino(5-methylpyridin-2-yl)methyl)morpholine-4-carboxylate (optically active substance D)

MS(ESI m/z): 308 (M+H)
RT(min): 0.90

Reference Example 23-8-10

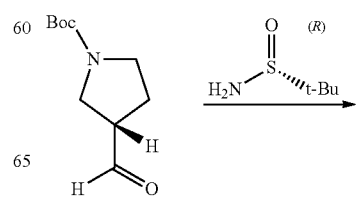

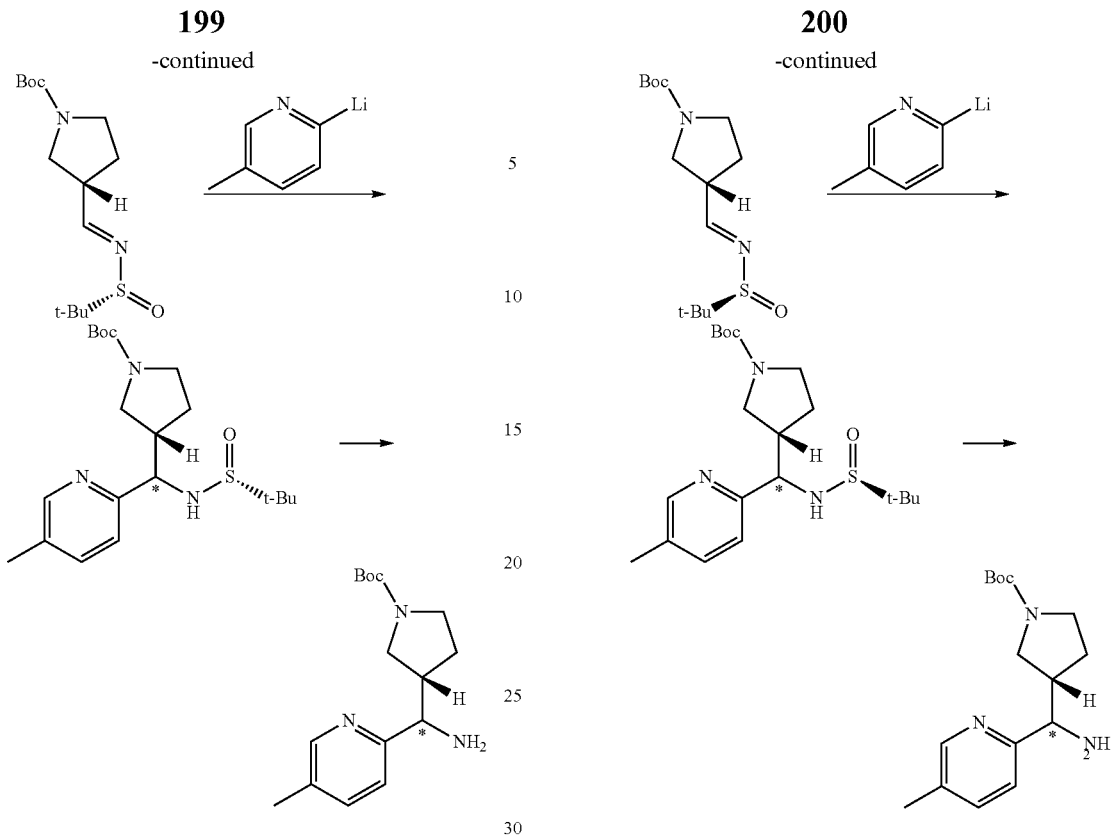

In the same manner as in Reference Example 23-8-1, the following compounds were obtained.

(S)-tert-butyl 3-((E)-(((R)-tert-butylsulfinyl)imino)methyl)pyrrolidine-1-carboxylate MS(ESI m/z): 303 (M+H)
RT(min): 1.41

(3 S)-tert-butyl 3-(((R)-1,1-dimethylethylsulfinamide)(5-methylpyridin-2-yl)methyl)pyrrolidine-1-carboxylate (optically active substance A)

MS(ESI m/z): 396 (M+H)
RT(min): 1.24

(3S)-tert-butyl 3-(amino(5-methylpyridin-2-yl)methyl)pyrrolidine-1-carboxylate (optically active substance A)

MS(ESI m/z): 292 (M+H)
RT(min): 0.91

Reference Example 23-8-11

In the same manner as in Reference Example 23-8-1, the following compounds were obtained.

(S)-tert-butyl 3-((E)-(((S)-tert-butylsulfinyl)imino)methyl)pyrrolidine-1-carboxylate MS(ESI m/z): 303 (M+H)
RT(min): 1.43

(3 S)-tert-butyl 3-(((S)-1,1-dimethylethylsulfinamide)(5-methylpyridin-2-yl)methyl)pyrrolidine-1-carboxylate (optically active substance B)

MS(ESI m/z): 396 (M+H)
RT(min): 1.23

(3S)-tert-butyl 3-(amino(5-methylpyridin-2-yl)methyl)pyrrolidine-1-carboxylate (optically active substance B)

MS(ESI m/z): 292 (M+H)
RT(min): 0.88

Reference Example 23-8-12

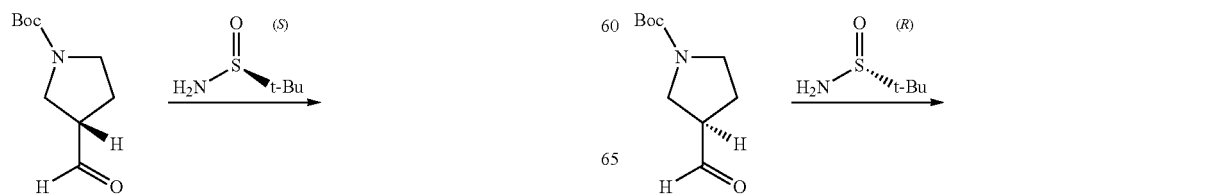

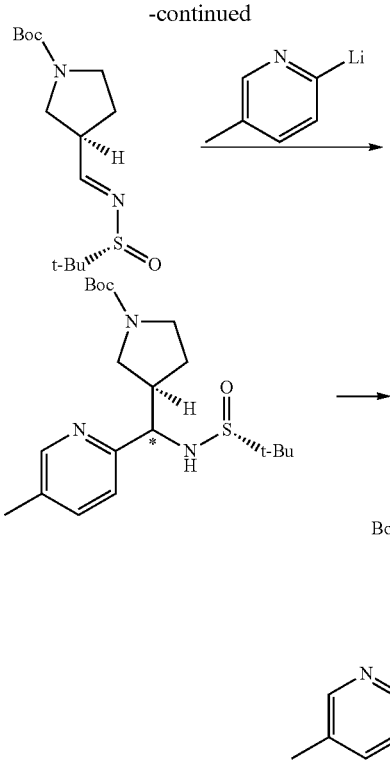

In the same manner as in Reference Example 23-8-1, the following compounds were obtained.

(R)-tert-butyl 3-((E)-(((R)-tert-butylsulfinyl)imino)methyl)pyrrolidine-1-carboxylate MS(ESI m/z): 303 (M+H)
RT(min): 1.43

(3R)-tert-butyl 3-(((R)-1,1-dimethylethylsulfinamide)(5-methylpyridin-2-yl)methyl)pyrrolidine-1-carboxylate (optically active substance C)

MS(ESI m/z): 396 (M+H)
RT(min): 1.23

(3R)-tert-butyl 3-(amino(5-methylpyridin-2-yl)methyl)pyrrolidine-1-carboxylate (optically active substance C)

MS(ESI m/z): 292 (M+H)
RT(min): 0.87

Reference Example 23-9-1

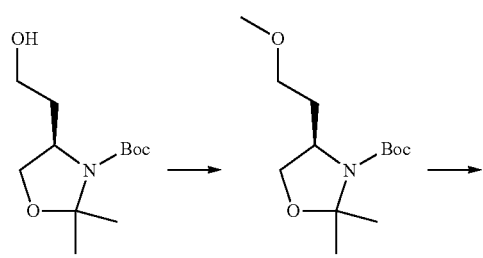

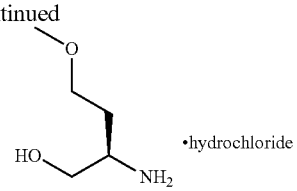

(1)
In the same manner as in Reference Example 21-20 (1), the following compound was obtained.

(R)-tert-butyl 4-(2-methoxyethyl)-2,2-dimethyl oxazolidine-3-carboxylate (2)
Methanol (1.14 mL) and 4.0 mol/L hydrogen chloride/1,4-dioxane (2.84 mL) were added to (R)-tert-butyl 4-(2-methoxyethyl)-2,2-dimethyl oxazolidine-3-carboxylate (147 mg), followed by stirring at room temperature for 3 hours. The solvent was distilled off under reduced pressure, whereby hydrochloride (94 mg) of (R)-2-amino-4-methoxybutane-1-ol was obtained.

Reference Example 23-9-2

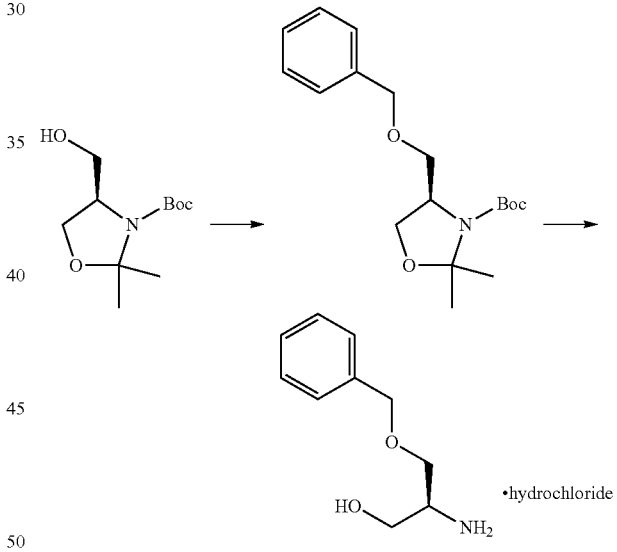

(1)
Under ice-cooling, sodium hydride (130 mg, 60%, dispersed in liquid paraffin) was added to a solution of (R)-tert-butyl 4-(hydroxymethyl)-2,2-dimethyl oxazolidine-3-carboxylate (500 mg) in tetrahydrofuran (10.8 mL), followed by stirring for 30 minutes. (Bromomethyl)benzene (385 µL) was added thereto, followed by stirring at room temperature for 2.5 hours. Sodium hydride (130 mg, 60%, dispersed in liquid paraffin) and (bromomethyl)benzene (385 µL) were added thereto, followed by stirring for 1.5 hours. Methanol and water were added sequentially thereto, and the resultant product was extracted with ethyl acetate. The organic layer was dried over anhydrous sodium sulfate, and the solvent was distilled off under reduced pressure. The obtained residues were purified by silica gel column chromatography (hexane:ethyl acetate=1:0→4:1), whereby (R)- tert-butyl 4-((benzyloxy)methyl)-2,2-dimethyl oxazolidine-3-carboxylate (564 mg) was obtained.

(2)
In the same manner as in Reference Example 23-9-1 (2), the following compound was obtained.

Hydrochloride of
(S)-2-amino-3-(benzyloxy)propane-1-ol

MS(ESI m/z): 182 (M+H)
RT(min): 0.57

Reference Example 23-10-1

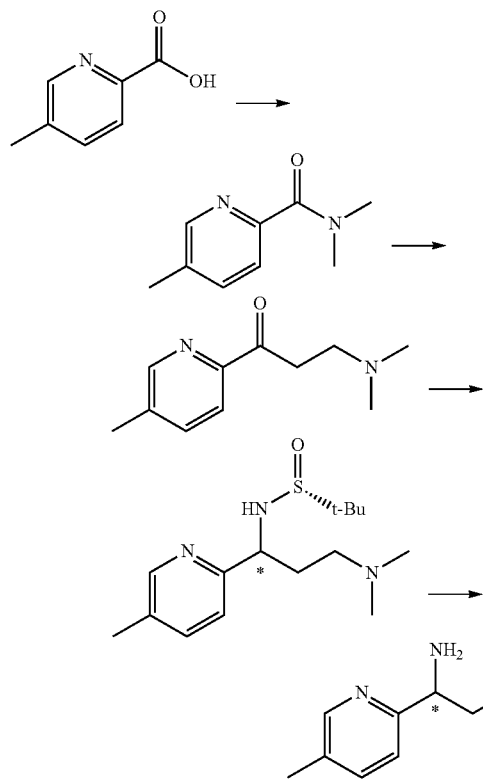

In the same manner as in Reference Example 23-1, 1-(5-methylpyridin-2-yl)-3-dimethylaminopropane-1-amine (optically active substance A) was obtained.
MS(ESI m/z): 194 (M+H)
RT(min): 0.21

Reference Example 23-10-2

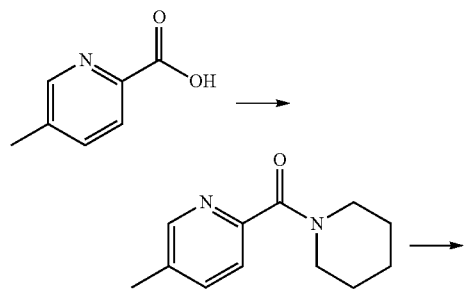

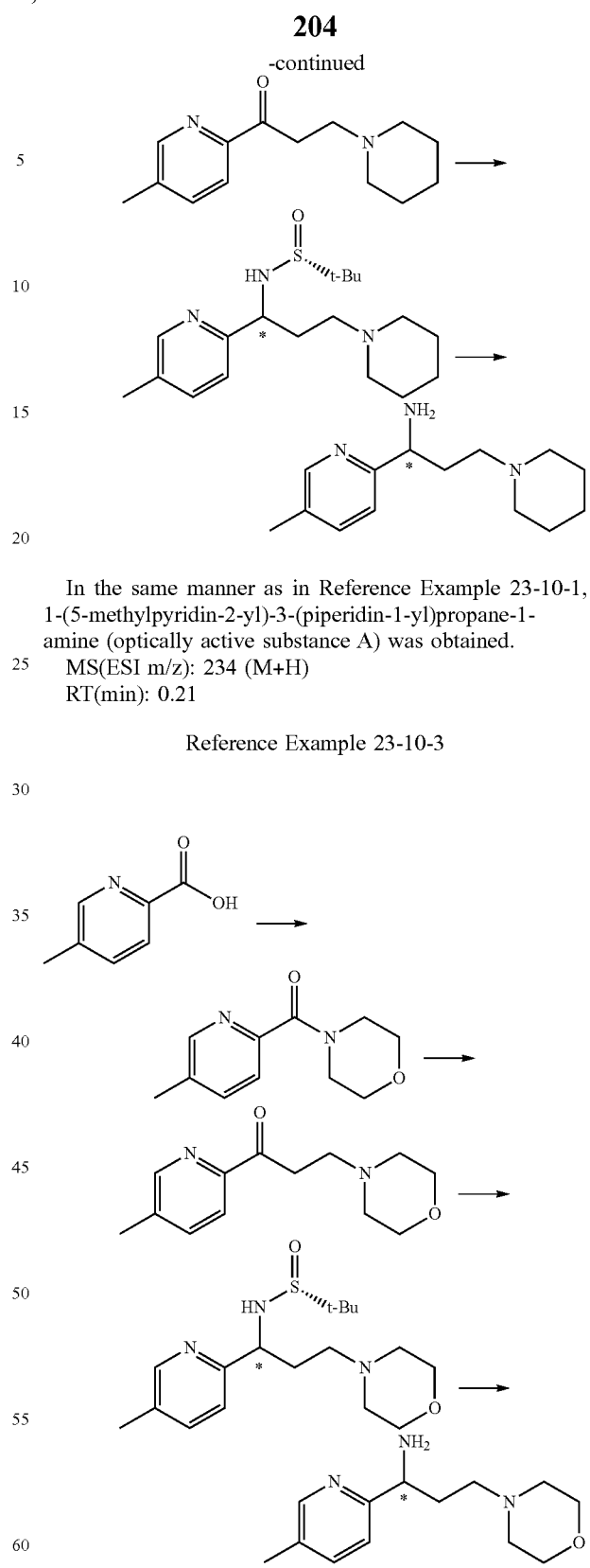

In the same manner as in Reference Example 23-10-1, 1-(5-methylpyridin-2-yl)-3-(piperidin-1-yl)propane-1-amine (optically active substance A) was obtained.
MS(ESI m/z): 234 (M+H)
RT(min): 0.21

Reference Example 23-10-3

In the same manner as in Reference Example 23-10-1, 1-(5-methylpyridin-2-yl)-3-morpholinopropane-1-amine (optically active substance A) was obtained.
MS(ESI m/z): 236 (M+H)
RT(min): 0.21

Reference Example 23-10-4

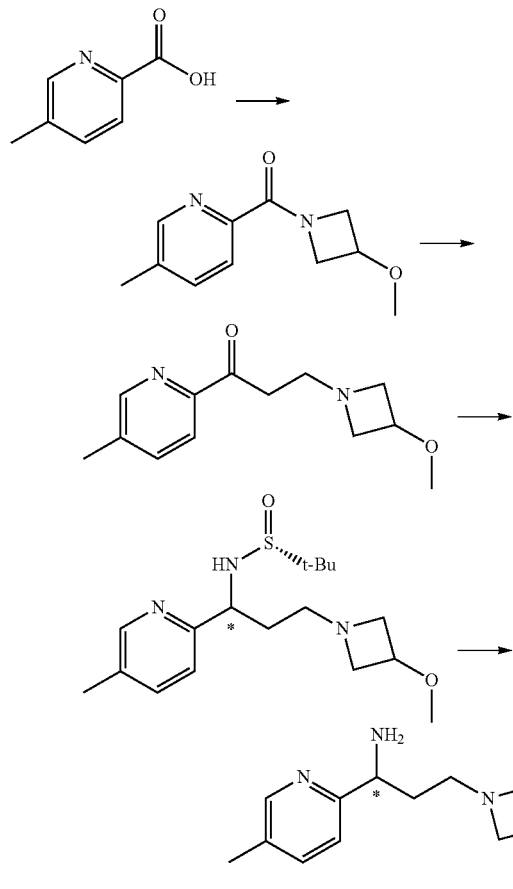

In the same manner as in Reference Example 23-10-1, 1-(5-methylpyridin-2-yl)-3-(3-methoxyazetidin-1-yl)propane-1-amine (optically active substance A) was obtained.
MS(ESI m/z): 236 (M+H)
RT(min): 0.21

Reference Example 23-10-5

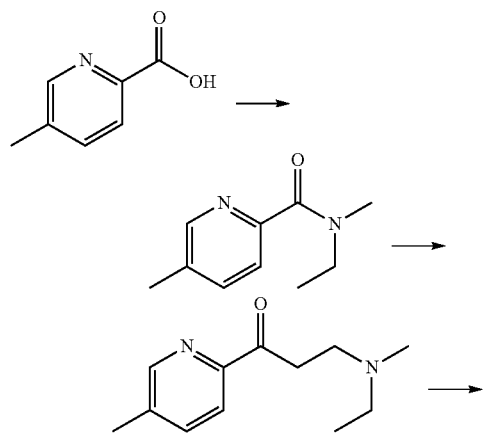

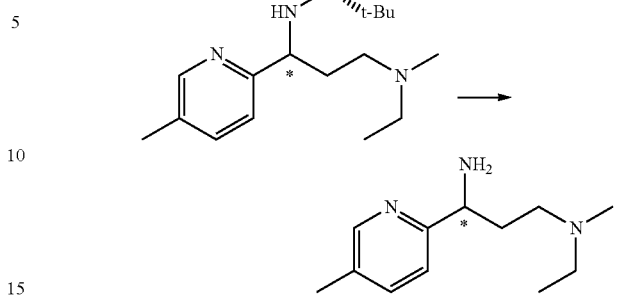

In the same manner as in Reference Example 23-10-1, 1-(5-methylpyridin-2-yl)-3-(ethyl(methyl)amino)propane-1-amine (optically active substance A) was obtained.
MS(ESI m/z): 208 (M+H)
RT(min): 0.21

Reference Example 23-10-6

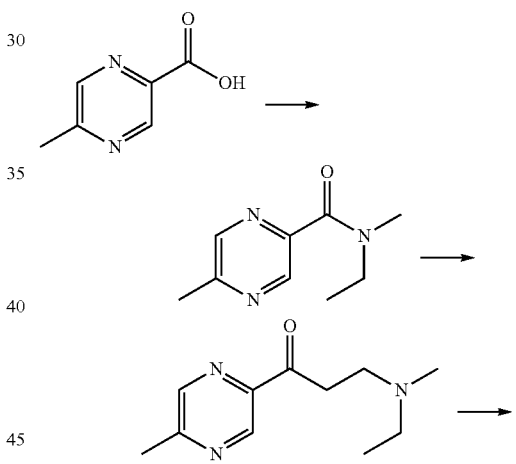

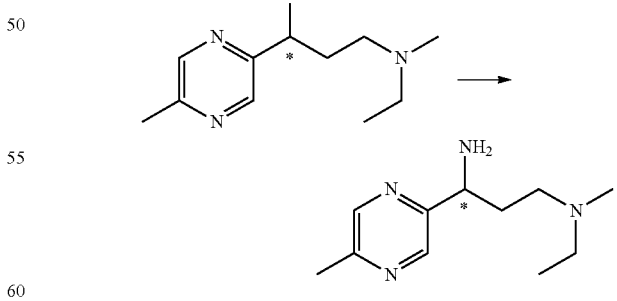

In the same manner as in Reference Example 23-10-1, 1-(5-methylpyrazin-2-yl)-3-(ethyl(methyl)amino)propane-1-amine (optically active substance A) was obtained.
MS(ESI m/z): 209 (M+H)
RT(min): 0.20

Reference Example 23-10-7

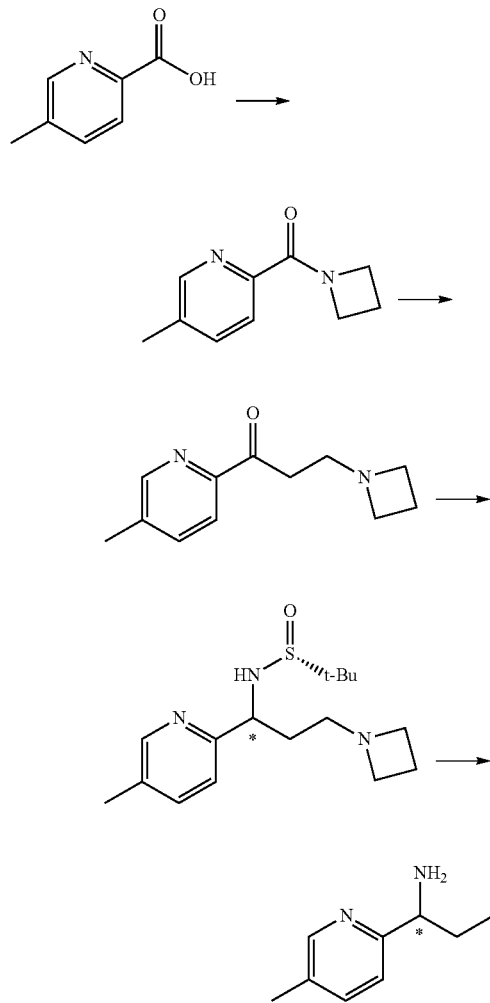

In the same manner as in Reference Example 23-10-1, 1-(5-methylpyridin-2-yl)-3-(azetidin-1-yl)propane-1-amine (optically active substance A) was obtained.

MS(ESI m/z): 207 (M+H)

RT(min): 0.20

Reference Example 23-11

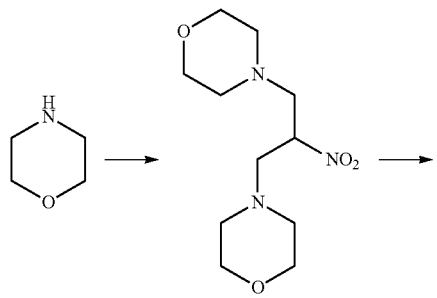

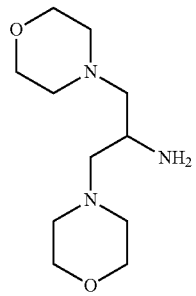

(1)

Nitromethane (270 μL) and a 40% benzyl trimethylammonium hydroxide aqueous solution (209 mg) were added to a solution of morpholine (871 μL) and a 37% formaldehyde aqueous solution (811 mg) in tetrahydrofuran (5 mL), followed by stirring at room temperature for 12 hours. A saturated sodium chloride aqueous solution was added to the reaction mixture, and the resultant product was extracted with ethyl acetate. The organic layer was dried over anhydrous sodium sulfate, then, the solvent was distilled off under reduced pressure, and the obtained residues were purified by silica gel column chromatography (ethyl acetate:hexane=1:1, NH silica), whereby 4,4'-(2-nitropropane-1,3-diyl)dimorpholine (1.02 g) was obtained.

MS(ESI m/z): 260 (M+H)

RT(min): 0.45

(2)

A 7.0 mol/L ammonia/methanol solution (4 mL) was added to a solution of 4,4'-(2-nitropropane-1,3-diyl)dimorpholine (518 mg) obtained in Reference Example 23-11 (1) in methanol (40 mL), and the resultant product was subjected to a hydrogenation reaction (30° C., FullH$_2$, flow rate of 1 mL/min, RaNi) using a flow type hydrogenation reaction apparatus. The solvent was distilled off under reduced pressure, and the obtained residues were purified by silica gel column chromatography (chloroform:methanol=9:1, NH silica), whereby 1,3-dimorpholinopropane-2-amine (408 mg) was obtained.

MS(ESI m/z): 230 (M+H)

RT(min): 0.22

Reference Example 23-12

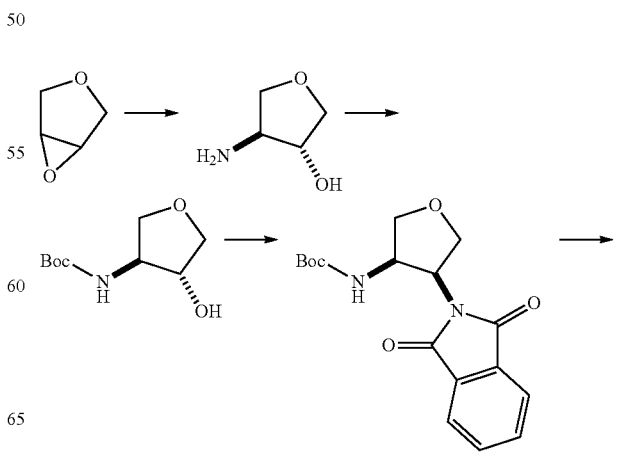

209
-continued

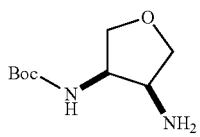

(1)

A 25% ammonia aqueous solution (15 mL) was added to a solution of 3,6-dioxabicyclo[3.1.0]hexane (2.4 g) in ethanol (15 mL), and the resultant product was stirred at 70° C. for 7.5 hours, and further stirred at 80° C. for 1.5 hours. The reaction mixture was cooled to room temperature, and the solvent was distilled off under reduced pressure, whereby trans-4-aminotetrahydrofuran-3-ol (2.9 g) was obtained.

(2)

Triethylamine (6 mL) and di-tert-butyl dicarbonate (9.8 mL) were added to a solution of trans-4-amino tetrahydrofuran-3-ol (2.9 g) obtained in Reference Example 23-12 (1) in tetrahydrofuran (40 mL), followed by stirring for 16 hours. A saturated sodium chloride aqueous solution was added to the reaction mixture, and the resultant product was extracted with ethyl acetate, followed by drying over anhydrous sodium sulfate. The solvent was distilled off under reduced pressure, and the obtained residues were purified by silica gel column chromatography (hexane:ethyl acetate=10: 1→1:9), whereby tert-butyl (trans-4-hydroxytetrahydrofuran-3-yl)carbamate (1.8 g) was obtained.

(3)

Triphenylphosphine (780 mg), phthalimide (440 mg), and 2.2 mol/L diethyl azodicarboxylate/toluene (1.3 mL) were added to a solution of tert-butyl (trans-4-hydroxytetrahydrofuran-3-yl)carbamate (200 mg) obtained in Reference Example 23-12 (2) in tetrahydrofuran (10 mL), followed by stirring at 60° C. for 3 hours. A saturated sodium hydrogen carbonate aqueous solution was added to the reaction mixture, and the resultant product was extracted with ethyl acetate, followed by drying over anhydrous sodium sulfate. The solvent was distilled off under reduced pressure, and the obtained residues were purified by silica gel column chromatography (hexane:ethyl acetate=10:1→2:1), whereby tert-butyl (cis-4-(1,3-dioxoisoindilin-2-yl)tetrahydrofuran-3-yl)carbamate (327 mg) was obtained.

(4)

Hydrazine monohydrate (1 mL) was added to a solution of tert-butyl (cis-4-(1,3-dioxoisoindolin-2-yl)tetrahydrofuran-3-yl)carbamate (327 mg) obtained in Reference Example 23-12 (3) in ethanol (10 mL), followed by stirring for 11.5 hours. The insolubles were filtered off, and the solvent was distilled off under reduced pressure. A saturated sodium chloride aqueous solution was added to the residues, and the resultant product was extracted with ethyl acetate, followed by drying over anhydrous sodium sulfate. The solvent was distilled off under reduced pressure, and the obtained residues were purified by silica gel column chromatography (chloroform:methanol=20:1→10:1), whereby tert-butyl (cis-4-aminotetrahydrofuran-3-yl)carbamate (138 mg) was obtained.

210
Reference Example 24

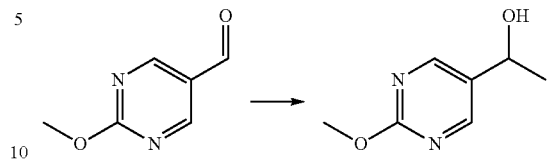

Under ice-cooling, 3.0 mol/L methyl magnesium bromide/diethyl ether (0.7 mL) was added to a solution of 2-methoxypyrimidine-5-carbaldehyde (138 mg) in tetrahydrofuran (5 mL), followed by stirring for 1 hour. Acetic acid was added thereto, and the solvent was distilled off under reduced pressure. The obtained residues were purified by silica gel column chromatography (hexane:ethyl acetate=1: 1), whereby 1-(2-methoxypyrimidin-5-yl)ethanol (126 mg) was obtained.

MS(ESI m/z): 155 (M+H)
RT(min): 0.52

Reference Example 25-1

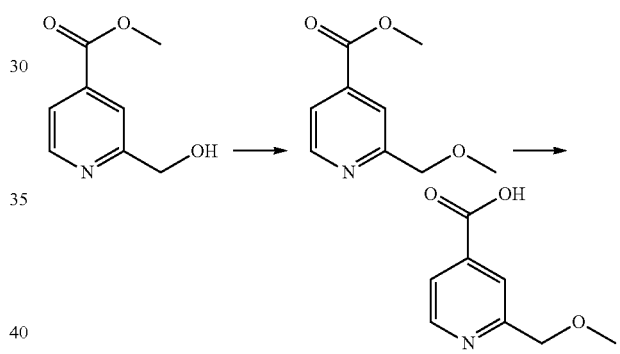

(1)

Under ice-cooling, sodium hydride (187 mg, 60%, dispersed in liquid paraffin) was added to a solution of methyl 2-(hydroxymethyl)isonicotinate (650 mg) in N,N-dimethyl formamide (8.0 mL), followed by stirring for 15 minutes. Methyl iodide (740 µL) was added thereto, followed by stirring for 1 hour. Ethyl acetate was added thereto, then, the organic layer was washed with a saturated aqueous sodium chloride solution, and dried over anhydrous sodium sulfate. The solvent was distilled off under reduced pressure, and the obtained residues were purified by silica gel column chromatography (hexane:ethyl acetate=9:1→1:1), whereby methyl 2-(methoxymethyl)isonicotinate (370 mg) was obtained as a colorless oily material.

(2)

Ethanol (1.0 mL) and a 5 mol/L sodium hydroxide aqueous solution (200 µL) were added to methyl 2-(methoxymethyl)isonicotinate (100 mg) obtained in Reference Example 25-1 (1), followed by stirring at room temperature for 6 hours. The solvent was distilled off under reduced pressure, then, concentrated hydrochloric acid (90 µL) was added to the obtained residues, and the precipitated solid was collected by filtration, whereby 2-(methoxymethyl)isonicotinic acid (53 mg) was obtained as a white solid.

Reference Example 25-2

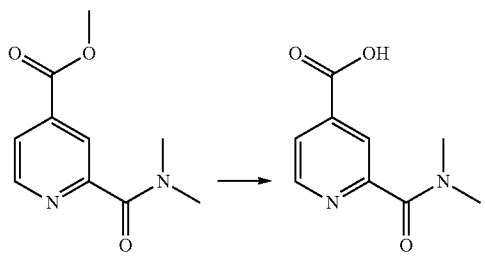

Ethanol (2.0 mL) and 5 mol/L sodium hydroxide aqueous solution (200 µL) were added to methyl 2-(dimethyl carbamoyl)isonicotinate (95 mg), followed by stirring at room temperature for 6 hours. Concentrated hydrochloric acid (90 µL) was added to the reaction mixture, then, the solvent was distilled off under reduced pressure, and ethyl acetate and a saturated sodium chloride aqueous solution were added thereto. All the solvents were distilled off under reduced pressure, then, ethanol was added thereto, and the precipitated solid was collected by filtration. The solvent was distilled off under reduced pressure, whereby 2-(dimethylcarbamoyl)isonicotinic acid (86 mg) was obtained.

Reference Example 25-3

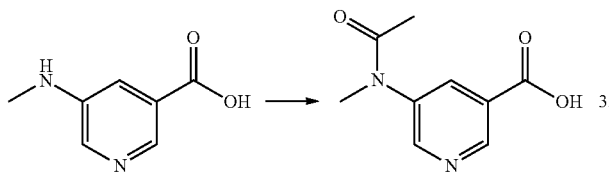

Acetic anhydride (500 µL) was added to a solution of 5-(methylamino)nicotinic acid (100 mg) in pyridine (1.0 mL), followed by stirring at room temperature for 22 hours. Water was added to the reaction mixture, and the solvent was distilled off under reduced pressure, whereby 5-(N-methylacetamide)nicotinic acid (70 mg) was obtained as a white solid.

Reference Example 26-1

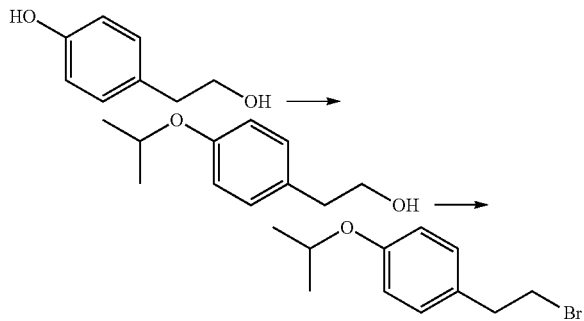

(1)
A mixture of 4-(2-hydroxyethyl)phenol (500 mg), N,N-dimethyl formamide (12 mL), potassium carbonate (600 mg), and 2-iodopropane (397 µL) was stirred at 80° C. for 7 hours. Water was added to the reaction mixture, and the resultant product was extracted with ethyl acetate. The organic layer was washed with a saturated sodium chloride aqueous solution, and the solvent was distilled off under reduced pressure, whereby 2-(4-isopropoxyphenyl)ethanol was obtained.

(2)
In the same manner as in Example 1-42-1 (2), the following compound was obtained.

1-(2-Bromoethyl)-4-isopropoxybenzene

Reference Example 26-2

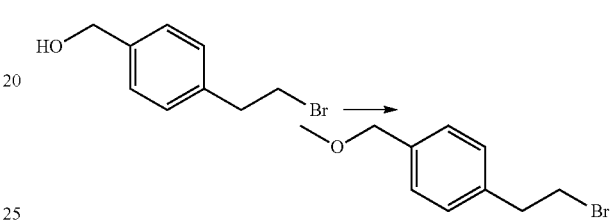

A solution of (4-(2-bromoethyl)phenyl)methanol (200 mg) in tetrahydrofuran (2.3 mL) and methyl iodide (87 µL) was added to a suspension of sodium hydride (56 mg, 60%, dispersed in liquid paraffin) in tetrahydrofuran (2.3 mL) under ice-cooling, followed by stirring at room temperature for 3 hours. Methanol and water were added to the reaction mixture, and the resultant product was extracted with ethyl acetate. The organic layer was washed with a saturated sodium chloride aqueous solution, then, the solvent was distilled off under reduced pressure, and the obtained residues were purified by silica gel column chromatography (hexane:ethyl acetate=9:1→1:1), whereby 1-(2-bromoethyl)-4-(methoxymethyl)benzene (147 mg) was obtained.

Reference Example 27-1

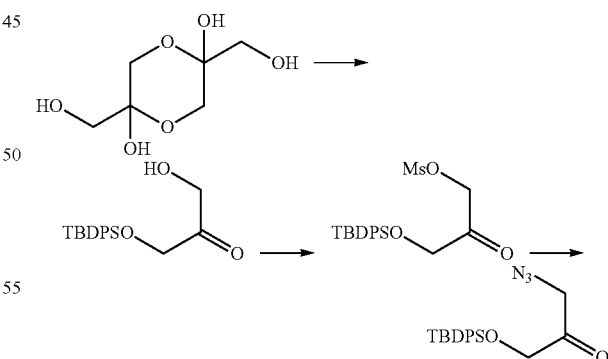

(1)
Imidazole (756 mg) and tert-butyldiphenyl chlorosilane (721 µL) was added to a solution of 2,5-bis(hydroxymethyl)-1,4-dioxane-2,5-diol (1.0 g) in N,N-dimethyl formamide (5.6 mL), followed by stirring for 3 hours. Water was added to the reaction mixture, and the resultant product was extracted with hexane and ethyl acetate. The organic layer was washed with a saturated sodium chloride aqueous solution, and the solvent was distilled off under reduced pressure. The obtained residues were purified by silica gel column chromatography (hexane:ethyl acetate=1:0→4:1), whereby 1-((tert-butyldiphenylsilyl)oxy)-3-hydroxypropan-2-one (329 mg) was obtained.

$^1$H-NMR (CDCl$_3$, 300 MHz) δ: 7.66-7.36 (10H, m), 4.60 (2H, d, J=5.0 Hz), 4.32 (2H, s), 2.99 (1H, t, J=5.0 Hz), 1.10 (9H, s).

(2)

In the same manner as in Example 1-59-1 (2), the following compound was obtained.

3-((tert-Butyldiphenylsilyl)oxy)-2-oxopropyl methanesulfonate $^1$H-NMR (CDCl$_3$, 300 MHz) δ: 7.73-7.36 (10H, m), 5.20 (2H, s), 4.30 (2H, s), 3.19 (3H, s), 1.10 (9H, s).

(3)

The temperature was changed to 50° C., and in the same manner as in Reference Example 22-31 (4), the following compound was obtained.

1-Azide-3-((tert-butyldiphenylsilyl)oxy)propan-2-one $^1$H-NMR (CDCl$_3$, 300 MHz) δ: 7.65-7.34 (10H, m), 4.27 (2H, s), 4.25 (2H, s), 1.10 (9H, s).

Reference Example 27-2

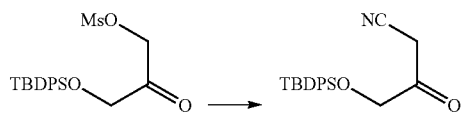

Potassium cyanide (43 mg) was added to a solution of 3-((tert-butyldiphenylsilyl)oxy)-2-oxopropyl methanesulfonate (133 mg) in dimethyl sulfoxide (3.3 mL), followed by stirring at 50° C. for 1 hour. The reaction mixture was cooled to room temperature, then, water was added thereto, and the resultant product was extracted with hexane and ethyl acetate. The organic layer was dried over anhydrous sodium sulfate, and the solvent was distilled off under reduced pressure. The obtained residues were purified by silica gel column chromatography (hexane:ethyl acetate=1:0→3:2), whereby 4-((tert-butyldiphenylsilyl)oxy)-3-oxobutanenitrile (8.6 mg) was obtained.

$^1$H-NMR (CDCl$_3$, 300 MHz) δ: 7.63-7.40 (10H, m), 4.26 (2H, s), 3.73 (2H, s), 1.11 (9H, s).

Reference Example 27-3

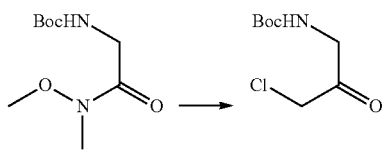

1.1 mol/L methyl lithium/diethyl ether (0.81 mL) was added to a solution of tert-butyl (2-(methoxy(methyl)amino)-2-oxoethyl)carbamate (100 mg) and chloroiodomethane (67 μL) in tetrahydrofuran (4.6 mL) at −78° C., and the resultant product was stirred for 20 minutes, and stirred at 0° C. for 20 minutes. An aqueous saturated ammonium chloride solution was added to the reaction mixture, then, the resultant product was extracted with ethyl acetate, and the solvent was distilled off under reduced pressure. The obtained residues were purified by silica gel column chromatography (hexane:ethyl acetate=9:1→2:3), whereby tert-butyl (3-chloro-2-oxopropyl)carbamate (8.7 mg) was obtained.

$^1$H-NMR (CDCl$_3$, 300 MHz) δ: 5.14 (1H, m), 4.24 (2H, d, J=5.3 Hz), 4.15 (2H, s), 1.45 (9H, s).

Reference Example 28-1-1

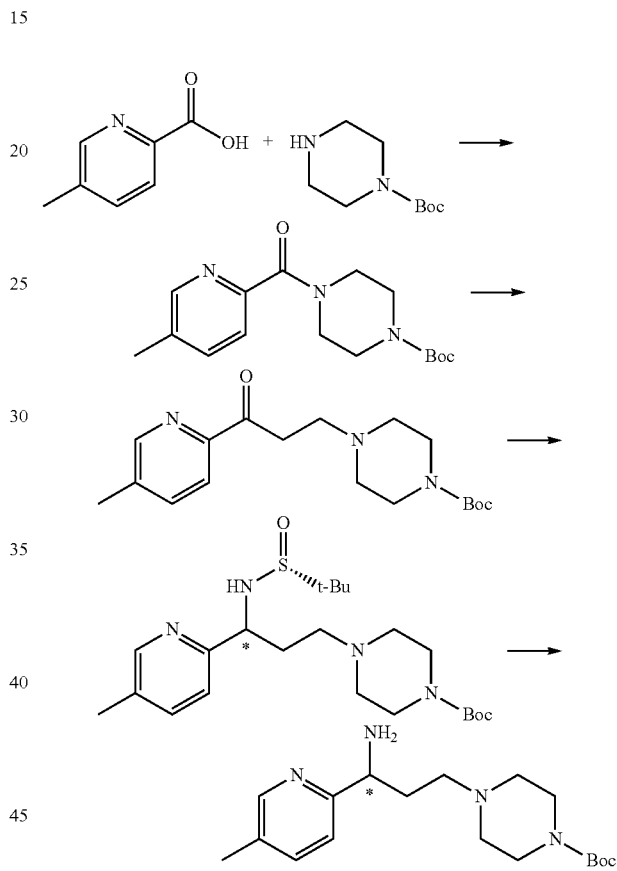

(1)

A mixture of 5-methyl picolinic acid (395 mg), tert-butyl piperazine-1-carboxylate (697 mg), 1-ethyl-3-(3-dimethylaminopropyl)carbodiimide hydrochloride (828 mg), pyridine (341 mg), and chloroform (10 mL) was stirred at room temperature for 1 hour, then, water was added thereto, and the resultant product was extracted with chloroform and ethyl acetate. The organic layer was dried over anhydrous sodium sulfate, and the solvent was distilled off under reduced pressure. The obtained residues were purified by silica gel column chromatography (hexane:ethyl acetate=6:4→0:1), whereby tert-butyl 4-(5-methylpicolinoyl)piperazine-1-carboxylate (725 mg) was obtained.

MS(ESI m/z): 306 (M+H)

RT(min): 0.8417

(2)

In the same manner as in Reference Example 23-1 (2), the following compound was obtained.

tert-Butyl 4-(3-(5-methylpyridin-2-yl)-3-oxopropyl)piperazine-1-carb-carboxylate MS(ESI m/z): 334 (M+H)
RT(min): 0.84

(3)
In the same manner as in Reference Example 23-1 (3), the following compound was obtained.

tert-Butyl 4-((3-((R)-1,1-dimethylethylsulfinamide)-3-(5-methylpyridin-2-yl)propyl)piperazine-1-carboxylate (optically active substance A)

MS(ESI m/z): 439 (M+H)
RT(min): 0.88

(4)
In the same manner as in Reference Example 23-1 (4), the following compound was obtained.

tert-Butyl 4-(3-amino-3-(5-methylpyridin-2-yl)propyl)piperazine-1-carboxylate (optically active substance A)

MS(ESI m/z): 335 (M+H)
RT(min): 0.63

Reference Example 28-1-2

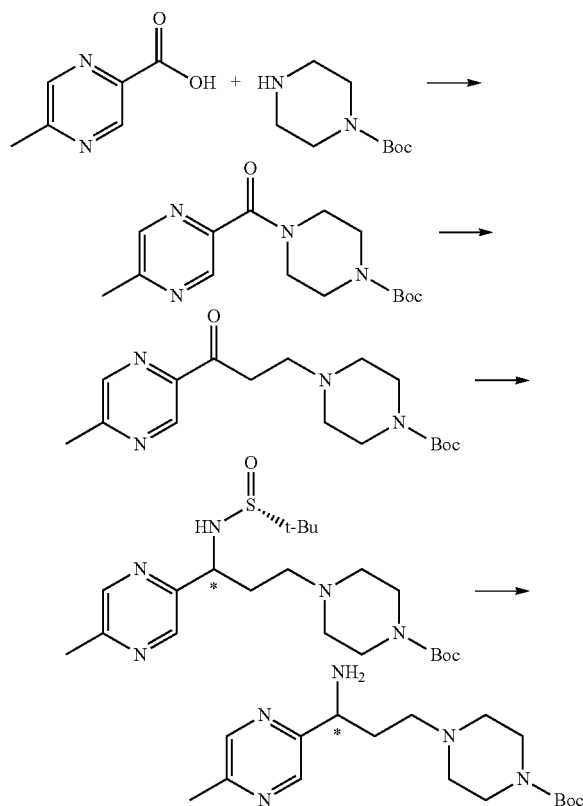

In the same manner as in Reference Example 28-1-1, the following compound was obtained.

tert-Butyl 4-(3-amino-3-(5-methylpyridin-2-yl)propyl)piperazine-1-carboxylate (optically active substance A)

MS(ESI m/z): 336 (M+H)
RT(min): 0.55

Reference Example 28-2-1

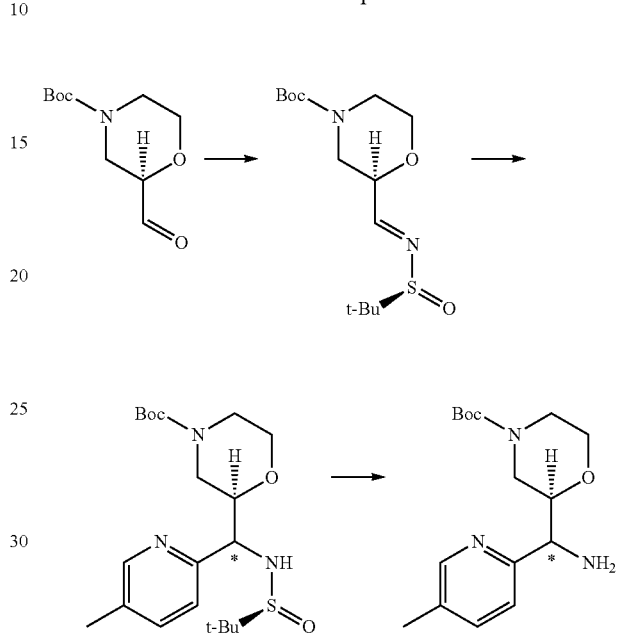

(1)
In the same manner as in Reference Example 23-3 (1), the following compound was obtained.

(R)-tert-butyl 2-((((S)-tert-butylsulfinyl)imino)methyl)morpholine-4-carboxylate (2)
In the same manner as in Reference Example 23-3 (2), the following compound was obtained.

(2R)-tert-butyl 2-(((S)-1,1-dimethylethylsulfinamide)(5-methylpyridin-2-yl)methyl)morpholine-4-carboxylate (optically active substance A)

MS(ESI m/z): 412 (M+H)
RT(min): 1.19

(3)
In the same manner as in Reference Example 23-3 (3), the following compound was obtained.

(2R)-tert-butyl 2-(amino(5-methylpyridin-2-yl)methyl)morpholine-4-carboxylate (optically active substance A)

MS(ESI m/z): 308 (M+H)
RT(min): 0.89

Reference Example 28-2-2

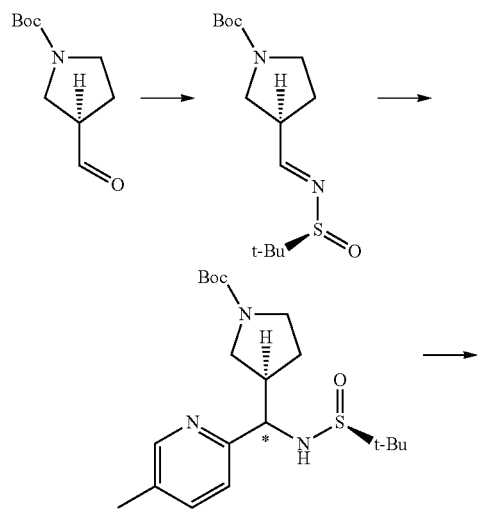

In the same manner as in Reference Example 28-2-1, the following compound was obtained.

(3R)-tert-butyl 3-(amino(5-methylpyridin-2-yl)methyl)pyrrolidine-1-carboxylate (optically active substance A)

MS(ESI m/z): 292 (M+H)
RT(min): 0.91

Reference Example 28-3-1

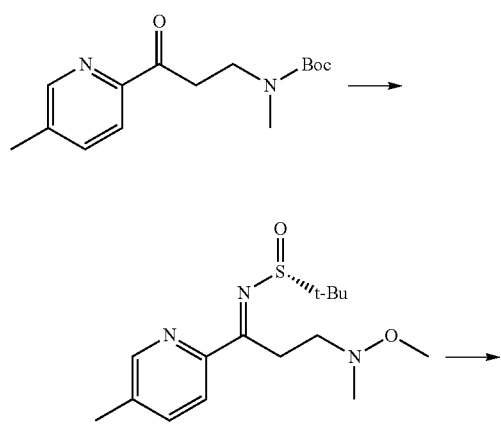

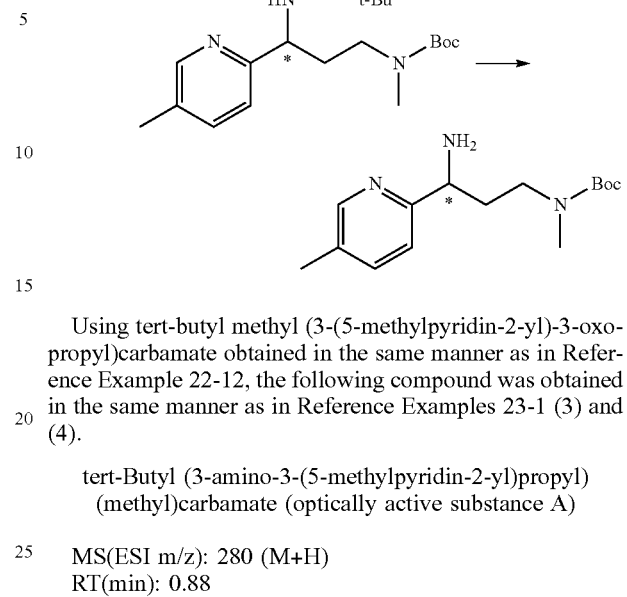

Using tert-butyl methyl (3-(5-methylpyridin-2-yl)-3-oxo-propyl)carbamate obtained in the same manner as in Reference Example 22-12, the following compound was obtained in the same manner as in Reference Examples 23-1 (3) and (4).

tert-Butyl (3-amino-3-(5-methylpyridin-2-yl)propyl)(methyl)carbamate (optically active substance A)

MS(ESI m/z): 280 (M+H)
RT(min): 0.88

Reference Example 28-3-2

In the same manner as in Reference Example 28-3-1, the following compound was obtained.

tert-Butyl (3-amino-3-(5-methylpyrazin-2-yl)propyl)(methyl)carbamate (optically active substance A)

MS(ESI m/z): 281 (M+H)
RT(min): 0.76

Reference Example 28-4

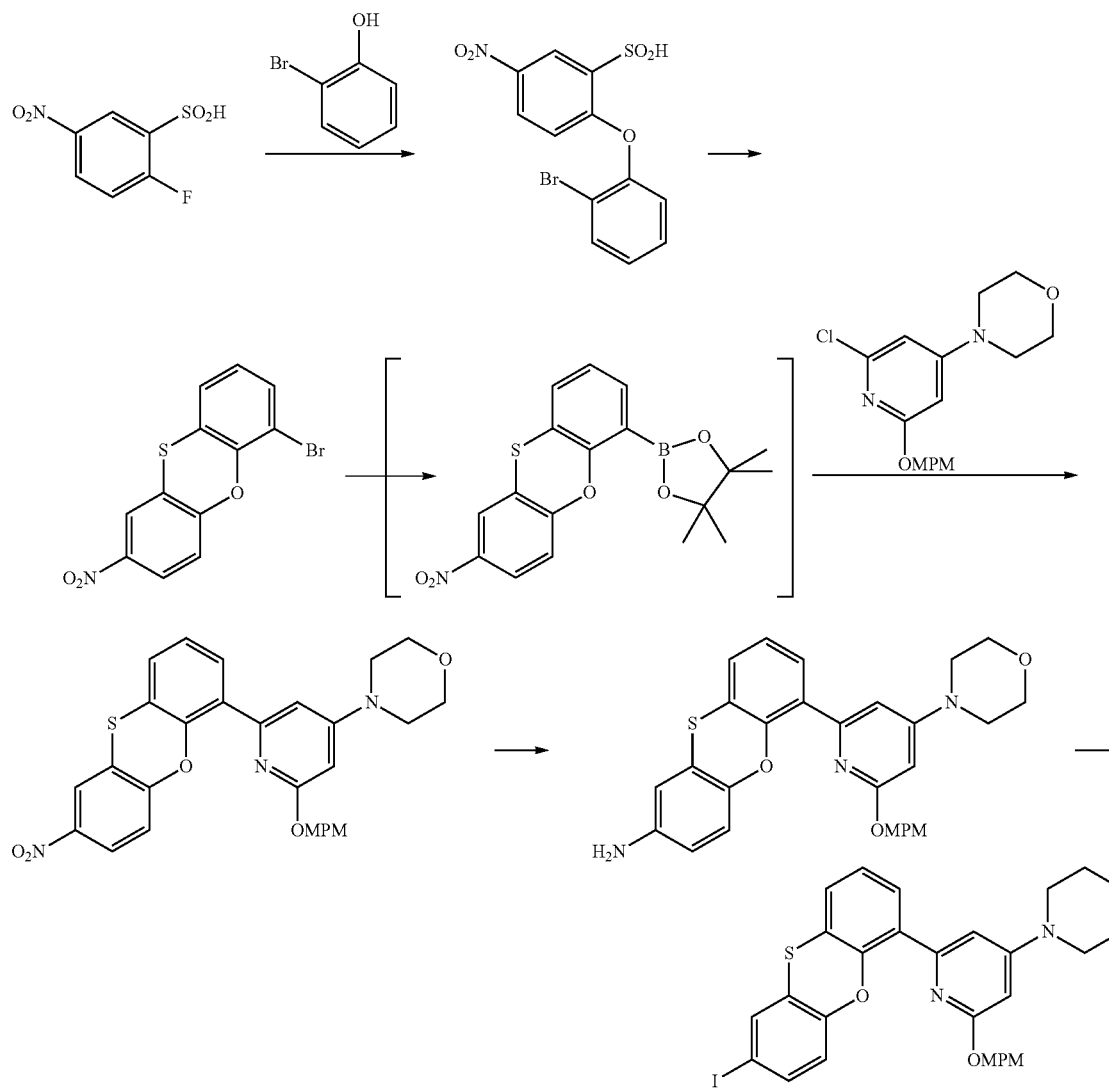

(1)
Using 2-bromophenol instead of 2-bromobenzenethiol, the following compound was obtained in the same manner as in Reference Example 3 (2).

2-(2-Bromophenoxy)-5-nitrobenzene sulfinic acid

MS(ESI m/z): 358 (M+H)
RT(min): 1.00
(2)
In the same manner as in Reference Example 3 (3), the following compound was obtained.

6-Bromo-2-nitrophenoxathiin

MS(ESI m/z): 324 (M+H)
RT(min): 1.97
(3)
In the same manner as in Reference Example 5 (1), the following compound was obtained.

4-(2-((4-Methoxybenzyl)oxy)-6-(8-nitrophenoxathiin-4-yl)pyridin-4-yl)morpholine

MS(ESI m/z): 544 (M+H)
RT(min): 1.80
(4)
In the same manner as in Reference Example 3 (4), the following compound was obtained.

6-(6-((4-Methoxybenzyl)oxy)-4-morpholinopyridin-2-yl)phenoxathiin-2-amine

MS(ESI m/z): 514 (M+H)
RT(min): 1.33
(5)
In the same manner as in Reference Example 6, the following compound was obtained.

4-(2-(8-Iodophenoxathiin-4-yl)-6-((4-methoxyben-zyl)oxy)pyridin-4-yl)morpholine

MS(ESI m/z): 625 (M+H)
RT(min): 2.02

Reference Example 28-5

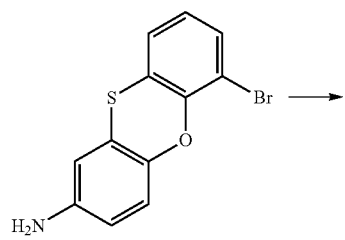

In the same manner as in Reference Example 6, the following compound was obtained.

6-Bromo-2-iodophenoxathiin

MS(ESI m/z): 407 (M+H)
RT(min): 2.32

Reference Example 29-1-1

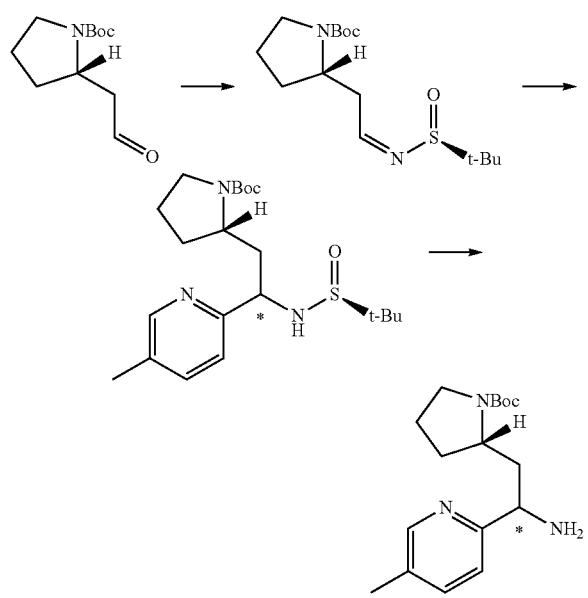

(1)
In the same manner as in Reference Example 23-2-1 (1), the following compound was obtained.

(S)-tert-butyl 2-(2-(((S)-tert-butylsulfinyl)imino)ethyl)pyrrolidine-1-carboxylate MS(ESI m/z): 317 (M+H)
RT(min): 1.52
(2)
In the same manner as in Reference Example 23-3 (2), the following compound was obtained.

(2S)-tert-butyl 2-(2-((S)-tert-butyl sulfinamide)-2-(5-methylpyridin-2-yl)ethyl)pyrrolidine-1-carboxy-late (optically active substance A)

MS(ESI m/z): 410 (M+H)
RT(min): 1.26
(3)
In the same manner as in Reference Example 23-3 (3), the following compound was obtained.

(2S)-tert-butyl 2-(2-amino-2-(5-methylpyridin-2-yl)ethyl)pyrrolidine-1-carboxylate (optically active substance A)

MS(ESI m/z): 306 (M+H)
RT(min): 0.99

Reference Example 29-1-2

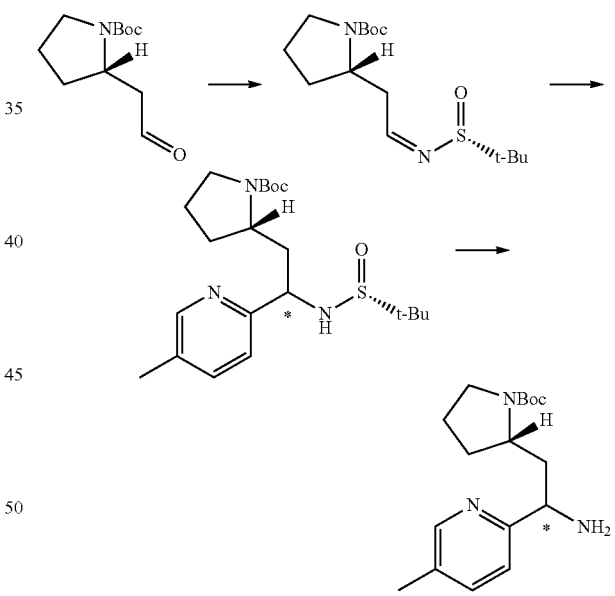

(1)
In the same manner as in Reference Example 23-2-1 (1), the following compound was obtained.

(S)-tert-butyl 2-(2-(((R)-tert-butylsulfinyl)imino)ethyl)pyrrolidine-1-carboxylate MS(ESI m/z): 317 (M+H)
RT(min): 1.54
(2)
In the same manner as in Reference Example 23-3 (2), the following compound was obtained.

(2S)-tert-butyl 2-(2-((R)-tert-butyl sulfinamide)-2-(5-methylpyridin-2-yl)ethyl)pyrrolidine-1-carboxylate (optically active substance B)

MS(ESI m/z): 410 (M+H)
RT(min): 1.32

(3)

In the same manner as in Reference Example 23-3 (3), the following compound was obtained.

(2S)-tert-butyl 2-(2-amino-2-(5-methylpyridin-2-yl)ethyl)pyrrolidine-1-carboxylate (optically active substance B)

MS(ESI m/z): 306 (M+H)
RT(min): 1.01

Reference Example 29-2

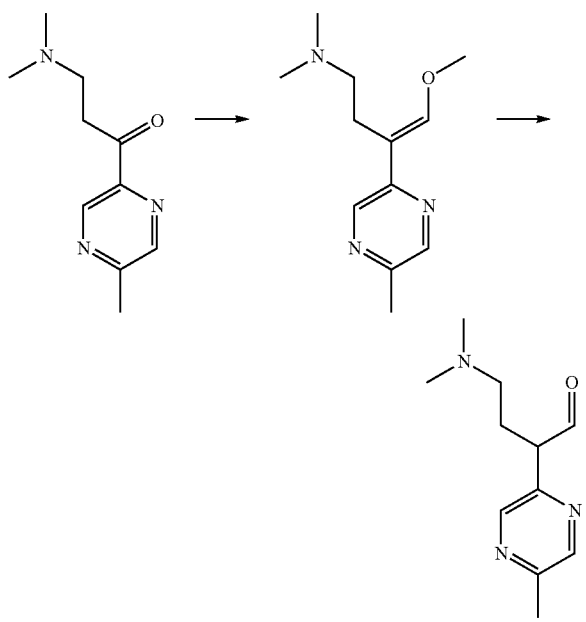

(1)

Under ice-cooling, a solution of 3-(dimethyl amino)-1-(5-methylpyrazin-2-yl)propan-1-one (190 mg) obtained in the same manner as in Reference Example 23-1 (2) in tetrahydrofuran (2 mL) was added to a mixture of (methoxymethyl)triphenylphosphonium chloride (675 mg), potassium tert-butoxide (221 mg), and tetrahydrofuran (4 mL), followed by stirring at room temperature for 15 hours. After a saturated sodium chloride aqueous solution was added to the reaction mixture, the resultant product was extracted with ethyl acetate, then, the organic layer was dried over anhydrous magnesium sulfate, and the solvent was distilled off under reduced pressure. The obtained residues were purified by silica gel column chromatography (ethyl acetate, methanol:chloroform=1:9), whereby 4-methoxy-N,N-dimethyl-3-(5-methylpyrazin-2-yl)-3-butene-1-amine (49 mg) was obtained.

MS(ESI m/z): 222 (M+H)
RT(min): 0.56

(2)

In the same manner as in Reference Example 22-15 (6), the following compound was obtained.

4-(Dimethylamino)-2-(5-methylpyrazin-2-yl)butanal

MS(ESI m/z): 208 (M+H)
RT(min): 0.36

Example 1-1

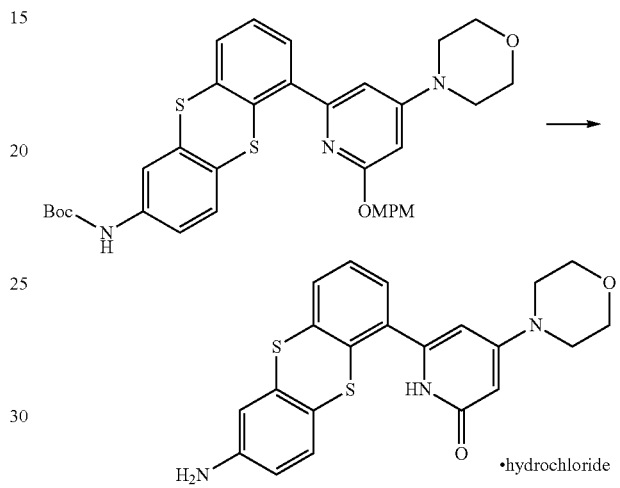

4.0 mol/L hydrogen chloride/1,4-dioxane (3.0 mL) was added to a solution of tert-butyl (6-(6-((4-methoxybenzyl)oxy)-4-morpholinopyridin-2-yl)thianthren-2-yl)carbamate (300 mg) in methanol (3.0 mL), followed by stirring at 60° C. for 1.5 hours. The reaction mixture was cooled to room temperature, then, the solvent was distilled off under reduced pressure, and the obtained residues were washed with ethyl acetate, whereby hydrochloride (130 mg) of 6-(7-aminothianthren-1-yl)-4-morpholinopyridin-2(1H)-one was obtained as a brown solid.

$^1$H-NMR (DMSO-d$_6$, 300 MHz) δ: 11.02 (1H, s), 7.62 (1H, t, J=4.5 Hz), 7.38-7.31 (2H, m), 7.11 (1H, d, J=8.3 Hz), 6.76 (1H, d, J=2.3 Hz), 6.48 (1H, dd, J=8.4, 2.1 Hz), 6.01 (1H, s), 5.48 (1H, s), 5.43 (2H, s), 3.67 (4H, t, J=4.6 Hz), 3.25 (4H, d, J=5.3 Hz).

MS(ESI m/z): 410 (M+H)
RT(min): 1.03

Example 1-2-1

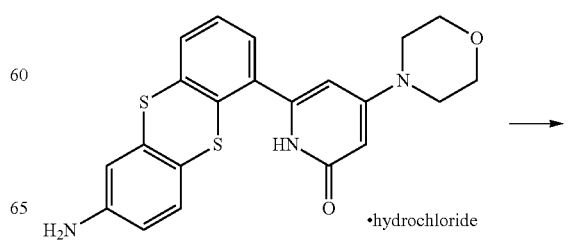

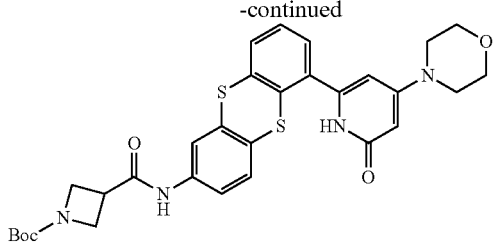

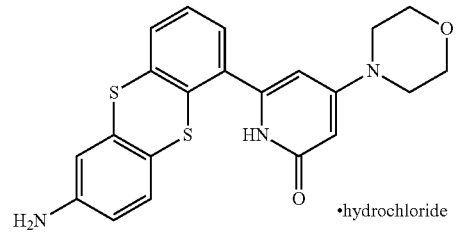

-continued

Example 1-2-2

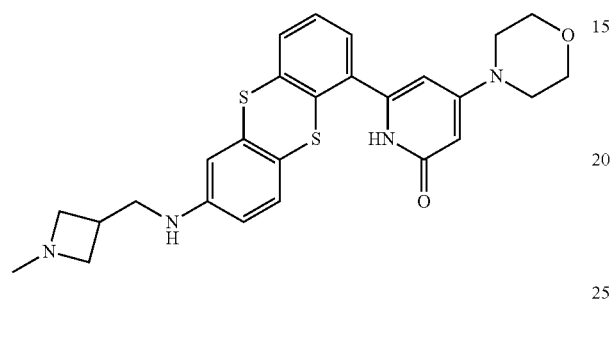

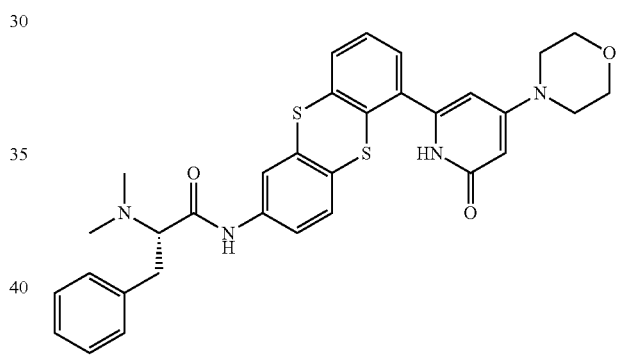

(1)

1-(tert-Butoxycarbonyl)azetidine-3-carboxylic acid (17 mg) and 2-(1H-7-azabenzotriazol-1-yl)-1,1,3,3-tetramethyluronium hexafluorophosphate methaneammonium (32 mg) were added to a solution of hydrochloride (20 mg) of 6-(7-aminothianthren-1-yl)-4-morpholinopyridin-2(1H)-one in N,N-dimethyl formamide (1 mL), followed by stirring for 2 hours. 1-(tert-Butoxycarbonyl)azetidine-3-carboxylic acid (8 mg) and 2-(1H-7-azabenzotriazol-1-yl)-1,1,3,3-tetramethyluronium hexafluorophosphate methaneammonium (16 mg) were added thereto, followed by stirring for 5 hours. A saturated sodium hydrogen carbonate aqueous solution was added to the reaction mixture, and the solid was collected by filtration, whereby tert-butyl 3-((6-(4-morpholino-6-oxo-1,6-dihydropyridin-2-yl)thianthren-2-yl)carbamoyl)azetidine-1-carboxylate (24 mg) was obtained.

MS(ESI m/z): 593 (M+H)

RT(min): 1.37

(2)

A 2 mol/L lithium aluminum hydride tetrahydrofuran solution (100 µL) was added to a solution of tert-butyl 3-((6-(4-morpholino-6-oxo-1,6-dihydropyridin-2-yl)thianthren-2-yl)carbamoyl)azetidine-1-carboxylate (11 mg) obtained in Example 1-2-1 (1) in tetrahydrofuran (3 mL), followed by refluxing for 3 hours. Methanol was added to the reaction mixture, then, the solvent was distilled off under reduced pressure, and the obtained residues were purified by preparative thin layer silica gel chromatography (chloroform:methanol=20:1, NH silica), whereby 6-(7-(((1-methylazetidin-3-yl)methyl)amino)thianthren-1-yl)-4-morpholinopyridin-2(1H)-one (1.8 mg) was obtained.

MS(ESI m/z): 493 (M+H)

RT(min): 0.95

(1)

In the same manner as in Example 1-2-1 (1), the following compound was obtained.

(S)-tert-butyl methyl (1-((6-(4-morpholino-6-oxo-1,6-dihydropyridin-2-yl)thianthren-2-yl)amino)-1-oxo-3-phenylpropan-2-yl)carbamate MS(ESI m/z): 671 (M+H)

RT(min): 1.72

(2)

In the same manner as in Example 1-2-1 (2), the following compound was obtained.

(S)-6-(7-((2-(dimethylamino)-3-phenylpropyl)amino)thianthren-1-yl)-4-morpholinopyridin-2(1H)-one MS(ESI m/z): 571 (M+H)

RT(min): 1.17

Example 1-3

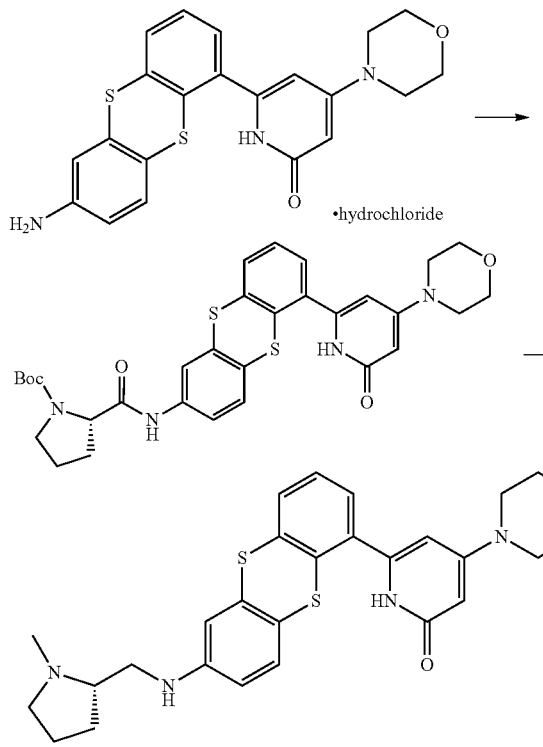

(1)

Isobutyl chloroformate (10 μL) was added to a solution of (S)-1-(tert-butoxycarbonyl)pyrrolidine-2-carboxylic acid (18 mg) in N,N-dimethyl formamide (1 mL), followed by stirring for 0.5 hours under ice-cooling. Hydrochloride (20 mg) of 6-(7-aminothianthren-1-yl)-4-morpholinopyridin-2 (1H)-one and N-methyl morpholine (45.6 μL) were added to the reaction mixture, followed by stirring for 1 hour under ice-cooling, then, the temperature was raised to room temperature, and a solution of (S)-1-(tert-butoxycarbonyl)pyrrolidine-2-carboxylic acid (90 mg) and isobutyl chloroformate (50 μL) in N,N-dimethyl formamide (1 mL) was added thereto, followed by stirring at room temperature for 2 hours. A saturated ammonium chloride aqueous solution and a saturated sodium hydrogen carbonate aqueous solution were added to the reaction mixture, and the solid was collected by filtration, whereby (S)-tert-butyl 2-((6-(4-morpholino-6-oxo-1,6-dihydropyridin-2-yl)thianthren-2-yl)carbamoyl)pyrrolidine-1-carboxylate (11 mg) was obtained.

MS(ESI m/z): 607 (M+H)

RT(min): 1.36

(2)

In the same manner as in Example 1-2-1 (2), the following compound was obtained.

(S)-6-(7-(((1-methylpyrrolidin-2-yl)methyl)amino) thianthren-1-yl)-4-morpholinopyridin-2(1H)-one MS(ESI m/z): 507 (M+H)

RT(min): 0.96

Example 1-4

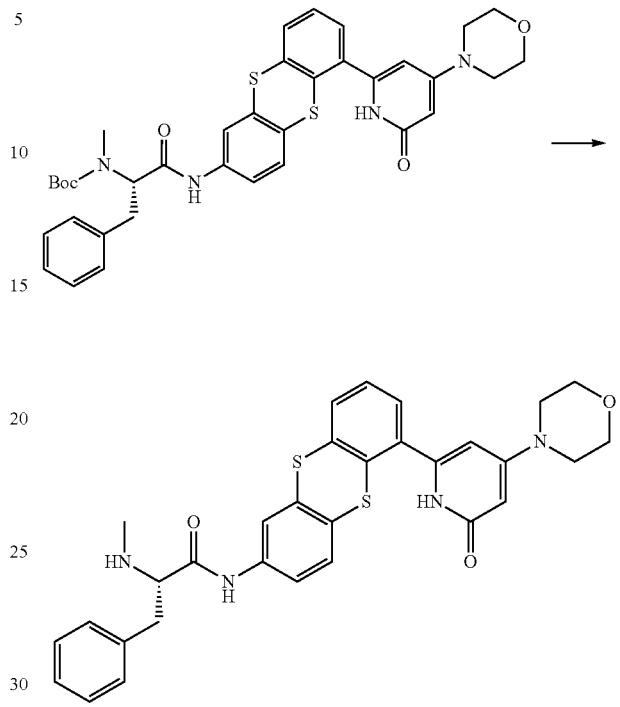

4 mol/L hydrogen chloride/1,4-dioxane (1 mL) was added to a solution of (S)-tert-butylmethyl (1-((6-(4-morpholino-6-oxo-1,6-dihydropyridin-2-yl)thianthren-2-yl)amino)-1-oxo-3-phenylpropan-2-yl)carbamate (4 mg) obtained in Example 1-2-2 (1) in 1,4-dioxane (1 mL), followed by stirring for 6 hours. After the solvent was distilled off under reduced pressure, a saturated sodium hydrogen carbonate aqueous solution was added to the obtained residues, then, the resultant product was extracted with chloroform, and the organic layer was dried over anhydrous sodium sulfate. The solvent was distilled off under reduced pressure, and the obtained residues were purified by preparative thin layer silica gel chromatography (chloroform:ethanol=30:1, NH silica), whereby (S)-2-(methylamino)-N-(6-(4-morpholino-6-oxo-1,6-dihydropyridin-2-yl)thianthren-2-yl)-3-phenyl propanamide (1.9 mg) was obtained.

MS(ESI m/z): 571 (M+H)

RT(min): 1.09

Example 1-5

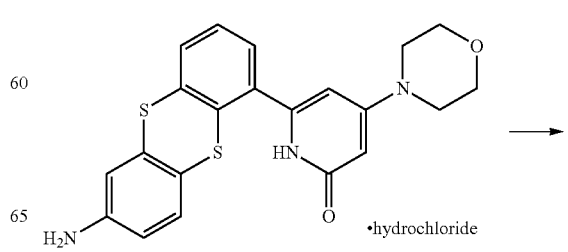

-continued

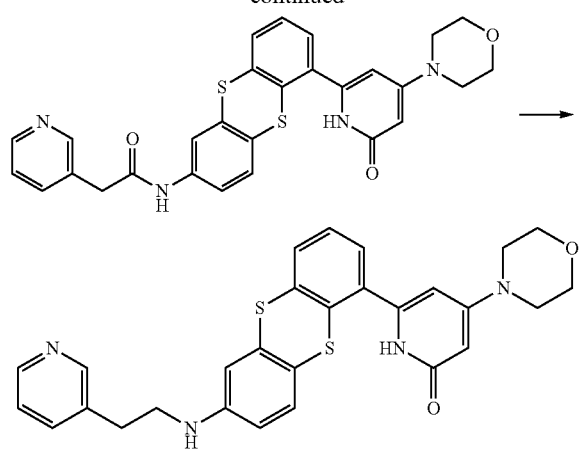

(1)

In the same manner as in Example 1-2-1 (1), the following compound was obtained.

N-(6-(4-morpholino-6-oxo-1,6-dihydropyridin-2-yl)thianthren-2-yl)-2-(pyridin-3-yl)acetamide (2)

In the same manner as in Reference Example 8 (3), the following compound was obtained.

4-morpholino-6-(7-((2-(pyridin-3-yl)ethyl)amino)thianthren-1-yl)pyridin-2(1H)-one MS(ESI m/z): 515 (M+H)
RT(min): 0.98

Example 1-6-1

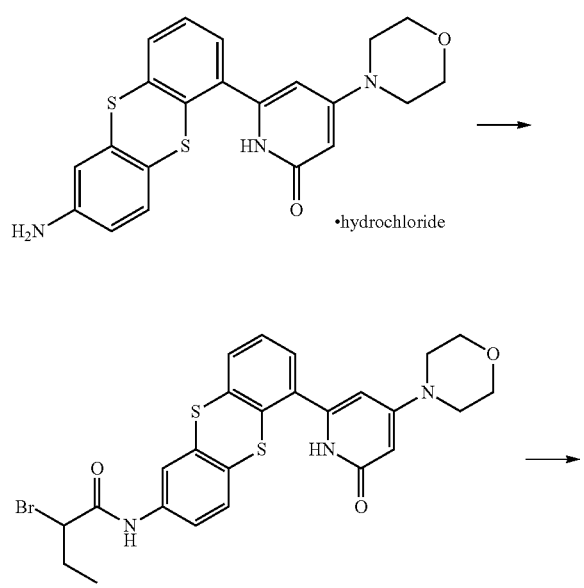

-continued

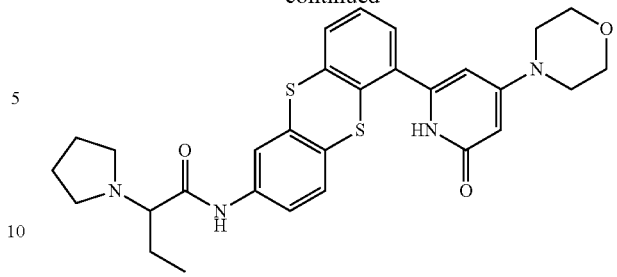

(1)

In the same manner as in Example 1-3 (1), the following compound was obtained.

2-Bromo-N-(6-(4-morpholino-6-oxo-1,6-dihydropyridin-2-yl)thianthren-2-yl)butanamide MS(ESI m/z): 560 (M+H)
RT(min): 1.39

(2)

Sodium iodide (7 mg) was added to a solution of 2-bromo-N-(6-(4-morpholino-6-oxo-1,6-dihydropyridin-2-yl)thianthren-2-yl)butanamide obtained in Example 1-6-1 (1) in pyrrolidine (1 mL), followed by stirring at for 10 hours. Ethyl acetate was added to the reaction mixture, then, the resultant product was washed with water, and the organic layer was dried over anhydrous sodium sulfate. The solvent was distilled off under reduced pressure, and the obtained residues were purified by preparative thin layer silica gel chromatography (chloroform:methanol=30:1, NH silica), whereby N-(6-(4-morpholino-6-oxo-1,6-dihydropyridin-2-yl)thianthren-2-yl)-2-(pyrrolidin-1-yl)butanamide (1.5 mg) was obtained.

MS(ESI m/z): 549 (M+H)
RT(min): 1.00

Example 1-6-2

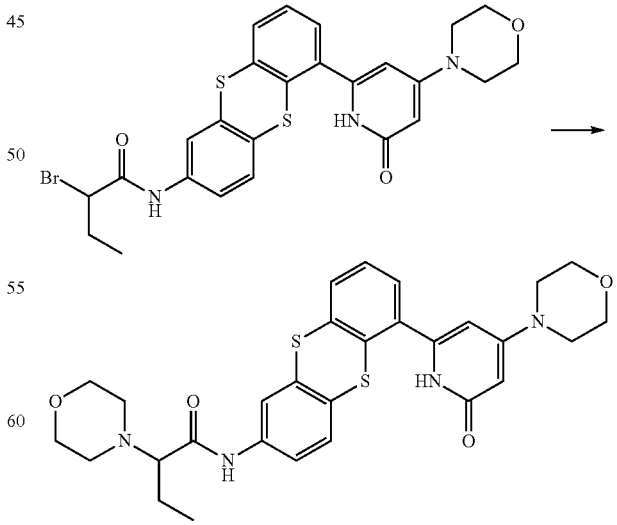

In the same manner as in Example 1-6-1 (2), the following compound was obtained.

2-Morpholino-N-(6-(4-morpholino-6-oxo-1,6-dihydropyridin-2-yl)thianthren-2-yl)butanamide MS(ESI m/z): 565 (M+H)
RT(min): 0.99

Example 1-7-1

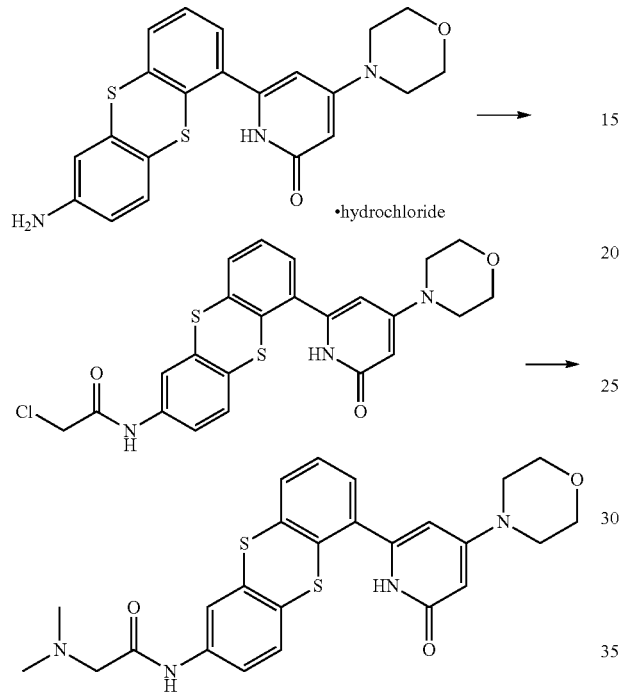

(1)
Chloroacetylchloride (33 μL) was added to a solution of hydrochloride (100 mg) of 6-(7-aminothianthren-1-yl)-4-morpholinopyridin-2(1H)-one and triethylamine (115 μL) in dichloromethane (10 mL), followed by stirring at the same temperature for 1 hour. Chloroacetyl chloride (20 μL) was added to the reaction mixture, followed by stirring at room temperature for 1 hour. Methanol was added to the reaction mixture, and the solvent was distilled off under reduced pressure. A saturated sodium hydrogen carbonate aqueous solution was added to the obtained residues, and the solid was collected by filtration, whereby 2-chloro-N-(6-(4-morpholino-6-oxo-1,6-dihydropyridin-2-yl)thianthren-2-yl)acetamide (86 mg) was obtained.
MS(ESI m/z): 486 (M+H)
RT(min): 1.19
(2)
Sodium iodide (7 mg) and a 2 mol/L dimethylamine tetrahydrofuran solution (0.5 mL) were added to a solution of 2-chloro-N-(6-(4-morpholino-6-oxo-1,6-dihydropyridin-2-yl)thianthren-2-yl)acetamide (20 mg) obtained in Example 1-7-1 (1) in N-methyl pyrrolidone (0.5 mL), followed by stirring for 3 hours. The reaction mixture was purified by silica gel column chromatography (ethyl acetate:methanol=1:0→10:1, NH silica), whereby 2-(dimethylamino)-N-(6-(4-morpholino-6-oxo-1,6-dihydropyridin-2-yl)thianthren-2-yl)acetamide (17 mg) was obtained.
MS(ESI m/z): 495 (M+H)
RT(min): 0.89

Example 1-7-2

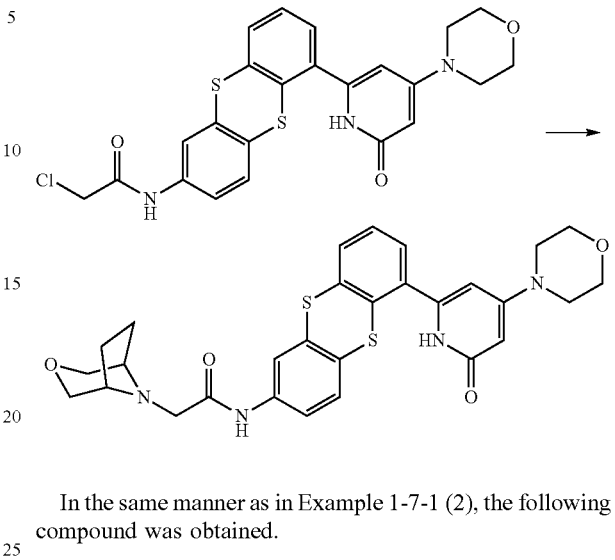

In the same manner as in Example 1-7-1 (2), the following compound was obtained.

2-(3-Oxa-8-azabicyclo[3.2.1]octan-8-yl)-N-(6-(4-morpholino-6-oxo-1,6-dihydropyridin-2-yl)thianthren-2-yl)acetamide MS(ESI m/z): 563 (M+H)
RT(min): 0.95

Example 1-7-3

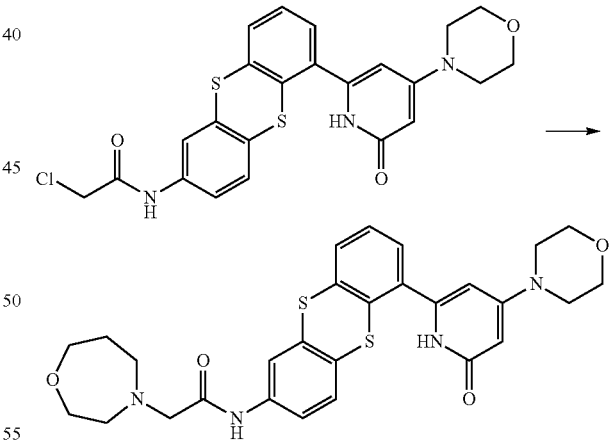

Using N,N-dimethyl formamide as a solvent, the following compound was obtained in the same manner as in Example 1-7-1 (2).

N-(6-(4-morpholino-6-oxo-1,6-dihydropyridin-2-yl)thianthren-2-yl)-2-(1,4-oxazepan-4-yl)acetamide MS(ESI m/z): 551 (M+H)
RT(min): 0.92

Example 1-7-4

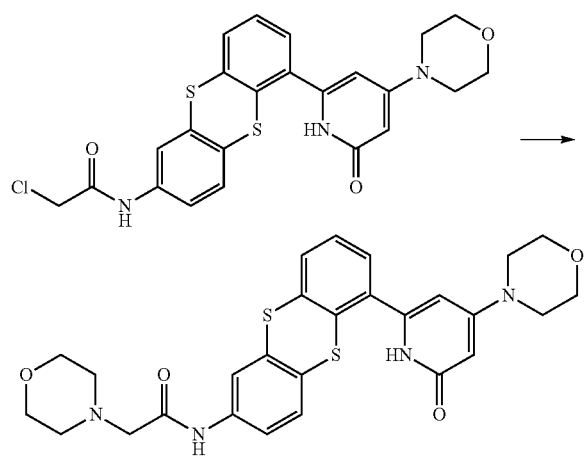

Using N,N-dimethyl acetamide as a solvent, the following compound was obtained in the same manner as in Example 1-7-1 (2).

2-Morpholino-N-(6-(4-morpholino-6-oxo-1,6-dihydropyridin-2-yl)thianthren-2-yl)acetamide MS(ESI m/z): 537 (M+H)
RT(min): 1.16

Example 1-8

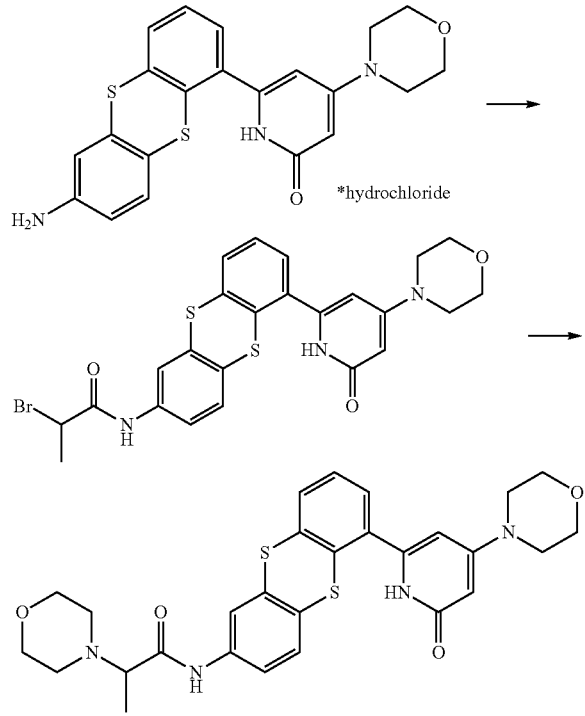 [SMILES: Nc1ccc2c(c1)Sc1cccc(-c3cc(N4CCOCC4)cc(=O)[nH]3)c1S2 ; CC(Br)C(=O)Nc1ccc2c(c1)Sc1cccc(-c3cc(N4CCOCC4)cc(=O)[nH]3)c1S2 ; CC(C(=O)Nc1ccc2c(c1)Sc1cccc(-c3cc(N4CCOCC4)cc(=O)[nH]3)c1S2)N1CCOCC1]

(1)

In the same manner as in Example 1-7-1 (1), the following compound was obtained.

2-Bromo-N-(6-(4-morpholino-6-oxo-1,6-dihydropyridin-2-yl)thianthren-2-yl)propanamide MS(ESI m/z): 546 (M+H)
RT(min): 1.32

(2)

In the same manner as in Example 1-7-3, the following compound was obtained.

2-Morpholino-N-(6-(4-morpholino-6-oxo-1,6-dihydropyridin-2-yl)thianthren-2-yl)propanamide MS(ESI m/z): 551 (M+H)
RT(min): 0.96

Example 1-9-1

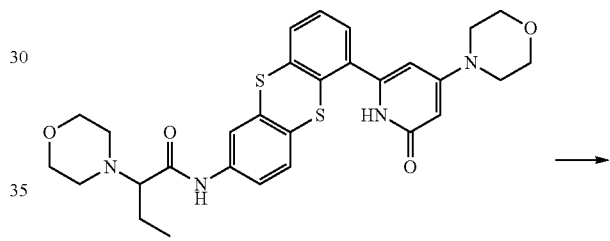

A 1.0 mol/L borane-tetrahydrofuran complex solution (127 µL) was added to a solution of 2-morpholino-N-(6-(4-morpholino-6-oxo-1,6-dihydropyridin-2-yl)thianthren-2-yl)butanamide (12 mg) obtained in Example 1-6-2 in tetrahydrofuran (1 mL), followed by stirring at 90° C. 2 hours. After the reaction mixture was cooled to room temperature, sodium hydrogen carbonate and water were added thereto, then, the resultant product was extracted with ethyl acetate, and the organic layer was dried over anhydrous sodium sulfate. The solvent was distilled off under reduced pressure, and the obtained residues were purified by preparative thin layer silica gel chromatography (chloroform:methanol=30:1, NH silica), whereby 4-morpholino-6-(7-((2-morpholinobutyl)amino)thianthren-1-yl)pyridin-2(1H)-one (1 mg) was obtained.

MS(ESI m/z): 551 (M+H)
RT(min): 1.00

Example 1-9-2-1

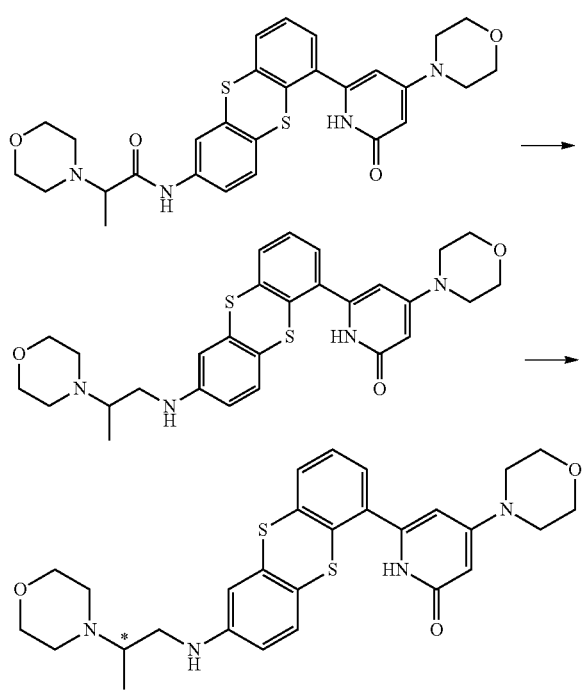

In the same manner as in Example 1-9-1, the following compound was obtained.

4-Morpholino-6-(7-((2-morpholinopropyl)amino)thianthren-1-yl)pyridin-2(1H)-one (racemic mixture)

$^1$H-NMR (DMSO-$d_6$, 300 MHz) δ: 11.02 (1H, brs), 7.65-7.57 (1H, m), 7.38-7.30 (2H, m), 7.17 (1H, d, J=8.5 Hz), 6.82 (1H, d, J=2.6 Hz), 6.54 (1H, dd, J=8.5 Hz, 2.6 Hz), 6.03 (1H, brs), 5.74 (1H, brs), 5.51 (1H, brs), 3.67 (4H, t, J=4.9 Hz), 3.57 (4H, brs), 3.26 (4H, d, J=4.9 Hz), 3.10-2.90 (2H, m), 2.75-2.65 (1H, m), 2.50-2.35 (4H, m), 0.97 (3H, d, J=6.6 Hz).

MS(ESI m/z): 537 (M+H)

RT(min): 0.98

Examples 1-9-2-2 and 1-9-2-3

Chiral resolution was performed on 4-morpholino-6-(7-((2-morpholinopropyl)amino)thianthren-1-yl)pyridin-2(1H)-one (racemic mixture) obtained in Example 1-9-2-1 by supercritical fluid chromatography, whereby an optically active substance A and an optically active substance B were obtained.

Example 1-9-2-2 (optically active substance A)

$^1$H-NMR (DMSO-$d_6$, 300 MHz) δ: 11.02 (1H, brs), 7.65-7.57 (1H, m), 7.38-7.30 (2H, m), 7.17 (1H, d, J=8.5 Hz), 6.82 (1H, d, J=2.6 Hz), 6.54 (1H, dd, J=8.5 Hz, 2.6 Hz), 6.03 (1H, brs), 5.74 (1H, brs), 5.51 (1H, brs), 3.67 (4H, t, J=4.9 Hz), 3.57 (4H, brs), 3.26 (4H, d, J=4.9 Hz), 3.10-2.90 (2H, m), 2.75-2.65 (1H, m), 2.50-2.35 (4H, m), 0.97 (3H, d, J=6.6 Hz).

MS(ESI m/z): 537 (M+H)

RT(min): 0.98

Example 1-9-2-3 (optically active substance B)

$^1$H-NMR (DMSO-$d_6$, 300 MHz) δ: 11.02 (1H, brs), 7.65-7.57 (1H, m), 7.38-7.30 (2H, m), 7.17 (1H, d, J=8.5 Hz), 6.82 (1H, d, J=2.6 Hz), 6.54 (1H, dd, J=8.5 Hz, 2.6 Hz), 6.03 (1H, brs), 5.74 (1H, brs), 5.51 (1H, brs), 3.67 (4H, t, J=4.9 Hz), 3.57 (4H, brs), 3.26 (4H, d, J=4.9 Hz), 3.10-2.90 (2H, m), 2.75-2.65 (1H, m), 2.50-2.35 (4H, m), 0.97 (3H, d, J=6.6 Hz).

MS(ESI m/z): 537 (M+H)

RT(min): 0.98

(Supercritical Fluid Chromatography Conditions)

Column: CHIRALPAK IB (manufactured by Daicel Chemical Industries, Ltd.)

Mobile phase: carbon dioxide/0.1% diethylamine-containing methanol (volume ratio: 75/25)

Flow rate: 20 mL/min

Detection wavelength: 254 nm

Temperature: 40° C.

Retention time: 22.02 min (optically active substance A), 23.96 min (optically active substance B)

Example 1-9-3

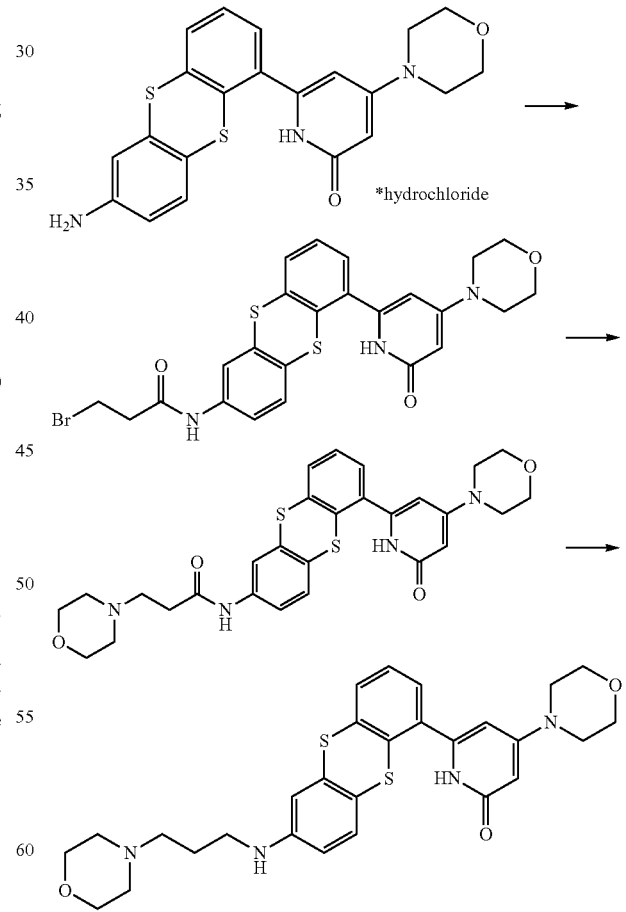

(1)

In the same manner as in Example 1-7-1, the following compound was obtained.-

3-Bromo-N-(6-(4-morpholino-6-oxo-1,6-dihydro-pyridin-2-yl)thianthren-2-yl)propanamide (2)

In the same manner as in Example 1-7-4, the following compound was obtained.

3-Morpholino-N-(6-(4-morpholino-6-oxo-1,6-dihydropyridin-2-yl)thianthren-2-yl)propanamide (3)

In the same manner as in Example 1-9-1, the following compound was obtained.

4-Morpholino-6-(7-((3-morpholinopropyl)amino)thianthren-1-yl)pyridin-2(1H)-one $^1$H-NMR (DMSO-$d_6$, 300 MHz) δ: 11.02 (1H, brs), 7.65-7.58 (1H, m), 7.38-7.30 (2H, m), 7.16 (1H, d, J=8.7 Hz), 6.82 (1H, d, J=2.3 Hz), 6.54 (1H, dd, J=8.7 Hz, 2.3 Hz), 6.08-5.97 (2H, m), 5.51 (1H, brs), 3.67 (4H, t, J=4.6 Hz), 3.58 (4H, t, J=4.6 Hz), 3.26 (4H, d, J=4.6 Hz), 3.03 (2H, q, J=6.5 Hz), 2.38-2.30 (6H, m), 1.65 (2H, q, J=6.5 Hz).
MS(ESI m/z): 537 (M+H)
RT(min): 0.91

(1)

In the same manner as in Example 1-7-1 (1), the following compound was obtained.

4-Bromo-N-(6-(4-morpholino-6-oxo-1,6-dihydro-pyridin-2-yl)thianthren-2-yl)butanamide (2)

In the same manner as in Example 1-7-4, the following compound was obtained.

4-Morpholino-N-(6-(4-morpholino-6-oxo-1,6-dihydropyridin-2-yl)thianthren-2-yl)butanamide (3)

In the same manner as in Example 1-9-1, the following compound was obtained.

4-Morpholino-6-(7-((4-morpholinobutyl)amino)thianthren-1-yl)pyridin-2(1H)-one

MS(ESI m/z): 551 (M+H)
RT(min): 0.94

Example 1-9-4

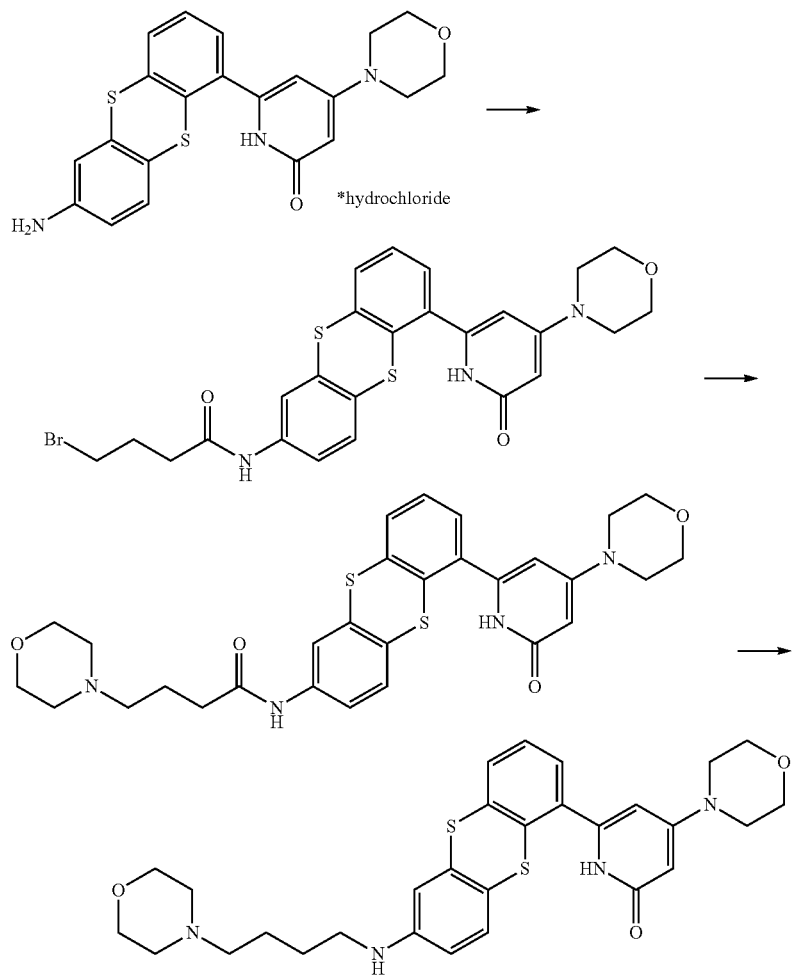

Example 1-10-1

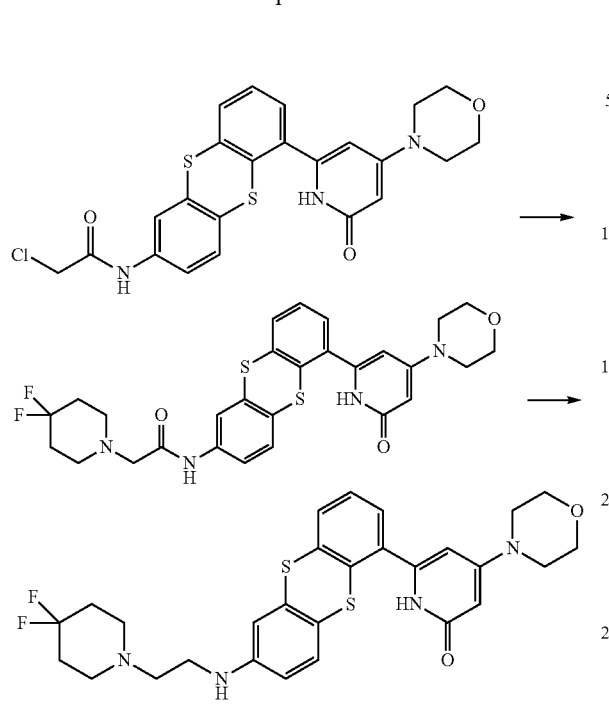

(1)
In the same manner as in Example 1-7-1 (2), the following compound was obtained.

2-(4,4-Difluoropiperidin-1-yl)-N-(6-(4-morpholino-6-oxo-1,6-dihydropyridin-2-yl)thianthren-2-yl)acetamide MS(ESI m/z): 571 (M+H)
RT(min): 1.07

(2)
In the same manner as in Example 1-9-1, the following compound was obtained.

6-(7-((2-(4,4-Difluoropiperidin-1-yl)ethyl)amino)thianthren-1-yl)-4-morpholinopyridin-2(1H)-one MS(ESI m/z): 557 (M+H)
RT(min): 1.03

Example 1-10-2

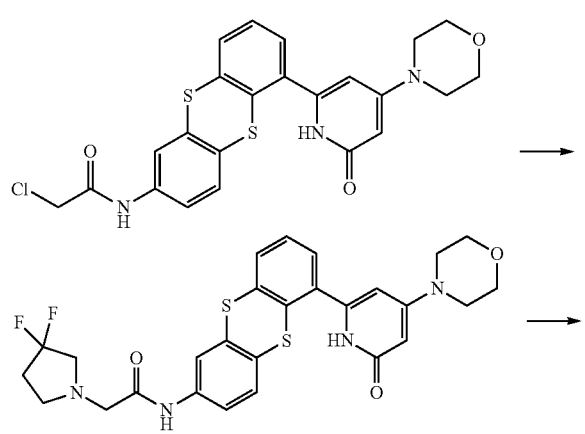

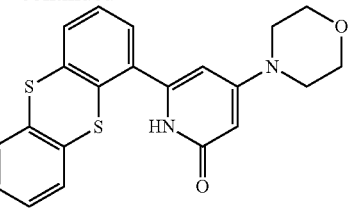

(1)
In the same manner as in Example 1-7-1 (2), the following compound was obtained.

2-(3,3-Difluoropyrrolidin-1-yl)-N-(6-(4-morpholino-6-oxo-1,6-dihydropyridin-2-yl)thianthren-2-yl)acetamide MS(ESI m/z): 557 (M+H)
RT(min): 1.16

(2)
In the same manner as in Example 1-9-1, the following compound was obtained.

6-(7-((2-(3,3-Difluoropyrrolidin-1-yl)ethyl)amino)thianthren-1-yl)-4-morpholinopyridin-2(1H)-one MS(ESI m/z): 543 (M+H)
RT(min): 1.02

Example 1-10-3

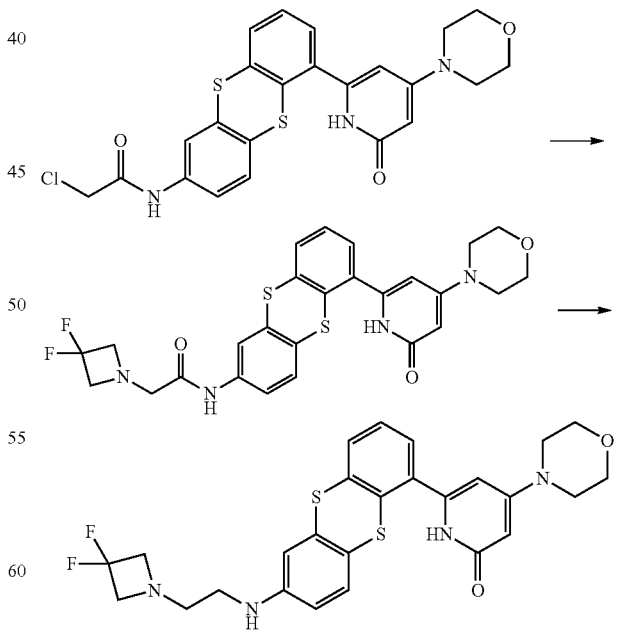

(1)
In the same manner as in Example 1-7-1 (2), the following compound was obtained.

2-(3,3-Difluoroazetidin-1-yl)-N-(6-(4-morpholino-6-oxo-1,6-dihydropyridin-2-yl)thianthren-2-yl)acetamide MS(ESI m/z): 543 (M+H)
RT(min): 1.13
(2)
In the same manner as in Example 1-9-1, the following compound was obtained.

6-(7-((2-(3,3-Difluoroazetidin-1-yl)ethyl)amino)thianthren-1-yl)-4-morpholinopyridin-2(1H)-one MS(ESI m/z): 529 (M+H)
RT(min): 0.99

Example 1-10-4

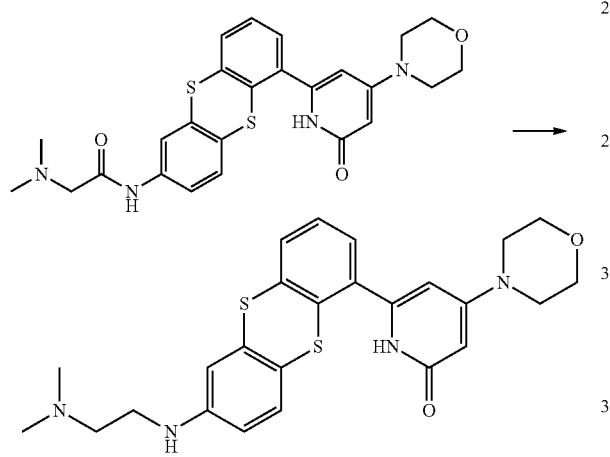

In the same manner as in Example 1-9-1, the following compound was obtained.

6-(7-((2-(Dimethylamino)ethyl)amino)thianthren-1-yl)-4-morpholinopyridin-2(1H)-one MS(ESI m/z): 481 (M+H)
RT(min): 0.92

Example 1-10-5

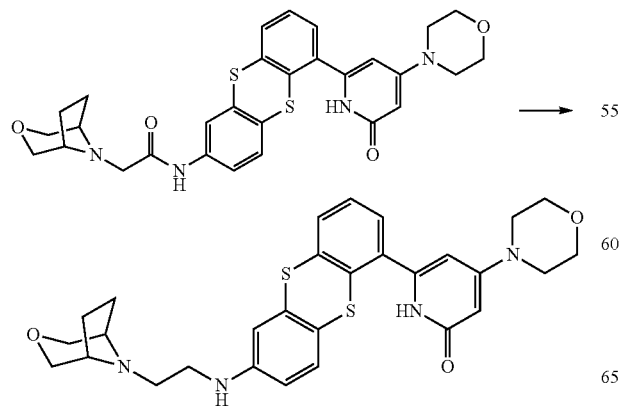

In the same manner as in Example 1-9-1, the following compound was obtained.

6-(7-((2-(3-oxa-8-azabicyclo[3.2.1]octan-8-yl)ethyl)amino)thianthren-1-yl)-4-morpholinopyridin-2(1H)-one $^1$H-NMR (CD$_3$OD, 300 MHz) δ: 7.63-7.56 (1H, m), 7.36-7.30 (2H, m), 7.16 (1H, d, J=8.6 Hz), 6.82 (1H, d, J=2.6 Hz), 6.56 (1H, dd, J=8.6, 2.0 Hz), 6.20 (1H, d, J=2.6 Hz), 5.75 (1H, d, J=2.6 Hz), 3.80 (4H, t, J=5.0 Hz), 3.72 (2H, d, J=10.6 Hz), 3.61-3.46 (2H, m), 3.40 (4H, t, J=4.6 Hz), 3.22-3.09 (4H, m), 2.54 (2H, t, J=6.3 Hz), 2.06-1.81 (4H, m).

MS(ESI m/z): 549 (M+H)
RT(min): 0.97

Example 1-10-6

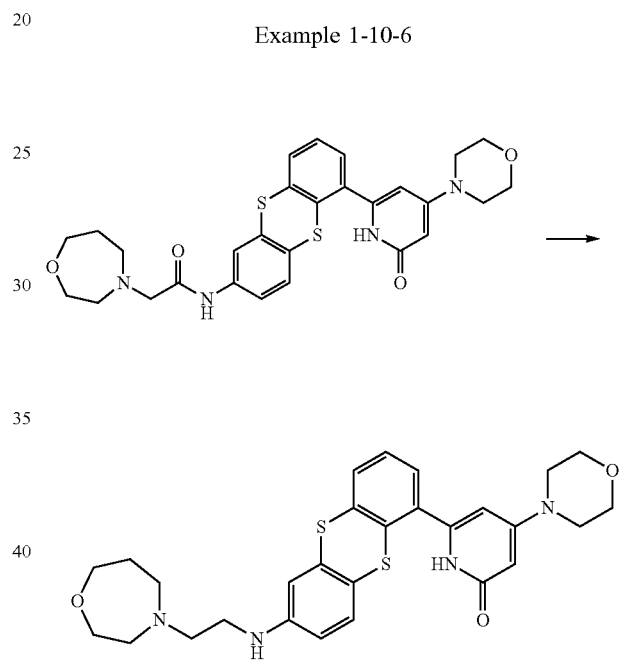

In the same manner as in Example 1-9-1, the following compound was obtained.

6-(7-((2-(1,4-Oxazepan-4-yl)ethyl)amino)thianthren-1-yl)-4-morpholinopyridin-2(1H)-one MS(ESI m/z): 537 (M+H)
RT(min): 0.93

Examples 1-10-7 to 1-10-15

In the same manner as in Example 1-10-1, the following compound was obtained.

TABLE 10

| Example No. | R$^b$ | Compound Name | Ms | RT (min) | $^1$H-NMR (300 MHz) (DMSO-d$_6$) δ: |
|---|---|---|---|---|---|
| 1-10-7 | 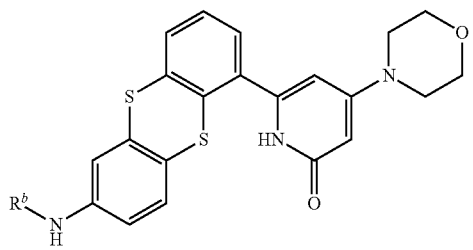 | 4-Morpholino-6-(7-((2-morpholinoethyl)amino) thianthren-1-yl)pyridin-2 (1H)-one | 523 | 0.87 | (CDCl$_3$): 7.56 (1H, dd, J = 6.3, 2.6 Hz), 7.30 (1H, s), 7.28 (1H, d, J = 4.02 Hz), 7.21 (1H, d J = 8.6 Hz), 6.78 (1H, d, J = 2.3 Hz), 6.50 (1H, dd, J = 8.6, 2.6 Hz), 5.98 (1H, d, J = 2.3 Hz), 5.70 (1H, d, J = 2.3 Hz), 3.81 (4H, t, J = 4.8 Hz), 3.71 (4H, t, J = 4.5 Hz), 3.32 (4H, t, J = 5.0 Hz), 3.14 (2H, t, J = 5.6 Hz), 2.62 (2H, t, J = 5.8 Hz), 2.45 (4H, t, J = 4.5 Hz). |
| 1-10-8 | 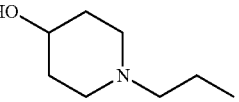 | 6-(7-((2-(4-Hydroxy piperidin-1-yl)ethyl)amino) thianthren-1-yl)-4-morpholino pyridin-2(1H)-one | 537 | 0.90 | |
| 1-10-9 | 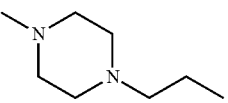 | 6-(7-((2-(4-Methyl piperazin-1-yl)ethyl)amino) thianthren-1-yl)-4-morpholino pyridin-2(1H)-one | 536 | 0.89 | 10.98 (1H, br, s), 7.65-7.58 (1H, m), 7.40-7.30 (2H, m), 7.16 (1H, d, J = 8.7 Hz), 6.79 (1H, d, J = 2.4 Hz), 6.54 (1H, dd, J = 8.7 Hz, 2.4 Hz), 6.03 (1H, br s), 5.80 (1H, t, J = 6.4 Hz), 5.51 (1H, br s), 3.67 (4H, t, J = 4.7 Hz), 3.26 (4H, t, J = 4.7 Hz), 3.10 (2H, q, J = 6.4 Hz), 2.55-2.25 (10 H, m), 2.14 (3H, s). |
| 1-10-10 | 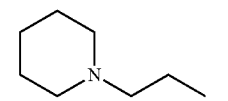 | 4-Morpholino-6-(7-((2-piperidin-1-yl)ethyl)amino) thianthren-1-yl)pyridin-2 (1H)-one | 521 | 0.96 | 10.99 (1H, br s), 7.65-7.58 (1H, m), 7.38-730 (2H, m), 7.16 (1H, d, J = 8.7 Hz), 6.79 (1H, d, J = 2.1 Hz), 6.52 (1H, dd, J = 8.7 Hz, 2.1 Hz), 6.03 (1H, br s), 5.80 (1H, t, J = 5.7 Hz), 5.51 (1H, br s), 3.67 (4H, t, J = 4.7 Hz), 3.26 (4H, t, J = 4.7 Hz, 3.10 (2H, g, J = 5.7 Hz), 2.45-2.30 (6H, m), 1.60-1.32 (6H, m). |
| 1-10-11 | 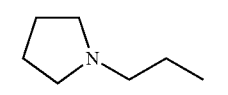 | 4-Morpholino-6-(7-((2-pyrrolidin-1-yl)ethyl)amino) thianthren-1-yl)pyridin-2 (1H)-one | 507 | 0.91 | |
| 1-10-12 | 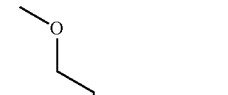 | 6-(7-((2-((2-Methoxy ethyl) (methyl)amino)ethyl)amino) thianthren-1-yl)-4-morpholino pyridin-2(1H)-one | 525 | 0.92 | |
| 1-10-13 | 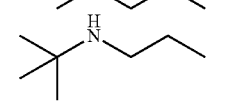 | 6-(7-((2-(tert-Butyl amino) ethyl)amino)thianthren-1-yl)-4-morpholino pyridin-2 (1H)-one | 509 | 0.95 | |
| 1-10-14 | 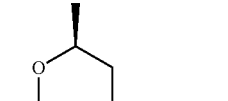 | 6-(7-((2-((2S,6R)-2,6-Dimethyl morpholino)ethyl) amino)thianthren-1-yl)-4-morpholino pyridin-2(1H)-one | 551 | 0.96 | 10.99 (1H, br s), 7.65-7.58 (1H, m), 7.38-7.30 (2H, m), 7.16 (1H, d, J = 8.7 Hz), 6.79 (1H, d, J = 2.3 Hz), 6.52 (1H, dd, J = 8.7 Hz, 2.3 Hz), 6.02 (1H, br s), 5.83 (1H, t, J = 6.0 Hz), 5.49 (1H, br s), 3.67 (4H, t, J = 4.8 Hz), 3.62-3.50 (2H, m), 3.26 (4H, t, J = 4.8 Hz), 3.11 (2H, q, J = 6.0 Hz, 2.76 (2H, d, J = 10.6 Hz), 2.43 (2H, d, J = 6.0 Hz), 1.63 (2H, d, J = 10.6 Hz), 1.03 (6H, d, J = 6.8 Hz). |
| 1-10-15 | 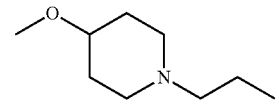 | 6-(7-((2-(4-Methoxy piperidin-1-yl)ethyl)amino) thianthren-1-yl)-4-morpholino pyridin-2(1H)-one | 551 | 0.94 | |

Example 1-11

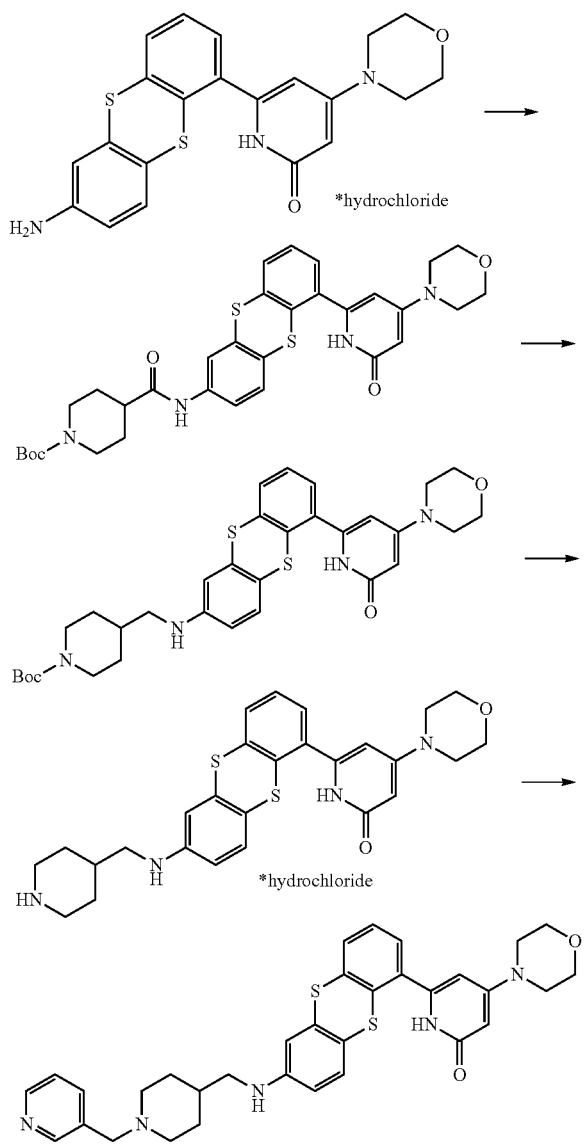 [SMILES: Nc1ccc2c(c1)Sc1cccc(-c3cc(N4CCOCC4)cc(=O)[nH]3)c1S2 ; CC(C)(C)OC(=O)N1CCC(C(=O)Nc2ccc3c(c2)Sc2cccc(-c4cc(N5CCOCC5)cc(=O)[nH]4)c2S3)CC1 ; CC(C)(C)OC(=O)N1CCC(CNc2ccc3c(c2)Sc2cccc(-c4cc(N5CCOCC5)cc(=O)[nH]4)c2S3)CC1 ; O=c1cc(N2CCOCC2)cc(-c2cccc3c2Sc2ccc(NCC4CCNCC4)cc2S3)[nH]1 ; O=c1cc(N2CCOCC2)cc(-c2cccc3c2Sc2ccc(NCC4CCN(Cc5cccnc5)CC4)cc2S3)[nH]1]

(1) and (2)

In the same manner as in Examples 1-5 (1) and 1-5 (2), the following compounds were obtained.

tert-Butyl 4-((6-(4-morpholino-6-oxo-1,6-dihydropyridin-2-yl)thianthren-2-yl)carbamoyl)piperidine-1-carboxylate tert-Butyl 4-(((6-(4-morpholino-6-oxo-1,6-dihydropyridin-2-yl)thianthren-2-yl)amino)methyl)piperidine-1-carboxylate (3)
4.0 mol/L hydrogen chloride/1,4-dioxane (1.0 mL) and methanol (1.0 mL) were added to tert-butyl 4-(((6-(4-morpholino-6-oxo-1,6-dihydropyridin-2-yl)thianthren-2-yl)amino)methyl)piperidine-1-carboxylate (33 mg) obtained in Example 1-11 (2), followed by stirring at room temperature for 17 hours. The solvent was distilled off under reduced pressure, whereby hydrochloride (22 mg) of 4-morpholino-6-(7-((piperidin-4-ylmethyl)amino)thianthren-1-yl)pyridin-2(1H)-one was obtained.

(4)
2-Picoline borane (5.2 mg) was added to a mixture of hydrochloride (20 mg) of 4-morpholino-6-(7-((piperidin-4-ylmethyl)amino)thianthren-1-yl)pyridin-2(1H)-one obtained in Example 1-11 (3), nicotinic aldehyde (4.2 mg), acetic acid (90 µL), and methanol (910 µL), followed by stirring at room temperature for 2 hours. Nicotinic aldehyde (4.2 mg) and 2-picoline borane (5.2 mg) were added thereto, followed by stirring at room temperature for 18 hours. 2 mol/L hydrochloric acid was added to the reaction mixture, and the solvent was distilled off under reduced pressure. A saturated sodium hydrogen carbonate aqueous solution was added to the obtained residues, then, the resultant product was extracted with chloroform, and the organic layer was dried over anhydrous sodium sulfate. The solvent was distilled off under reduced pressure, and the obtained residues were purified by preparative thin layer silica gel chromatography (chloroform:methanol=9:1, NH silica), whereby 4-morpholino-6-(7-(((1-(pyridin-3-ylmethyl)piperidin-4-yl)methyl)amino)thianthren-1-yl)pyridin-2(1H)-one (6.3 mg) was obtained.
MS(ESI m/z): 598 (M+H)
RT(min): 0.96

Example 1-12-1

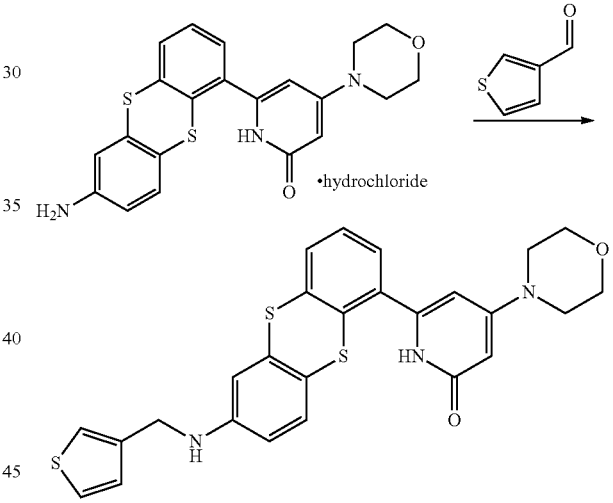

2-Picoline borane (1.6 mg) was added to a mixture of hydrochloride (4.1 mg) of 6-(7-aminothianthren-1-yl)-4-morpholinopyridin-2(1H)-one, thiophene-3-carbaldehyde (0.83 µL), acetic acid (9 µL), and methanol (91 µL), followed by stirring at room temperature for 1 hour. A saturated sodium hydrogen carbonate aqueous solution was added to the reaction mixture, then, the resultant product was extracted with chloroform, and the organic layer was dried over anhydrous sodium sulfate. The solvent was distilled off under reduced pressure, and the obtained residues were purified by silica gel column chromatography (chloroform:methanol=1:0→97:3, NH silica), whereby 4-morpholino-6-(7-((thiophen-3-ylmethyl)amino)thianthren-1-yl)pyridin-2 (1H)-one (1.8 mg) was obtained as a yellow solid.
MS(ESI m/z): 506 (M+H)
RT(min): 1.45

Examples 1-12-2 to 1-12-134

In the same manner as in Example 1-12-1, the following compounds were obtained.

TABLE 11

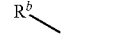

| Example No. | R$^b$ | Compound Name | MS | RT (min) | $^1$H-NMR (300 MHz) (DMSO-d$_6$) δ: |
|---|---|---|---|---|---|
| 1-12-2 | 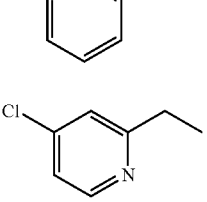 | 6-(7-(((6-Methylpyridin-2-yl)methyl)amino)thianthren-1-yl)-4-1-morpholino pyridin-2(1H)-one | 515 | 0.95 | 10.99 (1H, br s), 8.32 (1H, s), 7.62-7.56 (1H, m), 7.34-7.32 (2H, m), 7.18-7.05 (3H, m), 6.78 (1H, d, J = 2.3 Hz), 6.71 (1H, s), 6.50 (1H, d, J = 5.9 Hz), 3.66 (4H, t, J = 4.6 Hz), 3.33 (4H, t, J = 4.6 Hz), 2.46 (3H, s). |
| 1-12-3 | 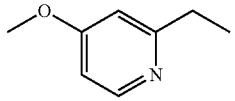 | 6-(7-(((4-Chloropyridin-2-yl)methyl)amino)thianthren-1-yl)-4-morpholino pyridin-2(1H)-one | 535 | 1.35 | 10.99 (1H, br s), 8.51 (1H, d, J = 6.0 Hz), 7.63-7.56 (1H, m), 7.43-7.38 (2H, m), 7.35-7.30 (2H, m) 7.17 (1H, d, J = 8.1 Hz), 6.80 (1H, d, J = 2.7 Hz), 6.75 (1H, t, J = 6.5 Hz), 6.51 (1H, dd, J = 8.7, 2.7 Hz), 6.02 (1H, br s), 5.49 (1H, br s), 4.39 (2H, d, J = 6.5 Hz), 3.66 (4H, t, J = 4.7 Hz), 3.25 (4H, t, J = 4.7 Hz). |
| 1-12-4 | 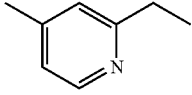 | 6-(7-(((4-Methoxy pyridin-2-yl)methl)amino)thianthren-1-yl)-4-morpholino pyridin-2(1H)-one | 531 | 0.95 | 11.00 (1H, br s), 8.34 (1H, d, J = 5.4 Hz), 7.64-7.57 (1H, m), 7.37-7.30 (2H, m), 7.16 (1H, d, J = 8.7 Hz), 6.89-6.82 (2H, m), 6.79 (1H, d, J = 2.7 Hz), 6.68 (1H, t, J = 5.9 Hz), 6.51 (1H, dd, J = 8.6, 1.9 Hz), 6.02 (1H, br s), 5.50 (1H, br s), 4.30 (2H, d, J = 5.9 Hz), 3.66 (4H, t, J = 4.7 Hz), 3.25 (4H, t, J = 4.7 Hz), 2.49 (3H, s). |
| 1-12-5 | 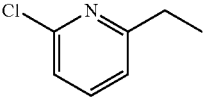 | 6-(7-(((4-Methyl pyridin-2-yl)methyl)amino)thianthren-1-yl)-4-morpholino pyridin-2(1H)-one | 515 | 0.98 | 11.02 (1H, br s), 8.37 (1H, d, J = 5.4 Hz), 7.64-7.58 (1H, m), 7.37-7.30 (2H, m), 7.17-7.13 (2H, m), 7.08 (1H, d, J = 4.8 Hz), 6.79 (1H, d, J = 2.7 Hz), 6.69 (1H, t, J = 6.2 Hz), 6.51 (1H, dd, J = 8.7, 2.7 Hz), 6.02 (1H, br s), 5.50 (1H, br s), 4.32 (2H, d, J = 6.2 Hz), 2.25 (3H, s). |
| 1-12-6 | 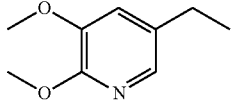 | 6-(7-(((6-Chloropyridin-2-yl)methyl)amino)thianthren-1-yl)-4-morpholino pyridin-2(1H)-one | 535 | 1.43 | 11.00 (1H, br s), 7.79 (1H, t, J = 7.9 Hz), 7.64-7.56 (1H, m), 7.39-7.27 (4H, m), 7.17 (1H, d, J = 8.6 Hz), 6.82-6.75 (2H, m), 6.50 (1H, dd, J = 8.6 Hz, 2.5 Hz), 6.02 (1H, br s), 5.50 (1H, br s), 4.36 (2H, d, J = 6.0 Hz), 3.66 (4H, t, J = 4.7 Hz), 3.25 (4H, t, J = 4.7 Hz). |
| 1-12-7 | 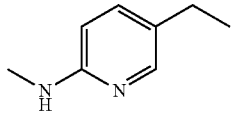 | 6-(7-(((5,6-Dimethoxy pyridin-3-yl)methyl)amino) thianthren-1-yl)-4-morpholino pyridin-2(1H)-one | 561 | 1.33 | |
| 1-12-8 | 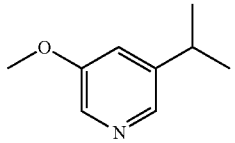 | 6-(7-(((6-(Methyl amino) pyridin-3-yl)methyl)amino) thianthren-1-yl)-4-morpholino pyridin-2(1H)-one | 530 | 0.96 | |
| 1-12-9 | 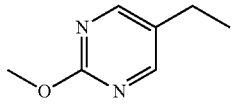 | 6-(7-((1-(5-Methoxy pyridin-3-yl)ethyl)amino) thianthren-1-yl)-4-morpholino pyridin-2(1H)-one | 545 | 1.09 | (CDCl$_3$): 9.59 (1H, s), 8.20-8.17 (2H, m), 7.50 (1H, dd, J = 6.6, 2.0 Hz), 7.29-7.22 (2.12, m), 7.14-7.10 (2H, m), 6.63 (1H, d, J = 2.6 Hz), 6.36 (1H, dd, J = 8.6, 2.6 Hz), 5.95 (1H, d J = 2.6 Hz), 5.69 (1H, d, J = 2.6 Hz), 4.49-4.42 (1H, m), 4.17 (1H, d, J = 5.3 Hz), 3.82 (3H, s), 3.80 (4H, t, J = 5.0 Hz), 3.30 (4H, t, J = 5.0 Hz), 1.52 (3H, d, J = 6.6 Hz). |
| 1-12-10 |  | 6-(7-(((2-Methoxy pyrimidin-5-yl)methyl)amino) thianthren-1-yl)-4-morpholino pyridin-2(1H)-one | 532 | 1.22 | |

TABLE 12

| Example No. | $R^b$ | Compound Name | MS | RT (min) | $^1$H-NMR (300 MHz) DMSO-$d_6$) δ: |
|---|---|---|---|---|---|
| 1-12-11 | 2-(dimethylamino)pyrimidin-5-yl | 6-(7-(((2-(Dimethyl amino) pyrimidin-5-yl)methyl) amino)thianthren-1-yl)-4-morpholino pyridin-2(1H)-one | 545 | 1.24 | 11.13 (1H, br s), 8.31 (2H, s), 7.65-7.58 (1H, m) 7.38-7.31 (2H, m), 7.17 (1H, d, J = 8.7 Hz), 6.81 (1H, d, J = 2.1 Hz), 6.54 (1H, dd, J = 8.7 Hz, 2.1 Hz), 6.43 (1H, br s), 6.07 (1H, br s), 5.54 (1H, br s), 4.08 (2H, br s), 3.67 (4H, t, J = 4.9 Hz), 3.27 (4H, t, J = 4.9 Hz), 3.07 (6H, s). |
| 1-12-12 | 5-methoxypyridin-2-yl | 6-(7-(((5-Methoxy pyridin-2-yl)methyl)amino) thianthren-1-yl)-4-morpholino pyridin-2(1H)-one | 531 | 1.14 | |
| 1-12-13 | 5-methylpyridin-2-yl | 6-(7-(((5-Methylpyridin-2-yl)methyl)amino)thianthren-1-yl)-4-morpholino pyridin-2(1H)-one | 515 | 1.02 | 11.04 (1H, br s), 8.35 (1H, d, J = 2.1 Hz), 7.64-7.56 (1H, m), 7.53 (1H, dd, J = 8.1 Hz, 2.1 Hz), 7.38-7.30 (2H, m), 7.20 (1H, d, J = 8.1 Hz), 7.15 (1H, d, J = 8.6 Hz), 6.77 (1H, d, J = 2.1 Hz), 6.71 (1H, br s), 6.54 (1H, dd, J = 8.6, 2.1 Hz), 6.03 (1H, br s), 5.51 (1H, br s), 4.31 (2H, br s), 3.66 (4H, t, J = 4.8 Hz), 3.25 (4H, t, J = 4.8 Hz), 2.25 (3H, s). |
| 1-12-14 | 4-cyclopropylpyridin-2-yl | 6-(7-(((4-Cyclopropyl pyridin-2-yl)methyl)amino) thianthren-1-yl)-4-morpholino pyridin-2(1H)-one | 541 | 1.03 | 10.99 (1H, br s), 8.31 (1H, d, J = 5.0 Hz), 7.64-7.56 (1H, m), 738-730 (2H, m), 7.16 (1H, d, J = 8.7 Hz), 7.07 (1H, s), 6.90 (1H, dd, J = 5.0 Hz, 1.7 Hz), 6.80 (1H, d, J = 2.4 Hz), 6.65 (1H, t, J = 6.0 Hz), 6.52 (1H, dd, J = 8.7, 2.4 Hz), 6.01 (1H, br s), 5.49 (1H, br s), 4.28 (2H, d, J = 6.0 Hz), 3.66 (4H, t, J = 4.7 Hz), 3.25 (4H, t, J = 4.7 Hz), 1.92-1.82 (1H, m), 1.05-0.98 (2H, m), 0.76-0.68 (2H, m). |
| 1-12-15 | 6-methylpyridin-3-yl | 6-(7-(((6-Methyl pyridin-3-yl)methyl)amino)thianthren-1-yl)-4-morpholino pyridin-2(1H)-one | 515 | 0.95 | 11.01 (1H, br s), 8.41 (1H, d, J = 2.1 Hz), 7.64-7.56 (2H, m), 7.38-7.30 (2H, m), 7.20 (1H, d, J = 7.8 Hz), 7.15 (1H, d, J = 8.4 Hz), 6.78 (1H, d, J = 2.4 Hz), 6.62 (1H, t, J = 5.9 Hz), 6.52 (1H, dd, J = 8.4, 2.4 Hz), 6.02 (1H, br s), 5.50 (1H, br s), 4.27 (2H, d, J = 5.9 Hz), 3.66 (4H, t, J = 4.7 Hz), 3.25 (4H, t, J = 4.7 Hz), 2.42 (3H, s). |
| 1-12-16 | 6-methoxypyridin-3-yl | 6-(7-(((6-Methoxy pyridin-3-yl)methyl)amino)thianthren-1-yl)-4-morpholino pyridin-2(1H)-one | 531 | 1.36 | |
| 1-12-17 | 1-(5-methoxypyridin-3-yl)propyl | 6-(7-((1-(5-Methoxy pyridin-3-yl)propyl)amino) thianthren-1-yl)-4-morpholino pyridin-2(1H)-one | 5.59 | 1.17 | |
| 1-12-18 | 2-chloropyridin-4-yl | 6-(7-(((2-Chloropyridin-4-yl) methyl)amino)thianthren-1-yl)-4-morpholino pyridin-3 (1H)-one | 535 | 1.35 | 11.00 (1H, br s), 8.32 (1H, d, J = 5.1 Hz), 7.63-7.57 (1H, m) 7.41 (1H, s), 7.36-7.30 (3H, m), 7.18 (1H, d, J = 8.6 Hz), 6.80-6.74 (2H, m), 6.49 (1H, dd, J = 8.6 Hz, 2.7 Hz), 6.02 (1H, br s), 5.50 (1H, br s), 4.38 (2H, d, J = 6.6 Hz), 3.66 (4H, t, J = 4.7 Hz), 3.25 (4H, t, J = 4.7 Hz). |

TABLE 13

| Example No. | R^b | Compound Name | MS | RT (min) | ¹H-NMR (300 MHz) (DMSO-d₆) δ: |
|---|---|---|---|---|---|
| 1-12-19 | (5-(1H-Pyrrol-1-yl)pyridin-3-yl) | 6-(7-(((5-(1H-Pyrrol-1-yl)pyridin-3-yl)methyl)amino)thianthren-1-yl)-4-morpholino pyridin-2(1H)-one | 566 | 1.35 | 10.94 (1H, br s), (8.76 (1H, d, J = 2.6 Hz) 8.42 (1H, d, J = 1.3 Hz), 7.97 (1H, t, J = 2.0 Hz), 7.64-7.56 (1H, m), 7.42 (2H, t, J = 2.2 Hz), 7.36-7.30 (2H, m), 7,18 (1H, d, J = 8.6 Hz), 6.85 (1H, d, J = 2.0 Hz), 6.67 (1H, t, J = 5.9 Hz), 6.57 (1H, dd, J = 8.6, 2.0 Hz), 6.32 (2H, t, J = 2.2 Hz), 6.02 (1H, br s), 5.50 (1H, br s), 4.38 (2H, d, J = 5.9 Hz), 3.66 (4H, t, J = 4.3 Hz), 3.25 (4H, t, J = 4.3 Hz). |
| 1-12-20 | (5-(1H-Imidazol-1-yl)pyridin-3-yl) | 6-(7-(((5-(1H-Imidazol-1-yl)pyridin-3-yl)methyl)amino)thianthren-1-yl)-4-morpholino pyridin-2(1H)-one | 567 | 0.96 | 11.00 (1H, br s), 8.82 (1H, d, J = 2.6 Hz), 8.53 (1H, d, J = 1.3 Hz), 8.32 (1H, s), 8.08 (1H, t, J = 2.3 Hz), 7.80 (1H, s), 7.64-7.56 (1H, m), 7.38-7.28 (2H, m), 7.18 (1H, d, J = 8.6 Hz), 7.16 (1H, s), 6.85 (1H, d, J = 2.3 Hz), 6.67 (1H, t, J = 6.1 Hz), 6.57 (1H, dd, J = 8.6, 2.3 Hz), 6.01 (1H, br s), 5.49 (1H, br s), 4.40 (2H, d, J = 6.1 Hz), 3.66 (4H, t, J = 4.6 Hz), 3.25 (4H, t, J = 4.6 Hz). |
| 1-12-21 | ([3,3'-Bipyridin]-5-yl) | 6-(7-((([3,3'-Bipyridin]-5-yl methyl)amino)thianthren-1-yl)-4-morpholino pyridin-2 (1H)-one | 578 | 1.05 | 10.99 (1H, br s), 8.92 (1H( d, J = 1.3 Hz), 8.82 (1H), d, J = 2.6 Hz), 8.63 (1H, dd, J = 4.6 Hz. 2.0 Hz), 8.60 (1H, d, J = 2.0 Hz), 8,16-8.10 (2H, m), 7,64-7.56 (1H, m), 7.53 (1H, dd, J = 7.9 Hz, 4.6 Hz), 7.38-7.30 (2H, m), 7.18 (1H, d, J = 8.6 Hz), 6.86 (1H, d, J = 2.6 Hz), 6.69 (1H, t, J = 5.9 Hz), 6.58 (1H, dd, J = 8.6 Hz, 2.6 Hz), 6.02 (1H, br s), 5.49 (1H, br s), 4.41 (2H, d, 6.1 Hz), 3.66 (4H, t, J = 4.6 Hz), 3.25 (4H, t, J = 4.6 Hz). |
| 1-12-22 | (5-(1-Methyl-1H-pyrazol-4-yl)pyridin-3-yl) | 6-(7-(((5-(1-Methyl-1H-pyrazol-4-yl)pyridin-3-yl)methyl)amino)thianthren-1-yl)-4-morpholino pyridin-2 (1H)-one | 581 | 1.01 | |
| 1-12-23 | (4-Methoxy pyridin-3-yl) | 6-(7-(((4-Methoxy pyridin-3-yl)methyl)amino)thianthren-1-yl)-4-morpholino pyridin-2 (1H)-one | 531 | 0.97 | |
| 1-12-24 | (2-(Methyl amino)pyridin-3-yl) | 6-(7-(((2-(Methyl amino)pyridin-3-yl)methyl)amino)thianthren-1-yl)-4-morpholino pyridin-2(1H)-one | 530 | 0.96 | |
| 1-12-25 | (pyridin-3-yl) | 4-Morpholino-6-(7-((pyridin-3-yl methyl)amino)thianthren-1-yl)pyridin-2 (1H)-one | 501 | 0.96 | |

TABLE 13-continued

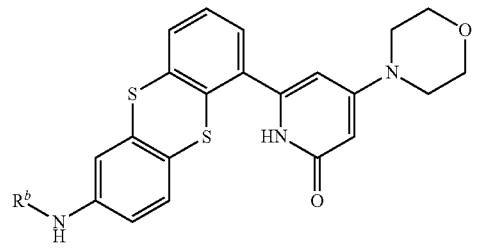

| Example No. | R$^b$ | Compound Name | MS | RT (min) | $^1$H-NMR (300 MHz) (DMSO-d$_6$) δ: |
|---|---|---|---|---|---|
| 1-12-26 | | 6-(7-((1-(5-Methoxy pyridin-3-yl)butyl)amino)thianthren-1-yl)-4-morpholino pyridin-2(1H)-one | 573 | 1.25 | |
| 1-12-27 | | 4-Morpholino-6-(7-((3-(pyridin-3-yl)propyl)amino)thianthren-1-yl)pyridin-2(1H)-one | 529 | 1.02 | |

TABLE 14

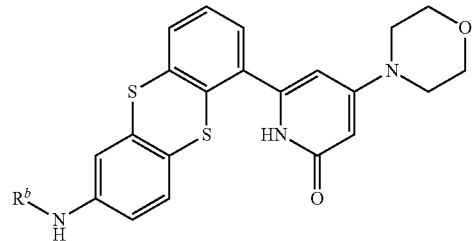

| Example No. | R$^b$ | Compound Name | MS | RT (min) | $^1$H-NMR (300 MHz) (DMSO-d$_6$) δ: |
|---|---|---|---|---|---|
| 1-12-28 | | 2-(((6-(4-Morpholino-6-oxo-1,6-dihydropyridin-2-yl)thianthren-2-yl)amino)methyl)isonicotinonitrile | 526 | 1.28 | (CD$_3$OD): 8.73 (1H, d, J = 4.8 Hz), 7.65 (1H, s), 7.62-7.55 (2H, m), 7.38-7.30 (2H, m), 7.15 (1H, d, J = 8.7 Hz), 6.76 (1H, d, J = 2.4 Hz), 6.52 (1H, dd, J = 8.7, 2.4 Hz), 6.21 (1H, d, J = 2.7 Hz), 5.74 (1H, d, J = 2.7 Hz), 4.49 (2H, s), 3.77 (4H, t, J = 4.7 Hz), 3.38 (4H, t, J = 4.7 Hz). |
| 1-12-29 | | 6-(7-((1-(4-Methyl pyridin-2-yl)ethyl)amino)thianthren-1-yl)-4-morpholino pyridin-2(1H-one | 529 | 1.01 | (CDCl$_3$): 8.41 (1H, d, J = 5.3 Hz), 7.56-7.52 (1H, m), 7.27-7.24 (2H, m, 7.15 (1H, d, J = 8.6 Hz), 7.10 (1H, s), 6.98 (1H, d, J = 5.3 Hz), 6.74 (1H, d, J = 2.6 Hz), 6.46 (1H, dd, J = 8.6, 2.6 Hz), 5.96 (1H, d, J = 2.6 Hz), 5.71 (1H, d, J = 2.6 Hz), 4.74-4.68 (1H, m), 4.58-4.48 (1H, m), 3.81 (4H, t, J = 5.0 Hz), 3.32 (4H, t, J = 5.0 Hz), 2.32 (3H, s), 1.51 (3H, d, J = 6.6 Hz). |

TABLE 14-continued

| Example No. | R^b | Compound Name | MS | RT (min) | ¹H-NMR (300 MHz) (DMSO-d₆) δ: |
|---|---|---|---|---|---|
| 1-12-30 | | 6-(7-((1-(6-Methyl pyridin-2-yl)ethyl) amino)thianthren-1-yl)-4-morpholino pyridin-2 (1H)-one | 529 | 1.02 | (CDCl₃): 9.61 (1H, s), 7.53-7.47 (2H, m),7.30-7.21 (2H, m), 7.13 (1H, d, J = 8.6 Hz), 7.06 (1H, d, J = 7.9 Hz), 7.01 (1H, d, J = 7.9 Hz), 6.74 (1H, d, J = 2.3 Hz), 6.45 (1H, dd, J = 8.6, 2.3 Hz), 5.96 (1H, d, J = 2.3 Hz), 5.67 (1H, d, J = 2.3 Hz), 4.78 (1H, d, J = 6.6 Hz), 4.60-4.49 (1H, m), 3.80 (4H, t, J = 5.0 Hz), 3.30 (4H, t, J = 5.0 Hz), 2.57 (3H, s), 1.51 (3H, d, J = 6.6 Hz). |
| 1-12-31 | | 6-(7-(((1-Methyl piperidin-4-yl) methyl)amino) thianthren-1-yl)-4-morpholino pyridin-2(1H)-one | 521 | 0.96 | |
| 1-12-32 | | 4-Morpholino-6-(7-(((6-morpholino pyridin-2-yl)methyl) amino)thianthren-1 yl)pyridin-2(1H)-one | 586 | 1.20 | |
| 1-12-33 | | 6-(7-(((6-(4-Methyl piperazin-1-yl)pyridin-2-yl)methyl)amino) thianthren-1-yl)-4-morpholino pyridin-2 (1H)-one | 599 | 1.06 | |
| 1-12-34 | | N,N-Diethyl-2-(4-(6-(((6-(4-morpholino-6-oxo-1,6-dihydro-pyridin-2-yl)thianthren-2-yl)amino)methyl) pyridin-2-yl)piperazin-1-yl) acetamide | 698 | 1.15 | |
| 1-12-35 | | 6-(7-(((6-(3-(Dimethyl amino)pyrrolidin-1-yl) pyridin-2-yl)methyl) amino)thianthren-1-yl)-4-morpholino pyridin-2 (1H)-one | 613 | 1.06 | |

TABLE 14-continued

| Example No. | R$^b$\ | Compound Name | MS | RT (min) | $^1$H-NMR (300 MHz) (DMSO-d$_6$) δ: |
|---|---|---|---|---|---|
| 1-12-36 | pyrimidin-4-yl methyl | 4-Morpholino-6-(7-((pyrimidin-4-yl methyl)amino)thianthren-1-yl)pyridin-2(1H)-one | 502 | 1.08 | |

TABLE 15

| Example No. | R$^b$\ | Compound Name | MS | RT (min) | $^1$H-NMR (300 MHz) (DMSO-d$_6$) δ: |
|---|---|---|---|---|---|
| 1-12-37 | 3-methylindolin-2-one | 3-((6-(4-Morpholino-6-oxo-1,6-dihydropyridin-2-yl)thianthren-2-yl)amino)indolin-2-one | 539 | 1.21 | |
| 1-12-38 | 6-cyanopyridin-2-yl methyl | 6-(((6-(4-Morpholino-6-oxo-1,6-dihydropyridin-2-yl)thianthren-2-yl)amino)methyl)picolinonitrile | 526 | 1.33 | 11.00 (1H, br s), 7.99 (1H, t, J = 7.9 Hz), 7.94-7.88 (1H, m), 7.65-7.56 (2H, m), 7.39-7.30 (2H, m), 7.17 (1H, d, J = 8.7 Hz), 6.83 (1H, t, J = 6.5 Hz), 6.80 (1H, d, J = 2.1 Hz), 6.50 (1H, dd, J = 8.7, 2.1 Hz), 6.02 (1H, br s), 5.50 (1H, br s), 4.44 (2H, d, J = 6.5 Hz), 3.66 (4H, t, J = 4.7 Hz), 3.25 (4H, t, J = 4.7 Hz). |
| 1-12-39 | 2-methylpyrimidin-4-yl methyl | 6-(7-(((2-Methyl pyrimidin-4-yl)methyl)amino)thianthren-1-yl)-4-morpholino pyridin-2(1H)-one | 516 | 1.09 | |
| 1-12-40 | 2-(dimethylamino)pyrimidin-4-yl methyl | 6-(7-(((2-(Dimethyl amino)pyrimidin-4-yl)methyl)amino)thianthren-1-yl)-4-morpholino pyridin-2(1H)-one | 545 | 1.20 | |
| 1-12-41 | 2-morpholinopyrimidin-4-yl methyl | 4-Morpholino-6-(7-(((2-morpholino pyrimidin-4-yl)methyl)amino)thianthren-1-yl)pyridin-2(1H)-one | 587 | 1.29 | |

TABLE 15-continued

| Example No. | R$^b$ | Compound Name | MS | RT (min) | $^1$H-NMR (300 MHz) (DMSO-d$_6$) δ: |
|---|---|---|---|---|---|
| 1-12-42 | | 4-Morpholino-6-(7-((pyrazin-2-yl methyl)amino)thianthren-1-yl)pyridin-2(1H)-one | 502 | 1.11 | |
| 1-12-43 | | 6-(7-((1-Cyclopropylethyl)araino)thianthren-1-yl)-4-morpholino pyridin-2(1H)-one | 478 | 1.45 | |
| 1-12-44 | | 4-Morpholino-6-(7-((pyridazin-3-yl methyl)amino)thianthren-1-yl)pyridin-2(1H)-one | 502 | 1.06 | |
| 1-12-45 | | 4-Morpholino-6-(7-((pyridazin-3-yl methyl)amino)thianthren-1-yl)pyridin-2(1H)-one | 502 | 1.03 | |
| 1-12-46 | | 6-(7-(((2-(Methyl amino)pyrimidin-5-yl)methyl)amino)thianthren-1-yl)-4-morpholino pyridin-2(1H)-one | 531 | 1.05 | (CDCl$_3$): 7.71-7.50 (1H, br m), 7.49-7.24 (4H, br m), 7.22-6.95 (2H, br m), 6.60-6.42 (1H, br m), 5.97 (1H, d, J = 2.0 Hz), 5.80 (1H, d, J = 2.0 Hz), 3.84 (4H, t, J = 5.0 Hz), 3.65 (2H, s), 3.36 (4H, t, J = 5.0 Hz), 2.98 (3H, s). |
| 1-12-47 | | 1,1-Dimethyl-3-(5-(((6-(4-morpholino-6-oxo-1,6-dihydropyridin-2-yl)thianthren-2-yl)amino)methyl)pyrimidin-2-yl)urea | 590 | 1.03 | |

TABLE 16

| Example No. | R$^b$ | Compound Name | MS | RT (min) | $^1$H-NMR (300 MHz) (DMSO-d$_6$) δ: |
|---|---|---|---|---|---|
| 1-12-48 | | N-(5-(((6-(4-Morpholino-6-oxo-1,6-dihydropyridin-2-yl)thianthren-2-yl)amino)methyl)pyrimidin-2-yl)pyrrolidine-1-carboxamide | 616 | 1.08 | |

TABLE 16-continued

| Example No. | R<sup>b</sup> | Compound Name | MS | RT (min) | ¹H-NMR (300 MHz) (DMSO-d₆) δ: |
|---|---|---|---|---|---|
| 1-12-49 | ethyl propanoate ester group | Ethyl 2-((6-(4-morpholino-6-oxo-1,6-dihydropyridin-2-yl)thianthren-2-yl)amino) acetate | 496 | 1.28 | (CDCl₃): 8.88 (1H, br s), 7.61-7.55 (1H, m), 7.31-7.27 (2H, m), 7.24 (1H, d, J = 8.6 Hz), 6.76 (1H, d, J = 2.6 Hz), 6.50 (1H, dd, J = 8.6, 2.6 Hz), 5.99 (1H, d, J = 2.0 Hz), 5.74 (1H, d, J = 2.0 Hz), 4.43 (1H, t, J = 3.9 Hz), 4.25 (2H, q, J = 7.2 Hz), 3.88 (2H, d, J = 3.9 Hz), 3.82 (4H, t, J = 5.0 Hz), 3.34 (4H, t, J = 5.0 Hz), 1.31 (3H, t, J = 7.2 Hz). |
| 1-12-50 | 5-methyl-3-isopropyl pyridine | 6-(7-((1-(5-Methyl pyridin-3-yl)ethyl)amino)thianthren-1-yl)-4-morpholino pyridin-2 (1H)-one | 529 | 1.01 | (CDCl₃): 8.40 (1H, d, J = 1.3 Hz), 8.33 (1H, d, J = 1.3 Hz), 7.53 (1H, t, J = 5.3 Hz), 7.43 (1H, s), 7.28-7.24 (2H, m), 7.14 (1H, d, J = 7.9 Hz), 6.64 (1H, d, J = 2.0 Hz), 6.37 (1H, dd, J = 8.6, 2.6 Hz), 5.97 (1H, d, J = 2.6 Hz), 5.73 (1H, d, J = 2.6 Hz), 4.47 (1H, q, J = 6.6 Hz), 4.14 (1H, br s), 3.81 (4H, t, J = 5.0 Hz), 3.32 (4H, t, J = 5.0 Hz), 2.31 (3H, s), 1.53 (3H, d, J = 6.6 Hz). |
| 1-12-51 | 5-ethyl-2-cyanothiophene | 5-(((6-(4-Morpholino-6-oxo-1,6-dihydropyridin-2-yl)thianthren-2-yl)amino) methyl)thiophene-2-carbonitrile | 531 | 1.36 | |
| 1-12-52 | 2-ethylthiazole | 4-Morpholino-6-(7-((thiazol-2-yl methyl) amino)thianthren-1-yl) pyridin-2 (1H)-one | 507 | 1.19 | |
| 1-12-53 | 4-ethylthiazole | 4-Morpholino-6-(7-((thiazol-4-yl methyl)amino) thianthren-1-yl)pyridin-2 (1H)-one | 507 | 1.20 | |
| 1-12-54 | 5-ethylthiazole | 4-Morpholino-6-(7-((thiazol-5-yl methyl)amino) thianthren-1-yl)pyridin-2 (1H)-one | 507 | 1.16 | |
| 1-12-55 | ethyl isobutyrate | Ethyl 2-((6-(4-morpholino-6-oxo-1,6-dihydropyridin-2-yl)thianthren-2-yl)amino) propanoate | 510 | 1.35 | |
| 1-12-56 | ethyl 6-ethylpicolinate | Ethyl 6-(((6-(4-morpholino-6-oxo-1,6-dihydropyridin-2-yl)thianthren-2-yl)amino) methyl)picol | 559 | 1.24 | |

TABLE 16-continued

| Example No. | R$^b$ | Compound Name | MS | RT (min) | $^1$H-NMR (300 MHz) (DMSO-d$_6$) δ: |
|---|---|---|---|---|---|
| 1-12-57 | | 6-(7-(((5-Methyl thiophen-2-yl)methyl)amino)thianthren-1-yl)-4-morpholino pyridin-2(1H)-one | 520 | 1.54 | |

TABLE 17

| Example No. | R$^b$ | Compound Name | MS | RT (min) | $^1$H-NMR (300 MHz) (DMSO-d$_6$) δ: |
|---|---|---|---|---|---|
| 1-12-58 | | 6-(7-(((4-Methyl thiophen-2-yl)methyl)amino)thianthren-1-yl)-4-morpholino pyridin-2(1H)-one | 520 | 1.53 | |
| 1-12-59 | | 6-(7-(((3-Methyl thiophen-2-yl)methyl)amino)thianthren-1-yl)-4-morpholino pyridin-2(1H)-one | 520 | 1.53 | |
| 1-12-60 | | 6-(7-(((6-Methyl pyrazin-2-yl)methyl)amino)thianthren-1-yl)-4-morpholino pyridin-2(1H)-one | 516 | 1.18 | |
| 1-12-61 | | 6-(7-(((3-Methyl pyrazin-2-yl)methyl)amino)thianthren-1-yl)-4-morpholino pyridin-2(1H)-one | 516 | 1.22 | |
| 1-12-62 | | 6-(7-(((5-Methyl pyrazin-2-yl)methyl)amino)thianthren-1-yl)-4-morpholino pyridin-2(1H)-one | 516 | 1.17 | (CDCl$_3$): 9.12 (1H, br s), 8.48 (1H, s), 8.40 (1H, s), 7.56 (1H, dd, J = 5.3, 3.3 Hz), 7.28 (1H, d, J = 5.3 Hz), 7.27 (1H, d, J = 3.3 Hz), 7.22 (1H, d, J = 8.6 Hz), 6.83 (1H, d, J = 2.6 Hz), 6.56 (1H, dd, J = 8.6, 2.6 Hz), 5.97 (1H, d, J = 2.0 Hz), 5.71 (1H, d, J = 2.0 Hz), 4.88 (1H, t, J = 5.5 Hz), 4.44 (2H, d, J = 5.5 Hz), 3.81 (4H, t, J = 5.0 Hz), 3.32 (4H, t, J = 5.0 Hz), 2.56 (3H, s). |

TABLE 17-continued

| Example No. | R^b | Compound Name | MS | RT (min) | ¹H-NMR (300 MHz) (DMSO-d₆) δ: |
|---|---|---|---|---|---|
| 1-12-63 | (2-isopropylpyrazine) | 4-Morpholino-6-(7-((1-(pyrazin-2-yl)ethyl)amino)thianthren-1-yl)pyridin-2(1H)-one | 516 | 1.19 | (CDCl₃): 9.66 (1H, br s), 8.60 (1H, s), 8.52 (1H, s), 8.46 (1H, s), 7.62-7.58 (1H, br m), 7.36-7.26 (2H, br m), 7.14 (1H, d, J = 7.9 Hz), 6.74 (1H, d, J = 2.6 Hz), 6.47 (1H, dd, J = 2.6, 7.9 Hz), 5.96 (1H, d, J = 2.0 Hz), 5.69 (1H, d, J = 2.0 Hz), 4.67 (1H, br s), 4.66 (1H, q, J = 5.9 Hz), 3.80 (4H, t, J = 5.0 Hz), 3.32 (4H, t, J = 5.0 Hz), 1.57 (3H, d, J = 5.9 Hz). |
| 1-12-64 | (2-isopropyl-5-methylpyrazine) | 6-(7-((1-(5-Methyl pyrazin-2-yl)ethyl)amino)thianthren-1-yl)-4-morpholino pyridin-2(1H)-one | 530 | 1.23 | (CDCl₃): 9.45 (1H, br s), 8.46 (1H, d, J = 1.3 Hz), 8.36 (1H, d, J = 1.3 Hz), 7.52 (1H, dd, J = 5.9, 2.6 Hz), 7.27 (1H, d, J = 5.9 Hz), 7.25 (1H, d, J = 2.6 Hz), 7.14 (1H, d, J = 8.6 Hz), 6.73 (1H, d, J = 2.6 Hz), 6.45 (1H, dd, J = 8.6, 2.6 Hz), 5.95 (1H, d, J = 2.0 Hz), 5.69 (1H, d, J = 2.0 Hz), 4.65 (1H, q, J = 5.9 Hz), 4.63 (1H, br s), 3.80 (4H, t, J = 5.0 Hz), 3.31 (4H, t, J = 5.0 Hz), 2.53 (3H, s), 1.54 (3H, d, J = 5.9 Hz). |
| 1-12-65 | (2-(1-hydroxymethylethyl)-4-methylpyridine) | 6-(7-((2-Hydroxy-1-(4-methyl pyridin-2-yl)ethyl)amino)thianthren-1-yl)-4-morpholino pyridin-2(1H)-one | 545 | 0.94 | (CDCl₃): 8.37 (1H, d, J = 4.6 Hz), 7.57-7.51 (1H, m), 7.28-7.23 (2H, m), 7.17-7.13 (2H, m), 7.02 (1H, d, J = 5.3 Hz), 6.81 (1H, d, J = 2.0 Hz), 6.52 (1H, dd, J = 8.6, 2.6 Hz), 5.96 (1H, d, J = 2.0 Hz), 5.71 (1H, d, J = 2.0 Hz), 5.08-5.02 (1H, m), 4.58-4.50 (1H, m), 4.02-3.89 (2H, m), 3.81 (4H, t, J = 5.0 Hz), 3.32 (4H, t, J = 5.0 Hz), 2.95-2.80 (1H, m), 2.32 (3H, s). |
| 1-12-66 | (3-(1-hydroxymethylethyl)-5-methylpyridine) | 6-(7-((2-Hydroxy-1-(5-methyl pyridin-3-yl)ethyl)amino)thianthren-1-yl)-4-morpholino pyridin-2(1H)-one | 545 | 0.92 | |
| 1-12-67 | (2-isopropylthiazole) | 4-Morpholino-6-(7-((1-(thiazol-2-yl)ethyl)amino)thianthren-1-yl)pyridin-2(1H)-one | 521 | 1.26 | |

TABLE 18

| Example No. | R^b | Compound Name | MS | RT (min) | ¹H-NMR (300 MHz) (DMSO-d₆) δ: |
|---|---|---|---|---|---|
| 1-12-68 | | 4-Morpholino-6-(7-((1-(pyrimidin-2-yl)ethyl)amino) thianthren-1-yl)pyridin-2 (1H)-one | 516 | 1.17 | |
| 1-12-69 | | 6-(7-((1-(4-Methyl pyrimidin-2-yl)ethyl)amino) thianthren-1-yl)-4-morpholino pyridin-2(1H)-one | 530 | 1.22 | (CDCl₃): 9.11 (1H, br s), 8.51 (1H, d, J = 5.3 Hz), 7.54 (1H, dd, J = 5.3, 4.0 Hz), 7.26 (1H, d, J = 5.3 Hz), 7.26 (1H, d, J = 4.0 Hz), 7.17 (1H, d, J = 8.6 Hz), 7.02 (1H, d, J = 5.3 Hz), 6.84 (1H, d, J = 2.6 Hz), 6.55 (1H, dd, J = 8.6, 2.6 Hz), 5.96 (1H, d, J = 2.6 Hz), 5.70 (1H, d, J = 2.6 Hz), 5.04 (1H, d, J = 8.6 Hz), 4.73 (1H, dq, J = 6.6, 8.6 Hz), 3.81 (4H, t, J = 5.0 Hz), 3.32 (4H, t, J = 5.0 Hz), 2.53 (3H, s), 1.55 (3H, d, J = 6.6 Hz). |
| 1-12-70 | | 6-(7-((1-(5-Methyl pyrimidin-2-yl)ethyl)amino) thianthren-1-yl)-4-morpholino pyridin-2(1H)-one | 530 | 1.24 | (CDCl₃): 9.51 (1H, br s), 8.47 (2H, s), 7.60-7.50 (1H, m), 7.35-7.25 (1H, m), 7.24 (1H, d, J = 3.3 Hz), 7.13 (1H, d, J = 7.9 Hz), 6.82 (1H, d, J = 3.3 Hz), 6.53 (1H, dd, J = 7.9, 3.3 Hz), 5.96 (1H, d, J = 2.6 Hz), 5.70 (1H, d, J = 2.6 Hz), 5.00 (1H, d, J = 7.9 Hz), 4.75 (1H, dq, J = 6.6, 7.9 Hz), 3.82 (4H, t, J = 5.0 Hz), 3.32 (4H, t, J = 5.0 Hz), 2.26 (3H, s), 1.55 (3H, d, J = 6.6 Hz). |
| 1-12-71 | | 6-(7-((2-Hydroxy-1-(6-methyl pyridin-2-yl)ethyl) amino)thianthren-1-yl)-4-morpholino pyridin-2(1H)-one | 545 | 0.93 | (CDCl₃): 7.57-7.51 (2H, m), 7.28-7.25 (2H, m), 7.18 (1H, d, J = 8.5 Hz), 7.12 (1H, d, J = 7.9 Hz), 7.06 (1H, d, J = 7.9 Hz), 6.83 (1H, d, J = 2.5 Hz), 6.54 (1H, dd, J = 8.5, 2.5 Hz), 5.97 (1H, d, J = 2.3 Hz), 5.72 (1H, d, J = 2.3 Hz), 5.02 (1H, br s), 4.55-4.51 (1H, br m), 4.00-3.95 (2H, m), 3.81 (4H, t, J = 5.0 Hz), 3.32 (4H, t, J = 5.0 Hz), 2.55 (3H, s). |
| 1-12-72 | | 6-(7-((2-Chlorocyclohexyl) amino)thianthren-1-yl)-4-morpholino pyridin-2(1H)-one | 526 | 1.63 | |
| 1-12-73 | | 6-(7-((1-(6-Methyl pyrazin-2-yl)ethyl)amino)thianthren-1-yl)-4-morpholino pyridin-2 (1H)-one | 530 | 1.25 | CDCl₃): 8.56 (1H, br s), 8.38-8.34 (2H, br m), 7.59-7.56 (1H, m), 7.32-7.17 (3H, m), 6.78-6.74 (1H, m), 6.49-6.46 (1H, m), 5.97 (1H, s), 5.36 (1H, br s), 4.66-4.62 (1H, m), 3.87-3.79 (4H, m), 3.38-3.30 (4H, m), 2.59 (3H, s), 1.29-1.25 (3H, br m). |
| 1-12-74 | | 4-Morpholino-6-(7-((1-(pyrimidin-4-yl)ethyl)amino) thianthren-1-yl)pyridin-2 (1H)-one | 516 | 1.14 | |

TABLE 18-continued

| Example No. | R<sup>b</sup> | Compound Name | MS | RT (min) | $^1$H-NMR (300 MHz) (DMSO-d$_6$) δ: |
|---|---|---|---|---|---|
| 1-12-75 | (6-methylpyrimidin-4-yl, isopropyl) | 6-(7-((1-(6-Methyl pyrimidin-4-yl)ethyl)amino)thianthren-1-yl)-4-morpholino pyridin-2(1H)-one | 530 | 1.17 | (CDCl$_3$): 9.04 (1H, s), 8.95 (1H, br s), 7.55 (1H, t, J = 4.3 Hz), 7.28-7.27 (2H, m), 7.18-7.16 (2H, m), 6.68 (1H, d, J = 2.0 Hz), 6.43 (1H, dd, J = 8.6, 2.0 Hz), 5.96 (1H, d, J = 2.6 Hz), 5.71 (1H, s), 4.51-4.47 (2H, m), 3.81 (4H, t, J = 4.6 Hz), 3.32 (4H, t, J = 4.6 Hz), 2.49 (3H, s), 1.53 (3H, d, J = 6.6 Hz). |
| 1-12-76 | (2-methoxypyrimidin-5-yl, isopropyl) | 6-(7-((1-(2-Methoxy pyrimidin-5-yl)ethyl)amino)thianthren-1-yl])-4-morpholino pyridin-2(1H)-one | 546 | 1.23 | |

TABLE 19

| Example No. | R<sup>b</sup> | Compound Name | MS | RT (min) | $^1$H-NMR (300 MHz) (DMSO-d$_6$) δ: |
|---|---|---|---|---|---|
| 1-12-77 | (4-methoxypyrimidin-2-yl, isopropyl) | 6-(7-((1-(4-Methoxy pyrimidin-2-yl)ethyl)amino)thianthren-1-yl)-4-morpholino pyridin-2(1H)-one | 546 | 1.31 | (CDCl$_3$): 8.60 (1H, br s), 8.36 (1H, d, J = 5.9 Hz), 7.57-7.55 (1H, m), 7.27-7.26 (2H, m), 7.19 (1H, d, J = 8.6 Hz), 6.86 (1H, d, J = 2.0 Hz), 6.59-6.55 (2H, m), 5.97 (1H, d, J = 2.0 Hz), 5.73 (1H, d, J = 2.0 Hz), 4.93-4.90 (1H, m), 4.70-4.62 (1H, m), 3.98 (3H, s), 3.82 (4H, t, J = 4.6 Hz), 3.33 (4H, t, J = 4.6 Hz), 1.54 (3H, d, J = 6.6 Hz). |
| 1-12-78 | (6-methoxypyrazin-2-yl, isopropyl) | 6-(7-((1-(6-Methoxy pyrazin-2-yl)ethyl)amino)thianthren-1-yl)-4-morpholino pyridin-2(1H)-one | 546 | 1.37 | |
| 1-12-79 | (6-methoxypyrazin-2-yl, 2-hydroxy-1-methylethyl) | 6-(7-((2-Hydroxy-1-(6-methoxy pyrazin-2-yl)ethyl)amino)thianthren-1-yl)-4-morpholino pyridin-2(1H)-one | 562 | 1.14 | |

TABLE 19-continued

| Example No. | R$^b$ | Compound Name | MS | RT (min) | $^1$H-NMR (300 MHz) (DMSO-d$_6$) δ: |
|---|---|---|---|---|---|
| 1-12-80 | 2-methylpyrimidin-4-yl with isopropyl | 6-(7-((1-(2-Methyl pyrimidin-4-yl)ethyl)amino) thianthren-1-yl)-4-morpholino pyridin-2(1H)-one | 530 | 1.17 | (CDCl$_3$): 8.56-8.54 (1H, m), 7.57-7.56 (1H, m), 7.29-7.26 (2H, m), 7.19-7.17 (1H, m), 7.11-7.09 (1H, m), 6.69 (1H, d, J = 2.6 Hz), 6.43 (1H, dd, J = 8.6, 2.6 Hz), 5.97 (1H, d, J = 2.0 Hz), 5.72 (1H, d, J = 2.0 Hz), 5.35 (1H, br s), 4.51-4.48 (1H, m), 3.83-3.82 (4H, m), 3.34-3.33 (4H, m), 2.76 (3H, s), 1.31-1.26 (3H, m). |
| 1-12-81 | 2-chloropyrimidin-4-yl with isopropyl | 6-(7-((1-(2-Chloropyrimidin-4-yl)ethyl)amino)thianthren-1-yl)-4-morpholino pyridin-2(1H)-one | 550 | 1.34 | |
| 1-12-82 | 2-cyanopyrimidin-4-yl with isopropyl | 4-(1-((6-(4-Morpholino-6-oxo-1,6-dihydropyridin-2-yl) thianthren-2-yl)amino)ethyl) pyrimidine-2-carbonitrile | 541 | 1.33 | |
| 1-12-83 | 6-chloropyrimidin-4-yl with isopropyl | 6-(7-((1-(6-Chloropyrimidin-4-yl)ethyl)amino)thianthren-1-yl)-4-morpholino pyridin-2 (1H)-one | 550 | 1.33 | |
| 1-12-84 | 6-cyanopyrimidin-4-yl with isopropyl | 6-(1-((6-(4-Morpholino-6-oxo-1,6-dihydropyridin-2-yl)thianthren-2-yl)amino) ethyl)pyrimidine-4-carbonitrile | 541 | 1.30 | |
| 1-12-85 | 4-(fluoromethyl)pyrimidin-2-yl with isopropyl | 6-(7-((1-(4-(Fluoromethyl) pyrimidin-2-yl)ethyl)amino) thianthren-1-yl)-4-morpholino pyridin-2(1H)-one | 548 | 1.28 | (CDCl$_3$): 8.74 (1H, d, J = 5.3 Hz), 7.56 (1H, t, J = 4.3 Hz), 7.35 (1H, d, J = 4.6 Hz), 7.30-7.23 (2H, m), 7.17 (1H, d, J = 7.9 Hz), 6.83 (1H, d, J = 2.4 Hz), 6.54 (1H, dd, J = 8.3, 2.4 Hz), 5.97 (1H, d, J = 2.3 Hz), 5.72 (1H, d, J = 2.3 Hz), 5.45 (2H, d, J = 46.2 Hz), 4.93-4.90 (1H, br m), 4.77-4.75 (1H, m), 3.81 (4H, t, J = 5.0 Hz), 3.32 (4H, t, J = 5.0 Hz), 1.55 (3H, d, J = 6.6 Hz). |
| 1-12-86 | 4-(hydroxymethyl)pyrimidin-2-yl with isopropyl | 6-(7-((1-(4-(Hydroxy methyl)pyrimidin-2-yl)ethyl) amino)thianthren-1-yl)-4-morpholino pyridin-2(1H)-one | 546 | 1.08 | |

TABLE 20

| Example No. | R^b | Compound Name | MS | RT (min) | ^1H-NMR (300 MHz) (DMSO-d_6) δ: |
|---|---|---|---|---|---|
| 1-12-87 | 4-(difluoromethyl)-2-isopropylpyrimidin-5-yl | 6-(7-((1-(4-(Difluoromethyl) pyrimidin-2-yl)ethyl)amino) thianthren-1-yl)-4-morpholino pyridin-2(1H)-one | 566 | 1.35 | (CDCl_3): 8.88 (1H, d, J = 5.3 Hz), 7.57-7.55 (1H, m), 7.48 (1H, d, J = 5.3 Hz), 7.29-7.25 (2H, m), 7.18 (1H, d, J = 7.9 Hz), 6.84 (1H, d, J = 2.6 Hz), 6.55 (1H, dd, J = 8.3, 2.6 Hz), 6.55 (1H, t, J = 55.0 Hz), 5.97 (1H, d, J = 2.3 Hz), 5.72 (1H, d, J = 2.3 Hz), 4.88-4.82 (2H, m), 3.81 (4H, t, J = 4.8 Hz), 3.33 (4H, t, J = 4.8 Hz), 1.26-1.25 (3H, m). |
| 1-12-88 | 2-methoxy-4-isopropylpyrimidin-5-yl | 6-(7-((1-(2-Methoxy pyrimidin-4-yl)ethyl)amino) thianthren-1-yl)-4-morpholino pyridin-2(1H)-one | 546 | 1.27 | |
| 1-12-89 | 2-(1-fluoromethyl)-4-methylpyrimidin | 6-(7-((2-Fluoro-1-(4-methyl pyrimidin-2-yl)ethyl)amino) thianthren-1-yl)-4-morpholino pyridin-2(1H)-one | 548 | 1.25 | (CDCl_3); 9.24 (1H, br s), 8.57 (1H, d, J = 5.3 Hz), 7.58 (1H, dd, J = 5.6, 3.6 Hz), 7.28 (1H, d, J = 5.6 Hz), 7.27 (1H, d, J = 3.6 Hz), 7.23 (1H, d, J = 8.6 Hz), 7.10 (1H, d, J = 5.3 Hz), 6.92 (H, d, J = 2.6 Hz), 6.63 (1H, dd, J = 8.6, 2.6 Hz), 5.98 (1H, d, J = 2.0 Hz), 5.74 (1H, d, J = 2.0 Hz), 5.32 (1H, d, J = 7.9 Hz), 4.98-4.83 (2H, m), 4.78-4.72 (1H, m), 3.82 (4H, t, J = 5.0 Hz), 3.34 (4H, t, J = 5.0 Hz), 2.55 (3H, s). |
| 1-12-90 | 2-(1-hydroxymethyl)-4-methylpyrimidin | 6-(7-((2-Hydroxy-1-(4-methyl pyrimidin-2-yl) ethyl) amino)thianthren-1-yl)-4-morpholino pyridin-2(1H)-one | 546 | 1.04 | (CDCl_3): 8.91 (1H, br s), 8.50 (1H, d, J = 4.9 Hz), 7.59-7.52 (1H, m), 7.29-7.27 (1H, m), 7.25-7.23 (1H, m), 7.20 (1H, d, J = 8.6 Hz), 7.09 (1H, d, J = 4.9 Hz), 6.95 (1H, d, J = 2.0 Hz), 6.67 (1H, dd, J = 8.6, 2.0 Hz), 5.98 (1H, d, J = 2.0 Hz), 5.73 (1H, d, J = 2.0 Hz), 5.47 (1H, br s), 4.71-4.63 (1H, br m), 4.00 (2H, ddd, J = 29.2, 11.1, 4.8 Hz), 3.82 (4H, t, J = 5.0 Hz), 3.57 (1H, br s), 3.33 (4H, t, J = 5.0 Hz), 2.54 (3H, s). |
| 1-12-91 | 6-(fluoromethyl)-4-isopropylpyrimidin | 6-(7-((1-(6-(Fluoromethyl) pyrimidin-4-yl)ethyl)amino) thianthren-1-yl)-4-morpholino pyridin-2(1H)-one | 548 | 1.23 | CD_3OD): 7.89-7.87 (1H, m), 7.58-7.55 (2H, m), 7.34-7.29 (2H, m), 7.11-7.08 (1H, m), 6.70-6.66 (1H, m), 6.46-6.40 (1H, m), 621-6.17 (1H, m), 5.74-5.69 (1H, m), 5.48-5.45 (1H, m), 5.34-5.28 (1H, m), 4.61-4.54 (1H, m), 3.77-3.74 (4H, m), 3.39-3.36 (4H, m), 1.53-1.51 (3H, m). |
| 1-12-92 | 5-(hydroxymethyl)-2-isopropylpyrimidin | 6-(7-((1-(5-(Hydroxy methyl)pyrimidin-2-yl)ethyl) amino)thianthren-1-yl)-4-morpholino pyridin-2(1H)-one | 546 | 1.06 | (CD_3OD): 8.70 (2H, s), 7.56 (1H, dd, J = 5.9, 3.3 Hz), 7.35-7.29 (2H, m), 7.06 (1H, d, J = 8.4 Hz), 6.75 (1H, d, J = 2.4 Hz), 6.50 (1H, dd, J = 8.4, 2.4 Hz), 6.19 (1H, d, J = 2.0 Hz), 5.73 (1H, d, J = 2.0 Hz), 4.69 (1H, q, J = 7.0 Hz), 4.61 (2H, s), 3.77 (4H, t, J = 5.0 Hz), 3.37 (4H, t, J = 5.0 Hz), 1.54 (3H, d, J = 7.0 Hz). |
| 1-12-93 | 2-(1-fluoromethyl)-5-methylpyrimidin | 6-(7-((2-Fluoro-1-(5-methyl pyrimidin-2-yl)ethyl)amino) thianthren-1-yl)-4-morpholino pyridin-2(1H)-one | 548 | 1.26 | (CDCl_3): 8.72 (1H, br s), 8.55 (2H, s), 7.60-7.53 (1H, m), 7.29-7.27 (1H, m), 7.26-7.23 (1H, m), 7.21 (1H, d, J = 8.6 Hz), 6.89 (1H, d, J = 2.6 Hz), 6.60 (1H, dd, J = 8.6, 2.6 Hz), 5.97 (1H, d, J = 2.0 Hz), 5.73 (1H, d, J = 2.0 Hz), 5.38-5.32 (1H, m), 5.25 (1H, d, J = 7.9 Hz), 4.90 (1H, t, J = 4.3 Hz), 4.74 (1H, t, J = 4.3 Hz), 3.82 (4H, t, J = 5.0 Hz), 3.33 (4H, t, J = 5.0 Hz), 2.31 (3H, s). |

TABLE 20-continued

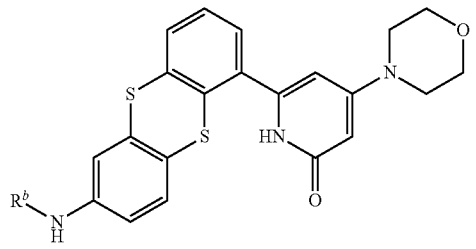

| Example No. | R<sup>b</sup> | Compound Name | MS | RT (min) | ¹H-NMR (300 MHz) (DMSO-d₆) δ: |
|---|---|---|---|---|---|
| 1-12-94 | | 4-Morpholino-6-(7-((1-(5-(pyrrolidin-1-yl methyl)pyrimidin-2-yl)ethyl)amino)thianthren-1-yl)pyridin-2(1H)-one | 599 | 0.99 | |

TABLE 21

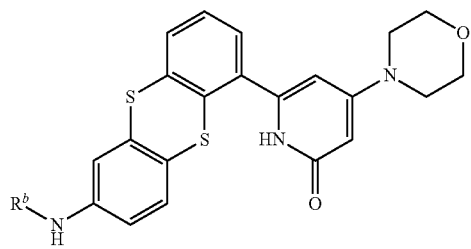

| Example No. | R<sup>b</sup> | Compound Name | MS | RT (min) | ¹H-NMR (300 MHz) (DMSO-d₆) δ: |
|---|---|---|---|---|---|
| 1-12-95 | | 4-Morpholino-6-(7-((1-(5-(morpholino methyl)pyrimidin-2-yl)ethyl)amino)thianthren-1-yl)pyridin-2(1H)-one | 581 | 0.90 | |
| 1-12-96 | | 6-(7-((2-Methoxy-1-(5-methyl pyrimidin-2-yl)ethyl)amino)thianthren-1-yl)-4-morpholino pyridin-2(1H)-one | 560 | 1.21 | (CDCl₃): 8.83 (1H, br s), 8.54 (2H, s), 7.59-7.53 (1H, m), 7.29-7.26 (1H, m), 7.27-7.24 (1H, m), 7.17 (1H, d, J = 8.3 Hz), 6.84 (1H, d, J = 2.6 Hz), 6.55 (1H, dd, J = 8.3, 2.6 Hz), 6.01 (1H, d, J = 2.0 Hz), 5.77 (1H, d, J = 2.0 Hz), 5.19-5.12 (1H, br m), 4.85-4.79 (1H, br m), 3.83 (2H, d, J = 5.1 Hz), 3.82 (4H, t, J = 5.0 Hz), 3.35 (4H, t, J = 5.0 Hz), 3.33 (3H, s), 2.29 (3H, s). |
| 1-12-97 | | 6-(7-((2-(2-Methoxy ethoxy)-1-(4-methyl pyrimidin-2-yl)ethyl)amino)thianthren-1-yl)-4-morpholino pyridin-2(1H)-one | 604 | 1.19 | (CDCl₃): 8.96 (1H, br s), 8.53 (1H, 3, J = 4.9 Hz), 7.54 (1H, dd, J = 5.3, 4.0 Hz), 7.29-7.25 (1H, m), 7.27-7.24 (1H, m), 7.16 (1H, d, J = 8.6 Hz), 7.04 (1H, d, J = 4.9 Hz), 6.86 (1H, d, J = 2.6 Hz), 6.56 (1H, dd, J = 8.6, 2.6 Hz), 5.98 (1H, d, J = 2.6 Hz), 5.72 (1H, d, J = 2.6 Hz), 5.22 (1H, d, J = 5.6 Hz), 4.82 (1H, dt, J = 5.3, 5.6 (Hz), 3.94 (2H, d, J = 5.3 Hz), 3.81 (4H, t, J = 5.0 Hz), 3.61 (2H, t, J = 4.6 Hz), 3.47 (2H, t, J = 4.6 Hz), 3.33 (4H, t, J = 5.0 Hz), 3.31 (3H, s), 2.53 (3H, s). |

TABLE 21-continued

| Example No. | $R^b$ | Compound Name | MS | RT (min) | $^1$H-NMR (300 MHz) (DMSO-$d_6$) δ: |
|---|---|---|---|---|---|
| 1-12-98 | (2-methoxyethoxymethyl-1-(5-methylpyrimidin-2-yl)ethyl) group | 6-(7-((2-(2-Methoxy ethoxy)-1-(5-methyl pyrimidin-2-yl)ethyl) amino)thianthren-1-yl)-4-morpholino pyridin-2(1H)-one | 604 | 1.20 | (CDCl$_3$): 9.25 (1H, br s), 8.53 (2H, s), 7.59-7.53 (1H, m), 7.30-7.27 (1H, m), 7.27-7.24 (1H, m), 7.16 (1H, d, J = 8.2 Hz), 6.84 (1H, d, J = 2.6 Hz), 6.54 (1H, dd, J = 8.2, 2.6 Hz), 6.04 (1H, d, J = 2.0 Hz), 5.80 (1H, d, J = 2.0 Hz), 5.16 (1H, br s), 4.86-4.80 (1H, m), 3.94 (2H, d, J = 5.3 Hz), 3.82 (4H, t, J = 5.0 Hz), 3.61 (2H, t, J = 4.6 Hz), 3.48 (2H, t, J = 4.6 Hz), 3.36 (4H, t, J = 5.0 Hz), 3.32 (3H, s), 2.29 (3H, s). |
| 1-12-99 | (2-hydroxy-1-(5-methylpyridin-2-yl)ethyl) group | 6-(7-((2-Hydroxy-1-(5-methyl pyridin-2-yl)ethyl) amino)thianthren-1-yl)-4-morpholino pyridin-2(1H)-one | 545 | 0.97 | |
| 1-12-100 | (2-methoxy-1-(5-methylpyridin-2-yl)ethyl) group | 6-(7-((2-Methoxy-1-(5-methyl pyridin-2-yl)ethyl) amino)thianthren-1-yl)-4-morpholino pyridin-2(1H)-one | 559 | 1.12 | (CDCl$_3$): 8.78 (1H, br s), 8.41 (1H, s), 7.54 (1H, dd, J = 5.3, 3.6 Hz), 7.43 (1H, dd, J = 7.9, 2.0 Hz), 7.28-7.24 (2H, m), 7.23 (1H, d, J = 7.9 Hz), 7.14 (1H, d, J = 8.6 Hz), 6.74 (1H, d, J = 2.6 Hz), 6.44 (1H, dd, J = 8.6, 2.6 Hz), 5.98 (1H, d, J = 2.0 Hz), 5.72 (1H, d, J = 2.0 Hz), 4.98 (1H, br s), 4.61 (1H, t, J = 5.7 Hz), 3.81 (4H, t, J = 5.0 Hz), 3.71 (2H, d, J = 5.7 Hz), 3.34 (3H, s), 3.32 (4H, t, J = 5.0 Hz), 2.32 (3H, s). |
| 1-12-101 | (2-ethoxy-1-(5-methylpyridin-2-yl)ethyl) group | 6-(7-((2-Ethoxy-1-(5-methyl pyridin-2-yl) ethyl)amino)thianthren-1-yl)-4-morpholino pyridin-2(1H)-one | 574 | 1.18 | |

TABLE 22

| Example No. | $R^b$ | Compound Name | MS | RT (min) | ¹H-NMR (300 MHz) (DMSO-d₆) δ: |
|---|---|---|---|---|---|
| 1-12-102 | 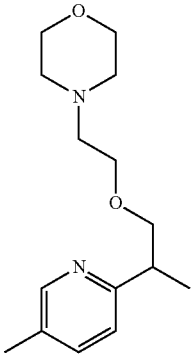 | 6-(7-((2-(2-Methoxy ethoxy)-1-(5-methyl pyridin-2-yl)ethyl)amino) thianthren-1-yl)-4-morpholino pyridin-2(1H)-one | 603 | 1.11 | (CDCl₃): 8.85 (1H, br s), 8.41 (1H, s), 7.54 (1H, dd, J = 5.0, 4.3 Hz), 7.42 (1H, dd, J = 7.9, 2.0 Hz), 7.28-7.24 (2H, m), 7.25-7.22 (1H, br m), 7.13 (1H, d, J = 8.6 Hz), 6.73 (1H, d, J = 2.0 Hz), 6.43 (1H, dd, J = 8.6, 2.0 Hz), 5.97 (1H, d, J = 2.6 Hz), 5.72 (1H, d, J = 2.6 Hz), 5.12 (1H, br s), 4.61 (1H, t, J = 5.6 Hz), 3.81 (4H, t, J = 5.0 Hz), 3.80 (2H, d, J = 5.6 Hz), 3.60 (2H, t, J = 4.5 Hz), 3.50 (2H, t, J = 4.5 Hz), 3.37 (3H, s), 3.32 (4H, t, J = 5.0 Hz), 2.32 (3H, s). |
| 1-12-103 | 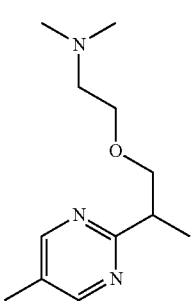 | 6-(7-((1-(5-Methyl pyridin-2-yl)-2-(2-morpholino ethoxy)ethyl)amino) thianthren-1-yl)-4-morpholino pyridin-2(1H-one | 658 | 1.15 | |
| 1-12-104 | | 6-(7-((2-(2-(Dimethyl amino)ethoxy)-1-(5-methyl pyrimidin-2-yl)ethyl)amino) thianthren-1-yl)-4-morpholino pyridin-2(1H)-one | 617 | 0.97 | |
| 1-12-105 | 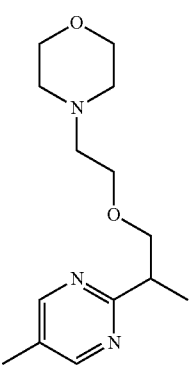 | 6-(7-((1-(5-Methyl pyrimidin-2-yl)-2-(2-morpholino ethoxy)ethyl) amino)thianthren-1-yl)-4-morpholino pyridin-2(1H) one | 659 | 1.00 | |

TABLE 22-continued

| Example No. | R$^b$ | Compound Name | MS | RT (min) | $^1$H-NMR (300 MHz) (DMSO-d$_6$) δ: |
|---|---|---|---|---|---|
| 1-12-106 | | 6-(7-((2-(Diethyl amino)-1-(5-methyl pyrimidin-2-yl) ethyl)amino)thianthren-1-yl)-4-morpholino pyridin-2(1H)-one | 601 | 1.03 | |
| 1-12-107 | | Methyl 2-(6-methyl pyridin 2-yl)-2-((6-(4-morpholino-6-oxo-1,6-dihydropyridin-2 yl)thianthren-2-yl)amino) acetate | 573 | 1.29 | (CDCl$_3$): 7.60-7.54 (2H, m), 7.28-7.20 (4H, m), 7.11 (1H, d, J = 7.9 Hz), 6.84 (1H, d, J = 2.6 Hz), 6.54 (1H, dd, J = 8.6, 2.6 Hz), 5.97 (1H, d, J = 2.6 Hz), 5.79 (1H, d, J = 7.3 Hz), 5.73 (1H, d, J = 2.6 Hz), 5.18 (1H, d, J = 7.3 Hz), 3.82 (4H, t, J = 5.0 Hz), 3.72 (3H, s), 3.33 (4H, t, J = 4.6 Hz), 2.59 (3H, s). |
| 1-12-108 | | Methyl 2-(5-methyl pyridin-2-yl)-2-((6-(4-morpholino-6-oxo-1,6-dihydropyridin-2-yl) thianthren-2-yl)amino) acetate | 573 | 1.30 | (CDCl$_3$): 8.44 (1H, d, J = 2.0 Hz), 7.58-7.48 (2H, m), 7.34 (1H, d, J = 8.6 Hz), 7.27-7.26 (2H, m), 7.20 (1H, d, J = 7.9 Hz), 6.81 (1H, d, J = 2.0 Hz), 6.51 (1H, dd, J = 8.3, 2.3 Hz), 5.96 (1H, d, J = 2.6 Hz), 5.72 (1H, d, J = 2.6 Hz), 5.63 (1H, d, J = 7.3 Hz), 5.19 (1H, d, J = 6.6 Hz), 3.81 (4H, t, J = 5.0 Hz), 3.72 (3H, s), 3.32 (4H, t, J = 4.6 Hz), 2.34 (3H, s). |

TABLE 23

| Example No. | R$^b$ | Compound Name | MS | RT (min) | $^1$H-NMR (300 MHz) (DMSO-d$_6$) δ: |
|---|---|---|---|---|---|
| 1-12-109 | | 4-Morpholino-6-(7-((1-(6-(piperidin-1-yl methyl) pyridin-2-yl)ethyl)amino) thianthren-1-yl)pyridin-2 (1H)-one | 612 | 1.07 | |

TABLE 23-continued

| Example No. | R$^b$ | Compound Name | MS | RT (min) | $^1$H-NMR (300 MHz) (DMSO-d$_6$) δ: |
|---|---|---|---|---|---|
| 1-12-110 | (pyrrolidin-1-yl methyl pyridin-2-yl, isopropyl) | 4-Morpholino-6-(7-((1-(6-(pyrrolidin-1-yl methyl) pyridin-2-yl)ethyl)amino) thianthren-1-yl)pyridin-2(1H)-one | 598 | 1.06 | |
| 1-12-111 | (dimethylaminomethyl pyridin-2-yl, isopropyl) | 6-(7-((1-(6-((Dimethyl amino)methyl)pyridin-2-yl) ethyl)amino)thianthren-1-yl)-4-morpholino pyridin-2(1H)-one | 572 | 1.03 | |
| 1-12-112 | (ethyl nicotinate methyl) | Ethyl 6-((((6-(4-morpholino-6-oxo-1,6-dihydropyridin-2-yl)thianthren-2-yl)amino) methyl)nicotinate | 573 | 1.36 | |
| 1-12-113 | (5-methyl pyridin-2-yl, isopropyl) | 6-(7-((1-(5-Methyl pyridin-2-yl)ethyl)amino)thianthren-1-yl)-4-morpholino pyridin-2(1H)-one | 530 | 1.06 | (CDCl$_3$): 8.66 (1H, br s), 8.39 (1H, d, J = 1.7 Hz), 7.55 (1H, dd, J = 5.3, 4.0 Hz), 7.43 (1H, dd, J = 7.6, 1.7 Hz), 7.32-7.27 (1H, m), 7.26-7.22 (1H, m), 7.17 (1H, d, J = 7.6 Hz), 7.15 (1H, d, J = 8.6 Hz), 6.73 (1H, d, J = 2.6 Hz), 6.45 (1H, dd, J = 8.6, 2.6 Hz), 5.96 (1H, d, J = 2.0 Hz), 5.72 (1H, d, J = 2.0 Hz), 4.69 (1H, br s), 4.56 (1H, q, J = 6.8 Hz), 3.81 (4H, t, J = 5.0 Hz), 3.32 (4H, t, J = 5.0 Hz), 2.31 (3H, s), 1.51 (3H, d, J = 6.8 Hz). |
| 1-12-114 | (5-methoxy pyrazin-2-yl, isopropyl) | 6-(7-((1-(5-Methoxy pyrazin-2-yl)ethyl)amino) thianthren-1-yl)-4-morpholino pyridin-2(1H) one | 546 | 1.36 | (CDCl$_3$): 9.42 (1H, br s), 8.16 (1H, d, J = 1.3 Hz), 8.06 (1H, d, J = 1.3 Hz), 7.53 (1H, dd, J = 6.6, 2.0 Hz), 7.27-7.23 (2H, m), 7.15 (1H, d, J = 8.6 Hz), 6.73 (1H, d, J = 2.6 Hz), 6.45 (1H, dd, J = 8.6, 2.6 Hz), 5.96 (1H, d, J = 2.6 Hz), 5.68 (1H, s), 4.62-4.58 (1H, m), 4.53-4.50 (1H, br m), 3.93 (3H, s), 3.80 (4H, t, J = 4.8 Hz), 3.30 (4H, t, J = 4.8 Hz), 1.53 (3H, d, J = 6.6 Hz). |
| 1-12-115 | (1-acetyl piperidin-4-yl) | 6-(7-((1-Acetyl piperidin-4-yl)amino)thianthren-1-yl)-4-morpholino pyridin-2(1H)-one | 535 | 1.13 | |
| 1-12-116 | (1-isopropyl piperidin-4-yl) | 6-(7-((1-Isopropyl piperidin-4-yl)amino)thianthren-1-yl)-4-morpholino pyridin-2(1H)-one | 535 | 1.00 | |

TABLE 24

| Example No. | R^b | Compound Name | MS | RT (min) | ¹H-NMR (300 MHz) (DMSO-d₆) δ: |
|---|---|---|---|---|---|
| 1-12-117 | (3-hydroxy-3-methyl-1-(5-methylpyrazin-2-yl)butyl) | 6-(7-((3-Hydroxy-3-methyl-1-(5-methyl pyrazin-2-yl)butyl)amino)thianthren-1-yl)-4-morpholino pyridin-2(1H)-one | 588 | 1.22 | |
| 1-12-118 | (1-(5-methylpyridin-2-yl)propyl) | 6-(7-((1-(5-Methyl pyridin-2-yl)propyl)amino)thianthren-1-yl)-4-morpholino pyridin-2(1H)-one | 543 | 1.13 | (CDCl₃): 9.89 (1H, br s), 8.33 (1H, d, J = 1.3 Hz), 7.50 (1H, dd, J = 6.6, 2.0 Hz), 7.40 (1H, dd, J = 7.9, 1.3 Hz), 7.24 (1H, d, J = 2.0 Hz), 7.23 (1H, d, J = 6.6 Hz), 7.13 (1H, d, J = 7.9 Hz), 7.09 (1H, d, J = 8.6 Hz), 6.73 (1H, d, J = 2.0 Hz), 6.44 (1H, dd, J = 8.6, 2.0 Hz), 5.94 (1H, d, J = 2.6 Hz), 5.67 (1H, d, J = 2.6 Hz), 4.76 (1H, d, J = 6.6 Hz), 4.39-4.30 (1H, m), 3.79 (4H, t, J = 5.0 Hz), 3.29 (4H, t, J = 5.0 Hz), 2.27 (3H, s), 1.88 (2H, dq, J = 14.0, 7.3 Hz), 0.90 (3H, t, J = 7.3 Hz). |
| 1-12-119 | (1-(5-methylpyridin-2-yl)butyl) | 6-(7-((1-(5-Methyl pyridin-2-yl)butyl)amino)thianthren-1-yl)-4-morpholino pyridin-2(1H)-one | 557 | 1.22 | |
| 1-12-120 | (3-methyl-1-(5-methylpyridin-2-yl)butyl) | 6-(7-((3-Methyl-1-(5-methyl pyridin-2-yl)butyl)amino)thianthren-1-yl)-4-morpholino pyridin-2(1H)-one | 571 | 1.31 | |
| 1-12-121 | (2-methyl-1-(5-methylpyridin-2-yl)propyl) | 6-(7-((2-Methyl-1-(5-methyl pyridin-2-yl)propyl)amino)thianthren-1-yl)-4-morpholino pyridin-2(1H)-one | 557 | 1.20 | |
| 1-12-122 | (2-methyl-1-(5-methylpyridin-2-yl)butyl) | 6-(7-((2-Methyl-1-(5-methyl pyridin-2-yl)butyl)amino)thianthren-1-yl)-4-morpholino pyridin-2(1H)-one | 571 | 1.29 | |

TABLE 24-continued

| Example No. | R^b | Compound Name | MS | RT (min) | ¹H-NMR (300 MHz) (DMSO-d₆) δ: |
|---|---|---|---|---|---|
| 1-12-123 | | 6-(7-((Cyclopropyl(5-methyl pyridin-2-yl)methyl)amino) thianthren-1-yl)-4-morpholino pyridin-2(1H)-one | 555 | 1.13 | |
| 1-12-124 | | 6-(7-((Cyclobutyl(5-methyl pyridin-2-yl)methyl)amino) thianthren-1-yl)-4-morpholino pyridin-2(1H)-one | 569 | 1.24 | |
| 1-12-125 | | 6-(7-((Cyclopentyl(5-methyl pyridin-2-yl)methyl)amino) thianthren-1-yl)-4-morpholino pyridin-2(1H)-one | 583 | 1.33 | |
| 1-12-126 | | 6-(7-((Cyclohexyl(5-methyl pyridin-2-yl)methyl)amino) thianthren-1-yl)-4-morpholino pyridin-2(1H)-one | 597 | 1.41 | |

TABLE 25

| Example No. | R$^b$ | Compound Name | MS | RT (min) | $^1$H-NMR (300 MHz) (DMSO-d$_6$) δ: |
|---|---|---|---|---|---|
| 1-12-127 | | 6-(7-((Cycloheptyl(5-methyl pyridin-2-yl)methyl)amino) thianthren-1-yl)-4-morpholino pyridin-2(1H)-one | 612 | 1.50 | |
| 1-12-128 | | 6-(7-((2-Cyclopropyl-1-(5-methyl pyridin-2-yl)ethyl) amino) thianthren-1-yl)-4-morpholino pyridin-2(1H)-one | 569 | 1.27 | |
| 1-12-129 | | 6-(7-((2-Cyclohexyl-1-(5-methyl pyridin-2-yl)ethyl) amino)thianthren-1-yl)-4-morpholino pyridin-2(1H) one | 612 | 1.52 | |
| 1-12-130 | | 6-(7-((4-Methoxy-1-(5-methyl pyridin-2-yl)butyl) amino)thianthren-1-yl)-4-morpholino pyridin-2(1H)-one | 587 | 1.12 | |
| 1-12-131 | | 6-(7-((3-(1,3-Dioxan-2-yl)-1-(5-methyl pyridin-2-yl) propyl)amino)thianthren-1-yl)-4-morpholino pyridin-2 (1H)-one | 629 | 1.14 | |

TABLE 25-continued

| Example No. | $R^b$ | Compound Name | MS | RT (min) | $^1$H-NMR (300 MHz) (DMSO-$d_6$) δ: |
|---|---|---|---|---|---|
| 1-12-132 | (HO, OMe-pyridinyl ethyl) | 6-(7-((2-Hydroxy-1-(6-methoxy pyridin-2-yl)ethyl) amino)thianthren-1-yl)-4-morpholino pyridin-2(1H)-one | 561 | 1.24 | (CDCl$_3$): 7.65-7.43 (2H, m), 7.30-7.25 (2H, m), 7.15 (1H, d, J = 8.6 Hz), 6.94-6.76 (2H, m), 6.64 (1H, d, J = 7.9 Hz), 6.58-6.43 (1H, m), 5.97 (1H, d, J = 2.0 Hz), 5.71 (1H, d, J = 2.0 Hz), 5.56-5.25 (1H, m), 5.09-4.70 (1H, m), 4.55-4.42 (1H, m), 4.04-3.87 (5H, m), 3.84-3.67 (4H, m), 3.36-3.26 (4H, m). |
| 1-12-133 | (F, 4-methylpyridinyl ethyl) | 6(7-((2-Fluoro-1-(4-methyl pyridin-2-yl)ethyl)amino) thianthren-1-yl)-4-morpholino pyridin-2(1H)-one | 547 | 1.13 | |
| 1-12-134 | (CD$_3$, F-pyridinyl ethyl) | 4-Morpholino-6-(7-((2,2,2-trideutero-1-(6-fluoropyridin-2-yl)ethyl) amino)thianthren-1-yl) pyridin-2(1H)-one | 536 | 1.41 | |

Examples 1-12-135-1 and 1-12-135-2

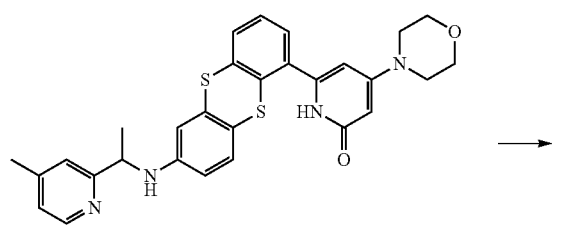

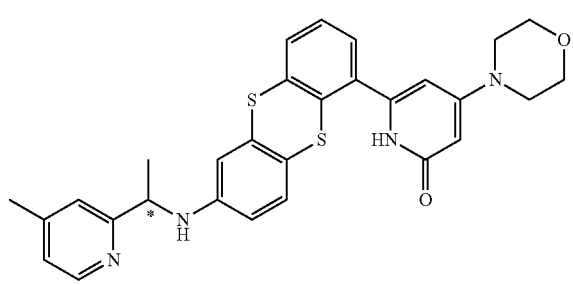

Chiral resolution was performed on 6-(7-((1-(4-methyl-pyridin-2-yl)ethyl)amino)thianthren-1-yl)-4-morpholin-opyridin-2(1H)-one (racemic mixture) by supercritical fluid chromatography, whereby an optically active substance A and an optically active substance B were obtained.

Example 1-12-135-1

Optically Active Substance A $^1$H-NMR (CDCl$_3$, 300 MHz) δ: 8.41 (1H, d, J=5.3 Hz), 7.56-7.52 (1H, m), 7.27-7.24 (2H, m), 7.15 (1H, d, J=8.6 Hz), 7.10 (1H, s), 6.98 (1H, d, J=5.3 Hz), 6.74 (1H, d, J=2.6 Hz), 6.46 (1H, dd, J=8.6, 2.6 Hz), 5.96 (1H, d, J=2.6 Hz), 5.71 (1H, d, J=2.6 Hz), 4.74-4.68 (1H, m), 4.58-4.48 (1H, m), 3.81 (4H, t, J=5.0 Hz), 3.32 (4H, t, J=5.0 Hz), 2.32 (3H, s), 1.51 (3H, d, J=6.6 Hz).
MS(ESI m/z): 529 (M+H)
RT(min): 1.01

Example 1-12-135-2

Optically Active Substance B $^1$H-NMR (CDCl$_3$, 300 MHz) δ: 8.41 (1H, d, J=5.3 Hz), 7.56-7.52 (1H, m), 7.27-7.24 (2H, m), 7.15 (1H, d, J=8.6 Hz), 7.10 (1H, s), 6.98 (1H, d, J=5.3 Hz), 6.74 (1H, d, J=2.6 Hz), 6.46 (1H, dd, J=8.6, 2.6 Hz), 5.96 (1H, d, J=2.6 Hz), 5.71 (1H, d, J=2.6 Hz), 4.74-4.68 (1H, m), 4.58-4.48 (1H, m), 3.81 (4H, t, J=5.0 Hz), 3.32 (4H, t, J=5.0 Hz), 2.32 (3H, s), 1.51 (3H, d, J=6.6 Hz).
MS(ESI m/z): 529 (M+H)
RT(min): 1.01
(Supercritical Fluid Chromatography Conditions)
Column: CHIRALCEL OJ-H (manufactured by Daicel Chemical Industries, Ltd.)

Mobile phase: carbon dioxide/methanol/diethylamine (volume ratio: 70/30/0.1)
Flow rate: 30 mL/min
Detection wavelength: 254 nm
Temperature: 40° C.
Retention time: 3.27 min (optically active substance A), 8.88 min (optically active substance B)

Examples 1-12-136-1 and 1-12-136-2

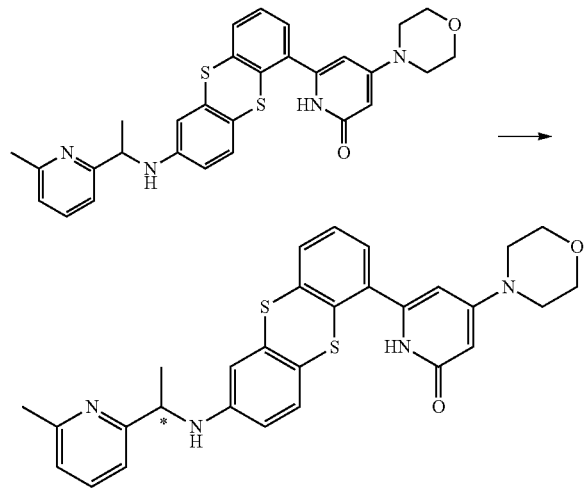 [SMILES: Cc1cccc(C(C)Nc2ccc3c(c2)Sc2cccc(-c4cc(N5CCOCC5)cc(=O)[nH]4)c2S3)n1 ; Cc1cccc(C(C)Nc2ccc3c(c2)Sc2cccc(-c4cc(N5CCOCC5)cc(=O)[nH]4)c2S3)n1]

Chiral resolution was performed on 6-(7-((1-(6-methylpyridin-2-yl)ethyl)amino)thianthren-1-yl)-4-morpholinopyridin-2(1H)-one (racemic mixture) by supercritical fluid chromatography, whereby an optically active substance A and an optically active substance B were obtained.

Example 1-12-136-1

Optically Active Substance A $^1$H-NMR (CDCl$_3$, 300 MHz) δ: 9.61 (1H, s), 7.53-7.47 (2H, m), 7.30-7.21 (2H, m), 7.13 (1H, d, J=8.6 Hz), 7.06 (1H, d, J=7.9 Hz), 7.01 (1H, d, J=7.9 Hz), 6.74 (1H, d, J=2.3 Hz), 6.45 (1H, dd, J=8.6, 2.3 Hz), 5.96 (1H, d, J=2.3 Hz), 5.67 (1H, d, J=2.3 Hz), 4.78 (1H, d, J=6.6 Hz), 4.60-4.49 (1H, m), 3.80 (4H, t, J=5.0 Hz), 3.30 (4H, t, J=5.0 Hz), 2.57 (3H, s), 1.51 (3H, d, J=6.6 Hz).
MS(ESI m/z): 529 (M+H)
RT(min): 1.01

Example 1-12-136-2

Optically Active Substance B $^1$H-NMR (CDCl$_3$, 300 MHz) δ: 9.61 (1H, s), 7.53-7.47 (2H, m), 7.30-7.21 (2H, m), 7.13 (1H, d, J=8.6 Hz), 7.06 (1H, d, J=7.9 Hz), 7.01 (1H, d, J=7.9 Hz), 6.74 (1H, d, J=2.3 Hz), 6.45 (1H, dd, J=8.6, 2.3 Hz), 5.96 (1H, d, J=2.3 Hz), 5.67 (1H, d, J=2.3 Hz), 4.78 (1H, d, J=6.6 Hz), 4.60-4.49 (1H, m), 3.80 (4H, t, J=5.0 Hz), 3.30 (4H, t, J=5.0 Hz), 2.57 (3H, s), 1.51 (3H, d, J=6.6 Hz).
MS(ESI m/z): 529 (M+H)
RT(min): 1.01

(Supercritical Fluid Chromatography Conditions)
Column: CHIRALCEL OJ-H (manufactured by Daicel Chemical Industries, Ltd.)
Mobile phase: carbon dioxide/methanol/diethylamine (volume ratio: 80/20/0.1)
Flow rate: 30 mL/min
Detection wavelength: 254 nm
Temperature: 40° C.
Retention time: 3.86 min (optically active substance A), 4.63 min (optically active substance B)

Examples 1-12-137-1 and 1-12-137-2

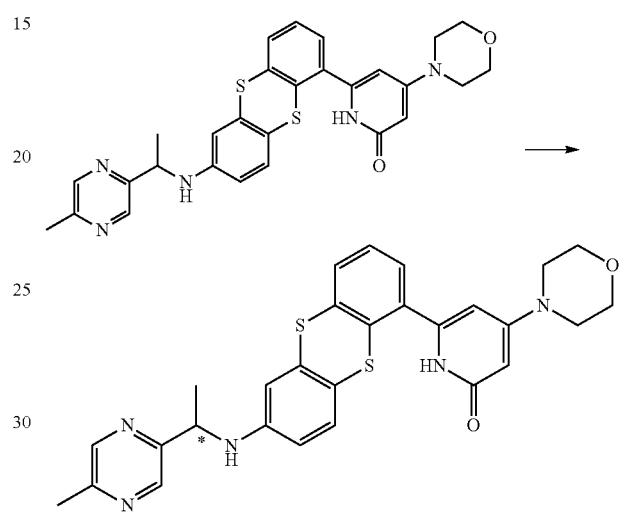

Chiral resolution was performed on 6-(7-((1-(5-methylpyrazin-2-yl)ethyl)amino)thianthren-1-yl)-4-morpholinopyridin-2(1H)-one (racemic mixture) by supercritical fluid chromatography, whereby an optically active substance A and an optically active substance B were obtained.

Example 1-12-137-1

Optically Active Substance A $^1$H-NMR (CDCl$_3$, 300 MHz) δ: 9.45 (1H, brs), 8.46 (1H, d, J=1.3 Hz), 8.36 (1H, d, J=1.3 Hz), 7.52 (1H, dd, J=5.9, 2.6 Hz), 7.27 (1H, d, J=5.9 Hz), 7.25 (1H, d, J=2.6 Hz), 7.14 (1H, d, J=8.6 Hz), 6.73 (1H, d, J=2.6H z), 6.45 (1H, dd, J=8.6, 2.6 Hz), 5.95 (1H, d, J=2.0 Hz), 5.69 (1H, d, J=2.0 Hz), 4.65 (1H, q, J=5.9 Hz), 4.63 (1H, brs), 3.80 (4H, t, J=5.0 Hz), 3.31 (4H, t, J=5.0 Hz), 2.53 (3H, s), 1.54 (3H, d, J=5.9 Hz).
MS(ESI m/z): 530 (M+H)
RT(min): 1.23

Example 1-12-137-2

Optically Active Substance B $^1$H-NMR (CDCl$_3$, 300 MHz) δ: 9.45 (1H, brs), 8.46 (1H, d, J=1.3 Hz), 8.36 (1H, d, J=1.3 Hz), 7.52 (1H, dd, J=5.9, 2.6 Hz), 7.27 (1H, d, J=5.9 Hz), 7.25 (1H, d, J=2.6 Hz), 7.14 (1H, d, J=8.6 Hz), 6.73 (1H, d, J=2.6 Hz), 6.45 (1H, dd, J=8.6, 2.6 Hz), 5.95 (1H, d, J=2.0 Hz), 5.69 (1H, d, J=2.0 Hz), 4.65 (1H, q, J=5.9 Hz), 4.63 (1H, brs), 3.80 (4H, t, J=5.0 Hz), 3.31 (4H, t, J=5.0 Hz), 2.53 (3H, s), 1.54 (3H, d, J=5.9 Hz).

MS(ESI m/z): 530 (M+H)
RT(min): 1.23
(Supercritical Fluid Chromatography Conditions)
Column: CHIRALCEL OJ-H (manufactured by Daicel Chemical Industries, Ltd.)
Mobile phase: carbon dioxide/0.1% diethylamine-containing methanol (volume ratio: 70/30)
Flow rate: 20 mL/min
Detection wavelength: 254 nm
Temperature: 40° C.
Retention time: 5.63 min (optically active substance A), 8.41 min (optically active substance B)

Examples 1-12-138-1 and 1-12-138-2

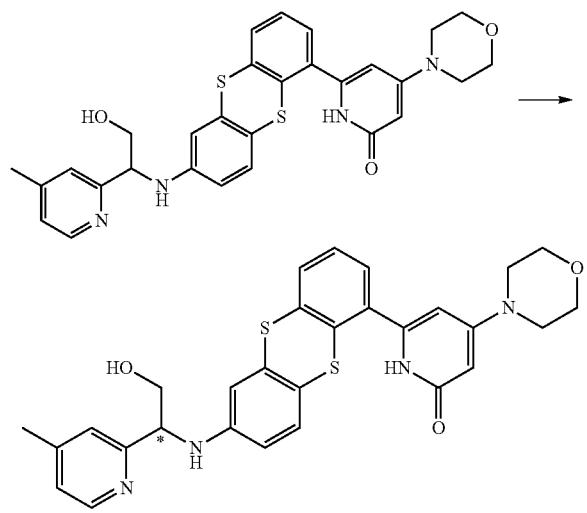

Chiral resolution was performed on 6-(7-((2-hydroxy-1-(4-methylpyridin-2-yl)ethyl)amino)thianthren-1-yl)-4-morpholinopyridin-2(1H)-one (racemic mixture) by supercritical fluid chromatography, whereby an optically active substance A and an optically active substance B were obtained.

Example 1-12-138-1

Optically Active Substance A $^1$H-NMR (CDCl$_3$, 300 MHz) δ: 8.37 (1H, d, J=4.6 Hz), 7.57-7.51 (1H, m), 7.28-7.23 (2H, m), 7.17-7.13 (2H, m), 7.02 (1H, d, J=5.3 Hz), 6.81 (1H, d, J=2.0 Hz), 6.52 (1H, dd, J=8.6, 2.6 Hz), 5.96 (1H, d, J=2.0 Hz), 5.71 (1H, d, J=2.0 Hz), 5.08-5.02 (1H, m), 4.58-4.50 (1H, m), 4.02-3.89 (2H, m), 3.81 (4H, t, J=5.0 Hz), 3.32 (4H, t, J=5.0 Hz), 2.95-2.80 (1H, m), 2.32 (3H, s).
MS(ESI m/z): 545 (M+H)
RT(min): 0.93

Example 1-12-138-2

Optically Active Substance B $^1$H-NMR (CDCl$_3$, 300 MHz) δ: 8.37 (1H, d, J=4.6 Hz), 7.57-7.51 (1H, m), 7.28-7.23 (2H, m), 7.17-7.13 (2H, m), 7.02 (1H, d, J=5.3 Hz), 6.81 (1H, d, J=2.0 Hz), 6.52 (1H, dd, J=8.6, 2.6 Hz), 5.96 (1H, d, J=2.0 Hz), 5.71 (1H, d, J=2.0 Hz), 5.08-5.02 (1H, m), 4.58-4.50 (1H, m), 4.02-3.89 (2H, m), 3.81 (4H, t, J=5.0 Hz), 3.32 (4H, t, J=5.0 Hz), 2.95-2.80 (1H, m), 2.32 (3H, s).
MS(ESI m/z): 545 (M+H)
RT(min): 0.93
(Supercritical Fluid Chromatography Conditions)
Column: CHIRALPAK IB (manufactured by Daicel Chemical Industries, Ltd.)
Mobile phase: carbon dioxide/0.1% diethylamine-containing methanol (volume ratio: 80/20)
Flow rate: 30 mL/min
Detection wavelength: 254 nm
Temperature: 40° C.
Retention time: 20.85 min (optically active substance A), 24.04 min (optically active substance B)

Examples 1-12-139-1 and 1-12-139-2

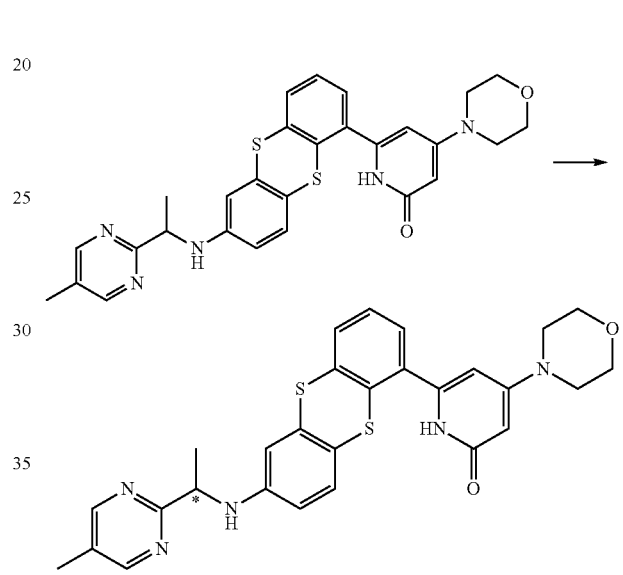

Chiral resolution was performed on 6-(7-((1-(5-methylpyrimidin-2-yl)ethyl)amino)thianthren-1-yl)-4-morpholinopyridin-2(1H)-one (racemic mixture) by supercritical fluid chromatography, whereby an optically active substance A and an optically active substance B were obtained.

Example 1-12-139-1

Optically Active Substance A $^1$H-NMR (CDCl$_3$, 300 MHz) δ: 9.51 (1H, brs), 8.47 (2H, s), 7.60-7.50 (1H, m), 7.35-7.25 (1H, m), 7.24 (1H, d, J=3.3 Hz), 7.13 (1H, d, J=7.9 Hz), 6.82 (1H, d, J=3.3 Hz), 6.53 (1H, dd, J=7.9, 3.3 Hz), 5.96 (1H, d, J=2.6 Hz), 5.70 (1H, d, J=2.6 Hz), 5.00 (1H, d, J=7.9 Hz), 4.75 (1H, dq, J=6.6, 7.9 Hz), 3.82 (4H, t, J=5.0 Hz), 3.32 (4H, t, J=5.0 Hz), 2.26 (3H, s), 1.55 (3H, d, J=6.6 Hz).
MS(ESI m/z): 530 (M+H)
RT(min): 1.24

Example 1-12-139-2

Optically Active Substance B $^1$H-NMR (CDCl$_3$, 300 MHz) δ: 9.51 (1H, brs), 8.47 (2H, s), 7.60-7.50 (1H, m), 7.35-7.25 (1H, m), 7.24 (1H, d, J=3.3 Hz), 7.13 (1H, d, J=7.9 Hz), 6.82 (1H, d, J=3.3 Hz), 6.53

(1H, dd, J=7.9, 3.3 Hz), 5.96 (1H, d, J=2.6 Hz), 5.70 (1H, d, J=2.6 Hz), 5.00 (1H, d, J=7.9 Hz), 4.75 (1H, dq, J=6.6, 7.9 Hz), 3.82 (4H, t, J=5.0 Hz), 3.32 (4H, t, J=5.0 Hz), 2.26 (3H, s), 1.55 (3H, d, J=6.6 Hz).

MS(ESI m/z): 530 (M+H)

RT(min): 1.24

(Supercritical Fluid Chromatography Conditions)

Column: CHIRALCEL OJ-H (manufactured by Daicel Chemical Industries, Ltd.)

Mobile phase: carbon dioxide/0.1% diethylamine-containing methanol (volume ratio: 70/30)

Flow rate: 20 mL/min

Detection wavelength: 254 nm

Temperature: 40° C.

Retention time: 6.04 min (optically active substance A), 10.40 min (optically active substance B)

Examples 1-12-140-1 and 1-12-140-2

7.06 (1H, d, J=7.9 Hz), 6.83 (1H, d, J=2.5 Hz), 6.54 (1H, dd, J=8.5, 2.5 Hz), 5.97 (1H, d, J=2.3 Hz), 5.72 (1H, d, J=2.3 Hz), 5.02 (1H, brs), 4.55-4.51 (1H, brm), 4.00-3.95 (2H, m), 3.81 (4H, t, J=5.0 Hz), 3.32 (4H, t, J=5.0 Hz), 2.55 (3H, s).

MS(ESI m/z): 545 (M+H)

RT(min): 0.94

(Supercritical Fluid Chromatography Conditions)

Column: CHIRALPAK AS-H (manufactured by Daicel Chemical Industries, Ltd.)

Mobile phase: carbon dioxide/0.1% diethylamine-containing methanol (volume ratio: 70/30)

Flow rate: 20 mL/min

Detection wavelength: 254 nm

Temperature: 40° C.

Retention time: 15.31 min (optically active substance A), 19.99 min (optically active substance B)

Examples 1-12-141-1 and 1-12-141-2

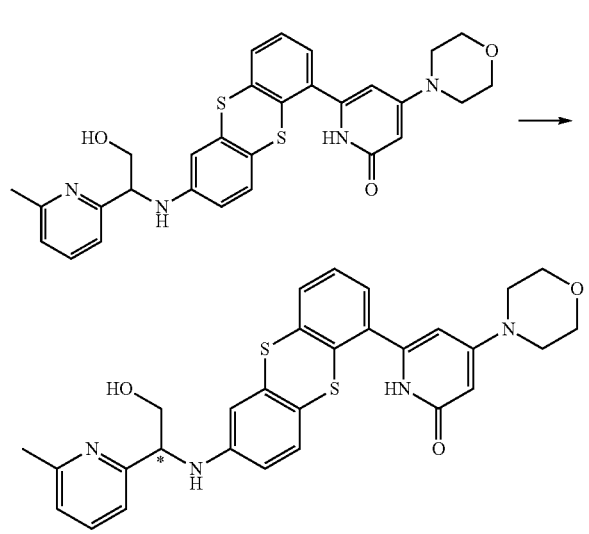

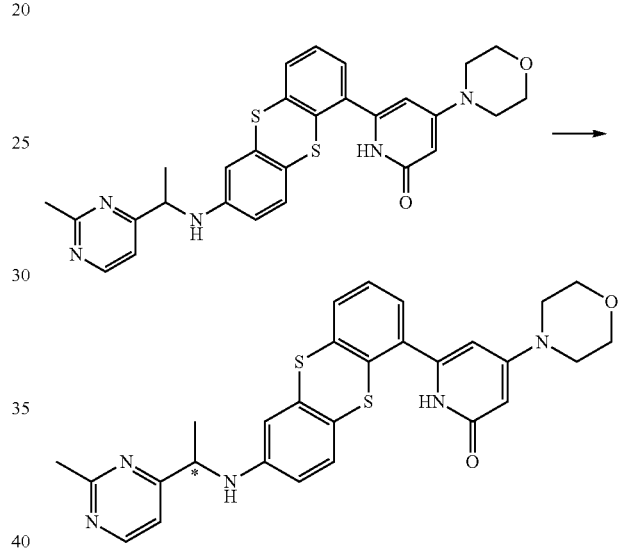

Chiral resolution was performed on 6-(7-((2-hydroxy-1-(6-methylpyridin-2-yl)ethyl)amino)thianthren-1-yl)-4-morpholinopyridin-2(1H)-one (racemic mixture) by supercritical fluid chromatography, whereby an optically active substance A and an optically active substance B were obtained.

Example 1-12-140-1

Optically Active Substance A

¹H-NMR (CDCl₃, 300 MHz) δ: 7.57-7.51 (2H, m), 7.28-7.25 (2H, m), 7.18 (1H, d, J=8.5 Hz), 7.12 (1H, d, J=7.9 Hz), 7.06 (1H, d, J=7.9 Hz), 6.83 (1H, d, J=2.5 Hz), 6.54 (1H, dd, J=8.5, 2.5 Hz), 5.97 (1H, d, J=2.3 Hz), 5.72 (1H, d, J=2.3 Hz), 5.02 (1H, brs), 4.55-4.51 (1H, brm), 4.00-3.95 (2H, m), 3.81 (4H, t, J=5.0 Hz), 3.32 (4H, t, J=5.0 Hz), 2.55 (3H, s).

MS(ESI m/z): 545 (M+H)

RT(min): 0.94

Example 1-12-140-2

Optically Active Substance B

¹H-NMR (CDCl₃, 300 MHz) δ: 7.57-7.51 (2H, m), 7.28-7.25 (2H, m), 7.18 (1H, d, J=8.5 Hz), 7.12 (1H, d, J=7.9 Hz),

Chiral resolution was performed on 6-(7-((1-(2-methylpyrimidin-4-yl)ethyl)amino)thianthren-1-yl)-4-morpholinopyridin-2(1H)-one (racemic mixture) by supercritical fluid chromatography, whereby an optically active substance A and an optically active substance B were obtained.

Example 1-12-141-1

Optically Active Substance A

¹H-NMR (CDCl₃, 300 MHz) δ: 8.56-8.54 (1H, m), 7.57-7.56 (1H, m), 7.29-7.26 (2H, m), 7.19-7.17 (1H, m), 7.11-7.09 (1H, m), 6.69 (1H, d, J=2.6 Hz), 6.43 (1H, dd, J=8.6, 2.6 Hz), 5.97 (1H, d, J=2.0 Hz), 5.72 (1H, d, J=2.0 Hz), 5.35 (1H, brs), 4.51-4.48 (1H, m), 3.83-3.82 (4H, m), 3.34-3.33 (4H, m), 2.76 (3H, s), 1.31-1.26 (3H, m).

MS(ESI m/z): 530 (M+H)

RT(min): 1.17

Example 1-12-141-2

Optically Active Substance B

¹H-NMR (CDCl₃, 300 MHz) δ: 8.56-8.54 (1H, m), 7.57-7.56 (1H, m), 7.29-7.26 (2H, m), 7.19-7.17 (1H, m), 7.11-7.09 (1H, m), 6.69 (1H, d, J=2.6 Hz), 6.43 (1H, dd, J=8.6, 2.6 Hz), 5.97 (1H, d, J=2.0 Hz), 5.72 (1H, d, J=2.0 Hz), 5.35 (1H, brs), 4.51-4.48 (1H, m), 3.83-3.82 (4H, m), 3.34-3.33 (4H, m), 2.76 (3H, s), 1.31-1.26 (3H, m).

MS(ESI m/z): 530 (M+H)

RT(min): 1.17

(Supercritical Fluid Chromatography Conditions)

Column: CHIRALCEL OJ-H (manufactured by Daicel Chemical Industries, Ltd.)

Mobile phase: carbon dioxide/0.1% diethylamine-containing methanol (volume ratio: 80/20)

Flow rate: 20 mL/min

Detection wavelength: 254 nm

Temperature: 40° C.

Retention time: 7.70 min (optically active substance A), 9.96 min (optically active substance B)

Examples 1-12-142-1 and 1-12-142-2

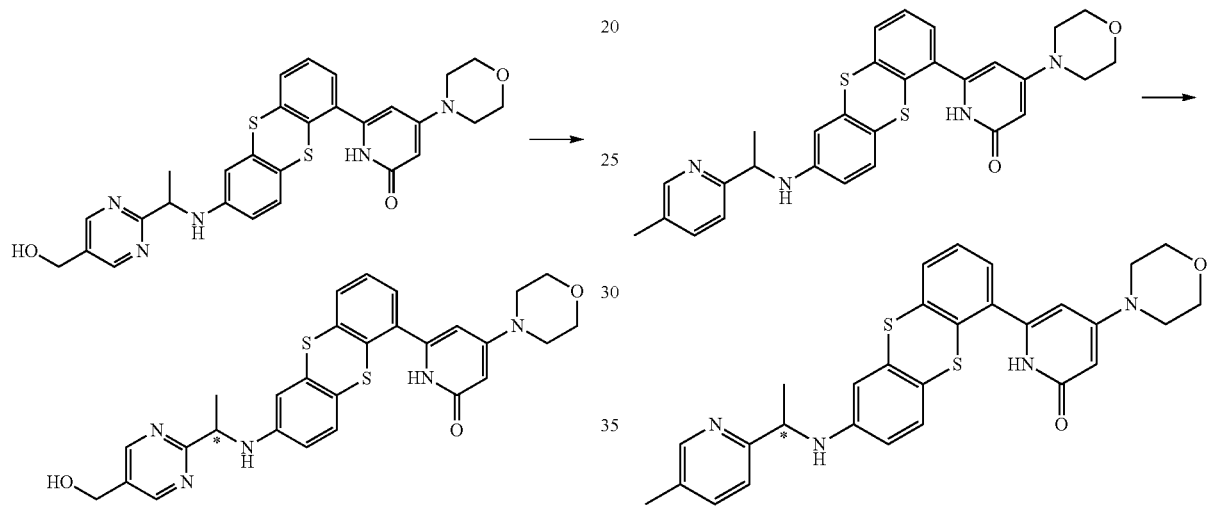

Chiral resolution was performed on 6-(7-((1-(5-(hydroxymethyl)pyrimidin-2-yl)ethyl)amino)thianthren-1-yl)-4-morpholinopyridin-2(1H)-one (racemic mixture) by supercritical fluid chromatography, whereby an optically active substance A and an optically active substance B were obtained.

Example 1-12-142-1

Optically Active Substance A $^1$H-NMR (CDCl$_3$, 300 MHz) δ: 8.70 (2H, s), 7.56 (1H, dd, J=5.9, 3.3 Hz), 7.35-7.29 (2H, m), 7.06 (1H, d, J=8.4 Hz), 6.75 (1H, d, J=2.4 Hz), 6.50 (1H, dd, J=8.4, 2.4 Hz), 6.19 (1H, d, J=2.0 Hz), 5.73 (1H, d, J=2.0 Hz), 4.69 (1H, q, J=7.0 Hz), 4.61 (2H, s), 3.77 (4H, t, J=5.0 Hz), 3.37 (4H, t, J=5.0 Hz), 1.54 (3H, d, J=7.0 Hz).

MS(ESI m/z): 546 (M+H)

RT(min): 1.06

Example 1-12-142-2

Optically Active Substance B $^1$H-NMR (CDCl$_3$, 300 MHz) δ: 8.70 (2H, s), 7.56 (1H, dd, J=5.9, 3.3 Hz), 7.35-7.29 (2H, m), 7.06 (1H, d, J=8.4 Hz), 6.75 (1H, d, J=2.4 Hz), 6.50 (1H, dd, J=8.4, 2.4 Hz), 6.19 (1H, d, J=2.0 Hz), 5.73 (1H, d, J=2.0 Hz), 4.69 (1H, q, J=7.0 Hz), 4.61 (2H, s), 3.77 (4H, t, J=5.0 Hz), 3.37 (4H, t, J=5.0 Hz), 1.54 (3H, d, J=7.0 Hz).

MS(ESI m/z): 546 (M+H)

RT(min): 1.06

(Supercritical Fluid Chromatography Conditions)

Column: CHIRALCEL OJ-H (manufactured by Daicel Chemical Industries, Ltd.)

Mobile phase: carbon dioxide/0.1% diethylamine-containing methanol (volume ratio: 70/30)

Flow rate: 20 mL/min

Detection wavelength: 254 nm

Temperature: 40° C.

Retention time: 6.04 min (optically active substance A), 10.03 min (optically active substance B)

Examples 1-12-143-1 and 1-12-143-2

Chiral resolution was performed on 6-(7-((1-(5-methylpyridin-2-yl)ethyl)amino)thianthren-1-yl)-4-morpholinopyridin-2(1H)-one (racemic mixture) by supercritical fluid chromatography, whereby an optically active substance A and an optically active substance B were obtained.

Example 1-12-143-1

Optically Active Substance A $^1$H-NMR (CDCl$_3$, 300 MHz) δ: 8.66 (1H, brs), 8.39 (1H, d, J=1.7 Hz), 7.55 (1H, dd, J=5.3, 4.0 Hz), 7.43 (1H, dd, J=7.6, 1.7 Hz), 7.32-7.27 (1H, m), 7.26-7.22 (1H, m), 7.17 (1H, d, J=7.6 Hz), 7.15 (1H, d, J=8.6 Hz), 6.73 (1H, d, J=2.6 Hz), 6.45 (1H, dd, J=8.6, 2.6 Hz), 5.96 (1H, d, J=2.0 Hz), 5.72 (1H, d, J=2.0 Hz), 4.69 (1H, brs), 4.56 (1H, q, J=6.8 Hz), 3.81 (4H, t, J=5.0 Hz), 3.32 (4H, t, J=5.0 Hz), 2.31 (3H, s), 1.51 (3H, d, J=6.8 Hz).

MS(ESI m/z): 529 (M+H)

RT(min): 1.06

Example 1-12-143-2

Optically Active Substance B $^1$H-NMR (CDCl$_3$, 300 MHz) δ: 8.66 (1H, brs), 8.39 (1H, d, J=1.7 Hz), 7.55 (1H, dd, J=5.3, 4.0 Hz), 7.43 (1H, dd, J=7.6, 1.7 Hz), 7.32-7.27 (1H, m), 7.26-7.22 (1H, m), 7.17

(1H, d, J=7.6 Hz), 7.15 (1H, d, J=8.6 Hz), 6.73 (1H, d, J=2.6 Hz), 6.45 (1H, dd, J=8.6, 2.6 Hz), 5.96 (1H, d, J=2.0 Hz), 5.72 (1H, d, J=2.0 Hz), 4.69 (1H, brs), 4.56 (1H, q, J=6.8 Hz), 3.81 (4H, t, J=5.0 Hz), 3.32 (4H, t, J=5.0 Hz), 2.31 (3H, s), 1.51 (3H, d, J=6.8 Hz).

MS(ESI m/z): 529 (M+H)
RT(min): 1.06
(Supercritical Fluid Chromatography Conditions)
Column: CHIRALCEL OJ-H (manufactured by Daicel Chemical Industries, Ltd.)
Mobile phase: carbon dioxide/0.1% diethylamine-containing methanol (volume ratio: 70/30)
Flow rate: 20 mL/min
Detection wavelength: 254 nm
Temperature: 40° C.
Retention time: 6.71 min (optically active substance A), 14.35 min (optically active substance B)

Examples 1-12-144-1 and 1-12-144-2

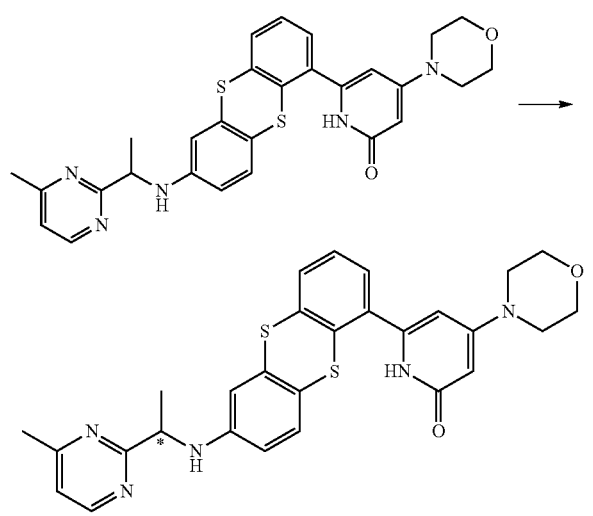

Chiral resolution was performed on 6-(7-((1-(4-methyl-pyrimidin-2-yl)ethyl)amino)thianthren-1-yl)-4-morpholin-opyridin-2(1H)-one (racemic mixture) by supercritical fluid chromatography, whereby an optically active substance A and an optically active substance B were obtained.

Example 1-12-144-1

Optically Active Substance A $^1$H-NMR (CDCl$_3$, 300 MHz) δ: 9.11 (1H, brs), 8.51 (1H, d, J=5.3 Hz), 7.54 (1H, dd, J=5.3, 4.0 Hz), 7.35-7.24 (2H, m), 7.17 (1H, d, J=8.6 Hz), 7.02 (1H, d, J=5.3 Hz), 6.84 (1H, d, J=2.6 Hz), 6.55 (1H, dd, J=8.6, 2.6 Hz), 5.96 (1H, d, J=2.6 Hz), 5.70 (1H, d, J=2.6 Hz), 5.04 (1H, d, J=8.6 Hz), 4.73 (1H, dq, J=6.6, 8.6 Hz), 3.81 (4H, t, J=5.0 Hz), 3.32 (4H, t, J=5.0 Hz), 2.53 (3H, s), 1.55 (3H, d, J=6.6 Hz).

MS(ESI m/z): 530 (M+H)
RT(min): 1.22

Example 1-12-144-2

Optically Active Substance B $^1$H-NMR (CDCl$_3$, 300 MHz) δ: 9.11 (1H, brs), 8.51 (1H, d, J=5.3 Hz), 7.54 (1H, dd, J=5.3, 4.0 Hz), 7.35-7.24 (2H, m), 7.17 (1H, d, J=8.6 Hz), 7.02 (1H, d, J=5.3 Hz), 6.84 (1H, d, J=2.6 Hz), 6.55 (1H, dd, J=8.6, 2.6 Hz), 5.96 (1H, d, J=2.6 Hz), 5.70 (1H, d, J=2.6 Hz), 5.04 (1H, d, J=8.6 Hz), 4.73 (1H, dq, J=6.6, 8.6 Hz), 3.81 (4H, t, J=5.0 Hz), 3.32 (4H, t, J=5.0 Hz), 2.53 (3H, s), 1.55 (3H, d, J=6.6 Hz).

MS(ESI m/z): 530 (M+H)
RT(min): 1.22
(Supercritical Fluid Chromatography Conditions)
Column: CHIRALCEL OJ-H (manufactured by Daicel Chemical Industries, Ltd.)
Mobile phase: carbon dioxide/0.1% diethylamine-containing methanol (volume ratio: 80/20)
Flow rate: 30 mL/min
Detection wavelength: 254 nm
Temperature: 40° C.
Retention time: 6.68 min (optically active substance A), 13.18 min (optically active substance B)

Examples 1-12-145-1 and 1-12-145-2

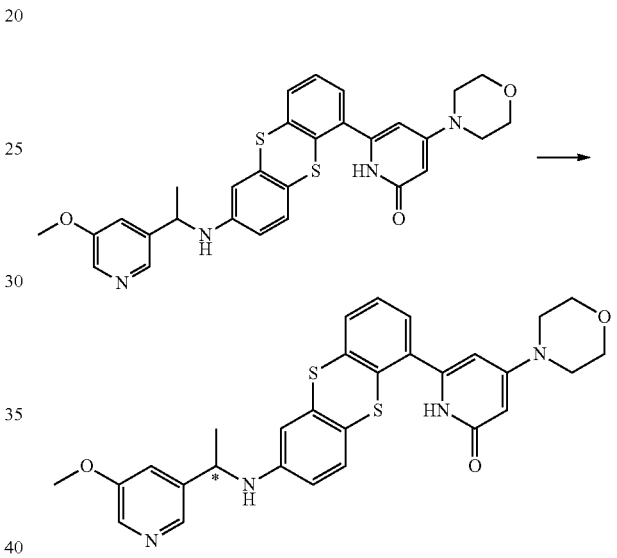

Chiral resolution was performed on 6-(7-((1-(5-methoxy-pyridin-3-yl)ethyl)amino)thianthren-1-yl)-4-morpholin-opyridin-2(1H)-one (racemic mixture) by supercritical fluid chromatography, whereby an optically active substance A and an optically active substance B were obtained.

Example 1-12-145-1

Optically Active Substance A $^1$H-NMR (CDCl$_3$, 300 MHz) δ: 9.59 (1H, s), 8.20-8.17 (2H, m), 7.50 (1H, dd, J=6.6, 2.0 Hz), 7.29-7.22 (2H, m), 7.14-7.10 (2H, m), 6.63 (1H, d, J=2.6 Hz), 6.36 (1H, dd, J=8.6, 2.6 Hz), 5.95 (1H, d, J=2.6 Hz), 5.69 (1H, d, J=2.6 Hz), 4.49-4.42 (1H, m), 4.17 (1H, d, J=5.3 Hz), 3.82 (3H, s), 3.80 (4H, t, J=5.0 Hz), 3.30 (4H, t, J=5.0 Hz), 1.52 (3H, d, J=6.6 Hz).

MS(ESI m/z): 545 (M+H)
RT(min): 1.08

Example 1-12-145-2

Optically Active Substance B $^1$H-NMR (CDCl$_3$, 300 MHz) δ: 9.59 (1H, s), 8.20-8.17 (2H, m), 7.50 (1H, dd, J=6.6, 2.0 Hz), 7.29-7.22 (2H, m), 7.14-7.10 (2H, m), 6.63 (1H, d, J=2.6 Hz), 6.36 (1H, dd, J=8.6, 2.6 Hz), 5.95 (1H, d, J=2.6 Hz), 5.69 (1H, d, J=2.6 Hz), 4.49-4.42 (1H, m), 4.17 (1H, d, J=5.3 Hz), 3.82 (3H, s), 3.80 (4H, t, J=5.0 Hz), 3.30 (4H, t, J=5.0 Hz), 1.52 (3H, d, J=6.6 Hz).

MS(ESI m/z): 545 (M+H)
RT(min): 1.08
(Supercritical Fluid Chromatography Conditions)
Column: CHIRALPAK IB (manufactured by Daicel Chemical Industries, Ltd.)
Mobile phase: carbon dioxide/0.1% diethylamine-containing methanol (volume ratio: 80/20)
Flow rate: 30 mL/min
Detection wavelength: 254 nm
Temperature: 40° C.
Retention time: 13.90 min (optically active substance A), 16.30 min (optically active substance B)

Examples 1-12-146-1 and 1-12-146-2

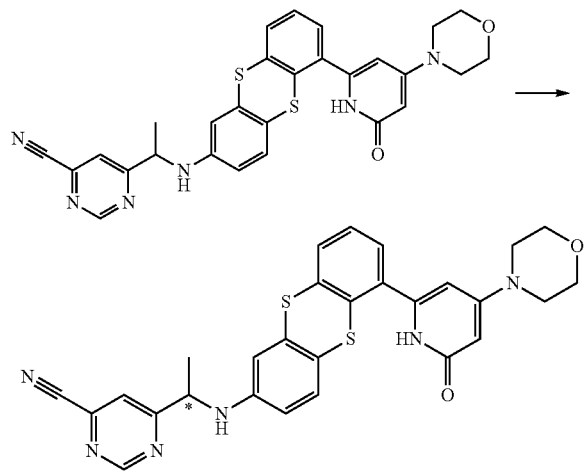

Chiral resolution was performed on 6-(1-((6-(4-morpholino-6-oxo-1,6-dihydropyridin-2-yl)thianthren-2-yl)amino)ethyl)pyrimidine-4-carbonitrile (racemic mixture) by supercritical fluid chromatography, whereby an optically active substance A and an optically active substance B were obtained.

Example 1-12-146-1

Optically Active Substance A

¹H-NMR (CDCl₃, 300 MHz) δ: 9.29 (1H, d, J=1.3 Hz), 7.67 (1H, d, J=1.3 Hz), 7.54 (1H, dd, J=6.3, 3.1 Hz), 7.29-7.27 (2H, m), 7.17 (1H, d, J=8.6 Hz), 6.63 (1H, d, J=2.3 Hz), 6.38 (1H, dd, J=8.6, 2.3 Hz), 5.97 (1H, d, J=2.0 Hz), 5.71 (1H, d, J=2.0 Hz), 4.64-4.55 (1H, m), 4.47 (1H, d, J=5.9 Hz), 3.81 (4H, t, J=5.0 Hz), 3.32 (4H, t, J=5.0 Hz), 1.59 (3H, d, J=7.3 Hz).

MS(ESI m/z): 541 (M+H)
RT(min): 1.30

Example 1-12-146-2

Optically Active Substance B

¹H-NMR (CDCl₃, 300 MHz) δ: 9.29 (1H, d, J=1.3 Hz), 7.67 (1H, d, J=1.3 Hz), 7.54 (1H, dd, J=6.3, 3.1 Hz), 7.29-7.27 (2H, m), 7.17 (1H, d, J=8.6 Hz), 6.63 (1H, d, J=2.3 Hz), 6.38 (1H, dd, J=8.6, 2.3 Hz), 5.97 (1H, d, J=2.0 Hz), 5.71 (1H, d, J=2.0 Hz), 4.64-4.55 (1H, m), 4.47 (1H, d, J=5.9 Hz), 3.81 (4H, t, J=5.0 Hz), 3.32 (4H, t, J=5.0 Hz), 1.59 (3H, d, J=7.3 Hz).

MS(ESI m/z): 541 (M+H)
RT(min): 1.30
(Supercritical Fluid Chromatography Conditions)
Column: CHIRALPAK IB (manufactured by Daicel Chemical Industries, Ltd.)
Mobile phase: carbon dioxide/0.1% diethylamine-containing methanol (volume ratio: 75/25)
Flow rate: 30 mL/min
Detection wavelength: 254 nm
Temperature: 40° C.
Retention time: 11.20 min (optically active substance A), 12.84 min (optically active substance B)

Example 1-13-1

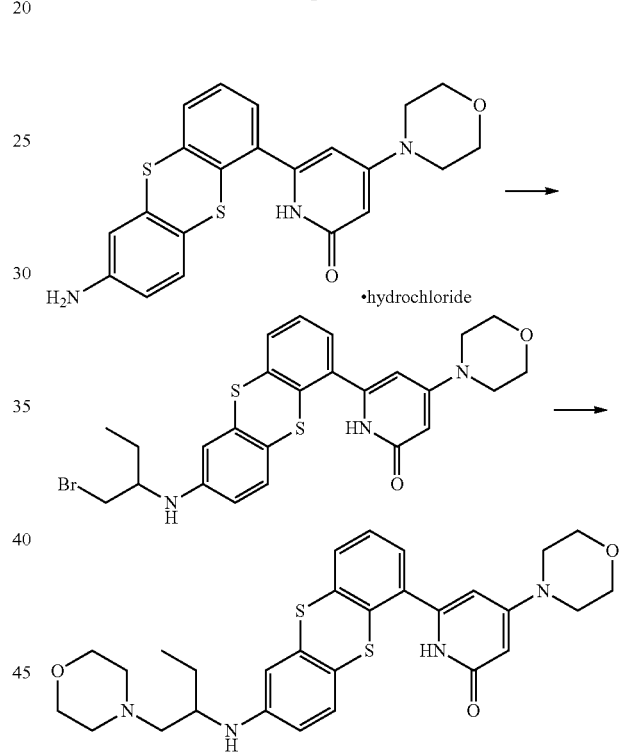

(1)
In the same manner as in Example 1-12-1, the following compounds were obtained.

6-(7-((1-Bromobutan-2-yl)amino)thianthren-1-yl)-4-morpholinopyridin-2(1H)-one

MS(ESI m/z): 546 (M+H)
RT(min): 1.59
(2)
In the same manner as in Example 1-6-1 (2), the following compound was obtained.

4-Morpholino-6-(7-((1-morpholinobutan-2-yl)amino)thianthren-1-yl)pyridin-2(1H)-one ¹H-NMR (CD₃OD, 300 MHz) δ: 7.65-7.53 (1H, m), 7.37-7.28 (2H, m), 7.19-7.06 (1H, m), 6.85-6.76 (1H, m), 6.60-6.48 (1H, m), 6.20 (1H, d, J=2.0 Hz), 5.73 (1H, d, J=2.6 Hz), 3.76 (4H, t, J=4.6 Hz), 3.72-3.59 (4H, m), 3.50-3.32 (4H, m), 2.88-2.76 (1H, m), 2.61-2.34 (6H, m), 1.71-0.90 (5H, m).

MS(ESI m/z): 551 (M+H)
RT(min): 1.02

Example 1-13-2

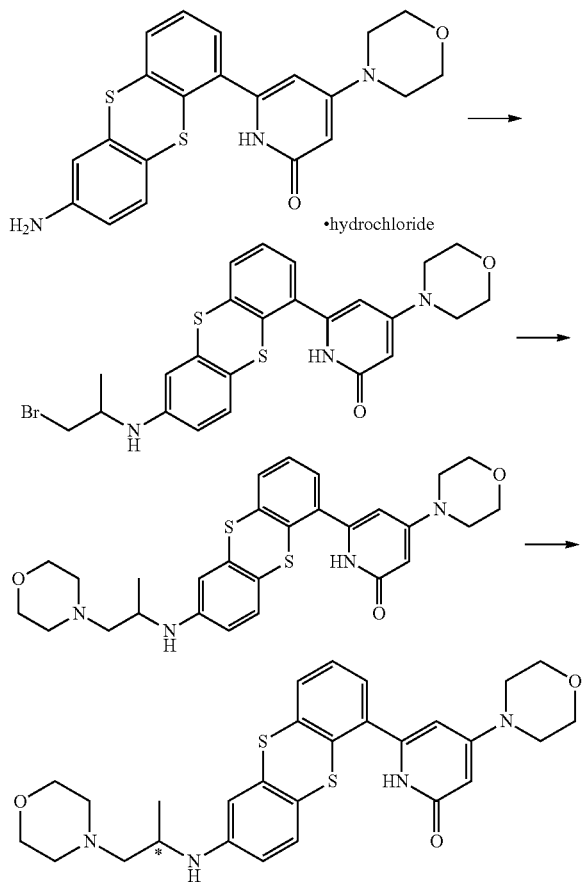

In the same manner as in Example 1-12-1, the following compounds were obtained.

6-(7-((1-Bromopropan-2-yl)amino))thianthren-1-yl)-4-morpholinopyridin-2(1H)-one

MS(ESI m/z): 532 (M+H)
RT(min): 1.49

Example 1-13-2-1

In the same manner as in Example 1-6-1 (2), the following compound was obtained.

4-Morpholino-6-(7-((1-morpholinopropan-2-yl)amino)thianthren-1-yl)pyridin-2(1H)-one (racemic mixture)

$^1$H-NMR (CDCl$_3$, 300 MHz) δ: 7.61-7.54 (1H, m), 7.30-7.24 (2H, m), 7.23 (1H, d, J=8.3 Hz), 6.83 (1H, s), 6.57 (1H, d, J=8.3 Hz), 5.98 (1H, d, J=2.4 Hz), 5.73 (1H, d, J=2.4 Hz), 3.90-3.50 (8H, m), 3.33 (4H, t, J=4.8 Hz), 2.80-2.35 (7H, m), 1.22 (3H, d, J=6.0 Hz).

MS(ESI m/z): 537 (M+H)
RT(min): 0.97

Examples 1-13-2-2 and 1-13-2-3

Chiral resolution was performed on 4-morpholino-6-(7-((1-morpholinopropan-2-yl)amino)thianthren-1-yl)pyridin-2(1H)-one (racemic mixture) obtained in Example 1-13-2-1 by supercritical fluid chromatography, whereby an optically active substance A and an optically active substance B were obtained.

Example 1-13-2-2

Optically Active Substance A $^1$H-NMR (CDCl$_3$, 300 MHz) δ: 7.61-7.54 (1H, m), 7.30-7.24 (2H, m), 7.23 (1H, d, J=8.3 Hz), 6.83 (1H, s), 6.57 (1H, d, J=8.3 Hz), 5.98 (1H, d, J=2.4 Hz), 5.73 (1H, d, J=2.4 Hz), 3.90-3.50 (8H, m), 3.33 (4H, t, J=4.8 Hz), 2.80-2.35 (7H, m), 1.22 (3H, d, J=6.0 Hz).

MS(ESI m/z): 537 (M+H)
RT(min): 0.97

Example 1-13-2-3

Optically Active Substance B $^1$H-NMR (CDCl$_3$, 300 MHz) δ: 7.61-7.54 (1H, m), 7.30-7.24 (2H, m), 7.23 (1H, d, J=8.3 Hz), 6.83 (1H, s), 6.57 (1H, d, J=8.3 Hz), 5.98 (1H, d, J=2.4 Hz), 5.73 (1H, d, J=2.4 Hz), 3.90-3.50 (8H, m), 3.33 (4H, t, J=4.8 Hz), 2.80-2.35 (7H, m), 1.22 (3H, d, J=6.0 Hz).

MS(ESI m/z): 537 (M+H)
RT(min): 0.97

(Supercritical Fluid Chromatography Conditions)
Column: CHIRALPAK IA (manufactured by Daicel Chemical Industries, Ltd.)
Mobile phase: carbon dioxide/0.1% diethylamine-containing methanol (volume ratio: 70/30)
Flow rate: 30 mL/min
Detection wavelength: 254 nm
Temperature: 40° C.
Retention time: 11.04 min (optically active substance A), 13.78 min (optically active substance B)

Example 1-13-3-1

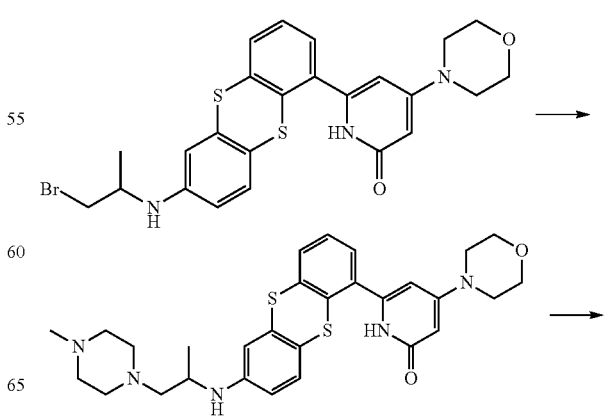

-continued

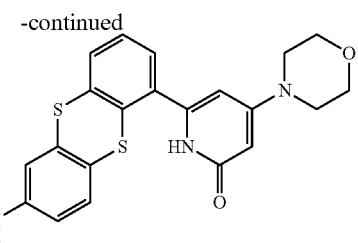

In the same manner as in Example 1-6-1 (2), the following compound was obtained.

6-(7-((1-(4-Methylpiperazin-1-yl)propan-2-yl)amino)thianthren-1-yl)-4-morpholinopyridin-2(1H)-one (racemic mixture)

$^1$H-NMR (CDCl$_3$, 300 MHz) δ: 7.61-7.54 (1H, m), 7.33-7.16 (3H, m), 6.80 (1H, d, J=2.6 Hz), 6.52 (1H, d d, J=8.3, 2.3 Hz), 5.98 (1H, d, J=2.6 Hz), 5.71 (1H, d, J=2.0 Hz), 4.55 (1H, brs), 3.82 (4H, t, J=5.0 Hz), 3.44 (1H, brs), 3.33 (4H, t, J=4.6 Hz), 2.59-2.29 (10H, m), 2.26 (3H, s), 1.18 (3H, d, J=5.9 Hz).

MS(ESI m/z): 550 (M+H)

RT(min): 1.02

Examples 1-13-3-2 to 1-13-3-3

Chiral resolution was performed on 6-(7-((1-(4-methyl piperazin-1-yl)propan-2-yl)amino)thianthren-1-yl)-4-morpholinopyridin-2(1H)-one (racemic mixture) obtained in Example 1-13-3-1 by supercritical fluid chromatography, whereby an optically active substance A and an optically active substance B were obtained.

Example 1-13-3-2

Optically Active Substance A $^1$H-NMR (CDCl$_3$, 300 MHz) δ: 7.61-7.54 (1H, m), 7.33-7.16 (3H, m), 6.80 (1H, d, J=2.6 Hz), 6.52 (1H, dd, J=8.3, 2.3 Hz), 5.98 (1H, d, J=2.6 Hz), 5.71 (1H, d, J=2.0 Hz), 4.55 (1H, brs), 3.82 (4H, t, J=5.0 Hz), 3.44 (1H, brs), 3.33 (4H, t, J=4.6 Hz), 2.59-2.29 (10H, m), 2.26 (3H, s), 1.18 (3H, d, J=5.9 Hz).

MS(ESI m/z): 550 (M+H)

RT(min): 1.02

Example 1-13-3-3

Optically Active Substance B $^1$H-NMR (CDCl$_3$, 300 MHz) δ: 7.61-7.54 (1H, m), 7.33-7.16 (3H, m), 6.80 (1H, d, J=2.6 Hz), 6.52 (1H, dd, J=8.3, 2.3 Hz), 5.98 (1H, d, J=2.6 Hz), 5.71 (1H, d, J=2.0 Hz), 4.55 (1H, brs), 3.82 (4H, t, J=5.0 Hz), 3.44 (1H, brs), 3.33 (4H, t, J=4.6 Hz), 2.59-2.29 (10H, m), 2.26 (3H, s), 1.18 (3H, d, J=5.9 Hz).

MS(ESI m/z): 550 (M+H)

RT(min): 1.02

(Supercritical Fluid Chromatography Conditions)

Column: CHIRALCEL OJ-H (manufactured by Daicel Chemical Industries, Ltd.)

Mobile phase: carbon dioxide/0.1% diethylamine-containing methanol (volume ratio: 80/20)

Flow rate: 30 mL/min

Detection wavelength: 254 nm

Temperature: 40° C.

Retention time: 4.12 min (optically active substance A), 7.07 min (optically active substance B)

Examples 1-13-4 to 1-13-17

In the same manner as in Example 1-6-1 (2), the following compounds were obtained.

TABLE 26

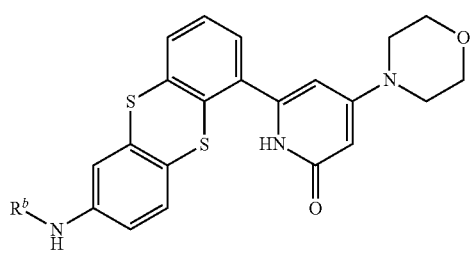

| Example No. | R$^b$ | Compound Name | MS | RT (min) | $^1$H-NMR (300 MHz) (DMSO-d$_6$) δ: |
|---|---|---|---|---|---|
| 1-13-4 | (piperidinyl-propyl) | 4-Morpholine-6-(7-((1-piperidin-1-yl)propan-2-yl)amino)thianthren-1-yl)pyridin-2(1H)-one | 535 | 1.05 | (CD$_3$OD): 7.66-7.53 (1H, m), 7.40-7.26 (2H, m), 7.22-7.06 (1H, m), 6.82-6.74 (1H, m), 6.58-6.46 (1H, m), 6.25-6.15 (1H, m), 5.77-5.68 (1H, m), 3.83-3.71 (4H, m), 3.67-3.48 (1H, m), 3.42-3.33 (4H, m), 3.32-3.29 (4H, m), 2.44 (2H, br s), 1.70-1.17 (6H, m), 1.14 (3H, d, J = 5.9 Hz). |
| 1-13-5 | (3-oxa-8-azabicyclo[3.2.1]octyl-propyl) | 6-(7-((1-(3-Oxa-8-azabicyclo[3.2.1]octan-8-yl)propan-2-yl)amino)thianthren-1-yl)-4-morpholino pyridin-2(1H)-one | 563 | 1.02 | |

TABLE 26-continued

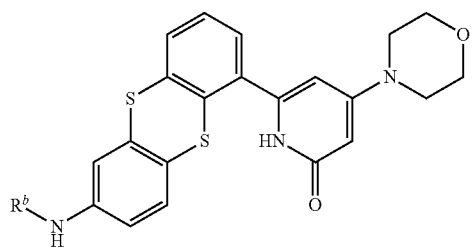

| Example No. | R$^b$ | Compound Name | MS | RT (min) | $^1$H-NMR (300 MHz) (DMSO-d$_6$) δ: |
|---|---|---|---|---|---|
| 1-13-6 | (3-hydroxypiperidinyl with isobutyl) | 6-(7-((1-(3-Hydroxy piperidin-1-yl)propan-2-yl)amino)thianthren-1-yl)-4-morpholino pyridin-2(1H)-one | 551 | 0.96 | |
| 1-13-7 | (cyclohexylamino with isobutyl) | 6-(7-((1-(Cyclohexyl amino)propan-2-yl)amino) thianthren-1-yl)-4-morpholino pyridin-2(1H)-one | 549 | 1.13 | |
| 1-13-8 | (cyclopentylamino with isobutyl) | 6-(7-((1-(Cyclopentyl amino)propan-2-yl)amino)thianthren-1-yl)-4-morpholino pyridin-2 (1H)-one | 535 | 1.07 | |
| 1-13-9 | (cyclohexyl(methyl)amino with isobutyl) | 6-(7-((1-(Cyxlohexyl(methyl) amino)propan-2-yl)amino) thianthren-1-yl)-4-morpholino pyridin-2(1H)-one | 563 | 1.15 | |
| 1-13-10 | (3-methylmorpholino with isobutyl) | 6-(7-((1-(3-Methyl morpholino)propan-2-yl) amino)thianthren-1-yl)-4-morpholino pyridin-2(1H)-one | 551 | 0.98 | |
| 1-13-11 | (2,6-dimethylmorpholino with isobutyl) | 6-(7-((1-(2,6-Dimethyl morpholino)propan-2-yl) amino)thianthren-1-yl)-4-morpholino pyridin-2(1H)-one | 565 | 1.08 | (CD$_3$OD): 7.64-7.56 (1H, m), 7.36-7.29 (2H, m), 7.14 (1H, d, J = 8.6 Hz), 6.82-6.77 (1H, m), 6.58-6.49 (1H, m), 6.22 (1H, d, J = 2.6 Hz), 5.75 (1H, d, J = 2.0 Hz), 3.78 (4H, t, J = 4.6 Hz), 3.72-3.53 (2H, m), 3.38 (4H, t, J = 5.0 Hz), 3.32-3.29 (2H, m), 3.13-2.61 (2H, m), 2.53-2.10 (3H, m), 1.22-1.00 (9H, m). |
| 1-13-12 | ((2S,6R)-2,6-dimethylmorpholino with isobutyl) | 6-(7-((1-((2S,6R)-2,6-Dimethyl morpholino)propan-2-yl)amino) thianthren-1-yl)-4-morpholino pyridin-2(1H)-one | 565 | 1.08 | (CD$_3$OD): 7.61 (1H, dd, J = 5.6, 3.6 Hz), 7.36-7.31 (2H, m), 7.15 (1H, d, J = 8.6 Hz), 6.83-6.79 (1H, m), 6.55 (1H, dd, J = 8.6, 2.0 Hz), 6.23 (1H, d, J = 2.0 Hz), 5.75 (1H, d, J = 2.6 Hz), 3.78 (4H, t, J = 4.6 Hz), 3.72-3.53 (2H, m), 3.39 (4H, t, J = 5.0 Hz), 3.33-3.28 (2H, m), 2.90-2.63 (2H, m), 2.55-2.14 (2H, m), 1.88-1.70 (1H, m), 1.18-1.03 (9H, m). |
| 1-13-13 | (4-ethylpiperazinyl with isobutyl) | 6-(7-((1-(4-Ethyl piperazin-1-yl)propan-2-yl)amino) thianthren-1-yl)-4-morpholino pyridin-2(1H)-one | 564 | 0.96 | |

TABLE 27

| Example No. | $R^b$ | Compound Name | MS | RT (min) | $^1$H-NMR (300 MHz) (DMSO-$d_6$) δ: |
|---|---|---|---|---|---|
| 1-13-14 | (1-isobutyl-4-isopropylpiperazine) | 6-(7-((1-(4-Isopropyl piperazin-1-yl)propan-2-yl) amino)thianthren-1-yl)-4-morpholino pyridin-2(1H)-one | 578 | 1.09 | |
| 1-13-15 | (1-isobutyl-4-phenylpiperazine) | 4-Morpholino-6-(7-((1-(4-phenyl piperazin-1-yl) propan-2-yl)amino) thianthren-1-yl)pyridin-2 (1H)-one | 612 | 1.19 | (CD$_3$OD): 7.60 (1H, t, J = 4.3 Hz), 7.36-7.29 (2H, m), 7.29-7.10 (3H, m), 7.03-6.89 (2H, m), 6.86-6.76 (2H, m), 6.60-6.50 (1H, m), 6.21 (1H, d, J = 2.0 Hz), 5.74 (1H, d, J = 2.6 Hz), 3.78 (4H, t, J = 4.6 Hz), 3.71-3.55 (1H, m), 3.37 (4H, dd, J = 9.9, 5.3 Hz), 3.23-3.10 (6H, m), 2.75-2.63 (4H, m), 1.19 (3H, d, J = 5.9 Hz). |
| 1-13-16 | (1-isobutyl-4-(pyridin-4-yl)piperazine) | 4-Morpholino-6-(7-((1-(4-(pyridin-4-yl)piperazin-1-yl) propan-2-yl)amino) thianthren-1-yl)pyridin-2 (1H)-one | 613 | 1.07 | |
| 1-13-17 | (1-isobutyl-4-(pyridin-2-yl)piperazine) | 4-Morpholino-6-(7-((1-(4-(pyridin-2-yl)piperazin-1-yl) propan-2-yl)amino) thianthren-1-yl)pyridin-2 (1H)-one | 613 | 1.12 | (CD$_3$OD): 8.09-8.02 (1H, m), 7.64-7.50 (2H, m), 7.37-7.29 (2H, m), 7.15 (1H, d, J = 8.6 Hz), 6.89-6.78 (2H, m), 6.72-6.64 (1H, m), 6.60-6.55 (1H, m), 6.22 (1H, d, J = 2.6 Hz), 5.74 (1H, d, J = 2.6 Hz), 3.78 (4H, t, J = 5.0 Hz), 3.51 (4H, t, J = 5.3 Hz), 3.38 (4H, t, J = 5.0 Hz), 3.36-3.29 (1H, m), 2.87-2.43 (6H, m), 1.19 (3H, d, J = 5.9 Hz). |

Example 1-13-18

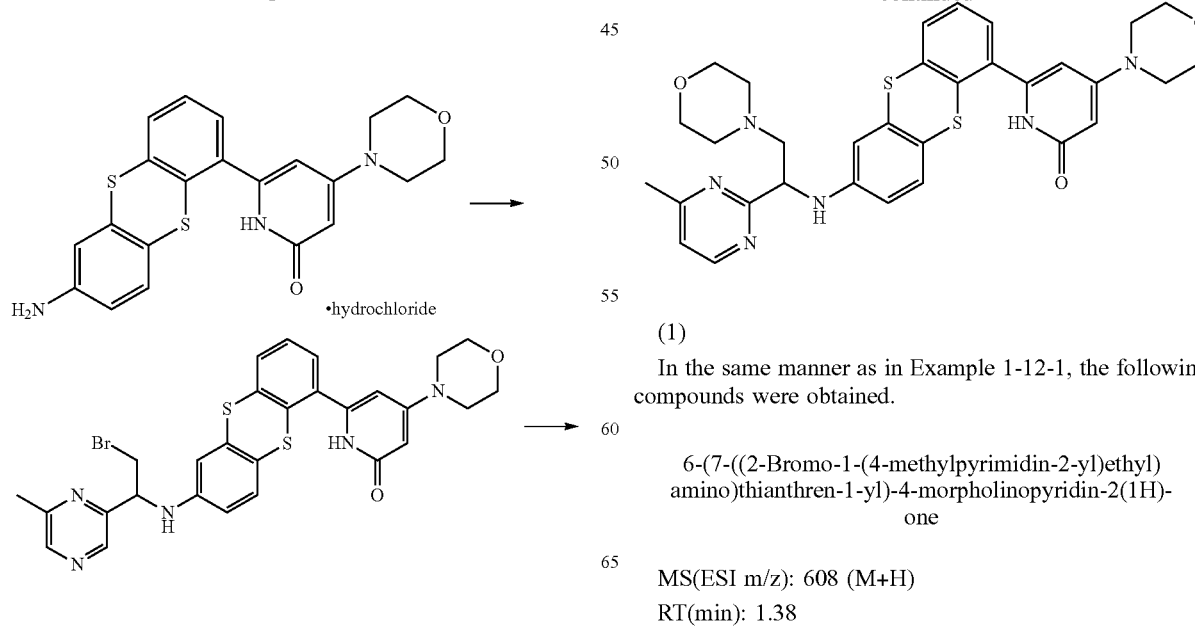

(1)

In the same manner as in Example 1-12-1, the following compounds were obtained.

6-(7-((2-Bromo-1-(4-methylpyrimidin-2-yl)ethyl) amino)thianthren-1-yl)-4-morpholinopyridin-2(1H)-one MS(ESI m/z): 608 (M+H)

RT(min): 1.38

(2)

In the same manner as in Example 1-6-1 (2), the following compound was obtained.

6-(7-((1-(4-Methylpyrimidin-2-yl)-2-morpholino-ethyl)amino)thianthren-1-yl)-4-morpholinopyridin-2(1H)-one MS(ESI m/z): 615 (M+H)
RT(min): 0.96

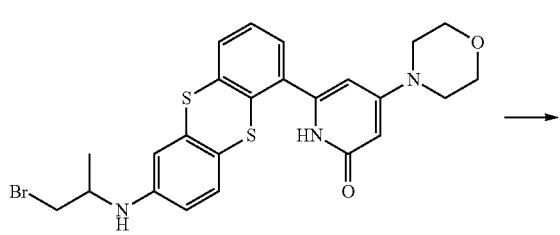

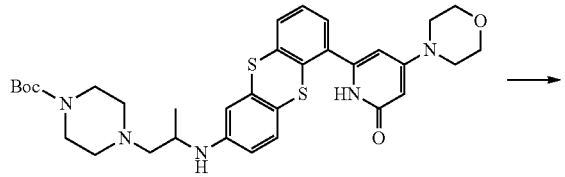

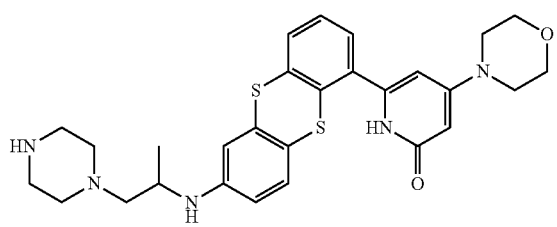

Example 1-14

(1)

Using N,N-dimethyl formamide as a solvent, the following compound was obtained in the same manner as in Example 1-7-1 (2).

tert-Butyl 4-(2-((6-(4-morpholino-6-oxo-1,6-dihydropyridin-2-yl)thianthren-2-yl)amino)propyl)piperazine-1-carboxylate MS(ESI m/z): 636 (M+H)
RT(min): 1.20

(2)

In the same manner as in Example 1-4, the following compound was obtained.

4-Morpholino-6-(7-((1-(piperazin-1-yl)propan-2-yl)amino)thianthren-1-yl)pyridin-2(1H)-one MS(ESI m/z): 536 (M+H)
RT(min): 0.95

Example 1-15-1

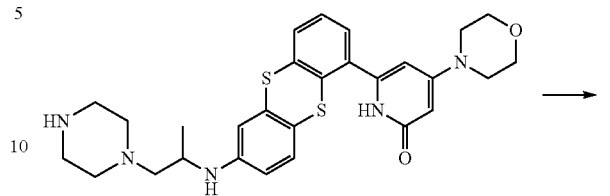

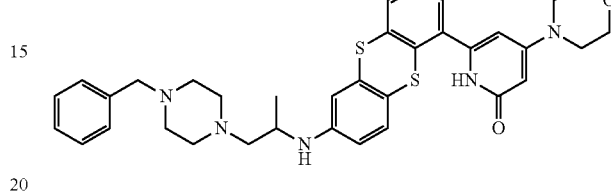

In the same manner as in Example 1-12-1, the following compound was obtained.

6-(7-((1-(4-Benzylpiperazin-1-yl)propan-2-yl)amino)thianthren-1-yl)-4-morpholinopyridin-2(1H)-one MS(ESI m/z): 626 (M+H)
RT(min): 1.16

Example 1-15-2

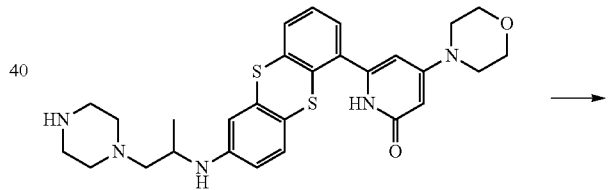

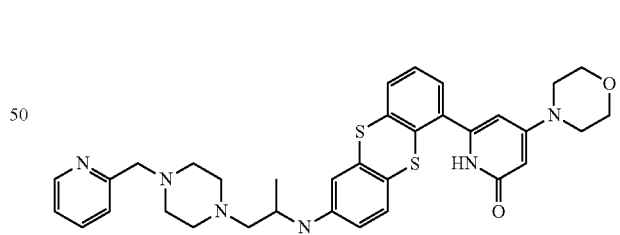

In the same manner as in Example 1-15-1, the following compound was obtained.

4-Morpholino-6-(7-((1-(4-(pyridin-2-ylmethyl)piperazin-1-yl)propan-2-yl)amino)thianthren-1-yl)pyridin-2(1H)-one MS(ESI m/z): 627 (M+H)
RT(min): 0.95

Example 1-15-3

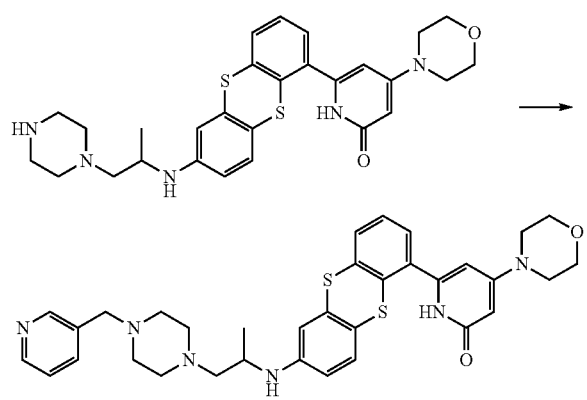

In the same manner as in Example 1-15-1, the following compound was obtained.

4-Morpholino-6-(7-((1-(4-(pyridin-3-ylmethyl)piper-azin-1-yl)propan-2-yl)amino)thianthren-1-yl)pyri-din-2(1H)-one MS(ESI m/z): 627 (M+H)
RT(min): 0.92

Example 1-15-4

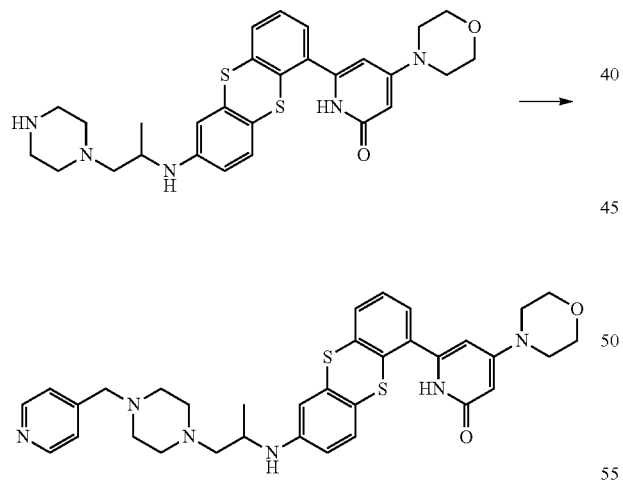

In the same manner as in Example 1-15-1, the following compound was obtained.

4-Morpholino-6-(7-((1-(4-(pyridin-4-ylmethyl)piper-azin-1-yl)propan-2-yl)amino)thianthren-1-yl)pyri-din-2(1H)-one MS(ESI m/z): 627 (M+H)
RT(min): 0.89

Example 1-16-1

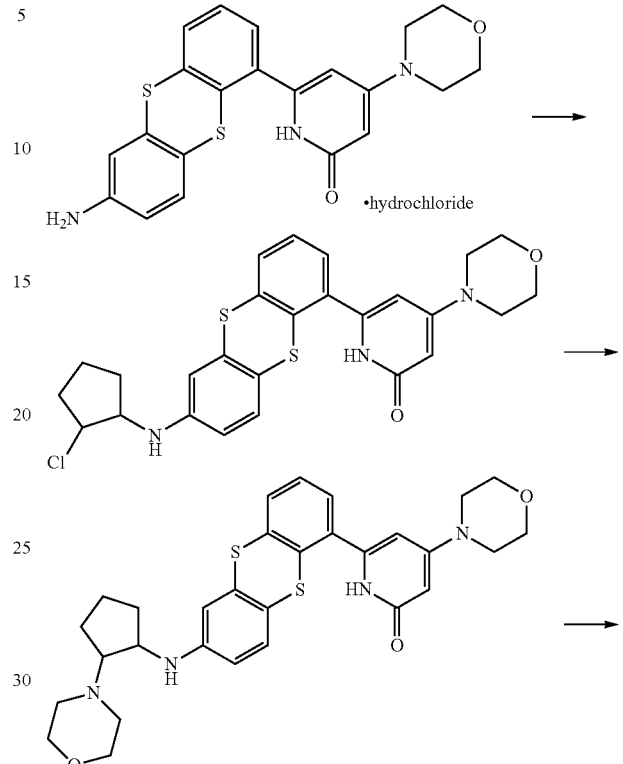

In the same manner as in Example 1-12-1, the following compound was obtained.

6-(7-((2-Chlorocyclopentyl)amino)thianthren-1-yl)-4-morpholinopyridin-2(1H)-one (diastereomer mixture)

MS(ESI m/z): 512 (M+H)
RT(min): 155

Example 1-16-1-1

Sodium iodide (7 mg) was added to a solution of 6-(7-((2-chlorocyclopentyl)amino)thianthren-1-yl)-4-morpholin-opyridin-2(1H)-one (diastereomer mixture) (20 mg) obtained in Example 1-16-1 in morpholine (1 mL), and the resultant product was irradiated with microwaves (Initiator™, 180° C., 0.8 hours, 2.45 GHz, 0 W to 240 W). The reaction mixture was cooled to room temperature, then, water was added thereto, and the solid was collected by filtration, and purified by preparative thin layer silica gel chromatography (chloroform:methanol=30:1, NH silica), whereby 4-morpholino-6-(7-((2-morpholinocyclopentyl)amino)thianthren-1-yl)pyridin-2(1H)-one (racemic mixture) (7.2 mg) was obtained.

MS(ESI m/z): 563 (M+H)
RT(min): 1.0

Examples 1-16-1-2 and 1-16-1-3

Chiral resolution was performed on 4-morpholino-6-(7-((2-morpholinocyclopentyl)amino)thianthren-1-yl)pyridin-2(1H)-one (racemic mixture) obtained in Example 1-16-1-1 by supercritical fluid chromatography, whereby an optically active substance A and an optically active substance B were obtained.

Example 1-16-1-2

Optically Active Substance A $^1$H-NMR (CD$_3$OD, 300 MHz) δ: 7.62-7.55 (1H, m), 7.35-7.29 (2H, m), 7.12 (1H, d, J=8.6 Hz), 6.78 (1H, d, J=2.6 Hz), 6.51 (1H, dd, J=8.6, 2.0 Hz), 6.21 (1H, d, J=2.6 Hz), 5.74 (1H, d, J=2.0 Hz), 3.81-3.73 (4H, m), 3.69-3.61 (4H, m), 3.37 (4H, t, J=5.0 Hz), 3.32-3.28 (2H, m), 2.64-2.48 (4H, m), 2.06-1.92 (2H, m), 1.76-1.26 (4H, m).
MS(ESI m/z): 563 (M+H)
RT(min): 1.04

Example 1-16-1-3

Optically Active Substance B $^1$H-NMR (CD$_3$OD, 300 MHz) δ: 7.62-7.55 (1H, m), 7.35-7.29 (2H, m), 7.12 (1H, d, J=8.6 Hz), 6.78 (1H, d, J=2.6 Hz), 6.51 (1H, dd, J=8.6, 2.0 Hz), 6.21 (1H, d, J=2.6 Hz), 5.74 (1H, d, J=2.0 Hz), 3.81-3.73 (4H, m), 3.69-3.61 (4H, m), 3.37 (4H, t, J=5.0 Hz), 3.32-3.28 (2H, m), 2.64-2.48 (4H, m), 2.06-1.92 (2H, m), 1.76-1.26 (4H, m).
MS(ESI m/z): 563 (M+H)
RT(min): 1.04
(Supercritical Fluid Chromatography Conditions)
Column: CHIRALPAK IB (manufactured by Daicel Chemical Industries, Ltd.)
Mobile phase: carbon dioxide/0.1% diethylamine-containing methanol (volume ratio: 75/25)
Flow rate: 30 mL/min
Detection wavelength: 254 nm
Temperature: 40° C.
Retention time: 13.06 min (optically active substance A), 14.82 min (optically active substance B)

Example 1-16-2

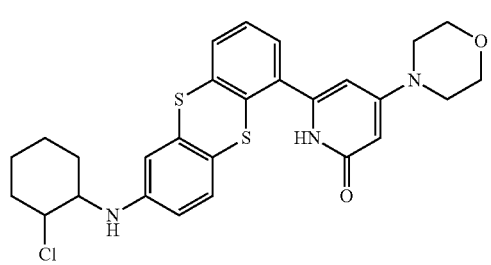

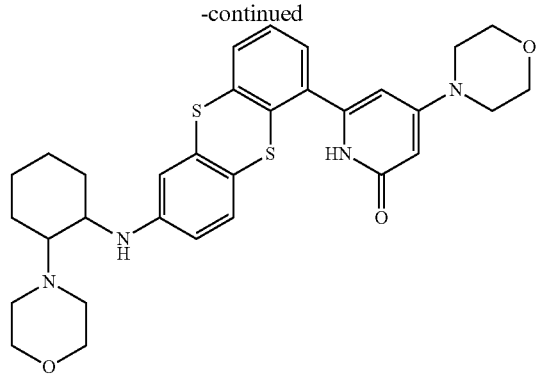

In the same manner as in Example 1-16-1-1, the following compound was obtained.

4-Morpholino-6-(7-((2-morpholinocyclohexyl)amino)thianthren-1-yl)pyridin-2(1H)-one MS(ESI m/z): 577 (M+H)
RT(min): 1.09

Example 1-16-3

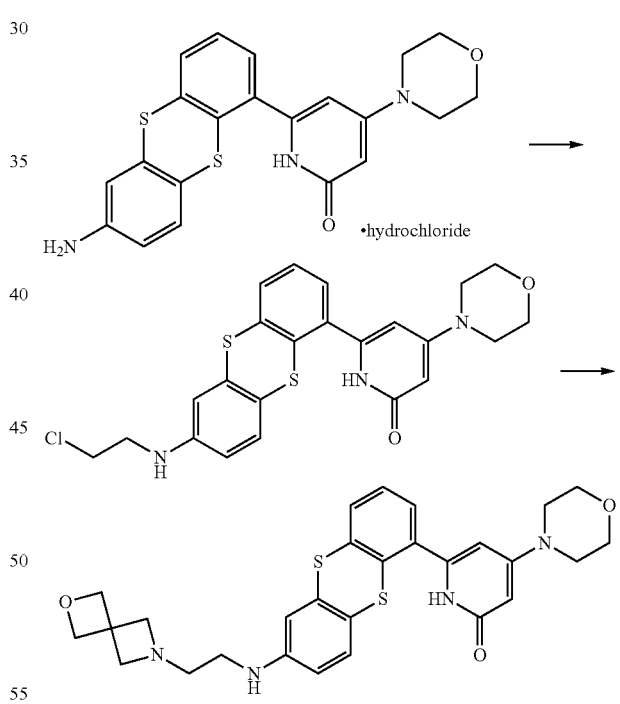

(1)
In the same manner as in Example 1-12-1, the following compound was obtained.

6-(7-((2-Chloroethyl)amino)thianthren-1-yl)-4-morpholinopyridin-2(1H)-one (2)
In the same manner as in Example 1-7-3, the following compound was obtained.

6-(7-((2-(2-Oxa-6-azaspiro[3.3]heptan-6-yl)ethyl)
amino)thianthren-1-yl)-4-morpholinopyridin-2(1H)-
one ¹H-NMR (CD₃OD, 300 MHz) δ: 7.63-7.56 (1H, m), 7.38-7.30 (2H, m), 7.17 (1H, d, J=8.4 Hz), 6.80 (1H, d, J=2.2 Hz), 6.54 (1H, dd, J=8.4 Hz, 2.2 Hz), 6.22 (1H, d, J=2.3 Hz), 5.75 (1H, d, J=2.3 Hz), 3.85-3.70 (8H, m), 3.45-3.13 (10H, m), 2.90-2.80 (2H, m).
MS(ESI m/z): 535 (M+H)
RT(min): 0.88

Example 1-16-4

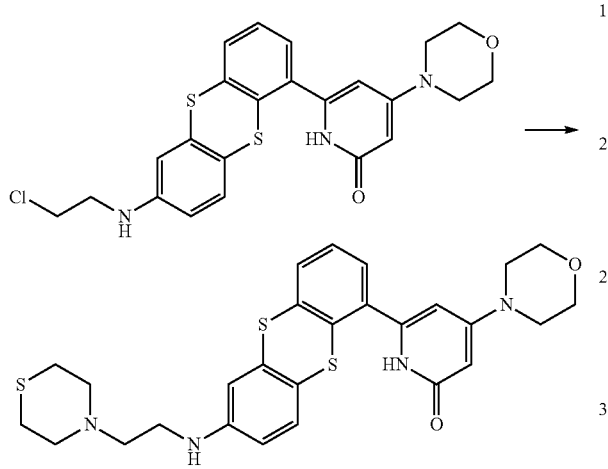

In the same manner as in Example 1-16-3 (2), the following compound was obtained.

4-Morpholino-6-(7-((2-thiomorpholinoethyl)amino)
thianthren-1-yl)pyridin-2(1H)-one ¹H-NMR (DMSO-d₆, 300 MHz) δ: 7.70-7.62 (1H, m), 7.44-7.34 (2H, m), 7.22 (1H, d, J=8.6 Hz), 6.88 (1H, d, J=2.7 Hz), 6.60 (1H, dd, J=8.6 Hz, 2.7 Hz), 6.38-6.28 (1H, m), 5.83-5.73 (1H, m), 3.80-2.75 (20H, m).
MS(ESI m/z): 539 (M+H)
RT(min): 0.94

Example 1-16-5

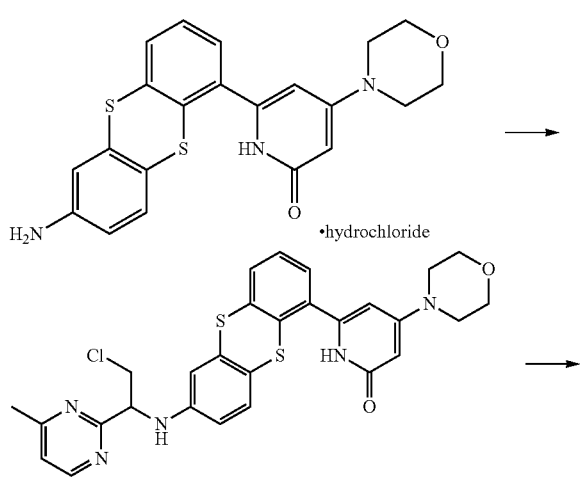

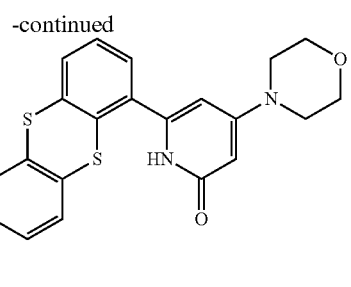

(1)
In the same manner as in Example 1-12-1, the following compound was obtained.

6-(7-((2-Chloro-1-(4-methylpyrimidin-2-yl)ethyl)
amino)thianthren-1-yl)-4-morpholinopyridin-2(1H)-
one (2)
In the same manner as in Example 1-16-1-1, the following compound was obtained.

6-(7-((2-(Methyl amino)-1-(4-methylpyrimidin-2-yl)
ethyl)amino)thianthren-1-yl)-4-morpholinopyridin-2
(1H)-one MS(ESI m/z): 559 (M+H)
RT(min): 0.95

Example 1-16-6

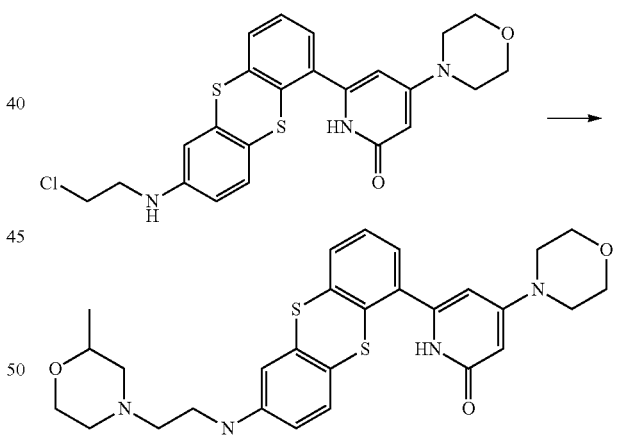

In the same manner as in Example 1-16-1-1, the following compound was obtained.

6-(7-((2-(2-Methylmorpholino)ethyl)amino)thian-
thren-1-yl)-4-morpholinopyridin-2(1H)-one ¹H-NMR (CD₃OD, 300 MHz) δ: 7.64-7.56 (1H, m), 7.38-7.30 (2H, m), 7.16 (1H, d, J=8.7 Hz), 6.80 (1H, d, J=2.4 Hz), 6.55 (1H, dd, J=8.7 Hz, 2.4 Hz), 6.23 (1H, d, J=2.0 Hz), 5.75 (1H, d, J=2.0 Hz), 3.79 (4H, t, J=4.9 Hz), 3.75-2.55 (11H, m), 3.39 (4H, t, J=4.9 Hz), 1.12 (3H, d, J=6.6 Hz).
MS(ESI m/z): 537 (M+H)
RT(min): 0.93

Example 1-16-7

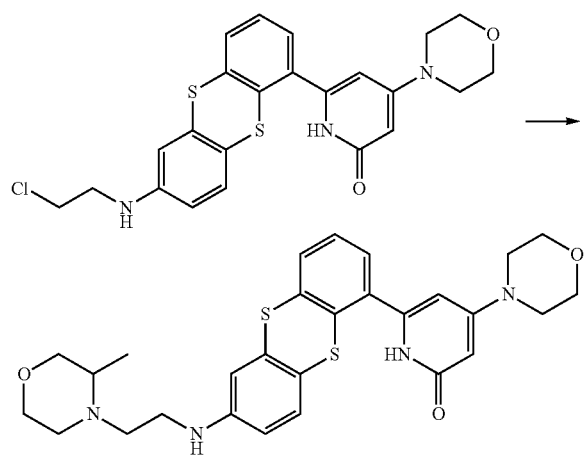

In the same manner as in Example 1-16-1-1, the following compound was obtained.

6-(7-((2-(3-Methylmorpholino)ethyl)amino)thian-thren-1-yl)-4-morpholinopyridin-2(1H)-one $^1$H-NMR (CDCl$_3$, 300 MHz) δ: 7.61-7.54 (1H, m), 7.30-7.24 (2H, m), 7.22 (1H, d, J=7.6 Hz), 6.83 (1H, d, J=2.1 Hz), 6.53 (1H, d, J=7.6 Hz), 5.98 (1H, d, J=2.3 Hz), 5.73 (1H, d, J=2.3 Hz), 3.90-2.20 (19H, m), 1.15-0.95 (3H, m).
MS(ESI m/z): 537 (M+H)
RT(min): 0.91

Example 1-16-8

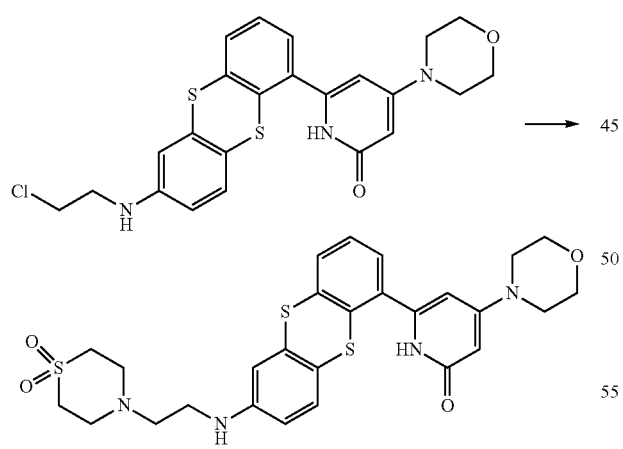

In the same manner as in Example 1-16-1-1, the following compound was obtained.

6-(7-((2-(1,1-Dioxidethiomorpholino)ethyl)amino)thianthren-1-yl)-4-morpholinopyridin-2(1H)-one MS(ESI m/z): 571 (M+H)
RT(min): 1.07

Example 1-17-1

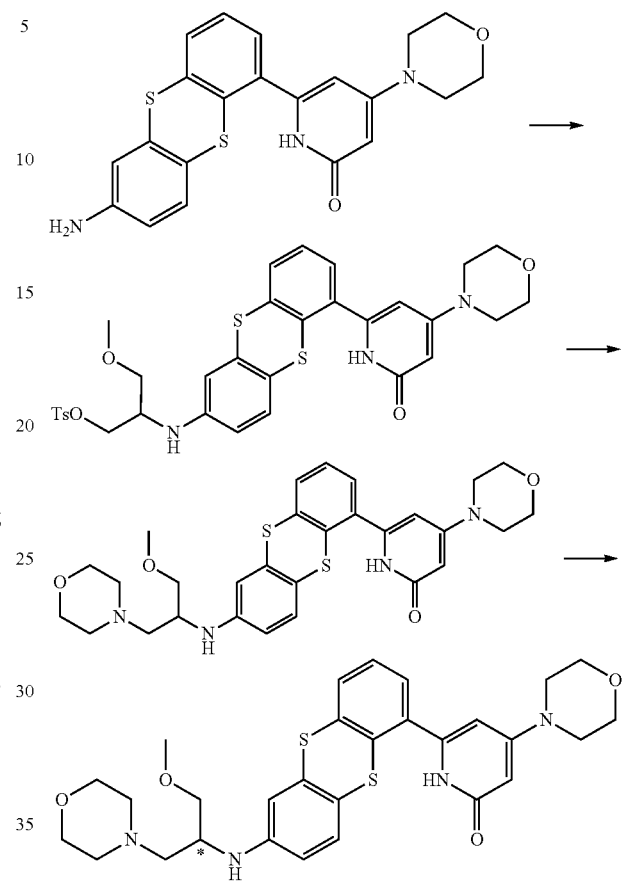

In the same manner as in Example 1-12-1, the following compound was obtained. 3-Methoxy-2-((6-(4-morpholino-6-oxo-1,6-dihydropyridin-2-yl)thianthren-2-yl)amino)propyl 4-methyl benzenesulfonate.
MS(ESI m/z): 652 (M+H)
RT(min): 1.52

Example 1-17-1-1

In the same manner as in Example 1-6-1 (2), the following compound was obtained.

6-(7-((1-Methoxy-3-morpholinopropan-2-yl)amino)thianthren-1-yl)-4-morpholinopyridin-2(1H)-one
(racemic mixture)

$^1$H-NMR (CDCl$_3$, 300 MHz) δ: 7.54 (1H, dd, J=7.6, 1.7 Hz), 7.36-7.24 (2H, m), 7.17 (1H, d, J=8.6 Hz), 6.82 (1H, d, J=2.0 Hz), 6.51 (1H, dd, J=8.6, 2.0 Hz), 5.97 (1H, d, J=2.6 Hz), 5.64 (1H, d, J=1.3 Hz), 4.41 (1H, s), 3.79 (4H, t, J=4.6 Hz), 3.66 (4H, t, J=4.6 Hz), 3.57-3.50 (2H, m), 3.46-3.38 (1H, m), 3.36 (3H, s), 3.28 (4H, t, J=4.6 Hz), 2.53 (2H, d, J=6.6 Hz), 2.45 (4H, t, J=4.3 Hz).
MS(ESI m/z): 567 (M+H)
RT(min): 0.99

Examples 1-17-1-2 and 1-17-1-3

Chiral resolution was performed on 6-(7-((1-methoxy-3-morpholinopropan-2-yl)amino)thianthren-1-yl)-4-morpholinopyridin-2(1H)-one (racemic mixture) obtained in Example 1-17-1-1 by supercritical fluid chromatography, whereby an optically active substance A and an optically active substance B were obtained.

Example 1-17-1-2

Optically Active Substance A

¹H-NMR (CDCl₃, 300 MHz) δ: 7.54 (1H, dd, J=7.6, 1.7 Hz), 7.36-7.24 (2H, m), 7.17 (1H, d, J=8.6 Hz), 6.82 (1H, d, J=2.0 Hz), 6.51 (1H, dd, J=8.6, 2.0 Hz), 5.97 (1H, d, J=2.6 Hz), 5.64 (1H, d, J=1.3 Hz), 4.41 (1H, s), 3.79 (4H, t, J=4.6 Hz), 3.66 (4H, t, J=4.6 Hz), 3.57-3.50 (2H, m), 3.46-3.38 (1H, m), 3.36 (3H, s), 3.28 (4H, t, J=4.6 Hz), 2.53 (2H, d, J=6.6 Hz), 2.45 (4H, t, J=4.3 Hz).

MS(ESI m/z): 567 (M+H)
RT(min): 0.99

Example 1-17-1-3

Optically Active Substance B

¹H-NMR (CDCl₃, 300 MHz) δ: 7.54 (1H, dd, J=7.6, 1.7 Hz), 7.36-7.24 (2H, m), 7.17 (1H, d, J=8.6 Hz), 6.82 (1H, d, J=2.0 Hz), 6.51 (1H, dd, J=8.6, 2.0 Hz), 5.97 (1H, d, J=2.6 Hz), 5.64 (1H, d, J=1.3 Hz), 4.41 (1H, s), 3.79 (4H, t, J=4.6 Hz), 3.66 (4H, t, J=4.6 Hz), 3.57-3.50 (2H, m), 3.46-3.38 (1H, m), 3.36 (3H, s), 3.28 (4H, t, J=4.6 Hz), 2.53 (2H, d, J=6.6 Hz), 2.45 (4H, t, J=4.3 Hz).

MS(ESI m/z): 567 (M+H)
RT(min): 0.99
(Supercritical Fluid Chromatography Conditions)
Column: CHIRALPAK AS-H (manufactured by Daicel Chemical Industries, Ltd.)
Mobile phase: carbon dioxide/0.1% diethylamine-containing methanol (volume ratio: 75/25)
Flow rate: 20 mL/min
Detection wavelength: 254 nm
Temperature: 40° C.
Retention time: 15.94 min (optically active substance A), 22.29 min (optically active substance B)

Example 1-17-2

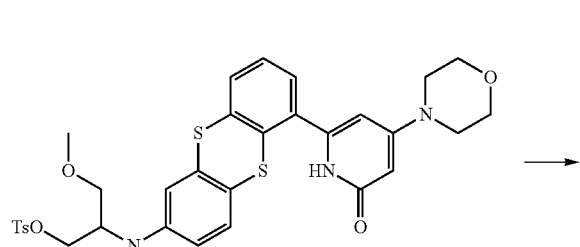

In the same manner as in Example 1-6-1 (2), the following compound was obtained.

6-(7-((1-Methoxy-3-(piperidin-1-yl)propan-2-yl) amino)thianthren-1-yl)-4-morpholinopyridin-2(1H)- one MS(ESI m/z): 565 (M+H)
RT(min): 1.06

Example 1-17-3

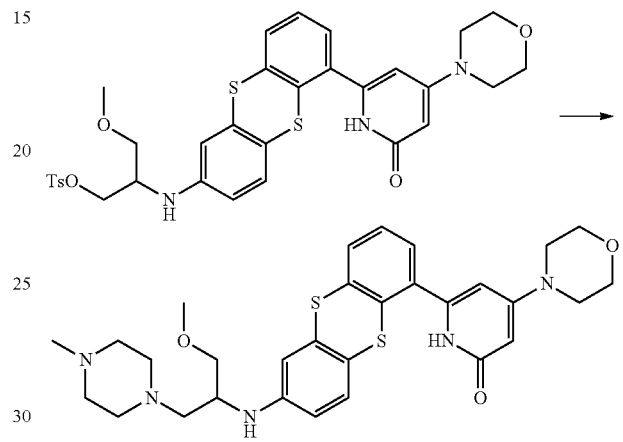

In the same manner as in Example 1-6-1 (2), the following compound was obtained.

6-(7-((1-Methoxy-3-(4-methylpiperazin-1-yl)propan-2-yl)amino)thianthren-1-yl)-4-morpholinopyridin-2 (1H)-one MS(ESI m/z): 580 (M+H)
RT(min): 1.07

Example 1-18-1

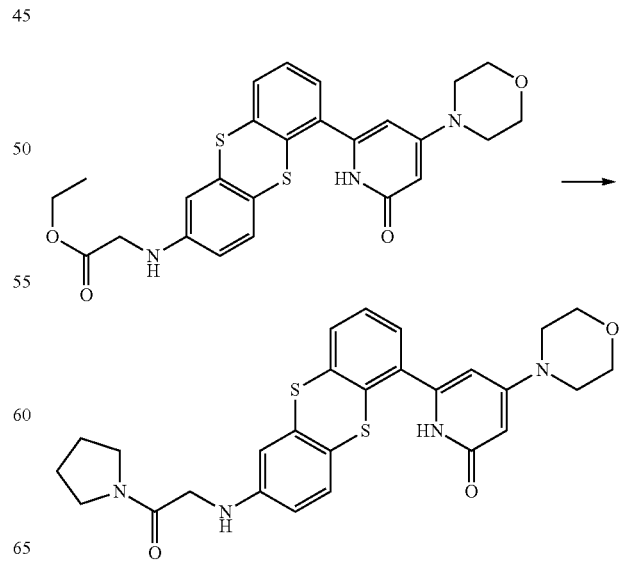

325

Pyrrolidine (0.6 mL) was added to ethyl 2-((6-(4-morpholino-6-oxo-1,6-dihydropyridin-2-yl)thianthren-2-yl)amino)acetate (4 mg), and the resultant product was irradiated with microwaves (Initiator™, 170° C., 0.5 hours, 2.45 GHz, 0 W to 240 W). The reaction mixture was cooled to room temperature, and purified by silica gel column chromatography (ethyl acetate:chloroform:methanol=1:0:0→0:19:1), whereby 4-morpholino-6-(7-((2-oxo-2-(pyrrolidin-1-yl)ethyl)amino)thianthren-1-yl)pyridin-2(1H)-one (1 mg) was obtained as a white solid.

MS(ESI m/z): 521 (M+H)

RT(min): 1.18

Examples 1-18-2 to 1-18-6

In the same manner as in Example 1-18-1, the following compound was obtained.

TABLE 28

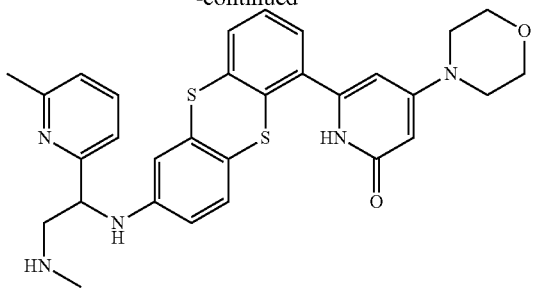

| Example No. | $R^b$ | MS | RT(min) |
|---|---|---|---|
| 1-18-2 | 2-Oxo-2-(piperidin-1-yl)ethyl | 535 | 1.31 |
| 1-18-3 | 2-(4-Methyl piperazin-1-yl)-2-oxoethyl | 550 | 0.87 |
| 1-18-4 | 1-Oxo-1-(pyrrolidin-1-yl)propan-2-yl | 535 | 1.18 |
| 1-18-5 | 1-Morpholino-1-oxopropan-2-yl | 551 | 1.14 |
| 1-18-6 | 1-(2-Methyl pyrrolidin-1-yl)-1-oxopropan-2-yl | 549 | 1.28 |

Example 1-19-1

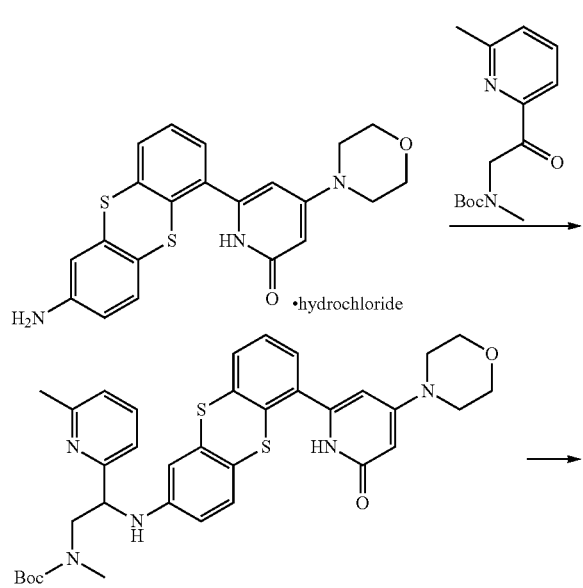

326

-continued

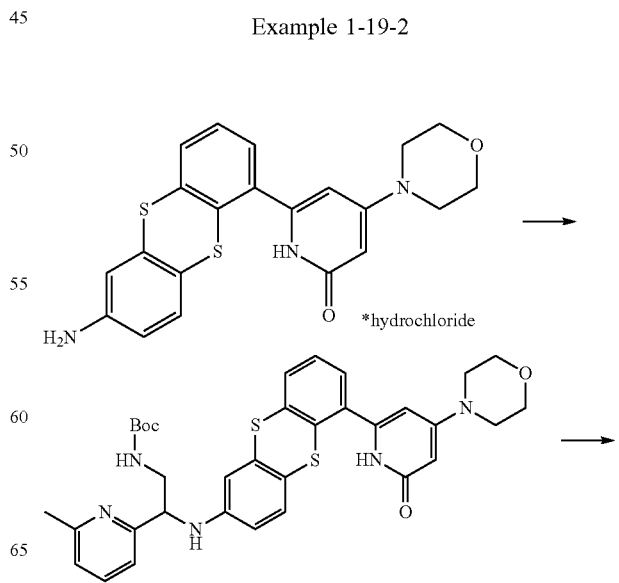

(1)

In the same manner as in Example 1-11 (4), the following compound was obtained.

tert-Butylmethyl (2-(6-methyl pyridin-2-yl)-2-((6-(4-morpholino-6-oxo-1,6-dihydropyridin-2-yl)thianthren-2-yl)amino)ethyl)carbamate MS(ESI m/z): 658 (M+H)

RT(min): 1.37

(2)

In the same manner as in Example 1-4, the following compound was obtained.

6-(7-((2-(Methylamino)-1-(6-methylpyridin-2-yl)ethyl)amino)thianthren-1-yl)-4-morpholinopyridin-2(1H)-one $^1$H-NMR (CDCl$_3$, 300 MHz) δ: 7.54 (1H, t, J=4.6 Hz), 7.50 (1H, t, J=7.3 Hz), 7.26-7.25 (2H, m), 7.16-7.10 (2H, m), 7.04 (1H, d, J=7.3 Hz), 6.76 (1H, d, J=2.6 Hz), 6.45 (1H, dd, J=8.6, 2.6 Hz), 5.96 (1H, d, J=2.6 Hz), 5.72 (1H, d, J=2.6 Hz), 5.45-5.27 (1H, m), 4.54-4.45 (1H, m), 3.82 (4H, t, J=4.6 Hz), 3.80-3.63 (1H, m), 3.32 (4H, t, J=4.6 Hz), 3.09-2.89 (2H, m), 2.59 (3H, s), 2.42 (3H, s).

MS(ESI m/z): 558 (M+H)

RT(min): 1.00

Example 1-19-2

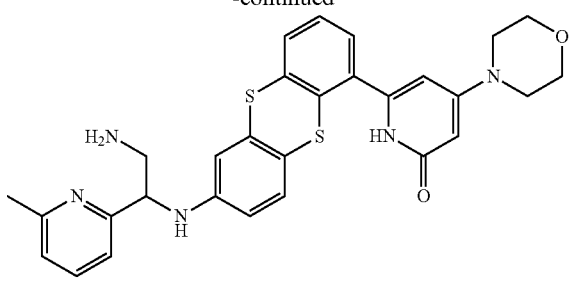

In the same manner as in Example 1-19-1, the following compounds were obtained.

tert-Butyl (2-(6-methyl pyridin-2-yl)-2-((6-(4-morpholino-6-oxo-1,6-dihydropyridin-2-yl)thianthren-2-yl)amino)ethyl)carbamate 6-(7-((2-Amino-1-(6-methylpyridin-2-yl)ethyl)amino)thianthren-1-yl)-4-morpholinopyridin-2(1H)-one MS(ESI m/z): 544 (M+H)
RT(min): 1.00

Example 1-19-3

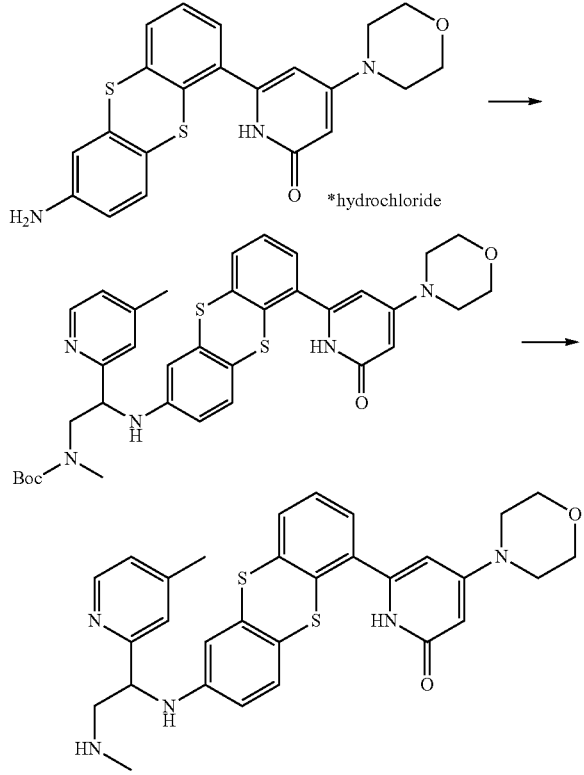

In the same manner as in Example 1-19-1, the following compounds were obtained.

tert-Butyl (2-(4-methyl pyridin-2-yl)-2-((6-(4-morpholino-6-oxo-1,6-dihydropyridin-2-yl)thianthren-2-yl)amino)ethyl) carbamate 6-(7-((2-(Methyl amino)-1-(4-methylpyridin-2-yl)ethyl)amino)thianthren-1-yl)-4-morpholinopyridin-2(1H)-one $^1$H-NMR (CDCl$_3$, 300 MHz) δ: 8.42 (1H, d, J=4.6 Hz), 7.54 (1H, t, J=4.6 Hz), 7.28-7.23 (2H, m), 7.13 (2H, d, J=8.6 Hz), 7.00 (1H, d, J=4.6 Hz), 6.76 (1H, d, J=2.6 Hz), 6.45 (1H, dd, J=8.6, 2.6 Hz), 5.95 (1H, d, J=2.6 Hz), 5.71 (1H, d, J=2.6 Hz), 5.44-5.21 (1H, m), 4.55-4.45 (1H, m), 3.81 (4H, t, J=5.0 Hz), 3.78-3.61 (1H, m), 3.31 (4H, t, J=5.0 Hz), 3.06-2.88 (2H, m), 2.42 (3H, s), 2.30 (3H, s).
MS(ESI m/z): 558 (M+H)
RT(min): 1.01

Example 1-19-4

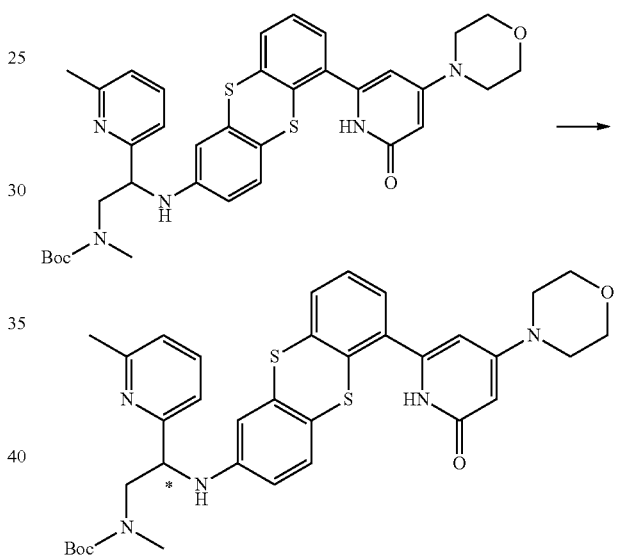

Chiral resolution was performed on tert-butyl methyl (2-(6-methyl pyridin-2-yl)-2-((6-(4-morpholino-6-oxo-1,6-dihydropyridin-2-yl)thianthren-2-yl)amino)ethyl) carbamate (racemic mixture) by supercritical fluid chromatography, whereby an optically active substance A and an optically active substance B were obtained.
Optically Active Substance A
MS(ESI m/z): 658 (M+H)
RT(min): 1.37
Optically Active Substance B
MS(ESI m/z): 658 (M+H)
RT(min): 1.37
(Supercritical Fluid Chromatography Conditions)
Column: CHIRALPAK IB (manufactured by Daicel Chemical Industries, Ltd.)
Mobile phase: carbon dioxide/0.1% diethylamine-containing methanol (volume ratio: 85/15)
Flow rate: 20 mL/min
Detection wavelength: 254 nm
Temperature: 40° C.
Retention time: 21.56 min (optically active substance A), 23.12 min (optically active substance B)

329
Example 1-19-4-1

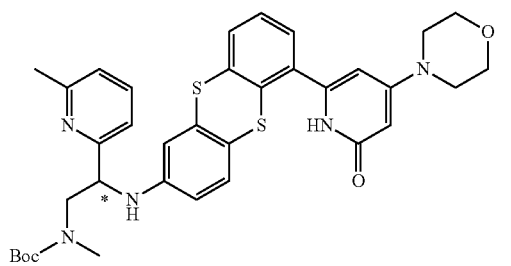

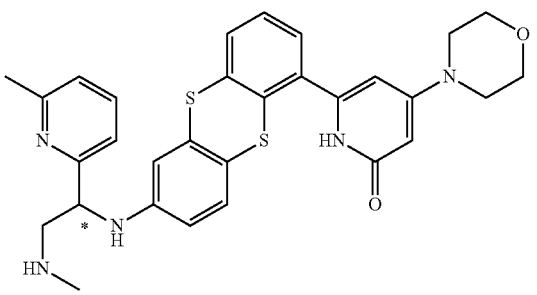

Using tert-butylmethyl (2-(6-methylpyridin-2-yl)-2-((6-(4-morpholino-6-oxo-1,6-dihydropyridin-2-yl)thianthren-2-yl)amino)ethyl)carbamate (optically active substance A) obtained in Example 1-19-4, the following compound was obtained in the same manner as in Example 1-19-1 (2).

6-(7-((2-(Methylamino)-1-(6-methylpyridin-2-yl)ethyl)amino)thianthren-1-yl)-4-morpholinopyridin-2(1H)-one (optically active substance A)

$^1$H-NMR (CDCl$_3$, 300 MHz) δ: 7.54 (1H, t, J=4.6 Hz), 7.50 (1H, t, J=7.3 Hz), 7.26-7.25 (2H, m), 7.16-7.10 (2H, m), 7.04 (1H, d, J=7.3 Hz), 6.76 (1H, d, J=2.6 Hz), 6.45 (1H, dd, J=8.6, 2.6 Hz), 5.96 (1H, d, J=2.6 Hz), 5.72 (1H, d, J=2.6 Hz), 5.45-5.27 (1H, m), 4.54-4.45 (1H, m), 3.82 (4H, t, J=4.6 Hz), 3.80-3.63 (1H, m), 3.32 (4H, t, J=4.6 Hz), 3.09-2.89 (2H, m), 2.59 (3H, s), 2.42 (3H, s).

MS(ESI m/z): 558 (M+H)
RT(min): 1.03

330
Example 1-19-4-2

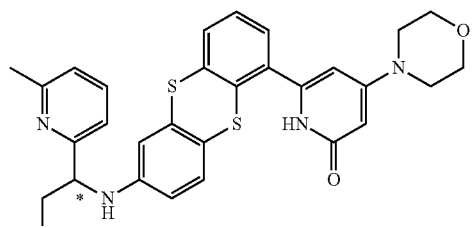

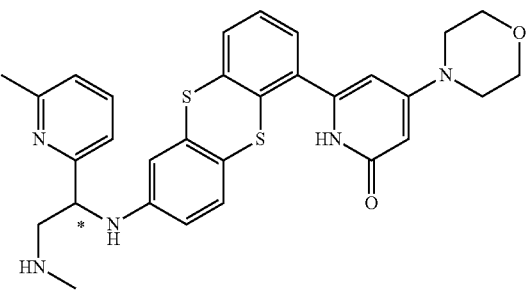

Using tert-butylmethyl (2-(6-methylpyridin-2-yl)-2-((6-(4-morpholino-6-oxo-1,6-dihydropyridin-2-yl)thianthren-2-yl)amino)ethyl)carbamate (optically active substance B) obtained in Example 1-19-4, the following compound was obtained in the same manner as in Example 1-19-1 (2).

6-(7-((2-(Methylamino)-1-(6-methylpyridin-2-yl)ethyl)amino)thianthren-1-yl)-4-morpholinopyridin-2(1H)-one (optically active substance B)

$^1$H-NMR (CDCl$_3$, 300 MHz) δ: 7.54 (1H, t, J=4.6 Hz), 7.50 (1H, t, J=7.3 Hz), 7.26-7.25 (2H, m), 7.16-7.10 (2H, m), 7.04 (1H, d, J=7.3 Hz), 6.76 (1H, d, J=2.6 Hz), 6.45 (1H, dd, J=8.6, 2.6 Hz), 5.96 (1H, d, J=2.6 Hz), 5.72 (1H, d, J=2.6 Hz), 5.45-5.27 (1H, m), 4.54-4.45 (1H, m), 3.82 (4H, t, J=4.6 Hz), 3.80-3.63 (1H, m), 3.32 (4H, t, J=4.6 Hz), 3.09-2.89 (2H, m), 2.59 (3H, s), 2.42 (3H, s).

MS(ESI m/z): 558 (M+H)
RT(min): 1.03

Example 1-20-1

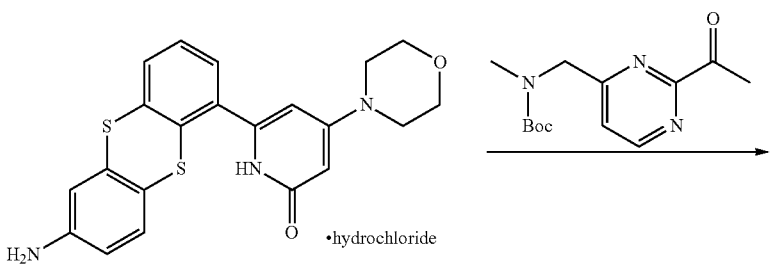

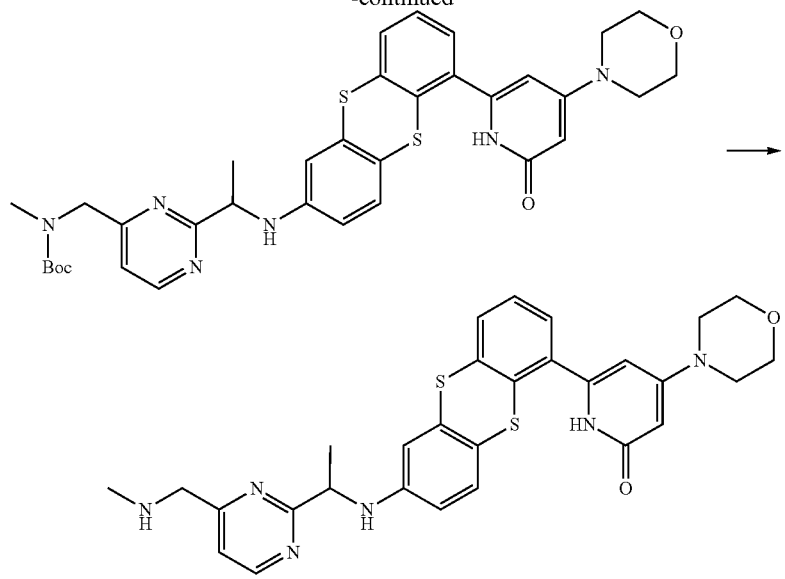

(1)
In the same manner as in Example 1-12-1, the following compounds were obtained.

tert-Butylmethyl ((2-(1-(((6-(4-morpholino-6-oxo-1,6-dihydropyridin-2-yl)thianthren-2-yl)amino)ethyl)pyrimidin-4-yl)methyl)carbamateter MS(ESI m/z): 659 (M+H)
RT(min): 1.46

(2)
Trifluoroacetic acid (1 mL) was added to a solution of tert-butyl methyl ((2-(1-(((6-(4-morpholino-6-oxo-1,6-dihydropyridin-2-yl)thianthren-2-yl)amino)ethyl)pyrimidin-4-yl)methyl)carbamate (21 mg) obtained in Example 1-20-1 (1) in dichloromethane (1 mL), followed by stirring at room temperature for 0.5 hours. The solvent was distilled off under reduced pressure, and the obtained residues were purified by silica gel column chromatography (chloroform: methanol=99:1→49:1, NH silica), whereby 6-(7-((1-(4-((methylamino)methyl)pyrimidin-2-yl)ethyl)amino)thianthren-1-yl)-4-morpholinopyridin-2(1H)-one (10 mg) was obtained.

MS(ESI m/z): 559 (M+H)
RT(min): 0.94

Examples 1-20-2 to 1-20-14

In the same manner as in Example 1-20-1, the following compounds were obtained.

TABLE 29

| Example No. | R$^b$ | Compound Name | MS | RT (min) | $^1$H-NMR (300 MHz) (DMSO-d$_6$) δ: |
|---|---|---|---|---|---|
| 1-20-2 | (H$_2$N-CH(CH$_3$)-CH$_2$-CH(CH$_3$)-CH$_2$CH$_3$) | 6-(7-(((2S)-2-Amino hexan-3-yl)amino)thianthren-1-yl)-4-morpholino pyridin-2(1H)-one | 509 | 1.06 | |

TABLE 29-continued

| Example No. | $R^b$ | Compound Name | MS | RT (min) | $^1$H-NMR (300 MHz) (DMSO-$d_6$) δ: |
|---|---|---|---|---|---|
| 1-20-3 | | 6-(7-(((2S)-2-Amino heptan-3-yl)amino)thianthren-1-yl)-4-morpholino pyridin-2(1H)-one | 523 | 1.14 | |
| 1-20-4 | | 6-(7-(((2S)-2-Amino-5-methyl hexan-3-yl)amino)thianthren-1-yl)-4-morpholino pyridin-2(1H)-one | 523 | 1.12 | |
| 1-20-5 | | 6-(7-(((3S)-3-Amino pentan-2-yl)amino)thianthren-1-yl)-4-morpholino pyridin-2(1H)-one | 495 | 0.98 | |
| 1-20-6 | | 6-(7-(((4S)-4-Amino hexan-3-yl)amino)thianthren-1-yl)-4-morpholino pyridin-2(1H)-one | 509 | 1.05 | |
| 1-20-7 | | 6-(7-(((5S)-5-Amino)-2-methyl heptan-4-yl)amino)thianthren-1-yl)-4-morpholino pyridin-2(1H)-one | 537 | 1.19 | |
| 1-20-8 | | 6-(7-((1-(6-((Methyl amino)methyl)pyridin-2-yl)ethyl)amino)thianthren-1-yl)-4-morpholino pyridin-2(1H)-one | 558 | 1.03 | |
| 1-20-9 | | 6-(7-((1-(6-(((2-Methoxy ethyl)amino)methyl)pyridin-2-yl)ethyl)amino)thianthren-1-yl)-4-morpholino pyridin-2(1H)-one | 602 | 1.03 | |

TABLE 29-continued

| Example No. | R^b\ | Compound Name | MS | RT (min) | ¹H-NMR (300 MHz) (DMSO-d$_6$) δ: |
|---|---|---|---|---|---|
| 1-20-10 | (2-methoxyethyl)(3-(6-methylpyridin-2-yl)butyl)amino | 6-(7-((3-((2-Methoxy ethyl) amino)-1-(6-methyl pyridin-2-yl)propyl)amino)thianthren-1-yl)-4-morpholino pyridin-2 (1H)-one | 616 | 1.01 | |
| 1-20-11 | methyl(3-(5-methylpyrazin-2-yl)butyl)amino | 6-(7-((3-(Methyl amino)-1-(5-methyl pyrazin-2-yl) propyl)amino)thianthren-1-yl)-4-morpholino pyridin-2 (1H)-one | 573 | 0.94 | |

TABLE 30

| Example No. | R^b\ | Compound Name | MS | RT (min) | ¹H-NMR (300 MHz) (DMSO-d$_6$) δ: |
|---|---|---|---|---|---|
| 1-20-12 | methyl(3-(6-methylpyridin-2-yl)butyl)amino | 6-(7-((3-(Methyl amino)-1 (6-methyl pyridin-2-yl) propyl)amino)thianthren-1-yl)-4-morpholino pyridin-2 (1H)-one | 572 | 1.04 | |
| 1-20-13 | ((6-methylpyridin-2-yl)(piperidin-3-yl)methyl)amino | 6-(7-(((6-Methyl pyridin-2-yl)(piperidin-3-yl)methyl) amino)thianthren-1-yl)-4-morpholino pyridin-2(1H)-one | 598 | 1.00 1.05 | |

TABLE 30-continued

| Example No. | R$^b$ | Compound Name | MS | RT (min) | $^1$H-NMR (300 MHz) (DMSO-d$_6$) δ: |
|---|---|---|---|---|---|
| 1-20-14 | | 6-(7-(((6-Methyl pyridin-2-yl)(pyrrolidin-3-yl)methyl)amino)thianthren-1-yl)-4-morpholino pyridin-2(1H)-one | 584 | 0.97 | |

Example 1-21-1

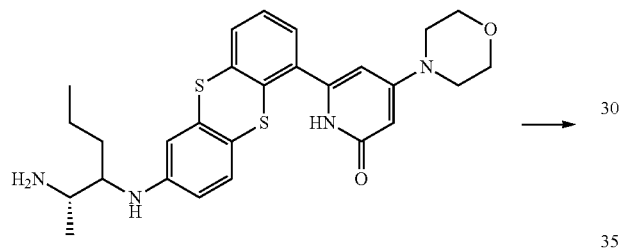

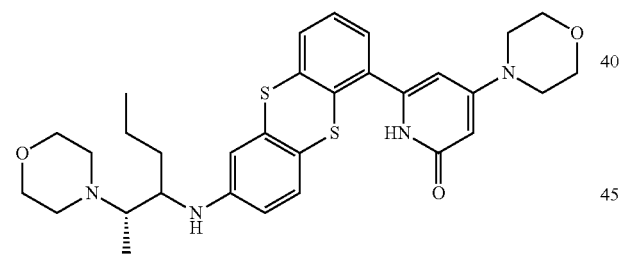

1-Iodo-2-(2-iodoethoxy)ethane (6.7 μL) and diisopropyl ethylamine (29 μL) were added to a solution of 6-(7-(((2S)-2-aminohexan-3-yl)amino)thianthren-1-yl)-4-morpholinopyridin-2(1H)-one (20 mg) in N,N-dimethyl formamide (1 mL), and the resultant product was irradiated with microwaves (microwave reaction apparatus, 100° C., 1 hour, 2.45 GHz, 0 W to 240 W). The reaction mixture was purified by silica gel column chromatography (hexane:ethyl acetate=1:0→0:1), whereby 6-(7-(((2S)-2-morpholinohexan-3-yl)amino)thianthren-1-yl)-4-morpholinopyridin-2(1H)-one (8 mg) was obtained.

MS(ESI m/z): 579 (M+H)

RT(min): 1.11

Examples 1-21-2 to 1-21-4

In the same manner as in Example 1-21-1, the following compounds were obtained.

TABLE 31
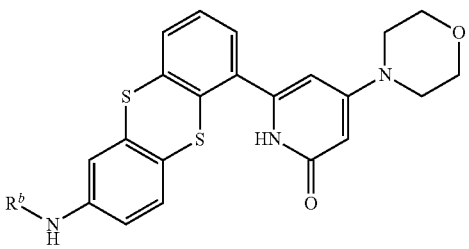
| Example No. | R$^b$ | Compound Name | MS | RT (min) | $^1$H-NMR (300 MHz) (DMSO-d$_6$) δ: |
|---|---|---|---|---|---|
| 1-21-2 | | 4-Morpholino-6-(7-(((2S)-2-morpholino heptan-3-yl) amino)thianthren-1-yl) pyridin-2(1H)-one | 593 | 1.19 | |
| 1-21-3 | | 4-Morpholino-6-(7-(((3S)-3-morpholino pentan-2-yl) amino)thianthren-1-yl) pyridin-2(1H)-one | 565 | 1.04 | |
| 1-21-4 | | 4-Morpholino-6-(7-(((4S)-4-morpholino hexan-3-yl) amino)thianthren-1-yl) pyridin-2(1H)-one | 579 | 1.11 | |
Example 1-21-5
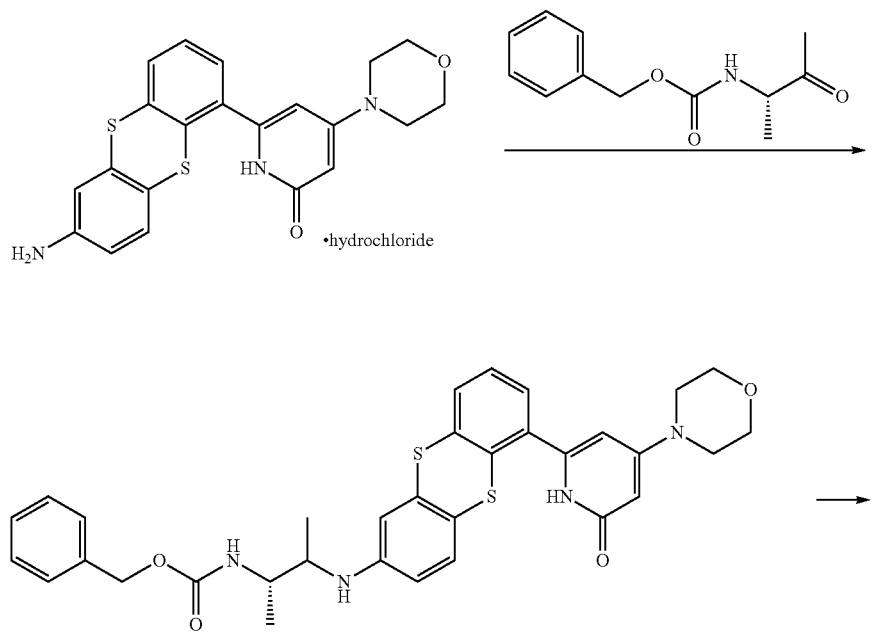

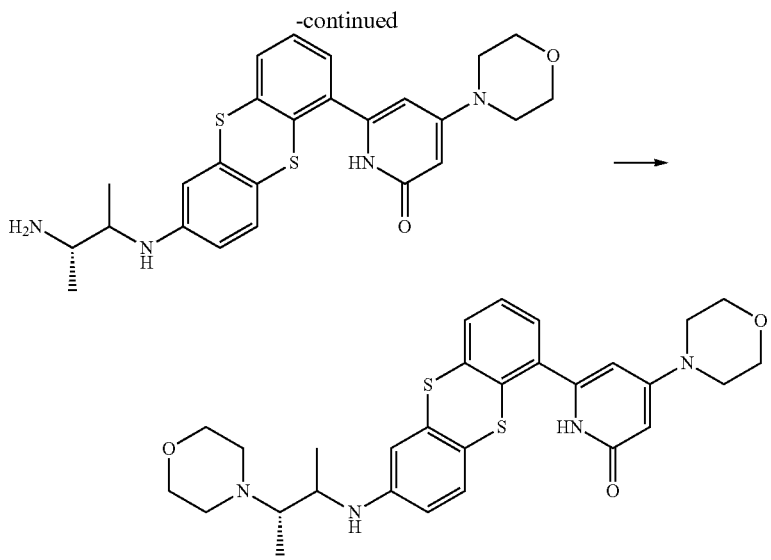

(1)
In the same manner as in Example 1-12-1, the following compounds were obtained.

Benzyl ((2S)-3-((6-(4-morpholino-6-oxo-1,6-dihydropyridin-2-yl)thianthren-2-yl)amino)butan-2-yl)carbamate MS(ESI m/z): 615 (M+H)
RT(min): 1.50

(2)
A solution of benzyl ((2S)-3-((6-(4-morpholino-6-oxo-1,6-dihydropyridin-2-yl)thianthren-2-yl)amino)butan-2-yl)carbamate (32 mg) obtained in Example 1-21-5 (1) in methanol was subjected to a hydrogenation reaction (50° C., FullH₂, flow rate of 1 mL/min, 20% Pd(OH)₂/C) using a flow type hydrogenation reaction apparatus. The reaction mixture was cooled to room temperature, then, the solvent was distilled off under reduced pressure, and the obtained residues were purified by silica gel column chromatography (ethyl acetate→chloroform:methanol=49:1→19:1, NH silica), whereby 6-(7-(((3 S)-3-aminobutan-2-yl)amino)thianthren-1-yl)-4-morpholinopyridin-2(1H)-one (6 mg) was obtained.

MS(ESI m/z): 481 (M+H)
RT(min): 0.94

(3)
Using 6-(7-(((3 S)-3-aminobutan-2-yl)amino)thianthren-1-yl)-4-morpholinopyridin-2(1H)-one obtained in Example 1-21-5 (2), the following compound was obtained in the same manner as in Example 1-21-1.

6-(7-(((3 S)-3-morpholinobutan-2-yl)amino)thianthren-1-yl)-4-morpholinopyridin-2(1H)-one MS(ESI m/z): 551 (M+H)
RT(min): 0.97

Example 1-22-1

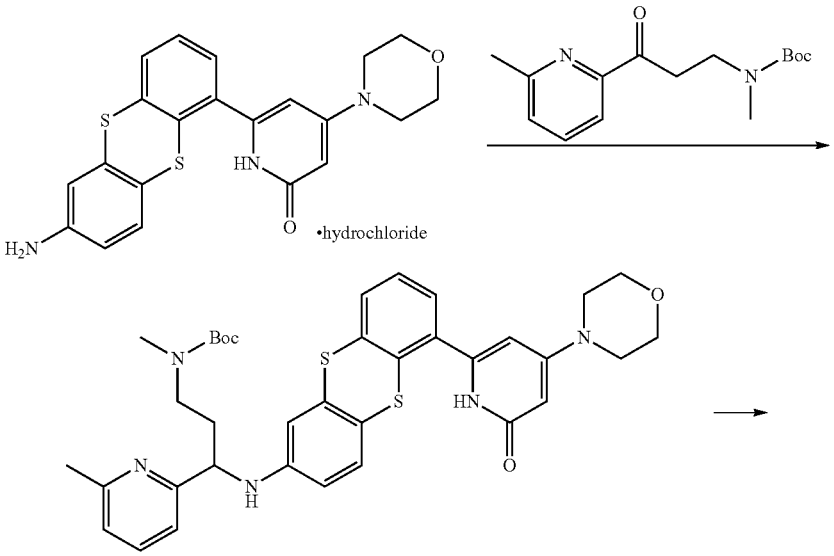

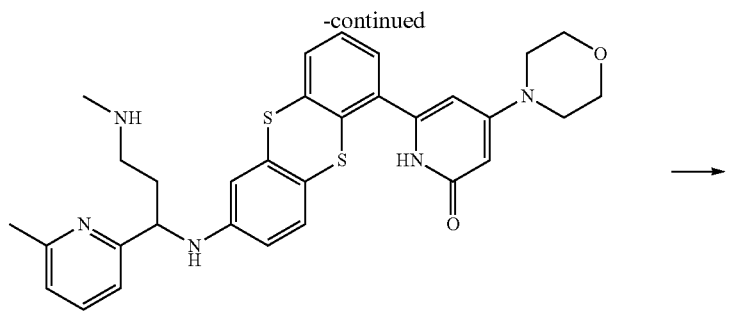

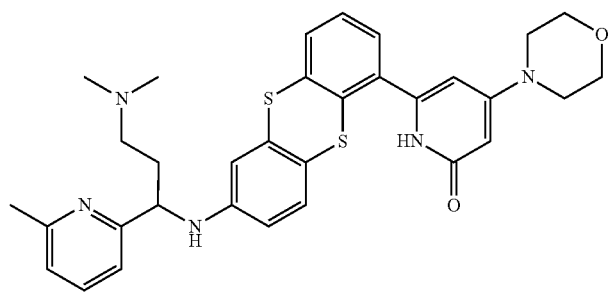

(1)
In the same manner as in Example 1-12-1, the following compounds were obtained.

tert-Butylmethyl (3-(6-methyltert-Butylmethyl (3-(6-methyl pyridin-2-yl)-3-((6-(4-morpholino-6-oxo-1,6-dihydropyridin-2-yl)thianthren-2-yl)amino)propyl)carbamate MS(ESI m/z): 672 (M+H)
RT(min): 1.33

(2)
In the same manner as in Example 1-20-1 (2), the following compound was obtained.

6-(7-((3-(Methylamino)-1-(6-methylpyridin-2-yl)propyl)amino)thianthren-1-yl)-4-morpholinopyridin-2(1H)-one MS(ESI m/z): 572 (M+H)
RT(min): 1.04

(3)
Potassium carbonate (4.1 mg) and methyl iodide (1.8 mg) were added to a solution of 6-(7-((3-(methylamino)-1-(6-methylpyridin-2-yl)propyl)amino)thianthren-1-yl)-4-morpholinopyridin-2(1H)-one (5.5 mg) obtained in Example 1-22-1 (2) in tetrahydrofuran (0.5 mL) and 1-methyl-2-pyrrolidone (0.5 mL), followed by stirring at room temperature for 0.5 hours. A saturated sodium hydrogen carbonate aqueous solution was added thereto, then, the resultant product was extracted with chloroform, and the organic layer was dried over anhydrous sodium sulfate. The solvent was distilled off under reduced pressure, the obtained residues were purified by silica gel column chromatography (chloroform:methanol=1:0→24:1, NH silica), and purified by preparative thin layer silica gel chromatography (chloroform:methanol=30:1, NH silica), whereby 6-(7-((3-(dimethylamino)-1-(6-methylpyridin-2-yl)propyl)amino)thianthren-1-yl)-4-morpholinopyridin-2(1H)-one (1.1 mg) was obtained as a yellow solid.

$^1$H-NMR (CDCl$_3$, 300 MHz) δ: 7.55 (1H, dd, J=5.9, 3.3 Hz), 7.48 (1H, t, J=7.6 Hz), 7.27-7.23 (2H, m), 7.12 (2H, t, J=8.6 Hz), 7.00 (1H, d, J=7.3 Hz), 6.69 (1H, d, J=2.3 Hz), 6.50 (1H, brs), 6.39 (1H, dd, J=8.6, 2.3 Hz), 5.95 (1H, d, J=2.6 Hz), 5.72 (1H, d, J=2.6 Hz), 4.49-4.47 (1H, m), 3.81 (4H, t, J=5.0 Hz), 3.32 (4H, t, J=5.0 Hz), 2.57 (3H, s), 2.46-2.33 (2H, m), 2.28 (6H, s), 2.21-2.01 (2H, m).

MS(ESI m/z): 586 (M+H)
RT(min): 1.03

Examples 1-22-2 to 1-22-10

In the same manner as in Example 1-22-1, the following compounds were obtained.

TABLE 32

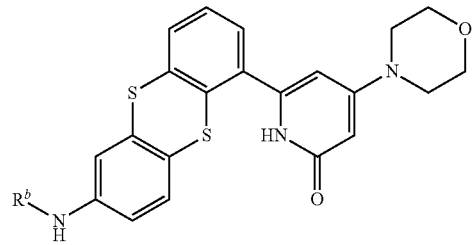

| Example No. | R$^b$ | Compound Name | MS | RT (min) | $^1$H-NMR (300 MHz) (DMSO-d$_6$) δ: |
|---|---|---|---|---|---|
| 1-22-2 | | 6-(7-((3-(Dimethyl amino)-1-(5-methyl pyrazin-2-yl) propyl)amino)thianthren-1-yl)-4-morpholino pyridin-2 (1H)-one | 587 | 0.96 | (CDCl$_3$): 8.46 (1H, s), 8.41 (1H, s), 7.57-7.51 (1H, m), 7.26 (2H, q, J = 5.3 Hz), 7.14 (1H, d, J = 7.9 Hz), 6.68 (1H, d, J = 2.6 Hz), 6.40 (1H, dd, J = 8.6, 2.6 Hz), 6.29 (1H, d, J = 6.0 Hz), 5.95 (1H, d, J = 2.6 Hz), 5.72 (1H, d, J = 2.6 Hz), 4.61-4.59 (1H, m), 3.81 (4H, t, J = 4.8 Hz), 3.32 (4H, t, J = 4.8 Hz), 2.54 (3H, s), 2.34 (2H, t, J = 5.9 Hz), 2.28-2.18 (6H, m), 2.09-1.90 (2H, m). |
| 1-22-3 | | 6-(7-((2-(Dimethyl amino)-1-(6-methyl pyridin-2-yl) ethyl)amino)thianthren-1-yl)-4-morpholino pyridin-2 (1H)-one | 572 | 1.02 | (CDCl$_3$): 8.81 (1H, br s), 7.54-7.47 (2H, m), 7.26-7.25 (2H, m), 7.20 (1H, d, J = 7.9 Hz), 7.11 (1H, d, J = 8.6 Hz), 7.03 (1H, d, J = 7.9 Hz), 6.71 (1H, d, J = 2.3 Hz), 6.39 (1H, dd, J = 8.6, 2.3 Hz), 5.94 (1H, d, J = 2.3 Hz), 5.71 (1H, d, J = 2.3 Hz), 5.40 (1H, d, J = 2.0 Hz), 4.34-4.32 (1H, m), 3.81 (4H, t, J = 4.8 Hz), 3.31 (4H, t, J = 4.8 Hz), 2.64-2.54 (5H, m), 2.24 (6H, s). |
| 1-22-4 | | 6-(7-(((1-Methyl piperidin-3-yl)(6-methyl pyridin-2-yl) methyl)amino)thianthren-1-yl)-4-morpholino pyridin-2 (1H)-one (Diastereomer A) | 612 | 0.99 | (CDCl$_3$): 8.63 (1H, br s), 7.54 (1H, t, J = 4.6 Hz), 7.47 (1H, t, J = 7.6 Hz), 7.27-7.25 (2H, m), 7.13 (1H, d, J = 7.9 Hz), 7.01-6.98 (2H, m), 6.77 (1H, d, J = 2.6 Hz), 6.47 (1H, dd, J = 8.6, 2.6 Hz), 5.95 (1H, d, J = 2.0 Hz), 5.71 (1H, d, J = 2.0 Hz), 5.10 (1H, d, J = 6.6 Hz), 4.30-4.27 (1H, m), 3.81 (4H, t, J = 5.0 Hz), 3.32 (4H, t, J = 5.0 Hz), 2.65 (1H, d, J = 10.6 Hz), 2.54 (3H, s), 2.46 (1H, d, J = 11.2 Hz), 2.23-2.19 (1H, m), 2.17 (3H, s), 1.99-1.95 (1H, m), 1.83-1.07 (5H, m). |
| 1-22-5 | | 6-(7-(((1-Methyl piperidin-3-yl)(6-methyl pyridin-2-yl) methyl)amino)thianthren-1-yl)-4-morpholino pyridin-2 (1H)-one (Diastereomer B) | 612 | 0.97 | (CDCl$_3$): 8.89 (1H, br s), 7.53 (1H, t, J = 4.6 Hz), 7.46 (1H, t, J = 7.9 Hz), 7.26-7.24 (2H, m), 7.12 (1H, d, J = 8.6 Hz), 7.00-6.97 (2H, m), 6.77 (1H, d, J = 2.6 Hz), 6.45 (1H, dd, J = 8.6, 2.6 Hz), 5.95 (1H, d, J = 2.6 Hz), 5.71 (1H, d, J = 2.6 Hz), 5.35 (1H, br s), 4.31-4.29 (1H, m), 3.80 (4H, t, J = 5.0 Hz), 3.31 (4H, t, J = 5.0 Hz), 2.77 (1H, d, J = 9.9 Hz), 2.57-2.53 (4H, m), 2.22 (3H, s), 2.14-1.98 (3H, m), 1.65-1.11 (4H, m). |
| 1-22-6 | | 6-(7-(((6-Methylpyridin-2-yl)(1-methyl pyrrolidin-3-yl) methyl)amino)thianthren-1-yl)-4-morpholino pyridin-2 (1H)-one (Diastereomer A) | 598 | 0.97 | (CDCl$_3$): 8.54 (1H, br s), 7.56-7.51 (1H, m), 7.46 (1H, t, J = 7.6 Hz), 7.28-7.22 (2H, m), 7.12-7.10 (2H, m), 7.00 (1H, d, J = 7.9 Hz), 6.65 (1H, d, J = 2.3 Hz), 6.34 (1H, dd, J = 8.6, 2.3 Hz), 6.26 (1H, d, J = 5.1 Hz), 5.95 (1H, d, J = 2.3 Hz), 5.71 (1H, d, J = 2.3 Hz), 4.28 (1H, t, J = 5.1 Hz), 3.81 (4H, t, J = 4.8 Hz), 3.32 (4H, t, J = 4.8 Hz), 3.00-2.72 (3H, m), 2.57 (3H, s), 2.33 (3H, s), 2.15-2.06 (3H, m), 1.85-1.73 (1H, m). |

TABLE 32-continued

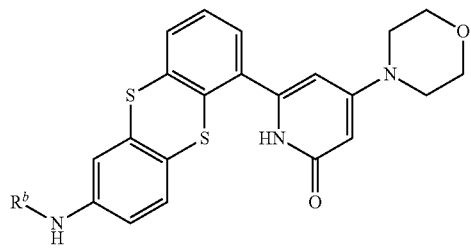

| Example No. | $R^b$ | Compound Name | MS | RT (min) | $^1$H-NMR (300 MHz) (DMSO-$d_6$) δ: |
|---|---|---|---|---|---|
| 1-22-7 | | 6-(7-(((6-Methyl pyridin-2-yl)(1-methyl pyrrolidin-3-yl)methyl)amino)thianthren-1-yl)-4-morpholino pyridin-2(1H)-one (Diastereomer B) | 598 | 0.98 | (CDCl$_3$): 8.89 (1H, br s), 7.55-7.52 (1H, m), 7.46 (1H, t, J = 7.6 Hz), 7.28-7.22 (2H, m), 7.12 (1H, d, J = 7.9 Hz), 7.06 (1H, d, J = 7.3 Hz), 7.00 (1H, d, J = 7.3 Hz), 6.67 (1H, d, J = 2.3 Hz), 6.35 (1H, dd, J = 8.6, 2.3 Hz), 5.95 (1H, d, J = 2.0 Hz), 5.85-5.80 (1H, m), 5.72 (1H, d, J = 2.0 Hz), 4.35 (1H, dd, J = 5.0, 5.0 Hz), 3.81 (4H, t, J = 5.0 Hz), 3.32 (4H, t, J = 5.0 Hz), 2.89-2.64 (3H, m), 2.57 (3H, s), 2.32 (3H, s), 2.21-2.05 (3H, m), 1.81-1.67 (1H, m). |

TABLE 33

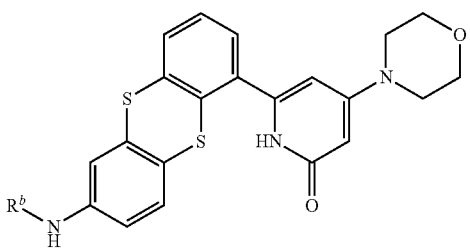

| Example No. | $R^b$ | Compound Name | MS | RT (min) | $^1$H-NMR (300 MHz) (DMSO-$d_6$) δ: |
|---|---|---|---|---|---|
| 1-22-8 | | 6-(7-(((1-Methyl azetidin-3-yl)(5-methyl pyridin-2-yl)methyl)amino)thianthren-1-yl)-4-morpholino pyridin-2(1H)-one | 584 | 0.99 | |
| 1-22-9 | | 6-(7-(((5-Methyl pyridin-2-yl)(1-methyl pyrrolidin-3-yl)methyl)amino)thianthren-1-yl)-4-morpholino pyridin-2(1H)-one (Diastereomer mixture) | 612 | 0.99 | |

TABLE 33-continued

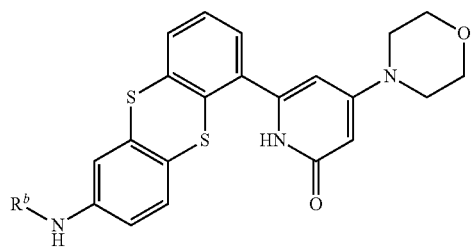

| Example No. | R[b] | Compound Name | MS | RT (min) | $^1$H-NMR (300 MHz) (DMSO-d$_6$) δ: |
|---|---|---|---|---|---|
| 1-22-10 | (N-methylpiperidin-3-yl with 1-(5-methylpyridin-2-yl)ethyl) | 6-(7-(((1-Methyl piperidin-3-yl)(5-methyl pyridin-2-yl) methyl)amino)thianthren-1-yl)-4-morpholino pyridin-2(1H)-one (Diastereomer mixture) | 612 | 1.00 | |

Examples 1-22-11-1 and 1-22-11-2

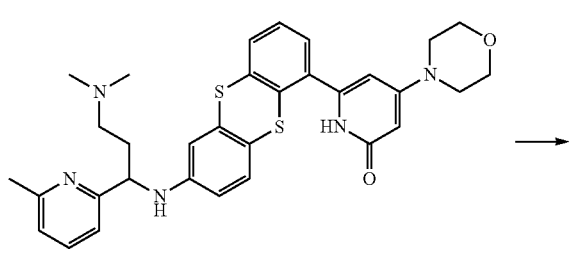

Chiral resolution was performed on 6-(7-((3-(dimethylamino)-1-(6-methylpyridin-2-yl)propyl)amino)thianthren-1-yl)-4-morpholinopyridin-2(1H)-one (racemic mixture) by supercritical fluid chromatography, whereby an optically active substance A and an optically active substance B were obtained.

Example 1-22-11-1

Optically Active Substance A

$^1$H-NMR (CDCl$_3$, 300 MHz) δ: 7.55 (1H, dd, J=5.9, 3.3 Hz), 7.48 (1H, t, J=7.6 Hz), 7.27-7.23 (2H, m), 7.12 (2H, t, J=8.6 Hz), 7.00 (1H, d, J=7.3 Hz), 6.69 (1H, d, J=2.3 Hz), 6.50 (1H, brs), 6.39 (1H, dd, J=8.6, 2.3 Hz), 5.95 (1H, d, J=2.6 Hz), 5.72 (1H, d, J=2.6 Hz), 4.49-4.47 (1H, m), 3.81 (4H, t, J=5.0 Hz), 3.32 (4H, t, J=5.0 Hz), 2.57 (3H, s), 2.46-2.33 (2H, m), 2.28 (6H, s), 2.21-2.01 (2H, m).

MS(ESI m/z): 586 (M+H)

RT(min): 1.03

Example 1-22-11-2

Optically Active Substance B

$^1$H-NMR (CDCl$_3$, 300 MHz) δ: 7.55 (1H, dd, J=5.9, 3.3 Hz), 7.48 (1H, t, J=7.6 Hz), 7.27-7.23 (2H, m), 7.12 (2H, t, J=8.6 Hz), 7.00 (1H, d, J=7.3 Hz), 6.69 (1H, d, J=2.3 Hz), 6.50 (1H, brs), 6.39 (1H, dd, J=8.6, 2.3 Hz), 5.95 (1H, d, J=2.6 Hz), 5.72 (1H, d, J=2.6 Hz), 4.49-4.47 (1H, m), 3.81 (4H, t, J=5.0 Hz), 3.32 (4H, t, J=5.0 Hz), 2.57 (3H, s), 2.46-2.33 (2H, m), 2.28 (6H, s), 2.21-2.01 (2H, m).

MS(ESI m/z): 586 (M+H)

RT(min): 1.03

(Supercritical Fluid Chromatography Conditions)

Column: CHIRALPAK AS-H (manufactured by Daicel Chemical Industries, Ltd.)

Mobile phase: carbon dioxide/0.1% diethylamine-containing methanol (volume ratio: 72/28)

Flow rate: 20 mL/min

Detection wavelength: 254 nm

Temperature: 40° C.

Retention time: 12.15 min (optically active substance A), 13.96 min (optically active substance B)

Examples 1-22-12-1 and 1-22-12-2

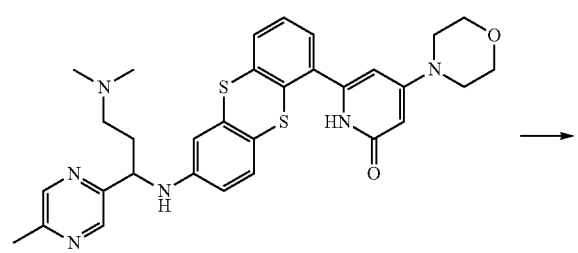

-continued

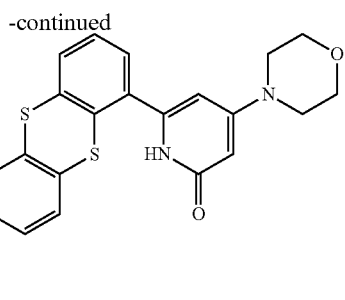

Chiral resolution was performed on 6-(7-((3-(dimethylamino)-1-(5-methylpyrazin-2-yl)propyl)amino)thianthren-1-yl)-4-morpholinopyridin-2(1H)-one (racemic mixture) by supercritical fluid chromatography, whereby an optically active substance A and an optically active substance B were obtained.

Example 1-22-12-1

Optically Active Substance A $^1$H-NMR (CDCl$_3$, 300 MHz) δ: 8.46 (1H, s), 8.41 (1H, s), 7.57-7.51 (1H, m), 7.26 (2H, q, J=5.3 Hz), 7.14 (1H, d, J=7.9 Hz), 6.68 (1H, d, J=2.6 Hz), 6.40 (1H, dd, J=8.6, 2.6 Hz), 6.29 (1H, d, J=6.0 Hz), 5.95 (1H, d, J=2.6 Hz), 5.72 (1H, d, J=2.6 Hz), 4.61-4.59 (1H, m), 3.81 (4H, t, J=4.8 Hz), 3.32 (4H, t, J=4.8 Hz), 2.54 (3H, s), 2.34 (2H, t, J=5.9 Hz), 2.28-2.18 (6H, m), 2.09-1.90 (2H, m).

MS(ESI m/z): 587 (M+H)

RT(min): 0.96

Example 1-22-12-2

Optically Active Substance B $^1$H-NMR (CDCl$_3$, 300 MHz) δ: 8.46 (1H, s), 8.41 (1H, s), 7.57-7.51 (1H, m), 7.26 (2H, q, J=5.3 Hz), 7.14 (1H, d, J=7.9 Hz), 6.68 (1H, d, J=2.6 Hz), 6.40 (1H, dd, J=8.6, 2.6 Hz), 6.29 (1H, d, J=6.0 Hz), 5.95 (1H, d, J=2.6 Hz), 5.72 (1H, d, J=2.6 Hz), 4.61-4.59 (1H, m), 3.81 (4H, t, J=4.8 Hz), 3.32 (4H, t, J=4.8 Hz), 2.54 (3H, s), 2.34 (2H, t, J=5.9 Hz), 2.28-2.18 (6H, m), 2.09-1.90 (2H, m).

MS(ESI m/z): 587 (M+H)

RT(min): 0.96

(Supercritical Fluid Chromatography Conditions)

Column: CHIRALPAK IB (manufactured by Daicel Chemical Industries, Ltd.)

Mobile phase: carbon dioxide/0.1% diethylamine-containing methanol (volume ratio: 70/30)

Flow rate: 20 mL/min

Detection wavelength: 254 nm

Temperature: 40° C.

Retention time: 18.38 min (optically active substance A), 20.62 min (optically active substance B)

Example 1-23-1

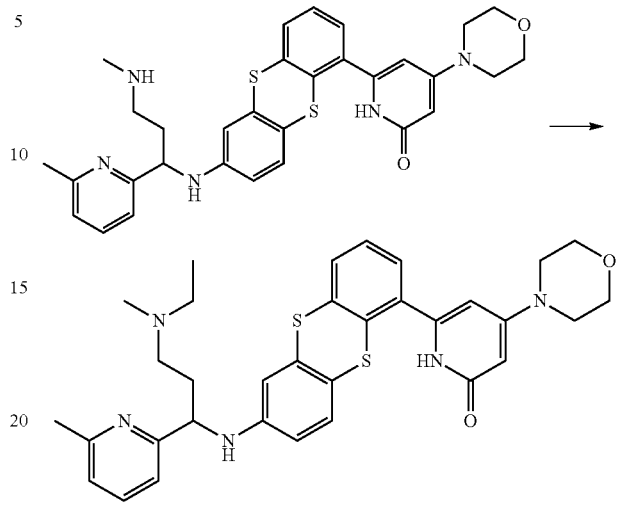

Potassium carbonate (7.2 mg) and ethyl iodide (3.5 mg) were added to a solution of 6-(7-((3-(methylamino)-1-(6-methylpyridin-2-yl)propyl)amino)thianthren-1-yl)-4-morpholinopyridin-2(1H)-one (10 mg) in tetrahydrofuran (0.66 mL) and 1-methyl-2-pyrrolidone (0.33 mL), followed by stirring at room temperature for 1.5 hours, and ethyl iodide (1.8 mg) was added thereto, followed by stirring for 16 hours. Water was added to the reaction mixture, then, the resultant product was extracted with chloroform, and the organic layer was dried over anhydrous sodium sulfate. The solvent was distilled off under reduced pressure, the obtained residues were purified by silica gel column chromatography (chloroform:methanol=1:0→97:3, NH silica), and purified by preparative thin layer silica gel chromatography (chloroform:methanol=30:1, NH silica), whereby 6-(7-((3-(ethyl(methyl)amino)-1-(6-methylpyridin-2-yl)propyl)amino)thianthren-1-yl)-4-morpholinopyridin-2(1H)-one (1.0 mg) was obtained.

$^1$H-NMR (CDCl$_3$, 300 MHz) δ: 8.89 (1H, brs), 7.52 (1H, dd, J=5.3, 3.3 Hz), 7.47 (1H, t, J=7.6 Hz), 7.28-7.24 (2H, m), 7.12-7.09 (2H, m), 7.00 (1H, d, J=7.3 Hz), 6.80 (1H, brs), 6.64 (1H, d, J=2.6 Hz), 6.35 (1H, dd, J=8.6, 2.6 Hz), 5.95 (1H, d, J=2.3 Hz), 5.70 (1H, d, J=2.3 Hz), 4.49-4.47 (1H, brm), 3.80 (4H, t, J=4.8 Hz), 3.31 (4H, t, J=4.8 Hz), 2.57 (3H, s), 2.48-2.37 (4H, m), 2.24 (3H, s), 2.12-2.05 (1H, m), 1.95-1.83 (1H, m), 1.08 (3H, t, J=6.9 Hz).

MS(ESI m/z): 600 (M+H)

RT(min): 0.96

Example 1-23-2

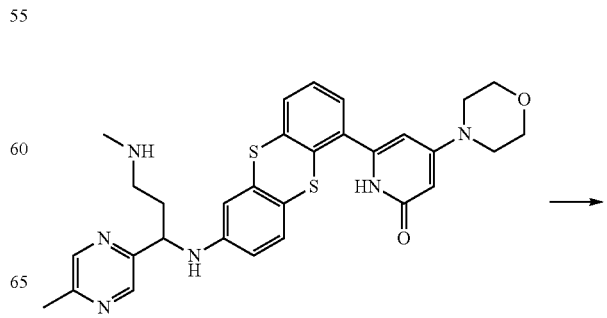

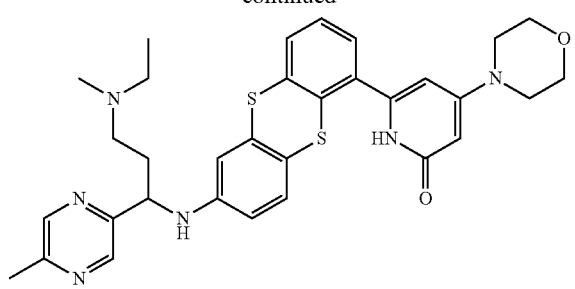

In the same manner as in Example 1-23-1, the following compounds were obtained.

6-(7-((3-(Ethyl(methyl)amino)-1-(5-methylpyrazin-2-yl)propyl)amino)thianthren-1-yl)-4-morpholinopyridin-2(1H)-one ¹H-NMR (CDCl₃, 300 MHz) δ: 8.95 (1H, brs), 8.46 (1H, d, J=1.3 Hz), 8.40 (1H, s), 7.53-7.51 (1H, m), 7.28-7.25 (2H, m), 7.11 (1H, d, J=8.6 Hz), 6.64 (1H, d, J=2.6 Hz), 6.61-6.59 (1H, m), 6.37 (1H, dd, J=8.6, 2.6 Hz), 5.95 (1H, d, J=2.3 Hz), 5.70 (1H, d, J=2.3 Hz), 4.60-4.56 (1H, brm), 3.80 (4H, t, J=5.0 Hz), 3.31 (4H, t, J=5.0 Hz), 2.54 (3H, s), 2.43-2.41 (4H, m), 2.24 (3H, s), 2.04-1.95 (2H, m), 1.08 (3H, t, J=7.3 Hz).

MS(ESI m/z): 601 (M+H)

RT(min): 0.97

Example 1-24-1

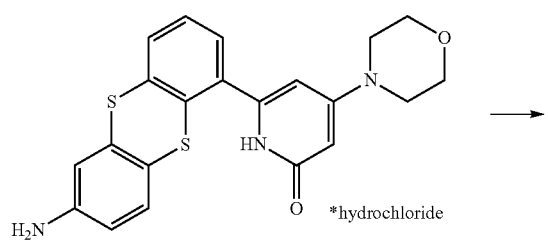

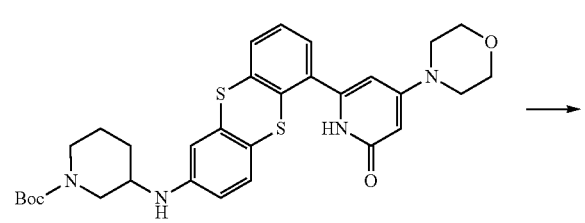

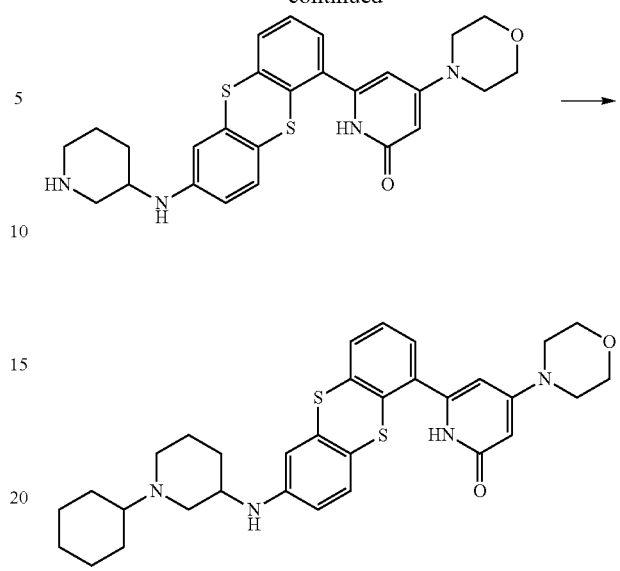

(1)

In the same manner as in Example 1-12-1, the following compound was obtained.

tert-Butyl 3-((6-(4-morpholino-6-oxo-1,6-dihydropyridin-2-yl)thianthren-2-yl)amino)piperidine-1-carboxylate MS(ESI m/z): 593 (M+H)

RT(min): 1.56

(2)

In the same manner as in Example 1-4, the following compound was obtained.

4-Morpholino-6-(7-(piperidin-3-ylamino)thianthren-1-yl)pyridin-2(1H)-one

MS(ESI m/z): 493 (M+H)

RT(min): 0.96

(3)

In the same manner as in Example 1-12-1, the following compound was obtained.

6-(7-((1-Cyclohexylpiperidin-3-yl)amino)thianthren-1-yl)-4-morpholinopyridin-2(1H)-one MS(ESI m/z): 575 (M+H)

RT(min): 1.08

Examples 1-24-2 to 1-24-8

In the same manner as in Example 1-24-1, the following compounds were obtained.

TABLE 34

| Example No. | R^b | Compound Name | MS | RT (min) | ¹H-NMR (300 MHz) (DMSO-$d_6$) δ: |
|---|---|---|---|---|---|
| 1-24-2 | 3-methylpiperidin-1-yl with pyridin-3-ylmethyl on N | 4-Morpholine-6-(7-((1-(pyridin-3-yl methyl) piperidin-3-yl)amino) thianthren-1-yl)pyridin-2 (1H)-one | 584 | 0.93 | 11.00 (1H, br s), 8.49 (1H, d, J = 1.5 Hz), 8.45 (1H, dd, J = 4.9 Hz, 1.6 Hz), 7.76-7.71 (1H, m), 7.62 (1H, dd, J = 5.7 Hz, 3.6 Hz), 7.38-7.30 (3H, m), 7.13 (1H, d, J = 8.4 Hz), 6.74 (1H, d, J = 2.4 Hz), 6.50 (1H, dd, J = 8.4 Hz, 2.4 Hz), 6.01 (1H, br s), 5.79 (1H, d, J = 8.4 Hz), 5.49 (1H, br s), 3.67 (4H, t, J = 4.7 Hz), 3.58-3.44 (2H, m), 3.42-3.30 (1H, m), 3.26 (4H, d, J = 4.7 Hz), 2.85-2.75 (1H, m), 2.65-2.55 (1H, m), 2.10-1.98 (1H, m), 1.88-1.75 (2H, m), 1.72-1.45 (2H, m), 1.25-1.10 (1H, m). |
| 1-24-3 | 3-methylpiperidin-1-yl with pyridin-2-ylmethyl on N | 4-Morpholino-6-(7-((1-(pyridin-2-yl methyl) piperidin-3-yl)amino) thianthren-1-yl)pyridin-2 (1H)-one | 584 | 0.97 | |
| 1-24-4 | 3-methylpiperidin-1-yl with pyridin-4-ylmethyl on N | 4-Morpholino-6-(7-((1-(pyridin-4-yl methyl) piperidin-3-yl)amino) thianthren-1-yl)pyridin-2 (1H)-one | 584 | 0.92 | 11.02 (1H, br s), 8.51-8.45 (2H, m), 7.66-7.58 (1H, m), 7.38-7.30 (4H, m), 7.13 (1H, d, J = 8.6 Hz), 6.77 (1H, d, J = 2.3 Hz), 6.51 (1H, dd, J = 8.6 Hz, 2.3 Hz), 6.02 (1H, br s), 5.81 (1H, d, J = 8.6 Hz), 5.51 (1H, br s), 3.67 (4H, t, J = 4.5 Hz), 3.59-3.44 (2H, m), 3.42-3.33 (1H, m), 3.26 (4H, d, J = 4.5 Hz), 2.85-2.75 (1H, m), 2.68-2.55 (1H, m), 2.12-2.00 (1H, m), 1.90-1.76 (2H, m), 1.74-1.48 (2H, m), 1.28-1.12 (1H, m). |
| 1-24-5 | 3-methyl-1-cyclopentylpiperidinyl | 6-(7-((1-Cyclopentyl piperidin-3-yl)amino) thianthren-1-yl)-4-morpholino pyridin-2(1H)-one | 561 | 1.07 | |
| 1-24-6 | 3-methyl-1-(oxetan-3-yl)piperidinyl | 4-Morpholino-6-(7-((1-(oxetan-3-yl)piperidin-3-yl) amino)thianthren-1-yl) pyridin-2(1H)-one | 549 | 0.93 | |

TABLE 34-continued

| Example No. | R[b] | Compound Name | MS | RT (min) | $^1$H-NMR (300 MHz) (DMSO-$d_6$) δ: |
|---|---|---|---|---|---|
| 1-24-7 | | 4-Morpholino-6-(7-((1-(tetrahydro-2H-pyran-4-yl)piperidin-3-yl)amino)thianthren-1-yl)pyridin-2(1H)-one | 577 | 0.99 | |
| 1-24-8 | | 4-Morpholino-6-(7-((1-(tetrahydrofuran-3-yl)piperidin-3-yl)amino)thianthren-1-yl)pyridin-2(1H)-one | 563 | 0.98 | |

Example 1-24-9

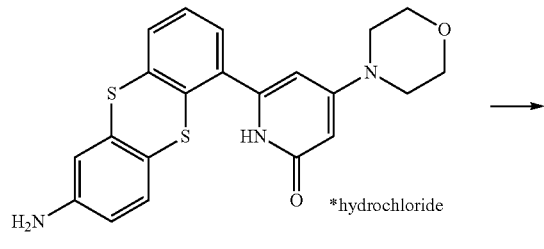

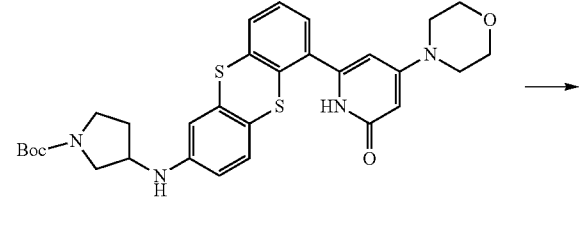

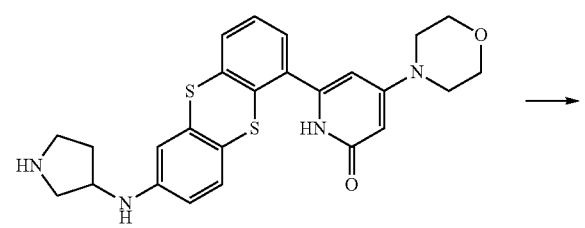

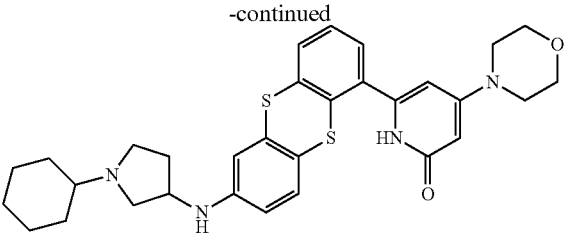

(1)

In the same manner as in Example 1-12-1, the following compound was obtained.

tert-Butyl 3-((6-(4-morpholino-6-oxo-1,6-dihydropyridin-2-yl)thianthren-2-yl)amino)pyrrolidine-1-carboxylate MS(ESI m/z): 579 (M+H)
RT(min): 1.52

(2)

In the same manner as in Example 1-4, the following compound was obtained.

4-Morpholino-6-(7-(pyrrolidin-3-ylamino)thianthren-1-yl)pyridin-2(1H)-one

MS(ESI m/z): 479 (M+H)
RT(min): 0.93

(3)

In the same manner as in Example 1-12-1, the following compound was obtained.

6-(7-((1-Cyclohexylpyrrolidin-3-yl)amino)thian-
thren-1-yl)-4-morpholinopyridin-2(1H)-one MS(ESI m/z): 561 (M+H)
RT(min): 1.14

Examples 1-24-10 to 1-24-14

In the same manner as in Example 1-24-9, the following compounds were obtained.

TABLE 35

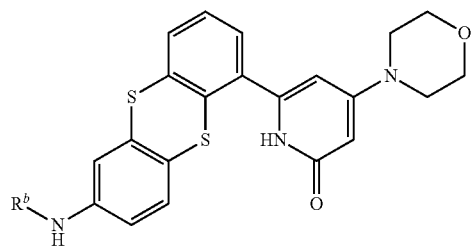

| Example No. | $R^b$ | Compound Name | MS | RT (min) | $^1$H-NMR (300 MHz) (DMSO-$d_6$) δ: |
|---|---|---|---|---|---|
| 1-24-10 | | 6-(7-((1-((4-Methoxy pyridin-3-yl)methyl) pyrrolidin-3-yl)amino) thianthren-1-yl)-4-morpholino pyridin-2(1H)-one | 600 | 0.82 | |
| 1-24-11 | | 4-Morpholino-6-(7-((1-(pyridin-3-yl methyl) pyrrolidin-3-yl)amino) thianthren-1-yl)pyridin-2 (1H)-one | 570 | 0.91 | 10.98 (1H, br s), 8.50 (1H, d, J = 1.8 Hz), 8.44 (1H, dd, J = 4.7 Hz, 1.9 Hz), 7.71 (1H, d, J = 8.1 Hz), 7.64-7.56 (1H, m), 7.38-7.30 (3H, m), 7.15 (1H, d, J = 8.6 Hz), 6.73 (1H, d, J = 2.0 Hz), 6.48 (1H, dd, J = 8.6 Hz, 2.0 Hz), 6.13 (1H, d, J = 6.6 Hz), 6.03 (1H, br s), 5.51 (1H, br s), 3.95-3.80 (1H, br s), 3.72-3.54 (6H, m), 3.26 (4H, t, J = 4.6 Hz), 2.80-2.70 (1H, m), 2.70-2.68 (1H, m), 2.50-2.32 (2H, m), 2.30-2.15 (1H, m), 1.62-1.50 (1H, m). |
| 1-24-12 | | 6-(7-((1-Cyclopentyl pyrrolidin-3-yl)amino) thianthren-1-yl)-4-morpholino pyridin-2(1H)-one | 547 | 1.09 | |
| 1-24-13 | | 4-Morpholino-6-(7-((1-(tetrahydro-2H-pyran-4-yl) pyrrolidin-3-yl)amino) thianthren-1-yl)pyridin-2 (1H)-one | 563 | 0.98 | |
| 1-24-14 | | 4-Morpholino-6-(7-((1-(tetrahydrofuran-3-yl) pyrrolidin-3-yl)amino) thianthren-1-yl)pyridin-2 (1H)-one | 549 | 0.94 | |

361

Example 1-24-15

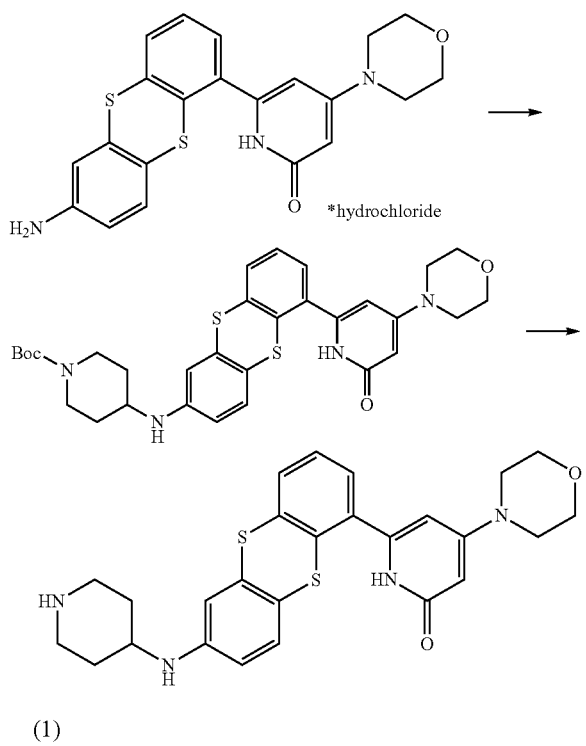

*hydrochloride (1)

In the same manner as in Example 1-12-1, the following compound was obtained.

tert-Butyl 4-((6-(4-morpholino-6-oxo-1,6-dihydro-pyridin-2-yl)thianthren-2-yl)amino)piperidine-1-carboxylate MS(ESI m/z): 593 (M+H)
RT(min): 1.57

(2)

In the same manner as in Example 1-4, the following compound was obtained.

362

4-Morpholino-6-(7-(piperidin-4-ylamino)thianthren-1-yl)pyridin-2(1H)-one

¹H-NMR (CDCl₃, 300 MHz) δ: 7.58 (1H, dd, J=5.8, 3.5 Hz), 7.29 (1H, s), 7.28 (1H, d, J=2.3 Hz), 7.18 (1H, d, J=8.3 Hz), 6.72 (1H, d, J=2.3 Hz), 6.43 (1H, dd, J=8.6, 2.3 Hz), 5.96 (1H, d, J=2.3 Hz), 5.71 (1H, d, J=2.3 Hz), 3.81 (4H, t, J=5.0 Hz), 3.60 (1H, d, J=8.9 Hz), 3.32 (4H, t, J=5.0 Hz), 3.06 (2H, d, J=12.6 Hz), 2.64 (2H, td, J=12.1, 2.2 Hz), 1.95 (2H, d, J=10.9 Hz), 1.19 (2H, d, J=8.9 Hz).
MS(ESI m/z): 493 (M+H)
RT(min): 0.91

Example 1-24-16

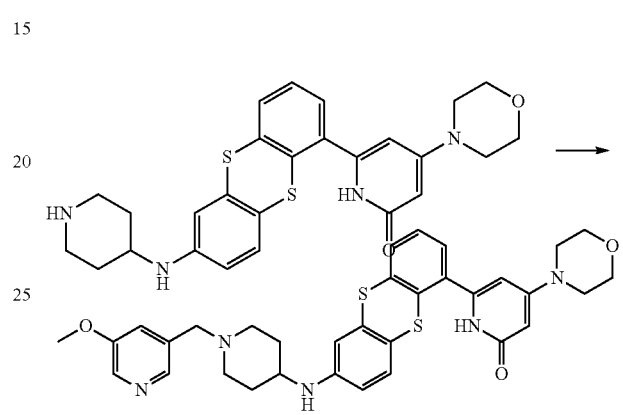

In the same manner as in Example 1-12-1, the following compound was obtained.

6-(7-((1-((5-Methoxypyridin-3-yl)methyl)piperidin-4-yl)amino)thianthren-1-yl)-4-morpholinopyridin-2(1H)-one MS(ESI m/z): 614 (M+H)
RT(min): 0.98

Examples 1-24-17 to 1-24-20

In the same manner as in Example 1-12-16, the following compound was obtained.

TABLE 36

| Example No. | $R^b$ | Compound Name | MS | RT (min) | ¹H-NMR (300 MHz) (DMSO-d₆) δ: |
|---|---|---|---|---|---|
| 1-24-17 | (pyridin-3-yl methyl)-(4-methylpiperidin-1-yl) | 4-Morpholino-6-(7-((1-(pyridin-3-yl methyl)piperidin-4-yl)amino)thianthren-1-yl)pyridin-2(1H)-one | 584 | 0.93 | 11.00 (1H, br s), 8.50-8.43 (2H, m), 7.72-7.67 (1H, m), 7.64-7.59 (1H, m), 7.38-7.30 (3H, m), 7.15 (1H, d, J = 8.4 Hz), 6.78 (1H, d, J = 2.4 Hz), 6.51 (1H, dd, J = 8.4, 2.4 Hz), 6.02 (1H, br s), 5.84 (1H, d, J = 7.8 Hz), 5.51 (1H, br s), 3.67 (4H, t, J = 4.8 Hz), 3.50 (2H, s), 3.30-3.10 (5H, m), 2.80-2.70 (2H, m), 2.20-2.00 (2H, m), 1.90-1.80 (2H, m), 1.45-1.20 (2H, m). |

TABLE 36-continued

| Example No. | R^b | Compound Name | MS | RT (min) | $^1$H-NMR (300 MHz) (DMSO-$d_6$) δ: |
|---|---|---|---|---|---|
| 1-24-18 | 1-Cyclopropyl-4-methylpiperidin-4-yl | 6-(7-((1-Cyclopropyl piperidin-4-yl)amino) thianthren-1-yl)-4-morpholino pyridin-2(1H)-one | 533 | 0.96 | 11.00 (1H, br s), 7.65-7.58 (1H, m), 7.38-7.30 (2H, m), 7.15 (1H, d, J = 8.6 Hz), 6.77 (1H, d, J = 2.7 Hz), 6.50 (1H, dd, J = 8.6, 2.7 Hz), 6.03 (1H, br s), 5.82 (1H, d, J = 7.8 Hz), 5.51 (1H, br s), 3.67 (4H, t, J = 4.7 Hz), 3.30-3.10 (5H, m), 2.92-2.82 (2H, m), 2.32-2.20 (2H, m), 1.88-1.76 (2H, m), 1.62-1.55 (1H, m), 1.32-1.18 (2H, m), 0.44-0.38 (2H, m), 0.30-0.22 (2H, m). |
| 1-24-19 | 1-(pyridin-2-ylmethyl)-4-methylpiperidin-4-yl | 4-Morpholino-6-(7-((1-(pyridin-2-yl methyl) piperidin-4-yl)amino) thianthren-1-yl)pyridin-2(1H)-one | 584 | 0.97 | |
| 1-24-20 | 1-(pyridin-4-ylmethyl)-4-methylpiperidin-4-yl | 4-Morpholino-6-(7-((1-(pyridin-4-yl methyl) piperidin-4-yl)amino) thianthren-1-yl)pyridin-2(1H)-one | 584 | 0.89 | |

Example 1-24-21

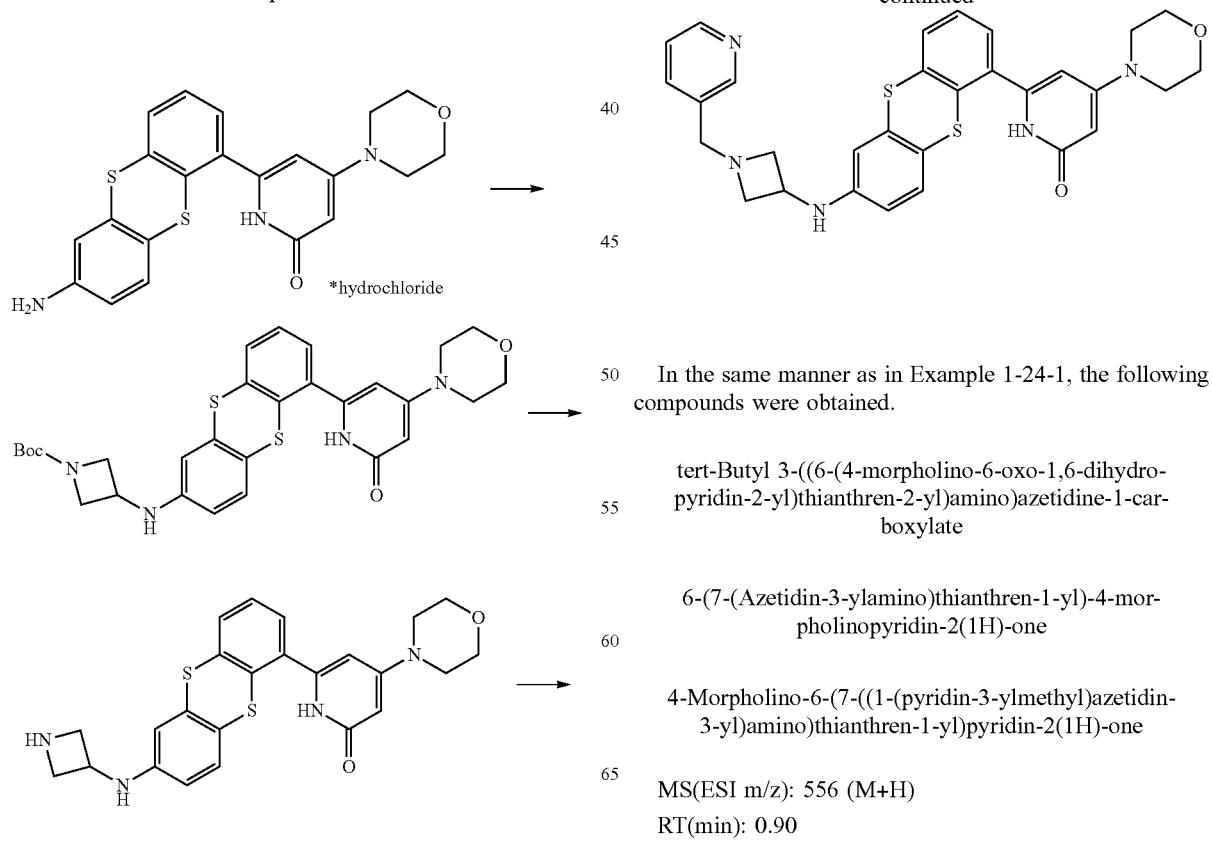

In the same manner as in Example 1-24-1, the following compounds were obtained.

tert-Butyl 3-((6-(4-morpholino-6-oxo-1,6-dihydropyridin-2-yl)thianthren-2-yl)amino)azetidine-1-carboxylate 6-(7-(Azetidin-3-ylamino)thianthren-1-yl)-4-morpholinopyridin-2(1H)-one 4-Morpholino-6-(7-((1-(pyridin-3-ylmethyl)azetidin-3-yl)amino)thianthren-1-yl)pyridin-2(1H)-one MS(ESI m/z): 556 (M+H)

RT(min): 0.90

Example 1-25

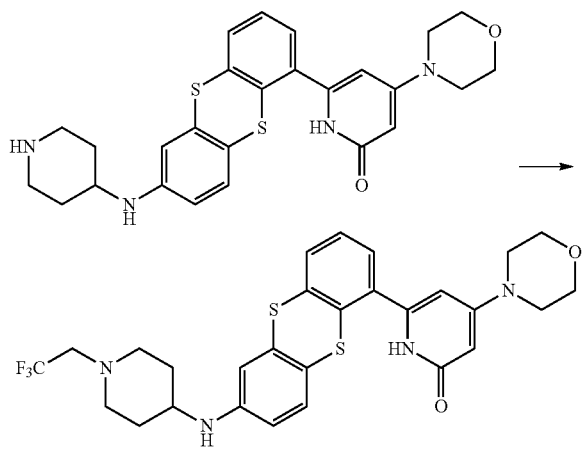

2,2,2-Trifluoroethyl trifluoromethanesulfonate (10 μL) and N,N-diisopropylethylamine (28 μL) were added to a solution of 4-morpholino-6-(7-(piperidin-4-ylamino)thianthren-1-yl)pyridin-2(1H)-one (20 mg) in N,N-dimethyl formamide (1 mL), followed by stirring at room temperature for 17 hours. 2,2,2-Trifluoroethyl trifluoromethanesulfonate (10 μL) was added thereto, followed by stirring at room temperature for 6 hours. Ethyl acetate was added to the reaction mixture, then, the resultant product was washed with a saturated sodium chloride aqueous solution, and the organic layer was dried over anhydrous sodium sulfate. The solvent was distilled off under reduced pressure, and the obtained residues were purified by silica gel column chromatography (chloroform:methanol=1:0→9:1, NH silica), whereby 4-morpholino-6-(7-((1-(2,2,2-trifluoroethyl)piperidin-4-yl)amino)thianthren-1-yl)pyridin-2(1H)-one (9 mg) was obtained as a white solid.

MS(ESI m/z): 575 (M+H)
RT(min): 1.37

Example 1-26-1

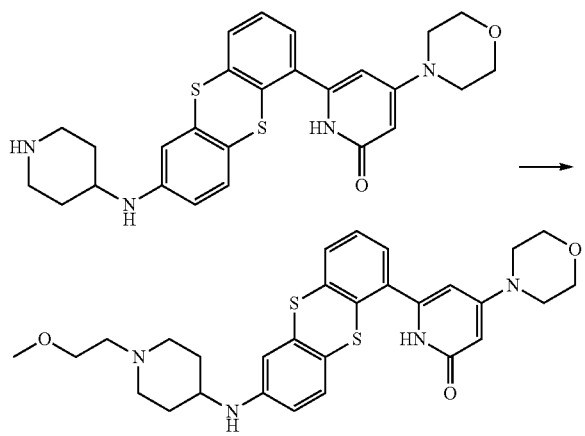

2-Bromoethyl methyl ether (6.9 mg) and potassium carbonate (18 mg) were added to a solution of 4-morpholino-6-(7-(piperidin-4-ylamino)thianthren-1-yl)pyridin-2(1H)-one (20 mg) in N,N-dimethyl formamide (1 mL), followed by stirring at 100° C. for 8 hours. After the reaction mixture was cooled to room temperature, ethyl acetate was added thereto, and the organic layer was washed with a saturated sodium chloride aqueous solution, and dried over anhydrous sodium sulfate. The solvent was distilled off under reduced pressure, and the obtained residues were purified by preparative thin layer silica gel chromatography (chloroform:methanol=30:1, NH silica), whereby 6-(7-((1-(2-methoxyethyl)piperidin-4-yl)amino)thianthren-1-yl)-4-morpholinopyridin-2(1H)-one (3.0 mg) was obtained as a white solid.

$^1$H-NMR (DMSO-$d_6$, 300 MHz) δ: 10.98 (1H, brs), 7.64-7.57 (1H, m), 7.38-7.30 (2H, m), 7.15 (1H, d, J=8.6 Hz), 6.77 (1H, d, J=2.3 Hz), 6.50 (1H, dd, J=8.6 Hz, 2.3 Hz), 6.03 (1H, brs), 5.83 (1H, d, J=7.8 Hz), 5.51 (1H, brs), 3.67 (4H, t, J=4.7 Hz), 3.41 (2H, t, J=5.9 Hz), 3.39-3.27 (1H, m), 3.26 (4H, d, J=4.7 Hz), 3.22 (3H, s), 2.85-2.75 (2H, m), 2.45 (2H, t, J=5.9 Hz), 2.13-2.03 (2H, m), 1.90-1.78 (2H, m), 1.45-1.20 (2H, m).

MS(ESI m/z): 551 (M+H)
RT(min): 0.96

Example 1-26-2

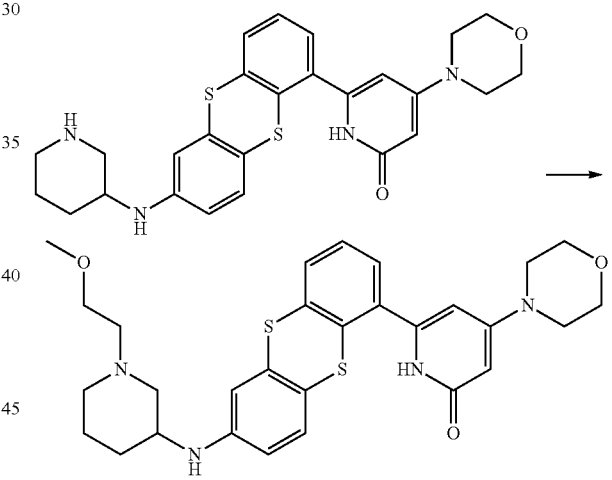

In the same manner as in Example 1-26-1, the following compound was obtained.

6-(7-((1-(2-Methoxyethyl)piperidin-3-yl)amino)thianthren-1-yl)-4-morpholinopyridin-2(1H)-one $^1$H-NMR (DMSO-$d_6$, 300 MHz) δ: 10.99 (1H, brs), 7.65-7.58 (1H, m), 7.38-7.30 (2H, m), 7.16 (1H, d, J=8.6 Hz), 6.78 (1H, d, J=2.2 Hz), 6.52 (1H, dd, J=8.6 Hz, 2.2 Hz), 6.03 (1H, brs), 5.77 (1H, d, J=8.7 Hz), 5.51 (1H, brs), 3.67 (4H, t, J=4.7 Hz), 3.41 (2H, d, J=5.8 Hz), 3.39-3.25 (1H, m), 3.26 (4H, d, J=4.7 Hz), 3.22 (3H, s), 2.95-2.85 (1H, m), 2.75-2.65 (1H, m), 2.50-2.43 (2H, m), 2.08-1.98 (1H, m), 1.90-1.75 (2H, m), 1.72-1.45 (2H, m), 1.25-1.10 (1H, m).

MS(ESI m/z): 551 (M+H)
RT(min): 0.96

Example 1-27

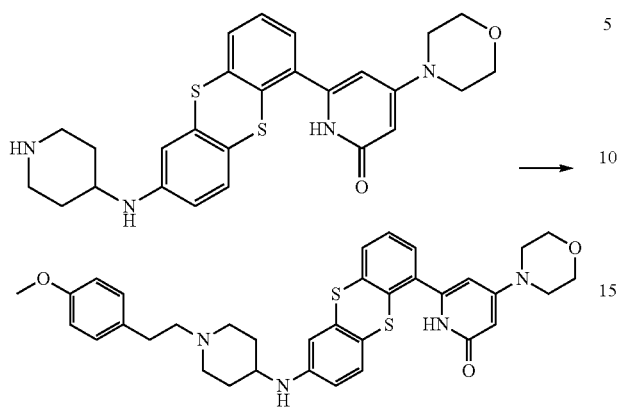

A mixture of 4-morpholino-6-(7-(piperidin-4-ylamino)thianthren-1-yl)pyridin-2(1H)-one (5 mg), sodium hydrogen carbonate (5 mg), N,N-dimethyl formamide (0.5 mL), and 1-(2-bromo ethyl)-4-methoxybenzene (4.7 μL) was stirred at 80° C. for 3 hours. After the reaction mixture was cooled to room temperature, water was added thereto, and the resultant product was extracted with ethyl acetate. The organic layer was washed with a saturated sodium chloride aqueous solution, then, the solvent was distilled off under reduced pressure, and the obtained residues were purified by preparative reversed phase HPLC (0.1% formic acid aqueous solution-0.1% solution of formic acid in acetonitrile), whereby 6-(7-((1-(4-methoxyphenethyl)piperidin-4-yl)amino)thianthren-1-yl)-4-morpholinopyridin-2(1H)-one (1.7 mg) was obtained.

MS(ESI m/z): 627 (M+H)
RT(min): 1.12

Example 1-28

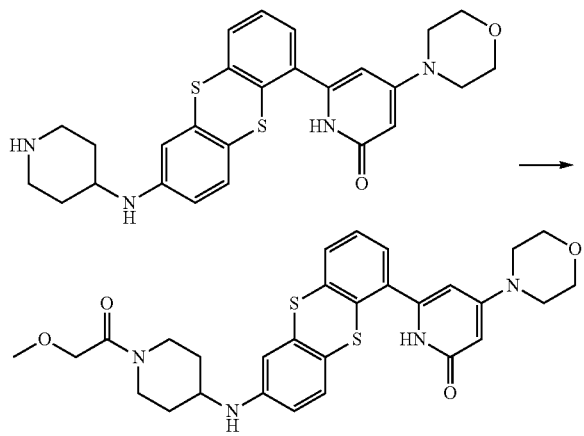

1-Ethyl-3-(3-dimethylaminopropyl)carbodiimide hydrochloride (60 mg), 1-hydroxybenzotriazole (43 mg), and N,N-diisopropyl ethylamine (107 μL) were added to a solution of 4-morpholino-6-(7-(piperidin-4-ylamino)thianthren-1-yl)pyridin-2(1H)-one (52 mg) and 2-methoxyacetic acid (32 mg) in N,N-dimethyl formamide (2 mL), followed by stirring at room temperature for 13.5 hours. A saturated sodium hydrogen carbonate aqueous solution was added to the reaction mixture, then, the resultant product was extracted with ethyl acetate, and the organic layer was dried over anhydrous sodium sulfate. The solvent was distilled off under reduced pressure, and the obtained residues were purified by silica gel column chromatography (ethyl acetate:methanol=10:1→5:1, NH silica), whereby 6-(7-((1-(2-methoxyacetyl)piperidin-4-yl)amino)thianthren-1-yl)-4-morpholinopyridin-2(1H)-one (36 mg) was obtained.

MS(ESI m/z): 565 (M+H)
RT(min): 1.13

Example 1-29-1

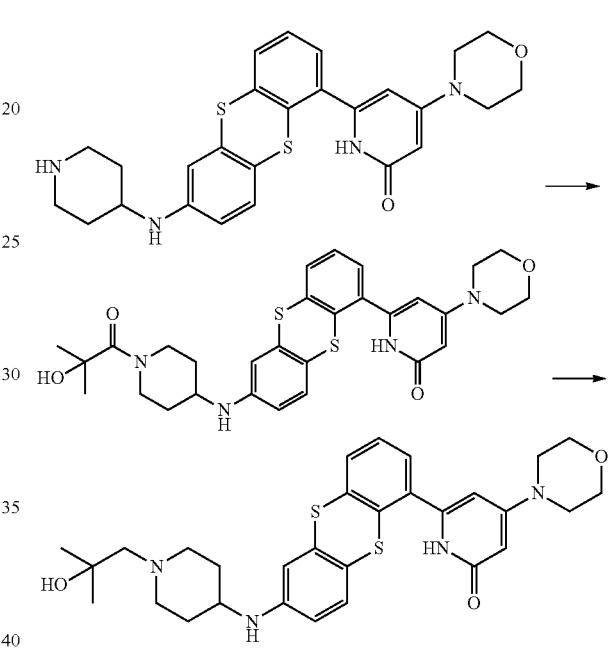

2-(7-aza-1H-benzotriazol-1-yl)-1,1,3,3-tetramethyluronium hexafluorophosphate (19 mg) was added to a solution of 4-morpholino-6-(7-(piperidin-4-ylamino)thianthren-1-yl)pyridin-2(1H)-one (20 mg), α-hydroxyisobutyric acid (4.2 mg), and N,N-diisopropyl ethylamine (23 μL) in N,N-dimethyl formamide (1.0 mL), followed by stirring at room temperature for 2 hours. Ethyl acetate was added to the reaction mixture, and the organic layer was washed sequentially with a saturated sodium hydrogen carbonate aqueous solution and a saturated sodium chloride aqueous solution, and dried over anhydrous sodium sulfate. The solvent was distilled off under reduced pressure, tetrahydrofuran (2.0 mL) and a 1.0 mol/L borane-tetrahydrofuran complex tetrahydrofuran (330 μL) was added to the obtained residues, followed by stirring at room temperature for 18 hours. 2 mol/L hydrochloric acid (500 μL) was added to the reaction mixture, followed by refluxing for 0.5 hours. After the reaction mixture was cooled to room temperature, ethyl acetate was added thereto, and the resultant product was washed with a saturated sodium hydrogen carbonate aqueous solution, and dried over anhydrous sodium sulfate. The solvent was distilled off under reduced pressure, and the obtained residues were purified by preparative thin layer silica gel chromatography (chloroform:ethanol=30:1, NH silica), whereby 6-(7-((1-(2-hydroxy-2-methylpropyl)piperidin-4-yl)amino)thianthren-1-yl)-4-morpholinopyridin-2 (1H)-one (4.7 mg) was obtained as a white solid.

MS(ESI m/z): 565 (M+H)
RT(min): 0.95

Example 1-29-2

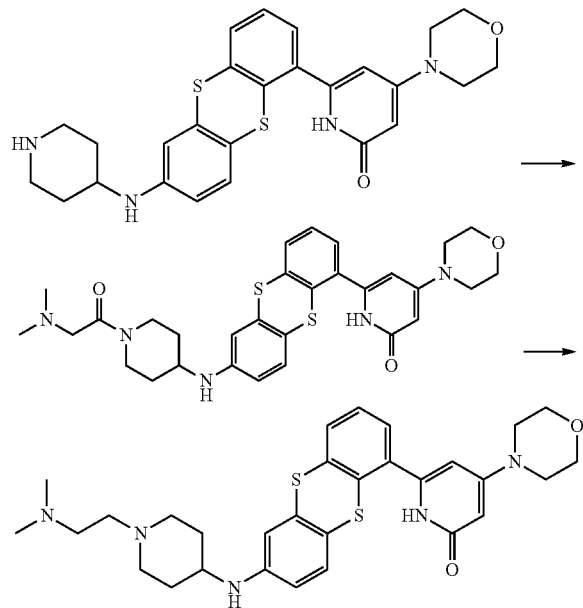

(1)

In the same manner as in Example 1-28, the following compound was obtained 6-(7-((1-(2-(Dimethylamino)acetyl)piperidin-4-yl)amino)thianthren-1-yl)-4-morpholinopyridin-2(1H)-one (2)

In the same manner as in Reference Example 8 (3), the following compound was obtained.

6-(7-((1-(2-(Dimethylamino)ethyl)piperidin-4-yl)amino)thianthren-1-yl)-4-morpholinopyridin-2(1H)-one MS(ESI m/z): 564 (M+H)
RT(min): 0.79

Example 1-30

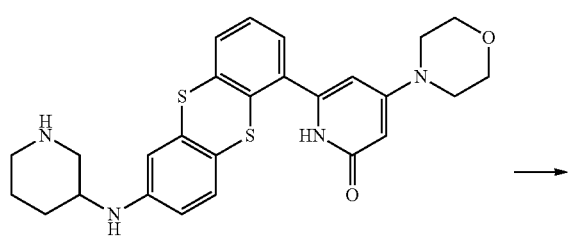

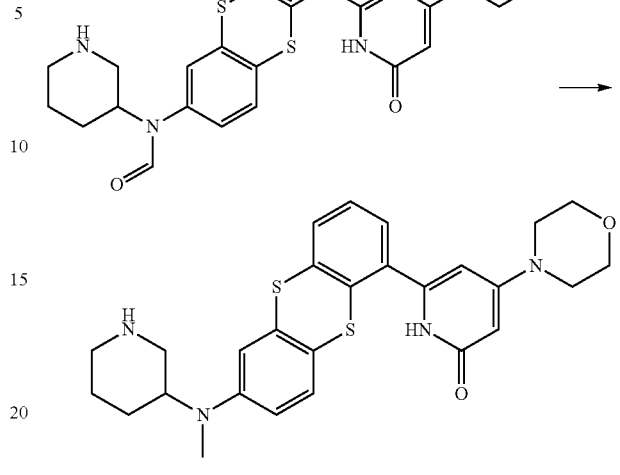

Formic acid (1.0 mL) was added to 4-morpholino-6-(7-(piperidin-3-ylamino)thianthren-1-yl)pyridin-2(1H)-one (20 mg), and the resultant product was irradiated with microwaves (microwave reaction apparatus, 130° C., 0.5 hours, 2.45 GHz, 0 W to 240 W). The reaction mixture was cooled to room temperature, and the solvent was distilled off under reduced pressure. Chloroform was added to the obtained residues, and the organic layer was washed with a saturated sodium hydrogen carbonate aqueous solution, and dried over anhydrous magnesium sulfate. The solvent was distilled off under reduced pressure, tetrahydrofuran (2.0 mL) and a 1.0 mol/L borane-tetrahydrofuran complex tetrahydrofuran solution (332 µL) was added to the obtained residues, followed by refluxing for 2 hours. 1.0 mol/L hydrochloric acid (500 µL) was added thereto, followed by refluxing for 1 hour. After the temperature of the reaction mixture was returned to room temperature, chloroform was added thereto, and the organic layer was washed with a saturated sodium hydrogen carbonate aqueous solution, and dried over anhydrous sodium sulfate. The solvent was distilled off under reduced pressure, and the obtained residues were purified by preparative thin layer silica gel chromatography (chloroform:ethanol=30:1, NH silica), whereby 6-(7-(methyl(piperidin-3-yl)amino)thianthren-1-yl)-4-morpholinopyridin-2(1H)-one (4.3 mg) was obtained.

MS(ESI m/z): 507 (M+H)
RT(min): 0.98

Example 1-31-1

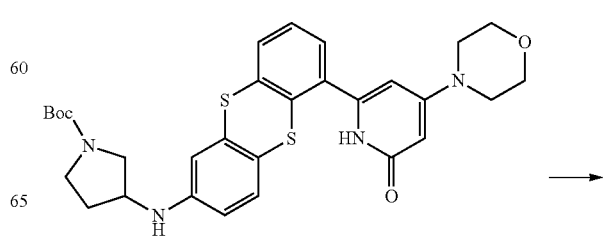

-continued

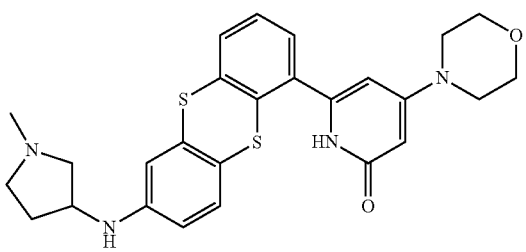

In the same manner as in Example 1-2-1 (2), the following compound was obtained.

6-(7-((1-Methylpyrrolidin-3-yl)amino)thianthren-1-yl)-4-morpholinopyridin-2(1H)-one MS(ESI m/z): 493 (M+H)
RT(min): 0.89

Example 1-31-2

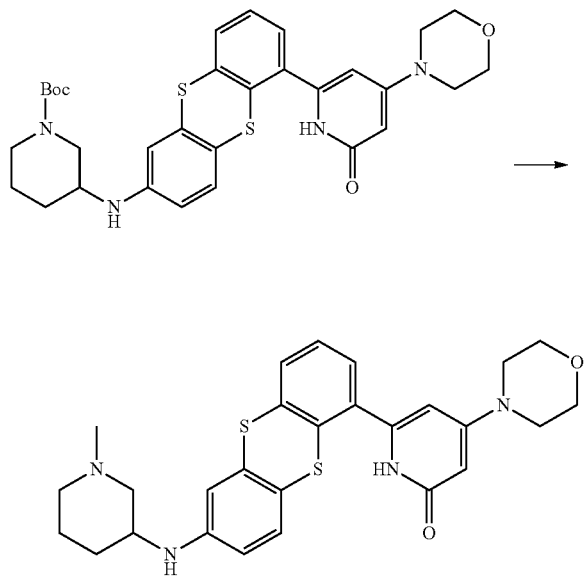

In the same manner as in Example 1-2-1 (2), the following compound was obtained.

6-(7-((1-Methylpiperidin-3-yl)amino)thianthren-1-yl)-4-morpholinopyridin-2(1H)-one $^1$H-NMR (CDCl$_3$, 300 MHz) δ: 7.59-7.54 (1H, m), 7.30-7.24 (2H, m), 7.19 (1H, d, J=8.6 Hz), 6.78 (1H, d, J=2.6 Hz), 6.48 (1H, dd, J=8.6 Hz, 2.6 Hz), 5.98 (1H, d, J=2.4 Hz), 5.71 (1H, d, J=2.4 Hz), 3.81 (4H, t, J=4.9 Hz), 3.60-3.50 (1H, m), 3.32 (4H, t, J=4.9 Hz), 2.70-2.55 (1H, m), 2.45-1.45 (11H, m).
MS(ESI m/z): 507 (M+H)
RT(min): 0.91

Example 1-32

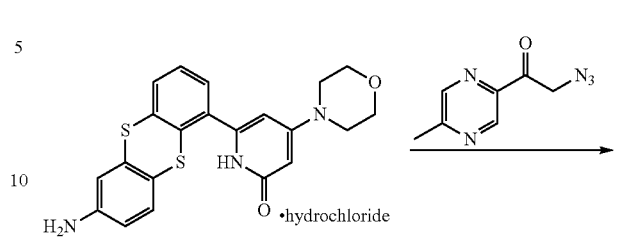

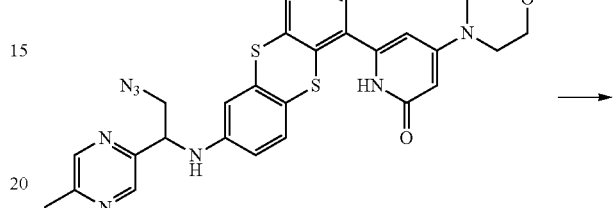

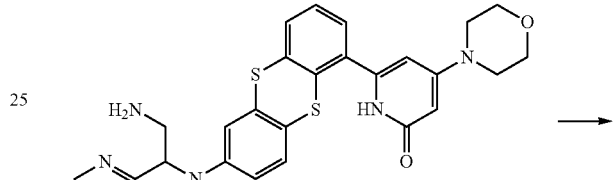

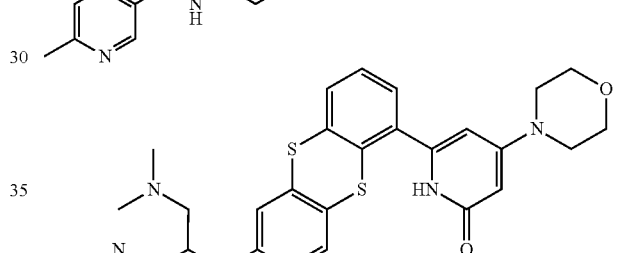

(1)
In the same manner as in Example 1-12-1, the following compound was obtained.

6-(7-((2-Azide-1-(5-methylpyrazin-2-yl)ethyl)amino)thianthren-1-yl)-4-morpholinopyridin-2(1H)-one MS(ESI m/z): 571 (M+H)
RT(min): 1.31

(2)
Water (1 mL) and triphenylphosphine (22 mg) were added to a solution of 6-(7-((2-azide-1-(5-methylpyrazin-2-yl)ethyl)amino)thianthren-1-yl)-4-morpholinopyridin-2(1H)-one (37 mg) obtained in Example 1-32 (1) in tetrahydrofuran (4 mL), and the resultant product was irradiated with microwaves (microwave reaction apparatus, 80° C., 20 minutes, 2.45 GHz, 0 W to 240 W). After the reaction mixture was cooled to room temperature, a saturated sodium chloride aqueous solution was added thereto, then, the resultant product was extracted with chloroform, and the organic layer was dried over anhydrous sodium sulfate. The solvent was distilled off under reduced pressure, whereby 6-(7-((2-amino-1-(5-methylpyrazin-2-yl)ethyl)amino)thianthren-1-yl)-4-morpholinopyridin-2(1H)-one was obtained.

Tetrahydrofuran (3.2 mL) was added to the obtained 6-(7-((2-amino-1-(5-methylpyrazin-2-yl)ethyl)amino)thianthren-1-yl)-4-morpholinopyridin-2(1H)-one, whereby a tetrahydrofuran solution was prepared.

MS(ESI m/z): 545 (M+H)
RT(min): 0.90

(3)

Tetrahydrofuran (0.4 mL), potassium carbonate (5.2 mg), and methyl iodide (3.5 mg) were added to a solution of 6-(7-((2-amino-1-(5-methylpyrazin-2-yl)ethyl)amino)thianthren-1-yl)-4-morpholinopyridin-2(1H)-one obtained in Example 1-32 (2) in tetrahydrofuran (0.63 mL), followed by stirring at room temperature for 16 hours. Methyl iodide (3.5 mg) was added thereto, followed by stirring for 1 hour, and methyl iodide (3.5 mg) was added thereto, followed by stirring for 10 minutes. A saturated sodium chloride aqueous solution was added to the reaction mixture, then, the resultant product was extracted with chloroform, and the organic layer was dried over anhydrous sodium sulfate. After the solvent was distilled off under reduced pressure, the obtained residues were purified by silica gel column chromatography (chloroform:methanol=100:0→99:1, NH silica), then, purified by preparative reversed phase HPLC (0.1% formic acid aqueous solution-0.1% solution of formic acid in acetonitrile), and purified by preparative thin layer silica gel chromatography (chloroform:ethanol=30:1, NH silica), whereby 6-(7-((2-(dimethylamino)-1-(5-methylpyrazin-2-yl)ethyl)amino)thianthren-1-yl)-4-morpholinopyridin-2(1H)-one (1 mg) was obtained.

MS(ESI m/z): 573 (M+H)
RT(min): 0.94

Example 1-33

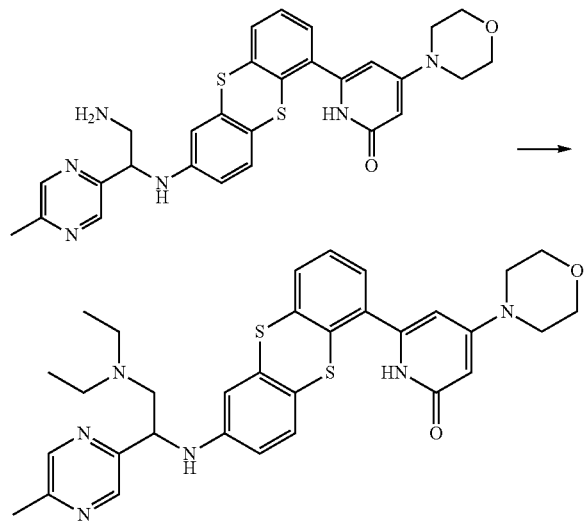

Acetic acid (45 µL), methanol (455 µL), acetaldehyde (1.36 mg), and 2-picoline borane (3 mg) were added to a solution (0.7 mL) of 6-(7-((2-amino-1-(5-methylpyrazin-2-yl)ethyl)amino)thianthren-1-yl)-4-morpholinopyridin-2 (1H)-one prepared in Example 1-32 (2) in tetrahydrofuran, followed by stirring at room temperature for 16 hours. A saturated sodium hydrogen carbonate aqueous solution was added thereto, then, the resultant product was extracted with chloroform, and the organic layer was dried over anhydrous sodium sulfate. The solvent was distilled off under reduced pressure, then, the obtained residues were purified by silica gel column chromatography (chloroform:methanol=100: 0→49:1, NH silica), and purified by preparative thin layer silica gel chromatography (chloroform:methanol=50:1, NH silica), whereby 6-(7-((2-(diethyl amino)-1-(5-methylpyrazin-2-yl)ethyl)amino)thianthren-1-yl)-4-morpholinopyridin-2(1H)-one (3.1 mg) was obtained.

MS(ESI m/z): 601 (M+H)
RT(min): 0.99

Example 1-34-1

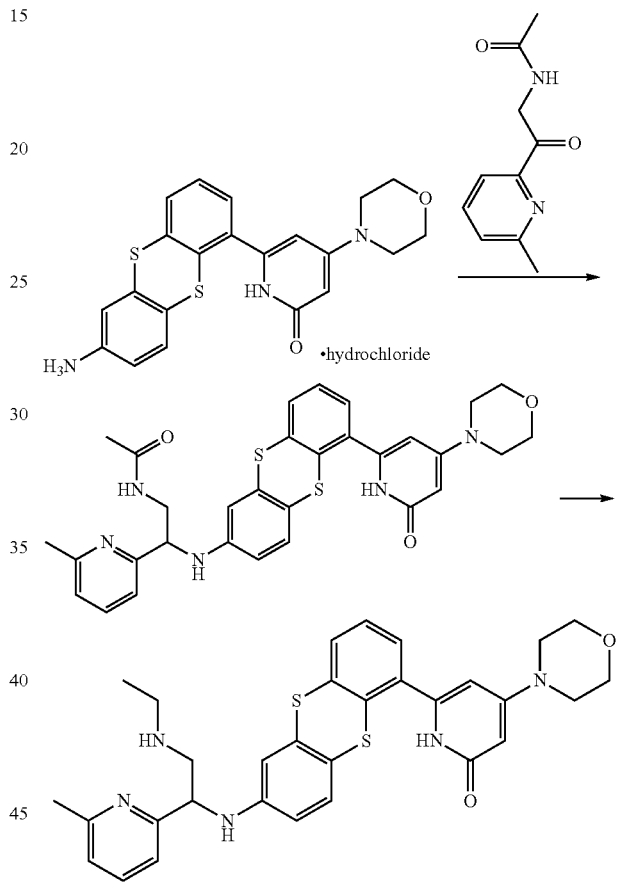

(1)

In the same manner as in Example 1-12-1, the following compound was obtained.

N-(2-(6-methylpyridin-2-yl)-2-((6-(4-morpholino-6-oxo-1,6-dihydropyridin-2-yl)thianthren-2-yl)amino) ethyl)acetamide MS(ESI m/z): 586 (M+H)
RT(min): 0.95

(2)

A 1.1 mol/L borane-tetrahydrofuran complex solution (52 µL) was added to a solution of N-(2-(6-methylpyridin-2-yl)-2-((6-(4-morpholino-6-oxo-1,6-dihydropyridin-2-yl)thianthren-2-yl)amino)ethyl)acetamide (6.8 mg) obtained in Example 1-34-1 (1) in tetrahydrofuran (1 mL), and the resultant product was irradiated with microwaves (microwave reaction apparatus, 80° C., 15 minutes, 2.45 GHz, 0 W to 240 W). A 1.1 mol/L borane-tetrahydrofuran complex solution (52 μL) was added thereto, and the resultant product was irradiated with microwaves (microwave reaction apparatus, 90° C., 0.5 hours, 2.45 GHz, 0 W to 240 W). After the reaction mixture was cooled to room temperature, a saturated sodium hydrogen carbonate aqueous solution and a saturated sodium chloride aqueous solution were added thereto, then, the resultant product was extracted with chloroform, and the organic layer was dried over anhydrous sodium sulfate. The solvent was distilled off under reduced pressure, and the obtained residues were purified by preparative reversed phase HPLC (0.1% formic acid aqueous solution-0.1% solution of formic acid in acetonitrile), whereby 6-(7-((2-(ethylamino)-1-(6-methylpyridin-2-yl)ethyl)amino)thianthren-1-yl)-4-morpholinopyridin-2(1H)-one (2.3 mg) was obtained.

MS(ESI m/z): 572 (M+H)
RT(min): 1.07

Examples 1-34-2 to 1-34-6

In the same manner as in Example 1-34-1, the following compounds were obtained.

TABLE 37

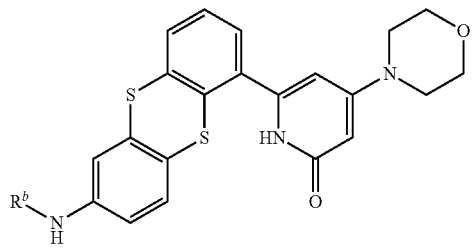

| Example No. | R$^b$ | Compound Name | MS | RT (min) | $^1$H-NMR (300 MHz) (DMSO-d$_6$) δ: |
|---|---|---|---|---|---|
| 1-34-2 | | 6-(7-((2-((2-Methoxy ethyl)amino)-1-(6-methyl pyridin-2-yl)ethyl)amino)thianthren-1-yl)-4-morpholino pyridin-2(1H)-one | 602 | 1.11 | |
| 1-34-3 | | 6-(7-((1-(6-Methyl pyridin-2-yl)-3-(piperidin-1-yl)propyl)amino)thianthren-1-yl)-4-morpholino pyridin-2(1H)-one | 626 | 1.32 | (CDCl$_3$): 8.32 (1H, br s), 7.54 (1H, dd, J = 5.6, 3.6 Hz), 7.47 (1H, t, J = 7.9 Hz), 7.28-7.22 (2H, m), 7.13-7.10 (3H, m), 7.00 (1H, d, J = 7.9 Hz), 6.64 (1H, d, J = 2.3 Hz), 6.36 (1H, dd, J = 8.6, 2.3 Hz), 5.95 (1H, d, J = 2.6 Hz), 5.72 (1H, d, J = 2.6 Hz), 4.48-4.46 (1H, m), 3.81 (4H, t, J = 5.0 Hz), 3.32 (4H, t, J = 5.0 Hz), 2.58 (3H, s), 2.44-2.37 (6H, br m), 2.13-2.07 (1H, br m), 1.93-1.86 (1H, br m), 1.71-1.49 (6H, br m). |
| 1-34-4 | | 6-(7-((1-(6-Methyl pyridin)-2-yl)-3-morpholino propyl)amino)thianthren-1-yl)-4-morpholino pyridin-2(1H)-one | 628 | 1.18 | (CDCl$_3$): 8.47 (1H, br s), 7.55-7.47 (2H, m), 7.28-7.25 (2H, m), 7.14 (1H, d, J = 8.6 Hz), 7.08 (1H, d, J = 7.6 Hz), 7.01 (1H, d, J = 7.6 Hz), 6.70 (1H, d, J = 2.0 Hz), 6.40 (1H, dd, J = 8.6, 2.0 Hz), 5.96 (1H, d, J = 2.0 Hz), 5.72 (1H, d, J = 2.0 Hz), 5.39-5.32 (1H, m), 4.53-4.49 (1H, m), 3.82-3.79 (8H, m), 3.32 (4H, t, J = 5.0 Hz), 2.56 (3H, s), 2.50-2.47 (4H, br m), 2.25-1.88 (2H, br m), 1.33-1.29 (2H, m). |

TABLE 37-continued
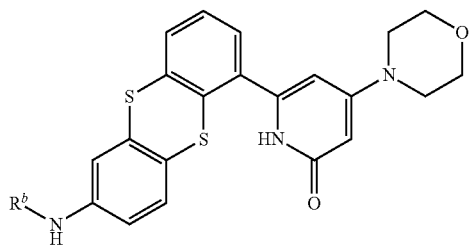
| Example No. | R$^b$ | Compound Name | MS | RT (min) | $^1$H-NMR (300 MHz) (DMSO-d$_6$) δ: |
|---|---|---|---|---|---|
| 1-34-5 | | 6-(7-((3-Hydroxy-1-(6-methyl pyridin-2-yl)propyl)amino)thianthren-1-yl)-4-morpholino pyridin-2(1H)-one | 559 | 0.94 | |
| 1-34-6 | | 6-(7-((1-(6-Methyl pyridin-2-yl)-3-(pyrrolidin-1-yl)propyl)amino)thianthren-1-yl)-4-morpholino pyridin-2(1H)-one | 612 | 1.24 | |
Example 1-35
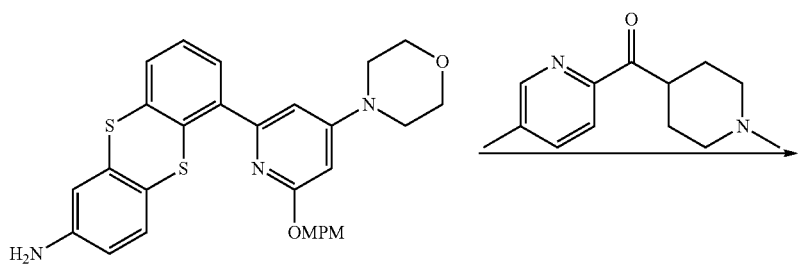
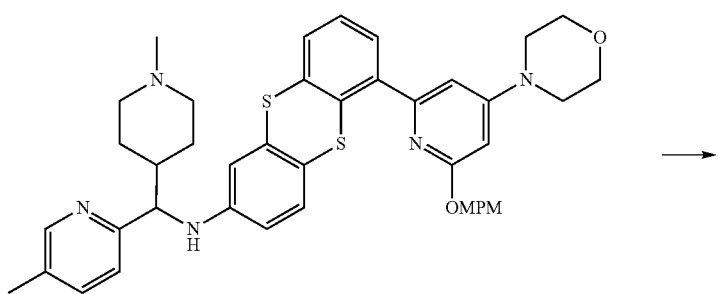

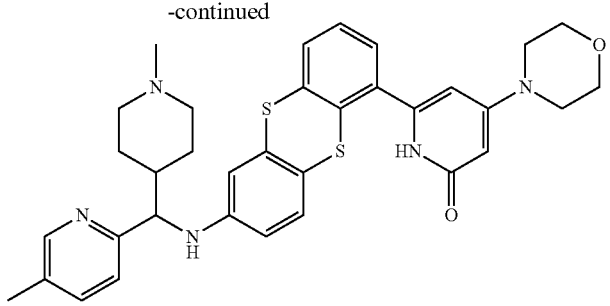

(1)

A solution of 6-(6-((4-methoxybenzyl)oxy)-4-morpholinopyridin-2-yl)thianthrene-2-amine (18 mg) and (1-methylpiperidin-4-yl)(5-methylpyridin-2-yl)methanone (17 mg) in toluene (1 mL) was stirred for 0.5 hours under reflux. Tetraethyl orthotitanate (50 μL) was added thereto, followed by stirring for 20 minutes under reflux. Methanol (0.3 mL) and sodium borohydride (9 mg) were added thereto under ice-cooling, followed by stirring for 10 minutes, and a saturated sodium chloride aqueous solution was added thereto. After the insoluble materials were filtered off, the resultant product was extracted with ethyl acetate, and the organic layer was dried over anhydrous sodium sulfate. The solvent was distilled off under reduced pressure, and the obtained residues were purified by silica gel column chromatography (hexane:ethyl acetate:methanol=1:1:0→0:1:0→0:9:1, NH silica), whereby 6-(6-((4-methoxybenzyl)oxy)-4-morpholinopyridin-2-yl)-N-((1-methylpiperidin-4-yl)(5-methylpyridin-2-yl)methyl)thianthrene-2-amine (16 mg) was obtained.

MS(ESI m/z): 732 (M+H)

RT(min): 1.40

(2)

Trifluoroacetic acid (0.3 mL) was added to a solution of 6-(6-((4-methoxybenzyl)oxy)-4-morpholinopyridin-2-yl)-N-((1-methylpiperidin-4-yl)(5-meth ylpyridin-2-yl)methyl)thianthrene-2-amine (16 mg) obtained in Example 1-35 (1) in chloroform (0.2 mL), followed by stirring at room temperature for 0.5 hours. After a saturated sodium hydrogen carbonate aqueous solution was added thereto, the resultant product was extracted with chloroform, and the organic layer was purified by silica gel column chromatography (chloroform:methanol=97:3, NH silica), and purified by preparative thin layer silica gel chromatography (chloroform:methanol=30:1, NH silica), whereby 6-(7-(((1-methylpiperidin-4-yl)(5-methylpyridin-2-yl)methyl)amino)thianthren-1-yl)-4-morpholinopyridin-2(1H)-one (2.2 mg) was obtained.

$^1$H-NMR (CDCl$_3$, 300 MHz) δ: 8.38 (1H, d, J=2.1 Hz), 7.55-7.53 (1H, m), 7.39 (1H, dd, J=7.6, 2.1 Hz), 7.28-7.23 (2H, m), 7.13-7.09 (2H, m), 6.73 (1H, d, J=2.6 Hz), 6.44 (1H, dd, J=8.6, 2.6 Hz), 5.95 (1H, d, J=2.0 Hz), 5.71 (1H, d, J=2.0 Hz), 4.77 (1H, d, J=7.9 Hz), 4.24 (1H, dd, J=7.9, 7.9 Hz), 3.81 (4H, t, J=4.8 Hz), 3.32 (4H, t, J=4.8 Hz), 2.89-2.79 (2H, m), 2.28 (3H, s), 2.23 (3H, s), 1.92-1.25 (7H, m).

MS(ESI m/z): 612 (M+H)

RT(min): 0.95

Example 1-36-1

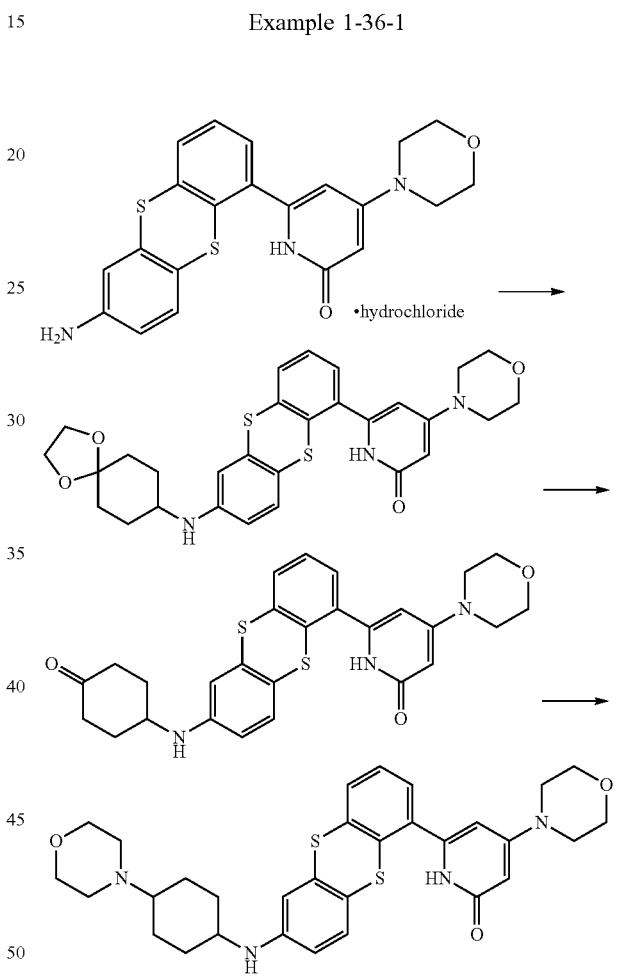

(1)

In the same manner as in Example 1-12-1, the following compounds were obtained.

6-(7-(1,4-dioxaspiro[4.5]decan-8-ylamino)thianthren-1-yl)-4-morpholinopyridin-2(1H)-one MS(ESI m/z): 550 (M+H)

RT(min): 1.36

(2)

2 mol/L hydrochloric acid (3 mL) was added to 6-(7-(1,4-dioxaspiro[4.5]decan-8-ylamino)thianthren-1-yl)-4-morpholinopyridin-2(1H)-one (40 mg) obtained in Example 1-36-1 (1), followed by refluxing for 5 hours. Sodium hydrogen carbonate was added to the reaction mixture, then, the resultant product was extracted with chloroform, and the organic layer was dried over anhydrous sodium sulfate. The solvent was distilled off under reduced pressure, whereby 4-morpholino-6-(7-((4-oxocyclohexyl)amino)thianthren-1-yl)pyridin-2(1H)-one was obtained.

MS(ESI m/z): 506 (M+H)
RT(min): 1.24

(3)

In the same manner as in Example 1-12-1, the following compound was obtained.

4-Morpholino-6-(7-((4-morpholinocyclohexyl)amino)thianthren-1-yl)pyridin-2(1H)-one (diastereomer mixture)

MS(ESI m/z): 577 (M+H)
RT(min): 0.95, 1.02

Example 1-36-2

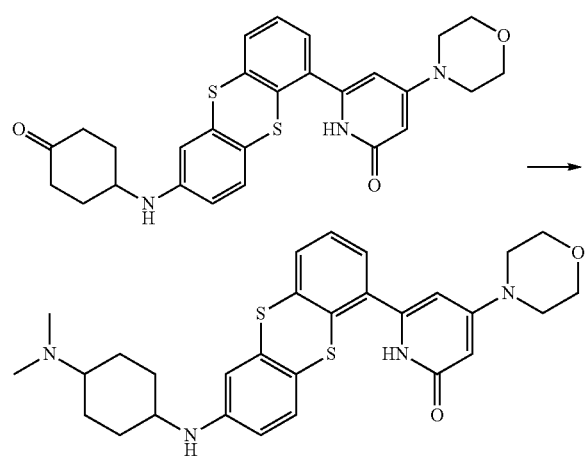

In the same manner as in Example 1-36-1 (3), the following compound was obtained.

6-(7-((4-(Dimethylamino)cyclohexyl)amino)thianthren-1-yl)-4-morpholinopyridin-2(1H)-one (diastereomer mixture)

MS(ESI m/z): 535 (M+H)
RT(min): 0.95, 1.02

Example 1-37-1

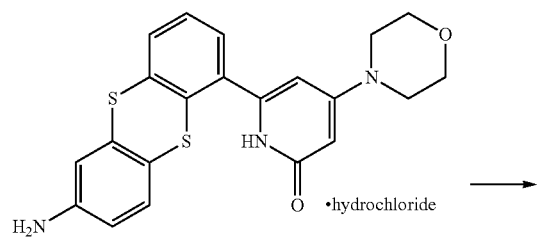

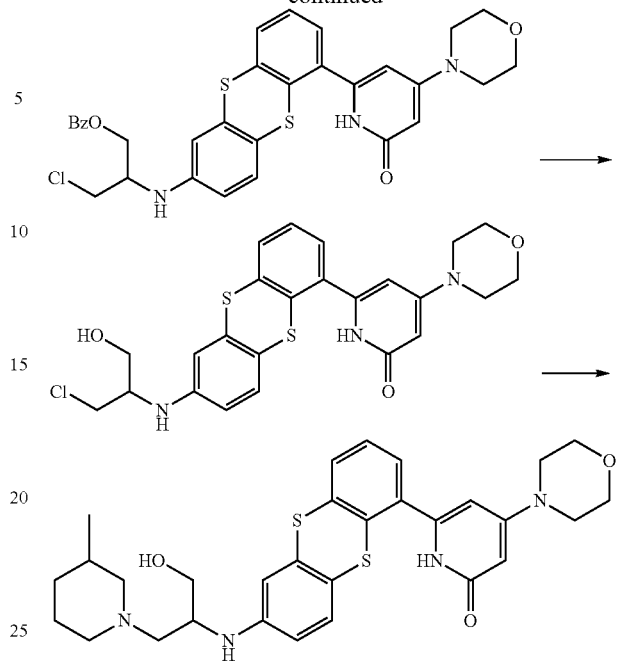

(1)
In the same manner as in Example 1-12-1, the following compounds were obtained.

3-Chloro-2-((6-(4-morpholino-6-oxo-1,6-dihydropyridin-2-yl)thianthren-2-yl)amino)propylbenzoate MS(ESI m/z): 606 (M+H)
RT(min): 1.55

(2)
A 2 mol/L sodium hydroxide aqueous solution (1 mL) was added to a solution of 3-chloro-2-((6-(4-morpholino-6-oxo-1,6-dihydropyridin-2-yl)thianthren-2-yl)amino)propylbenzoate (74 mg) obtained in Example 1-37-1 (1) in methanol (1 mL) and tetrahydrofuran (1 mL), followed by stirring at room temperature for 2.5 hours. The solvent was distilled off under reduced pressure, then, a saturated sodium chloride aqueous solution was added to the obtained residues, and the resultant product was extracted with ethyl acetate, whereby 6-(7-((1-chloro-3-hydroxypropan-2-yl)amino)thianthren-1-yl)-4-morpholinopyridin-2(1H)-one (300 mg) was obtained.
MS(ESI m/z): 502 (M+H)
RT(min): 1.21

(3)
3-Methyl piperidine (41 mg) and sodium iodide (10 mg) were added to a solution of 6-(7-((1-chloro-3-hydroxypropan-2-yl)amino)thianthren-1-yl)-4-morpholinopyridin-2(1H)-one (100 mg) obtained in Example 1-37-1 (2) in N-methyl pyrrolidone (1 mL), and the resultant product was irradiated with microwaves (microwave reaction apparatus, 130° C., 0.7 hours, 2.45 GHz, 0 W to 240 W). 3-Methyl piperidine (1 mL) was added to the reaction mixture, and the resultant product was irradiated with microwaves (microwave reaction apparatus, 180° C., 0.5 hours, 2.45 GHz, 0 W to 240 W). The reaction mixture was cooled to room temperature, and was purified by preparative reversed phase HPLC (0.1% formic acid aqueous solution-0.1% solution of formic acid in acetonitrile), whereby 6-(7-((1-hydroxy-3-(3-methylpiperidin-1-yl)propan-2-yl)amino)thianthren-1-yl)-4-morpholinopyridin-2(1H)-one (3.0 mg) was obtained.
MS(ESI m/z): 565 (M+H)
RT(min): 1.03

Examples 1-37-2 to 1-37-7

In the same manner as in Example 1-37-1, the following compounds were obtained.

TABLE 38

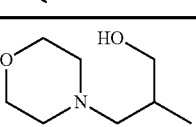

| Example No. | R$^b$ | Compound Name | MS | RT (min) | $^1$H-NMR (300 MHz) (DMSO-d$_6$) δ: |
|---|---|---|---|---|---|
| 1-37-2 | 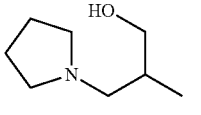 | 6-(7-((1-Hydroxy-3-morpholino propan-2-yl)amino)thianthren-1-yl)-4-morpholino pyridin-2(1H)-one | 553 | 0.89 | |
| 1-37-3 | | 6-(7-((1-Hydroxy-3-(pyrrolidin-1-yl)propan-2-yl)amino)thianthren-1-yl)-4-morpholino pyridin-2(1H)-one | 537 | 0.92 | |
| 1-37-4 | | 6-(7-((1-Hydroxy-3-(piperidin-1-yl)propan-2-yl)amino)thianthren-1-yl)-4-morpholino pyridin-2(1H)-one | 551 | 0.95 | |
| 1-37-5 | | 6-(7-((1-(3,5-Dimethyl piperidin-1-yl)-3-hydroxy propan-2-yl)amino)thianthren-1-yl)-4-morpholino pyridin-2(1H)-one | 579 | 1.07 | |
| 1-37-6 | | 6-(7-((1-Hydroxy-3-(2-methyl piperidin-1-yl)propan-2-yl)amino)thianthren-1-yl)-4-morpholino pyridin-2(1H)-one (Diastereomer A) | 565 | 1.02 | |
| 1-37-7 | | 6-(7-((1-Hydroxy-3-(2-methyl piperidin-1-yl)propan-2-yl)amino)thianthren-1-yl)-4-morpholino pyridin-2(1H)-one (Diastereomer B) | 565 | 0.99 | |

Example 1-38

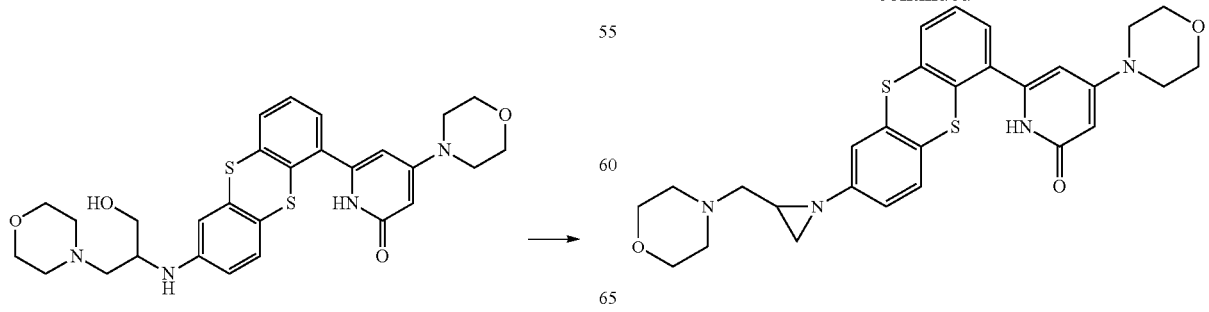

Bis(2-methoxyethyl)aminosulfur trifluoride (1.2 mg) was added to a solution of 6-(7-((1-hydroxy-3-morpholinopropan-2-yl)amino)thianthren-1-yl)-4-morpholinopyridin-2 (1H)-one (3 mg) in dichloromethane (1 mL) at −78° C., followed by stirring for 3 hours. A saturated sodium hydrogen carbonate aqueous solution was added to the reaction mixture, then, the resultant product was extracted with dichloromethane, and the organic layer was dried over anhydrous sodium sulfate. The solvent was distilled off under reduced pressure, and the obtained residues were purified by preparative thin layer silica gel chromatography (chloroform:ethanol=30:1, NH silica), whereby 4-morpholino-6-(7-(2-(morpholinomethyl)aziridin-1-yl)thianthren-1-yl)pyridin-2(1H)-one (3 mg) was obtained.

MS(ESI m/z): 535 (M+H)
RT(min): 0.93

Example 1-39

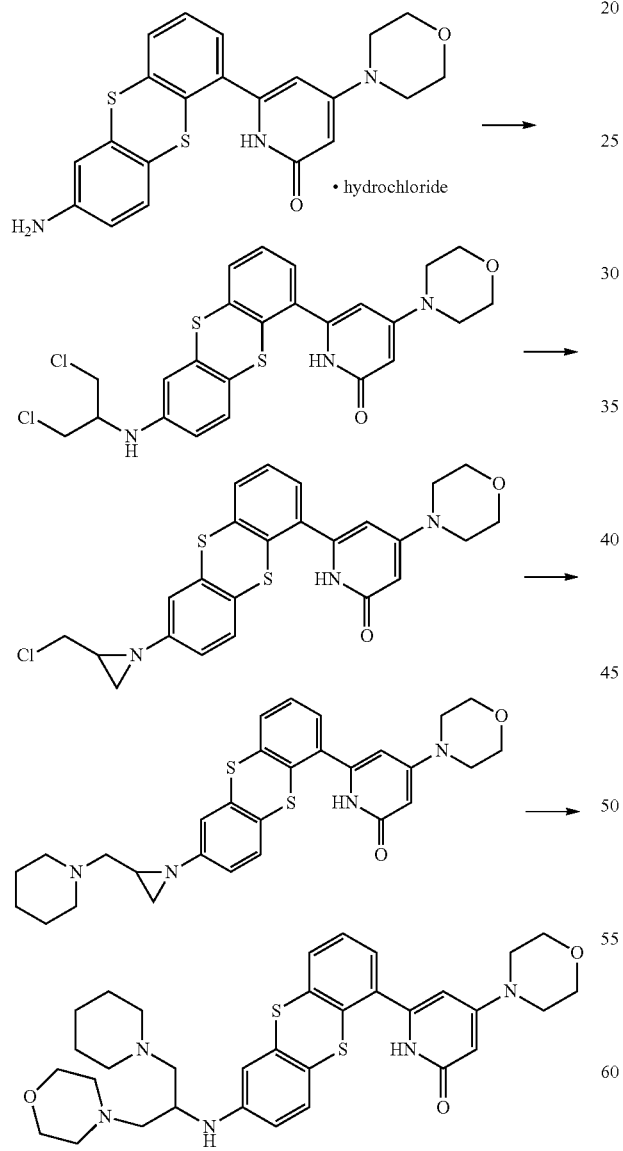

(1)
In the same manner as in Example 1-12-1, the following compound was obtained.

6-(7-((1,3-Dichloropropan-2-yl)amino)thianthren-1-yl)-4-morpholinopyridin-2(1H)-one MS(ESI m/z): 520 (M+H)
RT(min): 1.50

(2)
Sodium methoxide (50 mg) and sodium iodide (10 mg) were added to a solution of 6-(7-((1,3-dichloropropan-2-yl)amino)thianthren-1-yl)-4-morpholinopyridin-2(1H)-one (10 mg) obtained in Example 1-39 (1) in tetrahydrofuran (2 mL), followed by stirring at 60° C. for 4 hours. Methanol (1 mL) and sodium methoxide (50 mg) were added to the reaction mixture, followed by refluxing for 4 hours. After the reaction mixture was cooled to room temperature, the solvent was distilled off under reduced pressure, then, water was added to the obtained residues, and the resultant product was extracted with ethyl acetate. The solvent was distilled off under reduced pressure, whereby 6-(7-(2-(chloromethyl)aziridin-1-yl)thianthren-1-yl)-4-morpholinopyridin-2(1H)-one (4 mg) was obtained.

MS(ESI m/z): 484 (M+H)
RT(min): 1.37

(3)
Sodium iodide (15 mg) was added to a solution of 6-(7-(2-(chloromethyl)aziridin-1-yl)thianthren-1-yl)-4-morpholinopyridin-2(1H)-one (3 mg) obtained in Example 1-39 (2) in piperidine (2 mL), followed by stirring at 70° C. for 10 hours. After the reaction mixture was cooled to room temperature, water was added thereto, and the resultant product was extracted with ethyl acetate. The solvent was distilled off under reduced pressure, whereby 4-morpholino-6-(7-(2-(piperidin-1-ylmethyl)aziridin-1-yl)thianthren-1-yl)pyridin-2(1H)-one was obtained.

MS(ESI m/z): 533 (M+H)
RT(min): 0.96

(4)
A solution of 4-morpholino-6-(7-(2-(piperidin-1-ylmethyl)aziridin-1-yl)thianthren-1-yl)pyridin-2(1H)-one obtained in Example 1-39 (3) in morpholine (1 mL) was irradiated with microwaves (microwave reaction apparatus, 160° C., 0.5 hours, 2.45 GHz, 0 W to 240 W). The reaction mixture was cooled to room temperature, and was purified by preparative reversed phase HPLC (0.1% formic acid aqueous solution-0.1% solution of formic acid in acetonitrile), whereby 4-morpholino-6-(7-((1-morpholino-3-(piperidin-1-yl)propan-2-yl)amino)thianthren-1-yl)pyridin-2(1H)-one (0.9 mg) was obtained.

MS(ESI m/z): 620 (M+H)
RT(min): 1.00

Example 1-40

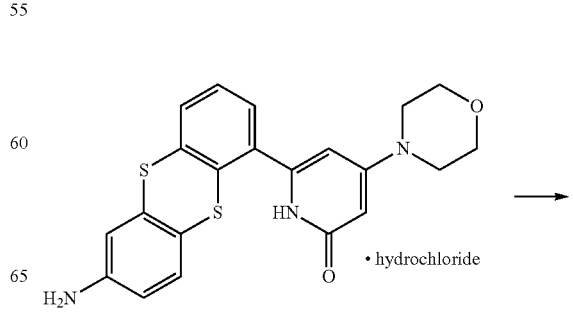

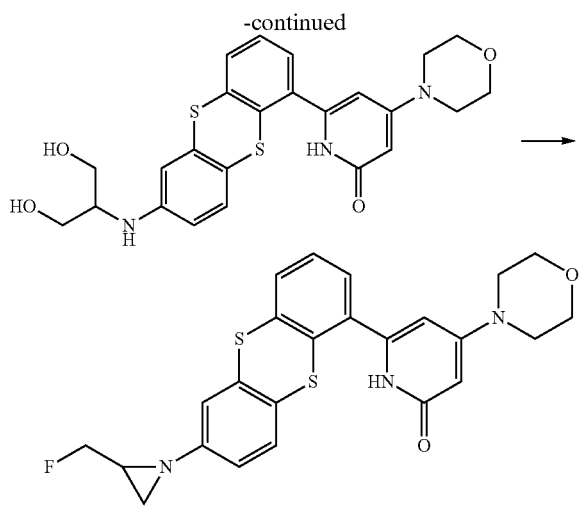

(1)

In the same manner as in Example 1-12-1, the following compound was obtained.

6-(7-((1,3-dihydroxypropan-2-yl)amino)thianthren-1-yl)-4-morpholinopyridin-2(1H)-one MS(ESI m/z): 484 (M+H)

RT(min): 0.97

(2)

A solution of bis(2-methoxyethyl)aminosulfur trifluoride (31 mg) in dichloromethane (0.5 mL) was added to a solution of 6-(7-((1,3-dihydroxypropan-2-yl)amino)thianthren-1-yl)-4-morpholinopyridin-2(1H)-one (27 mg) obtained in Example 1-40 (1) in dichloromethane (4 mL) at −78° C., followed by stirring for 6.5 hours. A saturated sodium hydrogen carbonate aqueous solution was added to the reaction mixture, then, the resultant product was extracted with dichloromethane, and the organic layer was dried over anhydrous sodium sulfate. The solvent was distilled off under reduced pressure, and the obtained residues were purified by preparative thin layer silica gel chromatography (chloroform:ethanol=30:1, NH silica), whereby 6-(7-(2-(fluoromethyl)aziridin-1-yl)thianthren-1-yl)-4-morpholinopyridin-2(1H)-one (8.6 mg) was obtained.

MS(ESI m/z): 468 (M+H)

RT(min): 1.27

Example 1-41-1

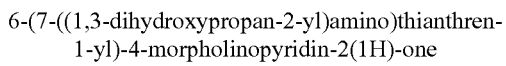

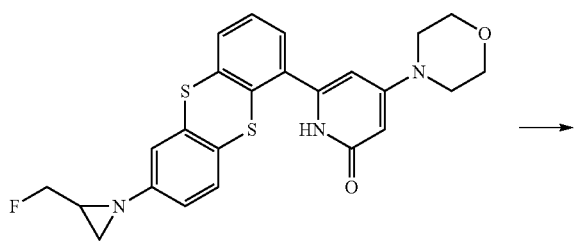

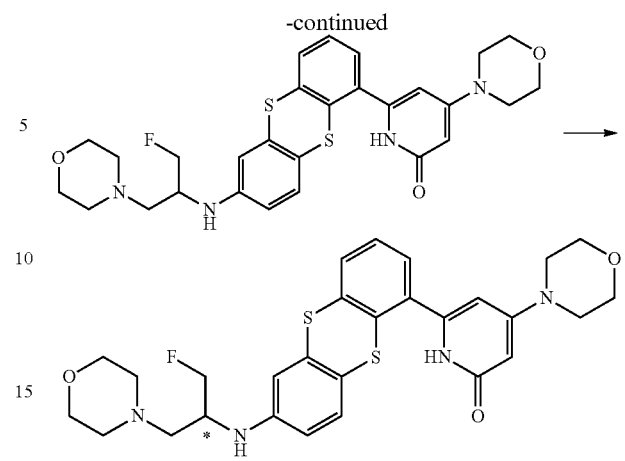

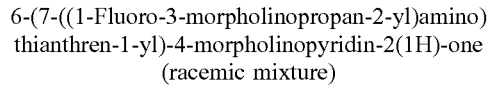

In the same manner as in Example 1-16-1-1, the following compound was obtained.

6-(7-((1-Fluoro-3-morpholinopropan-2-yl)amino)thianthren-1-yl)-4-morpholinopyridin-2(1H)-one (racemic mixture)

¹H-NMR (CD₃OD, 300 MHz) δ: 7.62-7.58 (1H, m), 7.34-7.32 (2H, m), 7.16 (1H, d, J=8.6 Hz), 6.87 (1H, d, J=2.6 Hz), 6.60 (1H, dd, J=8.6, 2.6 Hz), 6.22 (1H, d, J=2.6 Hz), 5.75 (1H, d, J=2.0 Hz), 4.62-4.34 (2H, m), 3.78 (4H, t, J=4.6 Hz), 3.65 (4H, t, J=4.6 Hz), 3.42-3.35 (5H, m), 2.64-2.38 (6H, m).

MS(ESI m/z): 555 (M+H)

RT(min): 0.97

Examples 1-41-1-2 and 1-41-1-3

Chiral resolution was performed on 6-(7-((1-fluoro-3-morpholinopropan-2-yl)amino)thianthren-1-yl)-4-morpholinopyridin-2(1H)-one (racemic mixture) obtained in Example 1-41-1-1 by supercritical fluid chromatography, whereby an optically active substance A and an optically active substance B were obtained.

Example 1-41-1-2

Optically Active Substance A

¹H-NMR (CD₃OD, 300 MHz) δ: 7.62-7.58 (1H, m), 7.34-7.32 (2H, m), 7.16 (1H, d, J=8.6 Hz), 6.87 (1H, d, J=2.6 Hz), 6.60 (1H, dd, J=8.6, 2.6 Hz), 6.22 (1H, d, J=2.6 Hz), 5.75 (1H, d, J=2.0 Hz), 4.62-4.34 (2H, m), 3.78 (4H, t, J=4.6 Hz), 3.65 (4H, t, J=4.6 Hz), 3.42-3.35 (5H, m), 2.64-2.38 (6H, m).

MS(ESI m/z): 555 (M+H)

RT(min): 0.97

Example 1-41-1-3

Optically Active Substance B

¹H-NMR (CD₃OD, 300 MHz) δ: 7.62-7.58 (1H, m), 7.34-7.32 (2H, m), 7.16 (1H, d, J=8.6 Hz), 6.87 (1H, d, J=2.6 Hz), 6.60 (1H, dd, J=8.6, 2.6 Hz), 6.22 (1H, d, J=2.6 Hz), 5.75 (1H, d, J=2.0 Hz), 4.62-4.34 (2H, m), 3.78 (4H, t, J=4.6 Hz), 3.65 (4H, t, J=4.6 Hz), 3.42-3.35 (5H, m), 2.64-2.38 (6H, m).

MS(ESI m/z): 555 (M+H)
RT(min): 0.97
(Supercritical Fluid Chromatography Conditions)
Column: CHIRALCEL OJ-H (manufactured by Daicel Chemical Industries, Ltd.)
Mobile phase: carbon dioxide/0.1% diethylamine-containing methanol (volume ratio: 70/30)
Flow rate: 20 mL/min
Detection wavelength: 254 nm
Temperature: 40° C.
Retention time: 9.22 min (optically active substance A), 12.08 min (optically active substance B)

Example 1-41-2

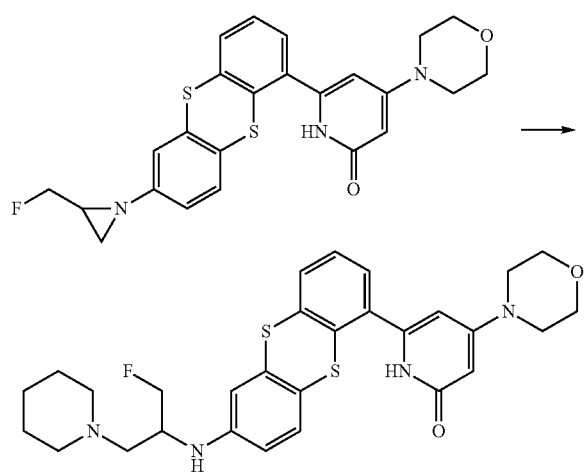

In the same manner as in Example 1-41-1-1, the following compound was obtained.

6-(7-((1-Fluoro-3-(piperidin-1-yl)propan-2-yl)amino)thianthren-1-yl)-4-morpholinopyridin-2(1H)-one $^1$H-NMR (CD$_3$OD, 300 MHz) δ: 7.65-7.58 (1H, m), 7.38-7.31 (2H, m), 7.22 (1H, d, J=8.6 Hz), 6.95 (1H, d, J=2.6 Hz), 6.68 (1H, dd, J=8.6, 2.6 Hz), 6.23 (1H, d, J=2.6 Hz), 5.75 (1H, d, J=2.0 Hz), 4.51 (1H, brs), 4.35 (1H, brs), 3.78 (4H, t, J=5.0 Hz), 3.39 (4H, t, J=5.0 Hz), 3.36-3.26 (1H, m), 3.22-3.01 (6H, m), 1.79 (4H, dd, J=10.6, 5.3 Hz), 1.61 (2H, d, J=6.6 Hz).
MS(ESI m/z): 553 (M+H)
RT(min): 1.02

Example 1-42-1

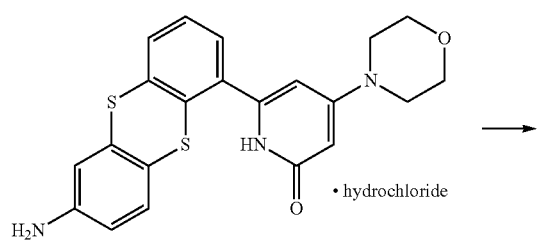

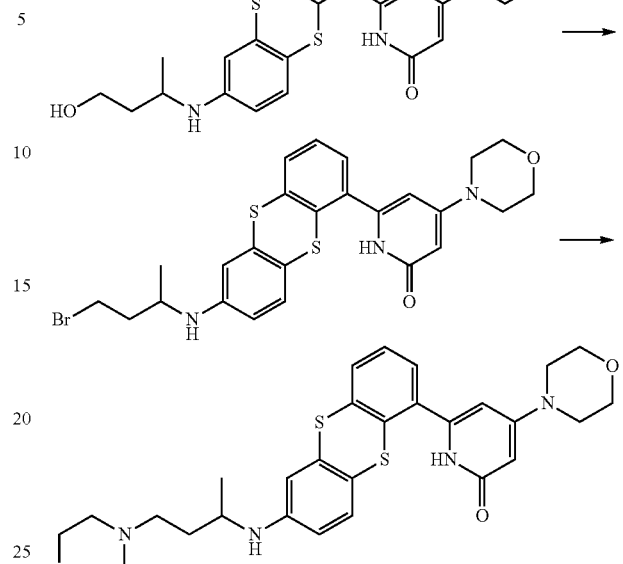

(1)
In the same manner as in Example 1-12-1, the following compound was obtained.

6-(7-((4-Hydroxybutan-2-yl)amino)thianthren-1-yl)-4-morpholinopyridin-2(1H)-one

MS(ESI m/z): 482 (M+H)
RT(min): 1.13
(2)
Carbon tetrabromide (123 mg) and triphenyl phosphine (98 mg) were added to a solution of 6-(7-((4-hydroxybutan-2-yl)amino)thianthren-1-yl)-4-morpholinopyridin-2(1H)-one (60 mg) obtained in Example 1-42-1 (1) in dichloromethane (2 mL), followed by stirring for 1 hour. The solvent was distilled off under reduced pressure, and the residues were purified by silica gel column chromatography (ethyl acetate:methanol=1:0→5:1, chloroform:methanol=10:1), whereby 6-(7-((4-bromobutan-2-yl)amino)thianthren-1-yl)-4-morpholinopyridin-2(1H)-one (120 mg) was obtained.
MS(ESI m/z): 546 (M+H)
RT(min): 1.54
(3)
In the same manner as in Example 1-16-1-1, the following compound was obtained.

4-Morpholino-6-(7-((4-morpholinobutan-2-yl)amino)thianthren-1-yl)pyridin-2(1H)-one $^1$H-NMR (CDCl$_3$, 300 MHz) δ: 7.56 (1H, dd, J=6.9, 2.3 Hz), 7.32-7.24 (2H, m), 7.17 (1H, d, J=8.6 Hz), 6.76 (1H, d, J=2.6 Hz), 6.44 (1H, dd, J=8.6, 2.6 Hz), 5.98 (1H, d, J=2.6 Hz), 5.70 (1H, d, J=2.6 Hz), 4.26-4.01 (1H, m), 3.81 (4H, t, J=5.0 Hz), 3.74 (4H, t, J=4.3 Hz), 3.37-3.28 (5H, m), 2.54-2.32 (6H, m), 2.05-1.57 (2H, m), 1.20 (3H, t, J=5.0 Hz).
MS(ESI m/z): 551 (M+H)
RT(min): 0.96

Examples 1-42-2 to 1-42-4

In the same manner as in Example 1-42-1, the following compound was obtained.

TABLE 39

| Example No. | R$^b$ | Compound Name | MS | RT (min) | $^1$H-NMR (300 MHz) (DMSO-d$_6$) δ: |
|---|---|---|---|---|---|
| 1-42-2 | | 6-(7-((4-(4-Methyl piperazin-1-yl)butan-2-yl) amino)thianthren-1-yl)-4-morpholino pyridin-2(1H)-one | 564 | 0.92 | |
| 1-42-3 | | 4-Morpholino-6-(7-((4-(piperidin-1-yl)butan-2-yl) amino)thianthren-1-yl) pyridin-2(1H)-one | 549 | 1.02 | |
| 1-42-4 | | 4-Morpholino-6-(7-((4-(pyrrolidin-1-yl)butan-2-yl) amino)thianthren-1-yl) pyridin-2(1H)-one | 535 | 0.99 | |

Example No. 1-43-1

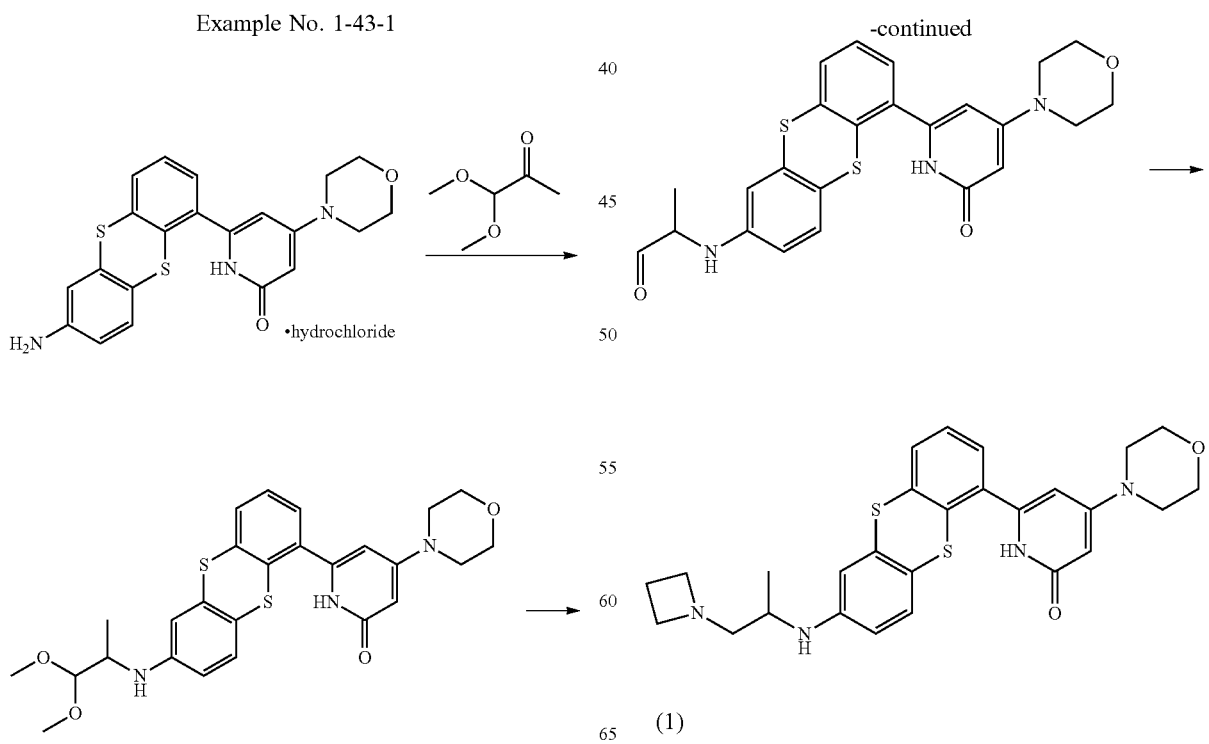

(1)

In the same manner as in Example 1-12-1, the following compound was obtained.

6-(7-((1,1-Dimethoxypropan-2-yl)amino)thianthren-1-yl)-4-morpholinopyridin-2(1H)-one MS(ESI m/z): 512 (M+H)
RT(min): 1.36

(2)

Water (50 µL) and lithium tetrafluoroborate (28 mg) were added to a solution of 6-(7-((1,1-dimethoxypropan-2-yl)amino)thianthren-1-yl)-4-morpholinopyridin-2(1H)-one (129 mg) obtained in Example 1-43-1 (1) in acetonitrile (2.5 mL), followed by stirring at 80° C. for 0.5 hours. After the reaction mixture was cooled to room temperature, a saturated sodium chloride aqueous solution was added thereto, and the resultant product was extracted with ethyl acetate, followed by drying over anhydrous sodium sulfate. The solvent was distilled off under reduced pressure, whereby 2-((6-(4-morpholino-6-oxo-1,6-dihydropyridin-2-yl)thianthren-2-yl)amino)propanal (90 mg) was obtained.

MS(ESI m/z): 466 (M+H)
RT(min): 1.18

(3)

Azetidine (50 µL) and 2-picoline borane (3 mg) were added to a solution of 2-((6-(4-morpholino-6-oxo-1,6-dihydropyridin-2-yl)thianthren-2-yl)amino)propanal (10 mg) obtained in Example 1-43-1 (2) in acetic acid (9 µL) and methanol (91 µL), followed by stirring at 80° C. for 1 hour. After the reaction mixture was cooled to room temperature, a saturated sodium hydrogen carbonate aqueous solution was added thereto, then, the resultant product was extracted with chloroform, and the organic layer was dried over anhydrous sodium sulfate. The solvent was distilled off under reduced pressure, and the obtained residues were purified by silica gel column chromatography (chloroform:methanol=1:0→97:3, NH silica), whereby 6-(7-((1-(azetidin-1-yl)propan-2-yl)amino)thianthren-1-yl)-4-morpholinopyridin-2(1H)-one (1.1 mg) was obtained.

MS(ESI m/z): 507 (M+H)
RT(min): 0.94

Examples 1-43-2 to 1-43-8

In the same manner as in Example 1-43-1, the following compounds were obtained.

TABLE 40

| Example No. | $R^b$ | Compound Name | MS | RT (min) | $^1$H-NMR (300 MHz) (DMSO-$d_6$) δ: |
|---|---|---|---|---|---|
| 1-43-2 | | 6-(7-((1-(2-Oxa-6-azaspiro[3.3]heptan-6-yl)propan-2-yl)amino)thianthren-1-yl)-4-morpholino pyridin-2(1H)-one | 549 | 0.91 | |
| 1-43-3 | | 6-(7-((1-(3-Methoxy azetidin-1-yl)propan-2-yl)amino)thianthren-1-yl)-4-morpholino pyridin-2(1H)-one | 537 | 0.95 | |
| 1-43-4 | | 6-(7-((1-(3,3-Difluoroazetidin-1-yl)propan-2-yl)amino)thianthren-1-yl)-4-morpholino pyridin-2(1H)-one | 543 | 1.02 | |
| 1-43-5 | | 4-Morpholino-6-(7-((1-(pyrrolidin-1-yl)propan-2-yl)amino)thianthren-1-yl) pyridin-2(1H)-one | 521 | 0.98 | |
| 1-43-6 | | 6-(7-((1-((S)-2-(Methoxymethyl)pyrrolidin-1-yl)propan-2-yl)amino)thianthren-1-yl)-4-morpholino pyridin-2(1H)-one | 565 | 1.08 | |

TABLE 40-continued

| Example No. | $R^b$ | Compound Name | MS | RT (min) | $^1$H-NMR (300 MHz) (DMSO-$d_6$) δ: |
|---|---|---|---|---|---|
| 1-43-7 | | 6-(7-((1-(3,3-Difluoropyrrolidin-1-yl)propan-2-yl)amino)thianthren-1-yl)-4-morpholino pyridin-2(1H)-one | 557 | 1.03 | |
| 1-43-8 | | 6-(7-((4-((S)-2-Methyl morpholino)propan-2-yl)amino)thianthren-1-yl)-4-morpholino pyridin-2(1H)-one | 551 | 0.87 | |

Example 1-44-1

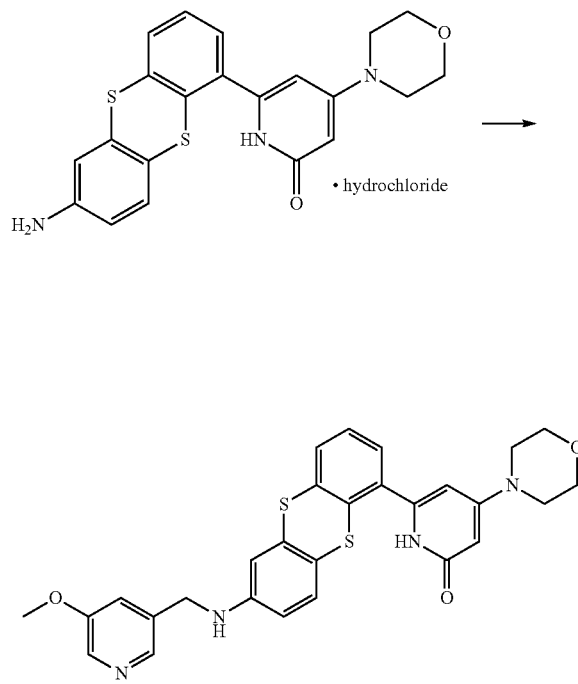

Acetic acid (0.3 mL), 5-methoxynicotinic aldehyde (7 mg), and sodium triacetoxyborohydride (21 mg) were added to a solution of 6-(7-aminothianthren-1-yl)-4-morpholin-opyridin-2(1H)-one (10 mg) in dichloromethane (3 mL), followed by stirring at room temperature for 2 hours. Dichloromethane was added to the reaction mixture, and the organic layer was washed with a saturated sodium hydrogen carbonate aqueous solution, and dried over anhydrous sodium sulfate. The solvent was distilled off under reduced pressure, and the obtained residues were purified by silica gel column chromatography (ethyl acetate:methanol=19:1→4:1, NH silica), whereby 6-(7-(((5-methoxypyridin-3-yl)methyl)amino)thianthren-1-yl)-4-morpholinopyridin-2(1H)-one (1.0 mg) was obtained as a white solid.

$^1$H-NMR (CDCl$_3$, 300 MHz) δ: 8.23 (1H, d, J=3.0 Hz), 8.21 (1H, d, J=1.7 Hz), 7.56 (1H, t, J=4.6 Hz), 7.30-7.25 (2H, m), 7.22 (1H, d, J=8.6 Hz), 7.16 (1H, t, J=2.1 Hz), 6.77 (1H, d, J=2.3 Hz), 6.50 (1H, dd, J=8.4, 2.5 Hz), 5.98 (1H, d, J=2.3 Hz), 5.73 (1H, d, J=2.6 Hz), 4.34 (2H, d, J=5.3 Hz), 3.84 (3H, s), 3.82 (4H, t, J=5.0 Hz), 3.33 (4H, t, J=5.0 Hz).

MS(ESI m/z): 531 (M+H)

RT(min): 1.01

Examples 1-44-2 to 1-44-6

In the same manner as in Example 1-44-1, the following compounds were obtained.

TABLE 41

| Example No. | R$^b$ | Compound Name | MS | RT (min) | $^1$H-NMR (300 MHz) (DMSO-d$_6$) δ: |
|---|---|---|---|---|---|
| 1-44-2 | 6-chloropyridin-3-yl methyl | 6-(7-(((6-Chloropyridin-3-yl)methyl)amino)thianthren-1-yl)-4-morpholino pyridin-2(1H)-one | 535 | 1.33 | 10.99 (1H, br s), 8.38 (1H, d, J = 2.3 Hz), 7.77 (1H, dd, J = 8.3, 2.3 Hz), 7.60 (1H, dd, J = 5.9, 3.3 Hz), 7.46 (1H, d, J = 7.9 Hz), 7.36-7.31 (2H, m), 7.17 (1H, d, J = 8.6 Hz), 6.79 (1H, d, J = 2.3 Hz), 6.67 (1H, t, J = 5.9 Hz), 6.52 (1H, dd, J = 8.6, 2.6 Hz), 6.01 (1H, s), 5.49 (1H, s), 4.33 (2H, d, J = 6.3 Hz), 3.66 (4H, t, J = 5.3 Hz), 3.25 (4H, t, J = 4.6 Hz). |
| 1-44-3 | 2-methylpyridin-4-yl methyl | 6-(7-(((2-Methyl pyridin-4-yl)methyl)amino)thianthren-1-yl)-4-morpholino pyridin-2(1H)-one | 515 | 0.91 | 10.99 (1H, br s), 8.33 (1H, d, J = 5.0 Hz), 7.60 (1H, t, J = 4.5 Hz), 7.35-7.31 (2H, m), 7.19-7.13 (2H, m), 7.09 (1H, d, J = 4.6 Hz), 6.74 (1H, d, J = 2.6 Hz), 6.71 (1H, t, J = 6.1 Hz), 6.48 (1H, dd, J = 8.4, 2.5 Hz), 5.99 (1H, s), 5.47 (1H, s), 4.28 (2H, d, J = 5.9 Hz), 3.66 (4H, t, J = 4.3 Hz), 3.25 (4H, t, J = 4.3 Hz), 2.41 (3H, s). |
| 1-44-4 | 2-methoxypyridin-4-yl methyl | 6-(7-(((2-Methoxy pyridin-4-yl)methyl amino)thianthren-1-yl)-4-morpholino pyridin-2(1H)-one | 531 | 1.28 | 10.98 (1H, br s), 8.06 (1H, d, J = 5.3 Hz), 7.60 (1H, dd, J = 5.8, 3.1 Hz), 7.35-7.30 (2H, m), 7.16 (1H, d, J = 8.6 Hz), 6.91 (1H, d, J = 5.3 Hz), 6.76-6.68 (3H, m), 6.48 (1H, dd, J = 8.6, 2.6 Hz), 6.01 (1H, s), 5.49 (1H, s), 4.29 (2H, d, J = 6.3 Hz), 3.80 (3H, s), 3.66 (4H, t J = 4.6 Hz), 3.25 (4H, t, J = 4.8 Hz). |
| 1-44-5 | 1-methylpiperidin-4-yl | 6-(7-((1-Methyl piperidin-4-yl)amino)thianthren-1-yl)-4-morpholino pyridin-2(1H)-one | 507 | 0.89 | (CDCl$_3$): 7.57 (1H, t, J = 4.5 Hz), 7.29 (1H, s), 7.27 (1H, s), 7.20 (1H, d, J = 8.6 Hz), 6.74 (1H, d, J = 2.3 Hz), 6.45 (1H, dd, J = 8.4, 2.5 Hz), 5.97 (1H, d, J = 2.6 Hz), 5.72 (1H, d, J = 2.6 Hz), 3.82 (4H, t, J = 5.0 Hz), 3.33 (4H, t, J = 5.0 Hz), 2.79 (2H, d, J = 11.9 Hz), 2.30 (3H, s), 2.12 (2H, t, J = 11.6 Hz), 2.00 (1H, br s), 1.68-1.42 (4H, br m). |
| 1-44-6 | tert-butyl pyrazole-pyridinyl | tert-Butyl 4-(5-(((6-(4-morpholino-6-oxo-1,6-dihydropyridin-2-yl)thianthren-2-yl)amino)methyl)pyridin-3-yl)-1H-pyrazole-1-carboxylate | 667 | 1.29 | (CDCl$_3$): 8.71 (1H, d, J = 2.0 Hz), 8.51 (1H, d, J = 2.0 Hz), 8.36 (1H, s), 7.99 (1H, s), 7.77 (1H, s), 7.54 (1H, dd, J = 6.8, 2.5 Hz), 7.29 (2H, s), 7.20 (1H, d, J = 8.6 Hz), 6.78 (1H, d, J = 2.6 Hz), 6.51 (1H, dd, J = 8.4, 2.5 Hz), 5.97 (1H, d, J = 2.3 Hz), 5.68 (1H, s), 4.38 (2H, s), 3.80 (4H, t, J = 4.6 Hz), 3.30 (4H, t, J = 4.1 Hz), 1.68 (9H, s). |

Example 1-45

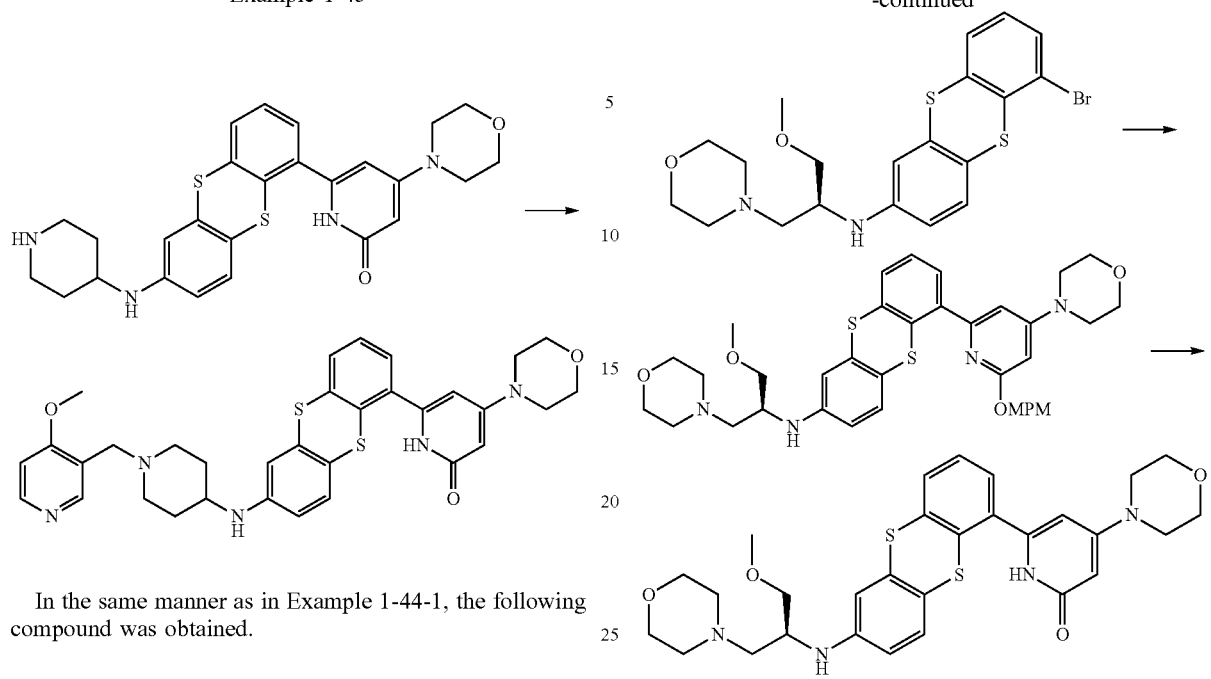

In the same manner as in Example 1-44-1, the following compound was obtained.

6-(7-((1-((4-Methoxypyridin-3-yl)methyl)piperidin-4-yl)amino)thianthren-1-yl)-4-morpholinopyridin-2(1H)-one MS(ESI m/z): 614 (M+H)
RT(min): 0.88

Example 1-46-1

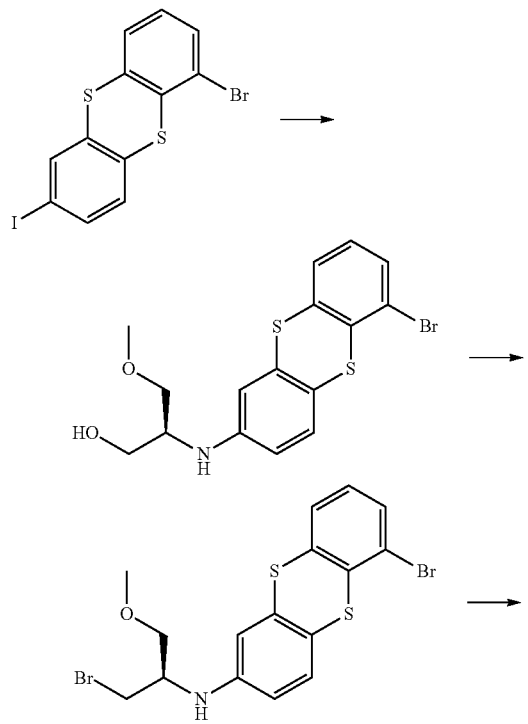

(1)

Copper (I) iodide (108 mg) and potassium phosphate (503 mg) were added to a solution of hydrochloride (167 mg) of 1-bromo-7-iodo thianthrene (140 mg) and (S)-2-amino-3-methoxy propane-1-ol in 2-propanol (2.4 mL) and ethylene glycol (0.6 mL), and the resultant product was irradiated with microwaves (microwave reaction apparatus, 100° C., 0.8 hours, 2.45 GHz, 0 W to 240 W), and irradiated with microwaves (microwave reaction apparatus, 110° C., 0.8 hours, 2.45 GHz, 0 W to 240 W). Copper (I) iodide (100 mg) was added to the reaction mixture, and the resultant product was irradiated with microwaves (Initiator™, 100° C., 1 hour, 2.45 GHz, 0 W to 240 W), and irradiated with microwaves (microwave reaction apparatus, 120° C., 1 hour, 2.45 GHz, 0 W to 240 W). The reaction mixture was cooled to room temperature, an aqueous saturated ammonium chloride solution was added thereto, and then extraction thereof was performed using ethyl acetate. The solvent was distilled off under reduced pressure, and the obtained residues were purified by silica gel column chromatography (hexane:ethyl acetate=1:0→0:1), whereby (S)-2-((6-bromothianthren-2-yl)amino)-3-methoxy propane-1-ol (59 mg) was obtained.

MS(ESI m/z): 400 (M+H)
RT(min): 1.70

(2)

In the same manner as in Example 1-42-1 (2), the following compound was obtained.

(R)-6-bromo-N-(1-bromo-3-methoxypropan-2-yl)thianthrene-2-amine

MS(ESI m/z): 462 (M+H)
RT(min): 2.13

(3)

The temperature was changed to 130° C., and in the same manner as in Example 1-6-1 (2), the following compound was obtained.

(S)-6-bromo-N-(1-methoxy-3-morpholinopropan-2-yl)thianthrene-2-amine

MS(ESI m/z): 469 (M+H)
RT(min): 1.30

(4)
Tetrakis(triphenylphosphine)palladium (0) (198 mg) was added to a solution of (S)-6-bromo-N-(1-methoxy-3-morpholinopropan-2-yl)thianthrene-2-amine (800 mg) and 4-(2-((4-methoxybenzyl)oxy)-6-(tributyl stannyl)pyridin-4-yl)morpholine (1.5 g) obtained in Example 1-46-1 (3) in 1,4-dioxane (10 mL), and the resultant product was irradiated with microwaves (microwave reaction apparatus, 140° C., 1.5 hours, 2.45 GHz, 0 W to 240 W). 4-(2-((4-Methoxybenzyl)oxy)-6-(tributyl stannyl)pyridin-4-yl)morpholine (480 mg) and tetrakis(triphenylphosphine)palladium (0) (98 mg) were added to the reaction mixture, and the resultant product was irradiated with microwaves (microwave reaction apparatus, 140° C., 1 hour, 2.45 GHz, 0 W to 240 W). The reaction mixture was cooled to room temperature, and purified by silica gel column chromatography (ethyl acetate:methanol=1:0→10:1), whereby (S)—N-(1-methoxy-3-morpholinopropan-2-yl)-6-(6-((4-methoxybenzyl)oxy)-4-morpholinopyridin-2-yl)thianthrene-2-amine (600 mg) was obtained.

MS(ESI m/z): 687 (M+H)
RT(min): 1.36

(5)
In the same manner as in Reference Example 18 (2), the following compound was obtained.

(S)-6-(7-((1-methoxy-3-morpholinopropan-2-yl)amino)thianthren-1-yl)-4-morpholinopyridin-2(1H)-one MS(ESI m/z): 567 (M+H)
RT(min): 0.96

Example 1-46-2

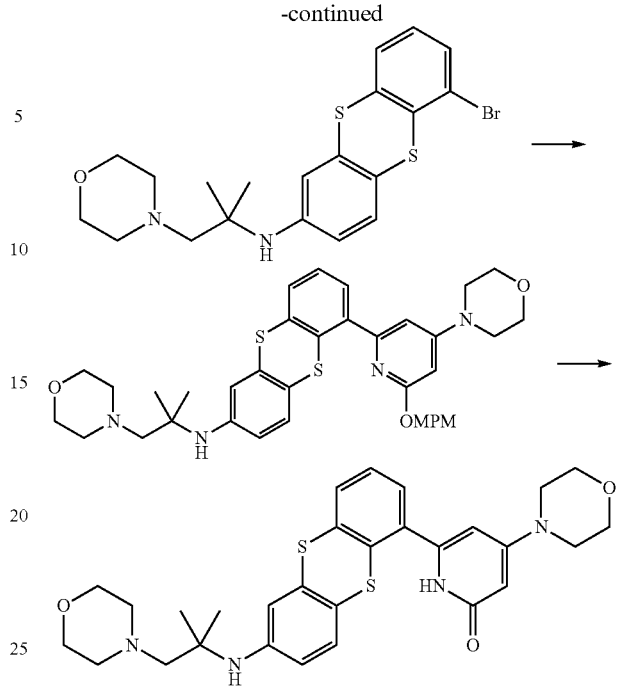

In the same manner as in Example 1-46-1, the following compound was obtained.

6-(7-((2-methyl-1-morpholinopropan-2-yl)amino)thianthren-1-yl)-4-morpholinopyridin-2(1H)-one MS(ESI m/z): 551 (M+H)
RT(min): 0.93

Example 1-46-3

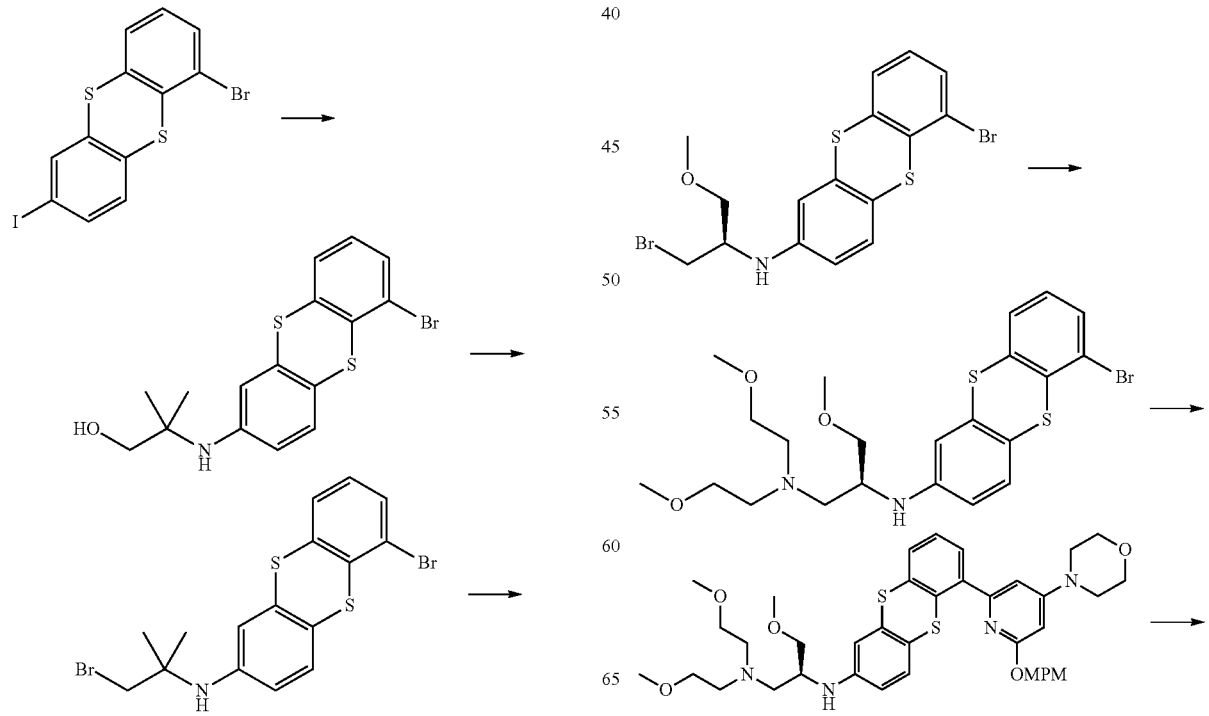

-continued

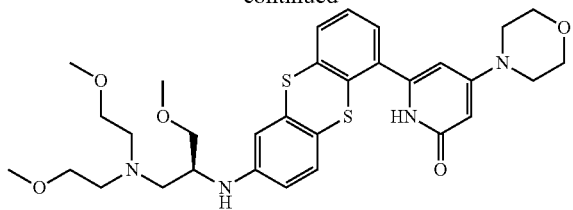

(1)
Using N,N-dimethyl formamide as a solvent, the following compound was obtained in the same manner as in Example 1-37-1 (3).

(S)—N²-(6-bromothianthren-2-yl)-3-methoxy-N¹,N¹-bis(2-methoxyethyl)propane-1,2-diamine MS(ESI m/z): 515 (M+H)
RT(min): 1.49
(2)
In the same manner as in Example 1-46-1 (4), the following compound was obtained.

(S)-3-methoxy-N²-(6-(6-((4-methoxybenzyl)oxy)-4-morpholinopyridin-2-yl)thianthren-2-yl)-N¹,N¹-bis(2-methoxyethyl)propane-1,2-diamine MS(ESI m/z): 733 (M+H)
RT(min): 1.49
(3)
In the same manner as in Reference Example 18 (2), the following compound was obtained.

(S)-6-(7-((1-(bis(2-methoxyethyl)amino)-3-methoxypropan-2-yl)amino)thianthren-1-yl)-4-morpholinopyridin-2(1H)-one MS(ESI m/z): 613 (M+H)
RT(min): 1.02

Examples 1-46-4 to 1-46-14

In the same manner as in Example 1-46-3, the following compounds were obtained.

TABLE 42

| Example No. | $R^b$ | Compound Name | MS | RT (min) | $^1$H-NMR (300 MHz) (DMSO-$d_6$) δ: |
|---|---|---|---|---|---|
| 1-46-4 | | 6-(7-(((S)-1-Methoxy-3-((R)-3-methyl morpholino)propan-2-yl)amino)thianthren-1-yl)-4-morpholino pyridin-2(1H)-one | 581 | 0.97 | (CDCl₃): 7.70-7.45 (1H, m), 7.39-7.15 (3H, m), 6.98-6.74 (1H, m), 6.66-6.44 (1H, m), 5.99 (1H, s), 5.73 (1H, s), 4.41 (1H, br s), 3.95-3.78 (4H, m), 3.78-3.46 (8H, m), 3.46-3.08 (5H, m), 3.02-1.92 (6H, m), 1.09-0.77 (3H, m). |
| 1-46-5 | | 6-(7-(((S)-1-Methoxy-3-((S)-3-methyl morpholino)propan-2-yl)amino)thianthren-1-yl)-4-morpholino pyridin-2(1H)-one | 581 | 0.97 | (CDCl₃): 7.55 (1H, dd, J = 6.9, 2.3 Hz), 7.35-7.25 (2H, m), 6.92-6.86 (1H, m), 6.81 (1H, dd, J = 7.3, 2.6 Hz), 6.51 (1H, td, J = 8.9, 2.6 Hz), 5.98 (1H, d, J = 2.6 Hz), 5.68 (1H, d, J = 2.6 Hz), 4.61 (1H, d, J = 4.6 Hz), 3.79 (8H, dd, J = 10.9, 4.3 Hz), 3.71-3.55 (4H, m), 3.49-3.41 (1H, m), 3.38-3.26 (8H, m), 3.19-2.23 (2H, m), 1.20-0.98 (3H, m). |
| 1-46-6 | | 6-(7-(((S)-1-Methoxy-3-((S)-2-methyl morpholino)propan-2-yl)amino)thianthren-1-yl)-4-morpholino pyridin-2(1H)-one | 581 | 0.99 | (CDCl₃): 7.61-7.54 (1H, m), 7.36-7.27 (2H, m), 6.89 (1H; d, J = 8.6 Hz), 6.81 (1H, d, J = 2.6 Hz), 6.52 (1H, dd, J = 8.6, 2.6 Hz), 5.99 (1H, d, J = 2.0 Hz), 5.69 (1H, d, J = 2.0 Hz), 4.62 (1H, s), 3.95-3.72 (11H, m), 3.63-3.50 (1H, m), 3.41-3.26 (9H, m), 3.16-2.45 (2H, m), 1.18-1.13 (3H, m). |
| 1-46-7 | | 6-(7-(((S)-1-Methoxy-3-((R)-2-methyl morpholino)propan-2-yl)amino)thianthren-1-yl)-4-morpholino pyridin-2(1H)-one | 581 | 0.99 | (CDCl₃): 7.61-7.56 (1H, m), 7.34-7.28 (2H, m), 6.88 (1H, d, J = 2.0 Hz), 6.81 (1H, d, J = 2.6 Hz), 6.52 (1H, dd, J = 8.6, 2.6 Hz), 6.07 (1H, d, J = 2.0 Hz), 5.79 (1H, d, J = 2.0 Hz), 4.62 (1H, s), 4.03-3.79 (11H, m), 3.64-3.50 (1H, m), 3.42-3.24 (9H, m), 3.18-2.26 (2H, m), 1.22-1.12 (3H, m). |

TABLE 42-continued

| Example No. | R<sup>b</sup> | Compound Name | MS | RT (min) | ¹H-NMR (300 MHz) (DMSO-d₆) δ: |
|---|---|---|---|---|---|
| 1-46-8 | 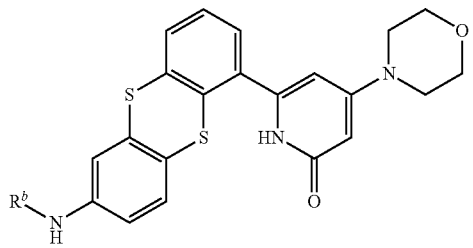 | (S)-6-(7-((1-Methoxy-3-(4-(trifluoromethyl)piperidin-1-yl)propan-2-yl)amino)thianthren-1-yl)-4-morpholino pyridin-2(1H)-one | 633 | 1.09 | (CDCl₃): 7.61-7.55 (1H, m), 7.36.-7.27 (2H, m), 6.93.-6.87 (1H, t, J = 4.6 Hz), 6.82 (1H, d, J = 2.0 Hz), 6.52 (1H, dd, J = 8.3, 2.3 Hz), 5.99 (1H, t, J = 2.3 Hz), 5.71 (1H, d, J = 2.6 Hz), 4.62 (1H, s), 3.84-3.78 (8H, m), 3.67 (1H, s), 3.55 (2H, dd, J = 9.2, 3.3 Hz), 3.39-3.29 (8H, m), 3.25-2.64 (2H, m), 2.01-1.50 (4H, m). |
| 1-46-9 | 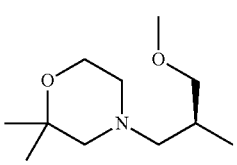 | (S)-6-(7-((1-(2,2-Dimethyl morpholino)-3-methoxy propan-2-yl)amino)thianthren-1-yl)-4-morpholino pyridin-2(1H)-one | 595 | 1.03 | (CDCl₃): 7.61-7.53 (1H, m), 7.34-7.28 (2H, m), 7.19 (1H, d, J = 8.6 Hz), 6.82 (1H, d, J = 2.6 Hz), 6.53 (1H, dd, J = 8.6, 2.6 Hz), 6.00 (1H, d, J = 2.0 Hz), 5.73 (1H, d, J = 2.6 Hz), 4.62 (1H, s), 3.81 (6H, t, J = 4.6 Hz), 3.75 (2H, t, J = 4.0 Hz), 3.56 (2H, t, J = 5.0 Hz), 3.41 (1H, dd, J = 9.6, 5.6 Hz), 3.36 (3H, s), 3.33 (2H, t, J = 5.0 Hz), 2.75-2.39 (4H, m), 2.31 (2H, s), 1.23 (6H, br s). |
| 1-46-10 | 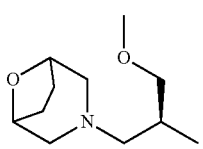 | 6-(7-(((2S)-1-(8-Oxa-3-azabicyclo[3.2.1]octan-3-yl)-3-methoxy propan-2-yl)amino)thianthren-1-yl)-4-morpholino pyridin-2(1H)-one | 593 | 0.99 | (CDCl₃): 7.63-7.54 (1H, m), 7.35-7.27 (2H, m), 7.20 (1H, d, J = 8.6 Hz), 6.83 (1H, d, J = 2.6 Hz), 6.55 (1H, dd, J = 8.3, 2.3 Hz), 6.04 (1H, d, J = 2.6 Hz), 5.76 (1H, d, J = 2.0 Hz), 4.62 (1H, s), 4.34-4.28 (2H, m), 3.88-3.77 (8H, m), 3.58-3.50 (2H, m), 3.41-3.31 (6H, m), 3.18-2.34 (4H, m), 2.26-1.76 (4H, m). |

TABLE 43

| Example No. | R<sup>b</sup> | Compound Name | MS | RT (min) | ¹H-NMR (300 MHz) (DMSO-d₆) δ: |
|---|---|---|---|---|---|
| 1-46-11 | 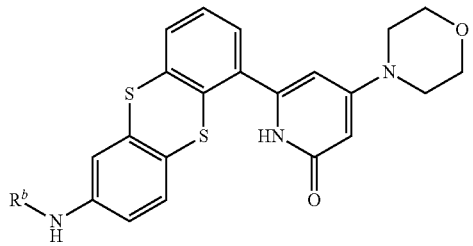 | 6-(7-(((S)-1-((2S,6R)-2,6-Dimethyl morpholino)-3-methoxy propan-2-yl)amino)thianthren-1-yl)-4-morpholino pyridin-2(1H)-one | 595 | 1.02 | (CDCl₃): 7.57-7.47 (1H, m), 7.33-7.28 (2H, m), 7.18 (1H, d, J = 8.6 Hz), 6.81 (1H, d, J = 2.0 Hz), 6.94-6.85 (1H, m), 5.99 (1H, d, J = 2.0 Hz), 5.68 (1H, d, J = 2.0 Hz), 4.62 (1H, s), 3.99-3.67 (8H, m), 3.55 (2H, dd, J = 9.2, 3.3 Hz), 3.44-3.26 (6H, m), 3.21-2.66 (4H, m), 2.34-1.98 (2H, m), 1.28-1.13 (6H, m). |
| 1-46-12 | 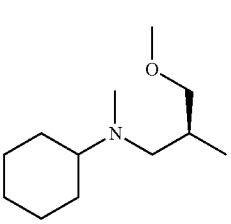 | (S)-6-(7-((1-(Cyclohexyl(methyl)amino)-3-methoxy propan-2-yl)amino)thianthren-1-yl)-4-morpholino pyridin-2 (1H)-one | 593 | 1.02 | |

TABLE 43-continued

| Example No. | R$^b$ | Compound Name | MS | RT (min) | $^1$H-NMR (300 MHz) (DMSO-d$_6$) δ: |
|---|---|---|---|---|---|
| 1-46-13 | (structure: (2R,6S)-2,6-dimethylpiperidine with methoxypropyl) | 6-(7-(((S)-1-((2R,6S)-2,6-Dimethyl piperidin-1-yl)-3-methoxy propan-2-yl)amino) thianthren-1-yl)-4-morpholino pyridin-2(1H)-one | 593 | 1.06 | |
| 1-46-14 | (structure: diisopropylamino methoxypropyl) | (S)-6-(7-((1-(Diisopropyl amino)-3-methoxy propan-2-yl) amino)thianthren-1-yl)-4-morpholino pyridin-2(1H)-one | 581 | 1.04 | |

Example 1-47

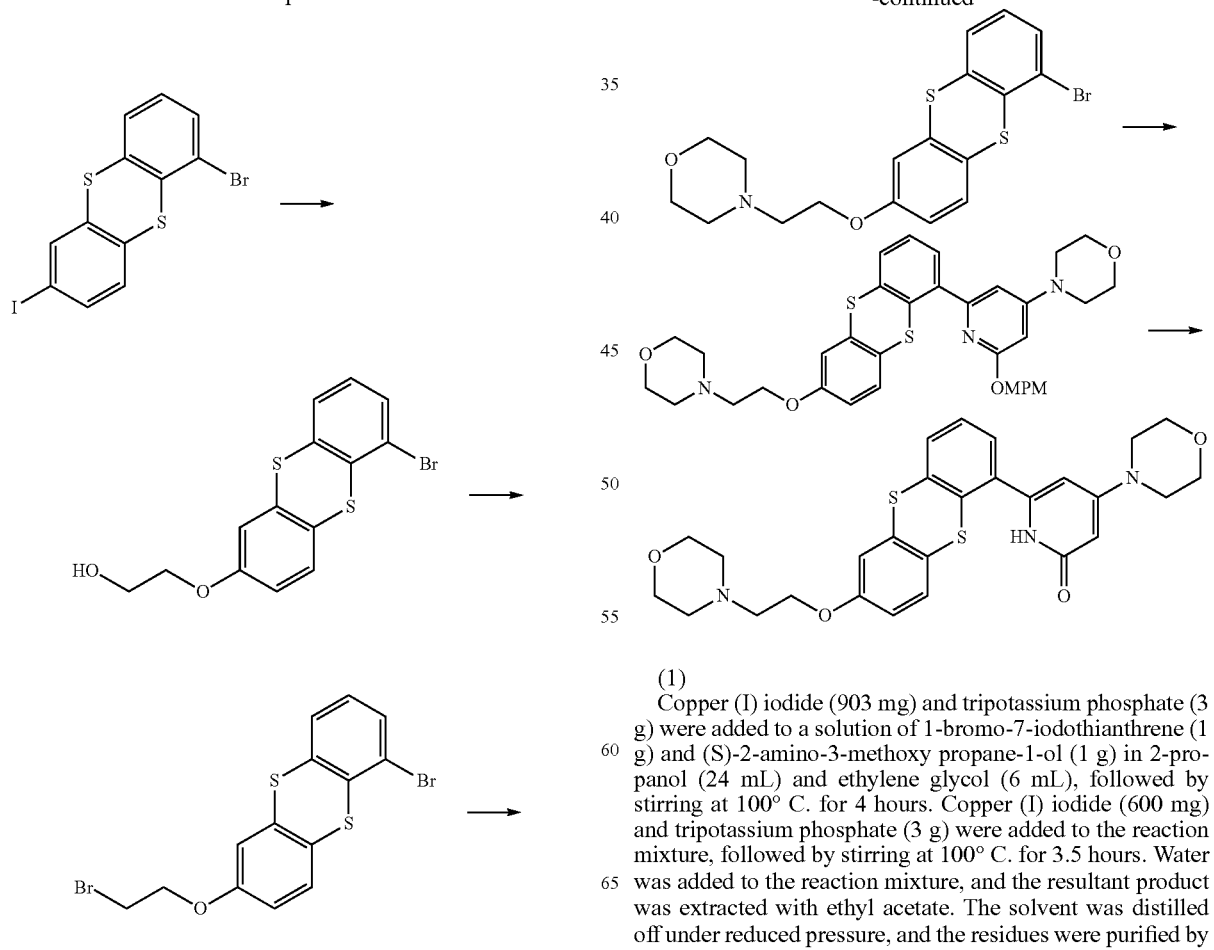

(1)
Copper (I) iodide (903 mg) and tripotassium phosphate (3 g) were added to a solution of 1-bromo-7-iodothianthrene (1 g) and (S)-2-amino-3-methoxy propane-1-ol (1 g) in 2-propanol (24 mL) and ethylene glycol (6 mL), followed by stirring at 100° C. for 4 hours. Copper (I) iodide (600 mg) and tripotassium phosphate (3 g) were added to the reaction mixture, followed by stirring at 100° C. for 3.5 hours. Water was added to the reaction mixture, and the resultant product was extracted with ethyl acetate. The solvent was distilled off under reduced pressure, and the residues were purified by silica gel column chromatography (hexane:ethyl acetate=1:0→5:1), whereby 2-((6-bromothianthren-2-yl)oxy)ethanol was obtained.

MS(ESI m/z): 354 (M+H)
RT(min): 1.66

(2)
In the same manner as in Example 1-42-1 (2), the following compound was obtained.

1-Bromo-7-(2-bromoethoxy)thianthrene (3)
The temperature was changed to 120° C., and in the same manner as in Example 1-6-1 (2), the following compound was obtained.

4-(2-((6-Bromothianthren-2-yl)oxy)ethyl)morpholine

MS(ESI m/z): 426 (M+H)
RT(min): 1.23

(4)
In the same manner as in Example 1-46-1 (4), the following compound was obtained.

4-(2-((6-(6-((4-Methoxybenzyl)oxy)-4-morpholinopyridin-2-yl)thianthren-2-yl)oxy)ethyl)morpholine MS(ESI m/z): 644 (M+H)
RT(min): 1.30

(5)
In the same manner as in Reference Example 18 (2), the following compound was obtained.

4-Morpholino-6-(7-(2-morpholinoethoxy)thianthren-1-yl)pyridin-2(1H)-one

MS(ESI m/z): 524 (M+H)
RT(min): 0.90

Example 1-48-1

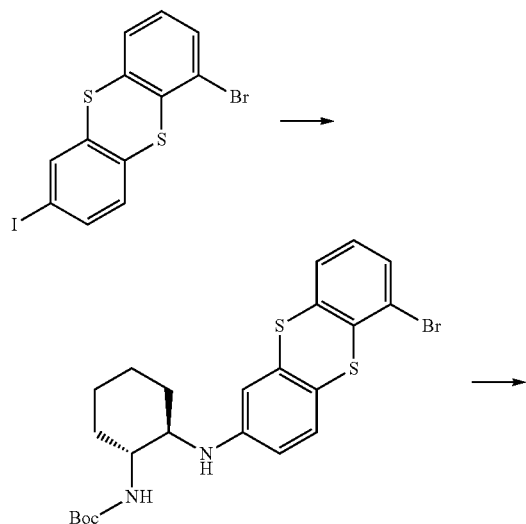

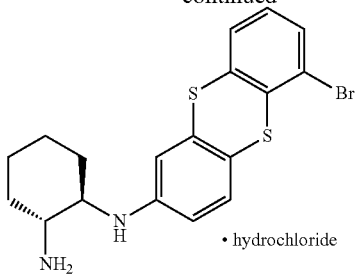

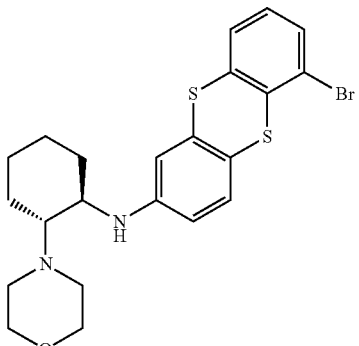

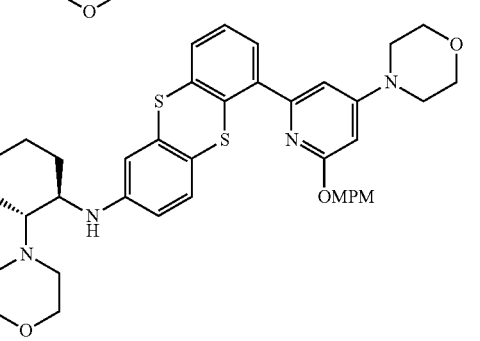

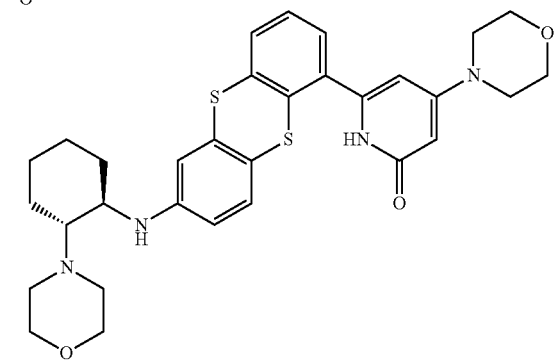

(1)
In a nitrogen atmosphere, a solution of 1-bromo-7-iodothianthrene (30 mg) and tert-butyl ((1R,2R)-2-aminocyclohexyl)carbamate (46 mg), cesium carbonate (139 mg), copper (I) iodide (14 mg), and 2-isobutyryl cyclohexanone (48 μL) in N,N-dimethyl formamide (2 mL) was stirred at room temperature for 6.5 hours. A saturated sodium chloride aqueous solution was added thereto, then, the resultant product was extracted with ethyl acetate, and the organic layer was dried over anhydrous sodium sulfate. The solvent was distilled off under reduced pressure, and the obtained residues were purified by silica gel column chromatography (hexane-ethyl acetate=1:0→0:1), whereby tert-butyl ((1R,2R)-2-((6-bromothianthren-2-yl)amino)cyclohexyl)carbamate (16 mg) was obtained.

MS(ESI m/z): 509 (M+H)
RT(min): 2.24

(2)

In the same manner as in Example 1-1, the following compound was obtained.

Hydrochloride of (1R,2R)—N¹-(6-bromothianthren-2-yl)cyclohexane-1,2-diamine

MS(ESI m/z): 409 (M+H)
RT(min): 1.40

(3)

1-Iodo-2-(2-iodoethoxy)ethane (6.7 µL) and diisopropyl ethylamine (29 µL) were added to a solution of hydrochloride (20 mg) of (1R,2R)—N¹-(6-bromothianthren-2-yl)cyclohexane-1,2-diamine obtained in Example 1-48-1 (2) in N,N-dimethyl formamide (1 mL), and the resultant product was irradiated with microwaves (microwave reaction apparatus, 100° C., 1 hour, 2.45 GHz, 0 W to 240 W). The reaction mixture was cooled to room temperature, and purified by silica gel column chromatography (hexane:ethyl acetate=1:0→0:1), whereby 6-bromo-N-((1R,2R)-2-morpholinocyclohexyl)thianthrene-2-amine (8 mg) was obtained.

MS(ESI m/z): 479 (M+H)
RT(min): 1.46

(4)

In the same manner as in Example 1-46-1 (4), the following compound was obtained.

6-(6-((4-Methoxybenzyl)oxy)-4-morpholinopyridin-2-yl)-N-((1R,2R)-2-morpholinocyclohexyl)thianthrene-2-amine MS(ESI m/z): 697 (M+H)
RT(min): 1.50

(5)

In the same manner as in Reference Example 18 (2), the following compound was obtained.

4-Morpholino-6-(7-(((1R,2R)-2-morpholinocyclohexyl)amino)thianthren-1-yl)pyridin-2(1H)-one ¹H-NMR (CDCl₃, 300 MHz) δ: 7.62-7.54 (1H, m), 7.32-7.27 (2H, m), 7.22 (1H, d, J=7.9 Hz), 6.80 (1H, d, J=2.6 Hz), 6.54 (1H, dd, J=8.6, 2.6 Hz), 5.98 (1H, d, J=2.6 Hz), 5.72 (1H, d, J=2.6 Hz), 5.14 (1H, s), 3.81 (4H, t, J=4.6 Hz), 3.71-3.54 (4H, m), 3.33 (4H, t, J=4.6 Hz), 2.63-2.48 (2H, m), 2.47-2.31 (4H, m), 2.04-1.66 (4H, m), 1.48-1.01 (4H, m).

MS(ESI m/z): 577 (M+H)
RT(min): 1.04

Example 1-48-2

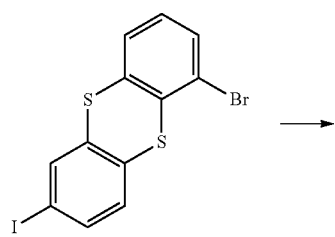

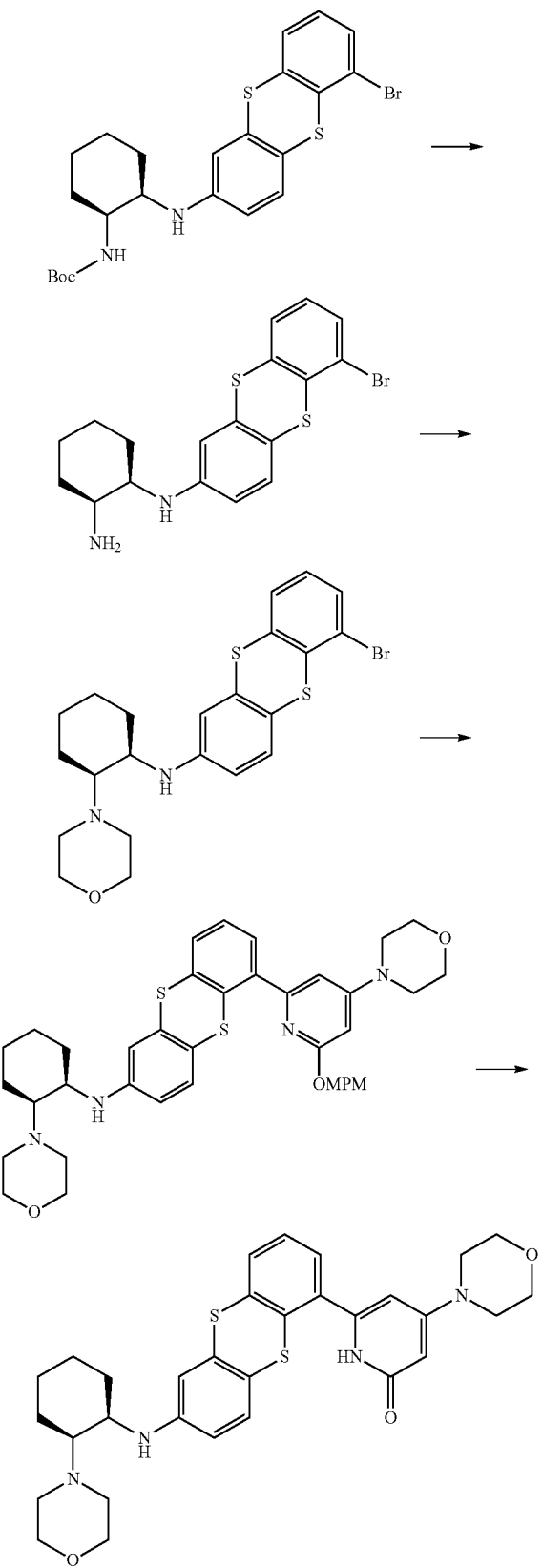

In the same manner as in Example 1-48-1, the following compound was obtained.

413

4-Morpholino-6-(7-(((1R,2S)-2-morpholinocyclo-hexyl)amino)thianthren-1-yl)pyridin-2(1H)-one MS(ESI m/z): 577 (M+H)
RT(min): 1.05

Example 1-49

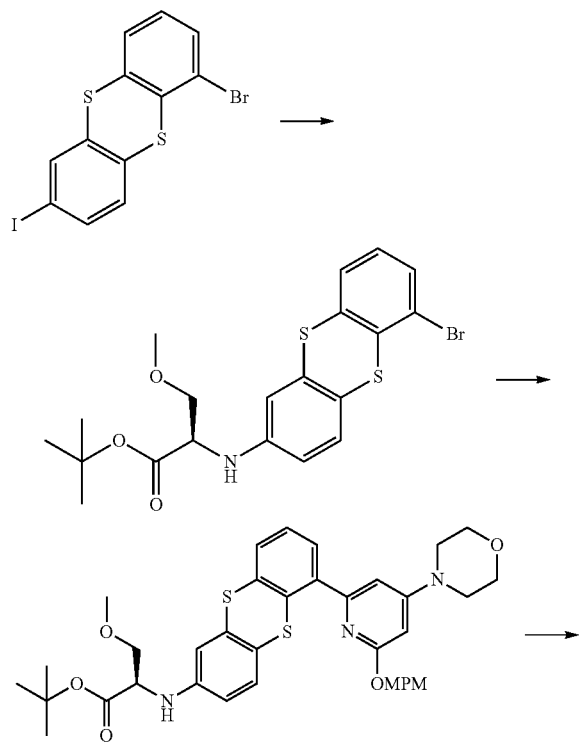

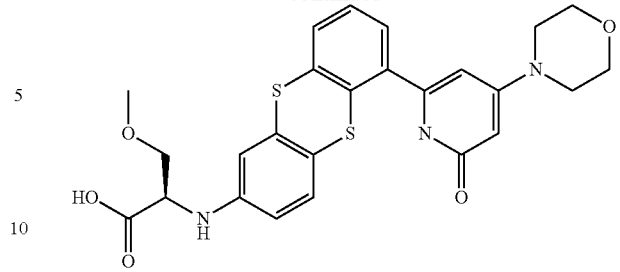

(1)
In the same manner as in Example 1-48-1 (1), the following compound was obtained.

(R)-tert-butyl 2-((6-bromothianthren-2-yl)amino)-3-methoxypropanoate

MS(ESI m/z): 468 (M+H)
RT(min): 2.08

(2)
In the same manner as in Example 1-46-1 (4), the following compound was obtained.

(R)-tert-butyl 3-methoxy-2-((6-(6-((4-methoxybenzyl)oxy)-4-morpholinopyridin-2-yl)thianthren-2-yl)amino)propanoate MS(ESI m/z): 688 (M+H)
RT(min): 2.02

(3)
In the same manner as in Example 1-4, the following compound was obtained.

(R)-3-methoxy-2-((6-(4-morpholino-6-oxo-1,6-dihydropyridin-2-yl)thianthren-2-yl)amino)propionic acid MS(ESI m/z): 512 (M+H)
RT(min): 1.10

Example 1-50-1

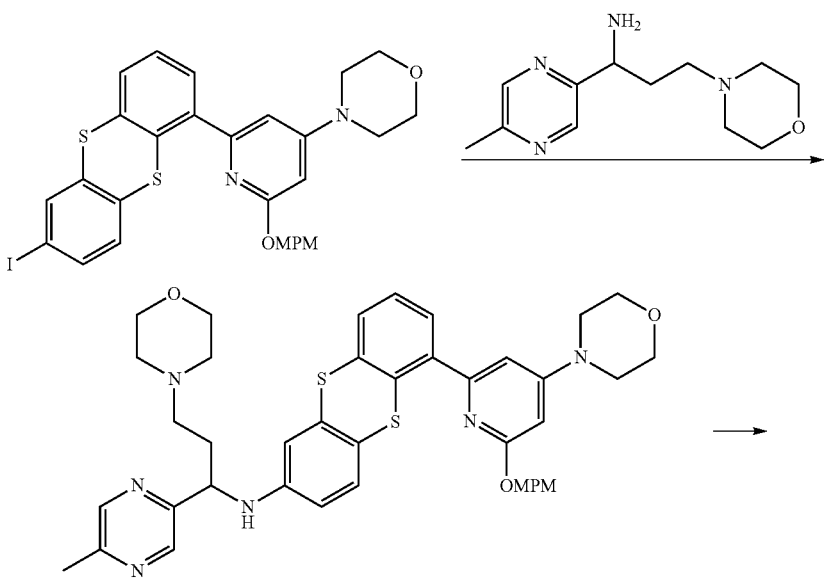

-continued

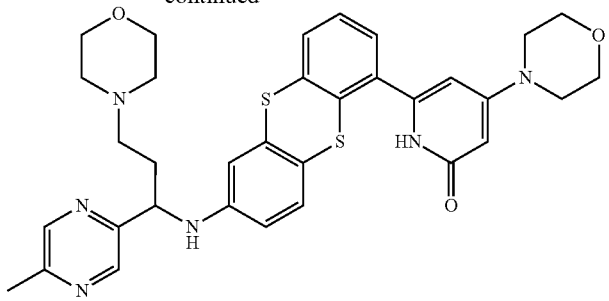

In a nitrogen atmosphere, a solution of 1-(5-methyl-pyrazin-2-yl)-3-morpholino propane-1-amine (49 mg), 4-(2-(7-iodothianthren-1-yl)-6-((4-methoxybenzyl)oxy)pyridin-4-yl)morpholine (44 mg), cesium carbonate (112 mg), copper (I) iodide (13 mg), and 2-isobutyryl cyclohexanone (46 μL) in N,N-dimethyl formamide (2 mL) was stirred at 50° C. for 5 hours. A saturated sodium hydrogen carbonate aqueous solution was added thereto, then, the resultant product was extracted with ethyl acetate, and the organic layer was dried over anhydrous sodium sulfate. The solvent was distilled off under reduced pressure, and the obtained residues were purified by silica gel column chromatography (hexane:ethyl acetate:methanol=2:1:0→0:1:0→0:9:1, NH silica), whereby 6-(6-((4-methoxybenzyl)oxy)-4-morpholinopyridin-2-yl)-N-(1-(5-methylpyrazin-2-yl)-3-morpholinopropyl)thianthrene-2-amine (40 mg) was obtained as a yellow oily material.

MS(ESI m/z): 749 (M+H)
RT(min): 1.37

(2)
Trifluoroacetic acid (1 mL) was added to a solution of 6-(6-((4-methoxybenzyl)oxy)-4-morpholinopyridin-2-yl)-N-(1-(5-methylpyrazin-2-yl)-3-morpholinopropyl)thianthrene-2-amine (40 mg) obtained in Example 1-50-1 (1) in dichloromethane (1 mL), followed by stirring at room temperature for 1 hour. The solvent was distilled off, then, the residues were purified by silica gel column chromatography (chloroform:methanol=1:0→49:1, NH silica), and purified by preparative thin layer silica gel chromatography (chloroform:methanol=30:1, NH silica), whereby 6-(7-((1-(5-methylpyrazin-2-yl)-3-morpholinopropyl)amino)thianthren-1-yl)-4-morpholinopyridin-2(1H)-one (16 mg) was obtained.

$^1$H-NMR (CDCl$_3$, 300 MHz) δ: 9.18 (1H, brs), 8.45 (1H, s), 8.39 (1H, s), 7.53-7.52 (1H, m), 7.28-7.26 (2H, m), 7.13-7.11 (1H, m), 6.69 (1H, d, J=2.6 Hz), 6.40 (1H, d, J=8.6 Hz), 6.19 (1H, d, J=5.9 Hz), 5.95 (1H, d, J=2.0 Hz), 5.70 (1H, brs), 4.64-4.62 (1H, m), 3.80-3.77 (8H, m), 3.32-3.30 (4H, m), 2.54 (3H, s), 2.48-2.41 (6H, m), 2.10-1.93 (2H, m).

MS(ESI m/z): 629 (M+H)
RT(min): 0.94

Examples 1-50-2 to 1-50-9

In the same manner as in Example 1-50-1, the following compounds were obtained.

TABLE 44

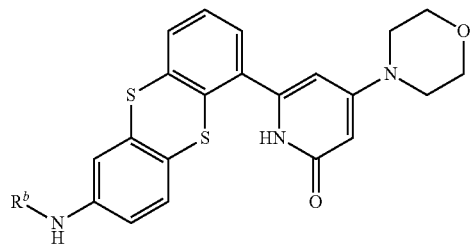

| Example No. | R$^b$ | Compound Name | MS | RT (min) | $^1$H-NMR (300 MHz) (DMSO-d$_6$) δ: |
|---|---|---|---|---|---|
| 1-50-2 | (5-methylpyridin-2-yl, dimethyl) | 6-(7-((2-(5-Methyl pyridin-2-yl)propan-2-yl)amino) thianthren-1-yl)-4-morpholino pyridin-2(1H)-one | 543 | 1.06 | (CDCl$_3$): 9.98 (1H, br s), 8.39 (1H, d, J = 1.8 Hz), 7.48 (1H, dd, J = 7.2, 2.0 Hz), 7.42 (1H, dd, J = 7.9, 1.8 Hz), 7.37 (1H, d, J = 7.9 Hz), 7.25 (1H, d, J = 2.0 Hz), 7.21 (1H, d, J = 7.2 Hz), 7.02 (1H, d, J = 8.6 Hz), 6.52 (1H, d, J = 2.6 Hz), 6.18 (1H, dd, J = 8.6, 2.6 Hz), 5.94 (1H, d, J = 2.0 Hz), 5.67 (1H, d, J = 2.0 Hz), 4.53 (1H, br s), 3.79 (4H, t, J = 5.0 Hz), 3.29 (4H, t, J = 5.0 Hz), 2.31 (3H, s), 1.66 (6H, s). |

TABLE 44-continued

| Example No. | $R^b$ | Compound Name | MS | RT (min) | $^1$H-NMR (300 MHz) (DMSO-d$_6$) δ: |
|---|---|---|---|---|---|
| 1-50-3 | | 6-(7-((1-(5-Methyl pyridin-2-yl)cyclobutyl)amino) thianthren-1-yl)-4-morpholino pyridin-2(1H)-one | 555 | 1.12 | |
| 1-50-4 | | 6-(7-((3-(5-Methyl pyridin-2-yl)oxetan-3-yl)amino) thianthren-1-yl)-4-morpholino pyridin-2(1H)-one | 557 | 1.18 | 8.52 (1H, d, J = 2.3 Hz), 7.62-7.56 (1H, m), 7.52 (1H, dd, J = 8.5, 2.3 Hz), 7.43 (1H, br s), 7.35-7.28 (2H, m), 7.20 (1H, d, J = 8.5 Hz), 7.11 (1H, d, J = 8.6 Hz), 6.43 (1H, d, J = 1.3 Hz), 6.03 (1H, dd, J = 8.6, 1.3 Hz), 5.97 (1H, d, J = 2.0 Hz), 5.45 (1H, d, J = 2.0 Hz), 5.08 (2H, d, J = 5.6 Hz), 4.65 (2H, d, J = 5.6 Hz), 3.65 (4H, t, J = 4.3 Hz), 3.24 (4H, t, J = 4.3 Hz), 2.28 (3H, s). |
| 1-50-5 | | 6-(7-((1-(5-Methyl pyridin-2-yl)cyclopropyl)amino) thianthren-1-yl)-4-morpholino pyridin-2(1H)-one | 541 | 1.12 | (CDCl$_3$): 9.23 (1H, br s), 8.31 (1H, d, J = 2.0 Hz), 7.53 (1H, dd, J = 5.9, 2.6 Hz), 7.31 (1H, dd, J = 7.9, 2.0 Hz), 7.30-7.27 (1H, m), 7.27-7.25 (1H, m), 7.23 (1H, d, J = 7.9 Hz), 7.17 (1H, d, J = 8.6 Hz), 6.80 (1H, d, J = 2.6 Hz), 6.52 (1H, dd, J = 8.6, 2.6 Hz), 5.98 (1H, d, J = 2.6 Hz), 5.71 (1H, d, J = 2.6 Hz), 4.76 (1H, br s), 3.81 (4H, t, J = 5.0 Hz), 3.32 (4H, t, J = 5.0 Hz), 2.27 (3H, s), 1.69 (2H, q, J = 3.5 Hz), 1.19 (2H, q, J = 3.5 Hz). |
| 1-50-6 | | 6-(7-((3-(5-Methyl pyridin-2-yl)pentan-3-yl)amino) thianthren-1-yl)-4-morpholino pyridin-2(1H)-one | 572 | 1.18 | |
| 1-50-7 | | 6-(7-((4-(Dimethyl amino)-1-(5-methyl pyridin-2-yl)butyl) amino)thianthren-1-yl)-4-morpholino pyridin-2(1H)-one | 600 | 0.93 | (CDCl$_3$): 9.20 (1H, br s), 8.37 (1H, s), 7.52-7.51 (1H, m), 7.39 (1H, dd, J = 7.9, 2.0 Hz), 7.25-7.24 (2H, m), 7.16 (1H, d, J = 7.9 Hz), 7.11 (1H, d, J = 8.6 Hz), 6.68 (1H, d, J = 2.3 Hz), 6.39 (1H, dd, J = 8.6, 2.3 Hz), 5.95 (1H, d, J = 1.7 Hz), 5.70 (1H, d, J = 1.7 Hz), 5.58 (1H, br s), 4.38-4.36 (1H, m), 3.80 (4H, t, J = 5.0 Hz), 3.31 (4H, t, J = 5.0 Hz), 2.29 (3H, s), 2.26-2.24 (2H, m), 2.20 (6H, s), 1.94-1.85 (2H, m), 1.58-1.44 (2H, m). |

TABLE 44-continued

| Example No. | $R^b$ | Compound Name | MS | RT (min) | $^1$H-NMR (300 MHz) (DMSO-$d_6$) δ: |
|---|---|---|---|---|---|
| 1-50-8 | | 6-(7-(((3-(Dimethyl amino) cyclobutyl)(5-methyl pyridin-2-yl)methyl)amino) thianthren-1-yl)-4-morpholino pyridin-2(1H)-one (Diastereomer A) | 612 | 0.98 | (CDCl$_3$): 8.93 (1H, br s), 8.34 (1H, d, J = 7.3 Hz), 7.53-7.52 (1H, m), 7.38 (1H, d, J = 7.9 Hz), 7.24-7.21 (2H, m), 7.16 (1H, d, J = 7.9 Hz), 7.11 (1H, dd, J = 8.5, 5.3 Hz), 6.85-6.82 (1H, m), 6.49 (1H, dd, J = 8.5, 2.3 Hz), 5.95 (1H, d, J = 2.0 Hz), 5.71-5.70 (1H, m), 5.64 (1H, d, J = 6.6 Hz), 4.47-4.44 (1H, m), 3.81 (4H, t, J = 4.0 Hz), 3.31 (4H, t, J = 4.0 Hz), 2.98-2.92 (1H, m), 2.71-2.64 (1H, m), 2.49 (6H, s), 2.25-2.16 (7H, br m). |

TABLE 45

| Example No. | $R^b$ | Compound Name | MS | RT (min) | $^1$H-NMR (300 MHz) (DMSO-$d_6$) δ: |
|---|---|---|---|---|---|
| 1-50-9 | | 6-(7-(((3-(Dimethyl amino) cyclobutyl)(5-methyl pyridin-2-yl)methyl)amino)thianthren-1-yl)-4-morpholino pyridin-2 (1H)-one (Diastereomer B) | 612 | 1.04 | (CDCl$_3$): 8.45 (1H, br s), 8.37 (1H, s), 7.54 (1H, dd, J = 5.9, 3.3 Hz), 7.41 (1H, dd, J = 7.9, 2.0 Hz), 7.28-7.22 (2H, m), 7.17-7.13 (2H, m), 6.76 (1H, d, J = 2.2 Hz), 6.46 (1H, dd, J = 8.3, 2.2 Hz), 5.94 (1H, d, J = 2.6 Hz), 5.72 (1H, d, J = 2.6 Hz), 4.51 (1H, d, J = 7.0 Hz), 4.37 (1H, dd, J = 9.9, 7.0 Hz), 3.81 (4H, t, J = 5.0 Hz), 3.32 (4H, t, J = 5.0 Hz), 2.80-2.70 (1H, m), 2.52-2.49 (1H, m), 2.29 (3H, s), 2.17-1.82 (10H, m). |

Example 1-51-1

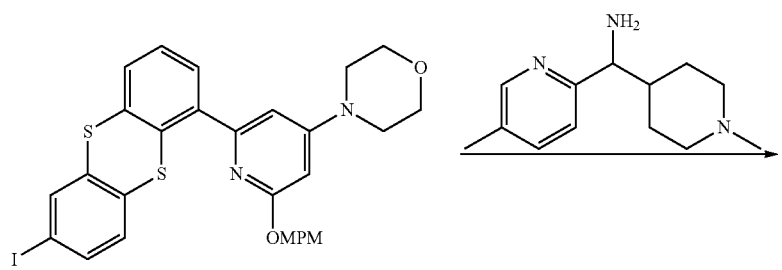

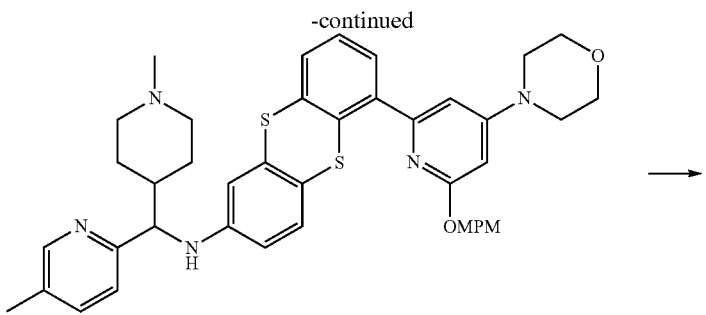

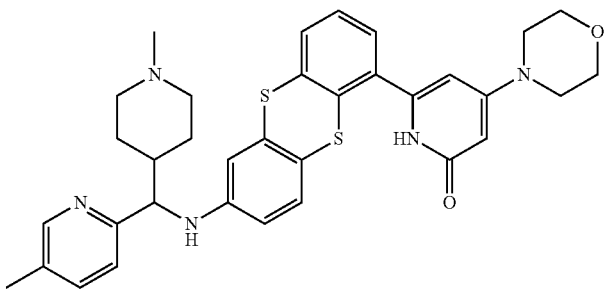

(1)

In the same manner as in Example 1-50-1 (1), the following compound was obtained.

6-(6-((4-methoxybenzyl)oxy)-4-morpholinopyridin-2-yl)-N-((1-methylpiperidin-4-yl) (5-methylpyridin-2-yl)methyl)thianthrene-2-amine MS(ESI m/z): 732 (M+H)
RT(min): 1.40

(2)

4.0 mol/L hydrogen chloride/1,4-dioxane (2 mL) was added to a solution of 6-(6-((4-methoxybenzyl)oxy)-4-morpholinopyridin-2-yl)-N-((1-methylpiperidin-4-yl)(5-meth yl pyridin-2-yl)methyl)thianthrene-2-amine (22 mg) obtained in Example 1-51-1 (1) in dichloromethane (2 mL), followed by stirring at room temperature for 1 hour. The solvent was distilled off, and 4.0 mol/L hydrogen chloride/1,4-dioxane (1 mL) and trifluoroacetic acid (1 mL) were added thereto, followed by stirring at room temperature for 15 minutes. After the solvent was distilled off under reduced pressure, a saturated sodium hydrogen carbonate aqueous solution was added thereto, then, the resultant product was extracted with chloroform, and the organic layer was purified by silica gel column chromatography (chloroform:methanol=97:3, NH silica), whereby 6-(7-(((1-methylpiperidin-4-yl)(5-methyl-pyridin-2-yl)methyl)amino)thianthren-1-yl)-4-morpholinopyridin-2(1H)-one (1.4 mg) was obtained.

$^1$H-NMR (CDCl$_3$, 300 MHz) δ: 8.38 (1H, d, J=2.1 Hz), 7.55-7.53 (1H, m), 7.39 (1H, dd, J=7.6, 2.1 Hz), 7.28-7.23 (2H, m), 7.13-7.09 (2H, m), 6.73 (1H, d, J=2.6 Hz), 6.44 (1H, dd, J=8.6, 2.6 Hz), 5.95 (1H, d, J=2.0 Hz), 5.71 (1H, d, J=2.0 Hz), 4.77 (1H, d, J=7.9 Hz), 4.24 (1H, dd, J=7.9, 7.9 Hz), 3.81 (4H, t, J=4.8 Hz), 3.32 (4H, t, J=4.8 Hz), 2.89-2.79 (2H, m), 2.28 (3H, s), 2.23 (3H, s), 1.92-1.25 (7H, m).

MS(ESI m/z): 612 (M+H)
RT(min): 0.95

Examples 1-51-2 to 1-51-12

In the same manner as in Example 1-51-1, the following compounds were obtained.

TABLE 46

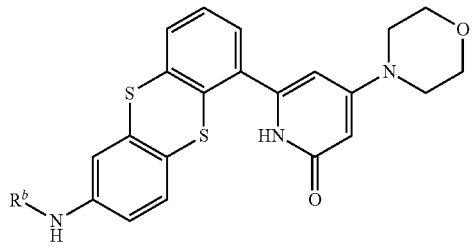

| Example No. | $R^b$ | Compound Name | MS | RT (min) | $^1$H-NMR (300 MHz) (DMSO-$d_6$) δ: |
|---|---|---|---|---|---|
| 1-51-2 | (1-methylpiperidin-4-yl with 5-methylpyridin-2-yl methyl group) | 6-(7-(((1-(Methyl piperidin-4-yl)(5-methyl pyridin-2-yl) methyl)amino)thianthren-1-yl)-4-morpholino pyridin-2 (1H)-one | 612 | 0.95 | (CDCl$_3$): 8.38 (1H, d, J = 2.1 Hz), 7.55-7.53 (1H, m), 7.39 (1H, dd, J = 7.6, 2.1 Hz), 7.28-7.23 (2H, m), 7.13-7.09 (2H, m), 6.73 (1H, d, J = 2.6 Hz), 6.44 (1H, dd, J = 8.6, 2.6 Hz), 5.95 (1H, d, J = 2.0 Hz), 5.71 (1H, d, J = 2.0 Hz), 4.77 (1H, d, J = 7.9 Hz), 4.24 (1H, dd, J = 7.9, 7.9 Hz), 3.81 (4H, t, J = 4.8 Hz), 3.32 (4H, t, J = 4.8 Hz), 2.89-2.79 (2H, m), 2.28 (3H, s), 2.23 (3H, s), 1.92-1.25 (7H, m). |
| 1-51-3 | (dimethylamino butyl with 5-methylpyridin-2-yl) | 6-(7-((4-(Dimethyl amino)-1-(5-methyl pyridin-2-yl)butyl) amino)thianthren-1-yl)-4-morpholino pyridin-2(1H)-one (Optically active substance A) | 600 | 0.93 | (CDCl$_3$): 9.20 (1H, br s), 8.37 (1H, s), 7.52-7.51 (1H, m), 7.39 (1H, dd, J = 7.9, 2.0 Hz), 7.25-7.24 (2H, m), 7.16 (1H, d, J = 7.9 Hz), 7.11 (1H, d, J = 8.6 Hz), 6.68 (1H, d, J = 2.3 Hz), 6.39 (1H, dd, J = 8.6, 2.3 Hz), 5.95 (1H, d, J = 1.7 Hz), 5.70 (1H, d, J = 1.7 Hz), 5.58 (1H, br s), 4.38-4.36 (1H, m), 3.80 (4H, t, J = 5.0 Hz), 3.31 (4H, t, J = 5.0 Hz), 2.29 (3H, s), 2.26-2.24 (2H, m), 2.20 (6H, s), 1.94-1.85 (2H, m), 1.58-1.44 (2H, m). |
| 1-51-4 | (dimethylamino butyl with 5-methylpyridin-2-yl) | 6-(7-((4-(Dimethyl amino)-1-(5-methyl pyridin-2-yl) butyl)amino)thianthren-1-yl)-4-morpholino pyridin-2(1H)-one (Optically active substance B) | 600 | 0.93 | (CDCl$_3$): 9.20 (1H, br s), 8.37 (1H, s), 7.52-7.51 (1H, m), 7.39 (1H, dd, J = 7.9, 2.0 Hz), 7.25-7.24 (2H, m), 7.16 (1H, d, J = 7.9 Hz), 7.11 (1H, d, J = 8.6 Hz), 6.68 (1H, d, J = 2.3 Hz), 6.39 (1H, dd, J = 8.6, 2.3 Hz), 5.95 (1H, d, J = 1.7 Hz), 5.70 (1H, d, J = 1.7 Hz), 5.58 (1H, br s), 4.38-4.36 (1H, m), 3.80 (4H, t, J = 5.0 Hz), 3.31 (4H, t, J = 5.0 Hz), 2.29 (3H, s), 2.26-2.24 (2H, m), 2.20 (6H, s), 1.94-1.85 (2H, m), 1.58-1.44 (2H, m). |
| 1-51-5 | (dimethylamino propyl with 5-methylpyridin-2-yl) | 6-(7-((3-(Dimethyl amino)-1-(5-methyl pyridin-2-yl) propyl)amino)thianthren-1-yl)-4-morpholino pyridin-2 (1H)-one (Optically active substance A) | 586 | 0.98 | (CDCl$_3$): 8.94 (1H, br s), 8.39 (1H, d, J = 2.0 Hz), 7.52 (1H, dd, J = 5.3, 4.0 Hz), 7.40 (1H, dd, J = 8.0, 2.0 Hz), 7.24 (1H, d, J = 4.0 Hz), 7.24 (1H, d, J = 5.3 Hz), 7.19 (1H, d, J = 8.0 Hz), 7.10 (1H, d, J = 8.6 Hz), 6.68 (1H, d, J = 2.0 Hz), 6.37 (1H, dd, J = 8.6, 2.0 Hz), 6.34 (1H, br s), 5.95 (1H, d, J = 2.0 Hz), 5.70 (1H, d, J = 2.0 Hz), 4.54-4.46 (1H, m), 3.80 (4H, t, J = 5.0 Hz), 3.31 (4H, t, J = 5.0 Hz), 2.35 (2H, t, J = 6.6 Hz), 2.30 (3H, s), 2.24 (6H, s), 2.10-1.83 (2H, m). |

TABLE 46-continued

| Example No. | $R^b\diagdown$ | Compound Name | MS | RT (min) | $^1$H-NMR (300 MHz) (DMSO-$d_6$) δ: |
|---|---|---|---|---|---|
| 1-51-6 | | 6-(7-((1-(5-Methyl pyridin-2-yl)-3-(piperidin-1-yl)propyl)amino)thianthren-1-yl)-4-morpholino pyridin-2(1H)-one (Optically active substance A) | 626 | 1.06 | |
| 1-51-7 | | 6-(7-((1-(5-Methyl pyridin-2-yl)-3-morpholino propyl)amino)thianthren-1-yl)-4-morpholino pyridin-2(1H)-one (Optically active substance A) | 628 | 1.02 | |
| 1-51-8 | | 6-(7-((3-(3-Methoxy azetidin-1-yl)-1-(5-methyl pyridin-2-yl)propyl)amino)thianthren-1-yl)-4-morpholino pyridin-2(1H)-one (Optically active substance A) | 628 | 1.05 | |

TABLE 47

| Example No. | R$^b$ | Compound Name | MS | RT (min) | $^1$H-NMR (300 MHz) (DMSO-d$_6$) δ: |
|---|---|---|---|---|---|
| 1-51-3 | (structure) | 6-(7-((3-(Ethyl(methyl)amino)-1-(5-methyl pyridin-2-yl)propyl)amino)thianthren-1-yl)-4-morpholino pyridin-2(1H)-one (Optically active substance A) | 600 | 1.01 | |
| 1-51-10 | (structure) | 6-(7-((3-(Ethyl(methyl)amino)-1-(5-methyl pyrazin-2-yl)propyl)amino)thianthren-1-yl)-4-morpholino pyridin-2(1H)-one (Optically active substance A) | 601 | 0.95 | |
| 1-51-11 | (structure) | 6-(7-((3-(Azetidin-1-yl)-1-(5-methyl pyrazin-2-yl)propyl)amino)thianthren-1-yl)-4-morpholino pyridin-2(1H)-one (Optically active substance A) | 599 | 0.95 | (CDCl$_3$): 8.45 (1H, s), 8.39 (1H, s), 8.28 (1H, br s), 7.55 (1H, dd, J = 5.9, 3.3 Hz), 7.31-7.22 (2H, m), 7.15 (1H, d, J = 8.6 Hz), 6.71 (1H, d, J = 2.0 Hz), 6.42 (1H, dd, J = 8.6, 2.0 Hz), 6.30 (1H, br s), 5.95 (1H, d, J = 2.6 Hz), 5.72 (1H, d, J = 2.6 Hz), 4.56 (1H, t, J = 6.3 Hz), 3.81 (4H, t, J = 5.0 Hz), 3.32 (4H, t, J = 5.0 Hz), 3.28-3.14 (4H, m), 2.53 (3H, s), 2.52-2.43 (2H, m), 2.15-2.06 (2H, m), 1.98-1.72 (2H, m). |
| 1-51-12 | (structure) | 6-(7-((1,3-Dimorpholino propan-2-yl)amino)thianthren-1-yl)-4-morpholino pyridin-2(1H)-one | 622 | 0.83 | (CDCl$_3$): 8.81 (1H, br s), 7.62-7.55 (1H, m), 7.32-7.25 (2H, m), 7.21 (1H, d, J = 8.6 Hz), 6.97 (1H, d, J = 2.6 Hz), 6.59 (1H, dd, J = 8.6, 2.6 Hz), 5.98 (1H, d, J = 2.0 Hz), 5.73 (1H, d, J = 2.0 Hz), 4.58 (1H, br, s), 3.82 (4H, t, J = 5.0 Hz), 3.70 (8H, t, J = 4.3 Hz), 3.54-3.43 (1H, m), 3.33 (4H, t, J = 5.0 Hz), 2.63-2.36 (12H, br m). |

Example 1-52

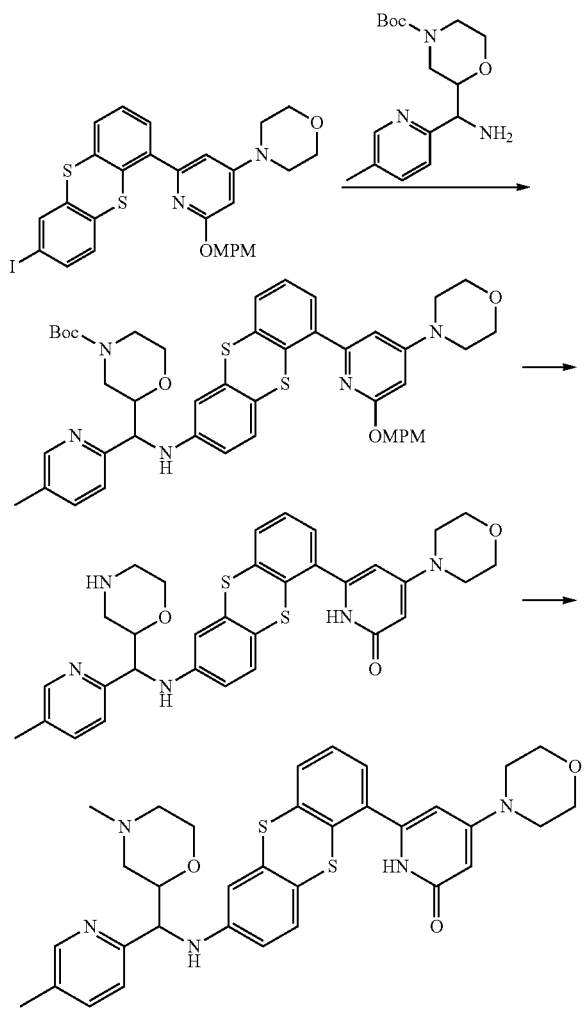

(1)

In the same manner as in Example 1-50-1 (1), the following compound was obtained.

tert-Butyl 2-(((6-(6-((4-methoxybenzyl)oxy)-4-morpholinopyridin-2-yl)thianthren-2-yl)amino)(5-methyl pyridin-2-yl)methyl)morpholine-4-carboxylate (diastereomer mixture)

MS(ESI m/z): 820 (M+H)
RT(min): 1.93, 1.97

(2)

4.0 mol/L hydrogen chloride/1,4-dioxane (0.5 mL) and trifluoroacetic acid (0.5 mL) were added to the diastereomer mixture (20 mg) obtained in Example 1-52 (1), followed by stirring at room temperature for 0.5 hours. The solvent was distilled off under reduced pressure, then, a saturated sodium hydrogen carbonate aqueous solution was added thereto, and the resultant product was extracted with chloroform. The organic layer was purified by silica gel column chromatography (chloroform:methanol=49:1→9:1, NH silica), whereby 6-(7-(((5-methylpyridin-2-yl)(morpholin-2-yl) methyl)amino)thianthren-1-yl)-4-morpholinopyridin-2 (1H)-one (diastereomer mixture) (9.5 mg) was obtained.

MS(ESI m/z): 600 (M+H)
RT(min): 1.00

Examples 1-52-1 and 1-52-2

2-Picoline borane (1.7 mg) was added to a solution of the diastereomer mixture (9.5 mg) obtained in Example 1-52 (2) and a 37% formaldehyde aqueous solution (1.28 mg) in acetic acid (14 µL) and methanol (136 µl), followed by stirring at room temperature for 0.5 hours. A sodium hydroxide aqueous solution was added thereto, then, the resultant product was extracted with chloroform, and the organic layer was dried over anhydrous sodium sulfate. The solvent was distilled off under reduced pressure, and the residues were purified by preparative thin layer silica gel chromatography (chloroform:methanol=40:1, NH silica), whereby a diastereomer A (3.0 mg) and a diastereomer B (2.2 mg) of 6-(7-(((4-methyl morpholin-2-yl)(5-methylpyridin-2-yl) methyl)amino)thianthren-1-yl)-4-morpholinopyridin-2 (1H)-one were obtained.

Example 1-52-1

Diastereomer A $^1$H-NMR (CDCl$_3$, 300 MHz) δ: 8.79 (1H, brs), 8.41 (1H, d, J=2.0 Hz), 7.53-7.51 (1H, m), 7.41 (1H, dd, J=7.9, 2.0 Hz), 7.28-7.21 (3H, m), 7.11 (1H, d, J=8.6 Hz), 6.72 (1H, d, J=2.6 Hz), 6.41 (1H, dd, J=8.6, 2.6 Hz), 5.94 (1H, d, J=2.6 Hz), 5.70 (1H, d, J=2.0 Hz), 5.13 (1H, d, J=5.9 Hz), 4.39 (1H, t, J=5.3 Hz), 3.94-3.85 (2H, m), 3.80 (4H, t, J=5.0 Hz), 3.62 (1H, td, J=11.4, 2.2 Hz), 3.31 (4H, t, J=5.0 Hz), 2.60 (2H, d, J=11.9 Hz), 2.31 (3H, s), 2.23 (3H, s), 2.15-2.06 (2H, m).

MS(ESI m/z): 614 (M+H)
RT(min): 1.00

Example 1-52-2

Diastereomer B $^1$H-NMR (CDCl$_3$, 300 MHz) δ: 8.57 (1H, brs), 8.37 (1H, s), 7.56-7.51 (1H, m), 7.40 (1H, dd, J=7.9, 2.0 Hz), 7.27-7.24 (2H, m), 7.17 (1H, d, J=8.6 Hz), 7.13 (1H, d, J=8.6 Hz), 6.78 (1H, d, J=2.6 Hz), 6.47 (1H, dd, J=8.6, 2.6 Hz), 5.94 (1H, d, J=2.6 Hz), 5.71 (1H, d, J=2.6 Hz), 5.15 (1H, d, J=7.3 Hz), 4.53 (1H, dd, J=7.3, 5.3 Hz), 3.94-3.89 (2H, m), 3.81 (4H, t, J=4.8 Hz), 3.65 (1H, td, J=11.4, 2.4 Hz), 3.31 (4H, t, J=4.8 Hz), 2.73 (1H, d, J=11.9 Hz), 2.58 (1H, d, J=9.9 Hz), 2.30 (3H, s), 2.22 (3H, s), 2.03 (1H, td, J=11.4, 3.5 Hz), 1.81 (1H, t, J=10.6 Hz).

MS(ESI m/z): 614 (M+H)
RT(min): 1.02

Example 1-53

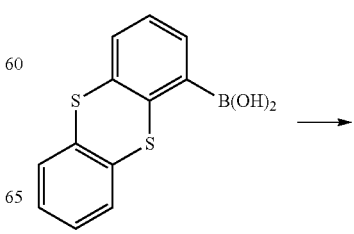

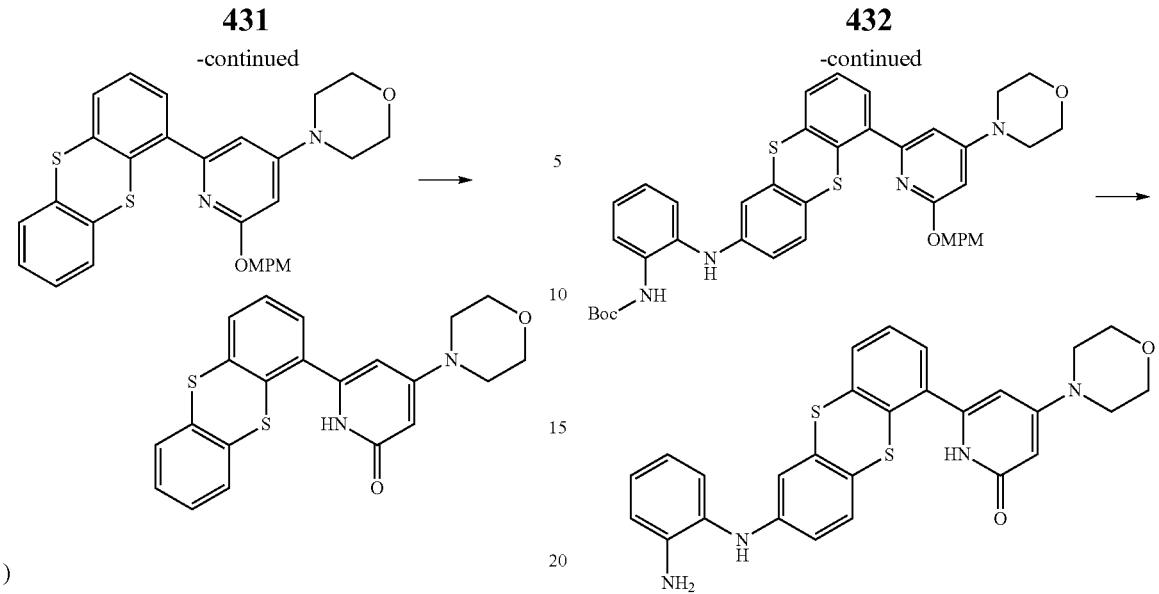

(1)

In the same manner as in Reference Example 3 (7), the following compound was obtained.

4-(2-((4-Methoxybenzyl)oxy)-6-(thianthren-1-yl)pyridin-4-yl)morpholine (2)

Trifluoroacetic acid (2 mL) was added to a solution of 4-(2-((4-methoxybenzyl)oxy)-6-(thianthren-1-yl)pyridin-4-yl)morpholine (45 mg) obtained in Example 1-53 (1) in chloroform (2 mL), followed by stirring at 50° C. for 2 hours. After the reaction mixture was cooled to room temperature, the solvent was distilled off under reduced pressure, then, saturated sodium hydrogen carbonate aqueous solution was added thereto, and the resultant product was extracted with ethyl acetate. The organic layer was washed with a saturated sodium chloride aqueous solution, and the solvent was distilled off under reduced pressure. The obtained residues were purified by preparative reversed phase HPLC (0.1% formic acid aqueous solution-0.1% solution of formic acid in acetonitrile), then, saturated sodium hydrogen carbonate aqueous solution was added thereto, and the resultant product was extracted with ethyl acetate. The organic layer was washed with a saturated sodium chloride aqueous solution, and dried over anhydrous sodium sulfate, and the solvent was distilled off under reduced pressure, whereby 4-morpholino-6-(thianthren-1-yl)pyridin-2(1H)-one (25 mg) was obtained as a white solid.

MS(ESI m/z): 395 (M+H)
RT(min): 1.32

Example 1-54

(1)

Chloro(2-(dicyclohexylphosphino)-3,6-dimethoxy-2',4',6'-triisopropyl-1,1'-biphenyl)(2-(2-aminoethyl)phenyl)palladium (II) (2.5 mg) and cesium carbonate (31 mg) were added to a solution of 4-(2-(7-iodothianthren-1-yl)-6-((4-methoxybenzyl)oxy)pyridin-4-yl)morpholine (20 mg) and tert-butyl (2-amino phenyl)carbamate (13 mg) in 1,4-dioxane (100 µL), followed by stirring at 90° C. for 5 hours. A saturated sodium hydrogen carbonate aqueous solution was added to the reaction mixture, then, the resultant product was extracted with ethyl acetate, and the organic layer was dried over anhydrous sodium sulfate. The solvent was distilled off under reduced pressure, and the obtained residues were purified by silica gel column chromatography (hexane:ethyl acetate=1:0→0:1), whereby tert-butyl (2-((6-(6-((4-methoxybenzyl)oxy)-4-morpholinopyridin-2-yl)thianthren-2-yl)amino)phenyl)carbamate (15 mg) was obtained.

MS(ESI m/z): 721 (M+H)
RT(min): 2.14

(2)

In the same manner as in Example 1-4, the following compound was obtained.

6-(7-((2-Aminophenyl)amino)thianthren-1-yl)-4-morpholinopyridin-2(1H)-one

MS(ESI m/z): 501 (M+H)
RT(min): 1.33

Examples 1-55-1 and 1-55-2

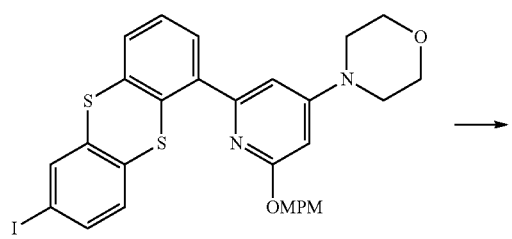

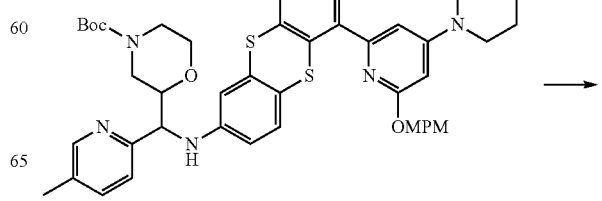

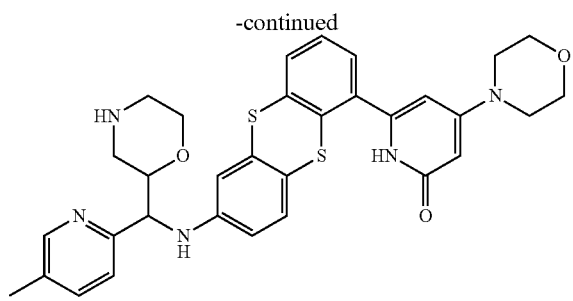

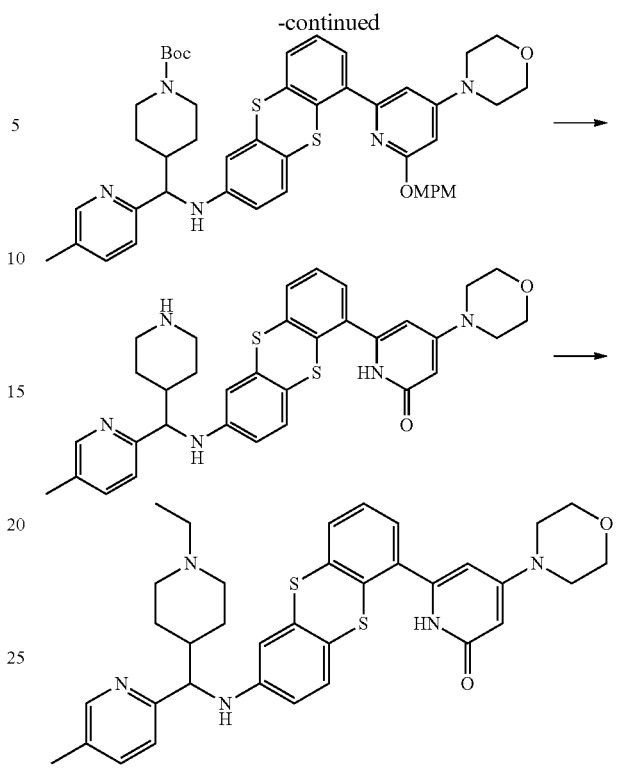

4.0 mol/L hydrogen chloride/1,4-dioxane (0.6 mL) was added to a mixed solution of tert-butyl 2-(((6-(6-((4-methoxybenzyl)oxy)-4-morpholinopyridin-2-yl)thianthren-2-yl)amino)(5-methyl pyridin-2-yl)methyl)morpholine-4-carboxylate (29 mg) in methanol (0.1 mL) and chloroform (0.1 mL), followed by stirring at 40° C. for 0.5 hours. The solvent was distilled off under reduced pressure, and the obtained residues were suspended in ethyl acetate. The solid was precipitated using a centrifugal separator, and the supernatant was removed. The obtained residues were neutralized with a sodium hydroxide aqueous solution, then, the resultant product was extracted with chloroform, and the organic layer was dried over anhydrous sodium sulfate. The solvent was distilled off under reduced pressure, and the obtained residues were purified by thin layer silica gel column chromatography (chloroform:methanol=30:1, NH silica), whereby 6-(7-(((5-methylpyridin-2-yl)(morpholin-2-yl)methyl)amino)thianthren-1-yl)-4-morpholinopyridin-2(1H)-one (diastereomer A) (5.2 mg) and 6-(7-(((5-methylpyridin-2-yl)(morpholin-2-yl)methyl)amino)thianthren-1-yl)-4-morpholinopyridin-2(1H)-one (diastereomer B) (4.7 mg) were obtained.

Example 1-55-1

Diastereomer A

MS(ESI m/z): 600 (M+H)
RT(min): 0.99

Example 1-55-2

Diastereomer B

MS(ESI m/z): 600 (M+H)
RT(min): 0.99

Example 1-56-1

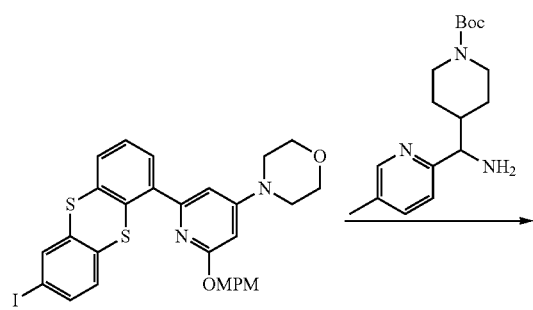

(1)
In the same manner as in Example 1-52 (1), the following compound was obtained.

tert-Butyl 4-(((6-(6-((4-methoxybenzyl)oxy)-4-morpholinopyridin-2-yl)thianthren-2-yl)amino)(5-methyl pyridin-2-yl)methyl)piperidine-1-carboxylate MS(ESI m/z): 818 (M+H)
RT(min): 1.97
(2)
In the same manner as in Example 1-55, the following compound was obtained.

6-(7-(((5-Methylpyridin-2-yl)(piperidin-4-yl)methyl)amino)thianthren-1-yl)-4-morpholinopyridin-2(1H)-one MS(ESI m/z): 598 (M+H)
RT(min): 0.93
(3)
2-Picoline borane (2.0 mg) was added to a mixture of 6-(7-(((5-methylpyridin-2-yl)(piperidin-4-yl)methyl)amino)thianthren-1-yl)-4-morpholinopyridin-2(1H)-one (5 mg) obtained in Example 1-56-1 (2) and acetaldehyde (0.44 mg) in acetic acid (50 μL) and methanol (500 μL), followed by stirring at room temperature for 1 hour. A saturated sodium hydrogen carbonate aqueous solution was added thereto, then, the resultant product was extracted with chloroform, and the organic layer was dried over anhydrous sodium sulfate. The solvent was distilled off under reduced pressure, and the obtained residues were purified by thin layer silica gel column chromatography (chloroform:methanol=30:1, NH silica), whereby 6-(7-(((1-ethyl piperidin-4-yl)(5-methylpyridin-2-yl)methyl)amino)thianthren-1-yl)-4-morpholinopyridin-2(1H)-one (2.7 mg) was obtained.
MS(ESI m/z): 626 (M+H)
RT(min): 1.02

Examples 1-56-2 to 1-56-16

In the same manner as in Example 1-56-1, the following compounds were obtained.

TABLE 48

| Example No. | R$^b$ | Compound Name | MS | RT (min) | $^1$H-NMR (300 MHz) (DMSO-d$_6$) δ: |
|---|---|---|---|---|---|
| 1-56-2 | | 6-(7-(((5-Methyl pyridin-2-yl)((S)-1-methyl pyrrolidin-2-yl)methyl)amino)thianthren-1-yl)-4-morpholino pyridin-2(1H)-one (Optically active substance A) | 598 | 1.05 | |
| 1-56-3 | | 6-(7-(((5-Methyl pyridin-2-yl)((S)-1-methyl pyrrolidin-2-yl)methyl)amino) thianthren-1-yl)-4-morpholino pyridin-2(1H)-one (Optically active substance B) | 598 | 1.04 | (CDCl$_3$): 8.61 (1H, br s), 8.43 (1H, d, J = 2.0 Hz), 7.55-7.52 (1H, m), 7.36 (1H, dd, J = 7.9, 2.0 Hz), 7.27-7.25 (2H, m), 7.19 (1H, d, J = 7.9 Hz), 7.15 (1H, d, J = 7.9 Hz), 6.70 (1H, d, J = 2.3 Hz), 6.41 (1H, dd, J = 8.6, 2.3 Hz), 5.96 (1H, d, J = 2.3 Hz), 5.72 (1H, d, J = 2.3 Hz), 5.55-5.52 (1H, br m), 4.38-4.35 (1H, br m), 3.81 (4H, t, J = 5.0 Hz), 3.32 (4H, t, J = 5.0 Hz), 3.16-3.14 (1H, m), 3.09-3.02 (1H, m), 2.34-2.24 (4H, m), 2.12-2.08 (1H, m), 1.89 (3H, s), 1.78-1.52 (3H, m). |
| 1-56-4 | | 6-(7-(((5-Methyl pyridin-2-yl)((R)-1-methyl pyrrolidin-2-yl)methyl)amino) thianthren-1-yl)-4-morpholino pyridin-2(1H)-one (Optically active substance C) | 598 | 1.04 | |
| 1-56-5 | | 6-(7-(((5-Methyl pyridin-2-yl)((R)-1-methyl pyrrolidin-2-yl)methyl)amino) thianthren-1-yl)-4-morpholino pyridin-2(1H)-one (Optically active substance D) | 598 | 1.05 | (CDCl$_3$): 10.23 (1H, br s), 8.42 (1H, d, J = 2.0 Hz), 7.48 (1H, dd, J = 7.3, 2.0 Hz), 7.39 (1H, dd, J = 7.9, 2.0 Hz), 7.28-7.21 (3H, m), 7.07 (1H, d, J = 8.6 Hz), 6.66 (1H, d, J = 2.6 Hz), 6.34 (1H, dd, J = 8.8, 2.6 Hz), 5.94 (1H, d, J = 2.3 Hz), 5.67 (1H, d, J = 2.3 Hz), 5.16 (1H, s), 4.42 (1H, d, J = 4.0 Hz), 3.79 (4H, t, J = 4.8 Hz), 3.29 (4H, t, J = 4.8 Hz), 3.12 (1H, t, J = 7.6 Hz), 2.77-2.74 (1H, m), 2.32 (3H, s), 2.29-2.21 (4H, m), 1.76-1.56 (3H, m), 1.23-1.19 (1H, m). |

TABLE 48-continued

| Example No. | R^b | Compound Name | MS | RT (min) | ¹H-NMR (300 MHz) (DMSO-d₆) δ: |
|---|---|---|---|---|---|
| 1-56-6 | (1-(2-fluoroethyl)piperidin-4-yl with 5-methylpyridin-2-yl)methyl | 6-(7-(((1-(2-Fluoroethyl) piperidin-4-yl)(5-methyl pyridin-2-yl)methyl)amino) thianthren-1-yl)-4-morpholino pyridin-2(1H)-one | 644 | 1.03 | (CDCl₃): 8.82 (1H, br s), 8.36 (1H, d, J = 2.0 Hz), 7.56-7.50 (1H, m), 7.39 (1H, dd, J = 7.9, 2.0 Hz), 7.24 (2H, d, J = 4.6 Hz), 7.12 (1H, d, J = 8.2 Hz), 7.08 (1H, d, J = 7.9 Hz), 6.72 (1H, d, J = 2.3 Hz), 6.44 (1H, dd, J = 8.2, 2.3 Hz), 5.95 (1H, d, J = 2.0 Hz), 5.71 (1H, d, J = 2.0 Hz), 4.80 (1H, d, J = 7.4 Hz), 4.53 (2H, dt, J = 47.6, 5.0 Hz), 4.24 (1H, dd, J = 7.4, 7.0 Hz), 3.80 (4H, t, J = 5.0 Hz), 3.31 (4H, t, J = 5.0 Hz), 2.96 (2H, dd, J = 17.5, 11.6 Hz), 2.64 (2H, dt, J = 28.2, 5.0 Hz), 2.28 (3H, s), 2.05-1.39 (7H, m). |
| 1-56-7 | (1-(2-methoxyethyl)piperidin-4-yl with 5-methylpyridin-2-yl)methyl | 6-(7-(((1-(2-Methoxy ethyl) piperidin-4-yl)(5-methyl pyridin-2-yl)methyl)amino) thianthren-1-yl)-4-morpholino pyridin-2(1H)-one | 656 | 1.05 | (CDCl₃): 8.74 (1H, br s), 8.37 (1H, d, J = 2.0 Hz), 7.56-7.51 (1H, m), 7.39 (1H, dd, J = 7.9, 2.0 Hz), 7.28-7.22 (2H, m), 7.12 (1H, d, J = 8.6 Hz), 7.08 (1H, d, J = 7.9 Hz), 6.71 (1H, d, J = 2.3 Hz), 6.43 (1H, dd, J = 8.6, 2.3 Hz), 5.95 (1H, d, J = 2.3 Hz), 5.71 (1H, d, J = 2.3 Hz), 4.79 (1H, d, J = 7.3 Hz), 4.24 (1H, dd, J = 7.3, 7.0 Hz), 3.81 (4H, t, J = 5.0 Hz), 3.47 (2H, t, J = 5.6 Hz), 3.34-3.31 (7H, m), 2.98-2.93 (2H, m), 2.52 (2H, t, J = 5.6 Hz), 2.28 (3H, s), 1.96-1.37 (7H, m). |

TABLE 49

| Example No. | R^b | Compound Name | MS | RT (min) | ¹H-NMR (300 MHz) (DMSO-d₆) δ: |
|---|---|---|---|---|---|
| 1-56-8 | (4-(2-methoxyethyl)morpholin-2-yl with 5-methylpyridin-2-yl)methyl | 6-(7-(((4-(2-Methoxy ethyl) morpholin-2-yl)(5-methyl pyridin-2-yl)methyl)amino) thianthren-1-yl)-4-morpholino pyridin-2(1H)-one (Diastereomer A) | 658 | 1.03 | (CDCl₃): 8.47 (1H, br s), 8.41 (1H, d, J = 2.0 Hz), 7.56-7.51 (1H, m), 7.40 (1H, dd, J = 7.9, 2.0 Hz), 7.26-7.22 (3H, m), 7.12 (1H, d, J = 8.6 Hz), 6.72 (1H, d, J = 2.3 Hz), 6.41 (1H, dd, J = 8.6, 2.3 Hz), 5.95 (1H, d, J = 2.3 Hz), 5.71 (1H, d, J = 2.3 Hz), 5.15 (1H, d, J = 5.3 Hz), 4.39 (1H, dd, J = 5.3, 5.2 Hz), 3.95-3.89 (2H, m), 3.81 (4H, t, J = 4.6 Hz), 3.66 (1H, t, J = 10.7 Hz), 3.45 (2H, t, J = 5.4 Hz), 3.33-3.31 (7H, m), 2.74 (2H, d, J = 10.7 Hz), 2.53 (2H, t, J = 5.4 Hz), 2.31 (3H, s), 2.20-2.16 (2H, m). |

TABLE 49-continued

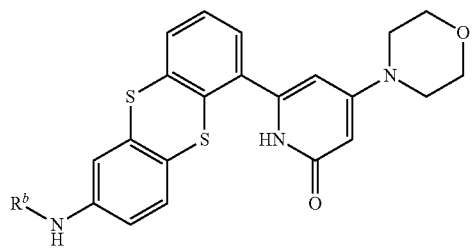

| Example No. | R$^b$ | Compound Name | MS | RT (min) | $^1$H-NMR (300 MHz) (DMSO-d$_6$) δ: |
|---|---|---|---|---|---|
| 1-56-9 | | 6-(7-(((4-(2-Methoxy ethyl) morpholin-2-yl)(5-methyl pyridin-2-yl)methyl)amino) thianthren-1-yl)-4-morpholino pyridin-2(1H)-one (Diastereomer B) | 658 | 1.04 | (CDCl$_3$): 8.46 (1H, br s), 8.37 (1H, d, J = 1.7 Hz), 7.55-7.52 (1H, m), 7.39 (1H, dd, J = 7.9, 1.7 Hz), 7.28-7.22 (2H, m), 7.17 (1H, d, J = 7.9 Hz), 7.12 (1H, d, J = 8.6 Hz), 6.78 (1H, d, J = 2.6 Hz), 6.47 (1H, dd, J = 8.6, 2.6 Hz), 5.95 (1H, d, J = 2.3 Hz), 5.71 (1H, d, J = 2.3 Hz), 5.19 (1H, d, J = 7.4 Hz), 4.53 (1H, dd, J = 7.4, 5.0 Hz), 3.98-3.97 (1H, m), 3.91-3.87 (1H, m), 3.81 (4H, t, J = 5.0 Hz), 3.74-3.66 (1H, m), 3.46 (2H, t, J = 5.3 Hz), 3.32-3.31 (7H, m), 2.84 (1H, d, J = 11.2 Hz), 2.71 (1H, d, J = 11.2 Hz), 2.51 (2H, t, J = 5.3 Hz), 2.30 (3H, s), 2.11 (1H, t, J = 10.4 Hz), 1.89 (1H, t, J = 10.4 Hz). |
| 1-56-10 | | 6-(7-((((S)-4-Methyl morpholin-2-yl)(5-methyl pyridin-2-yl)methyl)amino) thianthren-1-yl)-4-morpholino pyridin-2(1H)-one (Optically active substance A) | 614 | 0.98 | (CDCl$_3$): 8.57 (1H, br s), 8.37 (1H, s), 7.56-7.51 (1H, m), 7.40 (1H, dd, J = 7.9, 2.0 Hz), 7.27-7.24 (2H, m), 7.17 (1H, d, J = 8.6 Hz), 7.13 (1H, d, J = 8.6 Hz), 6.78 (1H, d, J = 2.6 Hz), 6.47 (1H, dd, J = 8.6, 2.6 Hz), 5.94 (1H, d, J = 2.6 Hz), 5.71 (1H, d, J = 2.6 Hz), 5.15 (1H, d, J = 7.3 Hz), 4.53 (1H, dd, J = 7.3, 5.3 Hz), 3.94-3.89 (2H, m), 3.81 (4H, t, J = 4.8 Hz), 3.65 (1H, td, J = 11.4, 2.4 Hz), 3.31 (4H, t, J = 4.8 Hz), 2.73 (1H, d, J = 11.9 Hz), 2.58 (1H, d, J = 9.9 Hz), 2.30 (3H, s), 2.22 (3H, s), 2.03 (1H, td, J = 11.4, 3.5 Hz), 1.81 (1H, t, J = 10.6 Hz). |
| 1-56-11 | | 6-(7-((((S)-4-Methyl morpholin-2-yl)(5-methyl pyridin-2-yl)methyl)amino) thianthren-1-yl)-4-morpholino pyridin-2(1H)-one (Optically active substance B) | 614 | 0.99 | (CDCl$_3$): 8.79 (1H, br s), 8.41 (1H, d, J = 2.0 Hz), 7.53-7.51 (1H, m), 7.41 (1H, dd, J = 7.9, 2.0 Hz), 7.28-7.21 (3H, m), 7.11 (1H, d, J = 8.8 Hz), 6.72 (1H, d, J = 2.6 Hz), 6.41 (1H, dd, J = 8.6, 2.6 Hz), 5.94 (1H, d, J = 2.6 Hz), 5.70 (1H, d, J = 2.0 Hz), 5.13 (1H, d, J = 5.9 Hz), 4.39 (1H, t, J = 5.3 Hz), 3.94-3.85 (2H, m), 3.80 (4H, t, J = 5.0 Hz), 3.62 (1H, td, J = 11.4, 2.2 Hz), 3.31 (4H, t, J = 5.0 Hz), 2.60 (2H, d, J = 11.9 Hz), 2.31 (3H, s), 2.23 (3H, s), 2.15-2.06 (2H, m). |
| 1-56-12 | | 6-(7-((((R)-4-Methyl morpholin-2-yl)(5-methyl pyridin-2-yl)methyl)amino) thianthren-1-yl)-4-morpholino pyridin-2(1H)-one (Optically active substance C) | 614 | 0.99 | (CDCl$_3$): 8.79 (1H, br s), 8.41 (1H, d, J = 2.0 Hz), 7.53-7.51 (1H, m), 7.41 (1H, dd, J = 7.9, 2.0 Hz), 7.28-7.21 (3H, m), 7.11 (1H, d, J = 8.6 Hz), 6.72 (1H, d, J = 2.6 Hz), 6.41 (1H, dd, J = 8.6, 2.6 Hz), 5.94 (1H, d, J = 2.6 Hz), 5.70 (1H, d, J = 2.0 Hz), 5.13 (1H, d, J = 5.9 Hz), 4.39 (1H, t, J = 5.3 Hz), 3.94-3.85 (2H, m), 3.80 (4H, t, J = 5.0 Hz), 3.62 (1H, td, J = 11.4, 2.2 Hz), 3.31 (4H, t, J = 5.0 Hz), 2.60 (2H, d, J = 11.9 Hz), 2.31 (3H, s), 2.23 (3H, s), 2.15-2.06 (2H, m). |

TABLE 50

| Example No. | R^b | Compound Name | MS | RT (min) | $^1$H-NMR (300 MHz) (DMSO-d$_6$) δ: |
|---|---|---|---|---|---|
| 1-56-13 | | 6-(7-((((R)-4-Methyl morpholin-2-yl)(5-methyl pyridin-2-yl)methyl)amino) thianthren-1-yl)-4-morpholino pyridin-2(1H)-one (Optically active substance D) | 614 | 0.99 | (CDCl$_3$) δ: 8.57 (1H, br s), 8.37 (1H, s), 7.56-7.51 (1H, m), 7.40 (1H, dd, J = 7.9, 2.0 Hz), 7.27-7.24 (2H, m), 7.17 (1H, d, J = 8.6 Hz), 7.13 (1H, d, J = 8.6 Hz), 6.78 (1H, d, J = 2.6 Hz), 6.47 (1H, dd, J = 8.6, 2.6 Hz), 5.94 (1H, d, J = 2.6 Hz), 5.71 (1H, d, J = 2.6 Hz), 5.15 (1H, d, J = 7.3 Hz), 4.53 (1H, dd, J = 7.3, 5.3 Hz), 3.94-3.89 (2H, m), 3.81 (4H, t, J = 4.8 Hz), 3.65 (1H, td, J = 11.4, 2.4 Hz), 3.31 (4H, t, J = 4.8 Hz), 2.73 (1H, d, J = 11.9 Hz), 2.58 (1H, d, J = 9.9 Hz), 2.30 (3H, s), 2.22 (3H, s), 2.03 (1H, td, J = 11.4, 3.5 Hz), 1.81 (1H, t, J = 10.6 Hz). |
| 1-56-14 | | 6-(7-(((5-Methyl pyridin-2-yl)((S)-1-methyl pyrrolidin-3-yl)methyl)amino) thianthren-1-yl)-4-morpholino pyridin-2(1H)-one (Optically active substance A) | 598 | 0.98 | (CDCl$_3$) δ: 8.64 (1H, br s), 8.40 (1H, s), 7.55-7.50 (1H, m), 7.39 (1H, dd, J = 7.9, 2.6 Hz), 7.24-7.23 (2H, m), 7.18 (1H, d, J = 7.9 Hz), 7.11 (1H, d, J = 7.9 Hz), 6.65 (1H, d, J = 2.0 Hz), 6.34 (1H, dd, J = 8.6, 2.0 Hz), 6.09 (1H, d, J = 5.3 Hz), 5.95 (1H, d, J = 2.6 Hz), 5.71 (1H, d, J = 2.0 Hz), 4.29 (1H, dd, J = 5.3, 4.8 Hz), 3.81 (4H, t, J = 5.0 Hz), 3.32 (4H, t, J = 5.0 Hz), 2.99-2.91 (1H, m), 2.78-2.71 (2H, m), 2.34 (3H, s), 2.30 (3H, s), 2.20-1.98 (3H, m), 1.83-1.74 (1H, m). |
| 1-56-15 | | 6-(7-(((5-Methyl pyridin-2-yl)((S)-1-methyl pyrrolidin-3-yl)methyl)amino) thianthren-1-yl)-4-morpholino pyridin-2(1H)-one (Optically active substance B) | 598 | 0.99 | (CDCl$_3$): 8.55 (1H, br s), 8.40 (1H, d, J = 2.0 Hz), 7.55-7.52 (1H, m), 7.39 (1H, dd, J = 7.3, 2.0 Hz), 7.25-7.24 (2H, m), 7.16 (1H, d, J = 7.9 Hz), 7.11 (1H, d, J = 8.6 Hz), 6.68 (1H, d, J = 2.0 Hz), 6.36 (1H, dd, J = 8.3, 2.3 Hz), 5.94 (1H, d, J = 2.6 Hz), 5.71 (1H, d, J = 2.0 Hz), 5.67 (1H, d, J = 4.6 Hz), 4.37-4.35 (1H, m), 3.81 (4H, t, J = 5.0 Hz), 3.32 (4H, t, J = 5.0 Hz), 2.84-2.79 (2H, m), 2.66-2.62 (1H, m), 2.32-2.24 (9H, m), 1.77-1.75 (1H, m). |
| 1-56-16 | | 6-(7-(((5-Methyl pyridin-2-yl)((R)-1-methyl pyrrolidin-3-yl)methyl)amino) thianthren-1-yl)-4-morpholino pyridin-2(1H)-one (Optically active substance C) | 598 | 0.98 | (CDCl$_3$): 8.55 (1H, br s), 8.40 (1H, d, J = 2.0 Hz), 7.55-7.52 (1H, m), 7.39 (1H, dd, J = 7.3, 2.0 Hz), 7.25-7.24 (2H, m), 7.16 (1H, d, J = 7.9 Hz), 7.11 (1H, d, J = 8.6 Hz), 6.68 (1H, d, J = 2.0 Hz), 6.36 (1H, dd, J = 8.3, 2.3 Hz), 5.94 (1H, d, J = 2.6 Hz), 5.71 (1H, d, J = 2.0 Hz), 5.67 (1H, d, J = 4.6 Hz), 4.37-4.35 (1H, m), 3.81 (4H, t, J = 5.0 Hz), 3.32 (4H, t, J = 5.0 Hz), 2.84-2.79 (2H, m), 2.66-2.62 (1H, m), 2.32-2.24 (9H, m), 1.77-1.75 (1H, m). |

Example 1-57-1

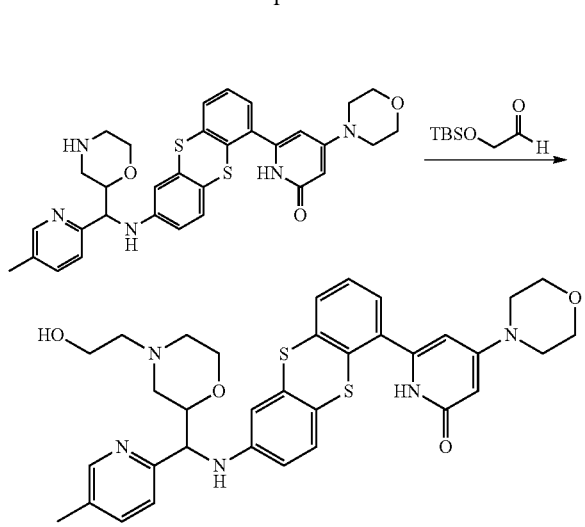

2-Picoline borane (3.0 mg) was added to a mixture of 6-(7-(((5-methylpyridin-2-yl)(morpholin-2-yl)methyl)amino)thianthren-1-yl)-4-morpholinopyridin-2(1H)-one (diastereomer A) (2.0 mg) obtained in Example 1-55 and 2-((tert-butyldimethylsilyl)oxy)acetaldehyde (0.70 mg) in acetic acid (45 μL) and methanol (450 μL), followed by stirring at room temperature for 1.5 hours. A 1.0 mol/L tetrabutylammonium fluoride-tetrahydrofuran solution (0.1 mL) was added to the reaction mixture, followed by stirring at room temperature for 5 hours. A saturated sodium hydrogen carbonate aqueous solution was added thereto, then, the resultant product was extracted with chloroform, and the organic layer was dried over anhydrous sodium sulfate. The solvent was distilled off under reduced pressure, and the obtained residues were purified by preparative thin layer silica gel chromatography (chloroform:methanol=30:1, NH silica), whereby 6-(7-(((4-(2-hydroxyethyl)morpholin-2-yl)(5-methylpyridin-2-yl)methyl)amino)thianthren-1-yl)-4-morpholinopyridin-2(1H)-one (racemic mixture A) (1.24 mg) was obtained.

$^1$H-NMR (CDCl$_3$, 300 MHz) δ: 8.66 (1H, brs), 8.41 (1H, d, J=2.0 Hz), 7.56-7.50 (1H, m), 7.42 (1H, dd, J=7.9, 2.0 Hz), 7.27-7.25 (3H, m), 7.12 (1H, d, J=7.9 Hz), 6.70 (1H, d, J=2.3 Hz), 6.40 (1H, dd, J=8.6, 2.3 Hz), 5.95 (1H, d, J=2.3 Hz), 5.71 (1H, d, J=2.3 Hz), 5.08 (1H, d, J=4.6 Hz), 4.65-4.59 (1H, m), 3.92-3.87 (2H, m), 3.80 (4H, t, J=5.0 Hz), 3.62-3.57 (3H, m), 3.31 (4H, t, J=5.0 Hz), 2.67-2.65 (1H, m), 2.60-2.52 (2H, m), 2.44-2.40 (3H, m), 2.32 (3H, s).

MS(ESI m/z): 644 (M+H)
RT(min): 1.00

Example 1-57-2

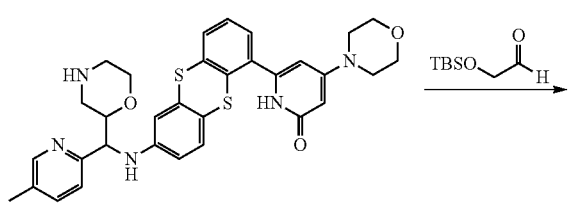

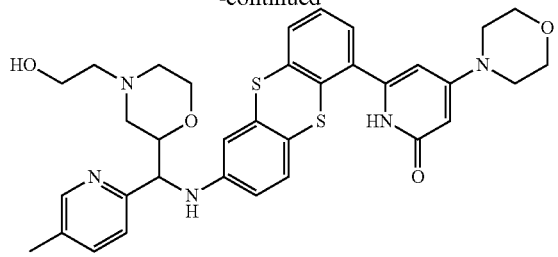

Using 6-(7-(((5-methylpyridin-2-yl)(morpholin-2-yl)methyl)amino)thianthren-1-yl)-4-morpholinopyridin-2(1H)-one (diastereomer B) obtained in Example 1-55, the following compound was obtained in the same manner as in Example 1-57-1.

6-(7-(((4-(2-Hydroxyethyl)morpholin-2-yl)(5-methylpyridin-2-yl)methyl)amino)thianthren-1-yl)-4-morpholinopyridin-2(1H)-one (racemic mixture B)

$^1$H-NMR (CDCl$_3$, 300 MHz) δ: 8.38 (1H, d, J=2.0 Hz), 7.55-7.53 (1H, m), 7.40 (1H, dd, J=7.3, 2.0 Hz), 7.28-7.23 (2H, m), 7.16-7.13 (2H, m), 6.78 (1H, d, J=2.3 Hz), 6.47 (1H, dd, J=8.6, 2.3 Hz), 5.95 (1H, d, J=2.0 Hz), 5.72 (1H, d, J=2.0 Hz), 5.12 (1H, d, J=7.3 Hz), 4.52-4.50 (1H, m), 3.95-3.87 (2H, m), 3.81 (4H, t, J=5.0 Hz), 3.64 (1H, td, J=11.2, 2.2 Hz), 3.57 (2H, t, J=5.3 Hz), 3.28 (4H, t, J=5.0 Hz), 2.81 (1H, d, J=11.2 Hz), 2.67 (1H, d, J=11.9 Hz), 2.49 (2H, t, J=5.3 Hz), 2.30 (3H, s), 2.21-2.14 (1H, m), 2.00-1.96 (1H, m).

MS(ESI m/z): 644 (M+H)
RT(min): 1.02

Example 1-58

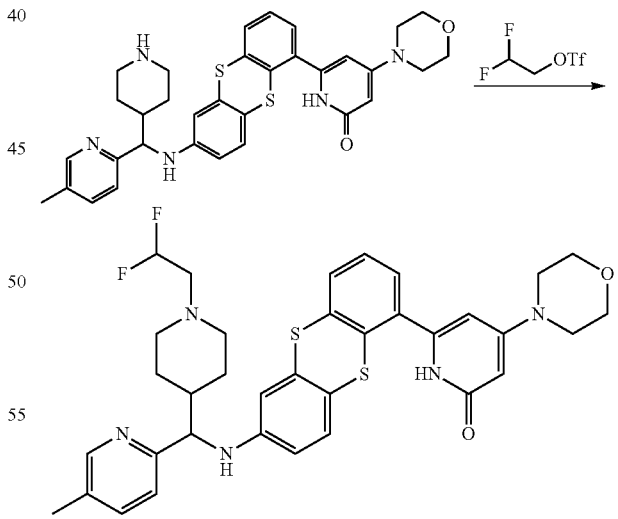

Potassium carbonate (2.9 mg) and 2,2-difluoroethyltrifluoro methanesulfonate (3.6 mg) were added to a solution of 6-(7-(((5-methylpyridin-2-yl)(piperidin-4-yl)methyl)amino)thianthren-1-yl)-4-morpholinopyridin-2(1H)-one (8.3 mg) obtained in Example 1-56-1 (2) in tetrahydrofuran (0.7 mL), followed by stirring at room temperature for 1 hour. A saturated sodium hydrogen carbonate aqueous solution was added thereto, then, the resultant product was extracted with chloroform, and the organic layer was dried over anhydrous sodium sulfate. The solvent was distilled off under reduced pressure, and the obtained residues were purified by preparative thin layer silica gel chromatography (chloroform: methanol=50:1, NH silica), whereby 6-(7-(((1-(2,2-difluoroethyl)piperidin-4-yl)(5-methylpyridin-2-yl)methyl) amino)thianthren-1-yl)-4-morpholinopyridin-2(1H)-one (2.9 mg) was obtained.

$^1$H-NMR (CDCl$_3$, 300 MHz) δ: 8.37 (1H, d, J=2.0 Hz), 7.57-7.52 (1H, m), 7.40 (1H, dd, J=7.9, 2.0 Hz), 7.27-7.25 (2H, m), 7.11-7.07 (2H, m), 6.73 (1H, d, J=2.3 Hz), 6.44 (1H, dd, J=8.6, 2.3 Hz), 6.01 (1H, d, J=2.6 Hz), 5.84 (1H, tt, J=56.1, 4.6 Hz), 5.76 (1H, d, J=2.6 Hz), 4.81 (1H, brs), 4.23 (1H, d, J=5.9 Hz), 3.81 (4H, t, J=4.8 Hz), 3.34 (4H, t, J=4.8 Hz), 2.96-2.89 (2H, m), 2.69 (2H, td, J=15.0, 4.6 Hz), 2.28 (3H, s), 2.17-1.79 (5H, m), 1.48-1.40 (2H, m).

MS(ESI m/z): 662 (M+H)
RT(min): 1.06

Example 1-59-1

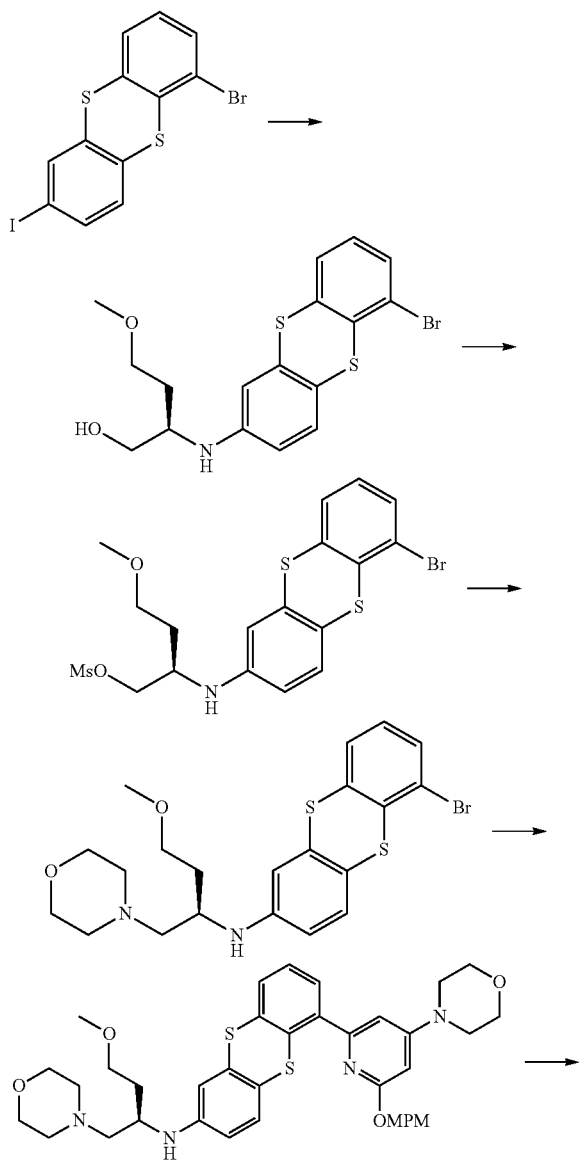

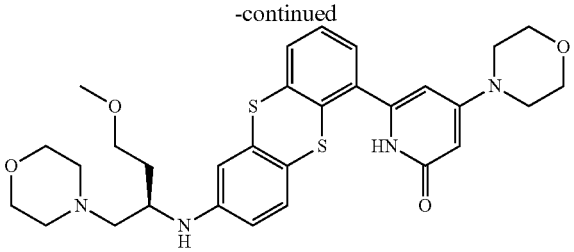

(1)

In the same manner as in Example 1-46-1 (1), the following compound was obtained.

(R)-2-((6-bromothianthren-2-yl)amino)-4-methoxybutane-1-ol

MS(ESI m/z): 414 (M+H+2)
RT(min): 1.74

(2)

Triethylamine (18 μL) and methanesulfonyl chloride (5.1 μL) were added a solution of (R)-2-((6-bromothianthren-2-yl)amino)-4-methoxybutane-1-ol (9.2 mg) in dichloromethane (1.0 mL), followed by stirring for 0.5 hours. Water was added to the reaction mixture, then, the resultant product was extracted with ethyl acetate, and the solvent was distilled off under reduced pressure. The obtained residues were purified by silica gel column chromatography (hexane:ethyl acetate=1:1), whereby (R)-2-((6-bromothianthren-2-yl) amino)-4-methoxybutyl methanesulfonate (23 mg) was obtained.

MS(ESI m/z): 492 (M+H+2)
RT(min): 1.87

(3)

The temperature was changed to 130° C., and in the same manner as in Example 1-6-1 (2), the following compound was obtained.

(R)-6-bromo-N-(4-methoxy-1-morpholinobutan-2-yl)thianthrene-2-amine

MS(ESI m/z): 483 (M+H+2)
RT(min):

(4)

In the same manner as in Example 1-46-1 (4), the following compound was obtained.

(R)—N-(4-methoxy-1-morpholinobutan-2-yl)-6-(6-((4-methoxybenzyl)oxy)-4-morpholinopyridin-2-yl) thianthrene-2-amine MS(ESI m/z): 701 (M+H)
RT(min): 1.41

(5)

In the same manner as in Reference Example 18 (2), the following compound was obtained.

(R)-6-(7-((4-methoxy-1-morpholinobutan-2-yl) amino)thianthren-1-yl)-4-morpholinopyridin-2(1H)-one $^1$H-NMR (CDCl$_3$, 300 MHz) δ: 7.58 (1H, dd, J=5.3, 4.0 Hz), 7.30-7.23 (2H, m), 7.21 (1H, d, J=8.6 Hz), 6.84 (1H, d, J=2.6 Hz), 6.53 (1H, dd, J=8.6, 2.6 Hz), 5.98 (1H, d, J=2.0 Hz), 5.74 (1H, d, J=2.0 Hz), 5.37-5.32 (1H, m), 3.82 (4H, t, J=5.0 Hz), 3.69-3.53 (5H, m), 3.46 (2H, t, J=5.9 Hz), 3.37-3.31 (7H, m), 2.51-2.39 (6H, m), 1.92-1.66 (2H, m).

MS(ESI m/z): 581 (M+H)

RT(min): 0.96

Example 1-59-2

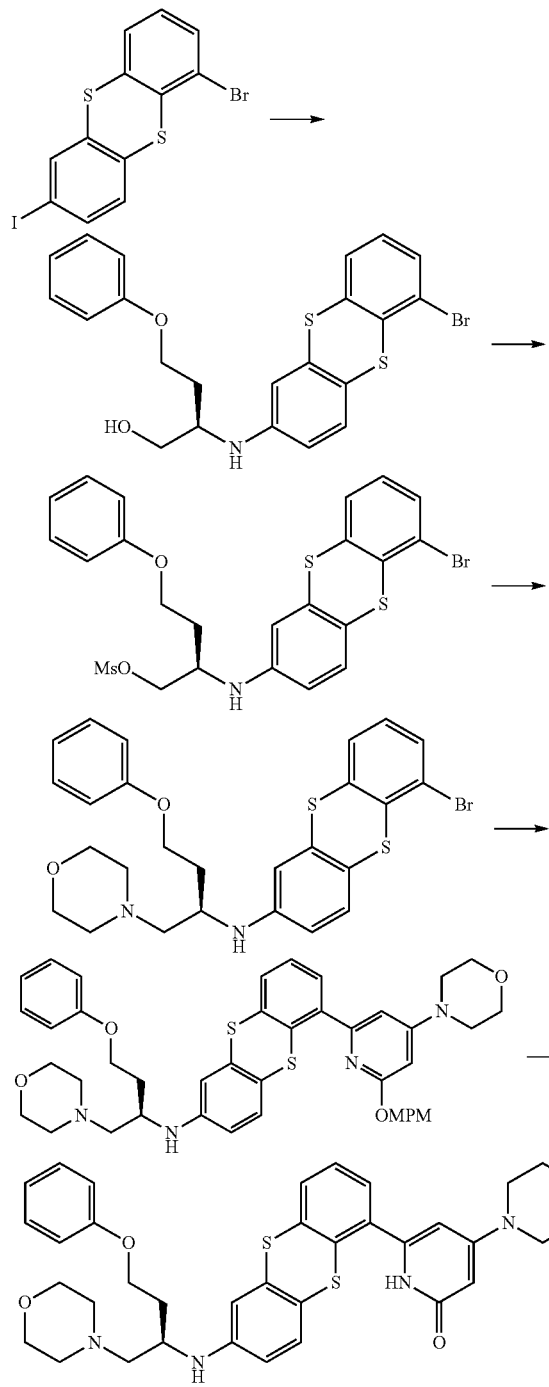

(1)
In the same manner as in Example 1-46-1 (1), the following compound was obtained.

(S)-3-(benzyloxy)-2-((6-bromothianthren-2-yl)amino)propane-1-ol

MS(ESI m/z): 476 (M+H+2)

RT(min): 1.73

(2)
In the same manner as in Example 1-59-1 (2), the following compound was obtained.

(R)-3-(benzyloxy)-2-((6-bromothianthren-2-yl)amino)propyl methanesulfonate

MS(ESI m/z): 552 (M+H)

RT(min): 2.08

(3)
The temperature was changed to 130° C., and in the same manner as in Example 1-6-1 (2), the following compound was obtained.

(S)—N-(1-(benzyloxy)-3-morpholinopropan-2-yl)-6-bromothianthrene-2-amine

MS(ESI m/z): 545 (M+H+2)

RT(min): 1.52

(4)
In the same manner as in Example 1-46-1 (4), the following compound was obtained.

(S)—N-(1-(benzyloxy)-3-morpholinopropan-2-yl)-6-(6-((4-methoxybenzyl)oxy)-4-morpholinopyridin-2-yl)thianthrene-2-amine MS(ESI m/z): 763 (M+H)

RT(min): 1.58

(5)
In the same manner as in Reference Example 18 (2), the following compound was obtained.

(S)-6-(7-((1-(benzyloxy)-3-morpholinopropan-2-yl)amino)thianthren-1-yl)-4-morpholinopyridin-2(1H)-one ¹H-NMR (CDCl₃, 300 MHz) δ: 7.58 (1H, t, J=4.6 Hz), 7.40-7.17 (8H, m), 6.82 (1H, d, J=2.6 Hz), 6.51 (1H, dd, J=8.6, 2.6 Hz), 5.99 (1H, d, J=2.6 Hz), 5.74 (1H, d, J=2.6 Hz), 5.37-5.32 (1H, m), 4.56 (1H, d, J=11.9 Hz), 4.50 (1H, d, J=11.9 Hz), 3.82 (4H, t, J=4.6 Hz), 3.70-3.45 (7H, m), 3.34 (4H, t, J=4.6 Hz), 2.60-2.40 (6H, m).

MS(ESI m/z): 643 (M+H)

RT(min): 1.14

Example 1-60

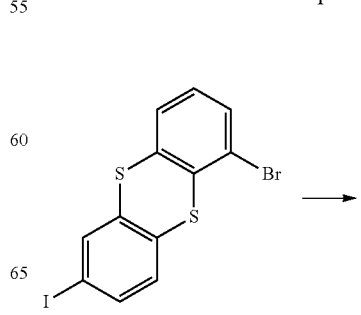

-continued

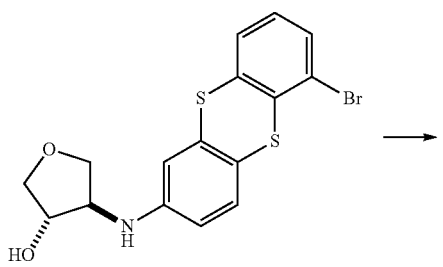

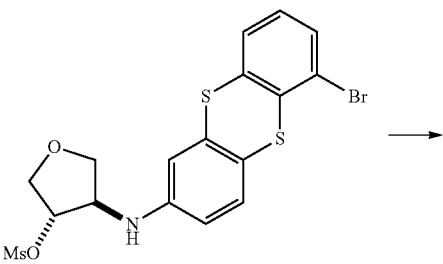

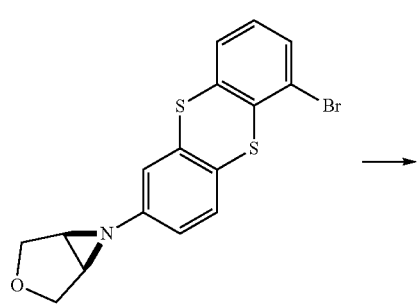

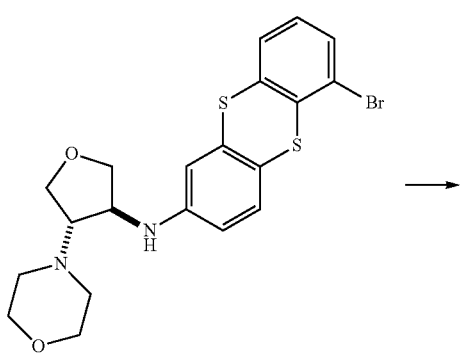

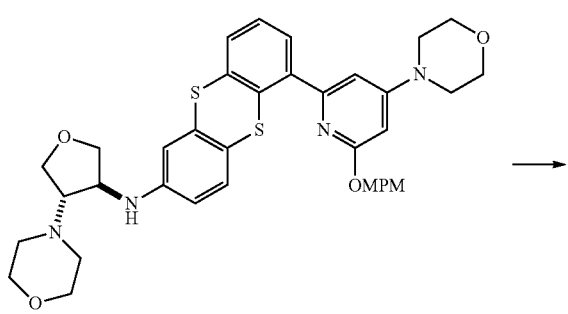

-continued

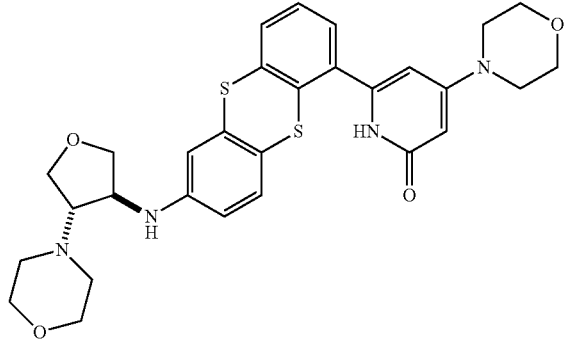

(1)
In the same manner as in Example 1-46-1 (1), the following compound was obtained.

Trans-4-((6-bromothianthren-2-yl)amino)tetrahydrofuran-3-ol

MS(ESI m/z): 398 (M+H)
RT(min): 1.59

(2)
In the same manner as in Reference Example 22-24-1 (1), the following compound was obtained.

Trans-4-((6-bromothianthren-2-yl)amino)tetrahydrofuran-3-yl methanesulfonate

MS(ESI m/z): 476 (M+H)
RT(min): 1.77

(3) and (4)
In the same manner as in Example 1-46-1 (3), the following compound was obtained.

Trans-N-(6-bromothianthren-2-yl)-4-morpholinotetrahydrofuran-3-amine

MS(ESI m/z): 467 (M+H)
RT(min): 1.38

(5)
In the same manner as in Example 1-46-1 (4), the following compound was obtained.

Trans-N-(6-(6-((4-methoxybenzyl)oxy)-4-morpholinopyridin-2-yl)thianthren-2-yl)-4-morpholinotetrahydrofuran-3-amine MS(ESI m/z): 685 (M+H)
RT(min): 1.42

(6)
In the same manner as in Reference Example 18 (2), the following compound was obtained.

Trans-4-morpholino-6-(7-((4-morpholinotetrahydrofuran-3-yl)amino)thianthren-1-yl)pyridin-2(1H)-one MS(ESI m/z): 565 (M+H)
RT(min): 0.94

Example 1-61

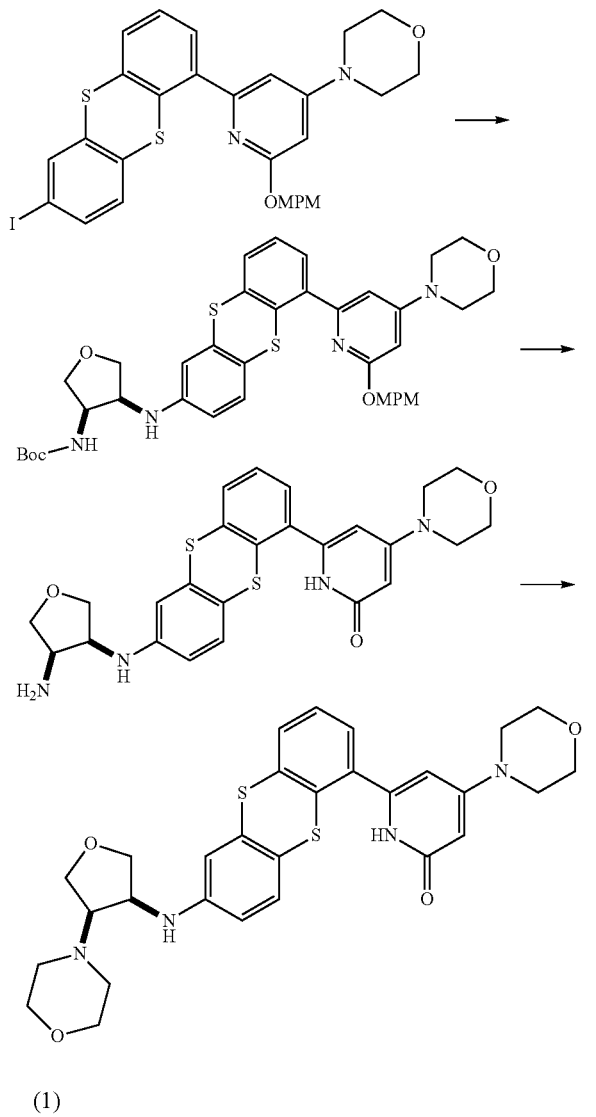

(1)
In the same manner as in Example 1-50-1 (1), the following compound was obtained.

Cis-N-(6-(6-(4-methoxybenzyl)oxy)-4-morpholinopyridin-2-yl)thianthren-2-yl)-4-morpholinotetrahydrofuran-3-amine MS(ESI m/z): 715 (M+H)
RT(min): 1.77
(2)
In the same manner as in Example 1-4, the following compound was obtained.

Cis-6-(7-((4-aminotetrahydrofuran-3-yl)amino)thianthren-1-yl)-4-morpholinopyridin-2(1H)-one MS(ESI m/z): 495 (M+H)
RT(min): 0.87
(3)
1-Iodo-2-(2-iodoethoxy)ethane (32 μL) and diisopropyl ethylamine (96 μL) were added to a solution of cis-6-(7-((4-aminotetrahydrofuran-3-yl)amino)thianthren-1-yl)-4-morpholinopyridin-2(1H)-one (37 mg) obtained in Example 1-61 (2) in N,N-dimethyl formamide (3 mL), followed by stirring at 90° C. for 2 hours. After the reaction mixture was cooled to room temperature, water was added thereto, then, the resultant product was extracted with ethyl acetate, and the organic layer was dried over anhydrous sodium sulfate. The solvent was distilled off under reduced pressure, and the obtained residues were purified by silica gel column chromatography (chloroform:methanol=20:1→6:1), whereby cis-4-morpholino-6-(7-((4-morpholinotetrahydrofuran-3-yl)amino)thianthren-1-yl)pyridin-2(1 H)-one (3.9 mg) was obtained.

MS(ESI m/z): 565 (M+H)
RT(min): 0.96

Example 2-1-1

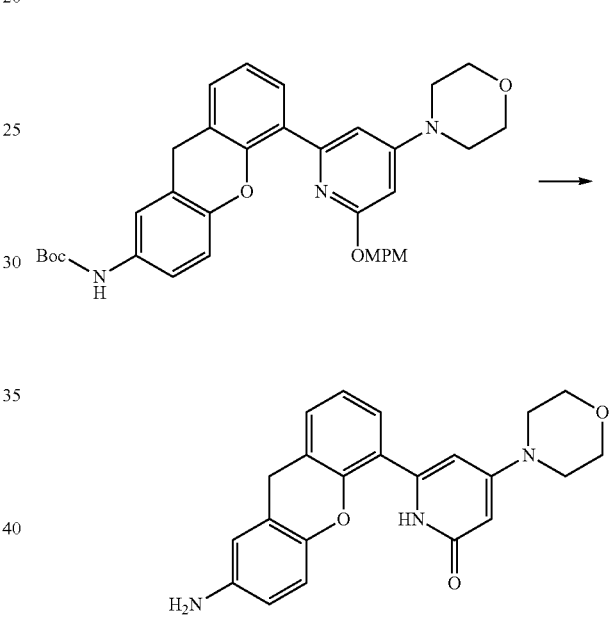

Under ice-cooling, 4.0 mol/L hydrogen chloride/1,4-dioxane (20 mL) was added to a solution of tert-butyl (5-(6-((4-methoxybenzyl)oxy)-4-morpholinopyridin-2-yl)-9H-xanthen-2-yl)carbamate (1.5 g) in methanol (10 mL), followed by stirring at room temperature for 13 hours. A saturated sodium hydrogen carbonate aqueous solution was added to the reaction mixture, then, the resultant product was extracted with chloroform, and the organic layer was dried over anhydrous sodium sulfate. The solvent was distilled off under reduced pressure, then, the obtained residues were purified by silica gel column chromatography (chloroform:methanol=1:0→9:1, NH silica), and purified by silica gel column chromatography (chloroform:methanol=9:1→4:1), whereby 5-6-(7-amino-9H-xanthen-4-yl)-4-morpholinopyridin-2(1H)-one (680 mg) was obtained as a white solid.

MS(ESI m/z): 376 (M+H)
RT(min): 0.75

Example 2-1-2

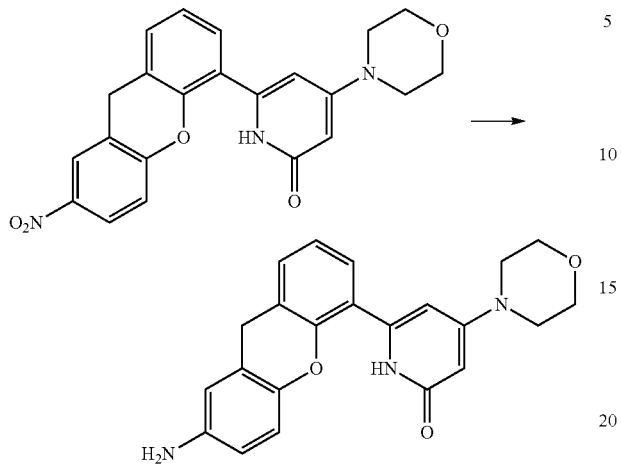

In the same manner as in Reference Example 3 (4), the following compound was obtained.

6-(7-Amino-9H-xanthen-4-yl)-4-morpholinopyridin-2(1H)-one

MS(ESI m/z): 376 (M+H)
RT(min): 0.75

Example 2-1-3

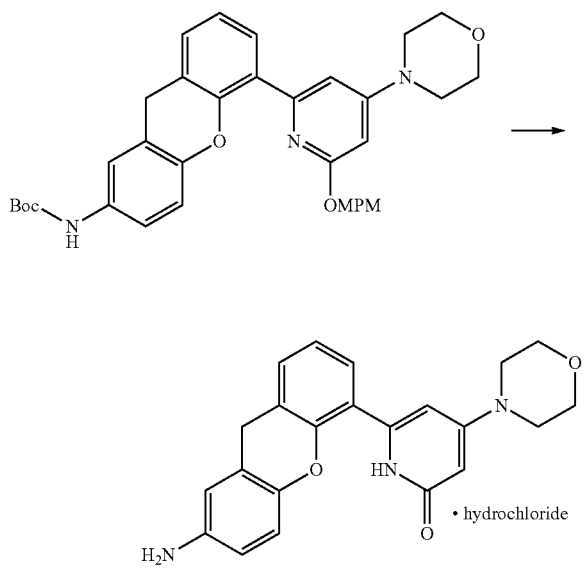

In the same manner as in Example 1-1, the following compound was obtained.

Hydrochloride of 6-(7-amino-9H-xanthen-4-yl)-4-morpholinopyridin-2(1H)-one

MS(ESI m/z): 376 (M+H)
RT(min): 0.75

Example 2-2-1

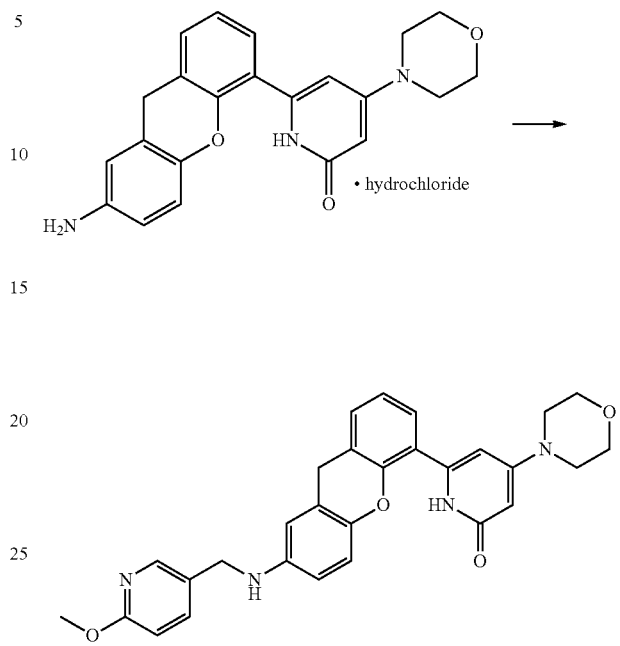

Sodium triacetoxyborohydride (57 mg) was added to a mixture of hydrochloride (80 mg) of 6-(7-amino-9H-xanthen-4-yl)-4-morpholinopyridin-2(1H)-one, 6-methoxynicotinic aldehyde (29 mg), triethylamine (36 mg), and dichloromethane (2.0 mL), followed by stirring at room temperature for 2.5 hours. Sodium triacetoxyborohydride (113 mg) was added thereto, followed by stirring at room temperature for 4 hours. Chloroform was added to the reaction mixture, and the organic layer was washed with a saturated sodium hydrogen carbonate aqueous solution, and dried over anhydrous sodium sulfate. The solvent was distilled off under reduced pressure, and the obtained residues were purified by silica gel column chromatography (chloroform:methanol=1:0→91:9), whereby 6-(7-(((6-methoxypyridin-3-yl)methyl)amino)-9H-xanthen-4-yl)-4-morpholinopyridin-2(1H)-one (66 mg) was obtained as a white solid.

$^1$H-NMR (DMSO-$d_6$, 300 MHz) δ: 10.87 (1H, brs), 8.15 (1H, d, J=1.8 Hz), 7.68 (1H, dd, J=8.6 Hz, 2.5 Hz), 7.31-7.24 (2H, m), 7.06 (1H, t, J=7.7 Hz), 6.78 (1H, d, J=8.7 Hz), 6.70 (1H, d, J=8.7 Hz), 6.52-6.46 (2H, m), 6.13 (1H, d, J=2.4 Hz), 6.00 (1H, t, J=6.0 Hz), 5.46 (1H, d, J=2.4 Hz), 4.18 (2H, d, J=6.0 Hz), 3.94 (2H, s), 3.81 (3H, s), 3.67 (4H, t, J=4.8 Hz), 3.25 (4H, t, J=4.8 Hz).

MS(ESI m/z): 497 (M+H)
RT(min): 1.17

Examples 2-2-2 to 2-2-75

In the same manner as in Example 2-2-1, the following compounds were obtained.

TABLE 51

| Example No. | R^b | Compound Name | MS | RT (min) | $^1$H-NMR (300 MHz) (DMSO-d$_6$) δ: |
|---|---|---|---|---|---|
| 2-2-2 | 6-Methylpyridin-3-yl | 6-(7-(((6-Methyl pyridin-3-yl)methyl)amino)-9H-xanthen-4-yl)-4-morpholino pyridin-2(1H)-one | 481 | 0.88 | 10.85 (1H, br s), 8.43 (1H, d, J = 2.1 Hz), 7.62 (1H, dd, J = 8.0 Hz, 2.0 Hz), 7.30-7.23 (2H, m), 7.18 (1H, d, J = 7.8 Hz), 7.05 1H, t, J = 7.5 Hz), 6.69 (1H, d, J = 8.4 Hz), 6.50-6.45 (2H, m), 6.13 (1H, d, J = 1.8 Hz), 6.07 (1H, t, J = 6.2 Hz), 5.46 (1H, d, J = 1.8 Hz), 4.23 (2H, d, J = 6.2 Hz), 3.94 (2H, s), 3.67 (4H, t, J = 4.6 Hz), 3.25 (4H, t, J = 4.6 Hz), 2.42 (3H, s). |
| 2-2-3 | 6-Chloropyridin-3-yl | 6-(7-(((6-Chloropyridin-3-yl)methyl)amino)-9H-xanthen-4-yl)-4-morpholino pyridin-2(1H)-one | 501 | 1.26 | 10.87 (1H, br s), 8.41 (1H, d, J = 2.1 Hz), 7.82 (1H, dd, J = 7.8 Hz, 2.7 Hz), 7.47 (1H, d, J = 7.8 Hz), 7.30-7.24 (2H, m), 7.06 (1H, t, J = 7.7 Hz), 6.70 (1H, d, J = 8.4 Hz), 6.52-6.45 (2H, m), 6.18-6.12 (2H, m), 5.46 (1H, d, J = 2.4 Hz), 4.29 (2H, d, J = 6.6 Hz), 3.94 (2H, s), 3.67 (4H, t, J = 4.8 Hz), 3.25 (4H, t, J = 4.8 Hz). |
| 2-2-4 | 6-((tetrahydro-2H-pyran-4-yl)oxy)pyridin-3-yl | 4-Morpholino-6-(7-(((6-((tetrahydro-2H-pyran-4-yl)oxy)pyridin-3-yl)methyl)amino)-9H-xanthen-4-yl)pyridin-2(1H)-one | 567 | 1.22 | |
| 2-2-5 | 4-Methyl-3,4-dihydro-2H-pyrido[3,2-b][1,4]oxazin-7-yl | 6-(7-(((4-Methyl-3,4-dihydro-2H-pyrido[3,2-b][1,4]oxazin-7-yl)methyl)amino)-9H-xanthen-4-yl)-4-morpholino pyridin-2(1H)-one | 538 | 0.93 | |
| 2-2-6 | 6-morpholinopyridin-3-yl | 4-Morpholino-6-(7-(((6-morpholino pyridin-3-yl)methyl)amino)-9H-xanthen-4-yl)pyridin-2(1H)-one | 552 | 0.93 | |
| 2-2-7 | 6-(Methylamino)pyridin-3-yl | 6-(7-(((6-(Methyl amino) pyridin-3-yl)methyl)amino)-9H-xanthen-4-yl)-4-morpholino pyridin-2(1H)-one | 496 | 0.88 | 10.87 (1H, br s), 7.97 (1H, d, J = 2.1 Hz), 7.37 (1H, dd, J = 8.2 Hz, 2.3 Hz), 7.31-7.23 (2H, m), 7.06 (1H, t, J = 7.5 Hz), 6.69 (1H, d, J = 8.7 Hz), 6.50-6.43 (2H, m), 6.39 (1H, d, J = 8.7 Hz), 6.33 (1H, q, J = 4.7 Hz), 6.13 (1H, d, J = 2.0 Hz), 5.82 (1H, t, J = 6.0 Hz), 5.46 (1H, d, J = 2.0 Hz), 4.02 (2H, d, J = 6.0 Hz), 3.95 (2H, s), 3.67 (4H, t, J = 4.8 Hz), 3.25 (4H, t, J = 4.8 Hz) 2.72 (3H, d, J = 4.7 Hz). |
| 2-2-8 | 6-(Dimethylamino)pyridin-3-yl | 6-(7-(((6-(Dimethyl amino)pyridin-3-yl)methyl)amino)-9H-xanthen-4-yl)-4-morpholino pyridin-2(1H)-one | 510 | 0.90 | |

TABLE 51-continued

| Example No. | R[b] | Compound Name | MS | RT (min) | $^1$H-NMR (300 MHz) (DMSO-d[6]) δ: |
|---|---|---|---|---|---|
| 2-2-9 | (5-methylpyridin-3-yl)methyl | 6-(7-(((5-Methyl pyridin-3-yl)methyl)amino)-9H-xanthen-4-yl)-4-morpholino pyridin-2(1H)-one | 481 | 0.90 | |

TABLE 52

| Example No. | R[b] | Compound Name | MS | RT (min) | $^1$H-NMR (300 MHz) (DMSO-d[6]) δ: |
|---|---|---|---|---|---|
| 2-2-10 | (5-fluoropyridin-3-yl)methyl | 6-(7-(((5-Fluoropyridin-3-yl)methyl)amino)-9H-xanthen-4-yl)-4-morpholino pyridin-2(1H)-one | 485 | 1.15 | |
| 2-2-11 | (6-fluoropyridin-3-yl)methyl | 6-(7-(((6-Fluoropyridin-3-yl)methyl)amino)-9H-xanthen-4-yl)-4-morpholino pyridin-2(1H)-one | 485 | 1.18 | 10.85 (1H, s), 8.22 (1H, d, J = 2.0 Hz), 7.95 (1H, td, J = 8.2, 2.5 Hz), 7.29 (1H, d, J = 7.6 Hz), 7.25 (1H, d, J = 7.6 Hz), 7.14 (1H, dd, J = 8.4, 2.8 Hz), 7.06 (1H, t, J = 7.6 Hz), 6.70 (1H, d, J = 8.6 Hz), 6.52-6.46 (2H, m), 6.14-6.09 (2H, m), 5.46 (1H, d, J = 2.3 Hz), 4.28 (2H, d, J = 5.9 Hz), 3.94 (2H, s), 3.67 (4H, t, J = 4.6 Hz), 3.25 (4H, t, J = 4.8 Hz). |
| 2-2-12 | (5-chloropyridin-3-yl)methyl | 6-(7-(((5-Chloropyridin-3-yl)methyl)amino)-9H-xanthen-4-yl)-4-morpholino pyridin-2(1H)-one | 501 | 1.24 | 10.85 (1H, s), 8.54 (1H, d, J = 1.7 Hz), 8.49 (1H, d, J = 2.6 Hz), 7.87 (1H, t, J = 2.0 Hz), 7.29 (1H, d, J = 7.6 Hz), 7.25 (1H, d, J = 7.6 Hz), 7.06 (1H, t, J = 7.4 Hz), 6.71 (1H, d J = 8.9 Hz), 6.52-6.46 (2H, m), 6.18 (1H, t, J = 6.4 Hz), 6.13 (1H, s), 5.46 (1H, s), 4.32 (2H, d, J = 6.3 Hz), 3.94 (2H, s), 3.67 (4H, t, J = 4.8 Hz), 3.25 (4H, t, J = 4 8 Hz). |
| 2-2-13 | (5-acetamidopyridin-3-yl)methyl | N-(5-(((5-(4-Morpholino-6-oxo-1,6-dihydropyridin-2-yl)-9H-xanthen-2-yl)amino)methyl)pyridin-3-yl)acetamide | 524 | 0.89 | |

TABLE 52-continued

| Example No. | R$^b$ | Compound Name | MS | RT (min) | $^1$H-NMR (300 MHz) (DMSO-d$_6$) δ: |
|---|---|---|---|---|---|
| 2-2-14 | 2-methoxypyrimidin-5-yl | 6-(7-(((2-Methoxy pyrimidin-5-yl)methyl)amino)-9H-xanthen-4-yl)-4-morpholino pyridin-2(1H)-one | 498 | 1.08 | 10.86 (1H, br s), 8.58 (2H, s), 7.31-7.24 (2H, m), 7.06 (1H, t, J = 7.7 Hz), 6.71 (1H, d, J = 9.3 Hz), 6.53-6.49 (2H, m), 6.13 (1H, d, J = 1.8 Hz), 8.02 (1H, t, J = 6.1 Hz), 5.46 (1H, d, J = 1.8 Hz), 4.21 (2H, d, J = 6.1 Hz), 3.96 (2H, s), 3.88 (3H, s), 3.67 (4H, t, J = 4.8 Hz), 3.25 (4H, t, J = 4.8 Hz). |
| 2-2-15 | 2-aminopyrimidin-5-yl | 6-(7-(((2-Amino pyrimidin-5-yl)methyl)amino)-9H-xanthen-4-yl)-4-morpholino pyridin-2(1H)-one | 483 | 0.89 | |
| 2-2-16 | 2-(methylamino)pyrimidin-5-yl | 6-(7-(((2-(Methyl amino) pyrimidin-5-yl)methyl) amino)-9H-xanthen-4-yl)-4-morpholino pyridin-2(1H)-one | 497 | 0.94 | 10.86 (1H, br s), 8.27 (2H, s), 7.31-7.24 (2H, m), 7.06 (1H, t, J = 7.7 Hz), 6.96 (1H, q, J = 5.2 Hz), 6.71 (1H, d, J = 8.7 Hz), 6.52-6.48 (2H, m), 6.13 (1H, d, J = 2.1 Hz), 5.84 (1H, t, J = 5.7 Hz), 5.46 (1H, d, J = 2.1 Hz), 4.02 (2H, d, J = 5.7 Hz), 3.96 (2H, s), 3.68 (4H, t, J = 4.8 Hz), 3.25 (4H, t, J = 4.8 Hz), 2.76 (3H, d, J = 5.2 Hz). |
| 2-2-17 | 2-(dimethylamino)pyrimidin-5-yl | 6-(7-(((2-(Dimethyl amino) pyrimidin-5-yl)methyl) amino)-9H-xanthen-4-yl)-4-morpholino pyridin-2(1H)-one | 511 | 1.06 | 10.86 (1H, br s), 8.34 (2H, s), 7.32-7.23 (2H, m), 7.06 (1H, t, J = 7.6 Hz), 6.71 (1H, d, J = 8.6 Hz), 6.52-6.46 (2H, m), 6.13 (1H, d, J = 2.3 Hz), 5.87 (1H, t, J = 5.8 Hz), 5.46 (1H, d, J = 2.3 Hz), 4.05 (2H, d, J = 5.8 Hz), 3.96 (2H, s), 3.67 (4H, t, J = 4.6 Hz), 3.25 (4H, t, J = 4.6 Hz), 3.08 (6H, s). |

TABLE 53

| Example No. | R$^b$ | Compound Name | MS | RT (min) | $^1$H-NMR (300 MHz) (DMSO-d$_6$) δ: |
|---|---|---|---|---|---|
| 2-2-18 | 5-fluoro-6-methoxypyridin-3-yl | 6-(7-(((5-Fluoro-6-methoxy pyridin-3-yl)methyl)amino)-9H-xanthen-4-yl)-4-morpholino pyridin-2(1H)-one | 515 | 1.31 | 10.87 (1H, br s), 7.99 (1H, d, J = 1.5 Hz), 7.64 (1H, dd, J = 11.6 Hz, 1.5 Hz), 7.32-7.23 (2H, m), 7.06 (1H, t, J = 7.6 Hz), 6.70 (1H, d, J = 8.6 Hz), 6.52-6.46 (2H, m), 6.13 (1H, d, J = 2.0 Hz), 6.08-6.00 (1H, br s), 5.46 (1H, d, J = 2.0 Hz), 4.21 (2H, d, J = 4.0 Hz), 3.95 (2H, s), 3.91 (3H, s), 3.67 (4H, t, J = 4.8 Hz), 3.25 (4H, t, J = 4.8 Hz). |

TABLE 53-continued

| Example No. | R<sup>b</sup> | Compound Name | MS | RT (min) | ¹H-NMR (300 MHz) (DMSO-d$_6$) δ: |
|---|---|---|---|---|---|
| 2-2-19 | 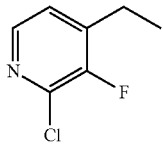 | 6-(7-(((2-Chloro-3-fluoropyridin-4-yl)methyl)amino)-9H-xanthen-4-yl)-4-morpholino pyridin-2(1H)-one | 519 | 1.36 | |
| 2-2-20 | 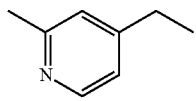 | 6-(7-(((2-Methyl pyridin-4-yl)methyl)amino)-9H-xanthen-4-yl)-4-morpholino pyridin-2(1H)-one | 481 | 0.87 | 10.85 (1H, br s), 8.34 (1H, d, J = 4.8 Hz), 7.30-7.20 (3H, m), 7.14 (1H, d, J = 4.8 Hz), 7.05 (1H, t, J = 7.7 Hz), 6.70 (1H, d, J = 7.8 Hz), 6.45-6.40 (2H, m), 6.19 (1H, t, J = 6.2 Hz), 6.13 (1H, d, J = 2.1 Hz), 5.46 (1H, d, J = 2.1 Hz), 4.25 (2H, d, J = 6.2 Hz), 3.93 (2H, s), 3.67 (4H, t, J = 4.6 Hz), 3.25 (4H, t, J = 4.6 Hz), 2.42 (3H, s). |
| 2-2-21 | 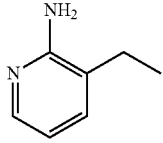 | 6-(7-(((2-Amino pyridin-3-yl)methyl)amino)-9H-xanthen-4-yl)-4-morpholino pyridin-2(1H)-one | 482 | 0.88 | |
| 2-2-22 | 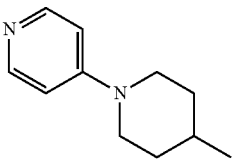 | 4-Morpholino-6-(7-((1-(pyridin-4-yl)piperidin-4-yl)amino)-9H-xanthen-4-yl)pyridin-2(1H)-one | 536 | 0.83 | (CDCl$_3$) δ: 9.03 (1H, br s), 8.27 (2H, d, J = 6.6 Hz), 7.34-7.26 (2H, m), 7.08 (1H, t, J = 7.6 Hz), 6.96 (1H, d, J = 8.9 Hz), 6.68 (2H, d, J = 6.6 Hz), 6.49 (1H, dd, J = 8.8, 2.5 Hz), 6.43 (1H, d, J = 2.6 Hz), 6.16 (1H, d, J = 2.3 Hz), 5.73 (1H, d, J = 2.3 Hz), 4.02 (2H, s), 3.83 (4H, t, J = 4.8 Hz), 3.49 (1H, s), 3.33 (4H, t, J = 4.8 Hz), 3.11-3.00 (2H, m), 2.16 (2H, d, J = 10.6 Hz), 1.75-1.26 (4H, m). |
| 2-2-23 | 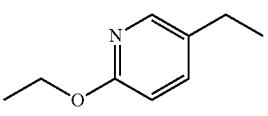 | 6-(7-(((6-Ethoxy pyridin-3-yl)methyl)amino)-9H-xanthen-4-yl)-4-morpholino pyridin-2(1H)-one | 511 | 1.26 | 10.86 (1H, br s), 8.13 (1H, d, J = 2.6 Hz), 7.67 (1H, dd, J = 8.6 Hz, 2.6 Hz), 7.32-7.23 (2H, m), 7.06 (1H, t, J = 7.6 Hz), 6.74 (1H, d, J = 8.6 Hz), 6.70 (1H, d, J = 8.6 Hz), 6.52-6.46 (2H, m), 6.13 (1H, d, J = 1.7 Hz), 5.99 (1H, t, J = 5.9 Hz), 5.46 (1H, d, J = 1.7 Hz), 4.26 (2H, q, J = 7.0 Hz), 4.17 (2H, d, J = 5.9 Hz), 3.94 (2H, s), 3.67 (4H, t, J = 4.6 Hz), 3.25 (4H, t, J = 4.6 Hz), 1.28 (3H, t, J = 7.0 Hz). |
| 2-2-24 | 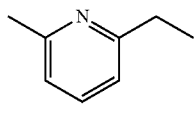 | 6-(7-(((6-Methyl pyridin-2-yl)methyl)amino)-9H-xanthen-4-yl)-4-morpholino pyridin-2(1H)-one | 481 | 0.89 | 10.86 (1H, br s), 7.60 (1H, t, J = 7.6 Hz), 7.32-7.22 (2H, m), 7.15-7.02 (3H, m), 6.70 (1H, d, J = 8.6 Hz), 6.50-6.40 (2H, m), 6.20-6.10 (2H, m), 5.46 (1H, d, J = 2.0 Hz), 4.28 (2H, d, J = 5.9 Hz), 3.93 (2H, s), 3.67 (4H, t, J = 4.8 Hz), 3.25 (4H, t, J = 4.8 Hz), 2.47 (3H, s). |
| 2-2-25 | 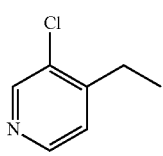 | 6-(7-(((3-Chloropyridin-4-yl)methyl)amino)-9H-xanthen-4-yl)-4-morpholino pyridin-2(1H)-one | 501 | 1.24 | |

TABLE 54

| Example No. | R$^b$ | Compound Name | MS | RT (min) | $^1$H-NMR (300 MHz) (DMSO-d$_6$) δ: |
|---|---|---|---|---|---|
| 2-2-26 | 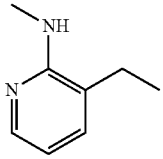 | 6-(7-(((2-(Methyl amino) pyridin-3-yl)methyl)amino)-9H-xanthen-4-yl)-4-morpholino pyridin-2(1H)-one | 496 | 0.90 | |
| 2-2-27 | 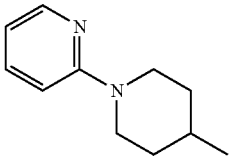 | 4-Morpholino-6-(7-((1-(pyridin-2-yl)piperidin-4-yl)amino)-9H-xanthen-4-yl) pyridin-2(1H)-one | 536 | 0.86 | |
| 2-2-28 | 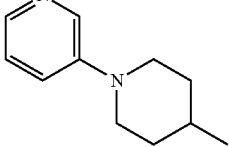 | 4-Morpholino-6-(7-((1-(pyridin-3-yl)piperidin-4-yl)amino)-9H-xanthen-4-yl) pyridin-2(1H)-one | 536 | 0.82 | |
| 2-2-29 | 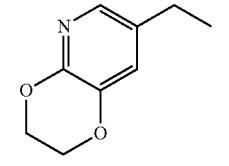 | 6-(7-(((2,3-Dihydro-[1,4]dioxino[2,3-b]pyridin-7-yl)methyl)amino)-9H-xanthen-4-yl)-4-morpholino pyridin-2(1H)-one | 525 | 1.08 | 10.85 (1H, br s), 7.74 (1H, d, J = 2.0 Hz), 7.32-7.22 (3H, m), 7.06 (1H, t, J = 7.6 Hz), 6.70 (1H, d, J = 8.6 Hz), 6.50-6.44 (2H, m), 6.13 (1H, d, J = 1.7 Hz), 6.01 (1H, t, J = 6.1 Hz), 5.46 (1H, d, J = 1.7 Hz), 4.37-4.32 (2H, m), 4.23-4.18 (2H, m), 4.16 (2H, d, J = 6.1 Hz), 3.94 (2H, s), 3.67 (4H, t, J = 4.6 Hz), 3.25 (4H, t, J = 4.6 Hz). |
| 2-2-30 | 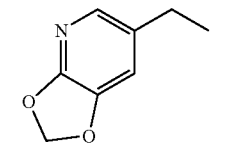 | 6-(7-(([1,3]Dioxolo[4,5-b]pyridin-6-yl methyl)amino)-9H-xanthen-4-yl)-4-morpholino pyridin-2(1H)-one | 511 | 1.11 | 10.87 (1H, br s), 7.60 (1H, d, J = 1.4 Hz), 7.31-7.24 (2H, m), 7.21 (1H, d, J = 1.4 Hz), 7.06 (1H, t, J = 7.8 Hz), 6.70 (1H, d, J = 9.3 Hz), 6.50-6.44 (2H, m), 6.13 (1H, d, J = 2.0 Hz), 6.10 (2H, s), 6.00 (1H, t, J = 6.0 Hz), 5.46 (1H, d, J = 2.0 Hz), 4.15 (2H, d, J = 6.0 Hz), 3.94 (2H, s), 3.67 (4H, t, J = 4.7 Hz), 3.25 (4H, t, J = 4.7 Hz). |
| 2-2-31 | 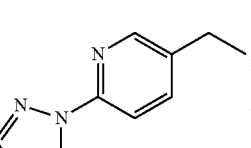 | 6-(7-(((6-(1H-Pyrazol-1-yl)pyridin-3-yl)methyl)amino)-9H-xanthen-4-yl)-4-morpholino pyridin-2(1H)-one | 533 | 1.29 | |
| 2-2-32 | 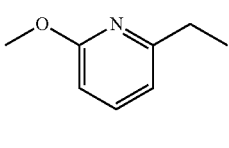 | 6-(7-(((6-Methoxy pyridin-2-yl)methyl)amino)-9H-xanthen-4-yl)-4-morpholino pyridin-2(1H)-one | 497 | 1.28 | 10.88 (1H, br s), 7.62 (1H, t, J = 7.6 Hz), 7.32-7.22 (2H, m), 7.06 (1H, t, J = 7.6 Hz), 6.92 (1H, d, J = 7.3 Hz), 6.71 (1H, d, J = 8.6 Hz), 6.65 (1H, d, J = 8.6 Hz), 6.52-6.45 (2H, m), 6.15-6.08 (2H, m), 5.46 (1H, d, J = 2.0 Hz), 4.25 (2H, d, J = 5.9 Hz), 3.94 (2H, s), 3.87 (3H, s), 3.67 (4H, t, J = 5.0 Hz), 3.25 (4H, t, J = 5.0 Hz). |

TABLE 54-continued

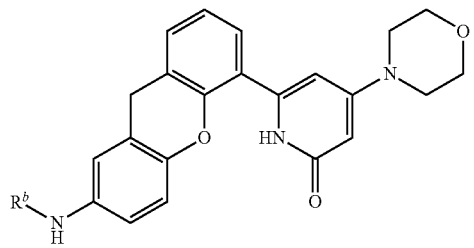

| Example No. | $R^b$ | Compound Name | MS | RT (min) | $^1$H-NMR (300 MHz) (DMSO-$d_6$) δ: |
|---|---|---|---|---|---|
| 2-2-33 | 5-(methoxymethyl)pyridin-3-yl | 6-(7-(((5-(Methoxy methyl)pyridin-3-yl)methyl)amino)-9H-xanthen-4-yl)-4-morpholino pyridin-2(1H)-one | 511 | 0.94 | |

TABLE 55

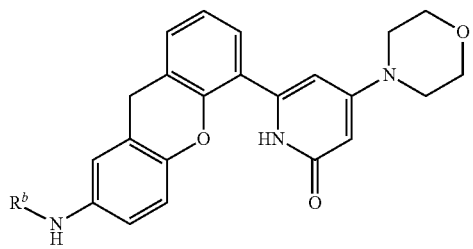

| Example No. | $R^b$ | Compound Name | MS | RT (min) | $^1$H-NMR (300 MHz) (DMSO-$d_6$) δ: |
|---|---|---|---|---|---|
| 2-2-34 | 4-methoxypyridin-3-yl | 6-(7-(((4-Methoxy pyridin-3-yl)methyl)amino)-9H-xanthen-4-yl)-4-morpholino pyridin-2(1H)-one | 497 | 0.90 | |
| 2-2-35 | 5,6-dimethoxypyridin-3-yl | 6-(7-(((5,6-Dimethoxy pyridin-3-yl)methyl)amino)-9H-xanthen-4-yl)-4-morpholino pyridin-2(1H)-one | 527 | 1.14 | 10.85 (1H, br s), 7.68 (1H, d, J = 2.0 Hz), 7.31-7.22 (3H, m), 7.06 (1H, t, J = 7.6 Hz), 6.71 (1H, d, J = 8.6 Hz), 6.53-5.47 (2H, m), 6.13 (1H, d, J = 2.3 Hz), 5.96 (1H, t, J = 5.9 Hz), 5.46 (1H, d, J = 2.3 Hz), 4.17 (2H, d, J = 5.9 Hz), 3.95 (2H, s), 3.82 (3H, s), 3.76 (3H, s), 3.67 (4H, t, J = 4.8 Hz), 3.25 (4H, t, J = 4.8 Hz). |
| 2-2-36 | 5-methoxypyrazin-2-yl | 6-(7-(((5-Methoxy pyrazin-2-yl)methyl)amino)-9H-xanthen-4-yl)-4-morpholino pyridin-2(1H)-one | 498 | 1.16 | 10.84 (1H, br s), 8.28 (1H, d, J = 1.3 Hz), 8.18 (1H, d, J = 1.3 Hz), 7.33-7.22 (2H, m), 7.06 (1H, t, J = 7.6 Hz), 6.71 (1H, d, J = 7.9 Hz), 6.54-6.47 (2H, m), 6.16-6.06 (2H, m), 5.46 (1H, br s), 4.32 (2H, d, J = 5.9 Hz), 3.95 (2H, s), 3.87 (3H, s), 3.68 (4H, t, J = 4.6 Hz), 3.25 (4H, t, J = 4.6). |
| 2-2-37 | 5-(dimethylamino)pyrazin-2-yl | 6-(7-(((5-Dimethyl amino)pyrazin-2-yl)methyl)amino)-9H-xanthen-4-yl)-4-morpholino pyridin-2(1H)-one | 511 | 1.07 | 10.88-10.80 (1H, m), 8.08 (1H, d, J = 1.3 Hz), 8.06 (1H, d, J = 1.3 Hz), 7.30 (1H, d, J = 7.9 Hz), 7.25 (1H, d, J = 7.9 Hz), 7.06 (1H, t, J = 7.9 Hz), 6.70 (1H, d, J = 8.0 Hz), 6.53-6.46 (2H, m), 6.13 (1H, br s), 5.98 (1H, t, J = 5.9 Hz), 5.46 (1H, br s), 4.20 (2H, d, J = 5.9 Hz), 3.94 (2H, s), 3.68 (4H, t, J = 4.6 Hz), 3.33 (4H, t, J = 4.6 Hz), 3.03 (6H, s). |

TABLE 55-continued

| Example No. | R^b | Compound Name | MS | RT (min) | ¹H-NMR (300 MHz) (DMSO-d₆) δ: |
|---|---|---|---|---|---|
| 2-2-38 | 4-methoxypyridin-2-yl-CH₂- | 6-(7-(((4-Methoxy pyridin-2-yl)methyl)amino)-9H-xanthen-4-yl)-4-morpholino pyridin-2(1H)-one | 497 | 0.89 | 10.85 (1H, br s), 8.34 (1H, d, J = 5.4 Hz), 7.30-7.23 (2H, m), 7.06 (1H, t, J = 7.5 Hz), 6.92 (1H, d, J = 2.6 Hz), 6.84 (1H, dd, J = 5.4 Hz, 2.6 Hz), 6.70 (1H, d, J = 8.7 Hz), 6.50-6.42 (2H, m), 6.18-6.10 (2H, m), 5.46 (1H, d, J = 2.1 Hz), 4.28 (2H, d, J = 6.0 Hz), 3.93 (2H, s), 3.77 (3H, s), 3.67 (4H, t, J = 4.5 Hz), 3.25 (4H, t, J = 4.5 Hz). |
| 2-2-39 | 6-(trifluoromethyl)pyridin-3-yl-CH₂- | 6-(7-((4,4-Difluoropiperidin-1-yl)methyl)-9H-xanthen-4-yl)-4-morpholino pyridin-2 (1H)-one | 535 | 1.36 | |
| 2-2-40 | 4-methylpyridin-2-yl-CH₂- | 6-(7-(((4-Methyl pyridin-2-yl)methyl)amino)-9H-xanthen-4-yl)-4-morpholino pyridin-2(1H)-one | 481 | 0.89 | 10.85 (1H, br s), 8.37 (1H, d, J = 5.3 Hz), 7.30-7.18 (3H, m), 7.09-7.01 (2H, m), 6.70 (1H, d, J = 8.6 Hz), 6.50-6.43 (2H, m), 6.18-6.10 (2H, m), 5.46 (1H, d, J = 2.0 Hz), 4.29 (2H, d, J = 5.9 Hz), 3.93 (2H, s), 3.67 (4H, t, J = 4.6 Hz), 3.25 (4H, t, J = 4.6 Hz), 2.27 (3H, s). |
| 2-2-41 | 5-methylpyridin-2-yl-CH₂- | 6-(7-(((5-Methyl pyridin-2-yl)methyl)amino)-9H-xanthen-4-yl)-4-morpholino pyridin-2(1H)-one | 481 | 0.91 | 10.85 (1H, br s), 8.35 (1H, s), 7.53 (1H, dd, J = 7.9 Hz, 2.0 Hz), 7.31-7.22 (3H, m), 7.05 (1H, t, J = 7.6 Hz), 6.69 (1H, d, J = 8.6 Hz), 6.48-6.42 (2H, m), 6.18-6.10 (2H, m), 5.45 (1H, d, J = 2.0 Hz), 4.29 (2H, d, J = 5.9 Hz), 3.92 (2H, s), 3.67 (4H, t, J = 5.0 Hz), 3.25 (4H, t, J = 5.0 Hz), 2.26 (3H, s). |

TABLE 56

| Example No. | R^b | Compound Name | MS | RT (min) | ¹H-NMR (300 MHz) (DMSO-d₆) δ: |
|---|---|---|---|---|---|
| 2-2-42 | 5-methoxypyridin-2-yl-CH₂- | 6-(7-(((5-Methoxy pyridin-2-yl)methyl)amino)-9H-xanthen-4-yl)-4-morpholino pyridin-2(1H)-one | 497 | 0.99 | 10.86 (1H, br s), 8.23 (1H, d, J = 2.0 Hz), 7.35-7.23 (4H, m), 7.05 (1H, t, J = 7.3 Hz), 6.69 (1H, d, J = 8.6 Hz), 6.50-6.40 (2H, m), 6.15-6.08 (2H, m), 5.46 (1H, d, J = 2.0 Hz), 4.27 (2H, d, J = 6.6 Hz), 3.93 (2H, s), 3.79 (3H, s), 3.67 (4H, t, J = 4.8 Hz), 3.25 (4H, t, J = 4.8 Hz). |
| 2-2-43 | 6-(methoxymethyl)pyridin-3-yl-CH₂- | 6-(7-(((6-(Methoxy methyl) pyridin-3-yl)methyl)amino)-9H-xanthen-4-yl)-4-morpholino pyridin-2(1H)-one | 511 | 0.96 | |

TABLE 56-continued

| Example No. | R$^b$ | Compound Name | MS | RT (min) | $^1$H-NMR (300 MHz) (DMSO-d$_6$) δ: |
|---|---|---|---|---|---|
| 2-2-44 | 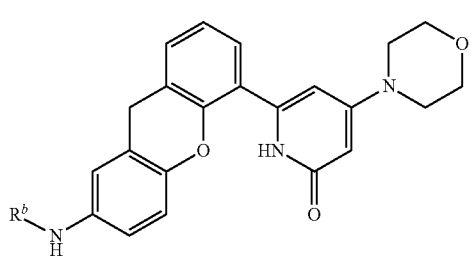 | 6-(7-((Furo[2,3-b]pyridin-5-yl methyl)amino)-9H-xanthen-4-yl)-4-morpholino pyridin-2(1H)-one | 507 | 1.17 | 10.86 (1H, br s), 8.32 (1H, d, J = 2.6 Hz), 8.10-8.05 (2H, m), 7.32-7.22 (2H, m), 7.05 (1H, t, J = 7.3 Hz), 7.00 (1H, d, J = 2.6 Hz), 6.70 (1H, d, J = 7.9 Hz), 6.53-6.47 (2H, m), 6.19-6.09 (2H, m), 5.46 (1H, s), 4.38 (2H, d, J = 5.9 Hz), 3.94 (2H, s), 3.67 (4H, t, J = 4.6 Hz), 3.25 (4H, t, J = 4.6 Hz). |
| 2-2-45 | 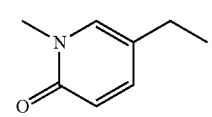 | 1-Methyl-5-(((5-(4-morpholino-6-oxo-1,6-dihydropyridin-2-yl)-9H-xanthen-2-yl)amino)methyl) pyridin-2(1H)-one | 497 | 0.93 | |
| 2-2-46 | 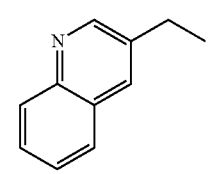 | 4-Morpholino-6-(7-((quinolin-3-yl methyl) amino)-9H-xanthen-4-yl) pyridin-2(1H)-one | 517 | 1.05 | 10.84 (1H, br s), 8.94 (1H, d, J = 2.0 Hz), 8.26 (1H, d, J = 2.0 Hz), 8.01 (1H, dd, J = 8.6, 1.3 Hz), 7.94 (1H, dd, J = 7.9, 1.3 Hz), 7.72 (1H, ddd, J = 8.6, 7.9, 1.3 Hz), 7.59 (1H, ddd, J = 7.9, 7.9, 1.3 Hz), 7.31-7.17 (2H, m) 7.06 (1H, t, J = 7.6 Hz), 6.72 (1H, d, J = 8.6 Hz), 6.58-6.50 (2H, m), 6.26 (1H, t, J = 5.9 Hz), 6.13 (1H, br s), 5.46 (1H, br s), 4.49 (2H, d, J = 5.9 Hz), 3.95 (2H, s), 3.68 (4H, t, J = 4.6 Hz), 3.25 (4H, t, J = 4.6 Hz). |
| 2-2-47 | 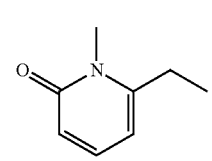 | 1-Methyl-6-(((5-(4-morpholino-6-oxo-1,6-dihydropyridin-2-yl)-9H-xanthen-2-yl)amino)methyl) pyridin-2(1H)-one | 497 | 1.06 | |
| 2-2-48 | 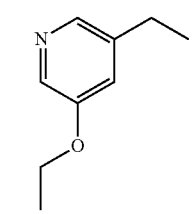 | 6-(7-(((5-Ethoxy pyridin-3-yl)methyl)amino)-9H-xanthen-4-yl)-4-morpholino pyridin-2(1H)-one | 511 | 1.04 | 10.87 (1H, br s), 8.17 (1H, d, J = 1.2 Hz), 8.13 (1H, d, J = 2.7 Hz), 7.34-7.24 (3H, m), 7.06 (1H, t, J = 7.5 Hz), 6.70 (1H, d, J = 8.4 Hz), 6.52-6.44 (2H, m), 6.13 (1H, d, J = 2.3 Hz), 6.09 (1H, t, J = 6.2 Hz), 5.46 (1H, d, J = 2.3 Hz), 4.26 (2H, d, J = 6.2 Hz), 4.07 (2H, q, J = 7.0 Hz), 3.94 (2H, s), 3.67 (4H, t, J = 4.9 Hz), 3.25 (4H, t, J = 4.9 Hz), 1.32 (3H, t, J = 7.0 Hz). |
| 2-2-49 | 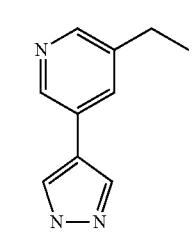 | 6-(7-(((5-(1-Methyl-1H-pyrazol-4-yl)pyridin-3-yl) methyl)amino)-9H-xanthen-4-yl)-4-morpholino pyridin-2(1H)-one | 547 | 0.95 | |

TABLE 57

| Example No. | R^b | Compound Name | MS | RT (min) | ¹H-NMR (300 MHz) (DMSO-d₆) δ: |
|---|---|---|---|---|---|
| 2-2-50 | 5-cyclopropylpyridin-3-yl | 6-(7-(((5-Cyclopropyl pyridin-3-yl)methyl) amino)-9H-xanthen-4-yl)-4-morpholino pyridin-2 (1H)-one | 507 | 1.00 | 10.93 (1H, br s), 8.34 (1H, d, J = 2.1 Hz), 8.26 (1H, d, J = 2.4 Hz), 7.42-7.40 (1H, m), 7.31-7.23 (2H, m), 7.06 (1H, t, J = 7.7 Hz), 6.70 (1H, d, J = 9.3 Hz), 6.51-6.47 (2H, m), 6.20-5.90 (2H, m), 5.48 (1H, d, J = 2.0 Hz), 4.22 (2H, s), 3.94 (2H, s), 3.68 (4H, t, J = 4.6 Hz), 3.26 (4H, t, J = 4.6 Hz), 1.99-1.88 (1H, m), 1.02-0.95 (2H, m), 0.73-0.69 (2H, m). |
| 2-2-51 | 4,6-dimethoxypyrimidin-2-yl | 6-(7-(((4,6-Dimethoxy pyrimidin-2-yl)methyl) amino)-9H-xanthen-4-yl)-4-morpholino pyridin-2 (1H)-one | 528 | 1.29 | 10.98 (1H, br s), 7.37-7.22 (2H, m), 7.07 (1H, t, J = 7.3 Hz), 6.76-6.54 (3H, m), 6.23-6.07 (2H, m), 6.00-5.77 (1H, m), 5.50 (1H, br s), 4.25 (2H, s), 3.97 (2H, s), 3.88 (6H, s), 3.74-3.62 (4H, br m), 3.34-3.33 (4H, m). |
| 2-2-52 | 2-chloropyridin-4-yl | 6-(7-(((2-Chloropyridin-4-yl)methyl)amino)-9H-xanthen-4-yl)-4-morpholino pyridin-2 (1H)-one | 501 | 1.28 | 10.87 (1H, br s), 8.33 (1H, d, J = 4.6 Hz), 7.44 (1H, s), 7.37 (1H, dd, J = 5.3 Hz, 1.Hz), 7.32-7.22 (2H, m), 7.06 (1H, t, J = 7.6 Hz), 6.72 (1H, d, J = 8.6 Hz), 6.48-6.40 (2H, m), 6.26 (1H, t, J = 6.2 Hz), 6.14 (1H, d, J = 2.3 Hz), 5.47 (1H, d, J = 2.3 Hz), 4.34 (2H, d, J = 6.1 Hz), 3.93 (2H, s), 3.67 (4H, t, J = 4.8 Hz), 3.25 (4H, t, J = 4.8 Hz). |
| 2-2-53 | 2-bromopyridin-4-yl | 6-(7-(((2-Bromopyridin-4-yl)methyl)amino)-9H-xanthen-4-yl)-4-morpholino pyridin-2 (1H)-one | 545 | 1.30 | 10.86 (1H, br s), 8.30 (1H, d, J = 5.3 Hz), 7.58 (1H, s), 7.42-7.38 (1H, m), 7.32-7.22 (2H, m), 7.06 (1H, t, J = 7.6 Hz), 6.71 (1H, d, J = 8.6 Hz), 6.48-6.40 (2H, m), 6.26 (1H, t, J = 6.1 Hz), 6.13 (1H, d, J = 2.0 Hz), 5.45 (1H, d, J = 2.0 Hz), 4.32 (2H, d, J = 6.1 Hz), 3.94 (2H, s), 3.67 (4H, t, J = 4.8 Hz), 3.25 (4H, t, J = 4.8 Hz). |
| 2-2-54 | benzyl carbamate cyclohexyl | Benzyl ((trans)-4-((5-(4-morpholino-6-oxo-1,6-dihydropyridin-2-yl)-9H-xanthen-2-yl)amino) cyclohexyl)carbamate | 607 | 1.12 | |
| 2-2-55 | 5-(1H-pyrazol-1-yl)pyridin-3-yl | 6-(7-(((5-(1H-Pyrazol-1-yl)pyridin-3-yl)methyl) amino)-9H-xanthen-4-yl)-4-morpholino pyridin-2 (1H)-one | 533 | 1.15 | |

TABLE 57-continued

| Example No. | R$^b$ | Compound Name | MS | RT (min) | $^1$H-NMR (300 MHz) (DMSO-d$_6$) δ: |
|---|---|---|---|---|---|
| 2-2-56 | (5-(1H-imidazol-1-yl)pyridin-3-yl)methyl | 6-(7-(((5-(1H-Imidazol-1-yl)pyridin-3-yl)methyl)amino)-9H-xanthen-4-yl)-4-morpholino pyridin-2(1H)-one | 533 | 0.90 | |
| 2-2-57 | ([3,3'-bipyridin]-5-yl)methyl | 6-(7-((([3,3'-Bipyridin]-5-yl methyl)amino)-9H-xanthen-4-yl)-4-morpholino pyridin-2(1H)-one | 544 | 0.98 | |

TABLE 58

| Example No. | R$^b$ | Compound Name | MS | RT (min) | $^1$H-NMR (300 MHz) (DMSO-d$_6$) δ: |
|---|---|---|---|---|---|
| 2-2-58 | (5-(1H-pyrrol-1-yl)pyridin-3-yl)methyl | 6-(7-(((5-(1H-Pyrrol-1-yl)pyridin-3-yl)methyl)amino)-9H-xanthen-4-yl)-4-morpholino pyridin-2(1H)-one | 532 | 1.26 | 10.85 (1H, br s), 8.76 (1H, d, J = 2.6 Hz), 8.46 (1H, d, J = 2.0 Hz), 8.00 (1H, t, J = 2.0 Hz), 7.43 (2H, t, J = 2.2 Hz), 7.32-7.22 (2H, m), 7.05 (1H, t, J = 7.6 Hz), 6.71 (1H, d, J = 8.6 Hz), 6.56-6.48 (2H, m), 6.33-6.30 (2H, m), 6.18-6.08 (2H, m), 5.45 (1H, d, J = 2.0 Hz), 4.35 (2H, d, J = 5.9 Hz), 3.95 (2H, s), 3.67 (4H, t, J = 4.8 Hz), 3.25 (4H, t, J = 4.8 Hz). |
| 2-2-59 | (5-(1H-1,2,4-triazol-1-yl)pyridin-3-yl)methyl | 6-(7-(((5-(1H-1,2,4-Triazol-1-yl)pyridin-3-yl)methyl)amino)-9H-xanthen-4-yl)-4-morpholino pyridin-2(1H)-one | 534 | 1.06 | |

TABLE 58-continued

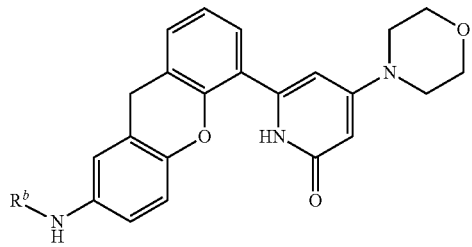

| Example No. | R$^b$ | Compound Name | MS | RT (min) | $^1$H-NMR (300 MHz) (DMSO-d$_6$) δ: |
|---|---|---|---|---|---|
| 2-2-60 | | 6-(7-(((5-(Cyclopent-2-en-1-yl)pyridin-3-yl)methyl) amino)-9H-xanthen-4-yl)-4-morpholino pyridin-2(1H)-one | 533 | 1.09 | 10.84 (1H, br s), 8.41 (1H, d, J = 1.3 Hz), 8.27 (1H, d, J = 2.0 Hz), 7.54 (1H, t, J = 2.0 Hz), 7.32-7.22 (2H, m), 7.06 (1H, t, J = 7.6 Hz), 6.70 (1H, d, J = 9.2 Hz), 6.52-6.44 (2H, m), 6.13 (1H, d, J = 2.0 Hz), 6.08 (1H, t, J = 5.9 Hz), 6.00-5.94 (1H, m), 5.80-5.72 (1H, m), 5.46 (1H, d, J = 2.0 Hz), 4.25 (2H, d, J = 5.9 Hz), 3.94 (2H, s), 3.67 (4H, t, J = 4.6 Hz), 3.25 (4H, t, J = 4.6 Hz), 2.56-2.26 (4H, m), 1.68-1.56 (1H, m). |
| 2-2-61 | | 6-(7-(((5-(Cyclopent-1-en-1-yl)pyridin-3-yl)methyl) amino)-9H-xanthen-4-yl)-4-morpholino pyridin-2(1H)-one | 533 | 1.16 | |
| 2-2-62 | | 6-(7-(1,4-Dioxaspiro[4.5] decan-8-yl amino)-9H-xanthen-4-yl)-4-morpholino pyridin-2(1H)-one | 516 | 0.93 | |
| 2-2-63 | | 4-Morpholino-6-(7-(((5-(pyrrolidin-1-yl)pyridin-3-yl)methyl)amino)-9H-xanthen-4-yl)pyridin-2(1H)-one | 536 | 1.03 | |
| 2-2-64 | | 6-(7-(((4-Chloropyridin-2-yl)methyl)amino)-9H-xanthen-4-yl)-4-morpholino pyridin-2(1H)-one | 501 | 1.21 | 10.85 (1H, br s), 8.52 (1H, d, J = 5.3 Hz), 7.45-7.38 (2H, m), 7.29 (1H, d, J = 7.6 Hz), 7.25 (1H, d, J = 7.6 Hz), 7.06 (1H, t, J = 7.6 Hz), 6.71 (1H, d, J = 8.6 Hz), 6.50-6.42 (2H, m), 6.26 (1H, t, J = 5.9 Hz), 6.13 (1H, br s), 5.46 (1H, br s), 4.36 (2H, d, J = 5.9 Hz), 3.94 (2H, s), 3.67 (4H, t, J = 4.6 Hz), 3.25 (4H, t, J = 4.6 Hz). |
| 2-2-65 | | 6-(7-(((5-Isopropoxy pyridin-3-yl)methyl)amino)-9H-xanthen-4-yl)-4-morpholino pyridin-2(1H)-one | 525 | 1.09 | |

TABLE 59

| Example No. | R<sup>b</sup> | Compound Name | MS | RT (min) | ¹H-NMR (300 MHz) (DMSO-d₆) δ: |
|---|---|---|---|---|---|
| 2-2-66 | 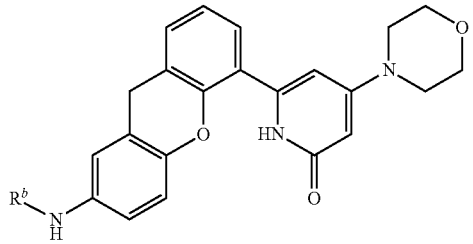 | 6-(7-(((5-Cyclopentyl pyridin-3-yl)methyl) amino)-9H-xanthen-4-yl)-4-morpholino pyridin-2(1H)-one | 535 | 1.11 | 10.87 (1H, br s), 8.39 (1H, d, J = 2.0 Hz), 8.33 (1H, d, J = 2.0 Hz), 7.64 (1H, t, J = 2.0 Hz), 7.31-7.23 (2H, m) 7.06 (1H, t, J = 7.2 Hz), 6.70 (1H, d, J = 9.3 Hz), 6.52-6.47 (2H, m), 6.13 (1H, d, J = 1.7 Hz), 6.07 (1H, t, J = 6.2 Hz), 5.46 (1H, d, J = 1.7 Hz), 4.25 (2H, d, J = 6.2 Hz), 3.95 (2H, s), 3.67 (4H, t, J = 4.7 Hz), 3.25 (4H, t, J = 4.7 Hz), 3.04-2.92 (1H, m), 2.08-1.95 (2H, m) 1.85-1.45 (6H, m). |
| 2-2-67 | 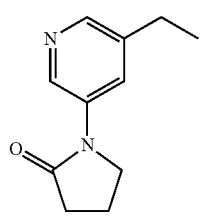 | 4-Morpholino-6-(7-(((5-(2-oxopyrrolidin-1-yl) pyridin-3-yl)methyl) amino)-9H-xanthen-4-yl)pyridin-2(1H)-one | 550 | 0.98 | |
| 2-2-68 | 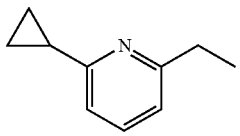 | 6-(7-(((6-Cyclopropyl pyridin-2-yl)methyl) amino)-9H-xanthen-4-yl)-4-morpholino pyridin-2(1H)-one | 507 | 0.99 | |
| 2-2-69 | 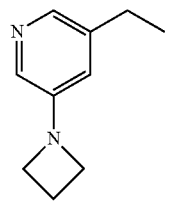 | 6-(7-(((5-(Azetidin-1-yl) pyridin-3-yl)methyl) amino)-9H-xanthen-4-yl)-4-morpholino pyridin-2(1H)-one | 522 | 0.98 | 10.86 (1H, br s), 7.92 (1H, d, J = 2.1 Hz), 7.65 (1H, d, J = 2.7 Hz), 7.31-7.23 (2H, m), 7.06 (1H, t, J = 7.5 Hz), 6.79-6.77 (1H, m), 6.70 (1H, d, J = 8.7 Hz), 6.50-6.45 (2H, m), 6.13 (1H, d, J = 1.8 Hz), 6.03 (1H, t, J = 6.0 Hz), 5.46 (1H, d, J = 1.8 Hz), 4.18 (2H, d, J = 6.0 Hz), 3.94 (2H, s), 3.83 (4H, t, J = 7.3 Hz), 3.67 (4H, t, J = 4.8 Hz), 3.25 (4H, t, J = 4.8 Hz), 2.33 (2H, quin, J = 7.3 Hz). |
| 2-2-70 | 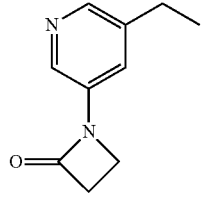 | 4-Morpholino-6-(7-(((5-(2-oxoazetidin-1-yl) pyridin-3-yl)methyl) amino)-9H-xanthen-4-yl)pyridin-2(1H)-one | 536 | 1.01 | |
| 2-2-71 | 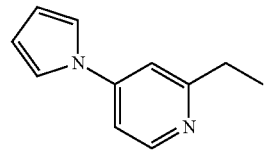 | 6-(7-(((4-(1H-Pyrrol-1-yl)pyridin-2-yl)methyl) amino)-9H-xanthen-4-yl)-4-morpholino pyridin-2(1H)-one | 532 | 1.06 | 11.83 (1H, br s), 8.51 (1H, d, J = 5.9 Hz), 7.61 (1H, d, J = 2.6 Hz), 7.56-7.48 (3H, m), 7.30-7.22 (2H, m), 7.05 (1H, t, J = 7.6 Hz), 6.71 (1H, d, J = 7.9 Hz), 6.56-6.48 (2H, m), 6.33 (2H, t, J = 2.3 Hz), 6.18-6.08 (2H, m), 5.46 (1H, d, J = 2.0 Hz), 4.36 (2H, d, J = 4.0 Hz), 3.94 (2H, s), 3.67 (4H, t, J = 4.8 Hz), 3.24 (4H, t, J = 4.8 Hz). |

TABLE 59-continued

| Example No. | R$^b$ | Compound Name | MS | RT (min) | $^1$H-NMR (300 MHz) (DMSO-d$_6$) δ: |
|---|---|---|---|---|---|
| 2-2-72 | (2,4'-bipyridinyl-methyl group) | 6-(7-(([2,4'-Bipyridin]-2'-yl methyl)amino)-9H-xanthen-4-yl)-4-morpholino pyridin-2(1H)-one | 544 | 0.97 | 10.84 (1H, br s), 8.94 (1H, d, J = 1.8 Hz), 8.67-8.63 (2H, m), 8.13 (1H, dt, J = 8.1 Hz, 1.9 Hz), 7.76 (1H, s), 7.66 (1H, dd, J = 5.3 Hz, 2.0 Hz), 7.54 (1H, dd, J = 8.0 Hz, 4.6 Hz), 7.30-7.22 (2H, m), 7.05 (1H, t, J = 7.7 Hz), 6.71 (1H, d, J = 9.3 Hz), 6.55-6.52 (2H, m), 6.20 (1H, t, J = 6.0 Hz), 6.12 (1H, d, J = 2.4 Hz), 5.45 (1H, d, J = 2.4 Hz), 4.42 (2H, s), 3.94 (2H, s), 3.67 (4H, t, J = 4.6 Hz), 3.24 (4H, t, J = 4.6 Hz). |

TABLE 60

| Example No. | R$^b$ | Compound Name | MS | RT (min) | $^1$H-NMR (300 MHz) (DMSO-d$_6$) δ: |
|---|---|---|---|---|---|
| 2-2-73 | (acetamidopyridinyl-methyl) | N-(6-(((5-(4-Morpholino-6-oxo-1,6-dihydropyridin-2-yl)-9H-xanthen-2-yl)amino)methyl)pyridin-2-yl) acetamide | 524 | 1.03 | |
| 2-2-74 | (1-methylpyrazolyl-pyridinyl-methyl) | 6-(7-(((4-(1-Methyl-1H-pyrazol-4-yl)pyridin-2-yl)methyl)amino)-9H-xanthen-4-yl)-4-morpholino pyridin-2(1H)-one | 547 | 0.89 | |
| 2-2-75 | (isopropylamino-pyridinyl-methyl) | 6-(7-(((5-(Isopropyl amino)pyridin-3-yl)methyl)amino)-9H-xanthen-4-yl)-4-morpholino pyridin-2(1H)-one | 524 | 1.00 | |

Example 2-2-76

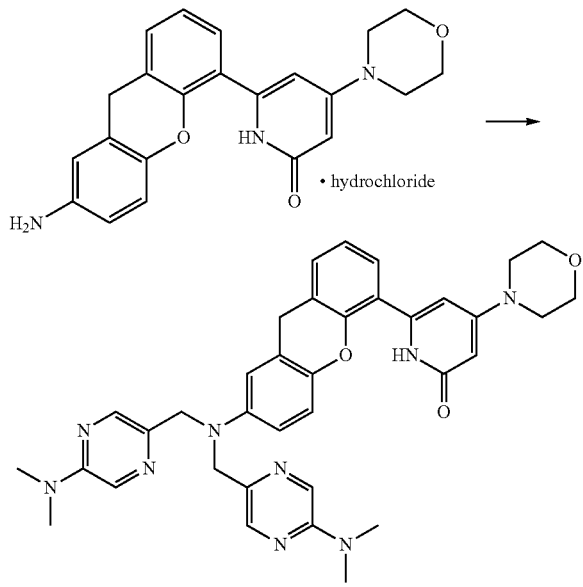

Using hydrochloride (30 mg) of 6-(7-amino-9H-xanthen-4-yl)-4-morpholinopyridin-2(1H)-one, 5-(dimethylamino)pyrazine-2-carbaldehyde (15 mg), and sodium triacetoxyborohydride (57 mg), 6-(7-(bis((5-(dimethylamino)pyrazin-2-yl)methyl)amino)-9H-xanthen-4-yl)-4-morpholinopyridin-2(1H)-one (8 mg) was obtained in the same manner as in Example 2-2-1.

$^1$H-NMR (DMSO-$d_6$, 300 MHz) δ: 10.86 (1H, brs), 8.10 (2H, d, J=1.3 Hz), 7.97 (2H, d, J=1.3 Hz), 7.32-7.22 (2H, m), 7.06 (1H, t, J=7.6 Hz), 6.76-6.64 (3H, m), 6.13 (1H, s), 5.46 (1H, s), 4.60 (4H, s), 3.94 (2H, s), 3.67 (4H, t, J=4.6 Hz), 3.25 (4H, t, J=4.6 Hz), 3.03 (12H, s).

MS(ESI m/z): 646 (M+H)

RT(min): 1.24

Examples 2-3-1 to 2-3-15

In the same manner as in Example 1-44-1, the following compounds were obtained.

TABLE 61

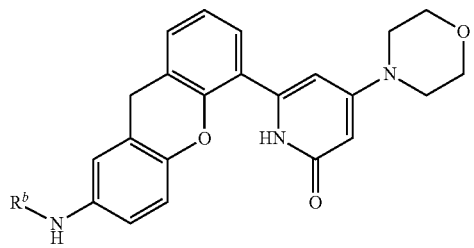

| Example No. | $R^b$ | Compound Name | MS | RT (min) | $^1$H-NMR (300 MHz) (DMSO-$d_6$) δ: |
|---|---|---|---|---|---|
| 2-3-1 | pyridin-3-yl | 4-Morpholino-6-(7-((pyridin-3-yl methyl)amino)-9H-xanthen-4-yl)pyridin-2(1H)-one | 467 | 0.89 | (CD$_3$OD): 8.64 (1H, d, J = 1.7 Hz), 8.54 (1H, dd, J = 5.0, 1.7 Hz), 7.70 (1H, dt, J = 8.0, 2.0 Hz), 7.34-7.21 (3H, m), 7.07 (1H, t, J = 7.6 Hz), 6.95 (1H, d, J = 8.9 Hz), 6.50 (1H, dd, J = 8.8, 2.8 Hz), 6.40 (1H, d, J = 3.0 Hz), 6.16 (1H, d, J = 2.6 Hz), 5.72 (1H, d, J = 2.3 Hz), 4.35 (2H, s), 3.99 (2H, s), 3.82 (4H, t, J = 5.0 Hz, 3.32 (4H, t, J = 5.0 Hz). |
| 2-3-2 | pyrimidin-5-yl | 4-Morpholino-6-(7-((pyrimidin-5-yl methyl)amino)-9H-xanthen-4-yl)pyridin-2(1H)-one | 468 | 1.01 | |
| 2-3-3 | pyridin-4-yl | 4-Morpholino-6-(7-((pyridin-4-yl-methyl)amino)-9H-xanthen-4-yl)pyridin-2(1H)-one | 467 | 0.85 | |
| 2-3-4 | pyrimidin-2-yl | 4-Morpholino-6-(7-((pyrimidin-2-yl methyl)amino)-9H-xanthen-4-yl)pyridin-2(1H)-one | 468 | 1.03 | |

TABLE 61-continued

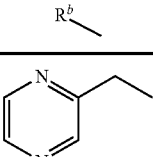

| Example No. | R^b | Compound Name | MS | RT (min) | $^1$H-NMR (300 MHz) (DMSO-$d_6$) δ: |
|---|---|---|---|---|---|
| 2-3-5 | 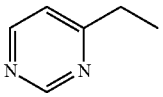 | 4-Morpholino-6-(7-((pyrazin-2-yl methyl)amino)-9H-xanthen-4-yl)pyridin-2(1H)-one | 468 | 1.05 | |
| 2-3-6 | 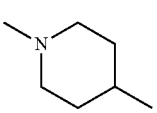 | 4-Morpholino-6-(7-((pyrimidin-4-yl methyl)amino)-9H-xanthen-4-yl)pyridin-2(1H)-one | 468 | 1.02 | |
| 2-3-7 | 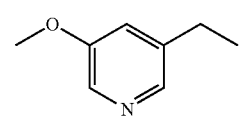 | 6-(7-((1-Methyl piperidin-4-yl)amino)-9H-xanthen-4-yl)-4-morpholino pyridin-2(1H)-one | 473 | 0.81 | |
| 2-3-8 | 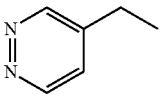 | 6-(7-(((5-Methoxy pyridin-3-yl)methyl)amino)-9H-xanthen-4-yl)-4-morpholino pyridin-2(1H)-one | 497 | 0.97 | (CDCl$_3$): 8.24 (2H, d, J = 2.6 Hz), 7.31 (1H, dd, J = 7.6, 1.7 Hz), 7.25-7.21 (2H, m), 7.07 (1H, t, J = 7.6 Hz), 6.95 (1H, d, J = 8.6 Hz), 6.51 (1H, dd, J = 8.9, 3.0 Hz), 6.40 (1H, d, J = 2.6 Hz), 6.16 (1H, d, J = 2.6 Hz), 5.71 (1H, d, J = 2.3 Hz), 4.33 (2H, s), 4.00 (2H, s), 3.85 (3H, s), 3.82 (4H, t, J = 5.0 Hz), 3.32 (4H, t, J = 5.0 Hz). |
| 2-3-9 | 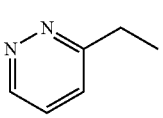 | 4-Morpholino-6-(7-((pyridazin-4-yl methyl)amino)-9H-xanthen-4-yl)pyridin-2(1H)-one | 468 | 0.98 | |
| 2-3-10 | 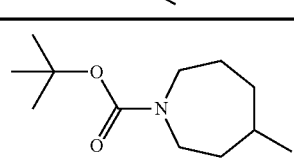 | 4-Morpholino-6-(7-((pyridazin-3-yl methyl)amino)-9H-xanthen-4-yl)pyridin-2(1H)-one | 468 | 0.98 | |

TABLE 62

| Example No. | R^b | Compound Name | MS | RT (min) | $^1$H-NMR (300 MHz) (DMSO-$d_6$) δ: |
|---|---|---|---|---|---|
| 2-3-11 | | tert-Butyl 4-((5-(4-morpholino-6-oxo-1,6-dihydropyridin-2-yl)-9H-xanthen-2-yl)amino)azepane-1-carboxylate | 573 | 1.22 | |

TABLE 62-continued

| Example No. | R$^b$ | Compound Name | MS | RT (min) | $^1$H-NMR (300 MHz) (DMSO-d$_6$) δ: |
|---|---|---|---|---|---|
| 2-3-12 |  | tert-Butyl 4-((5-(4-morpholino-6-oxo-1,6-dihydropyridin-2-yl)-9H-xanthen-2-yl)amino)piperidine-1-carboxylate | 559 | 1.24 | |
| 2-3-13 |  | 6-(7-((1-Acetyl piperidin-4-yl)amino)-9H-xanthen-4-yl)-4-morpholino pyridin-2(1H)-one | 501 | 0.86 | |
| 2-3-14 |  | 4-Morpholino-6-(7-((3-(trifluoromethyl)benzyl)amino)-9H-xanthen-4-yl)pyridin-2(1H)-one | 534 | 1.55 | (CDCl$_3$): 9.15 (1H, s), 7.64 (1H, s), 7.59-7.41 (3H, m), 7.31 (1H, dd, J = 7.8, 1.5 Hz), 7.25 (1H, d, J = 9.2 Hz), 7.07 (1H, t, J = 7.6 Hz), 6.94 (1H, d, J = 8.6 Hz), 6.49 (1H, dd, J = 8.8, 2.8 Hz), 6.40 (1H, d, J = 2.6 Hz), 6.15 (1H, d, J = 2.6 Hz), 5.71 (1H, d, J = 2.3 Hz), 4.38 (2H, s), 3.99 (2H, s), 3.82 (4H, t, J = 5.0 Hz), 3.31 (4H, t, J = 5.0 Hz). |
| 2-3-15 | 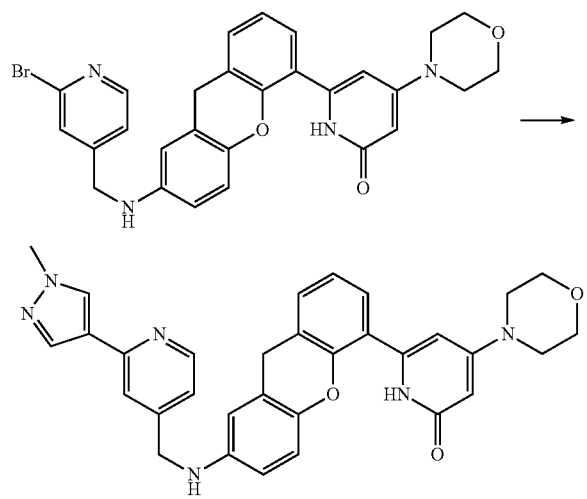 | 3-(((5-(4-Morpholino-6-oxo-1,6-dihydropyridin-2-yl)-9H-xanthen-2-yl)amino)methyl)benzonitrile | 491 | 1.32 | 10.84 (1H, s), 7.79 (1H, s), 7.72 (1H, s), 7.69 (1H, s), 7.54 (1H, t, J = 7.6 Hz), 7.28 (1H, t, J = 5.0 Hz), 7.24 (1H, s), 7.05 (1H, t, J = 7.6 Hz), 6.70 (1H, d, J = 8.3 Hz), 6.48-6.42 (2H, m), 6.20 (1H, d, J = 6.6 Hz), 6.12 (1H, s), 5.46 (1H, s) 4.32 (2H, d, J = 5.9 Hz), 3.93 (2H, s), 3.67 (4H, t, J = 4.8 Hz), 3.25 (4H, t, J = 4.6 Hz). |

Example 2-4

Bis(di-tert-butyl(4-dimethylaminophenyl)phosphine)dichloropalladium (II) (0.52 mg) was added to a suspension of 6-(7-(((2-bromopyridin-4-yl)methyl)amino)-9H-xanthen-4-yl)-4-morpholinopyridin-2(1H)-one (20 mg), 1-methyl pyrazole-4-boronic acid pinacol ester (9.2 mg), and sodium carbonate (78 mg) in 1,2-dimethoxyethane (4.0 mL) and water (1.0 mL), followed by refluxing for 2 hours. 1-Methyl pyrazole-4-boronic acid pinacol ester (7.7 mg) was added thereto, followed by refluxing for 3 hours, and 1-methyl pyrazole-4-boronic acid pinacol ester (7.7 mg) and bis(di-tert-butyl(4-dimethylaminophenyl)phosphine)dichloropalladium (II) (1.0 mg) were added thereto, followed by refluxing for 3 hours. After the reaction mixture was cooled to room temperature, chloroform was added thereto, and the resultant product was washed with water, and dried over anhydrous sodium sulfate. The solvent was distilled off under reduced pressure, and the obtained residues were purified by preparative thin layer silica gel chromatography (chloroform:methanol=30:1, NH silica), whereby 6-(7-(((2-(1-methyl-1H-pyrazol-4-yl)pyridin-4-yl)methyl)amino)-9H-xanthen-4-yl)-4-morpholinopyridin-2(1H)-one (2.5 mg) was obtained.

MS(ESI m/z): 547 (M+H)

RT(min): 0.95

Example 2-5

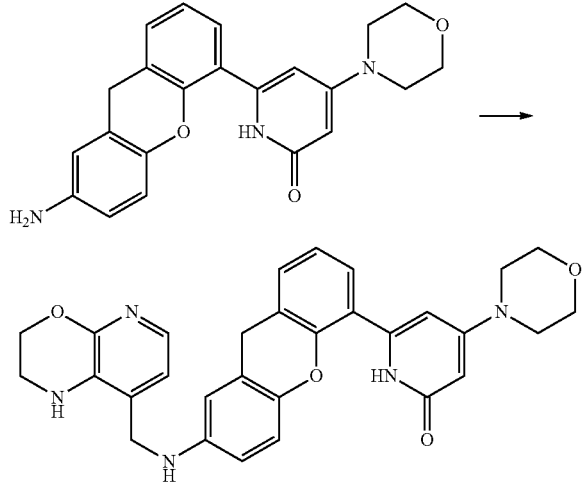 [SMILES: Nc1ccc2c(c1)Cc1cccc(-c3cc(N4CCOCC4)cc(=O)[nH]3)c1O2 ; O=c1cc(N2CCOCC2)cc(-c2cccc3c2Oc2ccc(NCc4ccnc5c4NCCO5)cc2C3)[nH]1]

Sodium triacetoxyborohydride (43 mg) was added to a mixture of 6-(7-amino-9H-xanthen-4-yl)-4-morpholinopyridin-2(1H)-one (30 mg), 2,3-dihydro-1H-pyrido[2,3-b][1,4]oxazine-8-carbaldehyde (11 mg), triethylamine (14 mg), and dichloromethane (2.0 mL), followed by stirring at room temperature for 5 hours. Chloroform was added thereto, and the organic layer was washed with a saturated sodium hydrogen carbonate aqueous solution, and dried over anhydrous sodium sulfate. The solvent was distilled off under reduced pressure, then, the obtained residues were purified by preparative thin layer silica gel chromatography (chloroform:methanol=30:1, NH silica), and methanol (2.0 mL) and sodium borohydride (10 mg) were added to the obtained residues, followed by stirring at room temperature for 4 hours. Chloroform was added thereto, and the organic layer was washed with a saturated sodium hydrogen carbonate aqueous solution, and dried over anhydrous sodium sulfate. The solvent was distilled off under reduced pressure, and the obtained residues were purified by preparative thin layer silica gel chromatography (chloroform:methanol=30:1, NH silica), whereby 6-(7-(((2,3-dihydro-1H-pyrido[3,4-b][1,4]oxazin-8-yl)methyl)amino)-9H-xanthen-4-yl)-4-morpholinopyridin-2(1H)-one (4.7 mg) was obtained as a white solid.

MS(ESI m/z): 524 (M+H)

RT(min): 0.88

Example 2-6-1

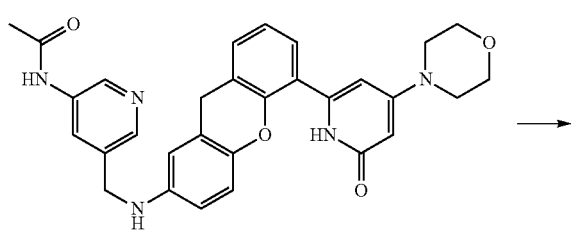

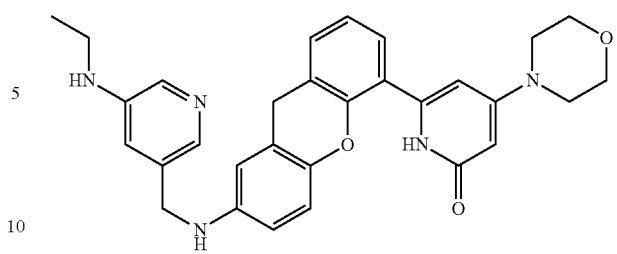

A 1.0 mol/L borane-tetrahydrofuran complex tetrahydrofuran solution (443 μL) was added to a solution of N-(5-(((5-(4-morpholino-6-oxo-1,6-dihydropyridin-2-yl)-9H-xanthen-2-yl)amino)methyl)pyridin-3-yl)acetamide (58 mg) in tetrahydrofuran (2.0 mL), followed by refluxing for 2 hours. 1 mol/L hydrochloric acid (2.0 mL) was added thereto, followed by refluxing for 1 hour. After the reaction mixture was cooled to room temperature, chloroform was added thereto, and the resultant product was washed with a saturated sodium hydrogen carbonate aqueous solution, and dried over anhydrous sodium sulfate. The solvent was distilled off under reduced pressure, and the obtained residues were purified by preparative thin layer silica gel chromatography (chloroform:ethanol=30:1, NH silica), whereby 6-(7-(((5-(ethylamino)pyridin-3-yl)methyl)amino)-9H-xanthen-4-yl)-4-morpholinopyridin-2(1H)-one (12 mg) was obtained.

MS(ESI m/z): 510 (M+H)

RT(min): 0.96

Example 2-6-2

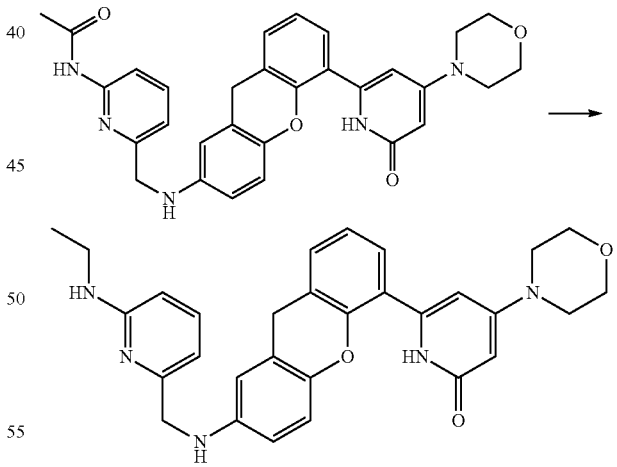

In the same manner as in Example 2-6-1, the following compound was obtained.

6-(7-(((6-(Ethylamino)pyridin-2-yl)methyl)amino)-9H-xanthen-4-yl)-4-morpholinopyridin-2(1H)-one MS(ESI m/z): 510 (M+H)

RT(min): 0.96

Example 2-7-1

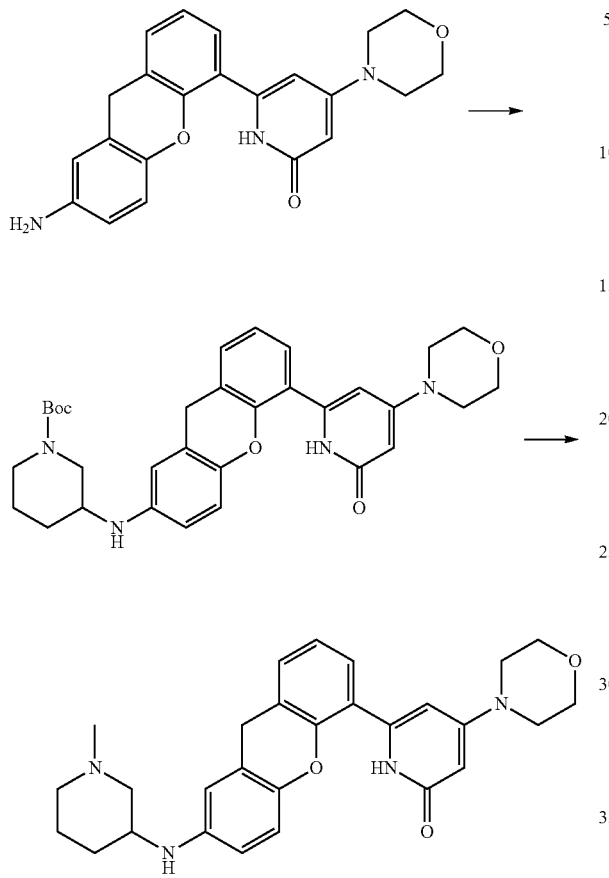

Sodium triacetoxyborohydride (51 mg) was added to a solution of 6-(7-amino-9H-xanthen-4-yl)-4-morpholinopyridin-2(1H)-one (30 mg), and tert-butyl 3-oxopiperidine-1-carboxylate (24 mg) in dichloromethane (1.5 mL), followed by stirring at room temperature for 13 hours. tert-Butyl 3-oxopiperidine-1-carboxylate (16 mg) and sodium triacetoxyborohydride (34 mg) were added thereto, followed by stirring at room temperature for 6 hours. Chloroform was added to the reaction mixture, and the organic layer was washed with a saturated sodium hydrogen carbonate aqueous solution, and dried over anhydrous sodium sulfate. The solvent was distilled off under reduced pressure, and the obtained residues were purified by silica gel column chromatography (chloroform:methanol=1:0→91:9). Tetrahydrofuran (2.0 mL) and lithium aluminium hydride (9.1 mg) were added to the obtained residues, followed by refluxing for 3 hours. After the reaction mixture was cooled to room temperature, chloroform was added thereto, and the resultant product was washed with water, and dried over anhydrous sodium sulfate. The solvent was distilled off under reduced pressure, and the obtained residues were purified by preparative thin layer silica gel chromatography (chloroform:methanol=15:1, NH silica), whereby 6-(7-((1-methylpiperidin-3-yl)amino)-9H-xanthen-4-yl)-4-morpholinopyridin-2(1H)-one (2.8 mg) was obtained.

MS(ESI m/z): 473 (M+H)
RT(min): 0.85

Example 2-7-2

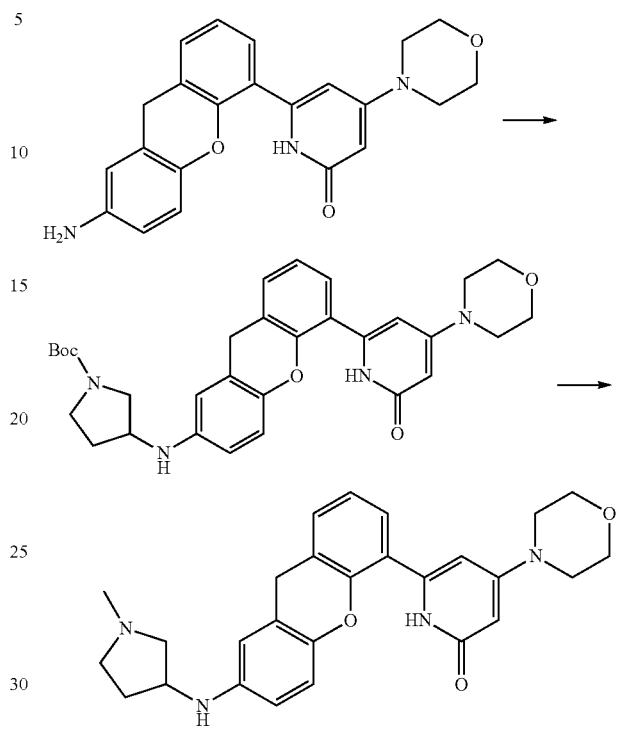

In the same manner as in Example 2-7-1, the following compound was obtained.

6-(7-((1-Methylpyrrolidin-3-yl)amino)-9H-xanthen-4-yl)-4-morpholinopyridin-2(1H)-one MS(ESI m/z): 459 (M+H)
RT(min): 0.83

Example 2-7-3

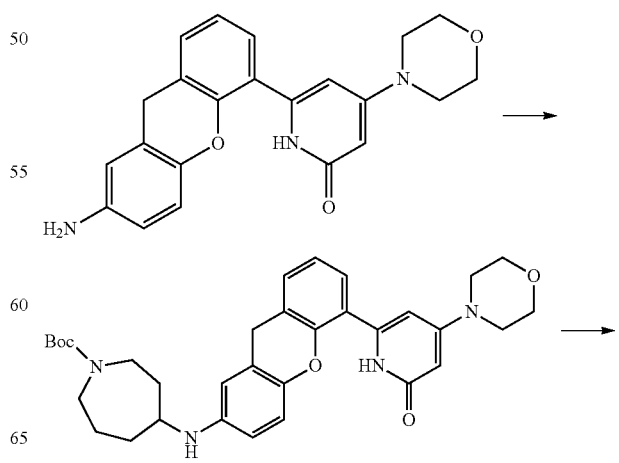

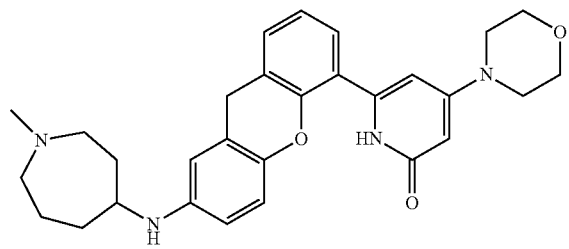

In the same manner as in Example 2-7-1, the following compound was obtained.

6-(7-((1-Methylazepan-4-yl)amino)-9H-xanthen-4-yl)-4-morpholinopyridin-2(1H)-one MS(ESI m/z): 487 (M+H)
RT(min): 0.80

Example 2-8-1

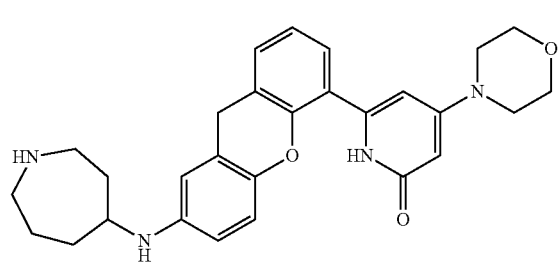

4.0 mol/L hydrogen chloride/1,4-dioxane (2.0 mL) and methanol (2.0 mL) were added to tert-butyl 4-((5-(4-morpholino-6-oxo-1,6-dihydropyridin-2-yl)-9H-xanthen-2-yl)amino)azepane-1-carboxylate (25 mg), followed by stirring at room temperature for 17 hours. A saturated sodium hydrogen carbonate aqueous solution was added to the reaction mixture, then, the resultant product was extracted with ethyl acetate, and the organic layer was dried over anhydrous sodium sulfate. The solvent was distilled off under reduced pressure, and the obtained residues were purified by preparative thin layer silica gel chromatography (chloroform:methanol=10:1, NH silica), whereby 6-(7-(azepan-4-ylamino)-9H-xanthen-4-yl)-4-morpholinopyridin-2(1H)-one (1.7 mg) was obtained.

MS(ESI m/z): 473 (M+H)
RT(min): 0.78

Example 2-8-2

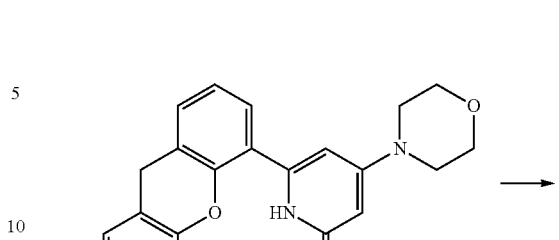

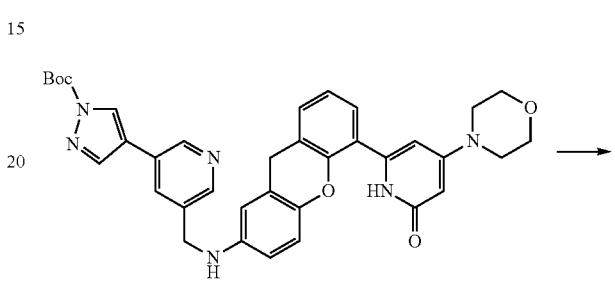

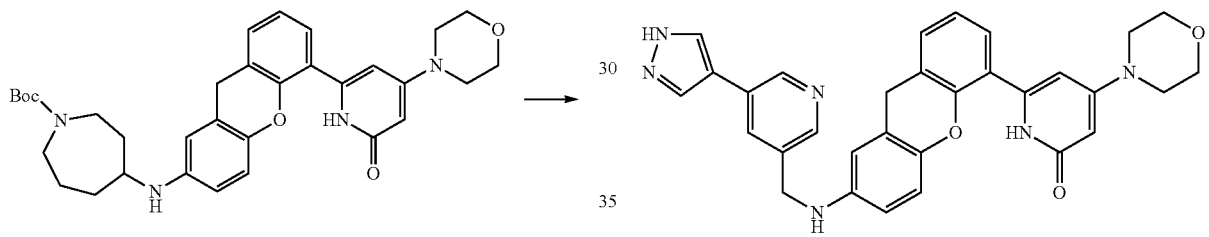

(1)

In the same manner as in Example 2-2-1, the following compound was obtained.

tert-Butyl 4-(5-(((5-(4-morpholino-6-oxo-1,6-dihydropyridin-2-yl)-9H-xanthen-2-yl)amino)methyl)pyridin-3-yl)-1H-pyrazole-1-carboxylate (2)

4.0 mol/L hydrogen chloride/1,4-dioxane (500 μL) and methanol (1.0 mL) were added to tert-butyl 4-(5-(((5-(4-morpholino-6-oxo-1,6-dihydropyridin-2-yl)-9H-xanthen-2-yl)amino)methyl)pyridin-3-yl)-1H-pyrazole-1-carboxylate (40 mg) obtained in Example 2-8-2 (1), followed by stirring at room temperature for 13 hours. Chloroform was added thereto, and the organic layer was washed with a saturated sodium hydrogen carbonate aqueous solution, and dried over anhydrous sodium sulfate. The solvent was distilled off under reduced pressure, and the obtained residues were purified by preparative thin layer silica gel chromatography (chloroform:methanol=15:1, NH silica), whereby 6-(7-(((5-(1H-pyrazol-4-yl)pyridin-3-yl)methyl)amino)-9H-xanthen-4-yl)-4-morpholinopyridin-2(1H)-one (12.7 mg) was obtained.

MS(ESI m/z): 533 (M+H)
RT(min): 0.88

Example 2-9-1

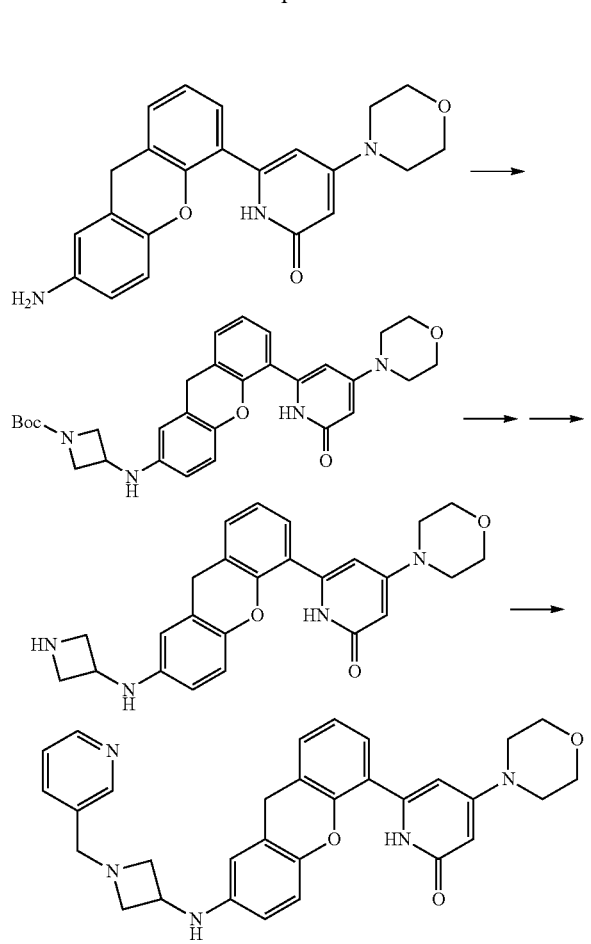

In the same manner as in Example 1-24-1, the following compounds were obtained.

tert-Butyl 3-((5-(4-morpholino-6-oxo-1,6-dihydro-pyridin-2-yl)-9H-xanthen-2-yl)amino)azetidine-1-carboxylate 6-(7-(Azetidin-3-ylamino)-9H-xanthen-4-yl)-4-morpholinopyridin-2(1H)-one 4-Morpholino-6-(7-((1-(pyridin-3-ylmethyl)azetidin-3-yl)amino)-9H-xanthen-4-yl)pyridin-2(1H)-one MS(ESI m/z): 522 (M+H)
RT(min): 0.82

Example 2-9-2

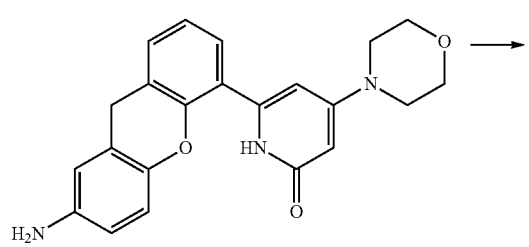

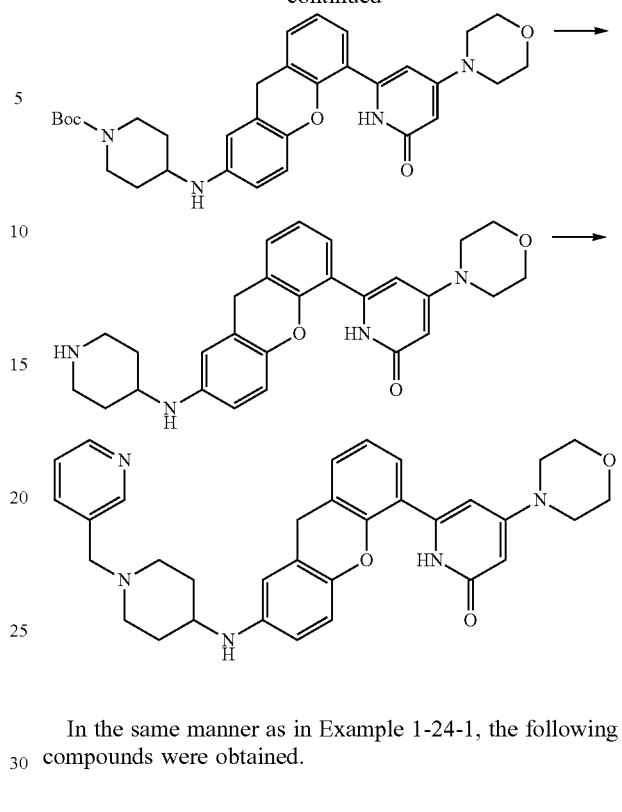

In the same manner as in Example 1-24-1, the following compounds were obtained.

tert-Butyl 4-((5-(4-morpholino-6-oxo-1,6-dihydro-pyridin-2-yl)-9H-xanthen-2-yl)amino)piperidine-1-carboxylate 4-Morpholino-6-(7-(piperidin-4-ylamino)-9H-xanthen-4-yl)pyridin-2(1H)-one 4-Morpholino-6-(7-((1-(pyridin-3-ylmethyl)piperidin-4-yl)amino)-9H-xanthen-4-yl)pyridin-2(1H)-one MS(ESI m/z): 550 (M+H)
RT(min): 0.82

Example 2-10

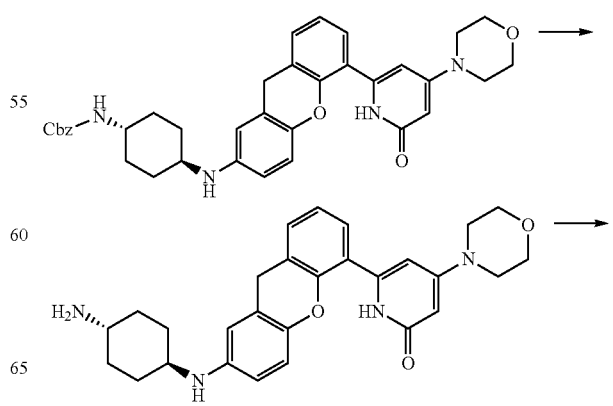

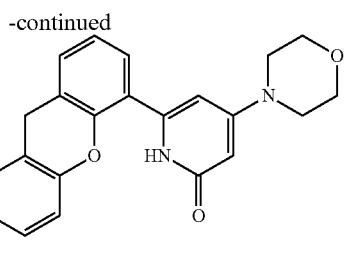

(1)

A mixture of benzyl ((trans)-4-((5-(4-morpholino-6-oxo-1,6-dihydropyridin-2-yl)-9H-xanthen-2-yl)amino)cyclohexyl)carbamate (26 mg), ammonium formate (14 mg), 10% palladium-carbon (3 mg), and methanol (3 mL) was refluxed for 2.5 hours. Ammonium formate (14 mg) and 10% palladium-carbon (3 mg) were added thereto, followed by refluxing for 3 hours. The reaction mixture was cooled to room temperature, the insoluble materials were filtered off, and the solvent was distilled off under reduced pressure. The obtained residues were purified by silica gel column chromatography (ethyl acetate:methanol=1:0→7:3, NH silica), whereby 6-(7-(((trans)-4-aminocyclohexyl)amino)-9H-xanthen-4-yl)-4-morpholinopyridin-2(1H)-one (18 mg) was obtained as a white solid.

MS(ESI m/z): 473 (M+H)
RT(min): 0.67

(2)

In the same manner as in Example 1-44-1, the following compound was obtained.

6-(7-(((Trans)-4-(dimethylamino)cyclohexyl)(methyl)amino)-9H-xanthen-4-yl)-4-morpholinopyridin-2(1H)-one MS(ESI m/z): 515 (M+H)
RT(min): 0.69

Example 2-11-1

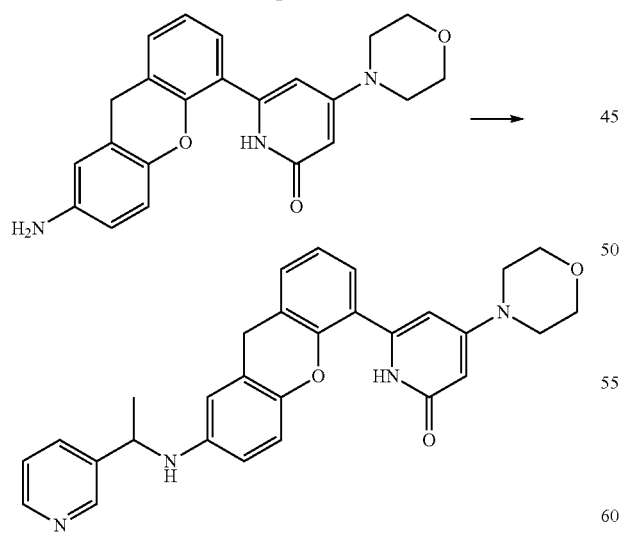

3-Acetyl pyridine (34 μL) and tetraisopropyl orthotitanate (180 μL) were added to a solution of 6-(7-amino-9H-xanthen-4-yl)-4-morpholinopyridin-2(1H)-one (77 mg) in methanol (2.0 mL) and chloroform (2.0 mL), the resultant product was stirred at room temperature for 1 hour, and refluxed for 1 hour. 3-Acetyl pyridine (34 μL) and tetraisopropyl orthotitanate (2.0 mL) was added thereto, and the resultant product was irradiated with microwaves (microwave reaction apparatus, 120° C., 0.5 hours, 2.45 GHz, 0 W to 240 W). The reaction mixture was cooled to room temperature, and ethanol (5.0 mL) and sodium borohydride (39 mg) were added thereto, followed by stirring at room temperature for 1 hour. After the insoluble materials were filtered off, chloroform was added thereto, then, the resultant product was washed with a saturated sodium chloride aqueous solution, and dried over anhydrous sodium sulfate. The solvent was distilled off under reduced pressure, and the obtained residues were purified by preparative thin layer silica gel chromatography (chloroform:methanol=20:1, NH silica), whereby 4-morpholino-6-(7-((1-(pyridin-3-yl)ethyl)amino)-9H-xanthen-4-yl)pyridin-2(1H)-one (racemic mixture) (18 mg) was obtained.

MS(ESI m/z): 481 (M+H)
RT(min): 0.91

Example 2-11-2

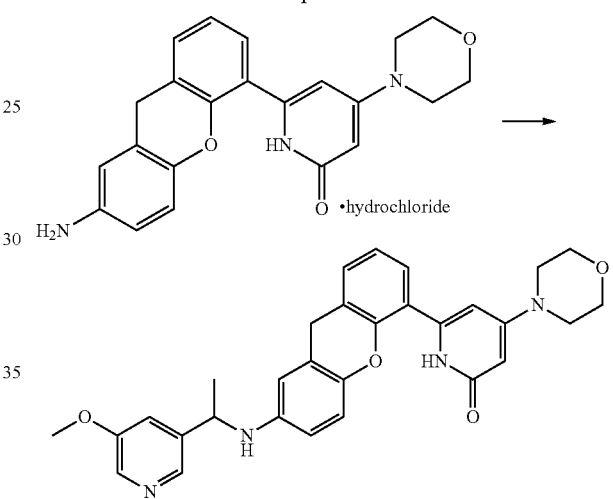

Using hydrochloride of 6-(7-amino-9H-xanthen-4-yl)-4-morpholinopyridin-2(1H)-one, the following compound was obtained in the same manner as in Reference Example 2-11-1.

6-(7-((1-(5-Methoxypyridin-3-yl)ethyl)amino)-9H-xanthen-4-yl)-4-morpholinopyridin-2(1H)-one (racemic mixture)

MS(ESI m/z): 511 (M+H)
RT(min): 0.98

Example 2-12

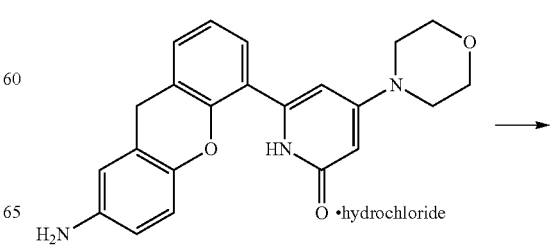

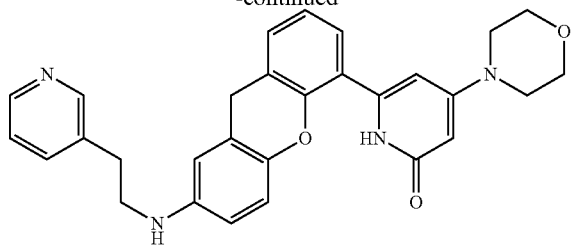
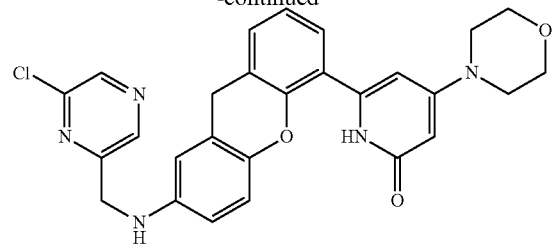

Ammonium formate (42 mg), triethylamine (31 μL), and 10% palladium carbon (50 mg) were added to a solution of hydrochloride (50 mg) of 6-(7-amino-9H-xanthen-4-yl)-4-morpholinopyridin-2(1H)-one and 3-pyridyl acetonitrile (13 μL) in methanol, followed by refluxing for 2 hours. Ammonium formate (70 mg) was added thereto, followed by refluxing for 1 hour, and 3-pyridyl acetonitrile (13 μL), ammonium formate (70 mg), and 10% palladium carbon (50 mg) were added thereto, followed by refluxing for 2 hours. After the insoluble materials were filtered off, the solvent was distilled off under reduced pressure, and the obtained residues were purified by preparative thin layer silica gel chromatography (chloroform:ethanol=30:1, NH silica), whereby 4-morpholino-6-(7-((2-(pyridin-3-yl)ethyl)amino)-9H-xanthen-4-yl)pyridin-2(1H)-one (3.6 mg) was obtained.

MS(ESI m/z): 481 (M+H)
RT(min): 0.88

Example 2-13-1

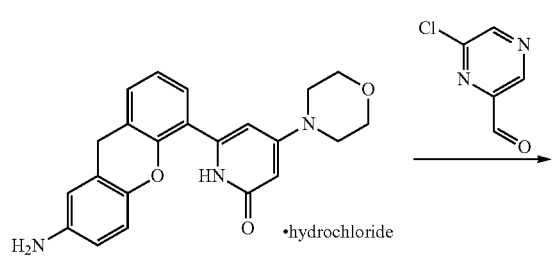

Iron (II) chloride (682 mg), sodium cyanoborohydride (628 mg), and methanol (50 mL) were mixed, whereby a 0.1 mol/L zinc cyanoborohydride-methanol solution was prepared.

A mixture of the 0.1 mol/L zinc cyanoborohydride-methanol solution (180 μL), hydrochloride (20 mg) of 6-(7-amino-9H-xanthen-4-yl)-4-morpholinopyridin-2(1H)-one, 6-chloropyrazine-2-carbaldehyde (6.4 mg), and methanol (0.90 mL) was stirred at room temperature for 12 hours. A saturated sodium hydrogen carbonate aqueous solution was added to the reaction mixture, and the solid was collected by filtration, and purified by preparative thin layer silica gel chromatography (chloroform:methanol=19:1), whereby 6-(7-(((6-chloropyrazin-2-yl)methyl)amino)-9H-xanthen-4-yl)-4-morpholinopyridin-2(1H)-one (16.7 mg) was obtained.

$^1$H-NMR (DMSO-$d_6$) δ: 10.85 (1H, brs), 8.67 (1H, s), 8.61 (1H, s), 7.29 (1H, d, J=7.6 Hz), 7.25 (1H, d, J=7.6 Hz), 7.06 (1H, t, J=7.6 Hz), 6.72 (1H, d, J=8.6 Hz), 6.54-6.46 (2H, m), 6.29 (1H, t, J=5.9 Hz), 6.13 (1H, s), 5.46 (1H, s), 4.43 (2H, d, J=5.9 Hz), 3.95 (2H, s), 3.68 (4H, t, J=4.6 Hz), 3.25 (4H, t, J=4.6 Hz).

MS(ESI m/z): 502 (M+H)
RT(min): 1.24

Examples 2-13-2 to 2-13-12

In the same manner as in Example 2-13-1, the following compounds were obtained.

TABLE 63

| Example No. | R$^b$ | Compound Name | MS | RT (min) | $^1$H-NMR (300 MHz) (DMSO-$d_6$) δ: |
|---|---|---|---|---|---|
| 2-13-2 | 4-methylthiazol-5-yl | 6-(7-(((4-Methyl thiazol-5-yl)methyl)amino)-9H-xanthen-4-yl)-4-morpholino pyridin-2(1H)-one | 487 | 1.08 | |

TABLE 63-continued

| Example No. | $R^b$ | Compound Name | MS | RT (min) | $^1$H-NMR (300 MHz) (DMSO-$d_6$) δ: |
|---|---|---|---|---|---|
| 2-13-3 | (5-(hydroxymethyl)furan-2-yl)methyl | 6-(7-(((5-(Hydroxy methyl) furan-2-yl)methyl)amino)-9H-xanthen-4-yl)-4-morpholino pyridin-2(1H)-one | 486 | 0.99 | |
| 2-13-4 | (5-(trifluoromethyl)pyridin-3-yl)methyl | 4-Morpholino-6-(7-(((5-(trifluoromethyl)pyridin-3-yl)methyl)amino)-9H-xanthen-4-yl)pyridin-2(1H)-one | 535 | 1.30 | 10.84 (1H, br s), 8.88 (1H, s), 8.84 (1H, s), 8.15 (1H, s), 7.29 (1H, d, J = 7.6 Hz), 7.25 (1H, d, J = 7.6 Hz), 7.06 (1H, t, J = 7.6 Hz), 6.71 (1H, d, J = 9.2 Hz), 6.54-6.47 (2H, m), 6.22 (1H, t, J = 5.9 Hz), 6.13 (1H, br s), 5.46 (1H, br s), 4.41 (2H, d, J = 5.9 Hz), 3.95 (2H, s), 3.67 (4H, t, J = 4.6 Hz), 3.25 (4H, t, J = 4.6 Hz). |
| 2-13-5 | (2-(dimethylamino)pyrimidin-4-yl)methyl | 6-(7-(((2-(Dimethyl amino) pyrimidin-4-yl)methyl) amino)-9H-xanthen-4-yl)-4-morpholino pyridin-2(1H)-one | 511 | 1.07 | 10.86 (1H, s), 8.23 (1H, s), 7.35-7.18 (2H, m), 7.12-7.00 (1H, m), 6.71 (1H, d, J = 7.3 Hz), 6.58-6.36 (3H, m), 6.13 (2H, br s), 5.46 (1H, br s), 4.15 (2H, br s), 3.94 (2H, br s), 3.67 (4H, br s), 3.25 (4H, br s), 3.12 (6H, s). |
| 2-13-6 | (thiophen-2-yl)methyl | 4-Morpholino-6-(7-((thiophen-2-yl methyl) amino)-9H-xanthen-4-yl) pyridin-2(1H)-one | 472 | 1.30 | 10.86 (1H, br s), 7.35 (1H, d, J = 4.3 Hz), 7.30 (1H, d, J = 7.3 Hz), 7.25 (1H, d, J = 7.3 Hz), 7.11-7.01 (2H, m), 6.96 (1H, t, J = 4.3 Hz), 6.71 (1H, d, J = 8.6 Hz), 6.56-6.47 (2H, m), 6.14 (1H, br s), 6.09 (1H, t, J = 5.9 Hz), 5.46 (1H, br s), 4.42 (2H, d, J = 5.9 Hz), 3.95 (2H, s), 3.69-3.66 (4H, br m), 3.29-3.22 (4H, br m). |
| 2-13-7 | (5-chlorothiophen-2-yl)methyl | 6-(7-(((5-Chlorothiophen-2-yl)methyl)amino)-9H-xanthen-4-yl)-4-morpholino pyridin-2(1H)-one | 506 | 1.48 | 10.86 (1H, s), 7.30 (1H, d, J = 7.6 Hz), 7.26 (1H, d, J = 7.6 Hz), 7.07 (1H, t, J = 7.6 Hz), 6.95 (1H, d, J = 4.0 Hz), 6.92 (1H, d, J = 4.0 Hz), 6.72 (1H, d, J = 8.6 Hz), 6.55-6.47 (2H, m), 6.19-6.10 (2H, m), 5.46 (1H, s), 4.37 (2H, d, J = 5.9 Hz), 3.96 (2H, s), 3.68 (4H, t, J = 4.6 Hz), 3.25 (4H, t, J = 4.6 Hz). |
| 2-13-8 | (4-methoxypyrimidin-2-yl)methyl | 6-(7-(((4-Methoxy pyrimidin-2-yl)methyl) amino)-9H-xanthen-4-yl)-4-morpholino pyridin-2(1H)-one | 498 | 1.10 | 10.86 (1H, br s), 8.47 (1H, d, J = 5.9 Hz), 7.30 (1H, d, J = 7.3 Hz), 7.26 (1H, d, J = 7.3 Hz), 7.06 (1H, t, J = 7.3 Hz), 6.81 (1H, d, J = 5.9 Hz), 6.71 (1H, d, J = 8.6 Hz), 6.61-6.52 (2H, m), 6.14 (1H, br s), 5.95 (1H, t, J = 5.9 Hz), 5.47 (1H, br s), 4.33 (2H, d, J = 5.9 Hz), 3.96 (2H, s), 3.92 (3H, s), 3.73-3.63 (4H, br m), 3.31-3.21 (4H, br m). |

TABLE 63-continued

| Example No. | R^b | Compound Name | MS | RT (min) | $^1$H-NMR (300 MHz) (DMSO-$d_6$) δ: |
|---|---|---|---|---|---|
| 2-13-9 | 6-methoxy pyrazin-2-yl (methylene) | 6-(7-(((6-Methoxy pyrazin-2-yl)methyl)amino)-9H-xanthen-4-yl)-4-morpholino pyridin-2(1H)-one | 498 | 1.18 | 10.85 (1H, br s), 8.16 (2H, s), 7.29 (1H, d, J = 7.6 Hz), 7.26 (1H, d, J = 7.6 Hz), 7.06 (1H, t, J = 7.6 Hz), 6.72 (1H, d, J = 9.2 Hz), 6.55-6.47 (2H, m), 6.21-6.08 (2H, m), 5.47 (1H, br s), 4.33 (2H, d, J = 6.6 Hz), 3.95 (2H, s), 3.93 (3H, s), 3.73-3.62 (4H, m), 3.29-3.20 (4H, m). |

TABLE 64

| Example No. | R^b | Compound Name | MS | RT (min) | $^1$H-NMR (300 MHz) (DMSO-$d_6$) δ: |
|---|---|---|---|---|---|
| 2-13-10 | 4-cyclopropyl pyridin-2-yl (methylene) | 6-(7-(((4-Cyclopropyl pyridin-2-yl)methyl)amino)-9H-xanthen-4-yl)-4-morpholino pyridin-2(1H)-one | 507 | 0.93 | 10.85 (1H, s), 8.32 (1H, d, J = 5.3 Hz), 7.29 (1H, d, J = 7.3 Hz), 7.25 (1H, d, J = 7.3 Hz), 7.11 (1H, d, J = 1.3 Hz), 7.06 (1H, t, J = 7.3 Hz), 6.91 (1H, dd, J = 5.3, 1.3 Hz), 6.70 (1H, d, J = 8.6 Hz), 6.51-6.42 (2H, m), 6.17-6.05 (2H, m), 5.46 (1H, s), 4.26 (2H, d, J = 5.9 Hz), 3.94 (2H, s), 3.68 (4H, t, J = 4.6 Hz), 3.25 (4H, t, J = 4.6 Hz), 1.87 (1H, tt, J = 8.6, 4.6 Hz), 1.02 (2H, ddd, J = 8.6, 6.2, 3.9 Hz), 0.72 (2H, ddd, J = 6.2, 4.6, 3.9 Hz). |
| 2-13-11 | 4-ethoxy pyridin-2-yl (methylene) | 6-(7-(((4-Ethoxy pyridin-2-yl)methyl)amino)-9H-xanthen-4-yl)-4-morpholino pyridin-2(1H)-one | 511 | 0.93 | 10.86 (1H, br s), 8.33 (1H, d, J = 5.3 Hz), 7.30 (1H, d, J = 7.6 Hz), 7.26 (1H, d, J = 7.6 Hz), 7.07 (1H, t, J = 7.6 Hz), 6.89 (1H, d, J = 2.0 Hz), 6.82 (1H, dd, J = 5.3, 2.0 Hz), 6.71 (1H, d, J = 7.9 Hz), 6.51-6.42 (2H, m), 6.20-6.10 (2H, m), 5.46 (1H, s), 4.28 (2H, d, J = 6.6 Hz), 4.06 (2H, q, J = 7.0 Hz), 3.94 (2H, s), 3.68 (4H, t, J = 4.6 Hz), 3.26 (4H, t, J = 4.6 Hz), 1.30 (3H, t, J = 7.0 Hz). |
| 2-13-12 | 2-methoxy pyridin-3-yl (methylene) | 6-(7-(((2-Methoxy pyridin-3-yl)methyl)amino)-9H-xanthen-4-yl)-4-morpholino pyridin-2(1H)-one | 497 | 1.19 | |

Examples 2-14-1 to 2-14-84

Using hydrochloride of 6-(7-amino-9H-xanthen-4-yl)-4-morpholinopyridin-2(1H)-one, the following compounds were obtained in the same manner as in Example 1-12-1.

TABLE 65

| Example No. | R$^b$ | Compound Name | MS | RT (min) | $^1$H-NMR (300 MHz) (DMSO-d$_6$) δ: |
|---|---|---|---|---|---|
| 2-14-1 | 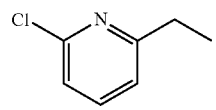 | tert-Butyl 3-fluoro-4-((5-(4-morpholino-6-oxo-1,6-dihydropyridin-2-yl)-9H-xanthen-2-yl)amino)piperidine-1-carboxylate | 577 | 1.39 1.45 | |
| 2-14-2 | 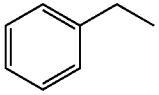 | 6-(7-(((6-Chloropyridin-2-yl)methyl)amino)-9H-xanthen-4-yl)-4-morpholino pyridin-2(1H)-one | 501 | 1.29 | |
| 2-14-3 | 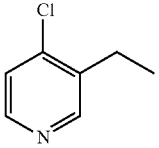 | 6-(7-(Benzyl amino)-9H-xanthen-4-yl)-4-morpholino pyridin-2(1H)-one | 466 | 1.34 | |
| 2-14-4 | 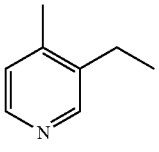 | 6-(7-(((4-Chloropyridin-3-yl)methyl)amino)-9H-xanthen-4-yl)-4-morpholino pyridin-2(1H)-one | 501 | 1.15 | |
| 2-14-5 | 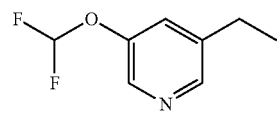 | 6-(7-(((4-Methyl pyridin-3-yl)methyl)amino)-9H-xanthen-4-yl)-4-morpholino pyridin-2(1H)-one | 481 | 0.89 | 10.85 (1H, s), 8.41 (1H, s), 8.32 (1H, d, J = 5.0 Hz), 7.30 (1H, d, J = 7.3 Hz), 7.26 (1H, d, J = 8.3 Hz), 7.20 (1H, d, J = 5.0 Hz), 7.06 (1H, t, J = 7.6 Hz), 6.72 (1H, d, J = 8.6 Hz), 6.54 (1H, d, J = 5.9 Hz), 6.50 (1H, s), 6.13 (1H, s), 5.90 (1H, t, J = 5.4 Hz), 5.46 (1H, s), 4.24 (2H, d, J = 5.3 Hz), 3.96 (2H, s), 3.68 (4H, t, J = 4.3 Hz), 3.25 (4H, t, J = 5.0 Hz), 2.35 (3H, s). |
| 2-14-6 | 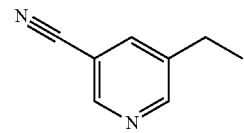 | 6-(7-(((5-(Difluoromethoxy)pyridin-3-yl)methyl)amino)-9H-xanthen-4-yl)-4-morpholino pyridin-2(1H)-one | 533 | 1.24 | |
| 2-14-7 |  | 5-(((5-(4-Morpholino-6-oxo-1,6-dihydropyridin-2-yl)-9H-xanthen-2-yl)amino)methyl)nicotinonitrile | 492 | 1.17 | 10.85 (1H, br s), 8.90 (1H, d, J = 1.9 Hz), 8.86 (1H, d, J = 1.9 Hz), 8.24 (1H, t, J = 1.9 Hz), 7.32-7.23 (2H, m), 7.06 (1H, t, J = 7.7 Hz), 6.71 (1H, d, J = 9.3 Hz), 6.52-6.45 (2H, m), 6.19 (1H, t, J = 6.5 Hz), 6.13 (1H, d, J = 2.4 Hz), 5.46 (1H, d, J = 2.4 Hz), 4.36 (2H, d, J = 6.5 Hz), 3.95 (2H, s), 3.67 (4H, t, J = 4.7 Hz), 3.25 (4H, t, J = 4.7 Hz). |

TABLE 65-continued

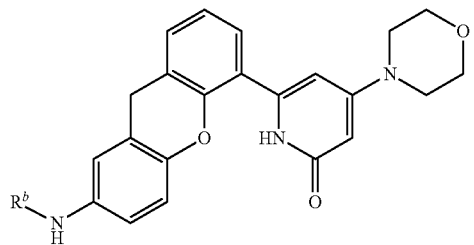

| Example No. | R$^b$ | Compound Name | MS | RT (min) | $^1$H-NMR (300 MHz) (DMSO-d$_6$) δ: |
|---|---|---|---|---|---|
| 2-14-8 | (2-ethyl-3-methoxypyridin-4-yl)methyl | 6-(7-(((3-Methoxy pyridin-2-yl)methyl)amino)-9H-xanthen-4-yl)-4-morpholino pyridin-2(1H)-one | 497 | 0.95 | 10.85 (1H, s), 8.12 (1H, t, J = 2.3 Hz), 7.43 (1H, d, J = 7.3 Hz), 7.32-7.24 (3H, m), 7.06 (1H, t, J = 7.6 Hz), 6.71 (1H, d, J = 8.9 Hz), 6.59 (2H, d, J = 7.6 Hz), 6.13 (1H, s), 5.78 (1H, t, J = 5.6 Hz), 5.46 (1H, s), 4.28 (2H, d, J = 5.6 Hz), 3.97 (2H, s), 3.88 (3H, s), 3.68 (4H, t, J = 4.8 Hz), 3.26 (4H, t, J = 4.8 Hz). |
| 2-14-9 | (4-ethyl-3-methoxypyridin-2-yl)methyl | 6-(7-(((3-Methoxy pyridin-4-yl)methyl)amino)-9H-xanthen-4-yl)-4-morpholino pyridin-2(1H)-one | 497 | 0.93 | 10.83 (1H, s), 8.32 (1H, s), 8.13 (1H, d, J = 4.6 Hz), 7.29-7.20 (3H, m), 7.05 (1H, t, J = 7.6 Hz), 6.70 (1H, d, J = 8.3 Hz), 6.44-6.38 (2H, m), 6.13-6.04 (2H, m), 5.45 (1H, s), 4.24 (2H, d, J = 5.9 Hz), 3.96 (3H, s), 3.93 (2H, s), 3.67 (4H, t, J = 4.8 Hz), 3.25 (4H, t, J = 4.8 Hz). |

TABLE 66

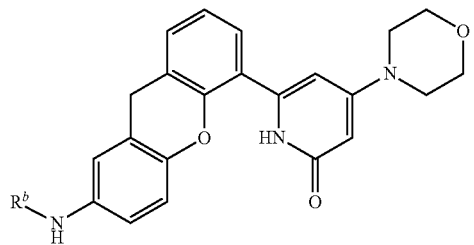

| Example No. | R$^b$ | Compound Name | MS | RT (min) | $^1$H-NMR (300 MHz) (DMSO-d$_6$) δ: |
|---|---|---|---|---|---|
| 2-14-10 | (5-ethyl-pyridin-3-yl with prop-1-en-2-yl) | 4-Morpholino-6-(7-(((5-(prop-1-en-2-yl)pyridin-3-yl)methyl)amino)-9H-xanthen-4-yl)pyridin-2(1H)-one | 507 | 1.07 | 10.87 (1H, br s), 8.58 (1H, d, J = 2.1 Hz), 8.49 (1H, d, J = 1.8 Hz), 8.24 (1H, t, J = 2.4 Hz), 7.32-7.22 (2H, m), 7.06 (1H, t, J = 7.5 Hz), 6.71 (1H, d, J = 9.3 Hz), 6.53-6.45 (2H, m), 6.18-6.08 (2H, m), 5.50 (1H, s), 5.46 (1H, d, J = 1.8 Hz), 5.19 (1H, d, J = 1.2 Hz), 4.29 (2H, d, J = 6.6 Hz), 3.95 (2H, s), 3.67 (4H, t, J = 4.6 Hz), 3.25 (4H, t, J = 4.6 Hz), 2.11 (3H, s). |
| 2-14-11 | (4-cyanopyridin-2-yl)methyl | 2-(((5-(4-Morpholino-6-oxo-1,6-dihydropyridin-2-yl)-9H-xanthen-2-yl)amino)methyl) isonicotinonitrile | 492 | 1.20 | 10.85 (1H, br s), 8.80 (1H, d, J = 6.0 Hz), 7.75-7.72 (2H, m), 7.32-7.22 (2H, m), 7.06 (1H, t, J = 7.5 Hz), 6.71 (1H, d, J = 8.7 Hz), 6.50-6.44 (2H, m), 6.27 (1H, t, J = 6.2 Hz), 6.13 (1H, d, J = 1.8 Hz), 5.46 (1H, d, J = 1.8 Hz), 4.42 (2H, d, J = 6.2 Hz), 3.94 (2H, s) 3.67 (4H, t, J = 4.7 Hz), 3.25 (4H, t, J = 4.7 Hz). |
| 2-14-12 | (5-(2-methoxypropan-2-yl)pyridin-3-yl)methyl | 6-(7-(((5-(2-Methoxy propan-2-yl)pyridin-3-yl)methyl)amino)-9H-xanthen-4-yl)-4-morpholino pyridin-2 (1H)-one | 539 | 1.01 | 10.89 (1H, br s), 8.47 (1H, d, J = 2.1 Hz), 8.45 (1H, d, J = 2.7 Hz), 7.77 (1H, t, J = 1.9 Hz), 7.32-7.22 (2H, m), 7.06 (1H, t, J = 7.5 Hz), 6.70 (1H, d, J = 8.7 Hz), 6.53-6.46 (2H, m), 6.18-6.08 (2H, m), 5.46 (1H, d, J = 2.7 Hz), 4.32-4.26 (2H, br s), 3.94 (2H, s), 3.67 (4H, t, J = 4.8 Hz), 3.25 (4H, t, J = 4.8 Hz), 2.96 (3H, s), 1.46 (6H, s). |

TABLE 66-continued

| Example No. | R^b | Compound Name | MS | RT (min) | $^1$H-NMR (300 MHz) (DMSO-d$_6$) δ: |
|---|---|---|---|---|---|
| 2-14-13 | (6-cyanopyridin-2-yl)methyl | 6-(((5-(4-Morpholino-6-oxo-1,6-dihydropyridin-2-yl)-9H-xanthen-2-yl)amino)methyl)picolinonitrile | 492 | 1.25 | 10.88 (1H, br s), 8.00 (1H, t, J = 7.7 Hz), 7.92-7.88 (1H, m), 7.67 (1H, dd, J = 7.7 Hz), 1.3 Hz), 7.32-7.22 (2H, m), 7.06 (1H, t, J = 7.5 Hz), 6.70 (1H, d, J = 7.8 Hz), 6.50-6.42 (2H, m), 6.38-6.28 (1H, br s), 6.13 (1H, d, J = 2.4 Hz), 5.46 (1H, d, J = 2.4 Hz), 4.44-4.36 (2H, br s), 3.93 (2H, s), 3.67 (4H, t, J = 4.6 Hz), 3.25 (4H, t, J = 4.6 Hz). |
| 2-14-14 | 3-(pyridin-3-yl)propyl | 4-Morpholino-6-(7-((3-(pyridin-3-yl)propyl)amino)-9H-xanthen-4-yl)pyridin-2(1H)-one | 495 | 0.82 | |
| 2-14-15 | (4,6-dimethylpyridin-2-yl)methyl | 6-(7-(((4,6-Dimethyl pyridin-2-yl)methyl)amino)-9H-xanthen-4-yl)-4-morpholino pyridin-2(1H)-one | 495 | 0.93 | |
| 2-14-16 | 1-(5-methoxypyridin-3-yl)propyl | 6-(7-((1-(5-Methoxy pyridin-3-yl)propyl)amino)-9H-xanthen-4-yl)-4-morpholino pyridin-2(1H)-one | 525 | 1.07 | 10.81 (1H, s), 8.19 (1H, d, J = 2.0 Hz), 8.10 (1H, d, J = 2.6 Hz), 7.37-7.34 (1H, m), 7.28-7.23 (2H, m), 7.04 (1H, t, J = 7.6 Hz), 6.64 (1H, d, J = 7.9 Hz), 6.45-6.42 (2H, m), 6.11 (1H, s), 6.00 (1H, d, J = 8.6 Hz), 5.45 (1H, s), 4.30 (1H, q, J = 7.9 Hz), 3.90-3.87 (2H, m), 3.78 (3H, s), 3.68-3.65 (4H, m), 3.26-3.22 (4H, m), 1.86-1.64 (2H, m), 0.91 (3H, t, J = 7.3 Hz). |
| 2-14-17 | 1-(5-methoxypyridin-3-yl)butyl | 6-(7-((1-(5-Methoxy pyridin-3-yl)butyl)amino)-9H-xanthen-4-yl)-4-morpholino pyridin-2(1H)-one | 539 | 1.17 | |

TABLE 67

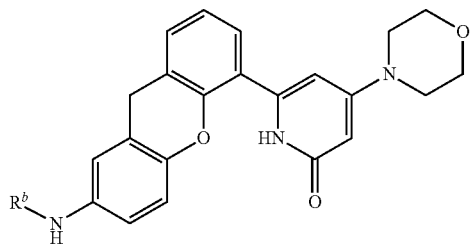

| Example No. | R[b] | Compound Name | MS | RT (min) | 1H-NMR (300 MHz) (DMSO-d6) δ: |
|---|---|---|---|---|---|
| 2-14-18 | 6-methyl pyridin-2-yl with isopropyl | 6-(7-((1-(6-Methyl pyridin-2-yl)ethyl)amino)-9H-xanthen-4-yl)-4-morpholino pyridin-2(1H)-one | 495 | 0.93 | (CDCl3): 9.13 (1H, s), 7.50 (1H, t, J = 7.6 Hz), 7.30-7.20 (2H, m), 7.12 (1H, d, J = 7.9 Hz), 7.05 (1H, d, J = 7.9 Hz), 7.00 (1H, d, J = 7.3 Hz), 6.88 (1H, d, J = 8.6 Hz), 6.44 (1H, dd, J = 8.6, 2.6 Hz), 6.34 (1H, d, J = 2.6 Hz), 6.14 (1H, d, J = 2.6 Hz) 5.70 (1H, d, J = 2.6 Hz), 4.53 (1H, q, J = 6.6 Hz), 4.41 (1H, br s), 3.94 (2H, s), 3.81 (4H, t, J = 4.8 Hz), 3.30 (4H, t, J = 4.8 Hz), 2.58 (3H, s), 1.52 (3H, d, J = 6.6 Hz). |
| 2-14-19 | 4-methyl pyridin-2-yl with isopropyl | 6-(7-((1-(4-Methyl pyridin-2-yl)ethyl)amino)-9H-xanthen-4-yl)-4-morpholino pyridin-2(1H)-one | 495 | 0.94 | (CDCl3): 9.00 (1H, s), 8.42 (1H, d, J = 5.3 Hz), 7.30-7.21 (2H, m), 7.15 (1H, s), 7.04 (1H, t, J = 7.6 Hz), 6.98 (1H, d, J = 4.6 Hz), 6.89 (1H, d, J = 8.6 Hz), 6.46 (1H, dd, J = 8.6, 2.6 Hz), 6.35 (1H, d, J = 2.6 Hz), 6.14 (1H, d, J = 2.6 Hz), 5.71 (1H, d, J = 2.6 Hz), 4.53 (1H, q, J = 6.6 Hz), 4.36 (1H, br s), 3.94 (2H, s), 3.82 (4H, t, J = 5.0 Hz), 3.31 (4H, t, J = 5.0 Hz), 2.32 (3H, s), 1.52 (3H, d, J = 6.6 Hz). |
| 2-14-20 | 4-methoxy pyridin-2-yl with isopropyl | 6-(7-((1-(4-Methoxy pyridin-2-yl)ethyl)amino)-9H-xanthen-4-yl)-4-morpholino pyridin-2(1H)-one | 511 | 0.93 | (CDCl3): 8.39 (1H, d, J = 5.3 Hz), 7.30-7.19 (2H, m), 7.04 (1H, t, J = 7.6 Hz), 6.87 (2H, dd, J = 5.6, 3.0 Hz), 6.68 (1H, dd, J = 5.3, 2.6 Hz), 6.43 (1H, dd, J = 8.6, 2.6 Hz), 6.33 (1H, d, J = 2.6 Hz), 6.15 (1H, d, J = 2.6 Hz), 5.70 (1H, d, J = 2.6 Hz), 4.50 (1H, q, J = 6.6 Hz), 3.93 (2H, s), 3.83-3.79 (7H, m), 3.31 (4H, t, J = 4.6 Hz), 1.53 (3H, d, J = 6.6 Hz). |
| 2-14-21 | 6-fluoropyridin-2-yl with isopropyl | 6-(7-((1-(6-Fluoropyridin-2-yl)ethyl)amino)-9H-xanthen-4-yl)-4-morpholino pyridin-2(1H)-one | 499 | 1.29 | (CDCl3): 9.20 (1H, s), 7.71 (1H, q, J = 7.9 Hz), 7.30-7.21 (3H, m), 7.05 (1H, t, J = 7.6 Hz), 6.88 (1H, d, J = 8.6 Hz), 6.79 (1H, dd, J = 7.9, 2.6 Hz), 6.43 (1H, dd, J = 8.6, 2.6 Hz), 6.31 (1H, d, J = 2.6 Hz), 6.14 (1H, d, J = 2.6 Hz), 5.70 (1H, d, J = 2.6 Hz), 4.55-4.47 (1H, m), 4.22 (1H, br s), 3.94 (2H, s), 3.81 (4H, t, J = 4.6 Hz), 3.30 (4H, t, J = 5.0 Hz), 1.53 (3H, d, J = 6.6 Hz). |
| 2-14-22 | 5-methyl pyridin-3-yl with isopropyl | 6-(7-((1-(5-Methyl pyridin-3-yl)ethyl)amino)-9H-xanthen-4-yl)-4-morpholino pyridin-2(1H)-one | 495 | 0.95 | |
| 2-14-23 | 4-chloropyridin-2-yl with isopropyl | 6-(7-((1-(4-Chloropyridin-2-yl)ethyl)amino)-9H-xanthen-4-yl)-4-morpholino pyridin-2(1H)-one | 515 | 1.28 | (CDCl3): 8.48 (1H, d, J = 5.9 Hz), 7.38 (1H, d, J = 2.0 Hz), 7.32-7.16 (3H, m), 7.06 (1H, t, J = 7.6 Hz), 6.86 (1H, d, J = 8.6 Hz), 6.42 (1H, dd, J = 8.6, 2.6 Hz), 6.31 (1H, d, J = 2.6 Hz), 6.21 (1H, d, J = 2.6 Hz), 5.75 (1H, d, J = 2.6 Hz), 4.54 (1H, q, J = 6.6 Hz), 3.95 (2H, s), 3.82 (4H, t, J = 5.0 Hz), 3.34 (4H, t, J = 5.0 Hz), 1.54 (3H, d, J = 6.6 Hz). |

TABLE 67-continued

[Structure: xanthene core with CH2-O linkage, bearing R^b-NH- group on one aromatic ring and a 4-morpholino-pyridin-2(1H)-one substituent]

| Example No. | R^b | Compound Name | MS | RT (min) | $^1$H-NMR (300 MHz) (DMSO-d$_6$) δ: |
|---|---|---|---|---|---|
| 2-14-24 | [5-methylpyrazin-2-yl with isopropyl linker] | 6-(7-((1-(5-Methyl pyrazin-2-yl)ethyl)amino)-9H-xanthen-4-yl)-4-morpholino pyridin-2(1H)-one | 496 | 1.12 | (CDCl$_3$): 8.50 (1H, d, J = 1.3 Hz), 8.41 (1H, s), 7.30-7.22 (2H, m), 7.06 (1H, t, J = 7.6 Hz), 6.85 (1H, d, J = 8.6 Hz), 6.45 (1H, dd, J = 8.6, 2.6 Hz), 6.35 (1H, d, J = 2.6 Hz), 6.22 (1H, d, J = 2.6 Hz), 5.75 (1H, d, J = 2.6 Hz), 4.62 (1H, q, J = 6.6 Hz), 3.95 (2H, s), 3.82 (4H, t, J = 5.0 Hz), 3.34 (4H, t, J = 5.0 Hz), 2.54 (3H, s), 1.55 (3H, d, J = 6.6 Hz). |

TABLE 68

[Structure: xanthene core with CH2-O linkage, bearing R^b-NH- group on one aromatic ring and a 4-morpholino-pyridin-2(1H)-one substituent]

| Example No. | R^b | Compound Name | MS | RT (min) | $^1$H-NMR (300 MHz) (DMSO-d$_6$) δ: |
|---|---|---|---|---|---|
| 2-14-25 | [2-fluoropyridin-4-yl with isopropyl linker] | 6-(7-((1-(2-(Fluoropyridin-4-yl)ethyl)amino)-9H-xanthen-4-yl)-4-morpholino pyridin-2(1H)-one | 499 | 1.26 | |
| 2-14-26 | [2-methoxypyridin-4-yl with isopropyl linker] | 6-(7-((1-(2-Methoxy pyridin-4-yl)ethyl)amino)-9H-xanthen-4-yl)-4-morpholino pyridin-2(1H)-one | 511 | 1.25 | (CDCl$_3$): 8.11 (1H, d, J = 5.3 Hz), 7.30-7.21 (2H, m), 7.05 (1H, t, J = 7.6 Hz), 6.88 (1H, dd, J = 5.3, 1.3 Hz), 6.84 (1H, d, J = 8.6 Hz), 6.74 (1H, s), 6.36 (1H, dd, J = 8.6, 2.6 Hz), 6.23-6.19 (2H, m), 5.74 (1H, d, J = 2.6 Hz), 4.36 (1H, q, J = 6.6 Hz), 3.93-3.91 (5H, m), 3.82 (4H, t, J = 5.0 Hz), 3.33 (4H, t, J = 5.0 Hz), 1.50 (3H, d, J = 6.6 Hz). |
| 2-14-27 | [5-chloropyridin-3-yl with isopropyl linker] | 6-(7-((1-(5-Chloropyridin-3-yl)ethyl)amino)-9H-xanthen-4-yl)-4-morpholino pyridin-2(1H)-one | 515 | 1.29 | |
| 2-14-28 | [2-methylpyridin-4-yl with isopropyl linker] | 6-(7-((1-(2-Methyl pyridin-4-yl)ethyl)amino)-9H-xanthen-4-yl)-4-morpholino pyridin-2(1H)-one | 495 | 0.92 | |

TABLE 68-continued

| Example No. | R$^b$ | Compound Name | MS | RT (min) | $^1$H-NMR (300 MHz) (DMSO-d$_6$) δ: |
|---|---|---|---|---|---|
| 2-14-29 | 5-fluoro-3-isopropylpyridin-3-yl | 6-(7-((1-(5-Fluoropyridin-3-yl)ethyl)amino)-9H-xanthan-4-yl)-4-morpholino pyridin-2(1H)-one | 499 | 1.2 | |
| 2-14-30 | 6-methoxy-2-isopropylpyridin-2-yl | 6-(7-((1-(6-Methoxy pyridin-2-yl)ethyl)amino)-9H-xanthen-4-yl)-4-morpholine pyridin-2(1H)-one | 511 | 1.29 | |
| 2-14-31 | thiazol-2-yl methyl | 4-Morpholino-6-(7-((thiazol-2-yl methyl) amino)-9H-xanthen-4-yl) pyridin-2(1H)-one | 473 | 1.12 | |
| 2-14-32 | 5-isocyanothiophen-2-yl methyl | 6-(7-(((5-Isocycanothiophen-2-yl)methyl)amino)-9H-xanthen-4-yl)-4-morpholino pyridin-2(1H)-one | 497 | 1.30 | (CDCl$_3$): 9.38 (1H, br s), 7.54-7.51 (1H, m), 7.36-7.23 (2H, m), 7.10-6.98 (3H, m), 6.52-6.45 (2H, m), 6.25-6.15 (1H, m), 5.80-5.70 (1H, m), 4.54 (2H, s), 4.20-4.14 (1H, br m), 4.00 (2H, s), 3.83-3.82 (4H, m), 3.32-3.31 (4H, m). |
| 2-14-33 | furan-2-yl methyl | 6-(7-((Furan-2-yl methyl) amino)-9H-xanthen-4-yl)-4-morpholino pyridin-2(1H)-one | 456 | 1.25 | |
| 2-14-34 | furan-3-yl methyl | 6-(7-((Furan-3-yl methyl) amino)-9H-xanthen-4-yl)-4-morpholino pyridin-2(1H)-one | 456 | 1.10 | |

TABLE 69

| Example No. | R$^b$ | Compound Name | MS | RT (min) | $^1$H-NMR (300 MHz) (DMSO-d$_6$) δ: |
|---|---|---|---|---|---|
| 2-14-35 | thiophen-3-yl methyl | 4-Morpholino-6-(7-((thiophen-3-yl methyl) amino)-9H-xanthen-4-yl) pyridin-2(1H)-one | 472 | 1.22 | |

TABLE 69-continued

| Example No. | R$^b$ | Compound Name | MS | RT (min) | $^1$H-NMR (300 MHz) (DMSO-d$_6$) δ: |
|---|---|---|---|---|---|
| 2-14-36 | | 4-Morpholino-6-(7-((thiazol-4-yl methyl) amino)-9H-xanthen-4-yl) pyridin-2(1H)-one | 473 | 1.06 | |
| 2-14-37 | | 4-Morpholino-6-(7-((thiazol-5-yl methyl) amino)-9H-xanthen-4-yl) pyridin-2(1H)-one | 473 | 1.06 | |
| 2-14-38 | | 6-(7-((2-Hydroxy-1-(6-methyl pyridin-2-yl)ethyl) amino)-9H-xanthen-4-yl)-4-morpholino pyridin-2 (1H)-one (Racemic mixture) | 511 | 0.86 | |
| 2-14-39 | | 6-(7-((2-Hydroxy-1-(4-methyl pyridin-2-yl)ethyl) amino)-9H-xanthen-4-yl)-4-morpholino pyridin-2 (1H)-one (Racemic mixture) | 511 | 0.88 | |
| 2-14-40 | | 6-(7-(((5-Methyl thiophen-2-yl)methyl)amino)-9H-xanthen-4-yl)-4-morpholino pyridin-2(1H)-one | 486 | 1.40 | |
| 2-14-41 | | 6-(7-(((4-Methyl thiophen-2-yl)methyl)amino)-9H-xanthen-4-yl)-4-morpholino pyridin-2(1H)-one | 486 | 1.41 | |
| 2-14-42 | | 6-(7-(((4-Methyl thiazol-2-yl)methyl)amino)-9H-xanthen-4-yl)-4-morpholino pyridin-2(1H)-one | 487 | 1.17 | |
| 2-14-43 | | 4-Morpholino-6-(7-((1-(thiazol-2-yl)ethyl)amino)-9H-xanthen-4-yl)pyridin-2 (1H)-one | 487 | 1.19 | |
| 2-14-44 | | 4-Morpholino-6-(7-((1-(thiophen-2-yl)ethyl) amino)-9H-xanthen-4-yl) pyridin-2(1H)-one | 486 | 1.36 | |

TABLE 70

| Example No. | R^b | Compound Name | MS | RT (min) | ¹H-NMR (300 MHz) (DMSO-d₆) δ: |
|---|---|---|---|---|---|
| 2-14-45 | (2-methoxy-1-(6-methylpyridin-2-yl)ethyl) group | 6-(7-((2-Methoxy-1-(6-methyl pyridin-2-yl)ethyl) amino)-9H-xanthen-4-yl)-4-morpholino pyridin-2 (1H)-one | 525 | 0.96 | (CDCl₃): 9.12 (1H, br s), 7.50 (1H, t, J = 7.9 Hz), 7.30-7.18 (3H, m), 7.07-7.02 (2H, m), 6.87 (1H, d, J = 8.8 Hz), 6.44 (1H, dd, J = 8.8, 2.6 Hz), 6.34 (1H, d, J = 2.6 Hz), 6.14 (1H, d, J = 2.6 Hz), 5.70 (1H, d, J = 2.6 Hz), 4.75 (1H, br s), 4.58 (1H, br s), 3.93 (2H, d, J = 3.3 Hz), 3.81 (4H, t, J = 5.0 Hz), 3.77-3.66 (2H, m), 3.37 (3H, s), 3.30 (4H, t, J = 5.0 Hz), 2.59 (3H, s). |
| 2-14-46 | Boc-aminomethyl-(6-methylpyridin-2-yl)ethyl group | tert-Butyl(2-(6-methyl pyridin-2-yl)-2-((5-(4-morpholino-6-oxo-1,6-dihydropyridin-2-yl)-9H-xanthen-2-yl)amino)ethyl) carbamate | 610 | 1.15 | |
| 2-14-47 | (5-methylthiazol-2-yl)methyl group | 6-(7-(((5-Methyl thiazol-2-yl)methyl)amino)-9H-xanthen-4-yl)-4-morpholino pyridin-2(1H)-one | 487 | 1.19 | |
| 2-14-48 | 1-(2-methylpyrimidin-4-yl)ethyl group | 6-(7-((1-(2-Methyl pyrimidin-4-yl)ethyl) amino)-9H-xanthen-4-yl)-4-morpholino pyridin-2 (1H)-one | 496 | 1.08 | |
| 2-14-49 | 1-(6-methylpyrazin-2-yl)ethyl group | 6-(7-((1-(6-Methyl pyrazin-2-yl)ethyl)amino)-9H-xanthen-4-yl)-4-morpholino pyridin-2(1H)-one | 496 | 1.13 | |
| 2-14-50 | 1-(pyrimidin-4-yl)ethyl group | 4-Morpholino-6-(7-((1-(pyrimidin-4-yl)ethyl) amino)-9H-xanthen-4-yl) pyridin-2(1H)-one | 482 | 1.06 | |
| 2-14-51 | 1-(5-methoxypyrazin-2-yl)ethyl group | 6-(7-((1-(5-Methoxy pyrazin-2-yl)ethyl)amino)-9H-xanthen-4-yl)-4-morpholino pyridin-2(1H)-one | 512 | 1.22 | (CDCl₃): 9.11 (1H, br s), 8.19 (1H, d, J = 1.3 Hz), 8.09 (1H, d, J = 1.3 Hz), 7.29 (1H, d, J = 7.9 Hz), 7.23 (1H, d, J = 7.9 Hz), 7.05 (1H, dd, J = 7.9, 7.9 Hz), 6.89 (1H, d, J = 8.6 Hz), 6.45 (1H, dd, J = 8.9, 2.3 Hz), 6.36 (1H, d, J = 2.3 Hz), 6.15 (1H, d, J = 2.0 Hz), 5.71 (1H, d, J = 2.0 Hz), 5.37-5.33 (1H, m), 4.60-4.58 (1H, m), 3.95 (2H, s), 3.93 (3H, s), 3.82 (4H, t, J = 4.8 Hz), 3.31 (4H, t, J = 4.8 Hz), 1.54 (3H, d, J = 6.6 Hz). |

TABLE 70-continued

| Example No. | $R^b$ | Compound Name | MS | RT (min) | $^1$H-NMR (300 MHz) (DMSO-d$_6$) δ: |
|---|---|---|---|---|---|
| 2-14-52 | 6-methyl-4-isopropyl pyrimidine | 6-(7-((1-(6-Methyl pyrimidin-4-yl)ethyl) amino)-9H-xanthen-4-yl)-4-morpholino pyridin-2(1H)-one | 496 | 1.08 | |

TABLE 71

| Example No. | $R^b$ | Compound Name | MS | RT (min) | $^1$H-NMR (300 MHz) (DMSO-d$_6$) δ: |
|---|---|---|---|---|---|
| 2-14-53 | 5-(dimethylamino)-2-isopropyl pyrazine | 6-(7-((1-(5-(Dimethyl amino) pyrazin-2-yl)ethyl)amino)-9H-xanthen-4-yl)-4-morpholino pyridin-2(1H)-one | 525 | 1.10 | |
| 2-14-54 | 2-(methylamino)-5-isopropyl pyrimidine | 6-(7-((1-(2-(Methyl amino) pyrimidin-5-yl)ethyl)amino)-9H-xanthen-4-yl)-4-morpholino pyridin-2(1H)-one | 511 | 0.99 | |
| 2-14-55 | 2-methoxy-5-isopropyl pyrimidine | 6-(7-((1-(2-Methoxy pyrimidin-5-yl)ethyl)amino)-9H-xanthen-4-yl)-4-morpholino pyridin-2(1H)-one | 512 | 1.12 | |
| 2-14-56 | 4-methoxy-2-isopropyl pyrimidine | 6-(7-((1-(4-Methoxy pyrimidin-2-yl)ethyl)amino)-9H-xanthen-4-yl)-4-morpholino pyridin-2(1H)-one | 512 | 1.15 | |

TABLE 71-continued

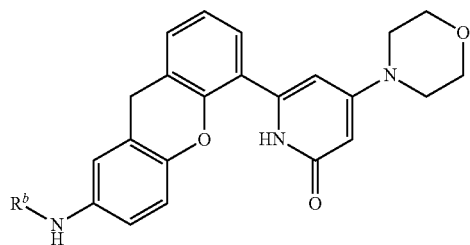

| Example No. | R$^b$ | Compound Name | MS | RT (min) | $^1$H-NMR (300 MHz) (DMSO-d$_6$) δ: |
|---|---|---|---|---|---|
| 2-14-57 | (6-methoxypyrazin-2-yl, isopropyl) | 6-(7-((1-(6-Methoxy pyrazin-2-yl)ethyl)amino)-9H-xanthen-4-yl)-4-morpholino pyridin-2(1H)-one | 512 | 1.24 | |
| 2-14-58 | (2-cyanopyrimidin-4-yl, isopropyl) | 4-(1-((5-(4-Morpholino-6-oxo-1,6-dihydropyridin-2-yl)-9H-xanthen-2-yl)amino)ethyl)pyrimidine-2-carbonitrile | 507 | 1.27 | |
| 2-14-59 | (6-chloropyrimidin-4-yl, isopropyl) | 6-(7-((1-(6-Chloropyrimidin-4-yl)ethyl)amino)-9H-xanthen-4-yl)-4-morpholino pyridin-2(1H)-one | 516 | 1.26 | |
| 2-14-60 | (4-cyanopyrimidin-6-yl, isopropyl) | 6-(1-((5-(4-Morpholino-6-oxo-1,6-dihydropyridin-2-yl)-9H-xanthen-2-yl)amino)ethyl)pyrimidine-4-carbonitrile | 507 | 1.23 | |
| 2-14-61 | (4-(fluoromethyl)pyrimidin-2-yl, isopropyl) | 6-(7-((1-(4-(Fluoromethyl)pyrimidin-2-yl)ethyl)amino)-9H-xanthen-4-yl)-4-morpholino pyridin-2(1H)-one | 514 | 1.15 | (CDCl$_3$): 9.08 (1H, br s), 8.75 (1H, d, J = 5.3 Hz), 7.32-7.26 (3H, m), 7.07-7.05 (1H, m), 6.91-6.88 (1H, m), 6.57-6.47 (2H, m), 6.17 (1H, s), 5.74 (1H, s), 5.45 (2H, d, J = 46.9 Hz), 4.79-4.73 (1H, m), 3.97 (2H, s), 3.82 (4H, t, J = 4.4 Hz), 3.33 (4H, t, J = 4.4 Hz), 1.27-1.24 (3H, m). |

TABLE 72

| Example No. | $R^b$ | Compound Name | MS | RT (min) | $^1$H-NMR (300 MHz) (DMSO-d$_6$) δ: |
|---|---|---|---|---|---|
| 2-14-62 | 4-(Difluoromethyl)-2-isopropylpyrimidine | 6-(7-((1-(4-(Difluoromethyl) pyrimidin-2-yl)ethyl)amino)-9H-xanthen-4-yl)-4-morpholino pyridin-2(1H)-one | 532 | 1.24 | (CDCl$_3$): 9.02 (1H, br s), 8.88 (1H, d, J = 4.6 Hz), 7.46 (1H, d, J = 5.3 Hz), 7.29-7.24 (2H, m), 7.05 (1H, t, J = 7.6 Hz), 6.89 (1H, d, J = 8.6 Hz), 6.55 (1H, t, J = 55.0 Hz), 6.52-6.49 (2H, m), 6.14 (1H, d, J = 2.3 Hz), 5.71 (1H, d, J = 2.3 Hz), 4.85-4.82 (1H, m), 4.59 (1H, br s), 4.00-3.93 (2H, m), 3.82 (4H, t, J = 4.8 Hz); 3.31 (4H, t, J = 4.8 Hz), 1.59-1.56 (3H, m). |
| 2-14-63 | 2-Methoxy-4-isopropylpyrimidine | 6-(7-((1-(2-Methoxy pyrimidin-4-yl)ethyl) amino)-9H-xanthen-4-yl)-4-morpholino pyridin-2(1H)-one | 512 | 1.18 | |
| 2-14-64 | 5-(Fluoromethyl)-2-isopropylpyrimidine | 6-(7-((1-(4-(Fluoromethyl) pyrimidin-2-yl)ethyl)amino)-9H-xanthen-4-yl)-4-morpholino pyridin-2(1H)-one | 514 | 1.13 | |
| 2-14-65 | 6-(Fluoromethyl)-4-isopropylpyrimidine | 6-(7-((1-(6-(Fluoromethyl) pyrimidin-4-yl)ethyl)amino)-9H-xanthen-4-yl)-4-morpholino pyridin-2(1H)-one | 514 | 1.15 | |
| 2-14-66 | 5-(Hydroxymethyl)-2-isopropylpyrimidine | 6-(7-((1-(5-(Hydroxy methyl) pyrimidin-2-yl)ethyl)amino)-9H-xanthen-4-yl)-4-morpholino pyridin-2(1H)-one | 512 | 0.94 | |
| 2-14-67 | 5-(morpholinomethyl)-2-isopropylpyrimidine | 4-Morpholino-6-(7-((1-(5-(morpholino methyl) pyrimidin-2-yl)ethyl)amino)-9H-xanthen-4-yl)pyridin-2(1H)-one | 581 | 0.90 | |
| 2-14-68 | 2-Methyl-4-ethylpyrimidine | 6-(7-(((2-Methyl pyrimidin-4-yl)methyl)amino)-9H-xanthen-4-yl)-4-morpholino pyridin-2(1H)-one | 482 | 1.02 | |
| 2-14-69 | 2-morpholino-4-ethylpyrimidine | 4-Morpholino-6-(7-(((2-morpholino pyrimidin-4-yl) methyl)amino)-9H-xanthen-4-yl)pyridin-2(1H)-one | 553 | 1.18 | |

TABLE 72-continued

| Example No. | R$^b$ | Compound Name | MS | RT (min) | $^1$H-NMR (300 MHz) (DMSO-d$_6$) δ: |
|---|---|---|---|---|---|
| 2-14-70 | 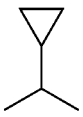 | 6-(7-((1-Cyclopropylethyl)amino)-9H-xanthen-4-yl)-4-morpholino pyridin-2(1H)-one | 444 | 0.94 | |

TABLE 73

| Example No. | R$^b$ | Compound Name | MS | RT (min) | $^1$H-NMR (300 MHz) (DMSO-d$_6$) δ: |
|---|---|---|---|---|---|
| 2-14-71 | 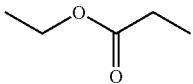 | Ethyl 2-((5-(4-morpholino-6-oxo-1,6-dihydropyridin-2-yl)-9H-xanthen-2-yl)amino)acetate | 462 | 1.19 | |
| 2-14-72 | 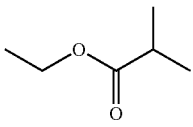 | Ethyl 2-((5-(4-morpholino-6-oxo-1,6-dihydropyridin-2-yl)-9H-xanthen-2-yl)amino)propanoate | 476 | 1.26 | |
| 2-14-73 | 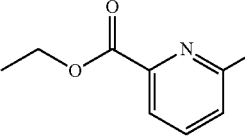 | Ethyl 6-(((5-(4-morpholino-6-oxo-1,6-dihydropyridin-2-yl)-9H-xanthen-2-yl)amino)methyl)picolinate | 539 | 1.14 | |
| 2-14-74 | 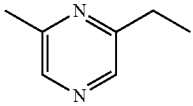 | 6-(7-(((6-Methyl pyrazin-2-yl)methyl)amino)-9H-xanthen-4-yl)-4-morpholino pyridin-2(1H)-one | 482 | 1.08 | |
| 2-14-75 | 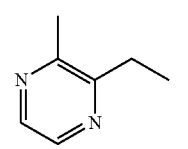 | 6-(7-(((3-Methyl pyrazin-2-yl)methyl)amino)-9H-xanthen-4-yl)-4-morpholino pyridin-2(1H)-one | 482 | 1.09 | |
| 2-14-76 | 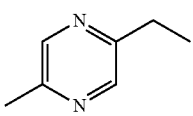 | 6-(7-(((5-Methyl pyrazin-2-yl)methyl)amino)-9H-xanthen-4-yl)-4-morpholino pyridin-2(1H)-one | 482 | 1.06 | |

TABLE 73-continued

| Example No. | R$^b$ | Compound Name | MS | RT (min) | $^1$H-NMR (300 MHz) (DMSO-d$_6$) δ: |
|---|---|---|---|---|---|
| 2-14-77 | 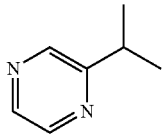 | 4-Morpholino-6-(7-((1-(pyrazin-2-yl)ethyl)amino)-9H-xanthen-4-yl)pyridin-2(1H)-one | 482 | 1.09 | |
| 2-14-78 | | 4-Morpholino-6-(7-((1-(pyrimidin-2-yl)ethyl)amino)-9H-xanthen-4-yl)pyridin-2(1H)-one | 482 | 1.04 | |
| 2-14-79 | | 6-(7-((1-(4-Methyl pyrimidin-2-yl)ethyl)amino)-9H-xanthen-4-yl)-4-morpholino pyridin-2(1H)-one | 496 | 1.08 | |
| 2-14-80 | | 6-(7-((1-(5-Methyl pyrimidin-2-yl)ethyl)amino)-9H-xanthen-4-yl)-4-morpholino pyridin-2(1H)-one | 496 | 1.10 | |

TABLE 74

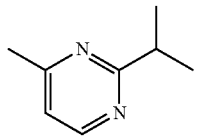

| Example No. | R$^b$ | Compound Name | MS | RT (min) | $^1$H-NMR (300 MHz) (DMSO-d$_6$) δ: |
|---|---|---|---|---|---|
| 2-14-81 | 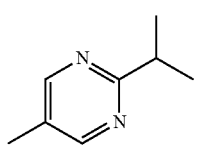 | 6-(7-((2-Fluoro-1-(4-methyl pyrimidin-2-yl)ethyl)amino)-9H-xanthen-4-yl)-4-morpholino pyridin-2(1H)-one | 514 | 1.16 | |

TABLE 74-continued

| Example No. | R$^b$ | Compound Name | MS | RT (min) | $^1$H-NMR (300 MHz) (DMSO-d$_6$) δ: |
|---|---|---|---|---|---|
| 2-14-82 | | 6-(7-((2-Hydroxy-1-(4-methyl pyrimidin-2-yl)ethyl)amino)-9H-xanthen-4-yl)-4-morpholino pyridin-2(1H)-one | 512 | 0.97 | |
| 2-14-83 | | 6-(7-((2-Fluoro-1-(5-methyl pyrimidin-2-yl)ethyl)amino)-9H-xanthen-4-yl)-4-morpholino pyridin-2(1H)-one | 514 | 1.17 | |
| 2-14-84 | | tert-Butyl 2-methyl-4-((5-(4-morpholino-6-oxo-1,6-dihydropyridin-2-yl)-9H-xanthen-2-yl)amino) piperidine-1-carboxylate | 573 | 1.28 1.37 | |

Examples 2-14-85-1 and 24-8-14-85-2

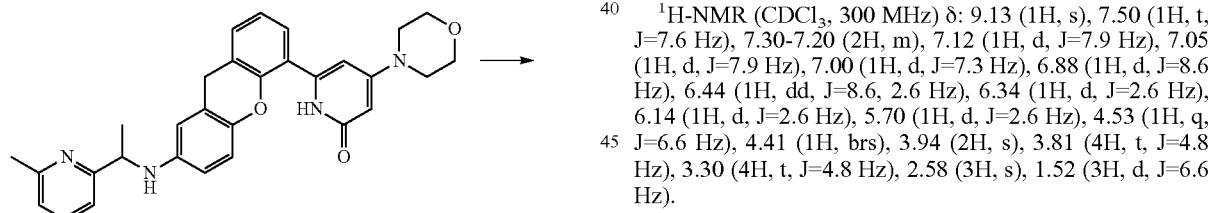

Chiral resolution was performed on 6-(7-((1-(6-methyl-pyridin-2-yl)ethyl)amino)-9H-xanthen-4-yl)-4-morpholinopyridin-2(1H)-one (racemic mixture) by supercritical fluid chromatography, whereby an optically active substance A and an optically active substance B were obtained.

Example 2-14-85-1

Optically Active Substance A $^1$H-NMR (CDCl$_3$, 300 MHz) δ: 9.13 (1H, s), 7.50 (1H, t, J=7.6 Hz), 7.30-7.20 (2H, m), 7.12 (1H, d, J=7.9 Hz), 7.05 (1H, d, J=7.9 Hz), 7.00 (1H, d, J=7.3 Hz), 6.88 (1H, d, J=8.6 Hz), 6.44 (1H, dd, J=8.6, 2.6 Hz), 6.34 (1H, d, J=2.6 Hz), 6.14 (1H, d, J=2.6 Hz), 5.70 (1H, d, J=2.6 Hz), 4.53 (1H, q, J=6.6 Hz), 4.41 (1H, brs), 3.94 (2H, s), 3.81 (4H, t, J=4.8 Hz), 3.30 (4H, t, J=4.8 Hz), 2.58 (3H, s), 1.52 (3H, d, J=6.6 Hz).

MS(ESI m/z): 495 (M+H)

RT(min): 0.93

Example 2-14-85-2

Optically Active Substance B $^1$H-NMR (CDCl$_3$, 300 MHz) δ: 9.13 (1H, s), 7.50 (1H, t, J=7.6 Hz), 7.30-7.20 (2H, m), 7.12 (1H, d, J=7.9 Hz), 7.05 (1H, d, J=7.9 Hz), 7.00 (1H, d, J=7.3 Hz), 6.88 (1H, d, J=8.6 Hz), 6.44 (1H, dd, J=8.6, 2.6 Hz), 6.34 (1H, d, J=2.6 Hz), 6.14 (1H, d, J=2.6 Hz), 5.70 (1H, d, J=2.6 Hz), 4.53 (1H, q, J=6.6 Hz), 4.41 (1H, brs), 3.94 (2H, s), 3.81 (4H, t, J=4.8 Hz), 3.30 (4H, t, J=4.8 Hz), 2.58 (3H, s), 1.52 (3H, d, J=6.6 Hz).

MS(ESI m/z): 495 (M+H)

RT(min): 0.93

(Supercritical Fluid Chromatography Conditions)

Column: CHIRALCEL OJ-H (manufactured by Daicel Chemical Industries, Ltd.)

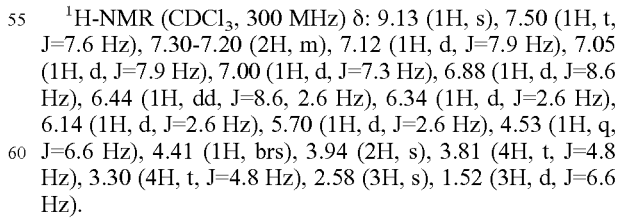

Mobile phase: carbon dioxide/methanol/diethylamine (volume ratio: 80/20/0.1)
Flow rate: 30 mL/min
Detection wavelength: 254 nm
Temperature: 40° C.
Retention time: 4.25 min (optically active substance A), 7.20 min (optically active substance B)

Examples 2-14-86-1 and 2-14-86-2

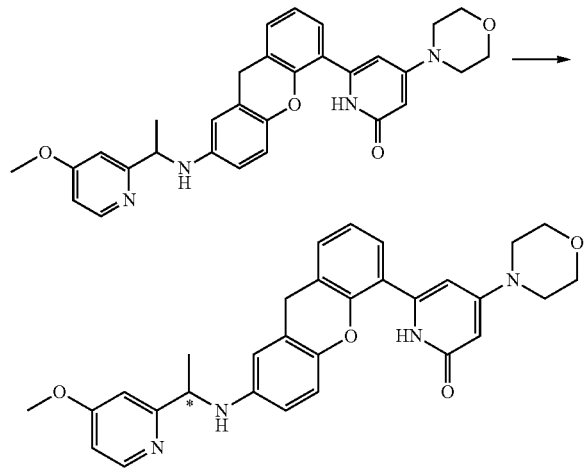

Chiral resolution was performed on 6-(7-((1-(4-methoxypyridin-2-yl)ethyl)amino)-9H-xanthen-4-yl)-4-morpholinopyridin-2(1H)-one (racemic mixture) by supercritical fluid chromatography, whereby an optically active substance A and an optically active substance B were obtained.

Example 2-14-86-1

Optically Active Substance A $^1$H-NMR (CDCl$_3$, 300 MHz) δ: 8.39 (1H, d, J=5.3 Hz), 7.30-7.19 (2H, m), 7.04 (1H, t, J=7.6 Hz), 6.87 (1H, d, J=2.6 Hz), 6.86 (1H, d, J=8.6 Hz), 6.68 (1H, dd, J=5.3, 2.6 Hz), 6.43 (1H, dd, J=8.6, 2.6 Hz), 6.33 (1H, d, J=2.6 Hz), 6.15 (1H, d, J=2.6 Hz), 5.70 (1H, d, J=2.6 Hz), 4.50 (1H, q, J=6.6 Hz), 3.93 (2H, s), 3.83-3.79 (7H, m), 3.31 (4H, t, J=4.6 Hz), 1.53 (3H, d, J=6.6 Hz).
MS(ESI m/z): 511 (M+H)
RT(min): 0.93

Example 2-14-86-2

Optically Active Substance B $^1$H-NMR (CDCl$_3$, 300 MHz) δ: 8.39 (1H, d, J=5.3 Hz), 7.30-7.19 (2H, m), 7.04 (1H, t, J=7.6 Hz), 6.87 (1H, d, J=2.6 Hz), 6.86 (1H, d, J=8.6 Hz), 6.68 (1H, dd, J=5.3, 2.6 Hz), 6.43 (1H, dd, J=8.6, 2.6 Hz), 6.33 (1H, d, J=2.6 Hz), 6.15 (1H, d, J=2.6 Hz), 5.70 (1H, d, J=2.6 Hz), 4.50 (1H, q, J=6.6 Hz), 3.93 (2H, s), 3.83-3.79 (7H, m), 3.31 (4H, t, J=4.6 Hz), 1.53 (3H, d, J=6.6 Hz).
MS(ESI m/z): 511 (M+H)
RT(min): 0.93
(Supercritical Fluid Chromatography Conditions)
Column: CHIRALCEL OJ-H (manufactured by Daicel Chemical Industries, Ltd.)

Mobile phase: carbon dioxide/methanol/diethylamine (volume ratio: 75/25/0.1)
Flow rate: 30 mL/min
Detection wavelength: 254 nm
Temperature: 40° C.
Retention time: 3.14 min (optically active substance A), 6.50 min (optically active substance B)

Examples 2-14-87-1 and 2-14-87-2

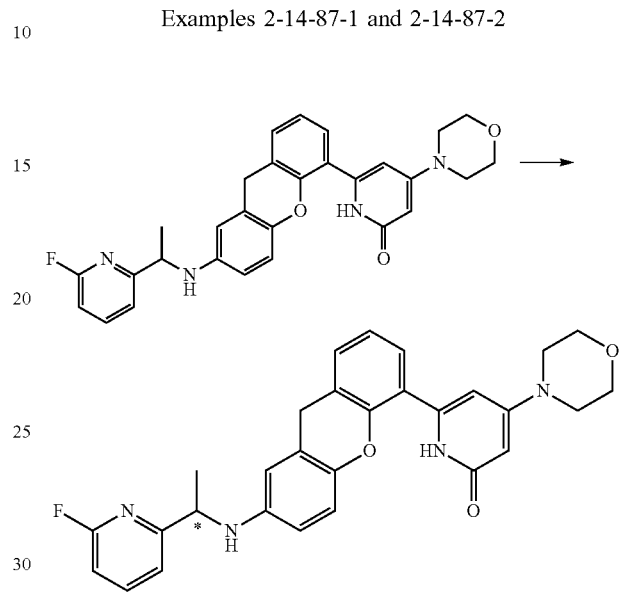

Chiral resolution was performed on 6-(7-((1-(6-fluoropyridin-2-yl)ethyl)amino)-9H-xanthen-4-yl)-4-morpholinopyridin-2(1H)-one (racemic mixture) by supercritical fluid chromatography, whereby an optically active substance A and an optically active substance B were obtained.

Example 2-14-87-1

Optically Active Substance A $^1$H-NMR (CDCl$_3$, 300 MHz) δ: 9.20 (1H, s), 7.71 (1H, q, J=7.9 Hz), 7.30-7.21 (3H, m), 7.05 (1H, t, J=7.6 Hz), 6.88 (1H, d, J=8.6 Hz), 6.79 (1H, dd, J=7.9, 2.6 Hz), 6.43 (1H, dd, J=8.6, 2.6 Hz), 6.31 (1H, d, J=2.6 Hz), 6.14 (1H, d, J=2.6 Hz), 5.70 (1H, d, J=2.6 Hz), 4.55-4.47 (1H, m), 4.22 (1H, brs), 3.94 (2H, s), 3.81 (4H, t, J=4.6 Hz), 3.30 (4H, t, J=5.0 Hz), 1.53 (3H, d, J=6.6 Hz).
MS(ESI m/z): 499 (M+H)
RT(min): 1.29

Example 2-14-87-2

Optically Active Substance B $^1$H-NMR (CDCl$_3$, 300 MHz) δ: 9.20 (1H, s), 7.71 (1H, q, J=7.9 Hz), 7.30-7.21 (3H, m), 7.05 (1H, t, J=7.6 Hz), 6.88 (1H, d, J=8.6 Hz), 6.79 (1H, dd, J=7.9, 2.6 Hz), 6.43 (1H, dd, J=8.6, 2.6 Hz), 6.31 (1H, d, J=2.6 Hz), 6.14 (1H, d, J=2.6 Hz), 5.70 (1H, d, J=2.6 Hz), 4.55-4.47 (1H, m), 4.22 (1H, brs), 3.94 (2H, s), 3.81 (4H, t, J=4.6 Hz), 3.30 (4H, t, J=5.0 Hz), 1.53 (3H, d, J=6.6 Hz).
MS(ESI m/z): 499 (M+H)
RT(min): 1.29

(Supercritical Fluid Chromatography Conditions)
Column: CHIRALPAK IB (manufactured by Daicel Chemical Industries, Ltd.)
Mobile phase: carbon dioxide/methanol/diethylamine (volume ratio: 80/20/0.1)
Flow rate: 30 mL/min
Detection wavelength: 254 nm
Temperature: 40° C.
Retention time: 11.70 min (optically active substance A), 13.64 min (optically active substance B)

Examples 2-14-88-1 and 2-14-88-2

Chiral resolution was performed on 6-(7-((1-(5-methyl-pyridin-3-yl)ethyl)amino)-9H-xanthen-4-yl)-4-morpholin-opyridin-2(1H)-one (racemic mixture) by supercritical fluid chromatography, whereby an optically active substance A and an optically active substance B were obtained.

Example 2-14-88-1

Optically Active Substance A

MS(ESI m/z): 495 (M+H)
RT(min): 0.95

Example 2-14-88-2

Optically Active Substance B

MS(ESI m/z): 495 (M+H)
RT(min): 0.96
(Supercritical Fluid Chromatography Conditions)
Column: CHIRALPAK AS-H (manufactured by Daicel Chemical Industries, Ltd.)
Mobile phase: carbon dioxide/methanol/diethylamine (volume ratio: 80/20/0.1)
Flow rate: 30 mL/min
Detection wavelength: 254 nm
Temperature: 40° C.
Retention time: 11.65 min (optically active substance A), 14.61 min (optically active substance B)

Examples 2-14-89-1 and 2-14-89-2

Chiral resolution was performed on 6-(7-((1-(4-chloro-pyridin-2-yl)ethyl)amino)-9H-xanthen-4-yl)-4-morpholin-opyridin-2(1H)-one (racemic mixture) by supercritical fluid chromatography, whereby an optically active substance A and an optically active substance B were obtained.

Example 2-14-89-1

Optically Active Substance A $^1$H-NMR (CDCl$_3$, 300 MHz) δ: 8.48 (1H, d, J=5.9 Hz), 7.38 (1H, d, J=2.0 Hz), 7.32-7.16 (3H, m), 7.06 (1H, t, J=7.6 Hz), 6.86 (1H, d, J=8.6 Hz), 6.42 (1H, dd, J=8.6, 2.6 Hz), 6.31 (1H, d, J=2.6 Hz), 6.21 (1H, d, J=2.6 Hz), 5.75 (1H, d, J=2.6 Hz), 4.54 (1H, q, J=6.6 Hz), 3.95 (2H, s), 3.82 (4H, t, J=5.0 Hz), 3.34 (4H, t, J=5.0 Hz), 1.54 (3H, d, J=6.6 Hz).
MS(ESI m/z): 515 (M+H)
RT(min): 1.28

Example 2-14-89-2

Optically Active Substance B $^1$H-NMR (CDCl$_3$, 300 MHz) δ: 8.48 (1H, d, J=5.9 Hz), 7.38 (1H, d, J=2.0 Hz), 7.32-7.16 (3H, m), 7.06 (1H, t, J=7.6 Hz), 6.86 (1H, d, J=8.6 Hz), 6.42 (1H, dd, J=8.6, 2.6 Hz), 6.31 (1H, d, J=2.6 Hz), 6.21 (1H, d, J=2.6 Hz), 5.75 (1H, d, J=2.6 Hz), 4.54 (1H, q, J=6.6 Hz), 3.95 (2H, s), 3.82 (4H, t, J=5.0 Hz), 3.34 (4H, t, J=5.0 Hz), 1.54 (3H, d, J=6.6 Hz).
MS(ESI m/z): 515 (M+H)
RT(min): 1.28
(Supercritical Fluid Chromatography Conditions)
Column: CHIRALCEL OJ-H (manufactured by Daicel Chemical Industries, Ltd.)
Mobile phase: carbon dioxide/methanol/diethylamine (volume ratio: 75/25/0.1)
Flow rate: 30 mL/min
Detection wavelength: 254 nm
Temperature: 40° C.

Retention time: 2.67 min (optically active substance A), 5.75 min (optically active substance B)

Examples 2-14-90-1 and 2-14-90-2

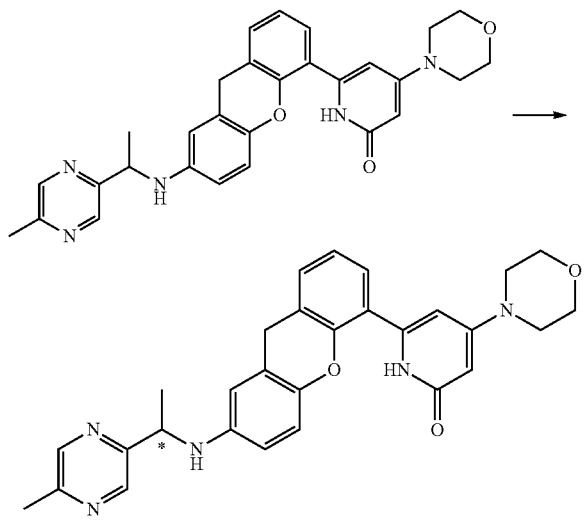

Chiral resolution was performed on 6-(7-((1-(5-methyl-pyrazin-2-yl)ethyl)amino)-9H-xanthen-4-yl)-4-morpholin-opyridin-2(1H)-one (racemic mixture) by supercritical fluid chromatography, whereby an optically active substance A and an optically active substance B were obtained.

Example 2-14-90-1

Optically Active Substance A

¹H-NMR (CDCl$_3$, 300 MHz) δ: 8.50 (1H, d, J=1.3 Hz), 8.41 (1H, s), 7.30-7.22 (2H, m), 7.06 (1H, t, J=7.6 Hz), 6.85 (1H, d, J=8.6 Hz), 6.45 (1H, dd, J=8.6, 2.6 Hz), 6.35 (1H, d, J=2.6 Hz), 6.22 (1H, d, J=2.6 Hz), 5.75 (1H, d, J=2.6 Hz), 4.62 (1H, q, J=6.6 Hz), 3.95 (2H, s), 3.82 (4H, t, J=5.0 Hz), 3.34 (4H, t, J=5.0 Hz), 2.54 (3H, s), 1.55 (3H, d, J=6.6 Hz).
MS(ESI m/z): 496 (M+H)
RT(min): 1.12

Example 2-14-90-2

Optically Active Substance B

¹H-NMR (CDCl$_3$, 300 MHz) δ: 8.50 (1H, d, J=1.3 Hz), 8.41 (1H, s), 7.30-7.22 (2H, m), 7.06 (1H, t, J=7.6 Hz), 6.85 (1H, d, J=8.6 Hz), 6.45 (1H, dd, J=8.6, 2.6 Hz), 6.35 (1H, d, J=2.6 Hz), 6.22 (1H, d, J=2.6 Hz), 5.75 (1H, d, J=2.6 Hz), 4.62 (1H, q, J=6.6 Hz), 3.95 (2H, s), 3.82 (4H, t, J=5.0 Hz), 3.34 (4H, t, J=5.0 Hz), 2.54 (3H, s), 1.55 (3H, d, J=6.6 Hz).
MS(ESI m/z): 496 (M+H)
RT(min): 1.12
(Supercritical Fluid Chromatography Conditions)
Column: CHIRALCEL OJ-H (manufactured by Daicel Chemical Industries, Ltd.)
Mobile phase: carbon dioxide/0.1% diethylamine-containing methanol (volume ratio: 75/25)
Flow rate: 20 mL/min
Detection wavelength: 254 nm
Temperature: 40° C.

Retention time: 5.32 min (optically active substance A), 11.76 min (optically active substance B)

Example 2-14-91

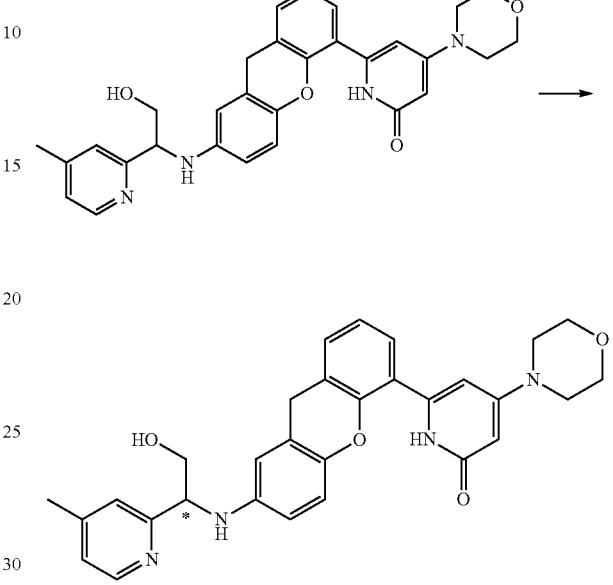

Chiral resolution was performed on 6-(7-((2-hydroxy-1-(4-methylpyridin-2-yl)ethyl)amino)-9H-xanthen-4-yl)-4-morpholinopyridin-2(1H)-one (racemic mixture) by supercritical fluid chromatography, whereby an optically active substance A was obtained.

MS(ESI m/z): 511 (M+H)
RT(min): 0.87
(Supercritical Fluid Chromatography Conditions)
Column: CHIRALPAK AS-H (manufactured by Daicel Chemical Industries, Ltd.)
Mobile phase: carbon dioxide/0.1% diethylamine-containing methanol (volume ratio: 80/20)
Flow rate: 30 mL/min
Detection wavelength: 254 nm
Temperature: 40° C.
Retention time: 19.98 min Examples 2-14-92-1 and 2-14-92-2

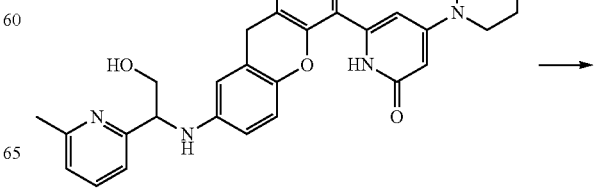

537
-continued

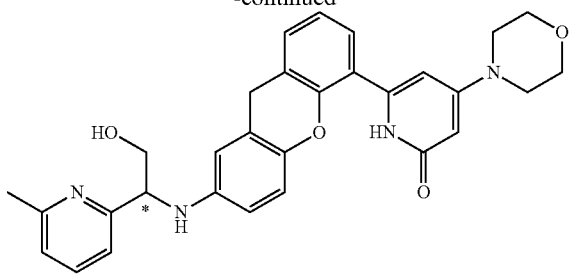

Chiral resolution was performed on 6-(7-((2-hydroxy-1-(6-methylpyridin-2-yl)ethyl)amino)-9H-xanthen-4-yl)-4-morpholinopyridin-2(1H)-one (racemic mixture) by supercritical fluid chromatography, whereby an optically active substance A and an optically active substance B were obtained.

Example 2-14-92-1

Optically Active Substance A

MS(ESI m/z): 511 (M+H)
RT(min): 0.87

Example 2-14-92-2

Optically Active Substance B

MS(ESI m/z): 511 (M+H)
RT(min): 0.87
(Supercritical Fluid Chromatography Conditions)
Column: CHIRALPAK AS-H (manufactured by Daicel Chemical Industries, Ltd.)
Mobile phase: carbon dioxide/0.1% diethylamine-containing methanol (volume ratio: 80/20)
Flow rate: 30 mL/min
Detection wavelength: 254 nm
Temperature: 40° C.
Retention time: 17.51 min (optically active substance A), 21.59 min (optically active substance B)

Examples 2-14-93-1 and 2-14-93-2

538

Chiral resolution was performed on 6-(7-((1-(4-methylpyridin-2-yl)ethyl)amino)-9H-xanthen-4-yl)-4-morpholinopyridin-2(1H)-one (racemic mixture) by supercritical fluid chromatography, whereby an optically active substance A and an optically active substance B were obtained.

Example 2-14-93-1

Optically Active Substance A $^1$H-NMR (CDCl$_3$, 300 MHz) δ: 9.00 (1H, s), 8.42 (1H, d, J=5.3 Hz), 7.30-7.21 (2H, m), 7.15 (1H, s), 7.04 (1H, t, J=7.6 Hz), 6.98 (1H, d, J=4.6 Hz), 6.89 (1H, d, J=8.6 Hz), 6.46 (1H, dd, J=8.6, 2.6 Hz), 6.35 (1H, d, J=2.6 Hz), 6.14 (1H, d, J=2.6 Hz), 5.71 (1H, d, J=2.6 Hz), 4.53 (1H, q, J=6.6 Hz), 4.36 (1H, brs), 3.94 (2H, s), 3.82 (4H, t, J=5.0 Hz), 3.31 (4H, t, J=5.0 Hz), 2.32 (3H, s), 1.52 (3H, d, J=6.6 Hz).
MS(ESI m/z): 495 (M+H)
RT(min): 0.95

Example 2-14-93-2

Optically Active Substance B $^1$H-NMR (CDCl$_3$, 300 MHz) δ: 9.00 (1H, s), 8.42 (1H, d, J=5.3 Hz), 7.30-7.21 (2H, m), 7.15 (1H, s), 7.04 (1H, t, J=7.6 Hz), 6.98 (1H, d, J=4.6 Hz), 6.89 (1H, d, J=8.6 Hz), 6.46 (1H, dd, J=8.6, 2.6 Hz), 6.35 (1H, d, J=2.6 Hz), 6.14 (1H, d, J=2.6 Hz), 5.71 (1H, d, J=2.6 Hz), 4.53 (1H, q, J=6.6 Hz), 4.36 (1H, brs), 3.94 (2H, s), 3.82 (4H, t, J=5.0 Hz), 3.31 (4H, t, J=5.0 Hz), 2.32 (3H, s), 1.52 (3H, d, J=6.6 Hz).
MS(ESI m/z): 495 (M+H)
RT(min): 0.95
(Supercritical Fluid Chromatography Conditions)
Column: CHIRALCEL OJ-H (manufactured by Daicel Chemical Industries, Ltd.)
Mobile phase: carbon dioxide/methanol/diethylamine (volume ratio: 80/20/0.1)
Flow rate: 30 mL/min
Detection wavelength: 254 nm
Temperature: 40° C.
Retention time: 14.42 min (optically active substance A), 18.41 min (optically active substance B)

Examples 2-14-94-1 and 2-14-94-2

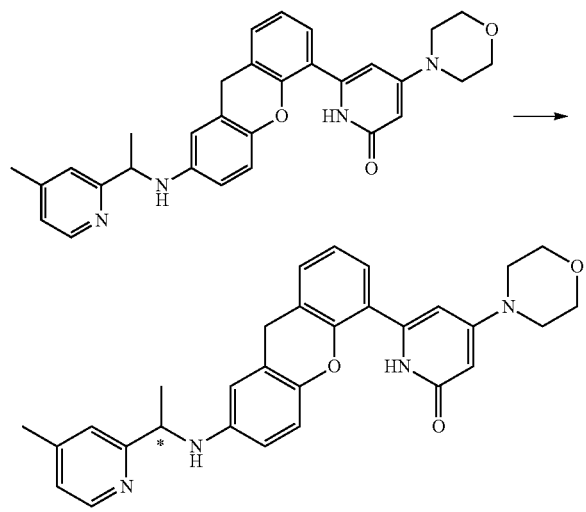

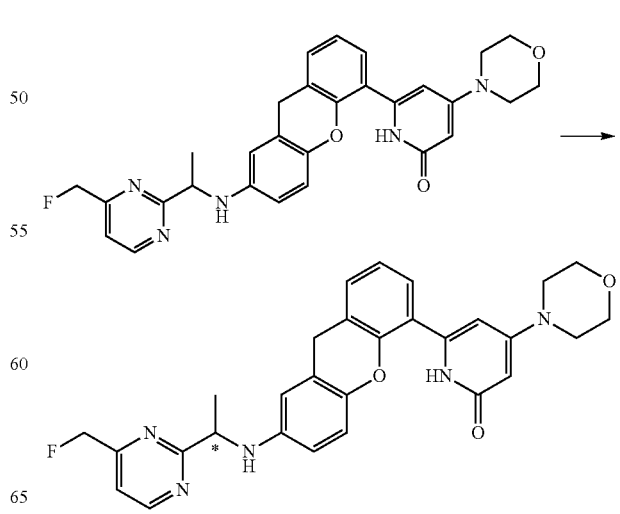

Chiral resolution was performed on 6-(7-((1-(4-(fluoromethyl)pyrimidin-2-yl)ethyl)amino)-9H-xanthen-4-yl)-4-morpholinopyridin-2(1H)-one (racemic mixture) by supercritical fluid chromatography, whereby an optically active substance A and an optically active substance B were obtained.

Example 2-14-94-1

Optically Active Substance A $^1$H-NMR (CDCl$_3$, 300 MHz) δ: 9.08 (1H, brs), 8.75 (1H, d, J=5.3 Hz), 7.32-7.26 (3H, m), 7.07-7.05 (1H, m), 6.91-6.88 (1H, m), 6.57-6.47 (2H, m), 6.17 (1H, s), 5.74 (1H, s), 5.45 (2H, d, J=46.9 Hz), 4.79-4.73 (1H, m), 3.97 (2H, s), 3.82 (4H, t, J=4.4 Hz), 3.33 (4H, t, J=4.4 Hz), 1.27-1.24 (3H, m).
MS(ESI m/z): 514 (M+H)
RT(min): 1.15

Example 2-14-94-2

Optically Active Substance B $^1$H-NMR (CDCl$_3$, 300 MHz) δ: 9.08 (1H, brs), 8.75 (1H, d, J=5.3 Hz), 7.32-7.26 (3H, m), 7.07-7.05 (1H, m), 6.91-6.88 (1H, m), 6.57-6.47 (2H, m), 6.17 (1H, s), 5.74 (1H, s), 5.45 (2H, d, J=46.9 Hz), 4.79-4.73 (1H, m), 3.97 (2H, s), 3.82 (4H, t, J=4.4 Hz), 3.33 (4H, t, J=4.4 Hz), 1.27-1.24 (3H, m).
MS(ESI m/z): 514 (M+H)
RT(min): 1.15
(Supercritical Fluid Chromatography Conditions)
Column: CHIRALCEL OJ-H (manufactured by Daicel Chemical Industries, Ltd.)
Mobile phase: carbon dioxide/0.1% diethylamine-containing methanol (volume ratio: 70/30)
Flow rate: 20 mL/min
Detection wavelength: 254 nm
Temperature: 40° C.
Retention time: 6.06 min (optically active substance A), 8.32 min (optically active substance B)

Example 2-15

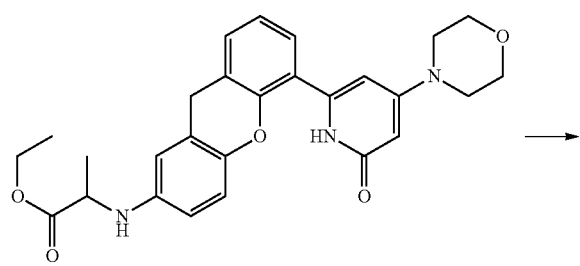

In the same manner as in Example 1-18-1, the following compound was obtained from ethyl 2-((5-(4-morpholino-6-oxo-1,6-dihydropyridin-2-yl)-9H-xanthen-2-yl)amino)propanate.

4-Morpholino-6-(7-((1-oxo-1-(pyrrolidin-1-yl)propan-2-yl)amino)-9H-xanthen-4-yl)pyridin-2(1H)-one MS(ESI m/z): 501 (M+H)
RT(min): 1.06

Example 2-16

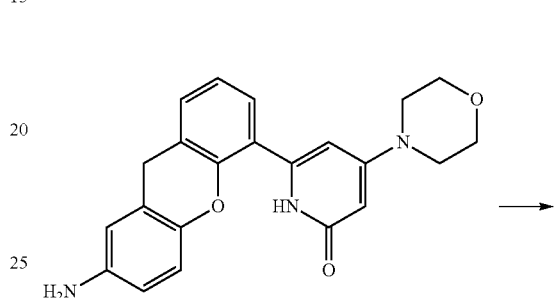

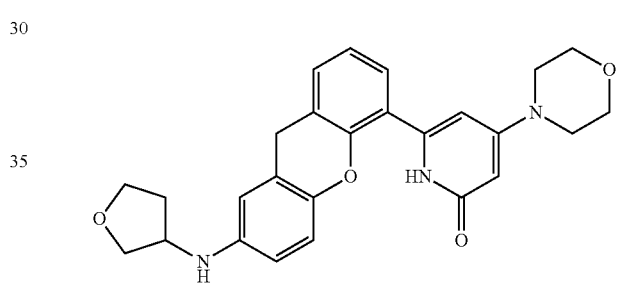

Using 6-(7-amino-9H-xanthen-4-yl)-4-morpholinopyridin-2(1H)-one, the following compound was obtained in the same manner as in Example 1-12-1.

4-Morpholino-6-(7-((tetrahydrofuran-3-yl)amino)-9H-xanthen-4-yl)pyridin-2(1H)-one MS(ESI m/z): 446 (M+H)
RT(min): 1.00

Example 2-17

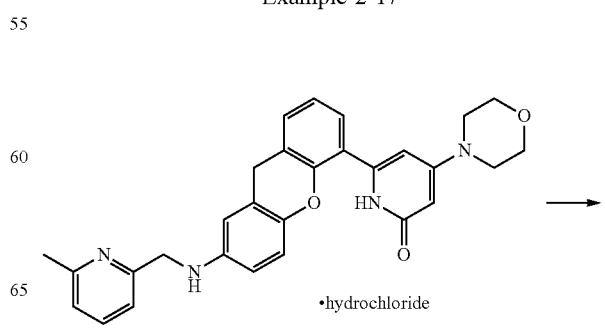

·hydrochloride

-continued

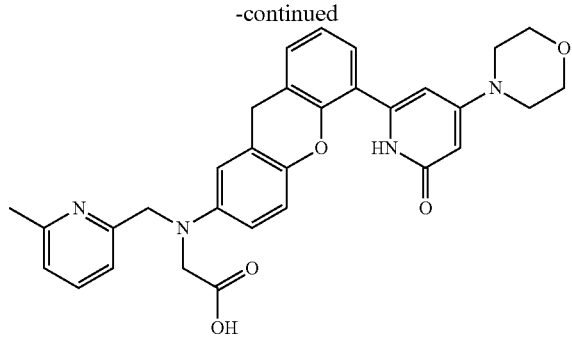

In the same manner as in Example 1-12-1, the following compound was obtained.

2-(((6-methylpyridin-2-yl)methyl)(5-(4-morpholino-6-oxo-1,6-dihydropyridin-2-yl)-9H-xanthen-2-yl)amino)acetic acid MS(ESI m/z): 539 (M+H)
RT(min): 0.88

Example 2-18

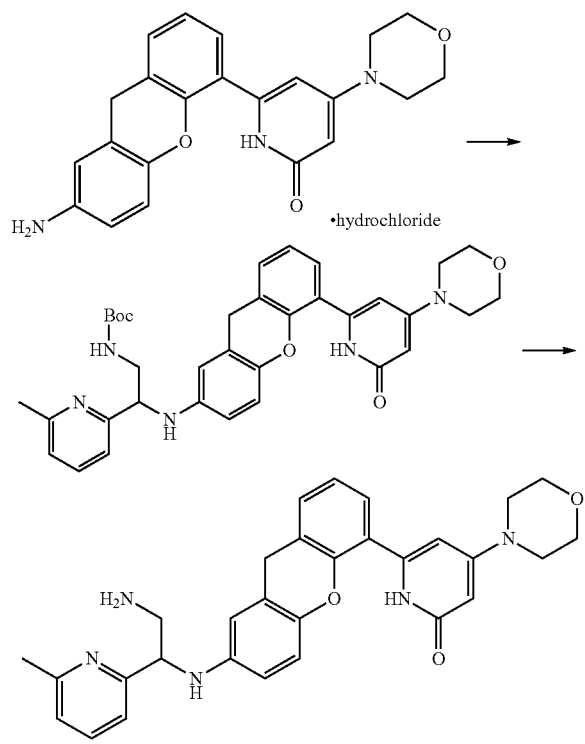

(1)
In the same manner as in Example 1-12-1, the following compound was obtained.

tert-Butyl (2-(6-methylpyridin-2-yl)-2-((5-(4-morpholino-6-oxo-1,6-dihydropyridin-2-yl)-9H-xanthen-2-yl)amino)ethyl)carbamate MS(ESI m/z): 610 (M+H)
RT(min): 1.15

(2)
In the same manner as in Example 2-8-1, the following compound was obtained.

6-(7-((2-Amino-1-(6-methylpyridin-2-yl)ethyl)amino)-9H-xanthen-4-yl)-4-morpholinopyridin-2(1H)-one MS(ESI m/z): 510 (M+H)
RT(min): 0.92

Example 2-19-1

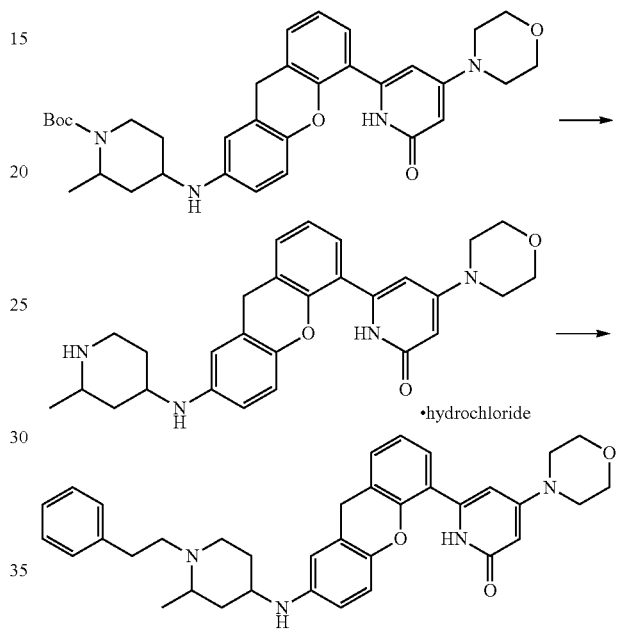

(1)
In the same manner as in Reference Example 10 (3), the following compound was obtained.

Hydrochloride of 6-(7-((2-Methylpiperidin-4-yl)amino)-9H-xanthen-4-yl)-4-morpholinopyridin-2(1H)-one MS(ESI m/z): 473 (M+H)
RT(min): 0.80

(2)
In the same manner as in Example 2-2-1, the following compound was obtained.

6-(7-((2-Methyl-1-phenethylpiperidin-4-yl)amino)-9H-xanthen-4-yl)-4-morpholinopyridin-2(1H)-one MS(ESI m/z): 577 (M+H)
RT(min): 1.06

Example 2-19-2

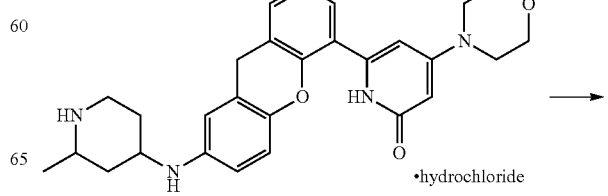

-continued

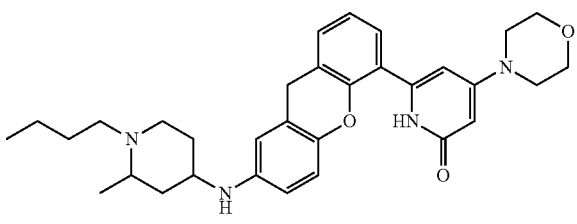

In the same manner as in Example 2-2-1, the following compound was obtained.

6-(7-((1-Butyl-2-methylpiperidin-4-yl)amino)-9H-xanthen-4-yl)-4-morpholinopyridin-2(1H)-one MS(ESI m/z): 529 (M+H)
RT(min): 0.98

Example 2-19-3

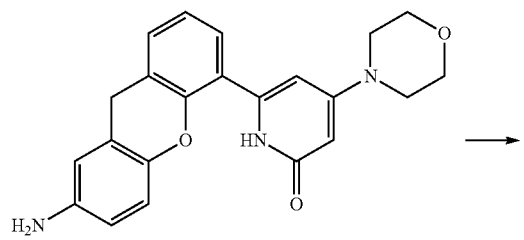

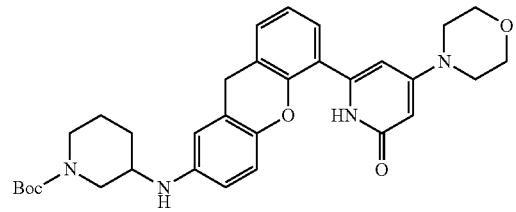

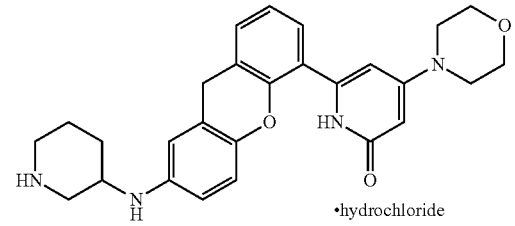

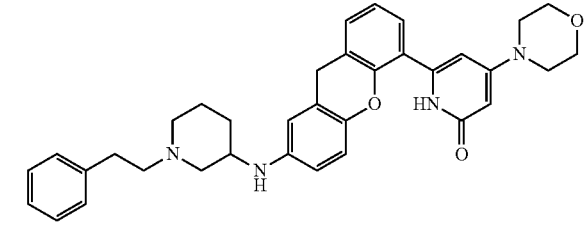

(1) and (2)
In the same manner as in Example 1-24-15 (1) and Reference Example 10 (3), the following compounds were obtained.

tert-Butyl 3-((5-(4-morpholino-6-oxo-1,6-dihydropyridin-2-yl)-9H-xanthen-2-yl)amino)piperidine-1-carboxylate MS(ESI m/z): 559 (M+H)
RT(min): 1.39

Hydrochloride of 4-morpholino-6-(7-(piperidin-3-ylamino)-9H-xanthen-4-yl)pyridin-2(1H)-one MS(ESI m/z): 459 (M+H)
RT(min): 0.83

(3)
In the same manner as in Example 1-44-1, the following compound was obtained.

4-Morpholino-6-(7-((1-phenethylpiperidin-3-yl)amino)-9H-xanthen-4-yl)pyridin-2(1H)-one MS(ESI m/z): 563 (M+H)
RT(min): 1.07

Example 2-19-4

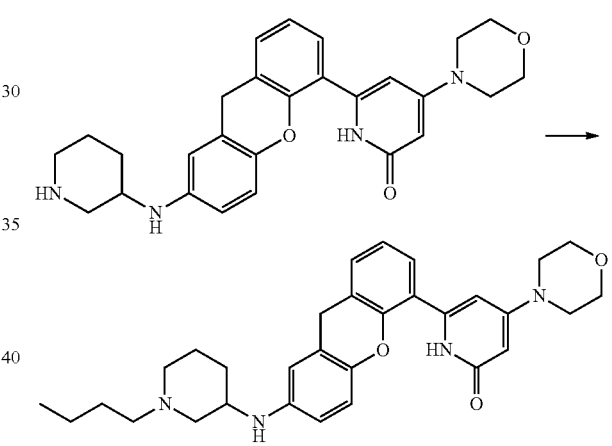

In the same manner as in Example 2-19-3 (3), the following compound was obtained.

6-(7-((1-Butylpiperidin-3-yl)amino)-9H-xanthen-4-yl)-4-morpholinopyridin-2(1H)-one MS(ESI m/z): 515 (M+H)
RT(min): 0.98

Example 2-19-5

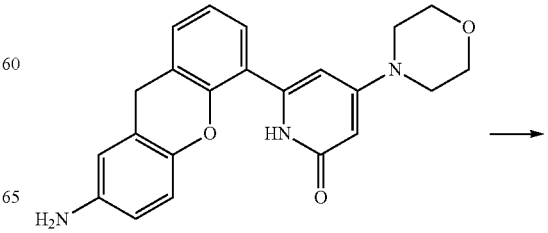

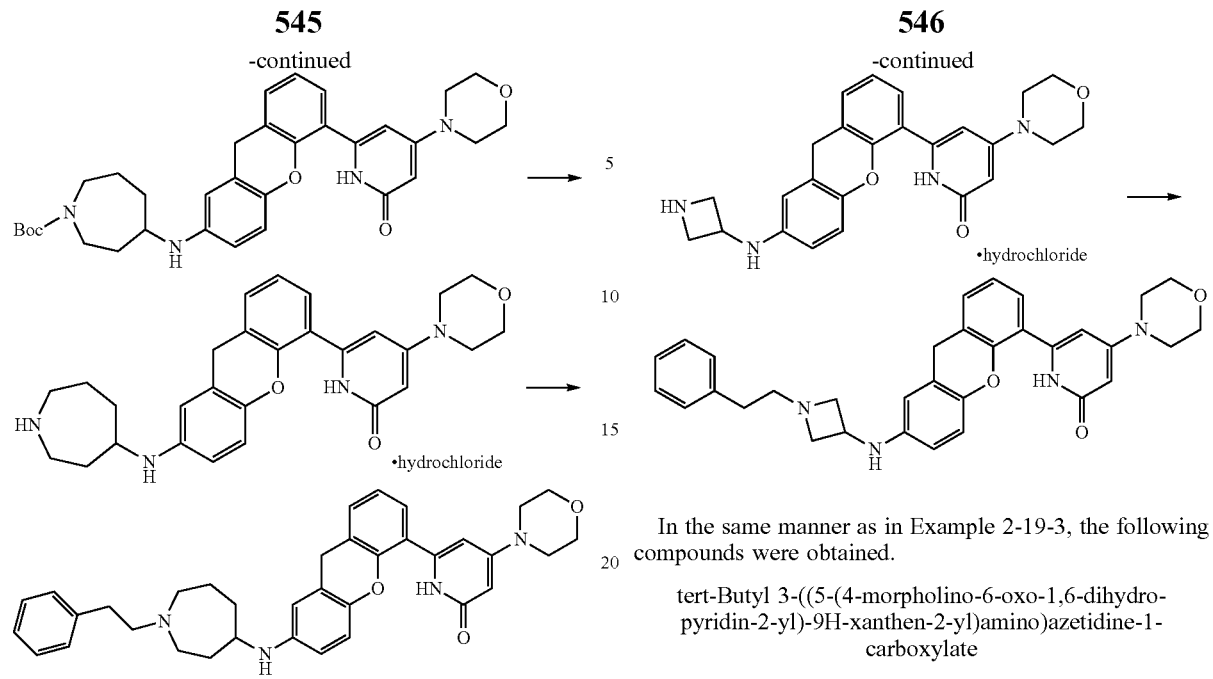

In the same manner as in Example 2-19-3, the following compounds were obtained.

tert-Butyl 4-((5-(4-morpholino-6-oxo-1,6-dihydro-pyridin-2-yl)-9H-xanthen-2-yl)amino)azepane-1-carboxylate MS(ESI m/z): 573 (M+H)
RT(min): 1.21

6-(7-(azepan-4-ylamino)-9H-xanthen-4-yl)-4-morpholinopyridin-2(1H)-one

MS(ESI m/z): 473 (M+H)
RT(min): 0.76

4-Morpholino-6-(7-((1-phenethylazepan-4-yl)amino)-9H-xanthen-4-yl)pyridin-2(1H)-one MS(ESI m/z): 577 (M+H)
RT(min): 1.00

Example 2-19-6

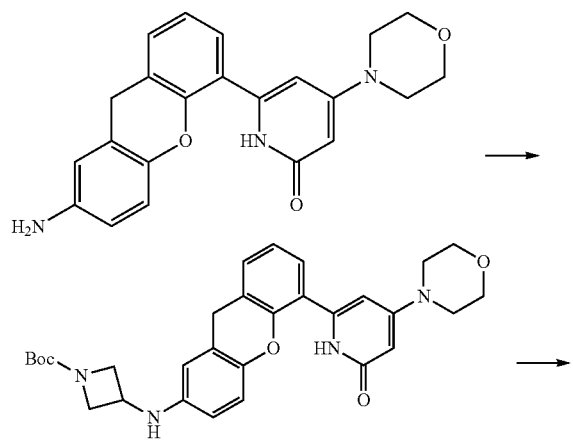

In the same manner as in Example 2-19-3, the following compounds were obtained.

tert-Butyl 3-((5-(4-morpholino-6-oxo-1,6-dihydro-pyridin-2-yl)-9H-xanthen-2-yl)amino)azetidine-1-carboxylate MS(ESI m/z): 531 (M+H)
RT(min): 1.35

Hydrochloride of 6-(7-(azetidin-3-ylamino)-9H-xanthen-4-yl)-4-morpholinopyridin-2(1H)-one MS(ESI m/z): 431 (M+H)
RT(min): 0.79

4-Morpholino-6-(7-((1-phenethylazetidin-3-yl)amino)-9H-xanthen-4-yl)pyridin-2(1H)-one MS(ESI m/z): 535 (M+H)
RT(min): 1.01

Example 2-19-7

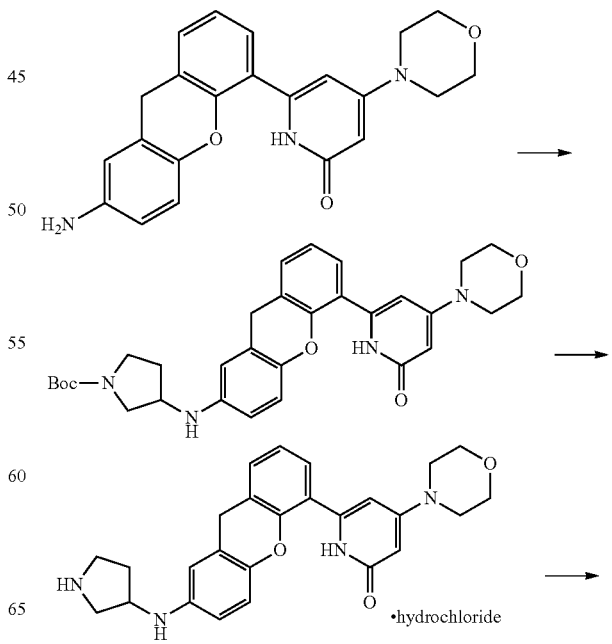

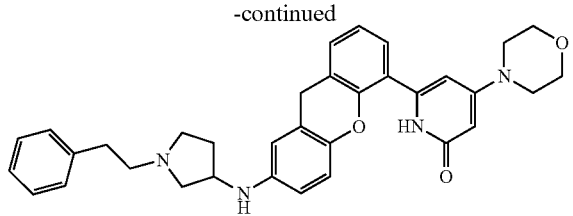

In the same manner as in Example 2-19-3, the following compounds were obtained.

tert-Butyl 3-((5-(4-morpholino-6-oxo-1,6-dihydro-pyridin-2-yl)-9H-xanthen-2-yl)amino)pyrrolidine-1-carboxylate MS(ESI m/z): 545 (M+H)
RT(min): 1.36

Hydrochloride of 4-morpholino-6-(7-(pyrrolidin-3-ylamino)-9H-xanthen-4-yl)pyridin-2(1H)-one MS(ESI m/z): 445 (M+H)
RT(min): 0.80

4-Morpholino-6-(7-((1-phenethylpyrrolidin-3-yl)amino)-9H-xanthen-4-yl)pyridin-2(1H)-one MS(ESI m/z): 549 (M+H)
RT(min): 1.02

Example 2-19-8

In the same manner as in Example 2-19-2, the following compound was obtained.

6-(7-((1-Butylpyrrolidin-3-yl)amino)-9H-xanthen-4-yl)-4-morpholinopyridin-2(1H)-one MS(ESI m/z): 501 (M+H)
RT(min): 0.94

Example 2-20-1

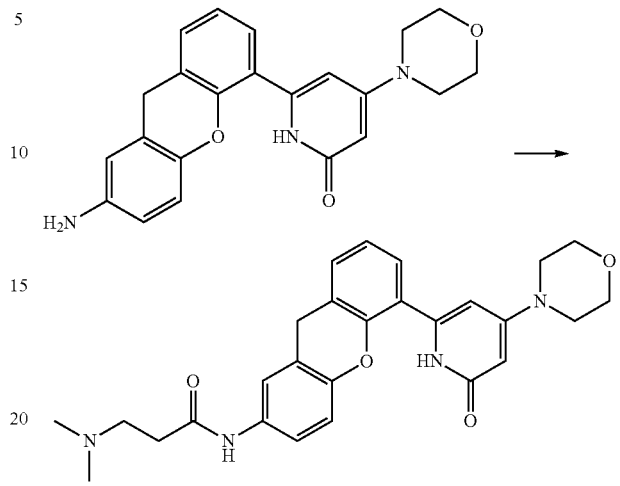

In the same manner as in Example 1-2-1 (1), the following compound was obtained.

3-(Dimethyl amino)-N-(5-(4-morpholino-6-oxo-1,6-dihydropyridin-2-yl)-9H-xanthen-2-yl)propanamide MS(ESI m/z): 475 (M+H)
RT(min): 0.81

Example 2-20-2

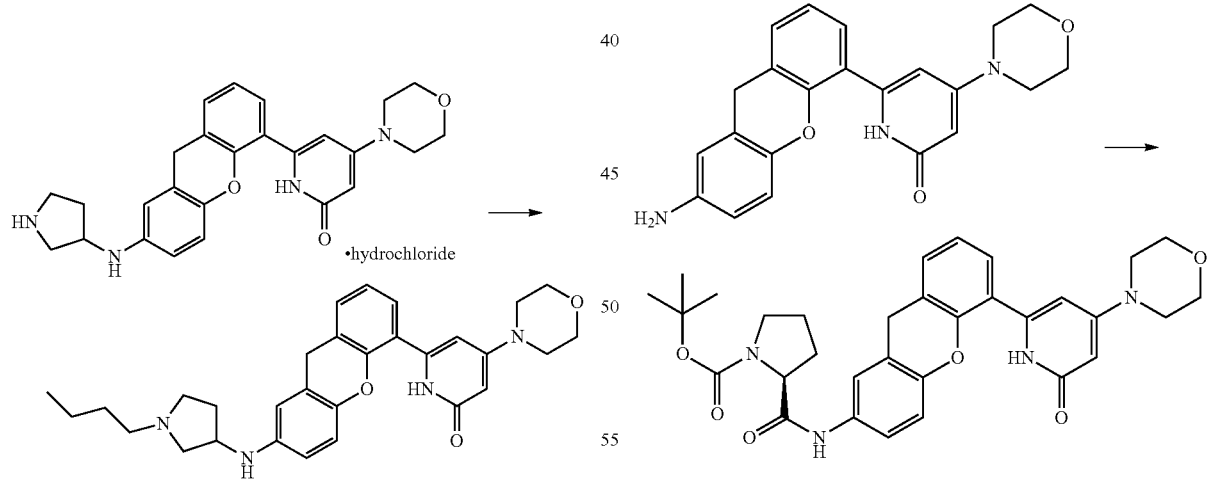

In the same manner as in Example 1-2-1 (1), the following compound was obtained.

(S)-tert-butyl 2-((5-(4-morpholino-6-oxo-1,6-dihydropyridin-2-yl)-9H-xanthen-2-yl)carbamoyl)pyrrolidine-1-carboxylate MS(ESI m/z): 573 (M+H)
RT(min): 1.26

Example 2-21-1

In the same manner as in Reference Example 8 (3), the following compound was obtained.

6-(7-((3-(Dimethylamino)propyl)amino)-9H-xanthen-4-yl)-4-morpholinopyridin-2(1H)-one MS(ESI m/z): 461 (M+H)
RT(min): 0.80

Example 2-21-2

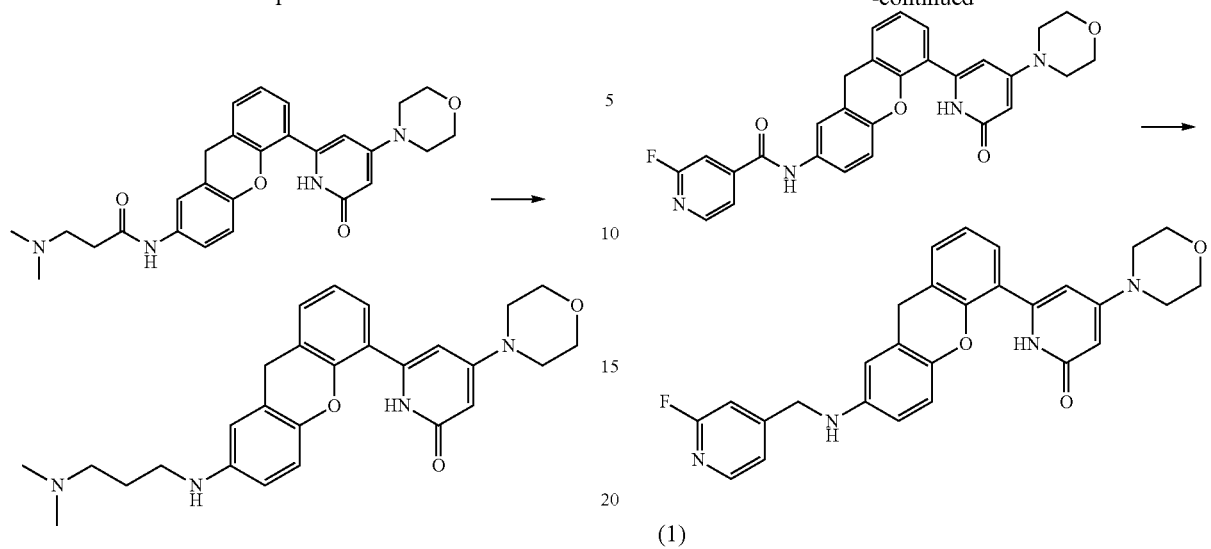

(1)
In the same manner as in Example 1-2-1 (1), the following compound was obtained.

2-Fluoro-N-(5-(4-morpholino-6-oxo-1,6-dihydropyridin-2-yl)-9H-xanthen-2-yl)isonicotinamide (2)
In the same manner as in Reference Example 8 (3), the following compound was obtained.

6-(7-(((2-Fluoropyridin-4-yl)methyl)amino)-9H-xanthen-4-yl)-4-morpholinopyridin-2 (1H)-one $^1$H-NMR (DMSO-$d_6$, 300 MHz) δ: 10.86 (1H, brs), 8.16 (1H, d, J=5.4 Hz), 7.33-7.23 (3H, m), 7.09-7.03 (2H, m), 6.71 (1H, d, J=7.8 Hz), 6.47-6.43 (2H, m), 6.28 (1H, t, J=6.2 Hz), 6.13 (1H, d, J=2.4 Hz), 5.45 (1H, d, J=2.4 Hz), 4.36 (2H, d, J=6.2 Hz), 3.93 (2H, s), 3.67 (4H, t, J=4.6 Hz), 3.25 (4H, t, J=4.6 Hz).
MS(ESI m/z): 485 (M+H)
RT(min): 1.21

Examples 2-21-3 to 2-21-9

In the same manner as in Example 2-21-2, the following compounds were obtained.

TABLE 75

| Example No. | $R^b$ | Compound Name | MS | RT (min) | $^1$H-NMR (300 MHz) (DMSO-$d_6$) δ: |
|---|---|---|---|---|---|
| 2-21-3 | 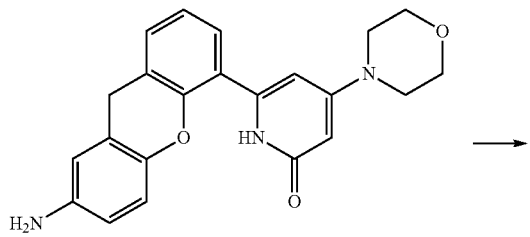 | (S)-tert-Butyl 2-(((5-(4-morpholino-6-oxo-1,6-dihydropyridin-2-yl)-9H-xanthen-2-yl)amino)methyl)pyrrolidine-1-carboxylate | 559 | 1.51 | |

TABLE 75-continued

| Example No. | $R^b$ | Compound Name | MS | RT (min) | $^1$H-NMR (300 MHz) (DMSO-$d_6$) δ: |
|---|---|---|---|---|---|
| 2-21-4 | | 6-(7-(((5-(Methyl amino) pyridin-3-yl)methyl)amino)-9H-xanthen-4-yl)-4-morpholino pyridin-2(1H)-one | 496 | 0.89 | |
| 2-21-5 | | 4-Morpholino-6-(7-(((1-(pyridin-4-yl)piperidin-4-yl)methyl)amino)-9H-xanthen-4-yl)pyridin-2(1H)-one | 550 | 0.88 | |
| 2-21-6 | | 6-(7-(((2-(Methoxy methyl) pyridin-4-yl)methyl)amino)-9H-xanthen-4-yl)-4-morpholino pyridin-2(1H)-one | 511 | 0.95 | 10.85 (1H, br s), 8.41 (1H, d, J = 5.4 Hz), 7.40 (1H, s), 7.30-7.23 (3H, m), 7.05 (1H, t, J = 7.7 Hz), 6.69 (1H, d, J = 8.4 Hz), 6.45-6.40 (2H, m), 6.24 (1H, t, J = 6.2 Hz), 6.13 (1H, d, J = 2.3 Hz), 5.45 (1H, d, J = 2.3 Hz), 4.46 (2H, s), 4.31 (2H, d, J = 6.2 Hz), 3.92 (2H, s), 3.67 (4H, t, J = 4.7 Hz), 3.42-3.28 (3H, m), 3.25 (4H, t, J = 4.7 Hz). |
| 2-21-7 | | 6-(7-(((5-(Dimethyl amino) pyridin-3-yl)methyl)amino)-9H-xanthen-4-yl)-4-morpholino pyridin-2(1H)-one | 510 | 0.94 | 10.85 (1H, br s), 7.97 (1H, d, J = 2.4 Hz), 7.89 (1H, d, J = 1.5 Hz), 7.31-7.23 (2H, m), 7.09-7.03 (2H, m), 6.70 (1H, d, J = 8.7 Hz), 6.52-6.47 (2H, m), 6.13 (1H, s), 6.03 (1H, t, J = 6.2 Hz), 5.46 (1H, d, J = 1.8 Hz), 4 20 (2H, d, J = 6.2 Hz), 3.94 (2H, s), 3.67 (4H, t, J = 4.7 Hz), 3.25 (4H, t, J = 4.7 Hz), 2.90 (6H, s). |
| 2-21-8 | | 6-(7-(((2-((Dimethyl amino) methyl)pyridin-4-yl)methyl)amino)-9H-xanthen-4-yl)-4-morpholino pyridin-2(1H)-one | 524 | 0.92 | |
| 2-21-9 | | 6-(7-(((5-(Ethyl(methyl) amino)pyridin-3-yl)methyl) amino)-9H-xanthen-4-yl)-4-morpholino pyridin-2(1H)-one | 524 | 0.99 | 10.86 (1H, br s), 7.93 (1H, d, J = 2.4 Hz), 7.85 (1H, s), 7.32-7.22 (2H, m), 7.10-7.02 (2H, m), 6.70 (1H, d, J = 8.7 Hz), 6.52-6.47 (2H, m), 6.13 (1H, d, J = 2.0 Hz), 6.08-5.98 (1H, br s), 5.46 (1H, d, J = 2.0 Hz), 4.19 (2H, s), 3.94 (2H, s), 3.67 (4H, t, J = 4.6 Hz), 3.25 (4H, t, J = 4.6 Hz), 2.86 (3H, s), 2.52-2.48 (2H, m), 1.01 (3H, t, J = 6.9 Hz). |

Example 2-22-1

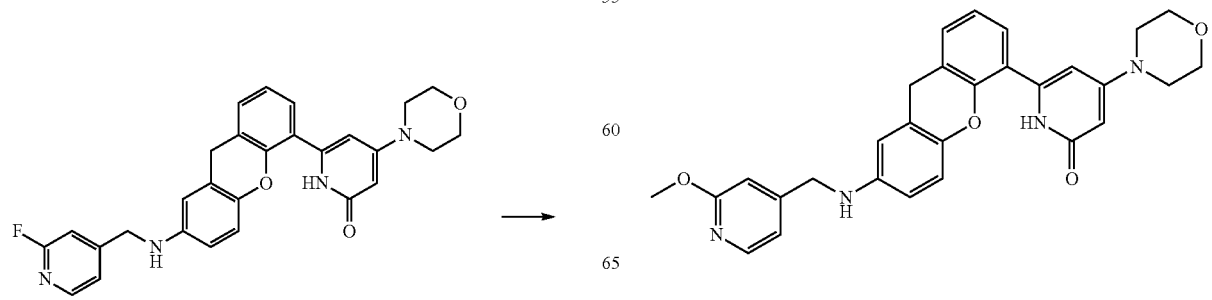

A 28% sodium methoxide methanol solution (60 μL) was added to a solution of 6-(7-(((2-fluoropyridin-4-yl)methyl)amino)-9H-xanthen-4-yl)-4-morpholinopyridin-2(1H)-one (15 mg) in methanol (2.0 mL), followed by heating and stirring at 80° C. for 16 hours. After the reaction mixture was cooled to room temperature, chloroform was added thereto, and the organic layer was washed with water, and dried over anhydrous sodium sulfate. The solvent was distilled off under reduced pressure, whereby 6-(7-(((2-methoxypyridin-4-yl)methyl)amino)-9H-xanthen-4-yl)-4-morpholinopyridin-2(1H)-one (13 mg) was obtained.

$^1$H-NMR (DMSO-$d_6$, 300 MHz) δ: 10.84 (1H, brs), 8.07 (1H, d, J=5.2 Hz), 7.30-7.20 (2H, m), 7.05 (1H, t, J=7.7 Hz), 6.95 (1H, dd, J=5.2 Hz, 1.3 Hz), 6.74 (1H, s), 6.69 (1H, d, J=8.4 Hz), 6.50-6.40 (2H, m), 6.20 (1H, t, J=6.3 Hz), 6.13 (1H, s), 5.46 (1H, d, J=1.8 Hz), 4.25 (2H, d, J=6.3 Hz), 3.93 (2H, s), 3.80 (3H, s), 3.67 (4H, t, J=4.6 Hz), 3.25 (4H, t, J=4.6 Hz).

MS(ESI m/z): 497 (M+H)

RT(min): 1.21

Example 2-22-2

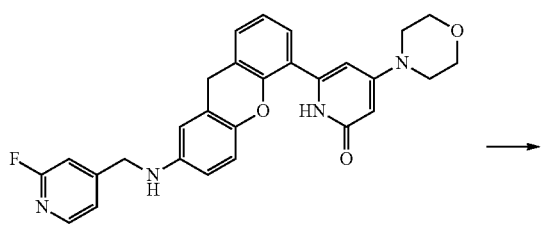

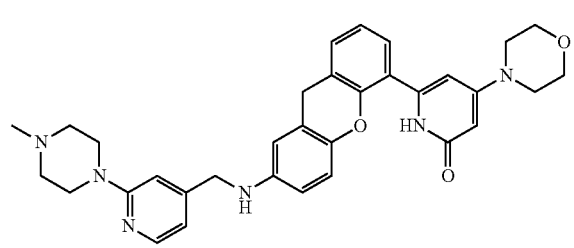

N-methyl piperazine (500 μL) was added to 6-(7-(((2-fluoropyridin-4-yl)methyl)amino)-9H-xanthen-4-yl)-4-morpholinopyridin-2(1H)-one (16 mg), and the resultant product was irradiated with microwaves (microwave reaction apparatus, 140° C., 0.5 hours→150° C., 0.5 hours 2.45 GHz, 0 W to 240 W). After the reaction mixture was cooled to room temperature, chloroform was added thereto, and the organic layer was washed with water, and dried over anhydrous sodium sulfate. The solvent was distilled off under reduced pressure, and the obtained residues were purified by preparative thin layer silica gel chromatography (chloroform:ethanol=30:1, NH silica), whereby 6-(7-(((2-(4-methylpiperazin-1-yl)pyridin-4-yl)methyl)amino)-9H-xanthen-4-yl)-4-morpholinopyridin-2(1H)-one (2.5 mg) was obtained.

MS(ESI m/z): 565 (M+H)

RT(min): 0.88

Example 2-23-1

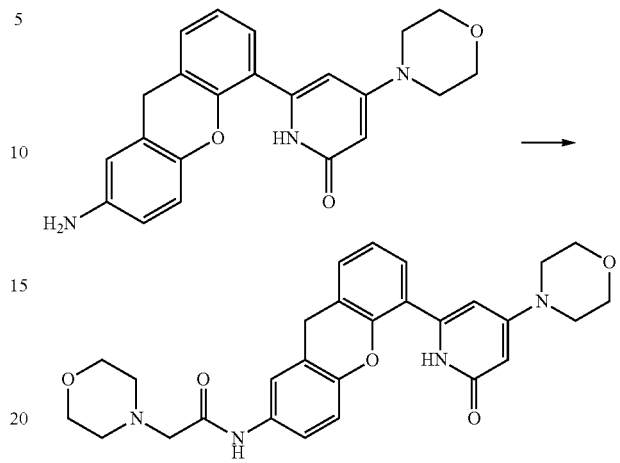

Chloroacetylchloride (12.7 μL) was added to a solution of 6-(7-amino-9H-xanthen-4-yl)-4-morpholinopyridin-2(1H)-one (30 mg) and triethylamine (33 μL) in tetrahydrofuran (2.0 mL) and N,N-dimethyl acetamide (1.0 mL), followed by stirring at room temperature for 0.5 hours. Chloroacetylchloride (12.7 μL) was added thereto, followed by stirring at room temperature for 1 hour, and morpholine (138 μL) was added thereto, followed by stirring at 80° C. for 3 hours. Ethyl acetate was added to the reaction mixture, then, the organic layer was washed with a saturated sodium chloride aqueous solution, and the aqueous layer was extracted with tetrahydrofuran. The organic layer and the extraction liquid were combined, and the resultant product was dried over anhydrous sodium sulfate. The solvent was distilled off under reduced pressure, and the obtained residues were purified by preparative thin layer silica gel chromatography (chloroform:methanol=20:1, NH silica), whereby 2-morpholino-N-(5-(4-morpholino-6-oxo-1,6-dihydropyridin-2-yl)-9H-xanthen-2-yl)acetamide (32 mg) was obtained.

MS(ESI m/z): 503 (M+H)

RT(min): 0.82

Example 2-23-2

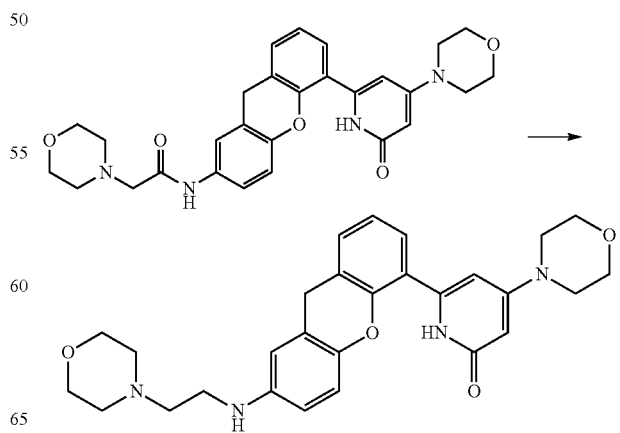

In the same manner as in Reference Example 8 (3), the following compound was obtained.

4-Morpholino-6-(7-((2-morpholinoethyl)amino)-9H-xanthen-4-yl)pyridin-2(1H)-one

MS(ESI m/z): 489 (M+H)
RT(min): 0.83

Example 2-24

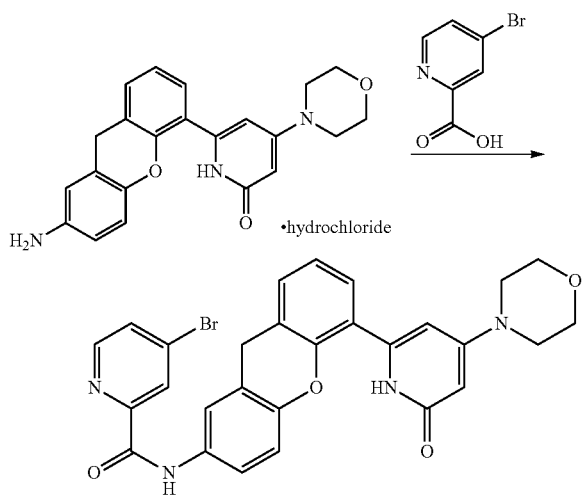

A mixture of hydrochloride (30 mg) of 6-(7-amino-9H-xanthen-4-yl)-4-morpholinopyridin-2(1H)-one, 4-bromopicolinic acid (27 mg), 1-ethyl-3-(3-dimethylaminopropyl)carbodiimide hydrochloride (26 mg), 1-hydroxybenzotriazole (18 mg), N,N-dimethyl formamide (0.67 mL), and N,N-diisopropyl ethylamine (70 µL) was stirred at 50° C. for 1 hour. After the reaction mixture was cooled to room temperature, water was added thereto, and the resultant product was extracted with ethyl acetate and methanol. The organic layer was washed with a saturated sodium chloride aqueous solution, and the solvent was distilled off under reduced pressure. The obtained residues were purified by silica gel column chromatography (chloroform:methanol=1:0→9:1, NH silica), whereby 4-bromo-N-(5-(4-morpholino-6-oxo-1,6-dihydropyridin-2-yl)-9H-xanthen-2-yl)picolinamide (56 mg) was obtained.

MS(ESI m/z): 561 (M+H+2)
RT(min): 1.40

Example 2-25-1

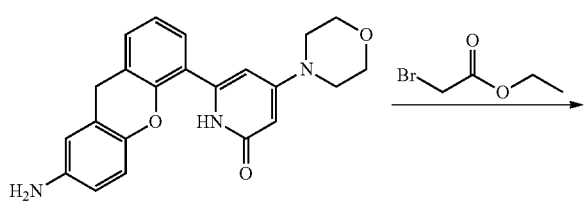

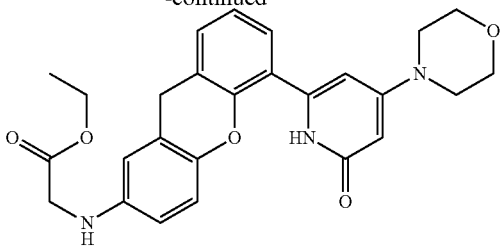

A mixture of 6-(7-amino-9H-xanthen-4-yl)-4-morpholinopyridin-2(1H)-one (38 mg), ethyl 2-bromoacetate (20 mg), potassium carbonate (28 mg), and N,N-dimethyl acetamide (1 mL) was stirred at room temperature for 40 hours. Chloroform was added to the reaction mixture, then, the resultant product was washed with water, and dried over anhydrous sodium sulfate. The solvent was distilled off under reduced pressure, and the obtained residues were purified by silica gel column chromatography (ethyl acetate:methanol=1:0→4:1), whereby ethyl 2-((5-(4-morpholino-6-oxo-1,6-dihydropyridin-2-yl)-9H-xanthen-2-yl)amino)acetate (22 mg) was obtained as a yellow solid.

$^1$H-NMR (DMSO-$d_6$, 300 MHz) δ: 10.88 (1H, s), 7.31 (1H, d, J=7.6 Hz), 7.26 (1H, d, J=6.3 Hz), 7.07 (1H, t, J=7.6 Hz), 6.72 (1H, d, J=8.6 Hz), 6.44 (2H, dd, J=11.9, 3.0 Hz), 6.14 (1H, s), 5.85 (1H, t, J=6.3 Hz), 5.47 (1H, d, J=2.0 Hz), 4.11 (2H, q, J=7.2 Hz), 3.97 (2H, s), 3.87 (2H, d, J=6.3 Hz), 3.68 (4H, t, J=4.6 Hz), 3.26 (4H, t, J=4.6 Hz), 1.19 (3H, t, J=7.1 Hz).

MS(ESI m/z): 462 (M+H)
RT(min): 1.23

Example 2-25-2

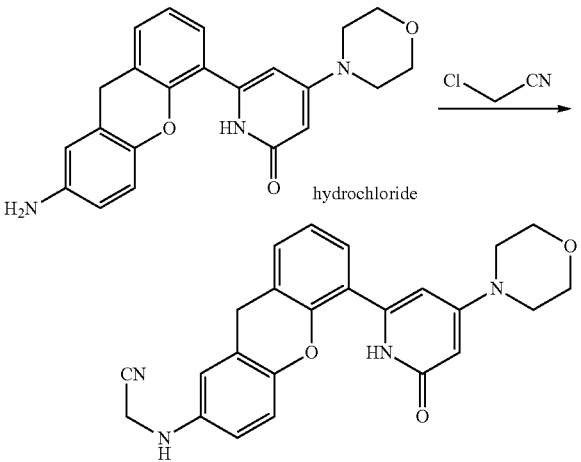

Hydrochloride (45 mg) of 2-Chloroacetonitrile (7.6 mg) was added to a mixture of 6-(7-amino-9H-xanthen-4-yl)-4-morpholinopyridin-2(1H)-one, potassium carbonate (55 mg), sodium iodide (15 mg), and acetonitrile (5 mL), followed by stirring at 120° C. for 2.5 hours. 2-Chloroacetonitrile (13 mg) was added thereto, followed by stirring for 4 hours. Ethyl acetate was added to the reaction mixture, and the resultant product was washed sequentially with a saturated sodium hydrogen carbonate aqueous solution and a saturated sodium chloride aqueous solution. The organic layer was dried over anhydrous sodium sulfate, then, the solvent was distilled off under reduced pressure, and the obtained residues were purified by silica gel column chromatography (ethyl acetate:methanol=9:1→7:3), whereby 2-((5-(4-morpholino-6-oxo-1,6-dihydropyridin-2-yl)-9H-xanthen-2-yl)amino)acetonitrile (33 mg) was obtained.

MS(ESI m/z): 415 (M+H)
RT(min): 1.08

Example 2-26

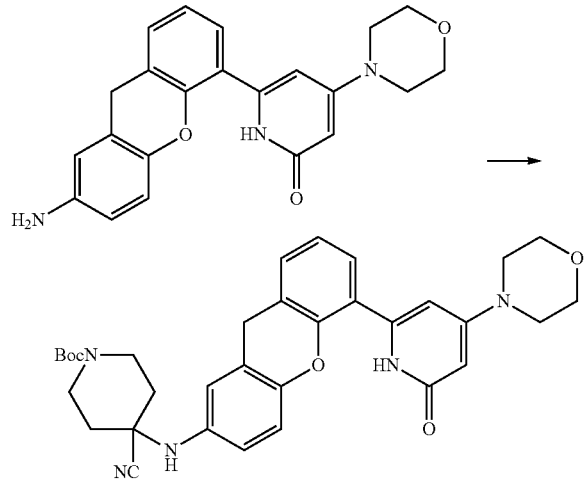

Trimethyl silylcyanide (6.9 µL) was added to a solution of 6-(7-amino-9H-xanthen-4-yl)-4-morpholinopyridin-2(1H)-one (20 mg) and tert-butyl 4-oxopiperidine-1-carboxylate (11 mg) in acetic acid (1 mL), followed by stirring at room temperature for 11 hours. tert-Butyl 4-oxopiperidine-1-carboxylate (11 mg) and trimethyl silylcyanide (6.9 µL) were added thereto, followed by stirring for 4 hours. After 25% ammonia water was added to the reaction mixture, the solid was collected by filtration, washed with hexane, and purified by preparative thin layer silica gel chromatography (chloroform:methanol=9:1), whereby tert-butyl 4-cyano-4-((5-(4-morpholino-6-oxo-1,6-dihydropyridin-2-yl)-9H-xanthen-2-yl)amino)piperidine-1-carboxylate (12.1 mg) was obtained.

MS(ESI m/z): 584 (M+H)
RT(min): 1.42

Example 2-27

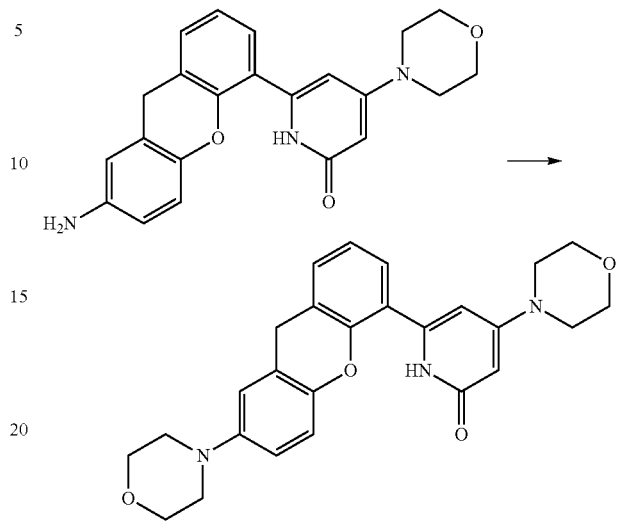

A mixture of 6-(7-amino-9H-xanthen-4-yl)-4-morpholinopyridin-2(1H)-one (30 mg), 1-bromo-2-(2-bromoethoxy)ethane (28 mg), N,N-diisopropyl ethylamine (31 mg), and N,N-dimethyl acetamide (1 mL) was stirred at 80° C. for 17 hours. Ethyl acetate was added to the reaction mixture, followed by washing with a saturated aqueous sodium chloride solution. The organic layer was dried over anhydrous sodium sulfate, then, the solvent was distilled off under reduced pressure, and the obtained residues were purified by preparative thin layer silica gel chromatography (chloroform:ethanol=10:1, NH silica), whereby 4-morpholino-6-(7-morpholino-9H-xanthen-4-yl)pyridin-2(1H)-one (11 mg) was obtained.

MS(ESI m/z): 446 (M+H)
RT(min): 1.09

Examples 2-28-1 to 2-28-38

Using hydrochloride of 4-morpholino-6-(7-(piperidin-4-ylamino)-9H-xanthen-4-yl)pyridin-2(1H)-one, the following compounds were obtained in the same manner as in Example 2-2-1.

TABLE 76

| Example No. | $R^b$ | Compound Name | MS | RT (min) | $^1$H-NMR (300 MHz) (DMSO-$d_6$) δ: |
|---|---|---|---|---|---|
| 2-28-1 | | 4-Morpholino-6-(7-((1-(pyridin-2-yl methyl)piperidin-4-yl)amino)-9H-xanthen-4-yl)pyridin-2(1H)-one | 550 | 0.88 | |

TABLE 76-continued

| Example No. | R^b | Compound Name | MS | RT (min) | ¹H-NMR (300 MHz) (DMSO-d₆) δ: |
|---|---|---|---|---|---|
| 2-28-2 | (5-methoxypyridin-3-yl)methyl-piperidine | 6-(7-((1-((5-Methoxy pyridin-3-yl)methyl) piperidin-4-yl)amino)-9H-xanthen-4-yl)-4-morpholino pyridin-2(1H)-one | 580 | 0.89 | |
| 2-28-3 | (pyrimidin-2-yl methyl)-piperidine | 4-Morpholino-6-(7-((1-(pyrimidin-2-yl methyl) piperidin-4-yl)amino)-9H-xanthen-4-yl)pyridin-2(1H)-one | 551 | 0.83 | |
| 2-28-4 | (pyrimidin-5-yl methyl)-piperidine | 4-Morpholino-6-(7-((1-(pyrimidin-5-yl methyl) piperidin-4-yl)amino)-9H-xanthen-4-yl)pyridin-2(1H)-one | 551 | 0.82 | |
| 2-28-5 | (2-methoxypyridin-3-yl)methyl-piperidine | 6-(7-((1-((2-Methoxy pyridin-3-yl)methyl)piperidin-4-yl) amino)-9H-xanthen-4-yl)-4-morpholino pyridin-2(1H)-one | 580 | 0.94 | |
| 2-28-6 | (6-methoxypyridin-3-yl)methyl-piperidine | 6-(7-((1-((6-Methoxy pyridin-3-yl)methyl) piperidin-4-yl)amino)-9H-xanthen-4-yl)-4-morpholino pyridin-2(1H)-one | 580 | 0.93 | |
| 2-28-7 | (pyrazin-2-yl methyl)-piperidine | 4-Morpholino-6-(7-((1-(pyrazin-2-yl methyl) piperidin-4-yl)amino)-9H-xanthen-4-yl)pyridin-2(1H)-one | 551 | 0.83 | |
| 2-28-8 | (6-(methylamino)pyridin-3-yl)methyl-piperidine | 6-(7-((1-((6-(Methyl amino)pyridin-3-yl)methyl) piperidin-4-yl)amino)-9H-xanthen-4-yl)-4-morpholino pyridin-2(1H)-one | 579 | 0.73 | |
| 2-28-9 | (6-(dimethylamino)pyridin-3-yl)methyl-piperidine | 6-(7-((1-((6-(Dimethyl amino) pyridin-3-yl)methyl)piperidin-4-yl)amino)-9H-xanthen-4-yl)-4-morpholino pyridin-2(1H)-one | 593 | 0.75 | |

TABLE 77

| Example No. | R^b | Compound Name | MS | RT (min) | ¹H-NMR (300 MHz) (DMSO-d_6) δ: |
|---|---|---|---|---|---|
| 2-28-10 | | 6-(7-((1-((6-Methyl pyridin-3-yl)methyl)piperidin-4-yl)amino)-9H-xanthen-4-yl)-4-morpholino pyridin-2(1H)-one | 564 | 0.77 | |
| 2-28-11 | | 6-(7-((1-((4-Methoxy pyridin-3-yl)methyl)piperidin-4-yl)amino)-9H-xanthen-4-yl)-4-morpholino pyridin-2(1H)-one | 580 | 0.71 | |
| 2-28-12 | | 6-(7-((1-((2-(Methyl amino)pyrimidin-5-yl)methyl)piperidin-4-yl)amino)-9H-xanthen-4-yl)-4-morpholino pyridin-2(1H)-one | 580 | 0.82 | |
| 2-28-13 | | 6-(7-((1-((2-(Dimethyl amino)pyrimidin-5-yl)methyl)piperidin-4-yl)amino)-9H-xanthen-4-yl)-4-morpholino pyridin-2(1H)-one | 594 | 0.89 | |
| 2-28-14 | | 6-(7-((1-((2-Methoxy pyrimidin-5-yl)methyl)piperidin-4-yl)amino)-9H-xanthen-4-yl)-4-morpholino pyridin-2(1H)-one | 581 | 0.84 | |
| 2-28-15 | | 4-Morpholino-6-(7-((1-((6-(trifluoromethyl)pyridin-3-yl)methyl)piperidin-4-yl)amino)-9H-xanthen-4-yl) pyridin-2(1H)-one | 618 | 0.98 | |
| 2-28-16 | | 6-(7-((1-((2-(Dimethyl amino)pyrimidin-4-yl)methyl)piperidin-4-yl)amino)-9H-xanthen-4-yl)-4-morpholino pyridin-2(1H)-one | 594 | 0.94 | |
| 2-28-17 | | 6-(7-((1-((5-Chloropyridin-3-yl)methyl)piperidin-4-yl)amino)-9H-xanthen-4-yl)-4-morpholino pyridin-2(1H)-one | 584 | 0.92 | |
| 2-28-18 | | 6-(7-((1-((5-Fluoropyridin-3-yl)methyl)piperidin-4-yl)amino)-9H-xanthen-4-yl)-4-morpholino pyridin-2(1H)-one | 568 | 0.88 | |

TABLE 78

| Example No. | R^b | Compound Name | MS | RT (min) | ¹H-NMR (300 MHz) (DMSO-d₆) δ: |
|---|---|---|---|---|---|
| 2-28-19 | | 6-(7-((1-((4-Methyl pyridin-2-yl)methyl)piperidin-4-yl)amino)-9H-xanthen-4-yl)-4-morpholino pyridin-2(1H)-one | 564 | 0.92 | |
| 2-28-20 | | 6-(7-((1-((4,6-Dimethoxy pyrimidin-2-yl)methyl) piperidin-4-yl)amino)-9H-xanthen-4-yl)-4-morpholino pyridin-2(1H)-one | 611 | 0.96 | |
| 2-28-21 | | 4-Morpholino-6-(7-((1-((6-((tetrahydro-2H-pyran-4-yl)oxy)pyridin-3-yl)methyl) piperidin-4-yl)amino)-9H-xanthen-4-yl)pyridin-2(1H)-one | 650 | 0.94 | |
| 2-28-22 | | 6-(7-((1-((5-Methyl pyridin-2-yl)methyl)piperidin-4-yl)amino)-9H-xanthen-4-yl)-4-morpholino pyridin-2(1H)-one | 564 | 0.90 | |
| 2-28-23 | | 6-(7-((1-((6-Methoxy pyrazin-2-yl)methyl) piperidin-4-yl)amino)-9H-xanthen-4-yl)-4-morpholino pyridin-2(1H)-one | 581 | 0.87 | 10.85 (1H, br s), 8.22 (1H, s), 8.18 (1H, s), 7.30 (1H, d, J = 7.6 Hz), 7.26 (1H, d, J = 7.6 Hz), 7.06 (1H, t, J = 7.6 Hz), 6.70 (1H, d, J = 8.6 Hz), 6.49-6.43 (2H, m), 6.14 (1H, br s), 5.47 (1H, br s), 5.24 (1H, d, J = 8.6 Hz), 3.96 (2H, s), 3.90 (3H, s), 3.68 (4H, t, J = 4.6 Hz), 3.60 (2H, s), 3.26 (4H, t, J = 4.6 Hz), 3.22-3.10 (1H, m), 2.85 (2H, d, J = 11.2 Hz), 2.21 (2H, t, J = 10.6 Hz), 2.04-1.85 (2H, m), 1.50-1.33 (2H, m). |
| 2-28-24 | | 6-(7-((1-Benzyl piperidin-4-yl)amino)-9H-xanthen-4-yl)-4-morpholino pyridin-2(1H)-one | 549 | 0.94 | |
| 2-28-25 | | 4-Morpholino-6-(7-((1-(thiophen-2-yl methyl) piperidin-4-yl)amino)-9H-xanthen-4-yl)pyridin-2(1H)-one | 555 | 0.92 | |
| 2-28-26 | | 4-Morpholino-6-(7-((1-(thiophen-3-yl methyl) piperidin-4-yl)amino)-9H-xanthen-4-yl)pyridin-2(1H)-one | 555 | 0.92 | |
| 2-28-27 | | 6-(7-((1-(Furan-2-yl methyl) piperidin-4-yl)amino)-9H-xanthen-4-yl)-4-morpholino pyridin-2(1H)-one | 539 | 0.88 | |

TABLE 79

| Example No. | R$^b$ | Compound Name | MS | RT (min) | $^1$H-NMR (300 MHz) (DMSO-d$_6$) δ: |
|---|---|---|---|---|---|
| 2-28-28 | 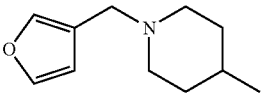 | 6-(7-((1-(Furan-3-yl methyl)piperidin-4-yl) amino)-9H-xanthen-4-yl)-4-morpholino pyridin-2(1H)-one | 539 | 0.89 | |
| 2-28-29 | 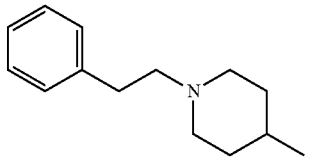 | 4-Morpholino-6-(7-((1-phenethyl piperidin-4-yl) amino)-9H-xanthen-4-yl) pyridin-2(1H)-one | 563 | 0.99 | |
| 2-28-30 | 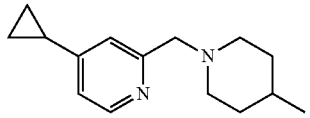 | 6-(7-((1-((4-Cyclopropyl pyridin-2-yl)methyl) piperidin-4-yl)amino)-9H-xanthen-4-yl)-4-morpholino pyridin-2(1H)-one | 590 | 1.00 | |
| 2-28-31 | 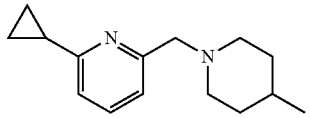 | 6-(7-((1-((6-Cyclopropyl pyridin-2-yl)methyl) piperidin-4-yl)amino)-9H-xanthen-4-yl)-4-morpholino pyridin-2(1H)-one | 590 | 1.03 | |
| 2-28-32 | 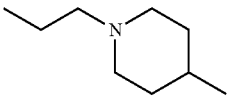 | 4-Morpholino-6-(7-((1-propyl piperidin-4-yl) amino)-9H-xanthen-4-yl) pyridin-2(1H)-one | 501 | 0.86 | 10.85 (1H, s), 7.30 (1H, d, J = 7.6 Hz), 7.26 (1H, d, J = 7.6 Hz), 7.06 (1H, t, J = 7.6 Hz), 6.70 (1H, d, J = 8.6 Hz), 6.50-6.41 (2H, m), 6.14 (1H, br s), 5.47 (1H, br s), 5.23 (1H, d, J = 7.9 Hz), 3.96 (2H, s), 3.68 (4H, t, J = 4.6 Hz), 3.26 (4H, t, J = 4.6 Hz), 3.22-3.08 (1H, m), 2.92-2.74 (2H, br m), 2.33-2.18 (2H, br m), 2.15-1.82 (4H, m), 1.51-1.20 (4H, m), 0.85 (3H, t, J = 7.3 Hz). |
| 2-28-33 | 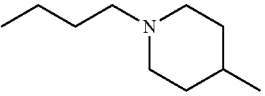 | 6-(7-((1-Butyl piperidin-4-yl)amino)-9H-xanthen-4-yl)-4-morpholino pyridin-2(1H)-one | 515 | 0.90 | |
| 2-28-34 | 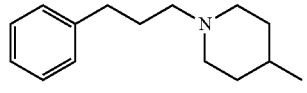 | 4-Morpholino-6-(7-((1-(3-phenyl propyl)piperidin-4-yl)amino)-9H-xanthen-4-yl) pyridin-2(1H)-one | 577 | 1.04 | |
| 2-28-35 | 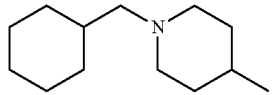 | 6-(7-((1-(Cyclohexylmethyl) piperidin-4-yl)amino)-9H-xanthen-4-yl)-4-morpholino pyridin-2(1H)-one | 555 | 1.04 | |
| 2-28-36 | 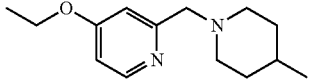 | 6-(7-((1-((4-Ethoxy pyridin-2-yl)methyl)piperidin-4-yl) amino)-9H-xanthen-4-yl)-4-morpholino pyridin-2(1H)-one | 594 | 0.94 | |

TABLE 80

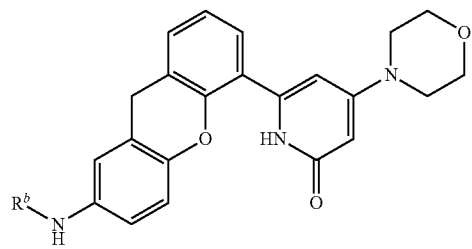

| Example No. | $R^b$ | Compound Name | MS | RT (min) | $^1$H-NMR (300 MHz) (DMSO-$d_6$) δ: |
|---|---|---|---|---|---|
| 2-28-37 | | 4-Morpholino-6-(7-((1-(2-phenyl propyl)piperidin-4-yl)amino)-9H-xanthen-4-yl)pyridin-2(1H)-one | 577 | 1.05 | |
| 2-28-38 | | 6-(7-((1-(2-(6-Methoxy pyridin-3-yl)ethyl)piperidin-4-yl)amino)-9H-xanthen-4-yl)-4-morpholino pyridin-2(1H)-one | 594 | 0.99 | |

Example 2-29

(1) and (2)

In the same manner as in Example 2-19-3 (1) and (2), the following compounds were obtained.

tert-Butyl 4-((5-(4-morpholino-6-oxo-1,6-dihydro-pyridin-2-yl)-9H-xanthen-2-yl)amino)piperidine-1-carboxylate Hydrochloride of 4-morpholino-6-(7-(piperidin-4-ylamino)-9H-xanthen-4-yl)pyridin-2(1H)-one (3)

In the same manner as in Example 1-26-1, the following compound was obtained.

6-(7-((1-(2-Methoxyethyl)piperidin-4-yl)amino)-9H-xanthen-4-yl)-4-morpholinopyridin-2(1H)-one MS(ESI m/z): 517 (M+H)
RT(min): 0.85

Example 2-30-1

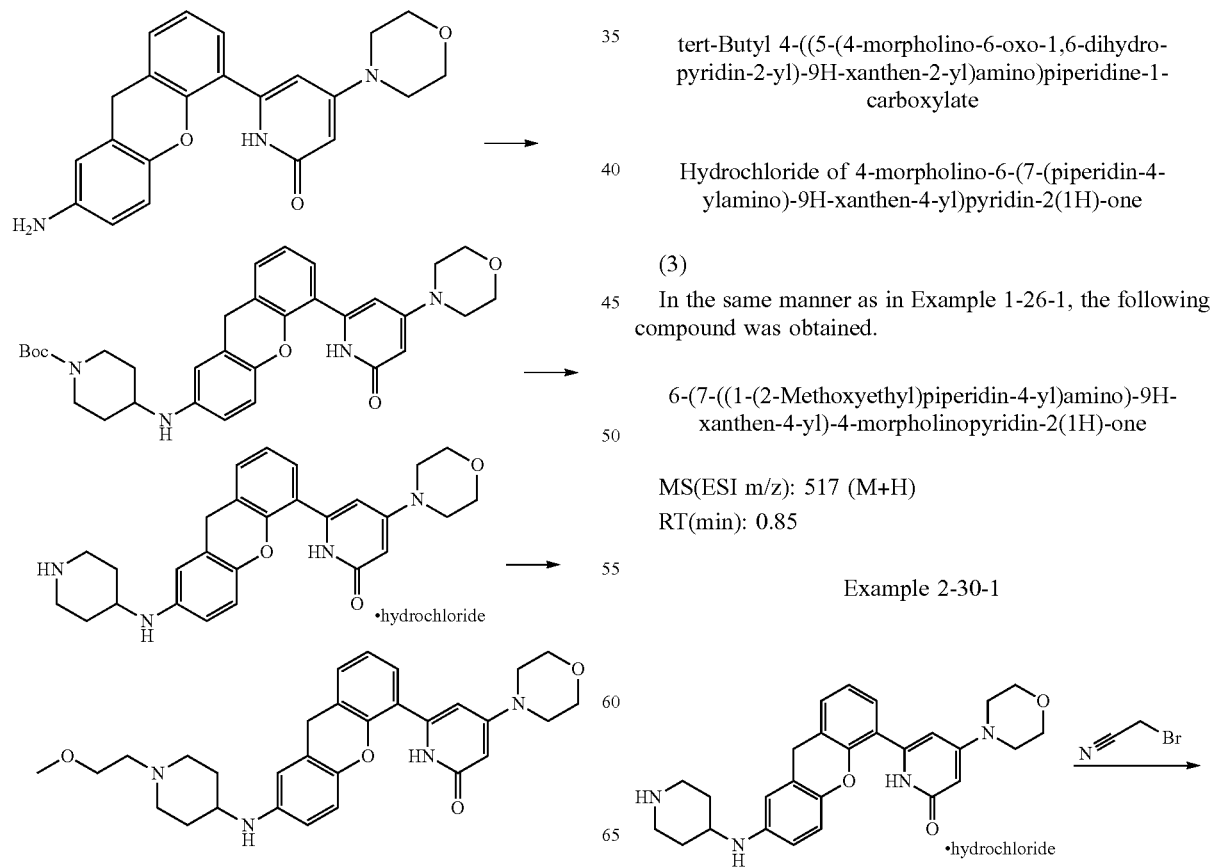

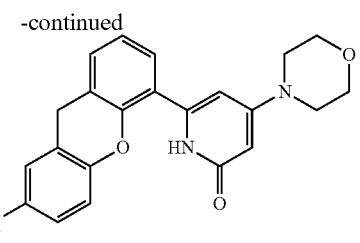

A mixture of hydrochloride (20 mg) of 4-morpholino-6-(7-(piperidin-4-ylamino)-9H-xanthen-4-yl)pyridin-2(1H)-one, sodium hydrogen carbonate (15 mg), N,N-dimethyl formamide (0.70 mL), and 2-bromoacetonitrile (2.7 μL) was stirred at 40° C. for 8 hours. After the reaction mixture was cooled to room temperature, water was added thereto, and the resultant product was extracted with ethyl acetate. The organic layer was washed with a saturated sodium chloride aqueous solution, then, the solvent was distilled off under reduced pressure, and the obtained residues were purified by preparative thin layer silica gel chromatography (chloroform:methanol=9:1), whereby 2-(4-((5-(4-morpholino-6-oxo-1,6-dihydropyridin-2-yl)-9H-xanthen-2-yl)amino)piperidin-1-yl)acetonitrile (5.1 mg) was obtained.

MS(ESI m/z): 498 (M+H)
RT(min): 0.88

Examples 2-30-2 to 2-30-20

In the same manner as in Example 2-30-1, the following compounds were obtained.

TABLE 81

| Example No. | $R^b$ | Compound Name | MS | RT (min) | $^1$H-NMR (300 MHz) (DMSO-$d_6$) δ: |
|---|---|---|---|---|---|
| 2-30-2 | 4-methoxyphenethyl | 6-(7-((1-(4-Methoxy phenethyl)piperidin-4-yl) amino)-9H-xanthen-4-yl)-4-morpholino pyridin-2 (1H)-one | 593 | 1.02 | |
| 2-30-3 | 2-(pyridin-2-yl)ethyl | 4-Morpholino-6-(7-((1-(2-(pyridin-2-yl)ethyl) piperidin-4-yl)amino)-9H-xanthen-4-yl)pyridin-2(1H)-one | 564 | 0.86 | |
| 2-30-4 | 2-methylphenethyl | 6-(7-((1-(2-Methyl phenethyl)piperidin-4-yl) amino)-9H-xanthen-4-yl)-4-morpholino pyridin-2 (1H)-one | 577 | 1.08 | |
| 2-30-5 | 2-cyclohexylethyl | 6-(7-((1-(2-Cyclohexylethyl)piperidin-4-yl)amino)-9H-xanthen-4-yl)-4-morpholino pyridin-2 (1H)-one | 569 | 1.21 | |
| 2-30-6 | 4-chlorophenethyl | 6-(7-((1-(4-Chlorophenethyl)piperidin-4-yl)amino)-9H-xanthen-4-yl)-4-morpholino pyridin-2 (1H)-one | 597 | 1.15 | |

TABLE 81-continued

| Example No. | R<sup>b</sup> | Compound Name | MS | RT (min) | $^1$H-NMR (300 MHz) (DMSO-d$_6$) δ: |
|---|---|---|---|---|---|
| 2-30-7 | | 4-Morpholino-6-(7-((1-(2-(pyridin-4-yl)ethyl)piperidin-4-yl)amino)-9H-xanthen-4-yl)pyridin-2(1H)-one | 564 | 0.72 | |
| 2-30-8 | | 6-(7-((1-(3-Methyl phenethyl)piperidin-4-yl)amino)-9H-xanthen-4-yl)-4-morpholino pyridin-2(1H)-one | 577 | 1.10 | |
| 2-30-9 | | 6-(7-((1-(2-Chlorophenethyl)piperidin-4-yl)amino)-9H-xanthen-4-yl)-4-morpholino pyridin-2(1H)-one | 597 | 1.11 | |
| 2-30-10 | | 6-(7-((1-(2-Methoxy phenethyl)piperidin-4-yl)amino)-9H-xanthen-4-yl)-4-morpholino pyridin-2(1H)-one | 593 | 1.04 | |

TABLE 82

| Example No. | R<sup>b</sup> | Compound Name | MS | RT (min) | $^1$H-NMR (300 MHz) (DMSO-d$_6$) δ: |
|---|---|---|---|---|---|
| 2-30-11 | | 6-(7-((1-(3-Methoxy phenethyl)piperidin-4-yl)amino)-9H-xanthen-4-yl)-4-morpholino pyridin-2(1H)-one | 593 | 1.04 | |

TABLE 82-continued

| Example No. | R$^b$ | Compound Name | MS | RT (min) | $^1$H-NMR (300 MHz) (DMSO-d$_6$) δ: |
|---|---|---|---|---|---|
| 2-30-12 | | 6-(7-((1-(3-Fluoropropyl) piperidin-4-yl)amino)-9H-xanthen-4-yl)-4-morpholino pyridin-2(1H)-one | 519 | 0.84 | |
| 2-30-13 | | 6-(7-((1-(2-Hydroxy-2-phenyl ethyl)piperidin-4-yl)amino)-9H-xanthen-4-yl)-4-morpholino pyridin-2(1H)-one | 579 | 0.96 | |
| 2-30-14 | | 6-(7-((1-(4-Fluorophenethyl) piperidin-4-yl)amino)-9H-xanthen-4-yl)-4-morpholino pyridin-2(1H)-one | 581 | 1.08 | |
| 2-30-15 | | 6-(7-((1-(3-Methoxy propyl)piperidin-4-yl) amino)-9H-xanthen-4-yl)-4-morpholino pyridin-2 (1H)-one | 531 | 0.86 | |
| 2-30-16 | | Methyl 5-(4-((5-(4-morpholino-6-oxo-1,6-dihydropyridin-2-yl)-9H-xanthen-2-yl)amino) piperidin-1-yl)pentanoate | 573 | 0.90 | |
| 2-30-17 | | 6-(7-((1-(4-(Hydroxy methyl)phenethyl)piperidin-4-yl)amino)-9H-xanthen-4-yl)-4-morpholino pyridin-2 (1H)-one | 593 | 0.91 | |
| 2-30-18 | | 6-(7-((1-(4-Isopropoxy phenethyl)piperidin-4-yl) amino)-9H-xanthen-4-yl)-4-morpholino pyridin-2(1H)-one | 621 | 1.20 | |
| 2-30-19 | | 4-(2-(4-((5-(4-Morpholino-6-oxo-1,6-dihydropyridin-2-yl)-9H-xanthen-2-yl) amino)piperidin-1-yl)ethyl) benzonitrile | 588 | 1.01 | |

TABLE 82-continued

| Example No. | $R^b$ | Compound Name | MS | RT (min) | $^1$H-NMR (300 MHz) (DMSO-$d_6$) δ: |
|---|---|---|---|---|---|
| 2-30-20 | (methoxymethyl-phenyl-ethyl-N-piperidinyl with methyl) | 6-(7-((1-(4-(Methoxy methyl) phenethyl)piperidin-4-yl) amino)-9H-xanthen-4-yl)-4-morpholino pyridin-2(1H)-one | 607 | 1.03 | |

Example 2-31

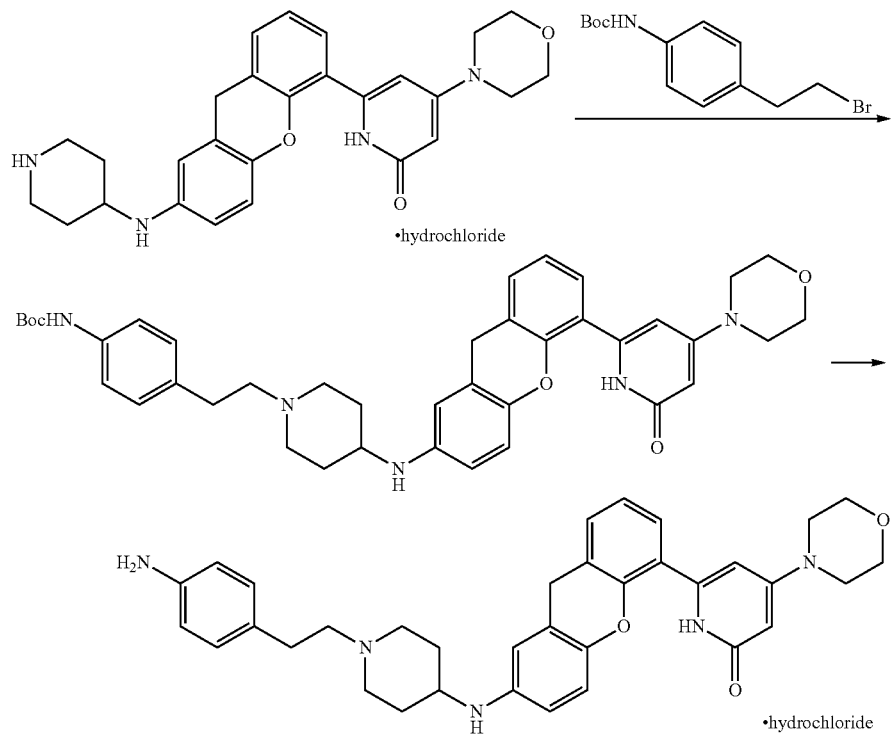

(1)
In the same manner as in Example 2-30-1, the following compound was obtained.

tert-Butyl (4-(2-(4-((5-(4-morpholino-6-oxo-1,6-dihydropyridin-2-yl)-9H-xanthen-2-yl)amino)piperidin-1-yl)ethyl)phenyl)carbamate MS(ESI m/z): 678 (M+H)
RT(min): 1.16

(2)
In the same manner as in Example 1-1, the following compound was obtained.

hydrochloride of 6-(7-((1-(4-aminophenethyl)piperidin-4-yl)amino)-9H-xanthen-4-yl)-4-morpholinopyridin-2(1H)-one MS(ESI m/z): 578 (M+H)
RT(min): 0.81

Example 2-32

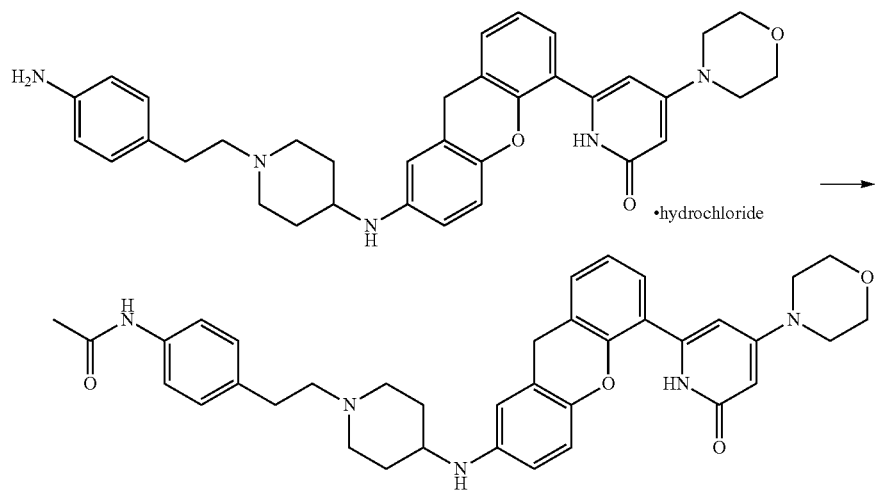

A mixture of hydrochloride (10 mg) of 6-(7-((1-(4-amino-phenethyl)piperidin-4-yl)amino)-9H-xanthen-4-yl)-4-morpholinopyridin-2(1H)-one, methanol (0.28 mL), acetic anhydride (1.3 μL), and sodium hydrogen carbonate (4.7 mg) was stirred at room temperature for 2 hours. Methanol (0.28 mL) and acetic anhydride (1.3 μL) were added thereto, followed by stirring for 2 hours. A saturated sodium hydrogen carbonate aqueous solution was added to the reaction mixture, and the resultant product was extracted with ethyl acetate. The organic layer was washed with a saturated sodium chloride aqueous solution, then, the solvent was distilled off under reduced pressure, and the obtained residues were purified by preparative thin layer silica gel chromatography (chloroform:methanol=9:1), whereby N-(4-(2-(4-((5-(4-morpholino-6-oxo-1,6-dihydropyridin-2-yl)-9H-xanthen-2-yl)amino)piperidin-1-yl)ethyl)phenyl)acetamide (2.7 mg) was obtained.
MS(ESI m/z): 620 (M+H)
RT(min): 0.91 mg) was stirred at room temperature for 5 minutes. A mixture of 6-(7-amino-9H-xanthen-4-yl)-4-morpholinopyridin-2(1H)-one (18 mg) and acetonitrile (100 μL) was added to the reaction mixture, followed by stirring at 40° C. for 2 hours. Lithium bromide (88 mg) was added thereto, followed by stirring for 1.5 hours. After the reaction mixture was cooled to room temperature, water was added thereto, and the resultant product was extracted with ethyl acetate. The organic layer was washed with a saturated sodium chloride aqueous solution, and the solvent was distilled off under reduced pressure. The obtained residues were purified by preparative reversed phase HPLC (0.1% formic acid aqueous solution-0.1% solution of formic acid in acetonitrile), whereby 6-(7-((trans-1-benzyl-3-hydroxypiperidin-4-yl)amino)-9H-xanthen-4-yl)-4-morpholinopyridin-2(1H)-one (2.3 mg) was obtained.
MS(ESI m/z): 565 (M+H)
RT(min): 0.93

Example 2-33

Example 2-34

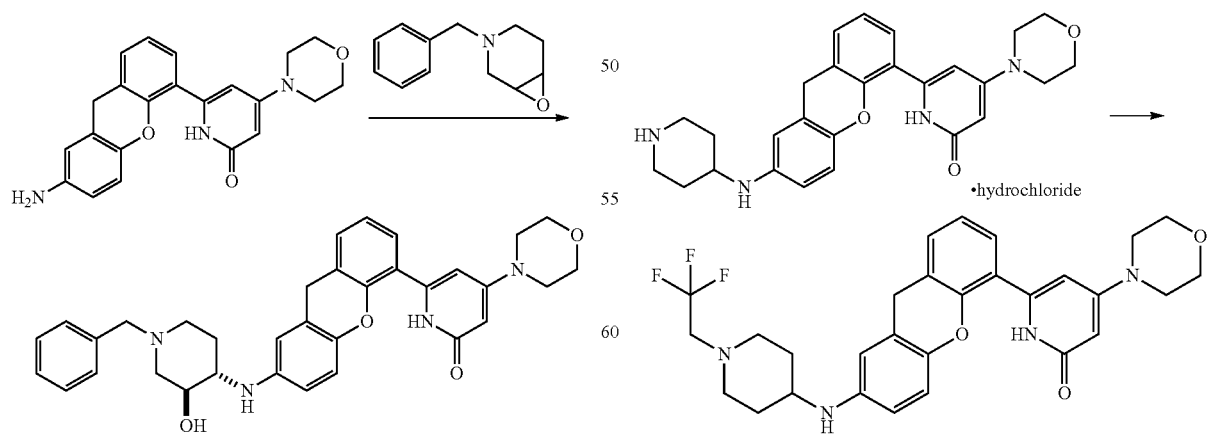

A mixture of lithium bromide (7.6 mg), acetonitrile (120 μL), and 3-benzyl-7-oxa-3-azabicyclo[4.1.0]heptane (7.9

In the same manner as in Example 1-25, the following compound was obtained.

4-Morpholino-6-(7-((1-(2,2,2-trifluoroethyl)piperidin-4-yl)amino)-9H-xanthen-4-yl)pyridin-2(1H)-one MS(ESI m/z): 541 (M+H)
RT(min): 1.09

Example 2-35

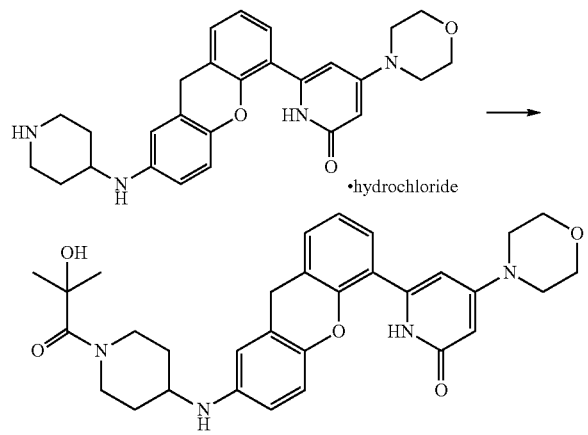

·hydrochloride

In the same manner as in Example 1-2-1 (1), the following compound was obtained.

6-(7-((1-(2-Hydroxy-2-methylpropanoyl)piperidin-4-yl)amino)-9H-xanthen-4-yl)-4-morpholinopyridin-2(1H)-one MS(ESI m/z): 545 (M+H)
RT(min): 0.89

Example 2-36-1

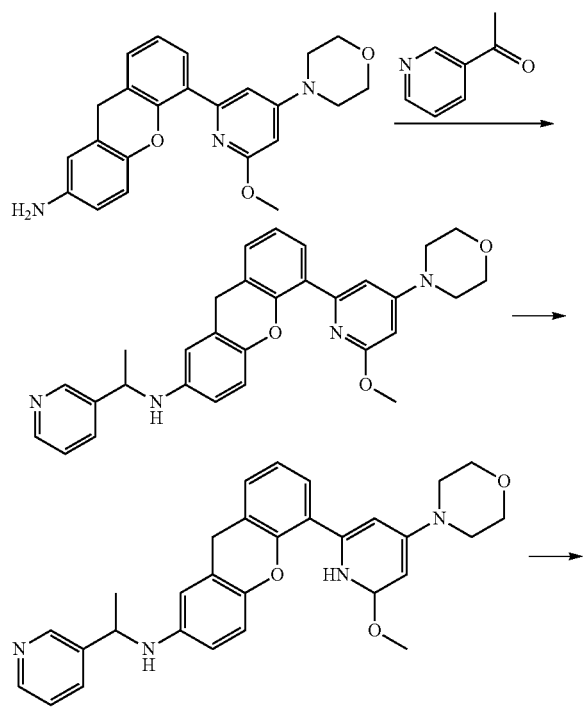

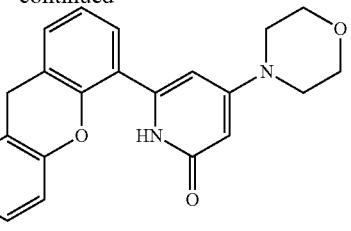

-continued (1)

1-(Pyridin-3-yl)ethanone (71 µL) and tetraisopropyl orthotitanate (1 mL) were added to a solution of 5-(6-methoxy-4-morpholinopyridin-2-yl)-9H-xanthene-2-amine (49 mg) in methanol (1.5 mL) and chloroform (0.5 mL), and the resultant product was irradiated with microwaves (microwave reaction apparatus, 140° C., 0.5 hours, 2.45 GHz, 0 W to 240 W). Sodium borohydride (49 mg) was added thereto, followed by stirring for 24 hours, and a saturated sodium chloride aqueous solution was added thereto, followed by stirring for 24 hours. The insoluble materials were filtered off, and ethyl acetate was added to the filtrate. The organic layer was washed with a saturated sodium chloride aqueous solution, and dried over anhydrous sodium sulfate. The solvent was distilled off under reduced pressure, and the obtained residues were purified by silica gel column chromatography (hexane:ethyl acetate=1:0→0:1), whereby 5-(6-methoxy-4-morpholinopyridin-2-yl)-N-(1-(pyridin-3-yl)ethyl)-9H-xanthene-2-amine (racemic mixture) (12 mg) was obtained.

MS(ESI m/z): 495 (M+H)
RT(min): 0.82

(2)

Chiral resolution was performed on 5-(6-methoxy-4-morpholinopyridin-2-yl)-N-(1-(pyridin-3-yl)ethyl)-9H-xanthene-2-amine (racemic mixture) obtained in Example 2-36-1 (1) by supercritical fluid chromatography, whereby an optically active substance A and an optically active substance B were obtained.

Optically Active Substance A
MS(ESI m/z): 495 (M+H)
RT(min): 0.83
Optically Active Substance B
MS(ESI m/z): 495 (M+H)
RT(min): 0.83

(Supercritical Fluid Chromatography Conditions)
Column: CHIRALPAK IB (manufactured by Daicel Chemical Industries, Ltd.)
Mobile phase: carbon dioxide/0.1% diethylamine-containing methanol (volume ratio: 85/15)
Flow rate: 30 mL/min
Detection wavelength: 254 nm
Temperature: 40° C.
Retention time: 19.5 min (optically active substance A), 21.4 min (optically active substance B)

(3)

A mixture of 5-(6-methoxy-4-morpholinopyridin-2-yl)-N-(1-(pyridin-3-yl)ethyl)-9H-xanthene-2-amine (optically active substance A) (3.6 mg) obtained in Example 2-36-1 (2), 6 mol/L hydrochloric acid (2 mL), and 1,4-dioxane (200 µL) was irradiated with microwaves (microwave reaction apparatus, 150° C., 0.5 hours, 2.45 GHz, 0 W to 240 W). The reaction mixture was cooled to room temperature, then, the solvent was distilled off under reduced pressure, and the obtained residues were purified by preparative thin layer silica gel chromatography (chloroform:methanol=39:1), whereby 4-morpholino-6-(7-((1-(pyridin-3-yl)ethyl)amino)-9H-xanthen-4-yl)pyridin-2(1H)-one (optically active substance A) (0.21 mg) was obtained.

MS(ESI m/z): 481 (M+H)
RT(min): 0.89

Example 2-36-2

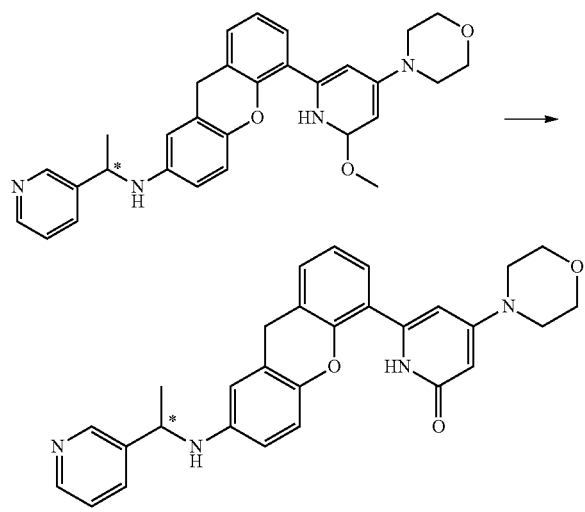

Using 5-(6-methoxy-4-morpholinopyridin-2-yl)-N-(1-(pyridin-3-yl)ethyl)-9H-xanthene-2-amine (optically active substance B) obtained in Example 2-36-1 (2), the following compound was obtained in the same manner as in Example 2-36-1 (3).

4-Morpholino-6-(7-((1-(pyridin-3-yl)ethyl)amino)-9H-xanthen-4-yl)pyridin-2(1H)-one (optically active substance B)

MS(ESI m/z): 481 (M+H)
RT(min): 0.89

Example 2-37

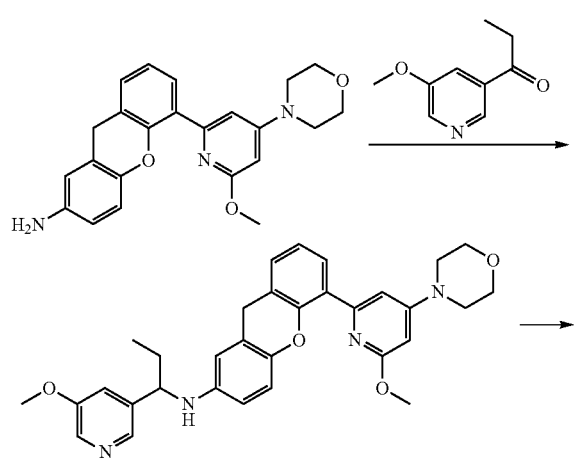

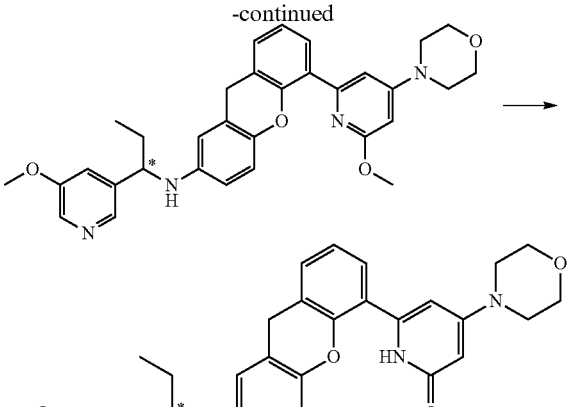

(1)

In the same manner as in Reference Example 1-12-1, the following compound was obtained.

5-(6-Methoxy-4-morpholinopyridin-2-yl)-N-(1-(5-methoxypyridin-3-yl)propyl)-9H-xanthene-2-amine (racemic mixture)

(2)

Chiral resolution was performed on 5-(6-methoxy-4-morpholinopyridin-2-yl)-N-(1-(5-methoxypyridin-3-yl)propyl)-9H-xanthene-2-amine (racemic mixture) obtained in Example 2-37 (1) by supercritical fluid chromatography, whereby an optically active substance A was obtained.

(Supercritical Fluid Chromatography Conditions)

Column: CHIRALPAK IC (manufactured by Daicel Chemical Industries, Ltd.)

Mobile phase: carbon dioxide/0.1% diethylamine-containing methanol (volume ratio: 70/30)

Flow rate: 30 mL/min

Detection wavelength: 254 nm

Temperature: 40° C.

Retention time: 12.3 min (3)

A mixture of 5-(6-methoxy-4-morpholinopyridin-2-yl)-N-(1-(5-methoxypyridin-3-yl)propy)-9H-xanthene-2-amine (optically active substance A) (5.0 mg), sodium iodide (3.0 mg), and acetic acid (2 mL) was irradiated with microwaves (microwave reaction apparatus, 140° C., 0.25 hours, 2.45 GHz, 0 W to 240 W). After the reaction mixture was cooled to room temperature, the solvent was evaporated under reduced pressure, then, a saturated sodium hydrogen carbonate aqueous solution was added thereto, and the resultant product was extracted with chloroform. The organic layer was dried over anhydrous sodium sulfate, and the solvent was distilled off under reduced pressure. The obtained residues were purified by preparative thin layer silica gel chromatography (chloroform:methanol=9:1), whereby 6-(7-((1-(5-methoxypyridin-3-yl)propyl)amino)-9H-xanthen-4-yl)-4-morpholinopyridin-2(1H)-one (optically active substance A) (1.62 mg) was obtained.

MS(ESI m/z): 525 (M+H)
RT(min): 1.09

Example 2-38

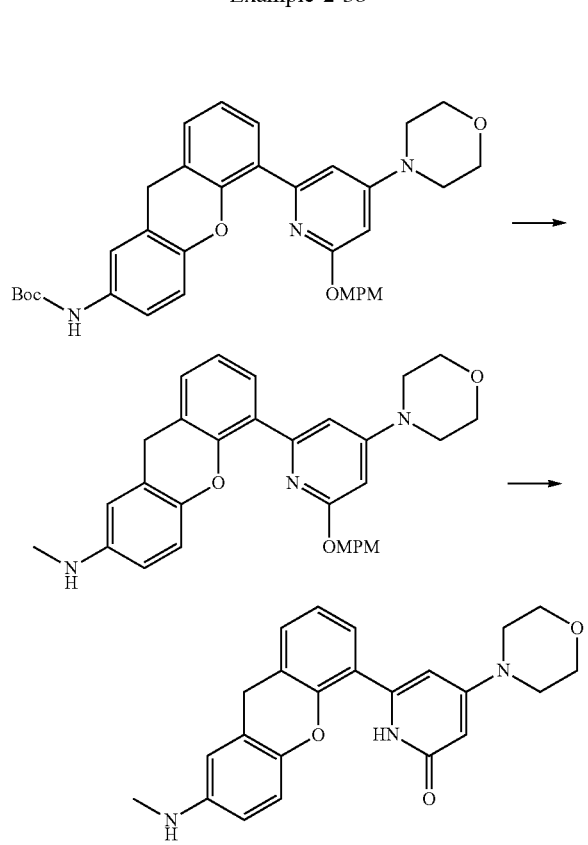

In the same manner as in Example 1-2-1 (2), the following compound was obtained.

5-(6-((4-Methoxybenzyl)oxy)-4-morpholinopyridin-2-yl)-N-methyl-9H-xanthene-2-amine In the same manner as in Example 1-46-1 (5), the following compound was obtained.

6-(7-(Methylamino)-9H-xanthen-4-yl)-4-morpholinopyridin-2(1H)-one

MS(ESI m/z): 390 (M+H)
RT(min): 0.81

Example 2-39

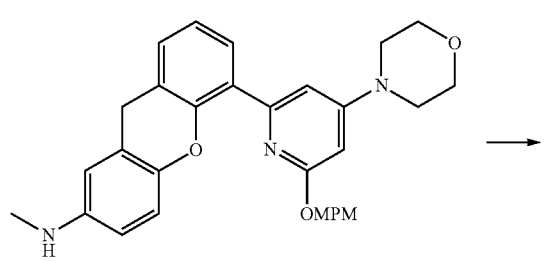

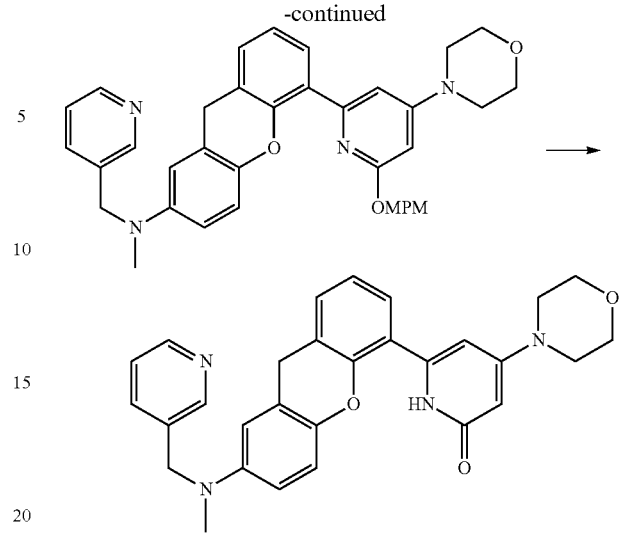

In the same manner as in Example 1-44-1, the following compound was obtained.

5-(6-((4-Methoxybenzyl)oxy)-4-morpholinopyridin-2-yl)-N-methyl-N-(pyridin-3-ylmethyl)-9H-xanthene-2-amine In the same manner as in Example 1-46 (5), the following compound was obtained.

6-(7-(Methyl(pyridin-3-ylmethyl)amino)-9H-xanthen-4-yl)-4-morpholinopyridin-2(1H)-one MS(ESI m/z): 481 (M+H)
RT(min): 0.96

Example 2-40

4.0 mol/mL hydrogen chloride/1,4-dioxane (20 mL) and methanol (10 mL) were added to tert-butyl (5-(6-((4-methoxybenzyl)oxy)-4-morpholinopyridin-2-yl)-9H-xanthen-2-yl)carbamate (1.5 g), followed by stirring at room temperature for 13 hours. A saturated sodium hydrogen carbonate aqueous solution was added to the reaction mixture, then, the resultant product was extracted with chloroform, and the organic layer was dried over anhydrous sodium sulfate. The solvent was distilled off under reduced pressure, and the obtained residues were purified by silica gel column chromatography (chloroform:methanol=1:0→4:1), whereby 6-(7-((4-methoxybenzyl)amino)-9H-xanthen-4-yl)-4-morpholinopyridin-2(1H)-one (70 mg) was obtained.

MS(ESI m/z): 496 (M+H)
RT(min): 1.23

Example 2-41-1

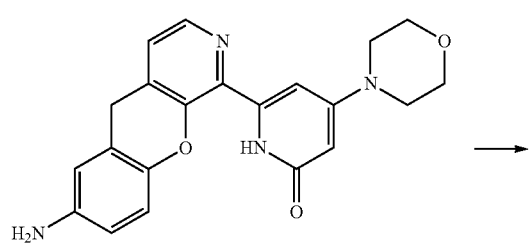

⟶

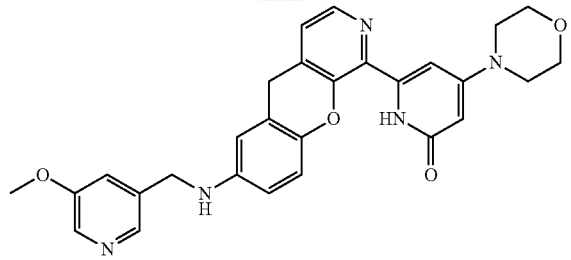

In the same manner as in Example 1-12-1, the following compound was obtained.

6-(7-(((5-Methoxypyridin-3-yl)methyl)amino)-5H-chromeno[2,3-c]pyridin-1-yl)-4-morpholinopyridin-2(1H)-one MS(ESI m/z): 498 (M+H)
RT(min): 0.21

Examples 2-41-2 to 2-41-17

In the same manner as in Example 2-41-1, the following compounds were obtained.

TABLE 83

| Example No. | $R^b$ | Compound Name | MS | RT (min) | $^1$H-NMR (300 MHz) (DMSO-$d_6$) δ: |
|---|---|---|---|---|---|
| 2-41-2 | 6-methylpyridin-2-ylmethyl | 6-(7-(((6-Methyl pyridin-2-yl)methyl)amino)-5H-chromeno[2,3-c]pyridin-1-yl)-4-morpholino pyridin-2(1H)-one | 482 | 0.79 | (CDCl$_3$): 10.23 (1H, s,), 8.25 (1H, d, J = 4.6 Hz). 7.55(1H, t, J = 7.6 Hz),7.49 (1H, d, J = 2.6 Hz), 7.16-7.05 (3H, m), 6.90 (1H, d, J = 9.2 Hz), 6.80 (1H, dd, J = 8.9, 3.0 Hz), 6.48 (1H, d, J = 2.6 Hz), 5.80 (1H, d, J = 2.0 Hz), 4.78 (1H, br s), 4.40 (2H, s), 4.02 (2H, s), 3.88 (4H, t, J = 5.0 Hz), 3.39 (4H, t, J = 5.0 Hz), 2.59 (3H, s) |
| 2-41-3 | 4-chloropyridin-2-ylmethyl | 6-(7-(((4-Chloropyridin-2-yl)methyl)amino)-5H-chromeno[2,3-c]pyridin-1-yl)-4-morpholino pyridin-2(1H)-one | 502 | 1.16 | (CDCl$_3$): 10.21 (1H, s), 8.50 (1H, d, J = 5.3 Hz) 8.25 (1H, d, J = 4.6 Hz), 7.48 (1H, d, J = 2.0 Hz), 7.37 (1H, d, J = 2.0 Hz), 7.24 (1H, dd, J = 5.3, 2.0 Hz), 7.15 (1H, d, J = 4.6 Hz), 6.90 (1H, d, J = 8.6 Hz), 6.58 (1H, dd, J = 8.6, 2.6 Hz), 6.45(1H, d, J = 2.6 Hz), 5.80 (1H, d, J = 2.6 Hz), 4.70 (1H, t, J = 5.9 Hz), 4.45 (2H, d, J = 5.3 Hz), 4.02 (2H, s), 3.88 (4H, t, J = 5.0 Hz), 3.39 (4H, t, J = 5.0 Hz). |
| 2-41-4 | 4-methoxypyridin-2-ylmethyl | 6-(7-(((4-Methoxy pyridin-2-yl)methyl)amino)-5H-chromeno[2,3-c]pyridin-1-yl)-4-morpholino pyridin-2(1H)-one | 498 | 0.78 | (CDCl$_3$): 10.23 (1H, s), 8.42 (1H, d, J = 5.9 Hz), 8.24 (1H, d, J = 4.6 Hz), 7.48 (1H, d, J = 2.6 Hz), 7.15 (1H, d, J = 4.6 Hz), 6.89-6.87 (2H, m), 6.74 (1H, dd, J = 5.9, 2.6 Hz), 6.59 (1H, dd, J = 8.6, 2.6 Hz), 8.47 (1H, d, J = 2.6 Hz) 5.80 (1H, d, J = 2.6 Hz), 4.74 (1H, s), 4.39 (2H, s), 4.01 (2H, s), 3.88 (4H, t, J = 5.0 Hz), 3.84 (3H, s), 3.39 (4H, t, J = 5.0 Hz). |
| 2-41-5 | 1-(4-methoxyphenethyl)-4-methylpiperidin-4-yl | 6-(7-((1-(4-Methoxy phenethyl)piperidin-4-yl)amino)-5H-chromeno[2,3-c]pyridin-1-yl)-4-morpholino pyridin-2(1H)-one | 594 | 0.99 | |

TABLE 83-continued

| Example No. | $R^b$ | Compound Name | MS | RT (min) | $^1$H-NMR (300 MHz) (DMSO-$d_6$) δ: |
|---|---|---|---|---|---|
| 2-41-6 | | 6-(7-(((4-Cyclopropyl pyridin-2-yl)methyl)amino)-5H-chromeno[2,3-c]pyridin-1-yl)-4-morpholino pyridin-2(1H)-one | 508 | 0.88 | |
| 2-41-7 | | 6-(7-(((4-Methyl pyridin-2-yl)methyl)amino)-5H-chromeno[2,3-c]pyridin-1-yl)-4-morpholino pyridin-2(1H)-one | 482 | 0.80 | |
| 2-41-8 | | 6-(7-(((6-Chloropyridin-2-yl)methlyl)anlino)-5H-chromeno[2,3-c]pyridin-1-yl)-4-morpholino pyridin-2(1H)-one | 502 | 1.25 | |
| 2-41-9 | | 6-(7-(((5-Chloropyridin-3-yl)methyl)amino)-5H-chromeno[2,3-c]pyridin-1-yl)-4-morpholino pyridin-2(1H)-one | 502 | 1.17 | |

TABLE 84

| Example No. | $R^b$ | Compound Name | MS | RT (min) | $^1$H-NMR (300 MHz) (DMSO-$d_6$) δ: |
|---|---|---|---|---|---|
| 2-41-10 | | 6-(7-(((5,6-Dimethoxy pyridin-3-yl)methyl)amino)-5H-chromeno[2,3-c]pyridin-1-yl)-4-morpholino pyridin-2(1H)-one | 528 | 1.10 | |
| 2-41-11 | | 6-(7-(((5-Cyclopropyl pyridin-3-yl)methyl)amino)-5H-chromeno[2,3-c]pyridin-1-yl)-4-morpholino pyridin-2(1H)-one | 508 | 0.89 | |

TABLE 84-continued

| Example No. | R$^b$ | Compound Name | MS | RT (min) | $^1$H-NMR (300 MHz) (DMSO-d$_6$) δ: |
|---|---|---|---|---|---|
| 2-41-12 | | 6-(7-(((3-Methoxy pyridin-2-yl)methyl)amino)-5H-chromeno[2,3-c]pyridin-1-yl)-4-morpholino pyridin-2(1H)-one | 498 | 0.89 | |
| 2-41-13 | | 6-(7-((1-(6-Fluoropyridin-2-yl)ethyl)amino)-5H-chromeno[2,3-c]pyridin-1-yl]-4-morpholino pyridin-2(1H)-one | 500 | 1.24 | |
| 2-41-14 | | 6-(7-((1-4-Methoxy pyridin-2-yl)ethyl)amino)-5H-chromeno[2,3-c]pyridin-1-yl)-4-morpholino pyridin-2(1H)-one | 512 | 0.83 | |
| 2-41-15 | | 6-(((1-(4-Morpholino-6-oxo-1,6-dihydropyridin-2-yl)-5H-chromeno[2,3-c]pyridin-7-yl)amino)methyl)picolinonitrile | 493 | 1.14 | |
| 2-41-16 | | 2-(((1-(4-Morpholino-6-oxo-1,6-dihydropyridin-2-yl)-5H-chromeno[2,3-c]pyridin-7-yl)amino)methyl)isonicotinonitrile | 493 | 1.08 | |
| 2-41-17 | | 5-(((1-(4-Morpholino-6-oxo-1,6-dihydropyridin-2-yl)-5H-chromeno[2,3-c]pyridin-7-yl)amino)methyl)thiophene-2-carbonitrile | 498 | 1.23 | |

Example 2-42-1

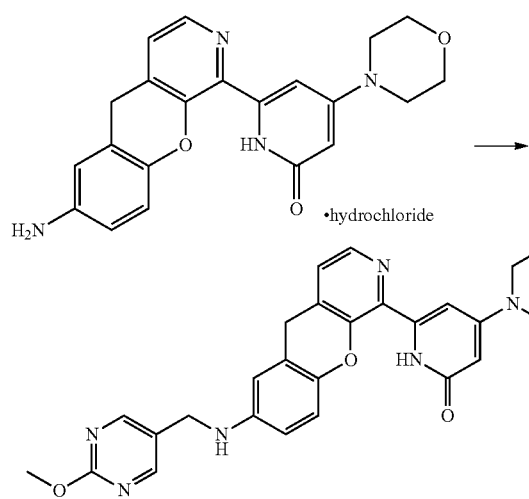

In the same manner as in Example 1-12-1, the following compound was obtained.

6-(7-(((2-Methoxypyrimidin-5-yl)methyl)amino)-5H-chromeno[2,3-c]pyridin-1-yl)-4-morpholinopyridin-2(1H)-one MS(ESI m/z): 499 (M+H)
RT(min): 1.00

Example 2-42-2

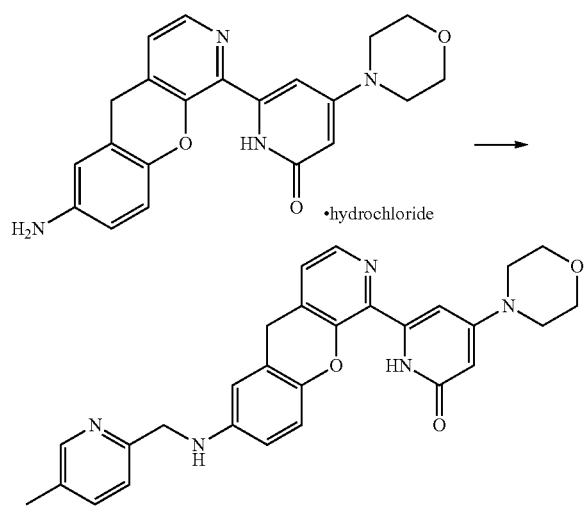

In the same manner as in Example 2-42-1, the following compound was obtained.

6-(7-(((5-Methylpyridin-2-yl)methyl)amino)-5H-chromeno[2,3-c]pyridin-1-yl)-4-morpholinopyridin-2(1H)-one MS(ESI m/z): 482 (M+H)
RT(min): 0.83

Example 2-42-3

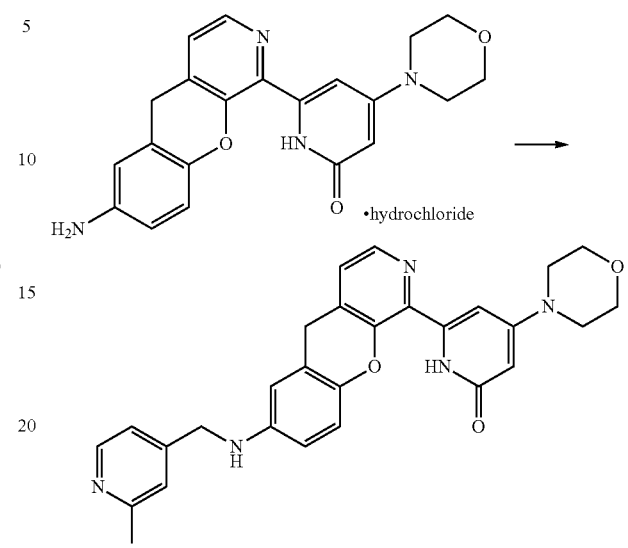

In the same manner as in Example 2-42-1, the following compound was obtained.

6-(7-(((2-Methylpyridin-4-yl)methyl)amino)-5H-chromeno[2,3-c]pyridin-1-yl)-4-morpholinopyridin-2(1H)-one MS(ESI m/z): 482 (M+H)
RT(min): 0.78

Example 2-42-4

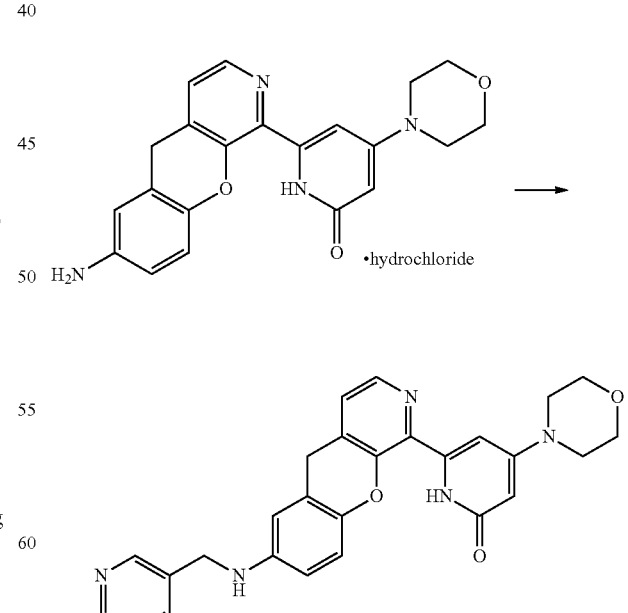

In the same manner as in Example 2-42-1, the following compound was obtained.

6-(7-(((6-Methylpyridin-3-yl)methyl)amino)-5H-chromeno[2,3-c]pyridin-1-yl)-4-morpholinopyridin-2(1H)-one MS(ESI m/z): 482 (M+H)
RT(min): 0.79

Example 2-42-5

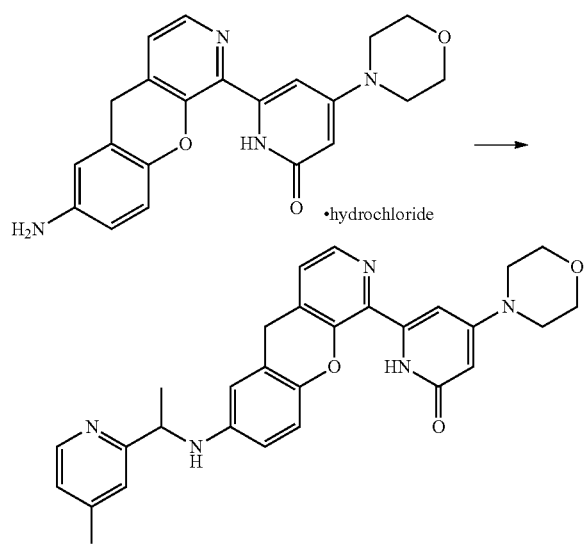

In the same manner as in Example 2-42-1, the following compound was obtained.

6-(7-((1-(4-Methylpyridin-2-yl)ethyl)amino)-5H-chromeno[2,3-c]pyridin-1-yl)-4-morpholinopyridin-2(1H)-one MS(ESI m/z): 496 (M+H)
RT(min): 0.85

Example 2-42-6

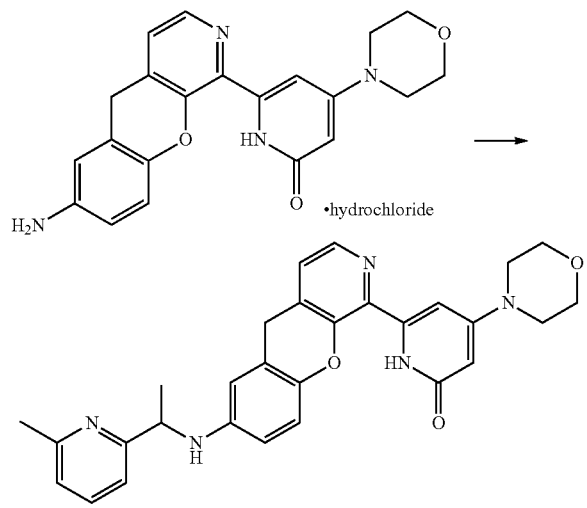

In the same manner as in Example 2-42-1, the following compound was obtained.

6-(7-(((1-(6-Methylpyridin-2-yl)ethyl)amino)-5H-chromeno[2,3-c]pyridin-1-yl)-4-morpholinopyridin-2(1H)-one MS(ESI m/z): 496 (M+H)
RT(min): 0.86

Example 2-42-7

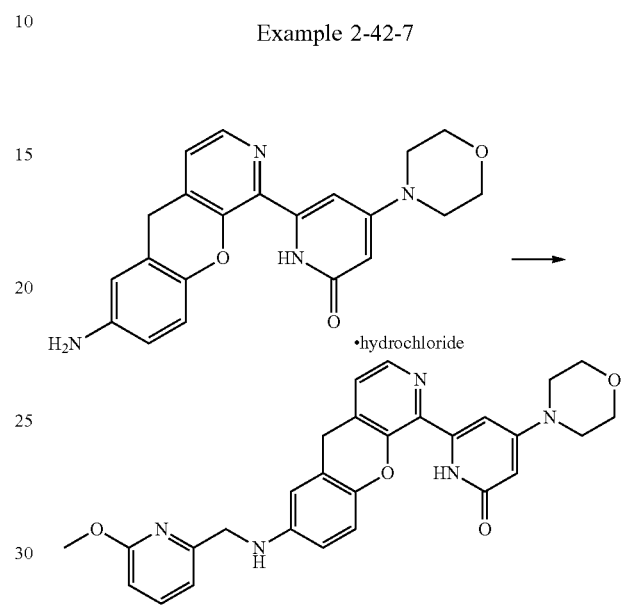

In the same manner as in Example 2-42-1, the following compound was obtained.

6-(7-(((6-Methoxypyridin-2-yl)methyl)amino)-5H-chromeno[2,3-c]pyridin-1-yl)-4-morpholinopyridin-2(1H)-one MS(ESI m/z): 498 (M+H)
RT(min): 1.25

Example 2-43

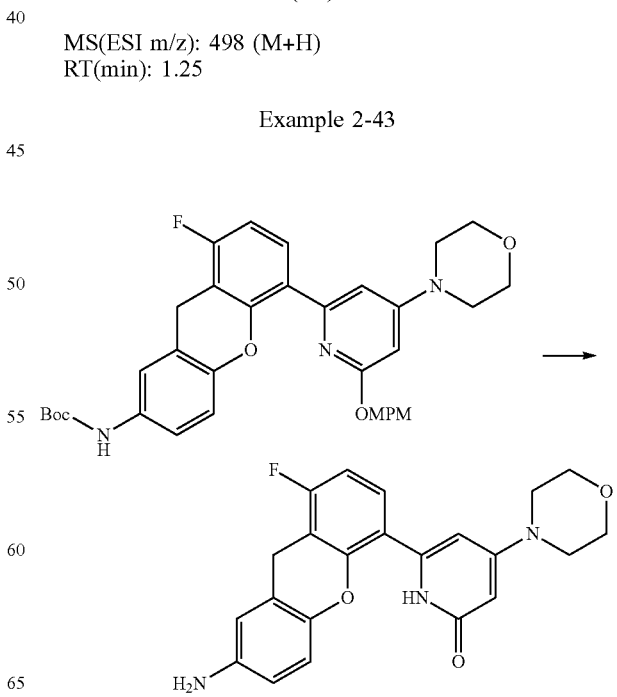

In the same manner as in Example 2-1-1, the following compound was obtained.

6-(7-Amino-1-fluoro-9H-xanthen-4-yl)-4-morpholinopyridin-2(1H)-one

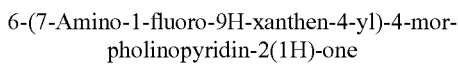

MS(ESI m/z): 394 (M+H)
RT(min): 0.80

Example 2-44-1

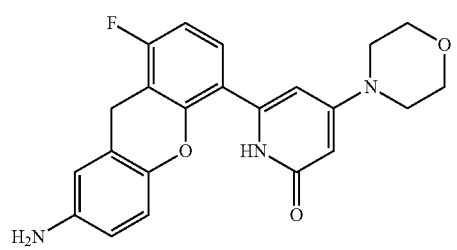

→

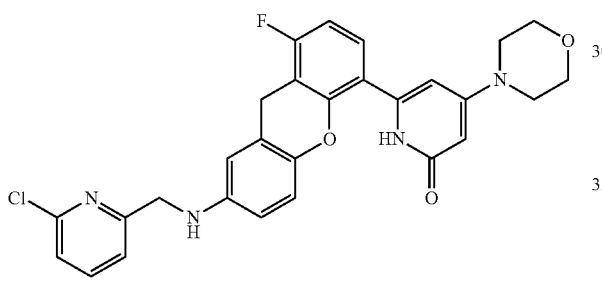

In the same manner as in Example 1-12-1, the following compound was obtained.

6-(7-(((6-Chloropyridin-2-yl)methyl)amino)-1-fluoro-9H-xanthen-4-yl)-4-morpholinopyridin-2(1H)-one MS(ESI m/z): 519 (M+H)
RT(min): 1.36

Example 2-44-2

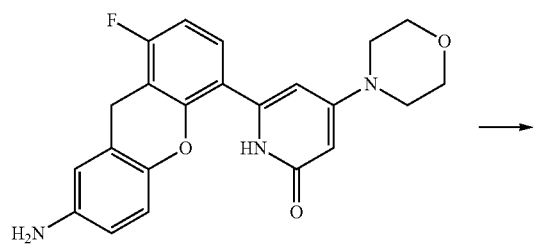

→

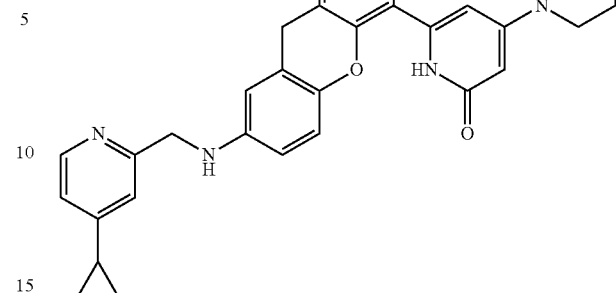

In the same manner as in Example 2-44-1, the following compound was obtained.

6-(7-(((4-Cyclopropylpyridin-2-yl)methyl)amino)-1-fluoro-9H-xanthen-4-yl)-4-morpholinopyridin-2(1H)-one MS(ESI m/z): 525 (M+H)
RT(min): 1.01

Example 2-44-3

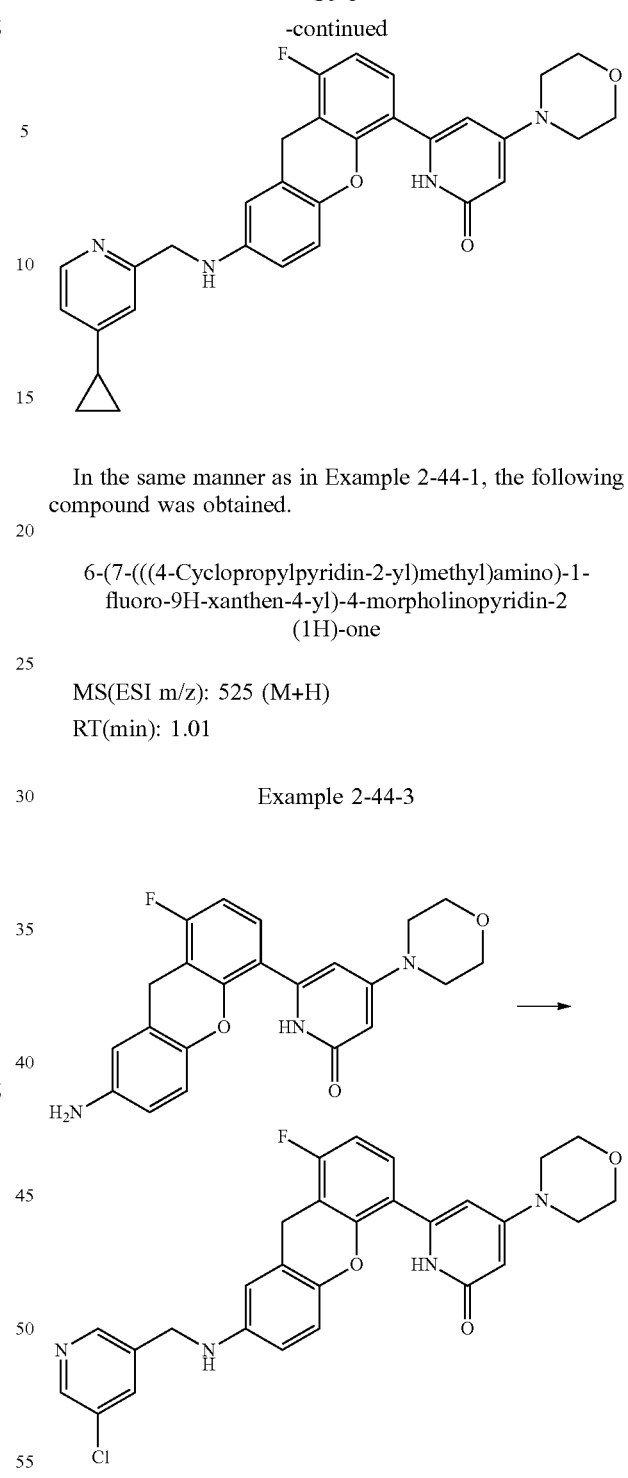

In the same manner as in Example 2-44-1, the following compound was obtained.

6-(7-(((5-Chloropyridin-3-yl)methyl)amino)-1-fluoro-9H-xanthen-4-yl)-4-morpholinopyridin-2(1H)-one MS(ESI m/z): 519 (M+H)
RT(min): 1.29

Example 2-45

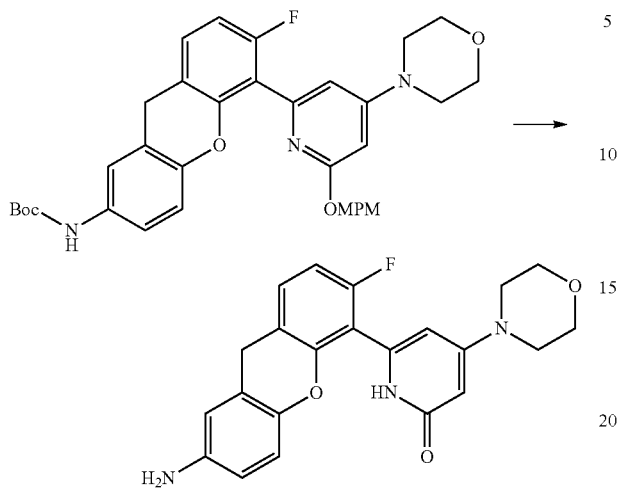

In the same manner as in Example 2-1-1, the following compound was obtained.

6-(7-Amino-3-fluoro-9H-xanthen-4-yl)-4-morpholinopyridin-2(1H)-one

MS(ESI m/z): 394 (M+H)
RT(min): 0.76

Example 2-46-1

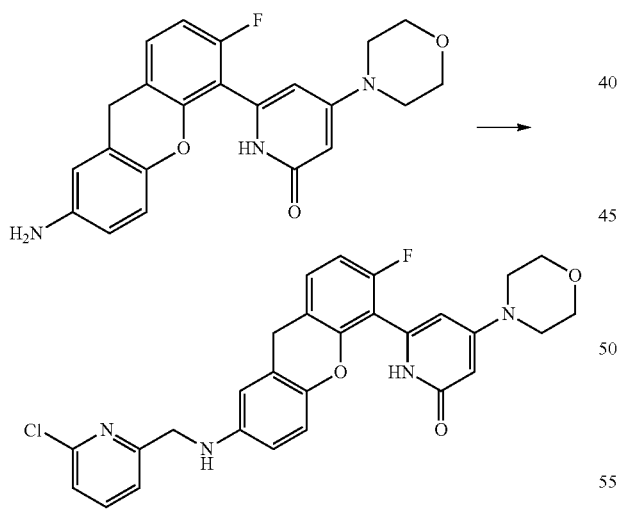

In the same manner as in Example 1-12-1, the following compound was obtained.

6-(7-(((6-Chloropyridin-2-yl)methyl)amino)-3-fluoro-9H-xanthen-4-yl)-4-morpholinopyridin-2(1H)-one ¹H-NMR (CDCl₃, 300 MHz) δ: 9.30 (1H, brs), 7.61 (1H, t, J=7.9 Hz), 7.29-7.15 (3H, m), 6.87 (1H, d, J=8.6 Hz), 6.84 (1H, dd, J=9.2, 8.6 Hz), 6.47 (1H, dd, J=8.6, 2.6 Hz), 6.39 (1H, d, J=2.6 Hz), 6.12 (1H, d, J=2.6 Hz), 5.66 (1H, d, J=2.6 Hz), 5.42-5.28 (1H, m), 4.41 (2H, d, J=4.6 Hz), 3.96 (2H, s), 3.80 (4H, t, J=5.0 Hz), 3.27 (4H, t, J=5.0 Hz).

MS(ESI m/z): 519 (M+H)
RT(min): 1.30

Example 2-46-2

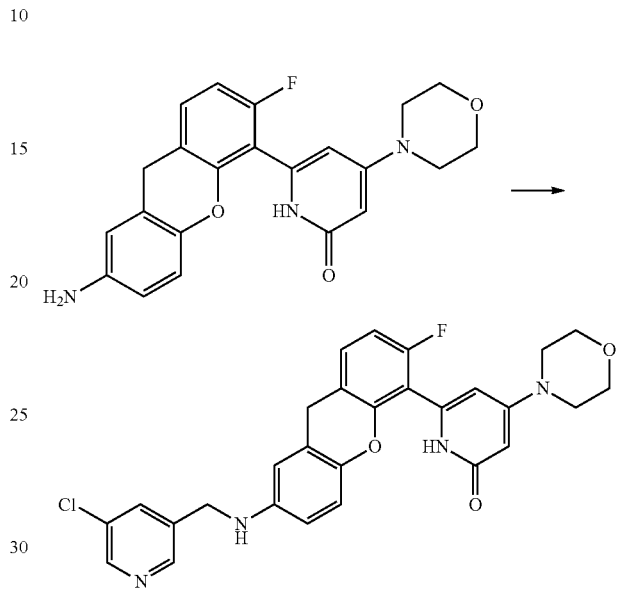

In the same manner as in Example 2-46-1, the following compound was obtained.

6-(7-(((5-Chloropyridin-3-yl)methyl)amino)-3-fluoro-9H-xanthen-4-yl)-4-morpholinopyridin-2(1H)-one ¹H-NMR (CDCl₃, 300 MHz) δ: 8.52-8.49 (2H, brm), 8.50-8.46 (1H, brm), 7.72-7.68 (1H, brm), 7.19 (1H, dd, J=8.6, 5.9 Hz), 6.89 (1H, d, J=9.2 Hz), 6.85 (1H, dd, J=8.8, 8.6 Hz), 6.48 (1H, dd, J=9.2, 2.6 Hz), 6.36 (1H, d, J=2.6 Hz), 6.14 (1H, d, J=2.0 Hz), 5.73 (1H, d, J=2.0 Hz), 4.35 (2H, s), 4.06-3.98 (1H, m), 3.96 (2H, s), 3.81 (4H, t, J=5.0 Hz), 3.31 (4H, t, J=5.0 Hz).

MS(ESI m/z): 519 (M+H)
RT(min): 1.23

Example 2-46-3

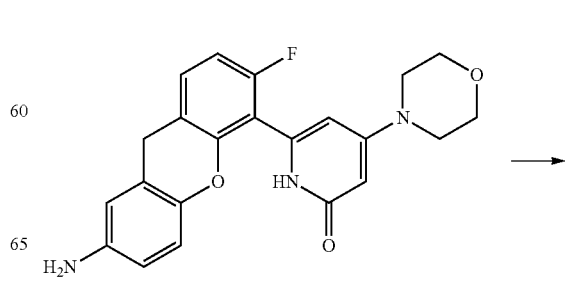

-continued

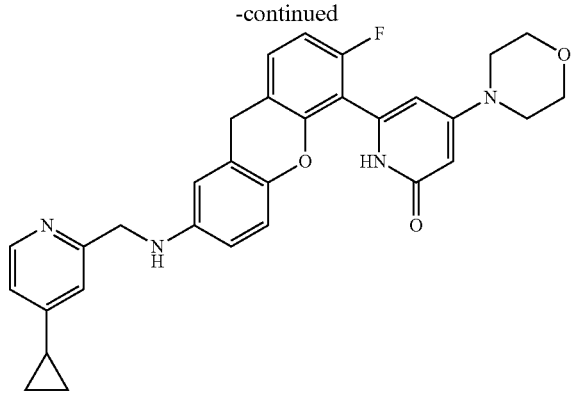

In the same manner as in Example 2-46-1, the following compound was obtained.

6-(7-(((4-Cyclopropylpyridin-2-yl)methyl)amino)-3-fluoro-9H-xanthen-4-yl)-4-morpholinopyridin-2(1H)-one ¹H-NMR (CDCl₃, 300 MHz) δ: 8.67 (1H, brs), 8.39 (1H, d, J=4.6 Hz), 7.19 (1H, dd, J=8.6, 5.9 Hz), 7.01 (1H, s), 6.92-6.80 (3H, m), 6.53 (1H, dd, J=8.9, 2.6 Hz), 6.44 (1H, d, J=2.6 Hz), 6.14 (1H, d, J=2.6 Hz), 5.72 (1H, d, J=2.6 Hz), 4.74-4.61 (1H, m), 4.35 (2H, s), 3.97 (2H, s), 3.81 (4H, t, J=5.0 Hz), 3.30 (4H, t, J=5.0 Hz), 1.85 (1H, tt, J=8.6, 4.6 Hz), 1.08 (2H, ddd, J=8.6, 6.6, 5.0 Hz), 0.78 (2H, ddd, J=6.6, 5.0, 4.6 Hz).
MS(ESI m/z): 525 (M+H)
RT(min): 0.97

Example 2-46-4

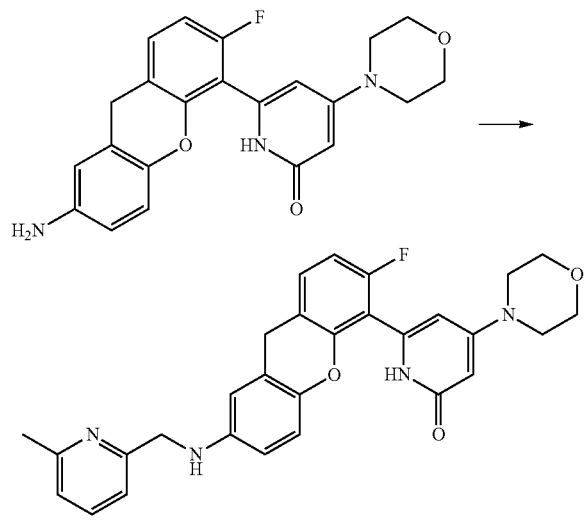

In the same manner as in Example 2-46-1, the following compound was obtained.

6-(3-Fluoro-7-(((6-methylpyridin-2-yl)methyl)amino)-9H-xanthen-4-yl)-4-morpholinopyridin-2(1H)-one ¹H-NMR (CDCl₃, 300 MHz) δ: 9.08 (1H, brs), 7.55 (1H, t, J=7.9 Hz), 7.20 (1H, dd, J=9.2, 5.9 Hz), 7.13 (1H, d, J=7.9 Hz), 7.06 (1H, d, J=7.3 Hz), 6.89 (1H, d, J=8.6 Hz), 6.85 (1H, t, J=9.2 Hz), 6.52 (1H, dd, J=8.6, 2.6 Hz), 6.45 (1H, d, J=2.6 Hz), 6.14 (1H, d, J=2.0 Hz), 5.70 (1H, d, J=2.0 Hz), 5.43-5.28 (1H, brm), 4.39 (2H, s), 3.98 (2H, s), 3.81 (4H, t, J=4.6 Hz), 3.30 (4H, t, J=4.6 Hz), 2.59 (3H, s).
MS(ESI m/z): 499 (M+H)
RT(min): 0.90

Example 2-46-5

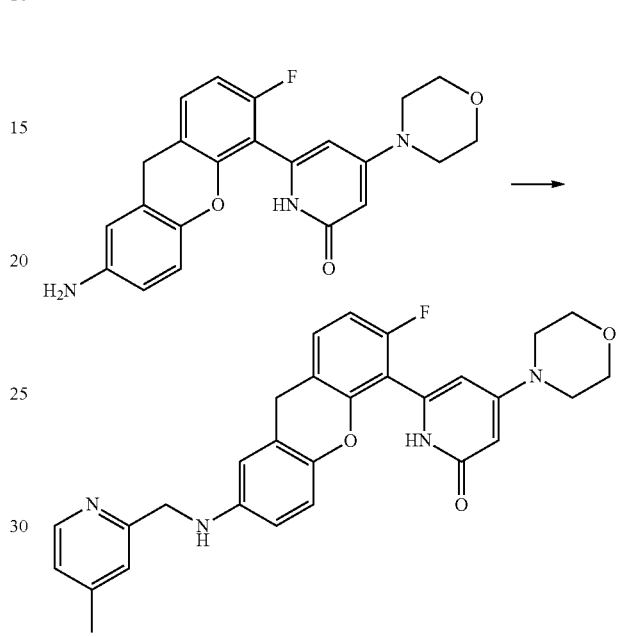

In the same manner as in Example 2-46-1, the following compound was obtained.

6-(3-Fluoro-7-(((4-methylpyridin-2-yl)methyl)amino)-9H-xanthen-4-yl)-4-morpholinopyridin-2(1H)-one ¹H-NMR (CDCl₃, 300 MHz) δ: 9.00 (1H, brs), 8.44 (1H, d, J=5.3 Hz), 7.20 (1H, dd, J=8.6, 5.9 Hz), 7.16 (1H, s), 7.03 (1H, d, J=5.3 Hz), 6.89 (1H, d, J=8.6 Hz), 6.85 (1H, dd, J=9.2, 8.6 Hz), 6.52 (1H, dd, J=8.6, 2.6 Hz), 6.45 (1H, d, J=2.6 Hz), 6.14 (1H, d, J=2.6 Hz), 5.70 (1H, d, J=2.6 Hz), 5.43-5.28 (1H, m), 4.39 (2H, s), 3.98 (2H, s), 3.81 (4H, t, J=4.6 Hz), 3.30 (4H, t, J=4.6 Hz), 2.35 (3H, s).
MS(ESI m/z): 499 (M+H)
RT(min): 0.91

Example 2-47

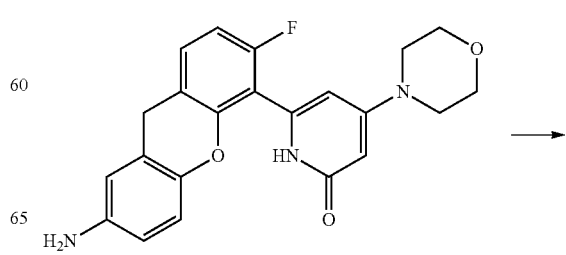

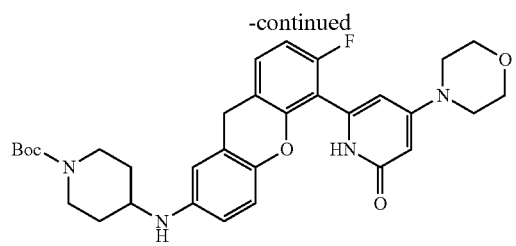

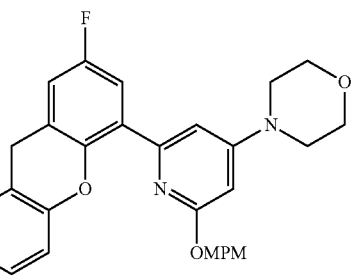

Example 2-48-1

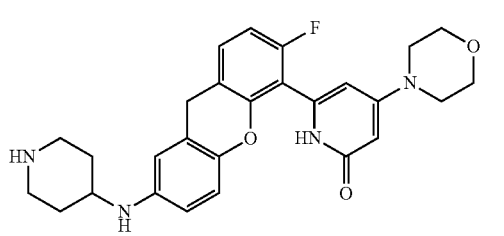

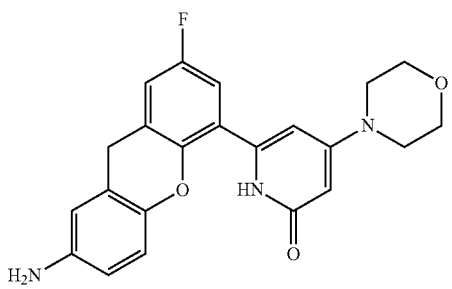

(1)

In the same manner as in Example 1-12-1, the following compound was obtained.

tert-Butyl 4-((6-fluoro-5-(4-morpholino-6-oxo-1,6-dihydropyridin-2-yl)-9H-xanthen-2-yl)amino)piperidine-1-carboxylate MS(ESI m/z): 577 (M+H)

RT(min): 1.26

(2)

In the same manner as in Example 1-4, the following compound was obtained.

6-(3-Fluoro-7-(piperidin-4-ylamino)-9H-xanthen-4-yl)-4-morpholinopyridin-2(1H)-one MS(ESI m/z): 477 (M+H)

RT(min): 0.78

(3)

In the same manner as in Example 1-27, the following compound was obtained.

6-(3-Fluoro-7-((1-(4-methoxyphenethyl)piperidin-4-yl)amino)-9H-xanthen-4-yl)-4-morpholinopyridin-2(1H)-one MS(ESI m/z): 611 (M+H)

RT(min): 1.03

A mixture of tert-butyl (7-fluoro-5-(6-((4-methoxybenzyl)oxy)-4-morpholinopyridin-2-yl)-9H-xanthen-2-yl)carbamate (181 mg) and 4.0 mol/L hydrogen chloride/1,4-dioxane (2.0 mL) was stirred at room temperature for 4 hours. Ethyl acetate was added to the reaction mixture, and the supernatant was removed by being decanted. A saturated sodium hydrogen carbonate aqueous solution was added to the obtained residue, and the resultant product was extracted with chloroform. The solvent was distilled off under reduced pressure, and the obtained residues were purified by silica gel column chromatography (chloroform:methanol=1:0→9:1, NH silica), whereby 6-(7-amino-2-fluoro-9H-xanthen-4-yl)-4-morpholinopyridin-2(1H)-one (81 mg) was obtained.

MS(ESI m/z): 394 (M+H)

RT(min): 0.79

Example 2-48-2

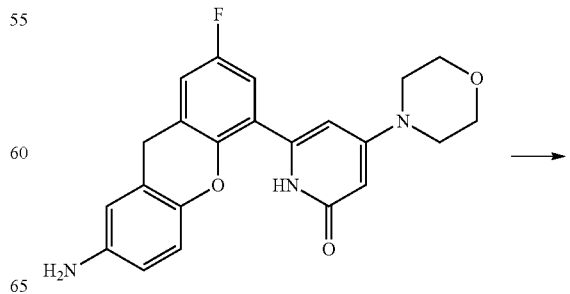

-continued

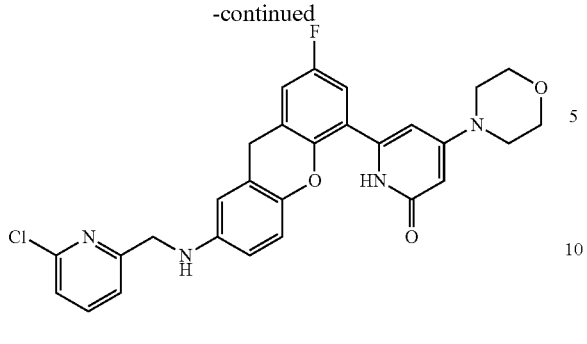

In the same manner as in Example 1-12-1, the following compound was obtained.

6-(7-(((6-Chloropyridin-2-yl)methyl)amino)-2-fluoro-9H-xanthen-4-yl)-4-morpholinopyridin-2(1H)-one MS(ESI m/z): 519 (M+H)
RT(min): 1.34

Example 2-48-3

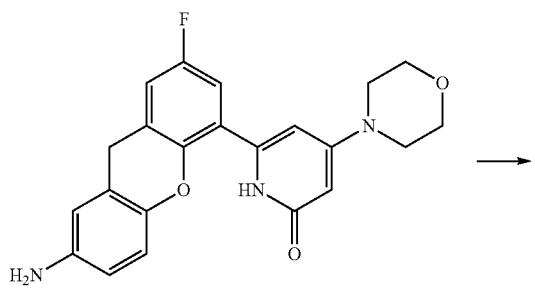

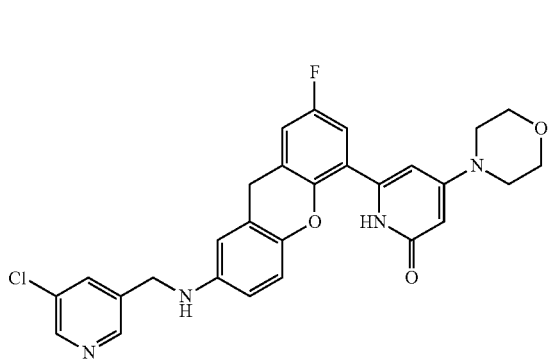

In the same manner as in Example 2-48-2, the following compound was obtained.

6-(7-(((5-Chloropyridin-3-yl)methyl)amino)-2-fluoro-9H-xanthen-4-yl)-4-morpholinopyridin-2(1H)-one MS(ESI m/z): 519 (M+H)
RT(min): 1.27

Example 2-48-4

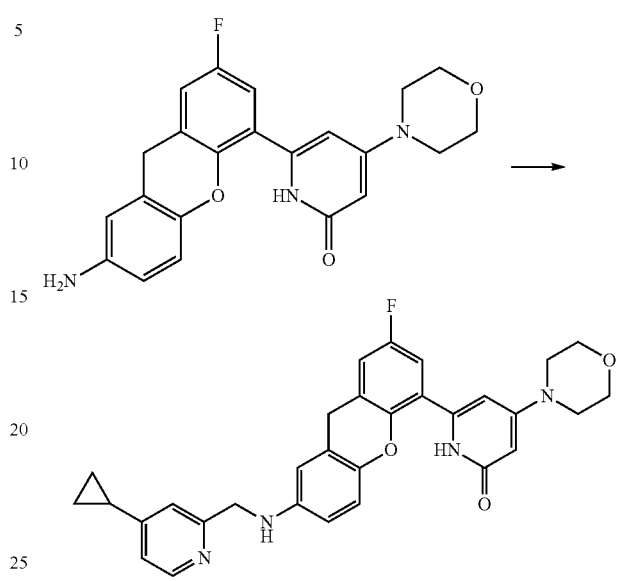

In the same manner as in Example 2-48-2, the following compound was obtained.

6-(7-(((4-Cyclopropylpyridin-2-yl)methyl)amino)-2-fluoro-9H-xanthen-4-yl)-4-morpholinopyridin-2(1H)-one MS(ESI m/z): 525 (M+H)
RT(min): 0.99

Example 2-49-1

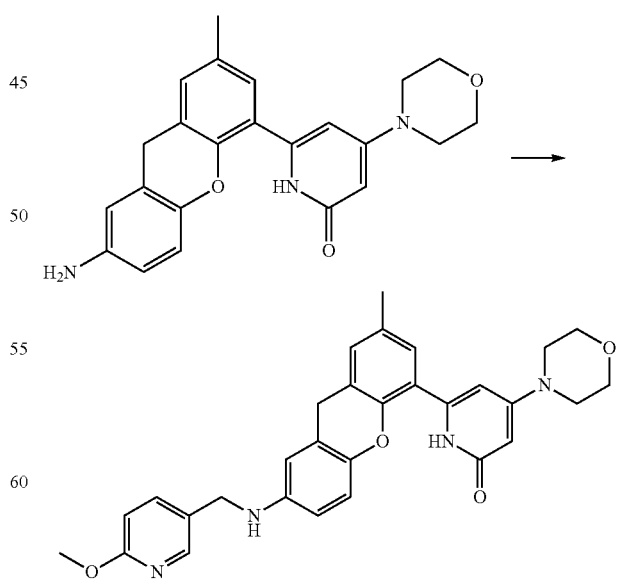

In the same manner as in Example 1-44-1, the following compound was obtained.

605

6-(7-(((6-Methoxypyridin-3-yl)methyl)amino)-2-methyl-9H-xanthen-4-yl)-4-morpholinopyridin-2(1H)-one MS(ESI m/z): 511 (M+H)
RT(min): 1.24

Example 2-49-2

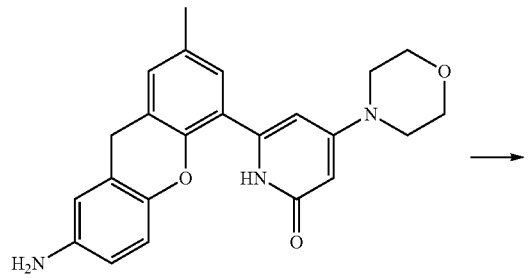

↓

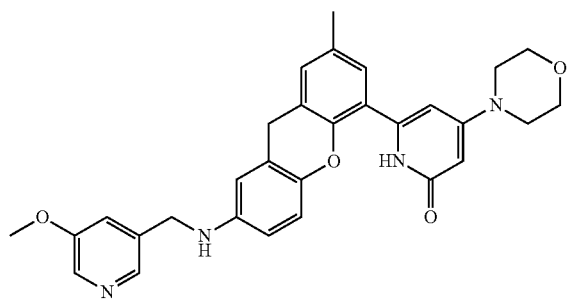

In the same manner as in Example 2-49-1, the following compound was obtained.

6-(7-(((5-Methoxypyridin-3-yl)methyl)amino)-2-methyl-9H-xanthen-4-yl)-4-morpholinopyridin-2(1H)-one MS(ESI m/z): 511 (M+H)
RT(min): 1.01

Example 2-50

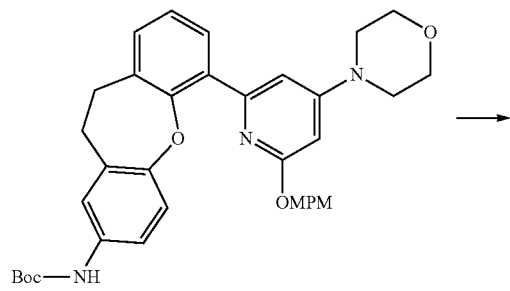

↓

606

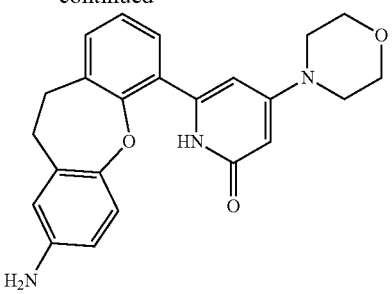

In the same manner as in Example 2-1-1, the following compound was obtained.

6-(8-Amino-10,11-dihydrodibenz[b,f]oxepin-4-yl)-4-morpholinopyridin-2(1H)-one

MS(ESI m/z): 390 (M+H)
RT(min): 0.82

Example 2-51-1

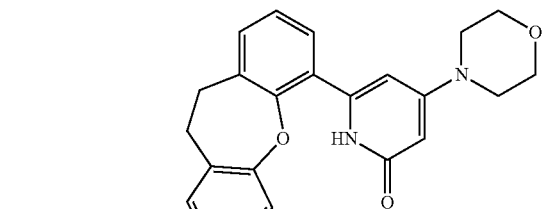

↓

In the same manner as in Example 1-44-1, the following compound was obtained.

6-(8-((1-Methylpiperidin-4-yl)amino)-10,11-dihydrodibenz[b,f]oxepin-4-yl)-4-morpholinopyridin-2(1H)-one MS(ESI m/z): 487 (M+H)
RT(min): 0.92

Example 2-51-2

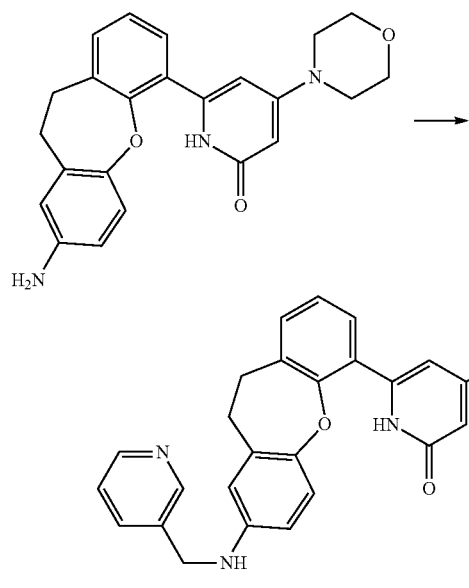

In the same manner as in Example 2-51-1, the following compound was obtained.

4-Morpholino-6-(8-((pyridin-3-ylmethyl)amino)-10,11-dihydrodibenz[b,f]oxepin-4-yl)pyridin-2(1H)-one MS(ESI m/z): 481 (M+H)
RT(min): 0.89

Example 2-51-3

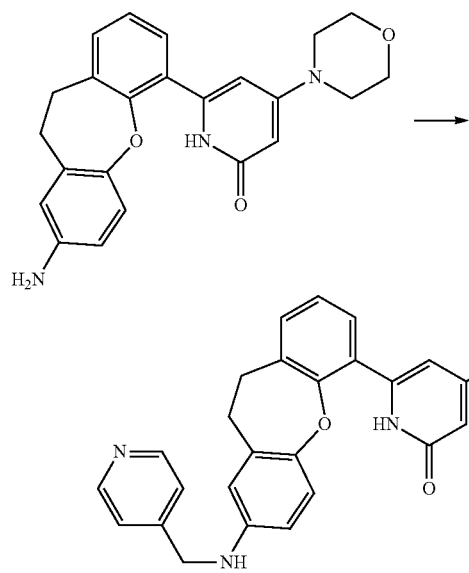

In the same manner as in Example 2-51-1, the following compound was obtained.

4-Morpholino-6-(8-((pyridin-4-ylmethyl)amino)-10,11-dihydrodibenz[b,f]oxepin-4-yl)pyridin-2(1H)-one MS(ESI m/z): 481 (M+H)
RT(min): 0.88

Example 2-52-1

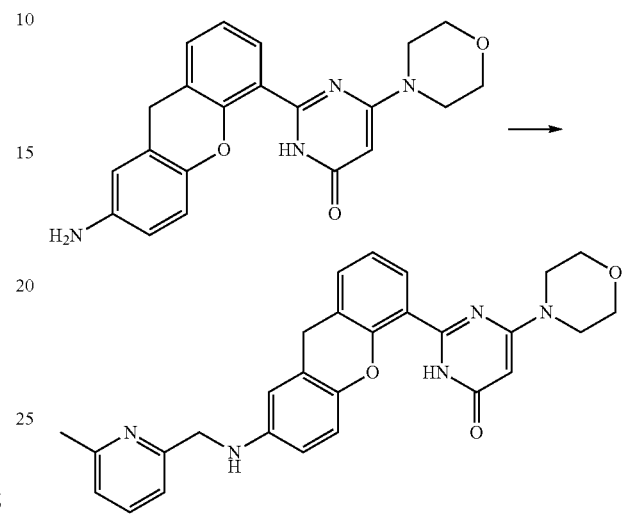

In the same manner as in Example 1-44-1, the following compound was obtained.

2-(7-(((6-Methylpyridin-2-yl)methyl)amino)-9H-xanthen-4-yl)-6-morpholino pyrimidine-4(3H)-one 1H-NMR (DMSO-$d_6$, 300 MHz) δ: 11.69 (1H, s), 7.60 (1H, t, J=7.6 Hz), 7.48-7.36 (2H, m), 7.15-7.05 (3H, m), 6.73 (1H, d, J=8.6 Hz), 6.49-6.43 (2H, m), 6.19 (1H, t, J=5.9 Hz), 4.74 (1H, s), 4.29 (2H, d, J=5.9 Hz), 3.95 (2H, s), 3.64 (4H, t, J=4.3 Hz), 3.49 (4H, d, J=4.3 Hz), 2.47 (3H, s).
MS(ESI m/z): 482 (M+H)
RT(min): 0.97

Example 2-52-2

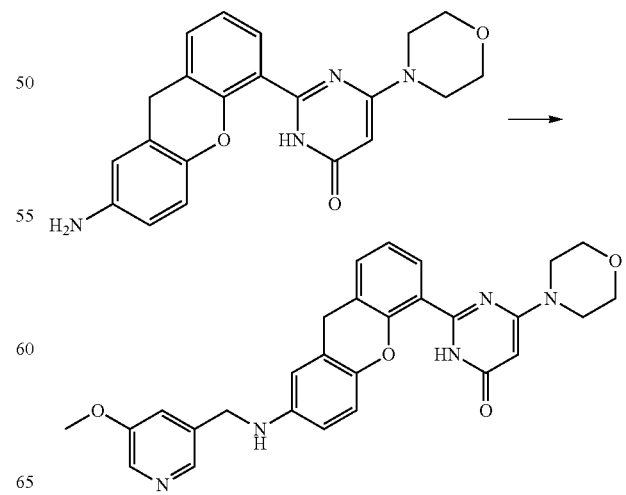

In the same manner as in Example 2-52-1, the following compound was obtained.

2-(7-(((5-Methoxypyridin-3-yl)methyl)amino)-9H-xanthen-4-yl)-6-morpholino pyrimidine-4(3H)-one ¹H-NMR (DMSO-d₆, 300 MHz) δ: 8.19 (1H, s), 8.15 (1H, d, J=6.8 Hz), 7.47-7.36 (3H, m), 7.10 (1H, t, J=7.4 Hz), 6.73 (1H, d, J=8.6 Hz), 6.53-6.47 (2H, m), 6.13 (1H, s), 5.31 (1H, s), 4.28 (2H, d, J=5.9 Hz), 3.96 (2H, s), 3.80 (3H, s), 3.65 (4H, t, J=4.6 Hz), 3.48 (4H, t, J=4.6 Hz).
MS(ESI m/z): 498 (M+H)
RT(min): 1.03

Example 2-52-3

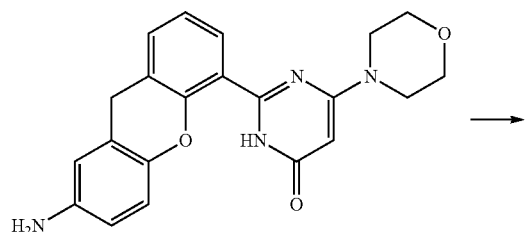

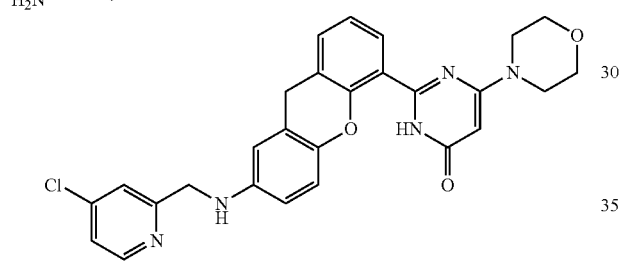

In the same manner as in Example 2-52-1, the following compound was obtained.

2-(7-(((4-Chloropyridin-2-yl)methyl)amino)-9H-xanthen-4-yl)-6-morpholinopyrimidine-4(3H)-one ¹H-NMR (DMSO-d₆, 300 MHz) δ: 11.70 (1H, s), 8.52 (1H, d, J=5.3 Hz), 7.48-7.36 (4H, m), 7.10 (1H, t, J=7.6 Hz), 6.74 (1H, d, J=8.6 Hz), 6.55-6.43 (2H, m), 6.28 (1H, t, J=6.3 Hz), 5.31 (1H, s), 4.37 (2H, d, J=6.3 Hz), 3.96 (2H, s), 3.65 (4H, t, J=4.6 Hz), 3.49 (4H, t, J=4.6 Hz).
MS(ESI m/z): 502 (M+H)
RT(min): 1.33

Example 2-52-4

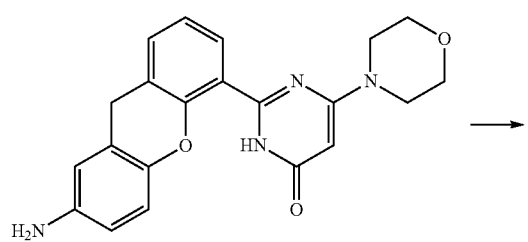

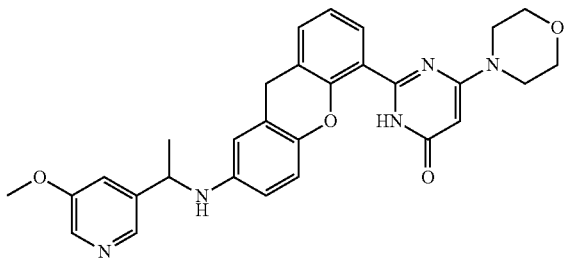

In the same manner as in Example 2-52-1, the following compound was obtained.

2-(7-((1-(5-Methoxypyridin-3-yl)ethyl)amino)-9H-xanthen-4-yl)-6-morpholinopyrimidine-4(3H)-one MS(ESI m/z): 512 (M+H)
RT(min): 1.09

Example 2-53

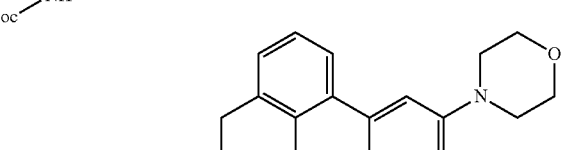

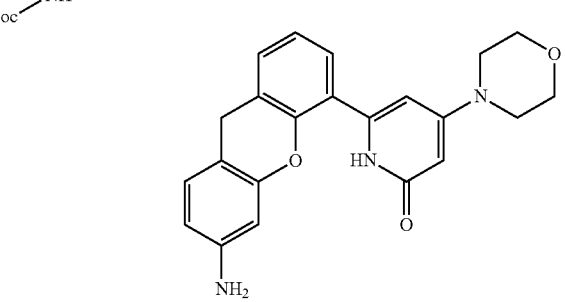

In the same manner as in Example 2-1-1, the following compound was obtained.

6-(6-Amino-9H-xanthen-4-yl)-4-morpholinopyridin-2(1H)-one

¹H-NMR (CDCl₃, 300 MHz) δ: 7.29 (1H, dd, J=7.6, 1.3 Hz), 7.24 (1H, dd, J=7.6, 1.3 Hz), 7.07 (1H, t, J=7.6 Hz), 6.92 (1H, d, J=7.9 Hz), 6.42 (1H, d, J=2.0 Hz), 6.37 (1H, dd, J=8.1, 2.1 Hz), 6.11 (1H, d, J=2.3 Hz), 5.57 (1H, d, J=2.3 Hz), 3.97 (2H, s), 3.79 (4H, t, J=5.0 Hz), 3.47 (2H, s), 3.25 (4H, t, J=4.8 Hz).
MS(ESI m/z): 376 (M+H)
RT(min): 0.93

Example 2-54-1

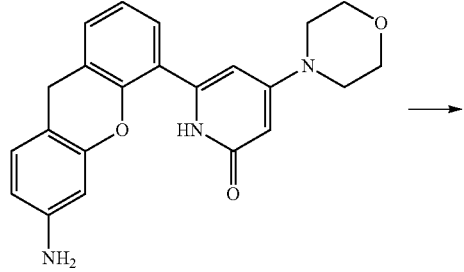

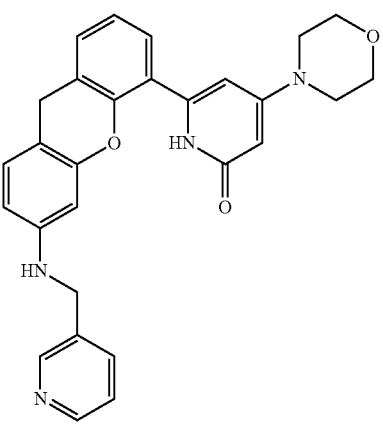

In the same manner as in Example 1-44-1, the following compound was obtained.

4-Morpholino-6-(6-((pyridin-3-ylmethyl)amino)-9H-xanthen-4-yl)pyridin-2(1H)-one

MS(ESI m/z): 467 (M+H)
RT(min): 0.80

Example 2-54-2

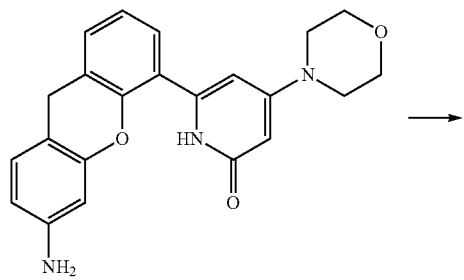

-continued

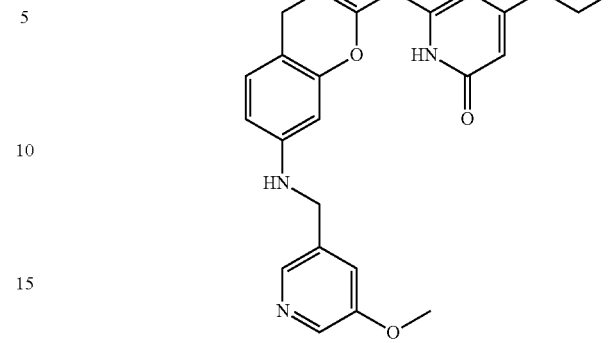

In the same manner as in Example 2-54-1, the following compound was obtained.

6-(6-(((5-Methoxypyridin-3-yl)methyl)amino)-9H-xanthen-4-yl)-4-morpholinopyridin-2(1H)-one $^1$H-NMR (CDCl$_3$, 300 MHz) δ: 8.20 (1H, d, J=3.0 Hz), 8.19 (1H, d, J=1.3 Hz), 7.30 (1H, d, J=7.6 Hz), 7.25 (1H, s), 7.17 (1H, s), 7.08 (1H, t, J=7.6 Hz), 6.96 (1H, d, J=8.3 Hz), 6.41 (1H, d, J=2.3 Hz), 6.35 (1H, dd, J=8.3, 2.3 Hz), 6.12 (1H, d, J=2.6 Hz), 5.68 (1H, d, J=2.3 Hz), 4.31 (2H, s), 3.98 (2H, s), 3.83 (3H, s), 3.81 (4H, t, J=5.4 Hz), 3.30 (4H, t, J=5.0 Hz).
MS(ESI m/z): 497 (M+H)
RT(min): 1.05

Example 2-55

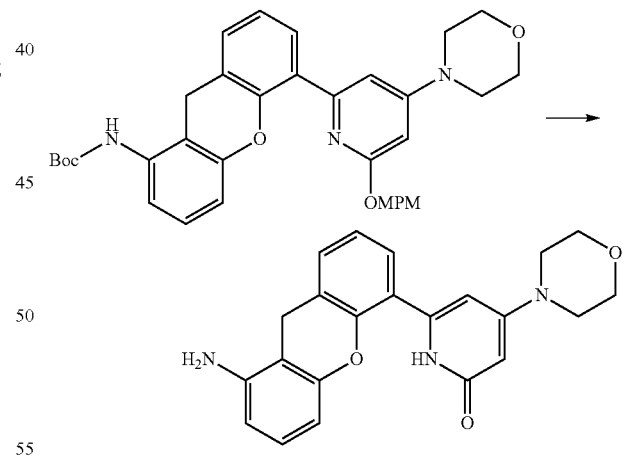

In the same manner as in Example 2-1-1, the following compound was obtained.

6-(8-Amino-9H-xanthen-4-yl)-4-morpholinopyridin-2(1H)-one $^1$H-NMR (CDCl$_3$, 300 MHz) δ: 7.33-7.26 (2H, m), 7.08 (1H, t, J=7.6 Hz), 6.98 (1H, t, J=8.1 Hz), 6.50 (1H, d, J=8.3 Hz), 6.44 (1H, dd, J=7.9, 1.0 Hz), 6.16 (1H, d, J=2.6 Hz), 5.69 (1H, d, J=2.3 Hz), 3.85 (2H, s), 3.82 (4H, t, J=5.0 Hz), 3.31 (4H, t, J=5.0 Hz).

MS(ESI m/z): 376 (M+H)
RT(min): 0.96

Example 2-56-1

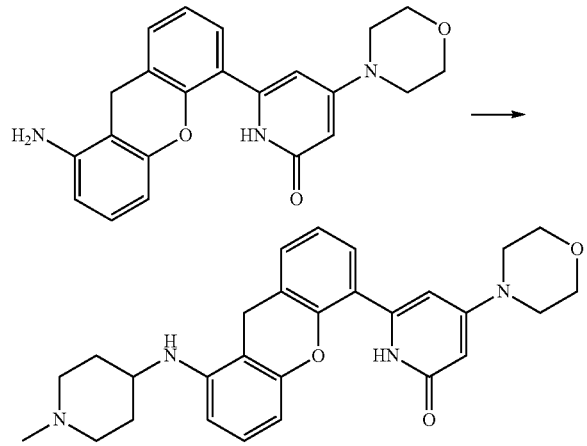

In the same manner as in Example 1-44-1, the following compound was obtained.

6-(8-((1-Methylpiperidin-4-yl)amino)-9H-xanthen-4-yl)-4-morpholinopyridin-2(1H)-one $^1$H-NMR (CDCl$_3$, 300 MHz) δ: 7.34-7.25 (2H, m), 7.10 (1H, d, J=7.6 Hz), 7.04 (1H, d, J=8.3 Hz), 6.45 (1H, d, J=7.6 Hz), 6.37 (1H, d, J=7.6 Hz), 6.18 (1H, d, J=2.3 Hz), 5.71 (1H, d, J=2.3 Hz), 3.82 (4H, t, J=5.0 Hz), 3.76 (2H, s), 3.49 (1H, br), 3.38 (1H, br), 3.32 (4H, t, J=5.0 Hz), 2.34 (3H, s), 2.27-1.52 (8H, m).
MS(ESI m/z): 473 (M+H)
RT(min): 0.83

Example 2-56-2

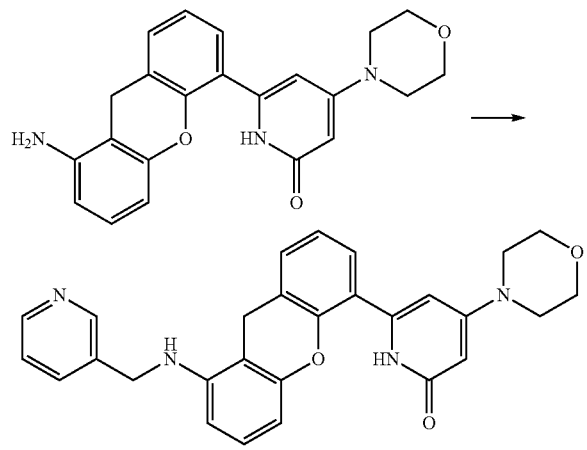

In the same manner as in Example 2-56-1, the following compound was obtained.

4-Morpholino-6-(8-((pyridin-3-ylmethyl)amino)-9H-xanthen-4-yl)pyridin-2(1H)-one

MS(ESI m/z): 467 (M+H)
RT(min): 0.87

Example 2-56-3

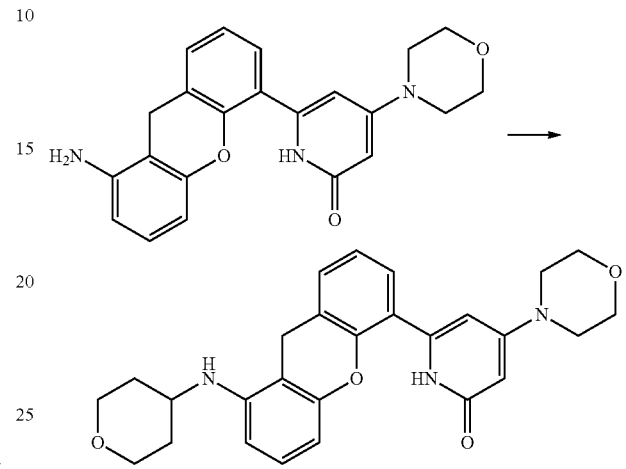

In the same manner as in Example 2-56-1, the following compound was obtained.

4-Morpholino-6-(8-((tetrahydro-2H-pyran-4-yl)amino)-9H-xanthen-4-yl)pyridin-2(1H)-one $^1$H-NMR (CDCl$_3$, 300 MHz) δ: 9.29 (1H, s), 7.35-7.25 (2H, m), 7.09 (1H, t, J=7.9 Hz), 7.06 (1H, t, J=8.6 Hz), 6.46 (1H, d, J=7.6 Hz), 6.40 (1H, d, J=7.9 Hz), 6.17 (1H, d, J=2.3 Hz), 5.70 (1H, d, J=2.6 Hz), 3.82 (4H, t, J=4.8 Hz), 3.78 (2H, s), 3.63 (1H, t, J=4.5 Hz), 3.59-3.51 (2H, m), 3.49 (1H, s), 3.31 (4H, t, J=5.0 Hz), 2.10 (2H, dd, J=12.9, 2.3 Hz), 1.67-1.51 (4H, m).
MS(ESI m/z): 460 (M+H)
RT(min): 1.18

Example 2-56-4

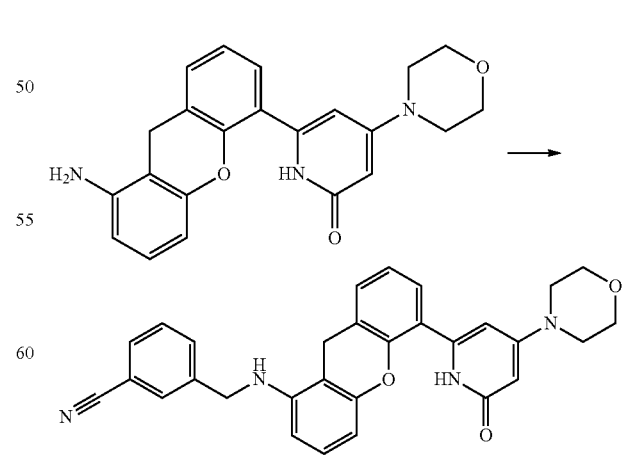

In the same manner as in Example 2-56-1, the following compound was obtained.

3-(((5-(4-Morpholino-6-oxo-1,6-dihydropyridin-2-yl)-9H-xanthen-1-yl)amino)methyl)benzonitrile ¹H-NMR (DMSO-d₆, 300 MHz) δ: 10.88 (1H, s), 7.81 (1H, s), 7.71 (2H, t, J=7.8 Hz), 7.53 (1H, t, J=7.6 Hz), 7.30 (2H, t, J=7.3 Hz), 7.11 (1H, t, J=7.6 Hz), 6.91 (1H, t, J=8.1 Hz), 6.17-6.06 (4H, m), 5.46 (1H, s), 4.44 (2H, d, J=5.9 Hz), 3.93 (2H, s), 3.68 (4H, t, J=4.8 Hz), 3.26 (4H, t, J=4.8 Hz).

MS(ESI m/z): 491 (M+H)

RT(min): 1.35

Example 2-57

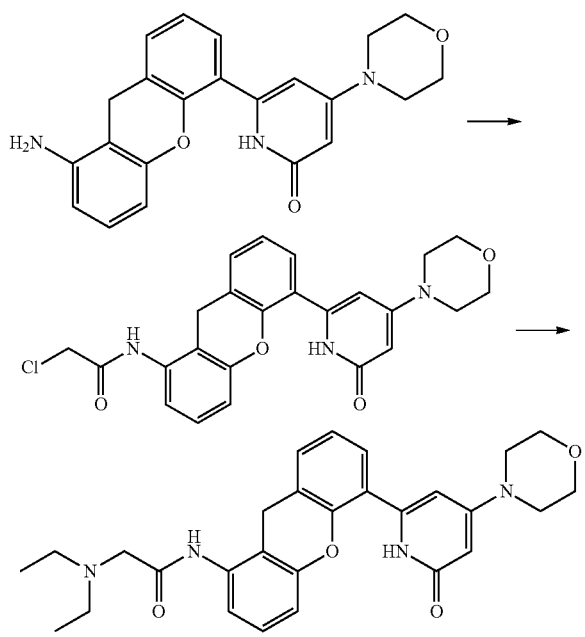

(1) and (2)

In the same manner as in Examples 1-7-1 (1) and 1-7-1 (2), the following compounds were obtained.

2-Chloro-N-(5-(4-morpholino-6-oxo-1,6-dihydropyridin-2-yl)-9H-xanthen-1-yl)acetamide MS(ESI m/z): 452 (M+H)

RT(min): 1.06

2-(Diethylamino)-N-(5-(4-morpholino-6-oxo-1,6-dihydropyridin-2-yl)-9H-xanthen-1-yl)acetamide ¹H-NMR (CDCl₃, 300 MHz) δ: 9.55 (1H, brs), 7.76 (1H, d, J=7.9 Hz), 7.34 (1H, d, J=7.6 Hz), 7.28 (1H, s), 7.20-7.09 (2H, m), 6.87 (1H, d, J=7.6 Hz), 6.15 (1H, d, J=2.6 Hz), 5.64 (1H, d, J=2.3 Hz), 3.99 (2H, s), 3.81 (4H, t, J=4.8 Hz), 3.29 (4H, t, J=5.0 Hz), 3.24 (2H, s), 2.73 (4H, q, J=7.2 Hz), 1.18 (6H, t, J=7.1 Hz).

MS(ESI m/z): 489 (M+H)

RT(min): 0.79

Example 2-58

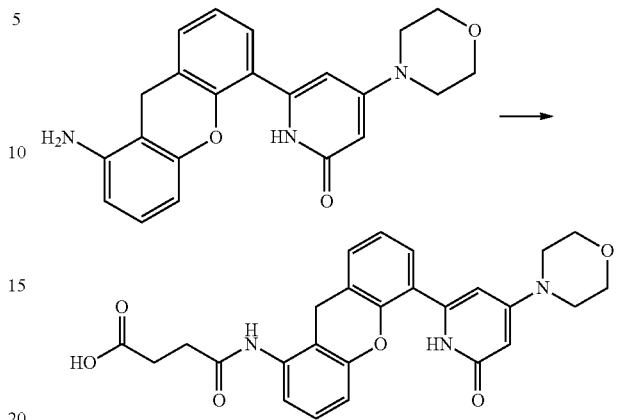

Pyridine (0.3 mL) was added to a solution of 6-(8-amino-9H-xanthen-4-yl)-4-morpholinopyridin-2(1H)-one (19 mg) and succinic anhydride (6 mg) in dichloromethane (3 mL), followed by stirring at the same temperature for 23 hours. The solid was collected by filtration, whereby 4-((5-(4-morpholino-6-oxo-1,6-dihydropyridin-2-yl)-9H-xanthen-1-yl)amino)-4-oxobutanoic acid (14 mg) was obtained.

¹H-NMR (DMSO-d₆, 300 MHz) δ: 12.13 (1H, brs), 10.87 (1H, brs), 7.28 (1H, s), 7.26 (1H, s), 7.08 (1H, t, J=7.6 Hz), 6.88 (1H, t, J=7.9 Hz), 6.37 (1H, dd, J=7.9, 1.0 Hz), 6.14 (1H, d, J=1.3 Hz), 6.10 (1H, d, J=7.3 Hz), 5.46 (1H, d, J=2.0 Hz), 5.16 (2H, s), 3.78 (2H, s), 3.68 (4H, t, J=4.6 Hz), 3.26 (4H, t, J=4.6 Hz), 2.41 (2H, s).

MS(ESI m/z): 476 (M+H)

RT(min): 0.95

Example 2-59

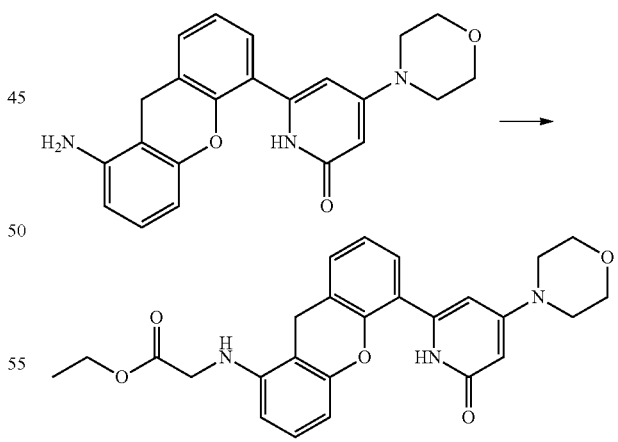

Bromoethyl acetate (20 mg) was added to a solution of 6-(8-amino-9H-xanthen-4-yl)-4-morpholinopyridin-2(1H)-one (37.5 mg) and potassium carbonate (28 mg) in N,N-dimethyl acetamide (5 mL), followed by stirring at the same temperature for 23 hours. Bromoethyl acetate (20 mg) was added thereto, followed by stirring at room temperature for 23 hours. Dichloromethane was added thereto, then, the resultant product was washed with water, and the organic layer was dried over anhydrous sodium sulfate. The solvent was distilled off under reduced pressure, and the obtained residues were purified by silica gel column chromatography (chloroform:methanol=1:0→4:1), whereby ethyl 2-((5-(4-morpholino-6-oxo-1,6-dihydropyridin-2-yl)-9H-xanthen-1-yl)amino)acetate (8 mg) was obtained as a white solid.

MS(ESI m/z): 462 (M+H)

RT(min): 1.25

Example 2-60

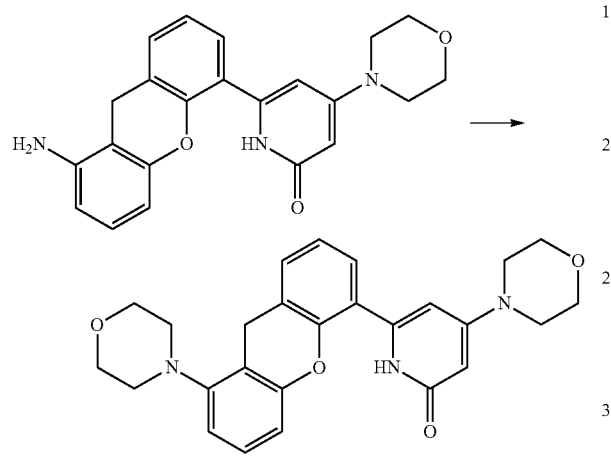

In the same manner as in Example 1-21-1, the following compound was obtained.

4-Morpholino-6-(8-morpholino-9H-xanthen-4-yl)pyridin-2(1H)-one

MS(ESI m/z): 446 (M+H)

RT(min): 1.24

Example 2-61

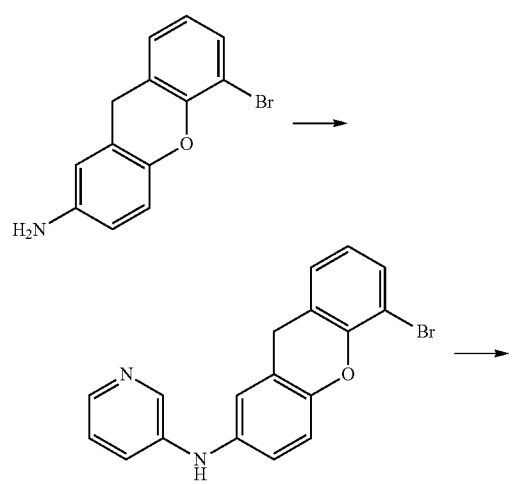

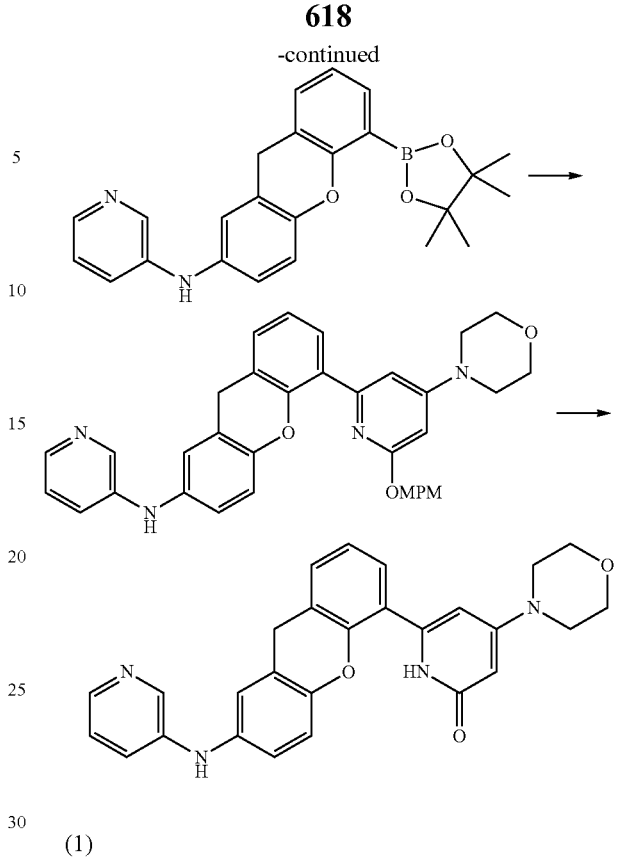

(1)

Copper (II) acetate (329 mg) was added to a solution of 5-bromo-9H-xanthene-2-amine (500 mg), 3-pyridylboronic acid (500 mg), and triethylamine (252 µL) in dichloromethane (10 mL), followed by stirring at the same temperature for 48 hours. Ethyl acetate was added to the reaction mixture, then, the resultant product was washed with a saturated sodium hydrogen carbonate aqueous solution and dried over anhydrous sodium sulfate, and the solvent was distilled off under reduced pressure. The obtained residues were purified by silica gel column chromatography (hexane:ethyl acetate=9:1→1:4), whereby N-(5-bromo-9H-xanthen-2-yl)pyridine-3-amine (330 mg) was obtained.

(2) and (3)

In the same manner as in Reference Examples 3 (6) and 3 (7), the following compounds were obtained.

N-(5-(4,4,5,5-tetramethyl-1,3,2-dioxaborolan-2-yl)-9H-xanthen-2-yl)pyridine-3-amine N-(5-(6-((4-methoxybenzyl)oxy)-4-morpholinopyridin-2-yl)-9H-xanthen-2-yl)pyridine-3-amine (4)

In the same manner as in Example 2-1-1, the following compound was obtained.

4-Morpholino-6-(7-(pyridin-3-ylamino)-9H-xanthen-4-yl)pyridin-2(1H)-one

MS(ESI m/z): 453 (M+H)

RT(min): 0.86

Example 2-62

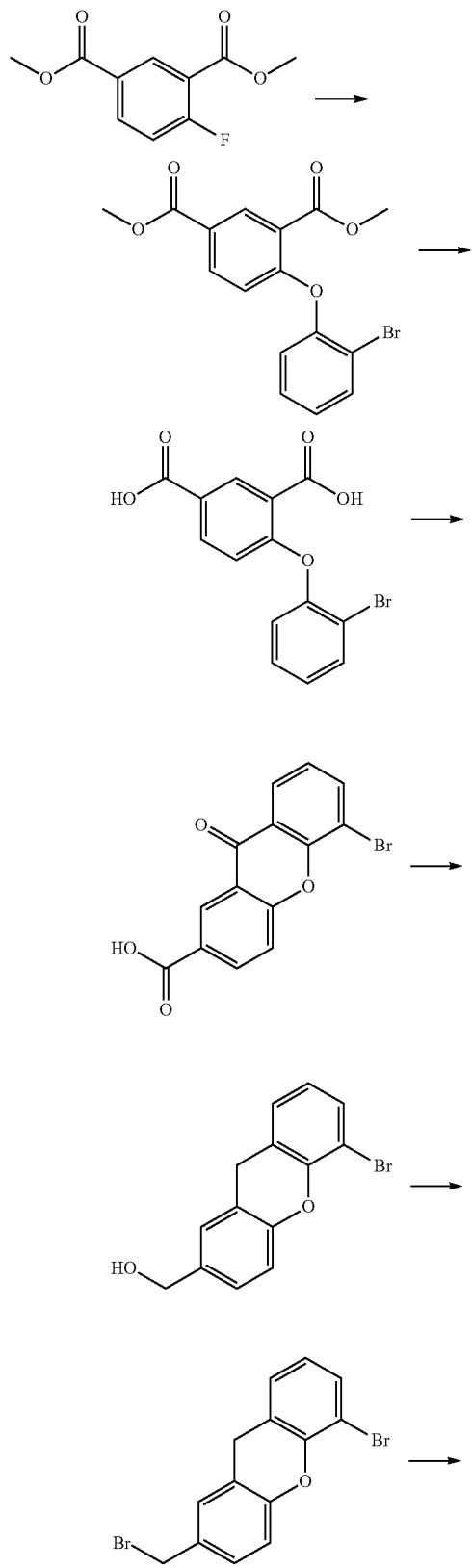

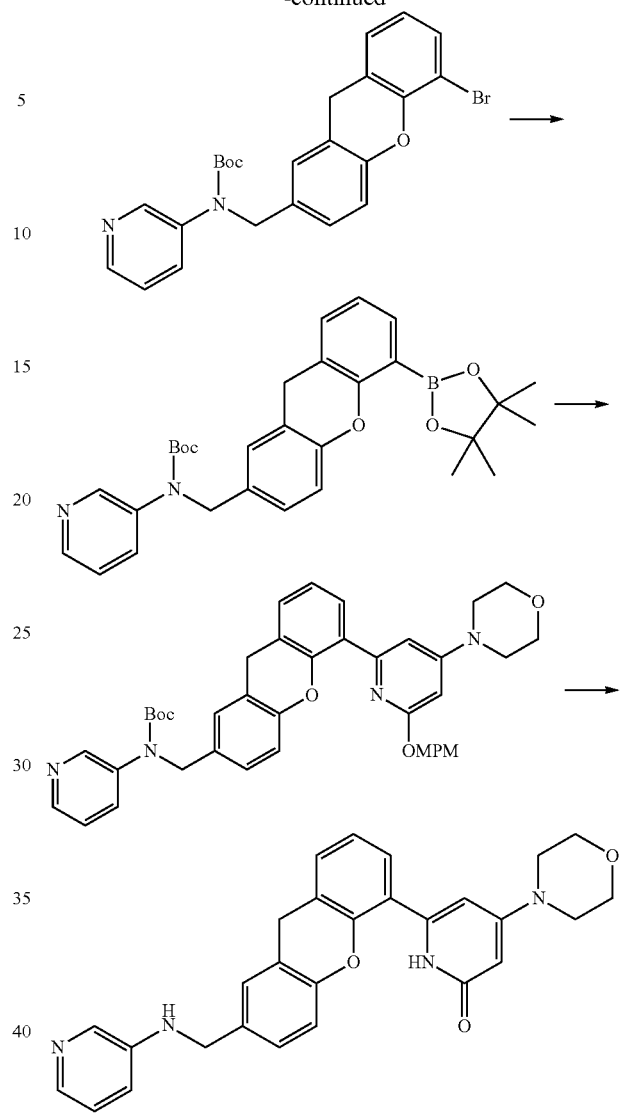

(1)
Potassium carbonate (1.43 g) was added to a solution of dimethyl 4-fluoroisophthalate (2.00 g) and 2-bromo phenol (1.79 g) in N,N-dimethyl acetamide (20 mL), followed by heating at 150° C. for 20 hours. After the reaction mixture was cooled to room temperature, ethyl acetate was added thereto, and the organic layer was washed with a saturated sodium chloride aqueous solution, and dried over anhydrous sodium sulfate. The solvent was distilled off under reduced pressure, and the obtained residues were purified by silica gel column chromatography (ethyl acetate:hexane=1:0→2:1), whereby dimethyl 4-(2-bromophenyl)isophthalic acid (3.05 g) was obtained.

(2)
A mixture of dimethyl 4-(2-bromophenoxy)isophthalic acid (3.03 g) obtained in Example 2-62 (1), ethanol (30 mL), and a 5 mol/L sodium hydroxide aqueous solution (10 mL) was stirred at room temperature for 4 hours. The solvent was distilled off under reduced pressure, then, 1 mol/L hydrochloric acid was added to the obtained residues, and the resultant product was extracted with ethyl acetate. The organic layer was dried over anhydrous magnesium sulfate, and the solvent was distilled off under reduced pressure, whereby 4-(2-bromophenyl)isophthalic acid (2.80 g) was obtained.

(3)

A mixture of 4-(2-bromophenyl)isophthalic acid (2.80 g) obtained in Example 2-62 (2) and methanesulfonic acid (30 mL) was stirred at 100° C. for 20 hours. The reaction mixture was poured into water, and the solid was collected by filtration, whereby 5-bromo-9-oxo-9H-xanthene-2-carboxylic acid (1.65 g) was obtained.

(4)

A 1.0 mol/L borane-tetrahydrofuran complex tetrahydrofuran solution (25 mL) was added dropwise to a solution of 5-bromo-9-oxo-9H-xanthene-2-carboxylic acid (1.65 g) obtained in Example 2-62 (3) in tetrahydrofuran (15 mL) under ice-cooling, followed by stirring at room temperature for 16 hours. Methanol was added to the reaction mixture, and the solvent was distilled off under reduced pressure. Ethyl acetate was added to the obtained residues, and the resultant product was washed with a saturated sodium hydrogen carbonate aqueous solution, and dried over anhydrous magnesium sulfate. The solvent was distilled off under reduced pressure, and the obtained residues were purified by silica gel column chromatography (hexane:ethyl acetate=9:1→1:2), whereby (5-bromo-9H-xanthen-2-yl)methanol (1.37 g) was obtained.

(5)

A mixture of (5-bromo-9H-xanthen-2-yl)methanol (200 mg) obtained in Example 2-62 (4), carbon tetrabromide (342 mg), triphenylphosphine (198 mg), and dichloromethane (5.0 mL) was stirred at room temperature for 12 hours. The solvent was distilled off under reduced pressure, and the obtained residues were purified by silica gel column chromatography (hexane:ethyl acetate=1:0→4:1), whereby 5-bromo-2-(bromomethyl)-9H-xanthene (135 mg) was obtained.

(6)

Under ice-cooling, sodium hydride (18 mg, 60%, dispersed in liquid paraffin) was added to a solution of tert-butyl (pyridin-3-yl)carbamate (86 mg) in N,N-dimethyl acetamide (2.0 mL), followed by stirring for 15 minutes, and a solution of 5-bromo-2-(bromomethyl)-9H-xanthene (135 mg) obtained in Example 2-62 (5) in N,N-dimethyl acetamide (2.0 mL) was added thereto, followed by stirring at room temperature for 4 hours. Ethyl acetate was added thereto, then, the organic layer was washed with a saturated aqueous sodium chloride solution, and dried over anhydrous sodium sulfate. The solvent was distilled off under reduced pressure, and the obtained residues were purified by silica gel column chromatography (hexane:ethyl acetate=4:1→1:2), whereby tert-butyl ((5-bromo-9H-xanthen-2-yl)methyl)(pyridin-3-yl)carbamate (135 mg) was obtained.

(7) to (9)

In the same manner as in Examples 2-61 (2) to 2-61 (4), the following compounds were obtained.

tert-Butyl (pyridin-3-yl)((5-(4,4,5,5-tetramethyl-1,3,2-dioxaborolan-2-yl)-9H-xanthen-2-yl)methyl)carbamate tert-Butyl ((5-(6-((4-methoxybenzyl)oxy)-4-morpholinopyridin-2-yl)-9H-xanthen-2-yl)methyl)(pyridin-3-yl)carbamate 4-Morpholino-6-(7-((pyridin-3-ylamino)methyl)-9H-xanthen-4-yl)pyridin-2(1H)-one MS(ESI m/z): 467 (M+H)
RT(min): 0.88

Examples 2-63

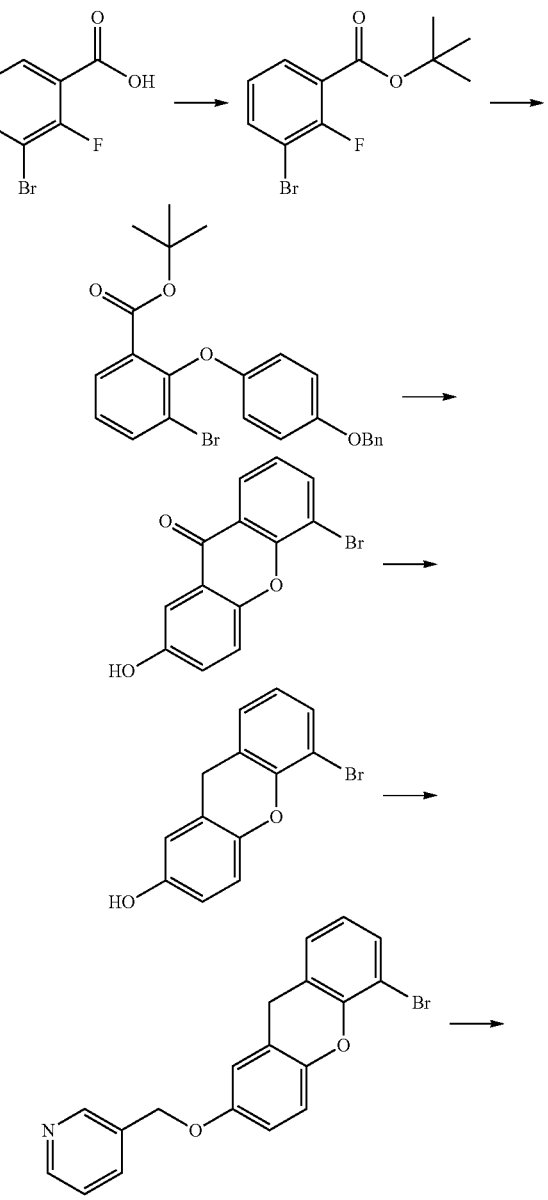

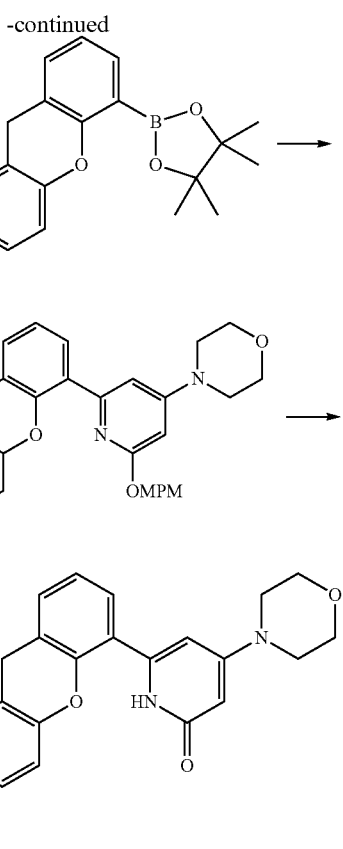

(1)

Di-tert-butyl dicarbonate (3.99 g) and N,N-dimethyl-4-amino pyridine (112 mg) were added to a solution of 3-bromo-2-fluorobenzoic acid (2.00 g) in tert-butyl alcohol (20 mL) and tetrahydrofuran (20 mL), followed by stirring at room temperature for 18 hours. The solvent was distilled off under reduced pressure, and the obtained residues were purified by silica gel column chromatography (hexane:ethyl acetate=9:1→1:1), whereby tert-butyl 3-bromo-2-fluorobenzoic acid (2.51 g) was obtained.

(2)

Potassium carbonate (1.89 g) was added to a solution of tert-butyl 3-bromo-2-fluorobenzoic acid (2.51 g) obtained in Reference Example 2-63 (1) and 4-(benzyloxy)phenol (2.74 g) in N-methyl pyrrolidone (50 mL), followed by stirring at 130° C. for 8 hours. After the reaction mixture was cooled to room temperature, ethyl acetate was added thereto, and the organic layer was washed with a saturated sodium chloride aqueous solution, and dried over anhydrous magnesium sulfate. The solvent was distilled off under reduced pressure, and the obtained residues were purified by silica gel column chromatography (hexane:ethyl acetate=1:0→17:3), whereby tert-butyl 2-(4-(benzyl oxy)phenoxy)-3-bromobenzoic acid (2.57 g) was obtained.

(3)

An Eaton reagent was added to tert-butyl 2-(4-(benzyloxy)phenoxy)-3-bromobenzoic acid (2.57 g) obtained in Reference Example 2-63 (2), followed by stirring at 50° C. for 1.5 hours. The reaction mixture was poured into ice water, and the solid was collected by filtration. The obtained solid, tetrahydrofuran (30 mL), methanol (10 mL), and a 5 mol/L sodium hydroxide aqueous solution (10 mL) were mixed. The solvent was distilled off under reduced pressure, then, 3 mol/L hydrochloric acid was added to the obtained residues, and the resultant product was extracted with ethyl acetate, followed by drying over anhydrous magnesium sulfate. The solvent was distilled off under reduced pressure, and the obtained residues were purified by silica gel column chromatography (hexane:ethyl acetate=9:1→2:1), whereby 5-bromo-2-hydroxy-9H-xanthen-9-one (800 mg) was obtained.

(4)

5-Bromo-2-hydroxy-9H-xanthen-9-one (800 mg) obtained in Reference Example 2-63 (3) was added to tetrahydrofuran (15 mL), and a 1.0 mol/L borane-tetrahydrofuran complex tetrahydrofuran solution (25 mL) was added thereto, followed by refluxing for 2 hours. The reaction mixture was cooled to room temperature, then, ethanol was added thereto, and the solvent was distilled off under reduced pressure. Ethyl acetate was added to the obtained residues, and the resultant product was washed with a saturated sodium hydrogen carbonate aqueous solution, and dried over anhydrous magnesium sulfate. The solvent was distilled off under reduced pressure, and the obtained residues were purified by silica gel column chromatography (hexane:ethyl acetate=9:1→1:2), whereby 5-bromo-9H-xanthene-2-ol (405 mg) was obtained.

(5)

3-(Chloromethyl)pyridine hydrochloride (65 mg) and potassium carbonate (105 mg) were added to a solution of 5-bromo-9H-xanthene-2-ol (100 mg) obtained in Reference Example 2-63 (4) in N,N-dimethyl acetamide (1.0 mL), and the resultant product was stirred at room temperature for 3 hours, and stirred at 60° C. for 4 hours. After the reaction mixture was cooled to room temperature, ethyl acetate was added thereto, and the resultant product was washed with a saturated sodium chloride aqueous solution, and dried over anhydrous magnesium sulfate. The solvent was distilled off under reduced pressure, and the obtained residues were purified by silica gel column chromatography (hexane:ethyl acetate=9:1-1:4), whereby 3-(((5-bromo-9H-xanthen-2-yl)oxy)methyl)pyridine (110 mg) was obtained.

(6) to (8)

In the same manner as in Examples 2-61 (2) to 2-61 (4), the following compounds were obtained.

3-(((5-(4,4,5,5-Tetramethyl-1,3,2-dioxaborolan-2-yl)-9H-xanthen-2-yl)oxy)methyl)pyridine 4-(2-((4-Methoxybenzyl)oxy)-6-(7-(pyridin-3-ylmethoxy)-9H-xanthen-4-yl)pyridin-4-yl)morpholine 4-Morpholino-6-(7-(pyridin-3-ylmethoxy)-9H-xanthen-4-yl)pyridin-2(1H)-one MS(ESI m/z): 468 (M+H)
RT(min): 0.96

Example 2-64

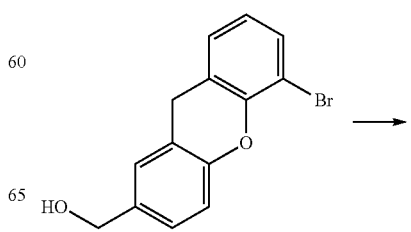

625

-continued

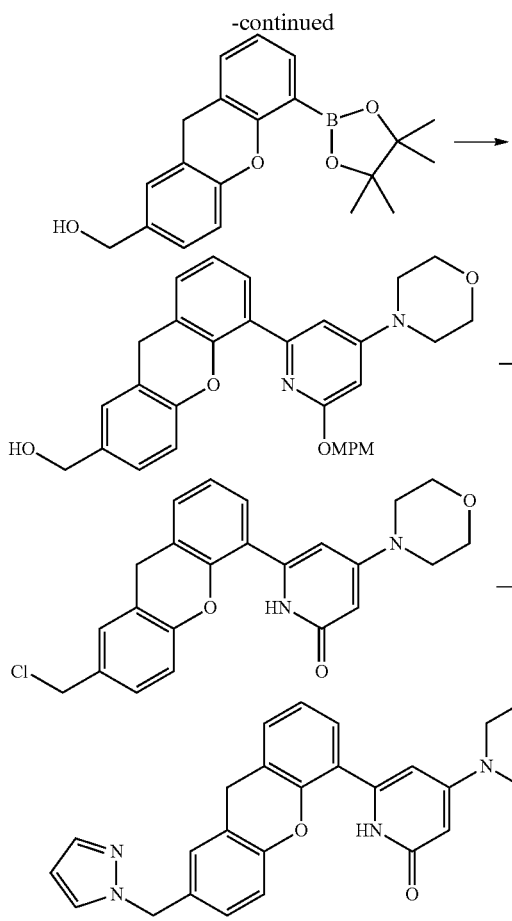

(1) and (2)

In the same manner as in Examples 2-61 (2) and 2-61 (3), the following compounds were obtained.

(5-(4,4,5,5-Tetramethyl-1,3,2-dioxaborolan-2-yl)-9H-xanthen-2-yl)methanol (5-(6-((4-Methoxybenzyl)oxy)-4-morpholinopyridin-2-yl)-9H-xanthen-2-yl)methanol (3)
4.0 mol/L hydrogen chloride/1,4-dioxane (3.0 mL) was added to (5-(6-((4-methoxybenzyl)oxy)-4-morpholinopyridin-2-yl)-9H-xanthen-2-yl)methanol (125 mg) obtained in Example 2-64 (2), followed by stirring at 60° C. for 6 hours. The solvent was distilled off under reduced pressure, and the obtained residues were washed with ethyl acetate, whereby 6-(7-(chloromethyl)-9H-xanthen-4-yl)-4-morpholinopyridin-2(1H)-one (85 mg) was obtained as a white solid.

(4)
Potassium carbonate (23 mg) and pyrazole (5.7 mg) were added to a solution of 6-(7-(chloro methyl)-9H-xanthen-4-yl)-4-morpholinopyridin-2(1H)-one (25 mg) obtained in Example 2-64 (3) in N,N-dimethyl acetamide (1.0 mL), followed by stirring at 80° C. for 14 hours. Pyrazole (11.4 mg) was added thereto, followed by stirring at 120° C. for 6 hours. After the reaction mixture was cooled to room temperature, ethyl acetate was added thereto, and the resultant product was washed with a saturated sodium chloride aqueous solution, and dried over anhydrous magnesium sulfate. The solvent was distilled off under reduced pressure,

626 and the obtained residues were purified by preparative thin layer silica gel chromatography (chloroform:methanol=50:1), whereby 6-(7-((1H-pyrazol-1-yl)methyl)-9H-xanthen-4-yl)-4-morpholinopyridin-2(1H)-one (9 mg) was obtained.
MS(ESI m/z): 441 (M+H)
RT(min): 1.14

Example 2-65

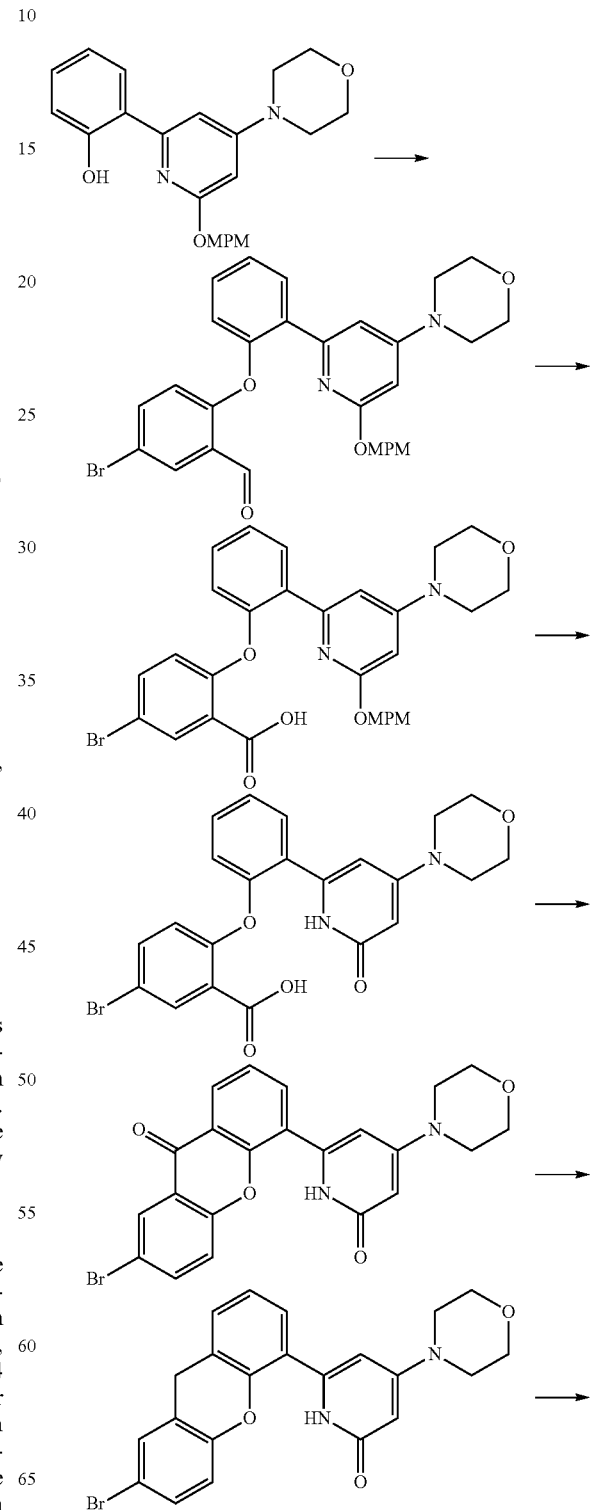

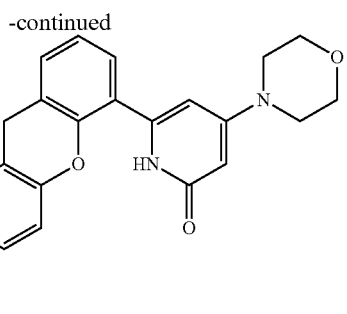

(1)

5-Bromo-2-fluorobenzaldehyde (211 μL) and potassium carbonate (245 mg) were added to a solution of 2-(6-((4-methoxybenzyl)oxy)-4-morpholinopyridin-2-yl)phenol (580 mg) in N,N-dimethyl acetamide (10 mL), followed by stirring at 100° C. for 9 hours. After the reaction mixture was cooled to room temperature, ethyl acetate was added thereto, and the organic layer was washed with a saturated sodium chloride aqueous solution, and dried over anhydrous magnesium sulfate. The solvent was distilled off under reduced pressure, and the obtained residues were purified by silica gel column chromatography (hexane:ethyl acetate=19:1→2:1), whereby 5-bromo-2-(2-(6-((4-methoxybenzyl)oxy)-4-morpholinopyridin-2-yl)phenoxy)benzaldehyde (980 mg) was obtained.

(2)

A solution of sodium dihydrogen phosphate (177 mg) and sodium chlorite (32 mg) in water (2.0 mL) was added dropwise to a mixture of 5-bromo-2-(2-(6-((4-methoxybenzyl)oxy)-4-morpholinopyridin-2-yl)phenoxy)benzaldehyde (170 mg) obtained in Example 2-65 (1), 2-methyl-2-butene (626 μL), tert-butyl alcohol (2.0 mL), and tetrahydrofuran (2.0 mL), followed by stirring at room temperature for 14 hours. Ethyl acetate was added to the reaction mixture, and the organic layer was washed with a saturated sodium chloride aqueous solution, and dried over anhydrous magnesium sulfate. The solvent was distilled off under reduced pressure, whereby 5-bromo-2-(2-(6-((4-methoxybenzyl)oxy)-4-morpholinopyridin-2-yl)phenoxy)benzoic acid (174 mg) was obtained.

(3)

A solution of 4.0 mol/L hydrogen chloride/1,4-dioxane (2.0 mL) was added to 5-bromo-2-(2-(6-((4-methoxybenzyl)oxy)-4-morpholinopyridin-2-yl)phenoxy)benzoic acid (667 mg) obtained in Example 2-65 (2), followed by stirring at 80° C. for 4 hours. The reaction mixture was cooled to room temperature, and the solvent was distilled off under reduced pressure. Methanol was added to the obtained residues, and the solvent was distilled off under reduced pressure. The obtained residues were washed with ethyl acetate, whereby 5-bromo-2-(2-(4-morpholino-6-oxo-1,6-dihydro pyridin-2-yl)phenoxy)benzoic acid (470 mg) was obtained.

(4)

An Eaton reagent (5.0 mL) was added to 5-bromo-2-(2-(4-morpholino-6-oxo-1,6-dihydropyridin-2-yl)phenoxy) benzoic acid (470 mg) obtained in Example 2-65 (3), followed by stirring at 80° C. for 1.5 hours. The reaction mixture was cooled to room temperature, and poured into ice water, and the solid was collected by filtration, whereby 6-(7-bromo-9-oxo-9H-xanthen-4-yl)-4-morpholinopyridin-2(1H)-one (270 mg) was obtained.

(5)

A 1.0 mol/L borane-tetrahydrofuran complex tetrahydrofuran solution (25 mL) was added to a solution of 6-(7-bromo-9-oxo-9H-xanthen-4-yl)-4-morpholinopyridin-2 (1H)-one (270 mg) obtained in Example 2-65 (4) in tetrahydrofuran (3.0 mL), followed by refluxing for 1 hour. After the reaction mixture was cooled to room temperature, the solvent was distilled off under reduced pressure, and the obtained residues were purified by silica gel column chromatography (chloroform:methanol=1:0→19:1), whereby 6-(7-bromo-9H-xanthen-4-yl)-4-morpholinopyridin-2(1H)-one (230 mg) was obtained.

(6)

3-Vinyl pyridine (18 μL), palladium acetate (2.6 mg), tri(o-tolyl)phosphine (6.9 mg), and triethylamine (24 μL) were added to a solution of 6-(7-bromo-9H-xanthen-4-yl)-4-morpholinopyridin-2(1H)-one (50 mg) obtained in Example 2-65 (5) in N-methyl pyrrolidone (1.0 mL), and the resultant product was irradiated with microwaves (microwave reaction apparatus, 180° C., 0.75 hours, 2.45 GHz, 0 W to 240 W). After the reaction mixture was cooled to room temperature, chloroform was added thereto, and the organic layer was washed with a saturated sodium chloride aqueous solution, and dried over anhydrous sodium sulfate. The solvent was distilled off under reduced pressure, and the obtained residues were purified by preparative thin layer silica gel chromatography (chloroform:methanol=30:1, NH silica), whereby (E)-4-morpholino-6-(7-(2-(pyridin-3-yl)vinyl)-9H-xanthen-4-yl)pyridin-2(1H)-one (9 mg) was obtained.

MS(ESI m/z): 464 (M+H)
RT(min): 0.99

Example 2-66

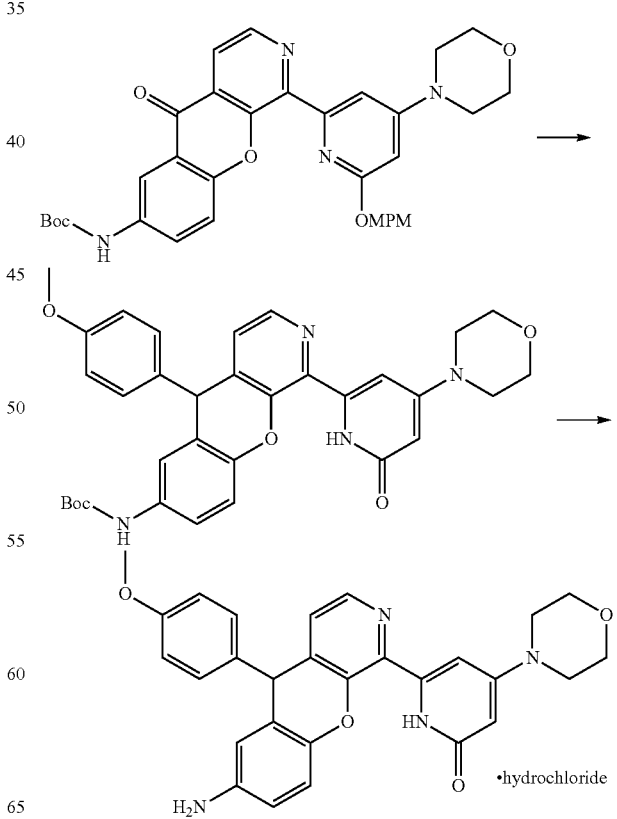

(1)

Methanol (35 mL) and sodium borohydride (19 mg) were added to a solution of tert-butyl (1-(6-((4-methoxybenzyl)oxy)-4-morpholinopyridin-2-yl)-5-oxo-5H-chromeno[2,3-c]pyridin-7-yl)carbamate (150 mg) in tetrahydrofuran (35 mL), followed by stirring at room temperature for 1 hour. Sodium borohydride (38 mg) was added thereto, followed by stirring at room temperature for 2 hours. After the reaction mixture was cooled to 0° C., a saturated ammonium chloride aqueous solution was added thereto, followed by stirring at for 0.5 hours, and the solvent was distilled off under reduced pressure. A saturated sodium hydrogen carbonate aqueous solution was added to the obtained residue, and the resultant product was extracted with chloroform. The organic layer was dried over anhydrous sodium sulfate, and the solvent was distilled off under reduced pressure. Triethylsilane (0.21 mL), trifluoroacetic acid (0.1 mL), and anisole (0.27 mL) were added to a solution of the obtained residues in dichloromethane (3 mL) under ice-cooling, followed by stirring for 5 hours. Triethylsilane (0.1 mL) and trifluoroacetic acid (0.04 mL) were added thereto, followed by stirring at room temperature for 1 hour. Triethylsilane (0.1 mL) and trifluoroacetic acid (0.04 mL) were added thereto, followed by stirring at room temperature for 1 hour. Triethylsilane (0.1 mL) and trifluoroacetic acid (0.04 mL) were added thereto, followed by stirring at room temperature for 1 hour. A saturated sodium hydrogen carbonate aqueous solution was added to the reaction mixture, and the resultant product was extracted with chloroform. The organic layer was dried over anhydrous sodium sulfate, and the solvent was distilled off under reduced pressure. The obtained residues were purified by silica gel column chromatography (chloroform:methanol=1:0→97:3, NH silica), and purified by preparative reversed phase HPLC (0.1% formic acid aqueous solution:0.1% solution of formic acid in acetonitrile=9:1→1:9), whereby tert-butyl (5-(4-methoxyphenyl)-1-(4-morpholino-6-oxo-1,6-dihydropyridin-2-yl)-5H-chromeno[2,3-c]pyridin-7-yl)carbamate (6.8 mg) was obtained as a pale yellow solid.

(2)

In the same manner as in Example 1-1, the following compound was obtained.

Hydrochloride of 6-(7-amino-5-(4-methoxyphenyl)-5H-chromeno[2,3-c]pyridin-1-yl)-4-morpholinopyridin-2(1H)-one MS(ESI m/z): 483 (M+H)
RT(min): 0.95

Example 2-67

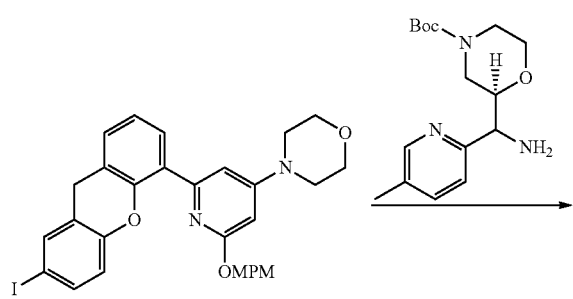

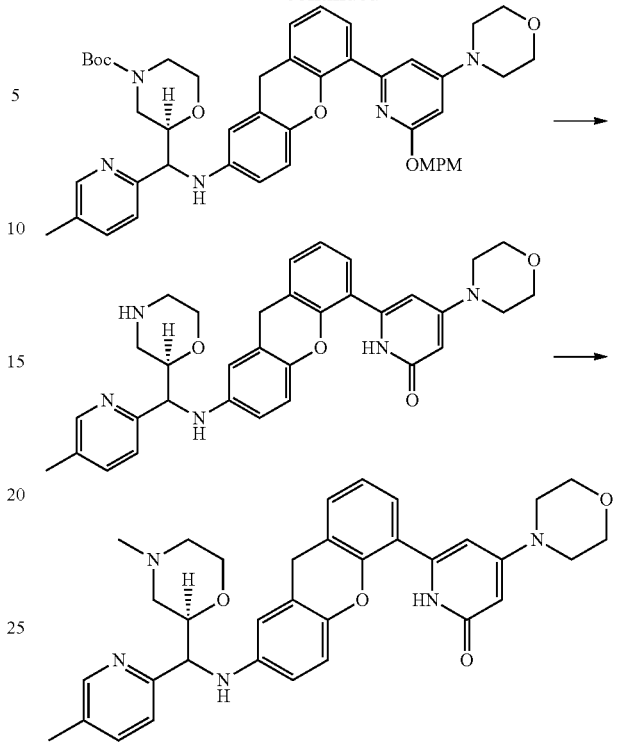

(1)

Dehydrated N,N-dimethyl formamide (0.5 mL) was added to a mixed solution of 4-(2-(7-iodo-9H-xanthen-4-yl)-6-((4-methoxybenzyl)oxy)pyridin-4-yl)morpholine (15 mg), (2R)-tert-butyl 2-(amino (5-methylpyridin-2-yl)methyl)morpholine-4-carboxylate (20 mg), copper (I) iodide (15 mg), cesium carbonate (50 mg), and 2-isobutyryl cyclohexanone (30 mg), and the resultant product was stirred at 100° C. for 1 hour, and stirred at 150° C. for 1 hour. Water was added thereto, then, the resultant product was extracted with ethyl acetate, and the organic layer was dried over anhydrous sodium sulfate. The solvent was distilled off under reduced pressure, and the obtained residues were purified by silica gel column chromatography (hexane:ethyl acetate=4:1→1:1, NH silica), whereby (2R)-tert-butyl 2-(((5-(6-((4-methoxybenzyl)oxy)-4-morpholinopyridin-2-yl)-9H-xanthen-2-yl)amino)(5-meth ylpyridin-2-yl)methyl)morpholine-4-carboxylate (7.6 mg) was obtained.

MS(ESI m/z): 786 (M+H)
RT(min): 1.58

(2)

4.0 mol/L hydrogen chloride/1,4-dioxane (0.3 mL) was added to a mixed solution of (2R)-tert-butyl 2-(((5-(6-((4-methoxybenzyl)oxy)-4-morpholinopyridin-2-yl)-9H-xanthen-2-yl)amino)(5-methylpyridin-2-yl)methyl)morpholine-4-carboxylate (7.6 mg) obtained in Example 2-67 (1) in methanol (50 μL) and chloroform (50 μL), followed by stirring at 40° C. for 0.5 hours. The solvent was distilled off under reduced pressure, and the obtained residues were suspended in ethyl acetate. The solid was precipitated using a centrifugal separator, and thereby supernatant was removed. The obtained residues were neutralized with a sodium hydroxide aqueous solution, then, the resultant product was extracted with chloroform, and the organic layer was dried over anhydrous sodium sulfate. The solvent was distilled off under reduced pressure, and the obtained residues were purified by preparative thin layer silica gel chromatography (chloroform:methanol=30:1, NH silica), whereby 6-(7-(((5-methylpyridin-2-yl)((R)-morpholin-2-yl)methyl)amino)-9H-xanthen-4-yl)-4-morpholinopyridin-2(1H)-one (0.5 mg) was obtained.

MS(ESI m/z): 566 (M+H)

RT(min): 0.92

(3)

2-Picoline borane (1.0 mg) was added to a mixture of 6-(7-(((5-methyl pyridin-2-yl)((R)-morpholin-2-yl)methyl)amino)-9H-xanthen-4-yl)-4-morpholinopyridin-2(1H)-one (0.5 mg) obtained in Example 2-67 (2) and 37% formaldehyde liquid (0.16 mg) in acetic acid (45 µL) and methanol (450 µL), followed by stirring at room temperature for 0.5 hours. A saturated sodium hydrogen carbonate aqueous solution was added thereto, then, the resultant product was extracted with chloroform, and the organic layer was dried over anhydrous sodium sulfate. The solvent was distilled off under reduced pressure, and the obtained residues were purified by preparative thin layer silica gel chromatography (chloroform:methanol=30:1, NH silica), whereby 6-(7-((((R)-4-methyl morpholin-2-yl)(5-methylpyridin-2-yl)methyl)amino)-9H-xanthen-4-yl)-4-morpholinopyridin-2(1H)-one (0.24 mg) was obtained.

¹H-NMR (CDCl₃, 300 MHz) δ: 8.93 (1H, brs), 8.39 (1H, d, J=2.0 Hz), 7.40 (1H, dd, J=8.6, 2.0 Hz), 7.22-7.19 (3H, m), 7.04 (1H, t, J=7.6 Hz), 6.86 (1H, d, J=8.6 Hz), 6.47 (1H, dd, J=8.6, 2.6 Hz), 6.37 (1H, d, J=2.6 Hz), 6.13 (1H, d, J=2.6 Hz), 5.71 (1H, d, J=2.0 Hz), 4.82 (1H, brs), 4.53-4.51 (1H, m), 3.94-3.90 (4H, m), 3.81 (4H, t, J=5.0 Hz), 3.72-3.63 (1H, m), 3.31 (4H, t, J=5.0 Hz), 2.81-2.76 (1H, m), 2.63-2.58 (1H, m), 2.30 (3H, s), 2.24 (3H, s), 2.06-2.03 (1H, m), 1.91-1.79 (1H, m).

MS(ESI m/z): 580 (M+H)

RT(min): 0.94

Example 3-1

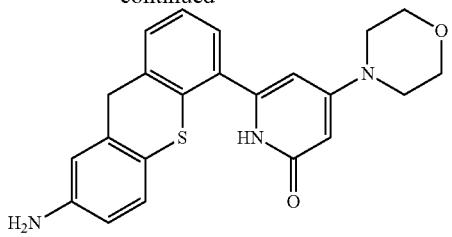

(1)

In the same manner as in Reference Example 3 (7), the following compound was obtained.

tert-Butyl (5-(6-((4-methoxybenzyl)oxy)-4-morpholinopyridin-2-yl)-9H-thioxanthen-2-yl)carbamate (2)

A mixture of tert-butyl (5-(6-((4-methoxybenzyl)oxy)-4-morpholinopyridin-2-yl)-9H-thioxanthen-2-yl)carbamate (680 mg) obtained in Example 3-1 (1) and trifluoroacetic acid (10 mL) was stirred at room temperature for 5 hours. After the solvent was distilled off under reduced pressure, ethyl acetate was added thereto, and the resultant product was washed with a saturated sodium hydrogen carbonate aqueous solution, and dried over anhydrous sodium sulfate. The solvent was distilled off under reduced pressure, and the obtained residues were purified by silica gel column chromatography (methanol:ethyl acetate=1:49→3:17), whereby 6-(7-amino-9H-thioxanthen-4-yl)-4-morpholinopyridin-2(1H)-one (250 mg) was obtained as a pale yellow solid.

MS(ESI m/z): 392 (M+H)

RT(min): 0.86

Example 3-2

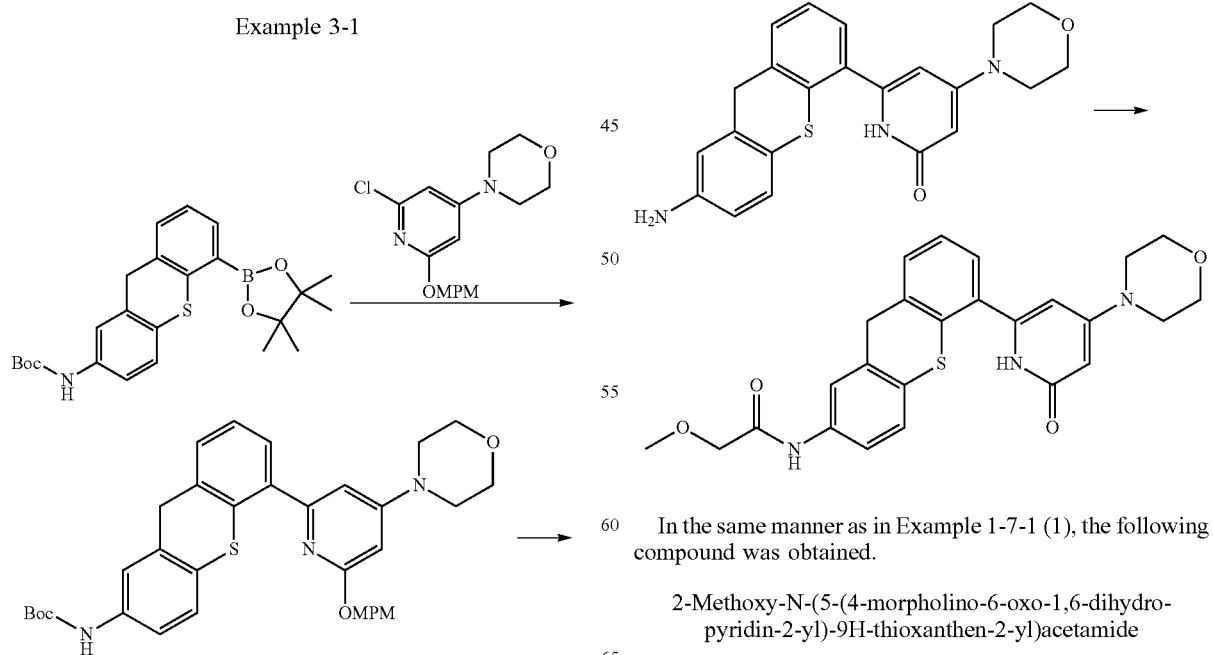

In the same manner as in Example 1-7-1 (1), the following compound was obtained.

2-Methoxy-N-(5-(4-morpholino-6-oxo-1,6-dihydropyridin-2-yl)-9H-thioxanthen-2-yl)acetamide MS(ESI m/z): 464 (M+H)

RT(min): 1.06

Example 3-3-1

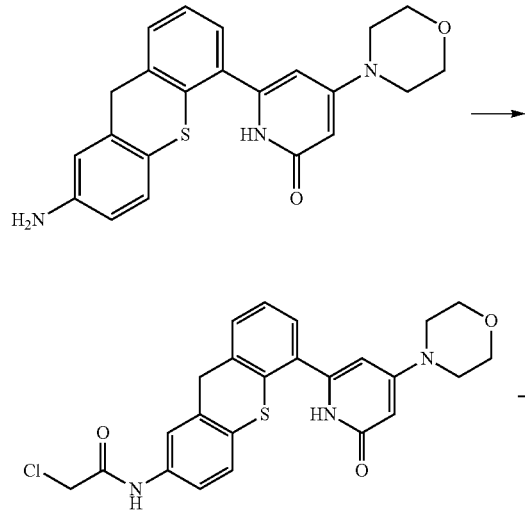

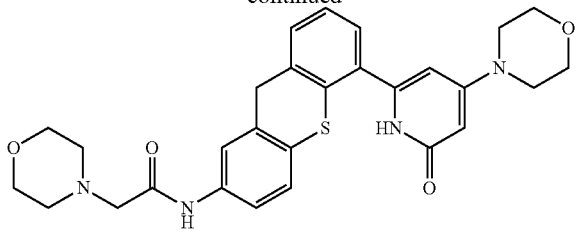

In the same manner as in Example 1-7-1, the following compounds were obtained.

2-Chloro-N-(5-(4-morpholino-6-oxo-1,6-dihydro-pyridin-2-yl)-9H-thioxanthen-2-yl)acetamide 2-Morpholino-N-(5-(4-morpholino-6-oxo-1,6-dihydropyridin-2-yl)-9H-thioxanthen-2-yl)acetamide MS(ESI m/z): 519 (M+H)
RT(min): 0.83

Examples 3-3-2 to 3-3-5

In the same manner as in Example 3-3-1, the following compounds were obtained.

TABLE 85

| Example No. | $R^b$ | Compound Name | MS | RT (min) | $^1$H-NMR (300 MHz) (DMSO-$d_6$) δ: |
|---|---|---|---|---|---|
| 3-3-2 | (2S,6R)-2,6-dimethylmorpholino-CH₂C(=O)- | 2-((2S,6R)-2,6-Dimethyl morpholino)-N-(5-(4-morpholino-6-oxo-1,6-dihydropyridin-2-yl)-9H-thioxanthen-2-yl)acetamide | 547 | 0.91 | |
| 3-3-3 | piperidin-1-yl-CH₂C(=O)- | N-(5-(4-Morpholino-6-oxo-1,6-dihydropyridin-2-yl)-9H-thioxanthen-2-yl)-2-(piperidin-1-yl)acetamide | 517 | 0.90 | (CD$_3$OD): 7.73 (1H, s), 7.51 (1H, d, J = 7.5 Hz), 7.41- 7.31 (4H, m), 6.24 (1H, d, J = 2.4 Hz), 5.75 (1H, d, J = 2.4 Hz), 3.90 (2H, s), 3.79 (4H, t, J = 5.0 Hz), 3.40 (4H, t, J = 5.0 Hz), 3.13 (2H, s), 2.60-2.52 (4H, m), 1.75-1.25 (6H, m). |
| 3-3-4 | 4-methylpiperazin-1-yl-CH₂C(=O)- | 2-(4-Methyl piperazin-1-yl)-N-(5-(4-morpholino-6-oxo-1,6-dihydropyridin-2-yl)-9H-thioxanthen-2-yl)acetamide | 532 | 0.85 | (CD$_3$OD): 7.74 (1H, s), 7.50 (1H, d, J = 5.7 Hz), 7.40- 7.26 (4H, m), 6.24 (1H, d, J = 2.4 Hz), 5.74 (1H, d, J = 2.4 Hz), 3.92 (2H, s), 3.79 (4H, t, J = 4.6 Hz), 3.39 (4H, t, J = 4.8 Hz), 3.18 (2H, s), 2.64-2.50 (8H, m), 2.42 (3H, s). |
| 3-3-5 | (Et)₂N-CH₂C(=O)- | 2-(Diethyl amino)-N-(5-(4-morpholino-6-oxo-1,6-dihydropyridin-2-yl)-9H-thioxanthen-2-yl)acetamide | 505 | 0.88 | (CD$_3$OD) δ: 7.73 (1H, d, J = 2.0 Hz), 7.51 (1H, dd, J = 7.1, 1.8 Hz) 7.41-7.29 (4H, m), 6.24 (1H, d, J = 2.3 Hz). 5.75 (1H, d, J = 2.3 Hz), 3.93 (2H, s), 3.79 (4H, t, J = 4.8 Hz) 3.40 (4H, t, J = 5.0 Hz), 3.21 (2H, s), 2.68 (4H, q, J = 7.2 Hz), 1.11 (6H, t, J = 7.3 Hz). |

Example 3-4-1

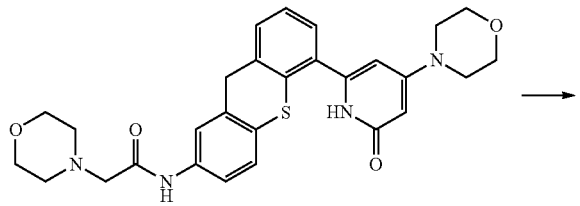

4-Morpholino-6-(7-((2-morpholinoethyl)amino)-9H-thioxanthen-4-yl)pyridin-2(1H)-one MS(ESI m/z): 505 (M+H)
RT(min): 0.88

Examples 3-4-2 to 3-4-4

In the same manner as in Example 3-4-1, the following compounds were obtained.

TABLE 86

| Example No. | $R^b$ | Compound Name | MS | RT (min) | $^1$H-NMR (300 MHz) (DMSO-$d_6$) δ: |
|---|---|---|---|---|---|
| 3-4-2 | N-piperidinylethyl | 4-Morpholino-6-(7-((2-(piperidin-1-yl)ethyl)amino)-9H-thioxanthen-4-yl)pyridin-2(1H)-one | 503 | 0.94 | (CD$_3$OD): 7.46 (1H, d, J = 7.6 Hz), 7.33-7.25 (2H, m), 7.09 (1H, d, J = 8.4 Hz), 6.71 (1H, s), 6.49 (1H, d, J = 7.6 Hz), 6.22 (1H, s), 5.74 (1H, s), 3.82 (2H, s), 3.79 (4H, t, J = 4.7 Hz), 3.39 (4H, t, J = 4.7 Hz), 3.26 (2H, t, J = 6.9 Hz), 2.52 (2H, t, J = 6.9 Hz), 2.51-2.45 (4H, m), 1.66-1.48 (6H, m). |
| 3-4-3 | N-(4-methylpiperazinyl)ethyl | 6-(7-((2-(4-Methyl piperazin-1-yl)ethyl)amino)-9H-thioxanthen-4-yl)-4-morpholino pyridin-2(1H)-one | 518 | 0.88 | (CD$_3$OD): 7.46 (1H, d, J = 6.9 Hz), 7.34-7.22 (2H, m), 7.10 (1H, d, J = 8.3 Hz), 6.72 (1H, d, J = 2.6 Hz), 6.50 (1H, dd, J = 8.4, 2.5 Hz), 6.22 (1H, d, J = 2.3 Hz), 5.74 (1H, d, J = 2.6 Hz), 3.82 (2H, s), 3.78 (4H, d, J = 5.0 Hz), 3.39 (4H, t, J = 5.0 Hz), 3.22 (2H, t, J = 6.4 Hz), 3.04 (2H, t, J = 9.6 Hz), 2.88-2.75 (4H, m) 2.72-2.62 (4H, m), 2.59 (3H, s). |
| 3-4-4 | N,N-diethylaminoethyl | 6-(7-((2-(Diethyl amino)ethyl)amino)-9H-thioxanthen-4-yl)-4-morpholino pyridin-2(1H)-one | 491 | 0.92 | (CD$_3$OD): 7.46 (1H, d, J = 6.9 Hz), 7.36-7.24 (2H, m), 7.10 (1H, d, J = 8.6 Hz), 6.71 (1H, d, J = 2.0 Hz), 6.49 (1H, dd, J = 8.4, 2.5 Hz), 6.22 (1H, d, J = 2.6 Hz), 5.74 (1H, d, J = 2.3 Hz), 3.82 (2H, s), 3.78 (4H, t, J = 4.8 Hz), 3.39 (4H, t, J = 5.0 Hz), 3.21 (2H, t, J = 6.9 Hz), 2.73-2.59 (6H, m), 1.07 (6H, t, J = 7.3 Hz). |

-continued

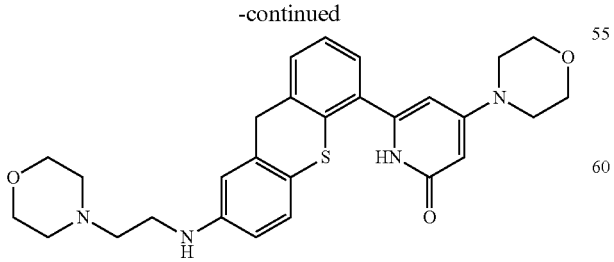

In the same manner as in Reference Example 8 (3), the following compound was obtained.

Example 3-5

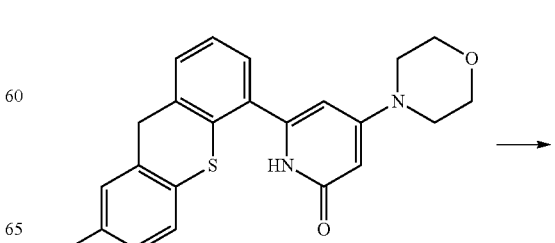

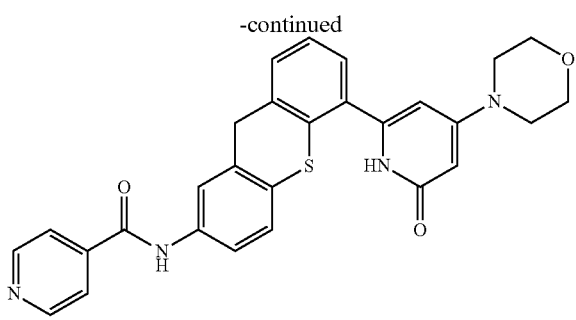

In the same manner as in Example 1-2-1 (1), the following compound was obtained.

N-(5-(4-Morpholino-6-oxo-1,6-dihydropyridin-2-yl)-9H-thioxanthen-2-yl)isonicotinamide MS(ESI m/z): 497 (M+H)
RT(min): 1.00

Example 3-6

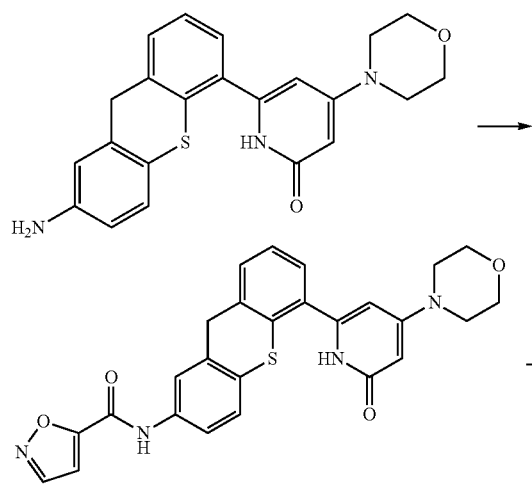

In the same manner as in Example 1-5, the following compounds were obtained.

N-(5-(4-morpholino-6-oxo-1,6-dihydropyridin-2-yl)-9H-thioxanthen-2-yl)isoxazole-5-carboxamide 6-(7-((isoxazol-5-ylmethyl)amino)-9H-thioxanthen-4-yl)-4-morpholinopyridin-2(1H)-one $^1$H-NMR (CDCl$_3$, 300 MHz) δ: 8.17 (1H, d, J=1.7 Hz), 7.38 (1H, dd, J=6.9, 2.0 Hz), 7.21 (1H, d, J=8.3 Hz), 6.74-6.69 (2H, m), 6.64 (1H, d, J=2.6 Hz), 6.50 (1H, dd, J=8.6, 2.6 Hz), 6.14 (1H, d, J=1.7 Hz), 6.01 (1H, d, J=2.3 Hz), 5.73 (1H, d, J=2.3 Hz), 4.52 (2H, d, J=5.6 Hz), 4.22 (1H, t, J=5.1 Hz), 3.84-3.79 (6H, m), 3.34 (4H, t, J=5.0 Hz).

MS(ESI m/z):473 (M+H)
RT(min): 1.17

Example 3-7

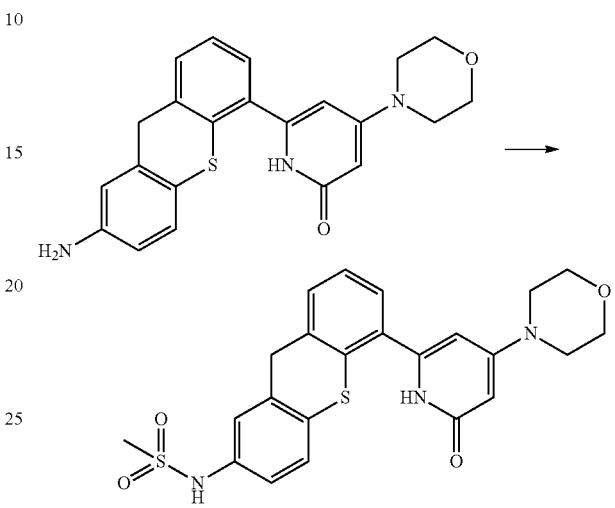

Methanesulfonyl chloride (4.4 mg) was added to a solution of 6-(7-amino-9H-thioxanthen-4-yl)-4-morpholinopyridin-2(1H)-one (15 mg) in pyridine (0.3 mL), followed by stirring at the same temperature for 18.5 hours. The solvent was distilled off under reduced pressure, and the obtained residues were purified by preparative thin layer silica gel chromatography (chloroform:methanol=9:1), whereby N-(5-(4-morpholino-6-oxo-1,6-dihydro pyridin-2-yl)-9H-thioxanthen-2-yl)methane sulfonamide (1.7 mg) was obtained.

MS(ESI m/z): 470 (M+H)
RT(min): 1.04

Example 3-8-1

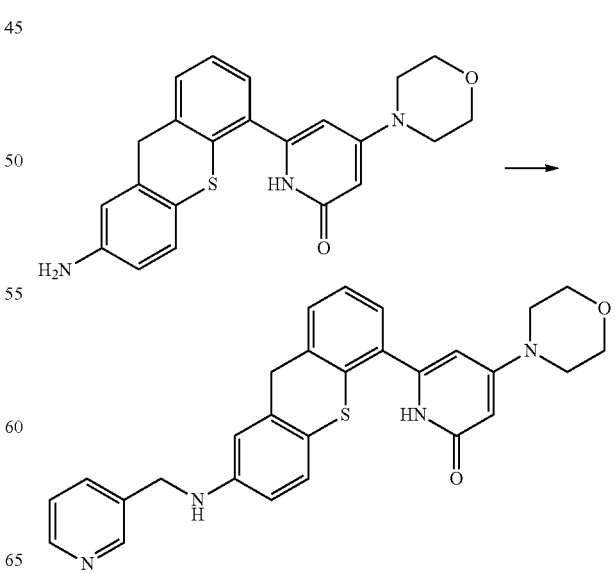

In the same manner as in Example 1-44-1, the following compound was obtained.

4-Morpholino-6-(7-((pyridin-3-ylmethyl)amino)-9H-thioxanthen-4-yl)pyridin-2(1H)-one ¹H-NMR (CD₃OD, 300 MHz) δ: 8.53 (1H, s), 8.38 (1H, d, J=4.6 Hz), 7.82 (1H, d, J=7.6 Hz), 7.49-7.20 (4H, m), 7.05 (1H, d, J=7.6 Hz), 6.70 (1H, s), 6.41 (1H, d, J=7.6 Hz), 6.19 (1H, s), 5.75 (1H, s), 4.82 (2H, s), 4.41 (2H, s), 3.76 (4H, t, J=4.8 Hz), 3.45 (4H, t, J=4.8 Hz).

MS(ESI m/z): 483 (M+H)

RT(min): 0.91

Examples 3-8-2 to 3-8-13

In the same manner as in Example 3-8-1, the following compounds were obtained.

TABLE 87

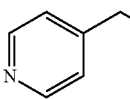

| Example No. | R^b | Compound Name | MS | RT (min) | ¹H-NMR (300 MHz) (DMSO-d₆) δ: |
|---|---|---|---|---|---|
| 3-8-2 | 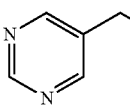 | 4-Morpholino-6-(7-((pyridin-4-yl methyl)amino)-9H-thioxanthen-4-yl)pyridin-2(1H)-one | 483 | 0.90 | (CDCl₃): 8.56 (2H, d, J = 6.3 Hz), 7.37 (1H, dd, J = 6.8, 2.1 Hz), 7.30-7.23 (4H, m), 7.18 (1H, d, J = 8.3 Hz), 6.57 (1H, d, J = 2.3 Hz), 6.44 (1H, dd, J = 8.4, 2.5 Hz), 6.00 (1H, d, J = 2.6 Hz), 5.73 (1H, d, J = 2.3 Hz), 4.39 (2H, s), 4.25 (1H, s), 3.82 (4H, t, J = 5.0 Hz), 3.78 (2H, s), 3.33 (4H, t, J = 5.0 Hz). |
| 3-8-3 | 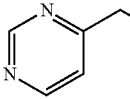 | 4-Morpholino-6-(7-((pyrimidin-5-yl methyl)amino)-9H-thioxanthen-4-yl)pyridin-2(1H)-one | 484 | 1.06 | (CDCl₃): 9.35 (1H, s), 9.13 (1H, s), 8.73 (2H, s), 7.35 (1H, t, J = 4.6 Hz), 7.26 (2H, d, J = 3.6 Hz), 7.17 (1H, d, J = 8.3 Hz), 6.61 (1H, d, J = 2.3 Hz), 6.46 (1H, dd, J = 8.4, 2.5 Hz), 6.00 (1H, d, J = 2.6 Hz), 5.69 (1H, d, J = 2.3 Hz), 4.38 (2H, d, J = 5.6 Hz), 4.25 (1H, t, J = 5.4 Hz), 3.80 (4H, t, J = 5.1 Hz), 3.78 (2H, s), 3.31 (4H, t, J = 5.0 Hz). |
| 3-8-4 | 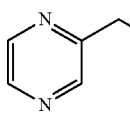 | 4-Morpholino-6-(7-((pyrimidin-4-yl methyl)amino)-9H-thioxanthen-4-yl)pyridin-2(1H)-one | 484 | 1.06 | (CDCl₃): 9.18 (1H, d, J = 1.3 Hz), 8.65 (1H, d, J = 5.0 Hz), 7.36-7.15 (5H, m), 6.62 (1H, d, J = 2.6 Hz), 6.48 (1H, dd, J = 8.4, 2.5 Hz), 6.00 (1H, d, J = 2.6 Hz), 5.71 (1H, d, J = 2.3 Hz), 4.78 (1H, t, J = 6.1 Hz), 4.46 (2H, d, J = 5.0 Hz), 3.81 (4H, t, J = 5.0 Hz), 3.80 (2H, s), 3.32 (4H, t, J = 5.0 Hz). |
| 3-8-5 | 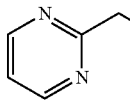 | 4-Morpholino-6-(7-((pyrazin-2-yl methyl)amino)-9H-thioxanthen-4-yl)pyridin-2 (1H)-one | 484 | 1.09 | (CDCl₃): 8.63 (1H, d, J = 1.3 Hz), 8.54 (1H, t, J = 2.1 Hz), 8.49 (1H, d, J = 2.6 Hz), 7.37 (1H, dd, J = 6.4, 2.8 Hz), 7.26-7.24 (2H, m), 7.20 (1H, d, J = 8.3 Hz), 6.69 (1H, d, J = 2.6 Hz), 6.54 (1H, dd, J = 8.4, 2.5 Hz), 6.00 (1H, d, J = 2.6 Hz). 5.71 (1H, d, J = 2.0 Hz), 4.79 (1H, t, J = 5.3 Hz), 4.51 (2H, d, J = 4.6 Hz) 3.84-3.78 (6H, m), 3.33 (4H, t, J = 4.8 Hz). |
| 3-8-6 | 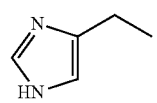 | 4-Morpholino-6-(7-((pyrimidin-2-yl methyl) amino)-9H-thioxanthen-4-yl) pyridin-2(1H)-one | 484 | 1.08 | (CDCl₃): 8.73 (2H, d, J = 5.0 Hz), 7.37 (1H, dd, J = 6.4, 2.5 Hz), 7.28-7.18 (4H, m), 6.75 (1H, d, J = 2.6 Hz), 6.59 (1H, dd, J = 6.3, 2.6 Hz), 6.01 (1H, d, J = 2.3 Hz), 5.72 (1H, d, J = 2.6 Hz), 5.16 (1H, s), 4.56 (2H, s), 3.85-3.80 (6H, m), 3.33 (4H, t, J = 5.0 Hz). |
| 3-8-7 |  | 6-(7-(((1H-Imidazol-4-yl) methyl)amino)-9H-thioxanthen-4-yl)-4-morpholino pyridin-2 1H)-one | 472 | 0.86 | (CD₃OD): 7.61 (1H, t, J = 1.5 Hz), 7.45 (1H, dd, J = 7.1, 1.8 Hz), 7.32-7.23 (2H, m), 7.09 (1H, d, J = 8.3 Hz), 6.94 (1H, s), 6.74 (1H, d, J = 2.3 Hz), 6.53 (1H, dd, J = 8.4, 2.5 Hz), 6.22 (1H, d, J = 2.6 Hz), 5.74 (1H, d, J = 2.3 Hz), 4.25 (2H, s), 3.80 (2H, s), 3.79 (4H, t, J = 5.1 Hz), 3.39 (4H, t, J = 5.0 Hz). |

TABLE 87-continued

| Example No. | R$^b$ | Compound Name | MS | RT (min) | $^1$H-NMR (300 MHz) (DMSO-d$_6$) δ: |
|---|---|---|---|---|---|
| 3-8-8 | 2-methoxy-3-methylene pyridine | 6-(7-(((2-Methoxy pyridin-3-yl)methyl)amino)-9H-thioxanthen-4-yl)-4-morpholino pyridin-2 (1H)-one | 513 | 1.33 | (CDCl$_3$): 8.06 (1H, dd, J = 5.0, 1.7 Hz), 7.51 (1H, dd, J = 7.3, 2.0 Hz), 7.34 (1H, t, J = 4.5 Hz), 7.25 (1H, s), 7.24 (1H, s), 7.16 (1H, d, J = 8.6 Hz), 6.82 (1H, dd, J = 7.3, 5.3 Hz), 6.60 (1H, d, J = 2.6 Hz), 6.46 (1H, dd, J = 8.4, 2.5 Hz), 6.01 (1H, d, J = 2.3 Hz), 5.71 (1H, d, J = 2.3 Hz), 4.30 (2H, s), 4.01 (3H, s), 3.81 (4H, t, J = 4.8 Hz), 3.78 (2H, s), 3.32 (4H, t, J = 5.0 Hz). |
| 3-8-9 | 5-methoxy-3-methylene pyridine | 6-(7-(((5-Methoxy pyridin-3-yl)methyl)amino)-9H-thioxanthen-4-yl)-4-morpholino pyridin-2 (1H)-one | 513 | 0.99 | (CDCl3): 8.23 (2H, d, J = 2.3 Hz), 7.36 (1H, dd J = 6.4, 2.5 Hz), 7.25-7.16 (4H, m), 6.62 (1H, d, J = 2.6 Hz) 6.48 (1H, dd, J = 8.6, 2.6 Hz). 6.00 (1H, d, J = 2.3 Hz), 5.72 (1H, d, J = 2.0 Hz), 4.35 (2H, s), 3.84 (3H, s), 3.81 (4H, t, J = 4.8 Hz), 3.79 (2H, s), 3.33 (4H, t, J = 4.8 Hz). |

TABLE 88

| Example No. | R$^b$ | Compound Name | MS | RT (min) | $^1$H-NMR (300 MHz) (DMSO-d$_6$) δ: |
|---|---|---|---|---|---|
| 3-8-10 | 6-methoxy-3-methylene pyridine | 6-(7-(((6-Methoxy pyridin-3-yl)methyl)amino)-9H-thioxanthen-4-yl)-4-morpholino pyridin-2(1H)-one | 513 | 1.28 | (CDCl$_3$): 8.14 (1H, d, J = 2.0 Hz), 7.57 (1H, dd, J = 8.6, 2.3 Hz), 7.37 (1H, dd, J = 6.8, 2.5 Hz), 7.26-7.22 (2H, m), 7.19 (1H, d, J = 8.3 Hz), 6.72 (1H, d, J = 8.6 Hz), 6.64 (1H, d, J = 2.3 Hz), 6.49 (1H, dd, J = 8.3, 2.6 Hz), 6.01 (1H, d, J = 2.3 Hz), 5.72 (1H, d J = 2.3 Hz), 4.25 (2H, s), 3.93 (3H, s), 3.82 (4H, t, J = 6.0 Hz), 3.80 (2H, s), 3.33 (4H, t, J = 4.8 Hz). |
| 3-8-11 | pyridazin-4-ylmethylene | 4-Morpholino-6-(7-((pyridazin-4-yl methyl)amino)-9H-thioxanthen-4-yl)pyridin-2(1H)-one | 484 | 1.01 | (CDCl$_3$): 9.22 (1H, s), 9.12 (1H, dd, J = 5.3, 1.0 Hz), 7.44 (1H, dd, J = 5.1, 2.5 Hz), 7.37 (1H, t, J = 3.6 Hz), 7.26-7.24 (2H, m), 7.20 (1H, d, J = 8.3 Hz), 6.54 (1H, d, J = 3.0 Hz), 6.44 (1H, dd, J = 8.4, 2.5 Hz), 6.00 (1H, d, J = 2.3 Hz), 5.73 (1H, d, J = 2.3 Hz), 4.45 (2H, d, J = 5.6 Hz), 4.31 (1H, t, J = 5.0 Hz), 3.82 (4H, t, J = 5.0 Hz), 3.78 (2H, s), 3.34 (4H, t, J = 5.0 Hz). |

TABLE 88-continued

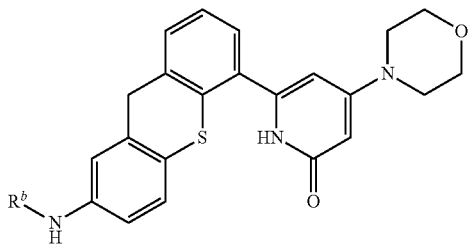

| Example No. | $R^b$ | Compound Name | MS | RT (min) | $^1$H-NMR (300 MHz) (DMSO-$d_6$) δ: |
|---|---|---|---|---|---|
| 3-8-12 | | 4-Morpholino-6-(7-(pyridazin-3-yl methyl) amino)-9H-thioxanthen-4-yl)pyridin-2(1H)-one | 484 | 1.02 | (CDCl$_3$): 9.13 (1H, dd, J = 4.8, 1.5 Hz), 7.51 (1H, dd, J = 8.4, 1.5 Hz), 7.44 (1H, dd, J = 8.3, 5.0 Hz), 7.37 (1H, t, J = 3.3 Hz), 7.29 (1H, s), 7.24 (1H, s), 7.20 (1H, d, J = 8.3 Hz), 6.67 (1H, d, J = 2.6 Hz), 6.53 (1H, dd, J = 8.3, 2.6 Hz), 6.01 (1H, d, J = 2.3 Hz), 5.73 (1H, d, J = 2.3 Hz), 4.90 (1H, s), 4.69 (2H, s), 3.82 (4H, t, J = 5.0 Hz), 3.80 (2H, s), 3.34 (4H, t, J = 5.0 Hz). |
| 3-8-13 | | 6-(7-((1-Methyl piperidin-4-yl)amino)-9H-thioxanthen-4-yl)-4-morpholino pyridin-2 (1H)-one | 489 | 0.85 | |

Examples 3-9

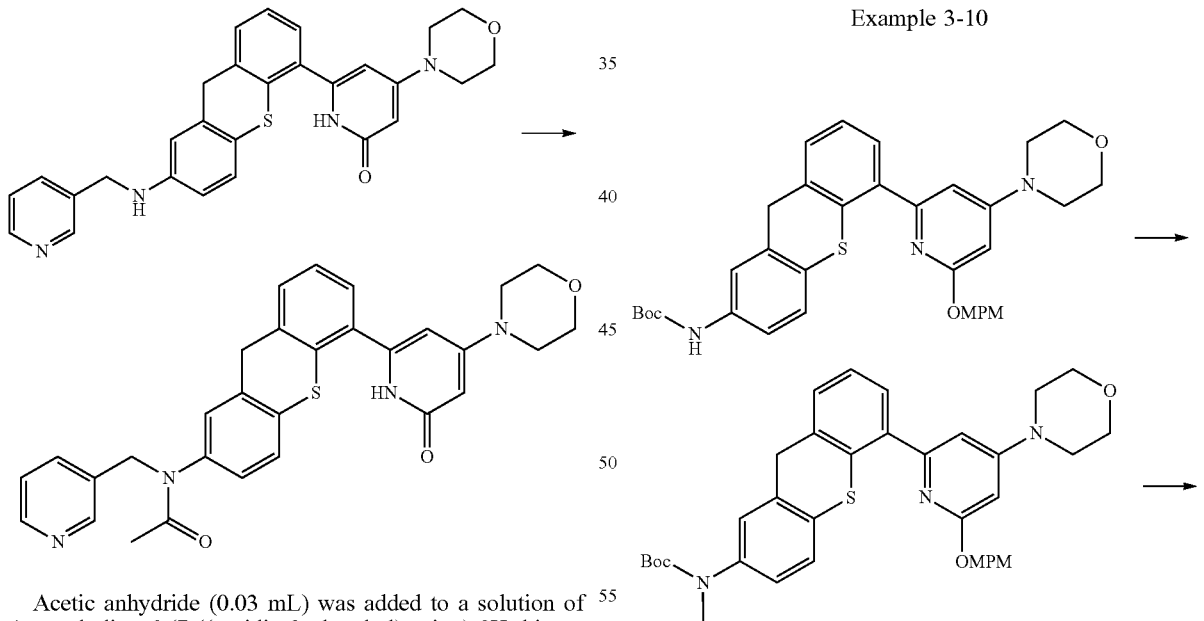

Acetic anhydride (0.03 mL) was added to a solution of 4-morpholino-6-(7-((pyridin-3-ylmethyl)amino)-9H-thioxanthen-4-yl)pyridin-2(1H)-one (15 mg) in pyridine (0.3 mL), followed by stirring at the same temperature for 2 hours. The solvent was distilled off under reduced pressure, and methanol (0.3 mL) and triethylamine (0.03 mL) were added to the obtained residues, followed by stirring at room temperature for 1.5 hours. The solvent was distilled off under reduced pressure, and the obtained residues were purified by preparative thin layer silica gel chromatography (chloroform:methanol=10:1), whereby N-(5-(4-morpholino-6-oxo-1,6-dihydropyridin-2-yl)-9H-thioxanthen-2-yl)-N-(pyridin-3-ylmethyl)acetamide (7.1 mg) was obtained.

MS(ESI m/z): 525 (M+H)

RT(min): 0.87

Example 3-10

(1)

Under ice-cooling, sodium hydride (3.6 mg, 60%, dispersed in liquid paraffin) was added to a solution of tert-butyl (5-(6-((4-methoxybenzyl)oxy)-4-morpholinopyridin-2-yl)-9H-thioxanthen-2-yl)carbamate (50 mg) in N,N-dimethyl formamide (1.0 mL), followed by stirring for 15 minutes, and iodomethane (12.8 mg) was added thereto, followed by stirring for 1.5 hours. Ethyl acetate was added to the reaction mixture, then, washed with a saturated sodium chloride aqueous solution, and dried over anhydrous magnesium sulfate. The solvent was distilled off under reduced pressure, and the obtained residues were purified by preparative thin layer silica gel chromatography (hexane:ethyl acetate=2:1), and purified by preparative thin layer silica gel chromatography (hexane:ethyl acetate=2:1, NH silica), whereby tert-butyl (5-(6-((4-methoxybenzyl)oxy)-4-morpholinopyridin-2-yl)-9H-thioxanthen-2-yl)(methyl) carba mate (17 mg) was obtained as a white solid.

(2)

Concentrated hydrochloric acid (0.5 mL) was added to a solution of tert-butyl (5-(6-((4-methoxybenzyl)oxy)-4-morpholinopyridin-2-yl)-9H-thioxanthen-2-yl)(methyl)carba mate (17 mg) obtained in Example 3-10 (1) in ethanol (0.5 mL), followed by stirring at room temperature for 4 hours. After the solvent was distilled off under reduced pressure, ethyl acetate was added to the obtained residues, and the resultant product was washed with a saturated sodium hydrogen carbonate aqueous solution, and dried over anhydrous sodium sulfate. The solvent was distilled off under reduced pressure, and the obtained residues were purified by preparative thin layer silica gel chromatography (chloroform:methanol=9:1), whereby 6-(7-(methylamino)-9H-thioxanthen-4-yl)-4-morpholinopyridin-2(1H)-one (7 mg) was obtained as a white solid.

MS(ESI m/z): 406 (M+H)
RT(min): 0.99

Example 4-1

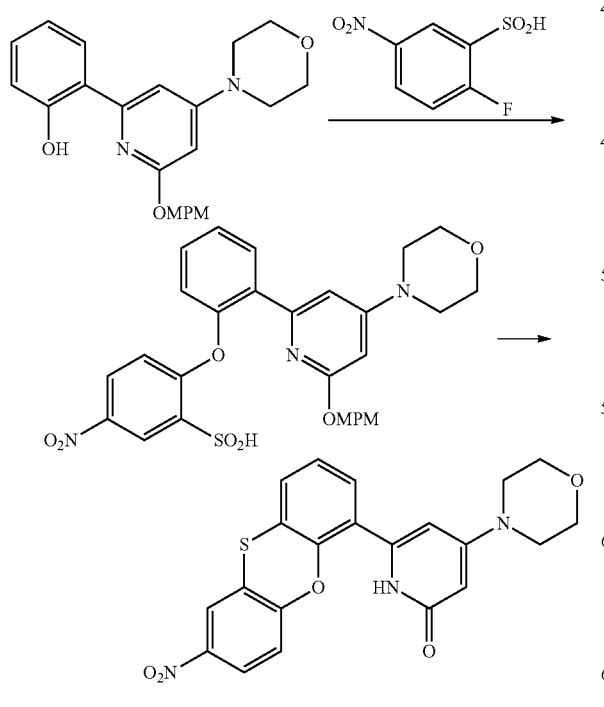

(1)

In the same manner as in Reference Example 9-1 (2), the following compound was obtained.

2-(2-(6-((4-Methoxybenzyl)oxy)-4-morpholinopyridin-2-yl)phenoxy)-5-nitrobenzene sulfinic acid MS(ESI m/z): 578 (M+H)
RT(min): 1.12

(2)

In the same manner as in Reference Example 9-1 (3), the following compound was obtained.

4-Morpholino-6-(8-nitrophenoxathiin-4-yl)pyridin-2(1H)-one

MS(ESI m/z): 424 (M+H)
RT(min): 1.25

Example 4-2

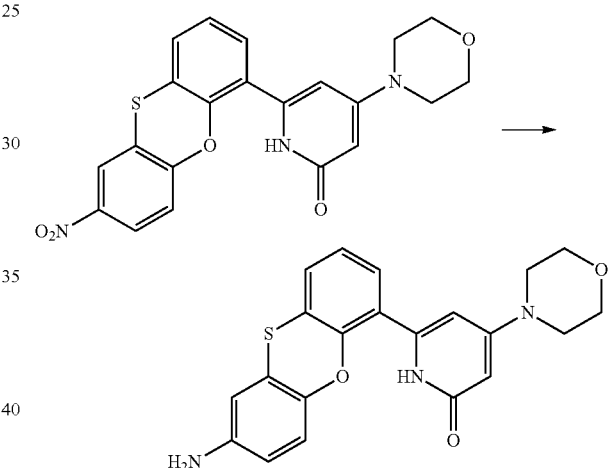

In the same manner as in Reference Example 3 (4), the following compound was obtained.

6-(8-Aminophenoxathiin-4-yl)-4-morpholinopyridin-2(1H)-one

MS(ESI m/z): 394 (M+H)
RT(min): 0.89

Example 4-3

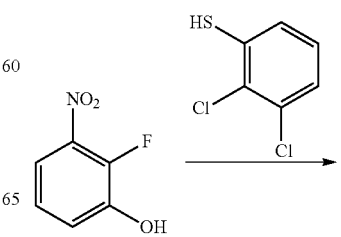

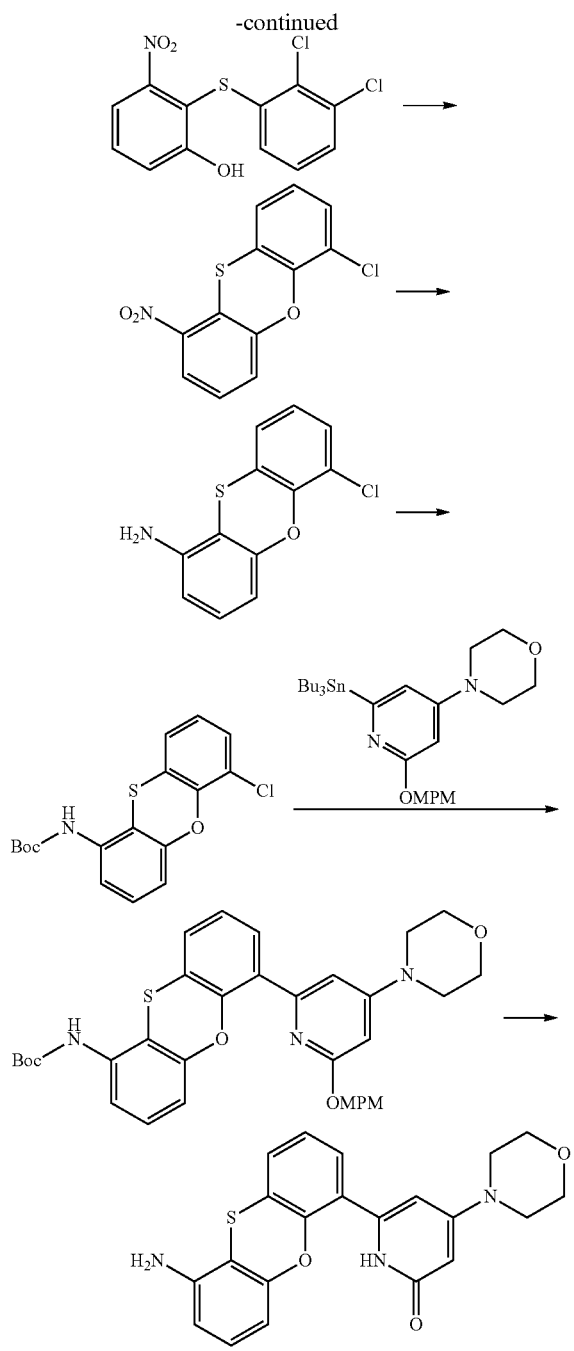

MS(ESI m/z): 317 (M+H)
RT(min): 1.59

(2)

Potassium carbonate (2.31 g) was added to a solution of 2-((2,3-dichlorophenyl)thio)-3-nitrophenol (2.64 g) obtained in Example 4-3 (1) in N-methyl pyrrolidone (15 mL), followed by stirring at 150° C. for 1.5 hours. After the reaction mixture was cooled to room temperature, 2 mol/L hydrochloric acid was added thereto, and the resultant product was extracted with ethyl acetate. The organic layer was washed with a saturated aqueous sodium chloride solution, and dried over anhydrous sodium sulfate. The solvent was distilled off under reduced pressure, whereby 6-chloro-1-nitrophenoxathiin was obtained as a yellow solid.

MS(ESI m/z): 280 (M+H)
RT(min): 1.90

(3)

In the same manner as in Reference Example 3 (4), the following compound was obtained.

6-Chlorophenoxathiin-1-amine

MS(ESI m/z): 250 (M+H)
RT(min): 1.66

(4)

In the same manner as in Reference Example 3 (5), the following compound was obtained.

tert-Butyl (6-chlorophenoxathiin-1-yl)carbamate

MS(ESI m/z): 350 (M+H)
RT(min): 1.97

(5)

In the same manner as in Reference Example 11 (6), the following compound was obtained.

tert-Butyl (6-(6-((4-methoxybenzyl)oxy)-4-morpholinopyridin-2-yl)phenoxathiin-1-yl)carbamate MS(ESI m/z): 614 (M+H)
RT(min): 1.74

(6)

In the same manner as in Example 2-1-1, the following compound was obtained.

6-(9-Aminophenoxathiin-4-yl)-4-morpholinopyridin-2(1H)-one $^1$H-NMR (CDCl$_3$, 300 MHz) δ: 7.31-7.25 (2H, m), 7.12 (1H, t, J=7.8 Hz), 6.98 (1H, t, J=7.9 Hz), 6.56-6.49 (2H, m), 6.16 (1H, d, J=2.3 Hz), 5.75 (1H, d, J=2.3 Hz), 3.83 (4H, t, J=5.0 Hz), 3.33 (4H, t, J=5.0 Hz).

MS(ESI m/z): 394 (M+H)
RT(min): 1.02

Example 4-4-1

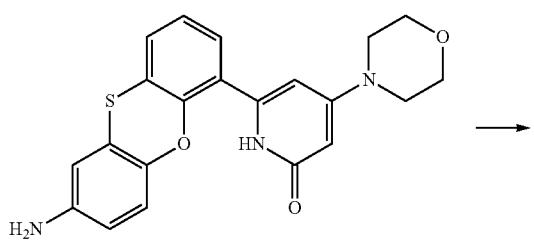

(1)

2-Fluoro-3-nitro phenol (1.57 g) and 2,3-dichlorobenzene thiol (1.79 g) were added to a solution of sodium hydroxide (0.80 g) in water (15 mL), and the resultant product was irradiated with microwaves (microwave reaction apparatus, 120° C., 1 hour, 2.45 GHz, 0 W to 240 W). After the reaction mixture was cooled to room temperature, 2 mol/L hydrochloric acid was added thereto, and the resultant product was extracted with ethyl acetate. The organic layer was washed with a saturated aqueous sodium chloride solution, and dried over anhydrous sodium sulfate. The solvent was distilled off under reduced pressure, and the obtained residues were purified by silica gel column chromatography (hexane:ethyl acetate=9:1→3:2), whereby 2-((2,3-dichlorophenyl)thio)-3-nitrophenol (2.64 g) was obtained as a yellow solid.

-continued

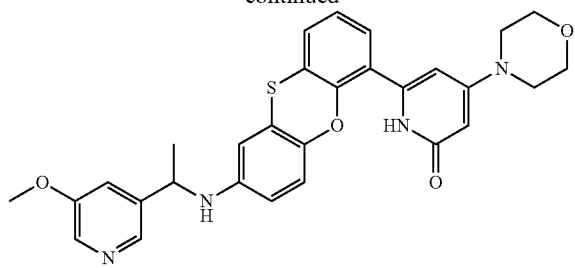

In the same manner as in Example 1-12-1, the following compound was obtained.

6-(8-((1-(5-Methoxypyridin-3-yl)ethyl)amino)phenoxathiin-4-yl)-4-morpholinopyridin-2(1H)-one MS(ESI m/z): 529 (M+H)
RT(min): 1.04

Examples 4-4-2 to 4-4-30

In the same manner as in Example 4-4-1, the following compounds were obtained.

TABLE 89

| Example No. | R$^b$ | Compound Name | MS | RT (min) | $^1$H-NMR (300 MHz) (DMSO-d$_6$) δ: |
|---|---|---|---|---|---|
| 4-4-2 | 4-Chloropyridin-2-yl, ethyl | 6-(8-(((4-Chloropyridin-2-yl)methyl)amino) phenoxathiin-4-yl)-4-morpholino pyridin-2(1H)-one | 519 | 1.29 | 10.87 (1H, s), 8.51 (1H, d, J = 5.9 Hz), 7.43-7.39 (2H, m), 7.30 (1H, dd, J = 7.6, 1.7 Hz), 7.23 (1H, d, J = 7.3 Hz), 7.10 (1H, t, J = 7.8 Hz), 6.66 (1H, d, J = 9.2 Hz), 6.46-6.43 (3H, m), 6.08 (1H, s), 5.46 (1H, s), 4.35 (2H, d, J = 6.3 Hz), 3.67 (4H, t, J = 4.6 Hz), 3.25 (4H, t, J = 4.6 Hz). |
| 4-4-3 | 2-Methylpyridin-4-yl, ethyl | 6-(8-(((2-Methyl pyridin-4-yl) methyl)amino)phenoxathiin-4-yl)-4-morpholino pyridin-2 (1H)-one | 499 | 0.90 | |
| 4-4-4 | 2-Methoxypyrimidin-5-yl, ethyl | 6-(8-(((2-Methoxy pyrimidin-5-yl)methyl) amino)phenoxathiin-4-yl)-4-morpholino pyridin-2 (1H)-one | 516 | 1.15 | (CDCl$_3$): 8.50 (2H, s), 7.36-7.18 (2H, m), 7.11 (1H, t, J = 7.6 Hz), 6.82 (1H, d, J = 8.6 Hz), 6.47-6.34 (3H, m), 6.02 (1H, d, J = 2.6 Hz), 5.43-5.25 (1H, m), 4.23 (2H, s), 4.00 (3H, s), 3.84 (4H, t, J = 4.6 Hz), 3.44 (4H, t, J = 4.6 Hz) |
| 4-4-5 | 2-(Dimethylamino)pyrimidin-5-yl, ethyl | 6-(8-(((2-(Dimethyl amino) pyrimidin-5-yl)methyl) amino)phenoxathiin-4-yl)-4-morpholino pyridin-2 (1H)-one | 529 | 1.16 | (CDCl$_3$): 8.49 (2H, s), 7.35 (1H, dd, J = 7.9, 1.3 Hz), 7.17 (1H, dd, J = 7.9, 1.3 Hz), 7.08 (1H, t, J = 7.9 Hz), 6.70 (1H, d, J = 8.6 Hz) 6.60 (1H, d, J = 2.0 Hz), 6.54-6.43 (2H, m), 6.32 (1H, d, J = 2.0 Hz), 5.38-5.31 (1H, m), 4.21 (2H, s), 3.86 (4H, t, J = 4.6 Hz), 3.55 (4H, t, J = 4.6 Hz), 3.33 (6H, s). |
| 4-4-6 | 6-(Methylamino)pyridin-3-yl, ethyl | 6-(8-(((6-(Methyl amino) pyridin-3-yl)methyl)amino) phenoxathiin-4-yl)-4-morpholino pyridin-2(1H)-one | 514 | 0.94 | 10.87 (1H, s), 7.96 (1H, s), 7.34 (1H, t, J = 4.3 Hz), 7.30 (1H, d, J = 7.6 Hz), 7.23 (1H, d, J = 6.6 Hz), 7.10 (1H, t, J = 7.6 Hz), 6.65 (1H, d, J = 8.6 Hz), 6.46-6.33 (4H, m), 6.09-6.03 (2H, m), 5.46 (1H, s), 4.02 (2H, d, J = 5.3 Hz), 3.67 (4H, t, J = 4.3 Hz), 3.26 (4H, t, J = 5.0 Hz), 2.73 (3H, s). |
| 4-4-7 | 5-(pyrrolidin-1-yl)pyridin-3-yl, ethyl | 4-Mmorpholino-6-(8-(((5-(pyrrolidin-1-yl)pyridin-3-yl) methyl)amino)phenoxathiin-4-yl)pyridin-2(1H)-one | 554 | 1.07 | 10.85 (1H, br s), 7.82 (1H, d, J = 1.2 Hz), 7.79 (1H, d, J = 3.3 Hz), 7.29 (1H, dd, J = 7.7, 1.7 Hz), 7.23 (1H, dd, J = 7.7, 1.7 Hz), 7.10 (1H, t, J = 7.5 Hz), 6.88-6.82 (1H, m), 6.65 (1H, d, J = 8.4 Hz), 6.50-6.44 (2H, m), 6.26 (1H, t, J = 6.0 Hz), 6.10 (1H, br s), 5.47 (1H, br s), 4.18 (2H, d, J = 6.0 Hz), 3.67 (4H, t, J = 4.9 Hz), 3.30-3.15 (8H, m), 2.00-1.90 (4H, m). |

TABLE 89-continued

| Example No. | $R^b$ | Compound Name | MS | RT (min) | $^1$H-NMR (300 MHz) (DMSO-$d_6$) δ: |
|---|---|---|---|---|---|
| 4-4-8 | 5-(1H-Pyrrol-1-yl)pyridin-3-yl | 6-(8-(((5-(1H-Pyrrol-1-yl)pyridin-3-yl)methyl)amino)phenoxathiin-4-yl)-4-morpholino pyridin-2(1H)-one | 550 | 1.32 | 10.86 (1H, br s), 8.76 (1H, d, J = 2.6 Hz), 8.44 (1H, d, J = 1.3 Hz) 7.98 (1H, t, J = 2.0 Hz), 7.44-7.40 (2H, m), 7.29 (1H, dd, J = 7.6, 1.7 Hz), 7.22 (1H, dd, J = 7.9, 1.3 Hz), 7.10 (1H, t, J = 7.5 Hz) 6.67 (1H, d, J = 9.9 Hz), 6.54-6.46 (2H, m) 6.38-6.30 (3H, m), 6.09 (1H, br s), 5.47 (1H, br s), 4.34 (2H, d, J = 5.9 Hz), 3.67 (4H, t, J = 4.6 Hz), 3.25 (4H, t, J = 4.6 Hz). |
| 4-4-9 | 5-(1H-Pyrazol-1-yl)pyridin-3-yl | 6-(8-(((5-(1H-Pyrazol-1-yl)pyridin-3-yl)methyl)amino)phenoxathiin-4-yl)-4-morpholino pyridin-2(1H)-one | 551 | 1.22 | |

TABLE 90

| Example No. | $R^b$ | Compound Name | MS | RT (min) | $^1$H-NMR (300 MHz) (DMSO-$d_6$) δ: |
|---|---|---|---|---|---|
| 4-4-10 | [3,3'-Bipyridin]-5-yl | 6-(8-((([3,3'-Bipyridin)-5-yl methyl)amino)phenoxathiin-4-yl)-4-morpholino pyridin-2(1H)-one | 562 | 103 | |
| 4-4-11 | 5-(1-Methyl-1H-pyrazol-4-yl)pyridin-3-yl | 6-(8-(((5-(1-Methyl-1H-pyrazol-4-yl)pyridin-3-yl)methyl)amino)phenoxathiin-4-yl)-4-morpholino pyridin-2(1H)-one | 565 | 1.00 | |
| 4-4-12 | 5,6-Dimethoxypyridin-3-yl | 6-(8-(((5,6-Dimethoxypyridin-3-yl)methyl)amino)phenoxathiin-4-yl)-4-morpholino pyridin-2(1H)-one | 545 | 1.26 | 10.87 (1H, br s), 7.66 (1H, d, J = 2.0 Hz), 7.33-7.19 (3H, m), 7.11 (1H, t, J = 7.6 Hz), 6.66 (1H, d, J = 9.2 Hz) 6.52-6.45 (2H, m), 6.18 (1H, t, J = 5.9 Hz), 6.09 (1H, br s), 5.47 (1H, br s), 4.16 (2H, d, J = 5.9 Hz), 3.82 (3H, s), 3.76 (3H, s), 3.67 (4H, t, J = 4.6 Hz), 3.26 (4H, t, J = 4.6 Hz). |

TABLE 90-continued

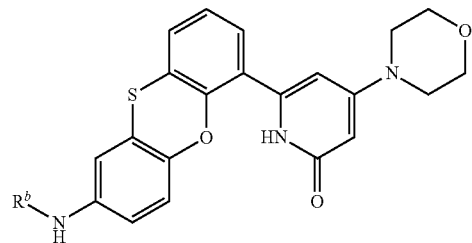

| Example No. | $R^b$ | Compound Name | MS | RT (min) | $^1$H-NMR (300 MHz) (DMSO-$d_6$) δ: |
|---|---|---|---|---|---|
| 4-4-13 | 2-(methylamino)pyrimidin-5-yl | 6-(8-(((2-(Methyl amino) pyrimidin-5-yl)methyl) amino)phenoxathiin-4-yl)-4-morpholino pyridin-2(1H)-one | 515 | 1.03 | 11.61 (1H, br s), 8.26 (2H, s), 7.35 (1H, dd, J = 7.3, 1.3 Hz), 7.27 (1H, dd, J = 7.3, 1.3 Hz). 7.14 (1H, t, J = 7.3 Hz), 7.07-6.97 (1H, m), 6.68-6.64 (1H, m), 6.51-6.43 (1H, m), 6.35 (1H, br s), 6.09 (1H, br s), 5.69 (1H, br s), 4.02 (2H, s), 3.69 (4H, t, J = 4.6 Hz), 3.35 (4H, t, J = 4.6 Hz), 2.76 (3H, d, J = 4.0 Hz). |
| 4-4-14 | 5-fluoro-6-methoxypyridin-3-yl | 6-(8-(((5-Fluoro-6-methoxy pyridin-3-yl)methyl)amino) phenoxathiin-4-yl)-4-morpholino pyridin-2(1H)-one | 533 | 1.38 | 10.92 (1H, br s), 7.97 (1H, d, J = 2.0 Hz), 7.62 (1H, dd, J = 11.2, 2.0 Hz), 7.30 (1H, dd, J = 7.9, 1.3 Hz), 7.24 (1H, dd, J = 7.9, 1.3 Hz). 7.11 (1H, t, J = 7.9 Hz), 6.66 (1H, m), 6.11 (1H, br s), 5.49 (1H, br s), 4.21 (2H, d, J = 4.6 Hz). 3.91 (3H, s), 3.67 (4H, t, J = 4.6 Hz), 3.26 (4H, t, J = 4.6 Hz). |
| 4-4-15 | quinolin-3-yl | 4-Morpholino-6-(8-((quinolin-3-yl methyl) amino)phenoxathiin-4-yl) pyridin-2(1H)-one | 535 | 1.13 | 10.86 (1H, br s), 8.91 (1H, d, J = 2.0 Hz), 8.24 (1H, d, J = 2.0 Hz), 8.00 (1H, d, J = 8.6 Hz), 7.93 (1H, d, J = 7.9 Hz), 7.72 (1H, dd, J = 7.9, 7.6 Hz), 7.58 (1H, dd, J = 8.6, 7.6 Hz), 7.28 (1H, dd, J = 7.9, 1.3 Hz), 7.22 (1H, dd, J = 7.9, 1.3 Hz), 7.09 (1H, t, J = 7.9 Hz), 6.74-6.60 (1H, m), 6.57-6.36 (3H, m), 6.09 (1H, br s), 5.47 (1H, br s), 4.47 (2H, d, J = 5.9 Hz), 3.66 (4H, t, J = 4.6 Hz), 3.25 (4H, t, J = 4.6 Hz). |
| 4-4-16 | 2-bromopyridin-4-yl | 6-(8-(((2-Bromopyridin-4-yl)methyl)amino) phenoxathiin-4-yl)-4-morpholino pyridin-2(1H)-one | 563 | 1.31 | 10.89 (1H, br s), 8.31 (1H, d, J = 5.3 Hz), 7.57 (1H, s), 7.38 (1H, d, J = 5.3 Hz), 7.29 (1H, dd, J = 7.3, 1.3 Hz), 7.23 (1H, dd, J = 7.3, 1.3 Hz), 7.11 (1H, t, J = 7.3 Hz), 6.67 (1H, d, J = 9.9 Hz), 6.49-6.40 (3H, m), 6.16-6.04 (1H, m), 5.52-5.43 (1H, m) 4.32 (2H, d, J = 5.9 Hz), 3.67 (4H, t, J = 4.6 Hz), 3.26 (4H, t, J = 4.6 Hz). |
| 4-4-17 | 5-(dimethylamino)pyrazin-2-yl | 6-(8-(((5-(Dimethyl amino) pyrazin-2-yl)methyl)amino) phenoxathiin-4-yl)-4-morpholino pyridin-2(1H)-one | 529 | 1.21 | (CDCl$_3$): 8.84 (1H, br s), 8.05 (1H, d, J = 2.0 Hz), 7.99 (1H, d, J = 2.0 Hz), 7.25-7.18 (2H, m), 7.06 (1H, t, J = 7.9 Hz), 6.92-6.85 (1H, m), 6.49-6.41 (2H, m), 6.13 (1H, d, J = 2.6 Hz), 5.73 (1H, d, J = 2.6 Hz), 5.38-5.32 (1H, m), 4.25 (2H, s), 3.82 (4H, t, J = 4.6 Hz), 3.33 (4H, t, J = 4.6 Hz), 3.12 (6H, s). |

TABLE 91

| Example No. | R$^b$ | Compound Name | MS | RT (min) | $^1$H-NMR (300 MHz) (DMSO-d$_6$) δ: |
|---|---|---|---|---|---|
| 4-4-18 | 4-Chloropyridin-3-yl | 6-(8-(((4-Chloropyridin-3-yl)methyl)amino) phenoxathiin-4-yl)-4-morpholino pyridin-2(1H)-one | 519 | 1.21 | |
| 4-4-19 | 4-Methylpyridin-3-yl | 6-(8-(((4-Methyl pyridin-3-yl)methyl)amino) phenoxathiin-4-yl)-4-morpholino pyridin-2(1H)-one | 499 | 0.95 | |
| 4-4-20 | 6-Chloropyridin-2-yl | 6-(8-(((6-Chloropyridin-2-yl)methyl)amino) phenoxathiin-4-yl)-4-morpholino pyridin-2(1H)-one | 519 | 1.36 | 10.87 (1H, s), 7.81 (1H, t, J = 7.9 Hz), 7.38-7.21 (4H, m) 7.12 (1H, d, J = 7.6 Hz), 6.66 (1H, d, J = 9.6 Hz), 6.45-6.43 (3H, m), 6.07 (1H, s), 5.45 (1H, s), 4.33 (2H, d, J = 6.6 Hz), 3.67 (4H, t, J = 4.5 Hz), 3.33 (4H, t, J = 4.5 Hz). |
| 4-4-21 | 6-Cyclopropylpyridin-2-yl | 6-(8-(((6-Cyclopropyl pyridin-2-yl)methyl)amino) phenoxathiin-4-yl)-4-morpholino pyrdin-2(1H)-one | 525 | 1.09 | 10.86 (1H, s), 7.56-7.53 (1H, m), 7.29-6.98 (5H, m), 6.64 (1H, d, J = 8.9 Hz), 6.55 (1H, s), 6.44 (1H, s), 6.31 (1H, s), 6.07 (1H, s), 5.45 (1H, s), 4.21 (2H, d, J = 5.9 Hz), 3.67 (4H, t, J = 4..8 Hz), 3.25 (4H, t, J = 4.8 Hz), 2.11-2.00 (1H, m), 0.96-0.88 (5H, m). |
| 4-4-22 | 3-Methoxypyridin-2-yl | 6-(8-(((3-Methoxy pyridin-2-yl)methyl)amino) phenoxathiin-4-yl)-4-morpholino pyridin-2(1H)-one | 515 | 1.03 | (CDCl$_3$): 8.16 (1H, d, J = 3.0 Hz), 7.26-7.14 (4H, m), 7.05 (1H, t, J = 7.8 Hz), 6.89 (1H, d, J = 9.2 Hz), 6.56-6.51 (2H, m), 6.14 (1H, d, J = 2.3 Hz), 5.70 (1H, d, J = 2.0 Hz), 4.33 (2H, s), 3.90 (3H, s), 3.81 (4H, t, J = 5.0 Hz), 3.31 (4H, t, J = 5.0 Hz). |
| 4-4-23 | 3-Methoxypyridin-4-yl | 6-(8-(((3-Methoxy pyridin-4-yl)methyl)amino) phenoxathiin-4-yl)-4-morpholino pyridin-2(1H)-one | 515 | 0.99 | 10.86 (1H, s), 8.32 (1H, s), 8.13 (1H, d, J = 4.6 Hz), 7.29 (1H, dd, J = 7.6, 1.7 Hz), 7.23 (1H, d, J = 6.6 Hz), 7.18 (1H, d, J = 4.6 Hz), 7.10 (1H, t, J = 7.6 Hz), 6.66 (1H, d, J = 8.9 Hz), 6.42-6.36 (2H, m), 6.26 (1H, s), 8.09 (1H, s), 5.46 (1H, s), 4.23 (2H, d, J = 6.3 Hz), 3.95 (3H, s), 3.67 (4H, t, J = 4.6 Hz), 3.25 (4H, t, J = 4.6 Hz). |
| 4-4-24 | pyridin-2-yl | 4-Morpholino-6-(8-((pyridin-2-yl methyl)amino)phenoxathiin-4-yl)pyridin-2(1H)-one | 485 | 0.98 | |
| 4-4-25 | 6-cyanopyridin-2-yl | 6-(((6-(4-Morpholino-6-oxo-1,6-dihydropyridin-2-yl)phenoxathiin-2-yl)amino) methyl)picolinonitrile | 510 | 1.31 | 10.87 (1H, br s), 8.01 (1H, t, J = 7.5 Hz), 7.91 (1H, d, J = 7.5 Hz), 7.67 (1H, d, J = 7.5 Hz), 7.30 (1H, dd, J = 7.8, 1.2 Hz), 7.23 (1H, dd, J = 7.5, 1.5 Hz), 7.10 (1H, t, J = 7.5 Hz), 6.66 (1H, d, J = 9.3 Hz), 6.51 (1H, br s), 5.44-5.40 (1H, br s), 4.41 (2H, d, J = 6.2 Hz), 3.67 (4H, t, J = 4.8 Hz), 3.25 (4H, t, J = 4.8 Hz). |

TABLE 91-continued

| Example No. | $R^b$ | Compound Name | MS | RT (min) | $^1$H-NMR (300 MHz) (DMSO-$d_6$) δ: |
|---|---|---|---|---|---|
| 4-4-26 | 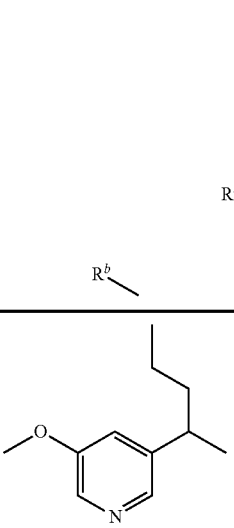 | 6-(8-((1-(5-Methoxy pyridin-3-yl)butyl)amino) phenoxathiin-4-yl)-4-morpholino pyridin-2(1H)-one | 557 | 1.23 | |

TABLE 92

| Example No. | $R^b$ | Compound Name | MS | RT (min) | $^1$H-NMR (300 MHz) (DMSO-$d_6$) δ: |
|---|---|---|---|---|---|
| 4-4-27 | 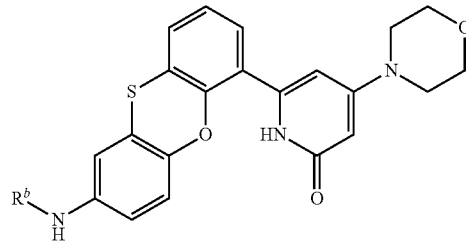 | 6-(8-((1-(5-Methoxy pyridin-3-yl)propyl)amino) phenoxathiin-4-yl)-4-morpholino pyridin-2(1 H)-one | 543 | 1.13 | |
| 4-4-28 | 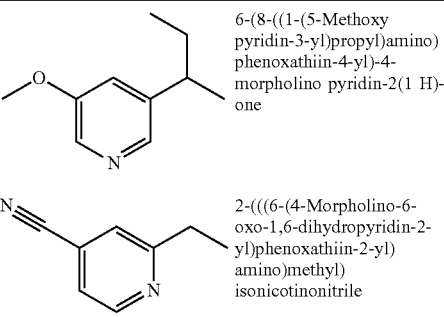 | 2-(((6-(4-Morpholino-6-oxo-1,6-dihydropyridin-2-yl)phenoxathiin-2-yl)amino)methyl) isonicotinonitrile | 510 | 1.26 | 10.87 (1H, br s), 8.79 (1H, d, J = 6.0 Hz), 7.75-7.72 (2H, m) 7.30 (1H, dd, J = 7.5, 1.5 Hz), 7.23 (1H, dd, J = 7.5, 1.5 Hz), 7.10 (1H, t, J = 7.6 Hz), 6.66 (1H, d, J = 8.4 Hz), 6.48-6.41 (3H, m), 6.10 (1H, s), 5.47 (1H, d, J = 2.1 Hz), 4.41 (2H, d, J = 6.0 Hz), 3.67 (4H, t, J = 4.8 Hz), 3.25 (4H, t, J = 4.8 Hz). |
| 4-4-29 | 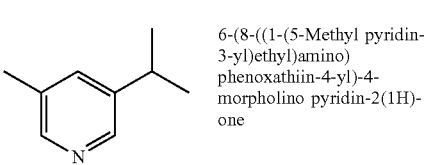 | 6-(8-((1-(5-Methyl pyridin-3-yl)ethyl)amino) phenoxathiin-4-yl)-4-morpholino pyridin-2(1H)-one | 513 | 0.99 | (CDCl$_3$): 9.32 (1H, br s), 8.39 (1H, d, J = 2.0 Hz), 8.31 (1H, d, J = 1.3 Hz), 7.45-7.42 (1H, m), 7.23-7.21 (1H, m), 7.17-7.14 (1H, m), 7.04 (1H, t, J = 7.3 Hz), 6.78 (1H, d, J = 8.6 Hz), 6.28-6.22 (2H, m), 6.11 (1H, d, J = 2.6 Hz), 5.70 (1H, d, J = 2.0 Hz), 4.48-4.38 (1H, m), 4.04-3.94 (1H, m), 3.80 (4H, t, J = 5.0 Hz), 3.30 (4H, t, J = 5.0 Hz), 2.31 (3H, s), 1.51 (3H, d, J = 6.6 Hz). |
| 4-4-30 | 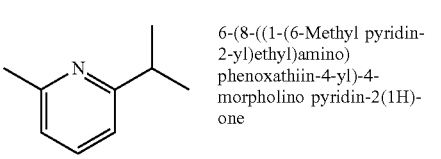 | 6-(8-((1-(6-Methyl pyridin-2-yl)ethyl)amino) phenoxathiin-4-yl)-4-morpholino pyridin-2(1H)-one | 513 | 1.00 | (CDCl$_3$): 9.12 (1H, br s), 7.50 (1H, t, J = 7.8 Hz), 7.27-6.98 (5H, m), 7.53 (1H, d, J = 9.3 Hz), 8.37-6.32 (2H, m), 6.11 (1H, d, J = 2.7 Hz), 5.70 (1H, d, J = 2.7 Hz), 4.56-4.40 (2H, m), 3.81 (4H, t, J = 4.5 Hz), 3.30 (4H, t, J = 4.5 Hz), 2.56 (3H, s), 1.50 (3H, d, J = 6.6 Hz). |

Example 4-5

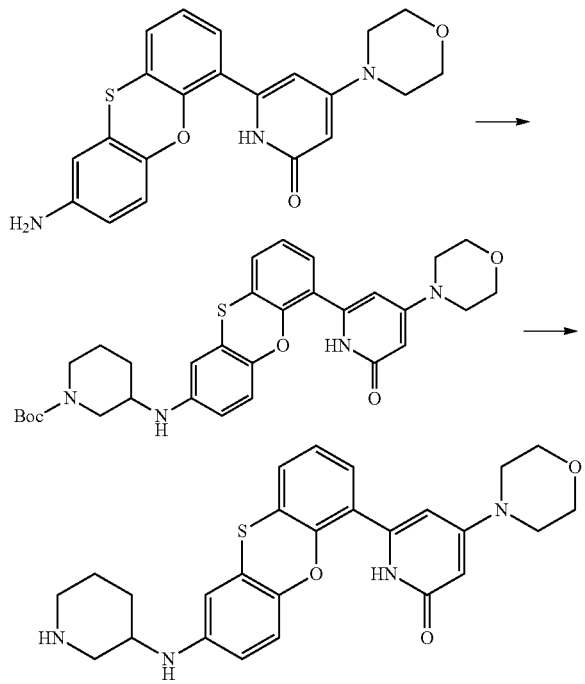

(1)
In the same manner as in Example 1-12-1, the following compound was obtained.

tert-Butyl 3-((6-(4-morpholino-6-oxo-1,6-dihydro-pyridin-2-yl)phenoxathiin-2-yl)amino)piperidine-1-carboxylate MS(ESI m/z): 577 (M+H)
RT(min): 1.50

(2)
4.0 mol/L hydrogen chloride/1,4-dioxane (2 mL) was added to a solution of tert-butyl 3-((6-(4-morpholino-6-oxo-1,6-dihydropyridin-2-yl)phenoxathiin-2-yl)amino)piperidine-1-carboxylate (13 mg) obtained in Example 4-5 (1) in methanol (1 mL), followed by stirring at room temperature for 3 hours. A sodium carbonate aqueous solution was added to the reaction mixture, and the resultant product was extracted with dichloromethane, followed by drying over anhydrous sodium sulfate. The solvent was distilled off under reduced pressure, and the obtained residues were purified by silica gel column chromatography (methanol: ethyl acetate=0:1→1:4, NH silica), whereby 4-morpholino-6-(8-(piperidin-3-ylamino)phenoxathiin-4-yl)pyridin-2 (1H)-one (11 mg) was obtained as a white solid.

$^1$H-NMR (CDCl$_3$, 300 MHz) δ: 7.23-7.19 (2H, m), 7.06 (1H, t, J=7.6 Hz), 6.86 (1H, d, J=9.2 Hz), 6.38-6.35 (2H, m), 6.12 (1H, d, J=2.3 Hz), 5.72 (1H, d, J=2.6 Hz), 3.82 (4H, t, J=5.0 Hz), 3.32 (4H, t, J=5.0 Hz), 3.17-3.13 (1H, m), 2.89-2.83 (1H, m), 2.72-2.68 (1H, m), 2.56-2.50 (1H, m), 1.88-1.48 (5H, m).

MS(ESI m/z): 477 (M+H)
RT(min): 0.91

Example 4-6-1

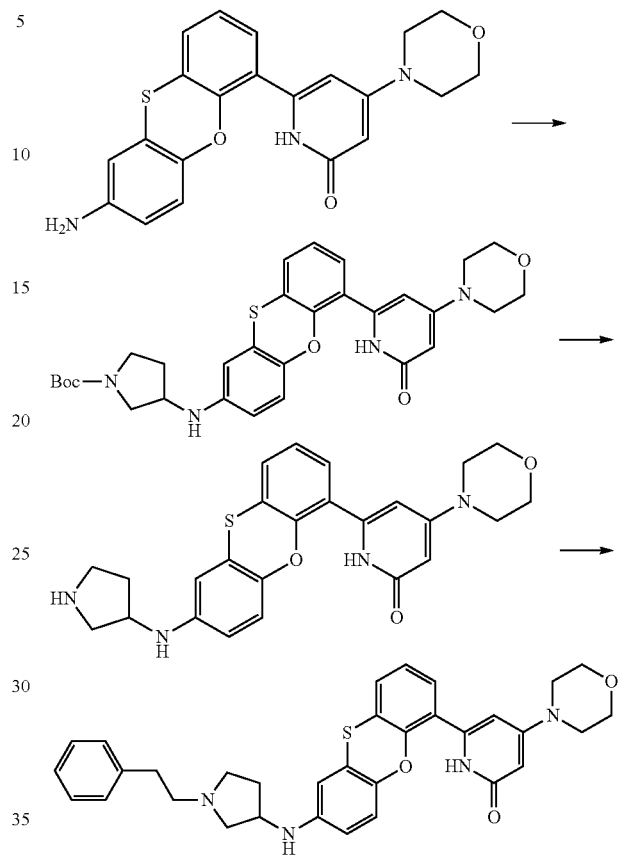

(1)
In the same manner as in Example 1-12-1, the following compound was obtained.

tert-Butyl 3-((6-(4-morpholino-6-oxo-1,6-dihydro-pyridin-2-yl)phenoxathiin-2-yl)amino)pyrrolidine-1-carboxylate MS(ESI m/z): 563 (M+H)
RT(min): 1.45

(2)
In the same manner as in Example 4-5 (2), the following compound was obtained.

4-Morpholino-6-(8-(pyrrolidin-3-ylamino)phenoxathiin-4-yl)pyridin-2(1H)-one

MS(ESI m/z): 463 (M+H)
RT(min): 0.87

(3)
In the same manner as in Example 1-44-1, the following compound was obtained.

4-Morpholino-6-(8-((1-phenethylpyrrolidin-3-yl)amino)phenoxathiin-4-yl)pyridin-2(1H)-one $^1$H-NMR (DMSO-d$_6$, 300 MHz) δ: 10.87 (1H, s), 7.33-7.08 (8H, m), 6.67 (1H, d, J=8.6 Hz), 6.55 (1H, s), 6.44-6.40 (2H, m), 6.10 (1H, s), 5.75 (1H, d, J=6.9 Hz), 3.68 (4H, t, J=4.8 Hz), 3.26 (4H, t, J=4.8 Hz), 2.86-2.61 (7H, m), 2.39-2.16 (3H, m), 1.54-1.51 (1H, m).

MS(ESI m/z): 567 (M+H)
RT(min): 1.15

Example 4-6-2

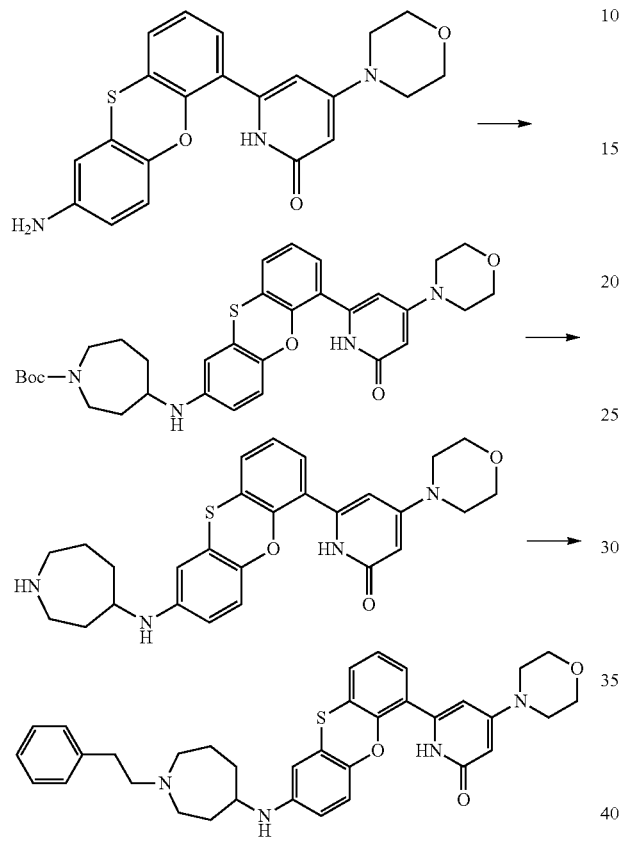

In the same manner as in Example 4-6-1, the following compounds were obtained.

tert-Butyl 4-((6-(4-morpholino-6-oxo-1,6-dihydro-pyridin-2-yl)phenoxathiin-2-yl)amino)azepane-1-carboxylate MS(ESI m/z): 591 (M+H)
RT(min): 1.50

6-(8-(Azepan-4-ylamino)phenoxathiin-4-yl)-4-morpholinopyridin-2(1H)-one

MS(ESI m/z): 491 (M+H)
RT(min): 0.91

4-Morpholino-6-(8-((1-phenethylazepan-4-yl)amino)phenoxathiin-4-yl)pyridin-2(1H)-one $^1$H-NMR (DMSO-d$_6$, 300 MHz) δ: 10.87 (1H, s), 7.33-7.11 (8H, m), 6.65 (1H, d, J=8.3 Hz), 6.55 (1H, d, J=8.1 Hz), 6.36-6.32 (2H, m), 6.09 (1H, s), 5.48-5.42 (1H, m), 3.70-3.65 (5H, m), 3.26 (4H, t, J=4.6 Hz), 2.68-2.58 (6H, m), 1.93-1.51 (8H, m).

MS(ESI m/z): 595 (M+H)
RT(min): 1.17

Example 4-6-3

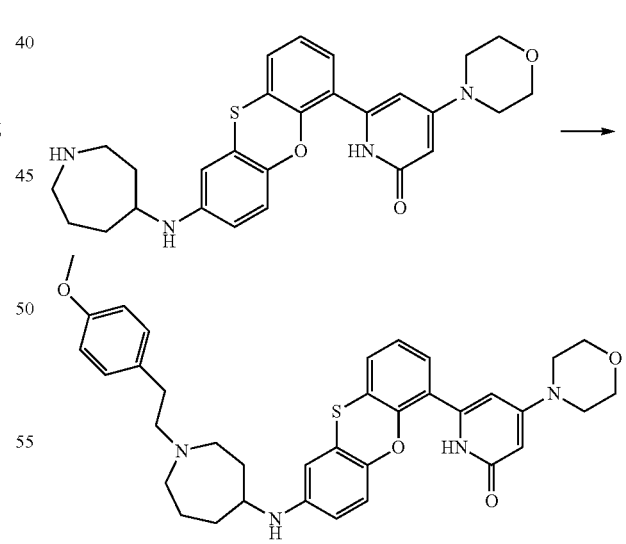

In the same manner as in Example 4-6-1 (3), the following compound was obtained.

4-Morpholino-6-(8-((1-phenethylpiperazin-3-yl)amino)phenoxathiin-4-yl)pyridin-2(1H)-one MS(ESI m/z): 581 (M+H)
RT(min): 1.16

Example 4-7

In the same manner as in Example 1-27, the following compound was obtained.

6-(8-((1-(4-Methoxyphenethyl)azepan-4-yl)amino)phenoxathiin-4-yl)-4-morpholinopyridin-2(1H)-one $^1$H-NMR (DMSO-d$_6$, 300 MHz) δ: 10.87 (1H, s), 7.31 (1H, dd, J=7.6, 1.7 Hz), 7.24 (1H, d, J=6.6 Hz), 7.16-7.08

(3H, m), 6.86-6.80 (2H, m), 6.68-6.62 (1H, m), 6.36-6.32 (2H, m), 6.10 (1H, s), 5.48-5.42 (2H, m), 3.72-3.60 (8H, m), 3.26 (4H, t, J=5.4 Hz), 2.64-2.55 (6H, m), 1.93-1.53 (8H, m).

MS(ESI m/z): 625 (M+H)

RT(min): 1.16

Example 4-8-1

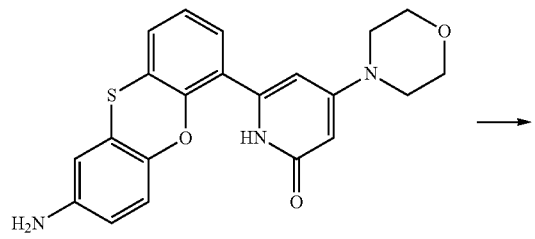

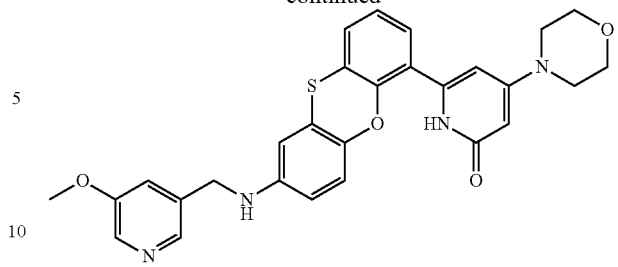

In the same manner as in Example 1-44-1, the following compound was obtained.

6-(8-(((5-Methoxypyridin-3-yl)methyl)amino)phenoxathiin-4-yl)-4-morpholinopyridin-2(1H)-one $^1$H-NMR (CDCl$_3$, 300 MHz) δ: 8.22 (1H, d, J=2.6 Hz), 8.21 (1H, d, J=1.7 Hz), 7.25 (1H, d, J=2.0 Hz), 7.22 (1H, s), 7.20 (1H, s), 7.07 (1H, t, J=7.4 Hz), 6.85 (1H, d, J=8.3 Hz), 6.37-6.32 (2H, m), 6.14 (1H, d, J=2.3 Hz), 5.75 (1H, d, J=2.3 Hz), 4.31 (2H, s), 3.85 (3H, s), 3.82 (4H, t, J=5.0 Hz), 3.33 (4H, t, J=4.8 Hz).

MS(ESI m/z): 515 (M+H)

RT(min): 1.01

Examples 4-8-2 to 4-8-26

In the same manner as in Example 4-8-1, the following compounds were obtained.

TABLE 93

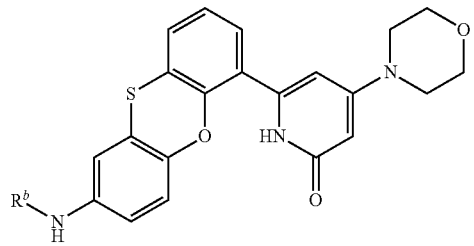

| Example No. | R$^b$ | Compound Name | MS | RT (min) | $^1$H-NMR (300 MHz) (DMSO-d$_6$) δ: |
|---|---|---|---|---|---|
| 4-8-2 | (1-methylpiperidin-4-yl) | 6-(8-((1-Methyl piperidin-4-yl)amino)phenoxathiin-4-yl)-4-morpholino pyridin-2(1H)-one | 491 | 0.87 | |
| 4-8-3 | (tert-butoxycarbonyl-piperidin-4-yl) | tert-Butyl 4-((6-(4-morpholino-6-oxo-1,6-dihydropyridin-2-yl)phenoxathiin-2-yl)amino)piperidin-1-carboxylate | 577 | 1.49 | |
| 4-8-4 | ((2-methoxypyridin-4-yl)methyl) | 6-(8-(((2-Methoxy pyridin-4-yl)methyl)amino)phenoxathiin-4-yl)-4-morpholino pyridin-2(1H)-one | 515 | 1.25 | (CDCl$_3$): 8.94 (1H, br s), 8.11 (1H, d, J = 5.3 Hz), 7.24 (1H, dd, J = 7.6, 1.7 Hz), 7.20 (1H, dd, J = 7.6, 1.7 Hz), 7.07 (1H, t, J = 7.8 Hz), 6.90-6.80 (2H, m), 6.70 (1H, s), 6.36 (1H, dd, J = 8.8, 2.8 Hz), 6.32 (1H, d, J = 2.6 Hz), 6.12 (1H, d, J = 2.3 Hz), 5.72 (1H, d, J = 2.3 Hz), 4.27 (1H, d, J = 5.6 Hz), 3.92 (3H, s), 3.82 (4H, t, J = 5.0 Hz), 3.32 (4H, t, J = 5.0 Hz). |

TABLE 93-continued

| Example No. | R$^b$ | Compound Name | MS | RT (min) | $^1$H-NMR (300 MHz) (DMSO-d$_6$) δ: |
|---|---|---|---|---|---|
| 4-8-5 | 6-Methyl pyridin-2-yl | 6-(8-(((6-Methyl pyridin-2-yl)methyl)amino) phenoxathiin-4-yl)-4-morpholino pyridin-2(1H)-one | 499 | 0.93 | (CDCl$_3$): 7.54 (1H, t, J = 7.8 Hz), 7.26-7.18 (2H, m), 7.22-7.03 (3H, m), 6.89 (1H, d, J = 8.9 Hz), 6.48-6.42 (2H, m) 6.13 (1H, d, J = 2.3 Hz), 5.73 (1H, d, J = 2.6 Hz), 4.34 (2H, s), 3.82 (4H, t, J = 4.8 Hz), 3.32 (4H, t, J = 5.0 Hz), 2.57 (3H, s). |
| 4-8-6 | 5-Chloropyridin-3-yl | 6-(8-(((5-Chloropyridin-3-yl)methyl)amino) phenoxathiin-4-yl)-4-morpholino pyridin-2(1H)-one | 519 | 1.29 | (CDCl$_3$): 8.50 (1H, d, J = 2.3 Hz), 8.48 (1H, d, J = 1.7 Hz), 7.67 (1H, t, J = 2.0 Hz), 7.24-7.18 (2H, m), 7.07 (1H, t, J = 7.8 Hz), 6.88 (1H, d, J = 8.6 Hz), 6.47-6.34 (2H, m), 6.12 (1H, d, J = 2.3 Hz), 5.72 (1H, d, J = 2.3 Hz), 4.33 (2H, d, J = 5.3 Hz), 3.82 (4H, t, J = 4.8 Hz), 3.32 (4H, t, J = 5.0 Hz). |
| 4-8-7 | 5-Cyclopropyl pyridin-3-yl | 6-(8-(((5-Cyclopropyl pyridin-3-yl)methyl)amino) phenoxathiin-4-yl)-4-morpholino pyridin-2(1H)-one | 525 | 1.02 | 10.87 (1H, s) 8.32 (1H, d, J = 2.0 Hz) 8.25 (1H, d, J = 2.3 Hz), 7.38 (1H, s), 7.30 (1H, dd, J = 7.6, 1.7 Hz), 7.23 (1H, d, J = 7.9 Hz), 7.10 (1H, t, J = 7.8 Hz), 6.66 (1H, d, J = 9.2 Hz), 6.58-6.42 (2H, m), 6.26 (1H, t, J = 6.3 Hz), 6.09 (1H, s), 5.47 (1H, s), 4.21 (2H, d, J = 5.9 Hz), 3.67 (4H, t, J = 4.8 Hz), 3.25 (4H, t, J = 5.0 Hz), 1.99-1.83 (1H, m), 1.08-0.95 (4H, m). |
| 4-8-8 | 4-Methoxy pyridin-2-yl | 6-(8-(((4-Methoxy pyridin-2-yl)methyl) amino)phenoxathiin-4-yl)-4-morpholino pyridin-2 (1H)-one | 515 | 0.93 | (CDCl$_3$): 8.39 (1H, d, J = 5.9 Hz), 7.26-7.19 (2H, m), 7.05 (1H, d, J = 7.9 Hz), 6.87 (1H, d, J = 8.9 Hz), 6.83 (1H, d, J = 2.6 Hz), 6.73 (1H, dd, J = 5.8, 2.5 Hz), 6.46-6.40 (2H, m), 6.13 (1H, d, J = 2.3 Hz), 5.73 (1H, d, J = 2.3 Hz), 4.34 (2H, s), 3.83 (3H, s), 3.82 (4H, t, J = 4.6 Hz), 3.32 (4H, t, J = 5.0 Hz). |
| 4-8-9 | 2-Methoxy pyridin-3-yl | 6-(8-(((2-Methoxy pyridin-3-yl)methyl) amino)phenoxathiin-4-yl)-4-morpholino pyridin-2 (1H)-one | 515 | 1.33 | (CDCl$_3$): 8.09-8.05 (1H, m), 7.51 (1H, d, J = 5.6 Hz), 7.27-7.18 (2H, m), 7.06 (1H, t, J = 7.8 Hz), 6.90-6.80 (2H, m ), 6.42-6.35 (2H, m), 6.12 (1H, d, J = 2.3 Hz), 5.72 (1H, d, J = 2.6 Hz), 4.25 (2H, s), 4.00 (3H, 2), (4H, t, J = 5.0 Hz), 3.32 (4H, t, J = 5.0 Hz). |

TABLE 94

| Example No. | R^b | Compound Name | MS | RT (min) | ¹H-NMR(300 MHz) (DMSO-d₆) δ: |
|---|---|---|---|---|---|
| 4-8-10 | 4-methoxypyridin-3-yl | 6-(8-(((4-Methoxy pyridin-3-yl)methyl)amino) phenoxathiin-4-yl)-4-morpholino pyridin-2(1H)-one | 515 | 0.94 | |
| 4-8-11 | 6-methoxypyridin-3-yl | 6-(8-(((6-Methoxy pyridin-3-yl)methyl)amino) phenoxathiin-4-yl)-4-morpholino pyridin-2(1H)-one | 515 | 1.28 | (CDCl₃): 8.12 (1H, d, J = 2.0 Hz), 7.56 (1H, dd, J = 8.6, 2.3 Hz), 7.26-7.18 (2H, m), 7.07 (1H, t, J = 7.8 Hz), 6.87 (1H, d, J = 9.2 Hz), 6.73 (1H, d, J = 8.3 Hz), 6.41-6.39 (2H, m), 6.12 (1H, d, J = 2.3 Hz), 5.72 (1H, d, J = 2.3 Hz), 4.20 (2H, s), 3.93 (3H, s), 3.82 (4H, t, J = 4.8 Hz), 3.32 (4H, t, J = 5.0 Hz). |
| 4-8-12 | 5-fluoropyridin-3-yl | 6-(8-(((5-Fluoropyridin-3-yl)methyl)amino) phenoxathiin-4-yl)-4-morpholino pyridin-2(1H)-one | 503 | 1.23 | 10.87 (1H, s), 8.46 (1H, s), 8.44 (1H, d, J = 2.6 Hz), 7.65 (1H, d, J = 9.2 Hz), 7.30 (1H, dd, J = 7.6, 1.7 Hz), 7.23 (1H, d, J = 6.6 Hz), 7.10 (1H, t, J = 7.8 Hz), 6.66 (1H, d, J = 9.2 Hz), 6.49-6.45 (2H, m), 6.37 (1H, t, J = 6.3 Hz), 6.09 (1H, s), 5.47 (1H, s), 4.34 (2H, d, J = 5.9 Hz), 3.67 (4H, t, J = 4.5 Hz), 3.25 (4H, t, J = 5.0 Hz). |
| 4-8-13 | 5-methylpyridin-2-yl | 6-(8-(((5-Methyl pyridin-2-yl)methyl)amino) phenoxathiin-4-yl)-4-morpholino pyridin-2(1H)-one | 499 | 0.96 | (CDCl₃): 8.39 (1H, d, J = 2.0 Hz), 7.46 (1H, dd, J = 8.1, 2.1 Hz), 7.25-7.16 (3H, m), 7.06 (1H, t, J = 7.6 Hz), 6.87 (1H, d, J = 8.9 Hz), 6.47-6.41 (2H, m), 6.13 (1H, d, J = 2.3 Hz), 5.72 (1H, d, J = 2.3 Hz), 4.35 (2H, s), 3.82 (4H, t, J = 4.8 Hz), 3.32 (4H, t, J = 5.0 Hz), 2.33 (3H, s). |
| 4-8-14 | 2-chloropyridin-4-yl | 6-(8-(((2-Chloropyridin-4-yl)methyl)amino) phenoxathiin-4-yl)-4-morpholino pyridin-2(1H)-one | 519 | 1.33 | |
| 4-8-15 | 5-cyclopentylpyridin-3-yl | 6-(8-(((5-Cyclopentyl pyridin-3-yl)methyl)amino) phenoxathiin-4-yl)-4-morpholino pyridin-2(1H)-one | 553 | 1.16 | 8.47 (2H, d, J = 2.1 Hz), 7.94 (1H, s), 7.33 (1H, dd, J = 7.6, 1.7 Hz), 7.26 (1H, dd, J = 7.5, 1.5 Hz), 7.13 (1H, t, J = 7.7 Hz), 6.66 (1H, d, J = 8.7 Hz), 6.51-6.45 (2H, m), 6.32 (1H, d, J = 1.8 Hz), 5.69 (1H, d, J = 1.8 Hz), 4.32 (2H, s), 3.69 (4H, t, J = 4.7 Hz), 3.34 (4H, t, J = 4.7 Hz), 3.15-3.00 (1H, m), 2.12-1.97 (2H, m), 1.85-145 (6H, m). |
| 4-8-16 | 5-(2-oxoazetidin-1-yl)pyridin-3-yl | 4-Morpholino-6-(8-(((5-(2-oxoazetidin-1-yl)pyridin-3-yl)methyl)amino) phenoxathiin-4-yl)pyridin-2 (1H)-one | 554 | 1.07 | |

TABLE 94-continued

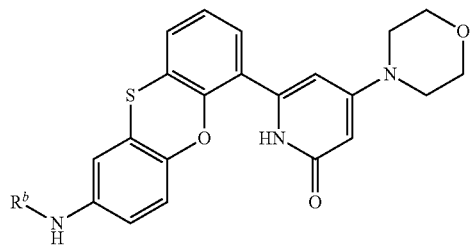

| Example No. | R$^b$ | Compound Name | MS | RT (min) | $^1$H-NMR(300 MHz) (DMSO-d$_6$) δ: |
|---|---|---|---|---|---|
| 4-8-17 | (5-methoxy-pyridin-2-yl)methyl | 6-(8-(((5-Methoxy pyridin-2-yl)methyl)amino) phenoxathiin-4-yl)-4-morpholino pyridin-2(1H)-one | 515 | 1.06 | 10.86 (1H, s), 6.22 (1H, d, J = 2.3 Hz), 7.34 (1H, dd, J = 8.6, 3.0 Hz), 7.31-7.26 (2H, m), 7.23 (1H, d, J = 7.6 Hz), 7.10 (1H, t, J = 7.6 Hz), 6.65 (1H, d, J = 8.9 Hz), 6.48-6.42 (2H, m), 6.33 (1H, t, J = 5.9 Hz), 6.09 (1H, s), 5.47 (1H, s), 4.25 (2H, d, J = 5.9 Hz), 3.79 (3H, s), 3.67 (4H, t, J = 4.6 Hz), 3.25 (4H, t, J = 4.6 Hz). |

TABLE 95

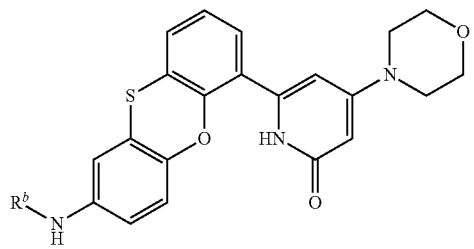

| Example No. | R$^b$ | Compound Name | MS | RT (min) | $^1$H-NMR(300 MHz) (DMSO-d$_6$) δ: |
|---|---|---|---|---|---|
| 4-8-18 | (6-methoxy-pyridin-2-yl)methyl | 6-(8-(((6-Methoxy pyridin-2-yl)methyl)amino)phenoxathiin-4-yl)-4-morpholino pyridin-2 (1H)-one | 515 | 1.39 | 10.87 (1H, s), 7.63 (1H, t, J = 7.8 Hz), 7.30 (1H, dd, J = 7.6, 1.7 Hz). 7.23 (1H, d, J = 6.3 Hz), 7.10 (1H, t, J = 7.6 Hz), 6.90 (1H, d, J = 7.3 Hz), 6.69-6.62 (2H, m), 6.49-6.43 (2H, m), 6.33 (1H, t, J = 5.8 Hz), 6.09 (1H, s), 5.47 (1H, s), 4.24 (2H, d, J = 5.9 Hz), 3.86 (3H, s), 3.67 (4H, t, J = 4.6 Hz), 3.25 (4H, t, J = 4.5 Hz). |
| 4-8-19 | (4-methyl-pyridin-2-yl)methyl | 6-(8-(((4-Methyl pyridin-2-yl)methyl)amino) phenoxathiin-4-yl)-4-morpholino pyridin-2(1H)-one | 499 | 0.94 | 10.88 (1H, s), 8.37 (1H, d, J = 4.6 Hz), 7.30 (1H, dd, J = 7.6, 1.7 Hz), 7.23 (1H, d, J = 5.9 Hz), 7.18 (1H, s), 7.10 (2H, dd, J = 9.6, 5.9 Hz), 6.65 (1H, d, J = 8.9 Hz), 6.48-6.42 (2H, m), 6.36 (1H, t, J = 6.3 Hz), 6.09 (1H, s), 5.47 (1H, s), 4.27 (1H, d, J = 5.9 Hz), 3.67 (4H, t, J = 4.6 Hz), 3.25 (4H, t, J = 5.0 Hz), 2.27 (3H, s). |
| 4-8-20 | (2-amino-pyridin-3-yl)methyl | 6-(8-(((2-Amino pyridin-3-yl)methyl)amino) phenoxathiin-4-yl)-4-morpholino pyridin-2(1H)-one | 500 | 1.01 | |

TABLE 95-continued

| Example No. | R^b | Compound Name | MS | RT (min) | $^1$H-NMR(300 MHz) (DMSO-d$_6$) δ: |
|---|---|---|---|---|---|
| 4-8-21 | 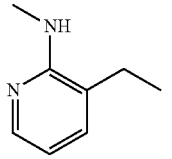 | 6-(8-(((2-(Methyl amino) pyridin-3-yl)methyl)amino) phenoxathiin-4-yl)-4-morpholino pyridin-2(1H)-one | 514 | 0.96 | |
| 4-8-22 | 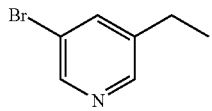 | 6-(8-(((5-Bromopyridin-3-yl)methyl)amino) phenoxathiin-4-yl)-4-morpholino pyridin-2(1H)-one | 563 | 1.31 | 10.87 (1H, s) 8.61 (1H, s), 8.56 (1H, t, J = 2.5 Hz), 7.99 (1H, s), 7.30 (1H, dd, J = 7.6, 1.7 Hz), 7.23 (1H, d, J = 6.6 Hz), 7.10 (1H, t, J = 7.6 Hz) 6.66 (1H, d, J = 9.6 Hz), 6.48-6.45 (2H, m), 6.37 (1H, t, J = 6.4 Hz), 6.08 (1H, s), 5.46 (1H, s), 4.31 (2H, d, J = 6.3 Hz), 3.67 (4H, t, J = 4.5 Hz), 3.25 (4H, t, J = 4.6 Hz). |
| 4-8-23 | 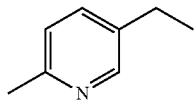 | 6-(8-(((6-Methyl pyridin-3-yl)methyl)amino) phenoxathiin-4-yl)-4-morpholino pyridin-2(1H)-one | 499 | 0.92 | 10.86 (1H, s), 8.41 (1H, s), 8.31 (1H, t, J = 3.0 Hz), 7.62-7.56 (2H, m), 7.29 (1H, d, J = 8.6 Hz), 7.22-7.07 (3H, m), 6.65 (1H, d, J = 9.2 Hz), 6.32-6.25 (1H, m), 6.08 (1H, s), 5.48 (1H, s), 4.22 (2H, d, J = 5.3 Hz), 3.67 (4H, t, J = 4.8 Hz), 3.25 (4H, t, J = 4.6 Hz), 2.41 (3H, s). |
| 4-8-24 | 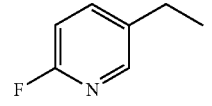 | 6-(8-(((6-Fluoropyridin-3-yl)methyl)amino) phenoxathiin-4-yl)-4-morpholino pyridin-2(1H)-one | 503 | 1.26 | 8.21 (1H, s), 7.93 (1H, td, J = 8.2, 2.8 Hz), 7.30 (1H, dd, J = 7.6, 1.7 Hz), 7.23 (1H, dd, J = 7.8, 1.6 Hz), 7.14-7.10 (2H, m), 6.66 (1H, d, J = 9.2 Hz), 6.48-6.46 (1H, m), 6.32 (1H, t, J = 6.3 Hz), 6.09 (1H, s), 5.47 (1H, s), 4.28 (2H, d, J = 5.9 Hz), 3.67 (4H, t, J = 4.8 Hz), 3.25 (4H, t, J = 4.8 Hz). |
| 4-8-25 | 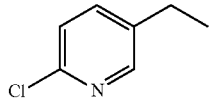 | 6-(8-(((6-Chloropyridin-3-yl)methyl)amino) phenoxathiin-4-yl)-4-morpholino pyridin-2(1H)-one | 519 | 1.31 | 10.86 (1H, s) 8.39 (1H, d, J = 2.3 Hz), 7.79 (1H, dd, J = 8.3, 2.6 Hz), 7.47 (1H, d, J = 8.3 Hz), 7.30 (1H, dd, J = 7.6, 1.7 Hz), 7.23 (1H, d, J = 5.9 Hz), 7.10 (1H, t, J = 7.8 Hz), 6.66 (1H, d, J = 9.2 Hz), 6.49-6.44 (2H, m), 6.35 (1H, t, J = 6.6 Hz), 6.09 (1H, s), 5.47 (1H, s), 4.29 (2H, d, J = 6.6 Hz), 3.67 (4H, t, J = 4.8 Hz), 3.25 (4H, t, J = 4.8 Hz). |
| 4-8-26 | 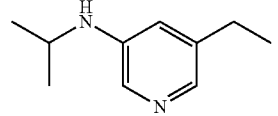 | 6-(8-(((5-Isopropyl amino) pyridin-3-yl)methyl)amino) phenoxathiin-4-yl)-4-morpholine pyridin-2(1H)-one | 542 | 1.04 | |

Example 4-9

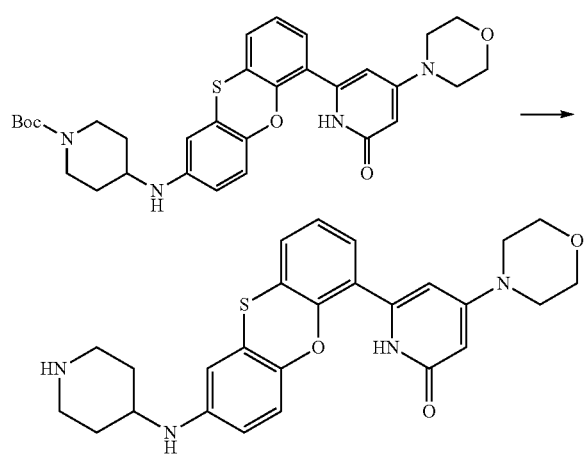

Using tert-butyl 4-((6-(4-morpholino-6-oxo-1,6-dihydro-pyridin-2-yl)phenoxathiin-2-yl)amino)piperidine-1-carboxylate, the following compound was obtained in the same manner as in Example 4-5 (2).

4-Morpholino-6-(8-(piperidin-4-ylamino)phenoxathiin-4-yl)pyridin-2(1H)-one

MS(ESI m/z): 477 (M+H)
RT(min): 0.88

Example 4-10

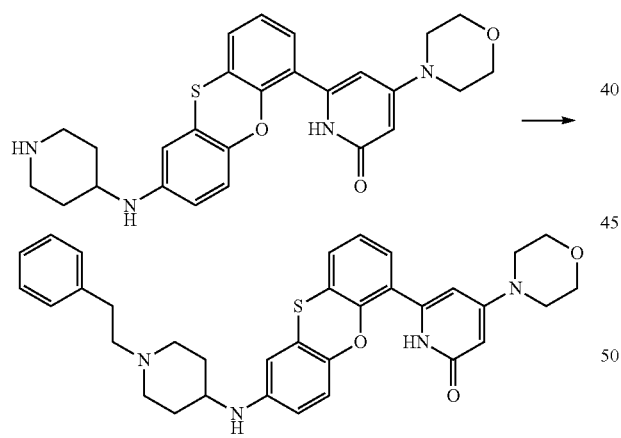

In the same manner as in Example 1-44-1, the following compound was obtained.

4-Morpholino-6-(8-((1-phenethylpiperidin-4-yl)amino)phenoxathiin-4-yl)pyridin-2(1H)-one ¹H-NMR (CDCl₃, 300 MHz) δ: 7.33-7.27 (2H, m), 7.25-7.20 (5H, m), 7.07 (1H, t, J=7.8 Hz), 6.87 (1H, d, J=9.6 Hz), 6.39-6.35 (2H, m), 6.12 (1H, d, J=2.3 Hz), 5.73 (1H, d, J=2.3 Hz), 3.82 (4H, t, J=5.0 Hz), 3.32 (4H, t, J=5.0 Hz), 2.96 (2H, d, J=11.6 Hz), 2.82 (2H, dd, J=10.6, 5.6 Hz), 2.61 (2H, dd, J=10.2, 5.6 Hz), 2.21 (2H, t, J=10.4 Hz), 2.08-2.01 (3H, brm), 1.50 (2H, t, J=11.1 Hz).

MS(ESI m/z): 581 (M+H)
RT(min): 1.14

Example 4-11

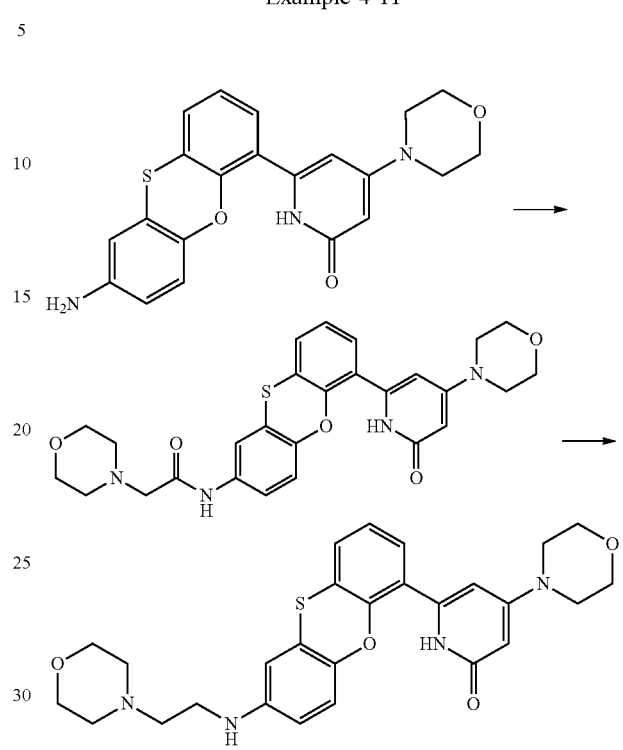

In the same manner as in Example 1-7-1 (1), the following compound was obtained.

2-Morpholino-N-(6-(4-morpholino-6-oxo-1,6-dihydropyridin-2-yl)phenoxathiin-2-yl)acetamide MS(ESI m/z): 521 (M+H)
RT(min): 0.85

(2)
In the same manner as in Reference Example 8 (3), the following compound was obtained.

4-Morpholino-6-(8-((2-morpholinoethyl)amino)phenoxathiin-4-yl)pyridin-2(1H)-one

MS(ESI m/z): 507 (M+H)
RT(min): 0.87

Example 4-12

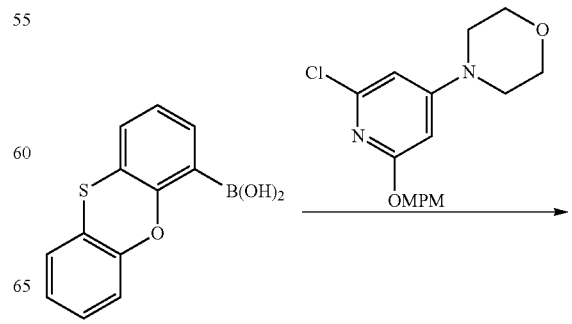

-continued

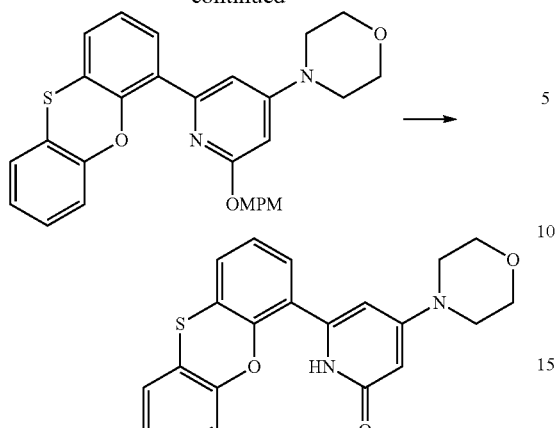

(1)

Using tetrakis(triphenylphosphine)palladium (0), the following compound was obtained in the same manner as in Reference Example 3 (7).

4-(2-((4-Methoxybenzyl)oxy)-6-(phenoxathiin-4-yl)pyridin-4-yl)morpholine (2)

In the same manner as in Example 1-53 (2), the following compound was obtained.

4-Morpholino-6-(phenoxathiin-4-yl)pyridin-2(1H)-one

MS(ESI m/z): 379 (M+H)

RT(min): 1.35

Example 5-1

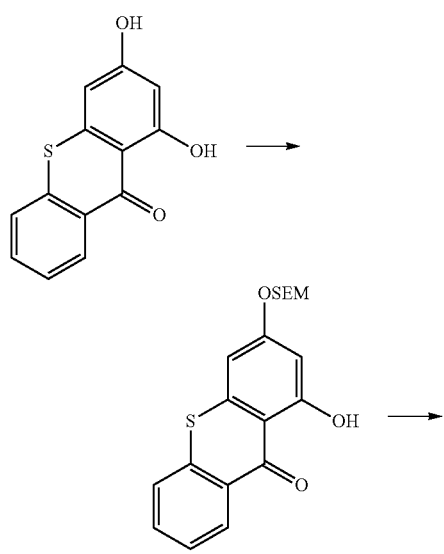

-continued

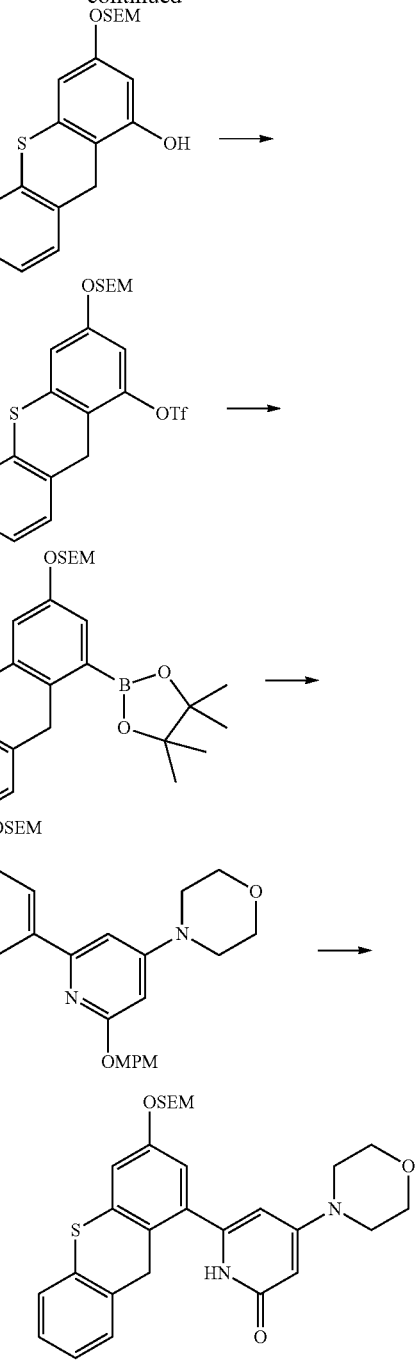

(1)

Cesium carbonate (1.60 g) and 2-(chloromethoxy)ethyl-trimethyl silane (0.69 mL) were added to a solution of 1,3-dihydroxy-9H-thioxanthen-9-one (798 mg) in acetonitrile (20 mL), followed by stirring at room temperature for 17 hours. An aqueous saturated ammonium chloride solution was added to the reaction mixture, and the resultant product was extracted with ethyl acetate. The organic layer was washed with a saturated sodium chloride aqueous solution, and dried over anhydrous sodium sulfate. The solvent was distilled off under reduced pressure, and the obtained residues were purified by silica gel column chromatography (hexane:ethyl acetate=1:0→9:1), whereby 1-hydroxy-3-((2-

(trimethylsilyl)ethoxy)methoxy)-9H-thioxanthen-9-one (258 mg) was obtained as a yellow oily material.

MS(ESI m/z): 375 (M+H)
RT(min): 2.35

(2)

In the same manner as in Reference Example 8 (3), the following compound was obtained.

3-((2-(Trimethyl silyl)ethoxy)methoxy)-9H-thioxanthene-1-ol

MS(ESI m/z): 359 (M–H)
RT(min): 2.12

(3)

Under ice-cooling, trifluoromethanesulfonic anhydride (0.21 mL) was added to a solution of 3-((2-(trimethyl silyl)ethoxy)methoxy)-9H-thioxanthene-1-ol (220 mg) obtained in Example 5-1 (2) in pyridine (3 mL), followed by stirring at room temperature for 17 hours. Water was added to the reaction mixture, and the resultant product was extracted with ethyl acetate. The organic layer was washed with a saturated aqueous sodium chloride solution, and dried over anhydrous sodium sulfate. The solvent was distilled off under reduced pressure, and the obtained residues were purified by silica gel column chromatography (hexane:ethyl acetate=1:0→9:1), whereby (3-((2-(trimethylsilyl)ethoxy) methoxy)-9H-thioxanthen-1-yl)trifluoro methanesulfonate (141 mg) was obtained as a yellow oily material.

(4) and (5)

In the same manner as in Reference Examples 3 (6) and 3 (7), the following compounds were obtained.

Trimethyl (2-(((1-(4,4,5,5-tetramethyl-1,3,2-dioxaborolan-2-yl)-9H-thioxanthen-3-yl)oxy)methoxy) ethyl)silane 4-(2-((4-Methoxybenzyl)oxy)-6-(3-((2-(trimethylsilyl)ethoxy)methoxy)-9H-thioxanthen-1-yl)pyridin-4-yl)morpholine MS(ESI m/z): 643 (M+H)
RT(min): 2.29

(6)

Under ice-cooling, 4-(2-((4-methoxybenzyl)oxy)-6-(3-((2-(trimethylsilyl)ethoxy)methoxy)-9H-thioxanthen-1-yl) pyridin-4-yl)morpholine (46 mg) obtained in Example 5-1 (5) and 10% hydrogen chloride/methanol (3 mL) were mixed, followed by stirring at room temperature for 15 hours.

The solvent was distilled off under reduced pressure, then, 10% ammonia water was added thereto, and the resultant product was extracted with chloroform. The organic layer was dried over anhydrous sodium sulfate. The solvent was distilled off under reduced pressure, and the obtained residues were purified by preparative thin layer silica gel chromatography (chloroform:methanol=9:1), whereby 6-(3-hydroxy-9H-thioxanthen-1-yl)-4-morpholinopyridin-2(1H)-one (1.8 mg) was obtained as a white solid.

MS(ESI m/z): 393 (M+H)
RT(min): 1.19

Example 5-2

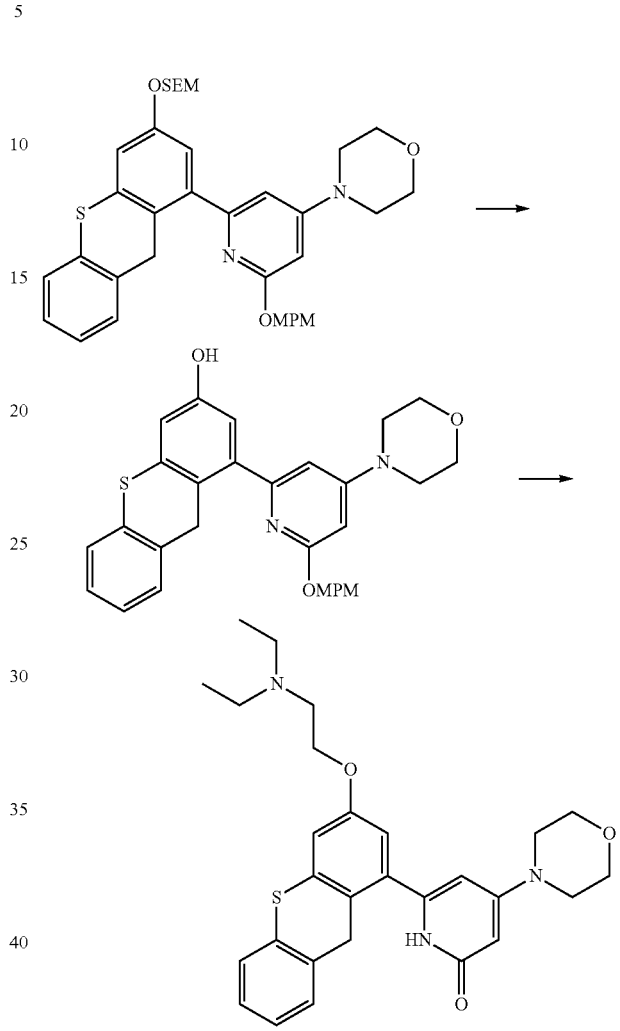

(1)

1 mol/L tetrabutylammonium fluoride/tetrahydrofuran (0.39 mL) was added to a solution of 4-(2-((4-methoxybenzyl)oxy)-6-(3-((2-(trimethylsilyl)ethoxy)methoxy)-9H-thioxanthen-1-yl)pyridin-4-yl)morpholine (49 mg) in tetrahydrofuran (2 mL), followed by stirring at 70° C. for 17 hours. 1 mol/L tetrabutylammonium fluoride/tetrahydrofuran (0.78 mL) was further added thereto, followed by stirring at 70° C. for 7 hours. After the reaction mixture was cooled to room temperature, the solvent was distilled off under reduced pressure, then, a saturated ammonium chloride aqueous solution was added thereto, and the resultant product was extracted with ethyl acetate. The organic layer was washed with a saturated aqueous sodium chloride solution, and dried over anhydrous sodium sulfate. The solvent was distilled off under reduced pressure, and the obtained residues were purified by silica gel column chromatography (hexane:ethyl acetate=1:0→1:1), whereby 1-(6-((4-methoxybenzyl)oxy)-4-morpholinopyridin-2-yl)-9H-thioxanthene-3-ol (16 mg) was obtained.

MS(ESI m/z): 513 (M+H)
RT(min): 1.47

(2)

Potassium carbonate (11 mg) and 2-bromo-N,N-diethyl-ethaneamine hydrobromide (8.3 mg) were added to a solution of 1-(6-(((4-methoxybenzyl)oxy)-4-morpholinopyridin-2-yl)-9H-thioxanthene-3-ol (8 mg) obtained in Example 5-2 (1) in N,N-dimethyl formamide (2.5 mL), followed by stirring at 70° C. for 15.5 hours. Potassium carbonate (33 mg) and 2-bromo-N,N-diethylethaneamine hydrobromide (19 mg) were further added thereto, followed by stirring at 60° C. for 23 hours. After the reaction mixture was cooled to room temperature, water was added thereto, and the resultant product was extracted with ethyl acetate. The organic layer was washed with a saturated aqueous sodium chloride solution, and dried over anhydrous sodium sulfate. The solvent was distilled off under reduced pressure, and 10% hydrogen chloride/methanol (3 mL) was added to the obtained residues, followed by stirring at 50° C. for 5 hours. The solvent was distilled off under reduced pressure, then, 10% ammonia water was added thereto, and the resultant product was extracted with chloroform. The organic layer was dried over anhydrous sodium sulfate. The solvent was distilled off under reduced pressure, and the obtained residues were purified by preparative thin layer silica gel chromatography (chloroform:methanol=9:1), whereby 6-(3-(2-(diethylamino)ethoxy)-9H-thioxanthen-1-yl)-4-morpholinopyridin-2(1H)-one (2.5 mg) was obtained as a white solid.

MS(ESI m/z): 492 (M+H)

RT(min): 1.02

Example 6

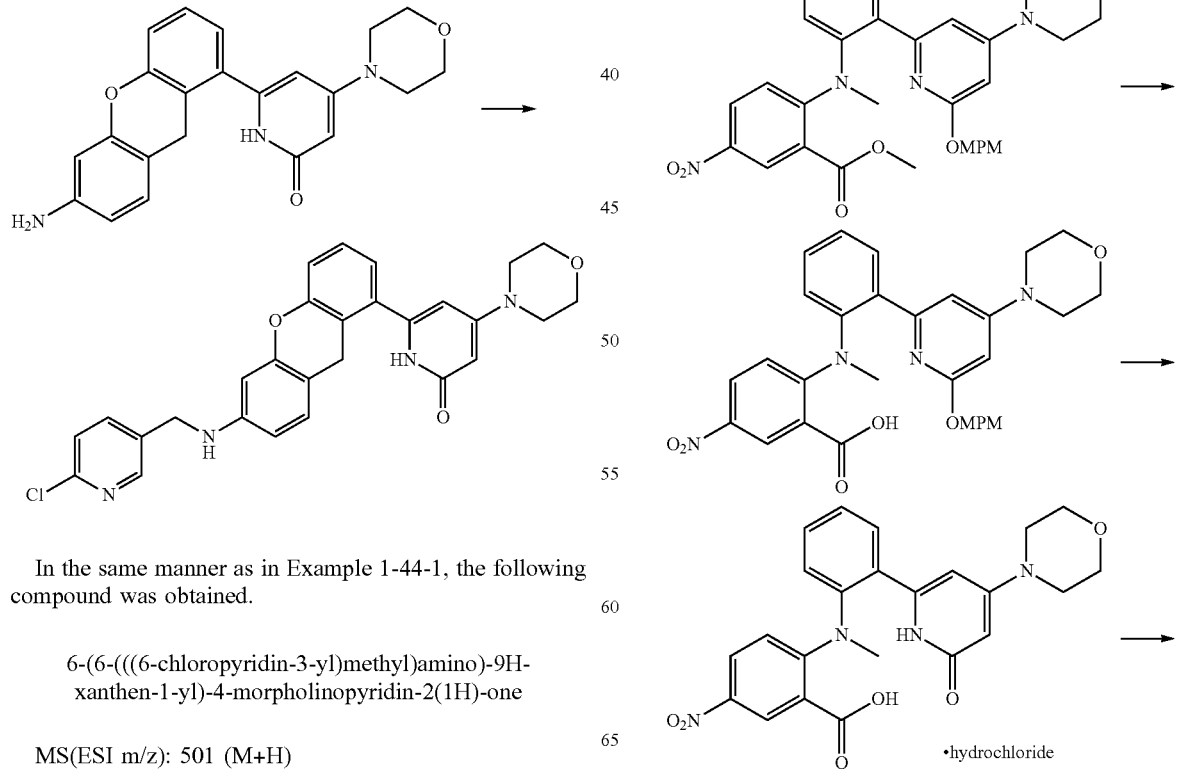

In the same manner as in Example 1-44-1, the following compound was obtained.

6-(6-(((6-chloropyridin-3-yl)methyl)amino)-9H-xanthen-1-yl)-4-morpholinopyridin-2(1H)-one MS(ESI m/z): 501 (M+H)

RT(min): 1.27

Example 7

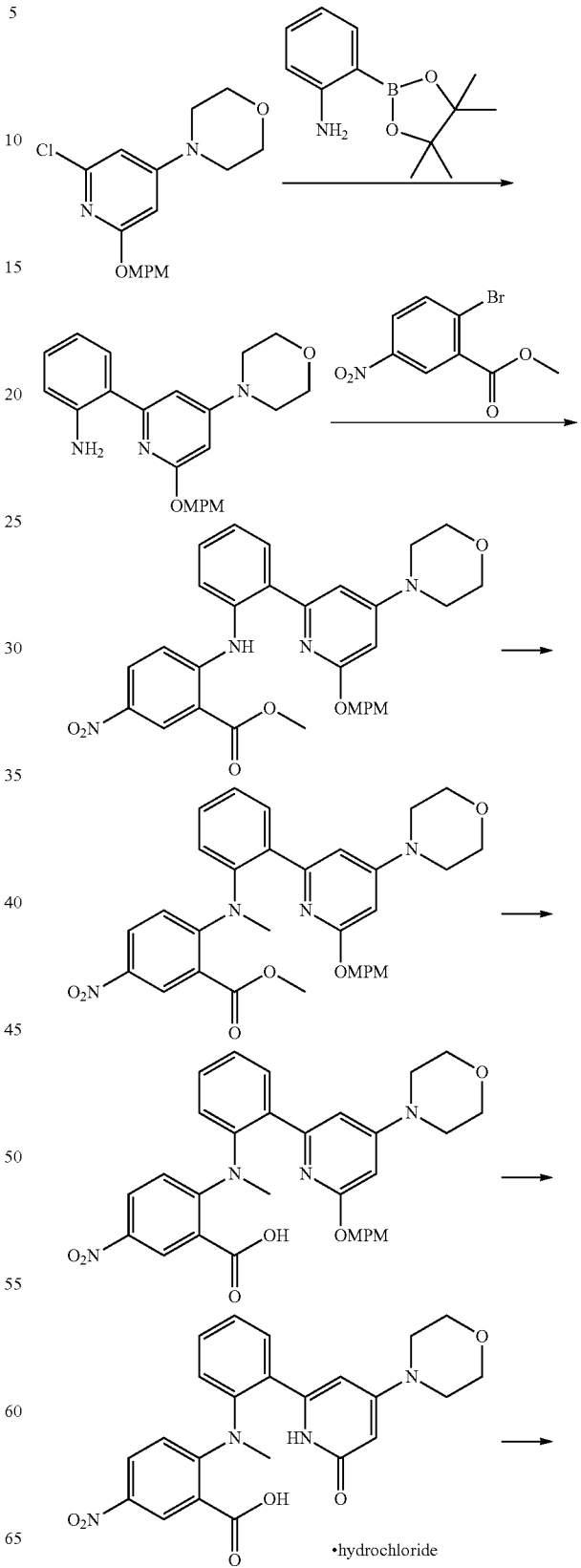

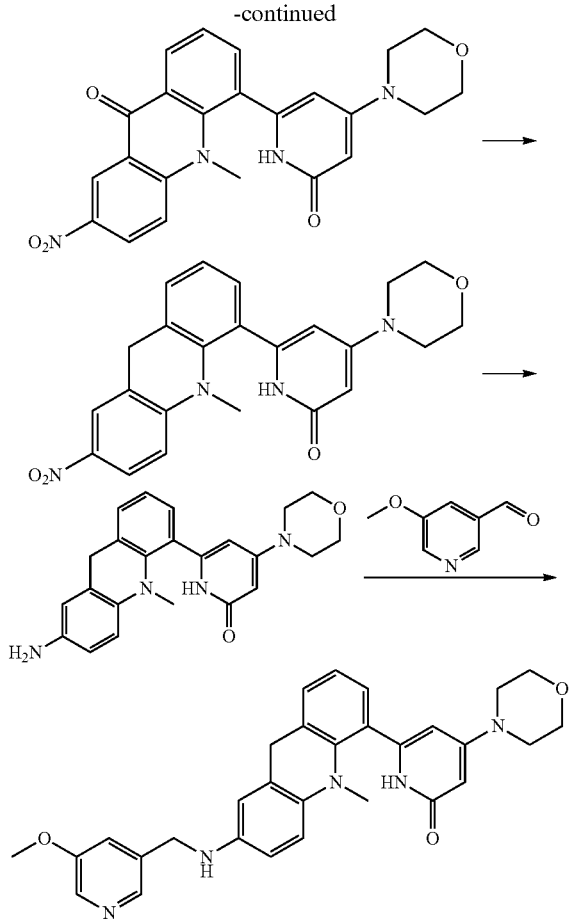

(1)

Water (5.0 mL) and bis(di-tert-butyl (4-dimethylaminophenyl)phosphine)dichloropalladium (II) (21 mg) were added to a solution of 4-(2-chloro-6-((4-methoxybenzyl) oxypyridin-4-yl)morpholine (1.00 g), 2-(4,4,5,5-tetramethyl-1,3,2-dioxaborolan-2-yl)aniline (720 mg), and sodium carbonate (633 mg) in 1,2-dimethoxyethane (20 mL), followed by refluxing for 2 hours. 2-(4,4,5,5-Tetramethyl-1,3, 2-dioxaborolan-2-yl)aniline (330 mg) was added thereto, followed by refluxing for 2.5 hours. After the reaction mixture was cooled to room temperature, ethyl acetate was added thereto, and the organic layer was washed with a saturated sodium chloride aqueous solution, and dried over anhydrous sodium sulfate. The solvent was distilled off under reduced pressure, and the obtained residues were purified by silica gel column chromatography (hexane:ethyl acetate=1:0→1:1), whereby 2-(6-((4-methoxybenzyl)oxy)-4-morpholinopyridin-2-yl)aniline (980 mg) was obtained as a brown solid.

(2)

Methyl 2-bromo-5-nitrobenzoate (773 mg), potassium carbonate (411 mg), and copper (I) iodide (142 mg) were added to a solution of 2-(6-((4-methoxybenzyl)oxy)-4-morpholinopyridin-2-yl)aniline (970 mg) obtained in Example 7 (1) in N-methyl pyrrolidone (20 mL), followed by stirring at 120° C. for 13 hours. After the reaction mixture was cooled to room temperature, ethyl acetate was added thereto, the organic layer was washed with a saturated sodium chloride aqueous solution, and the insoluble materials were filtered off, and dried over anhydrous sodium sulfate. The solvent was distilled off under reduced pressure, and the obtained residues were purified by silica gel column chromatography (chloroform:methanol=1:0→49:1), whereby methyl 2-((2-(6-((4-methoxybenzyl)oxy)-4-morpholinopyridin-2-yl)phenyl)amino)-5-nitrobenzoate (125 mg) was obtained as a yellow oily material.

(3)

Iodomethane (27 μL) and potassium carbonate (61 mg) were added to a solution of methyl 2-((2-(6-((4-methoxybenzyl)oxy)-4-morpholinopyridin-2-yl)phenyl)amino)-5-nitrobenzoate (125 mg) obtained in Example 7 (2) in N,N-dimethyl acetamide (3.0 mL), followed by stirring at 100° C. for 2.5 hours. Methyl iodide (14 μL) and potassium carbonate (30 mg) were added thereto, followed by stirring at 100° C. for 1 hour. After the reaction mixture was cooled to room temperature, ethyl acetate was added thereto, and the organic layer was washed with a saturated sodium chloride aqueous solution, and dried over anhydrous sodium sulfate. The solvent was distilled off under reduced pressure, and the obtained residues were purified by silica gel column chromatography (hexane:ethyl acetate=1:0→1:1), whereby methyl 2-((2-(6-((4-methoxybenzyl)oxy)-4-morpholinopyridin-2-yl)phenyl)(methyl)amino)-5-nitrobenzoate (90 mg) was obtained as a yellow oily material.

(4)

Ethanol (5.0 mL) and 3 mol/L sodium hydroxide aqueous solution (1.0 mL) were added to methyl 2-((2-(6-((4-methoxybenzyl)oxy)-4-morpholinopyridin-2-yl)phenyl) (methyl)amino)-5-nitrobenzoate (90 mg) obtained in Example 7 (3), followed by refluxing for 1.5 hours. After the reaction mixture was cooled to room temperature, acetic acid and ethyl acetate were added thereto, and the organic layer was washed with a saturated sodium chloride aqueous solution, and dried over anhydrous sodium sulfate. The solvent was distilled off under reduced pressure, and 4.0 mol/L hydrogen chloride/1,4-dioxane (2.0 mL) and methanol (2.0 mL) were added to the obtained residues, followed by stirring at 60° C. for 0.5 hours. After the reaction mixture was cooled to room temperature, ethanol was added thereto, and the solvent was distilled off under reduced pressure. The obtained residues were washed with ethyl acetate, whereby hydrochloride (62 mg) of 2-(methyl (2-(4-morpholino-6-oxo-1,6-dihydro pyridin-2-yl)phenyl)amino)-5-nitrobenzoic acid was obtained as a yellow solid.

(5)

In the same manner as in Reference Example 8 (2), the following compound was obtained.

10-Methyl-5-(4-morpholino-6-oxo-1,6-dihydropyridin-2-yl)-2-nitroacridin-9(10H)-one (6)

In the same manner as in Reference Example 8 (3), the following compound was obtained.

6-(10-Methyl-7-nitro-9,10-dihydroacridin-4-yl)-4-morpholinopyridin-2(1H)-one (7)

In the same manner as in Reference Example 3 (4), the following compound was obtained.

683

6-(7-Amino-10-methyl-9,10-dihydroacridin-4-yl)-4-morpholinopyridin-2(1H)-one (8)

In the same manner as in Example 1-44-1, the following compound was obtained.

6-(7-(((5-Methoxypyridin-3-yl)methyl)amino)-10-methyl-9,10-dihydroacridin-4-yl)-4-morpholinopyridin-2(1H)-one MS(ESI m/z): 510 (M+H)
RT(min): 0.98

Example 8-1

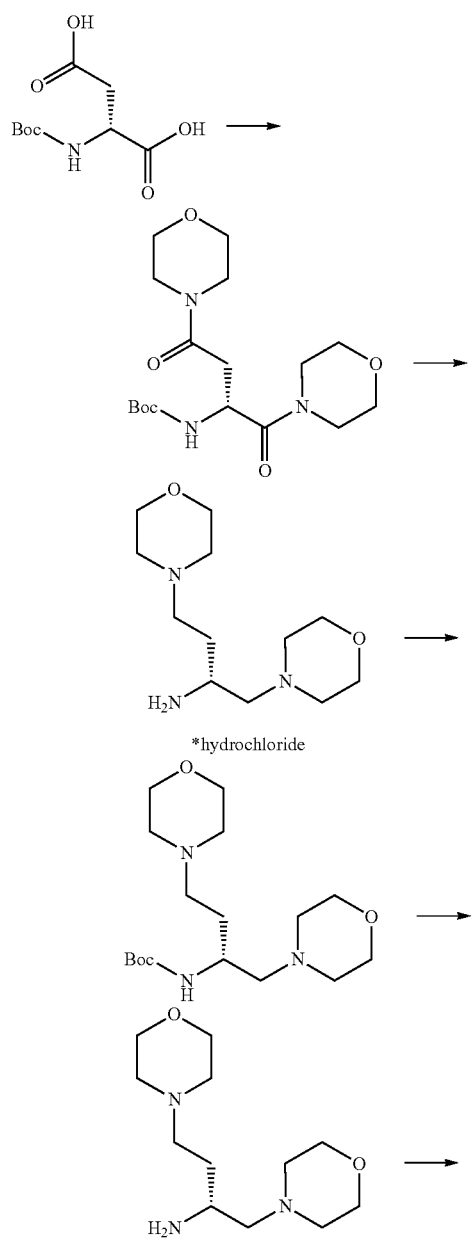

*hydrochloride

684

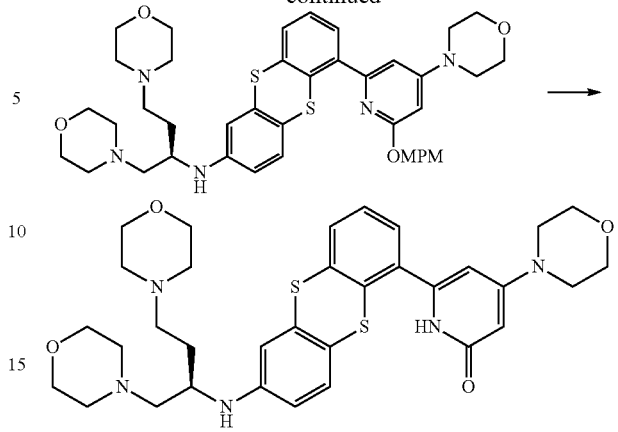

(1)
In the same manner as in Example 1-2-1 (1), the following compound was obtained.

(R)-tert-butyl (1,4-dimorpholino-1,4-dioxobutan-2-yl)carbamate

MS(ESI m/z): 372 (M+H)
RT(min): 0.89

(2)
A 1.0 mol/L borane-tetrahydrofuran complex/tetrahydrofuran solution (17.5 mL) was added to a solution of (R)-tert-butyl (1,4-dimorpholino-1,4-dioxobutan-2-yl)carbamate (1.3 g) obtained in Example 8-1 (1) in tetrahydrofuran (13 mL), followed by stirring at 80° C. for 3 hours. 1 mol/L hydrochloric acid (20 mL) was added thereto, followed by stirring for 2 hours, and the solvent was distilled off under reduced pressure, whereby hydrochloride of (R)-1,4-dimorpholinobutane-2-amine was obtained.

MS(ESI m/z): 244 (M+H)
RT(min): 0.19

(3)
In the same manner as in Reference Example 23-6 (7), the following compound was obtained.

(R)-tert-butyl (1,4-dimorpholinobutan-2-yl)carbamate

MS(ESI m/z): 344 (M+H)
RT(min): 0.45

(4)
In the same manner as in Example 1-4, the following compound was obtained.

(R)-1,4-dimorpholinobutane-2-amine

MS(ESI m/z): 244 (M+H)
RT(min): 0.19

(5)
In the same manner as in Example 1-50-1, the following compounds were obtained.

(R)—N-(1,4-dimorpholinobutan-2-yl)-6-(6-((4-methoxybenzyl)oxy)-4-morpholinopyridin-2-yl)thianthrene-2-amine MS(ESI m/z): 756 (M+H)
RT(min): 1.12

(R)-6-(7-((1,4-dimorpholinobutan-2-yl)amino)thianthren-1-yl)-4-morpholinopyridin-2(1H)-one MS(ESI m/z): 636 (M+H)
RT(min): 0.81

Example 8-2

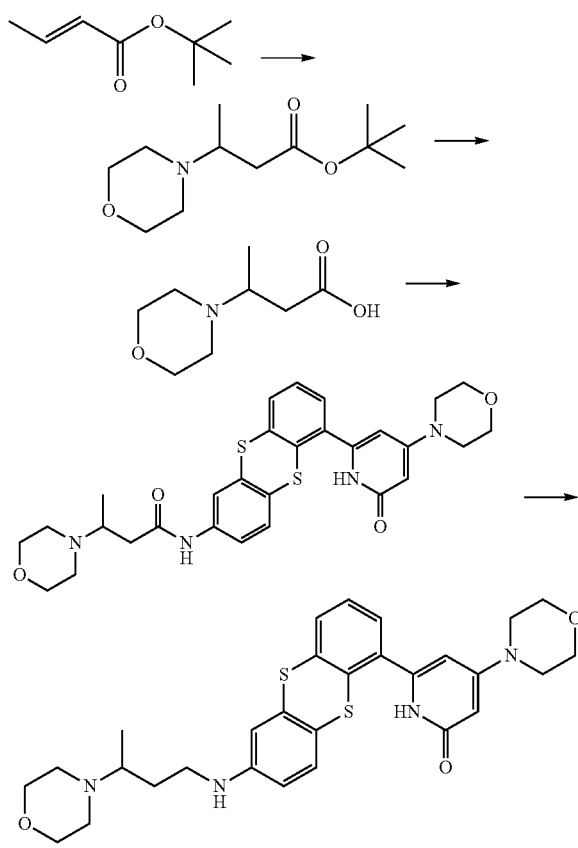

(1)
Morpholine (5 mL) was added to tert-butyl crotonate (500 mg), and the resultant product was irradiated with microwaves (microwave reaction apparatus, 100° C., 0.5 hours, 2.45 GHz, 0 W to 240 W). The resultant product was further irradiated with microwaves (microwave reaction apparatus, 110° C., 0.5 hours, 2.45 GHz, 0 W to 240 W). After the reaction mixture was cooled to room temperature, water was added thereto, and the resultant product was extracted with ethyl acetate. The solvent was distilled off under reduced pressure, and the obtained residues were purified by silica gel column chromatography (hexane:ethyl acetate=1:0→3:2), whereby tert-butyl 3-morpholinobutanoate (250 mg) was obtained as a colorless oily material.
MS(ESI m/z): 230 (M+H)
RT(min): 0.65
(2)
tert-Butyl 3-morpholinobutanoate (250 mg) obtained in Example 8-2 (1) and 4 mol/L hydrogen chloride/1,4-dioxane (10 mL) were mixed, followed by stirring at room temperature for 19.5 hours. The solvent was distilled off under reduced pressure, and the obtained residues were washed with ethyl acetate, whereby hydrochloride (200 mg) of 3-morpholinobutanoic acid was obtained as a white solid.

MS(ESI m/z): 174 (M+H)
RT(min): 0.22
(3)
In the same manner as in Example 1-2-1 (1), the following compound was obtained.

3-Morpholino-N-(6-(4-morpholino-6-oxo-1,6-dihydropyridin-2-yl)thianthren-2-yl)butanamide MS(ESI m/z): 565 (M+H)
RT(min): 0.90
(4)
In the same manner as in Reference Example 8 (3), the following compound was obtained.

4-Morpholino-6-(7-((3-morpholinobutyl)amino)thianthren-1-yl)pyridin-2(1H)-one

MS(ESI m/z): 551 (M+H)
RT(min): 0.94

Example 8-3

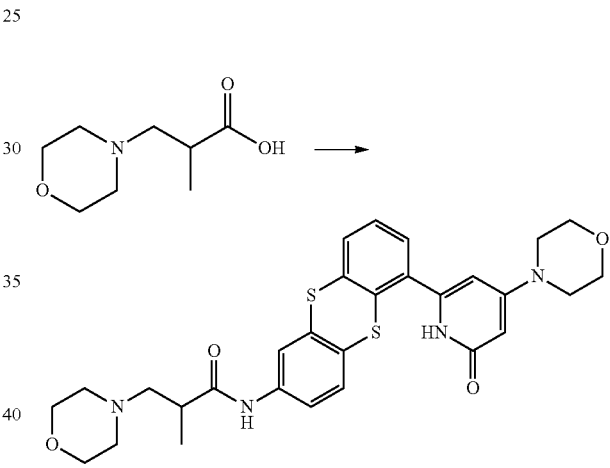

In the same manner as in Example 1-2-1 (1), the following compound was obtained.

2-Methyl-3-morpholino-N-(6-(4-morpholino-6-oxo-1,6-dihydropyridin-2-yl)thianthren-2-yl)propanamide MS(ESI m/z): 565 (M+H)
RT(min): 0.92

Example 8-4

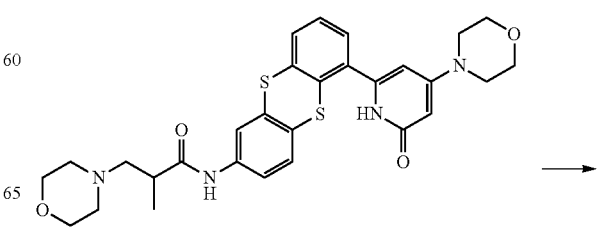

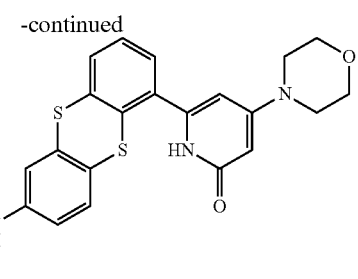

In the same manner as in Reference Example 8 (3), the following compound was obtained.

6-(7-((2-Methyl-3-morpholinopropyl)amino)thianthren-1-yl)-4-morpholinopyridin-2(1H)-one MS(ESI m/z): 551 (M+H)
RT(min): 0.96

Example 9-1

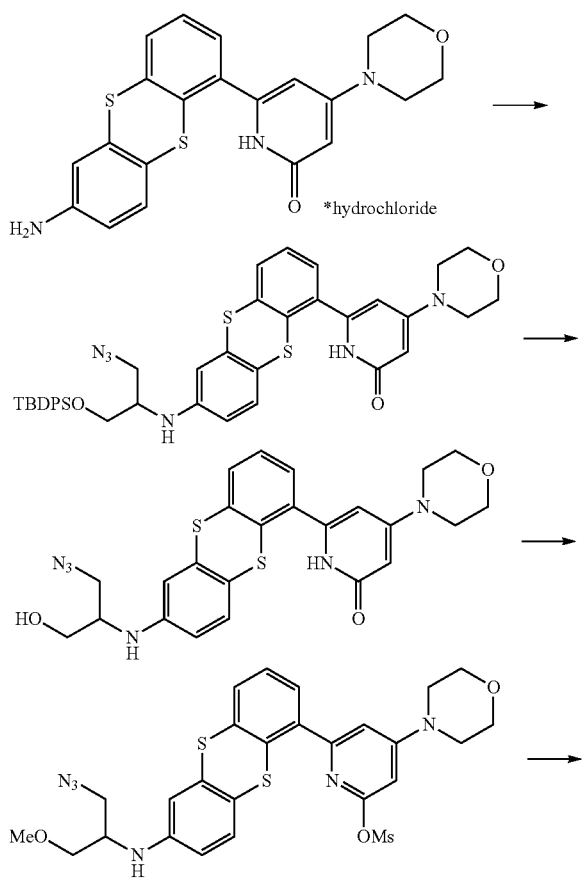

(1)
In the same manner as in Example 1-12-1, the following compounds were obtained.

6-(7-((1-Azide-3-((tert-butyldiphenylsilyl)oxy)propan-2-yl)amino)thianthren-1-yl)-4-morpholinopyridin-2(1H)-one MS(ESI m/z): 747 (M+H)
RT(min): 2.18

(2)
A 1.0 mol/L tetrabutylammonium fluoride-tetrahydrofuran solution (1.0 mL) were added to 6-(7-((1-azide-3-((tert-butyldiphenylsilyl)oxy)propan-2-yl)amino)thianthren-1-yl)-4-morpholinopyridin-2(1H)-one (10 mg) obtained in Example 9-1 (1), followed by stirring for 1 hour. An aqueous saturated ammonium chloride solution was added to the reaction mixture, then, the resultant product was extracted with ethyl acetate, and the solvent was distilled off under reduced pressure. The obtained residues were purified by silica gel column chromatography (chloroform:methanol=1:0→17:3, NH silica), whereby 6-(7-((1-azide-3-hydroxypropan-2-yl)amino)thianthren-1-yl)-4-morpholinopyridin-2(1H)-one (8.9 mg) was obtained.

MS(ESI m/z): 509 (M+H)
RT(min): 1.19

(3)
In the same manner as in Example 1-59-1 (2), the following compound was obtained.

3-Azide-2-((6-(6-((methylsulfonyl)oxy)-4-morpholinopyridin-2-yl)thianthren-2-yl)amino)propyl methanesulfonate MS(ESI m/z): 665 (M+H)
RT(min): 1.65

(4)
Morpholine (1.0 mL) was added to 3-azide-2-((6-(6-((methylsulfonyl)oxy)-4-morpholinopyridin-2-yl)thianthren-2-yl)amino)propyl methanesulfonate (11 mg) obtained in Example 9-1 (3), followed by stirring at 100° C. for 5 hours. Water was added to the reaction mixture, then, the resultant product was extracted with ethyl acetate, and the solvent was distilled off under reduced pressure. The obtained residues were purified by preparative thin layer silica gel chromatography (chloroform:methanol=95:5, NH silica), and purified by preparative thin layer silica gel chromatography (chloroform:methanol=98:2), whereby 6-(7-((1-azide-3-morpholinopropan-2-yl)amino)thianthren-1-yl)-4-morpholinopyridin-2(1H)-one (1.9 mg) was obtained.

MS(ESI m/z): 578 (M+H)
RT(min): 0.98

Example 9-2

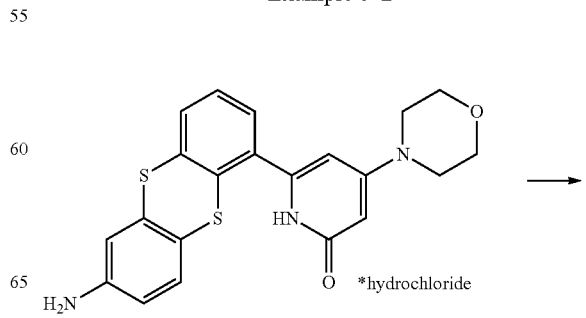

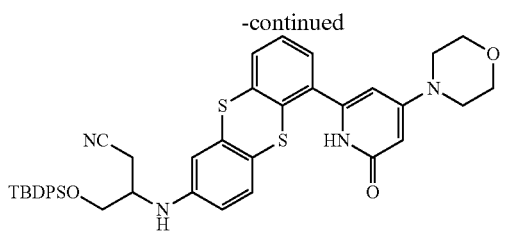

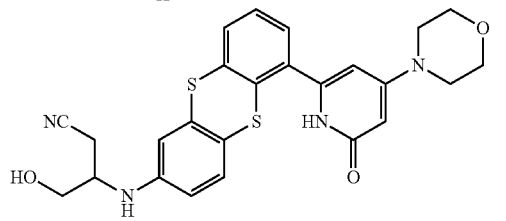

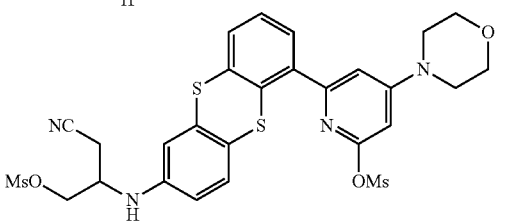

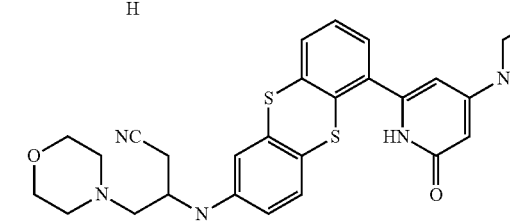

(1)
In the same manner as in Example 1-12-1, the following compound was obtained.

4-((tert-Butyldiphenylsilyl)oxy)-3-((6-(4-morpholino-6-oxo-1,6-dihydropyridin-2-yl)thianthren-2-yl)amino)butanenitrile MS(ESI m/z): 731 (M+H)
RT(min): 2.01
(2)
In the same manner as in Example 9-1 (2), the following compound was obtained.

4-Hydroxy-3-((6-(4-morpholino-6-oxo-1,6-dihydropyridin-2-yl)thianthren-2-yl)amino)butanenitrile MS(ESI m/z): 493 (M+H)
RT(min): 1.08
(3)
In the same manner as in Example 1-59-1 (2), the following compound was obtained.

3-Cyano-2-((6-(6-((methylsulfonyl)oxy)-4-morpholinopyridin-2-yl)thianthren-2-yl)amino)propyl methanesulfonate MS(ESI m/z): 649 (M+H)
RT(min): 1.53
(4)
In the same manner as in Example 9-1 (4), the following compound was obtained.

4-Morpholino-3-((6-(4-morpholino-6-oxo-1,6-dihydropyridin-2-yl)thianthren-2-yl)amino)butanenitrile MS(ESI m/z): 562 (M+H)
RT(min): 0.91

Example 9-3

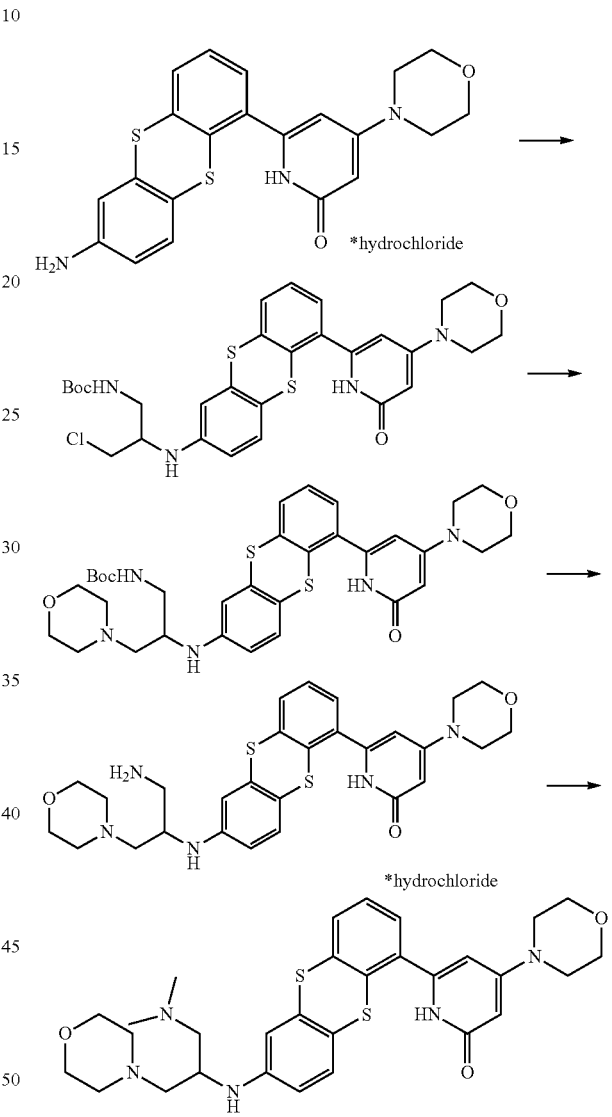

(1)
In the same manner as in Example 1-12-1, the following compound was obtained.

tert-Butyl (3-chloro-2-((6-(4-morpholino-6-oxo-1,6-dihydropyridin-2-yl)thianthren-2-yl)amino)propyl) carbamate MS(ESI m/z): 601 (M+H)
RT(min): 1.50
(2)
In the same manner as in Example 9-1 (4), the following compound was obtained.

tert-Butyl (3-morpholino-2-((6-(4-morpholino-6-oxo-1,6-dihydropyridin-2-yl)thianthren-2-yl)amino)propyl)carbamate MS(ESI m/z): 652 (M+H)
RT(min): 1.03

(3)
12 mol/L hydrochloric acid (0.5 mL) was added to a solution of tert-butyl (3-morpholino-2-((6-(4-morpholino-6-oxo-1,6-dihydropyridin-2-yl)thianthren-2-yl)amino)propyl) carbamate (17 mg) obtained in Example 9-3 (2) in methanol (1.0 mL), followed by stirring at room temperature for 2 hours. The solvent was distilled off under reduced pressure, whereby hydrochloride (13 mg) of 6-(7-((1-amino-3-morpholinopropan-2-yl)amino)thianthren-1-yl)-4-morpholinopyridin-2(1H)-one was obtained.
MS(ESI m/z): 552 (M+H)
RT(min): 0.79

(4)
In the same manner as in Example 1-52-1, the following compound was obtained.

6-(7-((1-(Dimethylamino)-3-morpholinopropan-2-yl)amino)thianthren-1-yl)-4-morpholinopyridin-2(1H)-one MS(ESI m/z): 580 (M+H)
RT(min): 0.83

Example 10-1

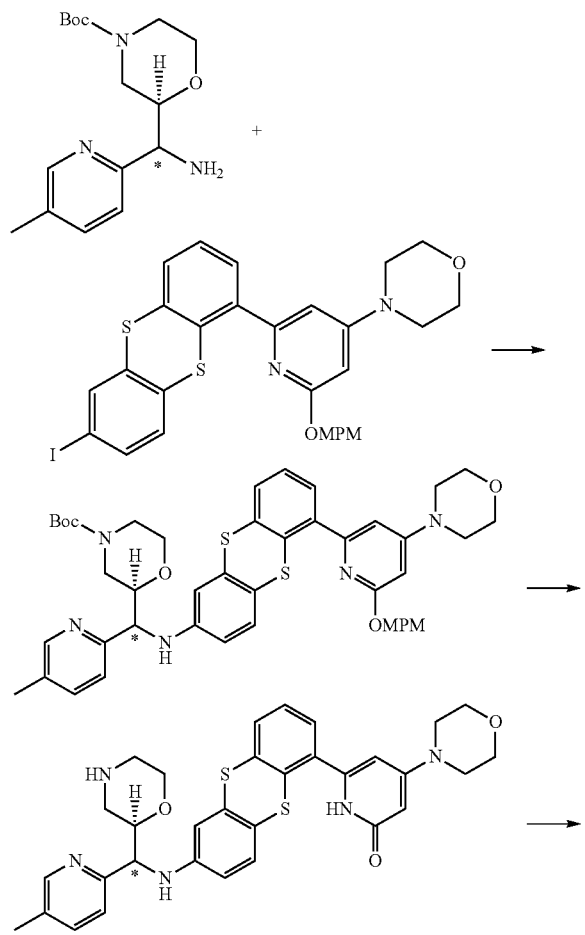

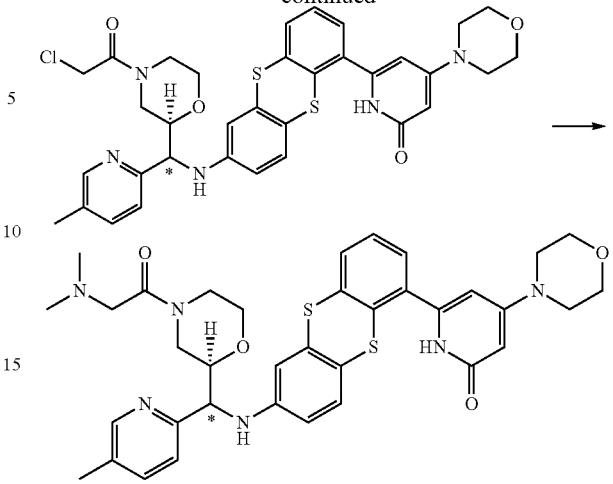

(1)
In the same manner as in Example 1-50-1 (1), the following compound was obtained.

(2R)-tert-butyl 2-(((6-(6-((4-methoxybenzyl)oxy)-4-morpholinopyridin-2-yl)thianthren-2-yl)amino)(5-methyl pyridin-2-yl)methyl)morpholine-4-carboxylate (optically active substance A)

MS(ESI m/z): 820 (M+H)
RT(min): 1.92

(2)
In the same manner as in Reference Example 18 (2), the following compound was obtained.

6-(7-(((5-Methyl pyridin-2-yl)((R)-morpholin-2-yl)methyl)amino)thianthren-1-yl)-4-morpholinopyridin-2(1H)-one (optically active substance A)

MS(ESI m/z): 600 (M+H)
RT(min): 0.96

(3)
Chloroacetylchloride (1 μL) was added to a solution of 6-(7-(((5-methyl pyridin-2-yl)((R)-morpholin-2-yl)methyl)amino)thianthren-1-yl)-4-morpholinopyridin-2(1H)-one (optically active substance A) (7.6 mg) and triethylamine (3.5 μL) obtained in Example 10-1 (2) in tetrahydrofuran (0.2 mL), followed by stirring for 0.5 hours. Methanol was added to the reaction mixture, and the solvent was distilled off under reduced pressure. The residues were purified by silica gel chromatography (chloroform:methanol=100:0→98:2, NH silica), whereby 6-(7-((((R)-4-(2-chloroacetyl)morpholin-2-yl)(5-methylpyridin-2-yl)methyl)amino)thianthren-1-yl)-4-morpholinopyridin-2(1H)-one (optically active substance A) (2.9 mg) was obtained.
MS(ESI m/z): 676 (M+H)
RT(min): 1.17

(4)
A 2 mol/L dimethyl amine-tetrahydrofuran solution (0.1 mL) was added to a solution of 6-(7-((((R)-4-(2-chloroacetyl)morpholin-2-yl)(5-methylpyridin-2-yl)methyl)amino)thianthren-1-yl)-4-morpholinopyridin-2(1H)-one (optically active substance A) (2.9 mg) obtained in Example 10-1 (3) in N,N-dimethyl formamide (0.1 mL), followed by stirring at 60° C. for 15 minutes. After the reaction mixture was cooled to room temperature, water was added thereto, and the resultant product was extracted with chloroform. The obtained organic layer was purified by silica gel chromatography (chloroform:methanol=100:0→98:2, NH silica), whereby 6-(7-((((R)-4-(2-(dimethylamino)acetyl)morpholin-2-yl)(5-methyl pyridin-2-yl)methyl)amino)thianthren-1-yl)-4-morpholinopyridin-2(1H)-one (optically active substance A) (0.5 mg) was obtained.

MS(ESI m/z): 685 (M+H)
RT(min): 0.97

Example 10-2

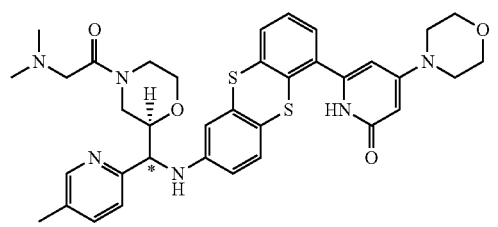

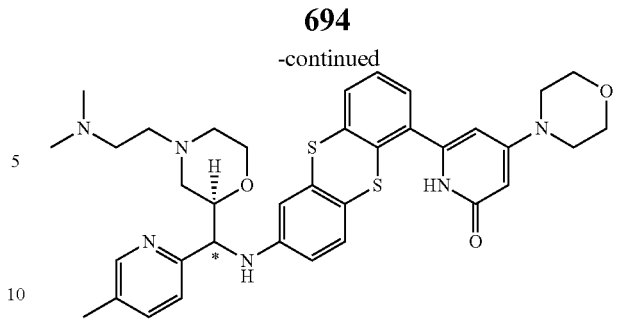

In the same manner as in Example 1-34-1 (2), the following compound was obtained.

6-(7-((((R)-4-(2-(dimethylamino)ethyl)morpholin-2-yl)(5-methylpyridin-2-yl)methyl)amino)thianthren-1-yl)-4-morpholinopyridin-2(1H)-one (optically active substance A)

MS(ESI m/z): 671 (M+H)
RT(min): 0.99

Examples 10-3-1 to 10-3-6

In the same manner as in Example 1-56-1, the following compounds were obtained.

TABLE 96

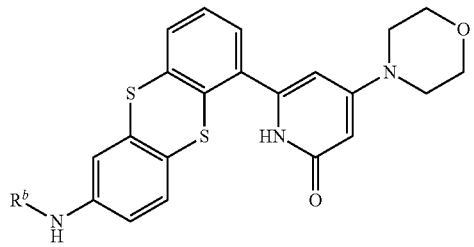

| Example No. | R$^b$ | Compound Name | MS (ESI m/z) (M + H) | RT (min) | $^1$H-NMR (300 MHz) (CDCl3) δ : |
|---|---|---|---|---|---|
| 10-3-1 | | 6-(7-((3-(4-Methyl piperazin-1-yl)-1-(5-methyl pyridin-2-yl)propyl)amino)thianthren-1-yl)-4-morpholino pyridin-2 (1H)-one (Optically active substance A) | 641 | 0.95 | 8.78 (1H, brs), 8.40 (1H, d, J = 2.0 Hz), 7.54 (1H, t, J = 4.6 Hz), 7.40 (1H, dd, J = 8.6, 2.0 Hz), 7.25 (2H, s), 7.18 (1H, d, J = 7.9 Hz), 7.12 (1H, d J = 8.6 Hz), 6.66 (1H, d, J = 2.6 Hz), 6.53 (1H, brs), 6.38 (1H, dd, J = 8.6, 2.0 Hz), 5.95 (1H, d, J = 2.0 Hz), 5.71 (1H, d, J = 2.6 Hz), 4.54-4.47 (1H, m), 3.81 (4H, t, J = 5.0 Hz), 3.32 (4H, t, J = 5.0 Hz), 2.56-2.42 (10H, m), 2.35 (3H, s), 2.31 (3H, s), 2.12-2.02 (1H, m), 1.96-1.87 (1H, m). |

TABLE 96-continued

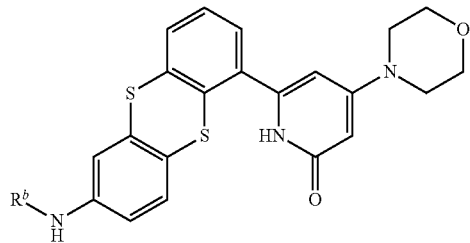

| Example No. | R[b] | Compound Name | MS (ESI m/z) (M + H) | RT (min) | $^1$H-NMR (300 MHz) (CDCl3) δ : |
|---|---|---|---|---|---|
| 10-3-2 | (1-methyl piperazine connected via propyl to 5-methylpyrazin-2-yl) | 6-(7-((3-(4-Methyl piperazin-1-yl)-1-(5-methyl pyrazin-2-yl)propyl)amino)thianthren-1-yl)-4-rnorpholino pyridin-2(1H)-one (Optically active substance A) | 642 | 0.93 | 8.44 (1H, s), 8.40 (1H, s), 7.55 (1H, t, J = 4.3 Hz), 7.29-7.25 (2H, m), 7.15 (1H, d, J = 8.6 Hz), 6.68 (1H, d, J = 2.5 Hz), 8.42 (1H, dd, J = 8.6, 2.0 Hz), 6.25 (1H, brs), 5.96 (1H, d, J = 2.0 Hz), 5.73 (1H, d, J = 2.6 Hz), 4.63-4.58 (1H, m), 3.81 (4H, t, J = 4.8 Hz), 3.32 (4H, t, J = 4.8 Hz), 2.71-2.38 (16H, m), 2.03-1.94 (1H, m), 1.91-1.81 (1H, m), 1.58 (1H, brs). |
| 10-3-3 | (2-methoxyethyl)(methyl)amino propyl linked to 5-methylpyridin-2-yl | 6-(7-((3-((2-Methoxy ethyl)(methyl)amino)-1-(5-methyl pyridin-2-yl)propyl)amino)thiarnthren-l-yl)-4-morpholino pyridin-2(1H)-one (Optically active substance A) | 630 | 1.02 | 8.50 (1H, brs), 8.39 (1H, s), 7.53 (1H, t, J = 4.6 Hz), 7.39 (1H, dd, J = 7.9, 2.0 Hz), 7.24 (2H, d, J = 4.6 Hz), 7.21 (1H, d, J = 7.9 Hz), 7.11 (1H, d, J = 7.9 Hz), 6.60 (1H, d, J = 2.0 Hz), 6.65 (1H, brs), 6.36 (1H, d, J = 8.6 Hz), 6.95 (1H, d, J = 2.6 Hz), 5.72 (1H, d, J = 2.0 Hz), 4.55-4.51 (1H, m), 3.81 (4H, t, J = 5.0 Hz), 3.50 (2H, t, J = 4.6 Hz), 3.38 (3H, s), 3.32 (4H, t, J = 5.0 Hz), 2.68-2.40 (4H, m), 2.30 (6H, s), 2.12-2.07 (1H, m), 1.96-1.91 (1H, m). |
| 10-3-4 | (2-methoxyethyl)(methyl)amino propyl linked to 5-methylpyrazin-2-yl | 6-(7-((3-((2-Methoxy ethyl)(methyl)amino)-1-(5-methyl pyrazin-2-yl)propyl)amino)thianthren-1-yl)-4-morpholino pyridin-2(1H)-one (Optically active substance A) | 631 | 0.96 | 8.63 (1H, brs), 8.47 (1H, d, J = 1.3 Hz), 8.40, (1H, s), 7.56-7.50 (1H, m), 7.28-7.23 (2H, m), 7.12 (1H, d, J = 8.6 Hz), 6.70 (1H, d, J = 2.0 Hz), 6.65-6.63 (1H, brm), 6.38 (1H, dd, J = 8.6, 2.6 Hz), 6.95 (1H, d, J = 2.6 Hz), 5.71 (1H, d, J = 2.0 Hz), 4.64-4.62 (1H, m), 3.81 (4H, t, J = 5.0 Hz), 3.50 (2H, t, J = 5.3 Hz), 3.38 (3H, s), 3.32 (4H, t, J = 5.0 Hz), 2.63-2.59 (2H, m), 2.53 (3H, s), 2.49-2.46 (2H, m), 2.30 (3H, s), 2.18-2.05 (1H, m), 1.99-1.92 (1H, m). |
| 10-3-5 | ((R)-1-methylpyrrolidin-3-yl)methyl linked to 5-methylpyridin-2-yl | 6-(7-(((5-Methyl pyridin-2-yl)((R)-1-methyl pyrrolidin-3-yl)methyl)amino)thianthren-l-yl)-4-morpholino pyridin-2(1H)-one (Optically active substance A) | 598 | 1.12 | 9.18 (1H, brs), 8.39 (1H, s), 7.53-7.50 (1H, m), 7.39 (1H, dd, J = 7.9, 2.0 Hz), 7.26-7.23 (2H, m), 7.18 (1H, d, J = 7.9 Hz), 7.09 (1H, d, J = 8.6 Hz), 6.84 (1H, d, J = 2.0 Hz), 6.33 (1H, dd, J = 8.6, 2.6 Hz), 6.13 (1H, d, J = 5.3 Hz), 5.95 (1H, d, J = 2.6 Hz), 5.70 (1H, s), 4.28 (1H, t, J = 5.0 Hz), 3.80 (4H, t, J = 5.0 Hz), 3.31 (4H, t, J = 4.6 Hz), 2.93 (1H, t, J = 7.9 Hz), 2.83-2.70 (2H, m), 2.33 (3H, s), 2.29 (3H, s), 2.21-2.01 (3H, m), 1.81-1.65 (1H, m). |

TABLE 96-continued

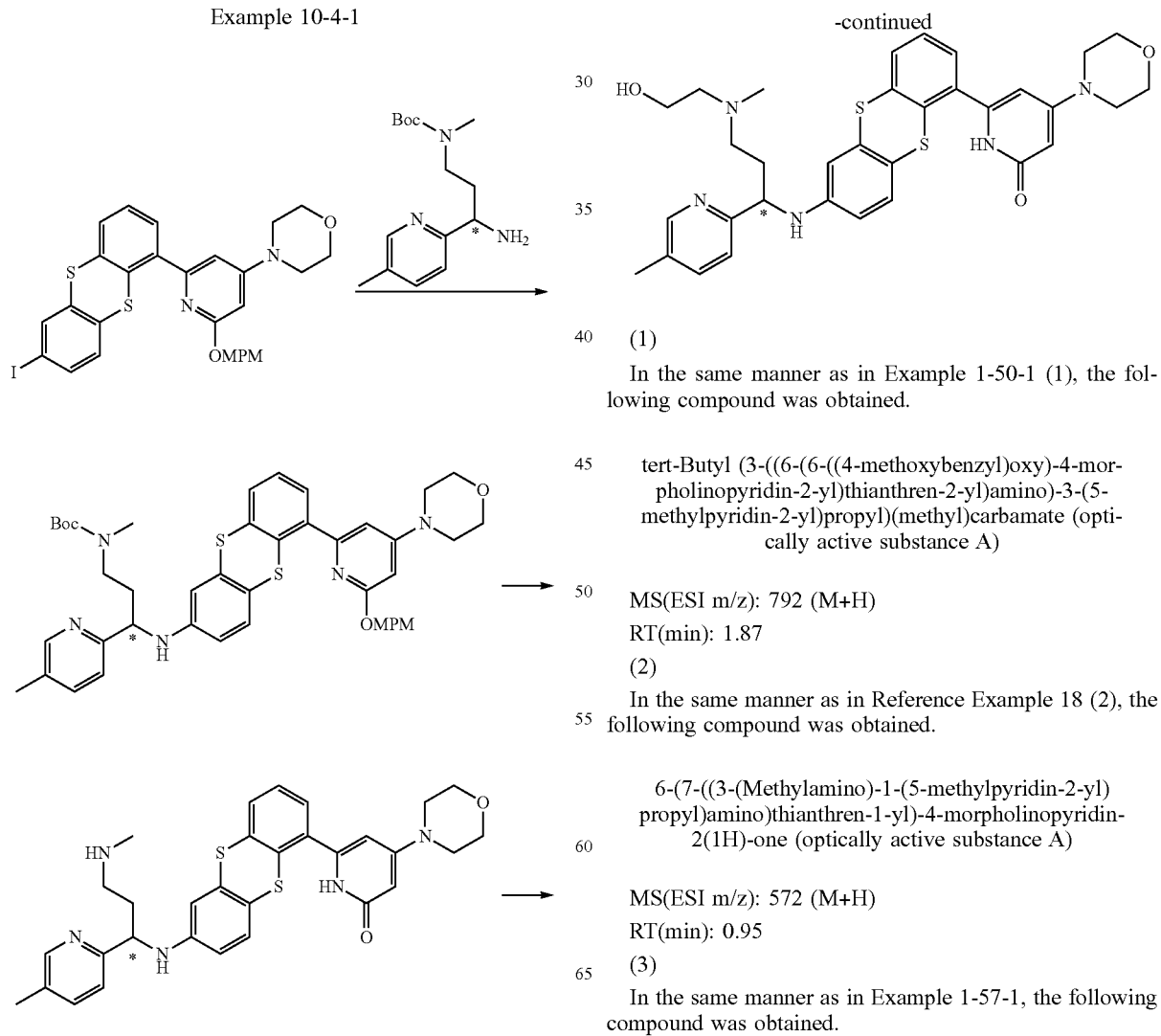

| Example No. | $R^b$ | Compound Name | MS (ESI m/z) (M + H) | RT (min) | $^1$H-NMR (300 MHz) (CDCl3) δ : |
|---|---|---|---|---|---|
| 10-3-6 | | 6-(7-((3-((2-Fluoroethyl) (methyl)amino)-1-(5-methyl pyrazin-2-yl)propyl)amino) thianthren-1-yl)-4-morpholino pyridin-2(1H)-one (Optically active substance A) | 619 | 0.96 | 8.59 (1H, brs), 8.46 (1H, d, J = 1.3 Hz), 8.40 (1H, s), 7.56-7.51 (1H, m), 7.26 (1H, s), 7.24 (1H, s), 7.13 (1H, d, J = 8.6 Hz), 6.68 (1H, d, J = 2.0 Hz), 6.40 (1H, dd, J = 8.6, 2.0 Hz), 6.24 (1H, d, J = 5.9 Hz), 5.95 (1H, d, J = 2.6 Hz), 5.71 (1H, s), 4.64-4.63 (2H, m), 4.48-4.47 (1H, m), 3.81 (4H, t, J = 5.0 Hz), 3.32 (4H, t, J = 4.6 Hz), 2.77-2.74 (1H, m), 2.67-2.65 (1H, m), 2.54 (3H, s), 2.50 (2H, t, J = 5.6 Hz), 2.34 (3H, s), 2.12-2.05 (1H, m), 1.99-1.94 (1H, m). |

Example 10-4-1

(1)

In the same manner as in Example 1-50-1 (1), the following compound was obtained.

tert-Butyl (3-((6-(6-((4-methoxybenzyl)oxy)-4-morpholinopyridin-2-yl)thianthren-2-yl)amino)-3-(5-methylpyridin-2-yl)propyl)(methyl)carbamate (optically active substance A)

MS(ESI m/z): 792 (M+H)

RT(min): 1.87

(2)

In the same manner as in Reference Example 18 (2), the following compound was obtained.

6-(7-((3-(Methylamino)-1-(5-methylpyridin-2-yl) propyl)amino)thianthren-1-yl)-4-morpholinopyridin-2(1H)-one (optically active substance A)

MS(ESI m/z): 572 (M+H)

RT(min): 0.95

(3)

In the same manner as in Example 1-57-1, the following compound was obtained.

6-(7-((3-((2-Hydroxyethyl)(methyl)amino)-1-(5-methylpyridin-2-yl)propyl)amino)thianthren-1-yl)-4-morpholinopyridin-2(1H)-one (optically active substance A)

MS(ESI m/z): 616 (M+H)
RT(min): 0.97
$^1$H-NMR (CDCl$_3$, 300 MHz) δ: 8.63 (1H, brs), 8.34 (1H, s), 7.52 (1H, t, J=4.6 Hz), 7.44 (1H, dd, J=7.9, 2.0 Hz), 7.24 (2H, d, J=4.6 Hz), 7.20 (1H, d, J=7.9 Hz), 7.10 (1H, d, J=7.9 Hz), 6.70 (1H, d, J=2.6 Hz), 6.40 (1H, dd, J=8.3, 2.3 Hz), 6.03 (1H, brs), 5.95 (1H, d, J=2.0 Hz), 5.71 (1H, d, J=2.6 Hz), 4.63 (1H, t, J=5.6 Hz), 3.81 (4H, t, J=4.8 Hz), 3.65-3.59 (2H, m), 3.31 (4H, t, J=4.8 Hz), 2.62-2.29 (10H, m), 2.17-2.12 (1H, m), 1.92-1.88 (1H, m), 1.63 (1H, brs).

Example 10-4-2

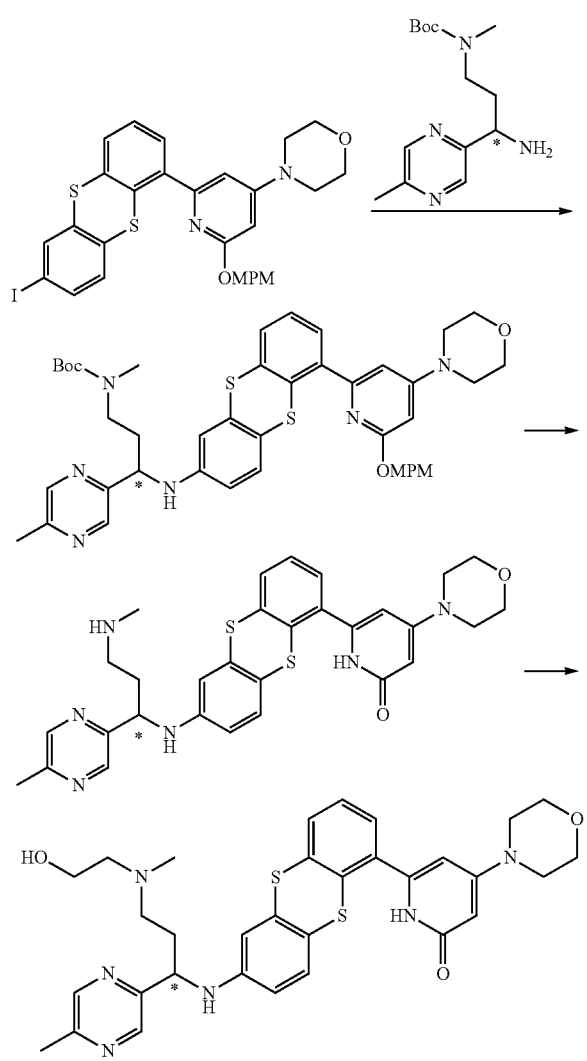

In the same manner as in Example 10-4-1, the following compound was obtained.

6-(7-((3-((2-Hydroxyethyl)(methyl)amino)-1-(5-methylpyrazin-2-yl)propyl)amino)thianthren-1-yl)-4-morpholinopyridin-2(1H)-one (optically active substance A)

MS(ESI m/z): 617 (M+H)
RT(min): 0.93

Example 10-5-1

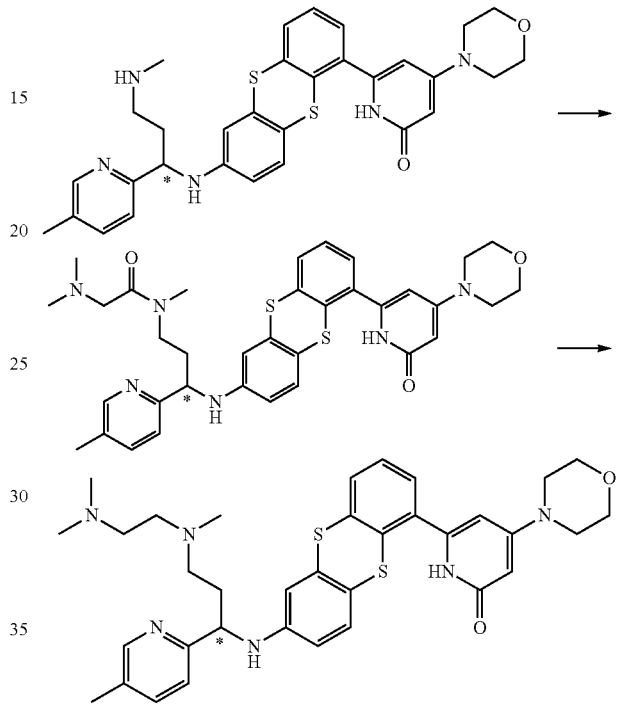

(1)
A mixture of 6-(7-((3-(methyl amino)-1-(5-methylpyridin-2-yl)propyl)amino)thianthren-1-yl)-4-morpholinopyridin-2(1H)-one (optically active substance A) (17 mg) obtained in Example 10-4-1 (2), N,N-dimethyl glycine (3.4 mg), 1-ethyl-3-(3-dimethylaminopropyl)carbodiimide hydrochloride (11 mg), pyridine (3 µL), chloroform (2 mL), tetrahydrofuran (0.1 mL), and N,N-dimethyl formamide (0.1 mL) was stirred at room temperature for 7 hours. Water was added to the reaction mixture, and extraction was carried out using chloroform. The organic layer was dried over anhydrous sodium sulfate, and the solvent was distilled off under reduced pressure. The obtained residues were purified by silica gel column chromatography (chloroform:methanol=100:0→98:2, NH silica), whereby 2-(dimethylamino)-N-methyl-N-(3-(5-methyl pyridin-2-yl)-3-((6-(4-morpholino-6-oxo-1,6-dihydropyridin-2-yl)thianthren-2-yl)amino)propyl)acetamide (optically active substance A) (16 mg) was obtained.
MS(ESI m/z): 657 (M+H)
RT(min): 0.93
(2)
In the same manner as in Example 1-34-1 (2), the following compound was obtained.

6-(7-((3-((2-(Dimethylamino)ethyl)(methyl)amino)-1-(5-methylpyridin-2-yl)propyl)amino)thianthren-1-yl)-4-morpholinopyridin-2(1H)-one (optically active substance A)

MS(ESI m/z): 643 (M+H)
RT(min): 1.06

Example 10-5-2
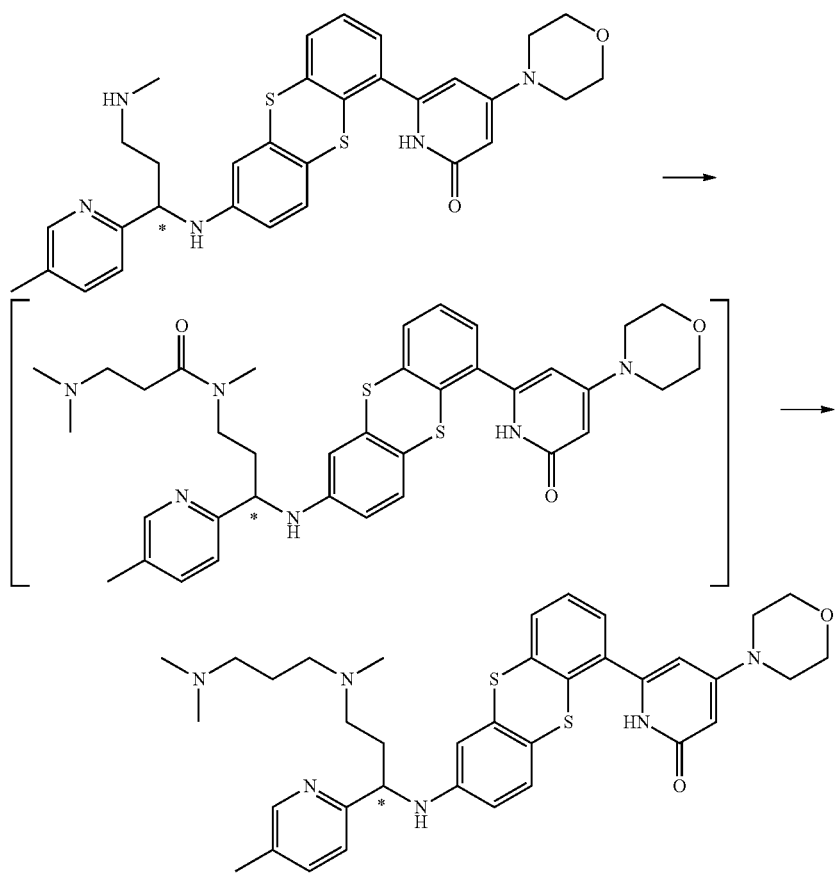
In the same manner as in Example 10-5-1, the following compound was obtained.
6-(7-((3-((3-(Dimethylamino)propyl)(methyl)amino)-1-(5-methylpyridin-2-yl)propyl)amino)thianthren-1-yl)-4-morpholinopyridin-2(1H)-one (optically active substance A)
MS(ESI m/z): 657 (M+H)
RT(min): 0.99
Example 10-6
-continued
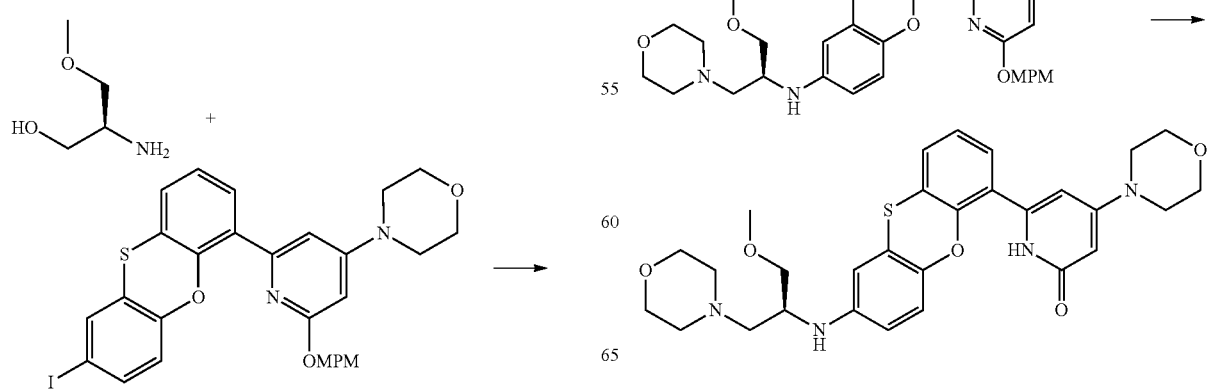

(1)

A solution of 4-(2-(8-iodophenoxathiin-4-yl)-6-((4-methoxybenzyl)oxy)pyridin-4-yl)morpholine (490 mg), (S)-2-amino-3-methoxypropane-1-ol (107 mg), cesium carbonate (1.27 g), copper (I) iodide (150 mg), and 2-isobutyryl cyclohexanone (400 mg) in N,N-dimethyl formamide (2 mL) was stirred at 80° C. for 1.5 hours in a nitrogen atmosphere. After the reaction mixture was cooled to room temperature, water was added thereto, then, the resultant product was extracted with ethyl acetate, and the organic layer was dried over anhydrous sodium sulfate. The solvent was distilled off under reduced pressure, and the obtained residues were purified by silica gel column chromatography (hexane:ethyl acetate=4:1→0:1), whereby (S)-3-methoxy-2-((6-(6-((4-methoxybenzyl)oxy)-4-morpholinopyridin-2-yl)phenoxathiin-2-yl)amino)propane-1-ol (250 mg) was obtained.

MS(ESI m/z): 602 (M+H)
RT(min): 2.03

(2)

Methanesulfonyl chloride (35 μL) was added to a mixed solution of (S)-3-methoxy-2-((6-(6-((4-methoxybenzyl)oxy)-4-morpholinopyridin-2-yl)phenoxathiin-2-yl)amino)propane-1-ol (250 mg) and triethylamine (87 μL) obtained in Example 10-6 (1) in dichloromethane (2 mL) at 0° C., followed by stirring for 20 minutes. The solvent was distilled off, and morpholine (3 mL) was added to the obtained residues, followed by heating to reflux for 1.5 hours. After the solvent was distilled off, water was added to the residues, then, the resultant product was extracted with ethyl acetate, and the organic layer was dried over anhydrous sodium sulfate. The solvent was distilled off under reduced pressure, and the obtained residues were purified by silica gel column chromatography (hexane:ethyl acetate=2:1), whereby (S)—N-(1-methoxy-3-morpholinopropan-2-yl)-6-(6-((4-methoxybenzyl)oxy)-4-morpholinopyridin-2-yl)phenoxathiin-2-amine (245 mg) was obtained.

MS(ESI m/z): 671 (M+H)
RT(min): 1.22

(3)

In the same manner as in Reference Example 18 (2), the following compound was obtained.

(S)-6-(8-((1-methoxy-3-morpholinopropan-2-yl)amino)phenoxathiin-4-yl)-4-morpholinopyridin-2(1H)-one MS(ESI m/z): 551 (M+H)
RT(min): 0.95

Example 10-7

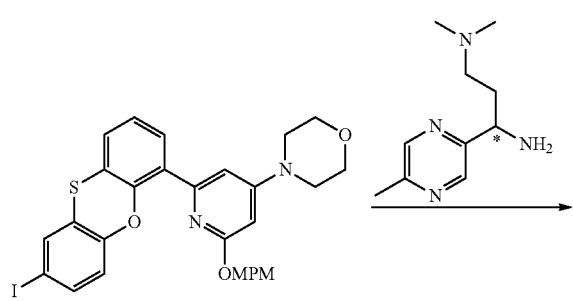

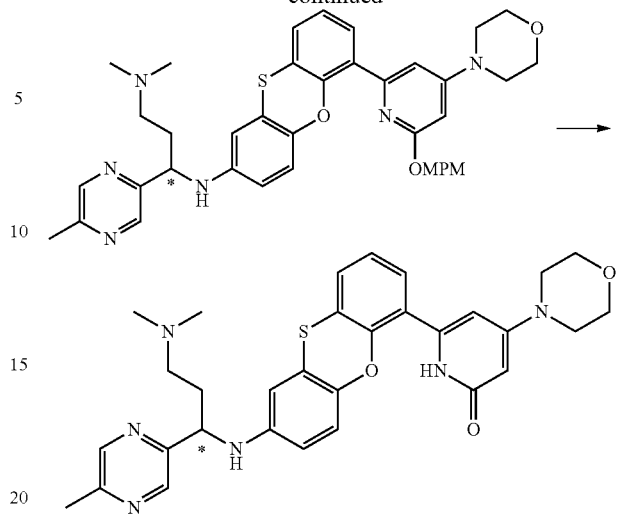

In the same manner as in Example 1-50-1, the following compound was obtained.

6-(8-((3-(Dimethylamino)-1-(5-methylpyrazin-2-yl)propyl)amino)phenoxathiin-4-yl)-4-morpholinopyridin-2(1H)-one (optically active substance A)

$^1$H-NMR (CDCl$_3$, 300 MHz) δ: 8.77 (1H, brs), 8.47 (1H, d, J=1.3 Hz), 8.41 (1H, s), 7.22-7.18 (2H, m), 7.05 (1H, t, J=7.6 Hz), 6.80 (1H, d, J=9.2 Hz), 6.30-6.30 (2H, m), 6.10 (1H, d, J=2.6 Hz), 5.96 (1H, brs), 5.72 (1H, d, J=2.6 Hz), 4.58-4.50 (1H, m), 3.81 (4H, t, J=4.8 Hz), 3.31 (4H, t, J=4.8 Hz), 2.55 (3H, s), 2.41-2.31 (2H, m), 2.26 (6H, s), 2.01-1.90 (2H, m).

MS(ESI m/z): 571 (M+H)
RT(min): 0.95

Example 10-8

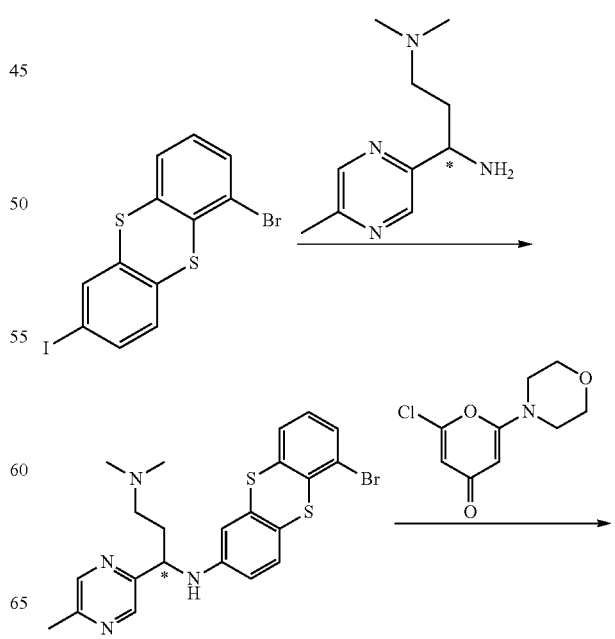

705

-continued

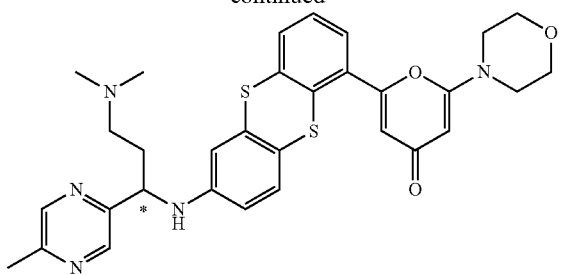

(1)

In the same manner as in Example 1-48-1 (1), the following compound was obtained.

$N^1$-(6-bromo thianthren-2-yl)-$N^3$,$N^3$-dimethyl-1-(5-methylpyrazin-2-yl)propane-1,3-diamine (optically active substance A)

MS(ESI m/z): 488 (M+H)

RT(min): 1.38

(2)

Bispinacolatodiboron (21 mg), a (2-dicyclohexylphosphino-2',4',6'-triisopropyl-1,1'-biphenyl)[2-(2'-amino-1,1'-biphenyl)]palladium (II) methanesulfonate complex (1.7 mg), and potassium acetate (12 mg) were added to a solution of $N^1$-(6-bromothianthren-2-yl)-$N^3$,$N^3$-dimethyl-1-(5-methylpyrazin-2-yl)propane-1,3-diamine (optically active substance A) (20 mg) obtained in Example 10-8 (1) in 1,4-dioxane (0.2 mL), followed by stirring at 90° C. for 2 hours under a nitrogen gas flow. 2-Chloro-6-morpholino-4H-pyran-4-one (13 mg), potassium carbonate (17 mg), and water (40 µL) were added to the reaction mixture, followed by stirring at 100° C. for 2.5 hours. After the reaction mixture was cooled to room temperature, chloroform was added thereto, and the resultant product was washed with water, and dried over anhydrous sodium sulfate. The solvent was distilled off under reduced pressure, the obtained residues were purified sequentially by silica gel column chromatography (chloroform:methanol=100:0→98:2, NH silica) and by silica gel column chromatography (chloroform:methanol=95:5→80:20), whereby 2-(7-((3-(dimethylamino)-1-(5-methylpyrazin-2-yl)propyl)amino)thianthren-1-yl)-6-morpholino-4H-pyran-4-one (optically active substance A) (13 mg) was obtained.

$^1$H-NMR (CDCl$_3$, 300 MHz) δ: 8.47 (1H, d, J=1.3 Hz), 8.40 (1H, s), 7.59 (1H, dd, J=7.6, 1.7 Hz), 7.34 (1H, dd, J=7.6, 1.7 Hz), 7.31-7.24 (1H, m), 7.14 (1H, d, J=7.9 Hz), 6.72 (1H, d, J=2.6 Hz), 6.44 (1H, dd, J=8.6, 2.0 Hz), 6.27 (1H, d, J=2.0 Hz), 6.09 (1H, brs), 5.50 (1H, d, J=1.3 Hz), 4.59 (1H, t, J=6.3 Hz), 3.80 (4H, t, J=4.6 Hz), 3.42 (4H, t, J=4.6 Hz), 2.67-2.50 (5H, m), 2.40 (6H, s), 2.21-2.03 (2H, m).

MS(ESI m/z): 588 (M+H)

RT(min): 0.98

706

Example 10-9

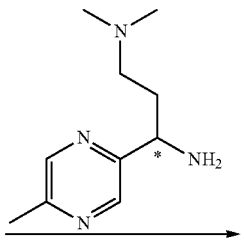

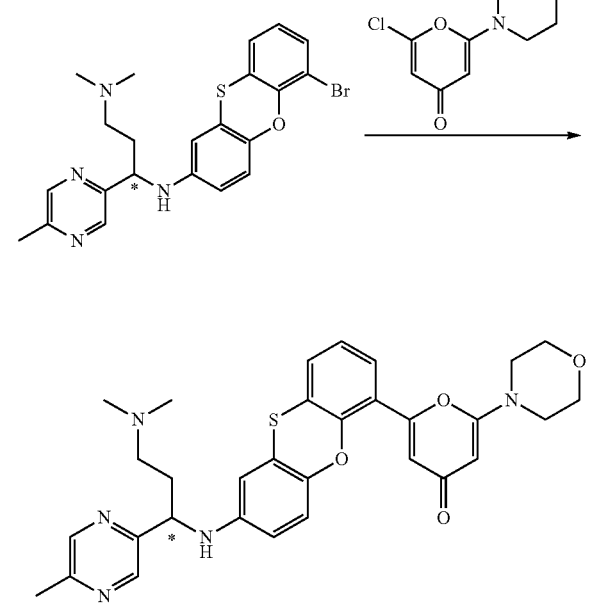

In the same manner as in Example 10-8, the following compound was obtained.

2-(8-((3-(Dimethylamino)-1-(5-methylpyrazin-2-yl)propyl)amino)phenoxathiin-4-yl)-6-morpholino-4H-pyran-4-one (optically active substance A)

$^1$H-NMR (CDCl$_3$, 300 MHz) δ: 8.48 (1H, d, J=1.3 Hz), 8.41 (1H, s), 7.30 (1H, dd, J=7.6, 1.7 Hz), 7.19 (1H, dd, J=7.9, 1.3 Hz), 7.05 (1H, t, J=7.6 Hz), 6.81 (1H, d, J=9.2 Hz), 6.65 (1H, d, J=2.0 Hz), 6.35-6.28 (2H, m), 5.77 (1H, brs), 5.47 (1H, d, J=2.0 Hz), 4.54 (1H, t, J=6.6 Hz), 3.79 (4H, t, J=5.0 Hz), 3.39 (4H, t, J=5.0 Hz), 2.62-2.48 (5H, m), 2.36 (6H, s), 2.13-1.99 (2H, m).

MS(ESI m/z): 572 (M+H)

RT(min): 0.98

Example 11-1

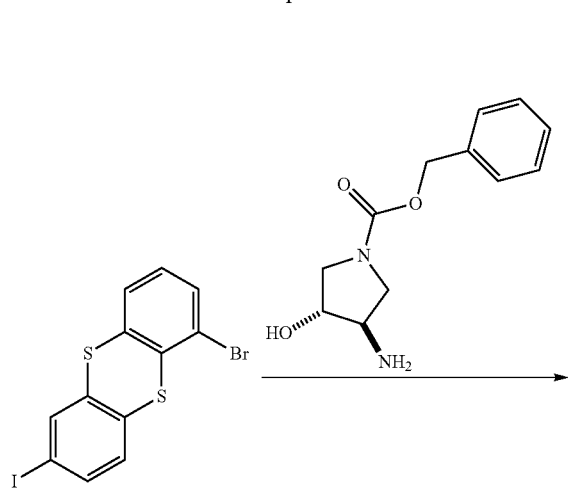

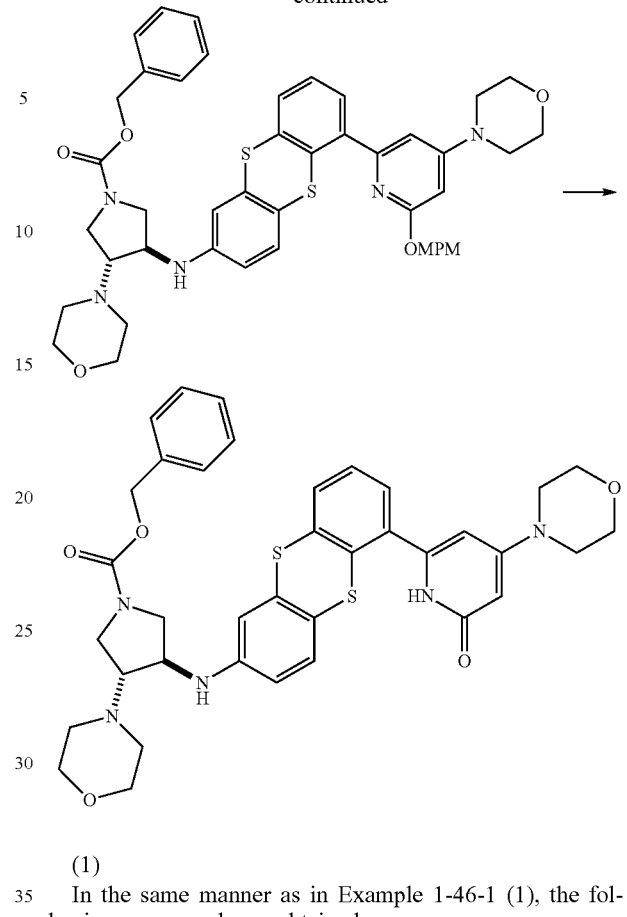

(1)
In the same manner as in Example 1-46-1 (1), the following compound was obtained.

Benzyl 3-((6-bromothianthren-2-yl)amino)-4-hydroxy-pyrrolidine-1-carboxylate (racemic mixture)

MS(ESI m/z): 531 (M+H)
RT(min): 1.91

(2)
In the same manner as in Example 1-46-1 (4), the following compound was obtained.

Benzyl 3-hydroxy-4-((6-(6-((4-methoxybenzyl)oxy)-4-morpholinopyridin-2-yl)thianthren-2-yl)amino)pyrrolidine-1-carboxylate (racemic mixture)

MS(ESI m/z): 749 (M+H)
RT(min): 1.79

(3)
In the same manner as in Reference Example 22-24-1 (1), the following compound was obtained.

Benzyl 3-((6-(6-((4-methoxybenzyl)oxy)-4-morpholinopyridin-2-yl)thianthren-2-yl)amino)-4-((methylsulfonyl)oxy)pyrrolidine-1-carboxylate (racemic mixture)

MS(ESI m/z): 827 (M+H)
RT(min): 1.87

(4)
In the same manner as in Example 1-46-1 (3), the following compound was obtained.

Benzyl 3-((6-(6-((4-methoxybenzyl)oxy)-4-morpholinopyridin-2-yl)thianthren-2-yl)amino)-4-morpholinopyrrolidine-1-carboxylate (racemic mixture)

MS(ESI m/z): 818 (M+H)
RT(min): 1.65

(5)
In the same manner as in Reference Example 18 (2), the following compound was obtained.

Benzyl 3-morpholino-4-((6-(4-morpholino-6-oxo-1,6-dihydropyridin-2-yl)thianthren-2-yl)amino)pyrrolidine-1-carboxylate (racemic mixture)

MS(ESI m/z): 698 (M+H)
RT(min): 1.19

Example 11-2

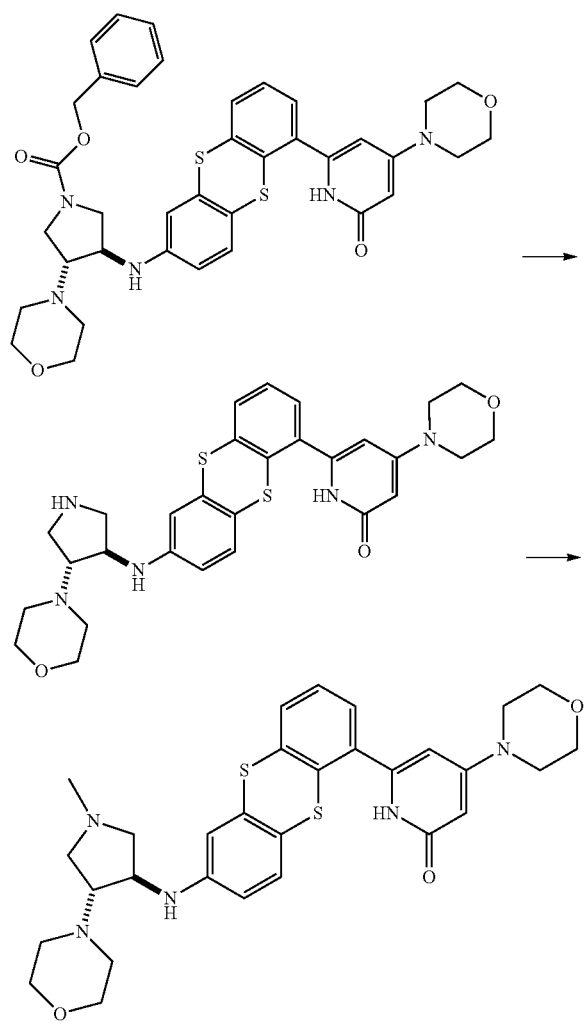

(1)
A 30% hydrogen bromide acetic acid solution (100 μL) was added to benzyl 3-morpholino-4-((6-(4-morpholino-6-oxo-1,6-dihydropyridin-2-yl)thianthren-2-yl)amino)pyrrolidine-1-carboxylate (racemic mixture) (5 mg) obtained in Example 11-1, followed by stirring for 0.5 hours. The obtained reaction mixture was used in the following reaction without purification.

(2)
In the same manner as in Example 1-52-1, the following compound was obtained.

6-(7-((1-Methyl-4-morpholinopyrrolidin-3-yl)amino)thianthren-1-yl)-4-morpholinopyridin-2(1H)-one (racemic mixture)

MS(ESI m/z): 578 (M+H)
RT(min): 0.90

Example 11-3

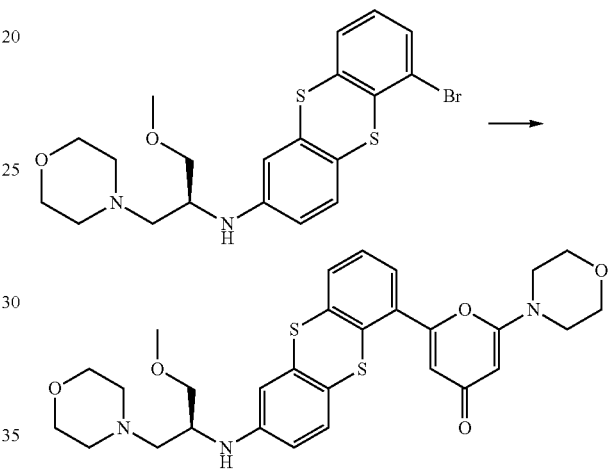

In the same manner as in Example 10-8 (2), the following compound was obtained.

(S)-2-(7-((1-methoxy-3-morpholinopropan-2-yl)amino)thianthren-1-yl)-6-morpholino-4H-pyran-4-one $^1$H-NMR (CDCl$_3$, 300 MHz) δ: 7.63 (1H, dd, J=7.6, 1.7 Hz), 7.36-7.31 (2H, m), 7.21 (1H, d, J=7.9 Hz), 6.84 (1H, d, J=2.6 Hz), 6.55 (1H, dd, J=8.6, 2.6 Hz), 6.30 (1H, d, J=2.0 Hz), 5.52 (1H, d, J=2.0 Hz), 3.85-3.78 (4H, m), 3.71-3.64 (5H, m), 3.57-3.51 (2H, m), 3.47-3.41 (5H, m), 3.36 (3H, s), 2.54 (2H, d, J=6.6 Hz), 2.49-2.42 (4H, m).
MS(ESI m/z): 568 (M+H)
RT(min): 1.01

Example 11-4

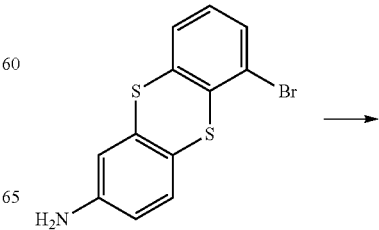

-continued (1)
In the same manner as in Example 1-12-1, the following compound was obtained.

6-Bromo-N-(1-bromopropan-2-yl)thianthrene-2-amine

MS(ESI m/z): 432 (M+H)
RT(min): 2.17
(2)
In the same manner as in Example 1-7-3, the following compound was obtained.

6-Bromo-N-(1-(4-methylpiperazin-1-yl)propan-2-yl)thianthrene-2-amine

MS(ESI m/z): 452 (M+H)
RT(min): 1.38
(3)
In the same manner as in Example 10-8 (2), the following compound was obtained.

2-(7-((1-(4-Methylpiperazin-1-yl)propan-2-yl)amino)thianthren-1-yl)-6-morpholino-4H-pyran-4-one MS(ESI m/z): 551 (M+H)
RT(min): 1.14

Example 12-1

-continued (1)
In the same manner as in Example 1-50-1 (1), the following compound was obtained.

(2S)-tert-butyl 2-(2-((6-(6-((4-methoxybenzyl)oxy)-4-morpholinopyridin-2-yl)thianthren-2-yl)amino)-2-(5-methylpyridin-2-yl)ethyl)pyrrolidine-1-carboxylate (optically active substance A)

MS(ESI m/z): 818 (M+H)
RT(min): 1.97
(2)
In the same manner as in Reference Example 18 (2), the following compound was obtained.

6-(7-((1-(5-Methylpyridin-2-yl)-2-((S)-pyrrolidin-2-yl)ethyl)amino)thianthren-1-yl)-4-morpholinopyridin-2(1H)-one (optically active substance A)

MS(ESI m/z): 598 (M+H)
RT(min): 1.02

Example 12-2

714

6-(7-((1-(5-Methylpyridin-2-yl)-2-((S)-1-methylpyr-rolidin-2-yl)ethyl)amino)thianthren-1-yl)-4-morpholinopyridin-2(1H)-one (optically active substance B)

MS(ESI m/z): 612 (M+H)

RT(min) 1.01

Example 12-3

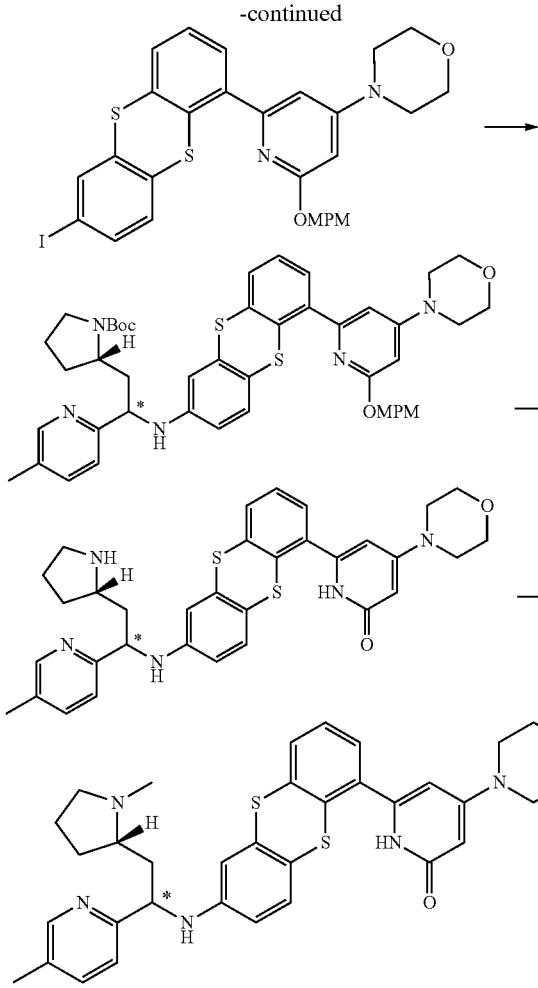

In the same manner as in Example 1-12-1, the following compound was obtained.

6-(7-((4-(Dimethylamino)-2-(5-methylpyrazin-2-yl)butyl)amino)thianthren-1-yl)-4-morpholinopyridin-2(1H)-one MS(ESI m/z): 601 (M+H)

RT(min): 0.95

713

(1)

In the same manner as in Example 12-1 (1), the following compound was obtained.

(2S)-tert-butyl 2-(2-((6-(6-((4-methoxybenzyl)oxy)-4-morpholinopyridin-2-yl)thianthren-2-yl)amino)-2-(5-methylpyridin-2-yl)ethyl)pyrrolidine-1-carboxy-late (optically active substance B)

MS(ESI m/z): 819 (M+H)

RT(min): 21.01

(2)

In the same manner as in Example 12-1 (2), the following compound was obtained.

6-(7-((1-(5-Methylpyridin-2-yl)-2-((S)-pyrrolidin-2-yl)ethyl)amino)thianthren-1-yl)-4-morpholinopyri-din-2(1H)-one (optically active substance B)

MS(ESI m/z): 598 (M+H)

RT(min): 0.96

(3)

In the same manner as in Example 1-52-1, the following compound was obtained.

Example 12-4

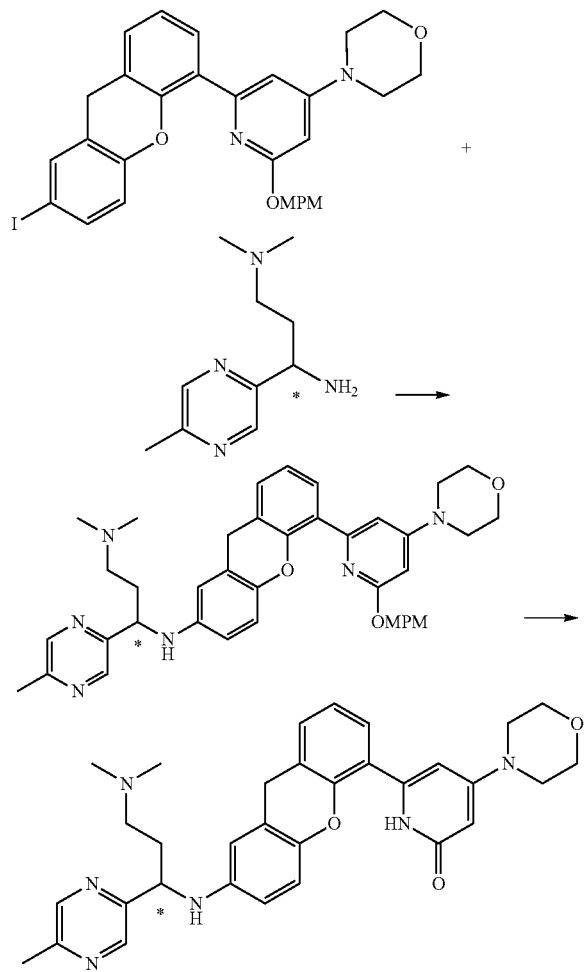

(1)
In the same manner as in Example 12-1 (1), the following compound was obtained.

N¹-(5-(6-((4-methoxybenzyl)oxy)-4-morpholin-opyridin-2-yl)-9H-xanthen-2-yl)-N³,N³-dimethyl-1-(5-methylpyrazin-2-yl)propane-1,3-diamine (optically active substance A)

MS(ESI m/z): 673 (M+H)
RT(min): 1.21

(2)
In the same manner as in Example 12-1 (2), the following compound was obtained.

6-(7-((3-(Dimethylamino)-1-(5-methylpyrazin-2-yl)propyl)amino)-9H-xanthen-4-yl)-4-morpholinopyridin-2(1H)-one (optically active substance A)

MS(ESI m/z): 553 (M+H)
RT(min): 0.92

Example 12-5

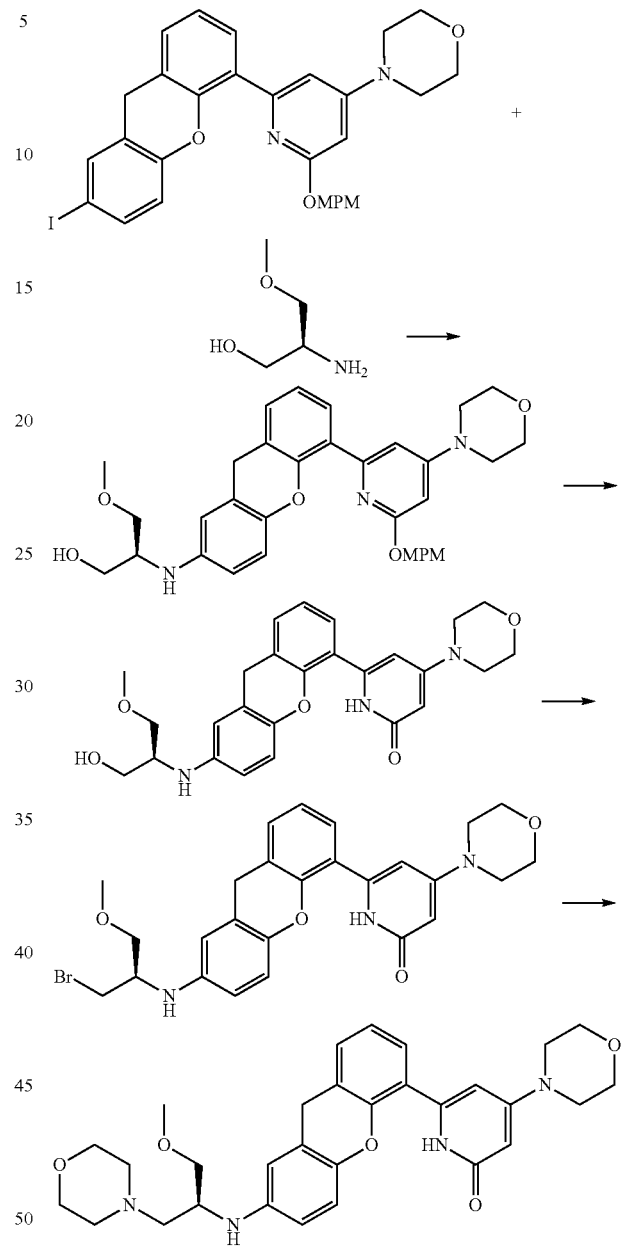

(1)
In the same manner as in Example 12-1 (1), the following compound was obtained.

(S)-3-Methoxy-2-((5-(6-((4-methoxybenzyl)oxy)-4-morpholinopyridin-2-yl)-9H-xanthen-2-yl)amino)propane-1-ol MS(ESI m/z): 584 (M+H)
RT(min): 1.20

(2)
In the same manner as in Example 12-1 (2), the following compound was obtained.

(S)-6-(7-((1-Hydroxy-3-methoxypropan-2-yl)amino)-9H-xanthen-4-yl)-4-morpholinopyridin-2(1H)-one MS(ESI m/z): 464 (M+H)
RT(min): 0.93
(3)
In the same manner as in Example 1-42-1 (2), the following compound was obtained.

(R)-6-(7-((1-bromo-3-methoxypropan-2-yl)amino)-9H-xanthen-4-yl)-4-morpholinopyridin-2(1H)-one MS(ESI m/z): 528 (M+H)
RT(min): 1.39
(4)
In the same manner as in Example 1-7-3, the following compound was obtained.

(S)-6-(7-((1-methoxy-3-morpholinopropan-2-yl)amino)-9H-xanthen-4-yl)-4-morpholinopyridin-2(1H)-one MS(ESI m/z): 533 (M+H)
RT(min): 0.93

Example 12-6

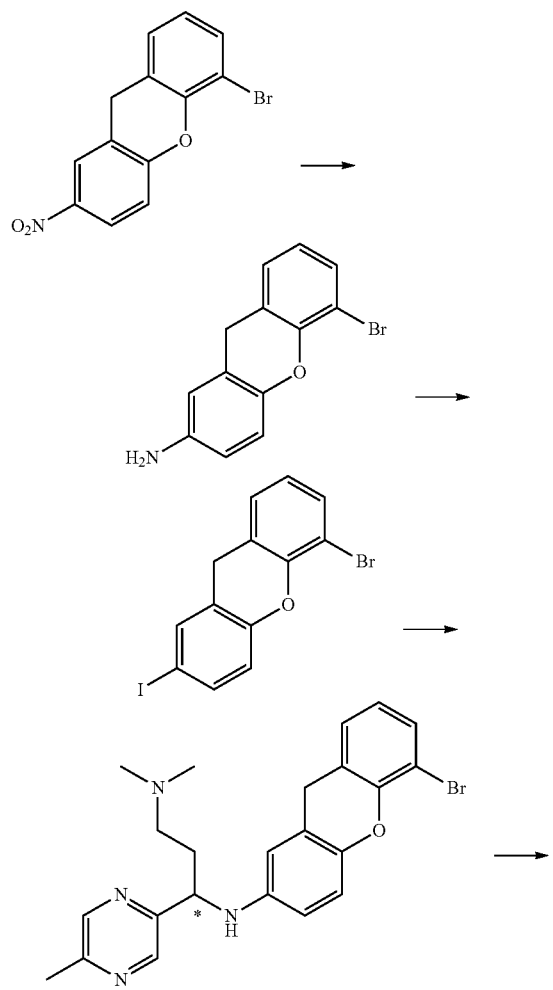

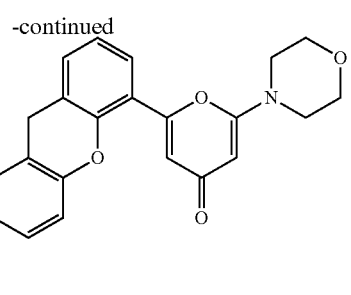

(1)
In the same manner as in Reference Example 3 (4), the following compound was obtained.

5-Bromo-9H-xanthene-2-amine

MS(ESI m/z): 278 (M+H)
RT(min): 1.12
(2)
In the same manner as in Reference Example 6, the following compound was obtained.

5-Bromo-2-iodo-9H-xanthene

MS(ESI m/z): 389 (M+H)
RT(min): 2.20
(3)
In the same manner as in Example 12-1 (1), the following compound was obtained.

$N^1$-(5-bromo-9H-xanthen-2-yl)-$N^3$,$N^3$-dimethyl-1-(5-methyl pyrazin-2-yl)propane-1,3-diamine (optically active substance A)

MS(ESI m/z): 455 (M+H)
RT(min): 1.22
(4)
In the same manner as in Example 10-8 (2), the following compound was obtained.

2-(7-((3-(Dimethylamino)-1-(5-methylpyrazine-2-yl)propyl)amino)-9H-xanthen-4-yl)-6-morpholino-4H-pyran-4-one (optically active substance A)

MS(ESI m/z): 554 (M+H)
RT(min): 0.93

The novel morpholine derivative of the present invention or a salt thereof has excellent ATM inhibitory activity, and is useful as an agent for treating a disease in which ATM is involved. In addition, the novel morpholine derivative of the present invention or a salt thereof is useful as a sensitivity-enhancing agent to an ionizing radiation or an anticancer agent having effects similar to the ionizing radiation.

The entirety of the disclosure of Japanese Patent Application No. 2013-177934 filed on Aug. 29, 2013 is incorporated into the present specification by reference.

All documents, patent application, and technology standards that are described in the present specification are incorporated by reference into the present specification to the same extent as in a case in which the incorporation of the individual documents, patent applications, and technology standards is specifically and individually described.

What is claimed is:
1. A morpholine derivative represented by formula [1A] or a salt thereof,

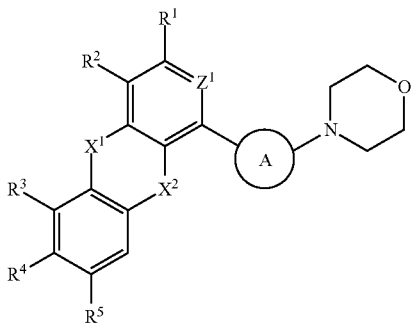

wherein, in the formula, a ring A represents a ring represented by formula [I] or a ring represented by formula [II];

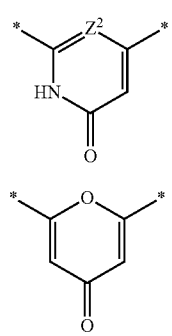

* represents a bonding position;
$Z^2$ represents CH or N;
$Z^1$ represents $CR^6$ or N;
$R^6$ represents a hydrogen atom, a halogen atom, or a $C_{1-8}$ alkyl group which may have a substituent;
$X^1$ represents $CHR^7$, $CHR^8$—$CHR^9$, O, or S;
$R^7$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent;
$R^8$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent;
$R^9$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent;
a carbon atom to which $R^8$ is bonded is bonded to a ring having $R^1$ and $R^2$;
$X^2$ represents $CH_2$, O, S, or $NR^{10}$;
$R^{10}$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent;
$R^1$ and $R^2$ are the same as or different from each other, and each of $R^1$ and $R^2$ represents a hydrogen atom, a halogen atom, a hydroxyl group which may have a protecting group, a $C_{1-8}$ alkyl group which may have a substituent, or a $C_{1-6}$ alkoxy group which may have a substituent;
$R^3$, $R^4$, and $R^5$ are the same as or different from each other, and each of $R^3$, $R^4$, and $R^5$ represents a hydrogen atom, a halogen atom, a nitro group, a hydroxyl group which may have a protecting group, a $C_{1-8}$ alkyl group which may have a substituent, a $C_{2-6}$ alkenyl group which may have a substituent, a $C_{2-6}$ alkynyl group which may have a substituent, a $C_{1-6}$ alkoxy group which may have a substituent, an acyl group which may have a substituent, an aryl group which may have a substituent, a heterocyclic group which may have a substituent, or $NR^aR^b$;
$R^a$ and $R^b$ are the same as or different from each other, and each of $R^a$ and $R^b$ represents a hydrogen atom, a $C_{1-8}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, an aryl group which may have a substituent, an ar $C_{1-6}$ alkyl group which may have a substituent, an acyl group which may have a substituent, a $C_{1-6}$ alkylsulfonyl group which may have a substituent, a heterocyclic group which may have a substituent, or a heterocyclic $C_{1-8}$ alkyl group which may have a substituent;
when the ring A is a ring represented by formula [II], $R^4$ represents $NR^{a1}R^{b1}$;
$R^{a1}$ represents a hydrogen atom, a $C_{1-8}$ alkyl group which may have one or more substituents selected from the substituent group f, a $C_{2-6}$ alkenyl group which may have one or more substituents selected from the substituent group f, a $C_{2-6}$ alkynyl group which may have one or more substituents selected from the substituent group f, a $C_{3-8}$ cycloalkyl group which may have one or more substituents selected from the substituent group f, an aryl group which may have one or more substituents selected from the substituent group f, an ar $C_{1-6}$ alkyl group which may have one or more substituents selected from the substituent group f, an acyl group which may have one or more substituents selected from the substituent group f, a $C_{1-6}$ alkylsulfonyl group which may have one or more substituents selected from the substituent group f, a heterocyclic group which may have one or more substituents selected from the substituent group f, or a heterocyclic $C_{1-8}$ alkyl group which may have one or more substituents selected from the substituent group f;
$R^{b1}$ represents a $C_{1-8}$ alkyl group which may have one or more substituents selected from the substituent group f, a $C_{2-6}$ alkenyl group which may have one or more substituents selected from the substituent group f, a $C_{2-6}$ alkynyl group which may have one or more substituents selected from the substituent group f, a $C_{3-8}$ cycloalkyl group which may have one or more substituents selected from the substituent group f, an aryl group which may have one or more substituents selected from the substituent group f, an ar $C_{1-6}$ alkyl group which may have one or more substituents selected from the substituent group f, a $C_{1-6}$ alkylsulfonyl group which may have one or more substituents selected from the substituent group f, a heterocyclic group which may have one or more substituents selected from the substituent group f, or a heterocyclic $C_{1-8}$ alkyl group which may have one or more substituents selected from the substituent group f;

in the substituent group f, $R^c$ and $R^d$ are the same as or different from each other, and each of $R^c$ and $R^d$ represents a hydrogen atom, a $C_{1-8}$ alkyl group which may have one or more substituents selected from the substituent group d, a $C_{2-6}$ alkenyl group which may have one or more substituents selected from the substituent group d, or a $C_{2-6}$ alkynyl group which may have one or more substituents selected from the substituent group d; or $R^c$ and $R^d$ may form a cyclic amino group which may be substituted with one or more substituents selected from the substituent group d, together with the nitrogen atom to which $R^c$ and $R^d$ are bonded;

$R^e$ and $R^f$ are the same as or different from each other, and each of $R^e$ and $R^f$ represents a hydrogen atom, a $C_{1-8}$ alkyl group which may have one or more substituents selected from the substituent group d, a $C_{2-6}$ alkenyl group which may have one or more substituents selected from the substituent group d, or a $C_{2-6}$ alkynyl group which may have one or more substituents selected from the substituent group d; or $R^e$ and $R^f$ may form a cyclic amino group which may have one or more substituents selected from the substituent group d, together with the nitrogen atom to which $R^e$ and $R^f$ are bonded;

in the substituent group e, $R^g$ and $R^h$ are the same as or different from each other, and each of $R^g$ and $R^h$ represents a hydrogen atom, a $C_{1-8}$ alkyl group, a $C_{2-6}$ alkenyl group, or a $C_{2-6}$ alkynyl group; or $R^g$ and $R^h$ may form a cyclic amino group together with the nitrogen atom to which $R^g$ and $R^h$ are bonded, wherein the substituent group f is selected from the group consisting of a deuterium atom, a halogen atom, a cyano group, a nitro group, a hydroxyl group which may have a protecting group, an amino group which may have a protecting group, a carboxyl group which may have a protecting group, a $C_{1-8}$ alkyl group which may have one or more substituents selected from the substituent group d, a $C_{2-6}$ alkenyl group which may have one or more substituents selected from the substituent group d, a $C_{2-6}$ alkynyl group which may have one or more substituents selected from the substituent group d, a $C_{3-8}$ cycloalkyl group which may have one or more substituents selected from the substituent group d, a $C_{3-8}$ cycloalkenyl group which may have one or more substituents selected from the substituent group d, an aryl group which may have one or more substituents selected from the substituent group d, an ar $C_{1-6}$ alkyl group which may have one or more substituents selected from the substituent group d, an $C_{1-6}$ alkoxy group which may have one or more substituents selected from the substituent group d, an acyl group which may have one or more substituents selected from the substituent group d, a $C_{1-6}$ alkylamino group which may have one or more substituents selected from the substituent group d, a di($C_{1-6}$ alkyl)amino group which may have one or more substituents selected from the substituent group d, a heterocyclic group which may have one or more substituents selected from the substituent group d, a heterocyclic $C_{1-8}$ alkyl group which may have one or more substituents selected from the substituent group d, a heterocyclic oxy group which may have one or more substituents selected from the substituent group d, $CONR^cR^d$, and $NHCONR^eR^f$, wherein the substituent group d is selected from the group consisting of a halogen atom, a cyano group, a nitro group, an oxo group, a hydroxyl group which may have a protecting group, an amino group which may have a protecting group, a carboxyl group which may have a protecting group, a $C_{1-8}$ alkyl group which may have one or more substituents selected from the substituent group e, a $C_{2-6}$ alkenyl group which may have one or more substituents selected from the substituent group e, a $C_{2-6}$ alkynyl group which may have one or more substituents selected from the substituent group e, a $C_{3-8}$ cycloalkyl group which may have one or more substituents selected from the substituent group e, an aryl group which may have one or more substituents selected from the substituent group e, a $C_{1-6}$ alkoxy group which may have one or more substituents selected from the substituent group e, an acyl group which may have one or more substituents selected from the substituent group e, a $C_{1-6}$ alkylamino group which may have one or more substituents selected from the substituent group e, a di($C_{1-6}$ alkyl)amino group which may have one or more substituents selected from the substituent group e, a heterocyclic group which may have one or more substituents selected from the substituent group e, and a heterocyclic oxy group which may have one or more substituents selected from the substituent group e, wherein the substituent group e is selected from the group consisting of a halogen atom, a hydroxyl group which may have a protecting group, a $C_{1-6}$ alkoxy group, and $CONR^gR^h$, wherein the protecting group of a hydroxyl group is selected from the group consisting of a $C_{1-6}$ alkyl group, a $C_{2-6}$ alkenyl group, an aralkyl group which contains a $C_{1-6}$ alkyl group, a $C_{1-6}$ alkoxy $C_{1-6}$ alkyl group, an aralkyl group which contains a $C_{1-6}$ alkoxy $C_{1-6}$ alkyl group, an acyl group, a $C_{1-6}$ alkoxycarbonyl group, an aralkyl group which contains a $C_{1-6}$ alkoxycarbonyl group, a $C_{1-6}$ alkylsulfonyl group, an arylsulfonyl group, a silyl group, a tetrahydrofuranyl group, and a tetrahydropyranyl group, wherein the protecting group of an amino group is selected from the group consisting of an aralkyl group which contains a $C_{1-6}$ alkyl group, a $C_{1-6}$ alkoxy $C_{1-6}$ alkyl group, an acyl group, a $C_{1-6}$ alkoxycarbonyl group, an aralkyl group which contains a $C_{1-6}$ alkoxycarbonyl group, an aryloxycarbonyl group, a $C_{1-6}$ alkylsulfonyl group, an arylsulfonyl group, and a silyl group, and wherein the protecting group of a carboxyl group is selected from the group consisting of a $C_{1-6}$ alkyl group, a $C_{2-6}$ alkenyl group, an aralkyl group which contains a $C_{1-6}$ alkyl group, a $C_{1-6}$ alkoxy $C_{1-6}$ alkyl group, an aralkyl group which contains a $C_{1-6}$ alkoxy $C_{1-6}$ alkyl group, an acyl group, a $C_{1-6}$ alkoxycarbonyl group, an aralkyl group which contains a $C_{1-6}$ alkoxycarbonyl group, a $C_{1-6}$ alkylsulfonyl group, an arylsulfonyl group, a silyl group, a tetrahydrofuranyl group, and a tetrahydropyranyl group.

2. The morpholine derivative or a salt thereof according to claim 1,
wherein the morpholine derivative is represented by formula [1],

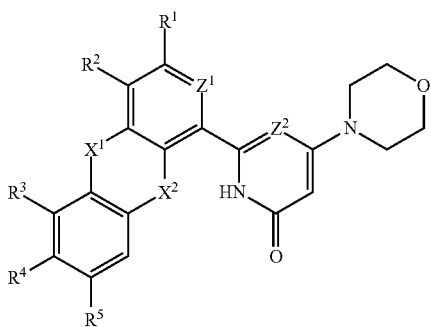

in the formula,
$Z^1$ represents $CR^6$ or N;
$R^6$ represents a hydrogen atom, a halogen atom, or a $C_{1-8}$ alkyl group which may have a substituent;
$Z^2$ represents CH or N;
$X^1$ represents $CHR^7$, $CHR^8$—$CHR^9$, O, or S;
$R^7$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent;
$R^8$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent;
$R^9$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent;
a carbon atom to which $R^8$ is bonded is bonded to a ring having $R^1$ and $R^2$;
$X^2$ represents $CH_2$, O, S, or $NR^{10}$;
$R^{10}$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent;
$R^1$ and $R^2$ are the same as or different from each other, and each of $R^1$ and $R^2$ represents a hydrogen atom, a halogen atom, a hydroxyl group which may have a protecting group, a $C_{1-8}$ alkyl group which may have a substituent, or a $C_{1-6}$ alkoxy group which may have a substituent;
$R^3$, $R^4$, and $R^5$ are the same as or different from each other, and each of $R^3$, $R^4$, and $R^5$ represents a hydrogen atom, a halogen atom, a nitro group, a hydroxyl group which may have a protecting group, a $C_{1-8}$ alkyl group which may have a substituent, a $C_{2-6}$ alkenyl group which may have a substituent, a $C_{2-6}$ alkynyl group which may have a substituent, a $C_{1-6}$ alkoxy group which may have a substituent, an acyl group which may have a substituent, an aryl group which may have a substituent, a heterocyclic group which may have a substituent, or a group represented by $NR^aR^b$; and $R^a$ and $R^b$ are the same as or different from each other, and each of $R^a$ and $R^b$ represents a hydrogen atom, a $C_{1-8}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, an aryl group which may have a substituent, an ar $C_{1-6}$ alkyl group which may have a substituent, an acyl group which may have a substituent, a $C_{1-6}$ alkylsulfonyl group which may have a substituent, a heterocyclic group which may have a substituent, or a heterocyclic $C_{1-8}$ alkyl group which may have a substituent.

3. The morpholine derivative or a salt thereof according to claim 1,
wherein $Z^1$ is CH.

4. The morpholine derivative or a salt thereof according to claim 1,
wherein $X^1$ is $CH_2$ or S.

5. The morpholine derivative or a salt thereof according to claim 1,
wherein $X^2$ is O or S.

6. The morpholine derivative or a salt thereof according to claim 1,
wherein $R^1$ is a hydrogen atom; and $R^2$ is a hydrogen atom.

7. The morpholine derivative or a salt thereof according to claim 2,
wherein $R^3$ is a hydrogen atom;
one of $R^4$ or $R^5$ is $NR^aR^b$;
the other $R^4$ or $R^5$ is a hydrogen atom; and
$R^a$ and $R^b$ are the same as or different from each other, and each of $R^a$ and $R^b$ represents a hydrogen atom, a $C_{1-8}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, an aryl group which may have a substituent, an ar $C_{1-6}$ alkyl group which may have a substituent, an acyl group which may have a substituent, a $C_{1-6}$ alkylsulfonyl group which may have a substituent, a heterocyclic group which may have a substituent, or a heterocyclic $C_{1-8}$ alkyl group which may have a substituent.

8. The morpholine derivative or a salt thereof according to claim 2,
wherein $R^3$ is a hydrogen atom;
$R^4$ is $NR^aR^b$;
$R^a$ and $R^b$ are the same as or different from each other, and each of $R^a$ and $R^b$ represents a hydrogen atom, a $C_{1-8}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, an aryl group which may have a substituent, an ar $C_{1-6}$ alkyl group which may have a substituent, an acyl group which may have a substituent, a $C_{1-6}$ alkylsulfonyl group which may have a substituent, a heterocyclic group which may have a substituent, or a heterocyclic $C_{1-8}$ alkyl group which may have a substituent; and
$R^5$ is a hydrogen atom.

9. The morpholine derivative or a salt thereof according to claim 2,
wherein $R^a$ is a hydrogen atom; and
$R^b$ is a hydrogen atom, a $C_{1-8}$ alkyl group which may have a substituent, a $C_{3-8}$ cycloalkyl group which may have a substituent, an ar $C_{1-6}$ alkyl group which may have a substituent, an acyl group which may have a substituent, a $C_{1-6}$ alkylsulfonyl group which may have a substituent, a heterocyclic group which may have a substituent, or a heterocyclic $C_{1-8}$ alkyl group which may have a substituent.

10. The morpholine derivative or a salt thereof according to claim 2,
wherein $R^a$ is a hydrogen atom; and
$R^b$ is a $C_{3-8}$ cycloalkyl group which may have a substituent, a heterocyclic group which may have a substituent, or a heterocyclic $C_{1-8}$ alkyl group which may have a substituent.

11. The morpholine derivative or a salt thereof according to claim 1,
wherein the morpholine derivative is represented by formula [1α],

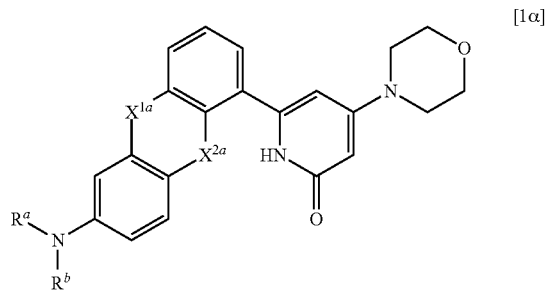

[1α]

in the formula,
$X^{1a}$ represents $CHR^7$, O, or S;
$R^7$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent;
$X^2$ represents $CH_2$, O, S, or $NR^{10}$;
$R^{10}$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent; and
$R^a$ and $R^b$ are the same as or different from each other, and each of $R^a$ and $R^b$ represents a hydrogen atom, a $C_{1-8}$ alkyl group which may have a substituent, a $C_{2-6}$ alkenyl group which may have a substituent, a $C_{2-6}$ alkynyl group which may have a substituent, a $C_{3-8}$ cycloalkyl group which may have a substituent, an aryl group which may have a substituent, an ar $C_{1-6}$ alkyl group which may have a substituent, an acyl group which may have a substituent, a $C_{1-6}$ alkylsulfonyl group which may have a substituent, a heterocyclic group which may have a substituent, or a heterocyclic $C_{1-8}$ alkyl group which may have a substituent.

12. The morpholine derivative or a salt thereof according to claim 11,
wherein $X^{1a}$ is $CH_2$ or S.

13. The morpholine derivative or a salt thereof according to claim 11,
wherein $X^2$ is O or S.

14. The morpholine derivative or a salt thereof according to claim 11,
wherein $R^a$ is a hydrogen atom; and
$R^b$ is a $C_{1-8}$ alkyl group which may have a substituent, a $C_{3-8}$ cycloalkyl group which may have a substituent, an ar $C_{1-6}$ alkyl group which may have a substituent, an acyl group which may have a substituent, a $C_{1-6}$ alkylsulfonyl group which may have a substituent, a heterocyclic group which may have a substituent, or a heterocyclic $C_{1-8}$ alkyl group which may have a substituent.

15. The morpholine derivative or a salt thereof according to claim 11,
wherein $R^a$ is a hydrogen atom; and
$R^b$ is a $C_{3-8}$ cycloalkyl group which may have a substituent, a heterocyclic group which may have a substituent, or a heterocyclic $C_{1-8}$ alkyl group which may have a substituent.

16. The morpholine derivative or a salt thereof according to claim 1,
wherein the morpholine derivative is represented by formula [1β],

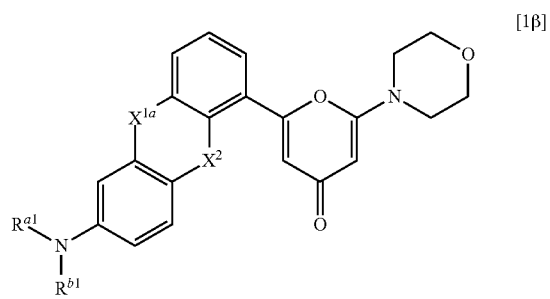

[1β]

in the formula,
$X^{1a}$ represents $CHR^7$, O, or S;
$R^7$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent;
$X^2$ represents $CH_2$, O, S, or $NR^{10}$;
$R^{10}$ represents a hydrogen atom, a $C_{1-8}$ alkyl group which may have a substituent, a $C_{2-6}$ alkenyl group which may have a substituent, a $C_{2-6}$ alkynyl group which may have a substituent, or an aryl group which may have a substituent;
$R^{a1}$ represents a hydrogen atom, a $C_{1-8}$ alkyl group which may have one or more substituents selected from the substituent group f, a $C_{2-6}$ alkenyl group which may have one or more substituents selected from the substituent group f, a $C_{2-6}$ alkynyl group which may have one or more substituents selected from the substituent group f, a $C_{3-8}$ cycloalkyl group which may have one or more substituents selected from the substituent group f, an aryl group which may have one or more substituents selected from the substituent group f, an ar $C_{1-6}$ alkyl group which may have one or more substituents selected from the substituent group f, an acyl group which may have one or more substituents selected from the substituent group f, a $C_{1-6}$ alkylsulfonyl group which may have one or more substituents selected from the substituent group f, a heterocyclic group which may have one or more substituents selected from the substituent group f, or a heterocyclic $C_{1-8}$ alkyl group which may have one or more substituents selected from the substituent group f;
$R^{b1}$ represents a $C_{1-8}$ alkyl group which may have one or more substituents selected from the substituent group f, a $C_{2-6}$ alkenyl group which may have one or more substituents selected from the substituent group f, a $C_{2-6}$ alkynyl group which may have one or more substituents selected from the substituent group f, a $C_{3-8}$ cycloalkyl group which may have one or more substituents selected from the substituent group f, an aryl group which may have one or more substituents selected from the substituent group f, an ar $C_{1-6}$ alkyl group which may have one or more substituents selected from the substituent group f, a $C_{1-6}$ alkylsulfonyl group which may have one or more substituents selected from the substituent group f, a heterocyclic group which may have one or more substituents selected from the substituent group f, or a heterocyclic $C_{1-8}$ alkyl group which may have one or more substituents selected from the substituent group f;

in the substituent group f, $R^c$ and $R^d$ are the same as or different from each other, and each of $R^c$ and $R^d$ represents a hydrogen atom, a $C_{1-8}$ alkyl group which may have one or more substituents selected from the substituent group d, a $C_{2-6}$ alkenyl group which may have one or more substituents selected from the substituent group d, or a $C_{2-6}$ alkynyl group which may have one or more substituents selected from the substituent group d; or $R^c$ and $R^d$ may form a cyclic amino group which may be substituted with one or more substituents selected from the substituent group d, together with the nitrogen atom to which $R^c$ and $R^d$ are bonded;

$R^e$ and $R^f$ are the same as or different from each other, and each of $R^e$ and $R^f$ represents a hydrogen atom, a $C_{1-8}$ alkyl group which may have one or more substituents selected from the substituent group d, a $C_{2-6}$ alkenyl group which may have one or more substituents selected from the substituent group d, or a $C_{2-6}$ alkynyl group which may have one or more substituents selected from the substituent group d; or $R^e$ and $R^f$ may form a cyclic amino group which may have one or more substituents selected from the substituent group d, together with the nitrogen atom to which $R^e$ and $R^f$ are bonded;

in the substituent group e, $R^g$ and $R^h$ are the same as or different from each other, and each of $R^g$ and $R^h$ represents a hydrogen atom, a $C_{1-8}$ alkyl group, a $C_{2-6}$ alkenyl group, or a $C_{2-6}$ alkynyl group; or $R^g$ and $R^h$ may form a cyclic amino group together with the nitrogen atom to which $R^g$ and $R^h$ are bonded, wherein the substituent group f is selected from the group consisting of a deuterium atom, a halogen atom, a cyano group, a nitro group, a hydroxyl group which may have a protecting group, an amino group which may have a protecting group, a carboxyl group which may have a protecting group, a $C_{1-8}$ alkyl group which may have one or more substituents selected from the substituent group d, a $C_{2-6}$ alkenyl group which may have one or more substituents selected from the substituent group d, a $C_{2-6}$ alkynyl group which may have one or more substituents selected from the substituent group d, a $C_{3-8}$ cycloalkyl group which may have one or more substituents selected from the substituent group d, a $C_{3-8}$ cycloalkenyl group which may have one or more substituents selected from the substituent group d, an aryl group which may have one or more substituents selected from the substituent group d, an ar $C_{1-6}$ alkyl group which may have one or more substituents selected from the substituent group d, an $C_{1-6}$ alkoxy group which may have one or more substituents selected from the substituent group d, an acyl group which may have one or more substituents selected from the substituent group d, a $C_{1-6}$ alkylamino group which may have one or more substituents selected from the substituent group d, a di($C_{1-6}$ alkyl)amino group which may have one or more substituents selected from the substituent group d, a heterocyclic group which may have one or more substituents selected from the substituent group d, a heterocyclic $C_{1-8}$ alkyl group which may have one or more substituents selected from the substituent group d, a heterocyclic oxy group which may have one or more substituents selected from the substituent group d, $CONR^cR^d$, and $NHCONR^eR^f$, wherein the substituent group d is selected from the group consisting of a halogen atom, a cyano group, a nitro group, an oxo group, a hydroxyl group which may have a protecting group, an amino group which may have a protecting group, a carboxyl group which may have a protecting group, a $C_{1-8}$ alkyl group which may have one or more substituents selected from the substituent group e, a $C_{2-6}$ alkenyl group which may have one or more substituents selected from the substituent group e, a $C_{2-6}$ alkynyl group which may have one or more substituents selected from the substituent group e, a $C_{3-8}$ cycloalkyl group which may have one or more substituents selected from the substituent group e, an aryl group which may have one or more substituents selected from the substituent group e, a $C_{1-6}$ alkoxy group which may have one or more substituents selected from the substituent group e, an acyl group which may have one or more substituents selected from the substituent group e, a $C_{1-6}$ alkylamino group which may have one or more substituents selected from the substituent group e, a di($C_{1-6}$ alkyl)amino group which may have one or more substituents selected from the substituent group e, a heterocyclic group which may have one or more substituents selected from the substituent group e, and a heterocyclic oxy group which may have one or more substituents selected from the substituent group e, and wherein the substituent group e is selected from the group consisting of a halogen atom, a hydroxyl group which may have a protecting group, a $C_{1-6}$ alkoxy group, and $CONR^gR^h$.

17. The morpholine derivative or a salt thereof according to claim 16, wherein $X^{1a}$ is $CH_2$ or S.

18. The morpholine derivative or a salt thereof according to claim 16, wherein $X^2$ is O or S.

19. The morpholine derivative or a salt thereof according to claim 16, wherein $R^{a1}$ is a hydrogen atom; and $R^{b1}$ is a $C_{1-8}$ alkyl group which may have one or more substituents selected from the substituent group f, a $C_{3-8}$ cycloalkyl group which may have one or more substituents selected from the substituent group f, an ar $C_{1-6}$ alkyl group which may have one or more substituents selected from the substituent group f, a $C_{1-6}$ alkylsulfonyl group which may have one or more substituents selected from the substituent group f, a heterocyclic group which may have one or more substituents selected from the substituent group f, or a heterocyclic $C_{1-8}$ alkyl group which may have one or more substituents selected from the substituent group f.

20. The morpholine derivative or a salt thereof according to claim 16,
wherein $R^{a1}$ is a hydrogen atom; and
$R^{b1}$ is a $C_{3-8}$ cycloalkyl group which may have one or more substituents selected from the substituent group f, a heterocyclic group which may have one or more substituents selected from the substituent group f, or a heterocyclic $C_{1-8}$ alkyl group which may have one or more substituents selected from the substituent group f.

21. A pharmaceutical composition containing the morpholine derivative or a salt thereof according to claim 1 and a pharmacologically acceptable additive.

22. A method for treating cancer or a disease, wherein the disease is caused by retroviral infection, the method including administrating an effective amount of the morpholine derivative or a salt thereof according to claim 1 to a subject.

23. A method for enhancing a sensitivity to an ionizing radiation or an anticancer agent having effects similar to the ionizing radiation, the method including administering an effective amount of the morpholine derivative or a salt thereof according to claim 1 to a subject.

* * * * *